US007157487B2

(12) United States Patent
Nakayama et al.

(10) Patent No.: US 7,157,487 B2
(45) Date of Patent: Jan. 2, 2007

(54) VLA-4 INHIBITORS

(75) Inventors: Atsushi Nakayama, Tokyo (JP); Nobuo Machinaga, Tokyo (JP); Yoshiyuki Yoneda, Tokyo (JP); Yuichi Sugimoto, Tokyo (JP); Jun Chiba, Tokyo (JP); Toshiyuki Watanabe, Tokyo (JP); Shin Iimura, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 68 days.

(21) Appl. No.: 10/451,159

(22) PCT Filed: Dec. 28, 2001

(86) PCT No.: PCT/JP01/11641

§ 371 (c)(1),
(2), (4) Date: Jun. 30, 2003

(87) PCT Pub. No.: WO02/053534

PCT Pub. Date: Jul. 11, 2002

(65) Prior Publication Data

US 2004/0110945 A1 Jun. 10, 2004

(30) Foreign Application Priority Data

Dec. 28, 2000 (JP) ............................. 2000-402890
May 18, 2001 (JP) ............................. 2001-149923

(51) Int. Cl.
*A61K 31/405* (2006.01)
*C07D 209/04* (2006.01)
(52) U.S. Cl. ...................................... 514/415; 548/490
(58) Field of Classification Search ................ 548/490; 514/415
See application file for complete search history.

(56) References Cited

U.S. PATENT DOCUMENTS

| 4,184,658 A | 1/1980 | Barahia |
| 4,221,815 A | 9/1980 | Weyer et al. |
| 6,117,901 A | 9/2000 | Wu et al. |
| 6,495,525 B1 * | 12/2002 | Lee et al. ............... 514/43 |
| 6,756,378 B1 * | 6/2004 | Baldwin et al. ....... 514/254.01 |

FOREIGN PATENT DOCUMENTS

| DE | 2500157 | 7/1976 |
| EP | 23569 | 2/1981 |
| EP | 585155 | 3/1994 |
| EP | 0 842 945 A2 | 5/1998 |
| JP | 60-181081 | 9/1985 |
| JP | 4-112868 | 4/1992 |
| JP | 5-43574 | 2/1993 |
| JP | 2000-344666 | 12/2000 |
| WO | 95/30673 | 11/1995 |
| WO | 96/04267 | 2/1996 |
| WO | WO 96/22966 | 8/1996 |
| WO | 97/02024 | 1/1997 |
| WO | WO 97/03094 | 1/1997 |
| WO | 97/22619 | 6/1997 |
| WO | WO 98/04247 | 2/1998 |
| WO | WO 98/04913 | 2/1998 |
| WO | 98/08818 | 3/1998 |
| WO | 98/22430 | 5/1998 |

(Continued)

OTHER PUBLICATIONS

Craig Zimmerman; "Peptide and peptidomimetic inhibitors of VLA-4," Exp. Opin. Ther. Patents (1999) 9(2); 129-133, especially p. 130.*

(Continued)

*Primary Examiner*—Joseph K. McKane
*Assistant Examiner*—Susannah L. Chung
(74) *Attorney, Agent, or Firm*—Oblon, Spivak, McClelland, Maier & Neustadt, P.C.

(57) ABSTRACT

The present invention relates to a compound represented by the following formula (I):

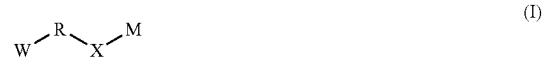

(wherein, W represents $W^A$-$A^1$-$W^B$- (in which, $W^A$ is substituted or unsubstituted aryl, etc., $A^1$ is —$NR^1$—, single bond, —C(O)—, etc., and $W^B$ is substituted or unsubstituted arylene, etc.), R is single bond, —NH—, —$OCH_2$—, alkenylene, etc., X is —C(O)—, —$CH_2$—, etc., and M is, for example, the following formula:

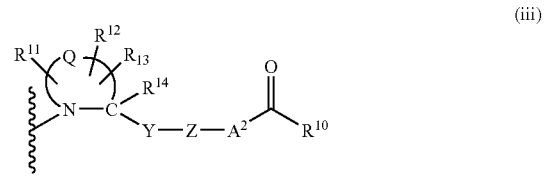

(in which, $R^{11}$, $R^{12}$ and $R^{13}$ each independently represents hydrogen, hydroxyl, amino, halogen, etc., $R^{14}$ is hydrogen or lower alkyl, Y represents —$CH_2$—O—, etc., Z is substituted or unsubstituted arylene, etc., $A^2$ is single bond, etc, and $R^{10}$ is hydroxyl or lower alkoxy)), or salt thereof; and a medicament containing the same.

This compound or salt thereof selectively inhibits binding of cell adhesion molecules to VLA-4 and exhibits high bioavailability so that it is useful as a preventive and/or remedy for inflammatory diseases, autoimmune diseases, metastasis, bronchial asthma, rhinostenosis, diabetes, and the like.

21 Claims, No Drawings

FOREIGN PATENT DOCUMENTS

| | | |
|---|---|---|
| WO | WO 99/33789 | 7/1999 |
| WO | 99/43672 | 9/1999 |
| WO | 99/64392 | 12/1999 |
| WO | WO 99/61421 | 12/1999 |
| WO | WO 00/00477 | 1/2000 |
| WO | 00/05223 | 2/2000 |
| WO | WO 00/05224 | 2/2000 |
| WO | WO 00/15612 | 3/2000 |
| WO | 00/18770 | 4/2000 |
| WO | 00/40088 | 7/2000 |
| WO | WO 00/49005 | 8/2000 |
| WO | WO 00/61580 | 10/2000 |
| WO | 00/66119 | 11/2000 |
| WO | WO 00/68195 | 11/2000 |
| WO | WO 00/68213 | 11/2000 |
| WO | WO 00/68223 | 11/2000 |
| WO | WO 01/00206 A1 | 1/2001 |
| WO | WO 01/12186 A1 | 2/2001 |
| WO | 01/34567 | 5/2001 |
| WO | 01/51487 | 7/2001 |
| WO | WO 01/53295 A1 | 7/2001 |
| WO | WO 01/58871 A1 | 8/2001 |
| WO | WO 01/64640 A1 | 9/2001 |
| WO | WO 01/64659 A2 | 9/2001 |
| WO | 02/04425 | 1/2002 |
| WO | 02/06222 | 1/2002 |
| WO | WO 03/004460 A2 | 1/2003 |

OTHER PUBLICATIONS

Duplantier et al., "Isooxazolyl, oxazolyl, and thiazdylpropionic acid derivatives as potent α4β1 Integrin Antagonists," Bioorganic & Med. Chem. Lett. 11 (2001) 2593-2596, especially p. 2593.*

Yang et al., "VLA-4 Antagonists: Potent Inhibitors of Lymphocyte Migration," Med. Res. Reviews, vol. 23, No. 3, 369-392 (2003), especially p. 370.*

Jefferson W. Tilley, et al., "VLA-4 antagonists", Drugs of the Future, vol. 26, No. 10, 2001, pp. 985-998.

Ginger X. Yang, et al., "VLA-4 Antagonists: Potent Inhibitors of Lymphocyte Migration", Medicinal Research Reviews, vol. 23, No. 3, 2003, pp. 369-392.

Craig N. Zimmerman, "Peptide and peptidomimetic inhibitors of VLA-4", Exp. Opin. Ther. Patents, vol. 9, No. 2 1999, pp. 129-133.

Allen J. Duplantier, et al., "Isoxazolyl, Oxazolyl, and Thiazolylpropionic Acid Derivatives as Potent $\alpha_4\beta_1$ Integrin Antagonists", Bioorganic and Medicinal Chemistry Letters, vol. 11, 2001, pp. 2593-2595.

E. Kudlacz, et al., "Pulmonary Eosinophilia in a Murine Model of Allergic Inflammation is Attenuated by Small Molecule_$\alpha_4\beta_1$ Antagonists", The Journal of Pharmacology and Experimental Therapeutics, vol. 301, No. 2, May 2002, pp. 747-752.

Daniel M. Scott, et al., "High-Affinity Antagonists of the A4B1 Integrin", 220th ACS National Meeting (Washington, DC)/MEDI, 178, 1 page, 2002.

J. Med. Chem., vol. 43, No. 3, pp. 392-400 2000.

* cited by examiner

VLA-4 INHIBITORS

TECHNICAL FIELD

The present invention relates to novel compounds or salts thereof having inhibitory action on VLA-4 (Very Late Antigen-4), and medicaments having these compounds as an effective ingredient.

BACKGROUND ART

A main pathological feature of inflammatory and autoimmune diseases resides in accumulation of activated leukocytes on a damaged tissue (inflammated tissue). A process of leukocytes from migration out of the circulatory system to transmigration on the inflammatory site involves four-step cascade reactions which interact each other: (1) adhesion and rolling, (2) activation, (3) firm adhesion and (4) transmigration (Springer, T., *Ann. Rev. Physiol.*, 57: 827(1995)).

First, leukocytes adhere to the vascular endothelium to a slight degree and roll on its surface. Then, activation of cells mediated by soluble chemoattractants occurs, which starts formation of firmer bonding between leukocytes to vascular endothelial cells. This firm bonding successively causes adhesion and transmigration of leukocytes across the space between the vascular endothelial cells. These steps occur continuously and each step is indispensable for occurrence of leukocyte transmigration. This also suggests that leukocyte transmigration is controlled at each step. This fact provides many interesting themes from the viewpoint of pharmaceutics.

A number of receptors in vivo are known. Among them, receptors taking part in leukocyte transmigration are characterized in that they belong to the cell adhesion molecule family (Carlos and Harlan, *Blood*, 82: 2068(1994)). The initial adhesion and rolling are mediated by an adhesion receptor called "selectin". Firm adhesion is mediated by mutual action between integrins on the leukocyte surface and immunoglobulin superfamily molecules expressed on the vascular endothelial surface. Both of these integrins and immunoglobulin type adhesion molecules mainly participate in leukocyte transmigration. Whether leukocytes pass through the extracellular matrix or stop at the inflammatory site after transmigration depends on integrins.

Integrins are a large family of heterodimeric glycoproteins in each of which two non-equivalent α and β-subunits are associated (Heynes, R., *Cell*, 69: 11(1992)). There exist at least 16 α-subunits (α-1 to α-9, αL, αM, αD, αX, αE, αIIb, αV) which are different each other and at least 9 β-subunits (β-1 to β9) which are different each other. Integrins are classified into subfamilies based on β-subunits. Leukocytes express many different integrins including α4β1, α5β1, α6β1, α4β7, αLβ2, αXβ2 and αVβ3.

The integrin α4β1 is known as a very late antigen (very late antigen-4; VLA-4) or CD49d/CD29. It is expressed by monocytes, lymphocytes, eosinophils and basocytes and serves as a modification factor to be a key in various inflammatory deficiencies (Helmer, M. *Ann. Rev. Immunol.*, 8: 365(1990)). The integrin α4β1 functions as a receptor for vascular cell adhesion molecule-1 (VCAM-1) and also as a receptor for fibronectin (FN) of extracellular protein (Elices, et al., *Cell*, 60: 577(1990)).

In recent years, it has been proved by the below-described studies that selective inhibition against adhesion mediated by α4β1/VCAM-1 will become a solving means for the treatment of autoimmune and allergic inflammatory diseases.

Described specifically, an in vivo experiment has proved that a monoclonal antibody which blocks the pathway of α4β1/ VCAM-1 has anti-inflammatory effects and retards the progress of the diseases (Lobb et al., *J. Clin., Invest.*, 94: 1722–28(1944)). In addition, reported are suppression, by an anti-α4 antibody, of both antigen-induced airway hypersensitivity and accumulation of leukocytes in airway alveolar secretion in guinea pigs used a pulmonary inflammation model (Pretolani, et al., *J. Exp. Med.*, 180: 795(1994); suppression, by α4 or VCAM-1 antibody, of eosinophil transmigration on the airway of mice used as an antigen-induced model (Nakajima et al., *J. Exp. Med.*, 179: 1145 (1994)), retardation or suppression, by α4 or VCAM-1 monoclonal antibody treatment, of onset of delayed dermal hypersensitivity in mice and monkeys (Chisholm et al., *Eur. J. Immunol.*, 179: 1145(1994), Silber et al., *J. Clin., Invest.*, 93: 1554(1993)); a model of cardiac transplantation rejection due to (incidental to) specific immunosuppressive action (Isobe et al., *J. Immunol.*, 153: 5810(1994)); graft versus host disease after bone marrow transplantation in mice (Yang et al., *Proc. Natl. Acad. Sci. USA*, 90; 10494 (1993)); and experimental autoimmune encephalomyelitis in rats and mice (Yednock, et al., *Nature.*, 356: 63(1992), Baron, et al., *J. Exp. Med.*, 177: 57(1993)).

In addition, there is a report on significant retardation of the onset of diabetes by administration, to nonobese diabetic mice used as an in vivo model, of soluble VCAM-immunoglobulin (Ig) fusion protein prepared by fusing two human N-terminal regions to the common portion of human IgG1 in accordance with Rational Drug Design (Significant delays the onset of adoptively transferred autoimmune diabetes in nonobese mice (Jakubowski et al., *J. Immunmol.*, 155: 938(1995)). Another report is that as a result of synthesis of a cyclic peptide antagonist by using the three-dimensional crystal structure of a VCAM-1 fragment for mimicking the binding loop portion of α4 integrin at the domain-1 of VCAM-1, CQIDSPC of the synthesized VCAM-1 peptide succeeded in inhibiting adhesion of VLA-4 expressed cells to purified VCAM-1 (Wang et al., *Proc. Natl. Acad. Sci. USA*, 92: 5714(1995)).

Reported as another strategy are blocking of adhesion of α4β1 to either one of binding sites of its corresponding receptor, that is, fibronectin including connecting segment-1 (CS-1) domain (E. A. Wayner, *J. Cell. Biol.*, 116; 489 (1992)); and in vitro inhibition, by synthetic CS-1 tetrapeptide (phenylacetic acid-Leu-Asp-Phe-d-Pro-amide), of leukocyte adhesion mediated by VLA-4 and amelioration of advance of coronary arterial diseases in cardiac transplantation of rabbits (Molossi et al., *J. Clin. Invest.*, 95: 2601 (1995)).

In addition, there are several reports on compounds exhibiting in vitro VLA-4 inhibitory activity (U.S. Pat. No. 5,821,231, WO96/22966, WO97/03094, WO98/04247 and WO98/04913)

Medicaments exhibiting sufficient effectiveness in oral administration and having clinical utility however have not yet been found.

An object of the present invention is therefore to provide a medicament which serves a selective inhibitor against VLA-4, exhibits effectiveness by oral administration and is administrable for a long period of time.

DISCLOSURE OF THE INVENTION

With the foregoing in view, the present inventors have carried out an investigation on low-molecular-weight and non-peptide compounds. As a result, it has been found that compounds represented by the below-described formula (I) selectively inhibit bonding of cell adhesion molecules to VLA-4 and are useful for prevention or treatment of various diseases mediated by migration and adhesion of leukocytes, leading to the completion of the present invention.

In the present invention, there are thus provided a compound represented by the following formula (I):

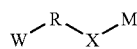
(I)

(wherein, W represents $W^A$-$A^1$-$W^B$- (in which, $W^A$ represents a substituted or unsubstituted aryl group or a substituted or unsubstituted monovalent heterocyclic group, $A^1$ represents —$NR^1$—, a single bond, —C(O)—, —C(O) $NR^1$—, a substituted or unsubstituted vinylene group, an ethynylene group, —$CR^{1a}R^{1b}$—O—, —$CR^{1a}$=$CR^{1b}$—C(O)$NR^1$— or —$CR^{1a}$=$CR^{1b}$—C(O)— (in which, $R^1$ represents a hydrogen atom or a lower alkyl group, and $R^{1a}$ and $R^{1b}$ each independently represents a hydrogen atom or a lower alkyl group), and $W^B$ represents a substituted or unsubstituted arylene group or a substituted or unsubstituted divalent heterocyclic group);

R represents a single bond, —NH—, —$OCH_2$—, an alkenylene group or —$(CH_2)_n$— (in which, n stands for 1 or 2);

X represents —C(O)—, —$CH_2$— or —$S(O)_2$—, and M represents the following formula (iii), (iv) or (v):

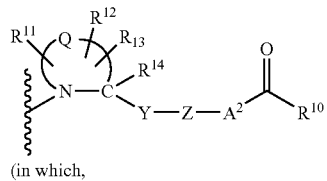
(iii)

(in which,

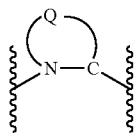
(iii-a)

represents a divalent 4-, 5-, 6- or 7-membered heterocyclic group (in which the nitrogen atom is bonded to X and Q represents a carbon, sulfur, oxygen or nitrogen atom), $R^{11}$, $R^{12}$ and $R^{13}$ each independently represents a hydrogen atom, a hydroxyl group, an amino group, a halogen atom, a cyano group, a carboxyl group, an alkoxycarbonyl group, a carbamoyl group, a substituted or unsubstituted mono- or dialkylaminocarbonyl group, a substituted or unsubstituted alkyl group, a substituted or unsubstituted aryl group, a substituted or unsubstituted heteroaryl group, a substituted or unsubstituted alkoxy group, a substituted or unsubstituted mono- or dialkylamino group, a substituted or unsubstituted cycloalkylamino group, a substituted or unsubstituted alkylsulfonylamino group, a substituted or unsubstituted arylsulfonylamino group, a substituted or unsubstituted aryloxy group, a substituted or unsubstituted heteroaryloxy group, a substituted or unsubstituted benzyloxy group, a substituted or unsubstituted alkylthio group, a substituted or unsubstituted cycloalkylthio group, a substituted or unsubstituted arylthio group, a substituted or unsubstituted alkylsulfonyl group, a substituted or unsubstituted cycloalkylsulfonyl group, or a substituted or unsubstituted arylsulfonyl group, or $R^{11}$ and $R^{12}$ or $R^{12}$ and $R^{13}$ may be coupled to form, together with the atom constituting the heterocyclic group to which $R^{11}$ to $R^{13}$ are bonded, a 3 to 7-membered cyclic hydrocarbon or heterocycle (the cyclic hydrocarbon and the heterocycle may have thereon 1 to 3 substituents selected from a hydroxyl group, halogen atoms, an amino group, alkyl groups, alkoxy groups, aryl groups, aryloxy groups, alkylamino groups, a benzyloxy group and heteroaryl groups), $R^{14}$ represents a hydrogen atom or a substituted or unsubstituted lower alkyl group, Y represents a single bond, —C(O)—, —C(O)NH—, or a linear or branched divalent aliphatic $C_{1-12}$ hydrocarbon group which may have a $C_{3-6}$ spiro ring or may have one or more carbon atoms substituted by —O—, —S—, —$S(O)_2$—, —C(O)— or —$NY^1$— (in which, $Y^1$ represents a hydrogen atom or a lower alkyl group), Z represents a substituted or unsubstituted arylene group, a substituted or unsubstituted heteroarylene group or a substituted or unsubstituted cycloalkylene group, $A^2$ represents a single bond, an alkenylene group, an alkynylene group, —$(CH_2)_t$— or —$O(CH_2)_v$— (in which, t stands for 1, 2 or 3 and v stands for 0, 1, 2 or 3), and $R^{10}$ represents a hydroxyl or a lower alkoxy group),

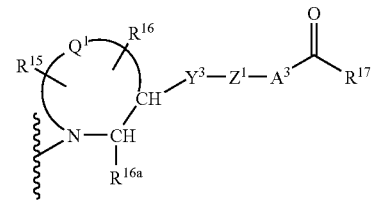
(iv)

(in which,

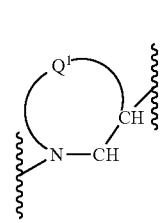
(iv-a)

represents a divalent 4-, 5-, 6- or 7-membered heterocyclic group (in which the nitrogen atom is bonded to X, and $Q^1$ represents a carbon, sulfur, oxygen or nitrogen atom), $R^{15}$ and $R^{16}$ each independently represents a hydrogen atom, a hydroxyl group, a halogen atom, a substituted or unsubstituted alkyl group or an alkoxy group, $R^{16a}$ represents a hydrogen atom or a substituted or unsubstituted alkyl group, $Y^3$ represents —O—, —S—, —$S(O)_2$—, —$(CH_2)_f$O— or —$NY^4$— (in which f stands for 1, 2 or 3 and $Y^4$ represents a hydrogen atom or a lower alkyl group), $Z^1$ represents a substituted or unsubstituted arylene group, a substituted or unsubstituted heteroarylene group or a substituted or unsubstituted cycloalkylene group, $A^3$ represents a single bond, an alkenylene group, an alkynylene group or —$(CH_2)_e$— (in which e stands for 1, 2 or 3), and $R^{17}$ represents a hydroxyl group or a lower alkoxy group),

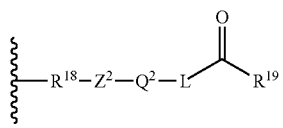

(in which, $R^{18}$ represents —$NR^{20}$— (in which $R^{20}$ represents a hydrogen atom, a substituted or unsubstituted alkyl group, a substituted or unsubstituted cycloalkyl group, a substituted or unsubstituted aryl group, a substituted or unsubstituted benzyl group, a substituted or unsubstituted lower alkenyl group or a substituted or unsubstituted alkynyl group), $Z^2$ represents a linear or branched divalent aliphatic $C_{1-12}$ hydrocarbon group which may have a $C_{3-6}$ Spiro ring, may have one or more carbon atoms substituted by a divalent $C_{3-8}$ cycloalkylene group or may have one or more carbon atoms substituted by —O—, —S—, —$S(O)_2$—, —C(O)— or —$NR^{21}$— (in which, $R^{21}$ represents a hydrogen atom or a substituted or unsubstituted lower alkyl group), $Q^2$ represents a single bond, a substituted or unsubstituted arylene group, a substituted or unsubstituted heteroarylene group or a substituted or unsubstituted cycloalkylene group, L stands for a single bond, a substituted or unsubstituted lower alkylene group or a substituted or unsubstituted lower alkenylene group, or $R^{19}$ represents a hydroxyl or a lower alkoxy group)); or salt thereof; and a medicament containing the same.

In the present invention, there are also provided a medicament and a composition, which comprise a pharmaceutically acceptable carrier and the above-described compound or salt.

In the present invention, there is also provided the use of the above-described compound or salt for the preparation of a medicament.

In the present invention, there is also provided a treating method of a disease caused by cell adhesion, which comprises administering the above-described compound or salt.

BEST MODE FOR CARRYING OUT THE INVENTION

The compound of the present invention is represented by the above-described formula (I). The alkyl group in the formula means a linear or branched saturated hydrocarbon group having 1 to 12, preferably 1 to 8 carbon atoms. Examples include methyl, ethyl, propyl, isopropyl, normal butyl, isobutyl, tertiary butyl, pentyl, heptyl and octyl groups.

The lower alkyl group means a linear or branched saturated hydrocarbon group having 1 to 8, preferably 1 to 6 carbon atoms. Examples include methyl, ethyl, propyl, isopropyl, normal butyl, isobutyl, tertiary butyl and pentyl groups.

The alkylene group means a divalent group formed of the above-exemplified alkyl group. Examples include methylene, ethylene, propylene, isopropylene, normal butylene, isobutylene, pentylene, hexylene, heptylene and octylene groups.

The alkenyl group means a linear or branched $C_{2-12}$, preferably $C_{2-8}$ group formed of an unsaturated hydrocarbon containing at least one double bond. Examples include vinyl, propenyl, isopropenyl, 1-butenyl, 2-butenyl, 1,3-butadienyl, 1-isobutenyl, 1-pentenyl, 1-heptenyl and 1-octenyl groups.

The alkenylene group means a divalent group formed of the above-exemplified alkenyl group. Examples include vinylene, propenylene, isopropenylene, 1-butenylene, 2-vinylene, 1-isobutenylene, 1-pentenylene, 1-heptenylene and 1-octenylene groups.

The alkynyl group means a linear or branched $C_{2-12}$, preferably $C_{2-8}$ group formed of an unsaturated hydrocarbon containing one triple bond. Examples include ethynyl, propynyl, 1-butynyl, 2-butynyl, 1-pentynyl, 1-heptynyl and 1-octynyl groups.

The alkynylene group means a divalent group formed of the above-exemplified alkynyl group. Examples include ethynylene, propynylene, 1-butynylene, 2-butynylene, 1-pentynylene, 1-heptynylene and 1-octynylene groups.

The cycloalkyl group means a cycloalkyl group having 3 to 10, preferably 3 to 6 carbon atoms. Examples include cyclopropyl, cyclobutyl, cyclopentyl and cyclohexyl groups.

The cycloalkylene group means a divalent group formed of the above-exemplified cycloalkyl group. The cycloalkyl group in this case is as described above. Examples include cyclopropylene, cyclobutylene, cyclopentylene and cyclohexylene groups.

The aliphatic hydrocarbon group means a linear, branched or cyclic hydrocarbon group having 1 to 18 carbon atoms, preferably 1 to 12 carbon atoms, and it includes alkyl, cycloalkyl, alkenyl, and alkynyl groups and combinations thereof. Examples include ethyl, propyl, propynyl and 2,4-heptadienyl groups.

The aryl group means an aromatic monocyclic or fused hydrocarbon group having 6 to 18, preferably 6 to 10 carbon atoms and examples include phenyl and naphthyl groups.

The arylene group means a divalent group formed of the above-exemplified aryl group and examples thereof include phenylene and naphthylene groups.

The cyclic hydrocarbon group means a saturated or unsaturated (including aromatic) monocyclic group having 3 to 7 carbon atoms, and examples include cyclopropane, cyclobutane, cyclopentane, cyclopentene, cyclohexane, cyclohexene, cycloheptane and benzene.

The heteroaryl group means a monovalent group formed of a monocyclic or fused aromatic heterocycle having, as the constituent of the ring, 5 to 18 atoms including at least one oxygen, nitrogen and/or sulfur atom, preferably a group formed of an aromatic heterocycle having 5 to 14 atoms. Examples of the monocyclic aromatic heterocycle include pyrrole, 2H-pyrrole, thiophene, furan, imidazole, pyrazole, isoxazole, isothiazole, thiazole, oxazole, oxadiazole, 1,3,4-thiadiazole, triazole, tetrazole, pyrimidine, pyrazine, pyrimidine, pyridazine, 2H-pyran and 4H-pyran. Among the fused aromatic heterocycles, examples of the bicyclic ones include indole, indolizine, isoindole, 1H-indazole, 2H-indazole, purine, 4H-quinolidine, isoquinoline, quinoline, phthalazine, naphthylidine, quinoxaline, quinazoline, cinnoline, benzopyran, benzo(b)thiophene, 2,3-benzofuran, 3,4-benzofuran, benzoxazole, benzothiazole, benzoisoxazole, benzoisothiazole, benzimidazole, benzotriazole, 1H-pyrrolo(2,3-b)pyridine, 1H-pyrrolo(2,3-c)pyridine, 1H-pyrrolo(3,2-c)pyridine, 1H-pyrrolo(3,2-b)pyridine, 3H-pyrrolo(2,3-b)pyridine, 3H-pyrrolo(2,3-c)pyridine, 3H-pyrrolo(3,2-c)pyridine, 3H-pyrrolo(3,2-b)pyridine, dihydropyrrolo(2,3-b)pyridine, dihydropyrrolo(2,3-c)pyridine, dihydropyrrolo(3,2-c)pyridine, dihydropyrrolo(3,2-b)pyridine, oxazolo(4,5-b)pyridine, oxazolo(4,5-c)pyridine, oxazolo(5,4-c)pyridine, oxazolo(5,4-b)pyridine, thiazolo(4,5-b)pyridine, thiazolo(4,5-c)pyridine, thiazolo(5,4-c)pyridine, thiazolo(5,4-b)pyridine and pyrido(1,2-a)pyrimidine. Examples of the tricyclic aromatic heterocycle include carbazole, carboline, phenoxazine, xanthene, xanthone, dibenzofuran and dibenzothiophene.

The heteroarylene group means a divalent group formed of the above-exemplified heteroaryl group.

The heterocyclic group means a group formed of a monocyclic or fused aliphatic or aromatic heterocycle having, as a constituent, 5 to 18 atoms, preferably 5 to 14 atoms including at least one oxygen, nitrogen and/or sulfur atom. Examples of the aromatic heterocyclic group are similar to those exemplified above as the heteroaryl group. Examples of the aliphatic heterocyclic group include pyrrolidine, pyrroline, imidazolidine, imidazoline, indoline, tetrahydrofuran, dihydrofuran, tetrahydrothiophene, dihydrothiophene, thiazolidine, thiazoline, oxazoline, oxazolidine, isoxazolidine, isoxazoline, piperidine, morpholine, thiamorpholine, piperazine, tetrahydropyrane, tetrahydrobenzimidazole, tetrahydrobenzofuran, tetrahydrobenzothiophene, tetrahydrobenzothiazole, tetrahydrobenzoxazole, tetrahydroquinoline, tetrahydroisoquinoline and tetrahydroquinazoline.

The halogen atom means a fluorine, chlorine, bromine or iodine atom.

Examples of the alkoxy group include methoxy, ethoxy, propoxy, isopropoxy, normal butoxy, isobutyloxy, tertiary-butoxy, pentyloxy, hexyloxy, heptyloxy and octyloxy groups.

The lower alkoxy group means a linear or branched alkoxy group having 1 to 8, preferably 1 to 6 carbon atoms and examples include methoxy, ethoxy, propoxy, isopropoxy, normal butoxy, isobutyloxy, tertiary butoxy, pentyloxy and hexyloxy groups.

Examples of the aryloxy group include phenoxy and naphthyloxy groups.

Examples of the heteroaryloxy group include pyridyloxy and indoleoxy groups.

Examples of the alkylthio group include methylthio, ethylthio, propylthio, isopropylthio, normal butylthio, isobutylthio, tertiary butylthio, pentylthio, hexylthio, heptylthio and octylthio groups.

Examples of the cycloalkylthio group include cyclopropylthio, cyclobutylthio, cyclopentylthio, cyclohexylthio and cyclooctylthio groups.

Examples of the arylthio group include phenylthio and naphthylthio groups.

Examples of the alkylsulfonyl group include methylsulfonyl, ethylsulfonyl, propylsulfonyl, isopropylsulfonyl, normal butylsulfonyl, isobutylsulfonyl, tertiary butylsulfonyl, pentylsulfonyl, hexylsulfonyl, heptylsulfonyl and octylsulfonyl groups.

Examples of the cycloalkylsulfonyl group include cyclopropylsulfonyl, cyclobutylsulfonyl, cyclopentylsulfonyl, cyclohexylsulfonyl and cyclooctylsulfonyl groups.

Examples of the arylsulfonyl group include phenylsulfonyl and naphthylsulfonyl groups.

The followings are specific examples of W-R-X- in the formula (I).

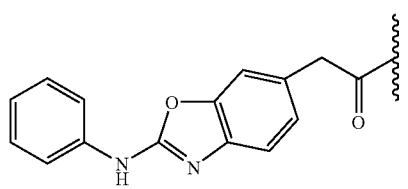

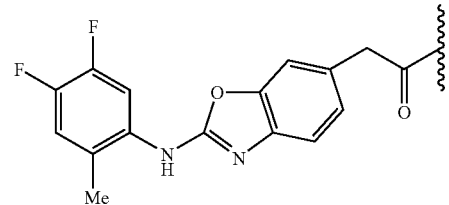

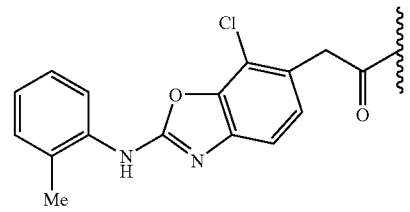

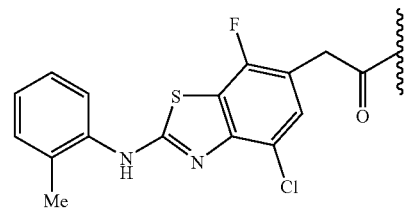

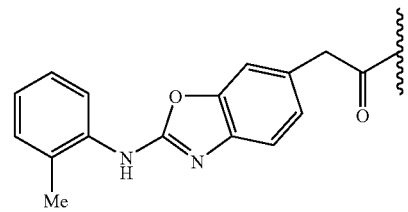

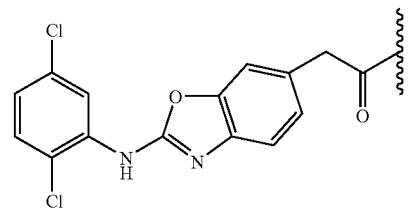

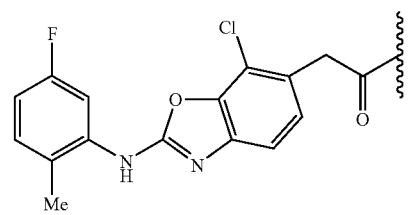

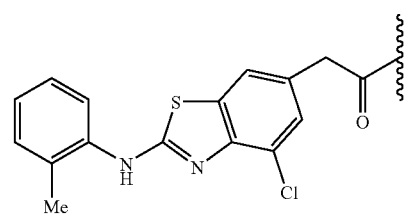

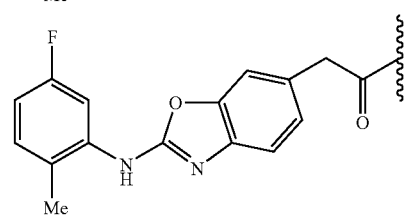

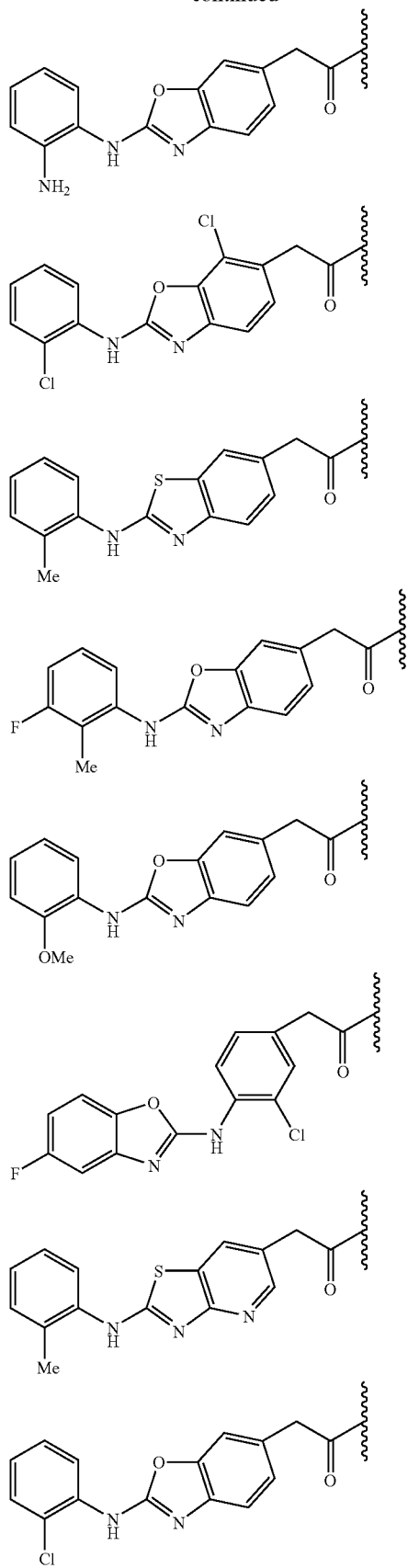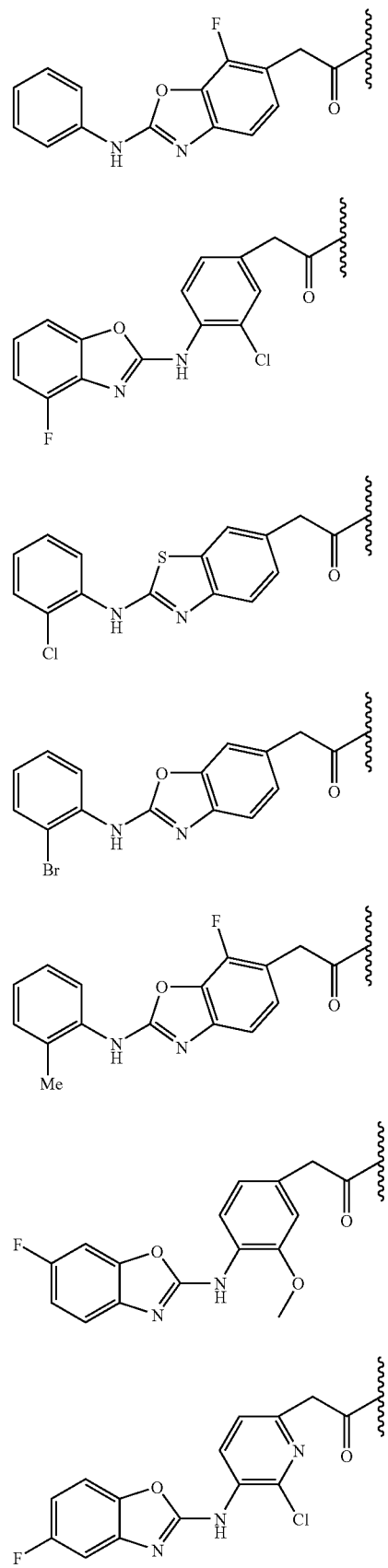

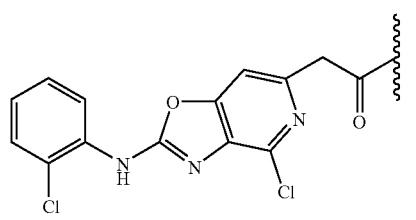
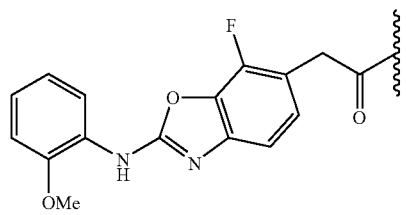
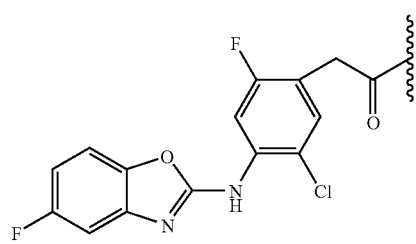
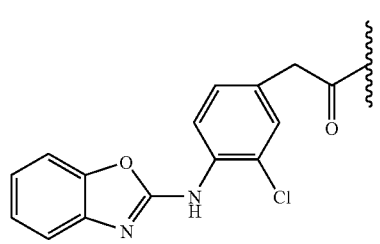
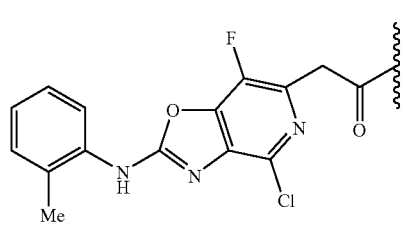
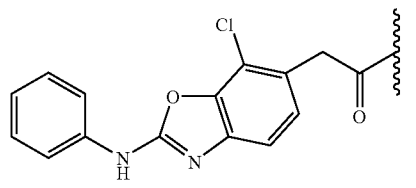
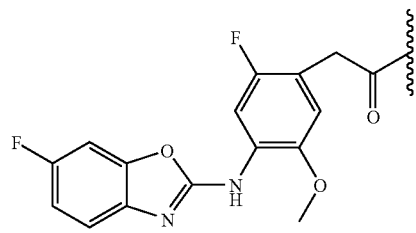
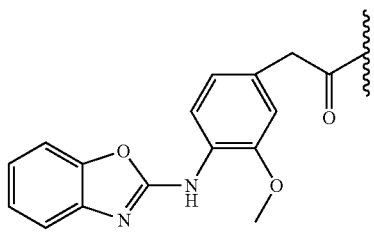
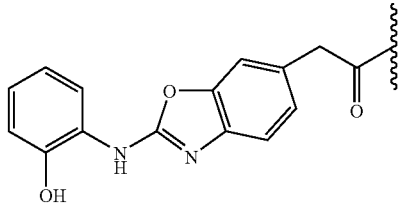
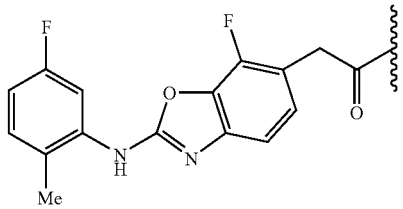
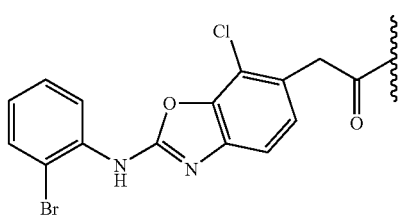
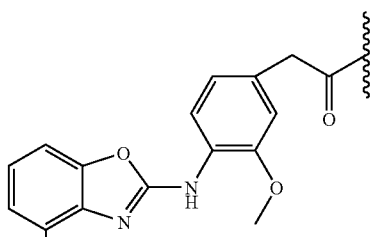
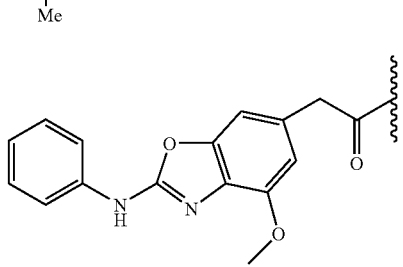
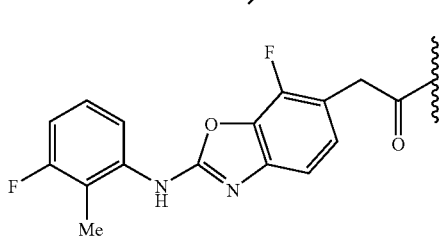

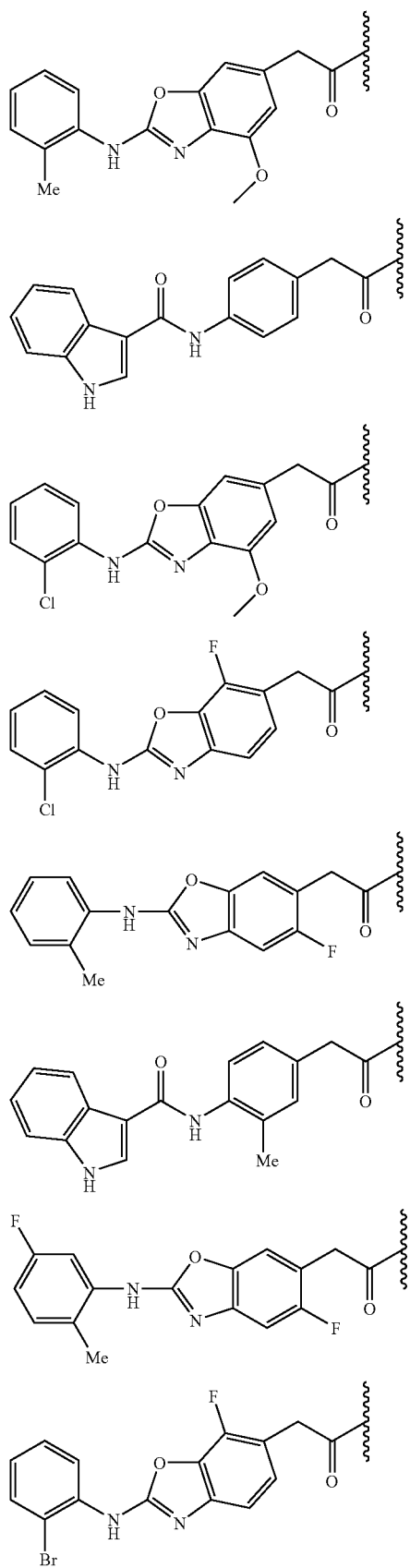
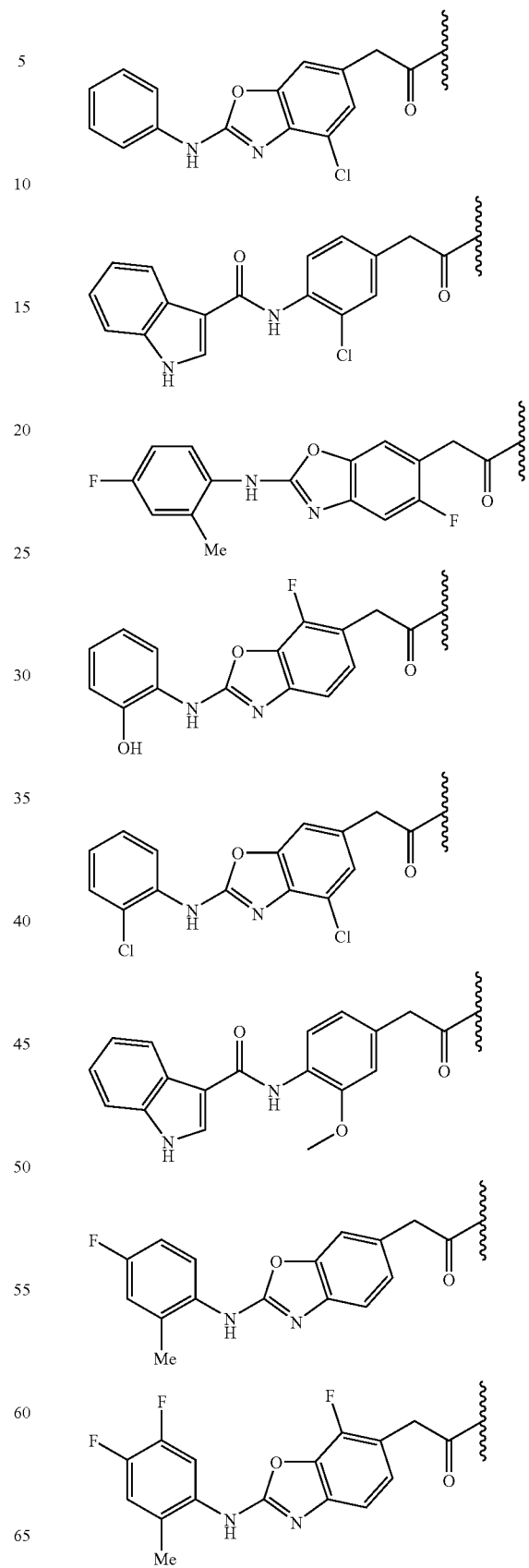

-continued
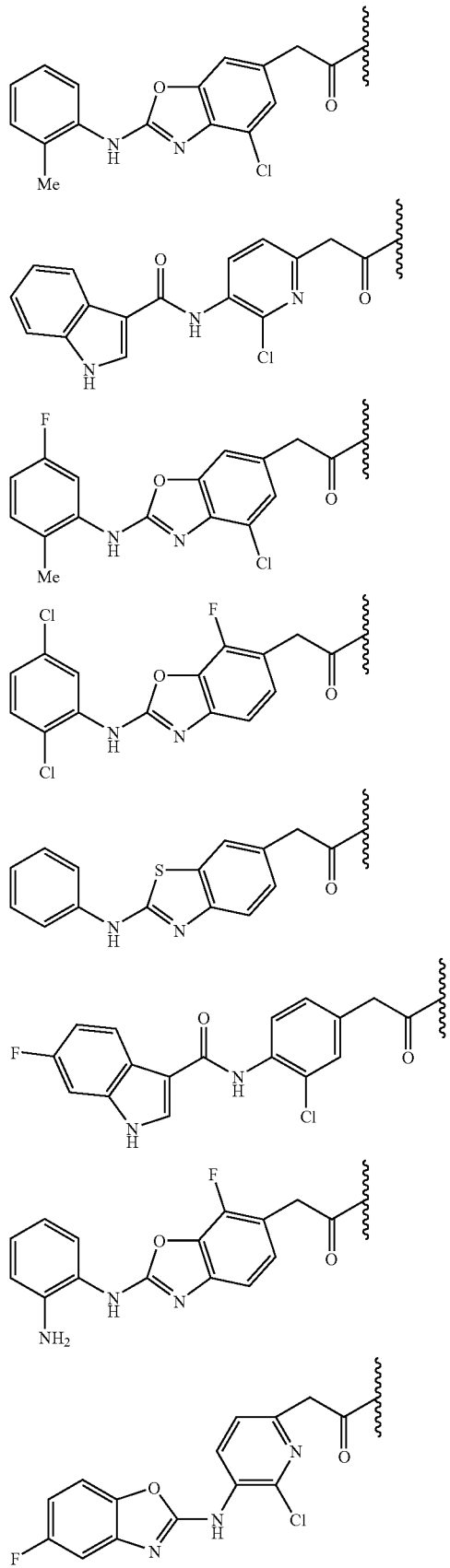
-continued
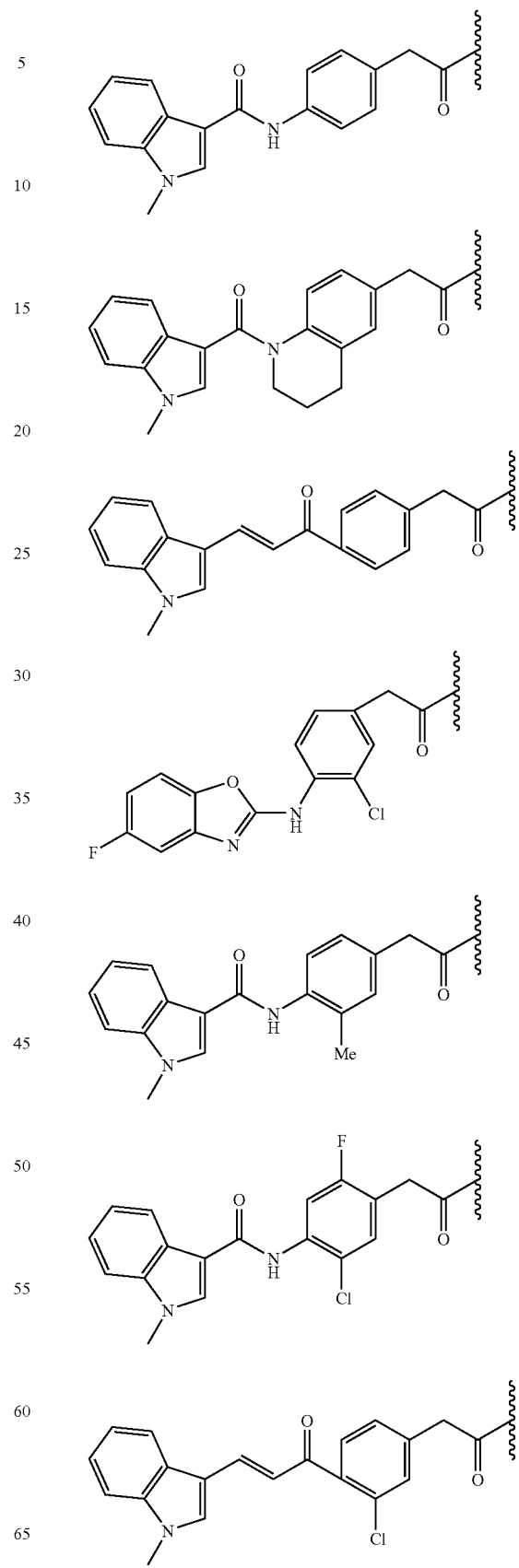

-continued
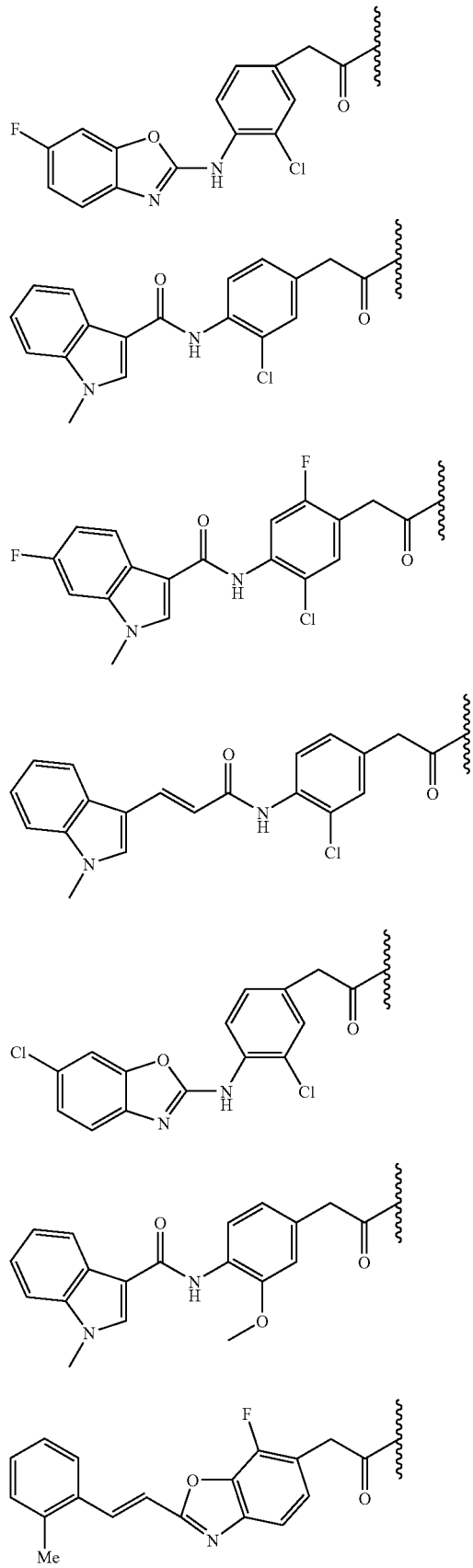
-continued
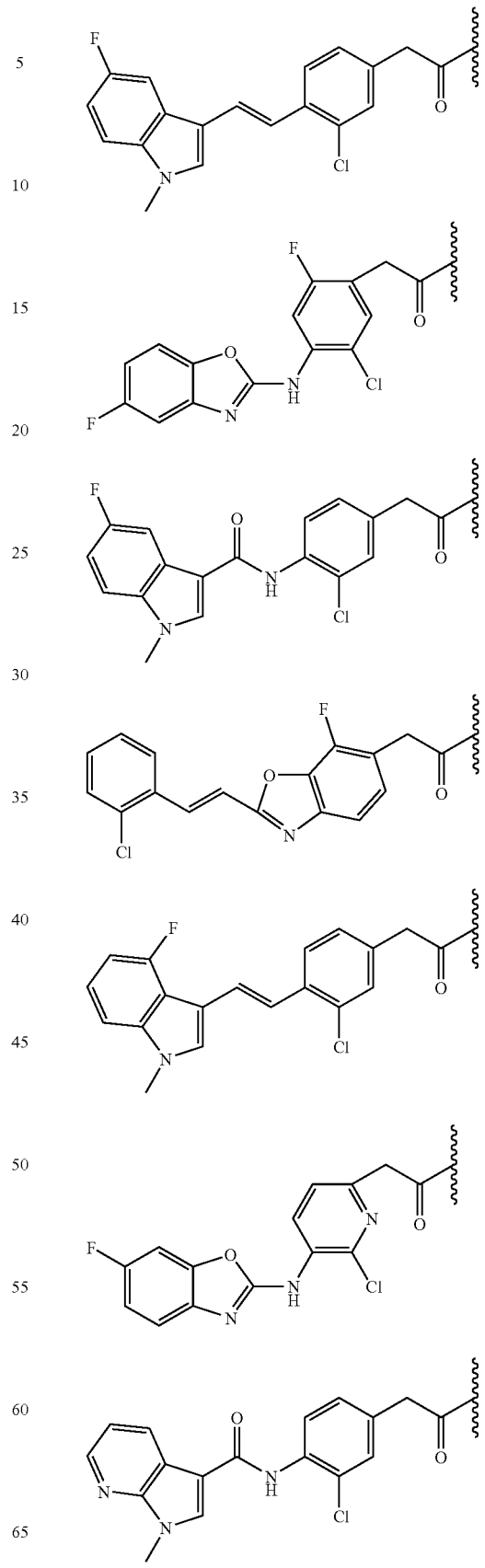

-continued
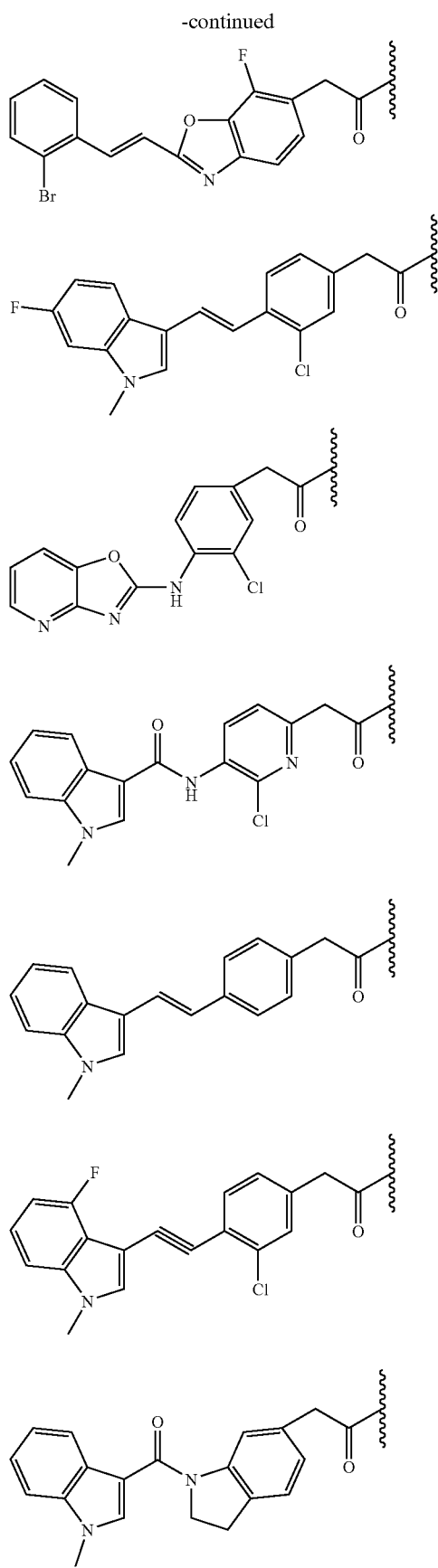
-continued
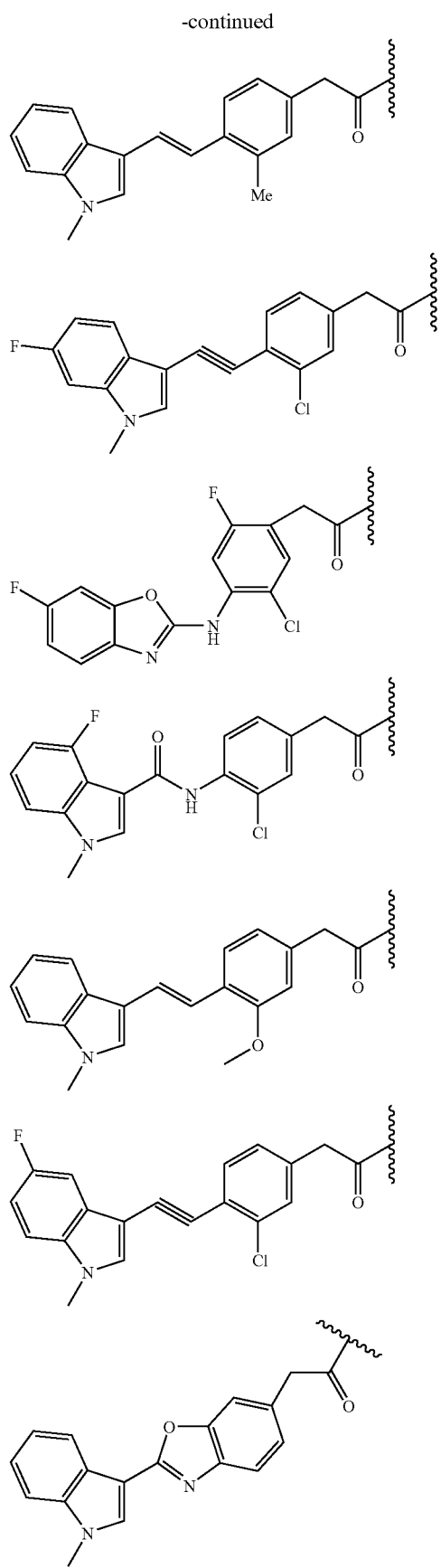

-continued
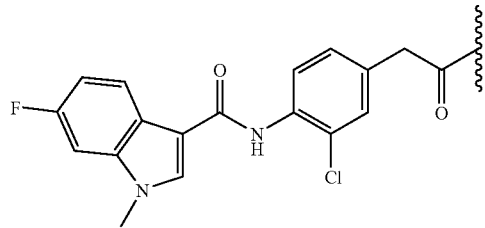
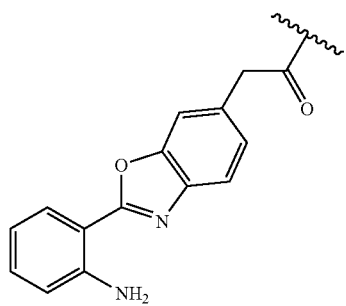
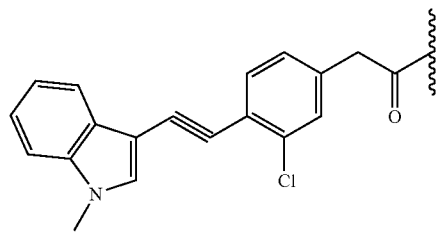
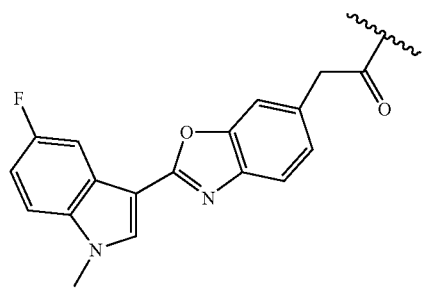
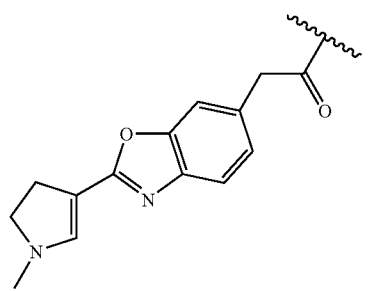
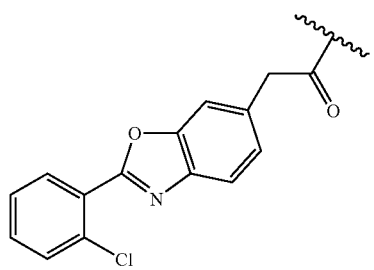
-continued
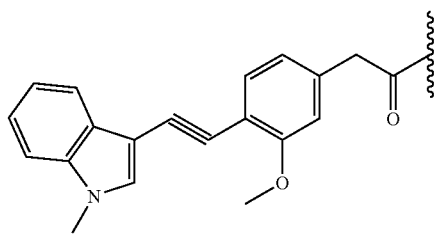
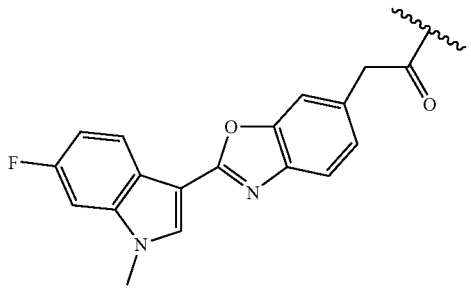
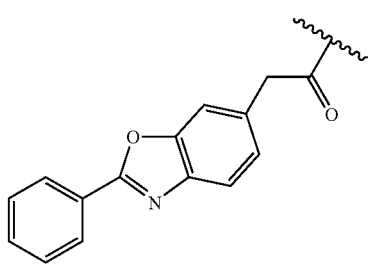
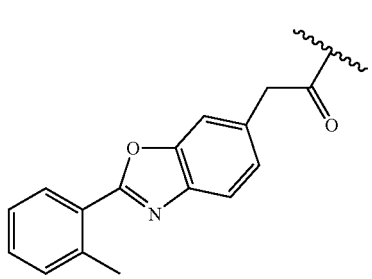
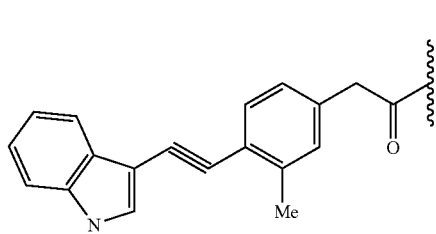
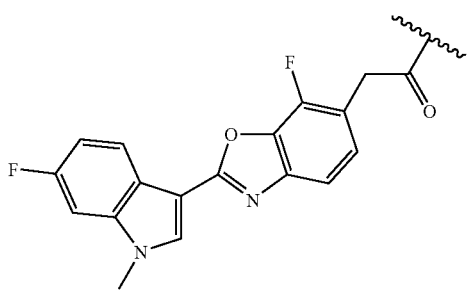

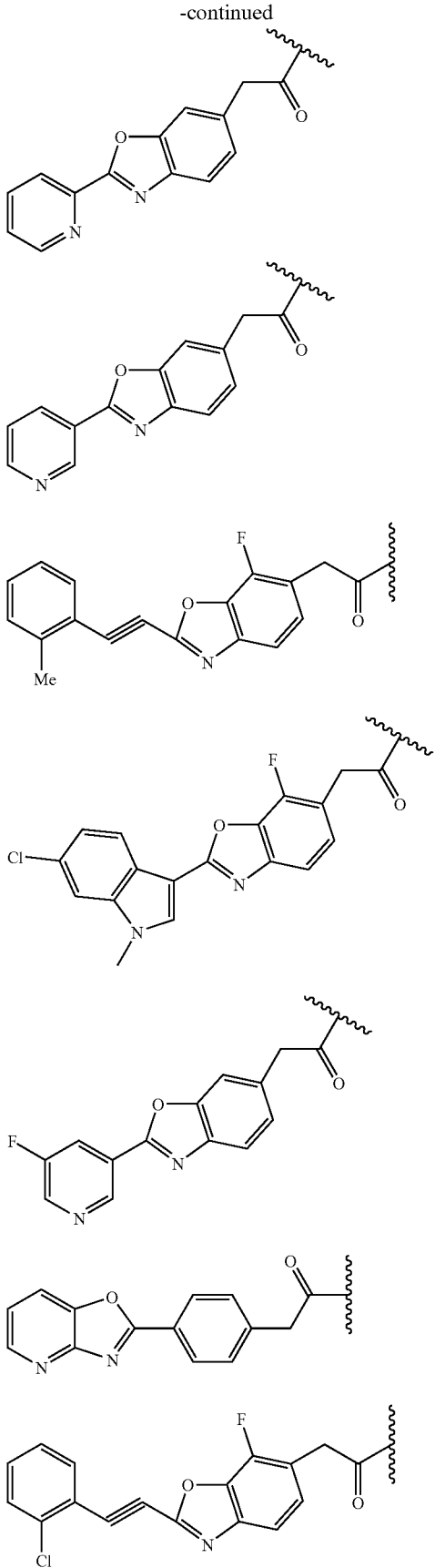
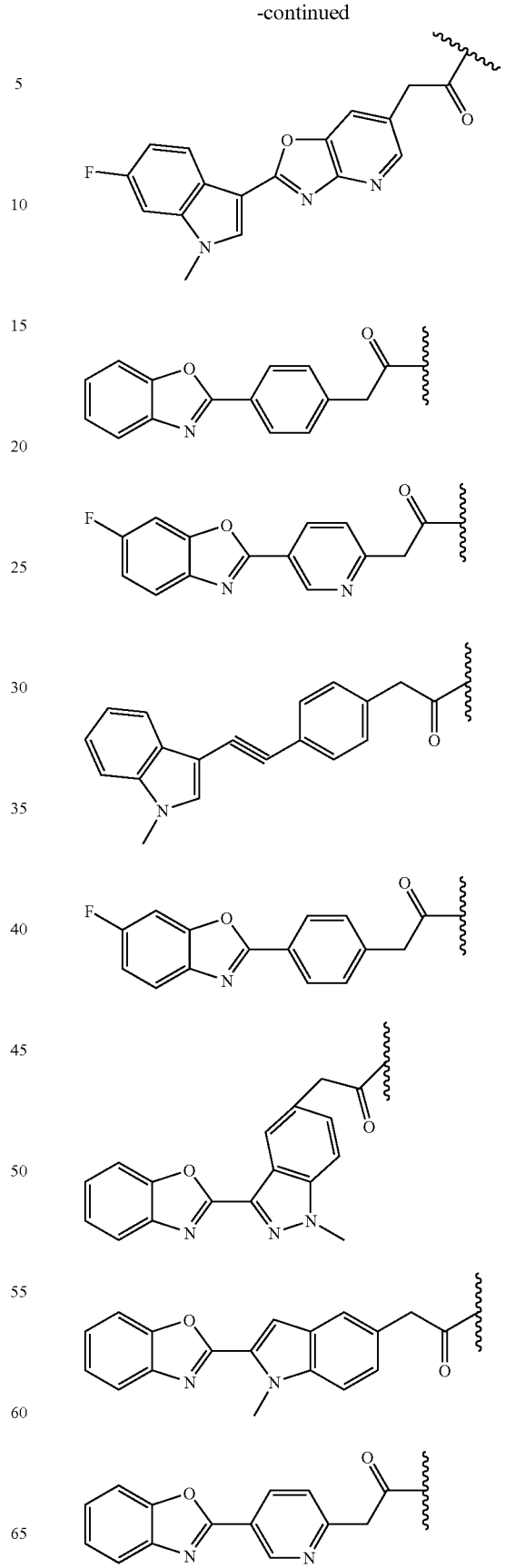

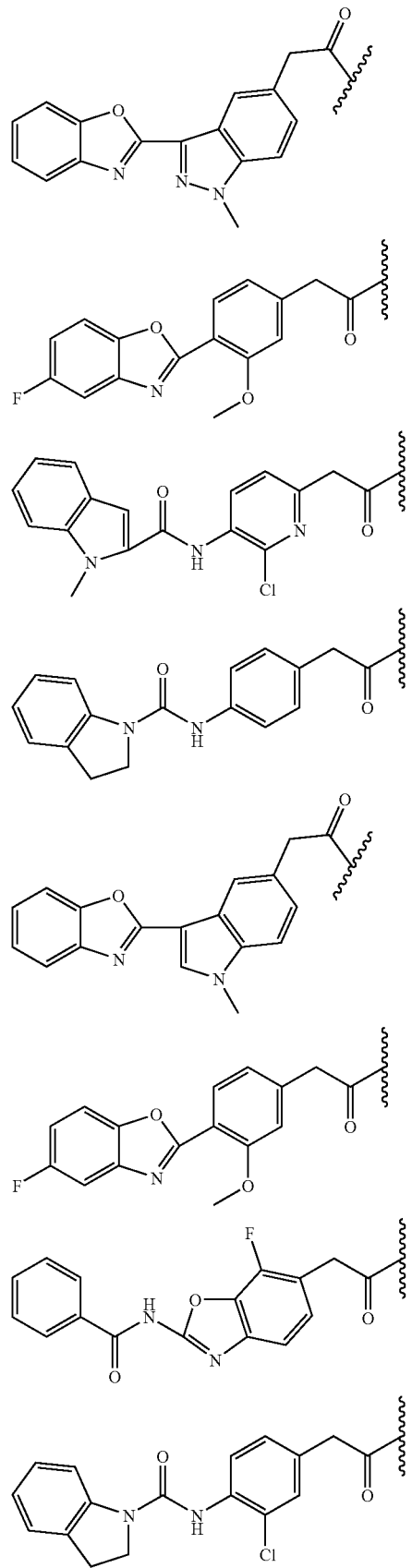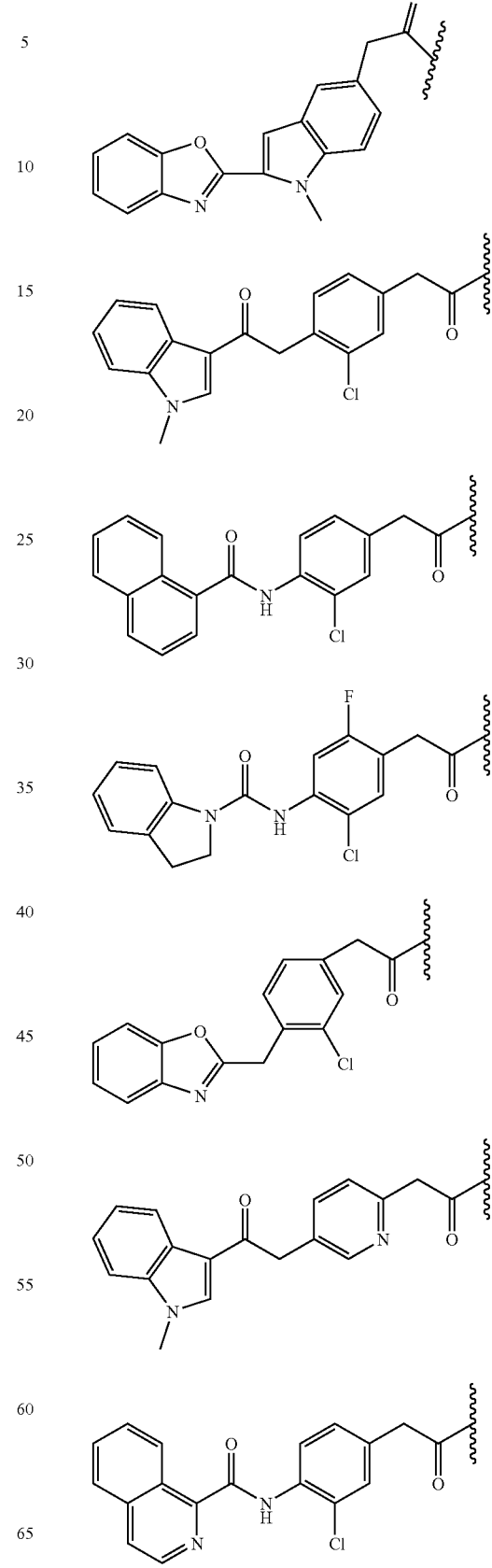

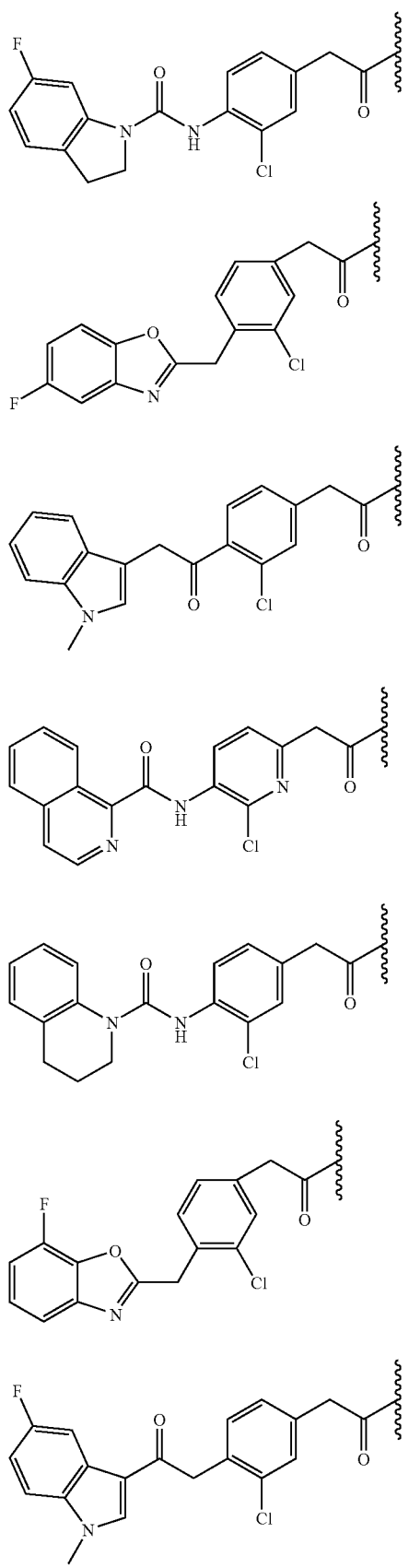
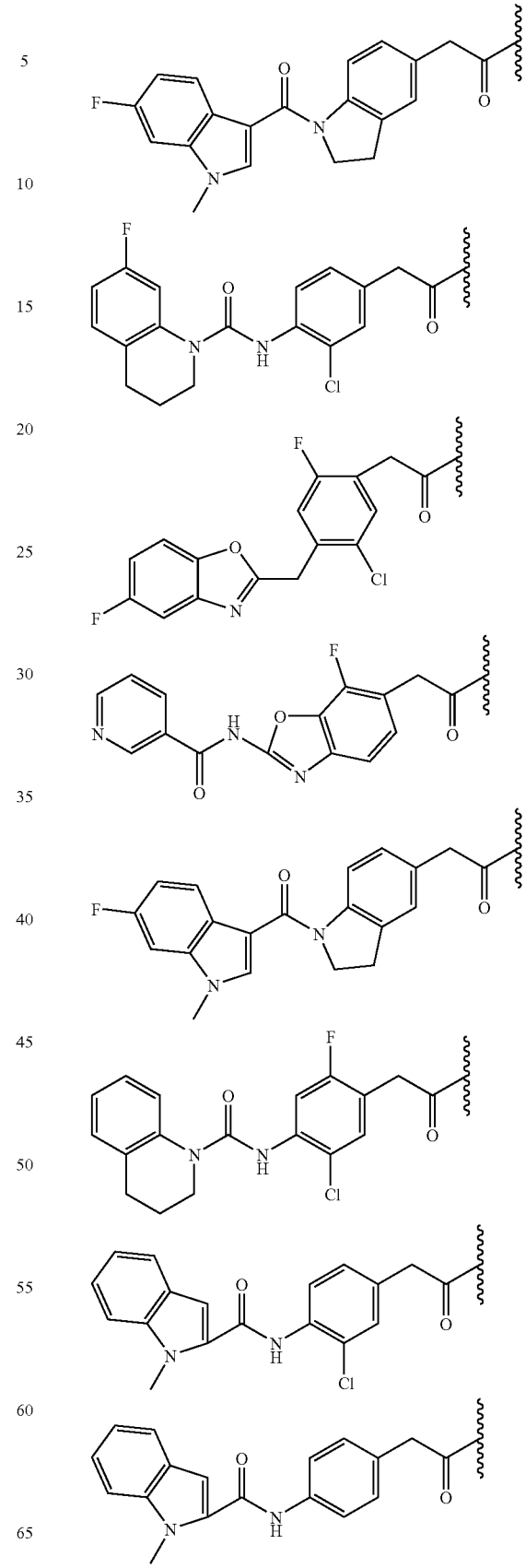

-continued
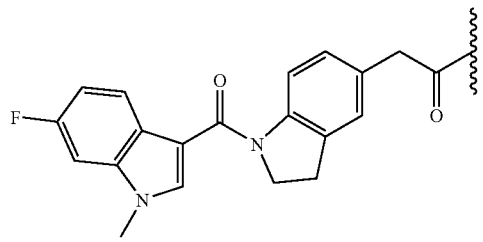 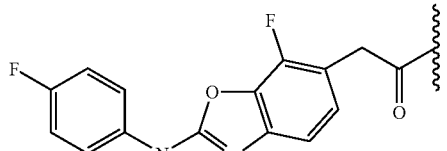
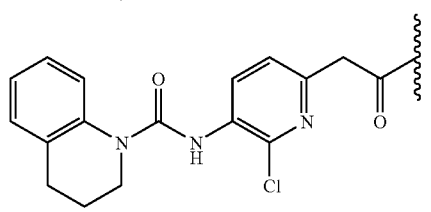 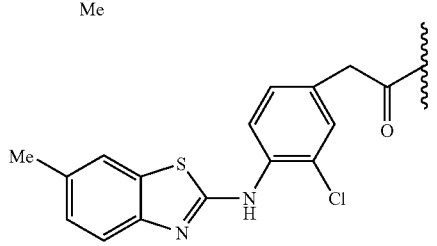
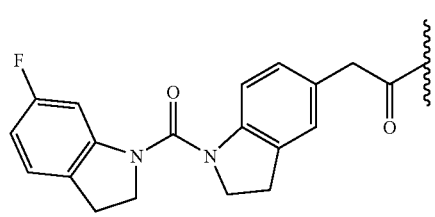 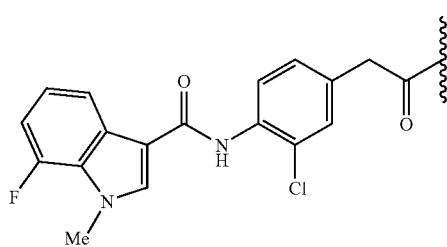
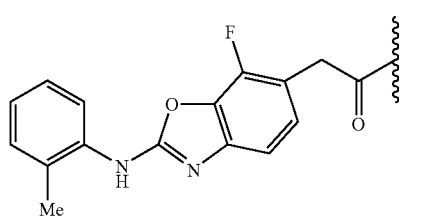 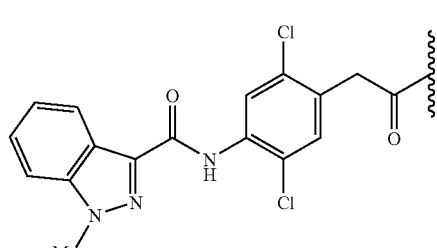
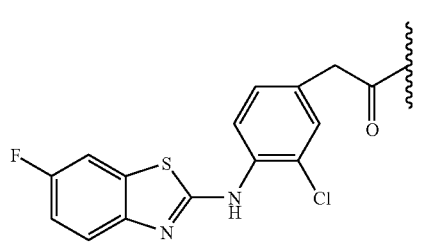 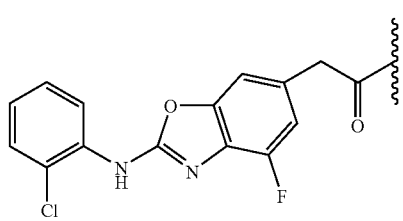
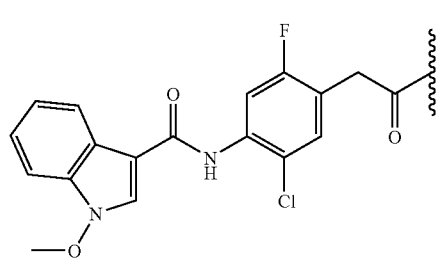 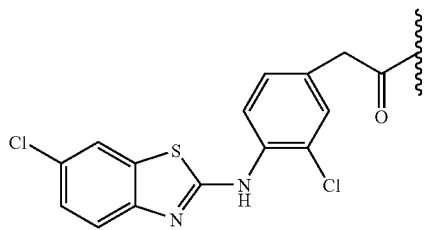
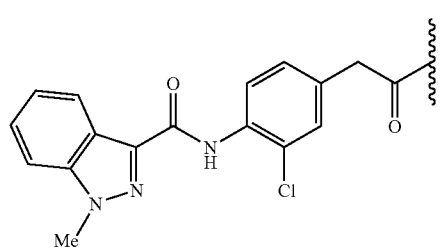 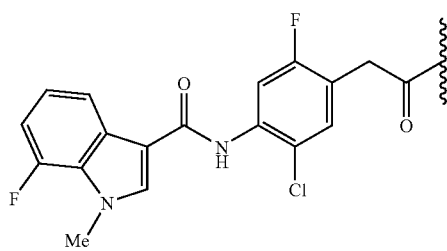

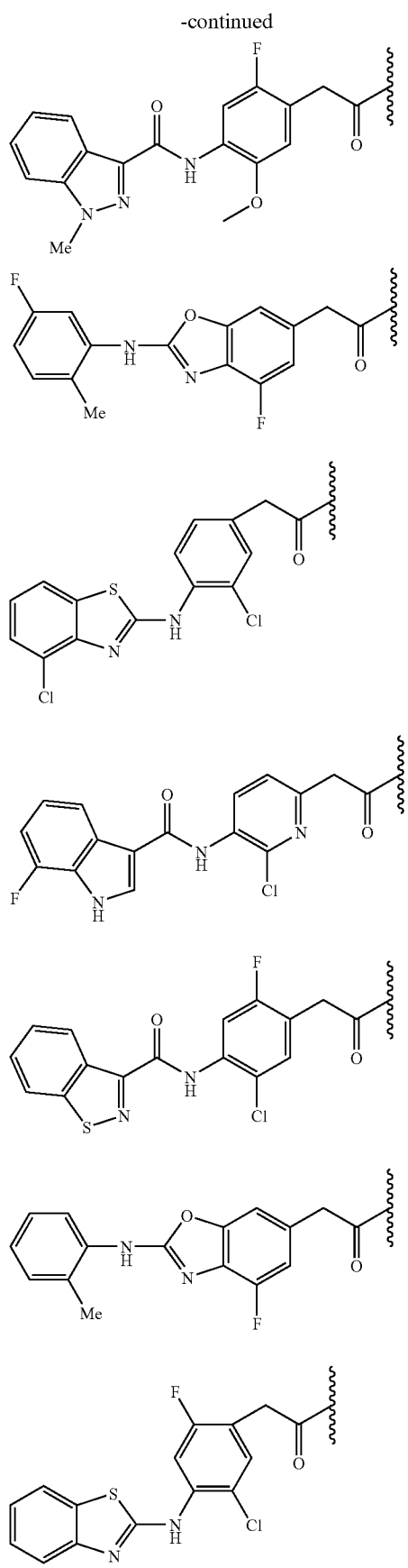

-continued

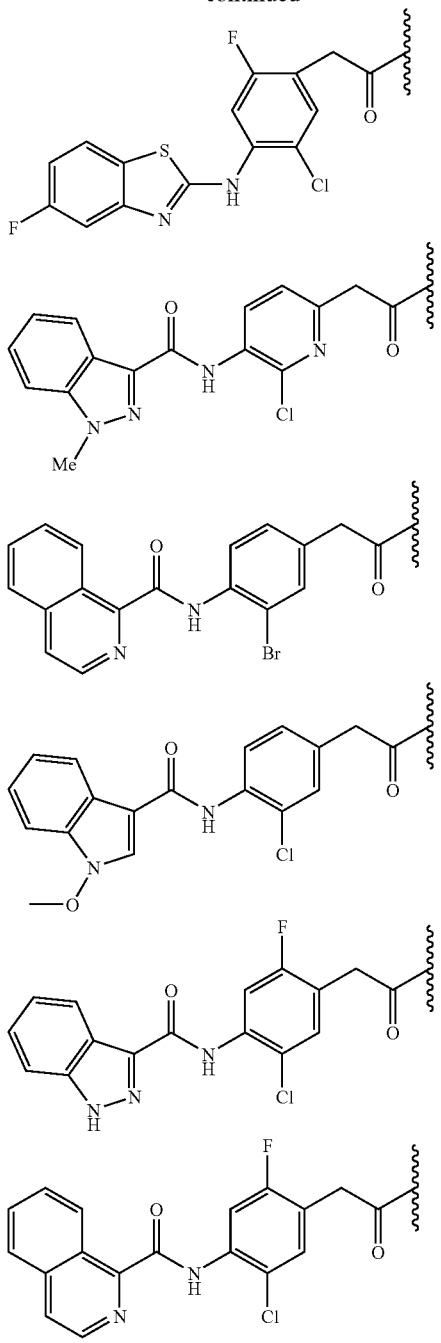

In the compound represented by the formula (I), W means the formula: $W^A$-$A^1$-$W^B$.

In the formula, $W^A$ is a substituted or unsubstituted aryl group or a substituted or unsubstituted monovalent heterocyclic group. This aryl group is similar to the above-described one, with a phenyl group being particularly preferred. As the heterocyclic group, preferred is a monovalent group formed, for example, of pyridine, thiazole, pyrimidine, pyrrole, indole, isoquinoline, quinoline, indoline, tetrahydroquinoline, indazole, benzisothiazole, benzisoxazole, benzothiazole or benzoxazole. Examples of the substituent for the aryl group or heterocyclic group include lower alkyl groups, lower alkoxy groups, halogen atoms, amino group and hydroxyl group. The aryl group or heterocyclic group may be substituted with at least one of these substituents.

$W^B$ is a substituted or unsubstituted arylene group or a substituted or unsubstituted divalent heterocyclic group. This arylene group is similar to the above-described one, with a phenylene group being particularly preferred. As the heterocyclic group, preferred is a divalent group formed, for example, of pyridine, thiazole, pyrimidine, pyrrole, indole, isoquinoline, quinoline, indoline, tetrahydroquinoline, benzothiazole or benzoxazole. Examples of the substituent for the arylene group or heterocyclic group include lower alkyl groups, lower alkoxy groups, halogen atoms, amino group and hydroxyl group. The arylene group or heterocyclic group may be substituted with at least one of these substituents.

$A^1$ represents —$NR^1$—, single bond, —C(O)—, —C(O)$NR^1$—, a substituted or unsubstituted vinylene group, an ethynylene group, —$CR^{1a}R^{1b}$—O—, —$CR^{1a}$=$CR^{1b}$—C(O)$NR^1$— or —$CR^{1a}$=$CR^{1b}$—C(O)— (in which, $R^1$ represents a hydrogen atom or a lower alkyl group, and $R^{1a}$ and $R^{1b}$ each independently represents a hydrogen atom or a lower alkyl group), of which single bond, —NH— or —C(O)NH— is preferred.

The formula: $W^A$-$A^1$-$W^B$ is preferably the following formula (i) or (ii).

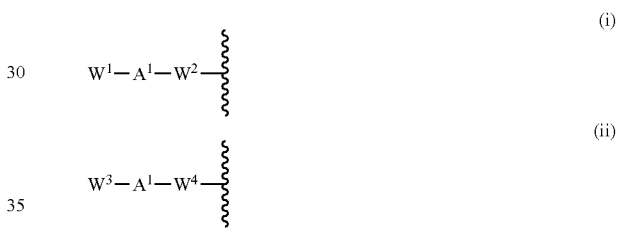

In the formula (i), $W^1$ represents a substituted or unsubstituted aryl group or a substituted or unsubstituted monovalent heterocyclic group and those exemplified above in $W^A$ are preferred. Particularly preferred examples include phenyl, pyridyl, indolyl, isoquinolinyl, indolinyl, tetrahydroquinolinyl, and benzoxazolyl groups, and phenyl, pyridyl, indolyl, isoquinolinyl, indolinyl, tetrahydroquinolinyl, indazolyl, benzisothiazolyl, benzisoxazolyl, benzothiazolyl and benzoxazolyl groups each substituted with a lower alkyl group, a lower alkoxy group or a halogen atom.

$W^2$ is a substituted or unsubstituted divalent bicyclic heterocyclic group and particularly preferred is that represented by the following formula (i-a), (i-b) or (i-c).

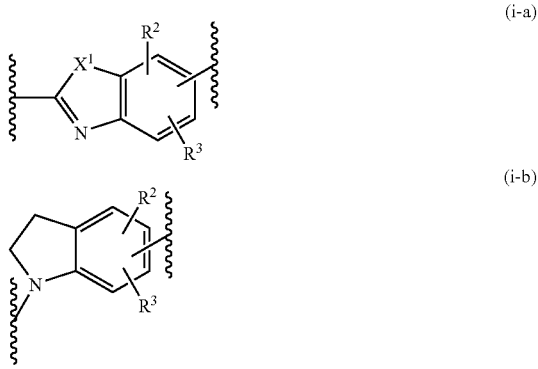

-continued

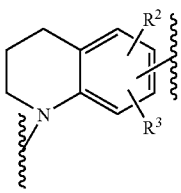
(i-c)

In the above formulas, $X^1$ represents an oxygen or sulfur atom, with oxygen atom being particularly preferred.

$R^2$ and $R^3$ each independently represents a hydrogen atom, a halogen atom, a lower alkyl group, a hydroxyl group, a lower alkoxy group or an amino group, of which a hydrogen atom, a halogen atom, a lower alkyl group or a lower alkoxy group is particularly preferred.

On the right side in the above-described formula (i-a), (i-b) or (i-c), the bonding to R is preferred and said bonding is preferably bonding to R at the para position on the benzene ring relative to the nitrogen atom in the formula (i-a), (i-b) or (i-c).

In the formula (ii), $W^3$ is a substituted or unsubstituted monovalent dicyclic heterocyclic group. Those represented by the following formulas (ii-a) to (ii-j) are preferred as $W^3$.

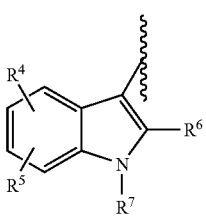
(ii-a)

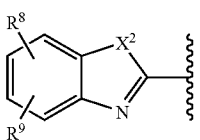
(ii-b)

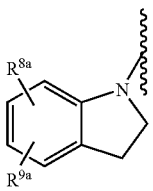
(ii-c)

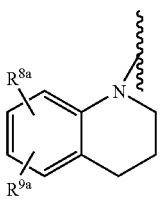
(ii-d)

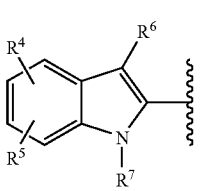
(ii-e)

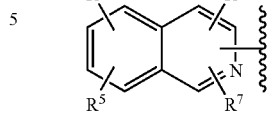
(ii-f)

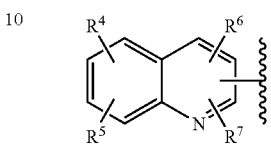
(ii-g)

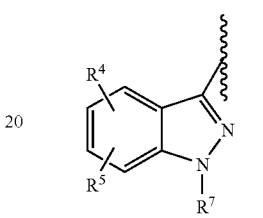
(ii-h)

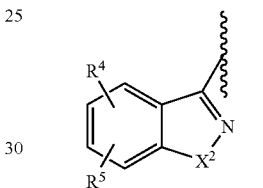
(ii-i)

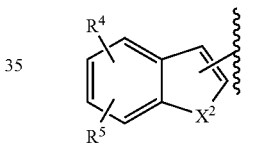
(ii-j)

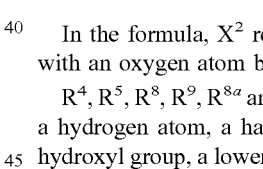

In the formula, $X^2$ represents an oxygen or sulfur atom, with an oxygen atom being particularly preferred.

$R^4$, $R^5$, $R^8$, $R^9$, $R^{8a}$ and $R^{9a}$ each independently represents a hydrogen atom, a halogen atom, a lower alkyl group, a hydroxyl group, a lower alkoxy group or an amino group, of which a hydrogen atom, a halogen atom, a lower alkyl group or a lower alkoxy group is preferred.

Of these, the formulas (ii-a), (ii-b), (ii-h) and (ii-i) are particularly preferred.

$W^4$ represents a substituted or unsubstituted arylene group or a substituted or unsubstituted divalent monocyclic heterocyclic group, preferably a phenylene group, a pyridylene group, or a phenylene or pyridylene group substituted with a lower alkyl group, a lower alkoxy group or a halogen atom.

$A^1$ and $R^1$ are preferably bonding at para position on the phenylene or pyridylene group.

R is a single bond, —NH—, —OCH$_2$—, an alkenylene group, or —(CH$_2$)$_n$— (in which n stands for 1 or 2), of which —CH$_2$— is particularly preferred.

X is —C(O)—, —CH$_2$— or —S(O)$_2$—, with —C(O)— being particularly preferred.

In the compound represented by the formula (I), M represents the below-described formula (iii), (iv) or (v):
Formula (iii):

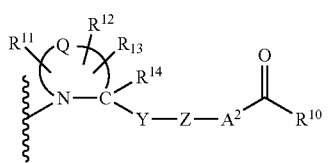
Specific examples of the formula (iii-b):
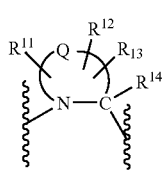
in the formula (ii) are exemplified below:
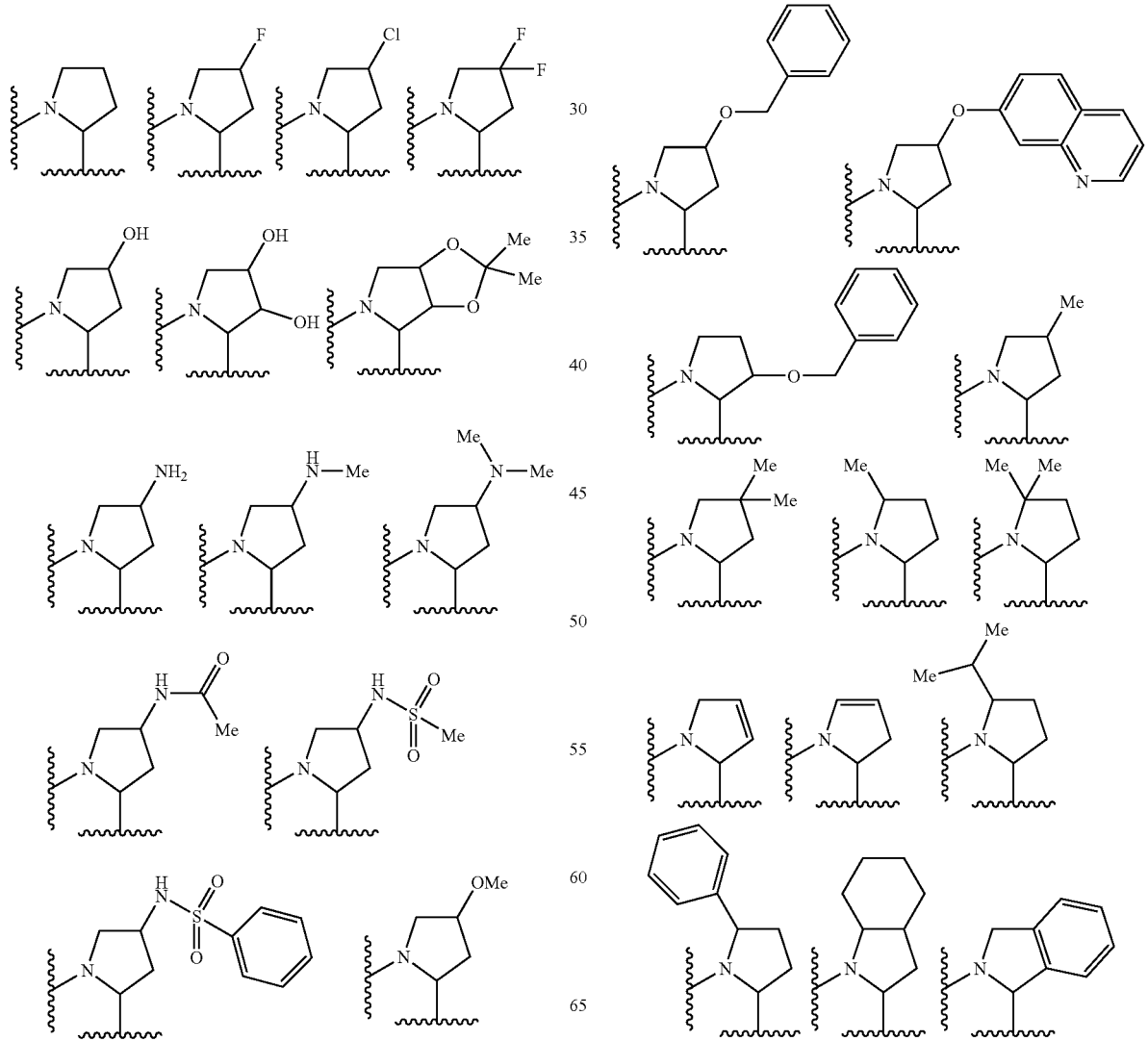

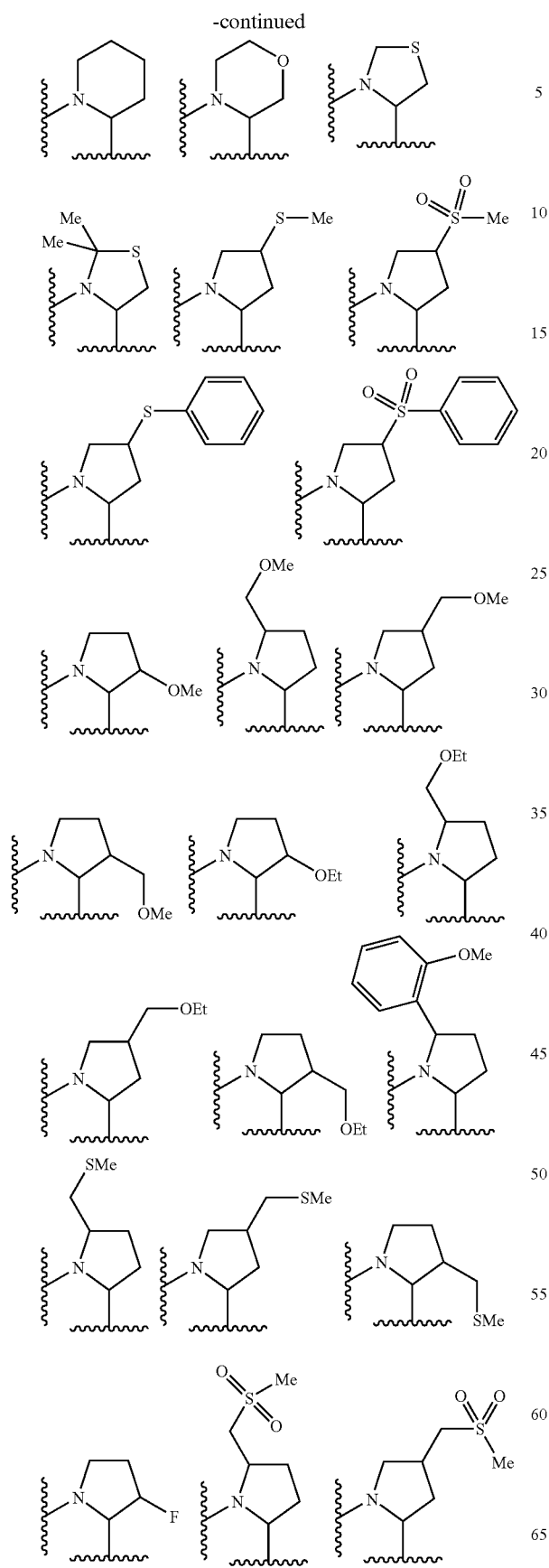
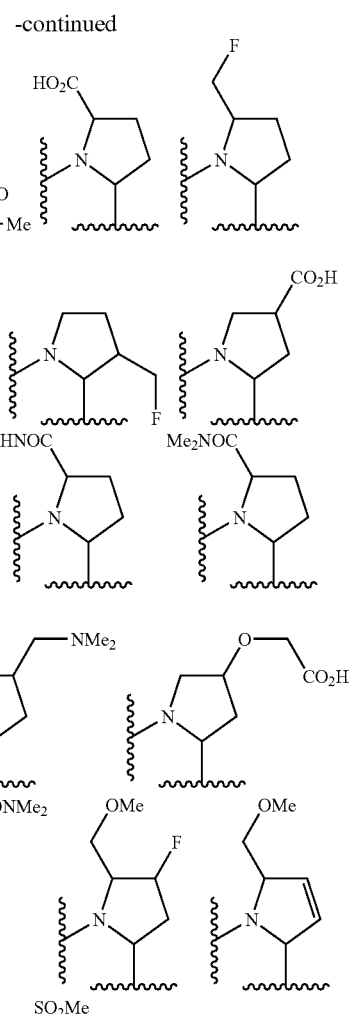

In this formula,

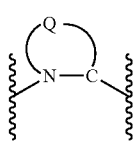

(iii-a)

represents a divalent 4-, 5-, 6- or 7-membered heterocyclic group, of which a 5- or 6-membered heterocyclic group having as Q a carbon, oxygen or nitrogen atom is preferred, with a divalent group formed of a pyrrolidine ring being particularly preferred.

Here, when Q is a divalent group formed of a pyrrolidine ring, it is most preferred that the absolute configuration of the 2-position to which a —Y-Z-A$^2$-C(O)—R$^{10}$ group is bonded is equal to that of the natural L-proline.

$R^{11}$, $R^{12}$ and $R^{13}$ each independently represents a hydrogen atom, a hydroxyl group, an amino group, a halogen atom, a cyano group, a carboxyl group, an alkoxycarbonyl group, a carbamoyl group, a substituted or unsubstituted mono- or dialkylaminocarbonyl group, a substituted or unsubstituted alkyl group, a substituted or unsubstituted aryl group, a substituted or unsubstituted heteroaryl group, a substituted or unsubstituted alkoxy group, a substituted or unsubstituted mono- or dialkylamino group, a substituted or unsubstituted cycloalkylamino group, a substituted or unsubstituted alkylsulfonylamino group, a substituted or unsubstituted arylsulfonylamino group, a substituted or unsubstituted aryloxy group, a substituted or unsubstituted heteroaryloxy group, a substituted or unsubstituted benzyloxy group, a substituted or unsubstituted alkylthio group, a substituted or unsubstituted cycloalkylthio group, a substituted or unsubstituted arylthio group, a substituted or unsubstituted alkylsulfonyl group, a substituted or unsubstituted cycloalkylsulfonyl group, or a substituted or unsubstituted arylsulfonyl group, or $R^{11}$ and $R^{12}$, or $R^{12}$ and $R^{13}$ may be coupled to form, together with the atom constituting the heterocyclic group to which $R^{11}$ to $R^{13}$ are bonded, a 3 to 7-membered cyclic hydrocarbon or heterocycle (the heterocycle may have thereon 1 to 3 substituents selected from a hydroxyl group, halogen atoms, an amino group, alkyl groups, alkoxy groups, aryl groups, aryloxy groups, alkylamino groups, a benzyloxy group and heteroaryl groups).

Examples of the alkyl, aryl, heteroaryl and alkoxy groups are similar to those described above. Examples of the mono- or dialkylamino group include monomethylamino, monoethylamino, isopropylamino, dimethylamino and diethylamino groups. Examples of the cycloalkylamino group include cyclopropylamino, cyclobutylamino and cyclopentylamino groups; those of the alkylsulfonylamino group include methanesulfonylamino, trifluoromethanesulfonylamino and ethanesulfonylamino groups; and those of the arylsulfonylamino group include benzenesulfonylamino and naphthylsulfonylamino groups. Examples of the substituent for them include halogen atoms, lower alkyl groups, lower alkoxy groups, hydroxyl group, amino group, acylamino groups and alkylamino groups.

In the case where $R^{11}$ and $R^{12}$, or $R^{12}$ and $R^{13}$ are coupled to form a 3- to 7-membered cyclic hydrocarbon or heterocycle together with the atom constituting the heterocyclic group to which $R^{11}$ to $R^{13}$ are bonded, examples of the thus formed ring include dihydroindole ring, tetrahydroindole ring, isoindoline ring and tetrahydroisoquinoline ring.

It is preferred that any one of $R^{11}$, $R^{12}$ and $R^{13}$ is a hydroxyl group, substituted or unsubstituted alkoxy group, substituted or unsubstituted alkyl group or halogen atom. Particularly, methoxyl group, methoxymethyl group or fluorine atom is preferred.

$R^{14}$ represents a hydrogen atom, or a substituted or unsubstituted alkyl group, of which a hydrogen atom and methyl group are preferred, particularly hydrogen atom is preferred.

In the formula (iii), Y represent a single bond, —C(O)—, —C(O)NH—, or a linear or branched divalent aliphatic $C_{1-12}$ hydrocarbon group which may have a $C_{3-6}$ spiro ring or may have one or more carbon atoms substituted by —O—, —S—, —S(O)$_2$—, —C(O)— or —NY$^1$— (in which, Y$^1$ represents a hydrogen atom or a lower alkyl group). Examples of the linear or branched divalent aliphatic hydrocarbon group formed of 1 to 12 carbon atoms include methylene, ethylene, propylene, isopropylene, 2,2-dimethylbutylene and 3,3-dimethylpentylene groups. When the aliphatic hydrocarbon group forms a spiro ring formed of 3 to 6 carbon atoms, the resulting ring is, for example, cyclopropane, cyclobutane or cyclohexane.

Of these, —CH$_2$O—, —CH$_2$S—, —CH$_2$S(O)$_2$—, —(CH$_2$)$_2$—, —CH=CH—, —C≡C— or —CH$_2$NY$^1$—, particularly —CH$_2$O— is preferred as Y.

Z represents a substituted or unsubstituted arylene group, a substituted or unsubstituted heteroarylene group or a substituted or unsubstituted cycloalkylene group. These arylene, heteroarylene and cycloalkylene groups are similar to those as exemplified above. Examples of the substituent for them include lower alkyl groups, lower alkoxy groups, halogen atoms, hydroxyl group, amino group and alkylamino groups. As Z, phenylene, pyridylene and cyclohexylene groups are preferred, with cyclohexylene group being particularly preferred. When Z represents a cyclohexylene group, it is most preferred that the relative configuration of the groups —Y— and -A$^2$- substituted on the cyclohexane ring is 1,4-trans configuration.

A$^2$ represents a single bond, alkenylene group, alkynylene group, —(CH$_2$)$_t$— or —O(CH$_2$)$_v$— (in which, t stands for 1, 2 or 3 and v stands for 0, 1, 2, or 3), of which a single bond is particularly preferred.

Formula (iv):

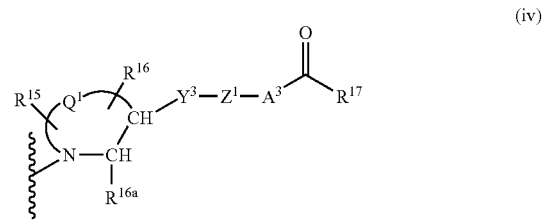

Specific examples of the formula (iv-b)

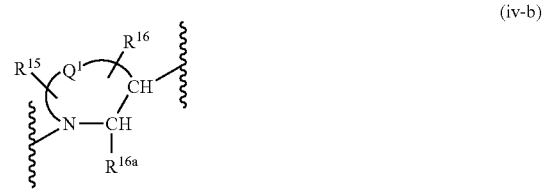

in the formula (iv) are exemplified below:

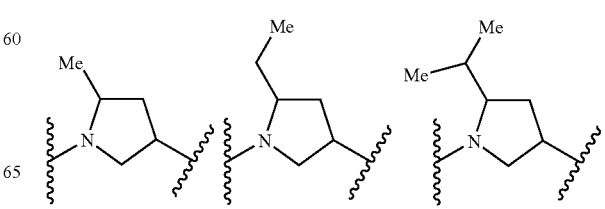

-continued
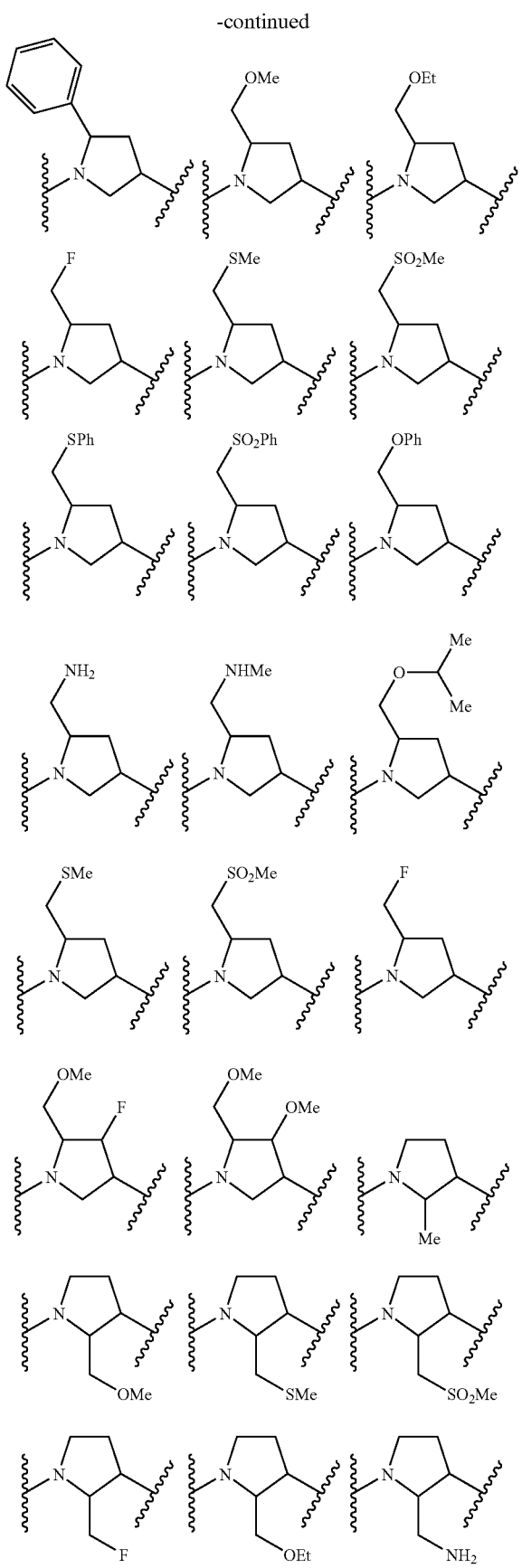
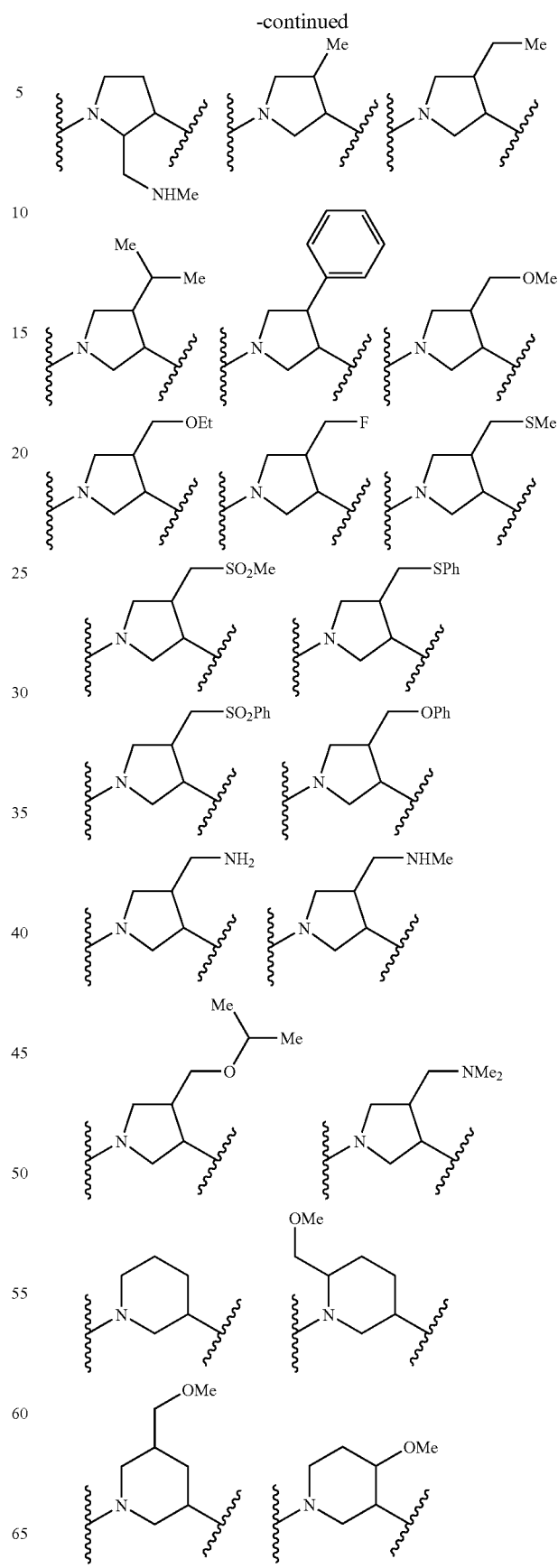

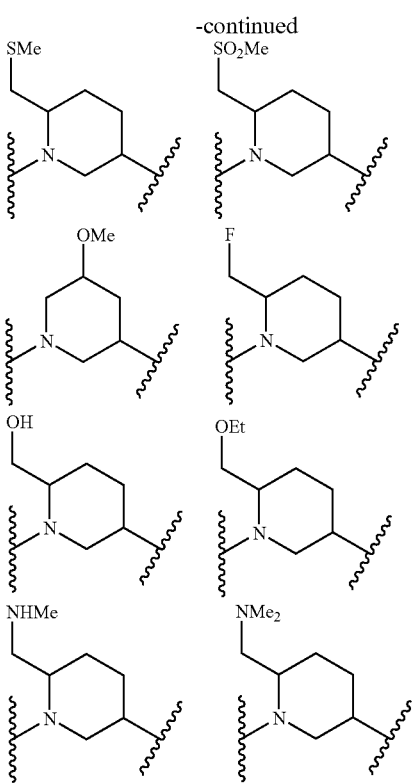

In the above formula,

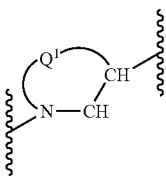
(iv-a)

represents a divalent 4-, 5-, 6- or 7-membered heterocyclic group, of which a 5- or 6-membered heterocyclic group having as $Q^1$ a carbon, oxygen or nitrogen atom is preferred, with a divalent group formed of a pyrrolidine ring being particularly preferred.

$R^{15}$ and $R^{16}$ each independently represents a hydrogen atom, a hydroxyl group, a halogen atom, a substituted or unsubstituted alkyl group or an alkoxy group, of which halogen atom, substituted or unsubstituted alkyl group or alkoxy group is preferred, with fluorine atom, methoxyl group or methoxymethyl group being particularly preferred.

$Y^3$ represents —O—, —S—, —S(O$_2$)—, —(CH$_2$)$_f$O— or —NY$^4$— (in which f stands for 1, 2 or 3 and $Y^4$ represents a hydrogen atom or a lower alkyl group), with —O— or —CH$_2$O— being particularly preferred.

$Z^1$ represents a substituted or unsubstituted arylene group, a substituted or unsubstituted heteroarylene group or a substituted or unsubstituted cycloalkylene group. Those exemplified above in Z are preferred.

$A^3$ represents a single bond, alkenylene group, alkynylene group or —(CH$_2$)$_e$— (in which, e stands for 1, 2 or 3), of which single bond is particularly preferred.

The formula (v):

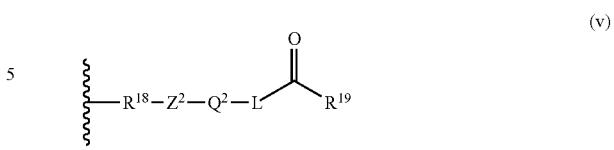
(v)

In the formula (v), $R^{18}$ represents —NR$^{20}$—, and $R^{20}$ represents a hydrogen atom, a substituted or unsubstituted alkyl group, a substituted or unsubstituted cycloalkyl group, a substituted or unsubstituted aryl group, a substituted or unsubstituted benzyl group, a substituted or unsubstituted lower alkenyl group or a substituted or unsubstituted alkynyl group. These alkyl, cycloalkyl, aryl, lower alkenyl and alkynyl groups are similar to those exemplified above. Substituents for them include alkoxy groups, alkyl groups, halogen atoms and hydroxyl group.

As $R^{20}$, preferred are substituted or unsubstituted alkyl groups, substituted or unsubstituted alkenyl groups and substituted or unsubstituted alkynyl groups, with methyl group, 2-fluoromethyl group, allyl group and propargyl group being particularly preferred.

$Z^2$ represents a linear or branched divalent aliphatic $C_{1-12}$ hydrocarbon group which may have a $C_{3-6}$ spiro ring, may have one or more carbon atoms substituted by a divalent $C_{3-8}$ cycloalkylene group, or may have one or more carbon atoms substituted by —O—, —S—, —S(O)$_2$—, —C(O)— or —NR$^{21}$ (in which, $R^{21}$ represents a hydrogen atom or a substituted or unsubstituted lower alkyl group). As $Z^2$, those exemplified above in Y of the formula (iii) are preferred.

$Q^2$ represents a single bond, a substituted or unsubstituted arylene group, a substituted or unsubstituted heteroarylene group or a substituted or unsubstituted cycloalkylene group. As $Q^2$, those exemplified above in Z are preferred.

L represents a single bond, a substituted or unsubstituted lower alkylene group or a substituted or unsubstituted lower alkenylene group. The lower alkylene and lower alkenylene group are similar to those as described above and substituents for them include lower alkyl groups and halogen atoms. As L, preferred are a single bond and a lower alkenylene group.

As M, the formula (iii) or (iv) is preferred. In the case where Z is a cyclohexylene group and $A^2$ is a single bond in the formula (iii), the formula (iii-c) is preferred.

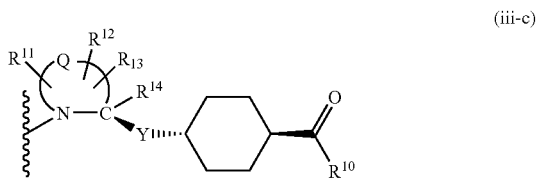
(iii-c)

Particularly, the formula (iii-d) is preferred.

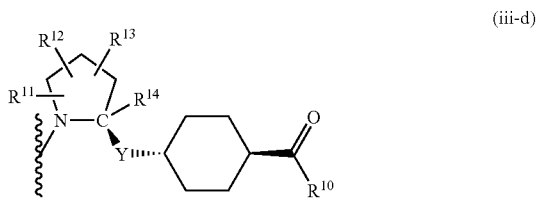
(iii-d)

In the case where $Z^1$ is a cyclohexylene group and $A^3$ is a single bond in the formula (iv), the formula (iv-c) is preferred.

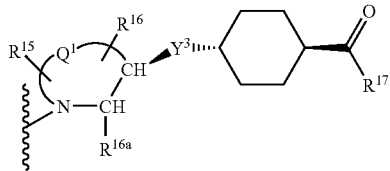

(iv-c)

Particularly, the formula (iv-d) is preferred.

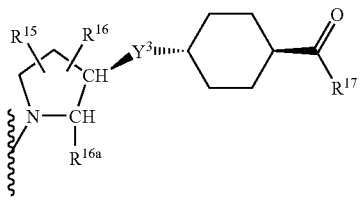

(iv-d)

As M, the formula (iii) is particularly preferred.

The invention compounds (I) can be converted into physiologically acceptable salts thereof as desired by using an inorganic acid such as hydrochloric acid, sulfuric acid or phosphoric acid, or an organic acid such as formic acid, acetic acid or methanesulfonic acid. When the invention compounds (I) have an acidic group such as carboxyl group, base addition salts can usually be formed. As physiologically acceptable salts, either organic salts or inorganic salts are possible. Preferred examples include alkali metal salts such as lithium salt, sodium salt and potassium salt, alkaline earth metal salts such as magnesium salt and calcium salt, ammonium salt, triethylamine salt, N-methylglucamine salt and tris(hydroxymethyl)aminomethane salt.

The invention compounds in the free form or salt form may exist as a solvate.

No particular limitation is imposed on the solvate insofar as it is a pharmaceutically acceptable one. Specific examples include hydrates and ethanolates. When the invention compounds (I) contain a nitrogen atom, they may exist as their N-oxides forms. These solvates and N-oxide forms are also embraced in the present invention.

Depending on the kind or combination of substituents, the invention compounds (I) or salts thereof have a variety of isomers, for example, geometrical isomers such as cis isomers and trans isomers, and optical isomers such as d-isomers and l-isomers. The present invention embraces all of these steric isomers and mixtures thereof at any ratio.

The invention compounds can be synthesized, for example, in accordance with any one of the below-described (Scheme 1) to (Scheme 18).

The compound of the formula (I) wherein X represents —C(O)— can be prepared by the coupling reaction of a carboxylic acid (1) and a cyclic amine (2), (3) or salt thereof, or a chain amine (4) or salt thereof (in the scheme,

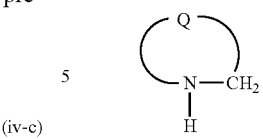

represents a 4-, 5-, 6- or 7-membered cyclic amine, and W, R, $R^{11}$, $R^{12}$, $R^{13}$, $R^{14}$, $R^{15}$, $R^{16}$, $R^{16a}$, Y, $Y^1$, Z, $Z^1$, $A^2$, $A^3$, $R^{10}$, $R^{17}$, $R^{20}$, $Z^2$, $Q^2$, L and $R^{19}$ have the same meanings as described above).

When in the compound of the formula (2), (3) or (4), $R^{10}$, $R^{17}$ or $R^{19}$ is a lower alkoxy group, the compounds obtained by the above-described coupling reaction can be converted into the corresponding free carboxylic acid type compound by alkaline hydrolysis.

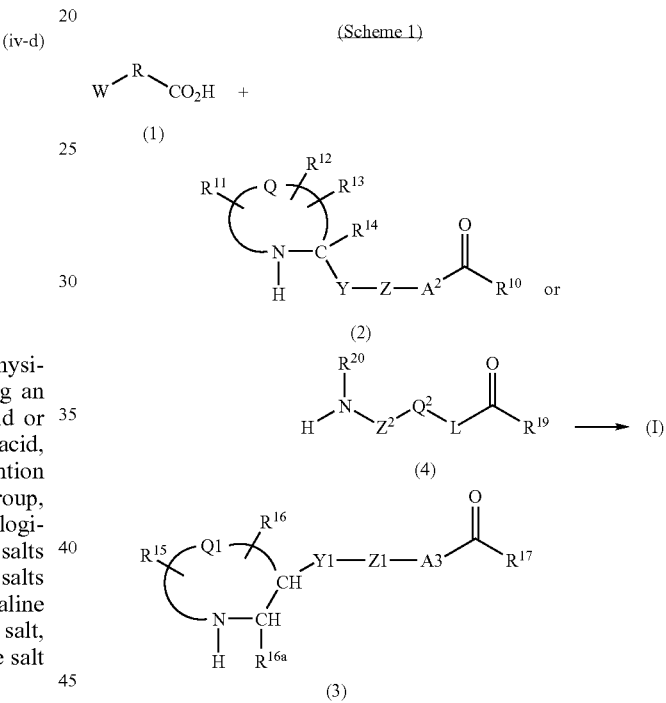

(Scheme 1)

The compound (I) in (Scheme 1) can be prepared in a known manner. The compound of the formula (I) can be prepared by reacting a carboxylic acid (1) with a cyclic amine (2) or (3), or a chain amine (4) in accordance with a known condensing method by using a condensing agent such as 1-ethyl-3-(3-dimethylaminopropyl)carbodiimide hydrochloride, N,N-dicyclohexylcarbodiimide or N,N-carbonyldiimidazole or an analogue thereto in an inert halogenated hydrocarbon solvent such as methylene chloride, an inert hydrocarbon solvent such as toluene, an inert ether solvent such as tetrahydrofuran or an inert polar solvent such as N,N-dimethylformamide at a temperature range of from −20° C. to the boiling point of the solvent, preferably 0° C. to room temperature. This reaction can also be conducted in the presence of an organic amine base such as triethylamine or 4-dimethylaminopyridine, or an organic amine base and 1-hydroxybenzotriazole.

In the below-described (Scheme 1A) to (Scheme 4), a synthesizing process of the carboxylic acid (1) used as a raw material for the above-described reaction will be indicated (in the schemes, $X^1$, R, $R^4$, $R^5$, $W^1$, $W^2$, $W^3$ and $W^4$ have the same meanings as described above, $R^{23}$s each independently represents a hydrogen atom, a halogen atom, a lower alkyl group, a hydroxyl group, a substituted or unsubstituted lower alkoxy group or an amino group, $R^{22}$ represents a lower alkyl or benzyl group, and $R^{24}$ represents a lower alkyl group).

In the below-described (Scheme 1A) and (Scheme 1B), a process for preparing a compound of the formula (I) wherein $A^1$ is a single bond is indicated.

Compounds of the formulas (1A-5) and (1B-5) can be prepared in a known manner. Compound (1A-4) is available, for example, by heating and refluxing—in the presence of an acid such as boric acid in an inert hydrocarbon solvent such as xylene—a compound of the formula (1A-1) which is commercially available or can be readily prepared in a known manner, preferably a compound of the formula (1A-2) which has been prepared by acting an acid halide such as oxalyl chloride, thionyl chloride, phosphorous trichloride or phosphorous pentachloride, preferably oxalyl chloride or thionyl chloride and a catalytic amount of N,N-dimethylformamide on the compound (1A-1) in an inert halogenated hydrocarbon solvent such as methylene chloride, an inert hydrocarbon solvent such as toluene or an inert ether solvent such as tetrahydrofuran at a temperature range of from −20° C. to the boiling point of the solvent, together with the compound of the formula (1A-3) (M.Terashima et al., *Synthesis*, 484 (1982)). And compound (1A-4) is also available, when carboxylic acid radical of the formula (1A-4) is formyl radical, via cyclization reaction using Ph- I(OAc)$_2$ (M. H. Jung et al., *J. Med. Chem.*, 9, 56(1999)). The carboxylic acid (1A-5) is then available by alkaline hydrolysis of the ester portion of the resulting compound in a known manner. In the case of a benzyl ester, the target product is available by, instead of the above-described alkaline hydrolysis, catalytic hydrogenation to remove the benzyl portion.

A compound of the formula (1B-4) can be prepared by effecting nucleophilic displacement reaction of a compound of the formula (1B-1) or (1B-2) (wherein, —H is bonded to the nitrogen atom of a nitrogen-containing heterocycle) and a compound of the formula (1B-3) in an inert hydrocarbon solvent such as xylene at a temperature range of from room temperature to the boiling point of the solvent. This reaction can be conducted in the presence of an organic base such as triethylamine or an inorganic base such as potassium carbonate. The reaction may be effected in a solventless manner at a temperature range of from room temperature to 200° C. By subjecting the resulting compound of the formula (1B-4) to hydrolysis or catalytic hydrogenation as indicated in (Scheme 1A), the compound of the formula (1B-5) can be prepared.

[Scheme 1A]

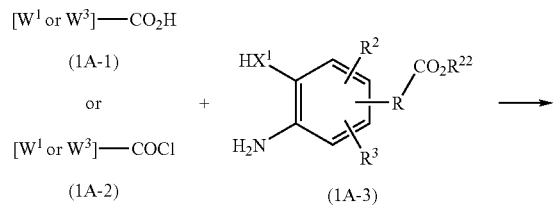

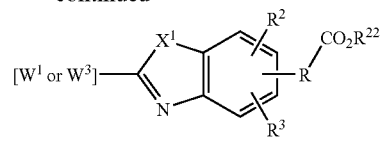

(1A-4)

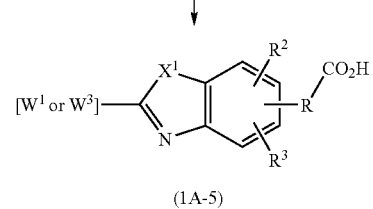

(1A-5)

[Scheme 1B]

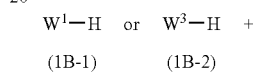

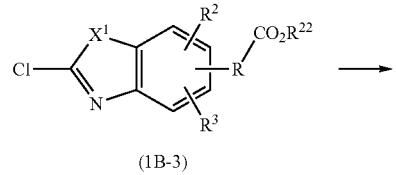

(1B-3)

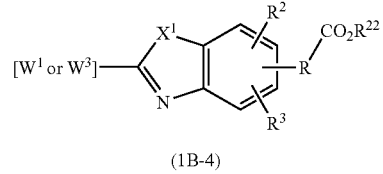

(1B-4)

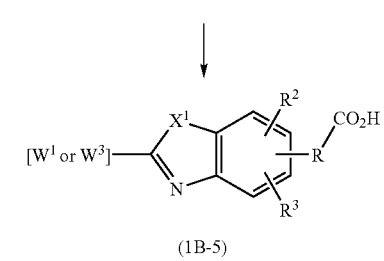

(1B-5)

The below-described (Scheme 1C) is a process for preparing a compound of the formula (I) wherein $A^1$ is —C(O)NR$^1$—.

A compound of the formula (1C-3) can be prepared in a known manner. For example, a compound of the formula (1-C2) can be prepared by reacting the compound (1A-2) as indicated in the above-described (Scheme 1A) with a compound of the formula (1C-1) in an inert halogenated hydrocarbon solvent such as methylene chloride, an inert hydrocarbon solvent such as toluene or an inert ether solvent such as tetrahydrofuran at a temperature range of from −20° C. to the boiling point of the solvent, preferably from room temperature to the boiling point of the solvent in the presence of an organic base such as triethylamine. Alternatively, the compound of the formula (1C-2) can be prepared by reacting the compound (1A-1) indicated in the above-described (Scheme 1A) with the compound of the formula (1C-1) by using a condensing agent such as 1-ethyl-3-(3-dimethylaminopropyl)carbodiimide hydrochloride, N,N-dicyclohexylcarbodiimide or N,N-carbonyldiimidazole or an analogue thereto in an inert halogenated hydrocarbon solvent such as methylene chloride, an inert hydrocarbon solvent such as toluene, an inert ether solvent such as tetrahydrofuran, or an inert polar solvent such as N,N-dimethylformamide at a temperature range of from −20° C. to the boiling point of the solvent. This reaction may be effected in the presence of an organic amine base such as triethylamine or 4-dimethylaminopyridine, or an inorganic base and 1-hydroxybenzotriazole. By subjecting the resulting compound of the formula (1C-2) to hydrolysis or catalytic hydrogenation as indicated in (Scheme 1A), the compound of the formula (1C-3) is available.

(Scheme 1C)

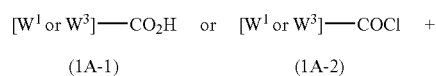

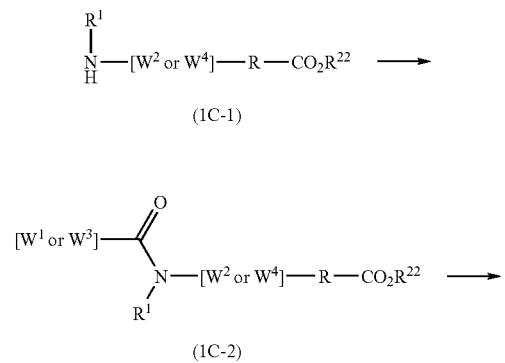

The below-described (Scheme 1D) is a preparation process of a compound of the formula (I) wherein $A^1$ represents —C(O)— (in the scheme, —H of each of the compounds (1D-2), (1D-5) and (1D-7) is bonded to the nitrogen atom of the nitrogen-containing heterocycle).

A compound of the formula (1D-4) can be prepared in a known manner. For example, a compound of the formula (1D-1) is prepared by acting phosgene or a phosgene equivalent such as triphosgene on the compound (1B-2) shown in (Scheme 1B) in an inert halogenated hydrocarbon solvent such as methylene chloride, an inert hydrocarbon solvent such as toluene or an inert ether solvent such as tetrahydrofuran at a temperature range of from −20° C. to the boiling point of the solvent, preferably from −20° C. to room temperature. Then, a compound of the formula (1D-2) is acted on the compound (1D-1), whereby a compound of the formula (1D-3) can be obtained. The compound of the formula (1D-3) is available in a similar manner by preparing a compound of the formula (1D-6) from a compound of the formula (1D-5) and then reacting the resulting compound with a compound of the formula (1D-7). The compound (1D-3) is also available by acting N,N-carbonyldiimidazole on the compound of the formula (1B-2) or (1D-5) in an inert polar solvent such as N,N-dimethylformamide at a temperature range of from −20° C. to the boiling point of the solvent, followed by the addition of the compound (1D-2) in the case of the compound of (1B-2) or the compound (1D-7) in the case of the compound (1D-5) to cause reaction. The compound of the formula (1D-3) is then subjected to hydrolysis or catalytic hydrogenation as shown in (Scheme 1A), whereby the compound of the formula (1D-4) can be prepared.

[Scheme 1D]

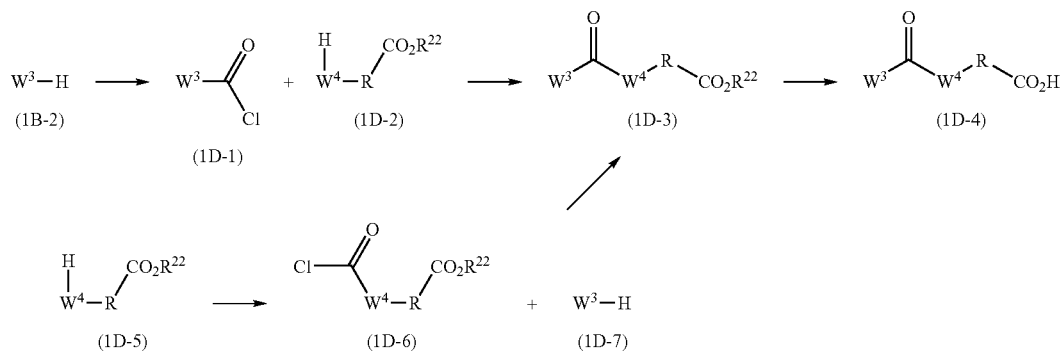

-continued

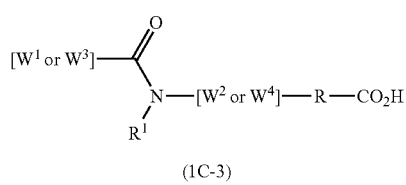

In the below-described (Scheme 1E), a compound of the formula (I) wherein $A^1$ represents vinylene is indicated.

A compound of the formula (1E-4) in (Scheme 1E) can be prepared by Wittig-Horner reaction. For example, the compound of the formula (1E-4) can be prepared by acting a trialkyl phosphite ester on a compound of the formula (1E-1), which is commercially available or can easily be prepared in a known manner, in a solventless manner at a temperature range of from room temperature to 200° C. to prepare the corresponding alkyl phosphite diester (1E-2);

acting thereon a base such as sodium hydride, lithium hexamethyl disilazane or sodium methoxide in an inert alcohol solvent such as ethanol, an inert hydrocarbon solvent such as toluene, an inert ether solvent such as tetrahydrofuran or inert polar solvent such as dimethylsulfoxide at a temperature range of from −78° C. to the boiling point of the solvent, preferably from −20° C. to room temperature, to generate a carbanion; and acting a compound of the formula (1E-3), which is commercially available or can easily prepared in a known manner, on the carbanion. By subjecting the resulting compound o f the formula (1E-4) to alkaline hydrolysis, a compound of the formula (1E-5) is available.

(1F-1) which is commercially available or can be prepared readily in a known manner is introduced into the corresponding dihalogeno-olefin in accordance with the Corey method and then, an organolithium such as butyl lithium is acted on the resulting compound, whereby a compound of the formula (1F-2) can be obtained. Alternatively, the compound of the formula (1F-2) can be prepared by reacting the compound (1F-1) with a carbanion easily available from trimethylsilyldiazomethane and an organolithium, followed by rearrangement (Y.Ito et al., *Synlett*, 1163 (1997)). Then, Heck type carbon-carbon coupling reaction is conducted with a compound of the formula (1F-3), whereby the com-

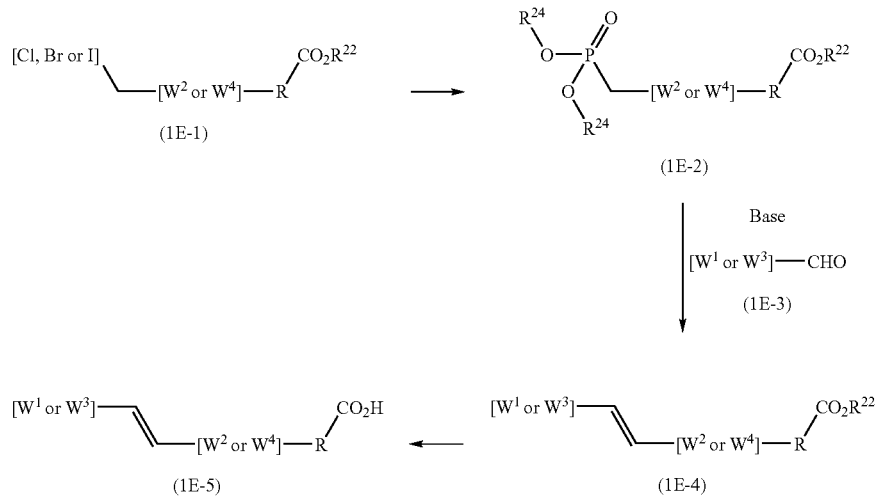

In the below-described (Scheme 1F), a compound of the formula (I) wherein A represents ethynylene is indicated.

A compound of the formula (IF-4) can be prepared in a known manner. For example, a compound of the formula pound of the formula (1F-4) can be obtained (T.Eckert et al., *Synth. Commun.*, 28, 327 (1998)). By subjecting the resulting compound of the formula (1F-4) to alkaline hydrolysis, a compound of the formula (1F-5) is available.

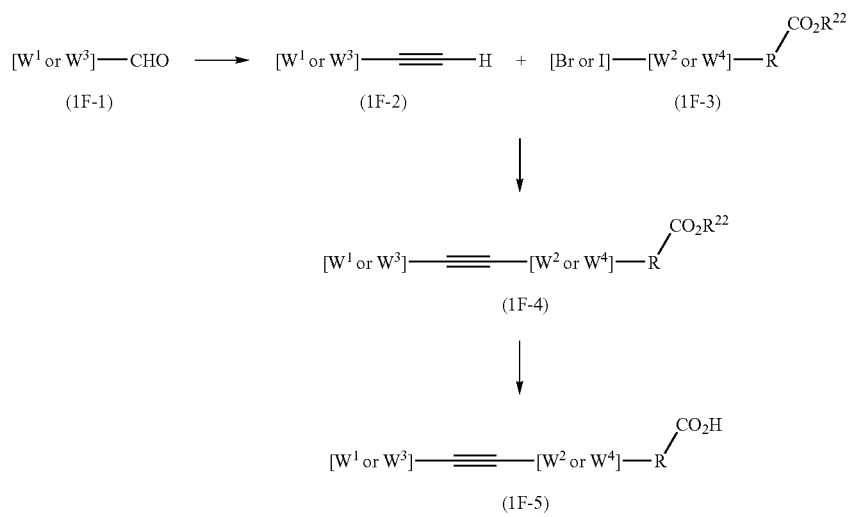

In the below-described (Scheme 2) to (Scheme 4), a compound of the formula (I) wherein $A^1$ represents $-NR^1$ is indicated.

A compound of the formula (1a) in the below-described (Scheme 2) can be prepared in a known manner. For example, an aniline derivative (6) which is known by itself or can be prepared in a known manner, and a thioisocyanate derivative (7) which is commercially available or can be prepared in a known manner or a xanthate derivative (8) which can be prepared in a known manner are treated in an inert halogenated hydrocarbon solvent such as methylene chloride, an inert hydrocarbon solvent such as toluene, an inert ether solvent such as tetrahydrofuran or an inert alcohol solvent such as ethanol at a temperature range of from $-20°$ C. to the boiling point of the solvent, preferably from $0°$ C. to room temperature, whereby the corresponding thiourea derivative (9) can be prepared. In a known manner, the resulting compound is then treated with $KO_2$ or $Ni_2O_3$, preferably mercuric oxide (yellow), each commercially available, in an inert hydrocarbon solvent such as toluene, inert ether solvent such as tetrahydrofuran or inert polar solvent such as N,N-dimethylformamide at a temperature range of from $-20°$ C. to the boiling point of the solvent, preferably from room temperature to the boiling point of the solvent, whereby the corresponding ring-closed compound (10) can be obtained (A. Koshiro et al., *Chem. Pharm. Bull.*, 7, 725 (1959); H. Ogura et al., ibid., 29, 1518 (1981); H. S. Chan et al., *Chem. Lett.*, 1291 (1986)). The resulting compound is then subjected to hydrolysis, or catalytic hydrogenation method as described in (Scheme 1), whereby the carboxylic acid (1a) can be obtained.

ably from $0°$ C. to the boiling point of the solvent. Then, for example, by treating the compound (13) with an organic acid such as pyridinium par-toluenesulfonate in an inert halogenated hydrocarbon solvent such as methylene chloride at a temperature range from room temperature to the boiling point of the solvent, the ring closed compound (10) is available (M. J. Suto et al., *Tetrahedron Lett.*, 36, 7213 (1995)).

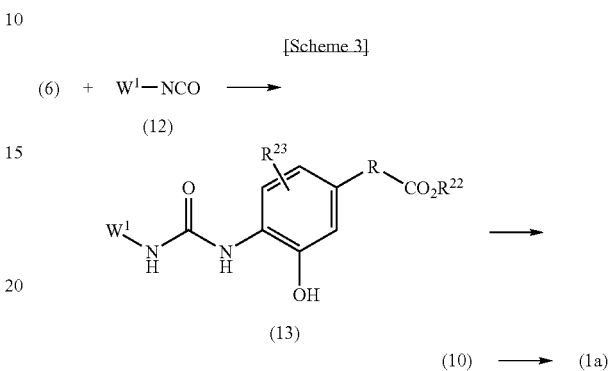

In the below-described (Scheme 4), a compound of the formula (1b) can be prepared in the following manner. A 2-benzazole chloride derivative (16) and an amine derivative (17) each available commercially or readily in a known manner are treated in an inert polar solvent such as N,N-dimethylformamide or an inert hydrocarbon solvent such as

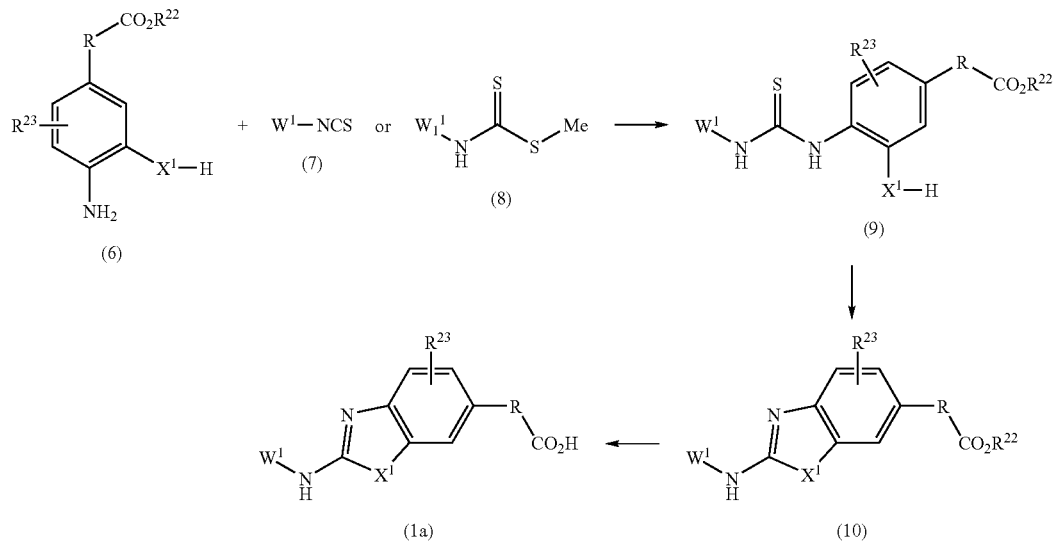

In the below-described (Scheme 3), another process for preparing the compound of the formula (10) is indicated. An urea derivative (13) is available by reacting the aniline derivative (6) with an isocyanate (12) which is commercially available or can be prepared in a known manner in an inert halogenated hydrocarbon solvent such as methylene chloride, an inert hydrocarbon solvent such as toluene or an inert ether solvent such as tetrahydrofuran at a temperature range of from $-20°$ C. to the boiling point of the solvent, preferxylene at a temperature range of from room temperature to the boiling point of the solvent, preferably from $100°$ C. to the boiling point of the solvent or treated in a solventless manner at a temperature range of from room temperature to $200°$ C., preferably from 100 to $200°$ C., whereby a compound of the formula (18) can be obtained. This reaction may be effected in the presence of an organic amine base such as triethylamine or an inorganic base such as potassium carbonate. Then, by hydrolysis or hydrogenolysis of an ester portion in accordance with the hydrolysis or catalytic hydrogenation method as shown in (Scheme 1A), the carboxylic acid (1b) can be obtained.

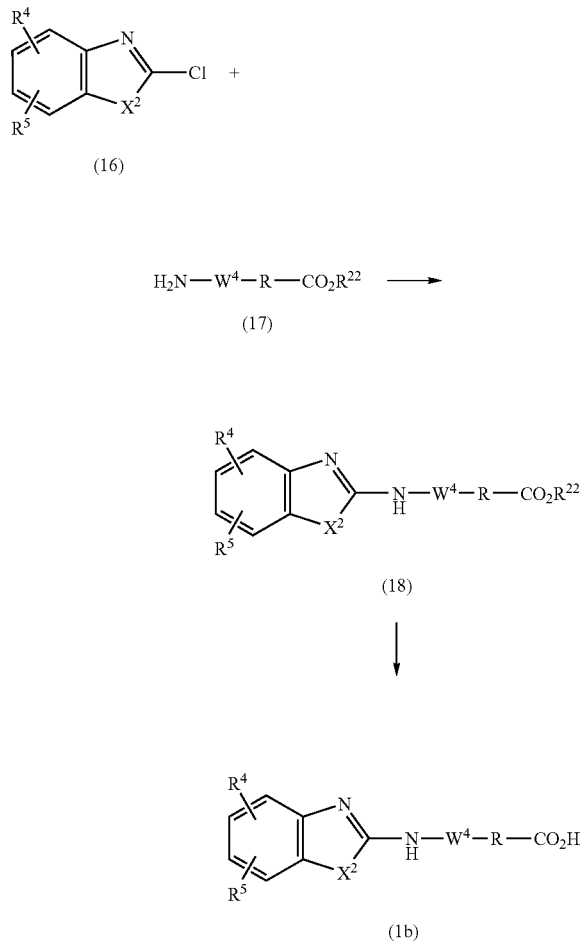

In the below-described (Scheme 5) to (Scheme 9), a preparation process of a compound of the formula (2) or (3) to be used in the above-described reaction as a raw material will be indicated (in the scheme, $R^{11}$, $R^{12}$, $R^{13}$, $R^{14}$, $R^{15}$, $R^{16}$, $A^2$, $A^3$, Z, $Z^1$, $R^{10}$ and $R^{17}$ have the same meanings as described above, $X^4$ represents a carbon or nitrogen atom, $Z^3$ represents a substituted or unsubstituted arylene group or a substituted or unsubstituted heteroarylene group, $Z^4$ represents a substituted or unsubstituted cycloalkylene group or a substituted or unsubstituted hetero cycloalkylene group, $Z^5$ represents a substituted or unsubstituted arylene group or a substituted or unsubstituted heteroarylene group, $R^{30}$ represents a lower alkyl group, E represents a protecting group (*Protective Groups in Organic Synthesis*, eds. by T. W. Greene and P. G. Wuts, John Wiley & Sons, Inc., New York, 1991) of a primary or secondary amine and $n^1$ stands for 0, 1 or 2).

In the below-described (Scheme 5), indicated is a process for preparing compounds of the formulas (2a) and (2b) including a step of forming an ether bond portion. An ester derivative (20) available commercially or in a known manner can be converted into the corresponding alcohol derivative (22) by known reduction. For example, the alcohol derivative (22) can be prepared by, after acidic or alkaline hydrolysis of the ester derivative (20) into the corresponding carboxylic acid (21), treating the resulting compound with borane or a reducing agent of such a kind in an inert halogenated hydrocarbon solvent such as methylene chloride, an inert hydrocarbon solvent such as toluene or an inert ether solvent such as tetrahydrofuran at a temperature range of from −20° C. to the boiling point of the solvent, preferably from 0° C. to the boiling point of the solvent. In this reduction, a preferable protecting group must be introduced as E of the ester derivative (20) and a tertiary butyloxycarbonyl group is preferred as it. Alternatively, the alcohol derivative (22) can be prepared not via the carboxylic acid (21) but directly from the ester derivative (20). For example, the alcohol derivative (22) can be prepared by treating the ester derivative (20) with a reducing agent such as diisobutyl aluminum hydride in an inert ether solvent such as tetrahydrofuran, preferably in an inert hydrocarbon solvent such as toluene or an inert halogenated hydrocarbon solvent such as methylene chloride at a temperature range of from −78° C. to the boiling point of the solvent, preferably from 0° C. to room temperature. Also in this case, a preferable protecting group must be introduced as E of the ester derivative (20) and, as it, a tertiary butyloxycarbonyl group is preferred. After formation of an ether bond by the Mitsunobu reaction with a phenol such as methyl 4-hydroxybenzoate and introduction of an aryl group or a heteroaryl group are conducted simultaneously, the protecting group E is removed. When E is a tertiary butyloxycarbonyl group, deprotection is performed by treating with trifluoroacetic acid in a solventless manner or in an inert halogenated hydrocarbon solvent such as methylene chloride, whereby the compound of the formula (2a) can be prepared. The ether bond formation of the compound (23) from the compound (22) can be conducted, instead of the above-described Mitsunobu reaction, by converting the primary hydroxy group of the compound (22) into an eliminating group such as mesyloxy group and then treating the resulting compound with a phenol such as methyl 4-hydroxybenzoate in an inert polar solvent such N,N-dimethylformamide at a temperature range from 0° C. to 90° C. in the presence of an inorganic base such as sodium hydride or potassium carbonate. In this case, a preferable protecting group E, for example, is a benzyloxycarbonyl group.

When $Z_3$ of the compound (23) is an phenylene group, a cyclohexane derivative (24) can be prepared by nuclear reduction of the benzene ring in a known manner. For example, a reduced derivative (24) can be prepared by catalytic hydrogenation of a compound of the formula (23) in an inert alcohol solvent such as methanol in the presence of a catalyst such as palladium, platinum oxide, preferably rhodium at 1 to 1000 atm, preferably 1 to 100 atm under a hydrogen atmosphere (R. A. Finnegan et al., *J. Org. Chem.*, 30, 4145 (1965); A. I. Meyers et al., *Org. Synth.*, 51, 103 (1971)). The above-described reduction is preferably conducted in the presence of acetic acid or trifluoroacetic acid. The protecting group E is then removed, for example, by treating, when E is a tertiary butyloxycarbonyl group, with trifluoroacetic acid in a solventless manner or an inert halogenated hydrocarbon solvent such as methylene chloride, whereby a compound of the compound (2b) can be prepared. The compound (2b) is also available by deprotection of E from the compound (23), followed by the above-described reduction.

[Scheme 5]

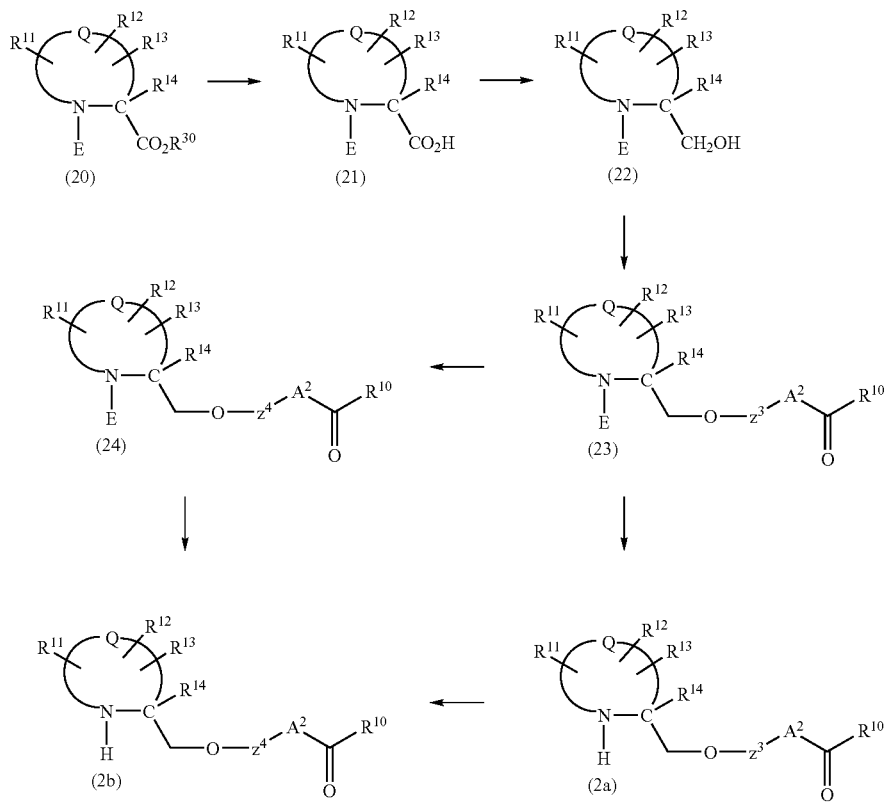

In the below-described (Scheme 5a), shown is a process permitting preparation of compounds of the formulas (3a) and (3b) in accordance with the preparation process of (Scheme 5) by using, as a raw material, a compound of the formula (22a) which is available commercially or in a known manner. Or, a primary alcohol derivative can be prepared in a known manner, for example, by converting the secondary hydroxy group of the compound (3a) into an eliminating group such as mesyloxy group, converting it into a cyano group by acting a cyanation agent such as potassium cyanide, then converting it into a formyl group by using diisopropyl aluminum hydride, and effecting reduction by sodium borohydride. An compound which is extended by one carbon between oxygen atom and ring in the compound (3b) can be prepared by using the resulting primary alcohol derivative as a raw material in accordance with the above-described ether bond formation method (A. Tarnowsky et al., *Bioorg. Med. Chem. Lett.*, 7, 573 (1997)).

[Scheme 5a]

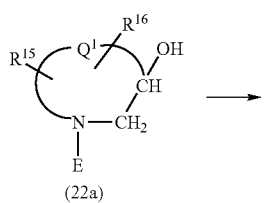

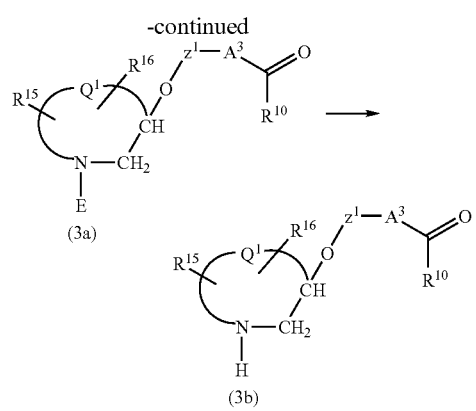

In the below-described (Scheme 6), indicated is a process for preparing a sulfide, sulfoxide or sulfone derivative (2m) in a known manner by using the alcohol derivative (22) as a starting material.

For example, a compound of the formula (25) can be prepared by converting a primary hydroxyl group of the alcohol derivative (22) into an eliminating group such as mesyloxy group and then treating the resulting compound with a thiol, which is available commercially or in a known manner, in an inert ether solvent such as tetrahydrofuran, an inert halogenated hydrocarbon solvent such as methylene chloride, preferably in an inert polar solvent such as N,N-dimethylformamide at a temperature range of from −20° C. to the boiling point of the solvent, preferably from room temperature to the boiling point of the solvent in the presence of a base such as potassium carbonate or sodium hydride. By subjecting the resulting compound to known oxidation reaction, its sulfide portion can be converted into a sulfoxide or sulfone group.

For example, the compound (25) can be converted into the corresponding sulfoxide or sulfone derivative by treating it with commercially available 3-chloroperbenzoic acid or peroxide such as hydrogen peroxide in an inert halogenated hydrocarbon solvent such as methylene chloride at a temperature range of from −78° C. to the boiling point of the solvent, preferably from −20° C. to room temperature. The protecting group E is then removed from the compound (25), or sulfoxide or sulfone derivative thereof, whereby a compound (2m) can be prepared.

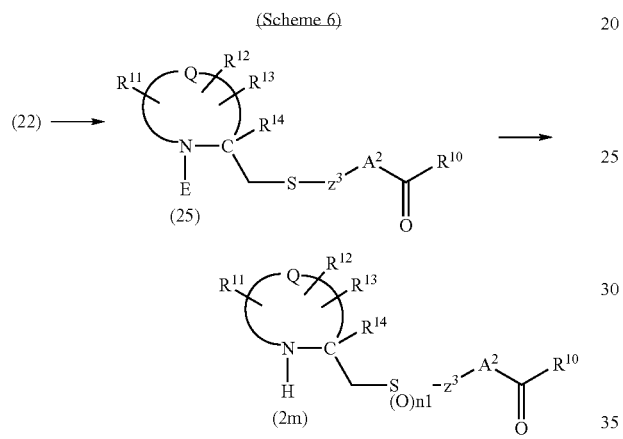

In the below-described (Scheme 7), a process for preparing compounds of the formulas (2c) and (2d) including a step of forming an amide bond is indicated. An amide derivative (27) or (29) can be prepared by reacting the carboxylic acid derivative (21) and a chain amine (26) or cyclic amine (28), which is available commercially or in a known manner, by using a condensing agent such as 1-ethyl-3-(3-dimethylaminopropyl)carbodiimide hydrochloride, N,N-dicyclohexylcarbodiimide or N,N-carbonyldiimidazole or an analogue thereto in an inert halogenated hydrocarbon solvent such as methylene chloride, an inert hydrocarbon solvent such as toluene, an inert ether solvent such as tetrahydrofuran or an inert polar solvent such as N,N-dimethylformamide at a temperature range of from −20° C. to the boiling point of the solvent, preferably from 0° C. to room temperature. This reaction can also be conducted in the presence of an organic amine base such as triethylamine or N,N-dimethylaminopyridine, or the organic amine base and 1-hydroxybenzotriazole. By deprotection of E, the compound of the formula (2c) or (2d) can be prepared.

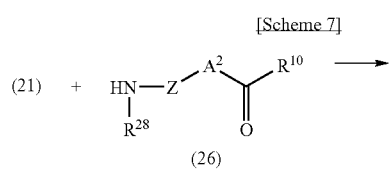

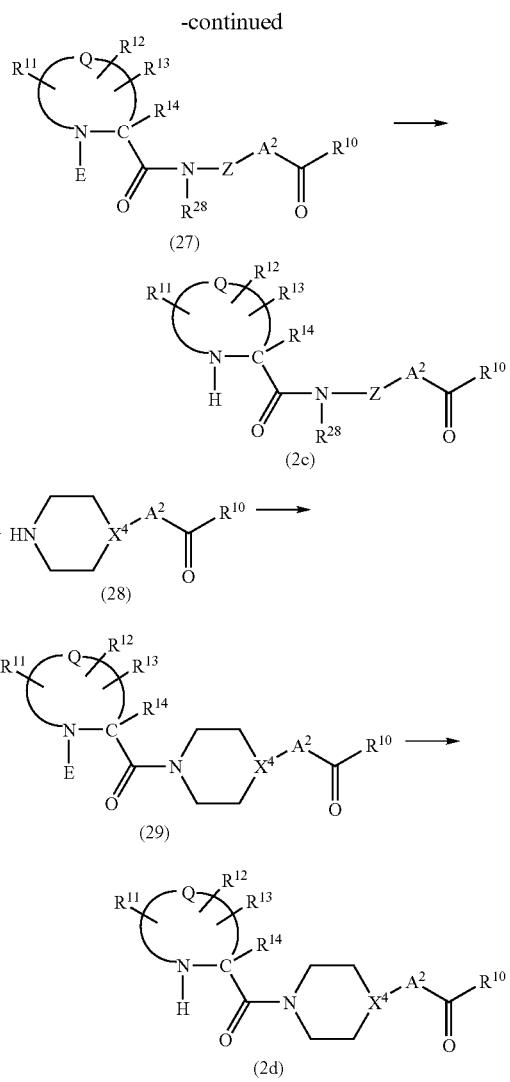

In the below-described (Scheme 8), a preparation process of a compound of the formula (2e) or (2f) including an N-alkylating step is indicated. The alcohol derivative (22) in (Scheme 5) can be converted into the corresponding aldehyde derivative (31) by oxidizing a primary hydroxyl group into an aldehyde in a known manner. For example, oxidation using a chromic acid, or oxidation using dimethylsulfoxide, for example, Swern oxidation is usable for conversion. The resulting aldehyde derivative (31) is then subjected to reductive N-alkylation reaction with the above-described amine derivative (26) or (28) in a known manner. This reducing reaction can be conducted using a reducing agent such as sodium cyanoborohydride or triacetoxy sodium borohydride in an inert alcohol solvent such as methanol or an inert ether solvent such as tetrahydrofuran. When sodium cyanoborohydride is used, reaction is preferably conducted under acidic conditions, for example, in the presence of acetic acid. The N-alkylation reaction can also be conducted by catalytic hydrogenation using a commercially available catalyst such as palladium-carbon. By the deprotection of protecting group E from the reduced derivative (32) or (34), a compound of the formula (2e) or (2f) can be prepared.

[Scheme 8]
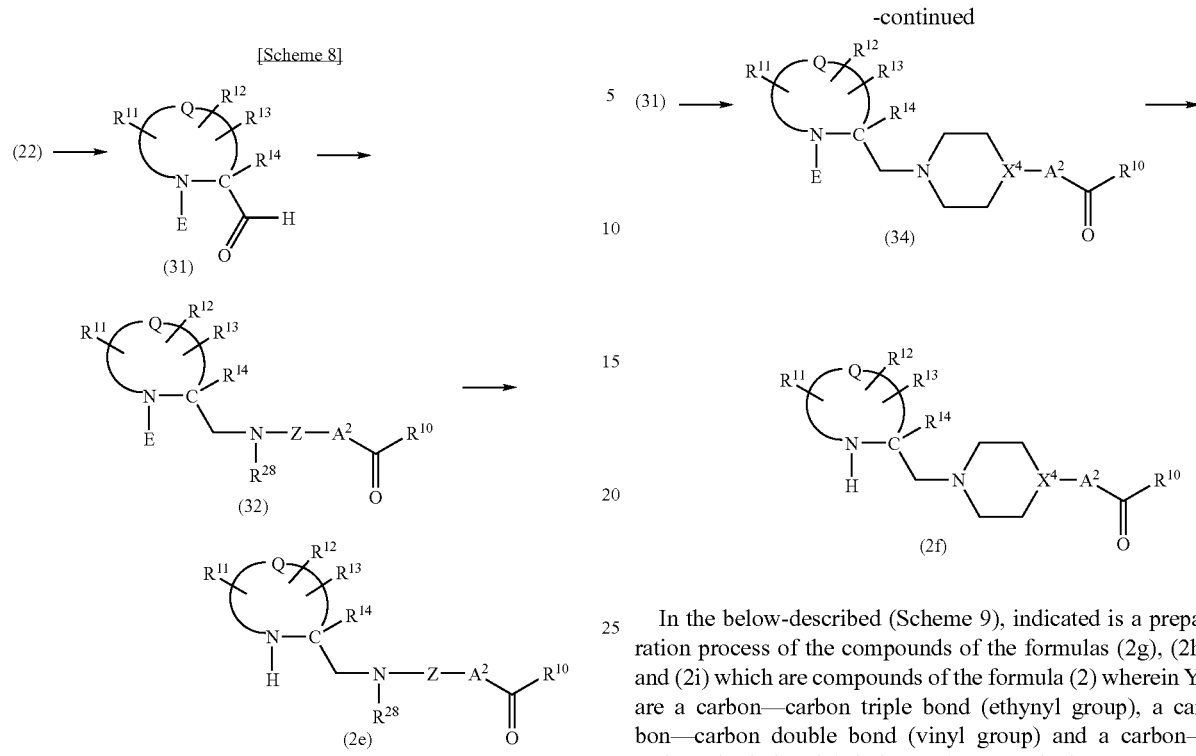
In the below-described (Scheme 9), indicated is a preparation process of the compounds of the formulas (2g), (2h) and (2i) which are compounds of the formula (2) wherein Ys are a carbon—carbon triple bond (ethynyl group), a carbon—carbon double bond (vinyl group) and a carbon—carbon single bond (ethyl group), respectively.
[Scheme 9]
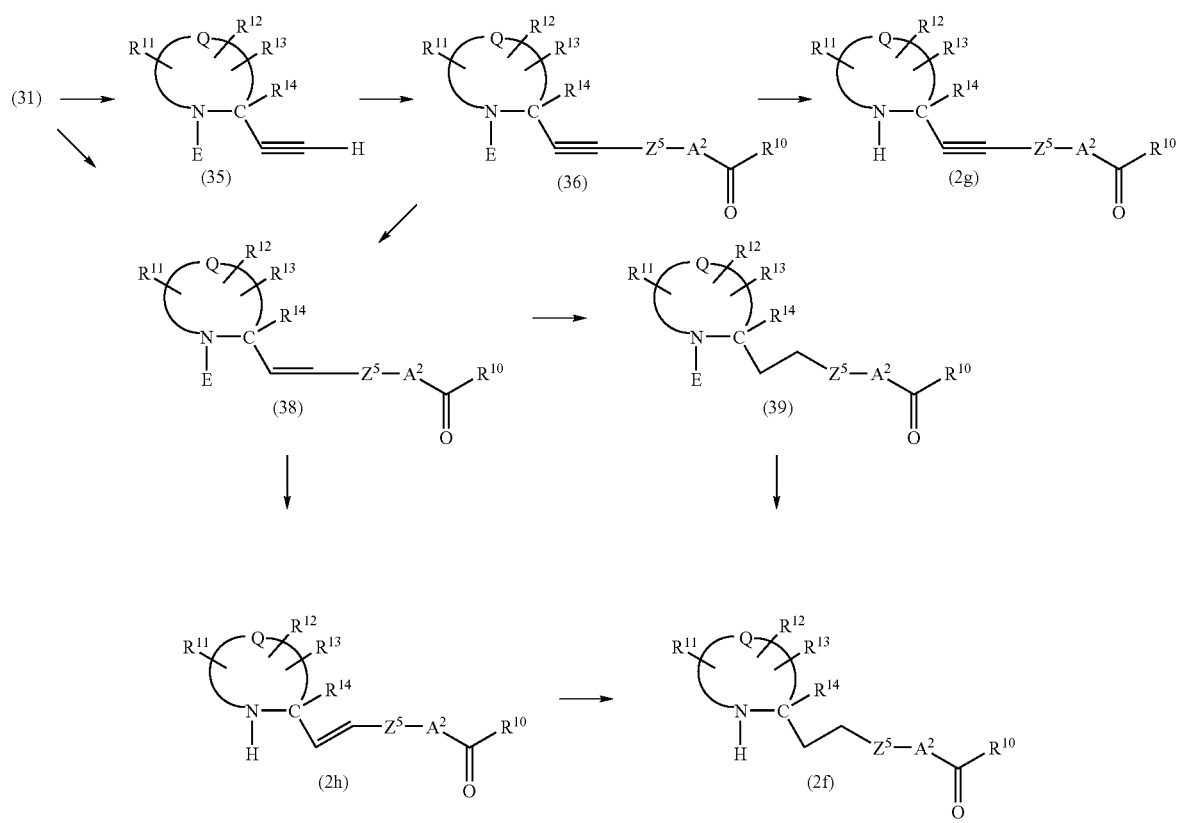

An acetylene derivative (35) can be prepared from the compound (31) in accordance with a known triple bond forming reaction, for example, by reacting trimethylsilyldiazomethane with a base such as lithium diisopropylamide in an inert ether solvent such as tetrahydrofuran at a temperature range of from −78° C. to the boiling point of the solvent and then reacting the resulting compound with the above-described aldehyde derivative (31) (Y. Ito et al., *Synlett*, 1163 (1997)). The acetylene derivative thus obtained is then reacted, in a known manner, with an aryl halide derivative or trifluoromethylsulfonyloxyaryl derivative, which is available commercially or in a known manner, in the presence of a palladium catalyst such as tetrakistriphenylphosphine palladium or palladium acetate and an organic base such as diisopropylamine or an inorganic base such as potassium carbonate in an inert polar solvent such as N,N-dimethylformamide at a temperature range of from −20° C. to the boiling point of the solvent, preferably from 0° C. to the boiling point, whereby the corresponding ethynyl derivative (36) can be prepared (T.Eckert et al., *Synth. Commun.*, 28, 327 (1998)). By deprotection of E from the resulting derivative, a compound of the formula (2g) can be prepared. As the preferable protecting group E, a tert-butoxycarbonyl group can be exemplified.

A vinyl derivative (38) is available in a known manner by using the above-described aldehyde derivative (31) as a raw material. The compound of the formula (38) can be prepared by reacting a Wittig-Horner reagent, which is available commercially or in a known manner, with a base such as lithium hexamethyldisilazane in an inert ether solvent such as tetrahydrofuran at a temperature range of from −78° C. to the boiling point of the solvent, preferably from −78° C. to room temperature and then reacting the resulting compound with the aldehyde derivative (31). Then, by deprotection of E, the compound of the formula (2h) can be prepared. Alternatively, the vinyl derivative (38) is available by subjecting the above-described ethynyl derivative (36) used as a raw material to known reducing reaction. For example, the ethynyl derivative (36) is subjected to catalytic hydrogenation in an inert alcohol solvent such as ethanol in the presence of a Lindlar catalyst and an organic amine base, such as quinoline, serving as a catalytic poison, whereby the vinyl derivative (38) can be prepared. Also upon preparation of the vinyl derivative, a preferable protecting group E must be used and as it, a tertiary butoxycarbonyl group is preferred.

An ethyl derivative (39) is available by catalytic hydrogenation of the ethynyl derivative (36) or vinyl derivative (38) used as a raw material. Then, the protecting group E is removed, whereby the compound of the formula (2i) can be prepared. Alternatively, the compound of the formula (2i) can be obtained by catalytic hydrogenation of the ethynyl derivative (2g) or vinyl derivative (2h).

In the below-described (Scheme 10) to (Scheme 13), a preparation process of a pyrrolidine is shown as a specific example of a preparation process of the compound of the formula (20) used as a raw material in (Scheme 5) (in the schemes, $R^{30}$ represents a lower alkyl group, $R^{31}$, $R^{33}$, $R^{36}$ and $R^{34}$ each independently represents a substituted or unsubstituted alkyl group, a substituted or unsubstituted aryl group or a substituted or unsubstituted heteroaryl group, $X^5$ represents a cyano group, an amino group, an azide group, a halogen atom, a substituted or unsubstituted monoalkylamino group, a substituted or unsubstituted dialkylamino group, a substituted or unsubstituted cycloalkylamino group, a substituted or unsubstituted alkylsulfonylamino group, a substituted or unsubstituted allyloxy group, a substituted or unsubstituted alkylthio group, a substituted or unsubstituted alkylsulfoxide group or a substituted or unsubstituted alkylsulfone group and E has the same meaning as described above).

In the below-described (Scheme 10), shown is a preparation process of a compound having a substituent introduced into the 4-position of pyrrolidine. An ester derivative (41) can be prepared by reacting commercially available 4-hydroxy-L-proline (40) with methanol hydrochloride, for example, at a temperature range of from room temperature to the boiling point of the solvent. The resulting ester derivative is then treated in an inert polar solvent mixture such as water and acetonitrile in the presence of an acid anhydride such as di-tert-butyl dicarbonate, an acyl-halide such as benzyloxycarbonyl chloride, an organic amine base such as triethylamine or an inorganic base such as potassium carbonate, whereby a compound of the formula (20a) can be prepared. The secondary hydroxyl group of the alcohol derivative (20a) can be converted into a secondary hydroxyl group having a contrary steric configuration by the Mitsunobu reaction. For example, the alcohol derivative (20a) and formic acid are subjected to the Mitsunobu reaction to introduce a formyloxy group into the secondary hydroxyl group portion, followed by alkaline hydrolysis by using an inorganic base such as potassium carbonate, preferably sodium bicarbonate, whereby the compound (20b) can be prepared.

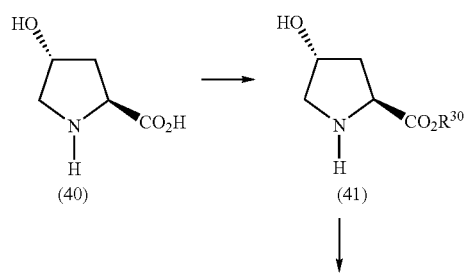

-continued

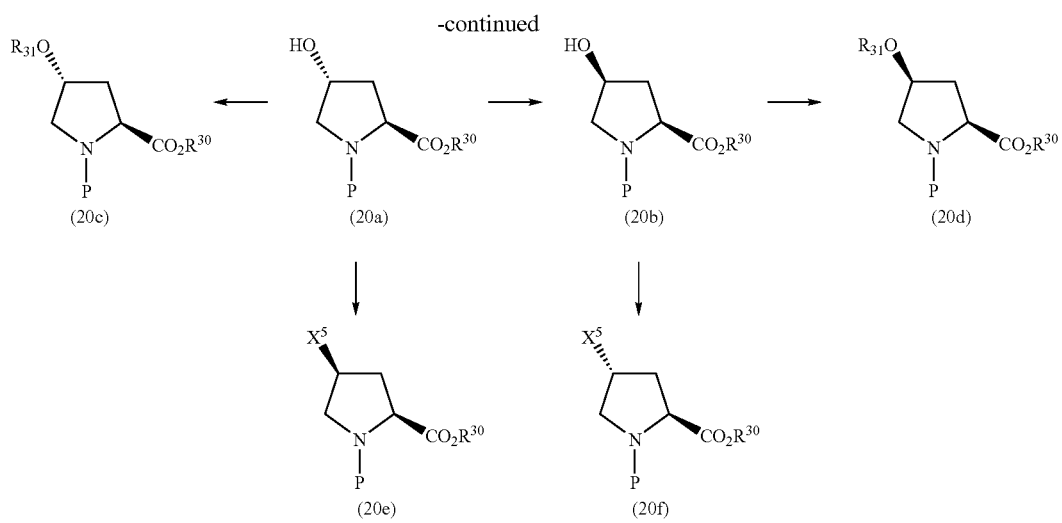

Alkoxy derivatives (20c) and (20d) can be prepared by treating the secondary hydroxyl group portion of the alcohol derivatives (20a) and (20b) in a known manner or while maintaining the steric structure in a known manner. For example, the alkoxy compounds (20c) and (20d) can be prepared by treating the alcohol compounds (20a) and (20b) in an inert ether solvent such as tetrahydrofuran or an inert polar solvent such as N,N-dimethylformamide at a temperature range of from −20° C. to the boiling point of the solvent, preferably from −20° C. to room temperature in the presence of an alkyl halide such as methyl iodide or benzyl bromide and an inorganic base such as sodium hydride. When the corresponding benzyloxy derivative is prepared by the above-described alkylation, it is preferred to add an inorganic base to the reaction mixture in the final stage of reaction at a temperature range of from −20° C. to room temperature. A compound of the formula (I) having a hydroxy group at 4-position of the pyrrolidine ring can be prepared, for example, by protecting the 4-hydroxyl group of the pyrrolidine ring of the compound (20a) or (20b) with a tertiary butyldimethylsilyl group and then using the resulting compound as a raw material.

By known $S_N 2$ type nucleophilic displacement reaction of the secondary hydroxyl groups of the compounds (20a) and (20b), these compounds can be converted into the compounds (20e) and (20f), respectively. For example, a fluorine atom can be introduced by treating, for example, the compound (20a) with a fluorinating agent such as diethylaminosulfur trifluoride in an inert halogenated hydrocarbon solvent such as methylene chloride at a temperature range of from −78° C. to the boiling point of the solvent, preferably from 0° C. to room temperature (L.Demange et al., Tetrahedron Lett., 39, 1169 (1998)).

Alternatively, a fluorine atom can be introduced by converting the secondary hydroxyl groups of the compounds (20a) and (20b) into an eliminating group such as alkyl or arylsulfonyloxy group, e.g., mesyloxy group and then treating the resulting compound with a fluoride of an alkali metal such as potassium fluoride or a fluoride of an alkaline earth metal such as cesium fluoride in an inert polar solvent such as N,N-dimethylformamide or ethylene glycol (G. Giardina et al., Synlett, 1, 57 (1995)). A cyano group can be introduced into the mesyloxy derivative by acting thereon a cyanation agent such as potassium cyanide. The secondary hydroxyl group of each of the compounds (20a) and (20b) can be converted into a chlorine atom by reacting it with triphenylphosphine in a carbon tetrachloride solvent at a temperature range of from −20° C. to the boiling point of the solvent, preferably from room temperature to the boiling point of the solvent (T. R. Webb et al., J. Org. Chem., 56, 3009 (1991)). It can also be converted into a phenoxy or phthaloyl group by the Mitsunobu reaction. This phthaloyl group can be converted into an amino group in a known manner by treating it with a commercially available hydrazine hydrate in an inert alcohol solvent such as ethanol. Furthermore, this amino group can be converted into a monoalkylamino or dialkylamino group by the above-described reductive amination reaction or treatment with a carbon halide such as iodomethane in the presence of an organic amine base such as triethylamine or an inorganic base such as potassium carbonate.

The above-described conversion into an amino group can be conducted by an alternative process. For example, after conversion of the secondary hydroxyl group of each of the compounds (20a) and (20b) into an eliminating group such as mesyloxy group, the compound is treated with lithium azide or sodium azide in an inert polar solvent such as N,N-dimethylformamide or inert ether solvent such as tetrahydrofuran at a temperature range of from −20° C. to the boiling point of the solvent, whereby the corresponding azide derivative can be obtained. It is then treated with triphenylphosphine and water in a known reducing method in an inert ether solvent such as tetrahydrofuran at a temperature range of from −20° C. to the boiling point of the solvent, preferably from room temperature to the boiling point of the solvent, or is subjected to catalytic hydrogenation or reduction with a reducing agent such as sodium borohydride in a known manner to convert the group into an amino group. An introduction of substituent at the 3-position of pyrrolidine ring can also be conducted by using commercially available trans-3-hydroxy-L-proline as a raw material in accordance with the manner described in (Scheme 10).

In the below-described (Scheme 11), a process for preparing dehydropyrrolidine (20g) in a known manner is indicated. For example, a 3,4-dihydropyrrolidine derivative (20g) can be prepared by converting the secondary hydroxyl group of the derivative (20a) into an eliminating group such as a mesyloxy group or bromine atom, preferably iodine atom, and then treating the resulting compound with an organic amine base such as 1,8-diazabicyclo(5,4,0)-7-undecene. Alternatively, the 3,4-dihydropyrrolidine derivative (20g) can be prepared by converting the secondary hydroxyl group of the derivative (20a) into the above-described eliminating group, treating with phenylselenyl sodium, which has been prepared from diphenyl diselenide and sodium borohydride, in methanol and then treating with a peroxide such as hydrogen peroxide in methylene chloride in the presence of pyridine (H.Rueger et al., *Can. J. Chem.*, 60, 2918 (1982)).

[Scheme 11]

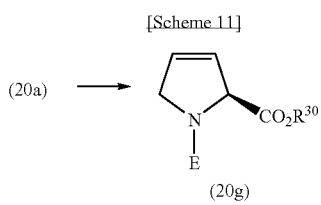

In the below-described (Scheme 12), a process for preparing a 3,4-dihydroxy derivative (20h) and a 3,4-dialkoxy derivative (20i) in a known manner by using, as a raw material, the compound (20g) shown in (Scheme 11) is specifically indicated.

The compound (20g) can be converted into its corresponding 3,4-dihydroxy derivative (20h) by treating it with a commercially available oxidizing agent such as 4-methylmorpholin-4-oxide derivative and osmium tetraoxide in a mixture of an inert polar solvent such as acetone with water or an inert ether solvent such as tetrahydrofuran with water, at a temperature range of from −20° C. to the boiling point of the solvent, preferably from 0° C. to room temperature. Then, the resulting compound can be converted into a dialkoxy derivative (20i) by treating with an alkyl halide such as methyl iodide or benzyl bromide in the presence of an inorganic base such as sodium hydride in an inert polar solvent such as N,N-dimethylformamide. Or, a derivative (20i) having a cyclic acetal or cyclic ketal introduced therein can be prepared by treating with a commercially available ketalization agent or acetalization agent in an inert polar solvent such as N,N-dimethylformamide or an inert halogenated hydrocarbon solvent such as methylene chloride in the presence of an organic acid such as tosylic acid (J. E. Baldwin et al., *Tetrahedron Lett.*, 35, 4649 (1994); D. M. Goli et al., *Carbohydr. Res.*, 259, 219 (1994)). The above-described ketal or acetal is usable as a protecting group for the secondary hydroxyl group at the 3,4-position. The ketal or acetal derivative can be used as a raw material for the preparation of a compound of the formula (I) having 3,4-dihydroxypyrrolidine.

[Scheme 12]

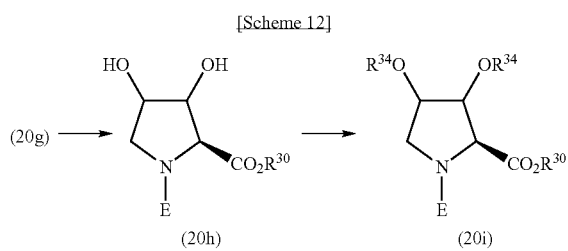

In the below-described (Scheme 13), a process for preparing a derivative (20j) having a substituent introduced at the 5-position of pyrrolidine in a known manner is indicated. For example, a commercially available N-(tertiary butyloxycarbonyl)-L-pyroglutamate ester (42) can be converted into the corresponding ring-opened derivative (43) by treating with an organolithium reagent such as phenyl lithium or a Grignard reagent such as methyl magnesium bromide in an inert ether solvent such as tetrahydrofuran at a temperature range of from −20° C. to the boiling point of the solvent, preferably from −20° C. to room temperature.

Then the resulting derivative can be converted into the corresponding cyclic imine derivative (44) by treating under acidic conditions, preferably, with trifluoroacetic acid to remove the tertiary butoxycarbonyl group. By catalytic hydrogenation of the resulting compound, the corresponding pyrrolidine derivative (20j) having a 2,5-cis configuration can be prepared (J. V. Betsbrugge et al., *Tetrahedron*, 54, 1753 (1998)). It can also be prepared by, instead of catalytic hydrogenation, reduction of imine with a reducing agent such as sodium cyanoborohydride. A pyrrolidine derivative having a 2,5-trans configuration can be prepared, for example, by using commercially available benzyl glycidyl ether as a starting material in accordance with Takano's procedure (S. Takano et al., *Tetrahedron Lett.*, 30, 3805 (1989)).

[Scheme 13]

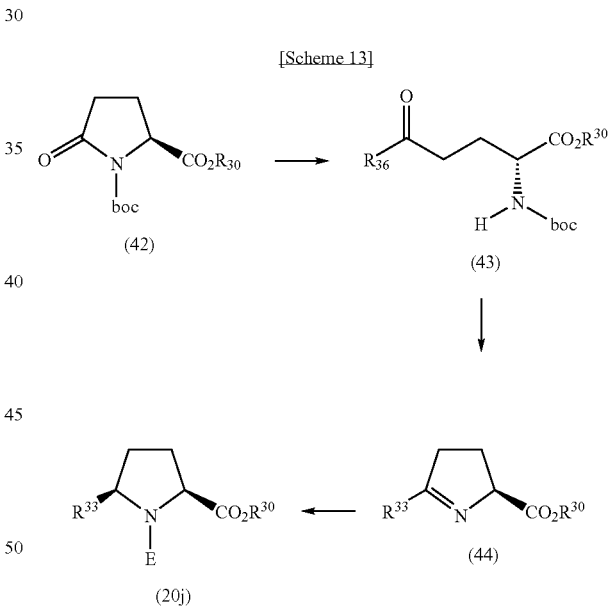

In the below-described (Scheme 14) to (Scheme 18), a process for preparing the compound of the formula (4) serving as a raw material in (Scheme 1) from commercially available amino acid, for example, glycine, is shown (in these schemes, E, $R^{20}$, $R^{10}$, $R^{28}$, $R^{20}$, Z, $Z^3$, $Z^4$, $A^2$, $X^4$, $n^1$ and $R^{19}$ have the same meanings as described above).

The below-described (Scheme 14) indicates that compounds of the formulas (4a), (4b) and (4c) can be synthesized in accordance with the preparation process as shown above in (Scheme 5) and (Scheme 6) by using as a raw material a glycine derivative (45) which can be prepared in a known manner.

[Scheme 14]

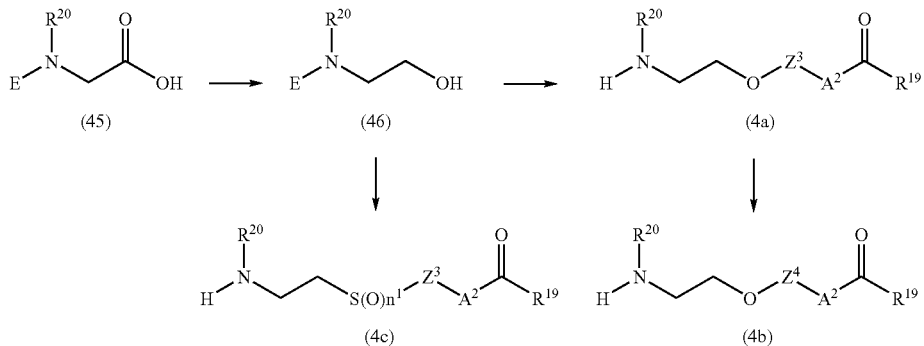

The below-described (Scheme 15) indicates that compounds of the formulas (4d) and (4e) can be prepared in accordance with a preparation process shown in (Scheme 7) by using the above-described glycine derivative (45) as a raw material.

[Scheme 15]

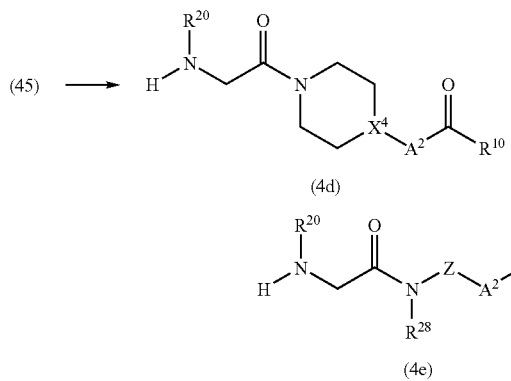

The below-described (Scheme 16) indicates that compounds of the formulas (4f) and (4g) can be prepared in accordance with a preparation process as shown in (Scheme 8) by using the above-described alcoholic derivative (46) as a raw material.

[Scheme 16]

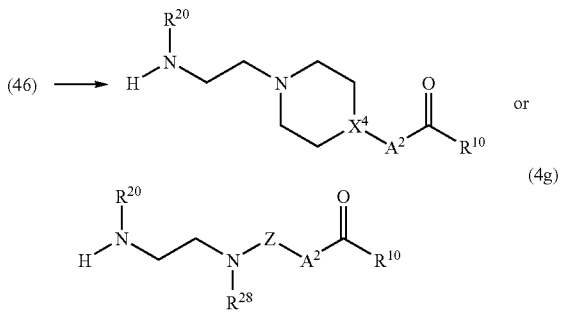

The below-described (Scheme 17) indicates that compounds of the formulas (4h), (4i) and (4j) can be prepared in accordance with a preparation process as shown in (Scheme 9) by using the above-described alcohol derivative (46) as a raw material.

[Scheme 17]

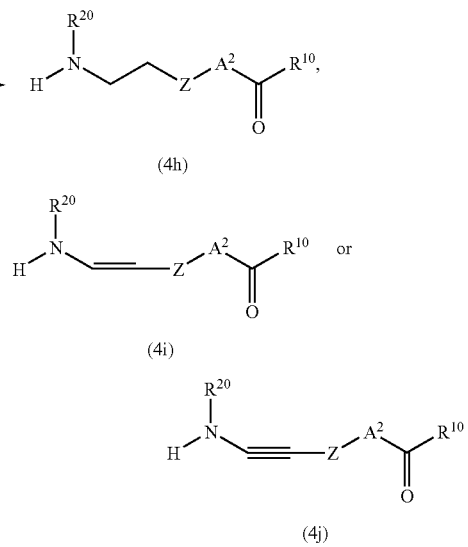

The below-described (Scheme 18) indicates that a primary amine (48) which is available commercially or in a known manner can be converted into a compound of the formula (4k) in accordance with the reductive N-alkylating reaction as shown in (Scheme 8) by reacting the primary amine with an aldehyde derivative (49) which is available commercially or in a known manner.

[Scheme 18]

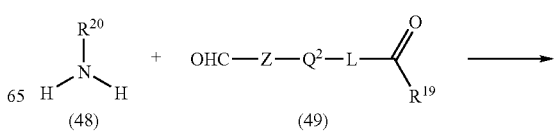

-continued

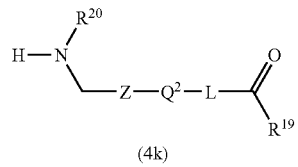

(4k)

As described later in Tests, the invention compounds or salts thereof thus obtained selectively inhibit the binding of cell adhesion molecules to VLA-4 and at the same time, exhibits high oral absorption. Accordingly, the invention compounds are useful as a preventive or remedy of diseases caused by VLA-4-related cell adhesion, that is, various diseases mediated by migration and adhesion of leukocytes, such as inflammatory diseases, autoimmune diseases, metastasis, bronchial asthma, rhinostenosis, diabetes, arthritis, psoriasis, multiple sclerosis, inflammatory intestinal diseases and rejection upon transplantation.

The medicament of the present invention can be administered through various administration routes including oral administration.

As an injection, they can be administered by any one of intravenous injection, intramuscular injection or subcutaneous administration.

Such formulations can be prepared by selecting a proper form depending on the administration route and adopting a usually employed method for it.

Examples of orally administrable formulations include tablets, powders, granules, capsules, solutions, syrups, elixirs, and oily or aqueous suspensions. Injections sometimes contain a stabilizer, antiseptic, solubilizing aid or the like. It is possible that after an injection solution which may contain such an aid is encapsulated in a container, it may be lyophilized into a solid formulation and reconstituted upon use if desired. Liquid formulations include solutions, suspensions and emulsions. Upon preparation of them, a suspending agent or emulsifying agent can be added as an additive.

The medicament containing the invention compound is preferably administered to adult by repeating once/day administration at proper intervals. Dosage falls within a range of 0.01 mg to 2000 mg, preferably 0.1 mg to 1000 mg.

To the medicament of the present invention, it is possible to use, in combination, an anti-inflammatory, anti-arthritic, adrenocortical steroid (corticosteroid), immunosuppressant, antipsoriatic, bronchodilator, a drug for bronchial asthma or antidiabetic as needed within an extent not damaging the effect of the invention.

EXAMPLES

The present invention will hereinafter be described in detail by Examples.

In Examples, "IR", "NMR" and "MS" mean "infrared absorption spectrum", "nuclear magnetic resonance spectrum" and "mass spectrometry", respectively. A ratio of an eluting solvent used for separation and purification by chromatography means a volumetric ratio. "IR" means the measurement by the KBr tablet method or ATR method. In the parentheses of "NMR" mean a measuring solvent with TMS (tetramethylsilane) used as an internal standard substance. "Anal. Calcd for rational formula" means a calculated value of elemental analysis, while a measured value is indicated after "Found". "HPLC" is an abbreviation of High Performance Liquid Chromatography and indicated in the parentheses are column and eluting solvent.

Example 1

4-((4S)-Fluoro-1-(2-phenylamino-6-benzoxazoly-lacetyl-(2S)-pyrrolidinylmethoxy)benzoic acid (Step 1) Synthesis of methyl 2-phenylaminobenzoxazol-6-acetate

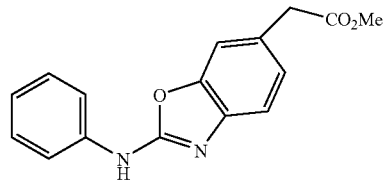

In ethanol (10 ml) was dissolved methyl 3-hydroxy-4-nitrophenylacetate (592 mg, 2.81 mmol), followed by the addition of 5% palladium/carbon (194 mg). The resulting mixture was subjected to catalytic hydrogenation overnight under stirring at room temperature and normal pressure. After removal the catalyst from the reaction mixture by filtration through Celite under reduced pressure, the filtrated cake was washed with ethanol (30 ml). The filtrate was stirred at room temperature. After addition of phenyl isothiocyanate (370 μl, 3.09 mmol) and stirring at room temperature for one hour, mercuric oxide (yellow) (1.1 g, 5.07 mmol) was added. The reaction mixture was heated under reflux for 3 hours. The mixture was then cooled and the insoluble matter was filtered out under reduced pressure. The filtrate was distilled under reduced pressure. The residue was purified by chromatography on a silica gel column, whereby methyl 2-phenylaminobenzoxazol-6-acetate (480 mg, 61%) was obtained as a white solid from chloroform-ethyl acetate (10:1, v/v) eluate fractions.

$^1$H-NMR (CDCl$_3$) δ: 3.69 (s, 2H), 3.70 (s, 3H), 7.11 (m, 2H), 7.24 (m, 1H), 7.30 (s, 1H), 7.50-7.38 (m, 3H), 7.59 (d, J=1.2 Hz, 2H).

(Step 2) Synthesis of 2-phenylaminobenzoxazol-6-acetic acid

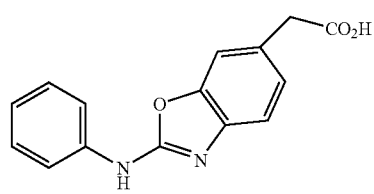

In tetrahydrofuran (which will hereinafter be abbreviated as "THF") (2 ml) and methanol (2 ml) was dissolved methyl 2-phenylaminobenzoxazol-6-acetate (460 mg, 1.63 mmol), followed by the addition of 1N NaOH (3.3 ml) under stirring at room temperature. After further stirring overnight at room temperature, the reaction mixture was concentrated into a small volume. The concentrate was acidified with acetic acid. The crystals thus obtained were collected by filtration, washed with water and then dried, whereby 2-phenylaminobenzoxazol-6-acetic acid (348 mg, 80%) was obtained as a pale yellow solid.

$^1$HNMR (DMSO-d$_6$) δ: 3.64 (s, 2H), 7.03 (t, J=7.6 Hz, 1H), 7.11 (dd, J=1.2, 8.0 Hz, 1H), 7.35–7.40 (m, 4H), 7.76 (d, J=8.8 Hz, 2H), 10.60 (brs, 1H), 12.4 (br, 1H).

(Step 3) Synthesis of methyl 4-((4S)-fluoro-1-(2-phenylamino-6-benzoxazolylacetyl)-(2S)-pyrrolidinylmethoxy)benzoate

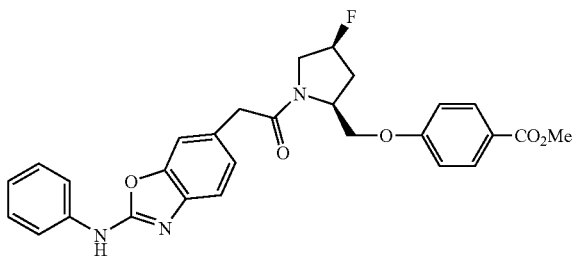

In N,N-dimethylformamide (which will hereinafter be abbreviated as "DMF") (12 ml) were dissolved 2-phenylaminobenzoxazol-6-acetic acid (309 mg, 1.15 mmol) and methyl 4-((4S)-fluoro-(2S)-pyrrolidinylmethoxy)benzoate (292 mg, 1.15 mmol), followed by the addition of 1-ethyl-3-(3-dimethylaminopropyl)carbodiimide hydrochloride (which will hereinafter be abbreviated as "EDC•HCl") (331 mg, 1.73 mmol), 1-hydroxybenzotriazole (which will hereinafter be abbreviated as "HOBt") and 4-dimethylaminopyridine (which will hereinafter be abbreviated as "DMAP") under stirring at room temperature. The reaction mixture was further stirred overnight at room temperature. The reaction mixture was diluted with ethyl acetate. The diluted mixture was then washed with saturated brine, dried over anhydrous magnesium sulfate and distilled under reduced pressure to remove the solvent. The residue was purified by chromatography on a silica gel column, whereby from chloroform-methanol (10:1, v/v) eluate fractions, methyl 4-((4S)-fluoro-1-(2-phenylamino-6-benzoxazolylacetyl)-(2S)-pyrrolidinylmethoxy)benzoate (560 mg, 96%) was obtained as a pale brown powder.

$^1$H-NMR (CDCl$_3$) δ: 1.20–1.25 (m, 1H), 2.02–2.22 (m, 1H), 2.32–2.56 (series of dd, J=15.0, 19.6 Hz, total 1H), 3.63–4.13 (m, total 4H), 3.85 (s, 3H), 4.51 (dd, J=4.4, 8.8 Hz, 1H), 4.62 (dt, J=4.4, 8.8 Hz, 1H), 5.29 (ABq, 1H), 6.84 (t, J=8.8 Hz, 1H), 6.95 (d, J=9.2 Hz, 2H), 7.08 (t, J=6.3 Hz, 2H), 7.31–7.42 (m, 3H), 7.60 (t, J=6.8 Hz, 2H), 7.90–8.00 (m, 2H).

(Step 4) Synthesis of 4-((4S)-fluoro-1-(2-phenylamino-6-benzoxazolylacetyl)-(2S)-pyrrolidinylmethoxy)benzoic acid

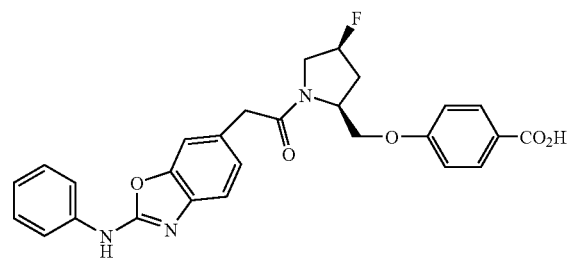

In THF (8 ml) and methanol (2 ml) was dissolved methyl 4-((4S)-fluoro-1-(2-phenylamino-6-benzoxazolylacetyl)-(2S)-pyrrolidinylmethoxy)benzoate (383 mg, 0.76 mmol). After addition of 0.25N NaOH (2 eq), the mixture was stirred overnight at room temperature. The reaction mixture was diluted with chloroform-methanol (5:1, v/v). The diluted mixture was washed with 1N HCl, dried over anhydrous magnesium sulfate and distilled under reduced pressure to remove the solvent. The residue was purified by chromatography on a silica gel column, whereby from chloroform-methanol (5:1, v/v) eluate fractions, 4-((4S)-fluoro-1-(2-phenylamino-6-benzoxazolylacetyl)-(2S)-pyrrolidinylmethoxy)benzoic acid (210 mg, 56%) was obtained as a pale brown powder.

IR (KBr) 2977, 1683, 1643, 1604 cm$^{-1}$;
$^1$H-NMR (DMSO-d$_6$) δ: 1.09 (t, J=7.0 Hz, 1H), 2.24–2.31 (m, 2H), 3.75–4.42 (m, total 7H), 5.44 (m, total 1H), 7.00–7.12 (m, 4H), 7.37 (m, 4H), 7.75 (d, J=8.4 Hz, 2H), 8.87 (d, J=8.4 Hz, 2H).

MS (FAB) m/z 490 (M$^+$+1);
Anal. Calcd for C$_{27}$H$_{24}$FN$_3$O$_5$·2.75H$_2$O: C, 60.16; H, 5.52; N, 7.80. Found: C, 60.46; H, 5.19; N, 7.24.

Example 2

4-((4S)-Fluoro-1-(2-(2-methylphenylamino)-6-benzoxazolylacetyl)-(2S)-pyrrolidinylmethoxy)benzoic acid (Step 1) Synthesis of benzyl 5-fluoro-2-nitrophenyl ether

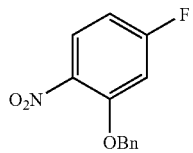

In DMF (300 ml), 5-fluoro-2-nitrophenol (10.0 g, 63.7 mmol), benzyl bromide (10.9 g, 63.7 mmol) and potassium carbonate (13.2 g, 95.6 mmol) were stirred at 80° C. for 4 hours. After cooling, the reaction mixture was poured in water (200 ml), followed by extraction with ether (2×200 ml). The extract was washed with saturated brine (200 ml), dried over anhydrous magnesium sulfate and distilled under reduced pressure to remove the solvent. The residue was purified by chromatography on a silica gel column, whereby from hexane-ethyl acetate (4:1) eluate fractions, the title compound (14.3 g, 91.3%) was obtained as a pale yellow amorphous substance.

$^1$H-NMR (CDCl$_3$) δ: 5.22 (s, 2H), 6.71–6.75 (m, 1H), 6.83 (dd, J=10.3, 2.5 Hz, 1H), 7.33–7.47 (m, 5H), 7.96 (dd, J=9.1, 5.4 Hz, 1H).

(Step 2) Synthesis of diethyl 3-benzyloxy-4-nitrophenylmalonate

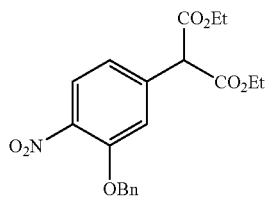

In DMF (100 ml) was suspended sodium hydride (4.63 g, 115.7 mmol). Under cooling at 0° C. and stirring, diethyl malonate (18.5 g, 115.7 mmol) was added dropwise. After vigorous evolution of a hydrogen gas stopped, a solution of benzyl 5-fluoro-2-nitrophenyl ether (14.3 g, 57.8 mmol) in DMF (100 ml) was added to the reaction mixture at 0° C. The reaction mixture was stirred for 15 hours at room temperature. Water (500 ml) was poured and the mixture was extracted with ethyl acetate (300 ml). The extract was washed with saturated brine (200 ml), dried over anhydrous magnesium sulfate and distilled under reduced pressure to remove the solvent. The residue was purified by chromatography on a silica gel column, whereby from hexane-ethyl acetate (3:1) eluate fractions, the title compound (22.0 g, 100%) was obtained as a yellow oil.

$^1$HNMR (CDCl$_3$) δ: 1.24–1.28 (m, 6H), 4.18-4.29 (m, 4H), 4.62 (s, 1H), 5.25 (s, 2H), 7.05 (dd, J=8.3, 1.7 Hz, 1H), 7.29–7.48 (m, 6H), 7.85 (d, J=8.3 Hz, 1H).

(Step 3) Synthesis of 3-hydroxy-4-nitrophenylacetic acid

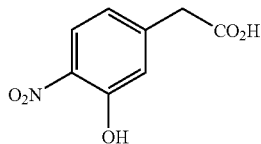

A mixture of diethyl 3-benzyloxy-4-nitrophenylmalonate (22.0 g, 57.8 mmol), acetic acid (200 ml) and concentrated hydrochloric acid (100 ml) was heated under reflux for 15 hours under stirring. After the reaction mixture was cooled to room temperature, the solvent was distilled off from the reaction mixture under reduced pressure. The solid thus obtained was collected by filtration under reduced pressure, followed by drying under reduced pressure, whereby the title compound (5.45 g, 48%) was obtained as a pale yellow amorphous substance.

$^1$H-NMR (DMSO-d$_6$) δ: 3.64 (s, 2H), 6.88 (dd, J=8.3, 1.6 Hz), 7.05 (s, 1H), 7.85 (d, J=8.3 Hz, 1H), 10.90 (s, 1H), 12.55 (br s, 1H).

(Step 4) Synthesis of methyl 3-hydroxy-4-nitrophenylacetate

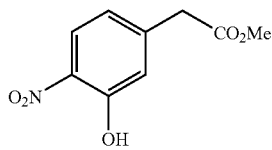

To 3-hydroxy-4-nitrophenylacetic acid (5.45 g, 27.6 mol) and methanol (100 ml) was added concentrated sulfuric acid (0.5 ml). The mixture was then heated under reflux for 4 hours under stirring. After cooling to room temperature, the reaction mixture was distilled under reduced pressure to remove the solvent. Water (100 ml) was added to the residue, followed by extraction with ether (300 ml). The extract was washed successively with a saturated aqueous solution (100 ml) of sodium bicarbonate and saturated brine (100 ml), dried over anhydrous magnesium sulfate and distilled under reduced pressure to remove the solvent, whereby the title compound (4.90 g, 84%) was obtained as a yellow crystalline powder.

$^1$H-NMR (CDCl$_3$) δ: 3.67 (s, 2H), 3.73 (s, 3H), 6.91 (d, J=8.3 Hz, 1H), 7.08 (s, 1H), 8.06 (d, J=8.3 Hz, 1H), 10.59 (s, 1H).

(Step 5) Synthesis of methyl 2-(2-methylphenylamino)-6-benzoxazolylacetate

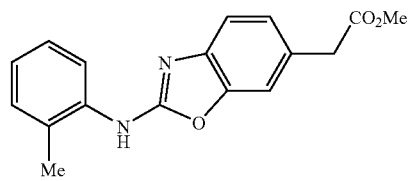

In ethanol (20 ml) was dissolved methyl 3-hydroxy-4-nitrophenylacetate (1.00 g, 4.74 mmol), followed by the addition of 5% palladium/carbon (500 mg). Under stirring at room temperature, the mixture was subjected to catalytic hydrogenation for 15 hours. After filtration of the reaction mixture through Celite to remove the insoluble matter, 2-tolyl isothiocyanate (765 μl, 5.69 mmol) was added to the filtrate while stirring at room temperature. The reaction mixture was stirred for 15 hours. After addition of mercuric oxide (yellow) (1.72 g, 7.94 mmol), the mixture was heated under reflux for 5 hours under stirring. The reaction mixture was then cooled to room temperature. After filtration of the reaction mixture through Celite under reduced pressure, the solvent was distilled off under reduced pressure from the filtrate. The residue was purified by chromatography on a silica gel column, whereby from chloroform-ethyl acetate (10:1) eluate fractions, the title compound (1.18 g, 84%) was obtained as a yellow oil.

$^1$H-NMR (CDCl$_3$) δ: 2.35 (s, 3H), 3.69 (s, 2H), 3.70 (s, 3H), 7.07 (t, J=8.1 Hz, 1H), 7.12 (dd, J=8.1, 1.5 Hz, 1H), 7.22–7.33 (m, 3H), 7.40 (d, J=8.1 Hz, 1H), 8.06 (d, J=8.1 Hz, 1H).

(Step 6) Synthesis of 2-(2-methylphenylamino)-6-benzoxazolylacetic acid

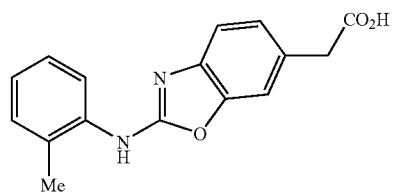

THF (30 ml) and 0.25N NaOH (32 ml, 8.00 mmol) were added to methyl 2-(2-methylphenylamino)-6-benzoxazolylacetate (1.18 g, 3.98 mmol), followed by stirring at room temperature for 5 hours. The reaction mixture was poured in 1N HCl (50 ml), followed by extraction with a chloroform-methanol (5:1, 2×200 ml) mixture. The extract was dried over anhydrous magnesium sulfate and distilled under reduced pressure to remove the solvent, whereby the title compound (867 mg, 77%) was obtained as a pale yellow amorphous substance.

$^1$H-NMR (DMSO-d$_6$) δ: 2.31 (s, 3H), 3.64 (s, 2H), 7.09–7.13 (m, 2H), 7.24-7.30 (m, 3H), 7.39 (d, J=1.0 Hz, 1H), 7.80 (dd, J=7.3, 1.5 Hz, 1H).

MS (ESI) m/z, 283 (M$^+$+1).

(Step 7) Synthesis of methyl 4-((4S)-fluoro-1-(2-(2-methylphenylamino)-6-benzoxazolylacetyl)-(2S)-pyrrolidinylmethoxy)benzoate

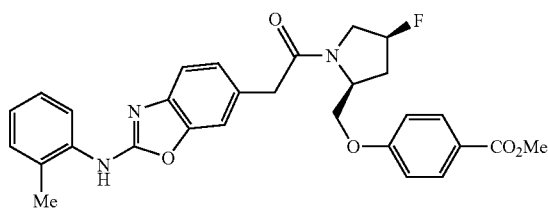

In DMF (10 ml) were dissolved 2-(2-methylphenylamino)-6-benzoxazolylacetic acid (300 mg, 1.06 mmol) and 4-((4S)-fluoro-(2S)-pyrrolidinylmethoxy)benzoate (269 mg, 1.06 mmol). After addition of EDC•HCl (305 mg, 1.59 mmol), HOBt (cat.) and DMAP (cat.) under stirring at room temperature, the mixture was stirred at room temperature for 15 hours. Water (200 ml) was added and the mixture was extracted with ethyl acetate (200 ml). The extract was washed with saturated brine (2×200 ml), dried over anhydrous magnesium sulfate and distilled under reduced pressure to remove the solvent. The residue was purified by chromatography on a silica gel column, whereby from chloroform-ethyl acetate (9:1) eluate fractions, the title compound (573 mg, 100%) was obtained as a yellow foam.

$^1$H-NMR (CDCl$_3$) δ: 2.06–2.59 (series of m, 5H), 3.68–4.15 (series of m, 8H), 4.52–4.65 (m, 2H), 5.24 and 5.37 (m, each, total 1H), 6.86–7.42 (series of m, 9H), 7.94–8.07 (m, 3H).

MS (ESI) m/z, 518 (M$^+$+1).

(Step 8) Synthesis of 4-((4S)-fluoro-1-(2-(2-methylphenylamino)-6-benzoxazolylacetyl)-(2S)-pyrrolidinylmethoxy)benzoic acid

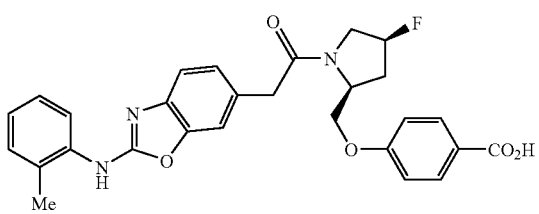

In THF (10 ml) was dissolved methyl 4-((4S)-fluoro-1-(2-(2-methylphenylamino)-6-benzoxazolylacetyl)-(2S)-pyrrolidinylmethoxy)benzoate (573 mg, 1.11 mmol). After addition of 0.25N NaOH (8.8 ml, 2.2 mmol) under stirring at room temperature, the mixture was stirred at room temperature for 15 hours. The reaction mixture was poured in 1N HCl (50 ml), followed by extraction with a chloroform-methanol (5:1, 2×200 ml). The extract was washed with anhydrous magnesium sulfate and then distilled under reduced pressure to remove the solvent. The residue was purified by chromatography on a silica gel column, whereby from chloroform-methanol (20:1 to 10:1) eluate fractions, the title compound (365 mg, 65%) was obtained as a colorless crystalline solid.

$^1$H-NMR (DMSO-d$_6$) δ: 2.25–2.51 (series of m, total 5H, including s, 3H, at d 2.30), 3.70–4.67 (series of m, 7H), 5.30–5.50 (m, total 1H), 7.03–7.09 (m, 4H), 7.24–7.34 (m, 4H), 7.81–7.91 (m, 3H), 9.61 (br s, 1H).

MS (ESI) m/z, 504 (M$^+$+1);

Anal. Calcd for C$_{28}$H$_{26}$FN$_3$O$_5$·0.5H$_2$O: C, 65.62; H, 5.31; N, 8.20. Found: C, 65.97; H, 5.61; N, 7.73.

Example 3

4-((4S)-Fluoro-1-(4-methoxy-2-(2-methylphenylamino)-6-benzoxazolylacetyl)-(2S)-pyrrolidinylmethoxy)benzoic acid (Step 1) Synthesis of 3,5-difluoro-2-nitrophenol

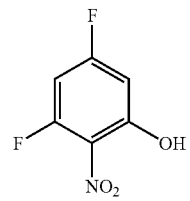

Dimethylsulfoxide (which will hereinafter be abbreviated as "DMSO") (50 ml) and 10N NaOH (12 ml, 120 mmol) were added to 1,3,5-trifluoro-2-nitrobenzene (10.0 g, 56.5 mmol). The mixture was stirred at room temperature for 15 hours. Water (100 ml) and ether (200 ml) were added to separate the reaction mixture into layers. The water layer thus obtained was acidified with 1N HCl, followed by extraction with ether (2×200 ml). The extract was dried over anhydrous magnesium sulfate and distilled under reduced pressure to remove the solvent. The residue was purified by chromatography on a silica gel column, whereby from chloroform-ethyl acetate (10:1) eluate fractions, the title compound (7.97 g, 81%) was obtained as a yellow crystalline powder.

$^1$H-NMR (CDCl$_3$) δ: 6.53–6.59 (m, 1H), 6.66–6.70 (m, 1H), 10.87 (d, J=1.2 Hz, 1H).

(Step 2) Synthesis of 3,5-difluoro-2-nitroanisole

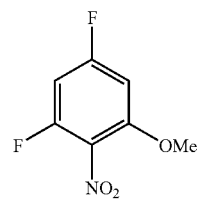

In DMF (50 ml) was dissolved 3,5-difluoro-2-nitrophenol. Potassium carbonate (10.4 g, 75.5 mmol) and methyl iodide (6.3 ml, 100.6 mmol) were added and the mixture was stirred for 15 hours at room temperature. Water (300 ml) was added, followed by extraction with ether (500 ml). The extract was washed with saturated brine (2×200 ml), dried over anhydrous magnesium sulfate and distilled under reduced pressure to remove the solvent, whereby the title compound (8.29 g, 87%) was obtained as a yellow crystalline powder.

$^1$H-NMR (DMSO-d$_6$) δ: 3.97 (s, 3H), 7.21–7.27 (m, 2H).

(Step 3) Synthesis of di-tert-butyl 3-fluoro-5-methoxy-4-nitrophenylmalonate

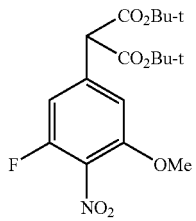

In DMF (60 ml) was suspended sodium hydride (2.75 g, 68.7 mmol). Under stirring at 0° C., di-tert-butyl malonate (14.9 g, 68.7 mmol) was added dropwise. After vigorous emission of a hydrogen gas stopped, a solution of 3,5-difluoro-2-nitroanisole (5.20 g, 27.5 mmol) in DMF (40 ml) was added. The reaction mixture was stirred at 80° C. for 4 hours. After cooling the reaction mixture to room temperature, water (200 ml) was added to terminate the reaction, followed by extraction with ether (300 ml). The extract was washed with saturated brine (200 ml), dried over anhydrous magnesium sulfate and distilled reduced pressure to remove the solvent. The residue was purified by chromatography on a silica gel column, whereby hexane-ethyl acetate (10:1) eluate fractions, the title compound (6.56 g, 62%) was obtained as an yellow oil.

$^1$H-NMR (CDCl$_3$) δ: 1.48 (s, 18H), 3.94 (s, 3H), 4.41 (s, 1H), 6.92 (m, 2H).

(Step 4) Synthesis of 3-fluoro-5-methoxy-4-nitrophenylacetic acid

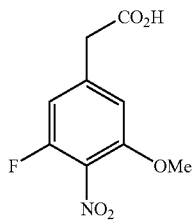

Acetic acid (7 ml) and concentrated hydrochloric acid (7 ml) were added to di-tert-butyl 3-fluoro-5-methoxy-4-nitrophenylmalonate (4.88 g, 12.7 mmol). The mixture was heated under reflux for 15 hours under stirring. After cooling, the reaction mixture was distilled under reduced pressure to remove the solvent. To the residue were added 1N NaOH (200 ml) and ether (200 ml) to separate it into layers. The water layer thus obtained was acidified with 1N HCl, followed by extraction with ether (200 ml). The extract was dried over anhydrous magnesium sulfate and distilled under reduced pressure to remove the solvent, whereby the title compound (2.83 g, 97%) was obtained as a pale brown solid.

$^1$H-NMR (CDCl$_3$) δ: 3.68 (s, 2H), 3.93 (s, 3H), 6.78 (m, 2H), 9.31 (br s, 1H).

(Step 5) Methyl 3-benzyloxy-5-methoxy-4-nitrophenylacetate

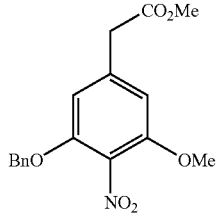

Sodium hydride (918 mg, 23.0 mmol) was added to benzyl alcohol (30 ml) in portions. After vigorous evolution of a hydrogen gas stopped, a solution of 3-fluoro-5-methoxy-4-nitrophenylacetic acid (2.63 g, 11.5 mmol) in benzyl alcohol (20 ml) was added to the reaction mixture. After stirring at 50° C. for 15 hours, the reaction mixture was cooled. To the mixture was added 1N NaOH (100 ml), followed by extraction with ether (200 ml). After addition of 1N HCl to the water layer, the mixture was extracted with ether (2×200 ml). The extract was dried over anhydrous magnesium sulfate and then, distilled under reduced pressure to remove the solvent, whereby a pale yellow oil was obtained. Methanol (50 ml) and concentrated sulfuric acid (0.5 ml) were added to the resulting oil and the mixture was heated and refluxed for 4 hours under stirring. The reaction mixture was then cooled to room temperature. After addition of a saturated aqueous solution of sodium bicarbonate for neutralization, the mixture was extracted with chloroform (2×250 ml). The extract was dried over anhydrous magnesium sulfate and then distilled under reduced pressure to remove the solvent. The residue was purified by chromatography on a silica gel column, whereby from chloroform eluate solutions, the title compound (2.77 g, 61%) was obtained as a yellow oil.

$^1$H-NMR (CDCl$_3$) δ: 3.58 (s, 2H), 3.69 (s, 3H), 3.88 (s, 3H), 5.15 (s, 2H), 6.55 (s, 1H), 6.60 (d, J=1.2 Hz, 1H), 7.36 (m, 5H).

(Step 6) Synthesis of methyl 4-methoxy-2-(2-methylphenylamino)-6-benzoxazolylacetate

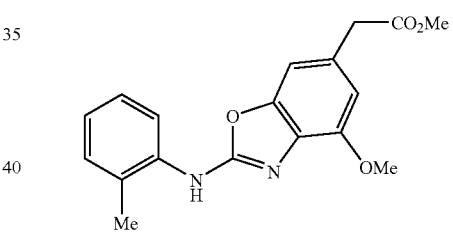

In ethanol (100 ml) was dissolved methyl 3-benzyloxy-5-methoxy-4-nitrophenylacetate (2.77 g, 8.36 mmol), followed by the addition of 5% palladium/carbon (1 g). Under stirring at room temperature, the resulting mixture was subjected to catalytic hydrogenation for 15 hours. The reaction mixture was filtered through Celite under reduced pressure to remove the insoluble matter. To the filtrate was added 2-tolyl thioisocyanate (1.35 ml, 10.0 mmol) under stirring at room temperature. The mixture was stirred at room temperature for 15 hours. Mercuric oxide (yellow) (3.08 g, 14.2 mmol) was added and the mixture was heated and refluxed for 4 hours under stirring. After the reaction mixture was cooled to room temperature, the insoluble matter was filtered off through Celite. The residue obtained by distilling off the solvent from the filtrate was purified by chromatography on a silica gel column, whereby from chloroform-ethyl acetate (4:1) eluate fractions, the title compound (1.30 g, 48%) was obtained as a brown oil.

$^1$H-NMR (CDCl$_3$) δ: 2.33 (s, 3H), 3.66 (s, 2H), 3.71 (d, J=0.49 Hz, 3H), 3.96 (s, 3H), 6.67 (s, 1H), 6.93 (d, J=0.49 Hz, 1H), 7.05 (t, J=7.3 Hz, 1H), 7.20 (d, J=7.3 Hz, 1H), 7.28 (m, 1H), 8.06 (d, J=8.1 Hz, 1H).

(Step 7) Synthesis of 4-methoxy-2-(2-(methylphenylamino)-6-benzoxazolylacetic acid

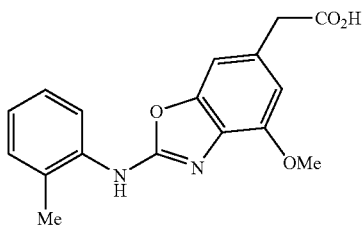

In THF (30 ml) was dissolved methyl 4-methoxy-2-(2-methylphenylamino)-6-benzoxazolylacetate (1.30 g, 3.98 mmol), followed by the addition of 0.25N NaOH (32 ml, 8.00 mmol). The mixture was stirred at room temperature for 15 hours. The reaction mixture was poured in 1N HCl (100 ml), followed by extraction with a chloroform-methanol (4:1, 2×200 ml) mixture. The extract was dried over anhydrous magnesium sulfate and distilled under reduced pressure to remove the solvent, whereby the title compound (1.24 g, 100%) was obtained as a brown amorphous substance.

$^1$H-NMR (CDCl$_3$) δ: 2.30 (s, 3H), 3.75 (m, 2H), 3.93 (s, 3H), 6.70 (s, 1H), 6.93 (s, 1H), 7.05 (s, 1H), 7.17–7.21 (m, 2H), 7.74 (d, J=7.1 Hz, 1H).

(Step 8) Synthesis of methyl 4-((4S)-fluoro-1-(4-methoxy-2-(2-methylphenylamino)-6-benzoxazolylacetyl)-(2S)-pyrrolidinylmethoxy)benzoate

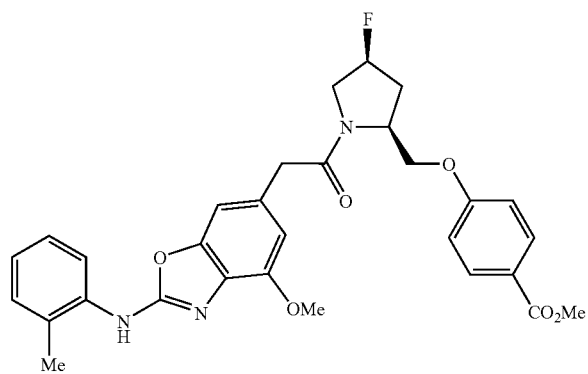

In DMF (10 ml) were dissolved 4-methoxy-2-(2-methylphenylamino)-6-benzoxazolylacetic acid (200 mg, 0.640 mmol) and methyl 4-((4S)-fluoro-(2S)-pyrrolidinylmethoxy)benzoate. EDC•HCl (184 mg, 0.960 mmol), HOBt (cat.) and DMAP (cat.) were added under stirring at room temperature and stirring was conducted for 15 hours. Water (200 ml) was added to the reaction mixture, followed by extraction with ethyl acetate (300 ml). The extract was washed with saturated brine (2×200 ml), dried over anhydrous magnesium sulfate and distilled under reduced pressure to remove the solvent. The residue was purified by chromatography on a silica gel column, whereby from chloroform-methanol (20:1) eluate fractions, the title compound (312 mg, 89%) was obtained as a yellow viscous oil.

$^1$H-NMR (CDCl$_3$) δ: 2.04–2.57 (series of m, 5H), 3.61–4.14 (series of m, 11H), 4.48–4.65 (m, 2H), 5.22 and 5.36 (m, each, total 1H), 6.66 (d, J=8.8 Hz, 2H), 7.03–7.08 (m, 1H), 7.20–7.29 (m, 2H), 7.51 (br s, 1H), 7.95–8.03 (m, 2H).

(Step 9) Synthesis of 4-((4S)-fluoro-1-(4-methoxy-2-(2-methylphenylamino)-6-benzoxazolylacetyl)-pyrrolidinylmethoxy)benzoic acid

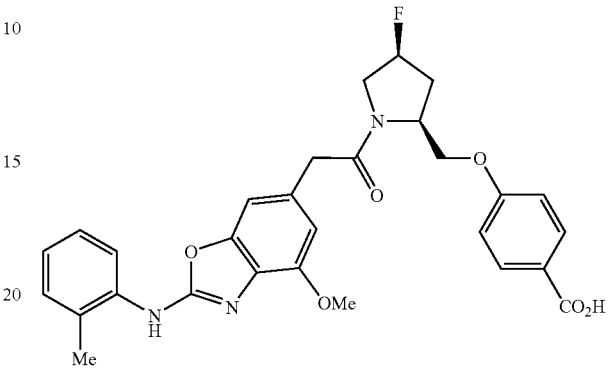

In THF (5 ml) was dissolved methyl 4-((4S)-fluoro-1-(4-methoxy-2-(2-methylphenylamino)-6-benzoxazolylacetyl)-(2S)-pyrrolidinylmethoxy)benzoate (312 mg, 0.570 mmol), followed by the addition of 0.25N NaOH (4.6 ml, 1.15 mmol). The resulting mixture was heated and refluxed for 4 hours under stirring. After the reaction mixture was cooled to room temperature, 1N HCl (100 ml) was poured therein. The crystals thus obtained were collected by filtration under reduced pressure, washed with water and dried under reduced pressure, whereby the title compound (100 mg, 33%) was obtained as a pale yellow amorphous substance.

$^1$H-NMR (DMSO-d$_6$) δ: 2.17–2.51 (series of m, total 5H, including s, 3H, at d 2.30), 3.35–4.66 (series of m, total 10H, including s, 3H, at d 3.89), 5.32–5.51 (m, 1H), 6.68 and 6.99 (s, each, total 1H), 7.03–7.09 (m, 3H), 7.23–7.27 (m, 2H), 7.85–7.92 (m, 3H).

MS (FAB) m/z, 534 (M$^+$+1);
Anal. Calcd for C$_{29}$H$_{28}$FN$_3$O$_6$·0.25H$_2$O: C, 64.74; H, 5.34; N, 7.81. Found: C, 64.68; H, 5.49; N, 7.67.

Example 4

4-(4,4-Difluoro-1-(2-(2-methylphenylamino)-6-benzoxazolylacetyl)-2S-pyrrolidinylmethoxy)benzoic acid (Step 1) Synthesis of methyl 4-(4,4-difluoro-1-(2-(2-methylphenylamino)-6-benzoxazolylacetyl)-(2S)-pyrrolidinylmethoxy)benzoate

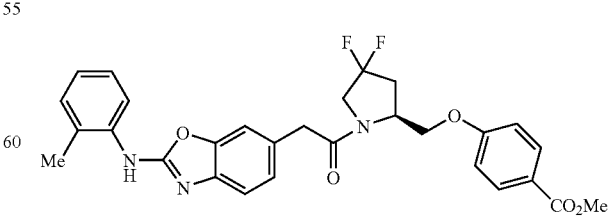

In DMF (6.6 ml) were dissolved methyl 4-(4,4-difluoro (2S)-pyrrolidinylmethoxy)benzoate (160.2 mg, 0.591 mmol), 2-(2-methylphenylamino)-6-benzoxazolylacetic acid (166.7 mg, 0.591 mmol) and HOBt (16.0 mg, 0.118 mmol). To the resulting solution was added EDC•HCl (169.8 mg, 0.886 mmol) at room temperature. The resulting mixture was stirred overnight at room temperature. After the reaction mixture was diluted with ethyl acetate, the diluted mixture was washed with saturated brine, dried over anhydrous sodium sulfate and distilled under reduced pressure to remove the solvent. The residue was purified by chromatography on a silica gel column, whereby from hexane-ethyl acetate (1:1, v/v) eluate fractions, the title compound (324.3 mg, 100%) was obtained as a light orange amorphous substance.

$^1$H-NMR (CDCl$_3$) δ: 2.37 (3H, s), 2.47–2.70 (2H, m), 3.67 (1H, d, J=15.2 Hz), 3.72 (1H, d, J=15.2 Hz), 3.74–4.02 (total 5H, m, including 3H, s at (3.84), 4.19 (1H, m), 4.38 (1H, m), 4.70 (1H, m), 6.80–7.43 (9H, series of m), 7.95 (2H, m), 8.08 (1H, d, J=8.0 Hz).

(Step 2) Synthesis of 4-(4,4-difluoro-1-(2-(2-methylphenylamino)-6-benzoxazolylacetyl)-2S-pyrrolidinylmethoxy)benzoic acid

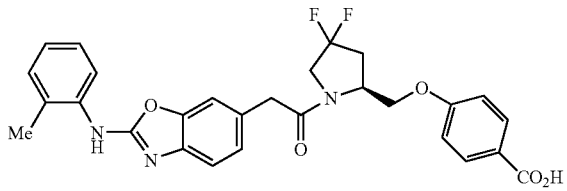

In THF (6.5 ml) was dissolved methyl 4-(4,4-difluoro-1-(2-(2-methylphenylamino)-6-benzoxazolylacety)-(2S)-pyrrolidinylmethoxy)benzoate (324.3 mg, 0.606 mmol). To the resulting solution was added 0.25N NaOH (6.5 ml) at 0° C. After stirring overnight at room temperature, the reaction mixture was further stirred overnight at 50° C. The reaction mixture was concentrated, followed by neutralization with 1N HCl. The crystals thus obtained were collected by filtration, washed with water and dried at 50° C., whereby the title compound (271.9 mg, 88% for 2 steps) was obtained as a pale brown solid.

IR (KBr) 3440, 1685, 1641, 1604, 1577 cm$^{-1}$;

$^1$H-NMR (DMSO-d$_6$) δ: 2.28 (3H, s), 2.38–2.86 (2H, m), 3.65–4.27 (6H, m), 4.54 (1H, m), 6.95–7.38 (8H, series of m), 7.79 (1H, d, J=8.0 Hz), 7.82–7.93 (3H, m), 9.62 (1H, broad s).

MS (ESI) m/z 522 (M$^+$+1).

Anal. Calcd for $C_{28}H_{25}F_2N_3O_5 \cdot 0.75H_2O$: C, 62.86; H, 4.99; N, 7.85; F, 7.10. Found: C, 63.09; H, 5.04; N, 7.66; F, 6.83.

Example 5

4-((2S, 4S)-1-(2-(2-Chlorophenylamino)-6-benzoxazolylacetyl)-4-fluoro-2-pyrrolidinylmethoxy)benzoic acid (Step 1) Synthesis of methyl 2-(2-chlorophenylamino)-6-benzoxazolylacetate

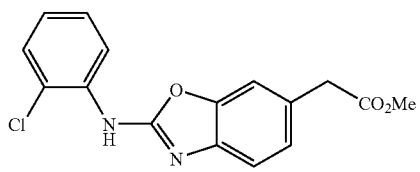

In methanol (50 ml) was dissolved methyl 4-amino-3-hydroxyphenylacetate (2.30 g, 12.7 mmol). After addition of 2-methylphenyl thioisocyanate (1.99 ml, 15.2 mmol) at room temperature, the mixture was stirred at room temperature for 3 hours. Mercuric oxide (yellow) (2.75 g, 15.2 mmol) was added to the reaction mixture. The mixture was then stirred at 50° C. for 50 minutes. After cooling to room temperature, the reaction mixture was concentrated under reduced pressure. The residue thus obtained was purified by chromatography on a silica gel column (silica gel: 100 g), whereby from chloroform/ethyl acetate (10/1) eluate fractions, the title compound (3.35 g, 83%) was obtained as a pale yellow solid.

$^1$H-NMR (CDCl$_3$) δ: 3.71 (s, 5H), 7.03 (dt, J=7.6,1.5 Hz, 1H), 7.16 (dd, J=8.1,1.7 Hz, 1H), 7.33 (d, J=1.0 Hz, 1H), 7.36–7.43 (m, 3H), 7.46 (d, J=8.1 Hz, 1H), 7.52 (br, 1H), 8.55 (dd, J=8.3,1.7 Hz, 1H).

(Step 2) Synthesis of 2-(2-chlorophenylamino)-6-benzoxazolylacetic acid

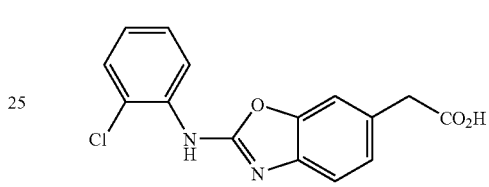

In THF (200 ml) was dissolved methyl 2-(2-chlorophenylamino)-6-benzoxazolylacetate (3.35 g, 10.6 mmol). After addition of 0.25N NaOH (200 ml), the mixture was stirred at room temperature for 16 hours. The reaction mixture was distilled under reduced pressure to remove the solvent. The residue was acidified with 1N HCl, followed by extraction with a chloroform/methanol (10/1) mixture. The extract was washed with saturated brine, dried over anhydrous sodium sulfate and distilled under reduced pressure to remove the solvent, whereby the title compound (2.94 g, 92%) was obtained as a pale brown solid.

$^1$H-NMR (DMSO-d$_6$) δ: 3.62 (s, 2H), 7.09 (d, J=7.8 Hz, 1H), 7.19 (t, J=7.1 Hz, 1H), 7.31 (d, J=8.1 Hz, 1H), 7.39 (s, 1H), 7.41 (d, J=7.6 Hz, 1H), 7.52 (d, J=7.3 Hz, 1H), 8.08 (d, J=6.8 Hz, 1H), 9.99 (br, 1H).

(Step 3) Synthesis of methyl 4-((2S,4S)-1-(2-(2-chlorophenylamino)-6-benzoxazolylacetyl)-4-fluoro-2-pyrrolidinylmethoxy)benzoate

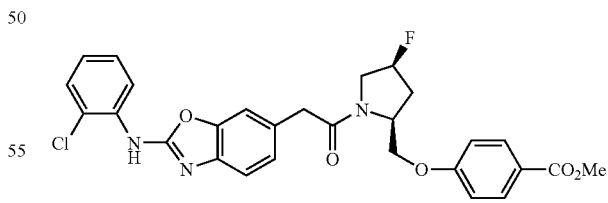

In DMF (5 ml), 2-(2-chlorophenylamino)-6-benzoxazolylacetic acid (303 mg, 1.0 mmol), methyl 4-((2S,4S)-4-fluoro-2-pyrrolidinylmethoxy)benzoate (253 mg, 1.0 mmol), EDC•HCl (288 mg, 1.5 mmol), HOBt (203 mg, 1.5 mmol) and triethylamine (0.70 ml, 5.0 mmol) were stirred at room temperature for 14 hours. The reaction mixture was poured in ice water (30 ml), followed by extraction with ethyl acetate. The extract was washed with saturated brine, dried over anhydrous sodium sulfate and distilled under reduced pressure to remove the solvent. The residue was purified by chromatography on a silica gel column (silica gel: 50 g), whereby from chloroform/acetone (10/1) eluate fractions, the title compound (360 mg, 67%) was obtained as a colorless amorphous substance.

$^1$H-NMR (CDCl$_3$) δ: 2.05–2.30 (m, 1H), 2.35–2.60 (m, 1H), 3.75 (d, J=4.6 Hz, 2H), 3.868 and 3.870 (each s, total 3H, amide isomers), 3.88–4.09 (m, 3H), 4.54–4.63 (m, 2H), 5.32 (dt, J=52.8,3.9 Hz, 1H), 6.87 and 6.99 (each d, J=8.8 and 9.0 Hz respectively, total 2H, amide isomers), 7.04 (t, J=6.4 Hz, 1H), 7.14 (d, J=8.1 Hz, 1H), 7.33 (s, 1H), 7.36–7.53 (m, 4H), 7.96 and 7.99 (each d, each J=9.0 Hz, total 2H, amide isomers), 8.54 (dd, J=8.3,1.2 Hz, 1H).

MS (ESI) m/z 538 (M$^+$+1), 540 (M$^+$+3).

(Step 4) Synthesis of 4-((2S,4S)-1-(2-(2-chlorophenylamino)-6-benzoxazolylacetyl)-4-fluoro-2-pyrrolidinylmethoxy)benzoic acid

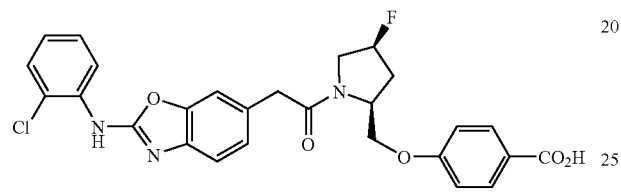

In THF (20 ml) was dissolved methyl 4-((2S,4S)-1-(2-(2-chlorophenylamino)-6-benzoxazolylacetyl)-4-fluoro-2-pyrrolidinylmethoxy)benzoate (360 mg, 0.669 mmol), followed by the addition of 0.25N NaOH (20 ml). The resulting mixture was stirred at room temperature for 18 hours. The reaction mixture was distilled under reduced pressure to remove the solvent. The residue was then acidified with 1N HCl, followed by extraction with a chloroform/methanol (10/1) mixture. The extract was washed with saturated brine, dried over anhydrous sodium sulfate and distilled under reduced pressure to remove the solvent. The residue was purified by thin-layer silica gel chromatography and separated using (chloroform/methanol (20/1)), whereby the title compound (273 mg, 78%) was obtained as a colorless amorphous substance.

IR (KBr) 3396, 2978, 2941, 1701, 1637, 1603, 1572 cm$^{-1}$;

$^1$H-NMR (DMSO-d$_6$) δ: 2.23–2.37 (m, 2H), 3.32 (br, 2H), 3.76–4.72 (m, 7H), 5.31–5.57 (m, 1H), 7.02–7.11 (m, 3H), 7.18 (t, J=6.1 Hz, 1H), 7.28–7.35 (m, 1H), 7.37 (s, 1H), 7.41 (dt, J=8.0,1.5 Hz, 1H), 7.52 (dd, J=8.0,1.2 Hz, 1H), 7.86 and 7.89 (each d, J=8.8 and 10.9 Hz respectively, total 2H, amide isomers), 8.09 (d, J=7.3 Hz, 1H), 8.31 (s, 1H).

MS (ESI) m/z 524 (M$^+$+1), 526 (M$^+$+3).

Example 6

4-((2S,4S)-1-(7-Fluoro-2-(2-methylphenylamino)-6-benzoxazolylacetyl)-4-fluoro-2-pyrrolidinylmethoxy)benzoic acid (Step 1) Synthesis of 1-benzyloxy-2,3-difluoro-6-nitrobenzene

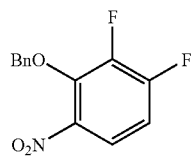

In THF (200 ml) was dissolved 2,3-difluoro-6-nitrophenol (10.0 g, 57.1 mmol), followed by the addition of potassium carbonate (15.8 g, 114.2 mmol) and benzyl bromide (7.47 ml, 62.8 mmol) at room temperature. The reaction mixture was stirred at 60° C. for 6 hours. DMF (100 ml) was added to the reaction mixture and the mixture was stirred at 60° C. for 24 hours. After cooling to room temperature, the reaction mixture was distilled under reduced pressure to remove the solvent. The residue was diluted with ether (100 ml), washed with saturated brine, dried over anhydrous sodium sulfate and distilled under reduced pressure to remove the solvent. The residue was purified by chromatography on a silica gel column (silica gel: 100 g), whereby from the hexane/ethyl acetate (4/1) eluate fractions, the title compound (4.17 g, 28%) was obtained as a yellow solid.

$^1$H-NMR (CDCl$_3$) δ: 5.29 (s, 2H), 7.00 (m, 1H), 7.38 (m, 3H), 7.46 (m, 2H), 7.66 (m, 1H).

(Step 2) Synthesis of di-tert-butyl (3-benzyloxy-2-fluoro-4-nitrophenyl)malonate

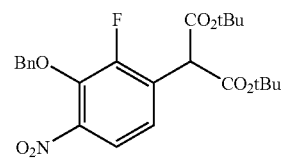

In THF (100 ml) were dissolved 1-benzyloxy-2,3-difluoro-6-nitrobenzene (4.17 g, 15.7 mmol) and di-tert-butyl malonate (3.52 ml, 15.7 mmol). To the resulting solution was added sodium hydride (60% in oil, 1.26 g, 31.4 mmol) in portions under stirring at 0° C. The reaction mixture was stirred at 0° C. for 30 minutes and then at 80° C. for 9 hours. Di-tert-butyl malonate (7.04 ml, 31.4 mmol) and sodium hydride (60%; 2.52 g, 52.8 mmol) were added and the mixture was stirred at 80° C. for 2 days. After cooling to room temperature, the reaction mixture was poured in ice water (100 ml), followed by extraction with ethyl acetate. The extract was washed with saturated brine, dried over anhydrous sodium sulfate and distilled under reduced pressure to remove the solvent. The residue was purified by chromatography on a silica gel column (silica gel: 200 g), whereby from hexane/ethyl acetate (8/1) eluate fractions, the title compound (6.87 g, 95%) was obtained as an orange solid.

$^1$H-NMR (CDCl$_3$) δ: 1.47 (s, 9H), 1.49 (s, 9H), 4.83 (s, 1H), 5.28 (s, 2H), 7.33–7.41 (m, 4H), 7.61 (d, J=8.5 Hz, 1H).

(Step 3) Synthesis of 2-fluoro-3-hydroxy-4-nitrophenylacetic acid

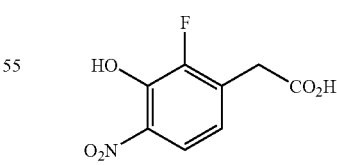

Di-tert-butyl (3-benzyloxy-2-fluoro-4-nitrophenyl)malonate (6.87 g, 14.9 mmol), acetic acid (200 ml) and concentrated hydrochloric acid (35 ml) were stirred at 120° C. for 6 hours. After cooling to room temperature, the reaction mixture was concentrated under reduced pressure, whereby the title compound was obtained as a brown oil (this compound was provided for the subsequent reaction without further purification).

(Step 4) Synthesis of methyl 2-fluoro-3-hydroxy-4-nitrophenylacetate

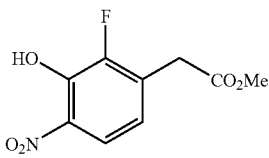

In methanol (300 ml), the above-described 1-benzyloxy-2-fluoro-6-nitrophenylacetic acid (14.9 mmol) and concentrated sulfuric acid (2 ml) were stirred at 70° C. for 4 hours. After cooling to room temperature, the reaction mixture was concentrated under reduced pressure. The residue was neutralized with a saturated aqueous solution of sodium bicarbonate, followed by extraction with chloroform. The extract was washed with saturated brine, dried over anhydrous sodium sulfate and distilled under reduced pressure to remove the solvent. The residue was purified by chromatography on a silica gel column (silica gel: 200 g), whereby from the hexane/ethyl acetate (4/1) eluate fractions, the title compound (5.22 g, 100% (2 steps)) was obtained as a brown solid.

$^1$H-NMR (CDCl$_3$) δ: 3.74 (s, 3H), 3.76 (d, J=1.2 Hz, 2H), 6.90 (dd, J=9.0,6.3 Hz, 1H), 7.88 (dd, J=9.0,2.0 Hz, 1H), 10.51 (s, 1H).

(Step 5) Synthesis of methyl 4-amino-3-hydroxy-2-fluorophenylacetate

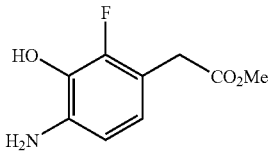

Methyl 2-fluoro-3-hydroxy-4-nitrophenylacetate (5.22 g, 14.9 mmol), reduced iron powder (2.66 g, 47.7 mmol), sodium acetate-trihydrate (2.03 g, 14.9 mmol) and acetic acid (5.54 ml) were heated and refluxed at 110° C. for 4 hours in methanol:water (1:4, 300 ml). After cooling to room temperature, the reaction mixture was filtered through Celite under reduced pressure to remove the insoluble matter. The filtrate was then concentrated, followed by extraction with ethyl acetate. The extract was washed with saturated brine, dried over anhydrous sodium sulfate and distilled under reduced pressure to remove the solvent. The residue was purified by chromatography on a silica gel column (silica gel: 50 g), whereby from hexane/ethyl acetate (2/1) eluate fractions, the title compound (1.29 g, 44%) was obtained as a brown oil.

$^1$H-NMR (CDCl$_3$) δ: 3.54 (s, 2H), 3.68 (s, 3H), 4.99 (s, 2H), 6.42 (d, J=7.6 Hz, 1H), 6.53 (d, J=7.1 Hz, 1H).

(Step 6) Synthesis of methyl 7-fluoro-2-(2-methylphenylamino)-6-benzoxazolylacetate

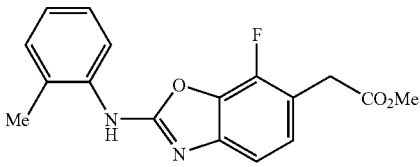

Methyl 4-amino-3-hydroxy-2-fluorophenylacetate (1.29 g, 6.48 mmol) was dissolved in methanol (20 ml). At room temperature, o-tolyl thioisocyanate (1.05 ml, 7.78 mmol) was added and the mixture was stirred for 5 hours. Mercuric oxide (yellow) (1.68 g, 7.77 mmol) was added to the reaction mixture, followed by stirring at 80° C. for further 3 hours. After the reaction mixture was cooled to room temperature, the solvent was distilled off under reduced pressure. The residue was purified by chromatography on a silica gel column (silica gel: 100 g), whereby chloroform/ethyl acetate (10/1) eluate fractions, the title compound (1.31 g, 64% (2 steps)) was obtained as a pale brown solid.

$^1$H-NMR (CDCl$_3$) δ: 2.34 (s, 3H), 3.72 (s, 3H), 3.74 (s, 2H), 7.05–7.10 (m, 2H), 7.15 (d, J=7.8 Hz, 1H), 7.21 (d, J=8.6 Hz, 1H), 7.29 (t, J=7.8 Hz, 1H), 7.32 (br, 1H), 8.01 (d, J=8.1 Hz, 1H).

(Step 7) Synthesis of 7-fluoro-2-(2-methylphenylamino)-6-benzoxazolylacetic acid

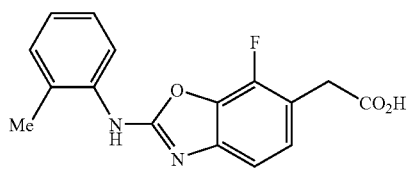

Methyl 7-fluoro-2-(2-methylphenylamino)-6-benzoxazolylacetate (1.31 g, 4.17 mmol) was dissolved in THF (30 ml), followed by the addition of 0.25N NaOH (30 ml). The resulting mixture was stirred at room temperature for 20 hours. The reaction mixture was distilled under reduced pressure to remove the solvent. The residue was acidified with 1N HCl, followed by extraction with a chloroform/methanol (10/1) mixture. The extract was washed with saturated brine, dried over anhydrous sodium sulfate and distilled under reduced pressure to remove the solvent, whereby the title compound (1.08 g, 86%) was obtained as a pale brown solid.

$^1$H-NMR (DMSO-d$_6$) δ: 2.30 (s, 3H), 3.68 (s, 2H), 7.09–7.18 (m, 3H), 7.25 (d, J=6.9 Hz, 2H), 7.80 (d, J=8.1 Hz, 1H), 8.30 (s, 1H) , 12.46 (br, 1H).

MS (ESI) m/z 301 (M$^+$+1).

(Step 8) Synthesis of methyl 4-((2S,4S)-1-(7-fluoro-2-(2-methylphenylamino)-6-benzoxazolylacetyl)-4-fluoro-2-pyrrolidinylmethoxy)benzoate

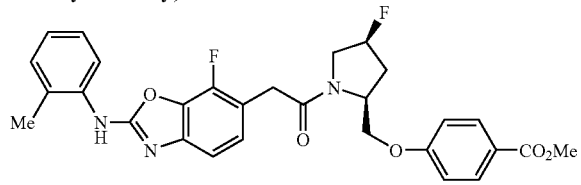

In DMF (5 ml), 7-fluoro-2-(2-methylphenylamino)-6-benzoxazolylacetic acid (300 mg, 1.0 mmol), methyl 4-((2S,4S)-4-fluoro-2-pyrrolidinylmethoxy)benzoate (253 mg, 1.0 mmol), EDC•HCl (288 mg, 1.5 mmol), HOBt (203 mg, 1.5 mmol) and triethylamine (0.70 ml, 5.0 mmol) were stirred at room temperature for 14 hours. After the reaction mixture was poured in ice water (20 ml), the mixture was extracted with ethyl acetate. The extract was washed with saturated brine, dried over anhydrous sodium sulfate and distilled under reduced pressure to remove the solvent. The residue was purified by chromatography on a silica gel column (silica gel: 50 g), whereby from chloroform/acetone (10/1) eluate fractions, the title compound (490 mg, 92%) was obtained as a colorless amorphous substance.

$^1$H-NMR (CDCl$_3$) δ: 2.10–2.30 (m, 1H), 2.35 (s, 3H), 2.58 (dd, J=19.8,15.2 Hz, 1H), 3.74 (s, 2H), 3.86 (s, 3H), 3.87–4.22 (m, 3H), 4.54–4.63 (m, 2H), 5.30–5.43 (m, 1H), 6.90 and 6.98 (each d, each J=9.1 Hz, total 2H, amide isomers), 7.04–7.13 (m, 3H), 7.21 (d, J=7.8 Hz, 2H), 7.30 (t, J=8.1 Hz, 1H), 7.94 (d, J=9.1 Hz, 2H), 8.05 (d, J=8.3 Hz, 1H).

MS (ESI) m/z 536 (M⁺+1).

(Step 9) Synthesis of 4-((2S,4S)-1-(7-fluoro-2-(2-methylphenylamino)-6-benzoxazolylacetyl)-4-fluoro-2-pyrrolidinylmethoxy)benzoic acid

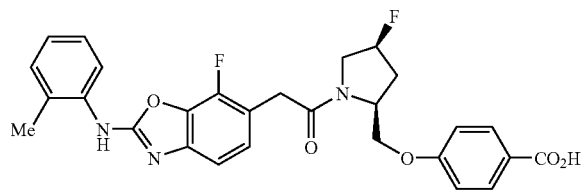

Methyl 4-((2S,4S)-1-(7-fluoro-2-(2-methylphenylamino)-6-benzoxazolylacetyl)-4-fluoro-2-pyrrolidinylmethoxy)benzoate (490 mg, 0.915 mmol) was dissolved in THF (40 ml). To the resulting solution was added 0.25N NaOH (40 ml), followed by stirring at room temperature for 14 hours. The reaction mixture was distilled under reduced pressure to remove the solvent. The residue was acidified with 1N HCl, followed by extraction with a chloroform/methanol (10/1) mixture. The extract was washed with saturated brine, dried over anhydrous sodium sulfate and distilled under reduced pressure to remove the solvent. The residue was purified by chromatography on a silica gel column (silica gel: 50 g), whereby from chloroform/methanol (20/1) eluate fractions, the title compound (394 mg, 83%) was obtained as a colorless amorphous substance.

IR (KBr) 3249, 3051, 2978, 1685, 1641, 1579, 1510 cm⁻¹;
¹H-NMR (DMSO-d₆) δ: 2.20–2.26 (m, 2H), 2.31 (s, 3H), 3.74–4.80 (m, 7H), 5.35–5.55 (m, 1H), 7.03–7.14 (m, 5H), 7.25 (t, J=6.6 Hz, 2H), 7.80 (d, J=8.0 Hz, 1H), 7.86 and 7.90 (each d, J=8.8 and 9.0 Hz respectively, total 2H, amide isomers), 9.89 (br, 1H), 12.62 (br, 1H).

MS (ESI) m/z 522 (M⁺+1).

Example 7

4-((4S)-Dimethylamino-1-(2-(2-methylphenylamino)-6-benzoxazolylacetyl)-(2S)-pyrrolidinylmethoxy)benzoic acid (Step 1) Synthesis of methyl 4-((4S)-dimethylamino-1-(2-(2-methylphenylamino)-6-benzoxazolylacetyl)-(2S)-pyrrolidinylmethoxy)benzoate

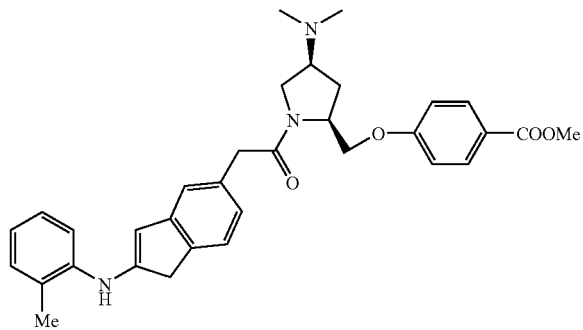

In methylene chloride (15 ml), EDC(HCl (144 mg, 0.5 mmol) was added to methyl 4-((4S)-dimethylamino-(2S)-pyrrolidinylmethoxy)benzoate (140 mg, 0.5 mmol), 2-(2-methylphenylamino)-6-benzoxazolylacetic acid (141 mg, 0.5 mmol), HOBt (68 mg, 0.5 mmol) and triethylamine (208 μl, 1.5 mmol) under stirring at 0° C. The reaction mixture was stirred at room temperature for 16 hours. Then, the solvent was distilled off under reduced pressure. Water (30 ml) was added to the residue and the mixture was extracted with ethyl acetate. The extract was washed with a saturated aqueous solution of sodium bicarbonate, dried over anhydrous sodium sulfate and distilled under reduced pressure to remove the solvent. The residue thus obtained was purified by thin-layer silica gel chromatography, whereby from methanol-methylene chloride (5:95, v/v) eluate fractions, the title compound (230 mg, 85%) was obtained as a colorless oil.

¹H-NMR (CDCl₃) δ: 2.24–2.61 (m, 11H), 3.17–3.22 (m, 1H), 3.71–3.87 (m, 5H), 4.11–4.21 (m, 1H), 4.42–4.52 (m, 1H), 6.86–7.37 (m, 9H), 7.94 (d, J=7.6 Hz, 2H), 8.10 (d, J=8.0 Hz, 1H).

(Step 2) Synthesis of 4-((4S)-dimethylamino-1-(2-(2-methylphenylamino)-6-benzoxazolylacetyl)-(2S)-pyrrolidinylmethoxy)benzoic acid

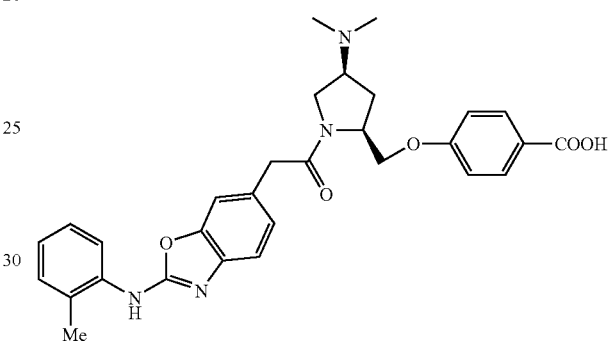

In THF (6.0 ml) and methanol (3.0 ml) was dissolved methyl 4-((4S)-dimethylamino-1-(2-(2-methylphenylamino)-6-benzoxazolylacetyl)-(2S)-pyrrolidinylmethoxy)benzoate (230 mg, 0.42 mmol), followed by the addition of 1N NaOH (1.5 ml, 1.5 mmol). The resulting mixture was stirred at 70° C. for 4 hours. The reaction mixture was concentrated under reduced pressure and the residue was acidified with water and 1N HCl. The crystals thus obtained were collected by filtration under reduced pressure, washed with water and dried under reduced pressure, whereby the title compound (130 mg, 59%) was obtained as a white crystalline substance.

IR (KBr) 2950, 1639, 1573, 1438, 1245, 1166;
¹H-NMR (DMSO-d₆) δ: 1.80–2.50 (m, 11H), 3.50–4.30 (m, 8H), 6.98–7.35 (m, 8H), 7.80–7.87 (m, 3H).

MS (FAB) m/z 529 (M+H)⁺;
Anal. Calcd for $C_{30}H_{32}N_4O_5 \cdot 1.3H_2O$: C, 65.27; H, 6.32; N, 10.15. Found: C, 65.48; H, 6.21; N, 9.88.

Example 8

4-((2S,4S)-4-Hydroxy-1-(2-(2-methylphenylamino)-6-benzoxazolylacetyl)-2-pyrrolidinylmethoxy)benzoic acid (Step 1) Synthesis of methyl 4-((2S,4S)-4-acetoxy-1-(2-(2-methylphenylamino)-6-benzoxazolylacetyl)-2-pyrrolidinylmethoxy)benzoate

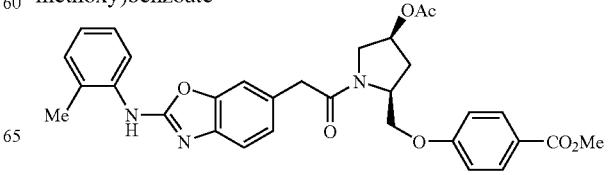

In DMF (10 ml), a mixture of 2-(2-methylphenylamino)-6-benzoxazolylacetic acid (318 mg, 1.13 mmol), 4-((2S,4S)-4-acetoxy-2-pyrrolidinylmethoxy)benzoate (330 mg, 1.13 mmol), EDC•HCl (325 mg, 1.70 mmol), HOBt (230 mg, 1.70 mmol) and triethylamine (1.18 ml, 8.50 mmol) was stirred at room temperature for 21 hours. The reaction mixture was poured in ice water (30 ml), followed by extraction with ethyl acetate. The extract was washed with saturated brine, dried over anhydrous sodium sulfate and distilled under reduced pressure to remove the solvent. The residue was purified by chromatography on a silica gel column (silica gel: 40 g), whereby from chloroform/acetone (20/1) eluate fractions, the title compound (610 mg, 97%) was obtained as a colorless amorphous substance.

$^1$H-NMR (CDCl$_3$) δ: 2.03 (s, 3H), 2.30 (d, J=2.9 Hz, 2H), 2.36 (s, 3H), 3.56 and 3.59 (each s, total 1H, amide isomers), 3.70 (s, 2H), 3.86 (s, 3H), 3.88 (m, 1H), 3.99–4.13 (m, 1H), 4.46–4.60 (m, 2H), 5.29–5.40 (m, 1H), 6.68 and 6.97 (each dd, each J=8.8 and 2.2 Hz respectively, total 2H, amide isomers), 7.08 (t, J=7.1 Hz, 2H), 7.22 and 7.24 (each s, total 2H, amide isomers), 7.27 and 7.30 (each s, total 2H, amide isomers), 7.36 (dd, JJ=7.8,2.7 Hz, 1H), 7.96 (dd, J=9.0,2.4 Hz, 2H), 8.01 and 8.04 (each s, total 1H, amide isomers).

MS (ESI) m/z 558 (M$^+$+1).

(Step 2) Synthesis of 4-((2S,4S)-4-hydroxy-1-(2-(2-methylphenylamino)-6-benzoxazolylacetyl)-2-pyrrolidinylmethoxy)benzoic acid

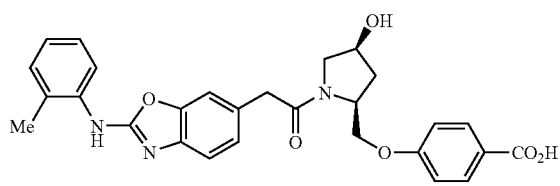

To a solution of methyl 4-((2S,4S)-4-acetoxy-1-(2-(2-methylphenylamino)-6-benzoxazolylacetyl)-2-pyrrolidinylmethoxy)benzoate (610 mg, 1.09 mmol) in THF (40 ml) was added 0.25N NaOH (40 ml). The resulting mixture was stirred at room temperature for 18 hours. The reaction mixture was concentrated under reduced pressure. The residue was acidified with 1N HCl, followed by extraction with a chloroform-methanol (10/1) mixture. The extract was washed with water and brine, dried over anhydrous sodium sulfate and concentrated under reduced pressure to remove the solvent, whereby the title compound (500 mg, 92%) was obtained as a pale pink amorphous substance.

IR (ATR) 3211, 2941, 2877, 1682, 1639, 1604, 1576, 1439 cm$^{-1}$;

$^1$H-NMR (DMSO-d$_6$) δ: 1.91–2.20 (m, 2H), 2.30 (s, 3H), 3.21 (d, J=13.2 Hz, 1H), 3.42 (d, J=11.3 Hz, 1H), 3.71 and 3.73 (each d, J=4.7 and 6.1 Hz respectively, total 1H, amide isomers), 4.18–4.59 (m, 4H), 5.16 and 5.18 (each d, each J=2.9 Hz, total 1H, amide isomers), 7.01 and 7.08 (each d, J=9.1 and 8.3 Hz, total 1H, amide isomers), 7.05 (d, J=9.1 Hz, 2H), 7.20–7.32 (m, 4H), 7.81 (d, J=7.8 Hz, 1H), 7.86 and 7.89 (each d, J=8.8 and 9.1 Hz, total 2H, amide isomers), 9.61 (br, 1H), 12.56 (br, 1H).

MS (ESI) m/z 502 (M$^+$+1).

Example 9

4-((3R,4S)-Isopropylidenedioxy-1-(2-(2-methylphenylamino)-6-benzoxazolylacetyl)-(2R)-pyrrolidinylmethoxy)benzoic acid (Step 1) Synthesis of 1-benzyloxycarbonyl-(3R,4S)-isopropylidenedioxy-(2S)-pyrrolidinylcarboxylic acid

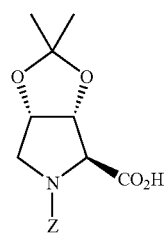

To a solution of methyl 1-benzyloxycarbonyl-(3R,4S)-isopropylidenedioxy-2-pyrrolidinylcarboxylate in THF (250 ml) was added 0.25N NaOH (255 ml). The resulting mixture was stirred overnight at room temperature. The reaction mixture was acidified with 1N HCl, followed by extraction with ethyl acetate. The extract was dried over anhydrous sodium sulfate and distilled under reduced pressure to remove the solvent, whereby the title compound (9.87 g, 96%) was obtained as a colorless oil.

$^1$H-NMR (CDCl$_3$) δ: 1.32 (s, 3H), 1.46 (d, J=2.7 Hz, 3H), 3.61 (m, 1H), 3.82 and 3.92 (each d, each J=12.7 Hz, total 1H, amide isomers), 4.58 and 4.64 (each s, total 1H, amide isomers), 4.77 (t, J=5.1 Hz, 1H), 4.83 and 4.89 (each d, each J=5.9 Hz, total 1H, amide isomers), 5.15 and 5.19 (d and s, J=2.4 Hz, total 2H, amide isomers), 7.31–7.37 (m, 5H).

(Step 2) Synthesis of 1-benzyloxycarbonyl-(3R,4S)-isopropylidenedioxy-(2R)-pyrrolidinylmethanol

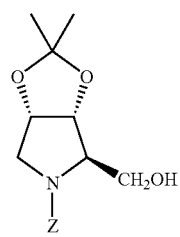

To a solution of 1-benzyloxycarbonyl-(3R,4S)-isopropylidenedioxy-(2S)-pyrrolidinylcarboxylic acid (9.87 g, 30.7 mmol) in THF (200 ml) was added a borane dimethyl sulfide solution (6.14 ml, 61.4 mmol) at 0° C. After stirring at room temperature for 2 hours, the reaction mixture was heated and refluxed for further 2 hours. The reaction mixture was then cooled to room temperature and concentrated under reduced pressure. Water (10 ml) was then added to the residue. The mixture was extracted with ethyl acetate. The extract was washed with water and saturated brine, dried over anhydrous sodium sulfate and distilled under reduced pressure to remove the solvent. The residue was purified by chromatography on a silica gel column (silica gel: 200 g), whereby from chloroform/methanol (20/1) eluate fractions, the title compound (10.1 g, 100%) was obtained as a colorless oil.

$^1$H-NMR (CDCl$_3$) δ: 1.31 (s, 3H), 1.45 (s, 3H), 3.56–4.74 (m, 7H), 5.14 (s, 2H), 7.34 (m, 5H).

(Step 3) Synthesis of methyl 4-(1-benzyloxycarbonyl-(3R,4S)-isopropylidenedioxy-(2R)-pyrrolidinylmethoxy)benzoate

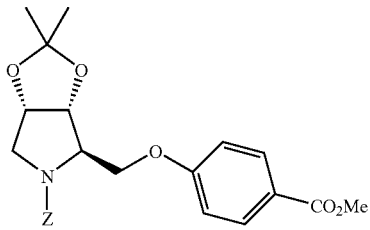

DIAD (138 ml, 0.70 mmol) was added dropwise to a solution of 1-benzyloxycarbonyl-(3R,4S)-isopropylidenedioxy-(2R)-pyrrolidinylmethanol (312 mg, 0.64 mmol), methyl 4-hydroxybenzoate (67 ml, 0.70 mmol) and triphenylphosphine (184 mg, 0.70 mmol) in THF (7 ml) under stirring at 0° C. in a nitrogen gas stream. The reaction mixture was stirred at room temperature for 3 hours. The residue obtained by concentration of the reaction mixture under reduced pressure was purified by chromatography on a silica gel column (silica gel: 10 g), whereby from hexane/ethyl acetate (4/1) eluate fractions, the title compound (321 mg, 83%) was obtained as a colorless oil.

$^1$H-NMR (CDCl$_3$) δ: 1.01 (s, 6H), 1.03 (s, 3H), 2.23 (m, 1H), 2.63 (m, 1H), 3.61 (d, J=12.5 Hz, 1H), 3.80–4.27 (m, 4H), 4.84 (br, 1H), 5.01 and 5.08 (ABq, each J=12.2 Hz, total 1H, amide isomers), 6.75–6.87 (m, 3H), 7.19–7.63 (m, 15H).

(Step 4) Synthesis of methyl 4-((3R,4S)-isopropylidenedioxy-(2R)-pyrrolidinylmethoxy)benzoate

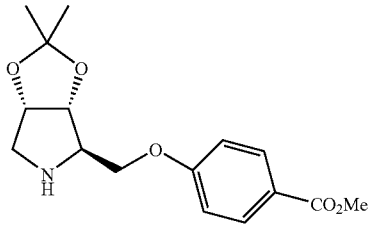

In ethanol (170 ml) were suspended methyl 4-(1-benzyloxycarbonyl-(3R,4S)-isopropylidenedioxy-(2R)-pyrrolidinylmethoxy)benzoate (2.37 g, 5.76 mmol) and 10% palladium/carbon (240 mg), followed by catalytic hydrogenation for one day under stirring at room temperature and normal pressure. The catalyst was filtered off and the filtrate was concentrated under reduced pressure. The residue thus obtained was purified by chromatography on a silica gel column (silica gel: 100 g), whereby from chloroform/acetone (20/1) eluate fractions, the title compound (930 mg, 53%) was obtained as a brown oil.

$^1$H-NMR (CDCl$_3$) δ: 1.35 (s, 3H), 1.50 (s, 3H), 3.02 (dd, J=13.7,4.1 Hz, 1H), 3.13 (d, J=13.7 Hz, 1H), 3.58 (t, J=6.3 Hz, 1H), 3.88 (s, 3H), 3.90 (dd, J=9.3,6.6 Hz, 1H), 4.02 (dd, J=9.5,3.9 Hz, 1H), 4.74 (d, J=5.6 Hz, 1H), 4.79 (m, 1H), 6.90 (d, J=9.0 Hz, 2H), 7.98 (d, J=9.0 Hz, 2H).

(Step 5) Synthesis of methyl 4-((3R,4S)-isopropylidenedioxy-1-(2-(2-methylphenylamino)-6-benzoxazolylacetyl)-(2R)-pyrrolidinylmethoxy)benzoate

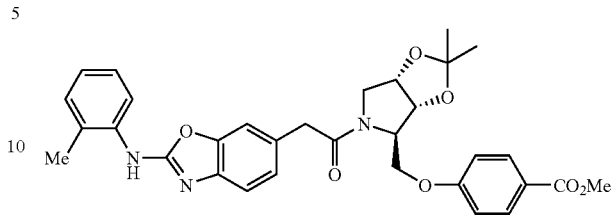

In DMF (10 ml), a mixture of 2-(2-methylphenylamino)-6-benzoxazolylacetic acid (184 mg, 0.651 mmol), methyl 4-((3R,4S)-isopropylidenedioxy-(2R)-pyrrolidinylmethoxy)benzoate (200 mg, 0.651 mmol), EDC•HCl (187 mg, 0.977 mmol), 1-hydroxybenzotriazole (132 mg, 0.977 mmol) and triethylamine (0.45 ml, 3.26 mmol) was stirred at room temperature for 22 hours. The reaction mixture was poured in ice water (30 ml) and the mixture was extracted with ethyl acetate. The extract was washed with water and saturated brine, dried over anhydrous sodium sulfate and distilled under reduced pressure to remove the solvent. The residue thus obtained was separated and purified by thin-layer silica gel chromatography with (chloroform/acetone (5/1)), whereby the title compound (389 mg, 100%) was obtained as a colorless amorphous substance.

$^1$H-NMR (CDCl$_3$) δ: 1.32 (s, 3H), 1.40 (s, 3H), 2.35 (s, 3H), 3.67–3.78 (m, 4H), 3.79 (s, 3H), 4.13 (dd, J=9.8,1.9 Hz, 1H), 4.43 (dd, J=9.8,3.4 Hz, 1H), 4.68 (s, 1H), 4.80 (d, J=6.1 Hz, 1H), 4.89 (t, J=5.4 Hz, 1H), 6.76 (d, J=8.8 Hz, 2H), 7.03 (d, J=8.1 Hz, 1H), 7.07 (d, J=7.3 Hz, 1H), 7.13 (s, 2H), 7.21 (d, J=7.3 Hz, 1H), 7.29–7.38 (m, 2H), 7.93 (dd, J=7.1,1.7 Hz, 2H), 8.05 (d, J=8.1 Hz, 1H).

MS (ESI) m/z 572 (M$^+$+1).

(Step 6) Synthesis of 4-((3R,4S)3,4-isopropylidenedioxy-1-(2-(2-methylphenylamino)-6-benzoxazolylacetyl)-(2R)-pyrrolidinylmethoxy)benzoic acid

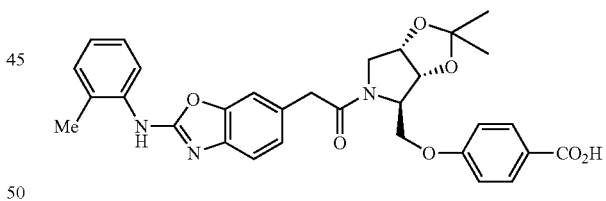

To a solution of methyl 4-((3R,4S)-isopropylidenedioxy-1-(2-(2-methylphenylamino)-6-benzoxazolylacetyl)-(2R)-pyrrolidinylmethoxy)benzoate (188 mg, 0.329 mmol) in THF (15 ml) was added 0.25 NaOH (15 ml). The resulting mixture was stirred at room temperature for 17 hours. The reaction mixture was then concentrated under reduced pressure. The residue thus obtained was acidified with 1N HCl. The crystals thus precipitated were collected by filtration under reduced pressure, washed with water and dried under reduced pressure, whereby the title compound (149 mg, 81%) was obtained as a colorless solid.

IR (ATR) 2989, 2939, 1685, 1639, 1604, 1576, 1510 cm$^{-1}$;

$^1$H-NMR (DMSO-d$_6$) δ: 1.18, 1.23, 1.25 and 1.30 (each s, total 6H, amide isomers), 2.39 (s, 3H), 3.65 and 3.69 (each d, J=6.1 and 5.4 Hz respectively, total 1H, amide isomers), 3.74 and 3.78 (each s, total 1H, amide isomers), 3.82 and 3.85 (each s, total 1H, amide isomers), 3.92 and 3.95 (each d, J=7.8 and 6.1 Hz respectively, total 1H, amide isomers), 4.11–4.20 (m, 2H), 4.43 and 4.54 (m and t, J=4.4 Hz, total 1H, amide isomers), 4.74 (dd, J=6.1,2.4 Hz, 1H), 4.84 and 4.92 (each t, J=4.4 and 3.9 Hz respectively, total 1H, amide isomers), 7.00 (s, 1H), 7.02 (s, 1H), 7.02 (s, 1H), 7.04 (s, 1H), 7.08 (d, J=7.1 Hz, 1H), 7.19–7.25 (m, 3H), 7.31 and 7.33 (each s, total 1H, amide isomers), 7.79 (d, J=7.8 Hz, 1H), 7.86 and 7.89 (each dd, each J=9.1,2.2 Hz, total 2H, amide isomers), 9.61 (br, 1H);

MS (ESI) m/z 558 (M$^+$+1);

Anal. Calcd for $C_{31}H_{31}N_{31}O_7 \cdot 0.7H_2O$: C, 65.30; H, 5.73; N, 7.37. Found: C, 65.46; H, 5.67; N, 7.04.

Example 10

4-((3R,4S)-Dihydroxy-1-(2-(2-methylphenylamino)-6-benzoxazolylacetyl)-(2R)-pyrrolidinylmethoxy)benzoic acid (Step 1) Synthesis of methyl 4-((3R,4S)-dihydroxy-1-(2-(2-methylphenylamino)-6-benzoxazolylacetyl)-(2R)-pyrrolidinylmethoxy)benzoate

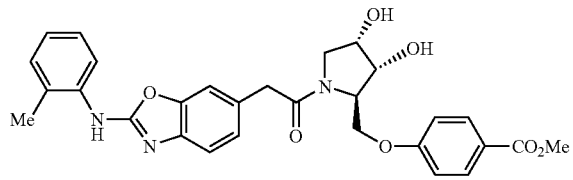

A mixture of methyl 4-((3R,4S)-isopropylidenedioxy-1-(2-(2-methylphenylamino)-6-benzoxazolylacetyl)-(2R)-pyrrolidinylmethoxy)benzoate (201 mg, 0.352 mmol) and an HCl-gas-introduced methanol (20 ml) was stirred at room temperature for 16 hours. The reaction mixture was concentrated under reduced pressure. Water (30 ml) was added to the residue and the mixture was extracted with ethyl acetate. The extract was washed with a saturated aqueous solution of sodium bicarbonate and saturated brine, dried over anhydrous sodium sulfate and distilled under reduced pressure to remove the solvent, whereby the title compound (144 mg, 77%) was obtained as an amorphous substance (this compound was provided for the subsequent reaction without further purification).

(Step 2) Synthesis of 4-((3R,4S)-dihydroxy-1-(2-(2-methylphenylamino)-6-benzoxazolylacetyl)-(2R)-pyrrolidinylmethoxy)benzoic acid

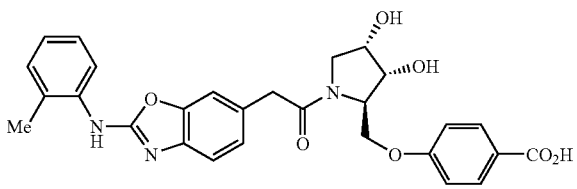

To a solution of methyl 4-((3R,4S)-dihydroxy-1-(2-(2-methylphenylamino)-6-benzoxazolylacetyl)-(2R)-pyrrolidinylmethoxy)benzoate (144 mg, 0.271 mmol) in THF (4 ml) was added 0.25N NaOH (4 ml). The resulting mixture was stirred at room temperature for 21 hours. The reaction mixture was concentrated under reduced pressure. After 1N HCl was added to the residue to acidify the same, the mixture was extracted with a chloroform/methanol (10/1) mixture. The extract was washed with saturated brine, dried over anhydrous sodium sulfate and distilled under reduced pressure to remove the solvent. The residue thus obtained was purified by chromatography on a thin-layer silica gel column with (chloroform/methanol (10/1)), whereby the title compound (24 mg, 17%) was obtained as a colorless amorphous substance.

IR (ATR) 3205, 3060, 2937, 1687, 1639, 1604, 1576, 1512, 1487, 1439 cm$^{-1}$;

$^1$H-NMR (DMSO-d$_6$) δ: 2.30 (s, 3H), 3.39 (m, 1H), 3.65–3.80 (m, 3H), 4.00 (d, J=2.9 Hz, 1H), 4.04 (s, 1H), 4.15–4.23 (m, 2H), 4.30 (d, J=3.9 Hz, 1H), 5.08 (br, 2H), 7.02 (d, J=8.8 Hz, 3H), 7.07 (t, J=7.3 Hz, 1H), 7.23 (d, J=7.6 Hz, 3H), 7.30 (s, 2H), 7.80 (d, J=8.1 Hz, 1H), 7.86 (d, J=8.8 Hz, 2H), 9.60 (br, 1H).

MS (ESI) m/z 518 (M$^+$+1).

Example 11

4-((2S,4S)-1-(2-(2-Methylphenylamino)-6-benzoxazolylacetyl)-4-(2-naphthyloxy)-2-pyrrolidinylmethoxy)benzoic acid (Step 1) Synthesis of methyl (2S,4S)-1-tertbutoxycarbonyl-4-(2-naphthyloxy)-2-pyrrolidinylcarboxylate

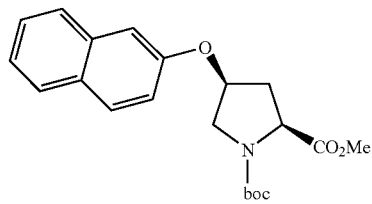

DIAD (3.72 ml, 18.9 mmol) was added to a solution of methyl (2S,4S)-1-tert-butoxycarbonyl-4-hydroxy-2-pyrrolidinylcarboxylate (4.22 g, 17.2 mmol), 2-naphthol (2.73 g, 18.9 mmol) and triphenylphosphine (4.96 g, 18.9 mmol) in THF (80 ml) under stirring at room temperature in a nitrogen gas stream. The mixture was stirred overnight at room temperature. The residue, which had been obtained by concentrating the reaction mixture under reduced pressure, was purified by chromatography on a silica gel column (silica gel: 600 g), whereby from chloroform/ethyl acetate (10/1) eluate fractions, the title compound (5.37 g) was obtained as an amorphous substance (this compound was provided for the subsequent reaction without further purification).

(Step 2) Synthesis of (2S,4S)-1-tert-butoxycarbonyl-4-(2-naphthyloxy)-2-pyrrolidinylcarboxylic acid

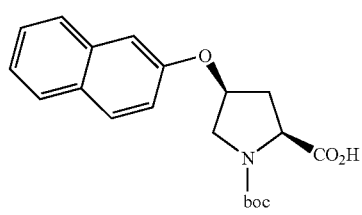

To a solution of methyl (2S,4S)-1-tert-butoxycarbonyl-4-(2-naphthyloxy)-2-pyrrolidinylcarboxylate (5.37 g) in THF (116 ml) was added 0.25N NaOH (116 ml, 29.0 mmol). The resulting mixture was stirred overnight at room temperature. The reaction mixture was concentrated under reduced pressure. The residue was acidified with 1N HCl, followed by extraction with chloroform. The extract was washed with saturated brine, dried over anhydrous sodium sulfate and distilled under reduced pressure to remove the solvent. The residue thus obtained was recrystallized from hexane-chloroform, whereby the title compound (4.44 g, 85% (2 steps)) was obtained as white crystalline powder.

$^1$H-NMR (DMSO-$d_6$) δ: 1.37 and 1.41 (each s, total 9H, amide isomers), 2.26 (d, J=13.9 Hz, 1H), 2.65 (m, 1H), 3.47 (d, J=11.5 Hz, 1H), 3.81 (m, 1H), 4.30 (m, 1H), 5.14 (m, 1H), 7.02–7.86 (m, 7H).

(Step 3) (2S,4S)-1-tert-Butoxycarbonyl-4-(2-naphthyloxy)-2-pyrrolidinylmethanol

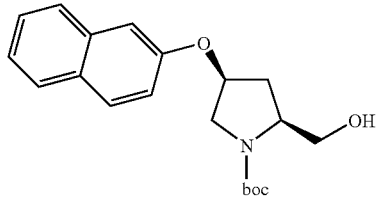

Borane-dimethyl sulfide (0.63 ml, 6.3 mmol) was added to a solution of (2S,4S)-1-tert-butoxycarbonyl-4-(2-naphthyloxy)-2-pyrrolidinylcarboxylic acid (1.12 g, 3.13 mmol) in THF (30 ml) under stirring at 0° C. The reaction mixture was stirred at 50° C. for 1.5 hours. After the reaction mixture was cooled to 0° C., water (20 ml) was added thereto. The mixture was then extracted with ethyl acetate. The extract was washed with saturated brine, dried over anhydrous sodium sulfate and distilled under reduced pressure to remove the solvent. The residue was purified by chromatography on a silica gel column (silica gel: 50 g), whereby from chloroform/methanol (50/1) eluate fractions, the title compound (1.10 g, 100%) was obtained as a pale yellow oil.

$^1$H-NMR (CDCl$_3$) δ: 1.48 (s, 9H), 2.45 (m, 1H), 3.58–4.80 (m, 4H), 5.01 (br, 1H), 7.04–7.99 (m, 7H).

(Step 4) Synthesis of methyl 4-((2S,4S)-1-tert-butoxycarbonyl-4-(2-naphthyloxy)-2-pyrrolidinylmethoxy)benzoate

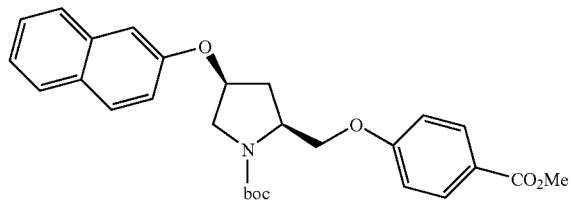

DIAD (0.37 ml, 1.86 mmol) was added to a solution of (2S,4S)-1-tert-butoxycarbonyl-4-(2-naphthyloxy)-2-pyrrolidinylmethanol (640 mg, 1.86 mmol), methyl 4-hydroxybenzoate (283 mg, 1.86 mmol) and triphenylphosphine (488 mg, 1.86 mmol) in THF (18 ml) under stirring at room temperature in a nitrogen gas stream. The reaction mixture was stirred overnight at room temperature. The residue obtained by concentrating the reaction mixture under reduced pressure was purified by chromatography on a silica gel column (silica gel: 100 g), whereby from hexane/ethyl acetate (2/1) eluate fractions, the title compound (830 mg, 93%) was obtained as a colorless oil.

$^1$H-NMR (CDCl$_3$) δ: 1.49 and 1.51 (each s, total 9H, amide isomers), 2.34 (m, 1H), 2.53 (d, J=14.2 Hz, 1H), 3.72–3.85 (m, 1H), 3.86 and 3.87 (each s, total 3H, amide isomers), 4.17 (m, 1H), 4.26–4.52 (m, 2H), 5.06 (br, 1H), 6.87 (d, J=8.8 Hz, 1H), 6.94 (d, J=8.8 Hz, 2H), 7.04 (br, 2H), 7.33 (t, J=7.3 Hz, 1H), 7.42 (t, J=7.3 Hz, 1H), 7.64–8.02 (m, 5H).

(Step 5) Synthesis of methyl 4-((2S,4S)-4-(2-naphthyloxy)-2-pyrrolidinylmethoxy)benzoate

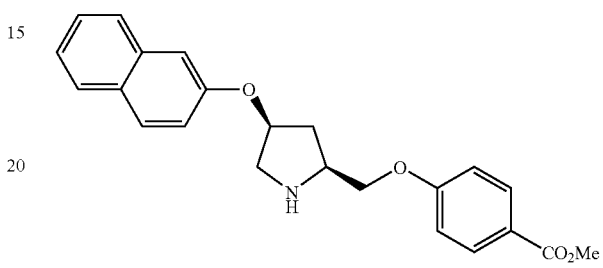

Trifluoroacetic acid (6 ml) was added to a solution of methyl 4-((2S,4S)-1-tert-butoxycarbonyl-4-(2-naphthyloxy)-2-pyrrolidinylmethoxy)benzoate (870 mg, 1.74 mmol) in methylene chloride (24 ml). The resulting mixture was stirred overnight at room temperature. To the residue obtained by concentrating the reaction mixture under reduced pressure was added 1N NaOH under ice cooling to make the residue alkaline, followed by extraction with methylene chloride. The extract was washed with saturated brine, dried over anhydrous sodium sulfate and distilled under reduced pressure to remove the solvent. The residue was purified by chromatography on a silica gel column (silica gel: 100 g), whereby from hexane/ethyl acetate (2/1) eluate fractions, the title compound (750 mg, 100%) was obtained as a black oil.

$^1$H-NMR (CDCl$_3$) δ: 1.99 (dd, J=14.2,5.6 Hz, 1H), 2.48 (m, 1H), 3.22 (dd, J=12.2,4.6 Hz, 1H), 3.43 (d, J=12.5 Hz, 1H), 3.67 (m, 1H), 3.86 and 3.87 (each s, total 3H, amide isomers), 4.11 (m, 2H), 5.04 (m, 1H), 6.83 (d, J=8.5 Hz, 1H), 6.89 (d, J=8.8 Hz, 2H), 7.07 (d, J=2.0 Hz, 1H), 7.12 (d, J=9.0 Hz, 1H), 7.33 (dt, J=8.1,1.2 Hz, 1H), 7.44 (dt, J=6.8,1.2 Hz, 1H), 7.70 (d, J=8.1 Hz, 1H), 7.75 (dd, J=9.0,5.1 Hz, 2H), 7.90 (d, J=8.5 Hz, 1H), 7.96 (dd, J=6.8,2.0 Hz, 2H).

(Step 6) Synthesis of methyl 4-((2S,4S)-1-(2-(2-methylphenylamino)-6-benzoxazolylacetyl)-4-(2-naphthyloxy)-2-pyrrolidinylmethoxy)benzoate

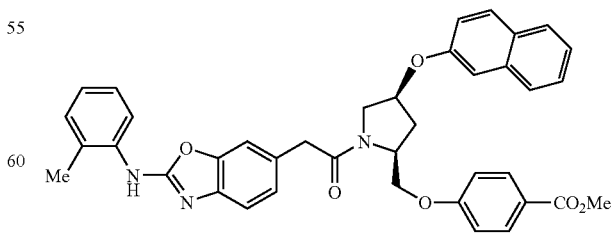

In DMF (10 ml), a mixture of 2-(2-methylphenylamino)-6-benzoxazolylacetic acid (141 mg, 0.50 mmol), methyl 4-((2S,4S)-4-(2-naphthyloxy)-2-pyrrolidinylmethoxy)benzoate (189 mg, 0.50 mmol), EDC•HCl (144 mg, 0.75 mmol), HOBt (101 mg, 0.75 mmol) and triethylamine was stirred at room temperature for 16 hours. The reaction mixture was poured in ice water (30 ml), followed by extraction with ethyl acetate. The extract was washed with ice water and saturated brine, dried over anhydrous sodium sulfate and distilled under reduced pressure to remove the solvent. The residue was separated and purified by chromatography on a thin-layer silica gel column with (chloroform/acetone (5/1)), whereby the title compound (312 mg, 97%) was obtained as a colorless amorphous substance.

$^1$H-NMR (CDCl$_3$) δ: 2.35 and 2.36 (each s, total 3H, amide isomers), 2.38 and 2.57 (m and d, J=14.5 Hz, total 1H, amide isomers), 3.74 (s, 2H), 3.86 (s, 3H), 3.88 and 3.94 (m and dd, J=12.7,5.2 Hz, total 1H, amide isomers), 4.17–4.31 (m, 2H), 4.56 (dd, J=9.3,3.7 Hz, 1H), 4.65 (m, 1H), 5.12 (br, 1H), 6.83 and 6.86 (br and d, J=8.8 Hz respectively, total 1H, amide isomers), 6.97 (d, J=8.8 Hz, 1H), 7.04–7.13 (m, 4H), 7.22 (d, J=7.3 Hz, 1H), 7.26–7.33 (m, 2H), 7.35 (d, J=8.0 Hz, 1H), 8.39 (t, J=8.1 Hz, 1H), 7.44 (t, J=6.9 Hz, 1H), 7.67 (d, J=8.1 Hz, 1H), 7.74 (t, J=10.3 Hz, 2H), 7.94 and 7.98 (each d, each J=8.6 Hz, total 2H, amide isomers), 8.08 (d, J=8.6 Hz, 1H).

MS (ESI) m/z 642 (M$^+$+1).

(Step 7) Synthesis of 4-((2S,4S)-1-(2-(2-methylphenylamino)-6-benzoxazolylacetyl)-4-(2-naphthyloxy)-2-pyrrolidinylmethoxy)benzoic acid

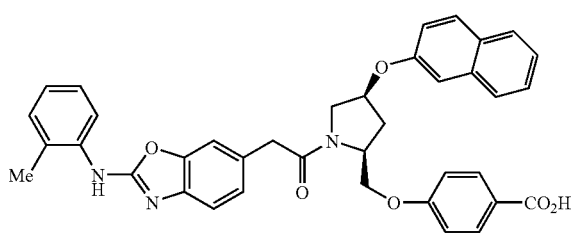

To a solution of methyl 4-((2S,4S)-1-(2-(2-methylphenylamino)-6-benzoxazolylacetyl)-4-(2-naphthyloxy)-2-pyrrolidinylmethoxy)benzoate (312 mg, 0.486 mmol) in THF (20 ml) was added 0.25N NaOH (20 ml). The resulting mixture was stirred at room temperature for 15 hours. The reaction mixture was then concentrated under reduced pressure. The residue was acidified with 1N HCl. The crystals thus precipitated were collected by filtration under reduced pressure, washed with water and dried under reduced pressure, whereby the title compound (253 mg, 83%) was obtained as a pale pink solid.

IR (ATR) 3060, 2941, 2879, 1682, 1639, 1603, 1576, 1510, 1439 cm$^{-1}$;

$^1$H-NMR (DMSO-d$_6$) δ: 2.30 (s, 3H), 2.31–2.44 (m, 1H), 3.78 (s, 2H), 3.86 and 3.89 (each s, total 1H, amide isomers), 3.99–4.78 (m, 5H), 5.25 and 5.32 (each m, total 1H, amide isomers), 7.02–7.10 (m, 4H), 7.16 (dd, J=9.2,2.2 Hz, 1H), 7.24 (m, 1H), 7.25 (s, 1H), 7.27 (m, 1H), 7.33–7.38 (m, 3H), 7.46 (t, J=7.1 Hz, 1H), 7.77–7.89 (m, 7H), 9.62 (br, 1H).

MS (ESI) m/z 470 (M$^+$+1);

Anal. Calcd for C$_{38}$H$_{33}$N$_3$O$_6$·1.0H$_2$O: C, 70.68; H, 5.46; N, 6.51. Found: C, 70.51; H, 5.41; N, 6.27.

Example 12

4-((2S,4S)-1-(2-(2-Methylphenylamino)-6-benzoxazolylacetyl)-4-phenoxy-2-pyrrolidinylmethoxy) benzoic acid (Step 1) Synthesis of methyl (2S,4S)-1-tert-butoxycarbonyl-4-phenoxy-2-pyrrolidinylcarboxylate

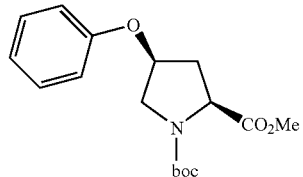

DIAD (4.13 ml, 21.0 mmol) was added to a solution of methyl (2S,4S)-1-tert-butoxycarbonyl-4-hydroxy-2-pyrrolidinylcarboxylate (4.69 g, 19.1 mmol), phenol (1.98 g, 21.0 mmol) and triphenylphosphine (5.51 g, 21.0 mmol) in THF (80 ml) under stirring at room temperature in a nitrogen gas stream. The reaction mixture was stirred overnight at room temperature. The residue obtained by concentrating the reaction mixture under reduced pressure was purified by chromatography on a silica gel column (silica gel: 700 g), whereby from chloroform/ethyl acetate (10/1) eluate fractions, the title compound (5.31 mg, 86%) was obtained as a colorless oil.

$^1$H-NMR (CDCl$_3$) δ: 1.43 and 1.48 (each br, total 9H, amide isomers), 2.48 (m, 1H), 3.75 (br, 3H), 4.42–4.96 (m, 2H), 6.88–7.35 (m, 5H).

(Step 2) Synthesis of (2S,4S)-1-tert-butoxycarbonyl-4-phenoxy-2-pyrrolidinylcarboxylic acid

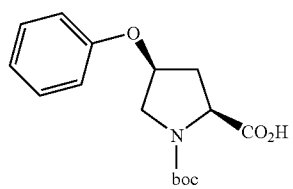

To a solution of methyl (2S,4S)-1-tert-butoxycarbonyl-4-phenoxy-2-pyrrolidinylcarboxylate (5.31 g, 16.5 mmol) in THF (132 ml) was added 0.25N NaOH (132 ml, 33.0 mmol). The reaction mixture was stirred overnight at room temperature. The residue obtained by concentrating the reaction mixture under reduced pressure was acidified with 1N HCl, followed by extraction with chloroform. The extract was washed with saturated brine, dried over anhydrous sodium sulfate and distilled under reduced pressure to remove the solvent. The crude crystals thus obtained were recrystallized from hexane-chloroform, whereby the title compound (2.96 g, 58%) was obtained as a white crystalline powder.

$^1$H-NMR (DMSO-d$_6$) δ: 1.36 (s, 9H), 2.16 (d, J=13.2 Hz, 1H), 2.56 (m, 1H), 3.46 (m, 1H), 3.71 (dt, J=12.0,5.4 Hz, 1H), 4.26 (dt, J=9.5,7.1 Hz, 1H), 4.99 (m, 1H), 6.85 (m, 2H), 6.94 (t, J=7.3 Hz, 1H), 7.28 (t, J=7.3 Hz, 1H).

(Step 3) Synthesis of (2S,4S)-1-tert-butoxycarbonyl-4-phenoxy-2-pyrrolidinylmethanol

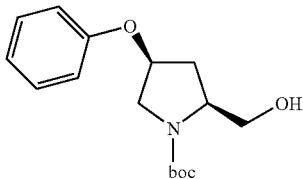

Borane-dimethyl sulfide (1.55 ml, 15.5 mmol) was added to a solution of (2S,4S)-1-tert-butoxycarbonyl-4-phenoxy-2-pyrrolidinylcarboxylic acid (2.39 g, 7.76 mmol) in THF (50 ml) under stirring at 0° C. The reaction mixture was stirred at the same temperature for 10 minutes and then at 50° C. for 2 hours. After cooling the reaction mixture to 0° C., water (30 ml) was added thereto, followed by extraction with ethyl acetate. The extract was washed with saturated brine, dried over anhydrous sodium sulfate and distilled under reduced pressure to remove the solvent. The residue was purified by chromatography on a silica gel column (silica gel: 60 g), whereby from chloroform/methanol (50/1) eluate fractions, the title compound (2.83 g, 100%) was obtained as a colorless oil.

$^1$H-NMR (CDCl$_3$) δ: 1.47 (s, 9H), 1.95 (br, 1H), 2.36 (m, 1H), 3.56–3.74 (m, 3H), 3.89–4.52 (m, 3H), 4.85 (br, 1H), 6.84 (dd, J=8.8,1.2 Hz, 2H), 6.97 (t, J=7.2 Hz, 1H), 7.29 (t, 2H, J=7.8 Hz).

(Step 4) Synthesis of methyl 4-((2S,4S)-1-tert-butoxycarbonyl-4-phenoxy-2-pyrrolidinylmethoxy)benzoate

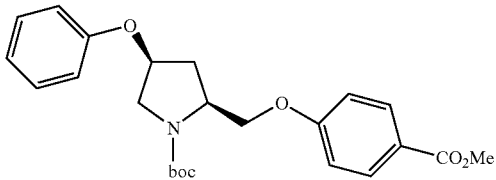

DIAD (0.64 ml, 3.25 mmol) was added dropwise while stirring a mixture of (2S,4S)-1-tert-butoxycarbonyl-4-phenoxy-2-pyrrolidinylmethanol (1.16 g, 3.25 mmol), methyl 4-hydoxybenzoate (494 mg, 3.25 mmol) and triphenylphosphine (852 mg, 3.25 mmol) in THF (30 ml) at room temperature in a nitrogen gas stream. After completion of the dropwise addition, the reaction mixture was stirred at room temperature for 20 minutes and at 80° C. for 8 hours. After cooling, the reaction mixture was concentrated under reduced pressure. The residue was purified by chromatography on a silica gel column (silica gel: 200 g), whereby from chloroform/acetone (20/1) eluate fractions, the title compound (2.07 g, 100%) was obtained as a colorless oil.

$^1$H-NMR (CDCl$_3$) δ: 1.56 (s, 9H), 2.30 (m, 1H), 2.47 and 2.49 (each br, total 1H, amide isomers), 3.69–3.80 (m, 3H), 3.88 (s, 3H), 4.08–4.49 (m, 2H), 4.94 (t, J=4.9 Hz, 1H), 6.82 (d, J=8.1 Hz, 2H), 6.96 (m, 3H), 7.27 (m, 2H), 7.96 (d, J=8.1 Hz, 2H).

(Step 5) Synthesis of methyl 4-((2S,4S)-4-phenoxy-2-pyrrolidinylmethoxy)benzoate

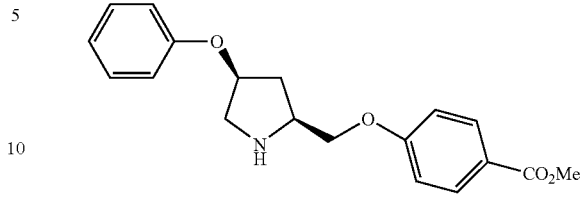

Trifluoroacetic acid (20 ml) was added to a solution of methyl 4-((2S,4S)-1-tert-butoxycarbonyl-4-phenoxy-2-pyrrolidinylmethoxy)benzoate (2.02 g, 3.25 mmol) in methylene chloride (100 ml). The resulting mixture was stirred at room temperature for 5 hours. The reaction mixture was then concentrated under reduced pressure. The residue was diluted with methylene chloride (50 ml), followed by washing with 1N NaOH. The organic layer was fractionated, followed by washing with saturated brine, drying over anhydrous sodium sulfate and distillation under reduced pressure to remove the solvent. The residue was purified by chromatography on a silica gel column (silica gel: 70 g), whereby from chloroform/acetone (10/1) chloroform/methanol (10/1) eluate fractions, the title compound (970 mg, 91%) was obtained as a brown oil.

$^1$H-NMR (CDCl$_3$) δ: 1.88 (dd, J=12.9,4.3 Hz, 1H), 2.39 (qq, J=6.8,6.8 Hz, 1H), 2.83 (br, 1H), 3.19 (dd, J=12.0,5.1 Hz, 1H), 3.33 (d, J=12.0 Hz, 1H), 3.64 (m, 1H), 3.87 (s, 3H), 4.07 (m, 2H), 4.88 (m, 1H), 6.86 (d, J=8.5 Hz, 2H), 6.90 (d, J=7.1 Hz, 2H), 6.94 (d, J=7.3 Hz, 1H), 7.26 (d, J=7.3 Hz, 2H), 7.96 (d, J=9.0 Hz, 2H).

(Step 6) Synthesis of methyl 4-((2S,4S)-1-(2-(2-methylphenylamino)-6-benzoxazolylacetyl)-4-phenoxy-2-pyrrolidinylmethoxy)benzoate

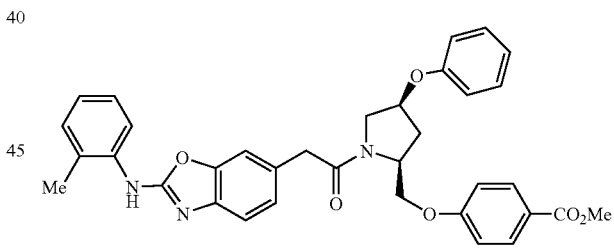

In DMF (10 ml), a mixture of 2-(2-methylphenylamino)-6-benzoxazolylacetic acid (351 mg, 1.07 mmol), methyl 4-((2S,4S)-4-phenoxy-2-pyrrolidinylmethoxy)benzoate (303 mg, 1.07 mmol), EDC•HCl (308 mg, 1.61 mmol), HOBt (218 mg, 1.61 mmol) and triethylamine (0.74 ml, 5.35 mmol) was stirred at room temperature for 21 hours. The reaction mixture was poured in ice water (30 ml), followed by extraction with ethyl acetate. The extract was washed with ice water and saturated brine, dried over anhydrous sodium sulfate and distilled under reduced pressure to remove the solvent. The residue was purified by chromatography on a silica gel column (silica gel: 40 g), whereby from chloroform/acetone (10/1) eluate fractions, the title compound (640 mg, 100%) was obtained as a yellow oil.

$^1$H-NMR (CDCl$_3$) δ: 2.17–2.52 (m, 5H), 3.68–3.80 (m, 3H), 3.86 (s, 3H), 3.88 (m, 1H), 4.12–4.29 (m, 1H), 4.53 (dd, J=13.0,3.9 Hz, 1H), 4.62 (m, 1H), 4.97 (m, 1H), 6.80 (d,

J=7.8 Hz, 2H), 6.86 (d, J=9.1 Hz, 1H), 6.95–6.99 (m, 2H), 7.07 (t, J=8.1 Hz, 2H), 7.21–7.33 (m, 5H), 7.39 (d, J=8.1 Hz, 1H), 7.94–7.99 (m, 2H), 8.01 (s, 1H), 8.08 (d, J=8.3 Hz, 1H).

MS (ESI) m/z 592 (M$^+$+1).

(Step 7) Synthesis of 4-((2S,4S)-1-(2-(2-methylphenylamino)-6-benzoxazolylacetyl)-4-phenoxy-2pyrrolidinylmethoxy)benzoic acid

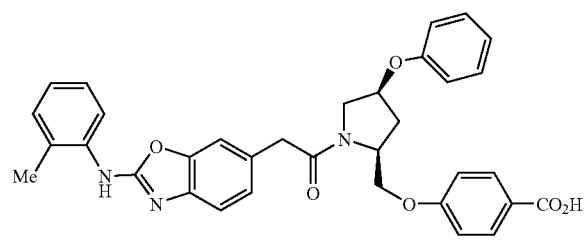

To a solution of methyl 4-((2S,4S)-1-(2-(2-methylphenylamino)-6-benzoxazolylacetyl)-4-phenoxy-2-pyrrolidinylmethoxy)benzoate (640 mg, 1.07 mmol) in THF (30 ml) was added 0.25N NaOH (30 ml). The resulting mixture was stirred at room temperature for 14 hours. The reaction mixture was then concentrated under reduced pressure. After addition of 1N HCl to the residue, the crystals thus precipitated were collected by filtration under reduced pressure, washed with water and dried under reduced pressure, whereby the title compound (366 mg, 60%) was obtained as a pale pink solid.

IR (ATR) 3060, 2985, 2941, 1687, 1639, 1603, 1576, 1489, 1439 cm$^{-1}$;

$^1$H-NMR (DMSO-d$_6$) δ: 2.17–2.25 (m, 2H), 2.30 (s, 3H), 3.39–4.27 (m, 7H), 5.09–5.20 (m, 1H), 6.93 (d, J=7.8 Hz, 2H), 7.01–7.10 (m, 5H), 7.25–7.33 (m, 7H), 7.80–7.89 (m, 3H), 9.64 (br, 1H).

MS (ESI) m/z 470 (M$^+$+1);

Anal. Calcd for C$_{34}$H$_{31}$N$_3$O$_6$·1.0H$_2$O: C, 68.56; H, 5.58; N, 7.05. Found: C, 68.77; H, 5.61; N, 7.00.

Example 13

4-((2S,4S)-4-Fluoro-1-(2-(2-methylphenylamino)-5-benzoxazolylacetyl)-2-pyrrolidinylmethoxy)benzoic acid (Step 1) Synthesis of methyl 4-hydroxy-3-nitrophenylacetate

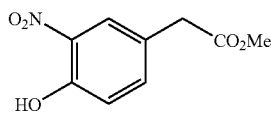

In methanol/toluene (1:10, 55 ml) was dissolved 4-hydroxy-3-nitrophenylacetic acid (2.0 g, 10.1 mmol). Trimethylsilyldiazomethane (2.0M hexane solution, 5.0 ml) was added dropwise to the resulting solution. After stirring at room temperature for 50 minutes, the reaction mixture was distilled under reduced pressure to remove the solvent. The residue was diluted with ethyl acetate. The ethyl acetate extract was then washed with a saturated aqueous solution of sodium bicarbonate and saturated brine, dried over anhydrous sodium sulfate and distilled under reduced pressure to remove the solvent, whereby the title compound (2.15 g, 100%) was obtained as a yellow solid (this compound was provided for the subsequent reaction without further purification).

$^1$H-NMR (CDCl$_3$) δ: 3.63 (s, 2H), 3.72 (s, 3H), 7.13 (d, J=8.5 Hz, 1H), 7.52 (dd, J=8.8,2.2 Hz, 1H), 10.53 (s, 1H).

(Step 2) Synthesis of methyl 3-amino-4-hydroxyphenylacetate

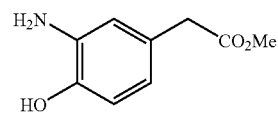

Methyl 4-hydroxy-3-nitrophenylacetate (2.15 g, 10.1 mmol) and 5% palladium/carbon (2.15 g) were suspended in methanol (100 ml). The resulting suspension was subjected to catalytic hydrogenation for 20 hours under stirring at room temperature and normal pressure. The catalyst was then filtered off from the reaction mixture. The filtrate was distilled under reduced pressure to remove the solvent, whereby the title compound (1.72 g, 93%) was obtained as a brown solid (this compound was provided for the subsequent reaction without further purification).

(Step 3) Synthesis of methyl 2-(2-methylphenylamino)-5-benzoxazolylacetate

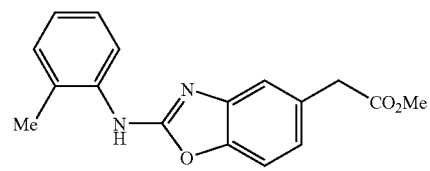

Methyl 3-amino-4-hydroxyphenylacetate (1.72 g, 9.49 mmol) was dissolved in methanol (100 ml). Under stirring at room temperature, o-tolyl thioisocyanate (1.91 ml, 14.3 mmol) was added, followed by stirring at room temperature for 24 hours. Mercuric oxide (yellow) (3.49 g, 16.1 mmol) was added to the reaction mixture. The reaction mixture was then stirred at room temperature for 2.5 hours. After cooling to room temperature, the reaction mixture was distilled under reduced pressure to remove the solvent. The residue was purified by chromatography on a silica gel column (silica gel: 100 g), whereby from hexane/ethyl acetate (2/1) eluate fractions, the title compound (2.33 g, 83% (2 steps)) was obtained as a yellow oil.

$^1$H-NMR (CDCl$_3$) δ: 2.35(s, 3H), 3.686(s, 2H), 3.692(s, 3H), 6.93(br, 1H), 7.02(dd, J=8.3,1.7 Hz, 1H), 7.07(t, J=7.3 Hz, 1H), 7.22(d, J=7.6 Hz, 1H), 7.25(d, J=3.2 Hz, 1H), 7.30(dt, J=8.6,0.5 Hz, 1H), 7.38(d, J=1.5 Hz, 1H), 8.05(d, J=8.1 Hz, 1H).

(Step 4) Synthesis of 2-(2-methylphenylamino)-5-benzoxazolylacetic acid

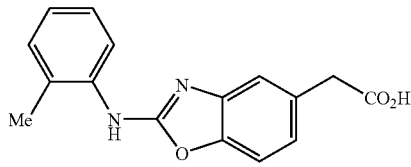

Methyl 2-(2-methylphenylamino)-5-benzoxazolylacetate (2.32 g, 7.86 mmol) was dissolved in THF (40 ml). After addition of 0.25N NaOH (40 ml) under stirring at room temperature, the mixture was stirred for 15 hours. The residue, which had been obtained by distilling the reaction mixture under reduced pressure to remove the solvent, was acidified with 1N HCl. The crystals thus obtained were collected by filtration under reduced pressure, washed with water, dried under reduced pressure, whereby the title compound (894 mg) was obtained as a pale black crystalline powder. The water layer was extracted with a chloroform/methanol (10/1) mixture. The extract was washed with saturated brine, dried over anhydrous sodium sulfate and distilled under reduced pressure to remove the solvent, whereby the title compound (1.03 g) was obtained as a colorless solid (total yield: 88%).

$^1$H-NMR (CDCl$_3$) δ: 2.29 (s, 3H), 3.50 (s, 2H), 6.96 (dd, J=8.1,1.7 Hz, 1H), 7.09 (t, J=7.6 Hz, 1H), 7.23 (m, 3H), 7.36 (d, J=8.1 Hz, 1H), 9.46 (br, 1H), 12.28 (br, 1H).

(Step 5) Synthesis of methyl 4-((2S,4S)-4-fluoro-1-(2-(2-methylphenylamino)-5-benzoxazolylacetyl)-2-pyrrolidinylmethoxy)benzoate

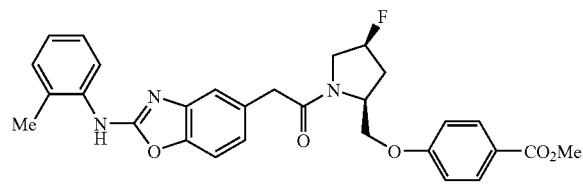

In DMF (5 ml), 2-(2-methylphenylamino)-5-benzoxazolylacetic acid (282 mg, 1.0 mmol), methyl 4-((2S,4S)-4-fluoro-1-2-pyrrolidinylmethoxy)benzoate (253 mg, 1.0 mmol), EDC•HCl (288 mg, 1.5 mmol), HOBT (203 mg, 1.5 mmol) and triethylamine (0.70 ml, 5.0 mmol) were stirred at room temperature for 18 hours. The reaction mixture was poured in water, followed by extraction with ethyl acetate. The extract was washed with ice water and saturated brine, dried over anhydrous sodium sulfate and distilled under reduced pressure to remove the solvent. The residue was purified by chromatography on a silica gel column (silica gel: 50 g), whereby from chloroform/acetone (10/1) eluate fractions, the title compound (405 mg, 78%) was obtained as a pale brown amorphous substance.

$^1$H-NMR (CDCl$_3$) δ: 2.03–2.26 (m, 1H), 2.49 (s, 3H), 2.53 (dd, J=19.5,15.1 Hz, 1H), 3.63–3.82 (m, 3H), 3.87 (s, 3H), 3.92 (d, J=9.5 Hz, 1H), 4.02–4.15 (m, 1H), 4.50–4.64 (m, 2H), 5.29 (d, J=52.7 Hz, 1H), 6.86 and 7.03 (each d, J=8.8 and 8.3 Hz respectively, total 1H, amide isomers), 7.99 (d, J=8.8 Hz, 2H), 7.08 (t, J=7.6 Hz, 1H), 7.21–7.34 (m, 5H), 7.96 (d, J=9.0 Hz, 2H), 8.01 (t, J=8.1 Hz, 1H).

MS (ESI) m/z 518 (M$^+$+1).

(Step 6) Synthesis of 4-((2S,4S)-4-fluoro-1-(2-(2-methylphenylamino)-5-benzoxazolylacetyl)-2-pyrrolidinylmethoxy)benzoic acid

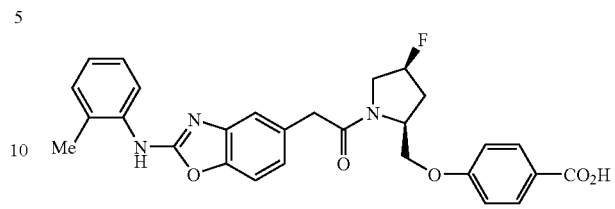

Methyl 4-((2S,4S)-4-fluoro-1-(2-(2-methylphenylamino)-5-benzoxazolylacetyl)-2-pyrrolidinylmethoxy)benzoate (405 mg, 0.783 mmol) was dissolved in THF (20 ml). To the resulting solution was added 0.25N NaOH (20 ml), followed by stirring at room temperature for 18 hours. The reaction mixture was distilled under reduced pressure to remove the solvent. The residue was acidified with 1N HCl. The crystals thus obtained were collected by filtration under reduced pressure, washed with water and dried under reduced pressure, whereby the title compound (200 mg, 81%) was obtained as a colorless crystalline powder.

IR (KBr) 3423, 3251, 2973, 2941, 1685, 1643, 1579 cm$^{-1}$;
$^1$H-NMR (DMSO-d$_6$) δ: 2.18–2.24 (m, 2H), 2.30 (s, 3H), 3.58–4.72 (m, 7H), 5.38 and 5.44 (each m, total 1H, amide isomers), 6.98 (d, J=8.3 Hz, 1H), 7.02–7.13 (m, 4H), 7.19–7.28 (m, 3H), 7.37 (m, 1H), 7.78 (d, J=8.8 Hz, 2H), 7.87 (d, J=8.8 Hz, 2H), 9.72 (br, 1H).
MS (ESI) m/z 470 (M$^+$+1);
Anal. Calcd for $C_{28}H_{26}FN_3O_5 \cdot 1.1H_2O$: C, 64.26; H, 5.43; F, 3.63; N, 8.03. Found: C, 64.07; H, 5.34; F, 3.66; N, 8.01.

Example 14

4-((2S,4S)-1-(4-(2-Benzoxazolylamino)phenylacetyl)-4-fluoro-2-pyrrolidinylmethoxy)benzoic acid (Step 1) Synthesis of ethyl 4-(2-benzoxazolylamino)phenylacetate

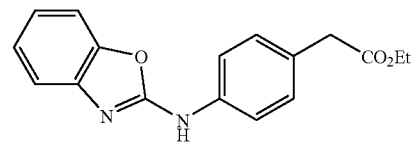

In xylene (10 mL), 2-chlorobenzoxazole (1.00 g, 6.51 mmol) and ethyl 4-aminophenylacetate (1.67 g, 6.51 mmol) were heated and refluxed for 10 hours. After cooling, water was added to the reaction mixture, followed by extraction with ethyl acetate. The extract was washed with saturated brine, dried over magnesium sulfate and distilled under reduced pressure to remove the solvent. The residue was purified by chromatography on a silica gel column, whereby from hexane-ethyl acetate (3:1, v/v) eluate fractions, ethyl 4-(2-benzoxazolylamino)phenylacetate (2.08 g, 99%) was obtained as a yellow solid.

$^1$H-NMR (CDCl$_3$) δ: 1.26 (t, J=7.1 Hz, 3H), 3.61 (2H, s), 4.16 (q, J=7.1 Hz, 2H), 7.13 (td, J=7.8,1.2 Hz, 1H), 7.24 (td, J=7.8,1.2 Hz, 1H), 7.31 (d, J=8.5 Hz, 2H), 7.34 (dd, J=7.8, 1.2 Hz, 1H), 7.49 (dd, J=7.8,1.2 Hz, 1H), 7.57 (d, J=8.5 Hz, 2H), 7.67 (1H, broad s).

MS (ESI) m/z 297 (M$^+$+1).

(Step 2) Synthesis of 4-(2-benzoxazolylamino)phenylacetic acid

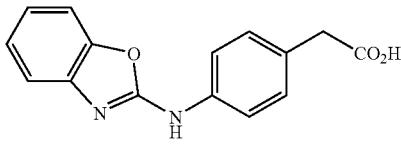

In THF (70 mL) was dissolved ethyl 4-(2-benzoxazolylamino)phenylacetate (2.08 g, 7.02 mmol), followed by the addition of 0.25N NaOH (42.0 mL, 10.5 mmol) at room temperature. After stirring for 24 hours, the reaction mixture was poured in 1N HCl (50 ml) at 0° C. The crystals thus precipitated were collected by filtration, whereby 4-(2-benzoxazolylamino)phenylacetic acid (1.85 g, 98%) was obtained as a solid.

$^1$H-NMR (DMSO-$d_6$) δ: 3.53 (2H, s), 7.12 (t, 1H, J=7.8 Hz, 1H), 7.21 (t, J=7.8 Hz, 1H), 7.25 (d, J=8.5 Hz, 2H), 7.44 (d, J=7.8 Hz, 1H), 7.47 (d, J=7.8 Hz, 1H), 7.68 (d, J=8.5 Hz, 2H), 10.56 (1H, s), 12.27 (1H, broad s).

MS (ESI) m/z 269 (M$^+$+1).

(Step 3) Synthesis of methyl 4-((2S,4S)-1-(4-(2-benzoxazolylamino)phenylacetyl)-4-fluoro-2-pyrrolidinylmethoxy)benzoate

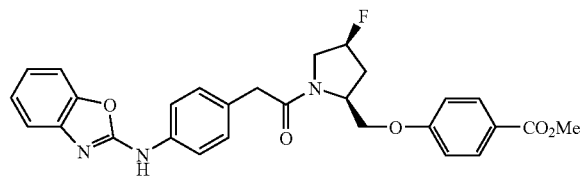

In DMF (8.8 mL) were dissolved 4-(2-benzoxazolylamino)phenylacetic acid (235 mg, 0.88 mmol), methyl 4-((4S)-fluoro-(2S)-pyrrolidinylmethoxy)benzoate (222 mg, 0.88 mmol), HOBt (24.0 mg, 0.18 mmol) and triethylamine (0.18 mL, 1.31 mmol). EDC•HCl (252 mg, 1.31 mmol) was then added to the resulting solution. After the resulting mixture was stirred for 3 hours, water (30 ml) was added thereto, followed by extraction with ethyl acetate. The extract was washed with saturated brine, dried over magnesium sulfate and distilled under reduced pressure to remove the solvent. The residue was purified by chromatography on a silica gel column, whereby from hexane-ethyl acetate (1:2, v/v) eluate fractions, methyl 4-((2S,4S)-1-(4-(2-benzoxazolylamino)phenylacetyl)-4-fluoro-2-pyrrolidinylmethoxy)benzoate (440 mg, 99%) was obtained as a pale yellow amorphous substance.

$^1$H-NMR (CDCl$_3$) δ: 2.14 (1H, m), 2.56 (1H, m), 3.63 (d, J=15.1 Hz, 1H), 3.80 (d, J=15.1 Hz, 1H), 3.87 (3H, s), 3.76–4.07 (3H, m), 4.55 (1H, m), 4.64 (1H, m), 5.31 (1H, m), 6.99 (d, J=8.8 Hz, 2H), 7.12 (t, J=7.6 Hz, 1H), 7.23 (t, J=7.6 Hz, 1H), 7.27 (d, J=8.6 Hz, 2H), 7.33 (d, J=7.6 Hz, 1H), 7.48 (d, J=7.6 Hz, 1H), 7.58 (d, J=8.6 Hz, 2H), 7.96 (d, J=8.8 Hz, 2H).

MS (ESI) m/z 504 (M$^+$+1).

(Step 4) Synthesis of 4-((2S,4S)-1-(4-(2-benzoxazolylamino)phenylacetyl)-4-fluoro-2-pyrrolidinylmethoxy)benzoic acid

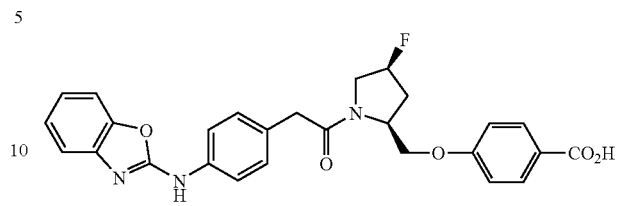

In THF (10 mL) was dissolved methyl 4-((2S,4S)-1-(4-(2-benzoxazolylamino)phenylacetyl)-4-fluoro-2-pyrrolidinylmethoxy)benzoate (440 mg, 0.87 mmol). At room temperature, 0.25N NaOH (5.24 ml, 1.31 mmol) was added to the resulting solution. After stirring at room temperature for 24 hours, the reaction mixture was poured in 1N HCl (30 ml) at 0° C. and the crystals thus obtained were collected by filtration. The crystals were dissolved in chloroform. The resulting solution was washed with saturated brine and then distilled under reduced pressure to remove the solvent. The crude crystals thus obtained were recrystallized from chloroform-hexane, whereby the title compound (388 mg, 91%) was obtained as a colorless amorphous substance.

IR (KBr) 3417, 3278, 3058, 2958, 1681, 1644, 1604, 1573, 1513, 1459, 1432 cm$^{-1}$;

$^1$H-NMR (DMSO-$d_6$) δ: 2.24–2.31 (2H, m), 3.63 (d, J=15.6 Hz, 1H), 3.68 (d, J=15.6 Hz, 1H), 3.77–3.92 (3H, m), 4.38–4.43 (2H, m), 5.44 (1H, m), 7.08 (d, J=8.5 Hz, 2H), 7.12(t, J=8.1 Hz, 1H), 7.22 (t, J=8.1 Hz, 1H), 7.25 (d, J=8.5 Hz, 2H), 7.44 (d, J=8.1 Hz, 1H), 7.48 (d, J=8.1 Hz, 1H), 7.70 (d, J=8.5 Hz, 2H), 7.88 (d, J=8.5 Hz, 2H), 10.57 (1H, broad s), 12.63 (1H, s; broad s).

MS (ESI) m/z 504 (M$^+$+1);

Anal. Calcd for $C_{27}H_{24}FN_3O_5 \cdot H_2O$: C, 63.90; H, 5.16; N, 8.28. Found C, 63.96; H, 5.48; N, 7.86.

Example 15

4-(1-(3-Chloro-4-(3-indolylcarbonylamino)phenylacetyl)-(4S)-fluoro-(2S)-pyrrolidinylmethoxy)benzoic acid (Step 1) Synthesis of ethyl 3-chloro-4-(3-indolylcarbonylamino)phenylacetate

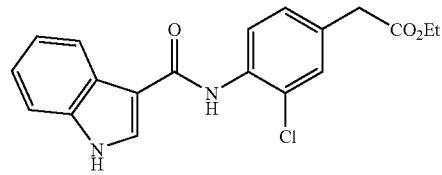

EDC•HCL (1.78 g, 9.28 mmol) was added to a solution of indole-3-carboxylic acid (1.00 g, 6.21 mmol), ethyl 4-amino-3-chlorophenylacetate (1.33 g, 6.22 mmol) and triethylamine (1.80 mL, 12.9 mmol). The mixture was stirred at 70° C. for 24 hours. After cooling to room temperature, the reaction mixture was added with water (30 ml), followed by extraction with ethyl acetate. The extract was washed with saturated brine, dried over anhydrous sodium sulfate and distilled under reduced pressure to remove the solvent. The residue was purified by chromatography on a silica gel column, whereby from hexane-ethyl acetate (1:1, v/v) eluate fractions, ethyl 3-chloro-4-(3-indolylcarbonylamino)phenylacetate (1.25 g, 56%) was obtained as a pale yellow solid.

¹H-NMR (CDCl₃) δ: 1.27 (t, J=7.1 Hz, 3H), 3.59 (s, 2H), 4.17 (q, J=7.1 Hz, 2H), 7.23 (m, 1H), 7.30–7.34 (m, 2H), 7.37 (d, J=2.0 Hz, 1H), 7.47 (m, 1H), 7.91 (d, J=2.9 Hz, 1H), 8.16 (m, 1H), 8.32 (broad s, 1H), 8.58 (d, J=8.5 Hz, 1H), 8.82 (broad s, 1H).

(Step 2) Synthesis of 3-chloro-4-(3-indolylcarbonylamino)phenylacetic acid

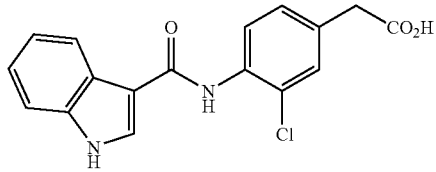

To a solution of ethyl 3-chloro-4-(3-indolylcarbonylamino)phenylacetate (1.25 g, 3.50 mmol) in THF (35 mL) was added 0.25N NaOH (21 mL, 5.23 mmol) under stirring. The reaction mixture was then stirred at room temperature for 24 hours. The reaction mixture was poured in 1N HCl (30 ml) under stirring at 0° C. The crystals thus precipitated were collected by filtration, whereby 3-chloro-4-(N-(3-indolylcarbonyl)amino)phenylacetic acid (1.05 g, 91%) was obtained as a colorless solid.

¹H-NMR (DMSO-d₆) δ: 3.61 (s, 2H), 7.12–7.20 (m, 2H), 7.24 (d, J=8.3 Hz, 1H), 7.44 (s, 1H), 7.47 (d, J=7.3 Hz, 1H), 7.67 (d, J=8.3 Hz, 1H), 8.14 (d, J=7.3 Hz, 1H), 8.29 (s, 1H), 9.32 (s, 1H), 11.75 (broads, 1H).

(Step 3) Synthesis of methyl 4-(1-(3-chloro-4-(3-indolylcarbonylamino)phenylacetyl)-(4S)-fluoro-(2S)-pyrrolidinylmethoxy)benzoate

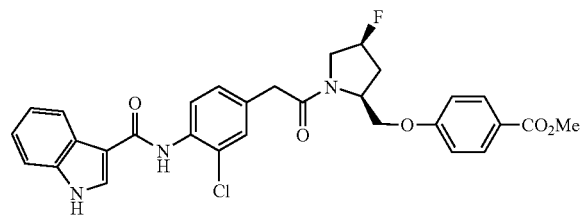

EDC•HCl (0.92 g, 4.79 mmol) was added to a solution of 3-chloro-4-(3-indolylcarbonylamino)phenylacetic acid (1.05 g, 3.19 mmol), methyl 4-((4S)-fluoro-(2S)-pyrrolidinylmethoxy)benzoate (0.81 g, 3.19 mmol), HOBt (86.3 mg, 0.64 mmol) and triethylamine (0.68 mL, 4.79 mmol) in DMF (30 mL). The mixture was then stirred at 60° C. for 10 hours. After cooling to room temperature, the reaction mixture was poured in water (30 ml), followed by extraction with ethyl acetate. The extract was washed with saturated brine, dried over anhydrous sodium sulfate and distilled under reduced pressure to remove the solvent. The crystals thus precipitated were collected by filtration, washed with water and dried under reduced pressure, whereby methyl 4-(1-(3-chloro-4-(3-indolylcarbonylamino)phenylacetyl)-(4S)-fluoro-(2S)-pyrrolidinylmethoxy)benzoate (0.73 g, 40%) was obtained as a brown solid.

¹H-NMR (DMSO-d₆) δ: 2.22–2.36 (m, 2H), 3.70 (d, J=16.1 Hz, 1H), 3.76 (d, J=16.1 Hz, 1H), 3.80 (s, 3H), 3.82–3.97 (m, 3H), 4.39–4.44 (m, 2H), 5.47 (m, 1H), 7.10 (d, J=8.8 Hz, 2H), 7.14–7.25 (m, 2H), 7.42 (d, J=1.5 Hz, 1H), 7.47 (d, J=7.8 Hz, 1H), 7.66 (d, J=8.1 Hz, 1H), 7.90 (d, J=8.8 Hz, 2H), 8.14 (d, J=7.8 Hz, 1H), 8.29 (s, 1H), 9.33 (s, 1H), 11.76 (broad s, 1H).

(Step 4) Synthesis of 4-(1-(3-chloro-4-(3-indolylcarbonylamino)phenylacetyl)-(4S)-fluoro-(2S)-pyrrolidinylmethoxy)benzoic acid

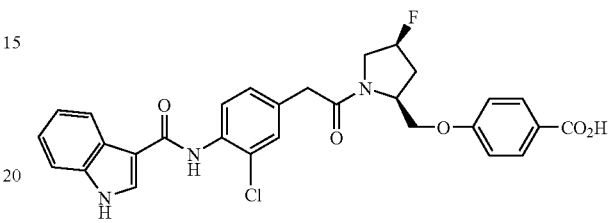

To a solution of methyl 4-(1-(3-chloro-4-(3-indolylcarbonylamino)phenylacetyl)-(4S)-fluoro-(2S)-pyrrolidinylmethoxy)benzoate (725 mg, 1.32 mmol) in THF-methanol (60 mL, 5:1, v/v) was added 0.25N NaOH (15.0 ml, 3.75 mmol). The resulting mixture was stirred at room temperature for 18 hours. The reaction mixture was poured in 1N HCl (20 ml) at 0° C. The crystals thus precipitated were collected by filtration, washed with water and dried under reduced pressure, whereby 4-(1-(3-chloro-4-(N-(3-indolylcarbonylamino)phenylacetyl)-4-fluoro-2-pyrrolidinylmethoxy)benzoic acid (399 mg, 55%) was obtained as a colorless solid.

IR (KBr) 3220, 2975, 1637, 1604, 1513, 14245, 1403 cm⁻¹;

¹H-NMR (DMSO-d₆) δ: 2.27–2.33 (m, 2H), 3.60 (d, J=15.9 Hz, 1H), 3.76 (d, J=15.9 Hz, 1H), 3.81–4.05 (m, 3H), 4.40–4.49 (m, 2H), 5.47 (m, 1H), 7.06 (d, J=8.6 Hz, 2H), 7.15–7.21 (m, 2H), 7.24 (d, J=8.2 Hz, 1H), 7.43 (s, 1H), 7.48 (d, J=7.8 Hz, 1H), 7.68 (d, J=8.2 Hz, 1H), 7.90 (d, J=8.6 Hz, 2H), 8.14 (d, J=7.8 Hz, 1H), 8.30 (s, 1H), 9.35 (s, 1H), 11.81 (broad s, 1H).

FAB-MS m/z 550 (M⁺+1);

Anal. Calcd for C₂₉H₂₅ClFN₃O₅.3.25H₂O: C, 57.24; H, 5.22; N, 6.91. Found: C, 57.29; H, 5.55; N, 6.50.

Example 16

4-((4S)-Fluoro-1-(4-methoxy-2-(2-methylphenylamino)-6-benzoxazolyl)oxyacetyl-(2S)-pyrrolidinylmethoxy)benzoic acid (Step 1) Synthesis of 5-fluoro-3-methoxy-2-nitrophenol

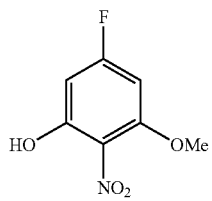

In 10N NaOH (13.1 ml, 131 mmol) and DMSO (25 ml), 3,5-difluoro-2-nitroanisole (8.29 g, 43.8 mmol) was stirred at 50° C. for 5 hours. After cooling, the reaction mixture was poured in 1N HCl (200 ml), followed by extraction with ethyl acetate (300 ml). The extract was washed with saturated brine (2×100 ml), dried over anhydrous magnesium sulfate and distilled under reduced pressure to remove the solvent. The residue was purified by chromatography on a silica gel column, whereby from hexane-ethyl acetate (4:1) eluate fractions, the title compound (4.14 g, 51%) was obtained as a yellow oil.

$^1$H-NMR (CDCl$_3$) δ: 3.94 (s, 3H), 6.28 (dd, J=10.5,2.7 Hz, 1H), 6.41 (dd, J=9.8,2.7 Hz, 1H), 10.92 (s, 1H).

(Step 2) Synthesis of benzyl 5-fluoro-3-methoxy-2-nitrophenyl ether

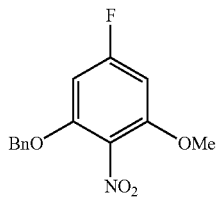

In DMF (20 ml), 5-fluoro-3-methoxy-2-nitrophenol (4.14 g, 22.1 mmol), benzyl bromide (3.2 ml, 26.5 mmol) and potassium carbonate (4.58 g, 33.2 mmol) were stirred at 70° C. for 5 hours. The reaction mixture was poured in water (200 ml), followed by extraction with ethyl acetate (300 ml). The extract was washed with saturated brine (200 ml), dried over anhydrous magnesium sulfate and distilled under reduced pressure to remove the solvent. The residue was purified by chromatography on a silica gel column, whereby from hexane-ethyl acetate (4:1) eluate fractions, the title compound (6.13 g, 100%) was obtained as a yellow oil.

$^1$H-NMR (CDCl$_3$) δ: 3.86 (s, 3H), 5.13 (s, 2H), 6.35 (dd, J=10.3,2.2 Hz, 1H), 6.38 (dd, J=10.3,2.2 Hz, 1H), 7.33–7.38 (m, 5H).

(Step 3) Synthesis of 3-benzyloxy-5-methoxy-4-nitrophenol

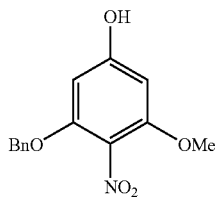

In 10N NaOH (5.8 ml, 58.0 mmol) and DMSO (20 ml), benzyl 5-fluoro-3-methoxy-2-nitrophenyl ether (5.35 g, 19.3 mmol) was stirred for 15 hours. The reaction mixture was poured in 1N HCl (100 ml), followed by extraction with ether (300 ml). The extract was washed with saturated brine (2×100 ml), dried over anhydrous magnesium sulfate and distilled under reduced pressure to remove the solvent. The residue was purified by chromatography on a silica gel column, whereby from chloroform-ethyl acetate (4:1) eluate fractions, the title compound (1.43 g, 27%) was obtained as a brown oil.

$^1$H-NMR (CDCl$_3$) δ: 3.81 (s, 3H), 5.08 (s, 2H), 6.10 (dd, J=10.8,2.2 Hz, 2H), 6.37 (s, 1H), 7.34 (m, 5H).

(Step 4) Synthesis of methyl 3-benzyloxy-5-methoxy-4-nitrophenoxyacetate

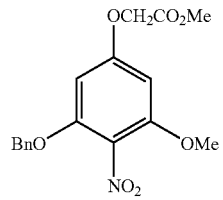

In DMF (10 ml), 3-benzyloxy-5-methoxy-4-nitrophenol (1.43 g, 5.20 mmol), potassium carbonate (1.08 g, 7.79 mmol) and methyl bromoacetate (591 µl, 6.24 mmol) were stirred at room temperature for 2 days. The reaction mixture was poured in water (200 ml), followed by extraction with ether (200 ml). The extract was washed with saturated brine (200 ml), dried over anhydrous magnesium sulfate and distilled under reduced pressure to remove the solvent. The residue was purified by chromatography on a silica gel column, whereby from chloroform-ethyl acetate (20:1) eluate fractions, the title compound (1.53 g, 85%) was obtained as a yellow crystalline solid.

$^1$H-NMR (CDCl$_3$) δ: 3.79 (s, 3H), 3.84 (s, 3H), 4.59 (s, 2H), 5.12 (s, 2H), 6.15 (s, 2H), 7.35 (m, 5H).

(Step 5) Synthesis of 3-benzyloxy-5-methoxy-4-nitrophenoxyacetic acid

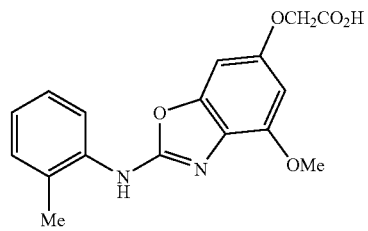

In ethanol (50 ml) was dissolved methyl 3-benzyloxy-5-methoxy-4-nitrophenoxyacetate (1.53 g, 4.41 mmol), followed by the addition of 5% palladium/carbon (1 g). At room temperature and normal pressure, the mixture was subjected to catalytic hydrogenation for 15 hours. The reaction mixture was filtered through Celite under reduced pressure to remove the insoluble matter. The filtrate was stirred at room temperature. To the filtrate was added 2-tolyl isothiocyanate (711 µl, 5.29 mmol). After stirring at room temperature for 15 hours, mercuric oxide (yellow) (1.62 g, 7.50 mmol) was added and the mixture was heated and refluxed for 4 hours. After cooling to room temperature, the reaction mixture was filtered through Celite under reduced pressure to remove the insoluble matter. The filtrate was then distilled under reduced pressure to remove the solvent. The resulting oily residue was dissolved in THF (35 ml). To the solution was added 0.25N NaOH (35 ml, 8.75 mmol) and the mixture was stirred at room temperature for 15 hours. The reaction mixture was poured in 1N HCl (100 ml), followed by extraction with a chloroform-methanol (4:1, 2×200 ml) mixture. The extract was dried over anhydrous magnesium sulfate and then distilled under reduced pressure to remove the solvent. Chloroform-hexane was added to the residue to crystallize the same, whereby the title compound (487 mg, 34%) was obtained as a pale yellow amorphous substance.

¹H-NMR (DMSO-d₆) δ: 2.29 (s, 3H), 3.89 (s, 3H), 4.70 (s, 2H), 6.48 (d, J=7.3 Hz, 1H), 6.78 (d, J=2.0 Hz, 1H), 7.06 (t, J=7.3 Hz, 1H), 7.22–7.24 (m, 2H), 7.85 (d, J=8.3 Hz, 1H).

(Step 6) Synthesis of methyl 4-((4S)-fluoro-1-(4-methoxy-2-(2-methylphenylamino)-6-benzoxazolyl)oxyacetyl-(2S)-pyrrolidinylmethoxy)benzoate

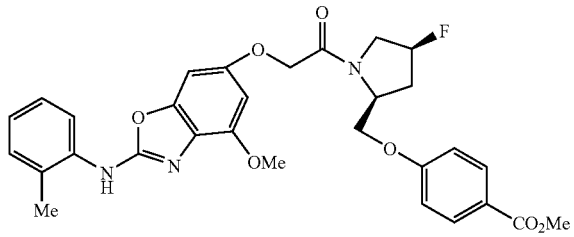

In DMF (4 ml) was dissolved (4-methoxy-2-(2-methylphenylamino)-6-benzoxazolyl)oxyacetic acid (160 mg, 0.49 mmol) and methyl 4-((4S)-fluoro-(2S)-pyrrolidinylmethoxy)benzoate (125 mg, 0.49 mmol). EDC·HCl (144 mg, 0.75 mmol), HOBt and DMAP were added to the resulting solution. The mixture was stirred overnight at room temperature. The reaction mixture was then diluted with ethyl acetate. The diluted mixture was washed with saturated brine, dried over anhydrous magnesium sulfate and distilled under reduced pressure to remove the solvent. The residue was purified by chromatography on a silica gel column and chloroform/methanol (20:1, v/v) eluate fractions were collected. They were purified further by thin-layer silica gel column chromatography (TLC) with chloroform-methanol (20:1, v/v), whereby methyl 4-((4S)-fluoro-1-(4-methoxy-2-(2-methylphenylamino)-6-benzoxazolyl)oxyacetyl-(2S)-pyrrolidinylmethoxy)benzoate (228 mg, 83%) was obtained as a pale brown solid.

IR (KBr) 2950, 1714, 1645, 1591 cm⁻¹;

¹H-NMR (CDCl₃) δ: 2.06 (m, 2H), 2.23 (s, 3H), 2.42 (dd, J=15.1,19.6 Hz, 1H), 3.74 (s, 3H), 3.80 (s, 3H), 3.86 (m, 1H), 3.94 (br, 1H), 4.39 (dd, J=4.0,9.2 Hz, 1H), 4.51 (br, 1H), 4.55 (m, 1H), 5.13–5.30 (series of m, total 1H), 6.37 (d, J=2.4 Hz, 1H), 6.47 (d, J=2.4 Hz, 1H), 6.86 (d, J=8.8 Hz, 2H), 6.94 (m, 1H), 7.08 (m, 2H), 7.15 (m, 1H), 7.35 (br, 1H), 7.87 (t, J=8.8 Hz, 2H), 7.94 (d, J=8.0 Hz, 1H).

MS (ESI) m/z 564 (M+H)⁺;

Anal. Calcd for C₃₀H₃₀FN₃O₇·H₂O: C, 61.96; H, 5.55; N, 7.22. Found: C, 61.77; H, 5.55; N, 6.97.

(Step 7) Synthesis of 4-((4S)-fluoro-1-(4-methoxy-2-(2-methylphenylamino)-6-benzoxazolyl)oxyacetyl-(2S)-pyrrolidinylmethoxy)benzoic acid

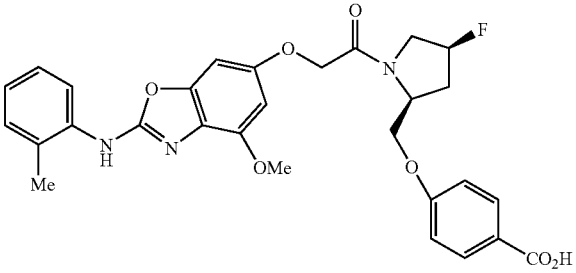

Methyl 4-((4S)-fluoro-1-(4-methoxy-2-(2-methylphenylamino)-6-benzoxazolyl)oxyacetyl-(2S)-pyrrolidinylmethoxy)benzoate (225 mg, 0.40 mmol) was dissolved in THF 4 ml) and methanol (1 ml), followed by the addition of 0.25N NaOH (two equivalents). The resulting mixture was stirred overnight at room temperature. The reaction mixture was diluted with chloroform-methanol (5:1, v/v). The diluted mixture was washed with 1N HCl, dried over anhydrous magnesium sulfate and distilled under reduced pressure to remove the solvent. The residue was purified by chromatography on a silica gel column. Chloroform-methanol (20:1, v/v) eluate fractions were collected and they were purified further by a thin-layer silica gel column chromatography (TLC) with chloroform-methanol (20:1, v/v), whereby 4-((4S)-fluoro-1-(4-methoxy-2-(2-methylphenylamino)-6-benzoxazolyl)oxyacetyl-(2S)-pyrrolidinylmethoxy)benzoic acid (161 mg, 73%) was obtained as white powder.

IR (KBr) 2951, 1645, 1593 cm⁻¹;

¹H-NMR (DMSO-d₆) δ: 2.29 (s, 3H), 2.31 (m, 2H), 2.40 (m, 1H), 3.57 (dd, J=13.6,31.9 Hz, 1H), 3.84 (m, 2H), 3.89 (s, 3H), 4.06–4.25 (series of m, total 1H), 4.48 (m, 1H), 5.49 (series of d, J=52.7 Hz, total 1H), 6.49 (series of d, J=2.4 Hz, total 1H), 6.79 (series of d, J=2.4 Hz, total 1H), 7.01 (m, 1H), 7.04 (d, J=8.8 Hz, 2H), 7.22 (d, J=7.6 Hz, 2H), 7.82 (d, J=8.8 Hz, 1H), 7.87 (d, J=8.8 Hz, 2H), 9.41 (br, 1H).

MS (ESI) m/z 550 (M+H)⁺;

Anal. Calcd for C₂₉H₂₈FN₃O₇·2H₂O: C, 59.48; H, 5.51; N, 7.18. Found: C, 59.61; H, 5.13; N, 6.89.

Example 17

4-(1-(2-(2-Methylphenylamino)-6-benzothiazolylacetyl)-(4S)-fluoro-(2S)-pyrrolidinylmethoxy)cyclohexanecarboxylic acid Isomer A and Isomer B (Step 1) Synthesis of di-tert-butyl (3-fluoro-4-nitrophenyl) malonate

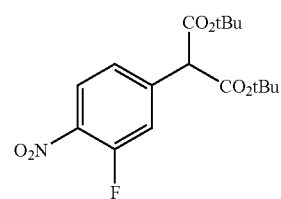

In THF (400 ml) were dissolved 2,4-difluoronitrobenzene (17.4 g, 109 mmol) and di-tert-butyl malonate (27.0 ml, 120 mmol). Under stirring at 0° C., sodium hydride (60% in oil, 4.82 g, 120 mmol) was added in portions. The reaction mixture was then stirred overnight at room temperature. The reaction mixture was poured in 1.0N-HCl (300 ml), followed by extraction with ethyl acetate. The extract was washed with saturated brine, dried over anhydrous magnesium sulfate and distilled under reduced pressure to remove the solvent. The residue was purified by chromatography on a silica gel column, whereby from hexane-ethyl acetate (20:1 to 10:1) eluate fractions, di-tert-butyl (3-fluoro-4-nitrophenyl)malonate (5.17 g, 13%) was obtained as a pale yellow oil.

¹H-NMR (CDCl₃) δ: 1.49 (s, 18H), 4.51 (s, 1H), 7.32 (d, J=8.4 Hz, 2H), 7.42 (dd, J=11.6,2.0 Hz, 1H), 8.05 (t, J=8.4 Hz, 1H).

(Step 2) Synthesis of ethyl 3-fluoro-4-nitrophenylacetate

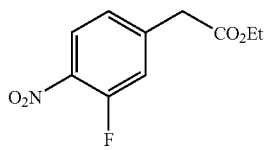

Trifluoroacetic acid (25 ml) was added to a solution of di-tert-butyl (3-fluoro-4-nitrophenyl)malonate (5.11 g, 14.4 mmol) in methylene chloride (50 ml). The resulting mixture was stirred at room temperature for 2 hours. The reaction mixture was concentrated under reduced pressure to yield a colorless solid substance. To the solid substance were added concentrated sulfuric acid (1 ml) and ethanol (50 ml) and the mixture was heated and refluxed for 2 hours. After cooling to room temperature, the reaction mixture was concentrated under reduced pressure. Ice water (100 ml) was poured in the residue, followed by extraction with ethyl acetate. The extract was washed with a saturated aqueous solution of sodium bicarbonate, dried over anhydrous sodium sulfate and distilled under reduced pressure to remove the solvent, whereby ethyl 3-fluoro-4-nitrophenylacetate (3.15 g, 96%) was obtained as a yellow oil.

$^1$H-NMR (CDCl$_3$) δ: 1.27 (t, J=7.2 Hz, 3H), 3.69 (s, 2H), 4.18 (q, J=14.4,7.2 Hz, 2H), 7.21 (d, J=8.8 Hz, 1H), 7.25 (d, J=10.0 Hz, 2H), 8.03 (t, J=8.0 Hz, 1H).

(Step 3) Synthesis of ethyl 3-(4-methoxybenzylthio)-4-nitrophenylacetate

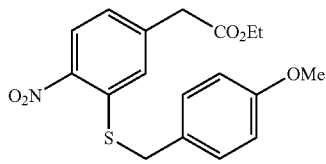

Sodium hydride (60% in oil, 440 mg, 11.0 mmol) was added in portions to a solution of ethyl 3-fluoro-4-nitrophenylacetate (2.09 g, 9.20 mmol) and 4-methoxyphenylbenzylthiol (3.85 ml, 27.6 mmol) in N-methylpyrrolidone (30 ml) under stirring at 0° C. After completion of the addition, the reaction mixture was stirred at room temperature for 5 hours. The reaction mixture was poured in 1.0 N-HCl (30 ml), followed by extraction with ether. The extract was washed with water (twice), dried over anhydrous sodium sulfate and distilled under reduced pressure to remove the solvent. The residue was purified by chromatography on a silica gel column, whereby from hexane-ethyl acetate (3:1) eluate fractions, ethyl 3-(4-methoxybenzylthio)-4-nitrophenylacetate (3.37 g, quant.) was obtained as a yellow oil.

$^1$H-NMR (CDCl$_3$) δ: 1.27 (t, J=6.8 Hz, 3H), 3.65 (s, 2H), 3.80 (s, 3H), 4.16 (s, 2H), 4.17 (q, J=14.4,7.2 Hz, 2H), 6.87 (d, J=8.4 Hz, 2H), 7.15 (dd, J=8.4,1.6 Hz, 1H), 7.33 (d, J=8.4 Hz, 2H), 8.17 (d, J=8.8 Hz, 1H).

(Step 4) Synthesis of ethyl 3-(4-methoxybenzylthio)-4-aminophenylacetate

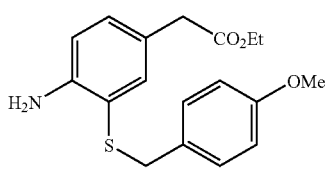

Under stirring, a solution of ethyl 3-(4-methoxybenzylthio)-4-nitrophenylacetate (3.33 g, 9.92 mmol), ammonium chloride (542 mg, 10.1 mmol) and reduced iron powder (2.57 g, 46.1 mmol) in ethanol/THF/water (2:2:1, 75 ml) was heated and refluxed for 1.5 hours. After the reaction mixture was cooled, the insoluble matter was filtered off. The filtrate was distilled under reduced pressure to remove the solvent. The residue was neutralized by pouring therein a saturated aqueous solution of sodium bicarbonate, followed by extraction with a chloroform-methanol mixture. The extract was dried over anhydrous sodium sulfate and distilled under reduced pressure to remove the solvent. The residue was purified by chromatography on a silica gel column, whereby from chloroform-ethyl acetate (20:1) eluate fractions, ethyl 3-(4-methoxybenzylthio)-4-aminophenylacetate (2.64 g, 86%) was obtained as a yellow oil.

$^1$H-NMR (CDCl$_3$) δ: 1.27 (t, J=6.8 Hz, 3H), 3.45 (s, 2H), 3.81 (s, 3H), 3.90 (s, 2H), 4.16 (q, J=14.0,7.2 Hz, 2H), 4.24 (brs, 2H), 6.69 (d, J=8.0 Hz, 1H), 6.80 (d, J=8.4 Hz, 2H), 7.06 (dd, J=8.4,2.0 Hz, 1H), 7.17 (s, 1H), 7.18 (s, 1H), 7.29 (s, 1H).

MS (ESI) m/z, 332 (M$^+$+H).

(Step 5) Synthesis of ethyl 4-(N'-(2-methylphenyl)thioureido)-3-(4-methoxybenzylthio)phenylacetate

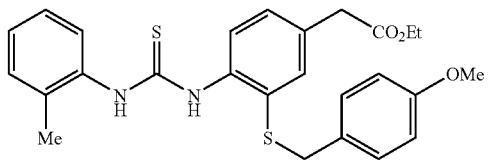

A solution of ethyl 3-(4-methoxybenzylthio)-4-aminophenylacetate (2.55 g, 7.69 mmol) and o-tolyl isocyanate (1.74 ml, 8.46 mmol) in acetonitrile (20 ml) was stirred overnight at 60° C. After the reaction mixture was cooled, the solvent was distilled off under reduced pressure. The residue was purified by chromatography on a silica gel column, whereby from hexane-ethyl acetate (3:1) eluate fractions, ethyl 4-(N'-(2-methylphenyl)thioureido)-3-(4-methoxybenzylthio)phenylacetate (1.66 g, 45%) was obtained as a yellow oil.

$^1$H-NMR (CDCl$_3$) δ: 1.24 (t, J=7.2 Hz, 3H), 3.51 (s, 2H), 3.73 (s, 2H), 3.77 (s, 3H), 4.13 (q, J=14.4,7.2 Hz, 2H), 6.69 (d, J=8.8 Hz, 1H), 6.84 (d, J=8.8 Hz, 2H), 7.21–7.34 (series of m, 6H), 7.60 (brs, 1H), 8.10 (brs, 1H), 8.32 (d, J=8.0 Hz, 2H).

MS (ESI) m/z, 481 (M$^+$+H).

(Step 6) Synthesis of ethyl 2-(2-methylphenylamino)-6-benzothiazolylacetate

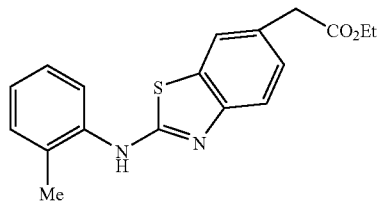

In ethanol (50 ml), ethyl 4-(N'-(2-methylphenyl)thioureido)-3-(4-methoxybenzylthio)phenylacetate (1.63 g, 3.40 mmol) and mercuric oxide (yellow) (1.10 g, 16.4 mmol) were stirred for one hour at 70° C. Water (50 ml) was added and the mixture was extracted with ethyl acetate. The extract was washed with water and a saturated aqueous solution of sodium bicarbonate, dried over anhydrous sodium sulfate and distilled under reduced pressure to remove the solvent. The residue was purified by chromatography on a silica gel column, whereby from hexane-ethyl acetate (3:1) eluate fractions, ethyl 2-(2-methylphenylamino)-6-benzothiazolylacetate (922 mg, 83%) was obtained as a pale yellow oil.

$^1$H-NMR (CDCl$_3$) δ: 1.25 (t, J=7.2 Hz, 3H), 2.78 (s, 3H), 3.64 (s, 2H), 4.14 (q, J=14.4,7.6 Hz, 2H), 7.17–7.22 (m, 2H), 7.29 (t, J=7.2 Hz, 2H), 7.43 (d, J=8.0 Hz, 1H), 7.51 (brs, 1H), 7.65 (d, J=8.0 Hz, 1H), 8.00 (brs, 1H).

MS (ESI) m/z, 327 (M$^+$+H).

(Step 7) Synthesis of 2-(2-methylphenylamino)-6-benzothiazolylacetic acid

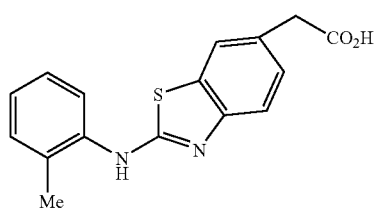

In THF-methanol (1:1, 20 ml) was dissolved ethyl 2-(2-methylphenylamino)-6-benzothiazolylacetate (907 mg, 2.78 mmol). To the resulting solution was added 1.0M-NaOH (8.34 ml, 8.34 mmol), followed by stirring overnight at room temperature. The reaction mixture was concentrated under reduced pressure. The residue was acidified with 1.0N HCl. The crystals thus obtained were collected by filtration under reduced pressure, washed with water and dried at 60° C. under reduced pressure, whereby 2-(2-methylphenylamino)-6-benzothiazolylacetic acid (675 mg, 81%) was obtained as a white crystalline powder.

$^1$H-NMR (DMSO-d$_6$) δ: 2.59 (s, 3H), 3.88 (s, 2H), 7.37 (t, J=7.2 Hz, 1H), 7.44–7.46 (m, 1H), 7.52 (t, J=7.6 Hz, 2H), 7.69 (d, J=8.0 Hz, 1H), 7.90 (s, 1H), 8.13 (d, J=8.0 Hz, 1H).

MS (ESI) m/z, 299 (M$^+$+H).

(Step 8) Synthesis of methyl 4-(1-(2-(2-methylphenylamino)-6-benzothiazolylacetyl)-(4S)-fluoro-(2S)-pyrrolidinylmethoxy)cyclohexanecarboxylate

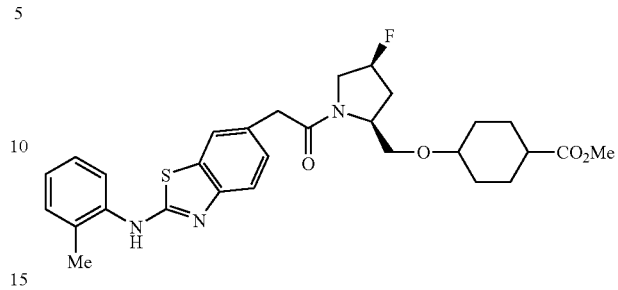

HOBt (14.0 mg, 0.10 mmol) was added to a solution of methyl 4-((4S)-fluoro-(2S)-pyrrolidinylmethoxy)cyclohexanecarboxylate (259 mg, 1.00 mmol), 2-(2-methylphenylamino)-6-benzothiazolylacetic acid (328 mg, 1.10 mmol) and EDC•HCl (288 mg, 1.50 mmol) in DMF (10 ml). The resulting mixture was stirred overnight at room temperature. The reaction mixture was poured in water (30 ml) and the mixture was extracted with ethyl acetate. The extract was washed with water, dried over anhydrous sodium sulfate and distilled under reduced pressure to remove the solvent. The residue was purified by chromatography on a silica gel column, whereby from hexane-ethyl acetate (1:4) eluate fractions, methyl 4-(1-(2-(2-methylphenylamino)-6-benzothiazolylacetyl)-(4S)-fluoro-(2S)-pyrrolidinylmethoxy)cyclohexanecarboxylate (409 mg, 76%), which was a mixture of two diastereomers, was obtained as a colorless amorphous substance.

$^1$H-NMR (CDCl$_3$), mixture of rotamars, δ: 1.20–1.30 (m, 1H), 1.39–1.55 (m, 2H), 1.56–1.72 (m, 2H), 1.77–1.92 (m, 3H), 1.99–2.15 (m, 3H), 2.20–2.55 (m, 2H), 2.34 (s, 3H), 3.20–3.40 (series of m, 6H), 3.66, 3.70 and 3.72 (s, total 3H), 5.15–5.30 (m, 1H), 7.16–7.20 (m, 2H), 7.26–7.28 (m, 3H), 7.45 (dd, J=8.4,3.6 Hz, 1H), 7.50–7.53 (m, 1H), 7.64–7.67 (m, 1H).

MS (ESI) m/z, 540 (M$^+$+H).

(Step 9) Synthesis of 4-(1-(2-(2-methylphenylamino)-6-benzothiazolylacetyl)-(4S)-fluoro-(2S)-pyrrolidinylmethoxy)cyclohexanecarboxylic acid, Isomer A and Isomer B

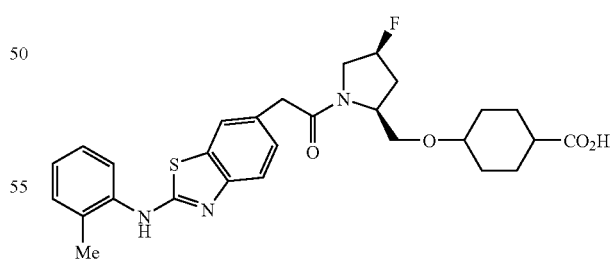

To a solution of methyl 4-(1-(2-(2-methylphenylamino)-6-benzothiazolylacetyl)-(4S)-fluoro-(2S)-pyrrolidinylmethoxy)cyclohexanecarboxylate (397 mg, 0.74 mmol), which was a mixture of two diastereomers, in methanol-THF (1:1, 10 ml) was added 0.25M-NaOH (8.83 ml, 2.21 mmol). The resulting mixture was stirred overnight at room temperature. The reaction mixture was poured in 1NHCl (20 ml) and the mixture was extracted with a chloroform-methanol mixture. The extract was washed with saturated brine, dried over anhydrous sodium sulfate and distilled under reduced pressure to remove the solvent, whereby 4-(1-(2-(2-methylphenylamino)-6-benzothiazolylacetyl)-(4S)-fluoro-(2S)-pyrrolidinylmethoxy)cyclohexanecarboxylic acid (468 mg, 89%), a mixture of two diastereomers, was obtained as a colorless amorphous substance. The mixture of these two diasteromers was separable by HPLC (Shimpack PRC-ODS/30 mm×250 mm, acetonitrile: 0.02N sodium acetate buffer=1:1, 20 ml/min) so that Isomer A and Isomer B were obtained each in the form of a colorless amorphous substance. Isomer A;

$^1$H-NMR (CDCl$_3$), mixture of rotamars, δ: 1.18–1.31 (m, 2H), 1.43–1.55 (m, 2H), 2.05–2.15 (m, 6H), 2.21–2.48 (m, 3H), 2.41 (s, 3H), 3.23–4.24 (series of m, 6H), 5.16–5.30 (m, 1H), 7.17–7.29 (m, 4H), 7.44–7.52 (m, 3H), 7.58 (s, 1H).

MS (ESI) m/z, 526 (M$^+$+H).

Isomer B;

$^1$H-NMR (CDCl$_3$), mixture of rotamars, δ: 1.22–1.30 (m, 2H), 1.43–1.52 (m, 2H), 1.68–2.02 (m, 6H), 2.10–2.18 (m, 1H), 2.30 (s, 3H), 2.22–2.50 (m, 2H), 3.33–4.48 (series of m, 6H), 5.14–5.29 (m, 1H), 7.17–7.27 (m, 5H), 7.43–7.50 (m, 3H);

MS (ESI) m/z, 526 (M$^+$+H).

Example 18

6-((4S)-Fluoro-1-(2-(2-methylphenylamino)-6-benzoxazolylacetyl)-(2S)-pyrrolidinylmethoxy)nicotinic acid (Step 1) Synthesis of methyl 6-((4S)-fluoro-1-(2-(2-methylphenylamino)-6-benzoxazolylacetyl)-(2S)-pyrrolidinylmethoxy)nicotinate

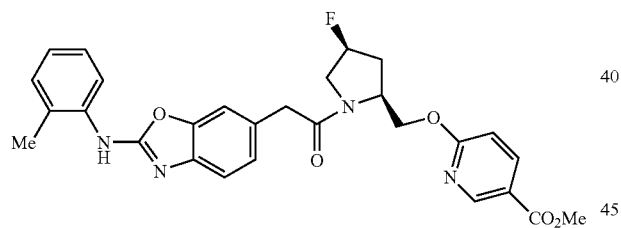

Methyl 6-((4S)-fluoro-(2S)-pyrrolidinylmethoxy)nicotinate (202.0 mg, 0.794 mmol), 2-(2-methylphenylamino)-6-benzoxazolylacetic acid (224.2 mg, 0.794 mmol) and HOBt (21.5 mg, 0.159 mmol) were dissolved in DMF (8.5 ml). Under stirring at room temperature, EDC•HCl (228.4 mg, 1.192 mmol) was added to the resulting solution. The reaction mixture was further stirred overnight at room temperature. Water (30 ml) was added and the mixture was extracted with ethyl acetate. The extract was washed with saturated brine, dried over anhydrous sodium sulfate and distilled under reduced pressure to remove the solvent. The residue was purified by chromatography on a silica gel column, whereby from chloroform-ethyl acetate (5:1, v/v) eluate fractions, the title compound (370.1 mg, 90%) was obtained as a colorless amorphous substance.

$^1$H-NMR (CDCl$_3$) δ: 2.02–2.30 (1H, m, CH$_2$), 2.34, 2.35 (total 3H, s, ArMe), 2.38–2.53 (1H, m, CH$_2$), 3.65–4.83 (total 10H, series of m, including 3H, s at (3.88, 3.90), 5.28 (1H, br d, J=53.9), 6.71–8.88 (total 11H, series of m, ArH, NH).

(Step 2) Synthesis of 6-((4S)-fluoro-1-(2-(2-methylphenylamino)-6-benzoxazolylacetyl)-(2S)-pyrrolidinylmethoxy)nicotinic acid

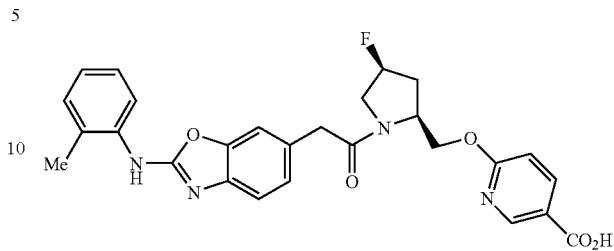

Methyl 6-((4S)-fluoro-1-(2-(2-methylphenylamino)-6-benzoxazolylacetyl)-(2S)-pyrrolidinylmethoxy)nicotinate (370.1 mg, 0.714 mmol) was dissolved in THF (7.5 ml). At room temperature, 0.25N NaOH (7.5 ml) was added at room temperature. The reaction mixture was stirred overnight at 50° C. The reaction mixture was concentrated under reduced pressure. The concentrate was acidified with 1N HCl. The crystals thus obtained were collected by filtration under reduced pressure, washed with water and dried at 50° C. under reduced pressure, whereby the title compound (214.8 mg, 60%) was obtained as a pale brown amorphous substance.

IR (KBr) 1683, 1637, 1600, 1573, 1244 cm$^{-1}$;

$^1$H-NMR (DMSO-d$_6$) δ: 2.13–2.41 (5H, m, including 3H, s at (2.31), 3.30–4.72 (total 7H, series of m), 5.43 (1H, br d, J=52.8 Hz), 6.86–7.42 (total 9H, series of m), 7.79 (1H, m), 8.10–8.22 (1H, m), 8.71 (1H, m).

MS (ESI) m/z 505 (M$^+$+1);

Anal. Calcd for C$_{27}$H$_{25}$FN$_4$O$_5$.0.25H$_2$O: C, 59.01; H, 5.50; N, 10.19; F, 3.46. Found: C, 59.38; H, 5.31; N, 9.73; F, 3.30.

Example 19

Methyl 6-((4S)-fluoro-1-(2-(2-methylphenylamino)-6-benzoxazolylacetyl)-(2S)-pyrrolidinylmethoxy)nicotinate

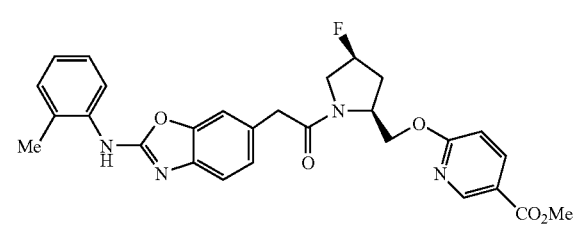

In methanol/benzene (1/1, v/v) (1.5 ml) was dissolved 6-((4S)-fluoro-1-(2-(2-methylphenylamino)-6-benzoxazolylacetyl)-(2S)-pyrrolidinylmethoxy)nicotinic acid (51.6 mg, 0.1023 mmol). Trimethylsilyldiazomethane (2.0M hexane solution, 0.08 ml, 0.1534 mmol) was added dropwise to the resulting solution under stirring at 0° C. After completion of the dropwise addition, the reaction mixture was stirred at room temperature for 3 hours. The solvent was distilled off under reduced pressure. The residue was purified by chromatography on a silica gel column, whereby from chloroform-methanol (10:1, v/v) eluate fractions, the title compound (44.4 mg, 84%) was obtained as a colorless amorphous substance.

¹H-NMR (CDCl₃) δ: 2.02–2.30 (1H, m), 2.34, 2.35 (total 3H, s), 2.38–2.53 (1H, m), 3.65–4.83 (total 10H, series of m, including total 3H, s at δ 3.88, 3.90), 5.28 (1H, br d, J=53.9), 6.71–8.88 (total 11H, series of m).

MS (ESI) m/z 519 (M⁺+1).

Example 20

4-((4S)-Methoxy-1-(2-(2-methylphenylamino)-6-benzoxazolylacetyl)-(2S)-pyrrolidinylmethoxy)cyclohexanecarboxylic acid, Isomer A and Isomer B (Step 1) Synthesis of methyl 4-(1-(tert-butoxycarbonyl)-(4S)-methoxy-(2S)-pyrrolidinylmethoxy)benzoate

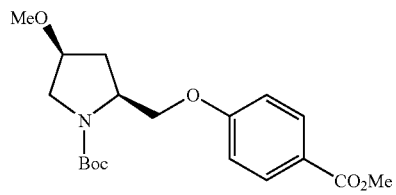

Methyl 4-(1-(tert-butoxycarbonyl)-(4S)-hydroxy-(2S)-pyrrolidinylmethoxy)benzoate (1.03 g, 2.92 mmol) and methyl iodide (300 μl, 5.91 mmol) were dissolved in DMF (20 ml). Under stirring at 0° C., sodium hydride (60% in oil, 145 g, 3.62 mmol) was added in portions. After the whole amount of sodium hydride was added, the reaction mixture was further stirred overnight at room temperature. The reaction mixture was then poured in water and the mixture was extracted with ethyl acetate. The extract was washed with saturated brine, dried over anhydrous magnesium sulfate and distilled under reduced pressure to remove the solvent. The residue was purified by chromatography on a silica gel column, whereby from hexane-ethyl acetate (4:1, v/v) eluate fractions, methyl 4-(1-(tert-butoxycarbonyl)-(4S)-methoxy-(2S)-pyrrolidinylmethoxy)benzoate (943 mg, 88%) was obtained as a pale yellow oil.

¹H-NMR (CDCl₃) δ: 1.46 (s, 9H), 2.03 (br, 1H), 2.27 (dd, J=1.6,14.0 Hz, 1H), 3.27 (s, 3H), 3.50 (m, 2H), 3.86 (s, 3H), 3.91–4.00 (br. m, 2H), 4.12–4.36 (br. m, 2H), 6.94 (br, 2H), 7.95 (d, J=8.8 Hz, 2H).

(Step 2) Synthesis of methyl 4-((4S)-methoxy-(2S)-pyrrolidinylmethoxy)cyclohexanecarboxylate

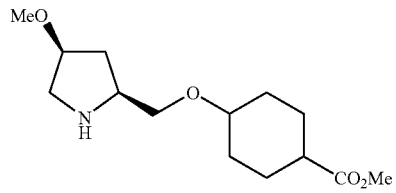

Methyl 4-(1-(tert-butoxycarbonyl)-(4S)-methoxy-(2S)-pyrrolidinylmethoxy)benzoate (943 mg, 2.56 mmol) was dissolved in ethanol (10 ml) and acetic acid (1 ml). To the resulting solution was added rhodium-alumina (500 mg) and the mixture was subjected to catalytic hydrogenation overnight at room temperature under 5 atm. The catalyst was filtered off and the filtrate was distilled under reduced pressure to remove the solvent. The residue was purified by chromatography on a silica gel column, whereby from hexane-ethyl acetate (3:1, v/v) eluate fractions, methyl 4-(1-(tert-butoxycarbonyl)-(4S)-methoxy-(2S)-pyrrolidinylmethoxy)cyclohexanecarboxylate (819 mg, 86%) was obtained as a pale yellow oil. The resulting methyl 4-(1-(tert-butoxycarbonyl)-(4S)-methoxy-(2S)-pyrrolidinylmethoxy)cyclohexanecarboxylate (819 mg, 2.20 mmol) was then dissolved in methylene chloride (9 ml). After addition of trifluoroacetic acid (4 ml) at 0° C., the mixture was stirred at room temperature for 1.5 hours. The reaction mixture was distilled under reduced pressure to remove the solvent. The residue was basified by the treatment with 1N NaOH, followed by extraction with chloroform. The extract was washed saturated with brine, dried over anhydrous magnesium sulfate and distilled under reduced pressure to remove the solvent, whereby methyl 4-((4S)-methoxy-(2S)-pyrrolidinylmethoxy)cyclohexanecarboxylate (2.53 g, 81%) was obtained as a pale yellow oil (a mixture of two diastereomers).

¹H-NMR (CDCl₃) δ: 1.47 (m, 3H), 1.61 (m, 2H), 1.81 (m, 4H), 2.03 (m, 2H), 2.32 (m, 1H), 2.84 (dd, J=5.1,11.5 Hz, 1H), 3.60 (d, J=11.5 Hz, 1H), 3.21 (br, 1H), 3.24 (s, 3H), 3.35–3.44 (m, 3H), 3.63 (s, 3H), 3.68 (br, 1H).

(Step 3) Synthesis of methyl 4-((4S)-methoxy-1-(2-(2-methylphenylamino)-6-benzoxazolylacetyl)-(2S)-pyrrolidinylmethoxy)cyclohexanecarboxylate

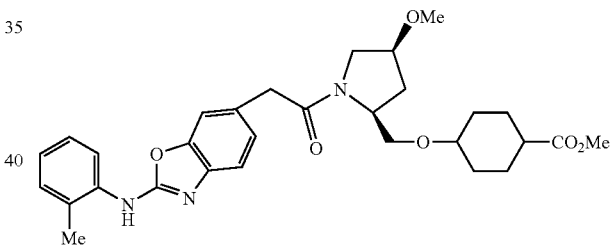

In DMF (7 ml) were dissolved 2-(2-methylphenylamino)-6-benzoxazolylacetic acid (218 mg, 0.77 mmol) and methyl 4-((4S)-methoxy-(2S)-pyrrolidinylmethoxy)cyclohexanecarboxylate (210 mg, 0.77 mmol). EDC•HCL (235 mg, 1.22 mmol), HOBt (5.0 mg, 0.04 mmol) and DMAP (5.0 mg, 0.04 mmol) were added to the resulting solution, followed by stirring overnight at room temperature. The reaction mixture was diluted with ethyl acetate. The diluted mixture was then washed with saturated brine, dried over anhydrous magnesium sulfate and distilled under reduced pressure to remove the solvent. The residue was purified by chromatography on a silica gel column, whereby from chloroform-methanol (10:1, v/v) eluate fractions, methyl 4-((4S)-methoxy-1-(2-(2-methylphenylamino)-6-benzoxazolylacetyl)-(2S)-pyrrolidinylmethoxy)cyclohexanecarboxylate (385 mg, 93%) was obtained as a pale brown oil (a mixture of two diastereomers).

IR (KBr) 2937, 1732, 1641, 1574 cm⁻¹;

¹H-NMR (CDCl₃) δ: 1.47 (m, 2H), 1.62 (m, 2H), 1.76–1.88 (m, 4H), 1.91–2.05 (m, 2H), 2.23 (m, 1H), 2.33 (d, 3H), 2.35 (m, 1H), 3.27 (d, 3H), 3.40–3.54 (m, 3H), 3.65

(d, 3H), 3.67 (m, 2H), 3.78–4.02 (series of m, total 2H), 4.12–4.26 (series of m, total 1H), 6.86 (br, 1H), 7.05 (q, J=7.6 Hz, 2H), 7.15 (d, J=7.6 Hz, 1H), 7.28 (m, 2H), 7.37 (dd, J=2.6,8.0 Hz, 1H), 8.07 (d, J=8.0 Hz, 1H).

MS (ESI) m/z 536 (M+H)+;

Anal. Calcd for $C_{30}H_{37}N_3O_6 \cdot 0.5H_2O$: C, 66.16; H, 7.03; N, 7.72. Found: C, 66.06; H, 6.96; N, 7.57.

(Step 4) Synthesis of 4-((4S)-methoxy-1-(2-(2-methylphenylamino)-6-benzoxazolylacetyl)-(2S)-pyrrolidinylmethoxy)cyclohexanecarboxylic acid, Isomer A and Isomer B

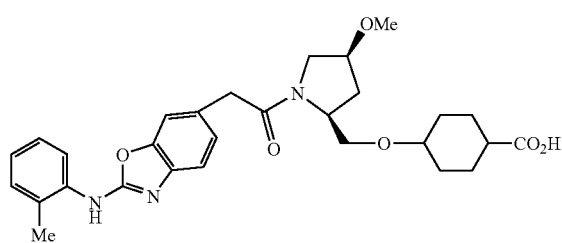

Methyl 4-((4S)-methoxy-1-(2-(2-methylphenylamino)-6-benzoxazolylacetyl)-(2S)-pyrrolidinylmethoxy)cyclohexanecarboxylate (940 mg, 1.79 mmol) was dissolved in THF (15 ml) and methanol (1 ml). To the resulting solution was added 0.25N NaOH (2 eq), followed by stirring overnight at room temperature. The reaction mixture was diluted with chloroform-methanol (5:1, v/v). The diluted mixture was washed with 1N HCl, dried over anhydrous magnesium sulfate and distilled under reduced pressure to remove the solvent. The residue was purified by chromatography on a silica gel column, whereby from chloroform-methanol (20:1, v/v) eluate fractions, 4-((4S)-methoxy-1-(2-(2-methylphenylamino)-6-benzoxazolylacetyl)-(2S)-pyrrolidinylmethoxy) cyclohexanecarboxylic acid (568 mg, 64%) was obtained as a mixture of two diastereomers. The mixture of two diastereomers was separable by HPLC (Shimpack PRC-ODS-30 mm×250 mm, acetonitrile : 0.02N sodium acetate buffer=1:1, 20 ml/min). Isomer A (39 mg, 11%) and Isomer B (246 mg, 67%) were obtained, each as a pale yellow crystalline powder.

Isomer A;

IR (KBr) 2933, 1697, 1641, 1574 cm$^{-1}$;

$^1$H-NMR (CDCl$_3$) δ: 1.18 (m, 4H), 1.40 (m, 2H), 1.96 (m, 4H), 2.19 (m, 2H), 2.28 (s, 3H), 3.15 (m, 1H), 3.21 (d, J=4.4 Hz, 3H), 3.40 (m, 2H), 3.60 (m, 3H), 3.64–3.90 (series of m, total 3H), 4.04–4.19 (m, 1H), 5.17 (br, 1H), 7.02 (t, J=7.4 Hz, 2H), 7.16 (m, 1H), 7.23 (m, 2H), 7.66 (d, J=8.0 Hz, 1H).

MS (ESI) m/z 522 (M+H)+;

Anal. Calcd for $C_{29}H_{35}N_3O_6 \cdot 1.75H_2O$: C, 62.97; H, 7.02; N, 7.60. Found: C, 63.39; H, 7.04; N, 6.90.

Isomer B;

IR (KBr) 2931, 1697, 1641, 1574 cm$^{-1}$;

$^1$H-NMR (CDCl$_3$) δ: 1.48 (m, 2H), 1.64–1.98 (series of m, total 8H), 2.23 (m, 1H), 2.27 (s, 3H), 2.38 (m, 1H), 3.27 (d, J=6.8 Hz, 1H), 3.39–3.47 (m, 3H), 3.54 (q, J=8.8 Hz, 1H), 3.66 (m, 2H), 3.88 (m, 2H), 4.20 (m, 1H), 7.05 (t, J=7.0 Hz, 2H), 7.19 (m, 1H), 7.30 (m, 2H), 7.81 (dd, J=8.0,44.4 Hz, 1H).

MS (ESI) m/z 522 (M+H)+;

Anal. Calcd for $C_{29}H_{35}N_3O_6 \cdot H_2O$: C, 64.55; H, 6.91; N, 7.79. Found: C, 64.81; H, 7.17; N. 7.00.

Example 21

4-(1-(2-(2-Methylphenylamino)-6-benzoxazolylacetyl)-(4S)-fluoro-(2S)-pyrrolidinylmethoxy)cyclohexanecarboxylic acid, Isomer G and Isomer H (Step 1) Synthesis methyl 4-(N-carbobenzoxy-(4S)-fluoro-(2S)-pyrrolidinylmethoxy)cyclohexanecarboxylate, Isomer A and Isomer B

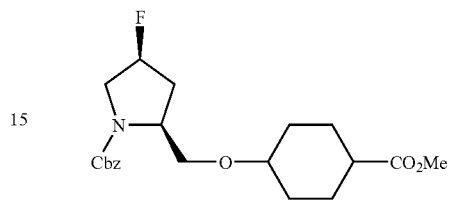

Methyl 4-((4S)-fluoro-(2S)-pyrrolidinylmethoxy)cycloehexanecarboxylate (529 mg, 2.04 mmol) and carbobenzoxy chloride (30 to 35% in toluene, 1.21 ml, 2.04 mmol) were dissolved in methylene chloride (20 ml). Under stirring, a saturated aqueous solution of sodium bicarbonate (5 ml) was added at room temperature. The reaction mixture was further stirred for 5.5 hours at room temperature. The reaction mixture was poured in water (20 ml) and the mixture was extracted with ethyl acetate. The extract was then dried over anhydrous sodium sulfate and distilled under reduced pressure to remove the solvent. The residue was purified by chromatography on a silica gel column, whereby from hexane-ethyl acetate (2:1) eluate fractions, methyl 4-(N-carbobenzoxy-(4S)-fluoro-(2S)-pyrrolidinylmethoxy)cyclohexanecarboxylate (648 mg, 85%), that is, a mixture of two diastereomers was obtained as a colorless oil. Since the mixture was separable into two diasteromers by medium-pressure chromatography on a silica gel column, from hexane-ethyl acetate (3:1) eluate fractions, two isomers were separated.

Isomer A:

$^1$H-NMR (CDCl$_3$) δ: 1.48 (brs, 2H), 1.64 (brs, 2H), 1.84 (brs, 4H), 2.01–2.18 (m, 1H), 2.41–2.51 (m, 1H), 3.33–3.51 (m, 2H), 4.60–3.75 (m, 3H), 3.67 (s, 3H), 4.11–4.15 (m, 1H), 5.10–5.29 (series of m, 3H), 7.30–7.37 (m, 5H).

MS (ESI) m/z, 394 (M+H).;

Isomer B:

$^1$H-NMR (CDCl$_3$) δ: 1.26 (brs, 2H), 1.44 (brs, 2H), 1.99–2.13 (m, 5H), 2.39 (brs, 1H), 2.39–2.48 (m, 1H), 3.18–3.36 (m, 2H), 3.61–3.86 (m, 3H), 3.67 (s, 3H), 4.14 (brs, 1H), 5.10–5.29 (series of m, 3H), 7.31–7.37 (m, 5H).

MS (ESI) m/z, 394 (M+H).

(Step 2) Synthesis of methyl 4-((4S)-fluoro-(2S)-pyrrolidinylmethoxy)cyclohexanecarboxylate (Isomer C)

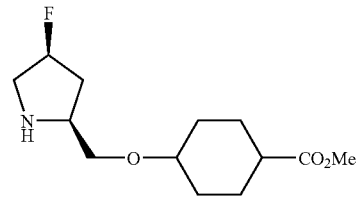

In methanol (10 ml), methyl 4-(N-carbobenzoxy-(4S)-fluoro-(2S)-pyrrolidinylmethoxy)cyclohexanecarboxylate (the above-described Isomer A, 451 mg, 1.15 mmol) and 20% palladium hydroxide/carbon (42 mg) were subjected to catalytic hydrogenation overnight at room temperature and 1 atm. The catalyst was filtered off from the reaction mixture and the filtrate was distilled under reduced pressure to remove the solvent, whereby methyl 4-((4S)-fluoro-(2S)-pyrrolidinylmethoxy)cyclohexanecarboxylate (311 mg, 100%) was obtained as a colorless solid (Isomer C).

As a result of X-ray structural analysis, the derivative of this compound was confirmed to be methyl cis-4-((4S)-fluoro-(2S)-pyrrolidinylmethoxy)cyclohexanecarboxylate whose substituents at the 1- and 4-positions on the cyclohexane ring had a cis relative configuration.

$^1$H-NMR (CDCl$_3$), mixture of rotamers, δ: 1.50 (brt, J=14.0 Hz, 2H), 1.61–1.66 (m, 2H), 1.80–2.01 (series of m, 5H), 2.17–2.37 (m, 2H), 3.05–3.18 (m, 1H), 3.40–3.61 (series of m, 5H), 3.64 (s, 3H), 5.01 (brs, 1H), 5.14–5.30 (m, 1H).

MS (ESI) m/z, 360 (M$^+$+H).

(Step 3) Synthesis methyl of 4-((4S)-fluoro-(2S)-pyrrolidinylmethoxy)cyclohexanecarboxylate (Isomer D)

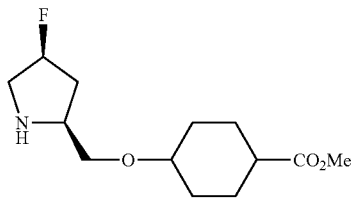

In methanol (5 ml), methyl 4-(N-carbobenzoxy-(4S)-fluoro-(2S)-pyrrolidinylmethoxy)cyclohexanecarboxylate (Isomer B, 121 mg, 0.31 mmol) and 20% palladium hydroxide/carbon (19 mg) were subjected to catalytic hydrogenation overnight at room temperature and 1 atm. The catalyst was filtered off from the reaction mixture and the filtrate was distilled under reduced pressure to remove the solvent, whereby methyl 4-((4S)-fluoro-(2S)-pyrrolidinylmethoxy)cyclohexanecarboxylate (311 mg, quant.) was obtained as a colorless solid (Isomer D).

As a result of X-ray structural analysis, the derivative of this compound was confirmed to be methyl trans-4-((4S)-fluoro-(2S)-pyrrolidinylmethoxy)cyclohexanecarboxylate whose substituents at the 1- and 4-positions on the cyclohexane ring had a trans relative configuration.

$^1$H-NMR (CDCl$_3$), mixture of rotamers, δ: 1.21–1.31 (m, 2H), 1.41–1.51 (m, 2H), 1.74–1.87 (m, 1H), 1.98–2.09 (m, 5H), 2.11–2.30 (m, 2H), 2.48 (brs, 1H), 2.85–2.98 (m, 1H), 3.22–3.59 (series of m, 5H), 5.12–5.26 (m, 1H).

MS (ESI) m/z, 360 (M$^+$+H).

(Step 4) Synthesis of methyl 4-(1-(2-(2-methylphenylamino)-6-benzoxazolylacetyl)-(4S)-fluoro-(2S)-pyrrolidinylmethoxy)cyclohexanecarboxylate (Isomer E)

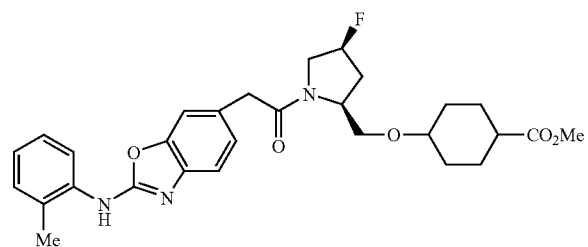

In DMF (10 ml), HOBT (5.2 mg, 0.04 mmol) was added to methyl 4-((4S)-fluoro-(2S)-pyrrolidinylmethoxy)cyclohexanecarboxylate (Isomer C, 50 mg, 0.19 mmol), 2-(2-methylphenylamino)-6-benzoxazolylacetic acid (59.9 g, 0.21 mmol) and EDC•HCl (55.5 mg, 0.29 mmol) under stirring at room temperature. After stirring overnight at room temperature, the reaction mixture was poured in water (10 ml) and the mixture was extracted with ethyl acetate. The extract was washed with saturated brine, dried over anhydrous sodium sulfate and distilled under reduced pressure to remove the solvent. The residue was purified by chromatography on a silica gel column, whereby from hexane-ethyl acetate (1:5) eluate fractions, methyl 4-(1-(2-(2-methylphenylamino)-6-benzoxazolylacetyl)-(4S)-fluoro-(2S)-pyrrolidinylmethoxy)cyclohexanecarboxylate (92.0 mg, 91%) was obtained as a colorless amorphous substance (Isomer E).

$^1$H-NMR (CDCl$_3$), mixture of rotamers, δ: 1.46–2.48 (series of m, 11H), 2.35 (s, 3H), 3.38–4.41 (series of m, 8H), 3.64–3.68 (m, 3H), 5.15–5.30 (m, 1H), 7.07 (dd, J=16.0,7.6 Hz, 2H), 7.21 (d, J=8.0 Hz, 1H), 7.30 (t, J=6.4 Hz, 2H), 7.32–7.40 (m, 1H), 8.07 (d, J=8.4 Hz, 1H).

(Step 5) Synthesis of methyl 4-(1-(2-(2-methylphenylamino)-6-benzoxazolylacetyl)-(4S)-fluoro-(2S)-pyrrolidinylmethoxy)cyclohexanecarboxylate (Isomer F)

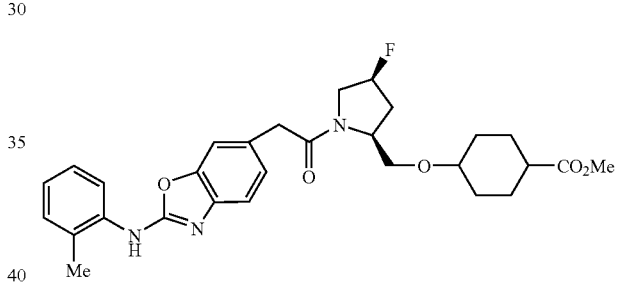

In DMF (10 ml), HOBT (8.0 mg, 0.04 mmol) was added to methyl 4-((4S)-fluoro-(2S)-pyrrolidinylmethoxy)cyclohexanecarboxylate (Isomer D, 77 mg, 0.30 mmol), 2-(2-methylphenylamino)-6-benzoxazolylacetic acid (92.2 mg, 0.33 mmol) and EDC•HCl (85.4 mg, 0.45 mmol) under stirring at room temperature. After further stirring overnight at room temperature, the reaction mixture was poured in water (10 ml) and the mixture was extracted with ethyl acetate. The extract was washed with saturated brine, dried over anhydrous sodium sulfate and distilled under reduced pressure to remove the solvent. The residue was purified by chromatography on a silica gel column, whereby from hexane-ethyl acetate (1:5) eluate fractions, methyl 4-(1-(2-(2-methylphenylamino)-6-benzoxazolylacetyl)-(4S)-fluoro-(2S)-pyrrolidinylmethoxy)cyclohexanecarboxylate (142 mg, 91%) was obtained as a colorless amorphous substance (Isomer F).

$^1$H-NMR (CDCl$_3$), mixture of rotamers, δ: 1.16–1.32 (m, 2H), 1.40–1.54 (m, 2H), 196–2.50 (series of m, 7H), 2.36 (s, 3H), 3.21–3.29 (m, 1H), 3.32–3.52 (m, 1H), 3.50–4.39 (series of m, 6H), 3.62–3.69 (m, 3H), 5.15–5.31 (m, 1H), 7.05–7.10 (m, 2H), 7.22 (d, J=7.2 Hz, 1H), 7.29–7.31 (m, 3H), 7.39–7.43 (m, 1H), 8.06 (d, J=8.0 Hz, 1H).

(Step 6) Synthesis of 4-(1-(2-(2-methylphenylamino)-6-benzoxazolylacetyl)-(4S)-fluoro-(2S)-pyrrolidinylmethoxy)cyclohexanecarboxylic acid (Isomer G)

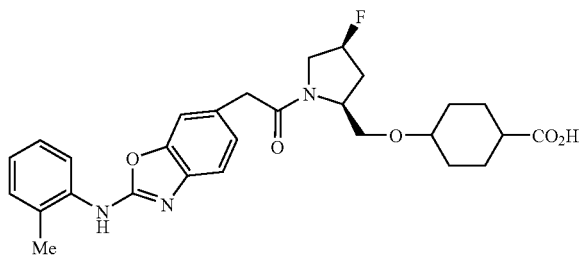

Methyl 4-(1-(2-(2-methylphenylamino)-6-benzoxazolylacetyl)-(4S)-fluoro-(2S)-pyrrolidinylmethoxy)cyclohexanecarboxylate (Isomer E, 92.0 mg, 0.18 mmol) was dissolved in methanol-THF (1:1, 10 ml). After addition of 0.25M-NaOH (0.53 ml, 2.11 mmol) under stirring at room temperature, the reaction mixture was stirred at room temperature for 15 hours. To the reaction mixture was further added 1.0M-NaOH (0.35 ml, 0.35 mmol), followed by stirring at 50° C. for 2.5 hours. The reaction mixture was poured in 1N-HCl (20 ml) and the mixture was extracted with a chloroform-methanol mixture. The extract was washed with saturated brine, dried over anhydrous sodium sulfate and distilled under reduced pressure to remove the solvent. The residue was purified by chromatography on a silica gel column, whereby from chloroform-methanol (10:1) eluate fractions, 4-(1-(2-(2-methylphenylamino)-6-benzoxazolylacetyl)-(4S)-fluoro-(2S)-pyrrolidinylmethoxy)cyclohexanecarboxylic acid (78.0 mg, 87%) was obtained as a colorless amorphous substance (Isomer G).

IR (KBr) 2933, 1693, 1641, 1575 cm$^{-1}$;

$^1$H-NMR (CDCl$_3$) δ: 1.45–1.58 (m, 2H), 1.63–2.01 (series of m, total 6H), 2.10–2.25 (m, 1H), 2.40–2.62 (m, 1H), 2.34 and 2.35 (s, total 3H), 3.30–4.48 (series of m, 9H), 5.14–5.29 (m, 1H), 7.05–7.12 (series of m, 2H), 7.20–7.33 (series of m, 5H), 7.70 and 7.75 (d, J=8.0 Hz, total 1H).

MS (FAB) m/z 510 (M$^+$+H)

(Step 7) Synthesis of 4-(1-(2-(2-methylphenylamino)-6-benzoxazolylacetyl)-(4S)-fluoro-(2S)-pyrrolidinylmethoxy)cyclohexanecarboxylic acid (Isomer H)

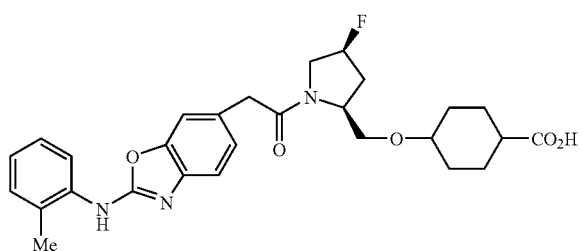

Methyl 4-(1-(2-(2-methylphenylamino)-6-benzoxazolylacetyl)-(4S)-fluoro-(2S)-pyrrolidinylmethoxy)cyclohexanecarboxylate (Isomer F, 130 mg, 0.25 mmol) was dissolved in methanol-THF (1:1, 10 ml). After addition of 0.25M-NaOH (1.99 ml, 0.50 mmol) at room temperature, the reaction mixture was stirred at room temperature for 1 hour. To the reaction mixture was added 1.0M-NaOH (0.74 ml, 0.74 mmol) and the mixture was stirred at 50° C. for 3 hours. The reaction mixture was poured in 1N-HCl (20 ml) and the mixture was extracted with a chloroform-methanol mixture. The extract was washed with saturated brine, dried over anhydrous sodium sulfate and distilled under reduced pressure to remove the solvent. The residue was purified by chromatography on a silica gel column, whereby from chloroform-methanol (10:1) eluate fractions, 4-(1-(2-(2-methylphenylamino)-6-benzoxazolylacetyl)-(4S)-fluoro-(2S)-pyrrolidinylmethoxy)cyclohexanecarboxylic acid (120 mg, 95%) was obtained as a colorless amorphous substance (Isomer H).

IR (KBr) 2937, 1699, 1641, 1574 cm$^{-1}$;

$^1$H-NMR (CDCl$_3$) δ: 1.20–1.31 (m, 2H), 1.43–1.56 (m, 2H), 2.10 (brs, 5H), 2.21–2.50 (m, 1H), 2.34 (s, 3H), 3.24–4.48 (series of m, 9H), 7.01 (brs, 1H), 7.11 (brs, 1H), 7.22–7.36 (series of m, 9H), 7.81 (brd, J=5.6 Hz, 1H).

MS (FAB) m/z 510 (M$^+$+H);

Anal. Calced for C$_{28}$H$_{32}$FN$_3$O$_5$: C, 66.00; H, 6.33; N, 8.25. Found: C, 65.71; H, 6.42; N, 8.08.

Example 22

4-(1-(2-(2-Methylphenylamino)-6-benzoxazolylacetyl)-(2S)-pyrrolidinylmethoxy)cyclohexanecarboxylic acid, Isomer A and Isomer B (Step 1) Synthesis of methyl 4-(1-(2-(2-methylphenylamino)-6-benzoxazolylacetyl)-(2S)-pyrrolidinylmethoxy)cyclohexanecarboxylate (cis and trans forms)

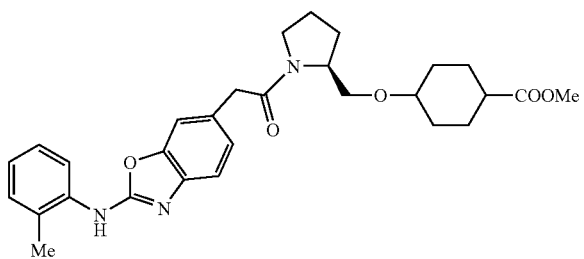

In methylene chloride (20 ml), EDC(HCl (691 mg, 3.6 mmol) was added at 0° C. to methyl 4-(1-(tert-butoxycarbonyl)-(2S)-pyrrolidinylmethoxy)cyclohexanecarboxylate (580 mg, 2.4 mmol), 2-(2-methylphenylamino)-6-benzoxazolylacetic acid (678 mg, 2.4 mmol), HOBt (324 mg, 2.4 mmol) and triethylamine (1.0 ml, 7.2 mmol). The reaction mixture was stirred at room temperature for 16 hours. Ice water (10 ml) was added and the mixture was extracted with ethyl acetate. The extract was washed with a saturated aqueous solution of sodium bicarbonate, a 2M aqueous citric acid solution and a saturated aqueous solution of sodium bicarbonate, dried over anhydrous sodium sulfate and distilled under reduced pressure to remove the solvent. The residue was purified by chromatography on a silica gel column, whereby from hexane-ethyl acetate (1:2, v/v) eluate fractions, the title compound (500 mg, 48%) was obtained as a colorless oil.

$^1$H-NMR (CDCl$_3$) δ: 1.30–2.10 (m, 12H), 2.36 (s, 3H), 3.30–3.90 (m, 7H), 4.10–4.25 (m, 2H), 7.00–7.40 (m, 7H), 8.04–8.06 (m, 1H).

(Step 2) Synthesis of 4-(1-(2-(2-methylphenylamino)-6-benzoxazolylacetyl)-(2S)-pyrrolidinylmethoxy)cyclohexanecarboxylic acid, Isomer A and Isomer B

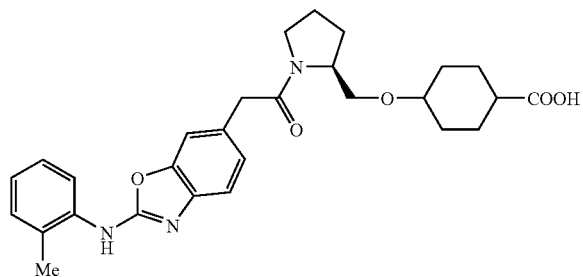

In THF (10 ml) and methanol (5 ml) was dissolved methyl 4-(1-(2-(2-methylphenylamino)-6-benzoxazolylacetyl)-(2S)-pyrrolidinylmethoxy)cyclohexanecarboxylate (580 mg, 1.1 mmol), that is, a mixture of two diastereomers (cis and trans forms). After addition of 1N NaOH (1.5 ml, 1.5 mmol), the mixture was stirred at 70° C. for 24 hours. The residue obtained by distilling off the solvent under reduced pressure, was acidified weakly with 1N HCl. The crystals thus precipitated were collected by filtration under reduced pressure. The resulting crystals were washed with water and dried under reduced pressure, whereby 4-(1-(2-(2-methylphenylamino)-6-benzoxazolylacetyl)-(2S)-pyrrolidinylmethoxy)cyclohexanecarboxylic acid was obtained as a mixture of two diastereomers. The mixture was separated by HPLC (C18 column, eluting with 0.02N acetate buffer-acetonitrile (1:1, v/v)), whereby Isomer A (150 mg, 27%) was obtained as a white crystalline solid.

IR (KBr) 2937, 2867, 1641, 1573, 1440, 1243 cm$^{-1}$;

$^1$H-NMR (DMSO-$d_6$) δ: 1.39–1.85 (m, 10H), 2.23–2.28 (m, 2H), 2.29 (s, 3H), 3.41–4.03 (m, 9H), 7.01–7.08 (m, 2H), 7.21–7.28 (m, 4H), 7.80–7.82 (m, 1H).

MS (FAB) m/z 492 (M+H)$^+$;

Anal. calcd for $C_{28}H_{33}N_3O_5 \cdot 0.2H_2O$: C, 67.91; H, 6.80; N, 8.49. Found: C, 67.79; H, 6.77; N, 8.25.

From HPLC (C18 column, eluting with 0.02N acetate buffer-acetonitrile (1:1, v/v)) eluate fractions, Isomer B (10 mg, 1.7%) was obtained as a white crystalline solid.

$^1$H-NMR (DMSO-$d_6$) δ: 1.11–1.30 (m, 5H), 1.80–2.11 (m, 7H), 2.29 (s, 3H), 3.44–4.00 (m, 9H), 7.02–7.08 (m, 2H), 7.21–7.29 (m, 4H), 7.79–7.81 (m, 1H).

Example 23

4-(1-(2-(2-Methylphenylamino)-6-benzoxazolylacetyl)-(4S)-fluoro-(2S)-pyrrolidinylmethoxy)-3-methylcyclohexanecarboxylic acid (Step 1) Synthesis of methyl 4-hydroxy-3-methylbenzoate

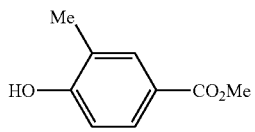

In DMSO (10 ml) and methanol (5 ml) were dissolved 4-hydroxy-3-methyliodobenzene (3.13 g, 13.4 mmol), triethylamine (4.11 ml, 29.5 mmol), palladium acetate (150 mg, 0.67 mmol) and 1,3-bis(diphenylphosphino)propane (276 mg, 0.67 mmol). Under stirring at room temperature, a carbon monoxide gas was introduced for 10 minutes. The reaction mixture was further stirred at 70° C. for 2 days under a carbon monoxide gas stream. After cooling to room temperature, the reaction mixture was concentrated. The concentrate was poured in water (20 ml), followed by extraction with ethyl acetate. The extract was washed successively with water (×2) and saturated brine (×2), dried over anhydrous sodium sulfate and distilled under reduced pressure to remove the solvent. The residue was purified by chromatography on a silica gel column, whereby from hexane-ethyl acetate (5:1) eluate fractions, methyl 4-hydroxy-3-methylbenzoate (2.00 g, 90%) was obtained as a white crystalline solid.

$^1$H-NMR (CDCl$_3$) δ: 2.28 (s, 3H), 3.90 (s, 3H), 6.20 (brs, 1H), 6.83 (d, J=8.4 Hz, 1H), 7.79 (d, J=8.4 Hz, 1H), 7.85 (s, 1H).

(Step 2) Synthesis of methyl 4-((4S)-fluoro-(2S)-pyrrolidinylmethoxy)-3-methylbenzoate

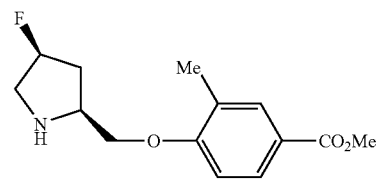

Methyl 4-hydroxy-3-methylbenzoate (1.98 g, 11.9 mmol), N-tert-butoxycarbonyl-(4S)-fluoro-(2S)-pyrrolidinylmethanol (2.87 g, 13.1 mmol) and triphenylphosphine (3.43 g, 13.1 mmol) were dissolved in THF (50 ml). Under stirring at room temperature, diisopropyl azodicarboxylate (2.57 ml, 13.1 mmol) was added and the reaction mixture was stirred overnight at 60° C. After cooling to room temperature, the reaction mixture was concentrated under reduced pressure. The residue was purified by chromatography on a silica gel column, whereby from hexane-ethyl acetate (4:1) eluate fractions, methyl 4-((4S)-fluoro-(2S)-pyrrolidinylmethoxy)-3-methylbenzoate was obtained. This compound was not purified further. Methylene chloride (50 ml) and trifluoroacetic acid (25 ml) were added. The mixture was then stirred at room temperature for 20 minutes. To the residue obtained by distilling off the solvent under reduced pressure, a saturated aqueous saturated solution of sodium bicarbonate was added to make it alkaline, followed by extraction with chloroform. The extract was dried over anhydrous sodium sulfate and dried under reduced pressure to remove the solvent, whereby methyl 4-((4S)-fluoro-(2S)-pyrrolidinylmethoxy)-3-methylbenzoate (551 mg, 17%) was obtained as a colorless solid (this compound was provided for the subsequent reaction without further purification).

$^1$H-NMR (CDCl$_3$) δ: 1.53 (brs, 1H), 1.63–1.76 (m, 1H), 1.86–2.01 (m, 1H), 1.92 (s, 3H), 2.58–2.71 (m, 1H), 3.01–3.10 (m, 1H), 3.26 (brs, 1H), 3.55 (s, 3H), 3.72–3.82 (m, 2H), 4.84–5.00 (m, 1H), 6.49 (d, J=8.4 Hz, 1H), 7.51 (s, 1H), 7.53 (dd, J=8.8, 2.8 Hz, 1H).

MS (ESI) m/z 309 (M$^+$+CH$_3$CN).

(Step 3) Methyl 4-(N-tert-butoxycarbonyl-(4S)-fluoro-(2S)-pyrrolidinylmethoxy)-3-methylbenzoate

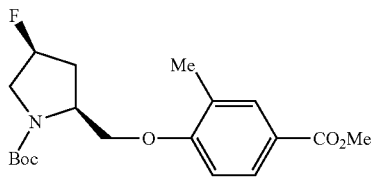

Methyl 4-((4S)-fluoro-(2S)-pyrrolidinylmethoxy)-3-methylbenzoate (2.04 g, 7.63 mmol) and di-tert-butyl dicarbonate (2.00 g, 9.16 mmol) were dissolved in acetonitrile (50 ml). At room temperature, 1.0M-NaOH (9.16 ml, 9.16 ml) was added and the mixture was stirred for 30 minutes. The reaction mixture was poured in 1.0N-HCl (20 ml), followed by extraction with ethyl acetate. The extract was dried over anhydrous sodium sulfate and distilled under reduced pressure to remove the solvent. The crude crystals thus obtained were recrystallized from ethyl acetate-hexane, whereby methyl 4-(N-tert-butoxycarbonyl-(4S)-fluoro-(2S)-pyrrolidinylmethoxy)-3-methylbenzoate (2.43 g, 86%) was obtained as a colorless crystalline powder.

MS (ESI) m/z, 368 ($M^+$+H).

(Step 4) Methyl 4-((4S)-fluoro-(2S)-pyrrolidinylmethoxy)-3-methylcyclohexanecarboxylate

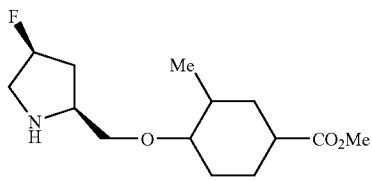

In ethanol-acetic acid (10:1, 16.5 ml), methyl 4-(N-tert-butoxycarbonyl-(4S)-fluoro-(2S)-pyrrolidinylmethoxy)-3-methylbenzoate (2.26 g, 6.17 mmol) and 5%-rhodium-alumina were subjected to catalytic hydrogenation at room temperature under stirring in a hydrogen gas stream of 5 atm. The catalyst was filtered off and from the filtrate, the solvent was distilled off under reduced pressure. The residue thus obtained was purified by chromatography on a silica gel column, whereby from hexane-ethyl acetate (4:1) eluate fractions, methyl 4-(N-tert-butoxycarbonyl-(4S)-fluoro-(2S)-pyrrolidinylmethoxy)-3-methylcyclohexanecarboxylate (2.22 g, 96%) was obtained as a colorless oil. The resulting methyl 4-(N-tert-butoxycarbonyl-(4S)-fluoro-(2S)-pyrrolidinylmethoxy)-3-methylcyclohexanecarboxylate (2.22 g, 5.94 mmol) was dissolved in methylene chloride (30 ml). Trifluoroacetic acid (10 ml) was added and the mixture was stirred at room temperature for 30 minutes. A saturated aqueous solution of sodium bicarbonate was added to the residue, which had been obtained by distilling off the solvent under reduced pressure, to neutralize it, followed by extraction with a chloroform-methanol (about 10:1). The extract was then dried over anhydrous sodium sulfate and the solvent was distilled off under reduced pressure, whereby methyl 4-((4S)-fluoro-(2S)-pyrrolidinylmethoxy)-3-methylcyclohexanecarboxylate (1.58 g, 98%), a mixture of diastereomers, was obtained as a colorless oil (this compound was provided for the subsequent reaction without further purification).

$^1$H-NMR (CDCl$_3$), mixture of diastereomers, δ: 0.97–1.00 (m, 3H), 1.23–1.33 (m, 1H), 1.54–1.69 (m, 5H), 1.80–1.94 (m, 1H), 2.05–2.22 (m, 3H), 2.28–2.35 (m, 1H), 2.78–2.91 (m, 1H), 3.24–3.37 (m, 4H), 3.59–3.69 (m, 1H), 3.65 and 3.66 (s, total 3H), 5.10–5.26 (m, 1H).

(Step 5) Synthesis of methyl 4-(1-(2-(2-methylphenylamino)-6-benzoxazolylacetyl)-(4S)-fluoro-(2S)-pyrrolidinylmethoxy)-3-methylcyclohexanecarboxylate

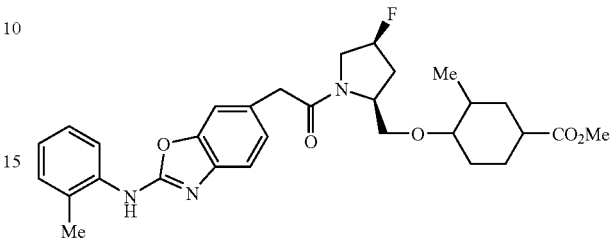

At room temperature, DMF (10 ml) and EDC•HCl (169 mg, 0.88 mmol) were added to methyl 4-((4S)-fluoro-(2S)-pyrrolidinylmethoxy)-3-methylcyclohexanecarboxylate (219 mg, 0.59 mmol), 2-(2-methylphenylamino)-6-benzoxazolylacetic acid (182 mg, 0.65 mmol), HOBt (8.0 mg, 0.06 mmol) and DMAP (7.2 mg, 0.06 mmol). The mixture was stirred overnight at room temperature. The reaction mixture was poured in water (30 ml), followed by extraction with ethyl acetate. The extract was washed with saturated brine (three times), dried over anhydrous sodium sulfate and distilled under reduced pressure to remove the solvent. The residue thus obtained was purified by chromatography on a silica gel column, whereby from hexane-ethyl acetate (1:5) eluate fractions, methyl 4-(1-(2-(2-methylphenylamino)-6-benzoxazolylacetyl)-(4S)-fluoro-(2S)-pyrrolidinylmethoxy)-3-methylcyclohexanecarboxylate (344 mg, quant.), a mixture of two diastereomers, was obtained as a colorless amorphous substance.

$^1$H-NMR (CDCl$_3$), mixture of diastereomers and rotamers, δ: 0.94–1.03 (m, 3H), 1.18–2.55 (series of m, 12H), 2.36 (s, 3H), 3.18–4.52 (series of m, 7H), 3.54–3.68 (m, 3H), 5.15–5.31 (m, 1H), 7.05–7.40 (series of m, 7H), 8.05 (d, J=8.4 Hz, 1H).

MS (ESI) m/z, 538 ($M^+$+H).

(Step 6) Synthesis of 4-(1-(2-(2-methylphenylamino)-6-benzoxazolylacetyl)-(4S)-fluoro-(2S)-pyrrolidinylmethoxy)-3-methylcyclohexanecarboxylic acid

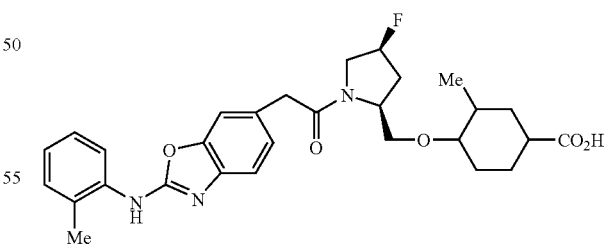

Methyl 4-(1-(2-(2-methylphenylamino)-6-benzoxazolylacetyl)-(4S)-fluoro-(2S)-pyrrolidinylmethoxy)-3-methylcyclohexanecarboxylate (329 mg, 0.61 mmol) was dissolved in methanol-THF (15:2, 17 ml). To the resulting solution was added 0.25M-NaOH (4.90 ml, 1.22 mmol) and the mixture was stirred overnight at room temperature. The reaction mixture was poured in 1N-HCl (10 ml), followed by extraction with a chloroform-methanol (10:1, v/v) mixture. The extract was washed with saturated brine, dried over anhydrous sodium sulfate and distilled under reduced pressure to remove the solvent. The residue was purified by chromatography on a silica gel column, whereby from hexane-ethyl acetate (1:4) eluate fractions, 4-(1-(2-(2-methylphenylamino)-6-benzoxazolylacetyl)-(4S)-fluoro-(2S)-pyrrolidinylmethoxy)-3-methylcyclohexanecarboxylic acid (259 mg, 81%), a mixture of diasteromers, was obtained as a colorless oil.

$^1$H-NMR (CDCl$_3$), mixture of diastereomers and rotamers, δ: 0.95–1.03 (m, 3H), 1.24–2.55 (series of m, 12H), 2.34, 2.35 and 2.36 (s, total 3H), 3.16–4.40 (series of m, 7H), 5.10–5.30 (m, 1H), 7.06–7.85 (series of m, 8H).

MS (ESI) m/z, 524 (M$^+$+H).

Example 24

4-(1-(2-(2-Chlorophenylamino)-6-benzoxazolylacetyl)-(4S)-fluoro-(2S)-pyrrolidinylmethoxy)cyclohexanecarboxylic acid, Isomer A and Isomer B (Step 1) Synthesis of methyl 4-(1-(2-(2-chlorophenylamino)-6-benzoxazolylacetyl)-(4S)-fluoro-(2S)-pyrrolidinylmethoxy)cyclohexanecarboxylate

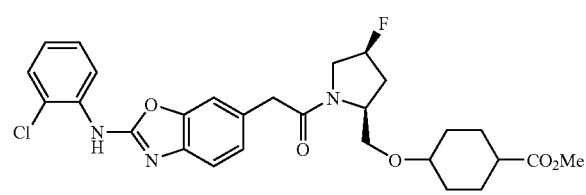

In DMF (10 ml), a mixture of 2-(2-chlorophenylamino)-6-benzoxazolylacetic acid (605 mg, 2.0 mmol), methyl 4-((4S)-fluoro-(2S)-pyrrolidinylmethoxy)cyclohexanecarboxylate (519 mg, 2.0 mmol, a mixture of cis and trans forms), EDC•HCl (575 mg, 3.0 mmol), HOBt (405 mg, 3.0 mmol) and triethylamine (1.39 ml, 10.0 mmol) was stirred at room temperature for 16 hours. The reaction mixture was poured in ice water (30 ml), followed by extraction with ethyl acetate. The extract was washed with saturated brine, dried over anhydrous sodium sulfate and distilled under reduced pressure to remove the solvent. The residue was purified by chromatography on a silica gel column (silica gel: 50 g), whereby from chloroform/acetone (10/1) eluate fractions, the title compound (770 mg, 71%), a mixture of diastereomers, was obtained as a brown oil (this compound was provided for the subsequent reaction without further purification).

(Step 2) Synthesis of 4-(1-(2-(2-chlorophenylamino)-6-benzoxazolylacetyl)-(4S)-fluoro-(2S)-pyrrolidinylmethoxy)cyclohexanecarboxylic acid, Isomer A and Isomer B

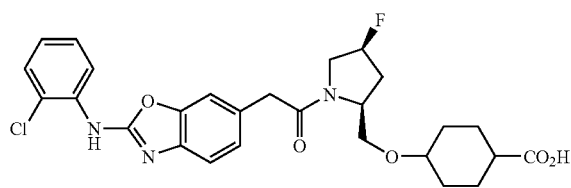

Methyl 4-(1-(2-(2-chlorophenylamino)-6-benzoxazolylacetyl)-(4S)-fluoro-(2S)-pyrrolidinylmethoxy)cyclohexanecarboxylate (770 mg, 1.42 mmol), a mixture of diasteromers, was dissolved in THF (20 ml). After addition of 0.25N NaOH (20 ml), the resulting mixture was stirred at room temperature for 18 hours. The reaction mixture was then concentrated under reduced pressure. The concentrate was acidified with 1N HCl, followed by extraction with a chloroform/methanol (10/1) mixture. The extract was washed with saturated brine, dried over anhydrous sodium sulfate and distilled under reduced pressure to remove the solvent. From the residue, two diasteromers were separated and purified by HPLC (C$_{18}$, 30×300 mm, 0.02M sodium acetate buffer/acetonitrile (1/1), 20 ml/min). Their fractions were distilled under reduced pressure to remove the solvent. After the residue was acidified with 1N HCl, extraction was performed with a chloroform/methanol (10/1) mixture. The extracts were washed with saturated brine, dried over anhydrous sodium sulfate and distilled under reduced pressure to remove the solvent, whereby Isomer A (161 mg, 21%) was obtained as a pale brown amorphous substance, while Isomer B (631 mg, 71%) was obtained as a pale brown amorphous substance.

Isomer A:

IR (KBr) 3406, 2937, 2862, 1724, 1703, 1637, 1587, 1572, 1533 cm$^{-1}$;

$^1$H-NMR (DMSO-d$_6$) δ: 0.82–1.41 (m, 4H), 1.83–2.20 (m, 6H), 3.16–4.32 (m, 9H), 5.22–5.43 (m, 1H), 706 (t, J=9.3 Hz, 1H), 7.18 (t, J=7.0 Hz, 1H), 7.32 (m, 2H), 7.41 (t, J=8.0 Hz, 1H), 8.67 (m, 1H).

MS (ESI) m/z, 530 (M$^+$+1), 532 (M$^+$+3).

Isomer B:

IR (KBr) 3404, 2939, 1868, 1720, 1701, 1637, 1597 cm$^{-1}$;

$^1$H-NMR (DMSO-d$_6$) δ: 1.44–1.72 (m, 7H), 2.12–2.36 (m, 3H), 3.14 (t, J=9.3 Hz, 1H), 3.37–4.42 (m, 8H), 5.24–5.44 (m, 1H), 7.06 (t, J=9.3 Hz, 1H), 7.18 (t, J=7.3 Hz, 1H), 7.29 and 7.31 (each s, total 1H, amide isomers), 7.32 and 7.33 (each s, total 1H, amide isomers), 7.41 (t, J=7.6 Hz, 1H), 7.52 (d, J=8.3 Hz, 1H), 8.08 (d, J=8.0 Hz, 1H).

MS (ESI), m/z 530 (M$^+$+1), 532 (M$^+$+3).

Example 25

4-(1-(2-(2-Bromophenylamino)-6-benzoxazolylacetyl)-(4S)-fluoro-(2S)-pyrrolidinylmethoxy)cyclohexanecarboxylic acid, Isomer A and Isomer B (Step 1) Synthesis of ethyl 2-(2-bromophenylamino)-6-benzoxazolylacetate

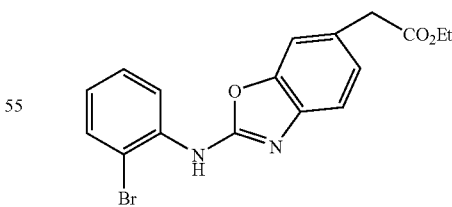

Methyl 3-hydroxy-4-aminophenylacetate (2.97 g, 16.4 mmol) was dissolved in methanol (30 ml). Under stirring at room temperature, 2-bromophenyl isothiocyanate (2.65 ml, 19.7 mmol) was added to the resulting solution. The reaction mixture was then stirred at room temperature for 1.5 hours. Mercuric oxide (yellow) (3.55 g, 16.4 mmol) was added to the reaction mixture, followed by heating and refluxing for 50 minutes. After cooling the reaction mixture to room temperature, the insoluble matter was filtered off through Celite under reduced pressure. The filtrate was distilled under reduced pressure to remove the solvent. The residue was then purified by chromatography on a silica gel column, whereby from hexane-ethyl acetate (4:1) eluate fractions, ethyl 2-(2-bromophenylamino)-6-benzoxazolylacetate (3.87 g, 66%) was obtained as a colorless solid.

$^1$H-NMR (CDCl$_3$) δ: 3.71 (s, 3H), 3.73 (d, J=16.8 Hz, 2H), 6.94–6.98 (m, 1H), 7.15 (d, J=8.0 Hz, 1H), 7.32 (s, 1H), 7.38–7.43 (m, 1H), 7.46 (d, J=8.4 Hz, 1H), 7.53 (brs, 1H), 7.55–7.58 (m, 1H), 8.52 (dd, J=8.4, 1.2 Hz, 1H).

MS (ESI) m/z 361 (M$^+$), 363 (M$^+$+2).

(Step 2) Synthesis of 2-(2-bromophenylamino)-6-benzoxazolylacetic acid

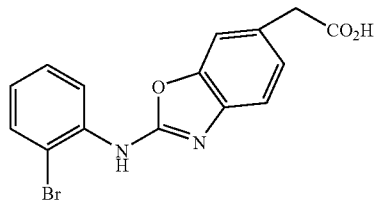

Ethyl 2-(2-bromophenylamino)-6-benzoxazolylacetate (3.82 g, 10.6 mmol) was dissolved in THF-methanol (1:1, 40 ml). To the resulting solution, 1.0M-NaOH (52.0 ml, 52.0 mmol) was added, followed by stirring at room temperature for 1.5 hours. To the residue, which had been obtained by distilling off the solvent under reduced pressure, was acidified with 1.0N-HCl. The crystals thus obtained were collected by filtration under reduced pressure, washed with water and dried overnight under reduced pressure at 60° C., whereby 2-(2-bromophenylamino)-6-benzoxazolylacetic acid (3.40 g, 93%) was obtained as a white crystalline powder.

$^1$H-NMR (DMSO-d$_6$) δ: 3.71 (s, 2H), 7.16 (d, J=8.0 Hz, 2H), 7.21 (t, J=8.0 Hz, 1H), 7.36 (d, J=8.0 Hz, 1H), 7.50 (s, 1H), 7.52 (t, J=7.6 Hz, 1H), 7.77 (d, J=8.0 Hz, 1H), 8.01 (d, J=7.6 Hz, 1H).

MS (ESI) m/z, 347 (M$^+$), 349 (M$^+$+2).

(Step 3) Synthesis of methyl 4-(1-(2-(2-bromophenylamino)-6-benzoxazolylacetyl)-(4S)-fluoro-(2S)-pyrrolidinylmethoxy)cyclohexanecarboxylate

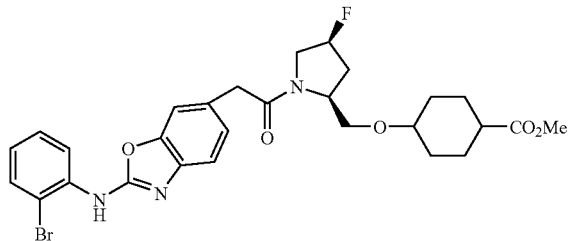

Methyl 4-((4S)-fluoro-(2S)-pyrrolidinylmethoxy)cyclohexanecarboxylate (267 mg, 1.03 mmol), 2-(2-bromophenylamino)-6-benzoxazolylacetic acid (357 mg, 1.03 mmol) and HOBt (14.0 mg, 0.10 mmol) were dissolved in DMF (10 ml). EDC•HCl (217 mg, 1.13 mmol) was added to the resulting solution and the mixture was stirred overnight at room temperature. The reaction mixture was poured in water (20 ml), followed by extraction with ethyl acetate. The extract was washed with saturated brine, dried over anhydrous sodium sulfate and distilled under reduced pressure to remove the solvent. The residue was purified by chromatography on a silica gel column, whereby from hexane-ethyl acetate (1:5) eluate fractions, methyl 4-(1-(2-(2-bromophenylamino)-6-benzoxazolylacetyl)-(4S)-fluoro-(2S)-pyrrolidinylmethoxy)cyclohexanecarboxylate (580 mg, 96%), a mixture of two diasteromers, was obtained as a colorless amorphous substance.

$^1$H-NMR (CDCl$_3$), mixture of diasteromers and rotamars, δ: 1.24–2.54 (series of m, 11H), 3.20–4.42 (series of m, 8H), 3.64–3.69 (m, 3H), 5.15–5.35 (m, 1H), 6.95 (t, J=7.8 Hz, 1H), 7.12 (t, J=8.1 Hz, 1H), 7.31–7.57 (m, 3H), 7.95 (d, J=9.0 Hz, 1H), 8.52 (d, J=8.3 Hz, 2H).

MS (ESI) m/z, 588 (M$^+$), 590 (M$^+$+2).

(Step 4) Synthesis of 4-(1-(2-(2-bromophenylamino)-6-benzoxazolylacetyl)-(4S)-fluoro-(2S)-pyrrolidinylmethoxy)cyclohexanecarboxylic acid, Isomer A and Isomer B

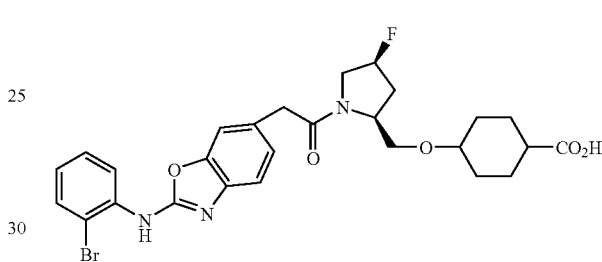

Methyl 4-(1-(2-(2-bromophenylamino)-6-benzoxazolylacetyl)-(4S)-fluoro-(2S)-pyrrolidinylmethoxy)cyclohexanecarboxylate (562 mg, 0.96 mmol), a mixture of two diasteromers, was dissolved in methanol-THF (15:2, 17 ml). To the resulting solution was added 0.25M-NaOH (7.64 ml, 1.191 mmol) and the mixture was stirred overnight at room temperature. The reaction mixture was poured in 1N-HCl (10 ml), followed by extraction with a chloroform-methanol mixture. The extract was washed with saturated brine, dried over anhydrous sodium sulfate and distilled under reduced pressure to remove the solvent. The residue was purified by chromatography on a silica gel column, whereby from ethyl acetate eluate fractions, 4-(1-(2-(2-bromophenylamino)-6-benzoxazolylacetyl)-(4S)-fluoro-(2S)-pyrrolidinylmethoxy)cyclohexanecarboxylic acid (345 mg, 63%), a mixture of two diasteromers, was obtained as a colorless amorphous substance. The mixture of two diastereomers was separable by HPLC (Shimpack PRC-ODS-30 mm×250 mm, acetonitrile:0.02N-sodium acetate buffer=1:1, 20 ml/min) so that Isomer A (polar fraction) and Isomer B (less polar fraction) were obtained, each as a colorless amorphous substance.

Isomer A;

$^1$H-NMR (CDCl$_3$), mixture of rotamars, δ: 1.23–1.35 (m, 2H), 1.43–1.53 (m, 2H), 2.01–2.48 (series of m, 6H), 3.28–3.53 (series of m, 2H), 3.63–3.92 (series of m, 6H), 4.01 (d, J=15.2 Hz, 1H), 4.22–4.42 (m, 1H), 5.17–5.33 (m, 1H), 6.98 (t, J=7.6 Hz, 1H), 7.12–7.14 (m, 1H), 7.27 (s, 1H), 7.34 (d, J=6.8 Hz, 1H), 7.40–7.47 (m, 2H), 7.58 (d, J=8.0 Hz, 1H), 8.47 (d, J=8.4 Hz, 1H).

MS (ESI) m/z 574 (M$^+$), 576 (M$^+$+2).

Isomer B;

$^1$H-NMR (CDCl$_3$), mixture of rotamars, δ: 1.26–1.55 (m, 2H), 1.67–1.75 (m, 2H), 1.81–1.93 (m, 4H), 2.00–2.53

(series of m, 3H), 3.34–4.09 (series of m, 7H), 4.22–4.43 (series of m, 1H), 5.17–5.32 (m, 1H), 6.95–6.99 (m, 1H), 7.13 (t, J=8.0 Hz, 1H), 7.26 (s, 1H), 7.34 (d, J=11.6 Hz, 1H), 7.39–7.46 (m, 2H), 7.58 (d, J=8.0 Hz, 1H), 8.47 (t, J=6.8 Hz, 1H).

MS (ESI) m/z, 574 (M$^+$), 576 (M$^+$+2).

Example 26

4-(1-(7-Fluoro-2-(2-methylphenylamino)-6-benzoxazolylacetyl)-(4S)-fluoro-(2S)-pyrrolidinylmethoxy)cyclohexanecarboxylic acid, Isomer A and Isomer B (Step 1) Synthesis of methyl 4-(1-(7-fluoro-2-(2-methylphenylamino)-6-benzoxazolylacetyl)-(4S)-fluoro-(2S)-pyrrolidinylmethoxy)cyclohexanecarboxylate

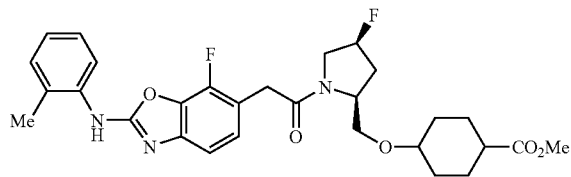

In DMF (5 ml), a mixture of 7-fluoro-2-(2-methylphenylamino)-6-benzoxazolylacetic acid (240 mg, 0.8 mmol), methyl 4-((4S)-fluoro-(2S)-pyrrolidinylmethoxy)cyclohexanecarboxylate (207 mg, 0.8 mmol, a mixture of cis and trans forms), EDC•HCl (230 mg, 1.2 mmol), HOBt (162 mg, 1.2 mmol) and triethylamine (0.56 ml, 4.0 mmol) was stirred at room temperature for 22 hours. The reaction mixture was poured in ice water (30 ml) and the mixture was extracted with ethyl acetate. The extract was washed with ice water and saturated brine, dried over anhydrous sodium sulfate and distilled under reduced pressure to remove the solvent. The residue was purified by chromatography on a silica gel column (silica gel: 40 g), whereby from chloroform/acetone (10/1) eluate fractions, the title compound (710 mg, 100%), a mixture of two diastereomers, was obtained as a colorless amorphous substance (this compound was provided for the subsequent reaction without further purification).

(Step 2) Synthesis of 4-(1-(7-fluoro-2-(2-methylphenylamino)-6-benzoxazolylacetyl)-(4S)-fluoro-(2S)-pyrrolidinylmethoxy)cyclohexanecarboxylic acid, Isomer A and Isomer B

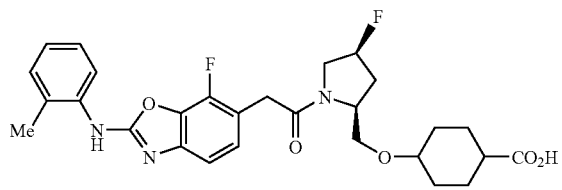

To a solution of methyl 4-(1-(7-fluoro-2-(2-methylphenylamino)-6-benzoxazolylacetyl)-(4S)-fluoro-(2S)-pyrrolidinylmethoxy)cyclohexanecarboxylate (710 mg, 0.80 mmol) in THF (40 ml) was added 0.25N NaOH (40 ml). The resulting mixture was stirred at room temperature for 16 hours. The reaction mixture was concentrated under reduced pressure. The residue was acidified with 1N HCl, followed by extraction with a chloroform/methanol (10/1) mixture. The extract was washed with saturated brine, dried over anhydrous sodium sulfate and distilled under reduced pressure to remove the solvent. From the residue, two diastereomers were separated and purified by HPLC ($C_{18}$, 30×300 mm, 0.02 M sodium acetate buffer/acetonitrile (1/1), 20 ml/min). Their fractions were distilled under reduced pressure to remove the solvent. The residue was acidified with 1N HCl, followed by extraction with a chloroform/methanol (10/1) mixture. The extracts were washed with saturated brine, dried over anhydrous sodium sulfate and distilled under reduced pressure to remove the solvent, whereby the title compound (Isomer A) (68 mg, 16% (2 steps)) was obtained as a colorless solid, while the title compound (Isomer B) (206 mg, 49% (2 steps), including 5% of Isomer A) was obtained as a colorless solid.

Isomer A:
IR (ATR) 2937, 2864, 2330, 1637, 1579 cm$^{-1}$;
$^1$H-NMR (DMSO-d$_6$) δ: 0.86 (t, J=5.4 Hz, 1H), 1.17–1.40 (m, 5H), 1.85–2.22 (m, 6H), 2.30 (s, 3H), 3.19 (t, J=8.3 Hz, 1H), 3.38–4.37 (m, 6H), 5.25–5.47 (m, 1H), 6.99–7.13 (m, 3H), 7.25 (d, J=6.8 Hz, 2H), 7.80 (d, J=8.6 Hz, 1H), 9.87 (br, 1H), 12.05 (br, 1H).

MS (ESI), m/z 528 (M$^+$+1).

Isomer B:
IR (ATR) 2939, 2870, 1722, 1699, 1639, 1579, 1454 cm$^{-1}$;
$^1$H-NMR (DMSO-d$_6$) δ: 0.86 (s, 1H), 1.18 (s, 1H), 1.24 (s, 1H), 1.40–1.82 (m, 6H), 1.91 and 1.99 (each s, total 1H, amide isomers), 2.10–2.29 (m, 2H), 2.37 (s, 3H), 3.17 (t, J=7.6 Hz, 1H), 3.44–4.50 (m, 6H), 5.33 and 5.41 (each d, J=54.8 and 53.6 Hz respectively, total 1H, amide isomers), 7.04 (m, 1H), 7.11 (s, 2H), 7.25 (s, 3H), 7.80 (d, J=7.3 Hz, 1H), 9.88 (br, 1H), 12.01 (br, 1H).

MS (ESI), m/z 528 (M$^+$+1).

Example 27

4-((2S,4S)-4-Fluoro-1-(2-(2-methylphenylamino)-6-benzoxazolylacetyl)-2-pyrrolidinylmethoxy)-n-butyric acid (Step 1) Synthesis of methyl 4-((2S,4S)-4-fluoro-1-(2-(2-methylphenylamino)-6-benzoxazolylacetyl)-2-pyrrolidinylmethoxy)-n-butyrate

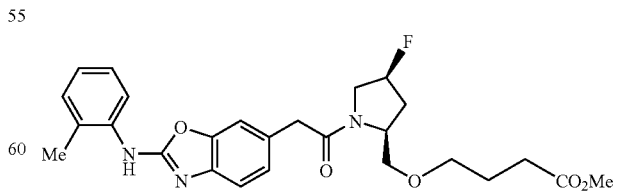

In DMF (4 ml), 2-(2-methylphenylamino)-6-benzoxazolyl-n-acetic acid (282 mg, 1.0 mmol), methyl 4-((4S)-fluoro-(2S)-pyrrolidinylmethoxy)-n-butyrate (219 mg, 1.0 mmol), EDC•HCl (288 mg, 1.5 mmol), HOBT (203 mg, 1.5 mmol) and triethylamine (5.0 ml, 0.70 mmol) were stirred at room temperature for 23 hours. The reaction mixture was poured in ice water, followed by extraction with ethyl acetate. The extract was washed with ice water and saturated brine. The organic layer was dried over anhydrous sodium sulfate and then, distilled under reduced pressure to remove the solvent. The residue was purified by chromatography on a silica gel column (silica gel: 50 g, chloroform/acetone (10/1)), followed by further separation and purification by thin-layer silica gel column chromatography (TLC) (chloroform/acetone (10/1)), whereby the title compound (378 mg, 78%) was obtained as a yellow oil.

$^1$H-NMR (CDCl$_3$) δ: 1.22 (t, J=6.9 Hz, 2H), 1.88–2.30 (m, 3H), 2.35 (s, 3H), 2.37–2.45 (m, 3H), 3.28–4.00 (m, 9H), 4.12–4.48 (m, 1H), 7.07 (m, 2H), 7.22 (d, J=7.3 Hz, 1H), 7.29–7.32 (m, 3H), 7.38 (dd, J=8.1, 4.9 Hz, 1H), 8.05 (d, J=8.1 Hz, 1H).

MS (ESI) m/z 484 (M$^+$+1).

(Step 2) Synthesis of 4-((2S,4S)-4-fluoro-1-(2-(2-methylphenylamino)-6-benzoxazolylacetyl)-2-pyrrolidinylmethoxy)-n-butyric acid

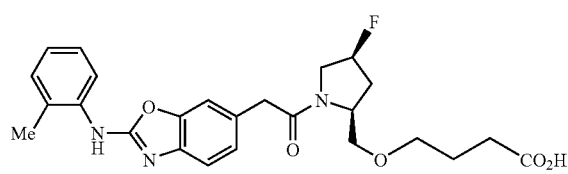

Methyl 4-((2S,4S)-4-fluoro-1-(2-(2-methylphenylamino)-6-benzoxazolylacetyl)-2-pyrrolidinylmethoxy)-n-butyrate (378 mg, 0.782 mmol) was dissolved in THF (20 ml). To the resulting solution was added 0.25N NaOH (20 ml) and the mixture was stirred at 50° C. for 18 hours. The reaction mixture was concentrated under reduced pressure. The residue was acidified with 1N HCl, followed by extraction with a chloroform/methanol (10/1) mixture. The extract was washed with saturated brine, dried over anhydrous sodium sulfate and distilled under reduced pressure to remove the solvent. The residue was then purified by thin-layer silica gel column chromatography (TLC), whereby from chloroform/methanol (10/1) eluate fractions, 4-((2S,4S)-4-fluoro-1-(2-(2-methylphenylamino)-6-benzoxazolylacetyl)-2-pyrrolidinylmethoxy)-n-butyric acid (99 mg, 27%) was obtained as a yellow oil. Ethanol (3 ml) and 1N NaOH (211 μl, 0.211 mmol) were added to the resulting 4-((2S,4S)-4-fluoro-1-(2-(2-methylphenylamino)-6-benzoxazolylacetyl)-2-pyrrolidinylmethoxy)-n-butyric acid (99 mg, 0.211 mmol) under stirring to dissolve the latter in the former. The resulting solution was concentrated to dryness. Ether was added to crystallize the residue, whereby sodium 4-((2S,4S)-4-fluoro-1-(2-(2-methylphenylamino)-6-benzoxazolylacetyl)-2-pyrrolidinylmethoxy)-n-butyrate (81 mg) was obtained as a solid.

Sodium salt IR (KBr) 3410, 3251, 2964, 2870, 1641, 1574, 1439 cm$^{-1}$;

$^1$H-NMR (DMSO-d$_6$) δ: 1.68–2.30 (m, 5H), 2.24 (s, 3H), 2.42 (m, 2H), 3.30–4.00 (m, 7H), 4.26 and 4.40 (q and m, J=6.8 Hz respectively, total 1H, amide isomers), 5.21 (dd, J=53.6, 3.9 Hz, 1H), 7.07 (d, J=6.6 Hz, 2H), 7.14–7.26 (m, 4H), 7.30 (d, J=7.6 Hz, 1H), 7.72 (m, 1H).

MS (ESI) m/z 470 (M$^+$+1);

Anal. Calcd for C$_{25}$H$_{27}$FN$_3$O$_5$·Na·3H$_2$O: C, 55.04; H, 6.10; N, 7.70. Found: C, 55.26; H, 5.95; N, 7.38.

Example 28

5-((2S,4S)-4-Fluoro-1-(2-(2-methylphenylamino)-6-benzoxazolylacetyl)-2-pyrrolidinyl)methoxypentanoic acid (Step 1) Synthesis of methyl 3-(1-tert-butoxycarbonyl-(4S)-fluoro-(2S)-pyrrolidinylmethoxy)propionate

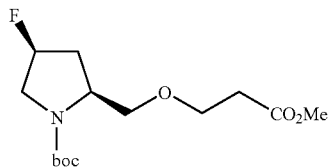

Sodium hydride (60% in oil, 365 mg, 9.12 mmol) was suspended in THF (20 ml). Under stirring at −50° C., a solution of (2S,4S)-1-(tert-butoxycarbonyl)-4-fluoro-2-prolinol (1.00 g, 4.56 mmol) in THF (15 ml) was added to the resulting suspension and the mixture was stirred at the same temperature for 5 minutes. To the reaction mixture was added methyl acrylate (0.95 ml, 10.5 mmol) at the same temperature. The reaction mixture was stirred for 15 minutes at the same temperature, followed by stirring for further 14 hours at −40° C. The reaction mixture was acidified with acetic acid (1 ml). After addition of water (20 ml), the mixture was extracted with ethyl acetate. The extract was washed with saturated brine, dried over anhydrous sodium sulfate and distilled under reduced pressure to remove the solvent. The residue was purified by chromatography on a silica gel column (silica gel: 50 g), whereby from hexane/ethyl acetate (2/1) eluate fractions, the title compound (670 mg, 48%) was obtained as a colorless oil.

$^1$H-NMR (CDCl$_3$) δ: 1.47 (s, 9H), 1.98–2.15 (m, 1H), 2.36 (dd, J=20.5, 5.6 Hz, 1H), 2.58 (t, J=6.6 Hz, 1H), 3.35 (t, J=9.0 Hz, 1H), 3.48–3.80 (m, 7H), 3.94–4.17 (m, 1H), 5.19 (d, J=53.1 Hz, 1H).

MS (ESI) m/z 306 (M$^+$+1).

(Step 2) Synthesis of methyl 3-((4S)-fluoro-(2S)-pyrrolidinylmethoxy)propionate

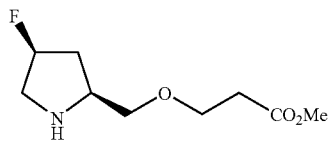

In methylene chloride (20 ml), trifluoroacetic acid (10 ml) was added to methyl 3-(1-tert-butoxycarbonyl-(4S)-fluoro-(2S)-pyrrolidinylmethoxy)propionate (670 mg, 2.19 mmol) and the mixture was stirred at room temperature for 7 hours. The reaction mixture was concentrated under reduced pressure. Under ice cooling, the residue was basified with 1N NaOH, followed by extraction with methylene chloride. The extract was washed with saturated brine, dried over anhydrous sodium sulfate and distilled under reduced pressure to remove the solvent, whereby the title compound (480 mg, 100%) was obtained as a yellow oil (this compound was provided for the subsequent reaction without further purification).

$^1$H-NMR (CDCl$_3$) δ: 1.79 (m, 1H), 2.02 (br, 1H), 2.04–2.21 (m, 1H), 2.60 (t, J=6.3 Hz, 2H), 2.90 (m, 1H), 3.31 (m, 1H), 3.49 (dd, J=9.5, 6.6 Hz, 1H), 3.56 (dd, J=9.5, 4.6 Hz, 1H), 3.69 (s, 3H), 3.75 (dt, J=6.6, 2.2 Hz, 2H), 5.18 (dt, J=54.8, 3.7 Hz, 1H).

(Step 3) Synthesis of 3-((2S,4S)-1-(tert-butoxycarbonyl)-4-fluoro-2-pyrrolidinylmethoxy)propionic acid

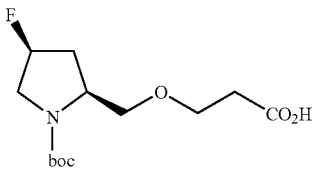

Methyl 3-((2S,4S)-1-(tert-butoxycarbonyl)-4-fluoro-2-pyrrolidinylmethoxy)propionate (2.84 g, 9.30 mmol) was dissolved in THF (40 ml). To the resulting solution was added 0.25N NaOH (40 ml) and the mixture was stirred at room temperature for 19 hours. The solvent was distilled off under reduced pressure. After the residue was acidified with 1N HCl, extraction was conducted with ethyl acetate. The extract was washed with ice water and brine, dried over anhydrous sodium sulfate and distilled under reduced pressure to remove the solvent, whereby the title compound (2.48 g, 92%) was obtained as a colorless oil (this compound was provided for the subsequent reaction without further purification).

(Step 4) Synthesis of 3-((2S,4S)-1-(tert-butoxycarbonyl)-4-fluoro-2-pyrrolidinylmethoxy)propanol

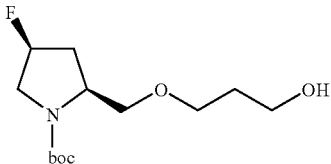

In THF (100 ml) was dissolved 3-((2S,4S)-1-(tert-butoxycarbonyl)-4-fluoro-2-pyrrolidinylmethoxy)propionic acid (2.48 g, 8.51 mmol). At room temperature, a 10.0M borane-dimethyl sulfide solution (2.79 ml, 27.9 mmol) was added and the mixture was stirred at room temperature for 3.5 hours and then, at 60° C. for 30 minutes. After cooling to room temperature, the reaction mixture was poured in ice water (100 ml), followed by extraction with ethyl acetate. The extract was washed with saturated brine, dried over anhydrous sodium sulfate and distilled under reduced pressure to remove the solvent. The residue was purified by chromatography on a silica gel column (silica gel: 50 g), whereby from chloroform/methanol (20/1) eluate fractions, the title compound (2.84 g, 100%) was obtained as a colorless oil.

$^1$H-NMR (CDCl$_3$) δ: 1.47 (s, 9H), 1.64–1.73 (m, 1H), 1.83 (br, 2H), 2.00–2.41 (m, 2H), 3.37 (t, J=9.1 Hz, 1H), 3.50–4.23 (m, 7H), 5.11 (d, J=53.1 Hz, 1H).

MS (ESI), m/z 278 (M$^+$+1).

(Step 5) Synthesis of 3-((2S,4S)-1-(tert-butoxycarbonyl)-4-fluoro-2-pyrrolidinylmethoxy)propionaldehyde

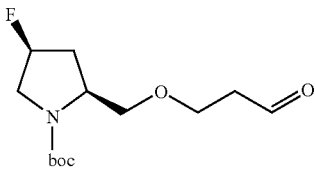

In methylene chloride (43 ml) were dissolved 3-((2S,4S)-1-(tert-butoxycarbonyl)-4-fluoro-2-pyrrolidinylmethoxy)propanol (2.84 g, 9.30 mmol), triethylamine (7.78 ml, 55.8 mmol) and DMSO (6.61 ml, 93.7 mmol). Under stirring at 0° C., a pyridine-sulfur trioxide complex (4.44 g, 27.9 mmol) was added dropwise to the resulting solution. After completion of the dropwise addition, the reaction mixture was stirred at room temperature for 2 hours. Water (50 ml) was added to the residue obtained by distilling off the solvent under reduced pressure, followed by extraction with ethyl acetate. The extract was washed with saturated brine, dried over anhydrous sodium sulfate and distilled under reduced pressure to remove the solvent. The residue was purified by chromatography on a silica gel column (silica gel: 50 g), whereby hexane/ethyl acetate (4/1) eluate fractions, the title compound (1.35 g, 53%) was obtained as a colorless oil.

$^1$H-NMR (CDCl$_3$) δ: 1.47 (s, 9H), 1.95–2.16 (m, 1H), 2.34 (t, J=17.1 Hz, 1H), 2.65 (br, 2H), 3.36 (t, J=9.8 Hz, 1H), 3.46–4.19 (m, 6H), 5.20 (d, J=53.7 Hz, 1H), 9.79 (s, 1H).

MS (ESI), m/z 278 (M$^+$+1).

(Step 6) Synthesis of methyl (E)-5-((2S,4S)-1-(tert-butoxycarbonyl)-4-fluoro-2-pyrrolidinylmethoxy)-2-pentenoate

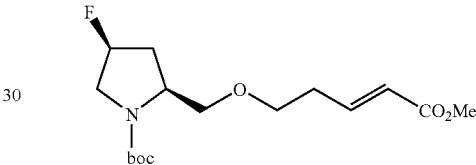

Trimethyl phosphonoacetate (0.95 ml, 5.88 mmol) was dissolved in THF (40 ml). Under a nitrogen gas stream, sodium hydride (60% in oil, 235 mg, 5.88 mmol) was added in portions to the resulting solution, while stirring at 0° C. After stirring the reaction mixture at the same temperature for 10 minutes, a solution of 3-((2S,4S)-1-(tert-butoxycarbonyl)-4-fluoro-2-pyrrolidinylmethoxy)propionaldehyde (1.35 g, 4.90 mmol) in THF (40 ml) was added dropwise at 0° C. The reaction mixture was further stirred for 2 hours at 0° C. and poured in ice water (50 ml), followed by extraction with ethyl acetate. The extract was washed with saturated brine, dried over anhydrous sodium sulfate and distilled under reduced pressure to remove the solvent. The residue was purified by chromatography on a silica gel column (silica gel: 50 g), whereby from chloroform/acetone (10/1) eluate fractions, the title compound (1.40 g, 86%) was obtained as a colorless oil.

$^1$H-NMR (CDCl$_3$) δ: 1.47 (s, 9H), 2.02–2.221 (m, 1H), 2.30–2.58 (m, 3H), 3.34 (t, J=10.0 Hz, 1H), 3.45–3.71 (m, 7H), 3.73 (s, 3H), 5.21 (d, J=55.3 Hz, 1H), 5.89 (d, J=15.9 Hz, 1H), 6.95 (dt, J=15.9, 7.1 Hz, 1H).

(Step 7) Synthesis methyl 5-((2S,4S)-1-(tert-butoxycarbonyl)-4-fluoro-2-pyrrolidinylmethoxy)pentanoate

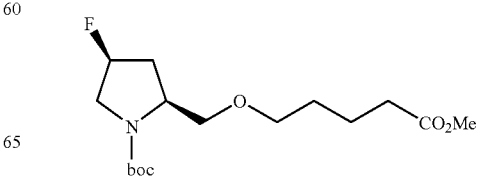

Methyl 5-((2S,4S)-1-(tert-butoxycarbonyl)-4-fluoro-2-pyrrolidinylmethoxy)-2-pentenoate (1.40 g, 4.22 mmol) and 5% palladium/carbon (wet.) (700 mg) were suspended in methanol (50 ml). Under stirring at room temperature, the resulting suspension was subjected to catalytic hydrogenation at normal pressure for 20 hours. The catalyst was filtered off and the filtrate was distilled under reduced pressure to remove the solvent. The residue was purified by chromatography on a silica gel column (silica gel: 20 g), whereby from hexane/ethyl acetate (4/1) eluate fractions, the title compound (1.09 g, 78%) was obtained as a colorless oil.

$^1$H-NMR (CDCl$_3$) δ: 1.47 (s, 9H), 1.61–1.74 (m, 3H), 1.98–2.18 (m, 2H), 2.31–2.42 (m, 3H), 3.31 (dt, J=7.9, 1.5 Hz, 1H), 3.40–3.66 (m, 4H), 3.67 (s, 3H), 3.73 (m, 1H), 4.09 (br, 1H), 5.20 (d, J=52.7 Hz, 1H).

(Step 8) Synthesis of methyl 5-((2S,4S)-4-fluoro-2-pyrrolidinylmethoxy)pentanoate

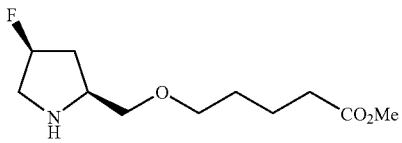

Methyl 5-((2S,4S)-1-(tert-butoxycarbonyl)-4-fluoro-2-pyrrolidinylmethoxy)pentanoate (1.09 g, 3.27 mmol) was dissolved in methylene chloride (50 ml). At room temperature, trifluoroacetic acid (10 ml) was added to the resulting solution. The mixture was stirred at the same temperature for 3.5 hours. The residue obtained by distilling off the solvent under reduced pressure was diluted with methylene chloride (50 ml). The solution was basified with 1N NaOH, followed by extraction with methylene chloride. The extract was washed with saturated brine, dried over anhydrous sodium sulfate and distilled under reduced pressure to remove the solvent, whereby the title compound (590 mg, 77%) was obtained as a yellow oil (this compound was provided for the subsequent reaction without further purification).

$^1$H-NMR (CDCl$_3$) δ: 1.59–1.96 (m, 5H), 2.15 (m, 1H), 2.34 (t, J=7.1 Hz, 2H), 2.86 (ddd, J=35.7, 13.2, 3.9 Hz, 1H), 3.27–3.35 (m, 2H), 3.42–3.53 (m, 4H), 3.67 (s, 3H), 5.18 (m, 1H).

MS (ESI), m/z 234 (M$^+$+1).

(Step 9) Synthesis of methyl 5-((2S,4S)-4-fluoro-1-(2-(2-methylphenylamino)-6-benzoxazolylacetyl)-2-pyrrolidinylmethoxy)pentanoate

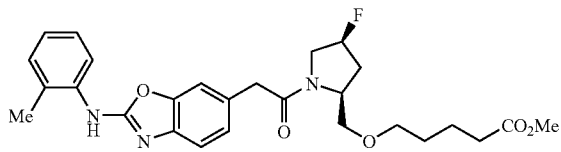

In DMF (5 ml), a mixture of 2-(2-methylphenylamino)-6-benzoxazolylacetic acid (357 mg, 1.26 mmol), methyl 5-((2S,4S)-4-fluoro-2-pyrrolidinylmethoxy)pentanoate (295 mg, 1.26 mmol), EDC•HCl (362 mg, 1.89 mmol), HOBt (255 mg, 1.89 mmol) and triethylamine (0.88 ml, 6.30 mmol) was stirred at room temperature for 1 hour. The reaction mixture was poured in ice water (50 ml), followed by extraction with ethyl acetate. The extract was washed with ice water and saturated brine, dried over anhydrous sodium sulfate and distilled under reduced pressure to remove the solvent. The residue was purified by chromatography on a silica gel column (silica gel: 70 g), whereby from chloroform/acetone (10/1) eluate fractions, the title compound (1.05 g, 100%) was obtained as a colorless oil.

$^1$H-NMR (CDCl$_3$) δ: 1.55–1.72 (m, 4H), 1.98–2.34 (m, 2H), 2.36 (s, 3H), 2.37–2.51 (m, 1H), 3.29–3.59 (m, 3H), 3.65 (s, 3H), 3.66–4.01 (m, 6H), 4.23–4.46 (m, 1H), 5.13–5.33 (m, 1H), 7.06 (t, J=7.1 Hz, 2H), 7.21 (d, J=7.3 Hz, 1H), 7.24–7.35 (m, 4H), 7.96 (m, 3H).

MS (ESI), m/z 497 (M$^+$+1).

(Step 10) Synthesis of 5-((2S,4S)-4-fluoro-1-((2-(2-methylphenylamino)-6-benzoxazolylacetyl)-2-pyrrolidinylmethoxy)pentanoic acid

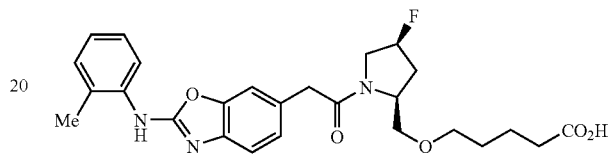

Methyl 5-((2S,4S)-4-fluoro-1-((2-(2-methylphenylamino)-6-benzoxazolylacetyl)-2-pyrrolidinylmethoxy)pentanoate (1.26 mmol) was dissolved in THF (40 ml). After addition of 0.25N NaOH (40 ml), the mixture was stirred at room temperature for 14 hours. The reaction mixture was distilled under reduced pressure to remove the solvent. The residue was acidified with 1N HCl. followed by extraction with a chloroform/methanol (10/1) mixture. The extract was washed with saturated brine, dried over anhydrous sodium sulfate and distilled under reduced pressure to remove the solvent, whereby 5-((2S,4S)-4-fluoro-1-((2-(2-methylphenylamino)-6-benzoxazolylacetyl)-2-pyrrolidinylmethoxy)pentanoic acid (390 mg, 60%) was obtained as a brown oil. Ethanol (10 ml) and 1N NaOH (0.750 ml, 0.750 mmol) were added to 5-((2S,4S)-4-fluoro-1-((2-(2-methylphenylamino)-6-benzoxazolylacetyl)-2-pyrrolidinylmethoxy)pentanoic acid (390 mg, 0.750 mmol). After stirring for 15 minutes, ether was added to the residue, which had been obtained by distilling off the solvent under reduced pressure, to solidify the same, whereby sodium 5-((2S,4S)-4-fluoro-1-((2-(2-methylphenylamino)-6-benzoxazolylacetyl)-2-pyrrolidinylmethoxy)pentanoate (283 mg) was obtained.

IR (KBr) 3425, 3251, 2939, 2868, 1643, 1574, 1439 cm$^{-1}$;
$^1$H-NMR (DMSO-d$_6$) δ: 1.01–1.30 (m, 3H), 1.45 (m, 4H), 1.86 (m, 2H), 2.03–2.23 (m, 2H), 2.28 (s, 3H), 3.15–4.43 (m, 6H), 5.23–5.41 (m, 1H), 6.99 (m, 2H), 7.19 (m, 5H), 7.85 (m, 1H).

MS (ESI), m/z 484 (M$^+$+1).

Example 29

Sodium 6-((2S,4S)-4-fluoro-1-(2-(2-methylphenylamino)-6-benzoxazolylacetyl)-2-pyrrolidinylmethoxy)hexanoate (Step 1) Synthesis of (Z)-4-benzyloxy-1-bromo-2-butene

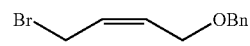

To a solution of (Z)-4-benzyloxy-2-buten-1-ol (2.0 g, 11.2 mmol) in methylene chloride (40 ml) were added carbon tetrabromide (4.46 g, 13.4 mmol) and triphenylphosphine (3.51 g, 13.4 mmol) at 0° C. under stirring in a nitrogen gas stream. After stirring at room temperature for 1.5 hours, the reaction mixture was concentrated under reduced pressure. The residue was purified by chromatography on a silica gel column (silica gel: 50 g), whereby from hexane/ethyl acetate (4/1) eluate fractions, the title compound (2.76 g, 100%) was obtained as a colorless oil.

$^1$H-NMR (CDCl$_3$) δ: 3.98 (d, J=8.3 Hz, 2H), 4.15 (d, J=6.1 Hz, 2H), 4.53 (s, 2H), 5.77 (m, 1H), 5.90 (m, 1H), 7.28–7.36 (m, 5H).

(Step 2) Synthesis of (Z)-(2S,4S)-2-(4-benzyloxy-2-butenyloxymethyl)-1-(tert-butoxycarbonyl)-4-fluoropyrrolidine

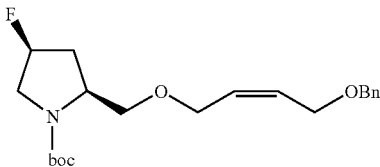

To a solution of (2S,4S)-1-(tert-butoxycarbonyl)-4-fluoro-2-pyrrolidinylmethanol (2.46 g, 11.2 mmol) in THF (100 ml), sodium hydride (60% in oil; 896 mg, 22.4 mmol) was added in portions under stirring at 0° C. in a nitrogen gas stream. After stirring at the same temperature for 20 minutes, a solution of (Z)-4-benzyloxy-1-bromo-2-butene (2.76 g, 11.2 mmol) in THF (100 ml) was added. The reaction mixture was stirred for 5 minutes. To the reaction mixture was added tetra-n-butyl ammonium iodide (100 mg, 0.27 mmol) at 0° C. and the mixture was stirred for 15 minutes. The reaction mixture was stirred further at room temperature for 19 hours. Water (50 ml) was added while stirring the reaction mixture under ice cooling, followed by extraction with ethyl acetate. The extract was washed with saturated brine, dried over anhydrous sodium sulfate and distilled under reduced pressure to remove the solvent. The residue was purified by chromatography on a silica gel column (silica gel: 120 g), whereby from hexane/ethyl acetate (4/1) eluate fractions, the title compound (3.30 g, 78%) was obtained as a colorless oil.

$^1$H-NMR (CDCl$_3$) δ: 1.47 (s, 9H), 1.98–2.25 (m, 1H), 2.39 (dd, J=20.6, 14.9 Hz, 1H), 3.31 (t, J=9.3 Hz, 1H), 3.48–3.81 (m, 3H), 3.95–4.18 (m, 5H), 4.51 (s, 2H), 5.20 (m, 1H), 5.70–5.84 (m, 2H), 7.27–7.53 (m, 5H).

MS (ESI) m/z 380 (M$^+$+1).

(Step 3) Synthesis of 4-((2S,4S)-1-(tert-butoxycarbonyl)-4-fluoro-2-pyrrolidinylmethoxy)-1-butanol

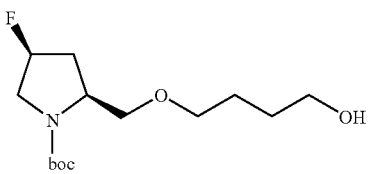

In ethanol (200 ml) were suspended (Z)-(2S,4S)-2-(4-benzyloxy-2-butenyloxymethyl)-1-(tert-butoxycarbonyl)-4-fluoropyrrolidine (4.58 g, 12.1 mmol) and 20% palladium hydroxide (4.0 g). The resulting suspension was subjected to catalytic hydrogenation at room temperature under normal pressure for 14 hours. The catalyst was then filtered off and the filtrate was distilled under reduced pressure to remove the solvent. The residue was purified by chromatography on a silica gel column (silica gel: 100 g), whereby from chloroform/acetone (10/1) eluate fractions, the title compound (2.42 g, 67%) was obtained as a colorless oil.

$^1$H-NMR (CDCl$_3$) δ: 1.47 (s, 9H), 1.6 (s, 2H), 1.98–2.23 (m, 2H), 2.38 (m, 1H), 3.36 (dt, J=10.5, 1.7 Hz, 1H), 3.52–3.82 (m, 8H), 4.01 and 4.13 (each br, total 1H, amide isomers), 5.21 (d, J=53.3 Hz, 1H).

(Step 4) Synthesis of 4-((2S,4S)-1-(tert-butoxycarbonyl)-4-fluoro-2-pyrrolidinylmethoxy)butylaldehyde

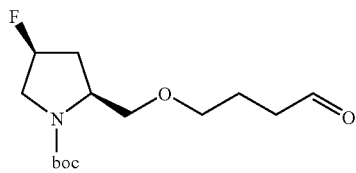

In methylene chloride (40 ml) were dissolved 4-((2S,4S)-1-(tert-butoxycarbonyl)-4-fluoro-2-pyrrolidinylmethoxy)-1-butanol (2.42 g, 8.31 mmol), triethylamine (6.95 ml, 49.9 mmol) and DMSO (5.90 ml, 83.1 mmol). Under stirring at 0° C., a pyridine-sulfur trioxide complex (3.97 g, 24.9 mmol) was added. The resulting mixture was stirred for 4 hours. The reaction mixture was distilled under reduced pressure to remove the solvent. To the residue was added water (50 ml), followed by extraction with ethyl acetate. The extract was washed with 1N HCl and saturated brine, dried over anhydrous sodium sulfate and distilled under reduced pressure to remove the solvent. The residue was purified by chromatography on a silica gel column (silica gel: 30 g), whereby from hexane/ethyl acetate (2/1) eluate fractions, the title compound (1.72 g, 72%) was obtained as a colorless oil.

$^1$H-NMR (CDCl$_3$) δ: 1.47 (s, 9H), 1.91 (t, J=6.6 Hz, 2H), 1.96–2.17 (m, 1H), 2.36 (t, J=15.4 Hz, 1H), 2.52 (t, J=7.1 Hz, 2H), 3.32 (t, J=9.8 Hz, 1H), 3.49–4.14 (m, 5H), 5.20 (d, J=53.5 Hz, 1H), 9.77 (s, 1H).

(Step 5) Synthesis of methyl (E)-6-((2S,4S)-1-(tert-butoxycarbonyl)-4-fluoro-2-pyrrolidinylmethoxy)-2-hexenoate

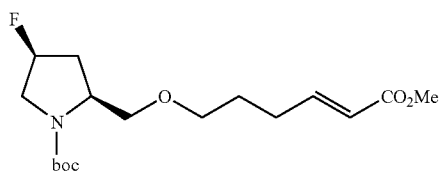

Trimethyl phosphonoacetate (1.15 ml, 7.13 mmol) was dissolved in THF (50 ml). Under a nitrogen gas stream, sodium hydride (60% in oil, 285 mg, 7.13 mmol) was added to the resulting solution in portions under stirring at 0° C. After stirring at the same temperature for 20 minutes, a solution of 4-((2S,4S)-1-(tert-butoxycarbonyl)-4-fluoro-2-pyrrolidinylmethoxy)butylaldehyde (1.72 g, 5.94 mmol) in THF (20 ml) was added dropwise. After completion of the dropwise addition, the reaction mixture was further stirred at the same temperature for 2.5 hours. The reaction mixture was poured in ice water (50 ml), followed by extraction with ethyl acetate. The extract was washed with saturated brine, dried over anhydrous sodium sulfate and distilled under reduced pressure to remove the solvent. The residue was purified by chromatography on a silica gel column (silica gel: 100 g), whereby from hexane/ethyl acetate (4/1) eluate fractions, the title compound (1.90 g, 93%) was obtained as a colorless oil.

¹H-NMR (CDCl₃) δ: 1.47 (s, 9H), 1.73 (br, 1H), 1.99–2.51 (m, 4H), 3.32 (dt, J=10.0, 1.7 Hz, 1H), 3.41–3.71 (m, 6H), 3.73 (s, 3H), 3.97–4.20 (m, 1H), 5.21 (d, J=53.1 Hz, 1H), 5.83 (d, J=15.4 Hz, 1H), 6.97 (dt, J=15.4, 6.8 Hz, 1H).

(Step 6) Methyl 6-((2S,4S)-1-(tert-butoxycarbonyl)-4-fluoro-2-pyrrolidinylmethoxy)hexenoate

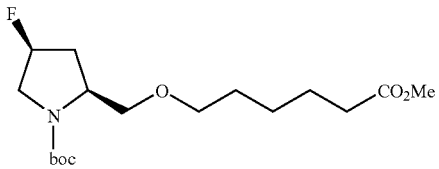

Methyl (E)-6-((2S,4S)-1-(tert-butoxycarbonyl)-4-fluoro-2-pyrrolidinylmethoxy)-2-hexenoate (1.90 g, 5.50 mmol) and 5% palladium/carbon (1.0 g) were suspended in methanol (80 ml). The resulting suspension was subjected to catalytic hydrogenation under normal pressure for 19 hours under stirring at room temperature. The catalyst was filtered off and the filtrate was distilled under reduced pressure to remove the solvent. The residue was purified by chromatography on a silica gel column (silica gel: 3 g), whereby from ethyl acetate eluate fractions, the title compound (1.92 g, 100%) was obtained as a colorless oil.

¹H-NMR (CDCl₃) δ: 1.38 (q, J=6.6 Hz, 2H), 1.48 (s, 9H), 1.57–1.70 (m, 4H), 1.98–2.18 (m, 1H), 2.31 (t, J=7.3 Hz, 3H), 2.39 (dd, J=20.7, 15.1 Hz, 1H), 3.31 (t, J=8.8 Hz, 1H), 3.41–3.60 (m, 3H), 3.67 (s, 3H), 3.68–4.18 (m, 2H), 5.20 (d, J=53.0 Hz, 1H).

(Step 7) Synthesis of methyl 6-((2S,4S)-4-fluoro-2-pyrrolidinylmethoxy)-2-hexanoate

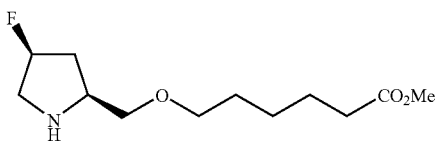

Methyl 6-((2S,4S)-1-(tert-butoxycarbonyl)-4-fluoro-2-pyrrolidinylmethoxy)hexanoate (1.92 g, 5.50 mmol) was dissolved in methylene chloride (100 ml). At room temperature, trifluoroacetic acid (10 ml) was added and the mixture was stirred for 1 hour. The reaction mixture was distilled under reduced pressure to remove the solvent. The residue was basified with 1N NaOH, followed by extraction with methylene chloride. The extract was washed with saturated brine, dried over anhydrous sodium sulfate and distilled under reduced pressure to remove the solvent, whereby the title compound (1.15 mg, 85%) was obtained as a pale yellow oil (this compound was provided for the subsequent reaction without further purification).

¹H-NMR (CDCl₃) δ: 1.38–1.70 (m, 6H), 2.21–2.30 (m, 1H), 2.34 (t, J=6.8 Hz, 2H), 2.46–2.61 (m, 1H), 3.50–3.74 (m, 9H), 4.15 (m, 1H), 5.30–5.45 (m, 1H).

MS (ESI), m/z 248 (M⁺+1).

(Step 8) Synthesis of methyl 6-((2S,4S)-4-fluoro-1-(2-(2-methylphenylamino)-6-benzoxazolyl)-2-pyrrolidinylmethoxy)hexanoate

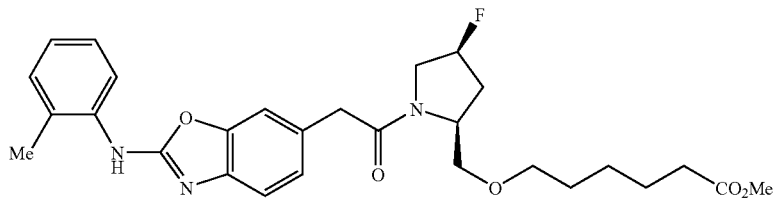

In DMF (10 ml), 2-(2-methylphenylamino)-6-benzoxazolylacetic acid (282 mg, 1.00 mmol), 6-((2S,4S)-4-fluoro-2-pyrrolidinylmethoxy)hexanoate (247 mg, 1.00 mmol), EDC·HCl (288 mg, 1.50 mmol), HOBT (203 mg, 1.50 mmol) and triethylamine (0.70 ml, 5.00 mmol) were stirred at room temperature for 22 hours. The reaction mixture was poured in ice water (50 ml), followed by extraction with ethyl acetate. The extract was washed with ice water and saturated brine, dried over anhydrous sodium sulfate and distilled under reduced pressure to remove the solvent. The residue thus obtained was purified by thin-layer silica gel chromatography, followed by separation by using chloroform/acetone (10/1), whereby the title compound (330 mg, 65%) was obtained as a yellow oil.

¹H-NMR (CDCl₃) δ: 1.35–1.47 (m, 2H), 1.53–1.74 (m, 4H), 1.90–2.32 (m, 4H), 2.35 (s, 3H), 3.29–3.50 (m, 3H), 3.57–4.48 (m, 9H), 5.12–5.29 (m, 1H), 7.07 (dt, J=8.3, 1.2 Hz, 2H), 7.21 (d, J=7.3 Hz, 1H), 7.29 (d, J=8.3 Hz, 2H), 7.36 (dd, J=7.8, 3.4 Hz, 2H), 8.01 (t, J=7.1 Hz, 1H).

MS (ESI), m/z 512 (M⁺+1).

(Step 9) Synthesis of sodium 6-((2S,4S)-4-fluoro-1-(2-(2-methylphenylamino)-6-benzoxazolylacetyl)-2-pyrrolidinylmethoxy)hexanoate

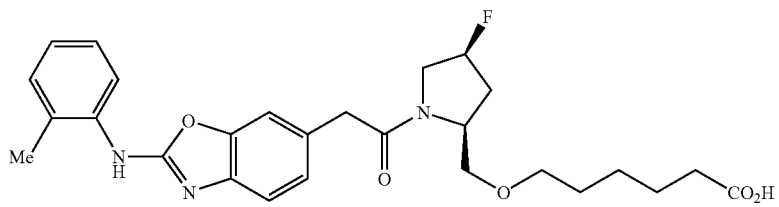

Methyl 6-((2S,4S)-4-fluoro-1-(2-(2-methylphenylamino)-6-benzoxazolylacetyl)-2-pyrrolidinylmethoxy)hexanoate (330 mg, 0.645 mmol) was dissolved in THF (30 ml). At room temperature, 0.25N NaOH (30 ml) was added and the mixture was stirred for 24 hours. The reaction mixture was distilled under reduced pressure to remove the solvent. The residue was acidified with 1N HCl, followed by extraction with a chloroform/methanol (10/1) mixture. The extract was washed with saturated brine, dried over anhydrous sodium sulfate and distilled under reduced pressure to remove the solvent. The residue was purified by thin-layer silica gel chromatography, followed by separation by using chloroform/methanol (20/1), whereby the title compound (238 mg, 74%) was obtained as a yellow oil. Ethanol (10 ml) and 1N NaOH (0.478 ml, 0.478 mmol) were added to the resulting carboxylic acid derivative (238 mg, 0.478 mmol). After stirring for 10 minutes, ether was added to crystallize the residue, which had been obtained by distilling off the solvent under reduced pressure, whereby sodium 6-((2S,4S)-4-fluoro-1-(2-(2-methylphenylamino)-6-benzoxazolylacetyl)-2-pyrrolidinylmethoxy)hexanoate (199 mg) was obtained.

IR (KBr) 3423, 3211, 2937, 2864, 1643, 1574, 1485, 1574 cm$^{-1}$;

$^1$H-NMR (DMSO-d$_6$) δ: 1.36–1.72 (m, 6H), 1.92–2.28 (m, 4H), 2.34 (s, 3H), 3.26–4.00 (m, 8H), 4.20–4.43 (m, 1H), 5.21 (dt, J=54.0, 4.6 Hz, 1H), 7.04–7.11 (m, 2H), 7.21–7.34 (m, 5H), 7.76 (t, J=7.3 Hz, 1H).

MS (ESI), m/z 498 (M$^+$+1);

Anal. Calcd for C$_{27}$H$_{32}$FN$_3$O$_5$·Na·1.0H$_2$O: C, 60.21; H, 6.36; F, 3.53; N, 7.80. Found: C, 60.11; H, 6.19; F, 3.28; N, 7.41.

Example 30

4-((4S)-Fluoro-1-(2-(2-methylphenylamino)-6-benzoxazolylacetyl)-(2S)-pyrrolidinylcarbonyl)-1-piperazinylacetic acid (Step 1) Synthesis of ethyl 4-((4S)-fluoro-1-(2-(2-methylphenylamino)-6-benzoxazolylacetyl)-(2S)-pyrrolidinylcarbonyl)-1-piperazinylacetate

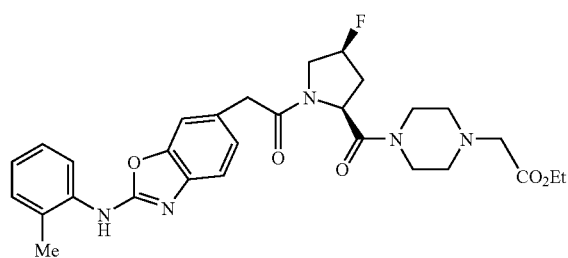

Ethyl 4-((4S)-fluoro-(2S)-pyrrolidinylcarbonyl)-1-pyrazinylacetate (300 mg, 1.04 mmol) was dissolved in DMF (10 ml). At room temperature, 2-(2-methylphenylamino)-6-benzoxazolylacetic acid (294 mg, 1.04 mmol), EDC•HCl (299 mg, 1.56 mmol), DMAP (cat.) and HOBt (cat.) were added successively to the resulting solution. The mixture was stirred for 15 hours. Saturated brine (100 ml) was added to the reaction mixture, followed by extraction with ethyl acetate. The extract was washed with saturated brine, dried over anhydrous magnesium sulfate and distilled under reduced pressure to remove the solvent. The residue thus obtained was purified by chromatography on a silica gel column, whereby from chloroform-methanol (20:1) eluate fractions, the title compound (107 mg, 19%) was obtained as a yellow oil.

(Step 2) Synthesis of 4-((4S)-fluoro-1-(2-(2-methylphenylamino)-6-benzoxazolylacetyl)-(2S)-pyrrolidinylcarbonyl)-1-piperazinylacetic acid.

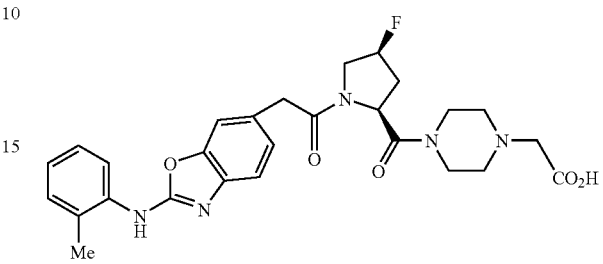

Ethyl 4-((4S)-fluoro-1-(2-(2-methylphenylamino)-6-benzoxazolylacetyl)-(2S)-pyrrolidinylcarbonyl)-1-piperazinylacetate (107 mg, 0.194 mmol) was dissolved in THF (4 ml). After addition of 0.25N NaOH (1.6 ml, 0.388 mmol), the mixture was stirred at room temperature for 15 hours. The reaction mixture was neutralized with 1N HCl and then concentrated under reduced pressure. The residue was purified using an ion exchange resin (HP20) and eluted with water and methanol, whereby the title compound (61 mg, 60%) was obtained as a yellow amorphous substance.

$^1$H-NMR (DMSO-d$_6$) δ: 1.75–2.61 (series of m, 9H, s, including 3H at δ 2.30), 2.80–4.00 (series of m, 10H), 4.82–6.02 (series of m, 2H), 6.98–7.46 (series of m, 6H), 7.82–7.94 (m, 1H).

MS (FAB) m/z, 524 (M$^+$+1).

Example 31

1-((4S)-Fluoro-1-(2-(2-methylphenylamino)-6-benzoxazolylacetyl)-(2S)-pyrrolidinylcarbonyl)-4-piperidinylacetic acid (Step 1) Synthesis of ethyl 4-piperidinylacetate

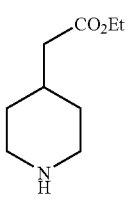

Ethyl 4-(1-(tert-butoxycarbonyl))piperidinylacetate (2.93 g, 10.8 mmol) was dissolved in methylene chloride (20 ml). After addition of trifluoroacetic acid (8 ml) at 0° C., the mixture was stirred at room temperature for 3 hours. The residue, which had been obtained by distilling the reaction mixture under reduced pressure to remove the solvent, was neutralized with a saturated aqueous solution of sodium bicarbonate, followed by extraction with a chloroform-methanol (5:1, v/v) mixture. The extract was washed with saturated brine, dried over anhydrous magnesium sulfate and distilled under reduced pressure to remove the solvent, whereby ethyl 4-piperidnylacetate (1.48 g, 80%) was obtained as a yellow solid.

¹H-NMR (CDCl₃) δ: 1.25 (t, J=7.2 Hz, 3H), 1.30 (m, 2H), 1.76 (d, J=13.2 Hz, 2H), 1.90 (m, 1H), 2.24 (d, J=7.2 Hz, 2H), 2.63 (dt, J=1.6, 13.1 Hz, 1H), 2.85 (br, 1H), 3.16 (d, J=12.4 Hz, 2H), 4.13 (q, J=7.5 Hz, 2H).

(Step 2) Synthesis of ethyl 1-(1-(tert-butoxycarbonyl)-(4S)-fluoro-(2S)-pyrrolidinylcarbonyl)-4-piperidinylacetate

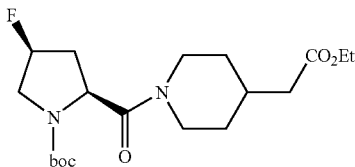

Ethyl 4-piperidinylacetate (1.48 g, 8.64 mmol) and 1-(tert-butoxycarbonyl)-(4S)-fluoro-(2S)-pyrrolidinecarboxylic acid (2.02 mg, 8.66 mmol) were dissolved in DMF (30 ml). EDC•HCl (2.49 g, 2.61 mmol), HOBt and DMAP were added to the resulting solution and the mixture was stirred overnight at room temperature. Water (50 ml) was added to the reaction mixture, followed by extraction with ethyl acetate. The extract was washed with saturated brine, dried over anhydrous magnesium sulfate and distilled under reduced pressure to remove the solvent. The residue was purified by chromatography on a silica gel column, whereby from chloroform-methanol (15:1, v/v) eluate fractions, ethyl 1-(1-(tert-butoxycarbonyl)-(4S)-fluoro-(2S)-pyrrolidinylcarbonyl)-4-piperidinylacetate (1.05 g, 32%) was obtained as a brown oil.

¹H-NMR (CDCl₃) δ: 1.17 (dt, J=4.0, 12.0 Hz, 1H), 1.26 (t, J=7.2 Hz, 3H), 1.47 (s, 9H), 1.70 (s, 2H), 1.75 (m, 2H), 2.03 (m, 1H), 2.20 (br, 1H), 2.24 (dd, J=4.4, 7.2 Hz, 2H), 2.43 (m, 1H), 2.57 (m, 1H), 3.02 (m, 1H), 3.77 (m, 2H), 4.14 (q, J=7.2 Hz, 2H), 4.60 (d, J=9.6 Hz, 1H), 5.20 (d, J=53.9 Hz, 1H).

(Step 3) Synthesis of ethyl 1-((4S)-fluoro-(2S)-pyrrolidinylcarbonyl)-4-piperidinylacetate

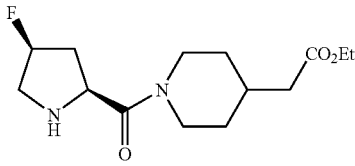

Ethyl 1-(1-(tert-butoxycarbonyl)-(4S)-fluoro-(2S)-pyrrolidinylcarbonyl)-4-piperidinylacetate (1.05 g, 2.74 mmol) was dissolved in methylene chloride (10 ml). After addition of trifluoroacetic acid (4 ml) to the resulting solution at 0° C., the reaction mixture was stirred at 50° C. for 3 hours. The reaction mixture was distilled under reduced pressure to remove the solvent. The residue was neutralized with a saturated aqueous solution of sodium bicarbonate, followed by extraction with a chloroform-methanol (5:1, v/v) mixture. The extract was washed with saturated brine, dried over anhydrous sodium sulfate and distilled under reduced pressure to remove the solvent, whereby ethyl 1-((4S)-fluoro-(2S)-pyrrolidinylcarbonyl)-4-piperidinylacetate (768 mg, 100%) was obtained as a yellow oil.

¹H-NMR (CDCl₃) δ: 1.17 (dt, J=4.0, 12.0 Hz, 1H), 1.26 (t, J=7.2 Hz, 3H), 1.79 (m, 2H), 2.02 (m, 3H), 2.24 (m, 2H), 2.38 (m, 1H), 2.66 (series of m, total 1H), 2.78 (ddd, J=2.8, 13.6, 37.5 Hz, 1H), 3.03 (ddd, J=2.4, 13.6, 18.8 Hz, 1H), 3.77 (m, 1H), 3.90 (m, 1H), 4.14 (q, J=7.2 Hz, 2H), 4.61 (br, 1H), 5.17 (d, J=53.9 Hz, 1H).

(Step 4) Synthesis of ethyl 1-((4S)-fluoro-1-(2-(2-methylphenylamino)-6-benzoxazolylacetyl)-(2S)-pyrrolidinylcarbonyl)-4-piperidinylacetate

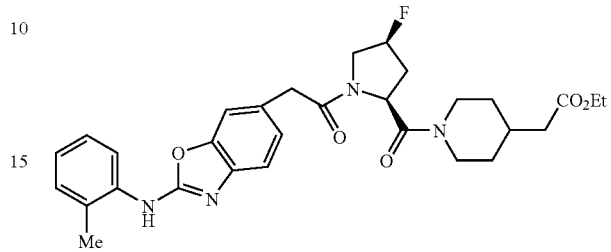

In DMF (9 ml) were dissolved 2-(2-methylphenylamino)-6-benzoxazolylacetic acid (350 mg, 1.24 mmol) and ethyl 1-((4S)-fluoro-(2S)-pyrrolidinylcarbonyl)-4-piperidinylacetate (357 mg, 1.24 mmol). EDC•HCl (356 mg, 1.86 mmol), HOBt and DMAP were added to the resulting solution. The mixture was stirred overnight at room temperature. Water (30 ml) was added to the reaction mixture, followed by extraction with ethyl acetate. The extract was washed with saturated brine, dried over anhydrous magnesium sulfate and distilled under reduced pressure to remove the solvent. The residue was purified by chromatography on a silica gel column, whereby from chloroform/methanol (10:1, v/v) eluate fractions, ethyl 1-((4S)-fluoro-1-(2-(2-methylphenylamino)-6-benzoxazolylacetyl)-(2S)-pyrrolidinylcarbonyl)-4-piperidinylacetate (525 mg, 77%) was obtained as a brown oil.

IR (ATR) 1726, 1637, 1573, 1440 cm⁻¹;
¹H-NMR (CDCl₃) δ: 1.15 (dt, J=4.0, 12.0 Hz, 1H), 1.26 (m, 3H), 1.78 (m, 2H), 2.03 (m, 1H), 2.29 (m, 3H), 2.35 (s, 3H), 2.44 (br, 1H), 2.56 (m, 1H), 3.02 (m, 1H), 3.79 (series of m, total 3H), 3.95 (m, 1H), 4.14 (m, 2H), 4.60 (m, 1), 5.01 (m, 1H), 5.25 (series of d, J=53.5 Hz, total 1H), 6.88 (br, 1H), 7.06 (d, J=8.0 Hz, 1H), 7.11 (d, J=8.0 Hz, 1H), 7.22 (d, J=8.0 Hz, 1H), 7.30 (t, J=8.0 Hz, 2H), 7.39 (m, 2H), 8.08 (d, J=8.0 Hz, 1H).
MS (ESI) m/z 551 (M+H)⁺.

(Step 5) Synthesis of 1-((4S)-fluoro-1-(2-(2-methylphenylamino)-6-benzoxazolylacetyl)-(2S)-pyrrolidinylcarbonyl)-4-piperidinylacetic acid

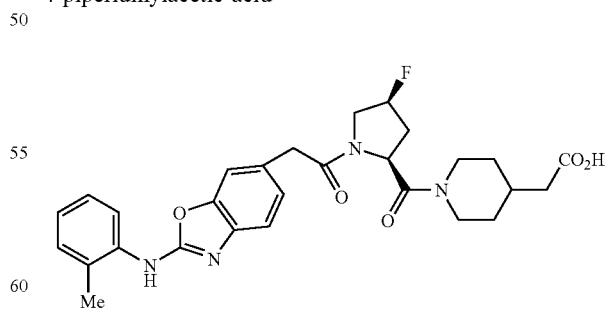

Ethyl 1-((4S)-fluoro-1-(2-(2-methylphenylamino)-6-benzoxazolylacetyl)-(2S)-pyrrolidinylcarbonyl)-4-piperidinylacetate (550 mg, 0.95 mmol) was dissolved in THF (6 ml). To the resulting solution was added 0.25N NaOH (2 eq) and the mixture was stirred overnight at room temperature.

Water (30 ml) was added to the reaction mixture, followed by extraction with a chloroform-methanol (5:1, v/v) mixture. The extract was washed with 1N HCl, dried over anhydrous magnesium sulfate and distilled under reduced pressure to remove the solvent. The residue was purified by chromatography on a silica gel column, whereby from chloroform-methanol (20:1, v/v) eluate fractions, 1-((4S)-fluoro-1-(2-(2-methylphenylamino)-6-benzoxazolylacetyl)-(2S)-pyrrolidinylcarbonyl)-4-piperidinylacetic acid (258 mg, 52%) was obtained as a white crystalline powder.

IR (ATR) 1712, 1639, 1573 cm$^{-1}$;

$^1$H-NMR (CDCl$_3$) δ: 1.26 (m, 2H), 1.80 (m, 2H), 2.04 (m, 1H), 2.29 (m, 3H), 2.35 (s, 3H), 2.44 (br, 1H), 2.61 (m, 1H), 3.06 (m, 1H), 3.77 (m, total 3H), 3.92 (m, 1H), 4.59 (br, 1H), 5.02 (t, J=8.0 Hz, 1H), 5.24 (m, 1H), 7.10 (m, 2H), 7.22 (d, J=7.6 Hz, 2H), 7.29 (m, 2H), 7.33 (m, 2H), 7.88 (d, J=8.8 Hz, 1H).

MS (ESI) m/z 523 (M+H)$^+$.

Example 32 cis-4-((4S)-Fluoro-1-(2-(2-methylphenylamino)-6-benzoxazolylacetyl)-(2S)-pyrrolidinylcarbonylamino)cyclohexanecarboxylic acid (Step 1) Synthesis of methyl cis-4-(1-(tert-butoxycarbonyl)-(4S)-fluoro-(2)-pyrrolidinylcarbonylamino)cyclohexanecarboxylate

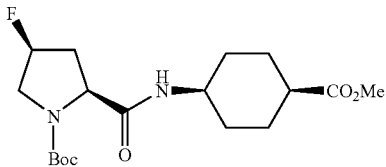

In acetonitrile-water (1:1, v/v, 60 ml) was dissolved cis-4-aminocyclohexanecarboxylic acid (1.32 g, 9.22 mmol). To the resulting solution were added di-tert-butyl dicarbonate (2.05 g, 9.39 mmol) and triethylamine (2.39 ml, 9.07 mmol) and the mixture was stirred at room temperature for 4 hours. The reaction mixture was concentrated under reduced pressure. The residue was acidified with 1N HCl, followed by extraction with a chloroform-methanol (5:1, v/v) mixture. The extract was dried over anhydrous magnesium sulfate and distilled under reduced pressure to remove the solvent, whereby cis-4-((tert-butoxycarbonyl)amino)cyclohexanecarboxylic acid (2.30 g, 97%) was obtained as a white crystalline powder. In methanol-benzene (5:1, v/v, 100 ml) was dissolved cis-4-((tert-butoxycarbonyl)amino)cyclohexanecarboxylic acid (2.30 g, 8.94 mmol). Trimethylsilyldiazomethane (a 2M hexane solution, 9 ml) was added dropwise to the resulting solution under stirring at room temperature. After completion of the dropwise addition, the reaction mixture was stirred at room temperature for 1 hour. The residue, which had been obtained by distilling the reaction mixture under reduced pressure to remove the solvent, was purified by chromatography on a silica gel column, whereby from hexane-ethyl acetate (3:1, v/v). eluate fractions, methyl cis-4-((tert-butoxycarbonyl)amino)cyclohexanecarboxylate (2.30 g, 100%) was obtained as a colorless oil. The resulting methyl cis-4-((tert-butoxycarbonyl)amino)cyclohexanecarboxylate (2.30 g, 8.93 mmol) was dissolved in methylene chloride (18 ml). After addition of trifluoroacetic acid (7 ml) to the resulting solution at 0° C., the reaction mixture was stirred at room temperature for 1.5 hours. The residue, which had been obtained by distilling the reaction mixture under reduced pressure to remove the solvent, was neutralized with a saturated aqueous solution of sodium bicarbonate, followed by extraction with a chloroform-methanol (5:1, v/v) mixture. The extract was washed with saturated brine, dried over anhydrous magnesium sulfate and distilled under reduced pressure to remove the solvent, whereby methyl cis-4-aminocyclohexanecarboxylate (1.39 g, 99%) was obtained as a colorless oil. In DMF (40 ml) were dissolved the resulting methyl cis-4-aminocyclohexanecarboxylate (1.39 g, 8.87 mmol) and 1-(tert-butoxycarbonyl)-(4S)-fluoro-(2S)-pyrrolidinecarboxylic acid (2.07 g, 8.87 mmol). EDC•HCl (2.56 g, 13.3 mmol), HOBt (5.0 mg, 0.04 mmol) and DMAP (5.0 mg, 0.04 mmol) were added to the resulting solution and the mixture was stirred overnight at room temperature. Saturated brine was poured in the reaction mixture, followed by extraction with ethyl acetate. The extract was dried over anhydrous magnesium sulfate and distilled under reduced pressure to remove the solvent. The residue was purified by chromatography on a silica gel column, whereby from chloroform-methanol (20:1, v/v) eluate fractions, methyl cis-4-(1-(tert-butoxycarbonyl)-(4S)-fluoro-(2S)-pyrrolidinylcarbonylamino)cyclohexanecarboxylate (2.96 g, 90%) was obtained as a pale yellow solid.

$^1$H-NMR (CDCl$_3$) δ: 1.47 (s, 9H), 1.56 (br, 2H), 1.72 (br, 4H), 1.88 (br, 2H), 2.27 (br, 1H), 2.49 (br, 2H), 2.56 (m, 1H), 3.68 (s, 3H), 3.78 (br, 1H), 3.95 (br, 1H), 5.13 (d, J=51.6 Hz, 1H), 7.72 (br, 1H).

(Step 2) Synthesis of methyl cis-4-((4S)-fluoro-(2S)-pyrrolidinylcarbonylamino)cyclohexanecarboxylate

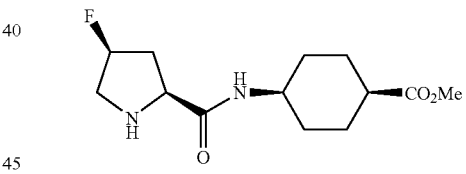

Methyl cis-4-(1-(tert-butoxycarbonyl)-(4S)-fluoro-(2S)-pyrrolidinylcarbonylamino)cyclohexanecarboxylate (440 mg, 1.18 mmol) was dissolved in methylene chloride (7 ml). Trifluoroacetic acid (3 ml) was added to the resulting solution at 0° C. The reaction mixture was then stirred at room temperature for 2 hours. From the reaction mixture, the solvent was distilled off under reduced pressure. The residue was neutralized with a saturated aqueous solution of sodium bicarbonate, followed by extraction with a chloroform-methanol (5:1, v/v) mixture. The extract was washed with saturated brine, dried over anhydrous magnesium sulfate and distilled under reduced pressure to remove the solvent, whereby methyl cis-4-((4S)-fluoro-(2S)-pyrrolidinylcarbonylamino)cyclohexanecarboxylate (270 mg, 84%) was obtained as a colorless oil.

$^1$H-NMR (CDCl$_3$) δ: 1.58 (m, 2H), 1.71 (m, 4H), 1.86 (m, 2H), 2.28 (m, 2H), 2.47 (m, 2H), 2.63 (series of dd, J=3.6, 35.5 Hz, total 1H), 3.31 (series of d, J=35.5 Hz, total 1H), 3.69 (s, 3H), 3.81 (dd, J=2.8, 10.4 Hz, 1H), 3.90 (br, 1H), 5.16 (d, J=53.1 Hz, 1H), 7.72 (br, 1H).

(Step 3) Synthesis of methyl cis-4-((4S)-fluoro-1-(2-(2-methylphenylamino)-6-benzoxazolylacetyl)-(2S)-pyrrolidinylcarbonylamino)cyclohexanecarboxylate

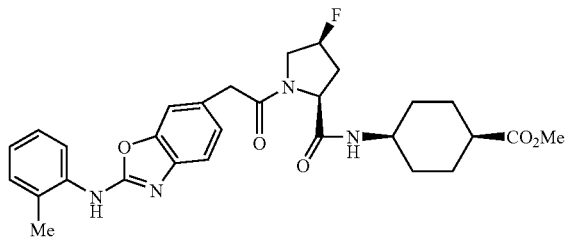

In DMF (5 ml) were dissolved 2-(2-methylphenylamino)-6-benzoxazolylacetic acid (147 mg, 0.52 mmol) and methyl cis-4-((4S)-fluoro-(2S)-pyrrolidinylcarbonylamino)cyclohexanecarboxylate (142 mg, 0.52 mmol). EDC•HCl (151 mg, 0.78 mmol), HOBt (5.0 mg, 0.04 mmol) and DMAP (5.0 mg, 0.04 mmol) were added to the resulting solution. The mixture was stirred overnight at room temperature. After dilution with ethyl acetate (50 ml), the mixture was washed with saturated brine, dried over anhydrous magnesium sulfate and distilled under reduced pressure to remove the solvent. The residue was purified by chromatography on a silica gel column, whereby from chloroform-methanol (10:1, v/v) eluate fractions, methyl cis-4-((4S)-fluoro-1-(2-(2-methylphenylamino)-6-benzoxazolylacetyl)-(2S)-pyrrolidinylcarbonylamino)cyclohexanecarboxylate (299 mg, 100%) was obtained as a brown oil.

IR (ATR) 1726, 1637, 1531, 1437 cm$^{-1}$;

$^1$H-NMR (CDCl$_3$) δ: 1.46 (m, 2H), 1.63 (m, 3H), 1.78 (m, 3H), 1.78 (m, 1H), 1.90 (m, 2H), 2.39 (s, 3H), 2.49 (m, 1H), 2.9 (series of m, total 2H), 3.70 (s, 3H), 3.76 (m, 1H), 3.82 (m, 1H), 5.21 (m, 1H), 7.08 (m, 2H), 7.22 (m, 1H), 7.28 (m, 1H), 7.44 (d, J=7.6 Hz, 1H), 8.01 (s, 2H), 8.15 (d, J=7.6 Hz, 1H).

MS (ESI) m/z 537 (M+H)$^+$;

Anal. Calcd for C$_{29}$H$_{33}$FN$_4$O$_5$.1.5H$_2$O: C, 61.80; H, 6.44; N, 9.94. Found: C, 62.21; H, 6.30; N, 9.02.

(Step 4) Synthesis of cis-4-((4S)-fluoro-1-(2-(2-methylphenylamino)-6-benzoxazolylacetyl)-(2S)-pyrrolidinylcarbonylamino)cyclohexanecarboxylic acid

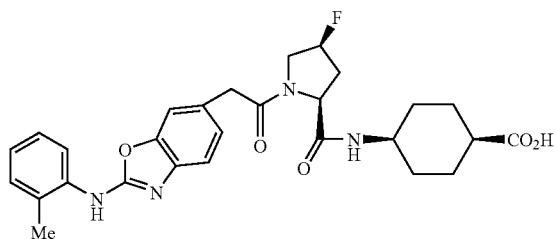

Methyl cis-4-((4S)-fluoro-1-(2-(2-methylphenylamino)-6-benzoxazolylacetyl)-(2S)-pyrrolidinylcarbonylamino)cyclohexanecarboxylate (299 mg, 0.55 mmol) was dissolved in THF (5 ml). To the resulting solution was added 0.25N NaOH (2 eq) and the mixture was stirred overnight at room temperature. After dilution with chloroform-methanol (5:1, v/v, 50 ml), the mixture was washed with 1N HCl, dried over anhydrous magnesium sulfate and distilled under reduced pressure to remove the solvent. The residue was purified by chromatography on a silica gel column, whereby chloroform-methanol (10:1, v/v) eluate fractions, cis-4-((4S)-fluoro-1-(2-(2-methylphenylamino)-6-benzoxazolylacetyl)-(2S)-pyrrolidinylcarbonylamino)cyclohexanecarboxylic acid (248 mg, 86%) was obtained as a white crystalline solid.

IR (ATR) 1639, 1573, 1428 cm$^{-1}$;

$^1$H-NMR (CDCl$_3$) δ: 1.24 (br, 2H), 1.54 (br, 1H), 1.66 (br, 4H), 1.76 (br, 2H), 1.99 (br, 1H), 2.17 (m, 1H), 2.31 (s, 3H), 2.44 (br, 1H), 2.83 (series of t, J=16.0 Hz, total 1H), 3.61–3.82 (series of m, total 4H), 3.86 (br, 2H), 5.24 (d, J=52.4 Hz, 1H), 7.10 (m, 2H), 7.20 (m, 1H), 7.25 (m, 2H), 7.32 (m, 2H), 7.80 (m, 1H).

MS (ESI) m/z 523 (M+H)$^+$;

Anal. Calcd for C$_{28}$H$_{31}$FN$_4$O$_5$.H$_2$O: C, 62.21; H, 6.15; N, 10.36. Found: C, 63.06; H, 6.23; N, 9.07.

Example 33

4-(1-(2-(2-Methylphenylamino)-6-benzoxazolylacetyl)-(4S)-fluoro-(2S)-pyrrolidinylmethylamino) benzoic acid (Step 1) Synthesis of N-tert-butoxycarbonyl-(4S)-fluoro-(2S)-prolinal

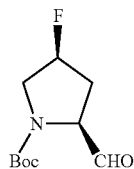

In methylene chloride (50 ml) was dissolved N-tert-butoxycarbonyl-(4S)-fluoro-(2S)-pyrrolidinylmethanol (1.22 g, 5.57 mmol). Under stirring at room temperature, 1,1,1-triacetoxy-1,1-dihydro-1,2-benziodoxol-3(1H)-one (Dess-Martin Periodinate, 2.84 g, 6.69 mmol) was added to the resulting solution in portions. After completion of the addition, the reaction mixture was stirred further for 2 hours at room temperature. The insoluble matter was filtered off under reduced pressure and then the filtrate was distilled under reduced pressure to remove the solvent. Ether was added to the residue. After filtering off the insoluble matter, the filtrate was distilled under reduced pressure. The above-described operation was repeated three times further to filter off the insoluble matter under reduced pressure, whereby N-tert-butoxycarbonyl-(4S)-fluoro-(2S)-prolinal (1.20 g, 99%) was obtained as a brown solid.

$^1$H-NMR (CDCl$_3$) δ: 1.63 and 1.68 (s, total 9H), 2.38–2.69 (m, 1H), 3.68–3.84 (m, 1H), 3.95–4.14 (m, 1H), 4.36–4.51 (m, 1H), 5.40 (brd, J=51.2 Hz, 1H), 9.78 (d, J=18.4 Hz, 1H).

MS (ESI) m/z, 218 (M$^+$+H).

(Step 2) Synthesis of methyl 4-((4S)-fluoro-(2S)-pyrrolidinylmethylamino)benzoate

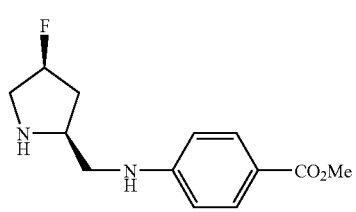

Methyl 4-aminobenzoate (728 mg, 4.82 mmol), acetic acid (290 ml, 4.82 mmol) and N-tert-butoxycarbonyl-(4S)-fluoro-(2S)-prolinal (6.97 mg, 3.21 mmol) were dissolved in methanol (15 ml). Under stirring at 0° C., sodium cyanoborohydride (95%, 320 mg, 4.82 mmol) was added to the resulting solution. The mixture was stirred overnight at room temperature. Water was added to the reaction mixture, followed by extraction with ethyl acetate. The extract was dried over anhydrous sodium sulfate and distilled under reduced pressure to remove the solvent. The residue thus obtained was dissolved in methylene chloride (10 ml). Trifluoroacetic acid (7 ml) was added to the resulting solution and the mixture was stirred at room temperature for 30 minutes. The reaction mixture was distilled under reduced pressure. After addition of a saturated aqueous solution of sodium bicarbonate to the residue, the resulting mixture was extracted with chloroform. The extract was dried over anhydrous sodium sulfate and distilled under reduced pressure to remove the solvent. The residue was purified by chromatography on a silica gel column, whereby from chloroform-methanol (10:1) eluate fractions, methyl 4-((4S)-fluoro-(2S)-pyrrolidinylmethylamino)benzoate (458 mg, 57%) was obtained as a colorless solid.

$^1$H-NMR (CDCl$_3$) δ: 1.80–1.92 (m, 1H), 2.15–2.31 (m, 1H), 2.90–3.03 (m, 1H), 3.18–3.23 (m, 1H), 3.28–3.37 (m, 2H), 3.45–3.51 (m, 1H), 3.84 (s, 3H), 4.63 (br s, 1H), 5.14–5.30 (m, 1H), 6.57 (d, J=6.8 Hz, 2H), 7.85 (d, J=7.2 Hz, 2H).

(Step 3) Synthesis of methyl 4-(1-(2-(2-methylphenylamino)-6-benzoxazolylacetyl)-(4S)-fluoro-(2)-pyrrolidinylmethylamino)benzoate

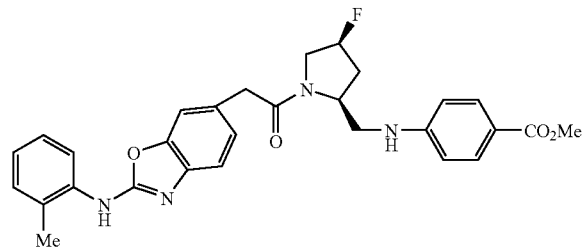

In DMF (10 ml), EDC•HCl (232 mg, 1.21 mmol) was added to methyl 4-((4S)-fluoro-(2S)-pyrrolidinylmethylamino)benzoate (277 mg, 1.10 mmol), 2-(2-methylphenylamino)-6-benzoxazolylacetic acid (310 mg, 1.10 mmol) and DMAP (148 mg, 1.21 mmol) at room temperature. The mixture was stirred overnight at room temperature. Water was added to the reaction mixture, followed by extraction with ethyl acetate. The extract was washed with saturated brine (three times), dried over anhydrous sodium sulfate and distilled under reduced pressure to remove the solvent. The residue was purified by chromatography on a silica gel column, whereby from hexane-ethyl acetate (1:4) eluate fractions, methyl 4-(1-(2-(2-methylphenylamino)-6-benzoxazolylacetyl)-(4S)-fluoro-(2S)-pyrrolidinylmethylamino) benzoate (580 mg, 100%) was obtained as a colorless amorphous substance.

$^1$H-NMR (CDCl$_3$) δ: 1.70 (br s, 1H), 2.07–2.23 (m, 2H), 2.37 (s, 3H), 3.24–3.28 (m, 1H), 3.57–3.75 (m, 1H), 3.61–3.85 (m, 2H), 3.83 (s, 3H), 4.54 (br d, J=6.8 Hz, 1H), 5.22–5.40 (m, 2H), 6.61 (d, J=8.8 Hz, 2H), 7.03–7.09 (m, 2H), 7.14 (s, 1H), 7.22 (d, J=7.2 Hz, 1H), 7.30 (t, J=8.0 Hz, 1H), 7.38 (d, J=8.0 Hz, 1H), 7.85 (d, J=8.8 Hz, 2H), 8.05 (d, J=8.0 Hz, 1H).

MS (ESI) m/z, 517 (M$^+$+H).

(Step 4) Synthesis of 4-(1-(2-(2-methylphenylamino)-6-benzoxazolylacetyl)-(4S)-fluoro-(2S)-pyrrolidinylmethylamino)benzoic acid

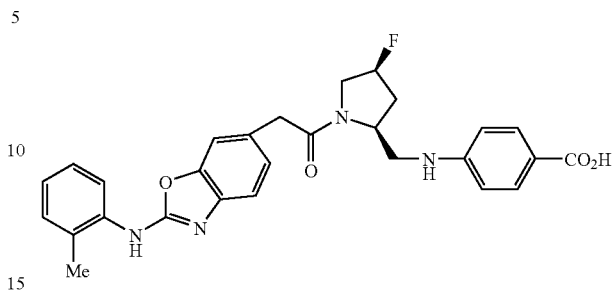

Methyl 4-(1-(2-(2-methylphenylamino)-6-benzoxazolylacetyl)-(4S)-fluoro-(2S)-pyrrolidinylmethylamino)benzoate (568 mg, 1.10 mmol) was dissolved in methanol-THF (1:1, 10 ml). After addition of 1.0M-NaOH (5.50 ml, 5.50 mmol) at room temperature, the resulting mixture was stirred at 60° C. for 3 hours. The reaction mixture was poured in 1N-HCl (10 ml), followed by extraction with a chloroform-methanol mixture. The extract was dried over anhydrous sodium sulfate and distilled under reduced pressure to remove the solvent. The residue was purified by chromatography on a silica gel column, whereby from chloroform-methanol (10:1) eluate fractions, 4-(1-(2-(2-methylphenylamino)-6-benzoxazolylacetyl)-(4S)-fluoro-(2S)-pyrrolidinylmethylamino)benzoic acid (409 mg, 74%) was obtained as a colorless amorphous substance.

$^1$H-NMR (DMSO-d$_6$), mixture of rotamars, δ: 2.02–2.26 (m, 2H), 2.29 and 2.30 (s, total 3H), 2.93–2.99 (m, 1H), 3.58–4.33 (series of m, 6H), 5.38–5.47 (m, 1H), 6.64–7.83 (series of m, 12H).

MS (ESI) m/z, 503 (M$^+$+H).

Example 34

4-(1-(2-(2-Methylphenylamino)-6-benzoxazolylacetyl)-(3R)-pyrrolidinyloxy)benzoic acid (Step 1) Synthesis of methyl 4-(1-(2-(2-methylphenylamino)-6-benzoxazolylacetyl)-(3R)-pyrrolidinyloxy)benzoate

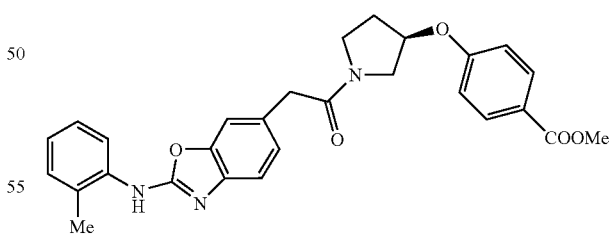

Methyl 4-(3R-pyrrolidinyl)oxybenzoate (221 mg, 1.0 mmol), 2-(2-methylphenylamino)-6-benzoxazolylacetic acid (282 mg, 1.0 mmol), HOBt (135 mg, 1.0 mmol) and triethylamine (417 μl, 3.0 mmol) were dissolved in methylene chloride (15 ml). At 0° C., EDC(HCl (288 mg, 1.5 mmol) was added and the mixture was stirred at room temperature for 16 hours. Ice water (20 ml) was added to the reaction mixture, followed by extraction with ethyl acetate. The extract was washed successively with a saturated aqueous solution of sodium bicarbonate, a 2M aqueous solution of citric acid and a saturated aqueous solution of sodium bicarbonate, dried over anhydrous sodium sulfate and distilled under reduced pressure to remove the solvent. The residue was purified by chromatography on a silica gel column, whereby from hexane-ethyl acetate (1:5, v/v) eluate fractions, the title compound (320 mg, 66%) was obtained as a colorless oil.

$^1$H-NMR (CDCl$_3$) δ: 2.20–2.40 (m, 5H), 3.60–4.00 (m, 6H), 4.95–5.05 (m, 1H), 6.80–7.41 (m, 9H), 7.94–8.09 (m, 3H).

(Step 2) Synthesis of 4-(1-(2-(2-methylphenylamino)-6-benzoxazolylacetyl)-(3R)-pyrrolidinyl)benzoic acid

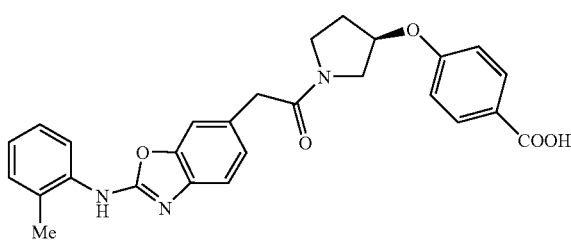

Methyl 4-(1-(2-(2-methylphenylamino)-6-benzoxazolylacetyl)-(3R)-pyrrolidinyloxy)benzoate (320 mg, 0.65 mmol) was dissolved in THF (5.0 ml) and methanol (3.0 ml). After addition of 1N NaOH (1.0 ml, 1.0 mmol) at room temperature, the reaction mixture was stirred for 18 hours at 70° C. From the reaction mixture, the solvent was distilled off under reduced pressure. The residue was acidified weakly with water (5 ml) and 1N HCl. The resulting crystals were collected by filtration under reduced pressure, washed with water and then dried under reduced pressure, whereby the title compound (240 mg, 77%) was obtained as a white crystalline solid.

$^1$H-NMR (DMSO-d$_6$) δ: 2.01–2.20 (m, 2H), 2.30 (s, 3H), 3.55–3.90 (m, 6H), 5.11–5.20 (m, 1H), 7.01–7.09 (m, 4H), 7.23–7.32 (m, 4H), 7.81–7.89 (m, 3H).

MS (FAB) m/z 472 (M+H)$^+$;

Anal. Calcd for C$_{27}$H$_{25}$N$_3$O$_5$·0.5H$_2$O: C, 67.49; H, 5.45; N, 8.74. Found: C, 67.33; H, 5.35; N, 8.57.

Example 35

4-(N-(3-Propinyl)-(2-(2-methylphenylamino)-6-benzoxazolylacetamido)methyl)cinnamic acid (Step 1) Synthesis of methyl 4-(N-(3-propinyl)-(2-(2-methylphenylamino)-6-benzoxazolylacetamido)methyl)cinnamate

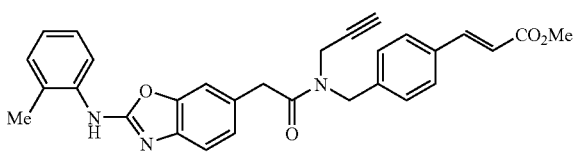

EDC·HCl (183 mg, 0.96 mmol) was added to a solution, in DMF (6 ml), of 2-(2-methylphenylamino)-6-benzoxazolylacetic acid (180 mg, 0.64 mmol), methyl 4-(N-(3-propinyl)aminomethyl)cinnamate (146 mg, 0.64 mmol), HOBt (17.0 mg, 0.13 mmol) and triethylamine (0.13 mL, 0.96 mmol). The resulting mixture was stirred overnight at room temperature. Water (20 ml) was added to the reaction mixture, followed by extraction with ethyl acetate. The extract was washed with saturated brine, dried over anhydrous sodium sulfate and distilled under reduced pressure to remove the solvent. The residue was purified by chromatography on a silica gel column, whereby from ethyl acetate eluate fractions, the title compound (313 mg, 99%) was obtained as a red amorphous substance.

$^1$H-NMR (CDCl$_3$) δ: 2.23, 2.33 (each s, total 1H), 2.38 (s, 3H), 3.82 (s, 3H), 3.83, 3.96 (each s, total 2H), 4.27 (s, 2H), 4.72, 4.74 (each s, total 2H), 6.44 (m, 1H), 6.95–7.56 (m, 10H), 7.68 (m, 1H), 8.08 (m, 1H).

(Step 2) Synthesis of 4-(N-(3-Propinyl)-(2-(2-methylphenylamino)-6-benzoxazolylacetamido)methyl)cinnamic acid:

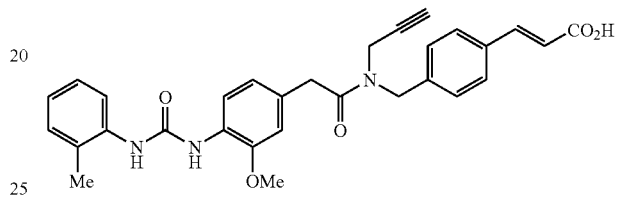

Under stirring at room temperature, 0.25N NaOH (4.70 mL, 1.17 mmol) was added to a solution of methyl 4-(N-(3-propionyl)-(2-(2-methylphenylamino)-6-benzoxazolylacetamido)methyl)cinnamate (313 mg, 0.63 mmol) in THF (8 mL). The reaction mixture was then stirred at 70° C. for 2 hours. Under stirring at 0° C., the reaction mixture was poured in 1N HCl (5 ml). The crystals thus obtained were collected by filtration, washed with water and dried under reduced pressure, whereby the title compound (609 mg, 82%) was obtained as a pale yellow solid.

IR (KBr) 3353, 3288, 2960, 2127, 2119, 1687, 1629, 1600, 1533, 1454, 1417 cm$^{-1}$;

$^1$H-NMR (DMSO-d$_6$) δ: 2.17 (s, 1H), 2.30 (s, 3H), 3.80, 3.92 (each s, total 2H), 4.12, 4.23 (each s, total 2H), 4.61, 4.76 (each s, total 2H), 6.50 (m, 1H), 7.00 (d, J=8.1 Hz, 1H), 7.08 (d, J=7.6 Hz, 2H), 7.23–7.29 (m, 6H), 7.52–7.67 (m, 3H), 7.81 (m, 1H), 9.64 (broad s, 1H).

ESI-MS 512 (M$^+$+1);

Anal. Calcd for C$_{30}$H$_{29}$N$_3$O$_5$·0.75H$_2$O: C, 68.62; H, 5.85; N, 8.00. Found: C, 68.76; H, 6.18; N, 7.16.

Example 36

4-(1-(3-Chloro-4-(1-indolinylcarbonylamino)phenylacetyl)-(4S)-fluoro-(2S)-pyrrolidinylmethoxy)cyclohexanecarboxylic acid (Step 1) Synthesis of ethyl 3-chloro-4-(1-indolinylcarbonylamino)phenylacetate

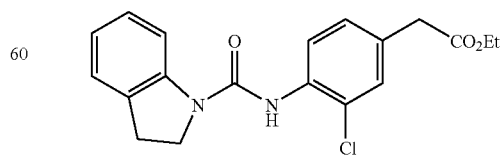

In methylene chloride (50 ml), triphosgene (926 mg, 3.12 mmol) and then pyridine (5 ml) were added to ethyl 4-amino-3-chlorophenylacetate (2.00 g, 9.36 mmol) under stirring at 0° C. After stirring at the same temperature for 15 minutes, indoline (1.05 ml, 9.36 mmol) was added. The reaction mixture was further stirred for 15 minutes at room temperature. Water (50 ml) was added to the reaction mixture, followed by extraction with ethyl acetate (300 ml). The extract was washed with saturated brine, dried over anhydrous magnesium sulfate and distilled under reduced pressure to remove the solvent, whereby ethyl 3-chloro-4-(1-indolinylcarbonylamino)phenylacetate (3.07 g, 91%) was obtained as a pale pink crystalline powder.

$^1$H-NMR (CDCl$_3$) δ: 1.25 (t, J=7.3 Hz, 3H), 3.20–3.26 (m, 2H), 3.54 (d, J=2.7 Hz, 2H), 4.08–4.18 (m, 4H), 6.93–6.98 (m, 1H), 7.09–7.31 (m, 5H), 7.94 (d, J=8.1 Hz, 1H), 8.28 (d, J=8.1 Hz, 1H);

MS (ESI) m/z 359 (M$^+$+1).

(Step 2) Synthesis of 3-chloro-4-(1-indolinylcarbonylamino)phenylacetic acid

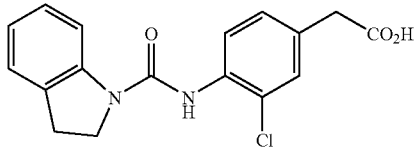

To ethyl 3-chloro-4-(1-indolinylcarbonylamino)phenylacetate (3.07 g, 8.56 mmol) were added 0.25N NaOH (68.4 ml, 17.1 mmol) and THF (70 ml). The mixture was heated and refluxed for 4 hours. After cooling, the reaction mixture was poured in 1N hydrochloric acid (50 ml). The crystals thus precipitated were collected by filtration, and dried under reduced pressure for 12 hours, whereby 3-chloro-4-(1-indolinylcarbonylamino)phenylacetic acid (1.71 g, 60%) was obtained as a colorless crystalline powder.

$^1$H-NMR (DMSO-d$_6$) δ: 3.19 (t, J=8.8 Hz, 2H), 3.61 (s, 2H), 4.13 (t, J=8.8 Hz, 2H), 6.90 (t, J=7.3 Hz, 1H), 7.11 (t, J=7.8 Hz, 1H), 7.19–7.23 (m, 2H), 7.41 (d, J=2.0 Hz, 1H), 7.54–7.58 (m, 1H), 7.82 (d, J=8.3 Hz, 1H), 8.21 (s, 1H);

MS (ESI) m/z 331 (M$^+$+1).

(Step 3) Synthesis of methyl 4-(1-(3-chloro-4-(1-indolinylcarbonylamino)phenylacetyl)-(4S)-fluoro-(2S)-pyrrolidinylmethoxy)cyclohexanecarboxylate

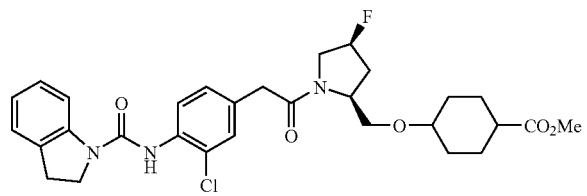

In DMF (10 ml), methyl ((4S)-fluoro-(2S)-pyrrolidinylmethoxy)cyclohexanecarboxylate (the compound synthesized in (Step 3) of Example 21) (143 mg, 0.55 mmol), 3-chloro-4-(1-indolinylcarbonylamino)phenylacetic acid (182 mg, 0.55 mmol), EDC•HCl (116 mg, 0.61 mmol) and HOBt (15 mg, 0.11 mmol) were stirred overnight at room temperature. Water (20 ml) was poured in the reaction mixture, followed by extraction with ethyl acetate. The extract was washed with saturated brine. The residue was purified by thin-layer column chromatography while using hexane/ethyl acetate (1/10) as a developing solvent, whereby methyl 4-(1-(3-chloro-4-(1-indolinylcarbonylamino))phenylacetyl)-(4S)-fluoro-(2S)-pyrrolidinylmethoxy)cyclohexanecarboxylate (259 mg, 82%) was obtained as a colorless amorphous substance.

$^1$H-NMR (CDCl$_3$), mixture of amide isomers, δ: 1.21–1.32 (m, 2H), 1.40–1.53 (m, 2H), 1.98–2.51 (series of m, 8H), 3.27 (t, J=8.4 Hz, 2H), 3.22–3.34 (m, 2H), 3.50–4.01 (series of m, 4H), 3.66 and 3.67 (s, total 3H), 4.14 (t, J=8.8 Hz, 2H), 4.10–4.38 (m, 1H), 5.16–5.33 (m, 1H), 6.98 (t, J=7.6 Hz, 1H), 7.12–7.24 (series of m, 4H), 7.34 (br s, 1H), 7.95 (d, J=8.0 Hz, 1H), 8.27 (t, J=8.4 Hz, 1H);

MS (ESI) m/z 572 (M$^+$+1).

(Step 4) Synthesis of 4-(1-(3-chloro-4-(1-indolinylcarbonylamino)phenylacetyl)-(4S)-fluoro-(2S)-pyrrolidinylmethoxy)cyclohexanecarboxylic acid

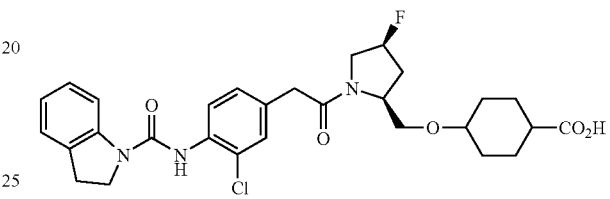

To methyl 4-(1-(3-chloro-4-(1-indolinylcarbonylamino)phenylacetyl)-(4S)-fluoro-(2S)-pyrrolidinylmethoxy)cyclohexanecarboxylate (224 mg, 0.39 mmol) were added 0.5N NaOH (4.7 ml), methanol (5 ml) and THF (5 ml). The mixture was stirred overnight at room temperature. The reaction mixture was poured in 1N hydrochloric acid (10 ml), followed by extraction with chloroform-methanol (10:1). The extract was dried over anhydrous sodium sulfate and distilled under reduced pressure to remove the solvent. The residue was purified by chromatography on a silica gel column, whereby from chloroform/methanol (10/1) eluate fractions, the title compound (221 mg, 100%) was obtained as a colorless amorphous substance.

$^1$H-NMR (CDCl$_3$), mixture of amide isomers, δ: 1.21–1.33 (m, 2H), 1.42–1.54 (m, 2H), 2.00–2.50 (series of m, 8H), 3.26 (t, J=8.8 Hz, 2H), 3.24–3.36 (m, 2H), 3.48–4.00 (series of m, 4H), 4.14 (t, J=8.8 Hz, 2H), 4.16–4.37 (m, 1H), 5.17–5.32 (m, 1H), 6.97 (t, J=7.6 Hz, 1H), 7.11–7.24 (series of m, 4H), 7.33 (s, 1H), 7.93 (d, J=8.0 Hz, 1H), 8.25 (t, J=9.2 Hz, 1H);

MS (ESI) m/z 558 (M$^+$+1).

Example 37

4-(1-(2-(2-Chlorophenyl)amino-7-fluoro-6-benzoxazolylacetyl)-(4S)-fluoro-(2S)-pyrrolidinylmethoxy)cyclohexanecarboxylic acid (Step 1) Synthesis of methyl 2-(2-chlorophenyl)amino-7-fluoro-6-benzoxazolylacetate

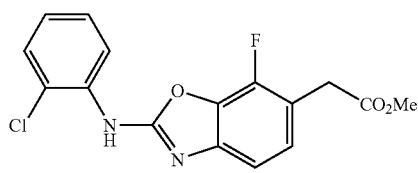

In methanol (50 ml) was dissolved 4-amino-2-fluoro-3-hydroxyphenylacetic acid (2.52 g, 12.7 mmol). At room temperature, 2-chlorophenyl isothiocyanate (1.99 ml, 12.7 mmol) was added to the resulting solution. After the resulting mixture was stirred at room temperature for 2.5 hours, mercuric oxide (yellow) (3.29 g, 15.2 mmol) was added thereto. The mixture was stirred further for 14 hours at 70° C. The reaction mixture was allowed to cool down to room temperature. The insoluble matter was filtered off through Celite under reduced pressure, followed by washing with methanol. From the filtrate, the solvent was distilled off under reduced pressure. The residue was purified by chromatography on a silica gel column (silica gel: 100 g, chloroform/ethyl acetate (30/1)), whereby from eluate fractions, methyl 2-(2-chlorophenyl)amino-7-fluoro-6-benzoxazolylacetate (2.12 g, 50%) was obtained as a pale pink solid.

$^1$H-NMR (CDCl$_3$) δ: 3.73 (s, 3H), 3.77 (s, 2H), 7.05 (tt, J=7.3, 1.0 Hz, 1H), 7.12 (t, J=7.1 Hz, 1H), 7.28 (s, 1H), 7.38 (dt, J=7.3, 0.7 Hz, 1H), 7.42 (d, J=8.0 Hz, 1H), 7.60 (br, 1H), 8.53 (d, J=8.3 Hz, 1H);

MS (ESI) m/z 335(M$^+$+1), 337 (M$^+$+3).

(Step 2) Synthesis of 2-(2-chlorophenyl)amino-7-fluoro-6-benzoxazolylacetic acid

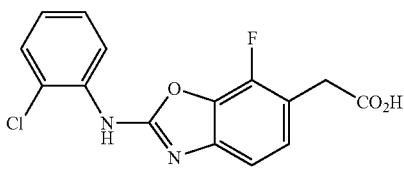

Methyl 2-(2-chlorophenyl)amino-7-fluoro-6-benzoxazolylacetate (2.12 g, 6.33 mmol) was dissolved in THF/methanol (2:1, 90 ml). To the resulting solution was added 1N NaOH (30 ml) and the mixture was stirred at room temperature for 3.5 hours. The solvent was distilled off under reduced pressure. The residue was acidified with 1N hydrochloric acid. The crystals thus precipitated were collected by filtration, washed with water and dried under reduced pressure, whereby 2-(2-chlorophenyl)amino-7-fluoro-6-benzoxazolylacetic acid (1.83 g, 90%) was obtained as a colorless solid.

$^1$H-NMR (DMSO-d$_6$) δ: 3.71 (s, 2H), 7.12–7.19 (m, 3H), 7.23 (dt, J=7.6,1.7 Hz, 1H), 7.43 (dt, J=7.6, 1.5 Hz, 1H), 7.55 (dd, J=8.1,1.5 Hz, 1H), 8.04 (d, J=8.3 Hz, 1H), 12.27 (br, 1H).

(Step 3) Synthesis of methyl 4-(1-(2-(2-chlorophenyl)amino-7-fluoro-6-benzoxazolylacetyl)-(4S)-fluoro-(2S)-pyrrolidinylmethoxy)cyclohexanecarboxylate:

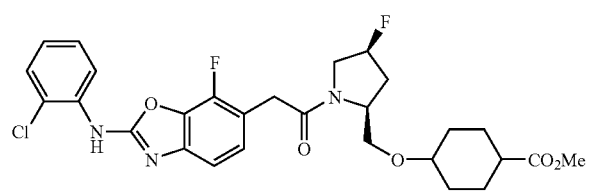

IN DMF (4 ml), methyl 4-((4S)-fluoro-(2S)-pyrrolidinylmethoxy)cyclohexanecarboxylate (the compound synthesized in Step 3 of Example 21) (210 mg, 0.81 mmol), 2-(2-chlorophenyl)amino-7-fluoro-6-benzoxazolylacetic acid (260 mg, 0.81 mmol), EDC•HCl (233 mg, 1.22 mmol), HOBT (165 mg, 1.22 mmol) and triethylamine (0.56 ml, 4.05 mmol) were stirred at room temperature for 15 hours. The reaction mixture was poured in ice water (30 ml), followed by extraction with ethyl acetate. The extract was washed with saturated brine, dried over anhydrous sodium sulfate and distilled under reduced pressure to remove the solvent. The residue was purified by chromatography on a silica gel column (silica gel: 50 g, chloroform/acetone (20/1)), whereby from eluate fractions, methyl 4-(1-(2-(2-chlorophenyl)amino-7-fluoro-6-benzoxazolylacetyl)-(4S)-fluoro-(2S)-pyrrolidinylmethoxy)cyclohexanecarboxylate (420 mg, 92%) was obtained as a colorless amorphous substance.

$^1$H-NMR (CDCl$_3$) δ: 1.17–1.54 (m, 5H), 1.92–2.53 (m, 7H), 3.28 (m, 1H), 3.35 and 3.54 (each m, total 1H, amide isomers), 3.64 and 3.67 (each s, total 3H, amide isomers), 3.70 (s, 1H), 3.72–4.04 (m, 3H), 4.31 and 4.38 (each m, total 1H, amide isomers), 5.26 and 5.30 (each m, total 1H, amide isomers), 7.04 (t, J=7.8 Hz, 1H), 7.13 (q, J=8.8 Hz, 1H), 7.26 (t, J=7.3 Hz, 1H), 7.37 (d, J=8.0 Hz, 1H), 7.41 (d, J=7.8 Hz, 1H), 7.62 (s, 1H), 8.52 (d, J=8.3 Hz, 1H);

MS (ESI) m/z 562 (M$^+$+1), 564 (M$^+$+3).

(Step 4) Synthesis of 4-(1-(2-(2-chlorophenyl)amino-7-fluoro-6-benzoxazolylacetyl)-(4S)-fluoro-(2S)-pyrrolidinylmethoxy)cyclohexanecarboxylic acid

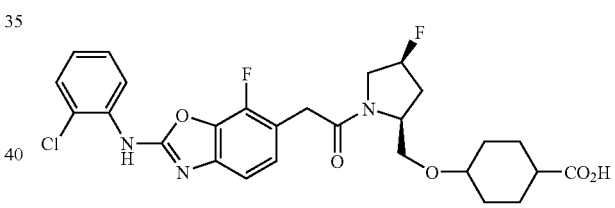

In THF/methanol (2:1, 15 ml) and 1N NaOH (5 ml), methyl 4-(1-(2-(2-chlorophenyl)amino-7-fluoro-6-benzoxazolylacetyl)-(4S)-fluoro-(2S)-pyrrolidinylmethoxy)cyclohexanecarboxylate (420 mg, 0.747 mmol) was stirred at room temperature for 17 hours. The solvent was distilled off under reduced pressure. The residue was acidified with 1N hydrochloric acid. The crystals thus obtained were collected by filtration under reduced pressure, washed with water and dried under reduced pressure, whereby the title compound (336 mg, 82%) was obtained as a pale brown solid.

IR (ATR) 3199, 2935, 2863, 1703, 1636, 1593, 1574, 1448 cm$^{-1}$;

$^1$H-NMR (DMSO-d$_6$) δ: 1.13–1.43 (m, 5H), 1.76–2.24 (m, 7H), 3.20 (t, J=8.8 Hz, 2H), 3.59–4.41 (m, 5H), 5.24–5.49 (m, 1H), 7.02–7.10 (m, 1H), 7.16 (d, J=8.1 Hz, 1H), 7.22 (t, J=7.6 Hz, 1H), 7.43 (t, J=7.6 Hz, 1H), 7.54 (d, J=7.8 Hz, 1H), 8.04 (d, J=8.1 Hz, 1H);

MS (ESI) m/z 548 (M$^+$+1), 550 (M$^+$+3);

Anal. Calcd for $C_{27}H_{28}ClF_2N_3O_5 \cdot 0.5H_2O$: C, 58.22; H, 5.25; N, 7.57; Cl, 6.37; F, 6.82. Found: C, 58.44; H, 5.17; N, 7.45; Cl, 6.55; F, 6.64.

Example 38

4-(1-(3-Chloro-4-(3-indolylcarbonylamino)phenylacetyl)-(4S)-fluoro-(2S)-pyrrolidinylmethoxy)cyclohexanecarboxylic acid (Step 1) Synthesis of methyl 4-(1-(3-chloro-4-(3-indolylcarbonylamino)phenylacetyl)-(4S)-fluoro-(2S)-pyrrolidinylmethoxy)cyclohexanecarboxylate

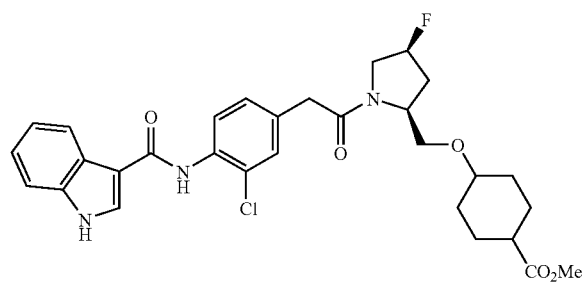

EDC·HCl (168 mg, 0.87 mmol) was added to a solution of 3-chloro-4-(3-indolylcarbonylamino)phenylacetic acid (240 mg, 0.67 mmol), methyl 4-((4S)-fluoro-(2S)-pyrrolidinylmethoxy)cyclohexanecarboxylate (the compound synthesized in (Step 3) of Example 21) (174 mg, 0.67 mmol), HOBt (18.0 mg, 0.13 mmol) and DMAP (16.0 mg, 0.13 mmol) in DMF (5.0 mL), followed by stirring at room temperature for 4 hours. Water (10 mL) was added to the reaction mixture. The precipitate was collected by filtration, washed with Et 20 and dried under reduced pressure, whereby methyl 4-(1-(3-chloro-4-(3-indolylcarbonylamino)phenylacetyl-(4S)-fluoro-(2S)-pyrrolidinylmethoxy)cyclohexanecarboxylate (320 mg, 84%) was obtained as a colorless solid.

$^1$H-NMR (DMSO-$d_6$) δ: 1.15–1.28 (m, 2H), 1.32–1.44 (m, 2H), 1.87–2.07 (m, 4H), 2.10–2.33 (m, 3H), 3.21 (m, 1H), 3.30 and 3.45 (each m, total 1H), 3.57 (s, 3H), 3.60–3.93 (m, 5H), 4.15 and 4.33 (each m, total 1H), 5.31 and 5.38 (each m, total 1H), 7.12–7.21 (m, 3H), 7.37 and 7.39 (each d, J=1.4 Hz, total 1H), 7.46 (d, J=7.8 Hz, 1H), 7.65 and 7.66 (each d, J=8.3 Hz, total 1H), 8.13 (d, J=7.8 Hz, 1H), 8.28 (s, 1H), 9.28 (s, 1H), 11.73 (broad s, 1H);

MS (ESI) m/z 570 (M$^+$+1), 572 (M$^+$+3).

(Step 2) Synthesis of 4-(1-(3-chloro-4-(3-indolylcarbonylamino)phenylacetyl)-(4S)-fluoro-(2S)-pyrrolidinylmethoxy)cyclohexanecarboxylic acid

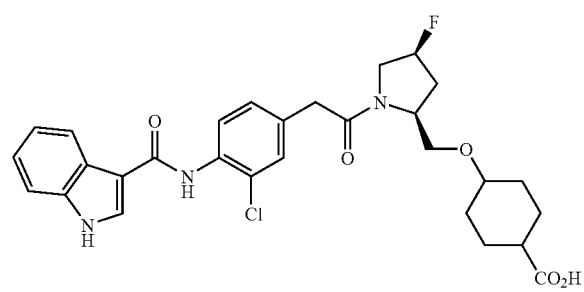

To a suspension of methyl 4-(1-(3-chloro-4-(3-indolylcarbonylamino)phenylacetyl)-(4S)-fluoro-(2S)-pyrrolidinylmethoxy)cyclohexanecarboxylate (320 mg, 0.56 mmol) in THF (14 mL) was added 0.25N NaOH (8.20 mL, 2.05 mmol). The mixture was stirred at room temperature for 5 hours. The reaction mixture was poured in 1N HCl under ice cooling. The crystals thus precipitated were collected by filtration, washed with water and dried under reduced pressure, whereby the title compound (295 mg, 88%) was obtained as a colorless solid.

IR (ATR) ν 3423, 3210, 2940, 2863, 1697, 1627, 1513, 1432 cm$^{-1}$;

$^1$H-NMR (DMSO-$d_6$) δ: 1.15–1.28 (m, 2H), 1.32–1.44 (m, 2H), 1.87–2.07 (m, 4H), 2.10–2.33 (m, 3H), 3.21 (m, 1H), 3.30 and 3.45 (each m, total 1H), 3.57 (s, 3H), 3.60–3.93 (m, 5H), 4.15 and 4.33 (each m, total 1H), 5.31 and 5.38 (each m, total 1H), 7.12–7.21 (m, 3H), 7.37 and 7.39 (each d, J=1.4 Hz, total 1H), 7.46 (d, J=7.8 Hz, 1H), 7.65 and 7.66 (each d, J=8.3 Hz, total 1H), 8.13 (d, J=7.8 Hz, 1H), 8.28 (s, 1H), 9.28 (s, 1H), 11.73 (broad s, 1H);

MS (ESI) m/z 556 (M$^+$+1), 558 (M$^+$+3);

Anal. Calcd for $C_{29}H_{31}ClFN_3O_5 \cdot H_2O$: C, 60.68; H, 5.79; N, 7.32. Found: C, 60.90; H, 5.29; N, 7.32.

Example 39

4-(1-(3-Chloro-4-(1-methyl-3-indolylcarbonylamino)phenylacetyl)-(4S)-fluoro-(2S)-pyrrolidinylmethoxy)cyclohexanecarboxylic acid (Step 1) Synthesis of ethyl 3-chloro-4-(1-methyl-3-indolylcarbonylamino)phenylacetate

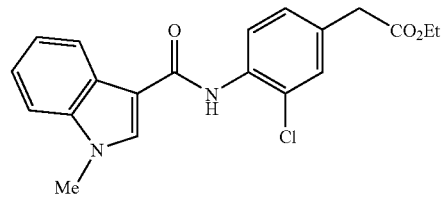

EDC·HCl (1.44 g, 7.49 mmol) was added to a solution of 1-methylindole-3-carboxylic acid (1.01 g, 5.71 mmol), ethyl 4-amino-3-chlorophenylacetate (1.22 g, 5.71 mmol), HOBt (0.86 g, 6.34 mmol) and DMAP (0.14 g, 1.15 mmol) in DMF (20 mL), followed by stirring at 70° C. for 18 hours. After cooling to room temperature, water (30 mL) was added to the reaction mixture, followed by extraction with ethyl acetate. The extract was washed with saturated brine, dried over anhydrous sodium sulfate and distilled under reduced pressure to remove the solvent. The residue was purified by chromatography on a silica gel column, whereby from hexane-ethyl acetate (1:1, v/v) eluate fractions, ethyl 3-chloro-4-(1-methyl-3-indolylcarbonylamino)phenyl acetate (639 mg, 30%) was obtained as a yellow solid.

$^1$H-NMR (CDCl$_3$) δ: 1.27 (t, J=7.1 Hz, 3H), 3.58 (s, 2H), 3.89 (s, 3H), 4.17 (q, J=7.1 Hz, 2H), 7.24 (dd, J=8.3, 2.0 Hz, 1H), 7.32–7.43 (m, 4H), 7.81 (s, 1H), 8.16 (m, 1H), 8.28 (broad s, 1H), 8.59 (d, J=8.3 Hz, 1H);

MS (ESI) m/z 371 (M$^+$+1), 373 (M$^+$+3).

(Step 2) Synthesis of 3-chloro-4-(1-methyl-3-indolylcarbonylamino)phenylacetic acid

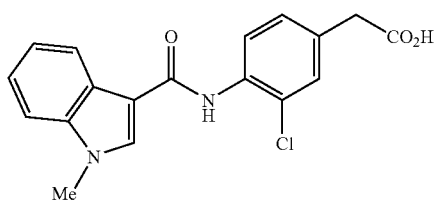

To a solution of ethyl 3-chloro-4-(1-methyl-3-indolylcarbonylamino)phenylacetate (639 mg, 1.72 mmol) in THF (17.5 mL) was added 0.25N NaOH (10.3 mL, 2.58 mmol). The resulting mixture was stirred at room temperature for 4 hours. Under ice cooling, the reaction mixture was poured in 1N HCl (15 ml). The crystals thus precipitated were collected by filtration, washed with water and dried under reduced pressure, whereby 3-chloro-4-(1-methyl-3-indolylcarbonylamino)phenylacetic acid (549 mg, 93%) was obtained as a colorless solid.

$^1$H-NMR (DMSO-$d_6$) δ: 3.61 (s, 2H), 3.89 (s, 3H), 7.17–7.28 (m, 3H), 7.43 (d, J=1.7 Hz, 1H), 7.53 (d, J=8.3 Hz, 1H), 7.69 (d, J=8.3 Hz, 1H), 8.14 (d, J=7.8 Hz, 1H), 8.26 (s, 1H), 9.26 (s, 1H).

(Step 3) Synthesis of methyl 4-(1-(3-chloro-4-(1-methyl-3-indolylcarbonylamino)phenylacetyl)-(4S)-fluoro-(2S)-pyrrolidinylmethoxy)cyclohexanecarboxylate

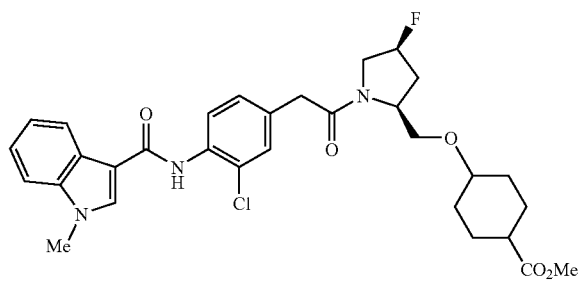

After addition of EDC•HCl (60.0 mg, 0.31 mmol) to a solution of 3-chloro-4-(1-methyl-3-indolylcarbonylamino) phenylacetic acid (82.0 mg, 0.24 mmol), methyl ((4S)-fluoro-(2S)-pyrrolidinylmethoxy)cyclohexanecarboxylate (the compound synthesized in (Step 3) of Example 21) (62.0 mg, 0.24 mmol), HOBt (6.0 mg, 0.05 mmol) and DMAP (6.0 mg, 0.05 mmol) in DMF (2.0 mL), the mixture was stirred at room temperature for 6 hours. The reaction mixture was poured in water (10 mL), followed by extraction with ethyl acetate. The extract was washed with saturated brine, dried over anhydrous sodium sulfate and distilled under reduced pressure to remove the solvent. The residue was purified by chromatography on a silica gel column, whereby from ethyl acetate eluate fractions, methyl 4-(1-(3-chloro-4-(1-methyl-3-indolylcarbonylamino)phenylacetyl)-(4S)-fluoro-(2S)-pyrrolidinylmethoxy)cyclohexanecarboxylate (115 mg, 82%) was obtained as a pale yellow amorphous substance.

$^1$H-NMR (CDCl$_3$) δ: 1.21–1.32 (m, 2H), 1.40–1.53 (m, 2H), 1.97–2.50 (m, 7H), 3.26 (m, 1H), 3.33 and 3.50 (each m, total 1H), 3.57–4.01 (m, 11H (3.64 and 3.66 (each s, total 3H), 3.88 (s, 3H)), 4.21 and 4.38 (each m, total 1H), 5.24 (m, 1H), 7.18 (m, 1H), 7.31–7.42 (m, 4H), 7.79 (s, 1H), 8.14 (m, 1H), 8.26 (broad s, 1H), 8.57 (d, J=8.3 Hz, 1H);

MS (ESI) m/z 584 (M$^+$+1), 586 (M$^+$+3).

(Step 4) Synthesis of 4-(1-(3-chloro-4-(1-methyl-3-indolylcarbonylamino)phenylacetyl)-(4S)-fluoro-(2S)-pyrrolidinylmethoxy)cyclohexanecarboxylic acid

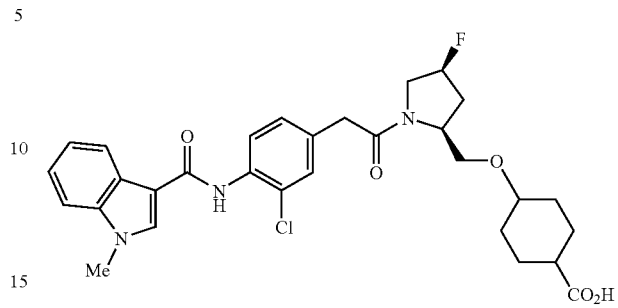

After addition of 0.25N NaOH (1.50 mL, 0.38 mmol) to a solution of methyl 4-(1-(3-chloro-4-(1-methyl-3-indolylcarbonylamino)phenylacetyl)-(4S)-fluoro-(2S)-pyrrolidinylmethoxy)cyclohexanecarboxylate (115 mg, 0.20 mmol) in THF (2.5 mL), the mixture was stirred at room temperature for 5 hours. Under ice cooling, the reaction mixture was poured in 1N HCl (3.0 mL). The crystals thus precipitated were collected by filtration, washed with water and dried under reduced pressure, whereby the title compound (94 mg, 88%) was obtained as a colorless solid.

IR (ATR) 2938, 2863, 1724, 1646, 1577, 1511, 1465 cm$^{-1}$;

$^1$H-NMR (DMSO-$d_6$) δ: 1.19–1.39 (m, 4H), 1.90–2.11 (m, 4H), 2.14–2.27 (m, 3H), 3.20 (m, 1H), 3.43–3.87 (m, 6H), 3.89 (s, 3H), 4.16 and 4.34 (each m, total 1H), 5.31 and 5.38 (each m, total 1H), 7.18–7.28 (m, 3H), 7.37 and 7.39 (each s, total 1H), 7.52 (d, J=8.1 Hz, 1H), 7.70 and 7.71 (each d, J=8.1 Hz, total 1H), 8.15 (d, J=7.8 Hz, 1H), 8.27 (d, J=7.8 Hz, 1H), 9.23 (s, 1H), 11.95 (broad s, 1H);

MS (ESI) m/z 570 (M$^+$+1), 572 (M$^+$+3);

Anal. Calcd for C$_{30}$H$_{33}$ClFN$_3$O$_5$·0.75H$_2$O: C, 61.75; H, 5.96; N, 7.20. Found: C, 61.85; H, 5.92; N, 6.83.

Example 40

4-((4S)-Fluoro-1-(2-(1-methyl-3-indolyl)-6-benzoxazolylacetyl)-(2S)-pyrrolidinylmethoxy)cyclohexanecarboxylic acid (Step 1) Synthesis of methyl 2-(1-methyl-3-indolyl)-6-benzoxazolylacetate

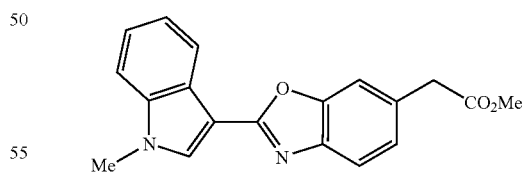

In xylene (20 mL), a mixture of 1-methyl-3-indolecarboxylic acid (1.00 g, 5.71 mmol), methyl 4-amino-3-hydroxyphenylacetate (1.03 g, 5.71 mmol) and boric acid (1.05 g, 17.1 mmol) was heated and refluxed for 24 hours by using a Dean-Stark trap. After the reaction mixture was cooled down to room temperature, the solvent was distilled off under reduced pressure. The residue was purified by chromatography on a silica gel column, whereby from chloroform-ethyl acetate (4:1, v/v) eluate fractions, methyl 2-(1-methyl-3-indolyl)-6-benzoxazolylacetate (0.20 g, 11%) was obtained as a yellow oil.

$^1$H-NMR (CDCl$_3$) δ: 3.72 (s, 3H), 3.76 (s, 2H), 3.88 (s, 3H), 7.21 (dd, J=8.1, 1.5 Hz, 1H), 7.32–7.40 (m, 3H), 7.49 (s, 1H), 7.65 (d, J=8.1 Hz, 1H), 7.91 (s, 1H), 8.45 (m, 1H);

MS (ESI) m/z 321 (M$^+$+1).

(Step 2) Synthesis of 2-(1-methyl-3-indolyl)-6-benzoxazolylacetic acid

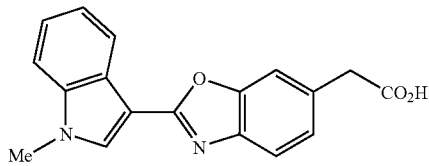

After addition of 0.25N NaOH (3.75 mL, 0.93 mmol) to a solution of methyl 2-(1-methyl-3-indolyl)-6-benzoxazolylacetate (200 mg, 0.62 mmol) in THF (6.5 mL), the mixture was stirred at room temperature for 2 hours. Under ice cooling, the reaction mixture was poured in 1N HCl (10 mL). The crystals thus precipitated were collected by filtration, washed with water and dried under reduced pressure, whereby 2-(1-methyl-3-indolyl)-6-benzoxazolylacetic acid (189 mg, 99%) was obtained as a colorless solid.

$^1$H-NMR (DMSO-d$_6$) δ: 3.73 (s, 2H), 3.94 (s, 3H), 7.24 (dd, J=7.8, 1.5 Hz, 1H), 7.31 (td, J=7.8, 1.5 Hz, 1H), 7.35 (td, J=7.8, 1.5 Hz, 1H), 7.60–7.64 (m, 3H), 8.32 (dd, J=8.1, 1.5 Hz, 1H), 8.34 (s, 1H), 12.37 (broad s, 1H);

MS (ESI) m/z 307 (M$^+$+1).

(Step 3) Synthesis of methyl 4-((4S)-fluoro-1-(2-(1-methyl-3-indolyl)-6-benzoxazolylacetyl)-(2S)-pyrrolidinylmethoxy)cyclohexanecarboxylate

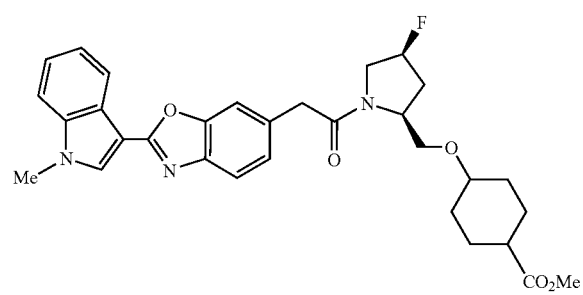

After addition of EDC•HCl (204 mg, 1.07 mmol) to a solution of 2-(1-methyl-3-indolyl)-6-benzoxazolylacetic acid (251 mg, 0.82 mmol), methyl ((4S)-fluoro-(2S)-pyrrolidinylmethoxy)cyclohexanecarboxylate (the compound synthesized in (Step 3) of Example 21) (212 mg, 0.82 mmol), HOBt (22.0 mg, 0.16 mmol) an DMAP (20.0 mg, 0.16 mmol) in DMF (5.0 mL), the resulting mixture was stirred at room temperature for 4 hours. The reaction mixture was poured in water (10 mL), followed by extraction with ethyl acetate. The extract was washed with saturated brine, dried over anhydrous sodium sulfate and distilled under reduced pressure to remove the solvent. The residue was purified by chromatography on a silica gel column, whereby from ethyl acetate fractions, methyl 4-((4S)-fluoro-1-(2-(1-methyl-3-indolyl)-6-benzoxazolylacetyl)-(2S)-pyrrolidinylmethoxy)cyclohexanecarboxylate (431 mg, 96%) was obtained as a yellow amorphous substance.

$^1$H-NMR (CDCl$_3$) δ: 1.21–1.34 (m, 2H), 1.40–1.53 (m, 2H), 1.96–2.15 (m, 4H), 2.19–2.50 (m, 3H), 3.26 (m, 1H), 3.35 and 3.50 (each m, total 1H), 3.64 and 3.66 (each s, total 3H), 3.69–3.87 (m, 3H), 3.90 (s, 3H), 3.94–4.06 (m, 2H), 4.25 and 4.39 (each m, total 1H), 5.23 (m, 1H), 7.19 (m, 1H), 7.34–7.41 (m, 3H), 7.49 (m, 1H), 7.64 (m, 1H), 7.93 (s, 1H), 8.44 (m, 1H);

MS (ESI) m/z 548 (M$^+$+1).

(Step 4) Synthesis of 4-((4S)-fluoro-1-(2-(1-methyl-3-indolyl)-6-benzoxazolylacetyl)-(2S)-pyrrolidinylmethoxy)cyclohexanecarboxylic acid

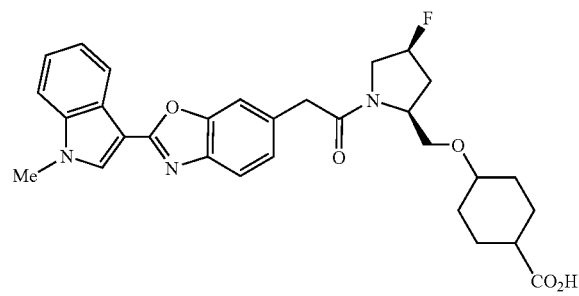

After addition of 0.25N NaOH (5.00 mL, 1.25 mmol) to a solution of methyl 4-((4S)-fluoro-1-(2-(1-methyl-3-indolyl)-6-benzoxazolylacetyl)-(2S)-pyrrolidinylmethoxy)cyclohexanecarboxylate (431 mg, 0.79 mmol) in THF (8.0 mL), the mixture was stirred at room temperature for 5 hours. Under ice cooling, the reaction mixture was poured in 1N HCl (10 mL). Crystals thus precipitated were collected by filtration, washed with water and dried under reduced pressure, whereby the title compound (396 mg, 94%) was obtained as a colorless solid.

IR (ATR) 2938, 2861, 1718, 1644, 1627, 1575, 1523, 1423 cm$^{-1}$;

$^1$H-NMR (DMSO-d$_6$) δ: 1.15–1.27 (m, 2H), 1.32–1.45 (m, 2H), 1.89–2.11 (m, 4H), 2.14–2.29 (m, 3H), 3.23 (m, 1H), 3.55 (m, 1H), 3.75–3.95 (m, 6H), 3.97 (s, 3H), 4.11 and 4.38 (each m, total 1H), 5.35 and 5.40 (each m, total 1H), 7.22 (m, 1H), 7.31–7.39 (m, 2H), 7.55–7.67 (m, 3H), 8.35 (s, 1H), 12.03 (broad s, 1H);

MS (ESI) m/z 534 (M$^+$+1);

Anal. Calcd for C$_{30}$H$_{32}$FN$_3$O$_5$: C, 67.53; H, 6.04; N, 7.87. Found: C, 67.33; H, 6.06; N, 7.70.

Example 41 trans-4-(1-((2-(5-Fluoro-2-methylphenylamino)-6-benzoxazolyl)acetyl)-(4S)-fluoro-(2S)-pyrrolidinylmethoxy)cyclohexanecarboxylic acid (Step 1) Synthesis of methyl (2-(5-fluoro-2-methylphenylamino)-6-benzoxazolyl)acetate

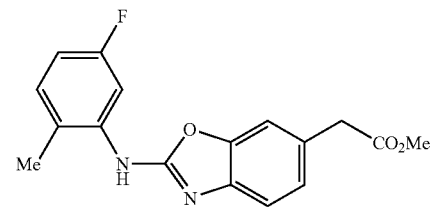

In methanol (50 ml), 5-fluoro-2-methylphenyl isothiocyanate (2.00 g, 12.0 mmol) was added to methyl 4-amino-3-hydroxyphenylacetate (2.17 g, 12.0 mmol) at room temperature. After stirring for 27 hours, mercuric oxide (yellow) (3.12 g, 14.4 mmol) was added to the reaction mixture and the resulting mixture was heated at 70° C. for 4 hours. After cooling to room temperature, the reaction mixture was filtered through Celite. The filtrate was washed with methanol. The filtrate was distilled under reduced pressure to remove the solvent. The residue was purified by chromatography on a silica gel column, whereby from chloroform/ethyl acetate (10/1) eluate fractions, methyl (2-(5-fluoro-2-methylphenylamino)-6-benzoxazolyl)acetate (1.73 g, 46%) was obtained as a pale brown oil.

$^1$H-NMR (CDCl$_3$) δ: 2.13 (s, 3H), 3.705 (s, 2H), 3.711 (s, 3H), 6.74 (dt, J=8.3, 2.7 Hz, 1H), 6.81 (br, 1H), 7.15 (dd, J=8.1, 1.7 Hz, 2H), 7.31 (d, J=1.2 Hz, 1H), 7.44 (d, J=8.1 Hz, 1H), 8.09 (dd, J=11.0, 2.7 Hz, 1H).

MS (ESI) m/z 315 (M$^+$+1).

(Step 2) (2-(5-Fluoro-2-methylphenylamino)-6-benzoxazolyl)acetic acid

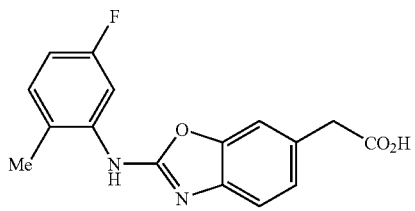

To a solution of methyl (2-(5-fluoro-2-methylphenylamino)-6-benzoxazolyl)acetate (1.73 g, 5.50 mmol) in THF/methanol (2:1, 30 ml) was added 1N NaOH (20 ml). After stirring at room temperature for 3.5 hours, the mixture was distilled under reduced pressure to remove the solvent. The residue was acidified with 1N HCl. The crystals thus precipitated were collected by filtration under reduced pressure, washed with water and dried under reduced pressure to give (2-(5-fluoro-2-methylphenylamino)-6-benzoxazolyl)acetic acid (1.60 g, 97%) as a colorless crystalline powder.

$^1$H-NMR (DMSO-d$_6$) δ: 2.49 (s, 3H), 3.64 (d, J=1.7 Hz, 2H), 6.87 (dt, J=8.3,1.5 Hz, 1H), 7.11 (d, J=8.1 Hz, 1H), 7.25 (t, J=7.3 Hz, 1H), 7.37 (d, J=8.1 Hz, 1H), 7.41 (s, 1H), 7.95 and 7.98 (each s, total 1H, amide isomers), 9.80 (br, 1H).

MS (ESI) m/z 301 (M$^+$+1).

(Step 3) Synthesis of methyl trans-4-(1-((2-(5-fluoro-2-methylphenylamino)-6-benzoxazolyl)acetyl)-(4S)-fluoro-(2S)-pyrrolidinylmethoxy)cyclohexanecarboxylate

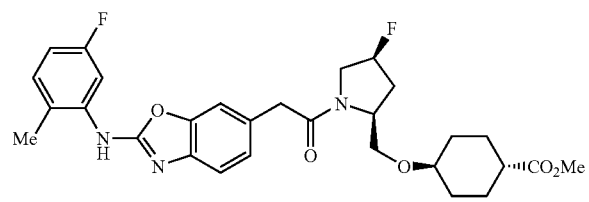

In DMF (5 ml), (2-(5-fluoro-2-methylphenyl)amino-6-benzoxazolyl)acetic acid, methyl trans-4-((4S)-fluoro-(2S)-pyrrolidinylmethoxy)cyclohexancarboxylate (compound synthesized in (Step 3) of Example 21) (259 mg, 1.0 mmol), EDC HCl (288 mg, 1.5 mmol), HOBt (203 mg, 1.5 mmol) and triethylamine (0.70 ml, 5.0 mmol) were stirred at room temperature for 18 hours. The reaction mixture was poured in ice water, followed by extraction with ethyl acetate. The extract was washed with saturated brine, dried over anhydrous sodium sulfate and distilled under reduced pressure to remove the solvent. The residue was purified by chromatography on a silica gel column, whereby from n-hexane/ethyl acetate (1/4) eluate fractions, methyl trans-4-(1-((2-(5-fluoro-2-methylphenylamino)-6-benzoxazolyl)acetyl)-(4S)-fluoro-(2S)-pyrrolidinylmethoxy)cyclohexanecarboxylate (540 mg, 100%) was obtained as a colorless amorphous substance.

$^1$H-NMR (CDCl$_3$) δ: 1.20–1.83 (m, 6H), 1.96–2.12 (m, 4H), 2.20–2.51 (m, 5H), 3.24 (m, 1H), 3.34 and 3.50 (t and dd, J=8.8 and 9.0, 6.8 Hz respectively, total 1H, amide isomers), 3.65 and 3.67 (each s, total 3H, amide isomers), 3.72–4.42 (m, 4H), 5.16–5.35 (m, 1H), 6.74 (t, J=7.8 Hz, 1H), 6.97 (br, 1H), 7.06–7.17 (m, 2H), 7.32 (d, J=7.3 Hz, 1H), 7.43 (t, J=6.8 Hz, 1H), 8.07 and 8.09 (each s, total 1H, amide isomers).

MS (ESI) m/z 542 (M$^+$+1).

(Step 4) Synthesis of trans-4-(1-((2-(5-fluoro-2-methylphenylamino)-6-benzoxazolyl)acetyl)-(4S)-fluoro-(2S)-pyrrolidinylmethoxy)cyclohexanecarboxylic acid.

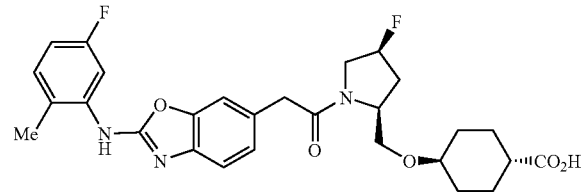

In THF/methanol (20/10 ml) was dissolved methyl trans-4-(1-((2-(5-fluoro-2-methylphenylamino)-6-benzoxazolyl)acetyl)-(4S)-fluoro-(2S)-pyrrolidinylmethoxy)cyclohexanecarboxylate (540 mg, 1.0 mmol), followed by the addition of 1N NaOH (20 ml). After stirring at room temperature for 14 hours, the mixture was distilled under reduced pressure to remove the solvent. The residue was acidified with 1N HCl. The crystals thus precipitated were collected by filtration under reduced pressure, washed with water and dried under reduced pressure to give the title compound (477 mg, 90%) as a colorless crystalline powder.

IR (ATR) ν 2939, 2864, 1701, 1639, 1610, 1576, 1437 cm$^{-1}$;

$^1$H-NMR (DMSO-d$_6$) δ: 1.10–1.41 (m, 4H), 1.82–2.01 (m, 4H), 2.10–2.21 (m, 3H), 2.29 (s, 3H), 3.14–3.57 (m, 3H), 3.62–3.95 (m, 4H), 4.14 and 4.32 (m and q, J=7.3 Hz, total 1H, amide isomers), 5.31 and 5.37 (each d, J=53.4 and 53.4 Hz respectively, total 1H, amide isomers), 6.87 (dt, J=8.4, 2.7 Hz, 1H), 7.05 and 7.08 (each d, each J=8.3 Hz, total 1H, amide isomers), 7.24 (t, J=6.8 Hz, 1H), 7.35 (t, J=8.3 Hz, 2H), 7.95 (d, J=11.5 Hz, 1H), 9.77 (br, 1H), 12.03 (br, 1H).

MS (ESI) m/z 528 (M$^+$+1);

Anal. Calcd for $C_{28}H_{31}F_2N_3O_5$ 0.2H$_2$O: C, 63.31; H, 5.96; N, 7.91; F, 7.15. Found: C, 63.13; H, 5.89; N, 7.71; F, 7.15.

Example 42 trans-4-(1-((2-(2-Chloro-6-methylphenylamino)-7-fluoro-6-benzoxazolyl)acetyl)-(4S)-fluoro-(2S)-pyrrolidinylmethoxy)cyclohexanecarboxylic acid (Step 1) Synthesis of methyl (2-(2-chloro-6-methylphenylamino)-7-fluoro-6-benzoxazolyl)acetate

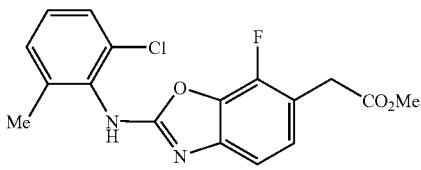

Methyl (4-amino-2-fluoro-3-hydroxyphenyl)acetate (1.0 g, 5.02 mmol) was dissolved in methanol (30 ml). To the resulting solution was added 2-chloro-6-methylphenyl isothiocyanate (841 mg, 4.58 mmol) at room temperature. After the resulting mixture was stirred for 5 days, mercuric oxide (yellow) (1.14 g, 4.36 mmol) was added thereto. The mixture was stirred at 70° C. for 23 hours. After cooling, the reaction mixture was filtered through Celite and washed with methanol. The filtrate was distilled under reduced pressure to remove the solvent. The residue was purified by chromatography on a silica gel column, whereby from chloroform/ethyl acetate (30/1) eluate fractions, methyl (2-(2-chloro-6-methylphenylamino)-7-fluoro-6-benzoxazolyl) acetate (1.45 g, 95%) was obtained as a red amorphous substance.

$^1$H-NMR (CDCl$_3$) δ: 2.38 (s, 3H), 3.71 (s, 2H), 3.74 (s, 3H), 7.05 (t, J=8.0 Hz, 1H), 7.14 (d, J=8.3 Hz, 1H), 7.20 (dd, J=7.6, 2.2 Hz, 1H), 7.23 (s, 1H), 7.34 (d, J=7.3 Hz, 1H).

MS (ESI) m/z 349 (M$^+$+1), 351 (M$^+$+3).

(Step 2) Synthesis of (2-(2-chloro-6-methylphenylamino)-7-fluoro-6-benzoxazolyl)acetic acid

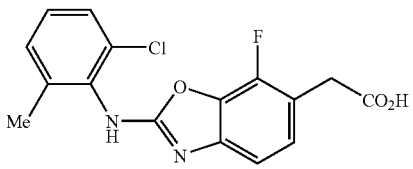

To a solution of methyl (2-(2-chloro-6-methylphenylamino)-7-fluoro-6-benzoxazolyl)acetate (1.45 g, 4.16 mmol) in THF/methanol (4:1, v/v 100 ml) was added 1N NaOH (40 ml). After stirring at room temperature for 17 hours, the reaction mixture was distilled under reduced pressure to remove the solvent. The residue was acidified with 1N HCl. The crystals thus precipitated were collected by filtration under reduced pressure, washed with water and dried under reduced pressure to give (2-(2-chloro-6-methylphenylamino)-7-fluoro-6-benzoxazolyl)acetic acid (1.30 g, 93%) as a colorless crystalline powder.

$^1$H-NMR (DMSO-d$_6$) δ: 2.28 (s, 3H), 3.36 (s, 2H), 7.01 and 7.03 (each s, total 1H, amide isomers), 7.07 (t, J=8.1 Hz, 1H), 7.29 (d, J=7.6 Hz, 1H), 7.32 (d, J=6.4 Hz, 1H), 7.42 (d, J=7.6 Hz, 1H).

MS (ESI) m/z 335 (M$^+$+1), 337 (M$^+$+3).

(Step 3) Synthesis of methyl trans-4-(1-((2-(2-chloro-6-methylphenylamino)-7-fluoro-6-benzoxazolyl)acetyl)-(4S)-fluoro-(2S)-pyrrolidinylmethoxy)cyclohexanecarboxylate


In DMF (4 ml), (2-(2-chloro-6-methylphenylamino)-7-fluoro-6-benzoxazolyl)acetic acid (167 mg, 0.50 mmol), methyl trans-4-((4S)-fluoro-(2S)-pyrrolidinylmethoxy)cyclohexanecarboxylate (the compound synthesized in (Step 3) of Example 21) (130 mg, 0.50 mmol), EDC HCl (144 mg, 0.75 mmol), HOBt (101 mg, 0.75 mmol) and triethylamine (0.35 ml, 2.50 mmol) were stirred at room temperature for 20 hours. The mixture was poured in ice water, followed by extraction with ethyl acetate. The extract was washed with saturated brine, dried over anhydrous sodium sulfate, and distilled under reduced pressure to remove the solvent. The residue was purified by thin-layer chromatography, whereby from chloroform/acetone (5/1) eluate fractions, methyl trans-4-(1-((2-(2-chloro-6-methylphenylamino)-7-fluoro-6-benzoxazolyl)acetyl)-(4S)-fluoro-(2S)-pyrrolidinylmethoxy)cyclohexanecarboxylate (238 mg, 83%) was obtained as a colorless amorphous substance.

$^1$H-NMR (CDCl$_3$) δ: 1.21–1.53 (m, 4H), 1.95–2.31 (m, 7H), 2.43 (s, 3H), 2.49 (m, 1H), 3.27 (m, 1H), 3.33 and 3.54 (t and dd, J=10.0 and 8.8, 6.4 Hz respectively, total 1H, amide isomers), 3.65 (s, 1H), 3.67 (s, 3H), 3.68–4.04 (m, 3H), 4.30 and 4.36 (q and m, J=6.8 Hz, total 1H, 5.25 and 5.30 (each dt, J=54.2, 3.8 and 53.2, 2.7 Hz respectively, total 1H, amide isomers), 7.00–7.22 (m, 3H), 7.32 (d, J=7.3 Hz, 1H).

MS (ESI) m/z 576 (M$^+$+1), 578 (M$^+$+3).

(Step 4) Synthesis of trans-4-(1-((2-(2-chloro-6-methylphenylamino)-7-fluoro-6-benzoxazolyl)acetyl)-(4S)-fluoro-(2S)-pyrrolidinylmethoxy)cyclohexanecarboxylic acid

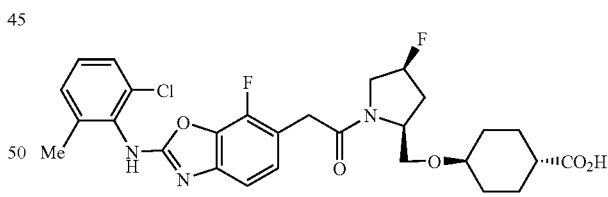

In THF/methanol (8/4, 12 ml) was dissolved methyl trans-4-(1-((2-(2-chloro-6-methylphenylamino)-7-fluoro-6-benzoxazolyl)acetyl)-(4S)-fluoro-(2S)-pyrrolidinylmethoxy)cyclohexanecarboxylate (238 mg, 0.413 mmol). To the resulting solution was added 1N NaOH (4 ml). After stirring at room temperature for 14 hours, the reaction mixture was distilled under reduced pressure to remove the solvent. The residue was acidified with 1N HCl. The crystals thus precipitated were collected by filtration under reduced pressure, washed with water and dried under reduced pressure to give the title compound (191 mg, 82%) as a colorless crystalline powder.

IR (ATR) ν 3743, 3674, 2939, 1704, 1635, 1583, 1504, 1452 cm$^{-1}$;

¹H-NMR (DMSO) δ: 1.10–1.42 (m, 5H), 1.81–2.22 (m, 6H), 2.28 (s, 3H), 3.18 (t, J=9.5 Hz, 1H), 3.42–4.02 (m, 6H), 4.11 and 4.35 (m and q, J=7.1 Hz, total 1H, amide isomers), 5.31 and 5.39 (each d, J=55.2 and 54.7 Hz respectively, total 1H, amide isomers), 6.96–7.03 (m, 2H), 7.28 (t, J=7.6 Hz, 1H), 7.32 (d, J=7.3 Hz, 1H), 7.42 (d, J=7.8 Hz, 1H).

MS (ESI) m/z 562 (M$^+$+1), 564 (M$^+$+3);

Anal. Calcd for $C_{28}H_{30}ClF_2N_3O_5$ 0.5H$_2$O: C, 58.90; H, 5.47; N, 7.36; Cl, 6.21; F, 6.65. Found: C, 58.85; H, 5.44; N, 7.19; Cl, 6.18; F, 6.47.

Example 43 trans-4-(1-((2-(5-Chloro-2-methylphenylamino)-7-fluoro-6-benzoxazolyl)acetyl)-(4S)-fluoro-(2S)-pyrrolidinylmethoxy)cyclohexanecarboxylic acid (Step 1) Synthesis of methyl (2-(5-chloro-2-methylphenylamino)-7-fluoro-6-benzoxazolyl)acetate

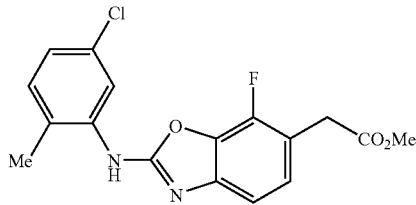

In methanol (30 ml) was dissolved methyl (4-amino-2-fluoro-3-hydroxyphenyl)acetate (1.0 g, 5.02 mmol). To the resulting solution was added 5-chloro-2-methylphenyl isothiocyanate (0.674 ml, 4.58 mmol). After the mixture was stirred at room temperature for 5 days, mercuric oxide (yellow) (1.14 g, 4.36 mmol) was added thereto. The resulting mixture was stirred at 70° C. for 6 hours. After cooling to room temperature, the reaction mixture was filtered through Celite and washed with methanol. The filtrate was distilled under reduced pressure to remove the solvent. The residue was purified by chromatography on a silica gel column, whereby from chloroform/ethyl acetate (30/1, v/v) eluate fractions, methyl (2-(5-chloro-2-methylphenylamino)-7-fluoro-6-benzoxazolyl)acetate (1.67 g, 100%) was obtained as a brown solid.

¹H-NMR (CDCl₃) δ: 2.32 (s, 3H), 3.73 (s, 3H), 3.76 (s, 2H), 7.04 (dd, J=8.1, 2.2 Hz, 1H), 7.10 (dd, J=7.8, 2.2 Hz, 1H), 7.13 (t, J=8.1 Hz, 2H), 8.30 (d, J=2.2 Hz, 1H).

MS (ESI) m/z 349 (M$^+$+1), 351 (M$^+$+3).

(Step 2) Synthesis of (2-(5-chloro-2-methylphenylamino)-7-fluoro-6-benzoxazolyl)acetic acid

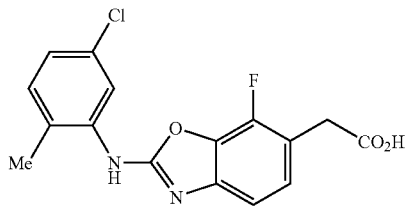

In THF/methanol (4:1, v/v, 100 ml) was dissolved methyl (2-(5-chloro-2-methylphenylamino)-7-fluoro-6-benzoxazolyl)acetate (1.67 g, 4.79 mmol). To the resulting solution was added 1N NaOH (40 ml). After stirring at room temperature for 12 hours, the reaction mixture was distilled under reduced pressure to remove the solvent. The residue was acidified with 1N HCl. The crystals thus precipitated were collected by filtration under reduced pressure, washed with water and dried under reduced pressure to give (2-(5-chloro-2-methylphenylamino)-7-fluoro-6-benzoxazolyl)acetic acid (1.39 g, 87%) as a colorless crystalline powder.

¹H-NMR (DMSO-d₆) δ: 2.30 (s, 3H), 3.71 (s, 2H), 7.12 (dd, J=8.1, 2.0 Hz, 1H), 7.15 (d, J=7.3 Hz, 1H), 7.23 (d, J=8.1 Hz, 1H), 7.26 (d, J=8.1 Hz, 1H), 8.09 (s, 1H), 10.06 (s, 1H), 12.46 (br, 1H).

MS (ESI) m/z 335 (M$^+$+1), 337 (M$^+$+3).

(Step 3) Synthesis of methyl trans-4-(1-((2-(5-chloro-2-methylphenylamino)-7-fluoro-6-benzoxazolyl)acetyl)-(4S)-fluoro-(2S)-pyrrolidinylmethoxy)cyclohexanecarboxylate

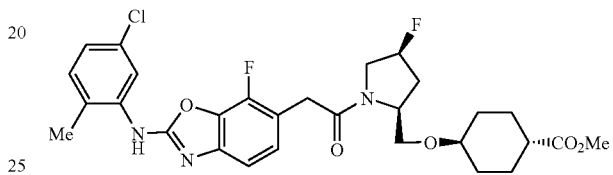

In DMF (4 ml), (2-(5-chloro-2-methylphenylamino)-7-fluoro-6-benzoxazolyl)acetic acid (167 mg, 0.50 mmol), methyl trans-4-((4S)-fluoro-(2S)-pyrrolidinylmethoxy)cyclohexanecarboxylate (the compound synthesized in (Step 3) of Example 21) (130 mg, 0.50 mmol), EDC HCl (144 mg, 0.75 mmol), HOBt (101 mg, 0.75 mmol) and triethylamine (0.35 ml, 2.50 mmol) were stirred at room temperature for 19 hours. The mixture was poured in ice water, followed by extraction with ethyl acetate. The extract was washed with saturated brine, dried over anhydrous sodium sulfate, and distilled under reduced pressure to remove the solvent. The residue was purified by chromatography using a thin-layer plate, whereby from chloroform/acetone (5/1, v/v) eluate fractions, methyl trans-4-(1-((2-(5-chloro-2-methylphenylamino)-7-fluoro-6-benzoxazolyl)acetyl)-(4S)-fluoro-(2S)-pyrrolidinylmethoxy)cyclohexanecarboxylate (261 mg, 91%) was obtained as a colorless amorphous substance.

¹H-NMR (CDCl₃) δ: 1.22–1.56 (m, 5H), 1.95–2.29 (m, 7H), 2.30 (s, 3H), 2.50 (m, 1H), 3.21–3.60 (m, 2H), 3.65 and 3.67 (each s, total 3H, amide isomers), 3.70 (s, 1H), 3.17–4.05 (m, 3H), 4.31–4.43 (m, 1H), 5.27 and 5.31(each dt, J=53.7, 4.4 and 52.7, 3.8 Hz respectively, total 1H, amide isomers), 7.02–7.14 (m, 4H), 7.22 (d, J=8.8 Hz, 1H), 8.26 (s, 1H).

MS (ESI) m/z 576 (M$^+$+1), 578 (M$^+$+3).

(Step 4) Synthesis of trans-4-(1-((2-(5-chloro-2-methylphenylamino)-7-fluoro-6-benzoxazolyl)acetyl)-(4S)-fluoro-(2S)-pyrrolidinylmethoxy)cyclohexanecarboxylic acid

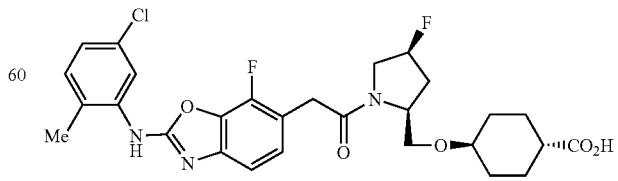

In THF/methanol (4:1, v/v, 12 ml) was dissolved methyl trans-4-(1-((2-(5-chloro-2-methylphenylamino)-7-fluoro-6- benzoxazolyl)acetyl)-(4S)-fluoro-(2S)-pyrrolidinyl-methoxy)cyclohexanecarboxylate (202 mg, 0.359 mmol). To the resulting solution was added 1N NaOH (4 ml). After stirring at room temperature for 14 hours, the reaction mixture was distilled under reduced pressure to remove the solvent. The residue was acidified with 1N HCl. The crystals thus precipitated were collected by filtration under reduced pressure, washed with water and dried under reduced pressure to give the title compound (202 mg, 79%) as a colorless crystalline powder.

IR (ATR) ν 3168, 2937, 1702, 1639, 1577, 1450 cm$^{-1}$;

$^1$H-NMR (DMSO-d$_6$) δ: 1.09–1.41 (m, 5H), 1.83–2.22 (m, 6H), 2.30 (s, 3H), 3.19 (t, J=9.8 Hz, 1H), 3.44–4.41 (m, 7H), 5.32 and 5.43 (each d, each J=54.4 Hz, total 1H, amide isomers), 7.05–7.10 (m, 1H), 7.12 (d, J=8.1 Hz, 1H), 7.22 (d, J=6.3 Hz, 1H), 7.27 (d, J=8.1 Hz, 1H), 8.10 (s, 1H), 10.04 (br, 1H).

MS (ESI) m/z 562 (M$^+$+1), 564 (M$^+$+3);

Anal. Calcd for C$_{28}$H$_{30}$ClF$_2$N$_3$O$_5$ 0.5H$_2$O: C, 58.90; H, 5.47; N, 7.36; Cl, 6.21; F, 6.65. Found: C, 59.13; H, 5.40; N, 7.15; Cl, 6.21; F, 6.48.

Example 44 trans-4-(1-((2-(5-Fluoro-2-methylphenylamino)-7-fluoro-6-benzoxazolyl)acetyl)-(4S)-fluoro-(2S)-pyrrolidinylmethoxy)cyclohexanecarboxylic acid (Step 1) Synthesis of methyl (2-(5-fluoro-2-methylphenylamino)-7-fluoro-6-benzoxazolyl)acetate

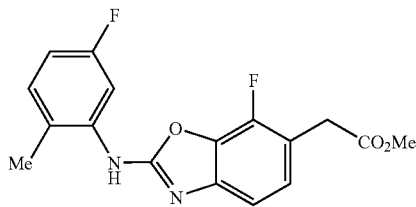

In methanol (30 ml) was dissolved methyl (4-amino-2-fluoro-3-hydroxyphenyl)acetate (1.0 g, 5.02 mmol). To the resulting solution was added 5-fluoro-2-methylphenyl isothiocyanate (1.0 g, 5.98 mmol). After the resulting mixture was stirred at room temperature for 5 days, mercuric oxide (yellow) (1.14 g, 4.36 mmol) was added thereto. The mixture was stirred at 70° C. for 6 hours. After cooling to room temperature, the reaction mixture was filtered through Celite and washed with methanol. The filtrate was distilled under reduced pressure to remove the solvent. The residue was purified by chromatography on a silica gel column, whereby from chloroform/ethyl acetate (30/1, v/v) eluate fractions, methyl (2-(5-fluoro-2-methylphenylamino)-7-fluoro-6-benzoxazolyl)acetate (810 mg, 56% (2 steps)) was obtained as a pink solid.

$^1$H-NMR (CDCl$_3$) δ: 2.32 (s, 3H), 3.72 (s, 3H), 3.76 (s, 2H), 6.75 (dt, J=8.1, 2.7 Hz, 1H), 6.87 (br, 1H), 7.11 (t, J=6.6 Hz, 1H), 7.15 (t, J=6.9 Hz, 1H), 8.11 (dd, J=11.0, 6.7 Hz, 1H).

MS (ESI) m/z 333 (M$^+$+1).

(Step 2) Synthesis of (2-(5-fluoro-2-methylphenylamino)-7-fluoro-6-benzoxazolyl)acetic acid

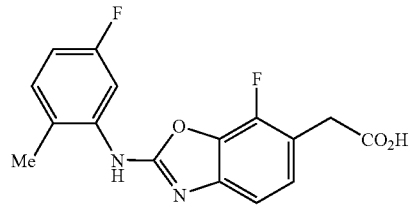

In THF/methanol (2:1, v/v, 90 ml) was dissolved methyl (2-(5-fluoro-2-methylphenylamino)-7-fluoro-6-benzoxazolyl)acetate (810 mg, 2.44 mmol). To the resulting solution was added 1N NaOH (30 ml). After stirring at room temperature for 12 hours, the reaction mixture was distilled under reduced pressure to remove the solvent. The residue was acidified with 1N HCl. The crystals thus precipitated were collected by filtration under reduced pressure, washed with water and dried under reduced pressure to give (2-(5-fluoro-2-methylphenylamino)-7-fluoro-6-benzoxazolyl) acetic acid (700 mg, 90%) as a pale brown solid.

$^1$H-NMR (DMSO-d$_6$) δ: 2.29 (s, 3H), 3.68 (s, 2H), 6.89 (dt, J=7.0, 1.7 Hz, 1H), 7.14 (t, J=6.4 Hz, 1H), 7.20 and 7.22 (each s, total 1H, amide isomers), 7.25 (t, J=7.4 Hz, 1H), 7.90 (d, J=11.3 Hz, 1H), 10.06 (br, 1H).

MS (ESI) m/z 319 (M$^+$+1).

(Step 3) Synthesis of methyl trans-4-(1-((2-(5-fluoro-2-methylphenylamino)-7-fluoro-6-benzoxazolyl)acetyl)-(4S)-fluoro-(2S)-pyrrolidinylmethoxy)cyclohexanecarboxylate

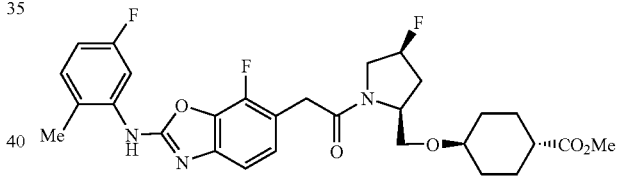

In DMF (4 ml) were dissolved (2-(5-fluoro-2-methylphenylamino)-7-fluoro-6-benzoxazolyl)acetic acid (159 mg, 0.50 mmol), methyl trans-4-((4S)-fluoro-(2S)-pyrrolidinylmethoxy)cyclohexanecarboxylate (the compound synthesized in (Step 3) of Example 21) (130 mg, 0.50 mmol), EDC HCl (144 mg, 0.75 mmol), HOBt (101 mg, 0.75 mmol) and triethylamine (0.35 ml, 2.50 mmol). The resulting solution was stirred at room temperature for 19 hours. The mixture was poured in ice water, followed by extraction with ethyl acetate. The extract was washed with saturated brine, dried over anhydrous sodium sulfate, and distilled under reduced pressure to remove the solvent. The residue was purified by chromatography using a thin plate, whereby from chloroform/acetone (5/1) eluate fractions, methyl trans-4-(1-((2-(5-fluoro-2-methylphenylamino)-7-fluoro-6-benzoxazolyl)acetyl)-(4S)-fluoro-(2S)-pyrrolidinylmethoxy)cyclohexanecarboxylate (243 mg, 87%) was obtained as a colorless amorphous substance.

$^1$H-NMR (CDCl$_3$) δ: 1.21–1.62 (m, 4H), 1.97–2.29 (m, 6H), 2.31 (s, 3H), 2.51 (m, 1H), 3.22–3.61 (m, 2H), 3.65 (s, 1H), 3.67 (s, 3H), 3.70 (s, 1H), 3.71–4.09 (m, 3H), 4.31–4.44 (m, 1H), 5.18–5.41 (m, 1H), 6.75 (t, J=6.3 Hz, 1H), 7.09–7.18 (m, 3H), 7.21 (d, J=9.5 Hz, 1H), 8.07 (dd, J=10.7, 2.2 Hz, 1H).

MS (ESI) m/z 560 (M$^+$+1).

(Step 4) Synthesis of trans-4-(1-((2-(5-fluoro-2-methylphenylamino)-7-fluoro-6-benzoxazolyl)acetyl)-(4S)-fluoro-(2S)-pyrrolidinylmethoxy)cyclohexanecarboxylic acid

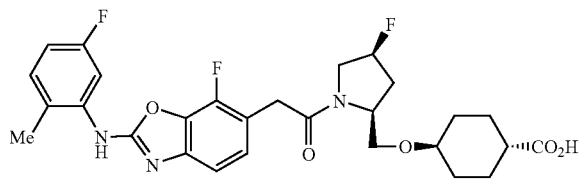

In THF/methanol (8/4 ml) was dissolved methyl trans-4-(1-((2-(5-fluoro-2-methylphenylamino)-7-fluoro-6-benzoxazolyl)acetyl)-(4S)-fluoro-(2S)-pyrrolidinylmethoxy)cyclohexanecarboxylate (243 mg, 0.434 mmol). To the resulting solution was added 1N NaOH (4 ml). After stirring at room temperature for 14 hours, the reaction mixture was distilled under reduced pressure to remove the solvent. The residue was acidified with 1N HCl. The crystals thus precipitated were collected by filtration under reduced pressure, washed with water and dried under reduced pressure to give the title compound (184 mg, 78%) as a colorless solid.

IR (ATR) ν 3224, 2937, 1720, 1703, 1639, 1610, 1579, 1452 cm$^{-1}$;

$^1$H-NMR (DMSO-d$_6$) δ: 1.12–1.43 (m, 4H), 1.82–2.22 (m, 7H), 2.30 (s, 3H), 3.20 (t, J=10.0 Hz, 1H), 3.40–4.08 (m, 6H), 4.13 and 4.36 (m and q, J=7.1 Hz, total 1H, amide isomers), 5.32 and 5.40 (dt and d, J=54.4, 4.4 and 53.5 Hz respectively, total 1H, amide isomers), 6.89 (dt, J=8.3,2.0 Hz, 1H), 7.05 and 7.08 (each t, J=7.1 and 7.3 Hz respectively, total 1H, amide isomers), 7.21 (dd, J=8.1, 2.4 Hz, 1H), 7.26 (t, J=7.8 Hz, 1H), 7.92 (d, J=11.5 Hz, 1H), 10.04 (br, 1H).

MS (ESI) m/z 546 (M$^+$+1);

Anal. Calcd for C$_{28}$H$_{30}$F$_3$N$_3$O$_5$ 0.4H$_2$O: C, 60.84; H, 5.62; N, 7.60; F, 10.31. Found: C, 60.91; H, 5.49; N, 7.41; F, 10.32.

Example 45 trans-4-(1-((2-(4-Fluoro-2-methylphenylamino)-7-fluoro-6-benzoxazolyl)acetyl)-(4S)-fluoro-(2S)-pyrrolidinylmethoxy)cyclohexanecarboxylic acid (Step 1) Synthesis of methyl (2-(4-fluoro-2-methylphenylamino)-7-fluoro-6-benzoxazolyl)acetate

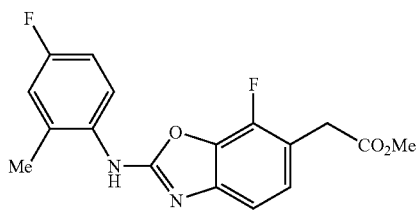

In methanol (30 ml) was dissolved methyl (4-amino-2-fluoro-3-hydroxyphenyl)acetate (1.0 g, 5.02 mmol). To the resulting solution was added 4-fluoro-2-methylphenyl isothiocyanate (0.74 ml, 5.23 mmol). After the mixture was stirred at room temperature for 5 days, mercuric oxide (yellow) (1.14 g, 4.36 mmol) was added thereto. The mixture was stirred at 70° C. for 6 hours. After cooling to room temperature, the reaction mixture was filtered through Celite and washed with methanol. The filtrate was distilled under reduced pressure to remove the solvent. The residue was purified by chromatography on a silica gel column, whereby from chloroform/ethyl acetate (30/1) eluate fractions, methyl (2-(4-fluoro-2-methylphenylamino)-7-fluoro-6-benzoxazolyl)acetate (1.32 g, 91%) was obtained as a colorless solid.

$^1$H-NMR (CDCl$_3$) δ: 2.34 (s, 3H), 3.72 (s, 3H), 3.75 (s, 2H), 6.71 (br, 1H), 6.92–7.01 (m, 2H), 7.09 (t, J=8.1 Hz, 1H), 7.18 (d, J=8.1 Hz, 1H), 7.93 (dd, J=8.8, 5.4 Hz, 1H).

MS (ESI) m/z 333 (M$^+$+1).

(Step 2) Synthesis of (2-(4-fluoro-2-methylphenylamino)-7-fluoro-6-benzoxazolyl)acetic acid

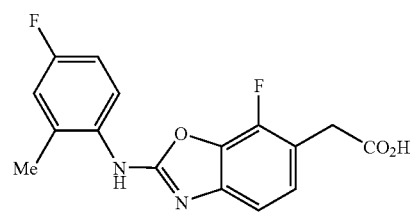

In THF/methanol (2:1, v/v, 120 ml) was dissolved methyl (2-(4-fluoro-2-methylphenylamino)-7-fluoro-6-benzoxazolyl)acetate (1.32 g, 3.97 mmol). To the resulting solution was added 1N NaOH (40 ml). After stirring at room temperature for 12 hours, the reaction mixture was distilled under reduced pressure to remove the solvent. The residue was acidified with 1N HCl. The crystals thus precipitated were collected by filtration under reduced pressure, washed with water and dried under reduced pressure to give (2-(4-fluoro-2-methylphenylamino)-7-fluoro-6-benzoxazolyl) acetic acid (1.38 g, 100%) as a colorless solid.

$^1$H-NMR (DMSO-d$_6$) δ: 2.26 (s, 3H), 3.68 (s, 2H), 7.06–7.14 (m, 4H), 7.75 (m, 1H), 9.91 (s, 1H).

MS (ESI) m/z 319 (M$^+$+1).

(Step 3) Synthesis of methyl trans-4-(1-((2-(4-fluoro-2-methylphenylamino)-7-fluoro-6-benzoxazolyl)acetyl)-(4S)-fluoro-(2S)-pyrrolidinylmethoxy)cyclohexanecarboxylate

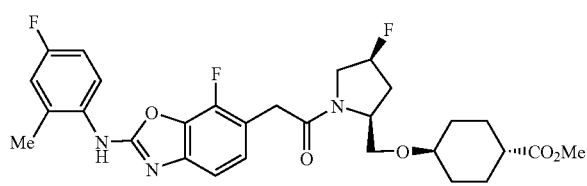

To a mixture of methyl (2-(4-fluoro-2-methylphenylamino)-7-fluoro-6-benzoxazolyl)acetate (159 mg, 0.50 mmol), methyl trans-4-((4S)-fluoro-(2S)-pyrrolidinylmethoxy)cyclohexanecarboxylate (the compound synthesized in (Step 3) of Example 21) (130 mg, 0.50 mmol), EDC HCl (144 mg, 0.75 mmol), HOBt (101 mg, 0.75 mmol) and triethylamine (0.35 ml, 2.50 mmol) was added DMF (4 ml). The resulting mixture was stirred at room temperature for 19 hours. The reaction mixture was poured in ice water, followed by extraction with ethyl acetate. The extract was washed with saturated brine, dried over anhydrous sodium sulfate, and distilled under reduced pressure to remove the solvent. The residue was purified by chromatography using a silica gel thin-layer plate (TLC), whereby from chloroform/acetone (5/1) eluate fractions, methyl trans-4-(1-((2-(4-fluoro-2-methylphenylamino)-7-fluoro-6-benzoxazolyl)acetyl)-(4S)-fluoro-(2S)-pyrrolidinylmethoxy)

cyclohexanecarboxylate (245 mg, 88%) was obtained as a colorless amorphous substance.

¹H-NMR (CDCl₃) δ: 1.27–1.57 (m, 5H), 1.96–2.28 (m, 7H), 2.32 (s, 3H), 2.45 and 2.51 (each d, J=15.7 and 14.9 Hz respectively, total 1H, amide isomers), 3.24–3.41 (m, 1H), 3.55 (m, 1H), 3.65 and 3.67 (each s, total 3H, amide isomers), 3.72–4.06 (m, 3H), 4.31–4.43 (m, 1H), 5.27 and 5.31 (each dt, J=54.0, 4.7 and 53.2, 4.3 Hz respectively, total 1H, amide isomers), 6.92–7.08 (m, 3H), 7.13 (t, J=8.1 Hz, 1H), 7.80 (m, 1H).

MS (ESI) m/z 560 (M⁺+1).

(Step 4) Synthesis of trans-4-(1-((2-(4-fluoro-2-methylphenylamino)-7-fluoro-6-benzoxazolyl)acetyl)-(4S)-fluoro-(2S)-pyrrolidinylmethoxy)cyclohexanecarboxylic acid

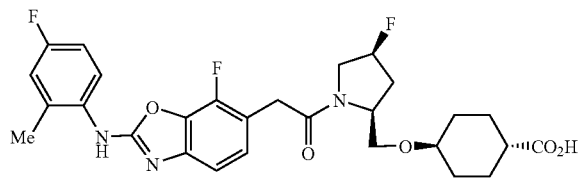

In THF/methanol (2:1, 12 ml) was dissolved methyl trans-4-(1-((2-(4-fluoro-2-methylphenylamino)-7-fluoro-6-benzoxazolyl)acetyl)-(4S)-fluoro-(2S)-pyrrolidinylmethoxy)cyclohexanecarboxylate (245 mg, 0.438 mmol). To the resulting solution was added 1N NaOH (4 ml). After stirring at room temperature for 14 hours, the reaction mixture was distilled under reduced pressure to remove the solvent. The residue was acidified with 1N HCl. The crystals thus precipitated were collected by filtration under reduced pressure, washed with water and dried under reduced pressure to give the title compound (199 mg, 83%) as a colorless solid.

IR (ATR) ν 3165, 2941, 1699, 1635, 1581, 1496, 1454 cm⁻¹; ¹H-NMR (DMSO-d₆) δ: 1.10–1.27 (m, 2H), 1.34 (t, J=12.4 Hz, 2H), 1.82–2.22 (m, 7H), 2.30 (s, 3H), 3.19 (t, J=8.8 Hz, 1H), 3.40–4.03 (m, 6H), 4.13 and 4.35 (m and q, J=7.1 Hz, total 1H, amide isomers), 5.32 and 5.40 (d and dt, J=54.9, 4.6 and 53.7 Hz respectively, total 1H, amide isomers), 6.99–7.16 (m, 4H), 7.76 (dd, J=8.8, 5.6 Hz, 1H), 9.89(br, 1H), 12.04(br, 1H).

MS (ESI) m/z 546 (M⁺+1);

Anal. Calcd for $C_{28}H_{30}F_3N_3O_5 \cdot 0.4H_2O$: C, 60.84; H, 5.62; N, 7.60; F, 10.31. Found: C, 61.15; H, 5.71; N, 7.15; F, 9.97.

Example 46 trans-4-(1-((2-(3-fluoro-2-methylphenylamino)-7-fluoro-6-benzoxazolyl)acetyl)-(4S)-fluoro-(2S)-pyrrolidinylmethoxy)cyclohexanecarboxylic acid (Step 1) Synthesis of methyl (2-(3-fluoro-2-methylphenylamino)-7-fluoro-6-benzoxazolyl)acetate

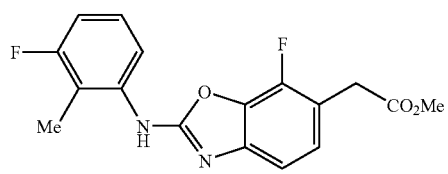

In THF (20 ml) was dissolved 3-fluoro-2-methylaniline (0.57 ml, 5.0 mmol). To the resulting solution was added thiophosgene (990 mg, 5.0 mmol) under stirring at room temperature. After the reaction mixture was stirred for 4 hours at room temperature, methyl (4-amino-2-fluoro-3-hydroxyphenyl)acetate (996 mg, 5.0 mmol) was added thereto. The resulting mixture was stirred further at room temperature for 2 days. Mercuric oxide (yellow) (1.08 g, 5.0 mmol) was added and the mixture was stirred at 70° C. for 4.5 hours. After cooling to room temperature, the reaction mixture was filtered through Celite and washed with methanol. The filtrate was distilled under reduced pressure to remove the solvent. The residue was purified by chromatography on a silica gel column, whereby from n-hexane/ethyl acetate (4/1) eluate fractions, methyl (2-(3-fluoro-2-methylphenylamino)-7-fluoro-6-benzoxazolyl)acetate (1.21 g, 73%) was obtained as a colorless solid.

¹H-NMR (CDCl₃) δ: 2.27 (s, 3H), 3.72 (s, 3H), 3.76 (s, 2H), 6.87 (t, J=8.8 Hz, 1H), 7.09 (t, J=6.6 Hz, 1H), 7.22 (d, J=7.8 Hz, 1H), 7.27 (m, 1H), 7.93 (d, J=7.8 Hz, 1H).

MS (ESI) m/z 333 (M⁺+1).

(Step 2) Synthesis of (2-(3-fluoro-2-methylphenylamino)-7-fluoro-6-benzoxazolyl)acetic acid

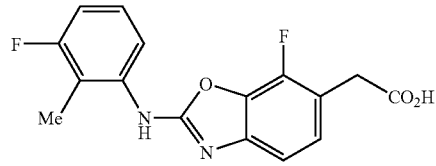

In THF/methanol (2:1, 60 ml) was dissolved methyl (2-(3-fluoro-2-methylphenylamino)-7-fluoro-6-benzoxazolyl)acetate (1.21 g, 3.64 mmol). To the resulting solution was added 1N NaOH (20 ml). After stirring at room temperature for 17 hours, the reaction mixture was distilled under reduced pressure to remove the solvent. The residue was acidified with 1N HCl. The crystals thus precipitated were collected by filtration under reduced pressure, washed with water and dried under reduced pressure to give (2-(3-fluoro-2-methylphenylamino)-7-fluoro-6-benzoxazolyl)acetic acid (1.10 g, 15%) as a colorless solid.

¹H-NMR (DMSO-d₆) δ: 2.21 (d, J=2.0 Hz, 3H), 3.66 (s, 2H), 7.00 (t, J=8.8 Hz, 1H), 7.10–7.16 (m, 2H), 7.26 and 7.30 (each d, J=7.8 and 8.1 Hz respectively, total 1H, amide isomers), 7.72 (d, J=7.1 Hz, 1H), 10.10 (br, 1H).

MS (ESI) m/z 319 (M⁺+1).

(Step 3) Synthesis of methyl trans-4-(1-((2-(3-fluoro-2-methylphenylamino)-7-fluoro-6-benzoxazolyl)acetyl)-(4S)-fluoro-(2S)-pyrrolidinylmethoxy)cyclohexanecarboxylate

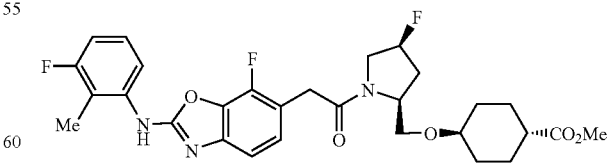

To a mixture of (2-(3-fluoro-2-methylphenylamino)-7-fluoro-6-benzoxazolyl)acetic acid (159 mg, 0.50 mmol), methyl trans-4-((4S)-fluoro-(2S)-pyrrolidinylmethoxy)cyclohexanecarboxylate (the compound synthesized in (Step 3) of Example 21) (130 mg, 0.50 mmol), EDC HCl (144 mg, 0.75 mmol), HOBt (101 mg, 0.75 mmol) and triethylamine (0.35 ml, 2.50 mmol) was added DMF (4 ml). The resulting mixture was stirred at room temperature for 18 hours. The reaction mixture was poured in ice water, followed by extraction with ethyl acetate. The extract was washed with saturated brine, dried over anhydrous sodium sulfate, and distilled under reduced pressure to remove the solvent. The residue was purified by chromatography using a thin-layer plate (TLC), whereby from chloroform/acetone (5/1) eluate fractions, methyl trans-4-(1-((2-(3-fluoro-2-methylphenylamino)-7-fluoro-6-benzoxazolyl)acetyl)-(4S)-fluoro-(2S)-pyrrolidinylmethoxy)cyclohexanecarboxylate (264 mg, 94%) was obtained as a colorless amorphous substance.

$^1$H-NMR (CDCl$_3$) δ: 1.91–1.58 (m, 4H), 1.96–2.21 (m, 5H), 2.25 (d, J=1.7 Hz, 3H), 2.27 and 2.48 (each m, total 1H, amide isomers), 3.22–3.33 (m, 1H), 3.35 and 3.56 (t and tt, J=8.5 and 9.3, 6.1 Hz respectively, total 1H, amide isomers), 3.65 and 3.67 (each s, total 3H, amide isomers), 3.69 (s, 1H), 3.70–4.02 (m, 5H), 4.33 and 4.39 (q and dt, J=7.6 and 7.8, 4.4 Hz, total 1H, amide isomers), 5.27 and 5.31 (each dt, =54.0, 4.1 and 53.0, 3.9 Hz, total 1H, amide isomers), 6.86 (t, J=8.3 Hz, 1H), 7.06 and 7.08 (each t, J=7.8 and 11.7 Hz respectively, total 1H, amide isomers), 7.16–7.29 (m, 2H), 7.88 (dd, J=8.1, 2.6 Hz, 1H).

MS (ESI) m/z 560 (M$^+$+1).

(Step 4) Synthesis of trans-4-(1-((2-(3-fluoro-2-methylphenylamino)-7-fluoro-6-benzoxazolyl)acetyl)-(4S)-fluoro-(2S)-pyrrolidinylmethoxy)cyclohexanecarboxylic acid

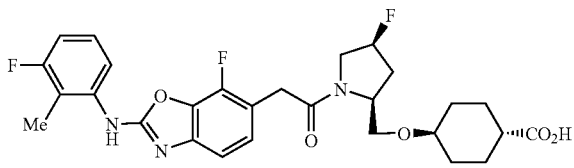

In THF/methanol (2:1, 63 ml) was dissolved methyl trans-4-(1-((2-(3-fluoro-2-methylphenylamino)-7-fluoro-6-benzoxazolyl)acetyl)-(4S)-fluoro-(2S)-pyrrolidinylmethoxy)cyclohexanecarboxylate (264 mg, 0.472 mmol). To the resulting solution was added 1N NaOH (10 ml). After stirring at room temperature for 17 hours, the reaction mixture was distilled under reduced pressure to remove the solvent. The residue was acidified with 1N HCl. The crystals thus precipitated were collected by filtration under reduced pressure, washed with water and dried under reduced pressure to give the title compound (199 mg, 83%) as a colorless solid.

IR (ATR) ν 3167, 2939, 1701, 1641, 1581, 1452 cm$^{-1}$;

$^1$H-NMR (DMSO-d$_6$) δ: 1.09–1.39 (m, 5H), 1.83–2.03 (m, 5H), 2.08–2.17 (m, 2H), 2.50 (d, J=2.0 Hz, 3H), 3.19 (t, J=8.8 Hz, 2H), 3.41–4.06 (m, 4H), 4.12 and 4.36 (m and q, J=6.8 Hz, total 1H, amide isomers), 5.32 and 5.40 (dt and d, J=54.5, 5.4 and 54.8 Hz respectively, total 1H, amide isomers), 7.00 (t, J=8.8 Hz, 1H), 7.05 (m, 1H), 7.13 and 7.15 (each d, J=2.7 and 2.9 Hz respectively, total 1H, amide isomers), 7/28 (dd, J=14.9, 8.1 Hz, 1H), 7.72 (d, J=8.1 Hz, 1H).

MS (ESI) m/z 546 (M$^+$+1);

Anal. Calcd for C$_{28}$H$_{30}$F$_3$N$_3$O$_5$ 0.1HCl.1.4H$_2$O: C, 58.55; H, 5.77; N, 7.32; F, 9.92. Found: C, 58.24; H, 5.38; N, 7.09; F, 9.63.

Example 47 trans-4-(1-((2-(5-Fluoro-2-methylphenylamino)-4-fluoro-6-benzoxazolyl)acetyl)-(4S)-fluoro-(2S)-pyrrolidinylmethoxy)cyclohexanecarboxylic acid (Step 1) Synthesis of 4,6-difluoro-2-hydroxynitrobenzene

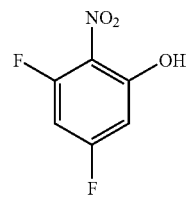

Under stirring at room temperature, 10N NaOH (18 ml, 180 mmol) was added dropwise to a solution of 2,4,6-trifluoronitrobenzne (15.0 g, 84.7 mmol) in DMSO (75 ml). After completion of the dropwise addition, the reaction mixture was stirred at room temperature for 18 hours. The reaction mixture was poured in 1N HCl to neutralize therewith, followed by extraction with ether. The extract was washed with saturated brine, dried over anhydrous sodium sulfate, and distilled under reduced pressure to remove the solvent. The residue was purified by chromatography on a silica gel column, whereby from ethyl acetate/chloroform (1/10) eluate fractions, 4,6-difluoro-2-hydroxynitrobenzene (12.5 g, 84%) was obtained as a yellow solid.

$^1$H-NMR (CDCl$_3$) δ: 6.55–6.60 (m, 1H), 6.68–6.71 (m, 1H), 10.90 (s, 1H).

(Step 2) Synthesis of 2-benzyloxy-4,6-difluoronitrobenzene

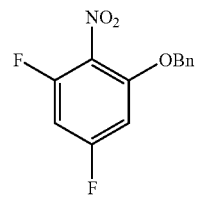

To a solution of 4,6-difluoro-2-hydroxynitrobenzene (12.5 g, 71.1 mmol) in DMF (150 ml) was added sodium hydride (60% in oil, 3.70 g, 92.4 mmol) under stirring at 0° C., and the reaction mixture was stirred for 15 minutes. Benzyl bromide (11.0 ml, 92.4 mmol) was added dropwise at 0° C. After completion of the dropwise addition, the reaction mixture was stirred at 80° C. for 18 hours. After cooling to room temperature, the mixture was poured in ice-1N HCl to neutralize therewith, followed by extraction with ether. The extract was washed with saturated brine, dried over anhydrous sodium sulfate, and distilled under reduced pressure to remove the solvent. The residue was purified by chromatography on a silica gel column, whereby from ethyl acetate/hexane (1/5) eluate fractions, 2-benzyloxy-4,6-difluoronitrobenzene (13.7 g, 73%) was obtained as a yellow solid.

$^1$H-NMR (CDCl$_3$) δ: 5.18 (s, 2H), 6.55–6.63 (m, 2H), 7.32–7.46 (m, 5H).

(Step 3) Synthesis of tert-butyl ethyl 5-benzyloxy-3-fluoro-4-nitrophenylmalonate

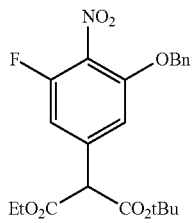

To a solution of tert-butyl ethyl malonate (10.0 g, 51.0 mmol) in DMF (200 ml) was added sodium hydride (60% in oil, 2.04 g, 51.0 mmol) at 0° C. under stirring. The reaction mixture was stirred at the same temperature for 30 minutes. A solution of 2-benzyloxy-4,6-difluoronitrobenzene (9.02 g, 34.0 mmol) in DMF (60 ml) was added dropwise to the reaction mixture at 0° C. The reaction mixture was then stirred at 80° C. for 18 hours. After cooling to room temperature, the reaction mixture was poured in ice-1N HCl to neutralize therewith, followed by extraction with ether. The extract was washed with saturated brine, dried over anhydrous sodium sulfate, then distilled under reduced pressure to remove the solvent. The residue was purified by chromatography on a silica gel column, whereby from with ethyl acetate/hexane (1/5) eluate fractions, tert-butyl ethyl 5-benzyloxy-3-fluoro-4-nitrophenylmalonate (2.91 g, 17%) was obtained as a yellow oil.

$^1$H-NMR (CDCl$_3$) δ: 1.24–1.30 (m, 3H), 1.47 (s, 9 H), 4.11–4.28 (m, 2H), 4.47 (s, 1H), 5.20 (s, 2H), 6.91 (d, J=9.6 Hz, 1H), 7.00 (s, 1H), 7.32–7.39 (m, 5 H).

(Step 4) Synthesis of ethyl 5-benzyloxy-3-fluoro-4-nitrophenylacetate

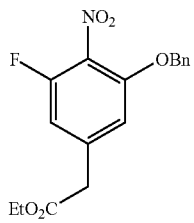

In methylene chloride (30 ml) was dissolved tert-butyl ethyl 5-benzyloxy-3-fluoro-4-nitrophenylmalonate (2.89 g, 6.67 mmol). To the resulting solution was added trifluoroacetic acid (30 ml). The resulting mixture was stirred at room temperature for 3.5 hours. The reaction mixture was distilled under reduced pressure to remove the solvent. The residue was neutralized with an aqueous saturated solution of sodium bicarbonate, followed by extraction with ethyl acetate. The extract was washed with saturated brine, dried over anhydrous sodium sulfate and distilled under reduced pressure to remove the solvent. The residue was purified by chromatography on a silica gel column, whereby from ethyl acetate/hexane (1/5) eluate fractions, ethyl 5-benzyloxy-3-fluoro-4-nitrophenylacetate (1.57 g, 70%) was obtained as a yellow oil.

$^1$H-NMR (CDCl$_3$) δ: 1.27 (t, J=7.2 Hz, 3H), 3.60 (s, 2H), 4.17 (q, J=7.2, 14.4 Hz, 2H), 5.20 (s, 2H), 6.80 (d, J=10.0 Hz, 1H), 6.84 (s, 1H), 7.27–7.40 (m, 5 H).

(Step 5) Synthesis of ethyl 4-amino-3-fluoro-5-hydroxyphenylacetate

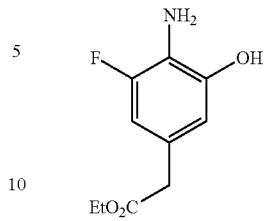

Ethyl 3-fluoro-4-nitro-5-benzyloxyphenylacetate (1.54 g, 4.62 mmol) and 10% palladium-carbon (122 mg) were subjected to catalytic hydrogenation for 20 hours under normal pressure while stirring at room temperature in EtOH (20 ml). From the reaction mixture, the catalyst was filtered off. The filtrate was distilled under reduced pressure to remove the solvent. The residue was purified by chromatography on a silica gel column, whereby from ethyl acetate/hexane (1/2) eluate fractions, ethyl 4-amino-3-fluoro-5-hydroxyphenylacetate (639 mg, 65%) was obtained as a brown oil.

$^1$H-NMR (CDCl$_3$) δ: 1.25 (t, J=7.2 Hz, 3H), 3.43 (s, 2H), 4.15 (q, J=7.2, 14.4 Hz, 2H), 6.48 (s, 1H), 6.54 (d, J=10.4 Hz, 1H).

(Step 6) Synthesis of 5-fluoro-2-methylphenyl isothiocyanate

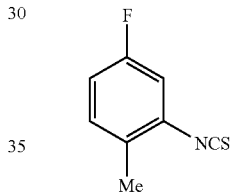

Under stirring at 0° C., a solution of 5-fluoro-2-methylaniline (1.23 g, 9.84 mmol) in methylene chloride (10 ml) was added dropwise to a mixture of calcium carbonate (2.46 g, 24.6 mmol) and thiophosgene (750 μl, 9.84 mmol) in a methylene chloride/water (1/1, 40 ml) mixture. After completion of the dropwise addition, the reaction mixture was stirred further at 0° C. for 35 minutes. The reaction mixture was poured in ice-1N HCR, followed by extraction with chloroform. The extract was washed with saturated brine, dried over anhydrous sodium sulfate, and distilled under reduced pressure to remove the solvent to give 5-fluoro-2-methylphenyl isothiocyanate (1.45 g, 88%) as a brown oil.

MS (ESI) m/z 167 (M$^+$).

(Step 7) Synthesis of ethyl (2-(5-fluoro-2-methylphenylamino)-4-fluoro-6-benzoxazolyl)acetate

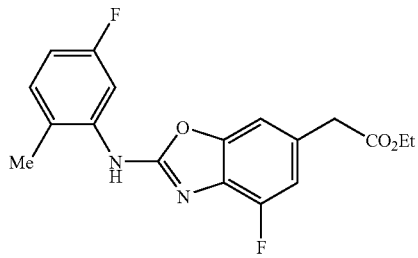

Under stirring at room temperature, ethyl 4-amino-3-fluoro-5-hydroxyphenylacetate (233 mg, 1.10 mmol) was added to a solution of 5-fluoro-2-methylphenyl isothiocyanate (184 mg, 1.10 mmol) in methanol (20 ml). The resulting mixture was stirred at 70° C. for 1 hour. To the reaction mixture was added mercuric oxide (yellow) (262 mg, 1.21 mmol), followed by stirring for further 30 minutes. After cooling to room temperature, the reaction mixture was filtered through Celite. The filtrate was washed with methanol and then, distilled under reduced pressure to remove the solvent. The residue was purified by chromatography on a silica gel column, whereby from chloroform/methanol (10/1) eluate fractions, ethyl (2-(5-fluoro-2-methylphenylamino)-4-fluoro-6-benzoxazolyl)acetate (216 mg, 57%) was obtained as a pale yellow solid.

$^1$H-NMR (CDCl$_3$) δ: 1.28 (t, J=7.2 Hz, 3H), 2.32 (s, 3H), 3.67 (s, 2H), 4.18 (q, J=6.8, 14.4 Hz, 2H), 6.74–6.79 (m, 1H), 6.92–6.97 (m, 2H), 7.14–7.17 (m, 2H), 8.05–8.09 (m, 1H).

MS (ESI) m/z 347 (M$^+$+1).

(Step 8) Synthesis of (2-(5-fluoro-2-methylphenylamino)-4-fluoro-6-benzoxazolyl)acetic acid

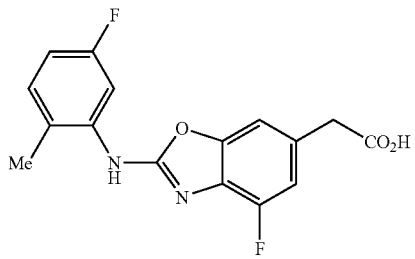

Ethyl (2-(5-fluoro-2-methylphenylamino)-4-fluoro-6-benzoxazolyl)acetate (215 mg, 0.62 mmol) was dissolved in THF/methanol (1/1, 20 ml). To the resulting solution was added 0.25N NaOH (12.4 ml, 3.10 mmol). The resulting mixture was stirred at room temperature for 1 hour. The reaction mixture was poured in 1N HCl to acidify the mixture, followed by extraction with chloroform/methanol (10/1). The extract was dried over anhydrous sodium sulfate, and distilled under reduced pressure to remove the solvent to give (2-(5-fluoro-2-methylphenylamino)-4-fluoro-6-benzoxazolyl)acetic acid (165 mg, 83%) as a pale brown solid.

$^1$H-NMR (CDCl$_3$) δ: 2.28 (s, 3H), 3.66 (s, 2H), 6.87–6.91 (m, 1H), 7.03 (d, J=11.6 Hz, 1H), 7.23–7.29 (m, 3H), 7.84–7.87 (m, 1H), 9.98 (brs, 1H).

MS (ESI) m/z 319 (M$^+$+1).

(Step 9) Synthesis of methyl trans-4-(1-((2-(5-fluoro-2-methylphenylamino)-4-fluoro-6-benzoxazolyl)acetyl)-(4S)-fluoro-(2S)-pyrrolidinylmethoxy)cyclohexanecarboxylate

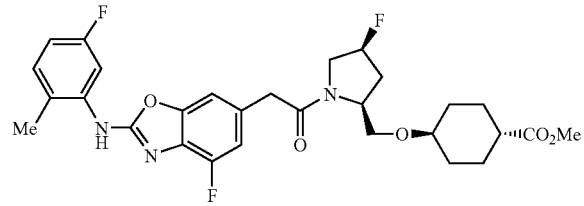

To a solution of (2-(5-fluoro-2-methylphenylamino)-4-fluoro-6-benzoxazolyl)acetic acid (165 mg, 0.52 mmol), methyl trans-4-((4S)-fluoro-(2S)-pyrrolidinylmethoxy)cyclohexanecarboxylate (the compound synthesized in (Step 3) of Example 21) (134 mg, 0.52 mmol) and EDC-HCl (119 mg, 0.62 mmol) in DMF (10 ml) was added HOBt (14.0 mg, 0.10 mmol). The resulting mixture was stirred at room temperature for 18 hours. Water was added to the reaction mixture, followed by extraction with ethyl acetate. The extract was washed with saturated brine, dried over anhydrous sodium sulfate, and distilled under reduced pressure to remove the solvent. The residue was purified by chromatography using a silica gel thin-layer plate (TLC), whereby from hexane/ethyl acetate (1/5) eluate fractions, methyl trans-4-(1-((2-(5-fluoro-2-methylphenylamino)-4-fluoro-6-benzoxazolyl)acetyl)-(4S)-fluoro-(2S)-pyrrolidinylmethoxy)cyclohexanecarboxylate (251 mg, 87%) was obtained as a colorless amorphous substance.

$^1$H-NMR (CDCl$_3$), mixture of amide-isomers, δ: 1.24–1.32 (m, 2H), 1.40–1.53 (m, 2H), 1.96–2.52 (series of m, 7H), 2.31 (s, 3H), 3.22–4.41 (series of m, 8H), 3.65 and 3.67 (s, total 3H), 4.28–4.42 (m, 1H), 5.17–5.36 (m, 1H), 6.73–6.77 (m, 1H), 6.89–6.92 (m, 1H), 7.12–7.16 (m, 3H), 8.01–8.05 (m, 1H).

MS (ESI) m/z 561 (M$^+$+2).

(Step 10) Synthesis of trans-4-(1-((2-(5-fluoro-2-methylphenylamino)-4-fluoro-6-benzoxazolyl)acetyl)-(4S)-fluoro-(2S)-pyrrolidinylmethoxy)cyclohexanecarboxylic acid

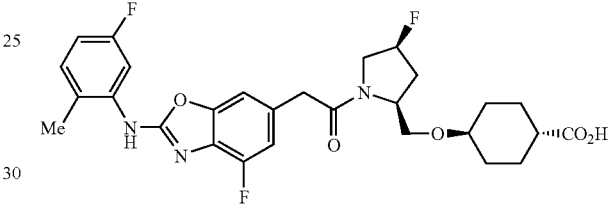

Methyl trans-4-(1-((2-(5-fluoro-2-methylphenylamino)-4-fluoro-6-benzoxazolyl)acetyl)-(4S)-fluoro-(2S)-pyrrolidinylmethoxy)cyclohexanecarboxylate (239 mg, 0.43 mmol) was dissolved in THF/methanol (1/1, 20 ml). To the resulting solution was added aqueous 0.25N NaOH (8.50 ml, 2.14 mmol). The resulting mixture was stirred at room temperature for 2 hours. The reaction mixture was acidified with 1N HCl, followed by extraction with chloroform/methanol (10/1). The extract was dried over anhydrous sodium sulfate, and distilled under reduced pressure to remove the solvent. The residue was purified by chromatography on a silica gel column, whereby from chloroform/methanol (15/1) eluate fractions, the title compound (233 mg, 100%) was obtained as a colorless amorphous substance.

$^1$H-NMR (CDCl$_3$), mixture of amide-isomers, δ: 1.22–1.33 (m, 2H), 1.42–1.52 (m, 2H), 2.02–2.62 (series of m, 7H), 2.31 (s, 3H), 3.23–4.42 (series of m, 8H), 4.28–4.42 (m, 1H), 5.17–5.36 (m, 1H), 6.74–6.78 (m, 1H), 6.89–6.92 (m, 1H), 7.11–7.15 (m, 3H), 7.75 (d, J=10.5 Hz, 1H).

MS (ESI) m/z 547 (M$^+$+2).

Example 48 trans-4-(1-((2-(1-Naphthylamino)-7-fluoro-6-benzoxazolyl)acetyl)-(4S)-fluoro-(2S)-pyrrolidinylmethoxy)cyclohexanecarboxylic acid (Step 1) Synthesis of methyl (2-(1-naphthylamino)-7-fluoro-6-benzoxazolyl)acetate

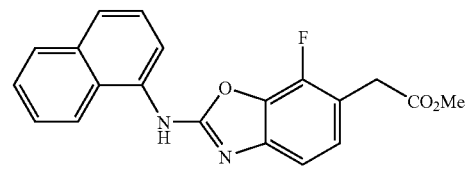

Methyl (4-amino-2-fluoro-3-hydroxyphenyl)acetate (996 mg, 5.00 mmol) was dissolved in methanol (50 ml). To the resulting solution was added 1-naphthyl isothiocyanate (926 mg, 5.00 mmol). After the resulting mixture was stirred at room temperature for 2 days, mercuric oxide (yellow) (1.08 g, 5.00 mmol) was added thereto. The mixture was stirred at 70° C. for 3.5 hours. After cooling to room temperature, the reaction mixture was filtered through Celite and washed with methanol. The filtrate was distilled under reduced pressure to remove the solvent. The crude crystals thus obtained were recrystallized from chloroform/n-hexane to give methyl (2-(1-naphthylamino)-7-fluoro-6-benzoxazolyl)acetate (1.41 g, 81%) as a pale gray crystalline powder.

$^1$H-NMR (CDCl$_3$) δ: 3.717 and 3.723 (each s, total 3H, amide isomers), 3.75 (d, J=1.2 Hz, 2H), 7.05 and 7.07 (each d, J=6.6 and 6.3 Hz respectively, total 1H, amide isomers), 7.53–7.59 (m, 3H), 7.73 (d, J=8.3 Hz, 1H), 7.92 (dd, J=7.1,2.4 Hz, 1H), 8.14 (dd, J=7.8,1.0 Hz, 1H).

MS (ESI) m/z 351 (M$^+$+1).

(Step 2) Synthesis of (2-(1-naphthylamino)-7-fluoro-6-benzoxazolyl)acetic acid

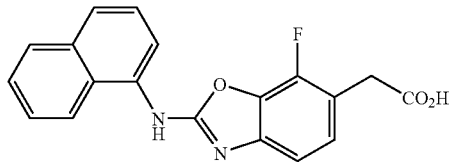

Methyl (2-(1-naphthylamino)-7-fluoro-6-benzoxazolyl)acetate (1.41 g, 4.02 mmol) was dissolved in THF/methanol (21, 30 ml). To the resulting solution was added 1N NaOH (10 ml). After stirring at room temperature for 12 hours, the reaction mixture was distilled under reduced pressure to remove the solvent. The residue was acidified with 1N HCl. The crystals thus precipitated were collected by filtration under reduced pressure, washed with water and dried under reduced pressure to give (2-(1-naphthylamino)-7-fluoro-6-benzoxazolyl)acetic acid (1.44 g, 100%) as a brown solid.

$^1$H-NMR (DMSO-d$_6$) δ: 3.70 (s, 2H), 7.15 (q, J=6.3 Hz, 1H), 7.16 (s, 1H), 7.55–7.61 (m, 3H), 7.78 (d, J=7.8 Hz, 1H), 7.97 and 7.98 (d and m, J=5.9 Hz, total 1H, amide isomers), 8.10 (d, J=7.6 Hz, 1H), 8.25–8.30 (m, 1H), 10.64 (br, 1H).

MS (ESI) m/z 337 (M$^+$+1).

(Step 3) Synthesis of methyl trans-4-(1-((2-(1-naphthylamino)-7-fluoro-6-benzoxazolyl)acetyl)-(4S)-fluoro-(2S)-pyrrolidinylmethoxy)cyclohexanecarboxylate

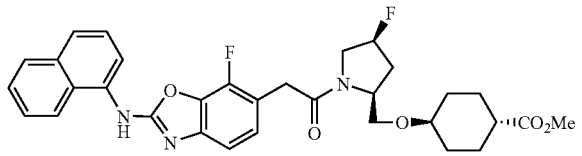

To a mixture of methyl (2-(1-naphthylamino)-7-fluoro-6-benzoxazolyl)acetate (168 mg, 0.50 mmol), methyl trans-4-((4S)-fluoro-(2S)-pyrrolidinylmethoxy)cyclohexanecarboxylate (the compound synthesized in (Step 3) of Example 21) (130 mg, 0.50 mmol), EDC HCl (144 mg, 0.75 mmol), HOBt (101 mg, 0.75 mmol) and triethylamine (0.35 ml, 2.50 mmol) was added DMF (5 ml). The resulting mixture was stirred at room temperature for 3 days. The reaction mixture was poured in ice water, followed by extraction with ethyl acetate. The extract was washed with saturated brine, dried over anhydrous sodium sulfate, and distilled under reduced pressure to remove the solvent. The residue was purified by chromatography using a thin-layer plate (TLC), whereby from chloroform/acetone (10/1) eluate fractions, methyl trans-4-(1-((2-(1-naphthylamino)-7-fluoro-6-benzoxazolyl)acetyl)-(4S)-fluoro-(2S)-pyrrolidinylmethoxy)cyclohexanecarboxylate (280 mg, 97%) was obtained as a pale brown oil.

$^1$H-NMR (CDCl$_3$) δ: 1.15–1.57 (m, 5H), 1.95–2.53 (m, 8H), 3.19–3.58 (m, 2H), 3.64 and 3.66 (each s, total 3H, amide isomers), 3.71–4.06 (m, 3H), 4.29–0.45 (m, 1H), 5.17–5.39 (m, 1H), 6.95–7.11 (m, 2H), 7.51–7.56 (m, 3H), 7.69 (d, J=7.3 Hz, 1H), 7.89 (m, 1H), 8.07–8.13 (m, 2H), 8.56 (br, 1H).

MS (ESI) m/z 578 (M$^+$+1).

(Step 4) Synthesis of trans-4-(1-((2-(1-naphthylamino)-7-fluoro-6-benzoxazolyl)acetyl)-(4S)-fluoro-(2S)-pyrrolidinylmethoxy)cyclohexanecarboxylic acid

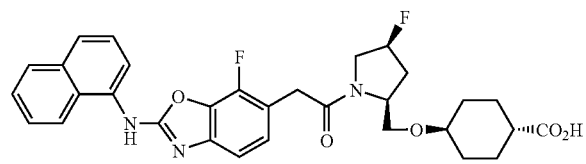

Methyl trans-4-(1-((2-(1-naphthylamino)-7-fluoro-6-benzoxazolyl)acetyl)-(4S)-fluoro-(2S)-pyrrolidinylmethoxy)cyclohexanecarboxylate (280 mg, 0.485 mmol) was dissolved in THF/methanol (2:1, v/v, 15 ml). To the resulting solution was added 1N NaOH (5 ml). After stirring at room temperature for 3 days, the reaction mixture was distilled under reduced pressure to remove the solvent. The residue was acidified with 1N HCl. The crystals thus precipitated were collected by filtration under reduced pressure, washed with water and dried under reduced pressure to give the title compound (204 mg, 74.6%) as a pale pink solid.

IR (ATR) ν 3278, 2935, 2864, 1701, 1637, 1572, 1452 cm$^{-1}$;

$^1$H-NMR (DMSO-d$_6$) δ: 1.09–1.41 (m, 4H), 1.82–2.36 (m, 7H), 3.19 (m, 2H), 3.36–4.39 (m, 6H), 5.25–5.50 (m, 1H), 7.01–7.09 (m, 1H), 7.15 and 7.16 (each d, J=2.9 and 3.2 Hz respectively, total 1H, amide isomers), 7.55–7.60 (m, 3H), 7.77 (d, J=8.3 Hz, 1H), 7.97 and 7.98 (each d, J=3.2 and 2.2 Hz respectively, total 1H, amide isomers), 8.11 (d, J=7.8 Hz, 1H), 8.28 and 8.29 (each d, J=5.1 and 4.2 Hz respectively, total 1H, amide isomers), 10.64 (br, 1H), 12.04 (br, 1H).

MS (ESI) m/z 564 (M$^+$+1).

Example 49 trans-4-(1-(4-(2-Benzoxazolyl)amino-3-chlorophenylacetyl)-(4S)-fluoro-(2S)-pyrrolidinylmethoxy)cyclohexanecarboxylic acid (Step 1) Synthesis of ethyl (4-(2-benzoxazolyl)amino-3-chlorophenyl)acetate

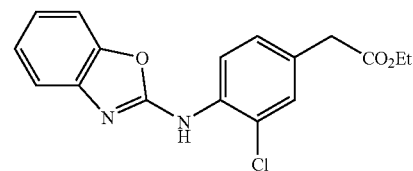

In xylene (10 ml), 2-chlorobenzoxazole (743 μl, 6.51 mmol) and ethyl 4-amino-3-chlorophenylacetate (1.30 g, 6.51 mmol) were heated under reflux for 2 hours. After cooling to room temperature, the reaction mixture was diluted with chloroform (50 ml). The mixture was washed with water, dried over anhydrous sodium sulfate, and distilled under reduced pressure to remove the solvent. The residue was purified by chromatography on a silica gel column, whereby from n-hexane/ethyl acetate (9:1, v/v) eluate fractions, ethyl (4-(2-benzoxazolyl)amino-3-chlorophenyl)acetate (1.70 g, 79%) was obtained as a pale yellow solid.

$^1$H-NMR (CDCl$_3$) δ: 1.25–1.28 (m, 3H), 3.58 (s, 2H), 4.14–4.19 (m, 2H), 7.15–7.19 (m, 1H), 7.24–7.30 (m, 3H), 7.36–7.38 (m, 2H), 7.52–7.54 (m, 1H), 8.51–8.53 (m, 1H).

MS (ESI) m/z 331 (M$^+$+1).

(Step 2) Synthesis of (4-(2-benzoxazolyl)amino-3-chlorophenyl)acetic acid

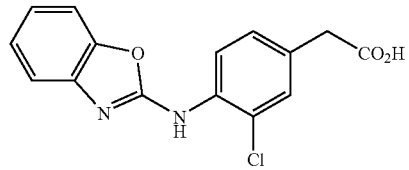

Ethyl (4-(2-benzoxazolyl)amino-3-chlorophenyl)acetate (1.70 g, 5.14 mmol) was dissolved in THF (30 ml). To the resulting solution was added 0.5N NaOH (30 ml, 15.0 mmol) under stirring. The resulting mixture was stirred at room temperature for 20 hours. The mixture was concentrated and the residue was acidified with ice-1N HCl. The crystals thus precipitated were collected by filtration under reduced pressure, washed with water and dried under reduced pressure to give (4-(2-benzoxazolyl)amino-3-chlorophenyl)acetic acid (1.24 g, 80%) as a pale yellow crystalline powder.

$^1$H-NMR (DMSO-d$_6$) δ: 3.62 (s, 2H), 7.10–7.19 (m, 1H), 7.21–7.28 (m, 1H), 7.30–7.31 (m, 1H), 7.38–7.40 (m, 1H), 7.45–7.49 (m, 3H), 7.94–7.96 (m, 1H).

(Step 3) Synthesis of methyl trans-4-(1-(4-(2-benzoxazolyl)amino-3-chlorophenylacetyl)-(4S)-fluoro-(2S)-pyrrolidinylmethoxy)cyclohexanecarboxylate

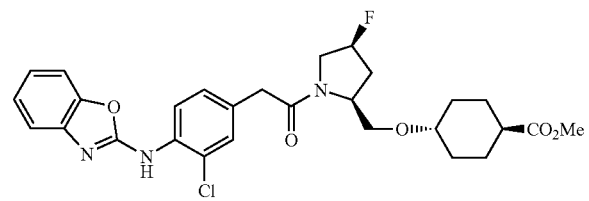

In DMF (5 ml), (4-(2-benzoxazolyl)amino-3-chlorophenyl)acetic acid (247 mg, 0.82 mmol), methyl trans-4-((4S)-fluoro-(2S)-pyrrolidinylmethoxy)cyclohexanecarboxylate (the compound synthesized in (Step 3) of Example 21) (225 mg, 0.87 mmol), EDC·HCl (235 mg, 1.23 mmol), HOBt (166 mg, 1.23 mmol), and triethylamine (171 μl, 1.23 mmol) were stirred at room temperature for 5 hours. To the reaction mixture was added water (20 ml), followed by extraction with ethyl acetate. The extract was washed with saturated brine, dried over anhydrous sodium sulfate, and distilled under reduced pressure to remove the solvent. The residue was purified by chromatography on a silica gel column, whereby from chloroform/methanol (60:1, v/v) eluate fractions, trans-4-(1-(4-(2-benzoxazolyl)amino-3-chlorophenylacetyl)-(4S)-fluoro-(2S)-pyrrolidinylmethoxy)cyclohexanecarboxylate (454 mg, 100%) was obtained as a pale yellow amorphous substance.

$^1$H-NMR (CDCl$_3$) δ: 1.18–1.53 (m, 4H), 1.97–2.51 (m, 7H), 3.23–3.36 and 3.49–3.59 (each m, total 2H), 3.63–4.01 (m, 8H), 4.19–4.24 and 4.35–4.41 (each m, total 1H), 5.17–5.20 and 5.30–5.33 (each m, total 1H), 7.15–7.19 (m, 1H), 7.24–7.27 (m, 2H), 7.36–7.38 (m, 2H), 7.52–7.54 (m, 1H), 8.47–8.53 (m, 1H).

MS (ESI) m/z 544 (M$^+$+1).

(Step 4) Synthesis of trans-4-(1-(4-(2-benzoxazolyl)amino-3-chlorophenylacetyl)-(4S)-fluoro-(2S)-pyrrolidinylmethoxy)cyclohexanecarboxylic acid

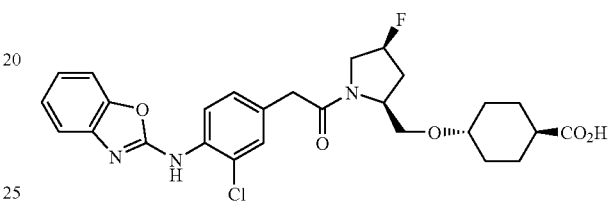

To methyl trans-4-(1-(4-(2-benzoxazolyl)amino-3-chlorophenylacetyl)-(4S)-fluoro-(2S)-pyrrolidinylmethoxy)cyclohexanecarboxylate (454 mg, 0.83 mmol) were added THF (5 ml) and 0.5N NaOH (5.0 ml, 2.50 mmol), followed by stirring at room temperature for 15 hours. The reaction mixture was poured in ice-1N HCl to acidify the mixture, followed by extraction with ethyl acetate. The extract was washed with saturated brine, dried over anhydrous sodium sulfate, and distilled under reduced pressure to remove the solvent. The residue was purified by chromatography on a silica gel column, whereby from chloroform/methanol (50:1, v/v) eluate fractions, the title compound (359 mg, 81%) was obtained as a colorless amorphous substance.

$^1$H-NMR (CDCl$_3$) δ: 1.21–1.34 (m, 2H), 1.43–1.55 (m, 2H), 2.02–2.51 (m, 7H), 3.24–3.37 and 3.47–3.52 (each m, total 2H), 3.58–4.01 (m, 5 H), 4.19–4.25 and 4.35–4.41 (each m, total 1H), 5.16–5.19 and 5.30–5.32 (each m, total 1H), 7.12–7.16 (m, 1H), 7.22–7.25 (m, 2H), 7.33–7.36 (m, 2H), 7.47–7.49 (m, 1H), 8.27–8.32 (m, 1H).

MS (ESI) m/z 530 (M$^+$+1);

Anal. Calcd for $C_{27}H_{29}ClFN_3O_5 \cdot 5/4H_2O$: C, 58.69; H, 5.75; N, 7.61. Found: C, 58.74; H, 5.17; N, 7.38.

Example 50 trans-4-(1-(4-(2-Benzoxazolyl)amino-3-methylphenylacetyl)-(4S)-fluoro-(2S)-pyrrolidinylmethoxy) cyclohexanecarboxylic acid (Step 1) Synthesis of tert-butyl (4-(2-benzoxazolyl)amino-3-methylphenyl)acetate

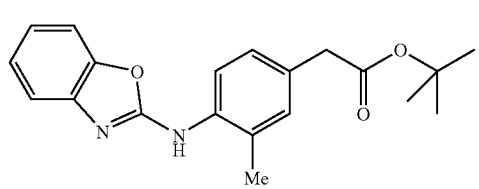

In xylene (20 ml), 2-chlorobenzoxazole (845 μl, 7.40 mmol) and tert-butyl 4-amino-3-methylphenylacetate (1.26 g, 5.69 mmol) were heated under reflux for 2 hours under stirring. After cooling to room temperature, the reaction mixture was distilled under reduced pressure to remove the solvent. The residue was dissolved in chloroform/methanol (9:1, v/v, 100 ml). The resulting solution was washed with water, dried over anhydrous sodium sulfate, and distilled under reduced pressure to remove the solvent. The residue was purified by chromatography on a silica gel column, whereby from n-hexane/ethyl acetate (4:1, v/v) eluate fractions, tert-butyl (4-(2-benzoxazolyl)amino-3-methylphenyl)acetate (1.17 g, 61%) was obtained as a yellow amorphous substance.

$^1$H-NMR (CDCl$_3$) δ: 1.46 (s, 9 H), 2.30 (s, 3H), 3.49 (s, 2H), 7.05–7.24 (m, 4H), 7.27–7.29 (m, 1H), 7.38–7.40 (m, 1H), 7.86–7.88 (m, 2H).

(Step 2) Synthesis of (4-(2-benzoxazolyl)amino-3-methylphenyl)acetic acid

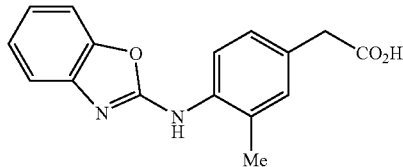

In methylene chloride (10 ml) was dissolved tert-butyl (4-(2-benzoxazolyl)amino-3-methylphenyl)acetate (1.17 g, 3.46 mmol). To the resulting solution was added trifluoroacetic acid (10 ml). The resulting mixture was stirred at room temperature for 20 hours. The reaction mixture was poured in ice water, followed by extraction with ethyl acetate. The extract was washed with saturated brine, dried over anhydrous sodium sulfate, and distilled under reduced pressure to remove the solvent. The residue was purified by chromatography on a silica gel column, whereby from chloroform/methanol (60:1 to 50:1, v/v) eluate fractions, (4-(2-benzoxazolyl)amino-3-methylphenyl)acetic acid (924 mg, 95%) was obtained as a pale yellow solid.

$^1$H-NMR (CDCl$_3$) δ: 2.38 (s, 3H), 3.68 (s, 2H), 7.22–7.29 (m, 4H), 7.36–7.42 (m, 3H), 7.48–7.52 (m, 1H).

MS (ESI) m/z 283 (M$^+$+1).

(Step 3) Synthesis of methyl trans-4-(1-(4-(2-benzoxazolyl)amino-3-methylphenylacetyl)-(4S)-fluoro-(2S)-pyrrolidinylmethoxy)cyclohexanecarboxylate

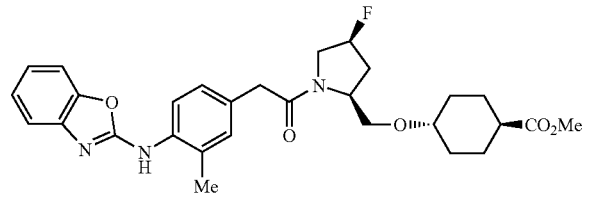

To a mixture of (4-(2-benzoxazolyl)amino-3-methylphenyl)acetic acid (220 mg, 0.78 mmol), methyl trans-4-((4S)-fluoro-(2S)-pyrrolidinylmethoxy)cyclohexanecarboxylate (the compound synthesized in (Step 3) of Example 21) (210 mg, 0.80 mmol), EDC•HCl (224 mg, 1.17 mmol), HOBt (158 mg, 1.17 mmol), and triethylamine (163 μl, 1.17 mmol) was added DMF (5 ml). The resulting mixture was stirred at room temperature for 15 hours. To the reaction mixture was added water, followed by extraction with ethyl acetate. The extract was washed with saturated brine, dried over anhydrous sodium sulfate, and distilled under reduced pressure to remove the solvent. The residue was purified by chromatography on a silica gel column, whereby from chloroform/methanol (60:1, v/v) eluate fractions, methyl trans-4-(1-(4-(2-benzoxazolyl)amino-3-methylphenylacetyl)-(4S)-fluoro-(2S)-pyrrolidinylmethoxy)cyclohexanecarboxylate (380 mg, 93%) was obtained as a colorless amorphous substance.

$^1$H-NMR (CDCl$_3$) δ: 1.26–1.46 (m, 4H), 1.99–2.46 (m, 10H), 3.25–3.89 (m, 10H), 4.23–4.25 and 4.38 (each m, total 1H), 5.19 and 5.32 (each m, total 1H), 7.08–7.21 (m, 4H), 7.28–7.29 (m, 1H), 7.41–7.43 (m, 1H), 7.67 (broad s, 1H), 7.87–7.93 (m, 1H).

MS (ESI) m/z 524 (M$^+$+1).

(Step 4) Synthesis of trans-4-(1-(4-(2-benzoxazolyl)amino-3-methylphenylacetyl)-(4S)-fluoro-(2S)-pyrrolidinylmethoxy)cyclohexanecarboxylic acid

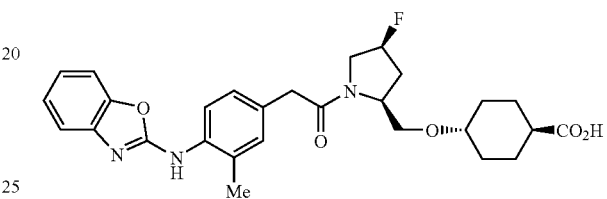

In THF (5 ml) was dissolved methyl trans-4-(1-(4-(2-benzoxazolyl)amino-3-methylphenylacetyl)-(4S)-fluoro-(2S)-pyrrolidinylmethoxy)cyclohexanecarboxylate (380 mg, 0.73 mmol). To the resulting solution was added 0.5N NaOH (5.0 ml, 2.50 mmol). The resulting mixture was stirred at room temperature for 3 hours. The reaction mixture was poured in ice 1N HCR, followed by extraction with ethyl acetate. The extract was washed with saturated brine, dried over anhydrous sodium sulfate, and distilled under reduced pressure to remove the solvent. The residue was purified by chromatography on a silica gel column, whereby from chloroform/methanol (60:1 to 50:1, v/v) eluate fractions, the title compound (155 mg, 42%) was obtained as a colorless amorphous substance.

$^1$H-NMR (CDCl$_3$) δ: 1.24–1.35 (m, 2H), 1.43–1.54 (m, 2H), 1.99–2.15 (m, 4H), 2.24–2.52 (m, total 6H), 3.25–4.02 (m, 7H), 4.21–4.27 and 4.37–4.43 (each m, total 1H), 5.17–5.21 and 5.30–5.34 (each m, total 1H), 7.07–7.23 (m, 4H), 7.30–7.40 (m, 2H), 7.69–7.74 (m, 1H).

MS (ESI) m/z 510 (M$^+$+1);

Anal. Calcd for C$_{28}$H$_{32}$FN$_3$O$_5$.1/2H$_2$O: C, 64.85; H, 6.41; N, 8.10. Found: C, 64.75; H, 6.56; N, 7.65.

Example 51 trans-4-(1-(3-(2-Benzoxazolyl)amino-2-chloro-6-pyridylacetyl)-(4S)-fluoro-(2S)-pyrrolidinylmethoxy)cyclohexanecarboxylic acid (Step 1) Synthesis of ethyl (3-(2-benzoxazolyl)amino-2-chloro-6-pyridyl)acetate

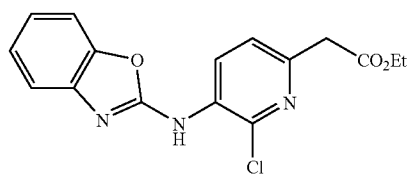

In xylene (100 ml), 2-chlorobenzoxazole (326 μl, 2.86 mmol) and ethyl (3-amino-2-chloro-6-pyridyl)acetate (557 mg, 2.59 mmol) were heated under reflux for 4 hours under stirring. After the reaction mixture was cooled to room temperature, the solvent was distilled off under reduced pressure. The residue was purified by chromatography on a silica gel column, whereby from n-hexane/ethyl acetate (3:1, v/v) eluate fractions, ethyl (3-(2-benzoxazolyl)amino-2-chloro-6-pyridyl)acetate (460 mg, 53%) was obtained as a colorless gum.

$^1$H-NMR (CDCl$_3$) δ: 1.25–1.28 (m, 3H), 3.79 (s, 2H), 4.16–4.21 (m, 2H), 7.14–7.18 (m, 1H), 7.22–7.26 (m, 1H), 7.31–7.36 (m, 3H) 7.49–7.51 (m, 1H), 8.86–8.89 (m, 1H).

MS (ESI) m/z 332 (M$^+$+1).

(Step 2) Synthesis of (3-(2-benzoxazolyl)amino-2-chloro-6-pyridyl)acetic acid

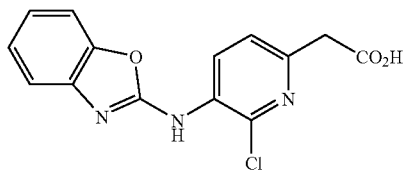

In THF (8 ml) was dissolved ethyl (3-(2-benzoxazolyl)amino-2-chloro-6-pyridyl)acetate (460 mg, 1.39 mmol). To the resulting solution was added 0.5N NaOH (8.0 ml, 4.00 mmol). The resulting mixture was stirred at room temperature for 1 hour. The reaction mixture was poured in ice-1N HCl to acidify the mixture. The crystals thus precipitated were collected by filtration under reduced pressure, washed with water and dried under reduced pressure to give (3-(2-benzoxazolyl)amino-2-chloro-6-pyridyl)acetic acid (332 mg, 79%) as a white solid.

$^1$H-NMR (DMSO-d$_6$) δ: 3.30 (s, 2H), 6.68–6.72 (m, 1H), 6.76–6.80 (m, 1H), 6.96–7.06 (m, 3H), 8.00–8.02 (m, 1H).

(Step 3) Synthesis of methyl trans-4-(1-(3-(2-benzoxazolyl)amino-2-chloro-6-pyridylacetyl)-(4S)-fluoro-(2S)-pyrrolidinylmethoxy)cyclohexanecarboxylate

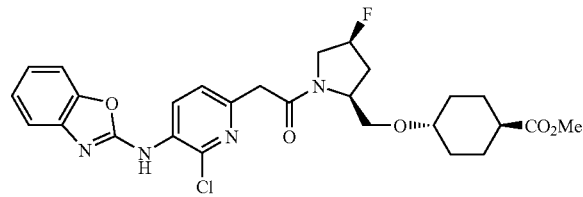

To a mixture of (3-(2-benzoxazolyl)amino-2-chloro-6-pyridyl)acetic acid (153 mg, 0.50 mmol), methyl trans-4-((4S)-fluoro-(2S)-pyrrolidinylmethoxy)cyclohexanecarboxylate (the compound synthesized in (Step 3) of Example 21) (131 mg, 0.51 mmol), EDC•HCl (145 mg, 0.76 mmol), HOBt (102 mg, 0.75 mmol), and triethylamine (105 μl, 0.75 mmol) was added DMF (5 ml). The resulting mixture was stirred at room temperature for 2 days. To the reaction mixture was added water, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (1:2, v/v) eluate fractions, methyl trans-4-(1-(3-(2-benzoxazolyl)amino-2-chloro-6-pyridylacetyl)-(4S)-fluoro-(2S)-pyrrolidinylmethoxy)cyclohexanecarboxylate (270 mg, 98%) was obtained as a colorless thick sticky liquid.

$^1$H-NMR (CDCl$_3$) δ: 1.24–1.29 (m, 2H), 1.39–1.53 (m, 2H), 1.96–2.52 (m, 7H), 3.22–3.36 and 3.50–3.54 (each m, total 2H), 3.64–4.14 (m, 8H), 4.38 and 4.45–4.47 (each m, total 1H), 5.20–5.23 and 5.34 (each m, total 1H), 7.15–7.27 (m, 2H), 7.35–7.39 (m, 2H), 7.50–7.52 (m, 1H), 7.72 (broad s, 1H), 8.83–8.89 (m, 1H).

MS (ESI) m/z 545 (M$^+$+1).

(Step 4) Synthesis of trans-4-(1-(3-(2-benzoxazolyl)amino-2-chloro-6-pyridylacetyl)-(4S)-fluoro-(2S)-pyrrolidinylmethoxy)cyclohexanecarboxylic acid

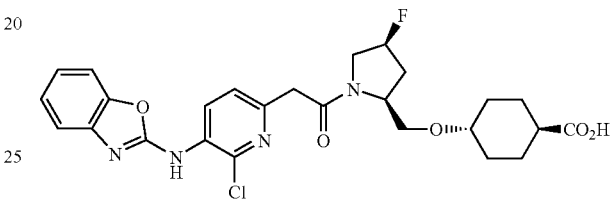

In THF (3.0 ml) was dissolved methyl trans-4-(1-(3-(2-benzoxazolyl)amino-2-chloro-6-pyridylacetyl)-(4S)-fluoro-(2S)-pyrrolidinylmethoxy)cyclohexanecarboxylate (270 mg, 0.50 mmol). To the resulting solution was added 0.5N NaOH (3.0 ml, 1.50 mmol). The resulting mixture was stirred at room temperature for 1 hour. The reaction mixture was poured in ice-1N HCl to acidify the mixture. The crystals thus precipitated were collected by filtration under reduced pressure, washed with n-hexane, and dried under reduced pressure to give the title compound (192 mg, 73%) as a pale yellow solid.

$^1$H-NMR (DMSO-d$_6$) δ: 1.21–1.36 (m, 4H), 1.83–2.23 (m, 7H), 3.18–4.07 (m, 7H), 4.12 and 4.38 (each m, total 1H), 5.25–5.31 and 5.39–5.45 (each m, total 1H), 7.11–7.15 (m, 1H), 7.19–7.23 (m, 1H), 7.36–7.40 (m, 2H), 7.47–7.49 (m, 1H), 8.42 (m, 1H).

MS (ESI) m/z 531 (M$^+$+1);

Anal. Calcd for $C_{26}H_{28}ClFN_4O_5 \cdot 1/2H_2O$: C, 57.83; H, 5.41; N, 10.38. Found: C, 58.03; H, 5.70; N, 9.62.

Example 52 trans-4-(1-(3-Chloro-4-(2-(4-methylbenzoxazolyl))aminophenylacetyl)-(4S)-fluoro-(2S)-pyrrolidinylmethoxy)cyclohexanecarboxylic acid (Step 1) Synthesis of 2-amino-3-methylphenol

In methanol (20 ml), 10% palladium-carbon (0.30 g, 20 wt %) was added to 3-methyl-2-nitrophenol (1.50 g, 9.80 mmol) and they were subjected to catalytic hydrogenation for 4 days. From the reaction mixture, an insoluble matter was filtered off through Celite. The filtrate was distilled under reduced pressure to remove the solvent to give 2-amino-3-methylphenol (1.19 g, 99%) as a brown oil.

$^1$H-NMR (CDCl$_3$) δ: 2.19 (s, 3H), 6.60–6.62 (m, 2H), 6.68–6.71 (m, 1H).

(Step 2) Synthesis of methyl 3-chloro-4-isothiocyanatophenylacetate

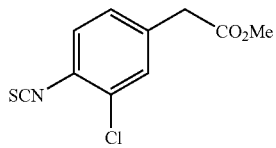

Calcium carbonate (626 mg, 6.25 mmol) and thiophosgene (191 μl, 2.51 mmol) were suspended in methylene chloride-water (10 ml, 1:1, v/v). To the resulting suspension was added a solution of methyl 4-amino-3-chlorophenylacetate (500 mg, 2.50 mmol) in methylene chloride (5 ml) under stirring at 0° C. The temperature of the reaction mixture was raised from 0° C. to room temperature over 1.5 hours. The reaction mixture was acidified with 1N HCl, followed by extraction with methylene chloride. The extract was washed with saturated brine, dried over anhydrous sodium sulfate, and distilled under reduced pressure to remove the solvent to give methyl 3-chloro-4-isothiocyanatophenylacetate (652 mg, 100%) as a yellow oil.

MS (ESI) m/z 241 (M$^+$).

(Step 3) Synthesis of methyl (3-chloro-4-(2-(4-methylbenzoxazolyl))aminophenyl)acetate

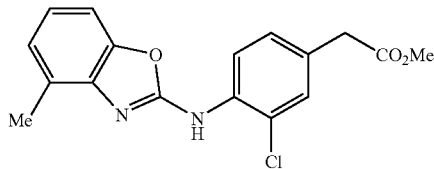

Toluene (15 ml) was added to a mixture of methyl 3-chloro-4-isothiocyanatophenylacetate (652 mg, 2.50 mmol) and 2-amino-3-methylphenol (307 mg, 2.50 mmol). The resulting mixture was heated under reflux for 2 hours. Mercuric oxide (yellow) (541 mg, 2.50 mmol) was added to the reaction mixture. The resulting mixture was heated under reflux for 5 hours. After cooling to room temperature, the reaction mixture was filtered through Celite, and washed with methanol. The filtrate was distilled under reduced pressure to remove the solvent. The residue wad purified by chromatography on a silica gel column, whereby from n-hexane/ethyl acetate (7:1, v/v) eluate fractions, methyl (3-chloro-4-(2-(4-methylbenzoxazolyl))aminophenyl)acetate (359 mg, 43%) was obtained as a black oil.

$^1$H-NMR (CDCl$_3$) δ: 2.55 (s, 3H), 3.58 (s, 2H), 3.70 (s, 3H), 7.02–7.06 (m, 2H), 7.11–7.19 (m, 1H), 7.25–7.28 (m, 1H), 7.33–7.34 (m, 1H), 7.50 (broad s, 1H), 8.54–8.56 (m, 1H).

MS (ESI) m/z 331 (M$^+$+1).

(Step 4) Synthesis of (3-chloro-4-(2-(4-methylbenzoxazolyl))aminophenyl)acetic acid

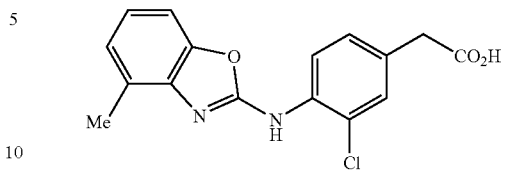

Methyl (3-chloro-4-(2-(4-methylbenzoxazolyl))aminophenyl)acetate (359 mg, 1.08 mmol) was dissolved in THF (6 ml). To the resulting solution was added 0.5N NaOH (6.5 ml, 3.25 mmol). The resulting mixture was stirred at room temperature for 4 hours. The reaction mixture was poured in ice-1N HCl to acidify the mixture, followed by extraction with ethyl acetate. The extract was washed with saturated brine, dried over anhydrous sodium sulfate, and distilled under reduced pressure to remove the solvent to give (3-chloro-4-(2-(4-methylbenzoxazolyl))aminophenyl)acetic acid (281 mg, 82%) as a brown solid.

$^1$H-NMR (CDCl$_3$) δ: 2.55 (s, 3H), 3.57 (s, 2H), 6.72–6.74 (m, 1H), 7.04–7.06 (m, 2H), 7.18–7.20 (m, 2H), 8.46–8.48 (m, 1H).

MS (ESI) m/z 317 (M$^+$+1).

(Step 5) Synthesis of methyl trans-4-(1-(3-chloro-4-(2-(4-methylbenzoxazolyl))aminophenylacetyl)-(4S)-fluoro-(2S)-pyrrolidinylmethoxy)cyclohexanecarboxylate

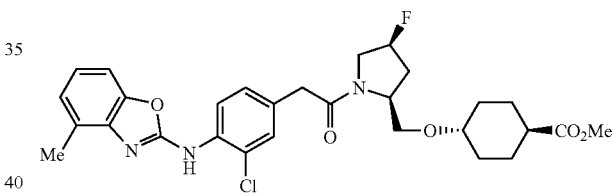

To a mixture of methyl (4-(2-(4-methylbenzoxazolyl))amino-3-chlorophenyl)acetate (281 mg, 0.89 mmol), methyl trans-4-((4S)-fluoro-(2S)-pyrrolidinylmethoxy)cyclohexanecarboxylate (the compound synthesized in (Step 3) of Example 21) (230 mg, 0.89 mmol), EDC•HCl (255 mg, 1.33 mmol), HOBt (180 mg, 1.33 mmol), and triethylamine (185 μl, 1.33 mmol) was added DMF (8 ml). The resulting mixture was stirred at room temperature for 15 hours. To the reaction mixture was added water, followed by extraction with ethyl acetate. The extract was washed with saturated brine, dried over anhydrous sodium sulfate, and distilled under reduced pressure to remove the solvent. The residue was purified by chromatography on a silica gel column, whereby from toluene/acetone (6:1, v/v) eluate fractions, methyl trans-4-(1-(3-chloro-4-(2-(4-methylbenzoxazolyl)) aminophenylacetyl)-(4S)-fluoro-(2S)-pyrrolidinylmethoxy) cyclohexanecarboxylate (368 mg, 74%) was obtained as a white amorphous substance.

$^1$H-NMR (CDCl$_3$) δ: 1.20–1.53 (m, 4H), 1.97–2.32 (m, 7H), 2.56 (s, 3H), 3.23–3.36 and 3.49–3.52 (each m, total 2H), 3.57–4.11 (m, 8H), 4.19–4.23 and 4.37 (each m, total 1H), 5.17–5.19 and 5.31–5.32 (each m, total 1H), 7.05–7.06 (m, 2H), 7.16–7.24 (m, 2H), 7.34–7.36 (m, 1H), 7.50 (broad s, 1H), 8.52–8.57 (m, 1H).

MS (ESI) m/z 558 (M$^+$+1).

(Step 6) Synthesis of trans-4-(1-(3-chloro-4-(2-(4-methyl-benzoxazolyl))aminophenylacetyl)-(4S)-fluoro-(2S)-pyrrolidinylmethoxy)cyclohexanecarboxylic acid

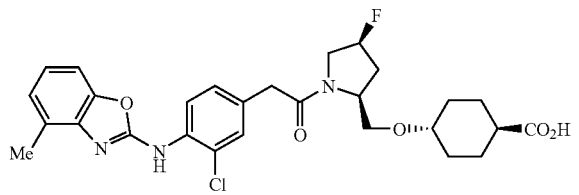

In THF (4 ml) was dissolved methyl trans-4-(1-(3-chloro-4-(2-(4-methylbenzoxazolyl))aminophenylacetyl)-(4S)-fluoro-(2S)-pyrrolidinylmethoxy)cyclohexanecarboxylate (368 mg, 0.66 mmol). To the resulting solution was added 0.5N NaOH (4.0 ml, 2.00 mmol). The resulting mixture was stirred at room temperature for 15 hours. The reaction mixture was poured in ice-1N HCl to acidify the mixture. The crystals thus precipitated were collected by filtration under reduced pressure, washed with water and dried under reduced pressure to give the title compound (139 mg, 39%) as a brown solid.

$^1$H-NMR (DMSO-$d_6$) δ: 1.15–1.36 (m, 4H), 1.87–2.20 (m, 7H), 2.39 (s, 3H), 3.15–3.87 (m, 7H), 4.13 and 4.32–4.34 (each m, total 1H), 5.24–5.31 and 5.37–5.44 (each m, total 1H), 6.97–7.02 (m, 2H), 7.21–7.26 (m, 2H), 7.37–7.38 (m, 1H), 7.89–7.93 (m, 1H).

MS (ESI) m/z 544 (M$^+$+1);

Anal. Calcd for $C_{28}H_{31}ClFN_3O_5 \cdot 1/4H_2O$: C, 61.31; H, 5.79; N, 7.66. Found: C, 61.14; H, 6.06; N, 6.97.

Example 53 trans-4-(1-(3-Chloro-4-(2-(7-fluorobenzoxazolyl))aminophenylacetyl)-(4S)-fluoro-(2S)-pyrrolidinylmethoxy)cyclohexanecarboxylic acid (Step 1) Synthesis of methyl (3-chloro-4-(2-(7-fluorobenzoxazolyl))aminophenyl)acetate

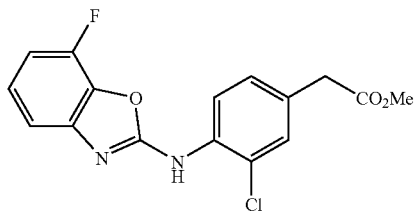

Toluene (15 ml) was added to a mixture of methyl 3-chloro-4-isothiocyanatophenylacetate (672 mg, 2.78 mmol) and 2-amino-6-fluorophenol (353 mg, 2.78 mmol). The resulting mixture was heated under reflux for 1.5 hours. Mercuric oxide (yellow) (1.03 g, 4.75 mmol) was added to the reaction mixture. The resulting mixture was heated under reflux for 10 hours. After cooling to room temperature, the reaction mixture was filtered through Celite. The filtrate was washed with methanol, and distilled under reduced pressure to remove the solvent. The residue was purified by chromatography on a silica gel column, whereby from n-hexane/ethyl acetate (7:1, v/v) eluate fractions, methyl (3-chloro-4-(2-(7-fluorobenzoxazolyl))aminophenyl)acetate (109 mg, 12%) was obtained as a yellow solid.

$^1$H-NMR (CDCl$_3$) δ: 3.60 (s, 2H), 3.71 (s, 3H), 6.91–6.96 (m, 1H), 7.15–7.21 (m, 1H), 7.27–7.32 (m, 2H), 7.37–7.38 (m, 1H), 7.59 (broad s, 1H), 8.49 (d, J=8.3 Hz, 1H).

MS (ESI) m/z 335 (M$^+$+1).

(Step 2) Synthesis of (3-chloro-4-(2-(7-fluorobenzoxazolyl))aminophenyl)acetic acid

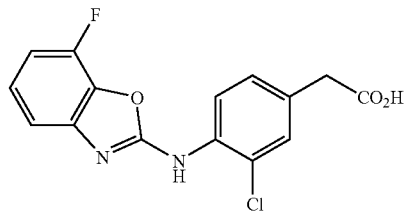

Methyl (3-chloro-4-(2-(7-fluorobenzoxazolyl))aminophenyl)acetate (109 mg, 0.33 mmol) was dissolved in THF (4 ml). To the resulting solution was added 0.25 N NaOH (4.0 ml, 1.00 mmol). The resulting mixture was stirred at room temperature for 1 hour. The reaction mixture was poured in -1N HCl to acidify the mixture. The crystals thus precipitated were collected by filtration under reduced pressure, washed with water and dried under reduced pressure to give (3-chloro-4-(2-(7-fluorobenzoxazolyl))aminophenyl)acetic acid (95 mg, 91%) as a brown solid.

MS (ESI), m/z 321 (M$^+$+1).

(Step 3) Synthesis of methyl trans-4-(1-(3-chloro-4-(2-(7-fluorobenzoxazolyl))aminophenylacetyl)-(4S)-fluoro-(2S)-pyrrolidinylmethoxy)cyclohexanecarboxylate

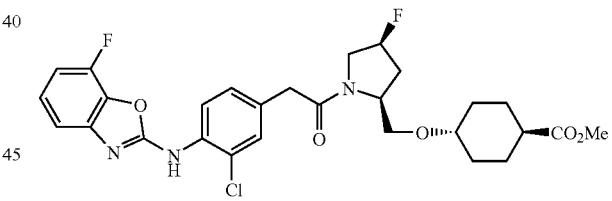

DMF (4 ml) was added to a mixture of (3-chloro-4-(2(7-fluorobenzoxazolyl))aminophenyl)acetic acid (95 mg, 0.30 mmol), methyl trans-4-((4S)-fluoro-(2S)-pyrrolidinylmethoxy)cyclohexanecarboxylate (the compound synthesized in (Step 3) of Example 21) (77 mg, 0.30 mmol), EDC•HCl (85 mg, 0.44 mmol), HOBt (60 mg, 0.44 mmol), and triethylamine (62 µl, 0.44 mmol). The resulting mixture was stirred at room temperature for 7 hours. To the reaction mixture was added water, followed by extraction with ethyl acetate. The extract was washed with saturated brine, dried over anhydrous sodium sulfate, and distilled under reduced pressure to remove the solvent. The residue was purified by chromatography on a silica gel column, whereby from toluene/acetone (6:1, v/v) eluate fractions, methyl trans-4-(1-(3-chloro-4-(2-(7-fluorobenzoxazolyl))aminophenylacetyl)-(4S)-fluoro-(2S)-pyrrolidinylmethoxy)cyclohexanecarboxylate (166 mg, 200%) was obtained as a pale yellow thick sticky liquid.

$^1$H-NMR (CDCl$_3$) δ: 1.18–1.32 (m, 2H), 1.39–1.53 (m, 2H), 1.97–2.08 (m, 4H), 2.19–2.52 (m, 3H), 3.23–3.29 and 3.32–3.54 (each m, total 2H), 3.58–4.01 (m, 8H), 4.19–4.25 and 4.35–4.41 (each m, total 1H), 5.17–5.20 and 5.30–5.34 (each m, total 1H), 6.91–6.96 (m, 1H), 7.15–7.31 (m, 3H), 7.36–7.38 (m, 1H), 7.62 (broad s, 1H), 8.44–8.49 (m, 1H).

MS (ESI) m/z 562 (M$^+$+1).

(Step 4) Synthesis of trans-4-(1-(3-chloro-4-(2-(7-fluorobenzoxazolyl))aminophenylacetyl)-(4S)-fluoro-(2S)-pyrrolidinylmethoxy)cyclohexanecarboxylic acid

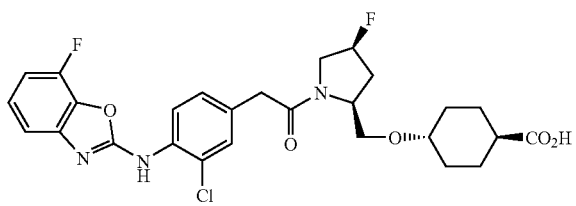

In THF (3.6 ml) was dissolved methyl trans-4-(1-(3-chloro-4-(2-(7-fluorobenzoxazolyl))aminophenylacetyl)-(4S)-fluoro-(2S)-pyrrolidinylmethoxy)cyclohexanecarboxylate (166 mg, 0.30 mmol). To the resulting solution was added 0.25 N NaOH (3.6 ml, 0.90 mmol). The resulting mixture was stirred at room temperature for 12 hours. The reaction mixture was poured in –1N HCl to acidify the mixture. The crystals thus precipitated were collected by filtration under reduced pressure, washed with water and dried under reduced pressure to give the title compound (101 mg, 62%) as a brown solid.

$^1$H-NMR (DMSO-d$_6$) δ: 1.15–1.39 (m, 4H), 1.84–2.28 (m, 7H), 3.14–3.88 (m, 7H), 4.12 and 4.30–4.34 (each m, total 1H), 5.23–5.30 and 5.37–5.44 (each m, total 1H), 7.00–7.05 (m, 1H), 7.18–7.25 (m, 3H), 7.37–7.39 (m, 1H), 7.87–7.90 (m, 1H).

MS (FAB) m/z 548 (M$^+$+1);

Anal. Calcd for C$_{27}$H$_{28}$ClF$_2$N$_3$O$_5$·1/4H$_2$O: C, 58.70; H, 5.20; N, 7.61. Found: C, 58.90; H, 5.59; N, 6.77.

Example 54 trans-4-(1-(3-Chloro-4-(2-(5-fluorobenzoxazolyl))aminophenylacetyl)-(4S)-fluoro-(2S)-pyrrolidinylmethoxy)cyclohexanecarboxylic acid (Step 1) Synthesis of 2-amino-4-fluorophenol

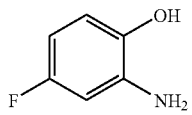

In methanol (20 ml) was dissolved 4-fluoro-2-nitrophenol (1.00 g, 6.37 mmol). To the resulting solution was added 10% palladium-carbon (0.20 g, 20 wt %). The resulting mixture was subjected to catalytic hydrogenation under stirring for 2 days. After the reaction mixture was filtered through Celite to remove the catalyst, the filtrate was distilled under reduced pressure to remove the solvent, whereby 2-amino-4-fluorophenol (850 mg, 100%) was obtained as a reddish brown solid.

$^1$H-NMR (CDCl$_3$) δ: 3.93 (broad s, 2H), 6.30–6.35 (m, 1H), 6.44–6.48 (m, 1H), 6.62–6.65 (m, 1H).

MS (ESI) m/z 169 (M$^+$+1+MeCN).

(Step 2) Synthesis of methyl (3-chloro-4-(2-(5-fluorobenzoxazolyl))aminophenyl)acetate

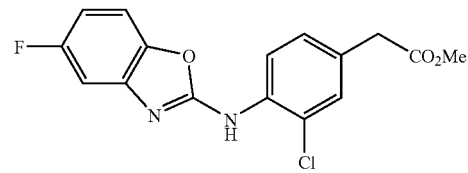

To a mixture of methyl 3-chloro-4-isothiocyanatophenylacetate (950 mg, 3.93 mmol) and 2-amino-4-fluorophenol (500 mg, 3.93 mmol) was added toluene (15 ml) and the mixture was heated under reflux for 2 hours. Mercuric oxide (yellow) (1.03 g, 4.75 mmol) was then added to the reaction mixture. The resulting mixture was heated under reflux for 2.5 hours. After cooling to room temperature, the reaction mixture was filtered through Celite. The filtrate was washed with methanol and then, distilled under reduced pressure to remove the solvent. The residue wad purified by chromatography on a silica gel column, whereby from n-hexane/ethyl acetate (7:1, v/v) eluate fractions, methyl (3-chloro-4-(2-(5-fluorobenzoxazolyl))aminophenyl)acetate (107 mg, 8%) was obtained as a brown solid.

$^1$H-NMR (CDCl$_3$) δ: 3.60 (s, 2H), 3.71 (s, 3H), 6.85–6.90 (m, 1H), 7.20–7.23 (m, 1H), 7.25–7.30 (m, 2H), 7.37–7.38 (m, 1H), 7.52 (broad s, 1H), 8.45–8.47 (m, 1H).

MS (ESI) m/z 335 (M$^+$+1).

(Step 3) Synthesis of (3-chloro-4-(2-(5-fluorobenzoxazolyl))aminophenyl)acetic acid

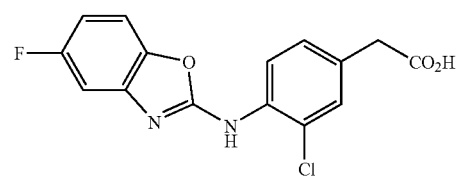

Methyl (3-chloro-4-(2-(5-fluorobenzoxazolyl))aminophenyl)acetate (148 mg, 0.44 mmol) was dissolved in THF (3 ml). To the resulting solution was added 0.5N NaOH (3.0 ml, 1.50 mmol), and the mixture was stirred at room temperature for 7 hours. The reaction mixture was poured in ice-1N HCl to acidify the mixture. The crystals thus precipitated were collected by filtration under reduced pressure, washed with water and dried under reduced pressure to give (3-chloro-4-(2-(5-fluorobenzoxazolyl))aminophenyl)acetic acid (129 mg, 91%) as a brown solid.

$^1$H-NMR (DMSO-d$_6$) δ: 3.62 (s, 2H), 6.89–6.94 (m, 1H), 7.21–7.30 (m, 2H), 7.45–7.49 (m, 2H), 7.85–7.87 (m, 1H), 10.16 (broad s, 1H), 12.44 (broad s, 1H).

MS (ESI) m/z 321 (M$^+$+1).

(Step 4) Synthesis of methyl trans-4-(1-(3-chloro-4-(2-(5-fluorobenzoxazolyl))aminophenylacetyl)-(4S)-fluoro-(2S)-pyrrolidinylmethoxy)cyclohexanecarboxylate

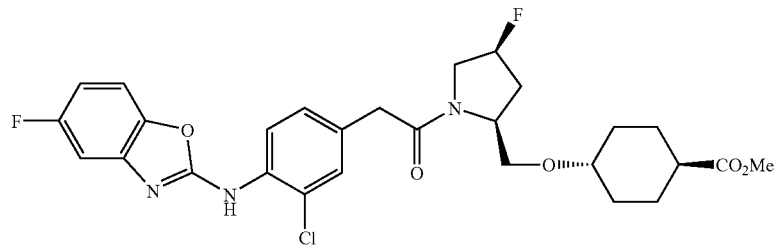

In DMF (5 ml), a mixture of (3-chloro-4-(2-(5-fluorobenzoxazolyl))aminophenyl)acetic acid (129 mg, 0.40 mmol), methyl trans-4-((4S)-fluoro-(2S)-pyrrolidinylmethoxy)cyclohexanecarboxylate (the compound synthesized in (Step 3) of Example 21) (104 mg, 0.40 mmol), EDC•HCl (116 mg, 0.61 mmol), HOBt (82 mg, 0.61 mmol) and triethylamine (84 μl, 0.60 mmol) was stirred at room temperature for 20 hours. The reaction mixture was poured in water, and the crystals thus precipitated were collected by filtration under reduced pressure. The crude crystals were dissolved in ethyl acetate. The solution was washed with saturated brine, dried over anhydrous sodium sulfate, and distilled under reduced pressure to remove the solvent. The residue was purified by chromatography on a silica gel column, whereby from toluene/acetone (6:1, v/v) eluate fractions, methyl trans-4-(1-(3-chloro-4-(2-(5-fluorobenzoxazolyl))aminophenylacetyl)-(4S)-fluoro-(2S)-pyrrolidinylmethoxy)cyclohexanecarboxylate (222 mg, 98%) was obtained as a pale yellow thick sticky liquid.

$^1$H-NMR (CDCl$_3$) δ: 1.14–1.32 (m, 2H), 1.39–1.53 (m, 2H), 1.96–2.51 (m, 7H), 3.21–3.37 and 3.49–3.54 (each m, total 2H), 3.58–4.01 (m, 8H), 4.19–4.25 and 4.35–4.40 (each m, total 1H), 5.17–5.20 and 5.30–5.33 (each m, total 1H), 6.83–6.89 (m, 1H), 7.13–7.28 (m, 3H), 7.36–7.37 (m, 1H), 7.52 (broad s, 1H), 8.40–8.46 (m, 1H).

MS (ESI) m/z 562 (M$^+$+1).

(Step 5) Synthesis of trans-4-(1-(3-chloro-4-(2-(5-fluorobenzoxazolyl))aminophenylacetyl)-(4S)-fluoro-(2S)-pyrrolidinylmethoxy)cyclohexanecarboxylic acid

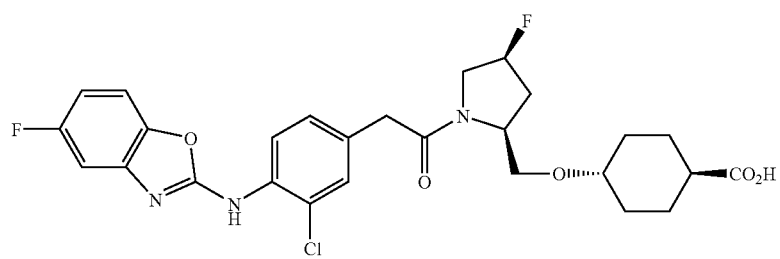

Methyl trans-4-(1-(3-chloro-4-(2-(5-fluorobenzoxazolyl))aminophenylacetyl)-(4S)-fluoro-(2S)-pyrrolidinylmethoxy)cyclohexanecarboxylate (222 mg, 0.40 mmol) was dissolved in THF (4.5 ml). To the resulting solution was added 0.25 N NaOH (4.5 ml, 1.13 mmol). The resulting mixture was stirred at room temperature for 13 hours. The reaction mixture was poured in –1N HCl to acidify the mixture. The crystals thus precipitated were collected by filtration under reduced pressure, washed with water and dried under reduced pressure to give the title compound (149 mg, 69%) as a pale yellow solid.

$^1$H-NMR (DMSO-d$_6$) δ: 1.16–1.38 (m, 4H), 1.88–1.95 (m, 4H), 2.15–2.21 (m, 3H), 3.16–3.88 (m, 7H), 4.13 and 4.33–4.35 (each m, total 1H), 5.25–5.33 and 5.39–5.46 (each m, total 1H), 6.89–6.93 (m, 1H), 7.21–7.25 (m, 2H), 7.39–7.40 (m, 1H), 7.46–7.49 (m, 1H), 7.83–7.86 (m, 1H).

MS (FAB) m/z 548 (M$^+$+1);

Anal. Calcd for C$_{27}$H$_{28}$ClF$_2$N$_3$O$_5$.1/2H$_2$O: C, 58.22; H, 5.25; N, 7.54. Found: C, 58.57; H, 5.49; N, 6.97.

Example 55 trans-4-(1-(4-(2-Benzoxazolyl)amino-5-chloro-2-fluorophenylacetyl)-(4S)-fluoro-(2S)-pyrrolidinylmethoxy)cyclohexanecarboxylic acid (Step 1) Synthesis of ethyl (4-(2-benzoxazolyl)amino-5-chloro-2-fluorophenyl)acetate

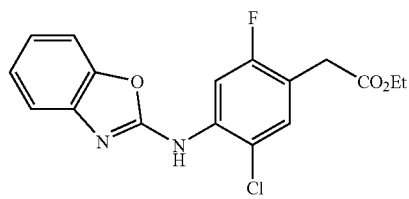

In xylene (4 ml), 2-chlorobenzoxazole (278 μl, 2.43 mmol) and ethyl (4-amino-5-chloro-2-fluorophenyl)acetate (512 mg, 2.21 mmol) were heated under reflux for 2 hours. After the reaction mixture was cooled to room temperature, the solvent was distilled off under reduced pressure. The residue was dissolved in ethyl acetate. The resulting solution was washed with a saturated aqueous solution of sodium bicarbonate, dried over anhydrous sodium sulfate, and distilled under reduced pressure to remove the solvent. The residue was purified by chromatography on a silica gel column, whereby from n-hexane/ethyl acetate (7:1, v/v)

eluate fractions, ethyl (4-(2-benzoxazolyl)amino-5-chloro-2-fluorophenyl)acetate (570 mg, 74%) was obtained as a pale yellow solid.

¹H-NMR (CDCl₃) δ: 1.27 (t, J=7.1 Hz, 3H), 3.62 (s, 2H), 4.19 (q, J=7.1 Hz, 2H), 7.16–7.38 (m, 3H), 7.53–7.56 (m, 2H), 8.47–8.50 (m, 1H).

MS (ESI) m/z 349 (M⁺+1).

(Step 2) Synthesis of (4-(2-benzoxazolyl)amino-5-chloro-2-fluorophenyl)acetic acid

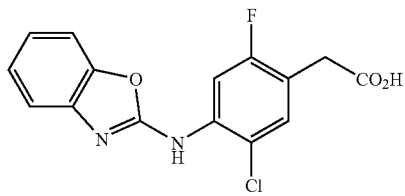

Ethyl (4-(2-benzoxazolyl)amino-5-chloro-2-fluorophenyl)acetate (570 mg, 1.63 mmol) was dissolved in THF (5 ml). To the resulting solution was added 1N NaOH (5.0 ml, 5.00 mmol), followed by stirring at room temperature for 20 hours. The reaction mixture was poured in ice-1N HCl to acidify therewith. The crystals thus precipitated were collected by filtration under reduced pressure, washed with water and dried under reduced pressure to give (4-(2-benzoxazolyl)amino-5-chloro-2-fluorophenyl)acetic acid (497 mg, 95%) as a brown solid.

¹H-NMR (DMSO-d₆) δ: 3.64 (s, 2H), 7.14–7.17 (m, 1H), 7.21–7.26 (m, 1H), 7.45–7.55 (m, 3H), 8.07–8.10 (m, 1H).

MS (ESI) m/z 321 (M⁺+1).

(Step 3) Synthesis of methyl trans-4-(1-(4-(2-benzoxazolyl)amino-5-chloro-2-fluorophenylacetyl)-(4S)-fluoro-(2S)-pyrrolidinylmethoxy)cyclohexanecarboxylate

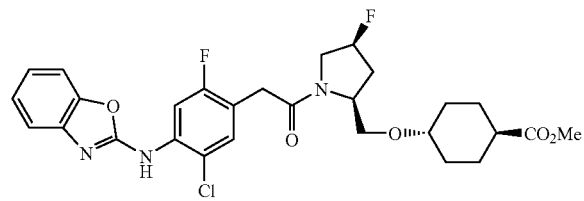

To a mixture of (4-(2-benzoxazolyl)amino-5-chloro-2-fluorophenyl)acetic acid (140 mg, 0.44 mmol), methyl trans-4-((4S)-fluoro-(2S)-pyrrolidinylmethoxy)cyclohexane-carboxylate (the compound synthesized in (Step 3) of Example 21) (104 mg, 0.40 mmol), EDC•HCl (115 mg, 0.60 mmol), HOBt (81 mg, 0.60 mmol), and triethylamine (84 μl, 0.60 mmol) was added DMF (5 ml). The resulting mixture was stirred at room temperature for 18 hours. Water was added to the reaction mixture. The crystals thus precipitated were collected by filtration under reduced pressure, washed with water and dried under reduced pressure to give methyl trans-4-(1-(4-(2-benzoxazolyl)amino-5-chloro-2-fluorophenylacetyl)-(4S)-fluoro-(2S)-pyrrolidinylmethoxy)-cyclohexanecarboxylate (223 mg, 99%) as a brown solid.

¹H-NMR (CDCl₃) δ: 1.23–1.46 (m, 4H), 1.97–2.32 (m, 7H), 3.24–3.58 (m, 2H), 3.65–3.98 (m, 8H), 4.30–4.37 (m, 1H), 5.20–5.24 and 5.33–5.37 (each m, total 1H), 7.17–7.21 (m, 1H), 7.25–7.29 (m, 1H), 7.37–7.41 (m, 2H), 7.54–7.56 (m, 1H), 8.44–8.50 (m, 1H).

MS (ESI) m/z 562 (M⁺+1).

(Step 4) Synthesis of trans-4-(1-(4-(2-benzoxazolyl)amino-5-chloro-2-fluorophenylacetyl)-(4S)-fluoro-(2S)-pyrrolidinylmethoxy)cyclohexanecarboxylic acid

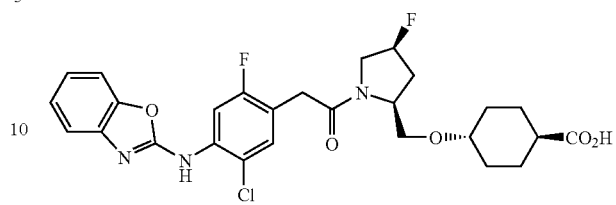

Methyl trans-4-(1-(4-(2-benzoxazolyl)amino-5-chloro-2-fluorophenylacetyl)-(4S)-fluoro-(2S)-pyrrolidinylmethoxy)cyclohexanecarboxylate (223 mg, 0.40 mmol) was dissolved in THF (3.0 ml). To the resulting solution was added 0.5N NaOH (2.5 ml, 1.25 mmol). The resulting mixture was stirred at room temperature for 1.5 hours. The reaction mixture was poured in ice-1N HCl to acidify the mixture. The crystals thus precipitated were collected by filtration under reduced pressure, washed with water and dried under reduced pressure to give the title compound (173 mg, 80%) as a brown solid.

¹H-NMR (DMSO-d₆) δ: 1.17–1.37 (m, 4H), 1.73–2.20 (m, 7H), 3.16–3.97 (m, 7H), 4.12 and 4.33 (each m, total 1H), 5.25–5.33 and 5.38–5.47 (each m, total 1H), 7.12–7.24 (m, 2H), 7.40–7.51 (m, 3H), 8.03 (m, 1H).

MS (ESI) m/z 548 (M⁺+1);

Anal. Calcd for C₃₀H₃₀FN₃O₅.1/2H₂O: C, 58.22; H, 5.25; N, 7.54. Found: C, 58.55; H, 5.41; N, 7.08.

Example 56 trans-4-(1-(4-(2-Benzothiazolyl)amino-3-chlorophenylacetyl)-(4S)-fluoro-(2S)-pyrrolidinylmethoxy)cyclohexanecarboxylic acid (Step 1) Synthesis of methyl (4-(2-benzothiazolyl)amino-3-chlorophenyl)acetate

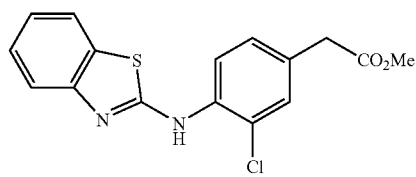

A mixture of 2-chlorobenzoxazole (489 mg, 2.88 mmol) and methyl 4-amino-3-chlorophenylacetate (567 mg, 2.84 mmol) and pyridinium•p-toluenesulfonate (pyridinium•p-toluenesulfonate (PPTS)) (214 mg, 0.85 mmol) was heated under reflux for 3 hours in xylene (10 ml). After the reaction mixture was cooled to room temperature, the solvent was distilled off under reduced pressure. The residue was purified by chromatography on a silica gel column, whereby from n-hexane/ethyl acetate (7:1, v/v) eluate fractions, methyl (4-(2-benzothiazolyl)amino-3-chlorophenyl)acetate (296 mg, 32%) was obtained as a white solid.

¹H-NMR (CDCl₃) δ: 3.58 (s, 2H), 3.71 (s, 3H), 7.16–7.24 (m, 2H), 7.33–7.38 (m, 2H), 7.63–7.69 (m, 2H), 8.33–8.35 (m, 1H).

MS (ESI) m/z 333 (M⁺+1).

(Step 2) Synthesis of (4-(2-benzothiazolyl)amino-3-chlorophenyl)acetic acid

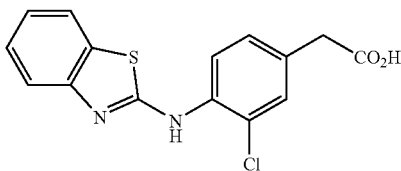

In THF (5 ml) was dissolved methyl (4-(2-benzothiazolyl)amino-3-chlorophenyl)acetate (296 mg, 0.89 mmol). To the resulting solution was added 0.5N NaOH (5.0 ml, 2.50 mmol). The resulting mixture was stirred at room temperature for 15 hours. The reaction mixture was poured in ice-1N HCl to acidify the mixture. The crystals thus precipitated were collected by filtration under reduced pressure, washed with water and dried under reduced pressure to give (4-(2-benzothiazolyl)amino-3-chlorophenyl)acetic acid (263 mg, 93%) as a white solid.

$^1$H-NMR (DMSO-$d_6$) δ: 3.59 (s, 2H), 7.11–7.15 (m, 1H), 7.25–7.31 (m, 2H), 7.42 (d, J=2.0 Hz, 1H), 7.52 (d, J=8.1 Hz, 1H), 7.77 (d, J=8.1 Hz, 1H), 8.11–8.13 (m, 1H).

MS (ESI) m/z 319 (M$^+$+1).

(Step 3) Synthesis of methyl trans-4-(1-(4-(2-benzothiazolyl)amino-3-chlorophenylacetyl)-(4S)-fluoro-(2S)-pyrrolidinylmethoxy)cyclohexanecarboxylate

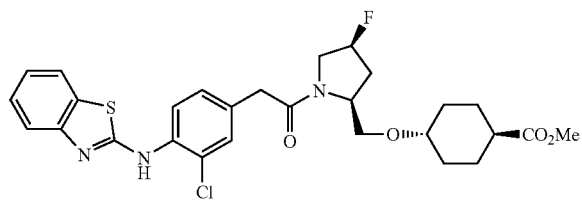

A mixture of (4-(2-benzothiazolyl)amino-3-chlorophenyl)acetic acid (263 mg, 0.83 mmol), methyl trans-4-((4S)-fluoro-(2S)-pyrrolidinylmethoxy)cyclohexanecarboxylate (the compound synthesized in (Step 3) of Example 21) (214 mg, 0.83 mmol), EDC·HCl (237 mg, 1.24 mmol), HOBt (167 mg, 1.24 mmol) and triethylamine (173 μl, 1.24 mmol) was stirred at room temperature for 3 days in DMF (7 ml). The reaction mixture was poured in water. The crystals thus precipitated were collected by filtration under reduced pressure, washed with water and dried under reduced pressure. The resulting crude crystals were purified by chromatography on a silica gel column, whereby from chloroform/methanol (60:1, v/v) eluate fractions, methyl trans-4-(1-(4-(2-benzothiazolyl)amino-3-chlorophenylacetyl)-(4S)-fluoro-(2S)-pyrrolidinylmethoxy)cyclohexanecarboxylate (460 mg, 100%) was obtained as a colorless amorphous substance.

$^1$H-NMR (CDCl$_3$) δ: 1.18–1.32 (m, 2H), 1.39–1.53 (m, 2H), 1.97–2.51 (m, 7H), 3.21–4.01 (m, 10H), 4.20–4.25 and 4.35–4.40 (each m, total 1H), 5.16–5.20 and 5.30–5.33 (each m, total 1H), 7.17–7.23 (m, 2H), 7.34–7.38 (m, 2H), 7.64–7.69 (m, 2H), 8.29–8.36 (m, 1H).

MS (ESI) m/z 560 (M$^+$+1).

(Step 4) Synthesis of trans-4-(1-(4-(2-benzothiazolyl)amino-3-chlorophenylacetyl)-(4S)-fluoro-(2S)-pyrrolidinylmethoxy)cyclohexanecarboxylic acid

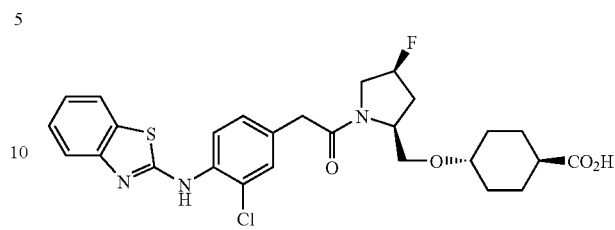

Methyl trans-4-(1-(4-(2-benzothiazolyl)amino-3-chlorophenylacetyl)-(4S)-fluoro-(2S)-pyrrolidinylmethoxy)cyclohexanecarboxylate (460 mg, 0.82 mmol) was dissolved in THF (5 ml). To the resulting solution was added 0.5N NaOH (5.0 ml, 2.50 mmol), followed by stirring at room temperature for 3 hours. The reaction mixture was poured in ice-1N HCl to acidify the mixture. The crystals thus precipitated were collected by filtration under reduced pressure, washed with water and dried under reduced pressure to give the title compound (314 mg, 70%) as a pale yellow solid.

$^1$H-NMR (DMSO-$d_6$) δ: 1.10–1.39 (m, 4H), 1.84–1.94 (m, 4H), 2.06–2.20 (m, 3H), 3.15–3.87 (m, 7H), 4.12 and 4.30–4.36 (each m, total 1H), 5.24–5.32 and 5.38–5.45 (each m, total 1H), 7.11–7.15 (m, 1H), 7.19–7.23 (m, 1H), 7.27–7.31 (m, 1H), 7.36–7.38 (m, 1H), 7.50–7.52 (m, 1H), 7.77–7.79 (m, 1H), 8.06–8.10 (m, 1H).

MS (ESI) m/z 546 (M$^+$+1);

Anal. Calcd for $C_{27}H_{29}ClFN_3O_4S·3/2H_2O$: C, 56.59; H, 5.63; N, 7.33. Found: C, 56.73; H, 5.58; N, 6.88.

Example 57 trans-4-(1-(3-Chloro-4-(6-fluoro-2-benzothiazolyl)aminophenylacetyl)-(4S)-fluoro-(2S)-pyrrolidinylmethoxy)cyclohexanecarboxylic acid (Step 1) Synthesis of 2-bromo-6-fluorobenzothiazole

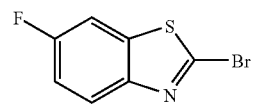

Copper (I) bromide (619 mg, 4.32 mmol) was suspended in acetonitrile (10 ml). To the resulting suspension was added tert-butyl nitrite (640 μl, 5.38 mmol), followed by stirring at 60° C. for 5 minutes. To the reaction mixture was added 2-amino-6-fluorobenzothiazole (605 mg, 3.60 mmol). The resulting mixture was stirred at 60° C. for 10 minutes. After cooling to the room temperature, the reaction mixture was diluted with ethyl acetate. The ethyl acetate solution was washed with 1N HCl, saturated brine, dried over anhydrous sodium sulfate, and distilled under reduced pressure to remove the solvent. The residue was purified by chromatography on a silica gel column, whereby from n-hexane/ethyl acetate (5:1, v/v) eluate fractions, 2-bromo-6-fluorobenzothiazole (330 mg, 40%) was obtained as a brown solid.

$^1$H-NMR (CDCl$_3$) δ: 7.19–7.24 (m, 1H), 7.49–7.52 (m, 1H), 7.92–7.96 (m, 1H).

MS (ESI) m/z 273.8 (M$^+$+1+MeCN).

(Step 2) Synthesis of methyl (3-chloro-4-(6-fluoro-2-benzothiazolyl)aminophenyl)acetate

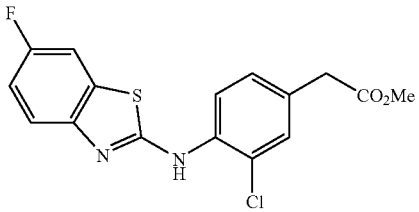

In xylene (8 ml), 2-bromo-6-fluorobenzothiazole (330 mg, 1.42 mmol), methyl 4-amino-3-chlorophenylacetate (284 mg, 1.42 mmol), and pyridinium p-toluenesulfonate (PPTS) (107 mg, 0.43 mmol) were heated under reflux for 10 hours. After cooling, the reaction mixture was distilled under reduced pressure to remove the solvent. The residue was purified by chromatography on a silica gel column, whereby from n-hexane/ethyl acetate (6:1, v/v) eluate fractions, methyl (3-chloro-4-(6-fluoro-2-benzothiazolyl)aminophenyl)acetate (158 mg, 32%) was obtained as a pale yellow solid.

$^1$H-NMR (CDCl$_3$) δ: 3.58 (s, 2H), 3.70 (s, 3H), 7.05–7.10 (m, 1H), 7.22–7.25 (m, 1H), 7.34–7.37 (m, 2H), 7.59–7.63 (m, 1H), 8.32–8.34 (m, 1H).

MS (ESI) m/z 351 (M$^+$+1).

(Step 3) Synthesis of (3-chloro-4-(6-fluoro-2-benzothiazolyl)aminophenyl)acetic acid

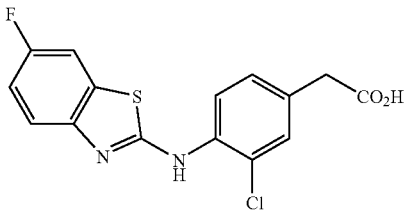

Methyl (3-chloro-4-(6-fluoro-2-benzothiazolyl)aminophenyl)acetate (158 mg, 0.45 mmol) was dissolved in THF (3 ml). To the resulting solution was added 0.5N NaOH (3.0 ml, 1.50 mmol), and the resulting mixture was stirred at room temperature for 18 hours. The mixture was poured in ice-1N HCl. The crystals thus precipitated were collected by filtration under reduced pressure, washed with water and dried under reduced pressure to give (3-chloro-4-(6-fluoro-2-benzothiazolyl)aminophenyl)acetic acid (127 mg, 84%) as a pale yellow solid.

$^1$H-NMR (DMSO-d$_6$) δ: 3.59 (s, 2H), 7.11–7.15 (m, 1H), 7.25–7.27 (m, 1H), 7.41–7.42 (m, 1H), 7.50–7.53 (m, 1H), 7.70–7.73 (m, 1H), 8.12–8.14 (m, 1H), 9.97 (broad s, 1H), 12.42 (broad s, 1H).

MS (ESI) m/z 337 (M$^+$+1).

(Step 4) Synthesis of methyl trans-4-(1-(3-chloro-4-(6-fluoro-2-benzothiazolyl)aminophenylacetyl)-(4S)-fluoro-(2S)-pyrrolidinylmethoxy)cyclohexanecarboxylate

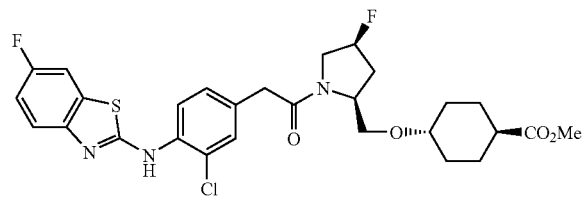

In DMF (8 ml), (3-chloro-4-(6-fluoro-2-benzothiazolyl)aminophenyl)acetic acid (127 mg, 0.38 mmol), methyl trans-4-((4S)-fluoro-(2S)-pyrrolidinylmethoxy)cyclohexanecarboxylate (the compound synthesized in (Step 3) of Example 21) (98 mg, 0.38 mmol), EDC•HCl (108 mg, 0.56 mmol), HOBt (76 mg, 0.56 mmol), and triethylamine (80 μl, 0.57 mmol) in DMF (8 ml) were stirred at room temperature for 18 hours. The reaction mixture was poured in water. The crystals thus precipitated were collected by filtration under reduced pressure, washed with water and dried under reduced pressure. The crude crystals were purified by chromatography on a silica gel column, whereby from chloroform/methanol (60:1, v/v) eluate fractions, methyl trans-4-(1-(3-chloro-4-(6-fluoro-2-benzothiazolyl) aminophenylacetyl)-(4S)-fluoro-(2S)-pyrrolidinylmethoxy) cyclohexanecarboxylate (266 mg, 100%) was obtained as a pale yellow thick sticky liquid.

$^1$H-NMR (CDCl$_3$) δ: 1.21–1.32 (m, 2H), 1.40–1.53 (m, 2H), 1.97–2.08 (m, 4H), 2.20–2.52 (m, 3H), 3.22–4.02 (m, 10H), 4.20–4.26 and 4.36–4.38 (each m, total 1H), 5.18–5.21 and 5.32–5.34 (each m, total 1H), 7.05–7.11 (m, 1H), 7.20–7.23 (m, 1H), 7.34–7.37 (m, 2H), 7.57–7.63 (m, 2H), 8.28–8.35 (m, 1H).

MS (ESI) m/z 578 (M$^+$+1).

(Step 5) Synthesis of trans-4-(1-(3-chloro-4-(6-fluoro-2-benzothiazolyl)aminophenylacetyl)-(4S)-fluoro-(2S)-pyrrolidinylmethoxy)cyclohexanecarboxylic acid

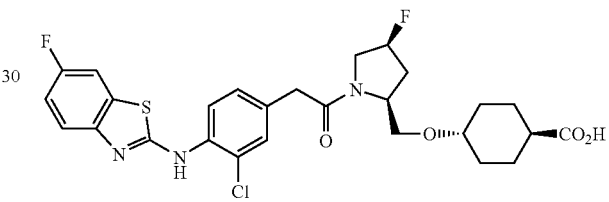

In THF (3 ml) was dissolved methyl trans-4-(1-(3-chloro-4-(6-fluoro-2-benzothiazolyl)aminophenylacetyl)-(4S)-fluoro-(2S)-pyrrolidinylmethoxy)cyclohexanecarboxylate (266 mg, 0.46 mmol). To the resulting solution was added 0.5N NaOH (3.0 ml, 1.50 mmol), followed by stirring at room temperature for 20 hours. The reaction mixture was poured in ice-1N HCl. The crystals thus precipitated were collected by filtration under reduced pressure, washed with water and dried under reduced pressure to give the title compound (189 mg, 73%) as a pale yellow solid.

$^1$H-NMR (DMSO-d$_6$) δ: 1.17–1.38 (m, 4H), 1.74–2.21 (m, 7H), 3.18–3.87 (m, 7H), 4.14 and 4.33–4.35 (each m, total 1H), 5.25–5.32 and 5.38–5.45 (each m, total 1H), 7.12–7.23 (m, 2H), 7.37–7.38 (m, 1H), 7.51–7.54 (m, 1H), 7.71–7.74 (m, 1H), 8.09–8.13 (m, 1H), 9.94 (broad s, 1H).

MS (ESI) m/z 564 (M$^+$+1).

Anal. Calcd for C$_{27}$H$_{28}$ClF$_2$N$_3$O$_4$S.1H$_2$O: C, 55.71; H, 5.19; N, 7.22; S, 5.51. Found: C, 55.88; H, 5.25; N, 6.74; S, 5.26.

Example 58 trans-4-(1-(3-Chloro-4-(6-methyl-2-benzothiazolyl) aminophenylacetyl)-(4S)-fluoro-(2S)-pyrrolidinylmethoxy)cyclohexanecarboxylic acid (Step 1) Synthesis of 2-bromo-6-methylbenzothiazole

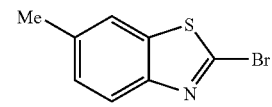

Copper (I) bromide (1.57 g, 10.9 mmol) was suspended in acetonitrile (25 ml). To the resulting suspension was added tert-butyl nitrite (1.63 ml, 13.7 mmol). The resulting mixture was stirred at 60° C. for 10 minutes. To the reaction mixture was added 2-amino-6-methylbenzothiazole (1.50 g, 9.13 mmol), followed by stirring at 60° C. for 1 hour. After cooling, the reaction mixture was diluted with ethyl acetate. The ethyl acetate solution was washed with 1N HCl and saturated brine, dried over anhydrous sodium sulfate, and distilled under reduced pressure to remove the solvent. The residue was purified by chromatography on a silica gel column, whereby from n-hexane/ethyl acetate (7:1, v/v) eluate fractions, 2-bromo-6-methylbenzothiazole (703 mg, 34%) was obtained as a brown oil.

$^1$H-NMR (CDCl$_3$) δ: 2.47 (s, 3H), 7.27–7.29 (m, 1H), 7.58–7.59 (m, 1H), 7.84–7.87 (m, 1H).

(Step 2) Synthesis of methyl (3-chloro-4-(6-methyl-2-benzothiazolyl)aminophenyl)acetate

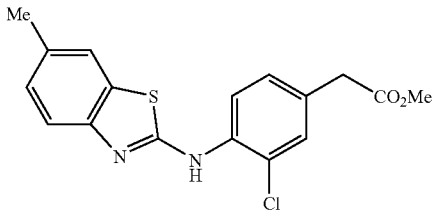

In xylene (10 ml), 2-bromo-6-methylbenzothiazole (703 mg, 3.08 mmol), methyl 4-amino-3-chlorophenylacetate (615 mg, 3.08 mmol), and pyridinium p-toluenesulfonate (PPTS) (232 mg, 0.92 mmol) were heated under reflux for 10 hours. After cooling, the reaction mixture was distilled under reduced pressure to remove the solvent. The residue was purified by chromatography on a silica gel column, whereby from n-hexane/ethyl acetate (6:1, v/v) eluate fractions, methyl (3-chloro-4-(6-methyl-2-benzothiazolyl)aminophenyl)acetate (274 mg, 26%) was obtained as a pale yellow solid.

$^1$H-NMR (CDCl$_3$) δ: 2.43 (s, 3H), 3.59 (s, 2H), 3.71 (s, 3H), 7.17–7.19 (m, 1H), 7.23–7.25 (m, 1H), 7.35 (m, 1H), 7.46 (s, 1H) , 7.58 (d, J=8.3 Hz, 1H) , 8.35 (d, J=8.3 Hz, 1H).

MS (ESI) m/z 347 (M$^+$+1).

(Step 3) Synthesis of (3-chloro-4-(6-methyl-2-benzothiazolyl)aminophenyl)acetic acid

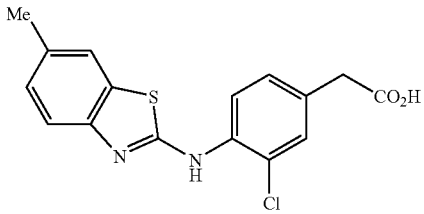

Methyl (3-chloro-4-(6-methyl-2-benzothiazolyl)aminophenyl)acetate (274 mg, 0.79 mmol) was dissolved in THF (5 ml). To the resulting solution was added 0.5N NaOH (5.0 ml, 2.50 mmol), followed by stirring at room temperature for 15 hours. The reaction mixture was poured in ice-1N HCR. The crystals thus precipitated were collected by filtration under reduced pressure, washed with water and dried under reduced pressure to give (3-chloro-4-(6-methyl-2-benzothiazolyl)aminophenyl)acetic acid (202 mg, 77%) as a pale yellow solid.

$^1$H-NMR (DMSO-d$_6$) δ: 2.35 (s, 3H), 3.60 (s, 2H), 7.10–7.13 (m, 1H), 7.25–7.27 (m, 1H), 7.41–7.42 (m, 2H), 7.59 (s, 1H), 8.13–8.15 (m, 1H).

(Step 4) Synthesis of methyl trans-4-(1-(3-chloro-4-(6-methyl-2-benzothiazolyl)aminophenylacetyl)-(4S)-fluoro-(2S)-pyrrolidinylmethoxy)cyclohexanecarboxylate

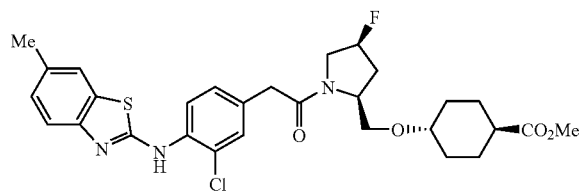

In DMF (5 ml), (3-chloro-4-(6-methyl-2-benzothiazolyl)aminophenyl)acetic acid (202 mg, 0.61 mmol), methyl trans-4-((4S)-fluoro-(2S)-pyrrolidinylmethoxy)cyclohexanecarboxylate (the compound synthesized in (Step 3) of Example 21) (157 mg, 0.61 mmol), EDC•HCl (175 mg, 0.91 mmol), HOBt (123 mg, 0.91 mmol), and triethylamine (130 μl, 0.93 mmol) were stirred at room temperature for 24 hours. The reaction mixture was poured in water. The crystals thus precipitated were collected by filtration under reduced pressure, washed with water and dried under reduced pressure. The crude crystals were purified by chromatography on a silica gel column, whereby from chloroform/methanol (60:1, v/v) eluate fractions, methyl trans-4-(1-(3-chloro-4-(6-methyl-2-benzothiazolyl)aminophenylacetyl)-(4S)-fluoro-(2S)-pyrrolidinylmethoxy)cyclohexanecarboxylate (331 mg, 95%) was obtained as a pale yellow oil.

$^1$H-NMR (CDCl$_3$) δ: 1.18–1.32 (m, 2H), 1.39–1.53 (m, 2H), 1.96–2.11 (m, 4H), 2.19–2.51 (m, total 6H, including s, 3H, at δ: 2.43), 3.22–3.53 (m, 2H), 3.57–4.01 (m, 8H), 4.19–4.25 and 4.35–4.40 (each m, total 1H), 5.17–5.20 and 5.30–5.33 (each m, total 1H), 7.16–7.23 (m, 2H), 7.33–7.35 (m, 1H), 7.46 (s, 1H), 7.52 (broad s, 1H), 7.56–7.59 (m, 1H), 8.30–8.38 (m, 1H).

(Step 5) Synthesis of trans-4-(1-(3-chloro-4-(6-methyl-2-benzothiazolyl)aminophenylacetyl)-(4S)-fluoro-(2S)-pyrrolidinylmethoxy)cyclohexanecarboxylic acid

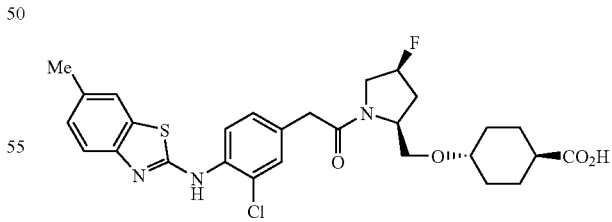

Methyl trans-4-(1-(3-chloro-4-(6-methyl-2-benzothiazolyl)aminophenylacetyl)-(4S)-fluoro-(2S)-pyrrolidinylmethoxy)cyclohexanecarboxylate (331 mg, 0.58 mmol) was dissolved in THF (3.5 ml). To the resulting solution was added 0.5N NaOH (3.5 ml, 1.75 mmol), followed by stirring at room temperature for 2 days. The reaction mixture was poured in ice-1N HCl. The crystals thus precipitated were collected by filtration under reduced pressure, washed with water and dried under reduced pressure to give the title compound (199 mg, 62%) as a brown solid.

¹H-NMR (DMSO-d₆) δ: 1.16–1.36 (m, 4H), 1.76–1.94 (m, 4H), 2.14–2.40 (m, total 6H, including s, 3H, at δ 2.34), 3.15–3.86 (m, 7H), 4.12 and 4.32–4.33 (each m, total 1H), 5.24–5.31 and 5.38–5.45 (each m, total 1H), 7.09–7.11 (m, 1H), 7.19–7.22 (m, 1H), 7.35–7.49 (m, 3H), 7.57 (s, 1H), 8.10–8.12 (m, 1H).

MS (ESI) m/z 560 (M⁺+1).

Anal. Calcd for $C_{28}H_{31}ClFN_3O_4S·3/2H_2O$: C, 57.28; H, 5.84; N, 7.16; S, 5.46. Found: C, 57.20; H, 5.66; N, 6.91; S, 5.39.

Example 59 trans-4-(1-(4-(6-Chloro-2-benzothiazolyl)amino-3-chlorophenylacetyl)-(4S)-fluoro-(2S)-pyrrolidinyl-methoxy)cyclohexanecarboxylic acid (Step 1) Synthesis of 2-bromo-6-chlorobenzothiazole

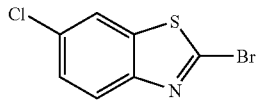

Copper (I) bromide (1.40 g, 9.76 mmol) was suspended in acetonitrile (25 ml). To the resulting suspension was added tert-butyl nitrite (1.45 ml, 12.2 mmol) and the mixture was stirred at 60° C. for 15 minutes. To the reaction mixture was added 2-amino-6-chlorobenzothiazole (1.50 g, 8.12 mmol), followed by stirring at 60° C. for 30 minutes. After cooling, the reaction mixture was diluted with ethyl acetate. The ethyl acetate solution was washed with 1N HCl and saturated brine, dried over anhydrous sodium sulfate, and distilled under reduced pressure to remove the solvent. The residue was purified by chromatography on a silica gel column, whereby from n-hexane/ethyl acetate (7:1, v/v) eluate fractions, 2-bromo-6-chlorobenzothiazole (1.39 g, 69%) was obtained as a yellow solid.

¹H-NMR (CDCl₃) δ: 7.42–7.46 (m, 1H), 7.76–7.90 (m, 2H).

(Step 2) Synthesis of methyl (4-(6-chloro-2-benzothiazolyl)amino-3-chlorophenyl)acetate

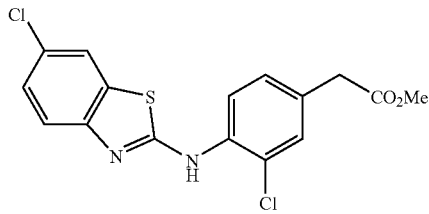

In xylene (10 ml), 2-bromo-6-chlorobenzothiazole (760 mg, 3.06 mmol), methyl 4-amino-3-chlorophenylacetate (610 mg, 3.06 mmol), and pyridinium•p-toluenesulfonate (PPTS) (230 mg, 0.92 mmol) were heated under reflux for 1 hour. After cooling, the reaction mixture was distilled under reduced pressure to remove the solvent. The residue was purified by chromatography on a silica gel column, whereby from n-hexane/ethyl acetate (6:1, v/v) eluate fractions, methyl (4-(6-chloro-2-benzothiazolyl)amino-3-chlorophenyl)acetate (271 mg, 24%) was obtained as a pale yellow solid.

¹H-NMR (CDCl₃) δ: 3.60 (s, 2H), 3.71 (s, 3H), 7.23–7.37 (m, 3H), 7.57–7.62 (m, 3H), 8.31–8.33 (m, 1H).

(Step 3) Synthesis of (4-(6-chloro-2-benzothiazolyl)amino-3-chlorophenyl)acetic acid

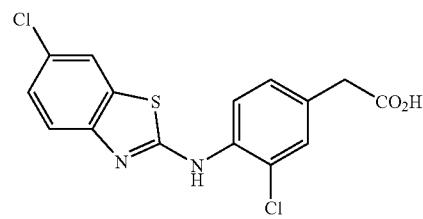

Methyl (4-(6-chloro-2-benzothiazolyl)amino-3-chlorophenyl)acetate (271 mg, 0.74 mmol) was dissolved in THF (4.5 ml). To the resulting solution was added 0.5N NaOH (4.5 ml, 2.25 mmol), followed by stirring at room temperature for 15 hours. The reaction mixture was poured in ice-1N HCl. The crystals thus precipitated were collected by filtration under reduced pressure, washed with water and dried under reduced pressure to give (4-(6-chloro-2-benzothiazolyl)amino-3-chlorophenyl)acetic acid (248 mg, 95%) as a pale yellow solid.

¹H-NMR (DMSO-d₆) δ: 3.61 (s, 2H), 7.26–7.33 (m, 2H), 7.43–7.44 (m, 1H), 7.50–7.52 (m, 1H), 7.92–7.93 (m, 1H), 8.08–8.10 (m, 1H).

(Step 4) Synthesis of methyl trans-4-(1-(4-(6-chloro-2-benzothiazolyl)amino-3-chlorophenylacetyl)-(4S)-fluoro-(2S)-pyrrolidinylmethoxy)cyclohexanecarboxylate

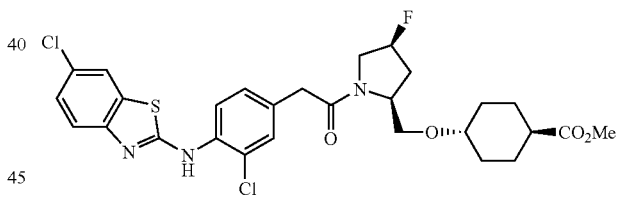

In DMF (6 ml), (4-(6-chloro-2-benzothiazolyl)amino-3-chlorophenyl)acetic acid (248 mg, 0.70 mmol), methyl trans-4-((4S)-fluoro-(2S)-pyrrolidinylmethoxy)cyclohexanecarboxylate (the compound synthesized in (Step 3) of Example 21) (182 mg, 0.70 mmol), EDC•HCl (202 mg, 1.05 mmol), HOBt (142 mg, 1.05 mmol), and triethylamine (150 μl, 1.08 mmol) were stirred at room temperature for 24 hours. The reaction mixture was poured in water. The crystals thus precipitated were collected by filtration under reduced pressure, washed with water and dried under reduced pressure. The crude crystals were dissolved in ethyl acetate. The resulting solution was washed with saturated brine, dried over anhydrous sodium sulfate, and distilled under reduced pressure to remove the solvent. The residue was purified by chromatography on a silica gel column, whereby from chloroform/methanol (60:1, v/v) eluate fractions, methyl trans-4-(1-(4-(6-chloro-2-benzothiazolyl)amino-3-chlorophenylacetyl)-(4S)-fluoro-(2S)-pyrrolidinyl-methoxy)cyclohexanecarboxylate (382 mg, 92%) was obtained as a colorless amorphous substance.

¹H-NMR (CDCl₃) δ: 1.23–1.50 (m, 4H), 1.97–2.52 (m, 7H), 3.25–4.03 (m, 10H), 4.23–4.24 and 4.39 (each m, total 1H), 5.19–5.22 and 5.33–5.35 (each m, total 1H), 7.21–7.36 (m, 3H), 7.56–7.69 (m, 3H), 8.26–8.34 (m, 1H).

MS (ESI) m/z 594 (M⁺+1).

(Step 5) Synthesis of trans-4-(1-(4-(6-chloro-2-benzothiazolyl)amino-3-chlorophenylacetyl)-(4S)-fluoro-(2S)-pyrrolidinylmethoxy)cyclohexanecarboxylic acid

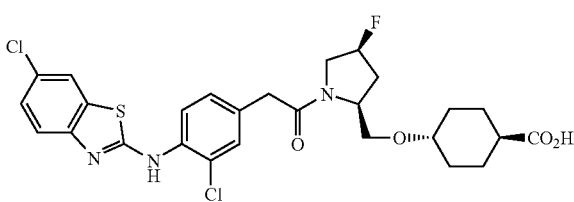

Methyl trans-4-(1-(4-(6-chloro-2-benzothiazolyl)amino-3-chlorophenylacetyl)-(4S)-fluoro-(2S)-pyrrolidinylmethoxy)cyclohexanecarboxylate (382 mg, 0.64 mmol) was dissolved in THF (4 ml). To the resulting solution was added 0.5N NaOH (4.0 ml, 2.00 mmol), followed by stirring at room temperature for 2 days. The reaction mixture was poured in ice-1N HCl. The crystals thus precipitated were collected by filtration under reduced pressure, washed with water and dried under reduced pressure. The crude crystals were purified by chromatography on a silica gel column, whereby from chloroform/methanol (30:1 to 15:1, v/v) eluate fractions, the title compound (320 mg, 86%) was obtained as a pale yellow amorphous substance.

¹H-NMR (DMSO-d₆) δ: 1.16–1.36 (m, 4H), 1.87–2.20 (m, 7H), 3.15–3.87 (m, 7H), 4.13 and 4.32–4.34 (each m, total 1H), 5.24–5.32 and 5.38–5.45 (each m, total 1H), 7.21–7.23 (m, 1H), 7.29–7.32 (m, 1H), 7.37–7.38 (m, 1H), 7.48–7.51 (m, 1H), 7.92 (s, 1H), 8.05–8.09 (m, 1H).

MS (ESI) m/z 580 (M⁺+1).

Anal. Calcd for $C_{27}H_{28}Cl_2FN_3O_4S \cdot 2H_2O$: C, 52.60; H, 5.23; N, 6.82; S, 5.20. Found: C, 52.37; H, 4.65; N, 6.62; S, 5.16.

Example 60 trans-4-(1-(4-(4-Chloro-2-benzothiazolyl)amino-3-chlorophenylacetyl)-(4S)-fluoro-(2S)-pyrrolidinylmethoxy)cyclohexanecarboxylic acid (Step 1) Synthesis of 2-bromo-4-chlorobenzothiazole

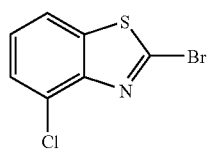

Copper (I) bromide (1.40 g, 9.76 mmol) was suspended in acetonitrile (25 ml). To the resulting suspension was added tert-butyl nitride (1.45 ml, 12.2 mmol) and the mixture was stirred at 60° C. for 10 minutes. To the reaction mixture was added 2-amino-4-chlorobenzothiazole (1.50 g, 8.12 mmol), followed by stirring at 60° C. for 2 hours. After cooling, the reaction mixture was diluted with ethyl acetate. The ethyl acetate solution was washed with 1N HCl and saturated brine, dried over anhydrous sodium sulfate, and distilled under reduced pressure to remove the solvent. The residue was purified by chromatography on a silica gel column, whereby from n-hexane/ethyl acetate (7:1, v/v) eluate fractions, 2-bromo-4-chlorobenzothiazole (1.32 g, 65%) was obtained as a pale yellow solid.

¹H-NMR (CDCl₃) δ: 7.33–7.38 (m, 1H), 7.49–7.53 (m, 1H), 7.67–7.71 (m, 1H).

(Step 2) Synthesis of methyl (4-(4-chloro-2-benzothiazolyl)amino-3-chlorophenyl)acetate

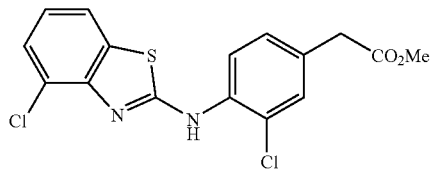

In xylene (7 ml), 2-bromo-4-chlorobenzothiazole (647 mg, 2.60 mmol), methyl 4-amino-3-chlorophenylacetate (520 mg, 2.60 mmol), and pyridinium•p-toluenesulfonate (PPTS) (200 mg, 0.80 mmol) were heated under reflux for 7 hours. After cooling, the reaction mixture was distilled under reduced pressure to remove the solvent. The residue was purified by chromatography on a silica gel column, whereby from n-hexane/ethyl acetate (6:1, v/v) eluate fractions, methyl (4-(4-chloro-2-benzothiazolyl)amino-3-chlorophenyl)acetate (556 mg, 58%) was obtained as a yellow amorphous substance.

¹H-NMR (CDCl₃) δ: 3.61 (s, 2H), 3.72 (s, 3H), 7.10–7.14 (m, 1H), 7.27–7.29 (m, 1H), 7.39–7.41 (m, 2H), 7.54–7.56 (m, 1H), 7.75 (broad s, 1H), 8.25–8.27 (m, 1H).

(Step 3) Synthesis of (4-(4-chloro-2-benzothiazolyl)amino-3-chlorophenyl)acetic acid

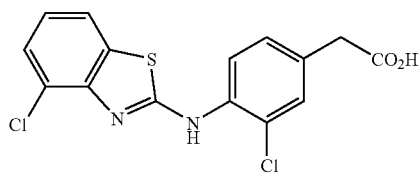

In THF (5 ml) was dissolved methyl (4-(4-chloro-2-benzothiazolyl)amino-3-chlorophenyl)acetate (556 mg, 1.51 mmol). To the resulting solution was added 1N NaOH (4.5 ml, 4.50 mmol), followed by stirring at room temperature for 20 hours. The mixture was poured in ice-1N HCl. The crystals thus precipitated were collected by filtration under reduced pressure, washed with water and dried under reduced pressure to give (4-(4-chloro-2-benzothiazolyl)amino-3-chlorophenyl)acetic acid (468 mg, 88%) as a pale yellow solid.

¹H-NMR (DMSO-d₆) δ: 3.63 (s, 2H), 7.12–7.16 (m, 1H), 7.29–7.31 (m, 1H), 7.38–7.41 (m, 1H), 7.46–7.47 (m, 1H), 7.76–7.78 (m, 1H), 8.18–8.21 (m, 1H), 10.26 (broad s, 1H), 12.45 (broad s, 1H).

(Step 4) Synthesis of methyl trans-4-(1-(4-(4-chloro-2-benzothiazolyl)amino-3-chlorophenylacetyl)-(4S)-fluoro-(2S)-pyrrolidinylmethoxy)cyclohexanecarboxylate

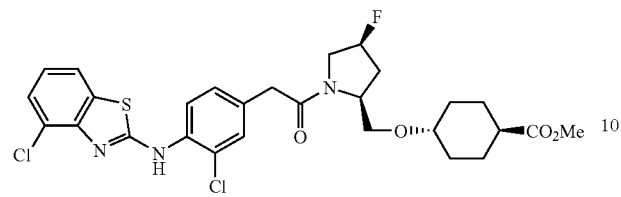

In DMF (7 ml), (4-(4-chloro-2-benzothiazolyl)amino-3-chlorophenyl)acetic acid (258 mg, 0.73 mmol), methyl trans-4-((4S)-fluoro-(2S)-pyrrolidinylmethoxy)cyclohexanecarboxylate (the compound synthesized in (Step 3) of Example 21) (189 mg, 0.73 mmol), EDC•HCl (210 mg, 1.10 mmol), HOBt (148 mg, 1.10 mmol), and triethylamine (155 μl, 1.11 mmol) were stirred at room temperature for 14 hours. The mixture was poured in water. The crystals thus precipitated were collected by filtration under reduced pressure, washed with water and dried under reduced pressure. The crude crystals were purified by chromatography on a silica gel column, whereby from n-hexane/ethyl acetate (1:1 to 1:2, v/v) eluate fractions, methyl trans-4-(1-(4-(4-chloro-2-benzothiazolyl)amino-3-chlorophenylacetyl)-(4S)-fluoro-(2S)-pyrrolidinylmethoxy)cyclohexanecarboxylate (430 mg, 99%) was obtained as a colorless amorphous substance.

$^1$H-NMR (CDCl$_3$) δ: 1.24–1.50 (m, 4H), 2.01–2.29 (m, 7H), 3.27–3.89 (m, 10H), 4.23–4.24 and 4.40 (each m, total 1H), 5.20 and 5.35 (each m, total 1H), 7.10–7.24 (m, 2H), 7.37–7.40 (m, 2H), 7.54–7.56 (m, 1H), 7.77 (m, 1H), 8.21–8.29 (m, 1H).

MS (ESI) m/z 594 (M$^+$+1).

(Step 5) Synthesis of trans-4-(1-(4-(4-chloro-2-benzothiazolyl)amino-3-chlorophenylacetyl)-(4S)-fluoro-(2S)-pyrrolidinylmethoxy)cyclohexanecarboxylic acid

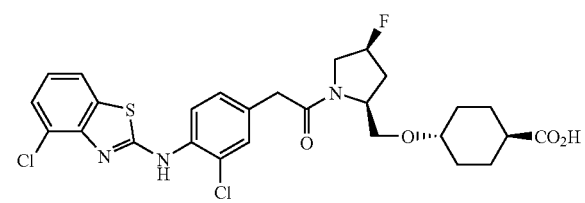

Methyl trans-4-(1-(4-(4-chloro-2-benzothiazolyl)amino-3-chlorophenylacetyl)-(4S)-fluoro-(2S)-pyrrolidinylmethoxy)cyclohexanecarboxylate (430 mg, 0.72 mmol) was dissolved in THF (4 ml). To the resulting solution was added 0.5N NaOH (4.2 ml, 2.10 mmol), followed by stirring at room temperature for 13 hours. The reaction mixture was poured in ice-1N HCl. The crystals thus precipitated were collected by filtration under reduced pressure, washed with water and dried under reduced pressure to give the title compound (375 mg, 89%) as a pale yellow solid.

$^1$H-NMR (DMSO-d$_6$) δ: 1.13–1.37 (m, 4H), 1.86–1.95 (m, 4H), 2.08–2.33 (m, 3H), 3.16–3.88 (m, 7H), 4.13 and 4.34–4.36 (each m, total 1H), 5.25–5.34 and 5.39–5.46 (each m, total 1H), 7.11–7.15 (m, 1H), 7.23–7.26 (m, 1H), 7.38–7.41 (m, 2H), 7.75–7.77 (m, 1H), 8.14–8.18 (m, 1H), 10.23 (broad s, 1H), 12.05 (broad s, 1H).

MS (FAB) m/z 580 (M$^+$+1).

Anal. Calcd for C$_{27}$H$_{28}$Cl$_2$FN$_3$O$_4$S.1/2H$_2$O: C, 55.01; H, 4.96; N, 7.13; S, 5.44. Found: C, 54.73; H, 5.00; N, 6.70; S, 5.28.

Example 61 trans-4-(1-(4-(2-Benzothiazolyl)amino-5-chloro-2-fluorophenylacetyl)-(4S)-fluoro-(2S)-pyrrolidinylmethoxy)cyclohexanecarboxylic acid (Step 1) Synthesis of 2-bromobenzothiazole

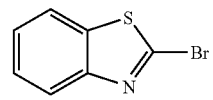

Copper (I) bromide (1.93 g, 13.5 mmol) was suspended in acetonitrile (30 ml). To the resulting suspension was added tert-butyl nitrite (2.00 ml, 16.8 mmol) and the mixture was stirred at 60° C. for 15 minutes. To the reaction mixture was added 2-aminobenzothiazole (1.68 g, 11.2 mmol) and the mixture was stirred at 60° C. for 1 hour. After cooling, the reaction mixture was poured in 1N HCl, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane/ethyl acetate (7:1, v/v) eluate fractions, 2-bromobenzothiazole (1.36 g, 57%) was obtained as a brown oil.

$^1$H-NMR (CDCl$_3$) δ: 7.39–7.51 (m, 2H), 7.77–7.82 (m, 1H), 7.94–8.00 (m, 1H).

(Step 2) Synthesis of methyl (4-(2-benzothiazolyl)amino-5-chloro-2-fluorophenyl)acetate

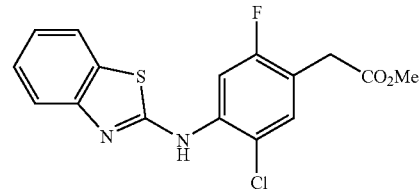

In xylene (10 ml), 2-bromobenzothiazole (740 mg, 3.46 mmol), methyl 4-amino-3-chloro-2-fluorophenylacetate (800 mg, 3.45 mmol), and pyridinium•p-toluenesulfonate (PPTS) (1.13 g, 4.50 mmol) were heated under reflux for 10 hours. After cooling, the reaction mixture was distilled under reduced pressure to remove the solvent. The residue was purified by chromatography on a silica gel column, whereby from n-hexane/ethyl acetate (7:1, v/v) eluate fractions, methyl (4-(2-benzothiazolyl)amino-5-chloro-2-fluorophenyl)acetate (559 mg, 44%) was obtained as a brown solid.

$^1$H-NMR (CDCl$_3$) δ: 1.26–1.30 (m, 3H), 3.62 (s, 2H), 4.10 (broad s, 1H), 4.15–4.21 (m, 2H), 7.21–7.42 (m, 3H), 7.67–7.76 (m, 2H), 8.47–8.50 (m, 1H).

MS (ESI) m/z 365 (M$^+$+1).

(Step 3) Synthesis of (4-(2-benzothiazolyl)amino-5-chloro-2-fluorophenyl)acetic acid

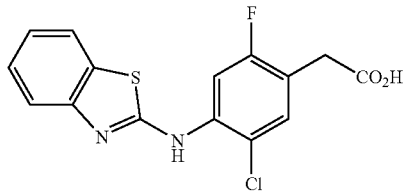

Methyl (4-(2-benzothiazolyl)amino-5-chloro-2-fluorophenyl)acetate (613 mg, 1.68 mmol) was dissolved in THF (5 ml). To the resulting solution was added 1N NaOH (5.0 ml, 5.00 mmol). The resulting mixture was stirred at room temperature for 17 hours. Water was added to the reaction mixture. The mixture was washed with ether. The water layer was poured in ice-1N HCl to acidify the water layer. The crystals thus precipitated were collected by filtration under reduced pressure, washed with water and dried under reduced pressure to give (4-(2-benzothiazolyl)amino-5-chloro-2-fluorophenyl)acetic acid (464 mg, 82%) as a pale yellow solid.

$^1$H-NMR (DMSO-$d_6$) δ: 3.63 (s, 2H), 7.17–7.21 (m, 1H), 7.32–7.39 (m, 1H), 7.52–7.54 (m, 1H), 7.61–7.63 (m, 1H), 7.82–7.84 (m, 1H), 8.38 (m, 1H), 10.17 (broad s, 1H), 12.52 (broad s, 1H).

(Step 4) Synthesis of methyl trans-4-(1-(4-(2-benzothiazolyl)amino-5-chloro-2-fluorophenylacetyl)-(4S)-fluoro-(2S)-pyrrolidinylmethoxy)cyclohexanecarboxylate

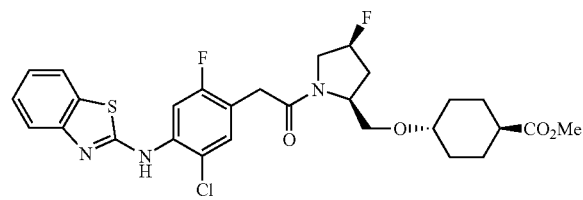

In DMF (8 ml), (4-(2-benzothiazolyl)amino-5-chloro-2-fluorophenyl)acetic acid (290 mg, 0.86 mmol), methyl trans-4-((4S)-fluoro-(2S)-pyrrolidinylmethoxy)cyclohexanecarboxylate (the compound synthesized in (Step 3) of Example 21) (223 mg, 0.86 mmol), EDC·HCl (247 mg, 1.29 mmol), HOBt (174 mg, 1.29 mmol), and triethylamine (180 μl, 1.29 mmol) were stirred at room temperature for 15 hours. The reaction mixture was poured in water. The crystals thus precipitated were collected by filtration under reduced pressure, and washed with water. The crude crystals were dissolved in ethyl acetate. The solution was washed with saturated brine, dried over anhydrous sodium sulfate, and distilled under reduced pressure to remove the solvent. The residue was purified by chromatography on a silica gel column, whereby from n-hexane/ethyl acetate (1:1, v/v) eluate fractions, methyl trans-4-(1-(4-(2-benzothiazolyl)amino-5-chloro-2-fluorophenylacetyl)-(4S)-fluoro-(2S)-pyrrolidinylmethoxy)cyclohexanecarboxylate (362 mg, 73%) was obtained as a colorless amorphous substance.

$^1$H-NMR (CDCl$_3$) δ: 1.21–1.53 (m, 4H), 1.97–2.54 (m, 7H), 3.23–4.02 (m, 10H), 4.28–4.41 (m, 1H), 5.20–5.24 and 5.34–5.38 (each m, total 1H), 7.21–7.30 (m, 1H), 7.35–7.44 (m, 2H), 7.63–7.83 (m, 3H), 8.42–8.50 (m, 1H).

MS (ESI) m/z 578 (M$^+$+1).

(Step 5) Synthesis of trans-4-(1-(4-(2-benzothiazolyl)amino-5-chloro-2-fluorophenylacetyl)-(4S)-fluoro-(2S)-pyrrolidinylmethoxy)cyclohexanecarboxylic acid

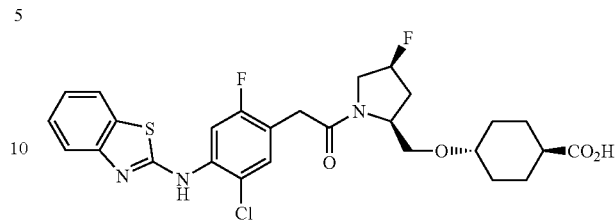

In THF (4 ml) was dissolved methyl trans-4-(1-(4-(2-benzothiazolyl)amino-5-chloro-2-fluorophenylacetyl)-(4S)-fluoro-(2S)-pyrrolidinylmethoxy)cyclohexanecarboxylate (362 mg, 0.63 mmol). To the resulting solution was added 0.5N NaOH (4.0 ml, 2.00 mmol). The resulting mixture was stirred at room temperature for 1 hour. The reaction mixture was poured in ice-1N HCR, followed by extraction with ethyl acetate. The extract was washed with saturated brine, dried over anhydrous sodium sulfate, and distilled under reduced pressure to remove the solvent. The residue was purified by chromatography on a silica gel column, whereby from chloroform/methanol (60:1 to 30:1, v/v) eluate fractions, the title compound (299 mg, 85%) was obtained as a colorless amorphous substance.

$^1$H-NMR (DMSO-$d_6$) δ: 1.16–1.38 (m, 4H), 1.89–2.23 (m, 7H), 3.17–3.93 (m, 7H), 4.13 and 4.34–4.36 (each m, total 1H), 5.26–5.35 and 5.40–5.48 (each m, total 1H), 7.17–7.21 (m, 1H), 7.32–7.36 (m, 1H), 7.40–7.45 (m, 1H), 7.61–7.63 (m, 1H), 7.82–7.84 (m, 1H), 8.32–8.34 (m, 1H).

MS (ESI) m/z 564 (M$^+$+1).

Anal. Calcd for $C_{27}H_{28}ClF_2N_3O_4S·2H_2O$: C, 54.04; H, 5.37; N, 7.00; S, 5.34. Found: C, 53.80; H, 4.63; N, 6.86; S, 5.17.

Example 62 trans-4-(1-(3-Chloro-4-(5-fluoro-2-benzothiazolyl)aminophenylacetyl)-(4S)-fluoro-(2)-pyrrolidinylmethoxy)cyclohexanecarboxylic acid (Step 1) Synthesis of 2-bromo-5-fluorobenzothiazole

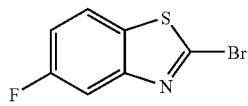

Copper (I) bromide (1.26 g, 7.31 mmol) was suspended in acetonitrile (25 ml). To the resulting suspension was added tert-butyl nitrite (1.47 ml, 10.9 mmol) and the mixture was stirred at 60° C. for 10 minutes. To the reaction mixture was added 2-amino-5-fluorobenzothiazole (1.23 g, 7.31 mmol), followed by stirring at 60° C. for 60 minutes. After cooling, the reaction mixture was poured in 1N HCl. The crystals thus precipitated were collected by filtration under reduced pressure. The crude crystals were dissolved in ethyl acetate. The solution was purified by chromatography on a silica gel column, whereby from n-hexane/ethyl acetate (7:1, v/v) eluate fractions, 2-bromo-5-fluorobenzothiazole (1.07 g, 63%) was obtained as a yellow solid.

$^1$H-NMR (CDCl$_3$) δ: 7.18–7.23 (m, 1H), 7.64–7.77 (m, 2H).

(Step 2) Synthesis of methyl (3-chloro-4-(5-fluoro-2-benzothiazolyl)aminophenyl)acetate

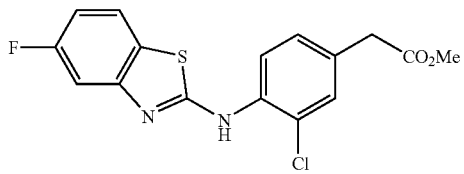

In xylene (5 ml), 2-bromo-5-fluorobenzothiazole (516 mg, 2.22 mmol), methyl 4-amino-3-chlorophenylacetate (444 mg, 2.22 mmol), and pyridinium·p-toluenesulfonate (PPTS) (168 mg, 0.67 mmol) were heated under reflux for 10 hours. After cooling, the reaction mixture was distilled under reduced pressure to remove the solvent. The residue was purified by chromatography on a silica gel column, whereby from n-hexane/ethyl acetate (7:1, v/v) eluate fractions, methyl (3-chloro-4-(5-fluoro-2-benzothiazolyl)aminophenyl)acetate (292 mg, 37%) was obtained as a pale yellow oil.

$^1$H-NMR (CDCl$_3$) δ: 3.61 (s, 2H), 3.72 (s, 3H), 6.93–6.98 (m, 1H), 7.25–7.27 (m, 1H), 7.37–7.41 (m, 2H), 7.55–7.58 (m, 1H), 7.65 (broad s, 1H), 8.31–8.33 (m, 1H).

(Step 3) Synthesis of (3-chloro-4-(5-fluoro-2-benzothiazolyl)aminophenyl)acetic acid In THF (5 ml) was dissolved methyl (3-chloro-4-(5-fluoro-2-benzothiazolyl)aminophenyl)acetate (292 mg, 0.83 mmol). To the resulting solution was added 0.5N NaOH (5.0 ml, 2.50 mmol). The resulting mixture was stirred at room temperature for 2 hours. The reaction mixture was poured in ice-1N HCl. The crystals thus precipitated were collected by filtration under reduced pressure, washed with water and dried under reduced pressure to give (3-chloro-4-(5-fluoro-2-benzothiazolyl)aminophenyl)acetic acid (226 mg, 81%) as a pale solid.

$^1$H-NMR (DMSO-d$_6$) δ: 3.61 (s, 2H), 6.98–7.03 (m, 1H), 7.27 (dd, J=2.0, 8.3 Hz, 1H), 7.34–7.37 (m, 1H), 7.44 (d, J=2.0 Hz, 1H), 7.78–7.82 (m, 1H), 8.05 (d, J=8.3 Hz, 1H).

(Step 4) Synthesis of methyl trans-4-(1-(3-chloro-4-(5-fluoro-2-benzothiazolyl)aminophenylacetyl)-(4S)-fluoro-(2S)-pyrrolidinylmethoxy)cyclohexanecarboxylate

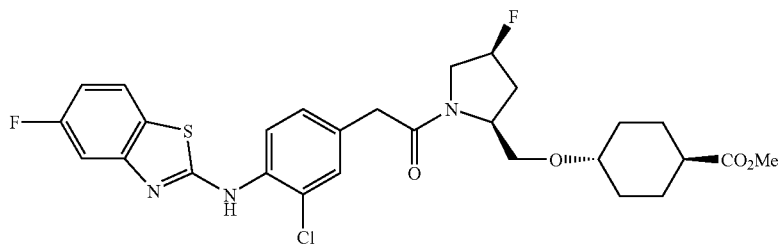

In DMF (5 ml), (3-chloro-4-(5-fluoro-2-benzothiazolyl)aminophenyl)acetic acid (216 mg, 0.64 mmol), methyl trans-4-((4S)-fluoro-(2S)-pyrrolidinylmethoxy)cyclohexanecarboxylate (the compound synthesized in (Step 3) of Example 21) (166 mg, 0.64 mmol), EDC·HCl (184 mg, 0.96 mmol), HOBt (130 mg, 0.96 mmol), and triethylamine (134 μl, 0.96 mmol) were stirred at room temperature for 2 days. The reaction mixture was poured in water. The crystals thus precipitated were collected by filtration under reduced pressure. The crude crystals were dissolved in ethyl acetate. The solution was washed with saturated brine, dried over anhydrous sodium sulfate, and distilled under reduced pressure to remove the solvent. The residue was purified by chromatography on a silica gel column, whereby from n-hexane/ethyl acetate (1:1 to 1:2, v/v) eluate fractions, methyl trans-4-(1-(3-chloro-4-(5-fluoro-2-benzothiazolyl)aminophenylacetyl)-(4S)-fluoro-(2S)-pyrrolidinylmethoxy)cyclohexanecarboxylate (355 mg, 96%) was obtained as a colorless amorphous substance.

$^1$H-NMR (CDCl$_3$) δ: 1.18–1.32 (m, 2H), 1.39–1.53 (m, 2H), 1.97–2.52 (m, 7H), 3.22–3.37 and 3.48–3.54 (each m, total 2H), 3.58–4.02 (m, 8H), 4.21–4.26 and 4.35–4.41 (each m, total 1H), 5.18–5.23 and 5.31–5.35 (each m, total 1H), 6.92–6.98 (m, 1H), 7.21–7.25 (m, 1H), 7.36–7.40 (m, 2H), 7.54–7.58 (m, 1H), 7.65 (broad s, 1H), 8.26–8.34 (m, 1H).

(Step 5) Synthesis of trans-4-(1-(3-chloro-4-(5-fluoro-2-benzothiazolyl)aminophenylacetyl)-(4S)-fluoro-(2S)-pyrrolidinylmethoxy)cyclohexanecarboxylic acid

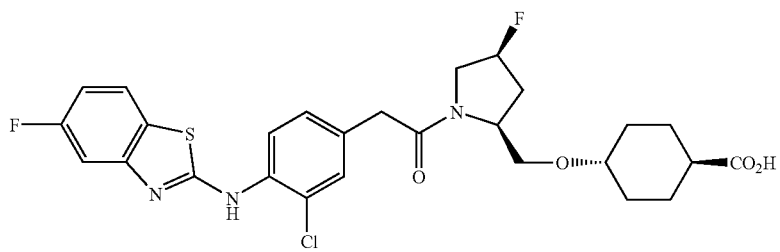

In THF (4 ml) was dissolved methyl trans-4-(1-(3-chloro-4-(5-fluoro-2-benzothiazolyl)aminophenylacetyl)-(4S)-fluoro-(2S)-pyrrolidinylmethoxy)cyclohexanecarboxylate (355 mg, 0.61 mmol). To the resulting solution was added 0.5N NaOH (4.0 ml, 2.00 mmol), followed by stirring at room temperature for 20 hours. The reaction mixture was poured in ice-1N HCl. The crystals thus precipitated were collected by filtration under reduced pressure, washed with water and dried under reduced pressure to give the title compound (287 mg, 83%) as a white solid.

$^1$H-NMR (DMSO-$d_6$) δ: 1.16–1.38 (m, 4H), 1.78–1.95 (m, 4H), 2.15–2.21 (m, 3H), 3.16–3.88 (m, 7H), 4.13 and 4.34–4.35 (each m, total 1H), 5.26–5.33 and 5.39–5.46 (each m, total 1H), 6.98–7.02 (m, 1H), 7.23–7.24 (m, 1H), 7.34–7.39 (m, 2H), 7.78–7.82 (m6, 1H), 8.01–8.05 (m, 1H), 10.11 (broad s, 1H), 12.06 (broad s, 1H).

MS (LC) m/z 564.4 (M$^+$+1).

Anal. Calcd for $C_{27}H_{28}ClF_2N_3O_4S.1H_2O$: C, 55.71; H, 5.19; N, 7.22; S, 5.51. Found: C, 56.00; H, 4.99; N, 6.89; S, 5.38.

Example 63 trans-4-(1-(5-Chloro-4-(5-fluoro-2-benzothiazolyl)amino-2-fluorophenylacetyl)-(4S)-fluoro-(2S)-pyrrolidinylmethoxy)cyclohexanecarboxylic acid (Step 1) Synthesis of 2-bromo-5-fluorobenzothiazole

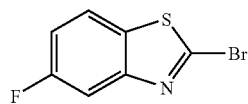

Copper (I) bromide (1.26 g, 7.31 mmol) was suspended in acetonitrile (25 ml). To the resulting suspension was added tert-butyl nitrite (1.47 ml, 10.9 mmol) and the mixture was stirred at 60° C. for 10 minutes. To the reaction mixture was added 2-amino-5-fluorobenzothiazole (1.23 g, 7.31 mmol), followed by stirring at 60° C. for 60 minutes. After cooling, the reaction mixture was poured in 1N HCl. The crystals thus precipitated were collected by filtration under reduced pressure. The crude crystals were dissolved in ethyl acetate. The resulting solution was washed successively with 1N HCl and saturated brine, dried over anhydrous sodium sulfate, and distilled under reduced pressure to remove the solvent. The residue was purified by chromatography on a silica gel column, whereby from n-hexane/ethyl acetate (7:1, v/v) eluate fractions, 2-bromo-5-fluorobenzothiazole (1.07 g, 63%) was obtained as a yellow solid.

$^1$H-NMR (CDCl$_3$) δ: 7.18–7.23 (m, 1H), 7.64–7.77 (m, 2H).

(Step 2) Synthesis of ethyl (5-chloro-4-(5-fluoro-2-benzothiazolyl)amino-2-fluorophenyl)acetate

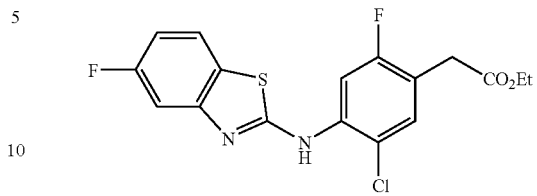

In xylene (5 ml), 2-bromo-5-fluorobenzothiazole (548 mg, 2.36 mmol), ethyl 4-amino-5-chloro-2-fluorophenylacetate (547 mg, 2.36 mmol), and pyridinium p-toluenesulfonate (PPTS) (178 mg, 0.71 mmol) were heated under reflux for 3 hours. After cooling, the reaction mixture was distilled under reduced pressure to remove the solvent. The residue was purified by chromatography on a silica gel column, whereby from n-hexane/ethyl acetate (7:1, v/v) eluate fractions, ethyl (5-chloro-4-(5-fluoro-2-benzothiazolyl)amino-2-fluorophenyl)acetate (298 mg, 33%) was obtained as a pale yellow solid.

$^1$H-NMR (CDCl$_3$) δ: 1.28 (t, J=7.1 Hz, 3H), 3.61 (s, 2H), 4.17 (q, J=7.1 Hz, 2H), 6.95–6.98 (m, 1H), 7.28–7.30 (m, 1H), 7.39–7.42 (m, 1H), 7.54–7.57 (m, 1H), 7.69 (broad s, 1H), 8.40–8.43 (m, 1H).

(Step 3) Synthesis of (5-chloro-4-(5-fluoro-2-benzothiazolyl)amino-2-fluorophenyl)acetic acid

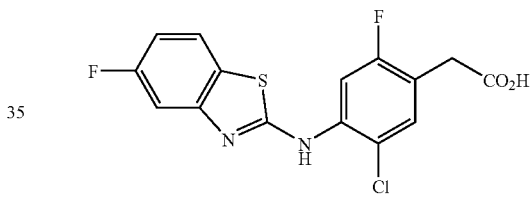

Ethyl (5-chloro-4-(5-fluoro-2-benzothiazolyl)amino-2-fluorophenyl)acetate (298 mg, 0.78 mmol) was dissolved in THF (5 ml). To the resulting solution was added 0.5N NaOH (5.0 ml, 2.50 mmol). The resulting mixture was stirred at room temperature for 3 hours. The reaction mixture was poured in ice-1N HCl. The crystals thus precipitated were collected by filtration under reduced pressure, washed with water and dried under reduced pressure to give (5-chloro-4-(5-fluoro-2-benzothiazolyl)amino-2-fluorophenyl)acetic acid (237 mg, 86%) as a pale yellow solid.

$^1$H-NMR (DMSO-$d_6$) δ: 3.64 (s, 2H), 7.03–7.08 (m, 1H), 7.45–7.55 (m, 2H), 7.83–7.86 (m, 1H), 8.28–8.31 (m, 1H), 10.26 (broad s, 1H), 12.56 (broad s, 1H).

(Step 4) Synthesis of methyl trans-4-(1-(5-chloro-4-(5-fluoro-2-benzothiazolyl)amino-2-fluorophenylacetyl)-(4S)-fluoro-(2S)-pyrrolidinylmethoxy)cyclohexanecarboxylate

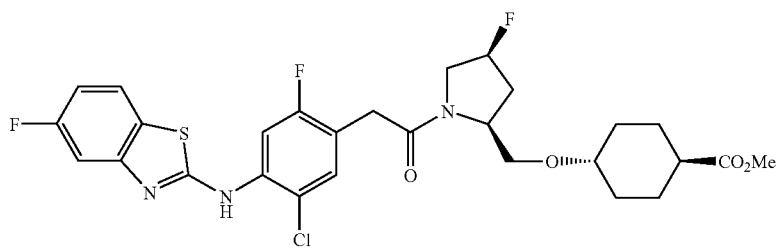

In DMF (5 ml), (5-chloro-4-(5-fluoro-2-benzothiazolyl) amino-2-fluorophenyl)acetic acid (233 mg, 0.66 mmol), methyl trans-4-((4S)-fluoro-(2S)-pyrrolidinylmethoxy)cyclohexanecarboxylate (the compound synthesized in (Step 3) of Example 21) (170 mg, 0.66 mmol), EDC•HCl (189 mg, 0.99 mmol), HOBt (133 mg, 0.98 mmol), and triethylamine (137 μl, 0.98 mmol) were stirred at room temperature for 3 hours. The reaction mixture was poured in water. The crystals thus precipitated were collected by filtration under reduced pressure. The crude crystals were dissolved in ethyl acetate. The resulting solution was washed with saturated brine, dried over anhydrous sodium sulfate, and distilled under reduced pressure to remove the solvent. The residue was purified by chromatography on a silica gel column, whereby from n-hexane/ethyl acetate (1:1 to 1:2, v/v) eluate fractions, methyl trans-4-(1-(5-chloro-4-(5-fluoro-2-benzothiazolyl)amino-2-fluorophenylacetyl)-(4S)-fluoro-(2S)-pyrrolidinylmethoxy)cyclohexanecarboxylate (368 mg, 94%) was obtained as a pale yellow amorphous substance.

$^1$H-NMR (CDCl$_3$) δ: 1.22–1.33 (m, 2H), 1.39–1.53 (m, 2H), 1.96–2.18 (m, 4H), 2.22–2.53 (m, 3H), 3.23–4.03 (m, 10H), 4.27–4.31 and 4.37 (each m, total 1H), 5.19 and 5.23–5.37 (each m, total 1H), 6.95–6.99 (m, 1H), 7.36–7.44 (m, 2H), 7.56–7.59 (m, 1H), 7.65 (broad s, 1H), 8.34–8.43 (m, 1H).

(Step 5) Synthesis of trans-4-(1-(5-chloro-4-(5-fluoro-2-benzothiazolyl)amino-2-fluorophenylacetyl)-(4S)-fluoro-(2S)-pyrrolidinylmethoxy)cyclohexanecarboxylic acid

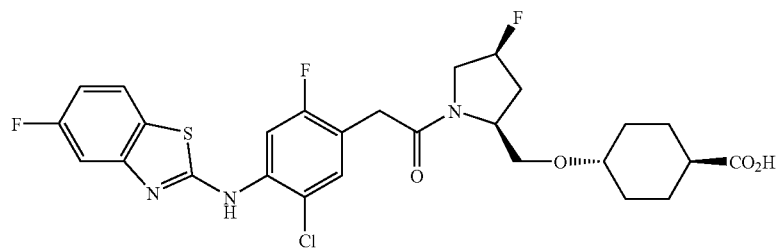

In THF (4 ml) was dissolved methyl trans-4-(1-(5-chloro-4-(5-fluoro-2-benzothiazolyl)amino-2-fluorophenylacetyl)-(4S)-fluoro-(2S)-pyrrolidinylmethoxy)cyclohexanecarboxylate (368 mg, 0.62 mmol). To the resulting solution was added 0.5N NaOH (4.0 ml, 2.00 mmol), followed by stirring at room temperature for 2 hours. The reaction mixture was poured in ice-1N HCl. The crystals thus precipitated were collected by filtration under reduced pressure, washed with water and dried under reduced pressure to give the title compound (266 mg, 74%) as a pale yellow solid.

$^1$H-NMR (DMSO-d$_6$) δ: 1.18–1.38 (m, 4H), 1.86–1.99 (m, 4H), 2.10–2.21 (m, 3H), 3.17–4.02 (m, 7H), 4.13 and 4.35–4.36 (each m, total 1H), 5.26–5.35 and 5.40–5.48 (each m, total 1H), 7.03–7.08 (m, 1H), 7.41–7.48 (m, 2H), 7.83–7.87 (m, 1H), 8.25–8.27 (m, 1H)

MS (LC) m/z 582.4 (M$^+$+1), 580.4 (M$^+$−1).

Anal. Calcd for C$_{27}$H$_{27}$ClF$_3$N$_3$O$_4$S.1/2H$_2$O: C, 54.87; H, 4.77; N, 7.11; S, 5.43. Found: C, 54.68; H, 4.62; N, 6.85; S, 5.45.

Example 64 trans-4-(1-((3-Bromo-4-((3-indolylcarbonyl)amino) phenyl)acetyl)-(4S)-fluoro-(2S)-pyrrolidinylmethoxy)cyclohexanecarboxylic acid (Step 1) Synthesis of ethyl (3-bromo-4-((3-indolylcarbonyl) amino)phenyl)acetate

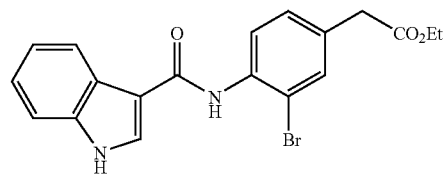

In DMF (20 ml) were dissolved indole-3-carboxylic acid (1.00 g, 6.21 mmol) and 4-amino-3-bromophenylacetic acid (1.60 g, 6.21 mmol). To the resulting solution was added EDC HCl (1.43 g, 7.45 mmol) under stirring at room temperature. After the reaction mixture was stirred at room temperature for 4 hours, water was added thereto, followed by extraction with ethyl acetate. The extract was washed with saturated brine, dried over anhydrous sodium sulfate, and distilled under reduced pressure to remove the solvent. The residue was purified by chromatography on a silica gel column, whereby from ethyl acetate eluate fractions, ethyl (3-bromo-4-((3-indolylcarbonyl)amino)phenyl)acetate (664 mg, 27%) was obtained as a pale yellow solid.

$^1$H-NMR (CDCl$_3$) δ: 1.29 (t, J=7.1 Hz, 3H), 3.59 (s, 2H), 4.19 (q, J=7.1 Hz, 2H), 7.24–7.33 (m, 3H), 7.41–7.51 (m, 2H), 7.82 (d, J=2.7 Hz, 1H), 8.20 (m, 1H), 8.31 (broad s, 1H), 8.48 (d, J=8.6 Hz, 1H), 9.35 (broad s, 1H).

(Step 2) Synthesis of (3-bromo-4-((3-indolylcarbonyl) amino)phenyl)acetic acid

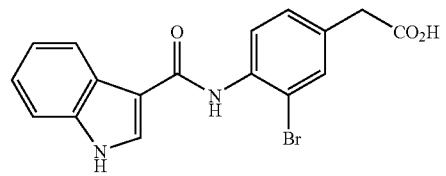

Ethyl (3-bromo-4-((3-indolylcarbonyl)amino)phenyl)acetate (664 mg, 1.65 mmol) was dissolved in THF (17 ml). To the resulting solution was added 0.25N NaOH (10.0 ml, 2.48 mmol). After stirring at room temperature for 24 hours, the reaction mixture was poured in 1N HCl to acidify the mixture. The crystals thus precipitated were collected by filtration under reduced pressure, washed with water, and dried under reduced pressure to give (3-bromo-4-((3-indolylcarbonyl)amino)phenyl)acetic acid (341 mg, 55%) as a brown solid.

$^1$H-NMR (DMSO-d$_6$) δ: 3.62 (s, 2H), 7.13–7.21 (m, 2H), 7.29 (dd, J=8.3, 1.7 Hz, 1H), 7.47 (d, J=8.3 Hz, 1H), 7.60 (d, J=1.7 Hz, 1H), 7.63 (d, J=8.3 Hz, 1H), 8.14 (d, J=7.6 Hz, 1H), 8.27 (d, J=3.2 Hz, 1H), 9.27 (s, 1H).

MS (ESI) m/z 373 (M$^+$+1), 375 (M$^+$+3).

(Step 3) Synthesis of methyl trans-4-(1-((3-bromo-4-((3-indolylcarbonyl)amino)phenyl)acetyl)-(4S)-fluoro-(2S)-pyrrolidinylmethoxy)cyclohexanecarboxylate (Step 4) Synthesis of trans-4-(1-((3-bromo-4-((3-indolylcarbonyl)amino)phenyl)acetyl)-(4S)-fluoro-(2S)-pyrrolidinylmethoxy)cyclohexanecarboxylic acid

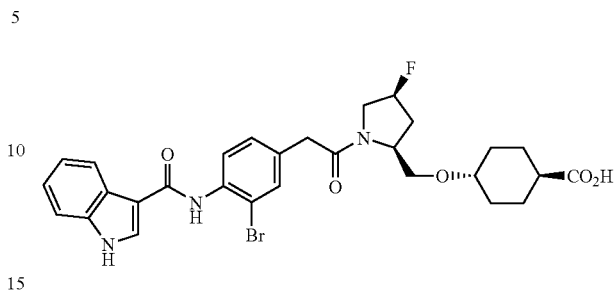

In THF (28 ml) was dissolved methyl trans-4-(1-((3-bromo-(3-indolylcarbonyl)amino)phenyl)acetyl)-(4S)-fluoro-(2S)-pyrrolidinylmethoxy)cyclohexanecarboxylate

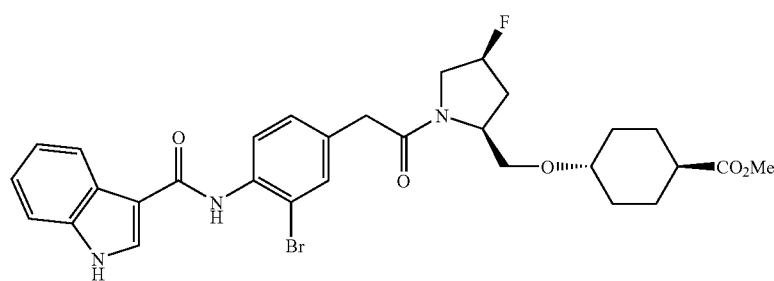

To a solution of 3-bromo-4-((3-indolylcarbonyl)amino) phenyl)acetic acid (341 mg, 0.91 mmol), methyl trans-4-((4S)-fluoro-(2S)-pyrrolidinylmethoxy)cyclohexanecarboxylate (the compound synthesized in (Step 3) of Example 21) (237 mg, 0.91 mmol), HOBt (25.0 mg, 0.18 mmol), and DMAP (22.0 mg, 0.13 mmol) in DMF (5.0 ml) was added EDC HCl (228 mg, 1.19 mmol) under stirring at room temperature. After the reaction mixture was stirred at room temperature for 20 hours, water was added thereto. The crystals thus precipitated were collected by filtration under reduced pressure, washed with water and dried under reduced pressure to give methyl trans-4-(1-((3-bromo-4-((3-indolylcarbonyl)amino)phenyl)acetyl)-(4S)-fluoro-(2S)-pyrrolidinylmethoxy)cyclohexanecarboxylate (500 mg, 89%) as a colorless solid.

$^1$H NMR (DMSO-d$_6$) δ: 1.15–1.28 (m, 2H), 1.32–1.45 (m, 2H), 1.87–2.33 (m, 7H), 3.21 (m, 1H), 3.46 (m, 1H), 3.57 (s, 3H), 3.59–3.93 (m, 5H), 4.16 and 4.34 (each m, total 1H), 5.31 and 5.38 (each m, total 1H), 7.12–7.20 (m, 2H), 7.24 (m, 1H), 7.47 (d, J=7.67 Hz, 1H), 7.54 and 7.56 (each d, J=1.5 Hz, total 1H), 7.62 and 7.64 (each d, J=8.3 Hz, total 1H), 8.14 (d, J=7.6 Hz, 1H), 8.26 (s, 1H), 9.24 (s, 1H), 11.73 (broad s, 1H).

MS (ESI) m/z 614 (M$^+$+1), 616 (M$^+$+3).

(500 mg, 0.81 mmol). To the resulting solution was added 0.25N NaOH (5.00 ml, 1.25 mmol), followed by stirring at room temperature for 3 hours. Methanol-water (1:1, v/v; 10 ml) was added to the reaction mixture. After the resulting mixture was stirred for 1 hour, the solvent was distilled off under reduced pressure. To the residue was added water and then, the mixture was acidified with 1N HCl (10 ml). The crystals thus precipitated were collected by filtration under reduced pressure, washed with water and dried under reduced pressure to give the title compound (390 mg, 80%) as a pale yellow solid.

IR (ATR) ν 3411, 3208, 2938, 2861, 1691, 1627, 1509, 1432 cm$^{-1}$;

$^1$H NMR (DMSO-d$_6$) δ: 1.19–1.42 (m, 4H), 1.87–2.28 (m, 7H), 3.19 (m, 1H), 3.42–3.93 (m, 6H), 4.14 and 4.34 (each m, total 1H), 5.32 and 5.38 (each m, total 1H), 7.12–7.21 (m, 2H), 7.24 (m, 1H), 7.47 (d, J=7.5 Hz, 1H), 7.54 and 7.56 (each d, J=1.7 Hz, total 1H), 7.62 and 7.64 (each d, J=8.0 Hz, total 1H), 8.14 (d, J=7.5 Hz, 1H), 8.26 (d, J=2.9 Hz, 1H), 9.24 (s, 1H), 11.73 (broad s, 1H), 12.01 (broad s, 1H).

MS (ESI) m/z 600 (M$^+$+1), 602 (M$^+$+3);

Anal. Calcd for $C_{29}H_{31}BrFN_3O_5 \cdot H_2O$: C, 56.32; H, 5.38; N, 6.79. Found: C, 56.10; H, 5.32; N, 6.68.

Example 65 trans-4-(1-((5-Chloro-2-fluoro-4-((1-methyl-3-indolylcarbonyl)amino)phenyl)acetyl)-(4S)-fluoro-(2S)-pyrrolidinylmethoxy)cyclohexanecarboxylic acid (Step 1) Synthesis of methyl trans-4-(1-((5-chloro-2-fluoro-4-((1-methyl-3-indolylcarbonyl)amino)phenyl)acetyl)-(4S)-fluoro-(2S)-pyrrolidinylmethoxy)cyclohexanecarboxylate

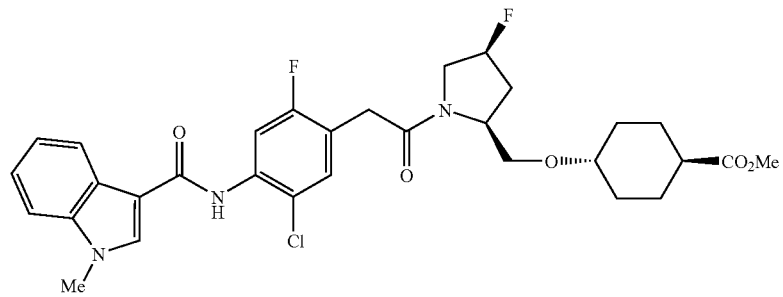

To a solution of (5-chloro-2-fluoro-4-((1-methyl-3-indolylcarbonyl)amino)phenyl)acetic acid (210 mg, 0.58 mmol), methyl trans-4-((4S)-fluoro-(2S)-pyrrolidinylmethoxy)cyclohexanecarboxylate (the compound synthesized in (Step 3) of Example 21) (151 mg, 0.58 mmol), HOBt (16.0 mg, 0.12 mmol), and DMAP (14.0 mg, 0.12 mmol) in DMF (6.0 ml) was added EDC HCl (167 mg, 0.87 mmol) under stirring at room temperature. The reaction mixture was stirred further for 13 hours at room temperature. The reaction mixture was diluted with water, followed by extraction with ethyl acetate. The extract was washed with saturated brine, dried over anhydrous sodium sulfate, and distilled under reduced pressure to remove the solvent. The residue was purified by chromatography on a silica gel column, whereby from ethyl acetate eluate fractions, methyl trans-4-(1-((5-chloro-2-fluoro-4-((1-methyl-3-indolylcarbonyl)amino)phenyl)acetyl)-(4S)-fluoro-(2S)-pyrrolidinylmethoxy)cyclohexanecarboxylate (354 mg, 100%) was obtained as a pale yellow amorphous substance.

$^1$H NMR (CDCl$_3$) δ: 1.20–1.28 (m, 2H), 1.31–1.52 (m, 2H), 1.96–2.52 (m, 7H), 3.25 (m, 1H), 3.34 and 3.52 (each m, total 1H), 3.57 (m, 1H), 3.64 and 3.66 (each s, total 3H), 3.71–3.99 (m, 7H, including singlet, 3H, at δ 3.87), 4.28 and 4.36 (each m, total 1H), 5.25 and 5.29 (each m, total 1H), 7.32–7.35 (m, 2H), 7.38–7.42 (m, 2H), 7.79 (m, 1H), 8.12 (m, 1H), 8.28 (m, 1H), 8.48 and 8.51 (each d, J=8.3 Hz, total 1H).

MS (ESI) m/z 602 (M$^+$+1).

(Step 2) Synthesis of trans-4-(1-((5-chloro-2-fluoro-4-((1-methyl-3-indolylcarbonyl)amino)phenyl)acetyl)-(4S)-fluoro-(2S)-pyrrolidinylmethoxy)cyclohexanecarboxylic acid

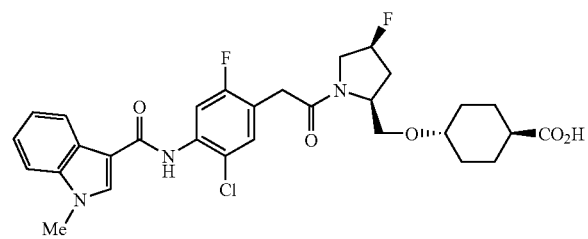

In THF (6.0 ml) was dissolved methyl trans-4-(1-((5-chloro-2-fluoro-4-((1-methyl-3-indolylcarbonyl)amino)phenyl)acetyl)-(4S)-fluoro-(2S)-pyrrolidinylmethoxy)cyclohexanecarboxylate (354 mg, 0.59 mmol). To the resulting solution was added 0.25N NaOH (3.53 ml, 0.88 mmol), followed by stirring for 6 hours at room temperature. The reaction mixture was poured in 1N HCl (10 ml) to acidify the mixture. The crystals thus precipitated were collected by filtration under reduced pressure, washed with water, and dried under reduced pressure to give the title compound (298 mg, 86%) as a colorless solid.

IR (ATR) ν 2940, 2863, 1718, 1652, 1585, 1521, 1465 cm$^{-1}$; $^1$H NMR (DMSO-d$_6$) δ: 1.16–1.41 (m, 4H), 1.86–2.32 (m, 7H), 3.17–3.84 (m, 6H), 3.89 (s, 3H), 4.13 and 4.35 (each m, total 1H), 5.32 and 5.40 (each m, total 1H), 7.21 (m, 1H), 7.27 (m, 1H), 7.42 and 7.45 (each d, J=7.3 Hz, total 1H), 7.54 (d, J=8.4 Hz, 1H), 7.70 and 7.72 (each d, J=5.6 Hz, total 1H), 8.15 (d, J=7.6 Hz, 1H), 8.30 (m, 1H), 9.28 (s, 1H), 12.01 (broad s, 1H).

MS (ESI) m/z 588 (M$^+$+1);

Anal. Calcd for C$_{30}$H$_{32}$ClF$_2$N$_3$O$_5$ 0.25H$_2$O: C, 60.81; H, 5.53; N, 7.09. Found: C, 61.07; H, 5.65; N, 6.71.

Example 66 trans-4-(1-(3-Chloro-4-((1-ethyl-3-indolylcarbonyl)amino)phenylacetyl)-(4S)-fluoro-(2S)-pyrrolidinylmethoxy)cyclohexanecarboxylic acid (Step 1) Synthesis of methyl 1-ethylindole-3-carboxylate

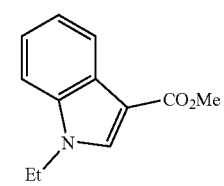

In DMF (8.0 ml) was suspended sodium hydride (60% in oil, 273.9 mg, 6.846 mmol). To the resulting suspension was added methyl indole-3-carboxylate (399.8 mg, 2.282 mmol) under stirring at 0° C. The reaction mixture was stirred for 40 minutes at the same temperature. To the mixture was added ethyl iodide (0.27 ml, 3.423 mmol) at 0° C., followed by stirring at the same temperature for further 2 hours. Water was added to the reaction mixture to terminate the reaction. The reaction mixture was extracted with ethyl acetate. The extract was washed successively with 1N HCl and saturated brine, dried over anhydrous sodium sulfate and distilled under reduced pressure to remove the solvent, whereby methyl 1-ethylindole-3-carboxylate was obtained. The resulting compound was provided for the subsequent reaction without further purification.

$^1$H-NMR (CDCl$_3$) δ: 1.52 (3H, t, J=7.2 Hz), 3.93 (3H, s), 4.20 (2H, q, J=7.2 Hz), 7.22–7.34 (2H, m), 7.38 (1H, m), 7.86 (1H, s), 8.20 (1H, m).

(Step 2) Synthesis of 1-ethylindole-3-carboxylic acid

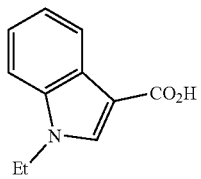

In THF (9.0 ml) was dissolved the methyl 1-ethylindole-3-carboxylate obtained in the above-described (Step 1). To the resulting solution was added 0.25N NaOH (9.0 ml) at room temperature. After the reaction mixture was stirred at 50° C. for 36 hours, 1N NaOH (1.0 ml) was added thereto, followed by stirring at 70° C. for 9 hours. The reaction mixture was cooled to room temperature, and then neutralized with 1N HCl (4.5 ml). The crystals thus precipitated were collected by filtration under reduced pressure, washed with water and dried under reduced pressure to give 1-ethylindole-3-carboxylic acid (388.0 mg, 90%, yield of 2 steps) as a pale pink amorphous substance.

$^1$H-NMR (DMSO-d$_6$) δ: 1.38 (3H, t, J=7.2 Hz), 4.26 (2H, q, J=7.2 Hz), 7.12–7.28 (2H, m), 7.55 (1H, d, J=8.0 Hz), 8.01 (1H, d, J=8.0 Hz), 8.07 (1H, s), 11.93 (1H, br s).

(Step 3) Synthesis of methyl 3-chloro-4-((1-ethyl-3-indolylcarbonyl)amino)phenylacetate

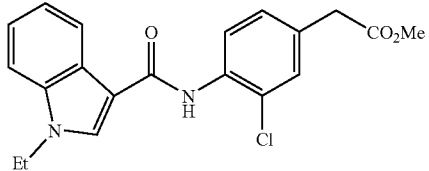

To 1-ethylindole-3-carboxylic acid (160.2 mg, 0.847 mmol) were added methylene chloride (3.5 ml) and oxalyl chloride (108.9 μl, 1.270 mmol) under stirring at 15° C. The reaction mixture was stirred for 2.5 hours at room temperature. The solvent was then distilled off under reduced pressure. To the residue was added methylene chloride (3.5 ml). Under stirring at room temperature, a solution of methyl 3-chloro-4-aminophenylacetate (177.5 mg, 0.889 mmol) in methylene chloride (3.5 ml) and triethylamine (0.37 ml, 2.667 mmol) were added and the mixture was heated under reflux for 18 hours. After the reaction mixture was cooled to room temperature, the solvent was distilled off under reduced pressure. The residue was dissolved in chloroform. The resulting solution was washed with 1N HCl ad saturated saline, and dried over anhydrous sodium sulfate. The solvent was distilled off under reduced pressure to give methyl 3-chloro-4-((1-ethyl-3-indolylcarbonyl)amino)phenylacetate (277.7 mg, 88%) as a brown amorphous substance. The resulting compound was provided for the subsequent reaction without further purification.

$^1$H-NMR (CDCl$_3$) δ: 1.54 (3H, t, J=7.6 Hz), 3.59 (2H, s), 3.71 (3H, s), 4.23 (2H, m), 7.15–7.49 (5H, m), 7.78 (1H, s), 8.14 (1H, m), 8.26 (1H, m), 8.59 (1H, d, J=8.4 Hz).

(Step 4) Synthesis of 3-chloro-4-((1-ethyl-3-indolylcarbonyl)amino)phenylacetic acid

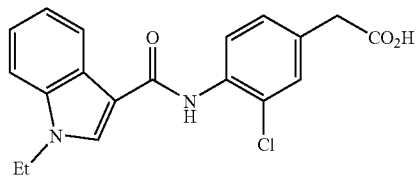

In THF (6.0 ml) was dissolved methyl 3-chloro-4-((1-ethyl-3-indolylcarbonyl)amino)phenylacetate. To the resulting solution was added 0.25N NaOH (6.0 ml) at room temperature. After stirring at 50° C. for 18 hours, the reaction mixture was cooled to room temperature and distilled under reduced pressure to remove the solvent. The residue was acidified with 1N HCl (2.0 ml). The crystals thus precipitated were collected by filtration under reduced pressure, washed with water and then, dried under reduced pressure to give 3-chloro-4-((1-ethyl-3-indolylcarbonyl)amino)phenylacetic acid (250.7 mg, 94%) as a brown amorphous substance.

$^1$H-NMR (DMSO-d$_6$) δ: 1.43 (3H, m, OCH$_2$Me), 3.62 (2H, s), 4.28 (2H, m, OCH$_2$Me), 7.12–7.30 (2H, m, ArH), 7.44 (1H, m), 7.58 (1H, m), 7.66 (1H, m), 7.91–8.10 (1H, m), 8.15 (1H, m), 8.35 (1H, m), 9.31 (1H, s).

(Step 5) Synthesis of methyl trans-4-(1-(3-chloro-4-((1-ethyl-3-indolylcarbonyl)amino)phenylacetyl)-(4S)-fluoro-(2S)-pyrrolidinylmethoxy)cyclohexanecarboxylate

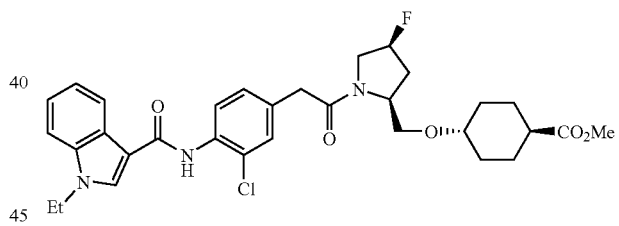

To a solution of methyl trans-4-((4S)-fluoro-(2S)-pyrrolidinylmethoxy)cyclohexanecarboxylate (the compound synthesized in (Step 3) of Example 21) (171.2 mg, 0.660 mmol), 3-chloro-4-((1-ethyl-3-indolylcarbonyl)amino)phenylacetic acid (235.6 mg, 0.660 mmol) and HOBt (17.8 mg, 0.132 mmol) in DMF (8.0 ml) was added EDC HCl (189.9 mg, 0.990 mmol) under stirring at room temperature. After stirring at room temperature for 18 hours, the reaction mixture was poured in ice-1-N HCl, followed by extraction with ethyl acetate. The extract was washed with a saturated aqueous solution of sodium bicarbonate, dried over anhydrous sodium sulfate, and distilled under reduced pressure to remove the solvent. The residue was purified by chromatography on a silica gel column, whereby from hexane-ethyl acetate (1:2, v/v) eluate fractions, methyl trans-4-(1-(3-chloro-4-((1-ethyl-3-indolylcarbonyl)amino)phenylacetyl)-(4S)-fluoro-(2S)-pyrrolidinylmethoxy)cyclohexanecarboxylate (334.1 mg, 85%) was obtained as a light brown amorphous substance.

$^1$H-NMR (CDCl$_3$) δ: 1.15–1.34 (2H, m), 1.36–1.58 (total 5H, m, including 3H, t, J=7.2 Hz, at δ: 1.53), 1.92–2.15 (5H, m), 2.16–2.50 (2H, m), 3.19–4.02 (total 10H, series of m, including total 3H, s at δ: 3.63, 3.65), 4.15–4.40 (total 3H, m, including 2H, q, J=7.2 Hz, at δ: 4.21), 5.24 (1H, m), 7.18 (1H, m), 7.32 (2H, m), 7.36 (1H, m), 7.42 (1H, m), 7.86 (1H, s), 8.13 (1H, m), 8.27 (1H, m), 8.56 (1H, dd, J=7.2, 8.4 Hz).

(Step 6) Synthesis of trans-4-(1-(3-chloro-4-((1-ethyl-3-indolylcarbonyl)amino)phenylacetyl)-(4S)-fluoro-(2S)-pyrrolidinylmethoxy)cyclohexanecarboxylic acid

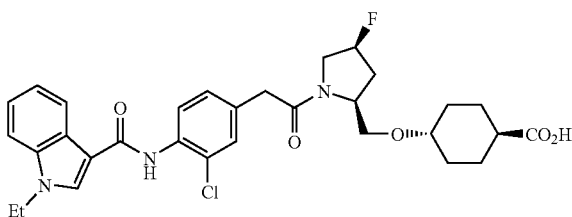

In THF (6.0 ml) was dissolved methyl 4-(1-(3-chloro-4-((1-ethyl-3-indolylcarbonyl)amino)phenylacetyl)-(4S)-fluoro-(2S)-pyrrolidinylmethoxy)cyclohexanecarboxylate (334.1 mg, 0.559 mmol). To the resulting solution was added 0.25N NaOH (6.0 ml), followed by stirring at room temperature for 18 hours. The reaction mixture was distilled under reduced pressure to remove the solvent. The residue thus obtained was acidified with 1N HCl (2.0 ml). The crystals thus precipitated were collected by filtration under reduced pressure, washed with water and dried under reduced pressure to give the title compound (293.6 mg, 90%) as a white amorphous substance.

IR (ATR) ν 2937, 1649, 1511 cm$^{-1}$;
$^1$H-NMR (DMSO-d$_6$) δ: 1.10–1.40 (4H, m), 1.45 (3H, t, J=7.2 Hz, OCH$_2$Me), 1.80–2.04 (4H, m), 2.04–2.36 (3H, m), 3.10–3.97 (total 7H, series of m), 4.07–4.39 (total 3H, m, including 2H, q, J=7.2 Hz, at δ: 4.29), 5.32 and 5.39 (total 1H, d, J=54.4 Hz), 7.10–7.30 (3H, m), 7.38 (1H, d, J=6.8 Hz), 7.59 (1H, d, J=8.0 Hz), 7.65 (1H, m), 8.16 (1H, d, J=8.0 Hz), 8.35 (1H, s), 9.31 (1H, s), 12.05 (1H, br s, CO$_2$H).

MS (ESI) m/z 584 (M$^+$+1);

Anal. Calcd for C$_{31}$H$_{35}$ClFN$_3$O$_5$ 0.25H$_2$O: C, 63.26; H, 6.08; N, 7.14; Cl, 6.02; F, 3.23. Found: C, 63.20; H, 6.08; N, 6.96; Cl, 5.86; F, 3.18.

Example 67 trans-4-(1-(3-Chloro-4-((1-isopropyl-3-indolylcarbonyl)amino)phenylacetyl)-(4S)-fluoro-(2S)-pyrrolidinylmethoxy)cyclohexanecarboxylic acid (Step 1) Synthesis of methyl 1-isopropylindole-3-carboxylate

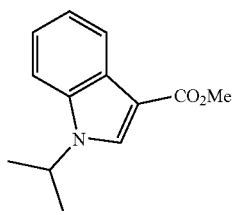

In DMF (8.0 ml) was suspended sodium hydride (60% in oil, 275.2 mg, 6.881 mmol). To the resulting suspension was added methyl indole-3-carboxylate (401.8 mg, 2.294 mmol) at 0° C. under stirring. After stirring for further 45 minutes at the same temperature, isopropyl iodide (0.34 ml, 3.440 mmol) was added to the reaction mixture. Stirring was then conducted for 1.5 hours at 0° C. and for 7 hours at room temperature. Water was added to the reaction mixture to terminate the reaction, followed by extraction with ethyl acetate. The extract was washed successively with 1N HCl and saturated saline, dried over anhydrous sodium sulfate and distilled under reduced pressure to remove the solvent. The residue was purified by chromatography on a silica gel column, whereby from hexane-ethyl acetate (3:1, v/v) eluate fractions, methyl 1-isopropylindole-3-carboxylate (387.6 mg, 78%) was obtained as a light yellow oil.

$^1$H-NMR (CDCl$_3$) δ: 1.56 (6H, d, J=6.8 Hz), 3.91 (3H, s,), 4.67 (1H, hep, J=6.8 Hz), 7.28 (2H, m), 7.40 (1H, m), 7.94 (1H, s), 8.19 (1H, m).

(Step 2) Synthesis of 1-isopropylindole-3-carboxylic acid

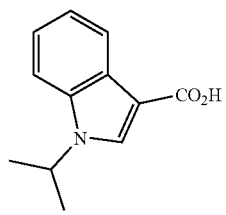

In THF (8.0 ml) was dissolved methyl 1-isopropylindole-3-carboxylate (387.6 mg, 1.784 mmol). To the resulting solution was added 0.25N NaOH (8.0 ml). The resulting mixture was stirred at 50° C. for 18 hours. After cooling to room temperature, the reaction mixture was acidified with 1N HCl (4.5 ml). The crystals thus precipitated were collected by filtration under reduced pressure, washed with water and dried under reduced pressure to give 1-isopropylindole-3-carboxylic acid (327.8 mg, 90%) as a pale pink amorphous substance.

$^1$H-NMR (DMSO-d$_6$) δ: 1.38 (6H, d, J=6.4 Hz), 4.78 (1H, m), 7.20 (2H, m), 7.59 (1H, d, J=8.0 Hz), 8.02 (1H, d, J=7.6 Hz), 8.12 (1H, s), 11.96 (1H, br s).

(Step 3) Synthesis of methyl 3-chloro-4-((1-isopropyl-3-indolylcarbonyl)amino)phenylacetate

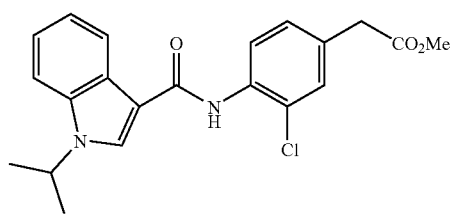

To a solution of 1-isopropylindole-3-carboxylic acid (159.6 mg, 0.785 mmol) in methylene chloride (3.5 ml) was added oxalyl chloride (101.0 μl, 1.178 mmol) under stirring at −15° C. The reaction mixture was stirred for 2.5 hours at room temperature and then distilled under reduced pressure to remove the solvent. The residue was dissolved in methylene chloride (3.5 ml), followed by the addition of a solution of methyl 3-chloro-4-aminophenylacetate (164.6 mg, 0.824 mmol) in methylene chloride (3.5 ml) and triethylamine (0.35 ml, 2.474 mmol) under stirring at room temperature. The reaction mixture was stirred at room temperature for 18 hours. The reaction mixture was then distilled under reduced pressure to remove the solvent. The residue was dissolved in chloroform. The resulting solution was washed successively with 1N HCl and saturated saline, dried over anhydrous sodium sulfate and distilled under reduced pressure to remove the solvent, whereby methyl 3-chloro-4-((1-isopropyl-3-indolylcarbonyl)amino)phenylacetate (275.3 mg, 91%) was obtained as a brown solid. The resulting compound was provided for the subsequent reaction without further purification.

$^1$H-NMR (CDCl$_3$) δ: 1.60 (6H, d, J=6.8 Hz), 3.60 (2H, s), 3.71 (3H, s), 4.73 (1H, m), 7.15–7.54 (5H, m), 8.00 (1H, s), 8.11 (1H, m), 8.28 (1H, m), 8.60 (1H, d, J=8.4 Hz).

(Step 4) Synthesis of 3-chloro-4-((1-isopropyl-3-indolylcarbonyl)amino)phenylacetic acid

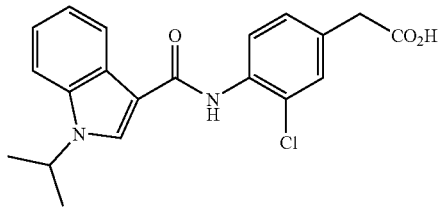

In THF (6.0 ml) was dissolved the methyl 3-chloro-4-((1-isopropyl-3-indolylcarbonyl)amino)phenylacetate obtained in the above-described (Step 3). To the resulting solution was added 0.25N NaOH (6.0 ml), followed by stirring at 50° C. for 18 hours. After cooling, the reaction mixture was distilled under reduced pressure to remove the solvent. The resulting residue was acidified with 1N HCl (2.0 ml). The crystals thus precipitated were collected by filtration under reduced pressure, washed with water and dried under reduced pressure to give 3-chloro-4-((1-isopropyl-3-indolylcarbonyl)amino)phenylacetic acid (246.2 mg, 93%) as a brown amorphous substance.

$^1$H-NMR (DMSO-d$_6$) δ: 1.52 (6H, d, J=6.4 Hz), 3.62 (2H, s), 4.84 (1H, hep, J=6.4 Hz), 7.13–7.30 (3H, m), 7.44 (1H, m), 7.62 (2H, m), 8.18 (1H, m), 8.48 (1H, s), 9.36 (1H, s), 12.32 (1H, br s).

(Step 5) Synthesis of methyl trans-4-(1-(3-chloro-4-((1-isopropyl-3-indolylcarbonyl)amino)phenylacetyl)-(4S)-fluoro-(2S)-pyrrolidinylmethoxy)cyclohexanecarboxylate

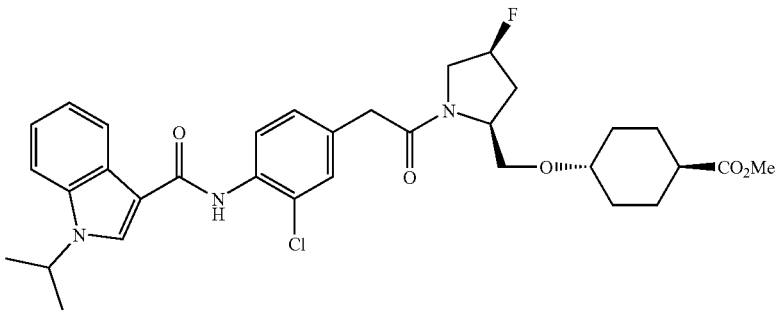

A mixture of methyl trans-4-((4S)-fluoro-(2S)-pyrrolidinylmethoxy)cyclohexanecarboxylate (the compound synthesized in (Step 3) of Example 21) (163.8 mg, 0.632 mmol), 3-chloro-4-((1-isopropyl-3-indolylcarbonyl)amino)phenylacetic acid (234.3 mg, 0.632 mmol) and HOBt (17.1 mg, 0.126 mmol) was dissolved in DMF (8.0 ml). To the resulting solution was added EDC HCl (181.7 mg, 0.948 mmol) under stirring at room temperature. The reaction mixture was stirred for further 18 hours at room temperature. The mixture was diluted with ethyl acetate, washed successively with 1N HCl and a saturated aqueous solution of sodium bicarbonate, dried over anhydrous sodium sulfate, and distilled under reduced pressure to remove the solvent. The residue was purified by chromatography on a silica gel column, whereby from hexane-ethyl acetate (1:2, v/v) eluate fractions, methyl trans-4-(1-(3-chloro-4-((1-isopropyl-3-indolylcarbonyl)amino)phenylacetyl)-(4S)-fluoro-(2S)-pyrrolidinylmethoxy)cyclohexanecarboxylate (322.9 mg, 84%) was obtained as a brown oil.

$^1$H-NMR (CDCl$_3$) δ: 1.10–1.33 (2H, m), 1.36–1.55 (2H, m), 1.58 (6H, d, J=6.8 Hz), 1.75 (1H, m), 1.92–2.15 (4H, m), 2.15–2.51 (2H, m), 3.19–4.02 (total 10H, series of m), 4.20 and 4.36 (total 1H, m), 4.72 (1H, hep, J=6.8 Hz), 5.23 (1H, d, J=54.4 Hz), 7.18 (1H, m), 7.28–7.40 (3H, m), 7.45 (1H, m), 7.98 (1H, s), 8.11 (1H, m), 8.29 (1H, s), 8.56 (1H, dd, J=7.2 Hz).

(Step 6) Synthesis of trans-4-(1-(3-chloro-4-((1-isopropyl-3-indolylcarbonyl)amino)phenylacetyl)-(4S)-fluoro-(2S)-pyrrolidinylmethoxy)cyclohexanecarboxylic acid

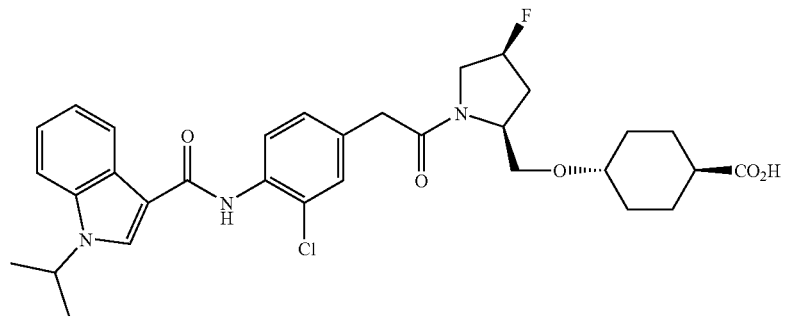

In THF (6.0 ml) was dissolved methyl trans-4-(1-(3-chloro-4-((1-isopropyl-3-indolylcarbonyl)amino)phenylacetyl)-(4S)-fluoro-(2S)-pyrrolidinylmethoxy)cyclohexanecarboxylate (322.9 mg, 0.528 mmol). To the resulting solution was added 0.25N NaOH (6.0 ml) and the mixture was stirred at room temperature for 18 hours. The reaction mixture was distilled under reduced pressure to remove the solvent. The resulting residue was acidified with 1N HCl (2.0 ml). The crystals thus precipitated were collected by filtration under reduced pressure, washed with water and dried under reduced pressure to give the compound (283.9 mg, 90%) as a white amorphous substance.

IR (ATR) ν 2933, 1643, 1511 cm$^{-1}$;
$^1$H-NMR (DMSO-d$_6$) δ: 1.08–1.44 (4H, m), 1.53 (6H, d, J=6.8 Hz), 1.80–2.05 (4H, m), 2.05–2.34 (3H, m), 3.12–4.40 (total 8H, series of m), 4.85 (1H, hep, J=6.8 Hz), 5.32 and 5.39 (total 1H, d, J=54.4 Hz), 7.12–7.28 (3H, m), 7.39 (1H, d, J=6.8 Hz), 7.60 (2H, m), 8.17 (1H, d, J=8.0 Hz), 8.48 (1H, s), 9.35 (1H, s), 12.04 (1H, s).

MS (ESI) m/z 598 (M$^+$+1);
Anal. Calcd for C$_{31}$H$_{35}$ClFN$_3$O$_5$ 0.25H$_2$O: C, 63.78; H, 6.27; N, 6.97; Cl, 5.88; F, 3.15. Found: C, 63.62; H, 6.32; N, 6.77; Cl, 5.72; F, 3.13.

Example 68 trans-4-(1-(4-((1-Benzyl-3-indolylcarbonyl)amino)-3-chlorophenylacetyl)-(4S)-fluoro-(2S)-pyrrolidinylmethoxy)cyclohexanecarboxylic acid (Step 1) Synthesis of methyl 1-benzylindole-3-carboxylate

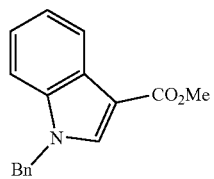

Sodium hydride (60% in oil, 274.1 mg, 6.853 mmol) was suspended in DMF (8.0 ml). To the resulting suspension was added methyl indole-3-carboxylate (400.2 mg, 2.284 mmol) under stirring at 0° C., followed by stirring at the same temperature for 30 minutes. To the reaction mixture was added benzyl bromide (0.41 ml, 3.427 mmol) at 0° C. After stirring at room temperature for 1 hour, the reaction mixture was added with water to terminate the reaction. The reaction mixture was then extracted with ethyl acetate. The extract was washed with 1N HCl, dried over anhydrous sodium sulfate and distilled under reduced pressure to remove the solvent. The residue was purified by chromatography on a silica gel column, whereby from hexane-ethyl acetate (6:1, v/v) eluate fractions, methyl 1-benzylindole-3-carboxylate (100%) was obtained as a gum.

$^1$H-NMR (CDCl$_3$) δ: 3.90 (3H, s), 5.31 (2H, s), 7.13 (2H, m), 7.18–7.38 (6H, m), 7.83 (1H, s), 8.19 (1H, d, J=8.0 Hz).

(Step 2) Synthesis of 1-benzylindole-3-carboxylic acid

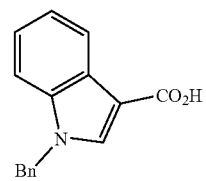

In THF (15 ml) was dissolved methyl 1-benzylindole-3-carboxylate (606.1 mg, 2.284 mmol). To the resulting solution was added 0.25N NaOH (8.0 ml) and the mixture was stirred at 70° C. for 18 hours. After the reaction mixture was cooled to room temperature, the solvent was distilled off under reduced pressure. The residue thus obtained was acidified with 1N HCl (5.5 ml). The crystals thus precipitated were collected by filtration under reduced pressure, washed with water and dried under reduced pressure to give 1-benzylindole-3-carboxylic acid (100%) as a light pink amorphous substance.

$^1$H-NMR (DMSO-d$_6$) δ: 5.49 (2H, s), 7.14–7.38 (7H, m), 7.52 (1H, m), 8.00 (1H, m), 8.21 (1H, s), 12.01 (1H, br s).

(Step 3) Synthesis of methyl 4-((1-benzyl-3-indolylcarbonyl)amino)-3-chlorophenylacetate

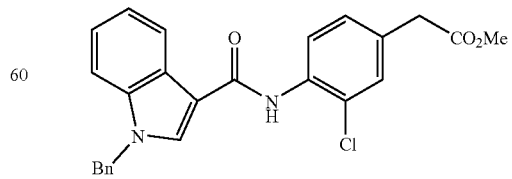

To a solution of 1-benzylindole-3-carboxylic acid (201.3 mg, 0.801 mmol) in methylene chloride (4.0 ml) was added oxalyl chloride (103.1 μl, 1.202 mmol) under stirring at −15° C. The reaction mixture was stirred at room temperature for 2.5 hours and then, distilled under reduced pressure to remove the solvent. The residue was dissolved in methylene chloride (4.0 ml) and to the resulting solution were added a solution of methyl 3-chloro-4-aminophenylacetate (167.9 mg, 0.841 mmol) in methylene chloride (4.0 ml) and triethylamine (0.35 ml, 2.523 mmol) under stirring at room temperature. The reaction mixture was stirred at room temperature for 18 hours. The reaction mixture was distilled under reduced pressure to remove the solvent. The residue was diluted with chloroform, washed with 1N HCl, dried over anhydrous sodium sulfate and distilled under reduced pressure to remove the solvent, whereby methyl 4-((1-benzyl-3-indolylcarbonyl)amino)-3-chlorophenylacetate (341.3 mg, 98%) was obtained. The compound was provided for the subsequent reaction without further purification.

$^1$H-NMR (CDCl$_3$) δ: 3.59 (2H, s), 3.71 (3H, s,), 5.38 (2H, s), 7.08–7.42 (10H, m), 7.87 (1H, s), 8.16 (1H, d, J=7.6 Hz), 8.29 (1H, s), 8.58 (1H, d, J=8.0 Hz).

(Step 4) Synthesis of 4-((1-benzyl-3-indolylcarbonyl)amino)-3-chlorophenylacetic acid

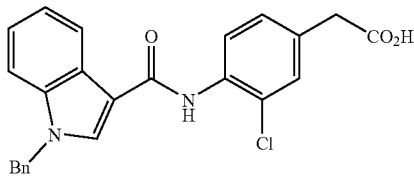

In THF (7.0 ml) was dissolved methyl 4-((1-benzyl-3-indolylcarbonyl)amino)-3-chlorophenylacetate (341.3 mg, 0.788 mmol). To the resulting solution was added 0.25N NaOH (7.0 ml). The resulting mixture was stirred at 50° C. for 18 hours. After the reaction mixture was cooled to room temperature, the solvent was distilled off under reduced pressure. The residue was acidified with 1N HCl (2.5 ml). The crystals thus precipitated were collected by filtration under reduced pressure, washed with water and dried under reduced pressure to give 4-((1-benzyl-3-indolylcarbonyl)amino)-3-chlorophenylacetic acid (285.8 mg, 86%) as a light pink amorphous substance.

$^1$H-NMR (DMSO-d$_6$) δ: 3.57 (2H, s), 5.52 (2H, s), 7.13–7.41 (8H, m), 7.44 (1H, s), 7.56 (1H, d, J=8.0 Hz), 7.64 (1H, d, J=8.0 Hz), 8.16 (1H, d, J=6.4 Hz), 8.43 (1H, s), 9.40 (1H, s).

(Step 5) Synthesis of methyl trans-4-(1-(4-((1-benzyl-3-indolylcarbonyl)amino)-3-chlorophenylacetyl)-(4S)-fluoro-(2S)-pyrrolidinylmethoxy)cyclohexanecarboxylate

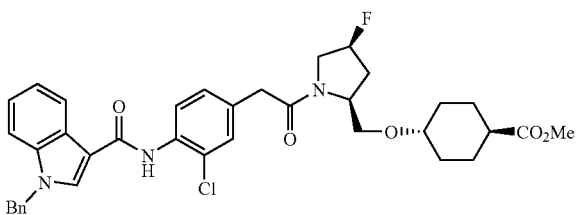

A mixture of methyl trans-4-(4S)-fluoro-(2S)-pyrrolidinylmethoxy)cyclohexanecarboxylate (the compound synthesized in (Step 3) of Example 21) (174.3 mg, 0.672 mmol), 4-((1-benzyl-3-indolylcarbonyl)amino)-3-chlorophenylacetic acid (281.5 mg, 0.672 mmol) and HOBt (18.2 mg, 0.134 mmol) was dissolved in DMF (8.0 ml). To the resulting solution was added EDC HCl (193.2 mg, 1.008 mmol), followed by stirring at room temperature for 18 hours. The reaction mixture was diluted with ethyl acetate, washed successively with 1N HCl and a saturated aqueous solution of sodium bicarbonate, dried over anhydrous sodium sulfate, and distilled under reduced pressure to remove the solvent. The residue was purified by chromatography on a silica gel column, whereby from hexane-ethyl acetate (1:2, v/v) to (10:1, v/v) eluate fractions, methyl trans-4-(1-(4-((1-benzyl-3-indolylcarbonyl)amino)-3-chlorophenylacetyl)-(4S)-fluoro-(2S)-pyrrolidinylmethoxy)cyclohexanecarboxylate (409.2 mg, 92%) was obtained as a brown oil.

$^1$H-NMR (CDCl$_3$) δ: 1.17–1.36 (2H, m), 1.40–1.56 (2H, m), 1.95–2.16 (5H, m), 2.17–2.54 (2H, m), 3.22–4.43 (total 11H, series of m), 5.16–5.38 (1H, m), 5.39 (2H, s), 7.14–7.43 (10H, m), 7.88 (1H, s), 8.17 (1H, d, J=7.2 Hz), 8.30 (1H, m), 8.59 (1H, dd, J=8.0 Hz).

(Step 6) Synthesis of trans-4-(1-(4-((1-benzyl-3-indolylcarbonyl)amino)-3-chlorophenylacetyl)-(4S)-fluoro-(2S)-pyrrolidinylmethoxy)cyclohexanecarboxylic acid

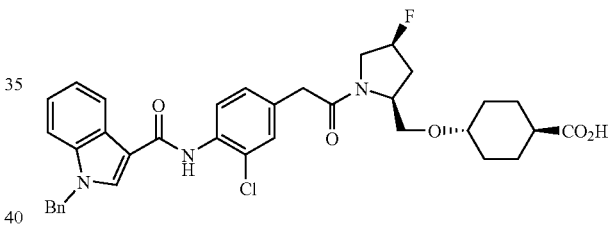

In THF (8.0 ml) was dissolved methyl trans-4-(1-(4-((1-benzyl-3-indolylcarbonyl)amino)-3-chlorophenylacetyl)-(4S)-fluoro-(2S)-pyrrolidinylmethoxy)cyclohexanecarboxylate (409.2 mg, 0.620 mmol). To the resulting solution was added 0.25N NaOH (8.0 ml) and the mixture was stirred at room temperature for 18 hours. The reaction mixture was then distilled under reduced pressure to remove the solvent. The residue was acidified with 1N HCl (2.5 ml). The crystals thus precipitated were collected by filtration under reduced pressure, washed with water and dried under reduced pressure to give the title compound (355.6 mg, 89%) as a white amorphous substance.

IR (ATR) ν2935, 1643, 1511 cm$^{-1}$;

$^1$H-NMR (DMSO-d$_6$) δ: 1.08–1.44 (4H, m), 1.80–2.05 (4H, m), 2.05–2.34 (3H, m), 3.11–3.94 (total 7H, series of m), 4.14 and 4.34 (total 1H, m), 5.32 and 5.46 (total 1H, d, J=55.2 Hz), 5.23 (2H, s), 7.12–7.45 (total 9H, series of m), 7.57 (1H, d, J=7.6 Hz), 7.65 (1H, m), 8.17 (1H, d, J=7.6 Hz), 8.43 (1H, s), 9.40 (1H, s), 12.05 (1H, s, CO$_2$H).

MS (ESI) m/z 646 (M$^+$+1);

Anal. Calcd for C$_{36}$H$_{37}$ClFN$_3$O$_5$ 0.25H$_2$O: C, 66.45; H, 5.81; N, 6.46; Cl, 5.45; F, 2.92. Found: C, 66.34; H, 5.83; N, 6.27; Cl, 5.35; F, 2.88.

Example 69 trans-4-(1-(2-Chloro-3-((1-methyl-3-indolylcarbonyl)amino)-6-pyridyl)acetyl)-(4S)-fluoro-(2S)-cyclohexanecarboxylic acid (Step 1) Synthesis of ethyl (2-chloro-3-(1-methyl-3-indolylcarbonyl)amino-6-pyridyl))acetate

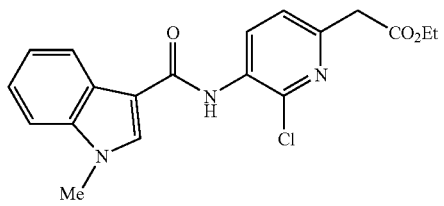

Oxalyl chloride (1.10 ml, 12.5 mmol) was added to a solution of 1-methylindole-3-carboxylic acid (2.00 g, 11.4 mmol) and DMF (0.18 ml, 2.28 mmol) in methylene chloride (25 ml) and the resulting mixture was stirred for 3 hours at room temperature. The reaction mixture was distilled under reduced pressure to remove the solvent to give 1-methylindole-3-carboxylic acid chloride (2.19 g, 99%) as a pale yellow solid. The resulting 1-methylindole-3-carboxylic acid chloride (752 mg, 3.88 mmol) was added in portions to a solution of ethyl 3-amino-2-chloro-6-pyridylacetate (833 mg, 3.88 mmol) and triethylamine (1.08 ml, 7.77 mmol) in methylene chloride (20 ml) under stirring at 0° C. The reaction mixture was heated under reflux for 8 hours. After cooling to room temperature and addition of water, the mixture was extracted with chloroform. The extract was washed with saturated brine, dried over anhydrous magnesium sulfate, and distilled under reduced pressure to remove the solvent. The residue was purified by chromatography on a silica gel column, whereby from n-hexane-ethyl acetate (2:1, v/v) eluate fractions, ethyl 2-chloro-3-(1-methyl-3-indolylcarbonyl)amino-6-pyridylacetate (859 mg, 60%) was obtained as a yellow solid.

$^1$H-NMR (DMSO-d$_6$) δ: 1.21 (t, J=7.1 Hz, 3H), 3.85 (s, 2H), 3.90 (s, 3H), 4.12 (q, J=7.1 Hz, 2H), 7.21 (m, 1H), 7.28 (m, 1H), 7.42 (d, J=8.1 Hz, 1H), 7.55 (d, J=8.1 Hz, 1H), 8.04 (m, 1H), 8.15 (m, 1H), 8.31 (m, 1H), 9.41 (broad s, 1H).

MS (ESI) m/z 372 (M$^+$+1).

(Step 2) Synthesis of (2-chloro-3-(1-methyl-3-indolylcarbonyl)amino-6-pyridyl)acetic acid

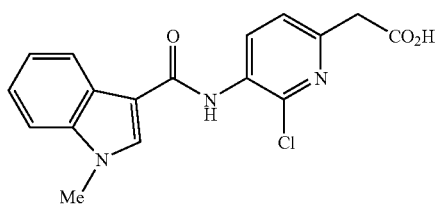

Ethyl 2-chloro-3-(1-methyl-3-indolylcarbonyl)amino-6-pyridylacetate (859 mg, 2.31 mmol) was dissolved in THF (25 ml). To the resulting solution was added 0.25N NaOH (13.9 ml, 3.47 mmol), followed by stirring at room temperature for 4 hours. Methanol-water (1:1, v/v, 10 ml) was added, and the mixture was stirred at 50° C. for 2 hours. The reaction mixture was acidified with 1N HCl (5.0 ml). The crystals thus precipitated were collected by filtration, washed with water, and dried under reduced pressure to give 2-chloro-3-(1-methyl-3-indolylcarbonyl)amino-6-pyridylacetyl acid (702 mg, 88%) as a colorless solid.

$^1$H-NMR (CDCl$_3$) δ: 3.76 (s, 2H), 3.89 (s, 3H), 7.21 (t, J=8.3 Hz, 1H), 7.28 (t, J=8.3 Hz, 1H), 7.41 (d, J=8.1 Hz, 1H), 7.55 (d, J=8.3 Hz, 1H), 8.15 (d, J=8.1 Hz, 1H), 8.31 (s, 1H), 9.40 (broad s, 1H), 12.50 (broad s, 1H).

MS (ESI) m/z 344 (M$^+$+1).

(Step 3) Synthesis of methyl trans-4-(1-(2-chloro-3-((1-methyl-3-indolylcarbonyl)amino)-6-pyridyl)acetyl)-(4S)-fluoro-(2S)-cyclohexanecarboxylate

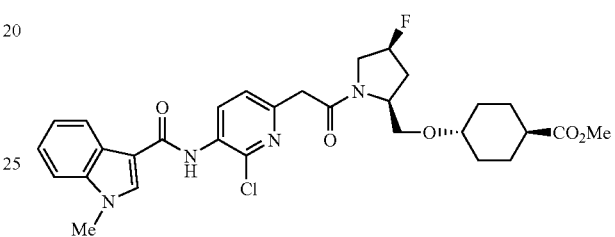

To a solution of (2-chloro-3-(1-methyl-3-indolylcarbonyl)amino-6-pyridyl)acetic acid (254 mg, 0.74 mmol), methyl trans-4-((4S)-fluoro-(2S)-pyrrolidinylmethoxy)cyclohexanecarboxylate (the compound synthesized in (Step 3) of Example 21) (192 mg, 0.74 mmol), HOBt (20.0 mg, 0.15 mmol), and DMAP (18.0 mg, 0.15 mmol) in DMF (8.0 ml) was added EDC HCl (212 mg, 1.11 mmol). After stirring at room temperature for 20 hours, the reaction mixture was added with water. The crystals thus precipitated were collected by filtration under reduced pressure, washed with water and dried under reduced pressure to give methyl trans-4-(1-(2-chloro-3-((1-methyl-3-indolylcarbonyl)amino)-6-pyridyl)acetyl)-(4S)-fluoro-(2S)-cyclohexanecarboxylate (377 mg, 887%) as a pale yellow solid.

$^1$H-NMR (CDCl$_3$) δ: 1.22–1.33 (m, 2H), 1.41–1.54 (m, 2H), 1.98–2.54 (m, 7H), 3.28 (m, 1H), 3.34 and 3.53 (each m, total 1H), 3.66 and 3.68 (each 2, total 3H), 3.70–3.89 (m, 4H), 3.91 (s, 3H), 3.92–4.12 (m, 2H), 4.39 and 4.46 (each m, total 1H), 5.28 (m, 1H), 7.30–7.39 (m, 2H), 7.44 (m, 1H), 7.83 (m, 1H), 8.13 (m, 1H), 8.24 (m, 1H), 8.92 and 8.95 (each d, J=8.3 Hz, total 1H).

MS (ESI) m/z 585 (M$^+$+1).

(Step 4) Synthesis of trans-4-(1-(2-chloro-3-((1-methyl-3-indolylcarbonyl)amino)-6-pyridyl)acetyl)-(4S)-fluoro-(2S)-cyclohexanecarboxylic acid

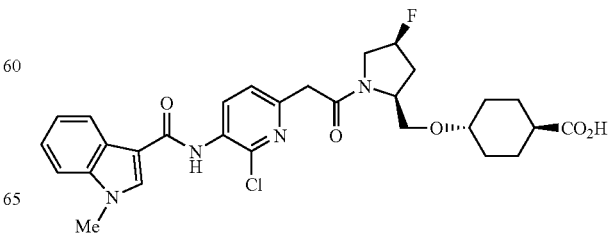

In THF (7.0 ml) was dissolved methyl trans-4-(1-(2-chloro-3-((1-methyl-3-indolylcarbonyl)amino)-6-pyridyl)acetyl)-(4S)-fluoro-(2S)-cyclohexanecarboxylate (377 mg, 0.64 mmol). To the resulting solution was added 0.25N NaOH (4.00 ml, 1.00 mmol), followed by stirring at room temperature for 19 hours. The reaction mixture was poured in 1N HCl (1.0 ml). The crystals thus precipitated were collected by filtration under reduced pressure, washed with water, and dried under reduced pressure to give the title compound (252 mg, 69%) as a pale yellow solid.

IR (ATR) ν 2940, 2861, 1710, 1654, 1617, 1581, 1519, 1488 cm$^{-1}$;

$^1$H-NMR (DMSO-d$_6$) δ: 1.17–1.38 (m, 4H), 1.86–2.21 (m, 7H), 3.18–3.87 (m. 6H), 3.90 (s, 3H), 3.93 (m, 1H), 4.14 and 4.40 (each m, total 1H), 5.33 and 5.40 (each m, total 1H), 7.21 (t, J=8.1 Hz, 1H), 7.27 (t, J=8.1 Hz, 1H), 7.34 (d, J=8.1 Hz, 1H), 7.55 (d, J=8.3 Hz, 1H), 8.12–8.17 (m, 2H), 8.30 (s, 1H), 9.39 (broad s, 1H), 12.00 (broad s, 1H).

MS (ESI) m/z 571 (M$^+$+1);

Anal. Calcd for $C_{29}H_{32}ClFN_4O_5$ 0.25H$_2$O: C, 60.52; H, 5.69; N, 9.73. Found: C, 60.46; H, 5.76; N, 9.43.

Example 70 trans-4-(1-(3-Fluoro-4-(1-methyl-3-indolyl)carbonylaminophenylacetyl)-(4S)-fluoro-(2S)-pyrrolidinylmethoxy)cyclohexanecarboxylic acid (Step 1) Synthesis of methyl trans-4-(1-(3-fluoro-4-(1-methyl-3-indolyl)carbonylaminophenylacetyl)-(4S)-fluoro-(2S)-pyrrolidinylmethoxy)cyclohexanecarboxylate

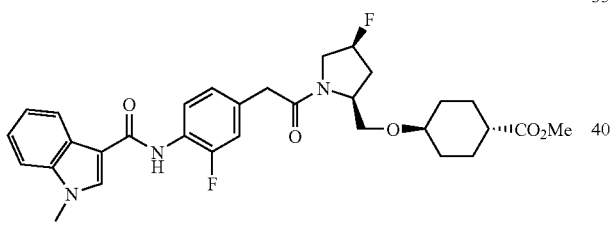

In THF (10 ml) and acetonitrile (10 ml) were dissolved methyl trans-4-((4S)-fluoro-(2S)-pyrrolidinylmethoxy)cyclohexanecarboxylate (the compound synthesized in (Step 3) of Example 21) (65 mg, 0.25 nnol), (3-fluoro-4-(1-methyl-3-indolyl)carbonylaminophenyl)acetic acid (90 mg, 0.25 mmol), HOBt (34 mg, 0.25 mmol), and triethylamine (104 μl, 0.75 mmol). After EDC•HCl (72 mg, 0.37 mmol) was added at 0° C., the mixture was stirred at room temperature for 16 hours. The reaction mixture was distilled under reduced pressure to remove the solvent. The residue was added with water, followed by extraction with ethyl acetate. The extract was washed successively with a saturated aqueous solution of sodium bicarbonate, a 2M aqueous citric acid solution, and a saturated aqueous solution of sodium bicarbonate, dried over anhydrous sodium sulfate, and distilled under reduced pressure to remove the solvent. The residue was purified by chromatography using a thin-layer plate, whereby from n-hexane-ethyl acetate (1:4, v/v) eluate fractions, methyl trans-4-(1-(3-fluoro-4-(1-methyl-3-indolyl)carbonylaminophenylacetyl)-(4S)-fluoro-(2S)-pyrrolidinylmethoxy)cyclohexanecarboxylate (130 mg, 90%) was obtained as a colorless oil.

$^1$H-NMR (CDCl$_3$) δ: 1.20–1.50 (m, 4H), 2.00–2.50 (m, 6H), 3.20–4.40 (m, 15H), 5.15–5.35 (m, 1H), 7.07–7.45 (m, 5H), 7.78 (s, 1H), 7.91 (br s, 1H), 8.03–8.06 (m, 1H), 8.45–8.47 (m, 1H).

(Step 2) Synthesis of 4-(1-(3-fluoro-4-(1-methyl-3-indolyl)carbonylaminophenylacetyl)-(4S)-fluoro-(2S)-pyrrolidinylmethoxy)cyclohexanecarboxylic acid

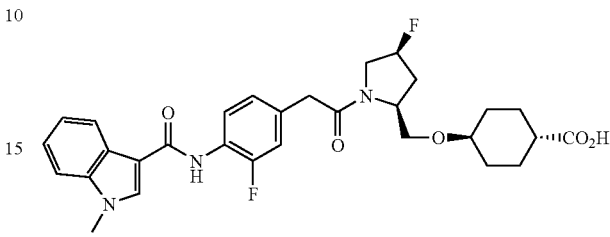

In THF (10 ml) and methanol (5.0 ml) was dissolved methyl trans-4-(1-(3-fluoro-4-(1-methyl-3-indolyl)carbonylaminophenylacetyl)-(4S)-fluoro-(2S)-pyrrolidinylmethoxy)cyclohexanecarboxylate (130 mg, 0.23 mmol). To the resulting solution was added 1N NaOH (0.8 ml, 0.8 mmol), followed by stirring at 70° C. for 18 hours. The reaction mixture was distilled under reduced pressure to remove the solvent. The residue was acidified with 1N HCl. The crystals thus precipitated were collected by filtration under reduced pressure, washed with water, and dried under reduced pressure to give the title compound (90 mg, 71%) as a white solid.

IR (ATR) ν 2933, 1639, 1627, 1521, 1427, 1099 cm$^{-1}$;
$^1$H-NMR (DMSO-d$^6$) δ: 1.16–1.37 (m, 4H), 1.88–2.18 (m, 6H), 3.10–4.30 (m, 12H), 5.22–5.45 (m, 1H), 7.00–7.27 (m, 4H), 7.53 (d, J=8.3 Hz, 1H), 7.60–7.63 (m, 1H), 8.14 (d, J=7.8 Hz, 1H), 8.25 (s, 1H), 9.46 (s, 1H).

MS (FAB) m/z 553 (M+H)$^+$;

Anal. calcd for $C_{30}H_{33}CFN_3O_5$ 0.4H$_2$O: C, 64.25; H, 6.07; N, 7.49. Found: C, 64.38; H, 6.16; N, 7.38.

Example 71 trans-4-(1-(2,5-Difluoro-4-((1-methyl-1H-3-indolylcarbonyl)amino)phenylacetyl)-(4S)-fluoro-(2S)-pyrrolidinylmethoxy)cyclohexanecarboxylic acid (Step 1) Synthesis of (2,5-difluoro-4-((1-methyl-1H-indolylcarbonyl)amino)phenyl)acetic acid

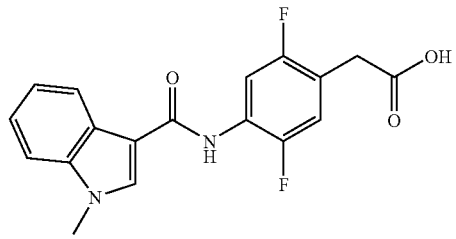

In methylene chloride (20 ml) were dissolved 1-methyl-1H-indole-3-carboxylic acid (814 mg, 4.65 mmol), triethylamine (2.6 ml, 18.6 mmol) and diphenylphosphinic chloride (1.72 ml, 9.3 mmol). The resulting solution was stirred for 3 days at room temperature. The reaction mixture was poured in 1M HCl, followed by extraction with chloroform.

The extract were washed with saturated brine, dried over anhydrous magnesium sulfate and distilled under reduced pressure to remove the solvent. To the residue were added THF (10 ml) and 0.25M NaOH (8 ml, 2 mmol) and the mixture was stirred at room temperature for 4 hours. The reaction mixture was poured in water and acidified with 1M HCl. The acidic solution was extracted with a chloroform/methanol mixture. The extract was dried over anhydrous magnesium sulfate and distilled under reduced pressure to remove the solvent to give 2,5-difluoro-4-((1-methyl-1H-3-indolylcarbonyl)amino)phenyl)acetic acid (483 mg, 30%) as a colorless solid.

$^1$H-NMR (DMSO-d$_6$) δ: 3.62 (s, 2H), 3.90 (s, 3H), 7.20 (t, J=7.5 Hz, 1H), 7.29 (t, J=7.5 Hz, 1H), 7.55 (d, J=8.1 Hz, 1H), 7.70 (dd, J=6.5, 8.8 Hz, 1H), 8.15 (d, J=7.5 Hz, 1H), 8.32 (s, 1H), 9.57 (s, 1H), 12.52 (br, 1H).

MS (ESI) m/z 345 (M+1)$^+$.

(Step 2) Synthesis of trans-4-(1-(2,5-difluoro-4-((1-methyl-1H-3-indolylcarbonyl)amino)phenylacetyl)-(4S)-fluoro-(2S)-pyrrolidinylmethoxy)cyclohexanecarboxylic acid

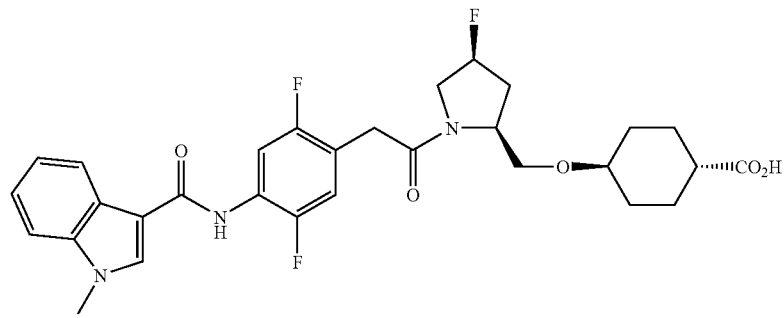

In DMF (10 ml) were dissolved 2,5-difluoro-4-((1-methyl-1H-3-indolylcarbonyl)amino)phenyl)acetic acid (480 mg, 1.39 mmol), methyl trans-4-((4S)-fluoro-(2S)-pyrrolidinylmethoxy)cyclohexanecarboxylate (the compound synthesized in (Step 3) of Example 21) (301 mg, 1.16 mmol), HOBt (357 mg, 2.64 mmol), DMAP (catalytic amount) and EDC·HCl (400 mg, 2.09 mmol). The resulting solution was stirred at room temperature for 18 hours. The reaction mixture was poured in 1M HCl, followed by extraction with ethyl acetate. The extract was washed with saturated brine, dried over anhydrous magnesium sulfate and distilled under reduced pressure to remove the solvent. The residue was purified by chromatography on a silica gel column (middle pressure Yamazen, linear gradient of chloroform and methanol form 100:0 to 95:5, 12 ml/min, φ 37 mm×300 mm), whereby a condensate was obtained. The resulting compound was added with THF (14 ml) and 0.25M NaOH (7 ml, 1.7 mmol), followed by stirring at room temperature for 18 hours. The reaction mixture was acidified with 1M HCl. The crystals thus precipitated were collected by filtration under reduced pressure. The crude crystals thus obtained were recrystallized from chloroform/n-hexane/acetone to give the title compound (329 mg, 50%) as a colorless solid.

$^1$H-NMR (DMSO-d$_6$) δ: 1.20 (m, 2H), 1.33 (m, 2H), 1.90 (m, 4H), 2.18 (m, 2H), 3.18 (t, J=9.5 Hz, 1H), 3.50 (m, 1H), 3.62 (m, 1H), 3.70 (m, 1H), 3.90 (s, 3H), 3.80–4.00 (m, 2H), 4.12 and 4.32 (2m, total 1H), 5.40 (m, 1H), 7.20 (m, 3H), 7.52 (d, J=8.1 Hz, 1H), 7.65 (m, 1H), 8.14 (d, J=7.8 Hz, 1H), 8.30 (s, 1H), 9.55 (s, 1H), 12.04 (br, 1H).

MS (ESI) m/z 572 (M+1)$^+$;

Anal. Calcd for $C_{30}H_{32}F_3N_3O_5 \cdot 1.0$ $H_2O$: C, 61.11; H, 5.81; N, 7.13. Found: C, 60.92; H, 5.55; N, 6.97.

Example 72 trans-4-(1-(2,5-Dichloro-4-((1-methyl-1H-3-indolylcarbonyl)amino)phenylacetyl)-(4S)-fluoro-(2S)-pyrrolidinylmethoxy)cyclohexanecarboxylic acid (Step 1) Synthesis of 2,5-dichloro-4-((1-methyl-1H-3-indolylcarbonyl)amino)phenyl)acetic acid

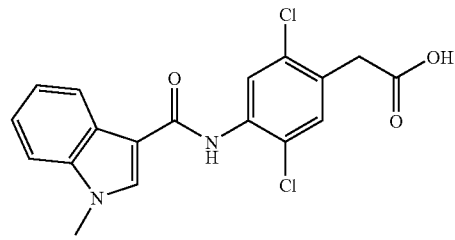

In methylene chloride (25 ml) was dissolved 1-methyl-1H-indole-3-carboxylic acid (794 mg, 4.53 mmol). Oxalyl chloride (0.79 ml, 9.1 mmol) was added to the solution under stirring at 0° C. The reaction mixture was stirred at room temperature for 1 hour and then, distilled under reduced pressure to remove the solvent. The residue was dissolved in methylene chloride (25 ml). The resulting solution was added to a solution of triethylamine (0.84 ml, 9.0 mmol) and ethyl 4-amino-2,5-dichlorophenylacetate (750 mg, 3.02 mmol) at 0° C. The reaction mixture was heated under reflux for 18 hours. After cooling to room temperature, the reaction mixture was poured in water, followed by extraction with chloroform. The extract was washed with saturated brine, dried over anhydrous magnesium sulfate and distilled under reduced pressure to remove the solvent. The residue was purified by chromatography on a silica gel column (middle pressure Yamazen, linear gradient of chloroform and methanol form 100:0 to 95:5, 12 ml/min, φ 37 mm×300 mm), whereby the purified ester was obtained. To the purified ester were added THF (45 ml) and 0.25M NaOH (18 ml, 4.5 mmol), followed by stirring at room temperature for 4 hours. Water and 1M HCl were added to acidify the reaction mixture. The crystals thus precipitated were collected by filtration under reduced pressure. The crude crystals were recrystallized from chloroform/n-hexane to give 2,5-dichloro-4-((1-methyl-1H-3-indolylcarbonyl)amino)phenyl)acetic acid (807 mg, 71%) as a colorless solid.

$^1$H-NMR (DMSO-d$_6$) δ: 3.72 (s, 2H), 3.90 (s, 3H), 7.22 (t, J=8.1 Hz, 1H), 7.28 (t, J=8.1 Hz, 1H), 7.56 (d, J=8.3 Hz, 1H), 7.64 (s, 1H), 7.92 (s, 1H), 8.15 (d, J=7.8 Hz, 1H), 8.31 (s, 1H), 9.39 (s, 1H).

MS (ESI) m/z 378 (M+1)$^+$.

(Step 2) Synthesis of trans-4-(1-(2,5-dichloro-4-((1-methyl-1H-3-indolylcarbonyl)amino)phenylacetyl)-(4S)-fluoro-(2S)-pyrrolidinylmethoxy)cyclohexanecarboxylic acid

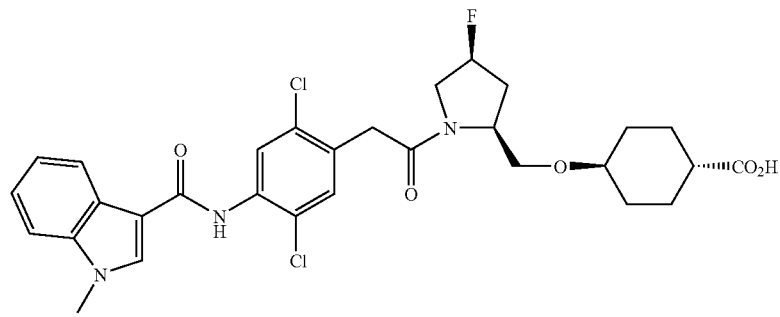

In DMF (10 ml) were dissolved (2,5-dichloro-4-((1-methyl-1H-3-indolylcarbonyl)amino)phenyl)acetic acid (438 mg, 1.16 mmol), methyl trans-4-((4S)-fluoro-(2S)-pyrrolidinylmethoxy)cyclohexanecarboxylate (the compound synthesized in (Step 3) of Example 21) (301 mg, 1.16 mmol), HOBt (357 mg, 2.64 mmol), DMAP (catalytic amount) and EDC•HCl salt (400 mg, 2.09 mmol). The resulting mixture was stirred at room temperature for 18 hours. The reaction mixture was poured in 1M HCl, followed by extraction with ethyl acetate. The extract was washed with saturated brine, dried over anhydrous magnesium sulfate, and distilled under reduced pressure to remove the solvent. The residue was purified by chromatography on a silica gel column (middle pressure Yamazen, linear gradient of chloroform and methanol form 100:0 to 95:5, 12 ml/min, φ 37 mm×300 mm). The purified ester was dissolved in THF (14 ml) and 0.25M NaOH (7 ml, 1.7 mmol). The resulting mixture was stirred for 18 hours at room temperature and poured in water. The solution was acidified with 1M HCl. Crystals thus precipitated were collected by filtration under reduced pressure. The crude crystals were recrystallized from chloroform/n-hexane/acetone to give the title compound (528 mg, 75%) as a colorless crystalline substance.

$^1$H-NMR (DMSO-d$_6$) δ: 1.20 (m, 2H), 1.32 (m, 2H), 1.90 (m, 4H), 2.20 (m, 2H), 3.21 (m, 1H), 3.49 (m, 1H), 3.65–4.00 (m, 4H), 3.90 (s, 3H), 4.12 and 4.40 (2m, total 1H), 5.40 (m, 1H), 7.21 (t, J=7.4 Hz, 1H), 7.28 (t, J=7.4 Hz, 1H), 7.50 (d, J=15.7 Hz, 1H), 7.55 (d, J=8.1 Hz, 1H), 7.88 (d, J=3.4 Hz, 1H), 8.14 (d, J=7.8 Hz, 1H), 8.30 (s, 1H), 9.38 (s, 1H), 12.04 (s, 1H).

MS (ESI) m/z 605 (M+1)$^+$.

Anal. Calcd for $C_{30}H_{32}Cl_2FN_3O_5 \cdot 0.25 H_2O$: C, 59.17; H, 5.38; N, 6.90. Found: C, 59.18; H, 5.38; N, 6.71.

Example 73 trans-4-(1-((5-Chloro-2-fluoro-4-((6-fluoro-1-methyl-3-indolylcarbonyl)amino)phenyl)acetyl)-(4S)-fluoro-(2S)-pyrrolidinylmethoxy)cyclohexanecarboxylic acid (Step 1) Synthesis of 6-fluoro-1-methylindole-3-carboxylic acid

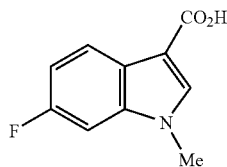

In acetone (200 ml) was dissolved 6-fluoro-1-methylindole-3-carbaldehyde (3.10 g, 17.5 mmol). To the resulting solution was added potassium permanganate (0.2M aqueous solution, 175 ml, 35.0 mmol) in portions under stirring at room temperature. After stirring at room temperature for 10 hours, the reaction mixture was filtered through Celite. After the filtrate was distilled under reduced pressure under reduced pressure, the residue was acidified with 1N HCl. The crystals thus precipitated were collected by filtration under reduced pressure, washed with water, and dried under reduced pressure to give 6-fluoro-1-methylindole-3-carboxylic acid (2.37 g, 70%) as a brown solid.

$^1$H-NMR (DMSO-d$_6$) δ: 3.82 (s, 3H), 7.05 (m, 1H), 7.41 (d, J=9.8 Hz, 1H), 7.98 (dd, J=8.6, 5.6 Hz, 1H), 8.04 (s, 1H), 12.03 (s, 1H).

MS (ESI) m/z 194 (M$^+$+1).

(Step 2) Synthesis of ethyl (5-chloro-2-fluoro-4-((6-fluoro-1-methyl-3-indolylcarbonyl)amino)phenyl)acetate

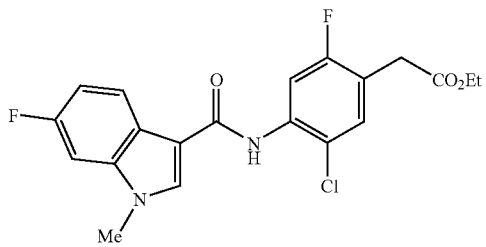

To a suspension of 6-fluoro-1-methylindole-3-carboxylic acid (500 mg, 2.59 mmol) and DMF (0.02 ml, 0.26 mmol) in methylene chloride (15 ml) was added dropwise oxalyl chloride (0.25 ml, 2.85 mmol) under stirring at room temperature. After completion of the dropwise addition, the reaction mixture was stirred at room temperature for 1 hour. The reaction mixture was then distilled under reduced pressure to remove the solvent. The residue was dissolved in methylene chloride (10.0 ml), followed by the dropwise addition to a solution of ethyl (4-amino-5-chloro-2-fluorophenyl)acetate (600 mg, 2.59 mmol) and triethylamine (1.08 ml, 7.77 mmol) in methylene chloride (5.0 ml). After completion of the dropwise addition, the reaction mixture was heated under reflux for 10 hours. After the reaction mixture was cooled to room temperature, the precipitated crystals were removed under reduced pressure. The filtrate was distilled under reduced pressure to remove the solvent. The residue was purified by chromatography on a silica gel column, whereby from n-hexane:ethyl acetate (2:1, v/v) eluate fractions, ethyl (5-chloro-2-fluoro-4-((6-fluoro-1-methyl-3-indolylcarbonyl)amino)phenyl)acetate (665 mg, 63%) was obtained as a yellow solid.

$^1$H-NMR (CDCl$_3$) δ: 1.28 (t, J=7.1 Hz, 3H), 3.62 (s, 2H), 3.84 (s, 3H), 4.19 (q, J=7.1 Hz, 2H), 7.07–7.12 (m, 2H), 7.34 (d, J=7.3 Hz, 1H), 7.74 (s, 1H), 8.10 (dd, J=9.1, 5.2 Hz, 1H), 8.19 (broad s, 1H), 8.49 (d, J=12.0 Hz, 1H).

MS (ESI) m/z 407 (M$^+$+1).

(Step 3) Synthesis of (5-chloro-2-fluoro-4-((6-fluoro-1-methyl-3-indolylcarbonyl)amino)phenyl)acetic acid

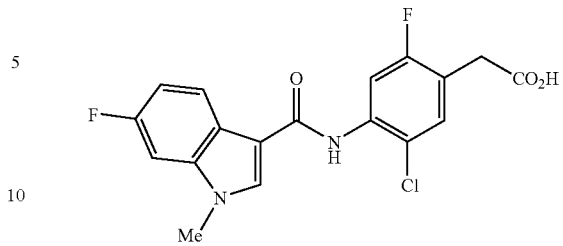

In THF (17 ml) was dissolved ethyl (5-chloro-2-fluoro-4-((6-fluoro-1-methyl-3-indolylcarbonyl)amino)phenyl)acetate (665 mg, 1.63 mmol). To the resulting solution was added 0.25N NaOH (9.81 ml, 2.45 mmol) and the mixture was stirred at room temperature for 14 hours. The reaction mixture was poured in 1N HCl (3.0 ml). The crystals thus precipitated were collected by filtration under reduced pressure, washed with water, and dried under reduced pressure to give (5-chloro-2-fluoro-4-((6-fluoro-1-methyl-3-indolylcarbonyl)amino)phenyl)acetic acid (600 mg, 97%) as a brown solid.

$^1$H-NMR (DMSO-d$_6$) δ: 3.65 (s, 2H), 3.86 (s, 3H), 7.06 (m, 1H), 7.44 (dd, J=10.3,2.5 Hz, 1H), 7.54 (d, J=7.6 Hz, 1H), 7.69 (d, J=11.2 Hz, 1H), 8.12 (dd, J=8.8,5.6 Hz, 1H), 8.32 (s, 1H), 9.38 (s, 1H), 12.58 (broad s, 1H).

MS (ESI) m/z 379 (M$^+$+1).

(Step 4) Synthesis of methyl trans-4-(1-((5-chloro-2-fluoro-4-((6-fluoro-1-methyl-3-indolylcarbonyl)amino)phenyl)acetyl)-(4S)-fluoro-(2S)-pyrrolidinylmethoxy)cyclohexanecarboxylate

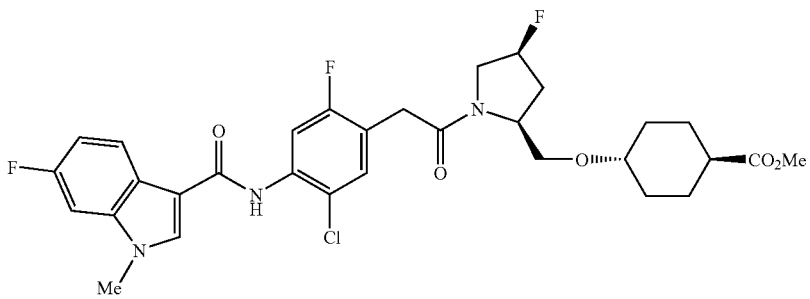

To a solution of (5-chloro-2-fluoro-4-((6-fluoro-1-methyl-3-indolylcarbonyl)amino)phenyl)acetic acid (200 mg, 0.53 mmol), methyl trans-4-((4S)-fluoro-(2S)-pyrrolidinylmethoxy)cyclohexanecarboxylate (the compound synthesized in (Step 3) of Example 21) (137 mg, 0.53 mmol), HOBt (14.0 mg, 0.11 mmol), and DMAP (13.0 mg, 0.11 mmol) in DMF (5.0 ml) was added EDC HCl (152 mg, 0.79 mmol). After stirring at room temperature for 18 hours, the reaction mixture was diluted with water, followed by extraction with ethyl acetate. The extract was washed saturated brine, dried over anhydrous sodium sulfate, and distilled under reduced pressure to remove the solvent. The residue was purified by chromatography on a silica gel column, whereby from ethyl acetate eluate fractions, methyl trans-4-(1-((5-chloro-2-fluoro-4-((6-fluoro-1-methyl-3-indolylcarbonyl)amino)phenyl)acetyl)-(4S)-fluoro-(2S)-pyrrolidinylmethoxy)cyclohexanecarboxylate (303 mg, 92%) as a yellow oil.

$^1$H-NMR (CDCl$_3$) δ: 1.18–1.53 (m, 4H), 1.93–2.53 (m, 7H), 3.23–3.98 (m, 13H), 4.30 and 4.37 (each m, total 1H), 5.26 and 5.28 (each m, total 1H), 7.06–7.11 (m, 2H), 7.39 and 7.40 (each d, J=7.1 Hz, total 1H), 7.73 (s, 1H), 8.10 (dd, J=9.0,4.9 Hz, 1H), 8.18 (m, 1H), 8.45 and 8.46 (each d, J=12.0 Hz, total 1H)

MS (ESI) m/z 620 (M$^+$+1).

(Step 5) Synthesis of trans-4-(1-((5-chloro-2-fluoro-4-((6-fluoro-1-methyl-3-indolylcarbonyl)amino)phenyl)acetyl)-(4S)-fluoro-(2S)-pyrrolidinylmethoxy)cyclohexanecarboxylic acid

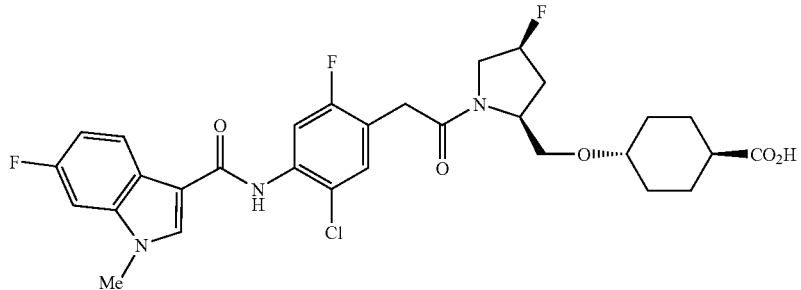

In THF (49 ml) was dissolved methyl trans-4-(1-((5-chloro-2-fluoro-4-((6-fluoro-1-methyl-3-indolylcarbonyl)amino)phenyl)acetyl)-(4S)-fluoro-(2S)-pyrrolidinylmethoxy)cyclohexanecarboxylate (303 mg, 0.49 mmol). To the resulting solution was added 0.25N NaOH (3.00 ml, 0.75 mmol) and the mixture was stirred at room temperature for 17 hours. The reaction mixture was poured in 1N HCl (1.0 ml). The crystals thus precipitated were collected by filtration, washed with water, and dried under reduce pressure to give the title compound (236 mg, 79%) as a colorless solid.

IR (ATR) ν 3417, 2940, 2865, 1708, 1619, 1646, 1585, 1517, 1467 cm$^{-1}$;

$^1$H-NMR (DMSO-d$_6$) δ: 1.18–1.41 (m, 4H), 1.86–2.33 (m, 7H), 3.17–3.98 (m, 10H), 4.13 and 4.35 (each m, total 1H), 5.32 and 5.41 (each m, total 1H), 7.06 (m, 1H), 7.42–7.46 (m, 2H), 7.65 and 7.66 (each d, J=11.2 Hz, total 1H), 8.12 (dd, J=8.6, 5.9 Hz, 1H), 8.31 (s, 1H), 9.37 (s, 1H), 12.03 (broad s, 1H).

MS (ESI) m/z 606 (M$^+$+1);

Anal. Calcd for C$_{30}$H$_{31}$ClF$_3$N$_3$O$_5$·0.75H$_2$O: C, 58.16; H, 5.29; N, 6.78. Found: C, 58.35; H, 5.23; N, 6.39.

Example 74 trans-4-(1-((5-Chloro-2-fluoro-4-(((5-fluoro-1-methyl-3-indolyl)carbonyl)amino)phenyl)acetyl)-(4S)-fluoro-(2S)-pyrrolidinylmethoxy)cyclohexanecarboxylic acid (Step 1) Synthesis of (5-fluoro-1-methylindol-3-carbaldehyde

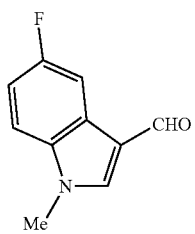

In DMF (100 ml) was dissolved 5-fluoroindol-3-carbaldehyde (5.17 g, 36.7 mmol). To the resulting solution was added sodium hydride (60% in oil, 1.39 g, 34.9 mmol) in portions under stirring at 0° C. After the reaction mixture was stirred at the same temperature for 1 hour, methyl iodide (4.57 ml, 73.4 mmol) was added thereto at 0° C. The resulting mixture was stirred at room temperature for 18 hours. The reaction mixture was poured in 1N HCl, followed by extraction with ether. The extract was washed with saturated brine, dried over anhydrous sodium sulfate, and distilled under reduced pressure to remove the solvent. The residue was crystallized by adding thereto chloroform/hexane. The crystals thus precipitated were collected by filtration under reduced pressure and dried under reduced pressure to give 5-fluoro-1-methylindole-3-carbaldehyde (2.53 g, 39%) as a white crystalline powder.

$^1$H-NMR (CDCl$_3$) δ: 3.86 (s, 3H), 7.08 (brt, J=9.2 Hz, 1H), 7.27 (dd, J=4.4,8.8 Hz, 1H), 7.68 (s, 1H), 7.95 (brd, J=9.6 Hz, 1H).

(Step 2) Synthesis of 5-fluoro-1-methylindole-3-carboxylic acid

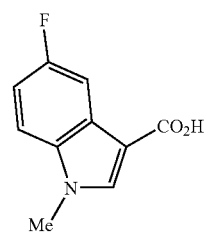

In acetone (50 ml) was dissolved 5-fluoro-1-methylindole-3-carbaldehyde (1.33 g, 7.52 mmol). To the resulting solution was added dropwise an 1N aqueous solution of potassium permanganate (7.15 ml, 7.15 mmol) under stirring at 0° C. After stirring at room temperature for 18 hours, another 1N aqueous solution of potassium permanganate (4.0 ml, 4.0 mmol) was added, and the mixture was stirred at room temperature for 18 hours. The mixture was filtered through Celite. After washing with water, the filtrate was added with 1N HCl. The crystals thus precipitated were collected by filtration under reduced pressure, washed with water and dried under reduced pressure to give 5-fluoro-1-methylindole-3-carboxylic acid (885 mg, 61%) as a white crystalline powder.

$^1$H-NMR (DMSO-d$_6$) δ: 3.86 (s, 3H), 7.06–7.11 (m, 1H), 7.53 (dd, J=4.8,9.2 Hz, 1H), 7.67 (brd, J=10.0 Hz, 1H), 8.08 (s, 1H), 12.00 (brs, 1H).

(Step 3) Synthesis of ethyl (5-chloro-2-fluoro-4-(((5-fluoro-1-methyl-3-indolyl)carbonyl)amino)phenyl)acetate

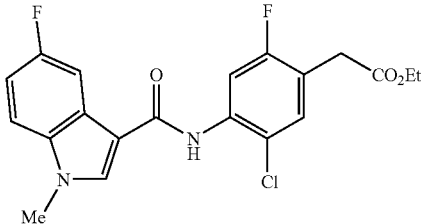

In methylene chloride (30 ml) was dissolved 5-fluoro-1-methylindole-3-carboxylic acid (885 mg, 4.58 mmol). To the resulting solution was added oxalyl chloride (600 μl, 6.87 mmol) under stirring at 0° C., and the resulting mixture was stirred at room temperature for 1 hour. From the reaction mixture, the solvent was distilled off under reduced pressure. The residue was dissolved in methylene chloride (50 ml). The resulting solution was added dropwise to a solution of ethyl (4-amino-5-chloro-2-fluorophenyl)acetate (1.06 g, 4.58 mmol) in methylene chloride (20 ml), followed by heating under reflux for 15 minutes. The reaction mixture was cooled and triethylamine (3.19 ml, 22.9 mmol) was added thereto. The resulting mixture was heated under reflux for 18 hours. The reaction mixture was cooled and poured in 1N HCl, followed by extraction with ethyl acetate. The extract was dried over anhydrous sodium sulfate, and distilled under reduced pressure to remove the solvent. The residue was purified by chromatography on a silica gel column, whereby from hexane/ethyl acetate (2/1) eluate fractions, ethyl (5-chloro-2-fluoro-4-(((5-fluoro-1-methyl-3-indolyl)carbonyl)amino)phenyl)acetate (868 mg, 47%) was obtained as a white solid.

$^1$H-NMR (CDCl$_3$) δ: 1.27 (t, J=7.2 Hz, 3H), 3.61 (s, 2H), 3.87 (s, 3H), 4.18 (dd, J=7.2,14.0 Hz, 2H), 7.08 (dt, J=2.0, 8.8 Hz, 1H), 7.29–7.34 (m, 2H), 7.5 (s, 1H), 7.83 (dd, J=2.4,9.6 Hz, 1H), 8.11 (brs, 1H), 8.80 (d, J=12 Hz, 1H).

MS (ESI) m/z 407 (M$^+$+1).

(Step 4) Synthesis of (5-chloro-2-fluoro-4-(((5-fluoro-1-methyl-3-indolyl)carbonyl)amino)phenyl)acetic acid

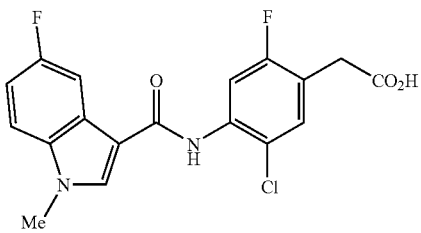

THF/methanol (1/1, 60 ml) and 0.25N NaOH (43 ml, 10.6 mmol) were added to ethyl (5-chloro-2-fluoro-4-(((5-fluoro-1-methyl-3-indolyl)carbonyl)amino)phenyl)acetate (865 mmol, 2.13 mmol) and the mixture was stirred at room temperature for 3 hours. The reaction mixture was poured in 1N HCl, followed by extraction with a chloroform/methanol (10/1) mixture. The extract was dried over anhydrous sodium sulfate, and distilled under reduced pressure to remove the solvent. The residue was solidified with methanol/chloroform/hexane. The crystals thus precipitated were collected by filtration under reduced pressure and dried under reduced pressure to give (5-chloro-2-fluoro-4-(((5-fluoro-1-methyl-3-indolyl)carbonyl)amino)phenyl)acetic acid (736 mg, 91%) as a white crystalline powder.

$^1$H-NMR (DMSO-d$_6$) δ: 3.72 (s, 2H), 3.90 (s, 3H), 7.11 (dt, J=2.8, 9.2 Hz, 1H), 7.53–7.58 (m, 2H), 7.83 (dd, J=2.4,9.6 Hz, 1H), 8.37.

MS (ESI) m/z 379 (M$^+$+1).

(Step 5) Synthesis of methyl trans-4-(1-((5-chloro-2-fluoro-4-(((5-fluoro-1-methyl-3-indolyl)carbonyl)amino)-phenyl)acetyl)-(4S)-fluoro-(2S)-pyrrolidinylmethoxy)cyclohexanecarboxylate

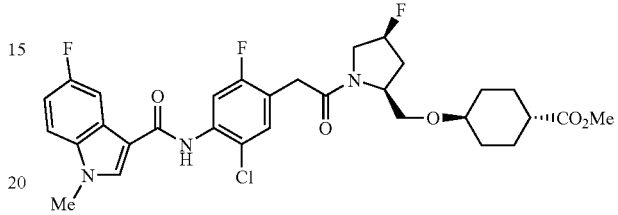

In DMF (20 ml) were dissolved (5-chloro-2-fluoro-4-(((5-fluoro-1-methyl-3-indolyl)carbonyl)amino)phenyl)acic acid (483 mg, 1.28 mmol), methyl trans-4-((4S)-fluoro-(2S)-pyrrolidinylmethoxy)cyclohexanecarboxylate (the compound synthesized in (Step 3) of Example 21) (331 mg, 1.28 mmol) and EDC-HCl (294 mg, 1.53 mmol). To the resulting solution was added HOBt (35.0 mg, 0.26 mmol), and the resulting mixture was stirred at room temperature for 18 hours. The reaction mixture was poured in water, followed by extraction with ethyl acetate. The extract was washed with saturated brine, dried over anhydrous sodium sulfate, and distilled under reduced pressure to remove the solvent. The residue was purified by chromatography on a silica gel column, whereby from hexane/ethyl acetate (1/2) eluate fractions, methyl trans-4-(1-((5-chloro-2-fluoro-4-(((5-fluoro-1-methyl-3-indolyl)carbonyl)amino)phenyl)acetyl)-(4S)-fluoro-(2S)-pyrrolidinylmethoxy)cyclohexanecarboxylate (718 mg, 91%) was obtained as a colorless amorphous substance.

$^1$H-NMR (CDCl$_3$), mixture of rotamars, δ: 1.23–1.31 (m, 2H), 1.40–1.52 (m, 2H), 1.96–2.52 (series of m, 7H), 3.20–4.00 (series of m, 7H), 3.65 and 3.67 (s, total 3H), 3.78 (s, 3H), 4.28–4.42 (m, 1H), 5.18–5.38 (m, 1H), 7.08 (brt, J=9.2 Hz, 1H), 7.31 (dd, J=4.4,9.2 Hz, 1H), 7.39 (dd, J=4.4,7.6 Hz, 1H), 7.75 (d, J=2.8 Hz, 1H), 7.84 (dd, J=2.8, 9.6 Hz, 1H), 8.11 (d, J=5.2 Hz, 1H), 8.43 and 8.46 (d, J=9.2 Hz, total 1H).

MS (ESI) m/z 621 (M$^+$+2).

(Step 6) Synthesis of trans-4-(1-((5-chloro-2-fluoro-4-(((5-fluoro-1-methyl-3-indolyl)carbonyl)amino)phenyl)acetyl)-(4S)-fluoro-(2S)-pyrrolidinylmethoxy)cyclohexanecarboxylic acid

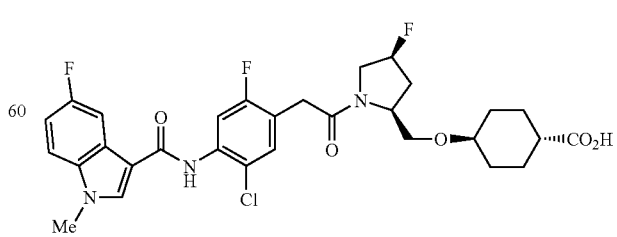

To the methyl ester (687 mg, 1.11 mmol) were added THF/methanol (1/1, 40 ml) and 0.25N NaOH (22 ml, 5.54 mmol), and the resulting mixture was stirred at room temperature for 3.5 hours. The reaction mixture was poured in 1N HCl, followed by extraction with chloroform/methanol (10/1). The extract was dried over anhydrous sodium sulfate, and distilled under reduced pressure to remove the solvent. The residue was purified by chromatography on a silica gel column, whereby from chloroform/methanol (10/1) eluate fractions, the title compound (694 mg, 100%) was obtained as a colorless amorphous substance.

$^1$H-NMR (DMSO-$d_6$), mixture of rotamars, δ: 1.18–1.39 (series of m, 4H), 1.87–2.51 (series of m, 7H), 3.16–4.40 (series of m, 8H), 3.90 (s, 3H), 5.23–5.55 (m, 1H), 7.08 (dt, J=2.8, 9.2 Hz, 1H), 7.41 and 7.44 (d, J=7.6 Hz, total 1H), 7.55 and 7.58 (d, J=4.4 Hz, total 1H), 7.66 and 7.69 (d, J=6.0 Hz, total 1H), 7.83 (dd, J=2.4,10.0 Hz, 1H), 8.38 (s, 1H), 9.33 (s, 1H).

MS (ESI) m/z 607 (M$^+$+1).

Example 75 trans-4-(1-((5-Chloro-2-fluoro-4-((4-fluoro-1-methyl-3-indolylcarbonyl)amino)phenyl)acetyl)-(4S)-fluoro-(2S)-pyrrolidinylmethoxy)cyclohexanecarboxylic acid (Step 1) Synthesis of 4-fluoro-1-methylindole

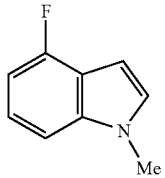

In DMF (40 ml) was dissolved 4-fluoroindole (2.00 g, 14.8 mmol). To the resulting solution was added sodium hydride (60% in oil, 0.71 g, 17.8 mmol) in portions under stirring at 0° C. After the reaction mixture was stirred for 40 minutes at the same temperature, methyl iodide (1.11 ml, 17.8 mmol) was added at 0° C. The reaction mixture was stirred further at the same temperature for 4 hours. A saturated aqueous solution of ammonium chloride was added to terminate the reaction. The reaction mixture was extracted with ether, and the extract was washed with saturated brine, dried over anhydrous sodium sulfate, and distilled under reduced pressure to remove the solvent. The residue was purified by chromatography on a silica gel column, whereby from n-hexane-ethyl acetate (5:1, v/v) eluate fractions, 4-fluoro-1-methylindole (2.20 g, 100%) was obtained as a yellow oil.

$^1$H-NMR (CDCl$_3$) δ: 3.78 (s, 3H), 6.55 (m, 1H), 6.77 (m, 1H), 7.01 (d, J=3.2 Hz, 1H), 7.08–7.15 (m, 2H).

MS (ESI) m/z 150 (M$^+$+1).

(Step 2) Synthesis of 4-fluoro-1-methylindole-3-carbaldehyde

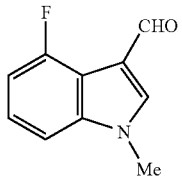

Under stirring at 0° C., phosphoryl chloride (2.07 ml, 22.1 mmol) was added dropwise to DMF (30 ml). After completion of the dropwise addition, a solution of 4-fluoro-1-methylindole (2.20 g, 14.7 mmol) in DMF (15 ml) was added dropwise and the reaction mixture was stirred at room temperature for 4 hours. The reaction mixture was poured in 1N NaOH (120 ml), followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (1:1, v/v) eluate fractions, 4-fluoro-1-methylindole-3-carbaldehyde (1.43 g, 55%) was obtained as a red solid.

$^1$H-NMR (CDCl$_3$) δ: 3.88 (s, 3H), 7.17 (d, J=7.1 Hz, 1H), 7.23–7.28 (m, 2H), 7.81 (s, 1H), 10.21 (s, 1H).

MS (ESI) m/z 178 (M$^+$+1).

(Step 3) Synthesis of 4-fluoro-1-methylindole-3-carboxylic acid

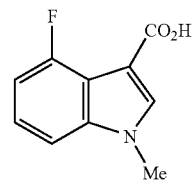

In acetone (95 ml) was dissolved 4-fluoro-1-methylindole-3-carbaldehyde (1.43 g, 8.08 mmol), followed by the addition of potassium permanganate (a 0.2M aqueous solution, 62.0 ml, 12.4 mmol) in portions at room temperature. After the reaction mixture was stirred at room temperature for 16 hours, the precipitate was filtered off through Celite. The filtrate was distilled under reduced pressure to remove the solvent. The residue was acidified with 1N HCl. The crystals thus precipitated were collected by filtration under reduced pressure, washed with water, and dried under reduced pressure to give 4-fluoro-1-methylindole-3-carboxylic acid (0.91 g, 58%) as a brown solid.

$^1$H-NMR (DMSO-$d_6$) δ: 3.85 (s, 3H), 6.93 (dd, J=11.5,7.8 Hz, 1H), 7.23 (m, 1H), 7.35 (d, J=8.3 Hz, 1H), 8.08 (s, 1H), 11.88 (broad s, 1H).

MS (ESI) m/z 194 (M$^+$+1).

(Step 4) Synthesis of ethyl (5-chloro-2-fluoro-4-((4-fluoro-1-methyl-3-indolylcarbonyl)amino)phenyl)acetate

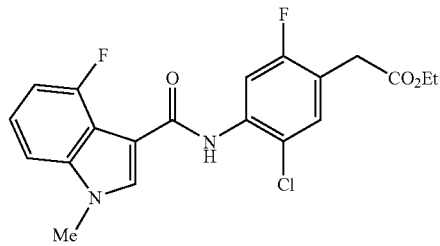

To a suspension of 4-fluoro-1-methylindole-3-carboxylic acid (700 mg, 3.62 mmol) and DMF (28.0 μl, 0.36 mmol) in methylene chloride (20 ml) was added oxalyl chloride (0.35 ml, 3.99 mmol) in portions under stirring at room temperature. After the reaction mixture was stirred at room temperature for 50 minutes, oxalyl chloride (30 μl) was added, and the mixture was stirred for further 40 minutes. To the reaction mixture, a solution of ethyl (4-amino-5-chloro-2-fluorophenyl)acetate (839 mg, 3.62 mmol) and triethylamine (1.52 ml, 10.9 mmol) in methylene chloride (5 ml) was added and the mixture was heated under reflux at room temperature for 4 hours. After cooling to room temperature, the reaction mixture was added with water, followed by extraction with chloroform. The extract was washed with brine, dried over anhydrous sodium sulfate, and distilled under reduced pressure to remove the solvent. The residue was purified by chromatography opn a silica gel column, whereby from n-hexane-ethyl acetate (2:1, v/v) eluate fractions, ethyl (5-chloro-2-fluoro-4-((4-fluoro-1-methyl-3-indolylcarbonyl)amino)phenyl)acetate (762 mg, 52%) was obtained as a yellow solid.

$^1$H-NMR (CDCl$_3$) δ: 1.27 (t, J=7.3 Hz, 3H), 3.61 (s, 2H), 3.87 (s, 3H), 4.18 (q, J=7.3 Hz, 2H), 7.02 (dd, J=12.2,8.1 Hz, 1H), 7.20 (d, J=8.1 Hz, 1H), 7.27 (m, 1H), 7.32 (d, J=7.3 Hz, 1H), 8.02 (s, 1H), 8.48 (d, J=12.2 Hz, 1H), 9.26 (m, 1H).

MS (ESI) m/z 407 (M$^+$+1).

(Step 5) Synthesis of (5-chloro-2-fluoro-4-((4-fluoro-1-methyl-3-indolylcarbonyl)amino)phenyl)acetic acid

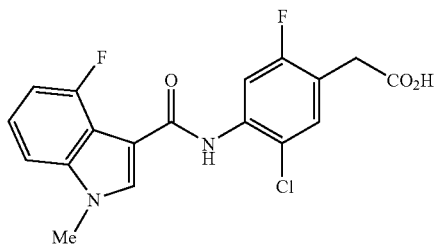

In THF (19 ml) was dissolved ethyl (5-chloro-2-fluoro-4-((4-fluoro-1-methyl-3-indolylcarbonyl)amino)phenyl)acetate (762 mg, 1.87 mmol). To the resulting solution was added 0.25N NaOH (11.2 ml, 2.81 mmol) and the mixture was stirred at room temperature for 3 hours. The reaction mixture was poured into 1N HCl (3.0 ml). The crystals thus precipitated were collected by filtration under reduced pressure, washed with water, and dried under reduced pressure to give (5-chloro-2-fluoro-4-((4-fluoro-1-methyl-3-indolylcarbonyl)amino)phenyl)acetic acid (698 mg, 99%) as a purple solid.

$^1$H-NMR (DMSO-d$_6$) δ: 3.64 (s, 2H), 3.90 (s, 3H), 7.07 (dd, J=12.5,7.8 Hz, 1H), 7.29 (m, 1H), 7.44 (d, J=8.4 Hz, 1H), 7.55 (d, J=7.8 Hz, 1H), 8.11 (d, J=11.7 Hz, 1H), 8.25 (s, 1H), 9.30 (d, J=10.3 Hz, 1H), 12.54 (broad s, 1H).

MS (LCMS) m/z 379 (M$^+$+1).

(Step 6) Synthesis of methyl trans-4-(1-((5-chloro-2-fluoro-4-((4-fluoro-1-methyl-3-indolylcarbonyl)amino)phenyl)acetyl)-(4S)-fluoro-(2S)-pyrrolidinylmethoxy)cyclohexanecarboxylate

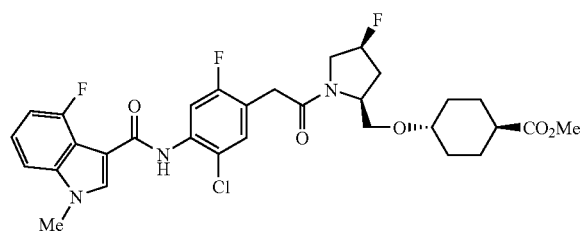

To a solution of (5-chloro-2-fluoro-4-((4-fluoro-1-methyl-3-indolylcarbonyl)amino)phenyl)acetic acid (200 mg, 0.53 mmol), methyl trans-4-((4S)-fluoro-(2S)-pyrrolidinylmethoxy)cyclohexanecarboxylate (the compound synthesized in (Step 3) of Example 21) (137 mg, 0.53 mmol), HOBt (14.0 mg, 0.11 mmol), and DMAP (13.0 mg, 0.11 mmol) in DMF (5.0 ml) was added EDC HCl (152 mg, 0.79 mmol). After stirring at room temperature for 23 hours, the reaction mixture was added with water, followed by extraction with ethyl acetate. The extract was washed with saturated brine, dried over anhydrous sodium sulfate, and distilled under reduced pressure to remove the solvent. The residue was purified by chromatography on a silica gel column, whereby from ethyl acetate eluate fractions, methyl trans-4-(1-((5-chloro-2-fluoro-4-((4-fluoro-1-methyl-3-indolylcarbonyl)amino)phenyl)acetyl)-(4S)-fluoro-(2S)-pyrrolidinylmethoxy)cyclohexanecarboxylate (332 mg, 100%) was obtained as a yellow solid.

$^1$H-NMR (CDCl$_3$) δ: 1.22–1.33 (m, 2H), 1.41–1.54 (m, 2H), 1.98–2.18 (m, 4H), 2.23–2.54 (m, 3H), 3.25–4.03 (m, 13H), 4.30 and 4.39 (each m, total 1H), 5.27 and 5.31 (each m, total 1H), 7.03 (dd, J=12.2,7.8 Hz, 1H), 7.21–7.31 (m, 2H), 7.38 and 7.39 (each d, J=7.3 Hz, total 1H), 8.03 (s, 1H), 8.46 and 8.48 (each d, J=12.2 Hz, total 1H), 9.26 (m, 1H).

MS (LCMS) m/z 620 (M$^+$+1).

(Step 7) Synthesis of trans-4-(1-((5-chloro-2-fluoro-4-((4-fluoro-1-methyl-3-indolylcarbonyl)amino)phenyl)acetyl)-(4S)-fluoro-(2S)-pyrrolidinylmethoxy)cyclohexanecarboxylic acid

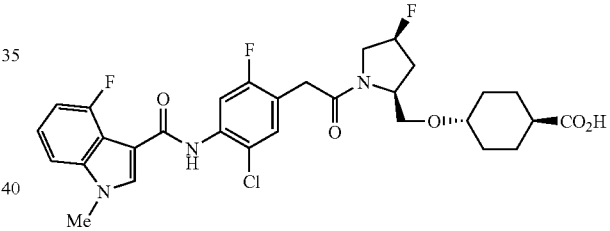

In THF (5.5 ml) was dissolved methyl trans-4-(1-((5-chloro-2-fluoro-4-((4-fluoro-1-methyl-3indolylcarbonyl)amino)phenyl)acetyl)-(4S)-fluoro-(2S)-pyrrolidinylmethoxy)cyclohexanecarboxylate (323 mg, 0.52 mmol). To the resulting solution was added 0.25N NaOH (3.13 ml, 0.78 mmol). The resulting mixture was stirred at room temperature for 16 hours. The reaction mixture was poured into 1N HCl (1.0 ml). The crystals thus precipitated were collected by filtration under reduced pressure, washed with water, and dried under reduced pressure to give the title compound (266 mg, 84%) as a yellow solid.

IR (ATR) ν 3399, 2937, 2863, 1724, 1648, 1621, 1587, 1521, 1450 cm$^{-1}$;

$^1$H-NMR (DMSO-d$_6$) δ: 1.16–1.41 (m, 4H), 1.86–2.00 (m, 4H), 2.10–2.32 (m, 3H), 3.17–3.88 (m, 7H), 3.90 (s, 3H), 4.13 and 4.35 (each m, total 1H), 5.32 and 5.40 (each m, total 1H), 7.07 (dd J=12.5,8.1 Hz, 1H), 7.29 (m, 1H), 7.42–7.45 (m, 2H), 8.10 (d, J=11.7 Hz, 1H), 8.26 (s, 1H), 9.28 (d, J=8.5 Hz, 1H), 12.03 (broad s, 1H).

MS (LCMS) m/z 606 (M$^+$+1);

Anal. Calcd for C$_{30}$H$_{31}$ClF$_3$N$_3$O$_5$ 0.5H$_2$O: C, 58.59; H, 5.24; N, 6.83. Found: C, 58.65; H, 5.27; N, 6.55.

Example 76 trans-4-((4S)-Fluoro-1-(2-fluoro-5-methoxy-4-((1-methyl-1H-3-indolylcarbonyl)amino)phenylacetyl)-(2S)-pyrrolidinylmethoxy)cyclohexanecarboxylic acid (Step 1) Synthesis of ethyl (4-amino-2-fluoro-5-methoxyphenyl)acetate

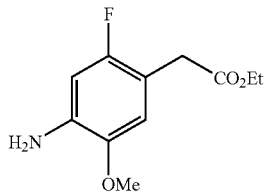

To 1,2-difluoro-4-methoxybenzene (5 g, 34.7 mmol) was added concentrated H$_2$SO$_4$ (9.25 ml, 174 mmol). Concentrated HNO$_3$ (2.64 ml, 34.7 mmol) was added dropwise under stirring at 0° C. After stirring for 3 hours at room temperature, the reaction mixture was poured into ice water, followed by extraction with ethyl acetate. The extract was washed with saturated brine, dried over anhydrous magnesium sulfate and distilled under reduced pressure to remove the solvent. The residue was dissolved in DMF (100 ml). Under stirring at 0° C., sodium hydride (4.16 g, 104 mmol) was added in portions. After the reaction mixture was stirred at the same temperature for 15 minutes, a solution of ethyl tert-butyl ethyl malonate (6.57 ml, 34.7 mmol) in DMF (50 ml) was added dropwise in portions thereto. After completion of the dropwise addition, stirring was conducted at room temperature for 18 hours. The reaction mixture was poured into ice water—an aqueous ammonium chloride solution, followed by extraction with ethyl acetate. The extract was washed with saturated brine, dried over anhydrous magnesium sulfate and distilled under reduced pressure to remove the solvent. The residue was added with methylene chloride-trifluoroacetic acid (100 ml, 1:1, v/v), followed by heating under reflux for 18 hours. After cooling to room temperature, the reaction mixture was distilled under reduced pressure to remove the solvent. An iron powder (6.2 g, 0.11 mol) was added to the residue and the mixture was sonicated for 5 minutes. To the reaction mixture were added methanol/water (175 ml, 1:4), sodium acetate (4.7 g, 35 mmol) and acetic acid (13.5 ml, 230 mmol), followed by heating under reflux for 3 hours (without using a stirrer). After cooling to room temperature, the reaction mixture was filtered through Celite under reduced pressure and the filtrate was washed with methanol. The filtrate was distilled under reduced pressure to remove the solvent. The residue was dissolved in ethyl acetate. The ethyl acetate solution was washed with saturated brine, dried over anhydrous magnesium sulfate, and distilled under reduced pressure to remove the solvent. The residue was purified by silica gel column chromatography (middle pressure chromatography system YAMAZEN YFLC-5404, hexane/ethyl acetate 9:1, φ 50 mm×500 mm, 15 ml/min) to give ethyl 4-amino-2-fluoro-5-methoxyphenylacetate (1.75 g, 22%) as a colorless oil.

$^1$H-NMR (CDCl$_3$) δ: 1.28 (t, J=7.1 Hz), 1.60 (br s), 3.52 (s, 2H), 3.80 (s, 3H), 3.92 (br s, 1H), 4.15 (q, J=7.1 Hz), 6.42 (d, J=10.5 Hz), 6.62 (d, J=6.8 Hz).

MS (ESI) m/z 228 (M+1)$^+$.

(Step 2) Synthesis of 2-fluoro-5-methoxy-4-((1-methyl-1H-3-indolylcarbonyl)amino)phenylacetic acid

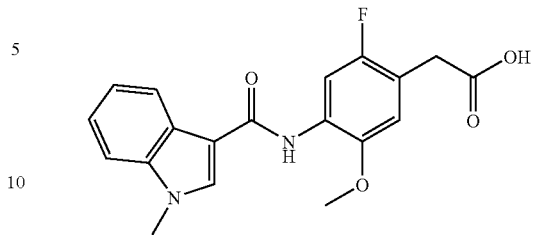

1-Methyl-1H-indole-3-carboxylic acid (700 mg, 4.0 mmol) was dissolved in methylene chloride (8 ml). Oxalyl chloride (0.53 ml, 6.1 mmol) was added dropwise to the solution under stirring at 0° C. After completion of the dropwise addition, the reaction mixture was stirred at room temperature for 1 hour and distilled under reduced pressure to remove the solvent. The residue was dissolved in methylene chloride (6 ml). The resulting solution was added to a solution of triethylamine (0.84 ml, 6.0 mmol) and ethyl 4-amino-2-fluoro-5-methoxyphenylacetate (909 mg, 4.0 mmol) in methylene chloride (3 ml) under stirring at 0° C. The reaction mixture was heated at reflux for 18 hours. After cooling to room temperature, the reaction mixture was poured into ice water, followed by extraction with chloroform. The extract was washed with saturated brine, dried over anhydrous magnesium sulfate and distilled under reduced pressure to remove the solvent. The residue was purified by silica gel column chromatography (middle pressure Yamazen, linear gradient of n-hexane/ethyl acetate form 9:1 to 7:3, 12 ml/min, φ 50 mm×300 mm, charged by dry silica gel method). The purified ester was added with THF (45 ml) and 0.25M NaOH (18 ml, 4.5 mmol), followed by stirring at room temperature for 4 hours. The reaction mixture was poured into water and 1M HCl was added to the resulting mixture to make it acidic. The crystals thus precipitated were collected by filtration under reduced pressure, washed with water and dried under reduced pressure to give 2-fluoro-5-methoxy-4-((1-methyl-1H-3-indolylcarbonyl)amino)phenylacetic acid (1.01 g, 71%) as a colorless solid.

$^1$H-NMR (CDCl$_3$) δ: 3.60 (s, 2H), 3.90 (s, 6H), 7.05 (d, J=6.8 Hz, 1H), 7.22 (t, J=7.5 Hz, 1H), 7.30 (t, J=7.5 Hz, 1H), 7.58 (d, J=7.6 Hz, 1H), 7.95 (d, J=11.5 Hz, 1H), 8.12 (d, J=7.3 Hz, 1H), 8.31 (s, 1H), 8.80 (s, 1H).

MS (ESI) m/z 357 (M+1)$^+$.

(Step 3) Synthesis of trans-4-((4S)-fluoro-1-(2-fluoro-5-methoxy-4-((1-methyl-1H-3-indolylcarbonyl)amino)phenylacetyl)-(2S)-pyrrolidinylmethoxy)cyclohexanecarboxylic acid

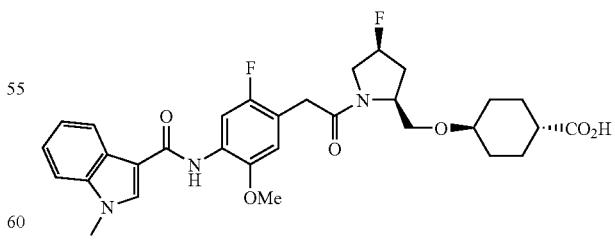

In DMF (5 ml) were dissolved 2-fluoro-5-methoxy-4-((1-methyl-1H-3-indolylcarbonyl)amino)phenyl)acetic acid (214 mg, 0.6 mmol), methyl trans-4-((4S)-fluoro-(2S)-pyrrolidinylmethoxy)cyclohexanecarboxylate (the compound synthesized in (Step 3) of Example 21) (155 mg, 0.6 mmol), HOBt (154 mg, 1.14 mmol), DMAP (catalytic amount) and EDC·HCl (173 mg, 0.9 mmol). The resulting solution was stirred at room temperature for 18 hours. The reaction mixture was poured in 1M HCl to acidify the mixture, followed by extraction with ethyl acetate. The extract was washed with saturated brine, dried over anhydrous magnesium sulfate, and distilled under reduced pressure to remove the solvent. The residue was purified by silica gel column chromatography (middle pressure Yamazen, chloroform, 10 ml/min, φ 15 mm×300 mm). To the purified ester were added THF (6 ml) and 0.25M NaOH (3.6 ml, 0.9 mmol) and the mixture was stirred for 18 hours at room temperature. Water was poured into the reaction mixture and the solution was acidified with 1M HCl. The crystals thus precipitated were collected by filtration under reduced pressure, washed with water and dried under reduced pressure to give the title compound (160 mg, 46%) as a colorless solid.

$^1$H-NMR (DMSO) δ: 1.10–1.40 (m, 4H), 1.85–2.25 (m, 6H), 3.20 (t, J=8.5 Hz, 1H), 3.42–3.80 (m, 7H), 3.88 (s, 3H), 3.90 (s, 3H), 4.15 and 4.33 (2m, total 1H), 3.35 (m, 1H), 6.95 (dd, J=6.9,14.7 Hz, 1H), 7.23 (t, J=7.5 Hz, 1H), 7.28 (t, J=7.5 Hz, 1H), 7.55 (d, J=7.8 Hz, 1H), 7.92 (dd, J=5.3,7.3 Hz, 1H), 8.12 (d, J=7.5 Hz, 1H), 8.30 (s, 1H), 8.88 (s, 1H).

MS (ESI) m/z 584 (M+1)$^+$.

Anal. Calcd for $C_{31}H_{35}F_2N_3O_6·0.25\ H_2O$: C, 63.31; H, 6.08; N, 7.14. Found: C, 63.07; H, 6.10; N, 7.05.

Example 77 trans-4-(1-(5-Chloro-2-fluoro-4-((1,2-dimethyl-1H-3-indolylcarbonyl)amino)phenylacetyl)-(4S)-fluoro-(2S)-pyrrolidinylmethoxy)cyclohexanecarboxylic acid (Step 1) Synthesis of 1,2-dimethyl-1H-indole-3-carboxylic acid

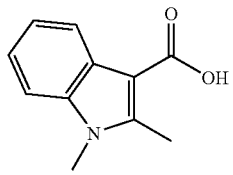

Diisopropylamine (2.83 ml, 20.0 mmol) was dissolved in THF (35 ml). Under stirring at −78° C., n-butyl lithium (12.7 ml, 20.0 mmol, a 1.57M hexane solution) was added to the resulting solution. After stirring at 0° C. for 15 minutes, the reaction mixture was cooled again to −78° C. Under stirring, a solution of 1-methyl-1H-indole-3-carboxylic acid (1.75 g, 10.0 mmol) in THF (5 ml) was added. After the reaction mixture was stirred at the same temperature for 30 minutes, methyl iodide (3.42 ml, 55.0 mmol) was added. The reaction mixture was caused to rise back to room temperature over 30 minutes. The reaction mixture was poured into water and the mixture was stirred for 18 hours at room temperature. The reaction mixture was washed with ether. The water layer was acidified with 1M HCl, followed by extraction with ether. The extract was washed with saturated brine, dried over anhydrous sodium sulfate and distilled under reduced pressure to remove the solvent. The residue was purified by silica gel chromatography (middle pressure, linear gradient of chloroform/methanol from 10:0 to 20:1, 20 ml/min, φ 50×300 mm) to give 1,2-dimethyl-1H-indole-3-carboxylic acid (180 mg, 10%) as a colorless solid.

$^1$H-NMR (DMSO-d$_6$) δ: 2.72 (s, 3H), 3.72 (s, 3H), 7.12 (t, J=7.8 Hz, 1H), 2.75 (t, J=8.3 Hz, 1H), 7.48 (d, J=7.8 Hz, 1H), 7.97 (d, J=7.1 Hz, 1H).

MS (ESI) m/z 190 (M+1)$^+$.

(Step 2) Synthesis of (5-chloro-2-fluoro-4-((1,2-dimethyl-1H-3-indolylcarbonyl)amino)phenyl)acetic acid

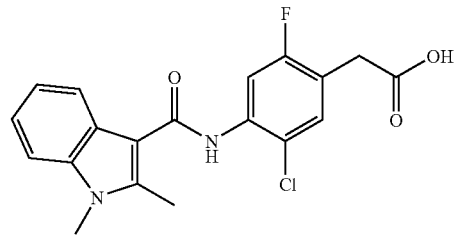

In methylene chloride (8 ml) was dissolved 1,2-dimethyl-1H-indole-3-carboxylic acid (270 mg, 1.43 mmol) was dissolved. Oxalyl chloride (0.19 ml, 2.1 mmol) was added to the solution under stirring at 0° C. The reaction mixture was stirred at room temperature for 1 hour and distilled under reduced pressure to remove the solvent. The residue was dissolved in methylene chloride (6 ml) and the resulting solution was added to a solution of triethylamine (0.56 ml, 4.3 mmol) and ethyl (4-amino-3-chloro-6-fluorophenyl)acetate (331 mg, 1.4 mmol) in methylene chloride (3 ml) under stirring at 0° C. The reaction mixture was heated at reflux for 18 hours. HOBt (catalytic amount) was added to the reaction mixture and the mixture was heated under reflux for 48 hours. After cooling, the reaction mixture was added with chloroform and a saturated aqueous solution of citric acid. The mixture was extracted with chloroform. The extract was washed with saturated brine, dried over anhydrous sodium sulfate and distilled under reduced pressure to remove the solvent. The residue was purified by silica gel column chromatography (middle pressure Yamazen, linear gradient of n-hexane/ethyl acetate form 9:1 to 7:3, 20 ml/min, φ 50 mm×150 mm, dry silica gel adsorption method). The purified product was dissolved in THF (15 ml) and to the resulting solution was added 0.25M NaOH (8.6 ml, 2.2 mmol). The mixture was stirred at room temperature for 18 hours. The reaction mixture was poured into 1M HCl to acidify therewith. The crystals thus precipitated were collected by filtration under reduced pressure, washed with water and dried under reduced pressure to give (5-chloro-2-fluoro-4-((1,2-dimethyl-1H-3-indolylcarbonyl)amino) phenyl)acetic acid (264 mg, 49%) as a colorless solid.

$^1$H-NMR (DMSO-d$_6$) δ: 2.70 (s, 3H), 3.65 (s, 2H), 3.77 (s, 3H), 7.21 (m, 2H), 7.58 (d, J=7.3 Hz, 1H), 7.93 (m, 1H), 7.99 (d, J=11.8 Hz, 1H), 9.06 (s, 1H).

MS (ESI) m/z 375 (M+1)$^+$.

(Step 3) Synthesis of trans-4-(1-(5-chloro-2-fluoro-4-((1,2-dimethyl-1H-3-indolylcarbonyl)amino)phenylacetyl)-(4S)-fluoro-(2S)-pyrrolidinylmethoxy)cyclohexanecarboxylic acid

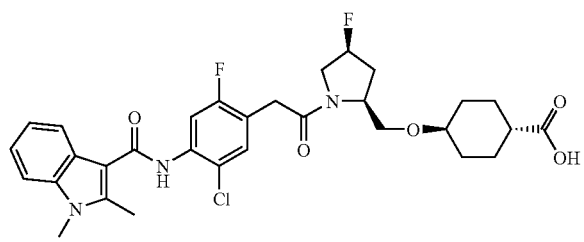

(5-Chloro-2-fluoro-4-((1,2-dimethyl-1H-3-indolylcarbonyl)amino)phenyl)acetic acid (191 mg, 0.51 mmol), methyl trans-4-((4S)-fluoro-(2S)-pyrrolidinylmethoxy)cyclohexanecarboxylate (the compound synthesized in (Step 3) of Example 21) (132 mg, 0.51 mmol), HOBt (131 mg, 0.97 mmol), DMAP (catalytic amount) and EDC·HCl salt (147 mg, 0.77 mmol) were dissolved in DMF (2.5 ml). The resulting solution was stirred at room temperature for 18 hours. The reaction mixture was poured into 1M HCl, followed by extraction with ethyl acetate. The extract was washed with saturated brine, dried over anhydrous magnesium sulfate, and distilled under reduced pressure to remove the solvent. The residue was purified by silica gel column chromatography (middle pressure Yamazen, linear gradient of chloroform/methanol from 10:0 to 20:1, 20 ml/min, φ 50 mm×150 mm). The residue was dissolved in THF (5 ml) and to the resulting solution was added 0.25M NaOH (3.1 ml, 0.77 mmol). The resulting mixture was stirred for 18 hours at room temperature. The reaction mixture was added to 1M HCl. The crystals thus precipitated were collected by filtration under reduced pressure, washed with water and dried under reduced pressure to give the title compound (227 mg, 74%) as a colorless solid.

$^1$H-NMR (DMSO-$d_6$) δ: 1.20–1.40 (m, 6H), 1.90 (m, 4H), 2.20 (m, 2H), 2.72 (s, 3H), 3.20 (t, J=10.0 Hz, 1H), 3.50 (m, 1H), 3.60–4.00 (m, 3H), 3.75 (s, 3H), 4.12 and 4.35 (2m, total 1H), 5.38 (dd, J=35,55 Hz, 1H), 7.20 (m, 2H), 7.48 (dd, J=7.3,11.8 Hz, 1H), 7.55 (d, J=8.6 Hz, 1H), 7.92 (d, J=8.3 Hz, 1H), 7.95 (d, J=5.6 Hz, 1H), 9.05 (s, 1H).

MS (ESI) m/z 603 (M+1)$^+$;

Anal. Calcd for $C_{31}H_{34}ClF_2N_3O_5 \cdot 0.5H_2O$: C, 60.93; H, 5.77; N, 6.88. Found: C, 61.12; H, 5.75; N, 6.84.

Example 78 trans-4-(1-((4-((2-Indolylcarbonyl)amino)-3-methoxyphenyl)acetyl)-(4S)-fluoro-(2S)-pyrrolidinylmethoxy)cyclohexanecarboxylic acid (Step 1) Synthesis of tert-butyl (4-((2-indolylcarbonyl)amino)-3-methoxyphenyl)acetate

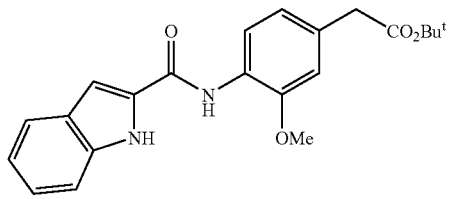

In DMF (10 ml), EDC HCl (1.43 g, 7.45 mmol) was added to indole-2-carboxylic acid (1.00 g, 6.21 mmol), tert-butyl 4-amino-3-methoxyphenylacetate (1.47 g, 6.21 mmol), HOBt (0.42 g, 3.10 mmol), and DMAP (0.38 g, 3.10 mmol). The resulting mixture was stirred at 60° C. for 16 hours. Water was added to the reaction mixture, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane:ethyl acetate (1:1, v/v) eluate fractions, tert-butyl (4-((2-indolylcarbonyl)amino)-3-methoxyphenyl)acetate (1.31 g, 55%) was obtained as a brown solid.

$^1$H-NMR (CDCl$_3$) δ: 1.45 (s, 9H), 3.51 (s, 2H), 3.97 (s, 3H), 6.89 (broad s, 1H), 6.91 (d, J=8.1 Hz, 1H), 7.00 (broad s, 1H), 7.16 (t, J=8.1 Hz, 1H), 7.31 (t, J=8.1 Hz, 1H), 7.46 (d, J=8.3 Hz, 1H), 7.69 (d, J=8.1 Hz, 1H), 8.42 (d, J=8.3 Hz, 1H), 8.54 (broad s, 1H), 9.31 (broad s, 1H).

MS (ESI) m/z 381 (M$^+$+1).

(Step 2) Synthesis of (4-((2-indolylcarbonyl)amino)-3-methoxyphenyl)acetic acid

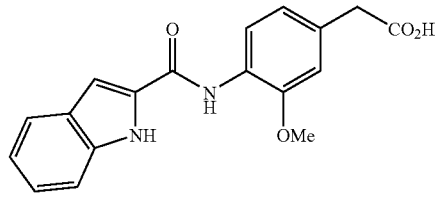

In methylene chloride (20 ml) was dissolved tert-butyl (4-((2-indolylcarbonyl)amino)-3-methoxyphenyl)acetate (1.31 g, 3.44 mmol). To the resulting solution was added TFA (10 ml) at 0° C. After the reaction mixture was stirred at room temperature for 1 hour, the reaction mixture was distilled under reduced pressure to remove the solvent, whereby (4-((2-indolylcarbonyl)amino)-3-methoxyphenyl) acetic acid (1.11 g, 99%) was obtained as a brown solid.

$^1$H-NMR (DMSO-$d_6$) δ: 3.57 (s, 2H), 3.86 (s, 3H), 6.87 (d, J=8.1 Hz, 1H), 7.01 (s, 1H), 7.06 (t, J=7.8 Hz, 1H), 7.21 (t, J=7.8 Hz, 1H), 7.32 (s, 1H), 7.45 (d, J=8.1 Hz, 1H), 7.64 (d, J=8.1 Hz, 1H), 7.74 (d, J=8.1 Hz, 1H), 9.32 (s, 1H), 11.72 (broad s, 1H).

MS (ESI) m/z 325 (M$^+$+1).

(Step 3) Synthesis of methyl trans-4-(1-((4-((2-indolylcarbonyl)amino)-3-methoxyphenyl)acetyl)-(4S)-fluoro-(2S)-pyrrolidinylmethoxy)cyclohexanecarboxylate

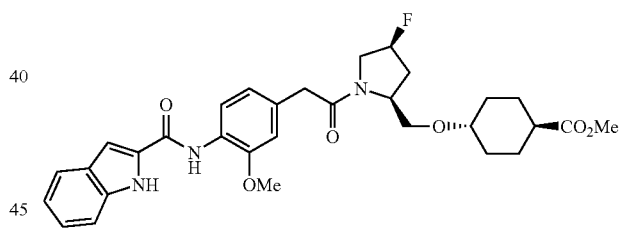

In DMF (6.0 ml) were dissolved (4-((2-indolylcarbonyl)amino)-3-methoxyphenyl)acetic acid (370 mg, 1.14 mmol), methyl trans-4-((4S)-fluoro-(2S)-pyrrolidinylmethoxy)cyclohexanecarboxylate (the compound synthesized in (Step 3) of Example 21) (296 mg, 1.14 mmol), HOBt (31.0 mg, 0.23 mmol), and DMAP (28.0 mg, 0.23 mmol). To the resulting solution was added EDC HCl (284 mg, 1.48 mmol), followed by stirring at room temperature for 21 hours. Water was added to the reaction mixture, followed by extraction with ethyl acetate. The extract was washed with saturated brine, dried over anhydrous sodium sulfate, and distilled under reduced pressure to remove the solvent. The residue was purified by chromatography on a silica gel column, whereby from ethyl acetate eluate fractions, methyl trans-4-(1-((4-((2-indolylcarbonyl)amino)-3-methoxyphenyl)acetyl)-(4S)-fluoro-(2S)-pyrrolidinylmethoxy)cyclohexanecarboxylate (514 mg, 80%) was obtained as a yellow amorphous substance.

$^1$H-NMR (CDCl$_3$) δ: 1.17–1.33 (m, 2H), 1.39–1.56 (m, 2H), 1.97–2.50 (m, 7H), 3.25 (m, 1H), 3.33 and 3.50 (each m, 1H), 3.62–3.91-(m, 8H), 3.96 (s, 3H), 4.25 and 4.38 (each m, total 1H), 5.24 (m, 1H), 6.86 (d, J=8.1 Hz, 1H), 6.94 (m, 1H), 7.02 (broad s, 1H), 7.17 (t, J=7.8 Hz, 1H), 7.31 (t, J=7.8 Hz, 1H), 7.47 (d, J=8.1 Hz, 1H), 7.69 (d, J=8.1 Hz, 1H), 8.42 (m, 1H), 8.55 (broad s, 1H), 9.52 (broad s, 1H).

MS (ESI) m/z 566 (M$^+$+1).

(Step 4) Synthesis of trans-4-(1-((4-((2-indolylcarbonyl)amino)-3-methoxyphenyl)acetyl)-(4S)-fluoro-(2S)-pyrrolidinylmethoxy)cyclohexanecarboxylic acid

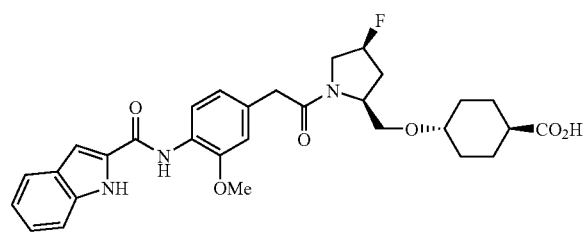

In THF (10 ml) was dissolved methyl trans-4-(1-((4-((2-indolylcarbonyl)amino)-3-methoxyphenyl)acetyl)-(4S)-fluoro-(2S)-pyrrolidinylmethoxy)cyclohexanecarboxylate (514 mg, 0.91 mmol). To the resulting solution was added 0.25N NaOH (5.50 ml, 1.36 mmol), followed by stirring at room temperature for 18 hours. The reaction mixture was poured into 1N HCl (5.0 ml) to acidify the mixture. The crystals thus precipitated were collected by filtration under reduced pressure, washed with water, and dried under reduced pressure to give the title compound (479 mg, 95%) as a colorless solid.

IR (ATR) ν 3662, 3415, 3278, 2987, 2942, 2900, 1724, 1702, 1658, 1600, 1536, 1486, 1450, 1413 cm$^{-1}$;

$^1$H-NMR (DMSO-d$_6$) δ: 1.12–1.38 (m, 4H), 1.86–2.26 (m, 7H), 3.18 (m, 1H), 3.43–3.91 (m, 9H), 4.15 and 4.32 (each m, total 1H), 5.31 and 5.37 (each m, total 1H), 6.83 (m, 1H), 6.94 and 6.97 (each d, J=1.5 Hz, total 1H), 7.06 (t, J=7.8 Hz, 1H), 7.21 (t, J=7.8 Hz, 1H), 7.32 (d, J=1.5 Hz, 1H), 7.45 (d, J=8.1 Hz, 1H), 7.64 (d, J=8.1 Hz, 1H), 7.71 and 7.72 (each d, J=8.1 Hz, total 1H), 9.34 (s, 1H), 11.74 (broad s, 1H), 12.02 (broad 1H).

MS (ESI) m/z 552 (M$^+$+1);

Anal. Calcd for C$_{30}$H$_{34}$FN$_3$O$_6$ 0.25H$_2$O: C, 64.79; H, 6.25; N, 7.56. Found: C, 64.77; H, 6.23; N, 7.40.

Example 79 trans-4-(1-((3-Bromo-4-((1-isoquinolinylcarbonyl)amino)phenyl)acetyl)-(4S)-fluoro-(2S)-pyrrolidinylmethoxy)cyclohexanecarboxylic acid (Step 1) Synthesis of ethyl (3-bromo-4-((1-isoquinolinylcarbonyl)amino)phenyl)acetate

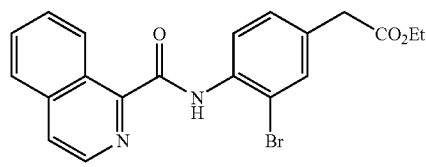

In DMF (15 ml) were dissolved 1-isoquinolinecarboxylic acid (1.00 g, 5.77 mmol), ethyl 4-amino-3-bromophenylacetate (1.49 g, 5.77 mmol), HOBt (0.39 g, 2.89 mmol), and DMAP (0.14 g, 1.15 mmol). To the resulting solution was added EDC HCl (1.33 g, 6.93 mmol). After stirring at 60° C. for 5 hours, the reaction mixture was cooled to room temperature. Water was added, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane:ethyl acetate (4:1, v/v) eluate fractions, ethyl (3-bromo-4-((1-isoquinolinylcarbonyl)amino)phenyl)acetate (1.64 g, 69%) was obtained as a yellow solid.

$^1$H-NMR (CDCl$_3$) δ: 1.28 (t, J=7.1 Hz, 3H), 3.60 (s, 2H), 4.17 (q, J=7.1 Hz, 2H), 7.32 (dd, J=8.5,2.0 Hz, 1H), 7.57 (d, J=2.0 Hz, 1H), 7.71–7.78 (m, 2H), 7.88–7.91 (m, 2H), 8.59 (d, J=5.6 Hz, 1H), 8.63 (d, J=8.5 Hz, 1H), 9.71 (m, 1H), 11.01 (broad s, 1H).

MS (ESI) m/z 413 (M$^+$+1), 415 (M$^+$+3).

(Step 2) Synthesis of (3-bromo-4-((1-isoquinolinylcarbonyl)amino)phenyl)acetic acid

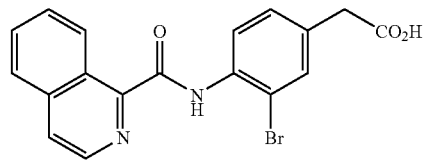

Ethyl (3-bromo-4-((1-isoquinolinylcarbonyl)amino)phenyl)acetate (1.64 g, 3.97 mmol) was dissolved in THF (40 ml). To the resulting solution was added 0.25N NaOH (24.0 ml, 5.95 mmol), and the mixture was stirred at room temperature for 8 hours. The reaction mixture was poured into 1N HCl (50 ml) to acidify the mixture. The crystals thus precipitated were collected by filtration under reduced pressure, washed with water, and dried under reduced pressure to give (3-bromo-4-((1-isoquinolinylcarbonyl)amino)phenyl)acetic acid (1.50 g, 98%) as a pale yellow solid.

$^1$H-NMR (DMSO-d$_6$) δ: 3.63 (s, 2H), 7.36 (d, J=8.5 Hz, 1H), 7.66 (s, 1H), 7.81 (m, 1H), 7.88 (m, 1H), 8.12 (d, J=8.3 Hz, 1H), 8.17 (d, J=5.4 Hz, 1H), 8.21 (d, J=8.5 Hz, 1H), 8.66 (d, J=5.4 Hz, 1H), 9.36 (d, J=8.5 Hz, 1H), 10.84 (s, 1H).

MS (ESI) m/z 385 (M$^+$+1), 387 (M$^+$+3).

(Step 3) Synthesis of methyl trans-4-(1-((3-bromo-4-((1-isoquinolinylcarbonyl)amino)phenyl)acetyl)-(4S)-fluoro-(2S)-pyrrolidinylmethoxy)cyclohexanecarboxylate

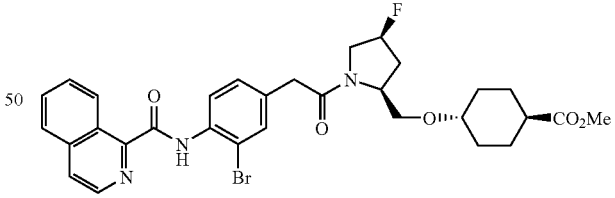

In DMF (5.0 ml) were dissolved (3-bromo-4-((1-isoquinolinylcarbonyl)amino)phenyl)acetic acid (350 mg, 0.91 mmol), methyl trans-4-((4S)-fluoro-(2S)-pyrrolidinylmethoxy)cyclohexanecarboxylate (the compound synthesized in (Step 3) of Example 21) (236 mg, 0.91 mmol), HOBt (25.0 mg, 0.18 mmol), and DMAP (22.0 mg, 0.18 mmol). To the resulting solution was added EDC HCl (226 mg, 1.18 mmol) and the mixture was stirred at room temperature for 22 hours. Water was added to the reaction mixture, followed by extraction with ethyl acetate. The extract was washed with saturated brine, dried over anhydrous sodium sulfate, and distilled under reduced pressure to remove the solvent. The residue was purified by chromatography on a silica gel column, whereby from ethyl acetate eluate fractions, methyl trans-4-(1-((3-bromo-4-((1-iso-quinolinylcarbonyl)amino)phenyl)acetyl)-(4S)-fluoro-(2S)-pyrrolidinylmethoxy)cyclohexanecarboxylate (575 mg, 100%) was obtained as a yellow solid.

$^1$H-NMR (CDCl$_3$) δ: 1.19–1.34 (m, 2H), 1.41–1.53 (m, 2H), 1.97–2.52 (m, 7H), 3.27 (m, 1H), 3.35 and 3.51 (each m, total 1H), 3.60–4.03 (m, 8H), 4.22 and 4.39 (each m, total 1H), 5.25 (m, 1H), 7.29 (m, 1H), 7.57 (m, 1H), 7.71–7.78 (m, 2H), 7.88–7.91 (m, 2H), 8.59–8.64 (m, 2H), 9.71 (m, 1H), 11.00 (m, 1H).

MS (ESI) m/z 626 (M$^+$+1), 628 (M$^+$+3).

(Step 4) Synthesis of trans-4-(1-((3-bromo-4-((1-isoquino-linylcarbonyl)amino)phenyl)acetyl)-(4S)-fluoro-(2S)-pyrro-lidinylmethoxy)cyclohexanecarboxylic acid

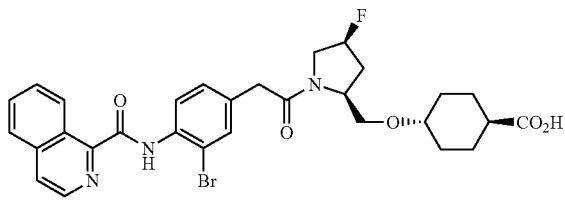

Methyl trans-4-(1-((3-bromo-4-((1-isoquinolinylcarbo-nyl)amino)phenyl)acetyl)-(4S)-fluoro-(2S)-pyrrolidinyl-methoxy)cyclohexanecarboxylate (575 mg, 0.92 mmol) was dissolved in THF (10 ml), followed by the addition of 0.25N NaOH (5.50 ml, 1.36 mmol). The resulting mixture was stirred at room temperature for 24 hours. The reaction mixture was poured into 1N HCl (5.0 ml) to acidify the mixture. The crystals thus precipitated were collected by filtration under reduced pressure, washed with water, and dried under reduced pressure to give the title compound (529 mg, 94%) as a pale yellow solid.

IR (ATR) ν 2938, 2857, 1720, 1687, 1596, 1513, 1450 cm$^{-1}$;

$^1$H-NMR (DMSO-d$_6$) δ: 1.14–1.42 (m, 4H), 1.86–2.27 (m, 7H), 3.17–3.92 (m, 7H), 4.15 and 4.34 (each m, total 1H), 5.31 and 5.38 (each m, total 1H), 7.32 (m, 1H), 7.58 and 7.60 (each d, J=1.2 Hz, total 1H), 7.80 (td, J=8.5, 1.2 Hz, 1H), 7.87 (td, J=8.5,1.2 Hz, 1H), 8.10 (d, J=8.3 Hz, 1H), 8.15 (d, J=5.6 Hz, 1H), 8.23 and 8.24 (each d, J=8.3 Hz, 1H), 8.65 (d, J=5.6 Hz, 1H), 9.39 (d, J=8.5 Hz, 1H), 10.84 (s, 1H), 12.00 (s, 1H).

MS (ESI) m/z 612 (M$^+$+1), 614 (M$^+$+3);

Anal. Calcd for C$_{30}$H$_{31}$BrFN$_3$O$_5$: C, 58.83; H, 5.10; N, 6.86. Found: C, 58.85; H, 5.27; N, 6.45.

Example 80 trans-4-(1-((3-Chloro-4-((1-isoquinolinylcarbonyl) amino)phenyl)acetyl)-(4S)-fluoro-(2S)-pyrrolidinyl-methoxy)cyclohexanecarboxylic acid (Step 1) Synthesis of methyl (3-chloro-4-((1-isoquinolinyl-carbonyl)amino)phenyl)acetate

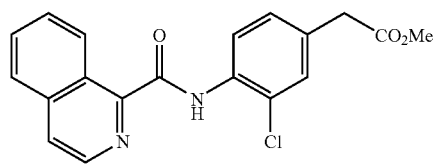

In DMF (15 ml) were dissolved 1-isoquinolinecarboxylic acid (1.00 g, 5.77 mmol), methyl 4-amino-3-chloropheny-lacetate (1.23 g, 6.16 mmol), HOBt (0.16 g, 1.15 mmol), and DMAP (0.14 g, 1.15 mmol). To the resulting solution was added EDC HCl (1.33 g, 6.93 mmol), followed by stirring at room temperature for 14 hours. The reaction mixture was poured into water (40 ml). The crystals precipitated were collected by filtration under reduced pressure, washed with water and ether, dried under reduced pressure to give methyl (3-chloro-4-((1-isoquinolinylcarbonyl)amino)phenyl)ac-etate (1.14 g, 56%) as a brown solid.

$^1$H-NMR (CDCl$_3$) δ: 3.62 (s, 2H), 3.72 (s, 3H), 7.29 (m, 1H), 7.40 (d, J=1.9 Hz, 1H), 7.71–7.78 (m, 2H), 7.88–7.91 (m, 2H), 8.58 (d, J=5.4 Hz, 1H), 8.65 (d, J=8.3 Hz, 1H), 9.71 (m, 1H), 11.02 (m, 1H).

MS (ESI) m/z 355 (M$^+$+1).

(Step 2) Synthesis of (3-chloro-4-((1-isoquinolinylcarbonyl) amino)phenyl)acetic acid

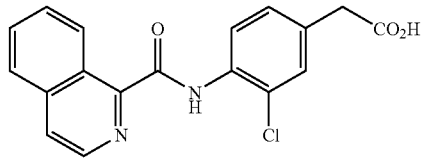

Methyl (3-chloro-4-((1-isoquinolinylcarbonyl)amino) phenyl)acetate (1.14 g, 3.21 mmol) was dissolved in THF (33 ml). To the resulting solution was added 0.25N NaOH (19.3 ml, 4.82 mmol), and the mixture was stirred at room temperature for 14 hours. The reaction mixture was poured into 1N HCl (5.0 ml). The crystals thus precipitated were collected by filtration under reduced pressure, washed with water, and dried under reduced pressure to give (3-chloro-4-((1-isoquinolinylcarbonyl)amino)phenyl)acetic acid (1.07 g, 98%) as a brown solid.

$^1$H-NMR (DMSO-d$_6$) δ: 3.63 (s, 2H), 7.33 (dd, J=8.3, 1.7 Hz, 1H), 7.51 (d, J=1.7 Hz, 1H), 7.81 (td, J=8.3,1.7 Hz, 1H), 7.88 (td, J=8.3,1.7 Hz, 1H), 8.12 (d, J=8.1 Hz, 1H), 8.16 (d, J=5.6 Hz, 1H), 8.24 (d, J=8.3 Hz, 1H), 8.67 (d, J=5.6 Hz, 1H), 9.34 (d, J=8.3 Hz, 1H), 10.85 (s, 1H), 12.48 (broad s, 1H).

MS (ESI) m/z 341 (M$^+$+1).

(Step 3) Synthesis of methyl trans-4-(1-((3-chloro-4-((1-isoquinolinylcarbonyl)amino)phenyl)acetyl)-(4S)-fluoro-(2S)-pyrrolidinylmethoxy)cyclohexanecarboxylate

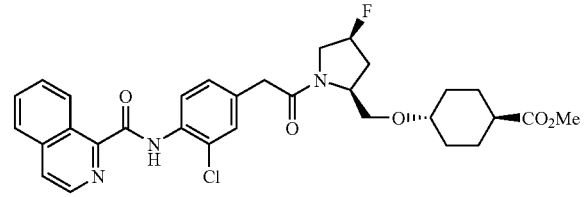

In DMF (7.5 ml) were dissolved (3-chloro-4-((1-iso-quinolinylcarbonyl)amino)phenyl)acetic acid (250 mg, 0.73 mmol), methyl trans-4-((4S)-fluoro-(2S)-pyrrolidinyl-methoxy)cyclohexanecarboxylate (the compound synthe-sized in (Step 3) of Example 21) (190 mg, 0.73 mmol), HOBt (20.0 mg, 0.15 mmol), and DMAP (18.0 mg, 0.15 mmol). To the resulting solution was added EDC HCl (211 mg, 1.10 mmol), followed by stirring at room temperature for 19 hours. Water was added to the reaction mixture, followed by extraction with ethyl acetate. The extract was washed with saturated brine, dried over anhydrous sodium sulfate, and distilled under reduced pressure to remove the solvent. The residue was purified by chromatography on a silica gel column, whereby from ethyl acetate eluate fractions, methyl trans-4-(1-((3-chloro-4-((1-isoquinolinylcarbonyl)amino)phenyl)acetyl)-(4S)-fluoro-(2S)-pyrrolidinylmethoxy)cyclohexanecarboxylate (399 mg, 94%) was obtained as a yellow amorphous substance.

$^1$H-NMR (CDCl$_3$) δ 1.21–1.30 (m, 2H), 1.44–1.50 (m, 2H), 1.98–2.48 (m, 7H), 3.27 (m, 1H), 3.35 and 3.52 (each m, total 1H), 3.60–3.93 (m, 8H, including each singlet, total 3H, at δ: 3.65 and 3.67), 4.23 and 4.39 (each m, total 1H), 5.26 (m, 1H), 7.24 (m, 1H), 7.40 (m, 1H), 7.71–7.78 (m, 2H), 7.88–7.91 (m, 2H), 8.59 (d, J=5.4 Hz, 1H), 8.64 (m, 1H), 9.71 (m, 1H), 11.02 (m, 1H).

MS (ESI) m/z 582 (M$^+$+1).

(Step 4) Synthesis of trans-4-(1-((3-chloro-4-((1-isoquinolinylcarbonyl)amino)phenyl)acetyl)-(4S)-fluoro-(2S)-pyrrolidinylmethoxy)cyclohexanecarboxylic acid

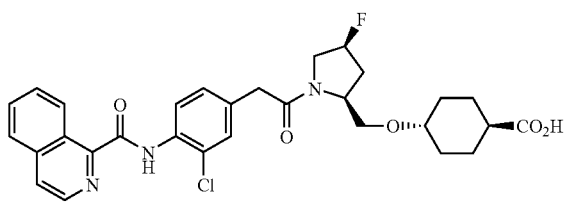

Methyl trans-4-(1-((3-chloro-4-((1-isoquinolinylcarbonyl)amino)phenyl)acetyl)-(4S)-fluoro-(2S)-pyrrolidinylmethoxy)cyclohexanecarboxylate (399 mg, 0.69 mmol) was dissolved in THF (7.0 ml). To the resulting solution was added 0.25N NaOH (4.11 ml, 1.03 mmol), followed by stirring at room temperature for 18 hours. The reaction mixture was poured into 1N HCl (1.1 ml). The crystals thus precipitated were collected by filtration under reduced pressure, washed with water, and dried under reduced pressure to give the title compound (347 mg, 89%) as a yellow solid.

IR (ATR) ν 2935, 2861, 1716, 1596, 1527, 1442 cm$^{-1}$;

$^1$H-NMR (DMSO-d$_6$) δ: 1.13–1.41 (m, 4H), 1.85–2.25 (m, 7H), 3.17–3.89 (m, 7H), 4.14 and 4.34 (each m, total 1H), 5.32 and 5.39 (each m, total 1H), 7.28 (m, 1H), 7.44 and 7.45 (m, total 1H), 7.81 (t, J=7.1 Hz, 1H), 7.88 (t, J=7.1 Hz, 1H), 8.12 (d, J=8.1 Hz, 1H), 8.16 (d, J=5.6 Hz, 1H), 8.22 (m, 1H), 8.67 (d, J=5.6 Hz, 1H), 9.31 (d, J=8.5 Hz, 1H), 10.84 (s, 1H), 12.02 (broad s, 1H).

MS (ESI) m/z 568 (M$^+$+1);

Anal. Calcd for C$_{30}$H$_{31}$ClFN$_3$O$_5$: C, 63.43; H, 5.50; N, 7.40. Found: C, 63.40; H, 5.62; N, 7.40.

Example 81 trans-4-(1-((5-Chloro-2-fluoro-4-((1-isoquinolinylcarbonyl)amino)phenyl)acetyl)-(4S)-fluoro-(2S)-pyrrolidinylmethoxy)cyclohexanecarboxylic acid (Step 1) Synthesis of ethyl (5-chloro-2-fluoro-4-((1-isoquinolinylcarbonyl)amino)phenyl)acetate

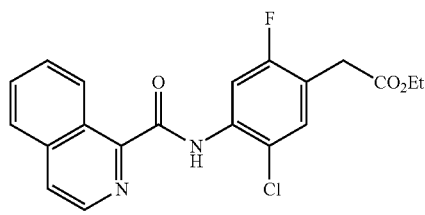

In methylene chloride (15 ml), diphenylphosphinic chloride (0.99 ml, 5.19 mmol) was added to 1-isoquinolinecarboxylic acid (375 mg, 2.17 mmol), ethyl 4-amino-3-chlorophenylacetate (501 mg, 2.17 mmol), and triethylamine (1.32 ml, 9.53 mmol), followed by stirring at room temperature for 24 hours. Water was added to the reaction mixture to separate therefrom an organic layer. The methylene chloride layer was washed with water, dried over anhydrous sodium sulfate, and distilled under reduced pressure to remove the solvent. The residue was purified by chromatography on a silica gel column, whereby from n-hexane-ethyl acetate (3:1, v/v) eluate fractions, ethyl (5-chloro-2-fluoro-4-((1-isoquinolinylcarbonyl)amino)phenyl)acetate (690 mg, 82%) was obtained as a yellow solid.

$^1$H-NMR (CDCl$_3$) δ: 1.28 (t, J=7.1 Hz, 3H), 3.64 (s, 2H), 4.19 (q, J=7.1 Hz, 2H), 7.36 (d, J=7.2 Hz, 1H), 7.72–7.78 (m, 2H), 7.88–7.91 (m, 2H), 8.57–8.60 (m, 2H), 9.68 (m, 1H), 11.11 (broad s, 1H).

MS (ESI) m/z 387 (M$^+$+1).

(Step 2) Synthesis of (5-chloro-2-fluoro-4-((1-isoquinolinylcarbonyl)amino)phenyl)acetic acid

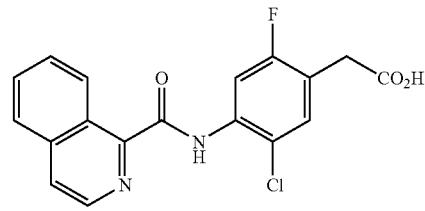

Ethyl (5-chloro-2-fluoro-4-((1-isoquinolinylcarbonyl)amino)phenyl)acetate (690 mg, 1.78 mmol) was dissolved in THF (18 ml). To the resulting solution was added 0.25N NaOH (10.7 ml, 2.68 mmol), and the resulting mixture was stirred at room temperature for 7 hours. The reaction mixture was poured into 1N HCl (3.0 ml). The crystals thus precipitated were collected by filtration under reduced pressure, washed with water, and dried under reduced pressure to give (5-chloro-2-fluoro-4-((1-isoquinolinylcarbonyl)amino)phenyl)acetic acid (583 mg, 91%) as a pale yellow solid.

$^1$H-NMR (DMSO-d$_6$) δ: 3.66 (s, 2H), 7.62 (d, J=7.5 Hz, 1H), 7.82 (m, 1H), 7.88 (m, 1H), 8.12 (d, J=8.5 Hz, 1H), 8.18 (d, J=5.6 Hz, 1H), 8.23 (d, J=11.5 Hz, 1H), 8.67 (d, J=5.6 Hz, 1H), 9.38 (d, J=8.5 Hz, 1H), 10.98 (broad s, 1H), 12.59 (broad s, 1H).

MS (ESI) m/z 359 (M$^+$+1).

(Step 3) Synthesis of methyl trans-4-(1-((5-chloro-2-fluoro-4-((1-isoquinolinylcarbonyl)amino)phenyl)acetyl)-(4S)-fluoro-(2S)-pyrrolidinylmethoxy)cyclohexanecarboxylate

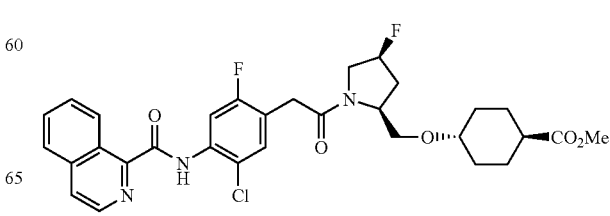

In DMF (5.5 ml) were dissolved (5-chloro-2-fluoro-4-((1-isoquinolinylcarbonyl)amino)phenyl)acetic acid (200 mg, 0.56 mmol), methyl trans-4-((4S)-fluoro-(2S)-pyrrolidinylmethoxy)cyclohexanecarboxylate (the compound synthesized in (Step 3) of Example 21) (145 mg, 0.56 mmol), HOBt (15.0 mg, 0.11 mmol), and DMAP (14.0 mg, 0.11 mmol). To the resulting solution was added EDC HCl (160 mg, 0.84 mmol), followed by stirring at room temperature for 21 hours. The reaction mixture was added with water, followed by extraction with ethyl acetate. The extract was washed with saturated brine, dried over anhydrous sodium sulfate, and distilled under reduced pressure to remove the solvent. The residue was purified by chromatography on a silica gel column, whereby from ethyl acetate eluate fractions, methyl trans-4-(1-((5-chloro-2-fluoro-4-((1-isoquinolinylcarbonyl)amino)phenyl)acetyl)-(4S)-fluoro-(2S)-pyrrolidinylmethoxy)cyclohexanecarboxylate (341 mg, 100%) was obtained as a yellow amorphous substance.

$^1$H-NMR (CDCl$_3$) δ: 1.18–1.33 (m, 2H), 1.40–1.54 (m, 2H), 1.97–2.54 (m, 7H), 3.28 (m, 1H), 3.36 and 3.53 (each m, total 1H), 3.64 and 3.66 (each s, total 3H), 3.66–4.03 (m, 5H), 4.31 and 4.37 (each m, total 1H), 5.27 and 5.29 (each m, total 1H), 7.41 and 7.43 (each d, J=7.3 Hz, total 1H), 7.72–7.78 (m, 2H), 7.88–7.91 (m, 2H), 8.54 and 8.58 (each d, J=9.7 Hz, total 1H), 8.56 (d, J=5.6 Hz, 1H), 9.68 (m, 1H), 11.09 (d, J=8.1 Hz, 1H).

MS (ESI) m/z 600 (M$^+$+1).

(Step 4) Synthesis of trans-4-(1-((5-chloro-2-fluoro-4-((1-isoquinolinylcarbonyl)amino)phenyl)acetyl)-(4S)-fluoro-(2S)-pyrrolidinylmethoxy)cyclohexanecarboxylic acid

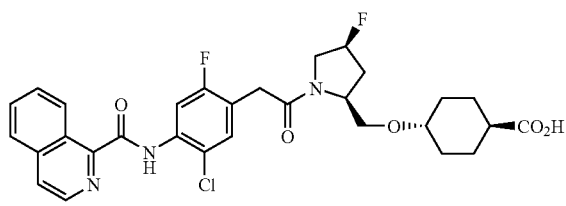

To methyl trans-4-(1-((5-chloro-2-fluoro-4-((1-isoquinolinylcarbonyl)amino)phenyl)acetyl)-(4S)-fluoro-(2S)-pyrrolidinylmethoxy)cyclohexanecarboxylate (341 mg, 0.57 mmol) were added THF (5.8 ml) was added 0.25N NaOH (3.40 ml, 0.85 mmol), followed by stirring at room temperature for 14 hours. The reaction mixture was poured into 1N HCl (1.0 ml). The crystals thus precipitated were collected by filtration under reduced pressure, washed with water, and dried under reduced pressure to give the title compound (291 mg, 87%) as a yellow solid.

IR (ATR) ν 3282, 2940, 2863, 1722, 1693, 1650, 1619, 1581, 1517 cm$^{-1}$;

$^1$H-NMR (DMSO-d$_6$) δ: 1.15–1.41 (m, 4H), 1.86–2.33 (m, 7H), 3.17–4.00 (m, 7H), 4.13 and 4.36 (each m, total 1H), 5.32 and 5.41 (each m, total 1H), 7.49 and 7.53 (each d, J=7.3 Hz, total 1H), 7.82 (t, J=7.3 Hz, 1H), 7.88 (t, J=7.3 Hz, 1H), 8.12 (d, J=8.1 Hz, 1H), 8.18–8.23 (m, 2H), 8.67 (d, J=5.6 Hz, 1H), 9.38 (d, J=8.8 Hz, 1H), 10.95 (m, 1H), 12.02 (broad s, 1H).

MS (ESI) m/z 586 (M$^+$+1);

Anal. Calcd for C$_{30}$H$_{30}$ClF$_2$N$_3$O$_5$ 0.25H$_2$O: C, 61.02; H, 5.21; N, 7.12. Found: C, 61.01; H, 5.17; N, 7.00.

Example 82 trans-4-(1-((3-Chloro-4-((7-fluoro-1-isoquinolinylcarbonyl)amino)phenyl)acetyl)-(4S)-fluoro-(2S)-pyrrolidinylmethoxy)cyclohexanecarboxylic acid (Step 1) Synthesis of methyl (3-chloro-4-((7-fluoro-1-isoquinolinylcarbonyl)amino)phenyl)acetate

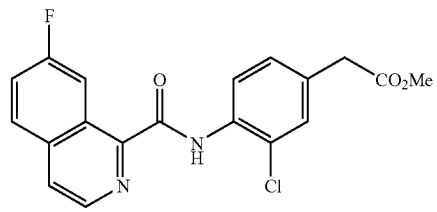

In DMF (5 ml) were dissolved 7-fluoro-1-isoquinolinecarboxylic acid (250 mg, 1.31 mmol), methyl 4-amino-3-chlorophenylacetate (262 mg, 1.31 mmol), HOBt (catalytic amount), and DMAP (192 m g, 1.57 mmol). To the resulting solution was added EDC HCl (290 mg, 6.93 mmol), followed by stirring at room temperature for 14 hours. The reaction mixture was poured into water (20 ml). The crystals thus precipitated were collected by filtration under reduced pressure, washed with ether and then dried under reduced pressure to give methyl (3-chloro-4-((7-fluoro-1-isoquinolinylcarbonyl)amino)phenyl)acetate (250 mg, 51%) as a colorless crystalline powder.

$^1$H-NMR (CDCl$_3$) δ: 3.62 (s, 2H), 3.72 (s, 3H), 7.25 9.45 (series of m, 9H).

MS (ESI) m/z 323 (M$^+$+1).

(Step 2) Synthesis of (3-chloro-4-((7-fluoro-1-isoquinolinylcarbonyl)amino)phenyl)acetic acid

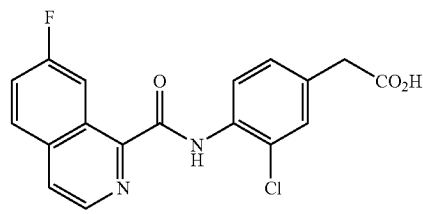

In THF (5 ml), 0.25N NaOH (4 ml, 4.82 mmol) was added to methyl (3-chloro-4-((7-fluoro-1-isoquinolinylcarbonyl)amino)phenyl)acetate (100 mg, 0.27 mmol) and the resulting mixture was stirred at room temperature for 18 hours. The reaction mixture was poured into 1N HCl (2.0 ml). The crystals thus precipitated were collected by filtration under reduced pressure, washed with water, and dried under reduced pressure to give (3-chloro-4-((7-fluoro-1-isoquinolinylcarbonyl)amino)phenyl)acetic acid (75 mg, 78%) as a colorless solid.

MS (ESI) m/z 359 (M$^+$+1).

(Step 3) Synthesis of methyl trans-4-(1-((3-chloro-4-((7-fluoro-1-isoquinolinylcarbonyl)amino)phenyl)acetyl)-(4S)-fluoro-(2S)-pyrrolidinylmethoxy)cyclohexanecarboxylate

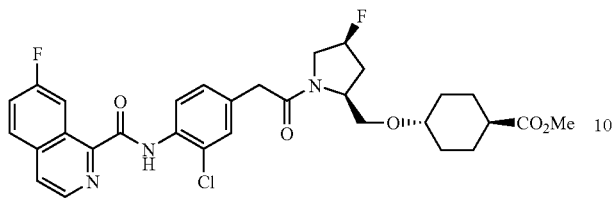

In DMF (5 ml) were suspended (3-chloro-4-((7-fluoro-1-isoquinolinylcarbonyl)amino)phenyl)acetic acid (57 mg, 0.159 mmol), methyl trans-4-((4S)-fluoro-(2S)-pyrrolidinylmethoxy)cyclohexanecarboxylate (the compound synthesized in (Step 3) of Example 21) (42 mg, 0.159 mmol), HOBt (catalytic amount), and DMAP (24 mg, 0.191 mmol). To the resulting suspension was added EDC HCl (37 mg, 0.191 mmol), followed by stirring at room temperature for 20 hours. The reaction mixture was poured into water, followed by extraction with ethyl acetate. The extract was washed with saturated brine, dried over anhydrous sodium sulfate, and distilled under reduced pressure to remove the solvent. The residue was purified by chromatography on a silica gel column, whereby from ethyl acetate eluate fractions, methyl trans-4-(1-((3-chloro-4-((7-fluoro-1-isoquinolinylcarbonyl)amino)phenyl)acetyl)-(4S)-fluoro-(2S)-pyrrolidinylmethoxy)cyclohexanecarboxylate (105 mg, 100%) was obtained as a colorless amorphous substance.

$^1$H-NMR (CDCl$_3$) δ 1.21–1.31 (m, 2H), 1.44–1.51 (m, 2H), 1.98–2.49 (m, 7H), 3.27 (m, 1H), 3.35 and 3.52 (each m, total 1H), 3.60–3.93 (m, 8H), 4.23 and 4.39 (each m, total 1H), 5.26 (m, 1H), 7.26 (m, 1H), 7.41 (m, 1H), 7.56 (m, 1H), 7.90 and 7.92 (each m, 2H), 8.59 and 8.63 (each m, 2H), 9.46 (m, 1H), 11.01 (br d, 1H).

MS (ESI) m/z 560 (M$^+$+1).

(Step 4) Synthesis of trans-4-(1-((3-chloro-4-((7-fluoro-1-isoquinolinylcarbonyl)amino)phenyl)acetyl)-(4S)-fluoro-(2S)-pyrrolidinylmethoxy)cyclohexanecarboxylic acid

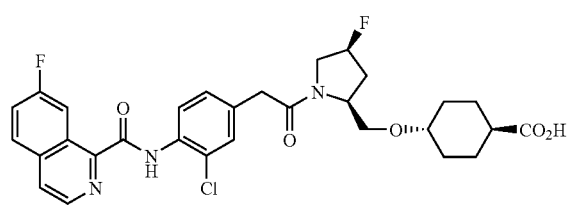

In THF (5 ml), 0.25N NaOH (1.9 ml) was added to methyl trans-4-(1-((3-chloro-4-((7-fluoro-1-isoquinolinylcarbonyl)amino)phenyl)acetyl)-(4S)-fluoro-(2S)-pyrrolidinylmethoxy)cyclohexanecarboxylate (95 mg, 0.15 mmol), followed by stirring at room temperature for 18 hours. The reaction mixture was poured into 1N HCl (2 ml). The crystals thus precipitated were collected by filtration under reduced pressure, washed with water, and dried under reduced pressure to give the title compound (65 mg, 71%) as a colorless crystalline powder.

$^1$H-NMR (CDCl$_3$) δ: 1.13–1.40 (m, 4H), 1.80–2.30 (m, 7H), 3.15–3.90 (m, 7H), 4.10 and 4.35 (each m, total 1H), 5.30 and 5.40 (each m, total 1H), 7.25 (m, 1H), 7.41 (m, 1H), 7.54 (m, 1H), 7.89 (m, 1H), 7.92 (m, 1H), 8.59 (m, 1H), 8.62 (m, 1H), 9.45 (m, 1H), 11.01 (br d, 1H).

MS (ESI) m/z 586 (M$^+$+1).

Example 83 trans-4-(1-(3-Chloro-4-((3-benzo(d)isothiazolylcarbonyl)amino)phenylacetyl)-(4S)-fluoro-(2S)-pyrrolidinylmethoxy)cyclohexanecarboxylic acid (Step 1) Synthesis of 3-chloro-4-((3-benzo(d)isothiazolylcarbonyl)amino)phenylacetic acid

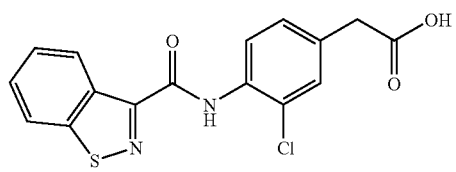

Methyl 4-amino-3-chlorphenylacetate (50 mg, 0.25 mmol), 3-benzo(d)isothiazole-3-carboxylic acid (45 mg, 0.25 mmol), HOBt (64 mg, 0.475 mmol), EDC (72 mg, 0.38 mmol) and DMAP (catalytic amount) were dissolved in DMF (2 ml). The resulting solution was stirred for 8 hours. The reaction mixture was poured into 1M HCl, followed by extraction with ethyl acetate. The extract was washed with saturated brine, dried over anhydrous magnesium sulfate and distilled under reduced pressure to remove the solvent. To the residue were added THF/methanol (4 ml, 3:1) and 1M NaOH (1 ml) and the resulting mixture was stirred for 18 hours at room temperature. The reaction mixture was distilled under reduced pressure to remove the solvent. The residue was acidified with 1M HCl.The crystals thus precipitated were collected by filtration under reduced pressure, washed with water and dried under reduced pressure to give 3-chloro-4-((3-benzo(d)isothiazolylcarbonyl)amino)phenylacetic acid (80 mg, 92%) as a colorless solid.

$^1$H-NMR (DMSO-d$_6$) δ: 3.62 (s, 2H), 7.30 (d, J=8.1 Hz, 1H), 7.50 (s, 1H), 7.64 (d, J=8.1 Hz, 1H), 7.70 (d, J=8.1 Hz, 1H), 7.95 (d, J=8.3 Hz, 1H), 8.36 (d, J=8.1 Hz, 1H), 8.80 (d, J=8.1 Hz, 1H), 10.27 (s, 1H).

MS (ESI) m/z 347 (M+1)$^+$.

(Step 2) Synthesis of trans-4-(1-(3-chloro-4-((3-benzo(d)isothiazolylcarbonyl)amino)phenylacetyl)-(4S)-fluoro-(2S)-pyrrolidinylmethoxy)cyclohexanecarboxylic acid

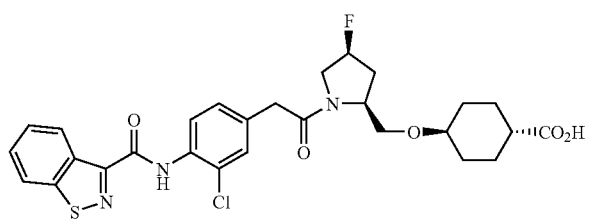

In DMF (1.2 ml) were dissolved 3-chloro-4-((3-benzo(d)isothiazolylcarbonyl)amino)phenylacetic acid (80 mg, 0.23 mmol), methyl trans-4-((4S)-fluoro-(2S)-pyrrolidinylmethoxy)cyclohexanecarboxylate (the compound synthesized in (Step 3) of Example 21) (60 mg, 0.23 mmol), HOBt (59 mg, 0.44 mmol), DMAP (catalytic amount) and EDC•HCl (66 mg, 0.35 mmol). The resulting solution was stirred at room temperature for 18 hours. The reaction mixture was poured in 1M HCl, followed by extraction with ethyl acetate. The extract was washed with saturated brine, dried over anhydrous magnesium sulfate and distilled under reduced pressure to remove the solvent. To the residue were added THF (2.1 ml) and 0.25M NaOH (1.26 ml, 0.32 mmol) and the mixture was stirred at room temperature for 18 hours. The reaction mixture was poured in ice water and acidified with 1M HCl. The crystals thus precipitated were collected by filtration under reduced pressure, washed with water and dried under reduced pressure. The crude crystals thus obtained were recrystallized from chloroform/n-hexane to give the title compound (85 mg, 64%) as a colorless solid.

$^1$H-NMR (DMSO-$d_6$) δ: 1.10–1.40 (m, 6H), 1.82–2.20 (m, 6H), 3.20 (m, 1H), 3.50–4.40 (m, 6H), 5.36 (m, 1H), 7.26 (t, J=7.7 Hz, 1H), 7.64 (t, J=7.4 Hz, 1H), 7.71 (t, J=7.4 Hz, 1H), 7.94 (dd, J=4.9,8.3 Hz, 1H), 8.36 (d, J=8.3 Hz, 1H), 8.80 (d, J=8.3 Hz, 1H), 10.27 (s, 1H).

MS (ESI) m/z 575 (M+1)$^+$.

Anal. Calcd for $C_{28}H_{29}ClFN_3O_5S$: C, 58.58; H, 5.13; N, 7.02. Found: C, 58.58; H, 5.13; N, 7.02.

Example 84 trans-4-(1-(5-Chloro-2-fluoro-4-((4-fluoro-3-benzo (d)isothiazolylcarbonyl)amino)phenylacetyl)-(4S)-fluoro-(2S)-pyrrolidinylmethoxy)cyclohexanecarboxylic acid (Step 1) Synthesis of 4-fluorobenzo(d)isothiazole-3-carboxylic acid

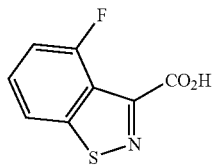

3-Fluorobenzenethiol (5.0 g, 39.0 mmol) was dissolved in methylene chloride (200 ml), and oxalyl chloride (3.57 ml, 41.0 mmol) and triethylamine (5.71 ml, 41.0 mmol) were added to the solution under stirring at 0° C. The reaction mixture was stirred for 24 hours at room temperature. The reaction mixture was distilled under reduced pressure to remove the solvent. The residue was suspended in methylene chloride (100 ml). After aluminum chloride (7.8 g, 58.5 mmol) was added to the reaction mixture under cooling at 0° C., the reaction mixture was stirred at room temperature for 4 hours. The reaction mixture was poured in ice water, followed by extraction with chloroform. The extract was washed with saturated brine, dried over anhydrous magnesium sulfate and distilled under reduced pressure to remove the solvent. To the residue were added concentrated aqueous ammonia (28%, 50 ml) and hydrogen peroxide (35% in water, 50 ml) and the mixture was stirred at room temperature for 24 hours. The crystals thus precipitated were collected by filtration and added with THF (100 ml) and 0.25M NaOH (60 ml, 15 mmol). The resulting mixture was heated under reflux for 24 hours. The reaction mixture was cooled to room temperature and poured in 1M HCl. The mixture was concentrated to dryness under reduced pressure. The residue was purified with chromatography on a silica gel column (middle pressure chromatography system Yamazen, C-18 column, linear gradient of H$_2$0 (0.1% HCOOH) and methanol (0.1% HCOOC) from 10% to 90%, 10 ml/min) to give 4-fluorobenzo(d)isothiazole-3-carboxylic acid (590 mg, 8%) as a colorless solid.

$^1$H-NMR (DMSO-$d_6$) δ: 7.51 (dt, J=2.5,9.1 Hz, 1H), 8.19 (dd, J=2.5,8.8 Hz, 1H), 8.66 (dd, J=5.1,9.1 Hz, 1H).

MS (ESI) m/z 198 (M+1)$^+$.

(Step 2) Synthesis of (5-chloro-2-fluoro-4-((4-fluoro-3-benzo(d)isothiazolylcarbonyl)amino)phenyl)acetic acid

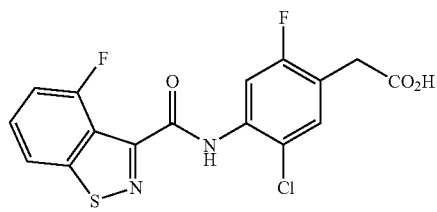

In DMF (10 ml) were dissolved 4-fluorobenzo(d)isothiazole-3-carboxylic acid (240 mg, 1.22 mmol), ethyl 4-amino-5-chloro-2-fluorophenylacetate (282 mg, 1.22 mmol), HOBt (313 mg, 2.32 mmol), EDC HCl (351 mg, 1.83 mmol) and DMAP (catalytic amount). The resulting solution was stirred for 4 days at room temperature. The reaction mixture was poured in 1M HCl, followed by extraction with ethyl acetate. The extract was washed with saturated brine, dried over anhydrous magnesium sulfate and distilled under reduced pressure to remove the solvent. The residue was purified by silica gel column chromatography (middle pressure chromatography system from Yamazen, chloroform, 8 ml/min, φ 15 mm×300 mm). To the resulting ester were added THF (12 ml) and 0.25M NaOH (7.32 ml, 1.83 mmol), followed by stirring at room temperature for 4 hours. The reaction mixture was poured in 1M HCl to acidify the mixture. The crystals thus precipitated were collected by filtration under reduced pressure, washed with water, and dried under reduced pressure to give (5-chloro-2-fluoro-4-((4-fluoro-3-benzo(d)isothiazolylcarbonyl)amino)phenyl) acetic acid (105 mg, 22%) as a colorless solid.

$^1$H-NMR (DMSO-$d_6$) δ: 1.28 (t, J=7.2 Hz, 3H), 3.64 (s, 2H), 4.19 (q, J=7.2 Hz, 2H), 7.34 (dt, J=2.2,9.1 Hz, 1H), 7.37 (d, J=7.1 Hz, 1H), 7.64 (dd, J=2.2,8.3 Hz, 1H), 8.48 (d, J=11.5 Hz, 1H), 9.00 (dd, J=5.1, 9.0 Hz, 1H), 9.92 (s, 1H).

(Step 3) Synthesis of trans-4-(1-(5-chloro-2-fluoro-4-((4-fluoro-3-benzo(d)isothiazolylcarbonyl)amino)phenylacetyl)-(4S)-fluoro-(2S)-pyrrolidinylmethoxy)cyclohexanecarboxylic acid

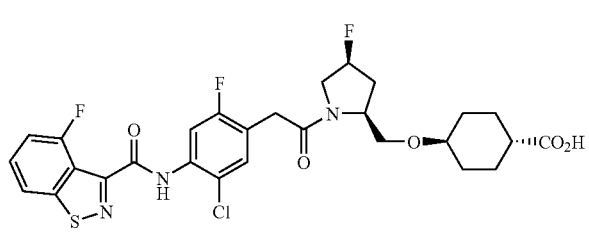

In DMF (3 ml) were dissolved (5-chloro-2-fluoro-4-((4-fluoro-3-benzo(d)isothiazolylcarbonyl)amino)phenyl)acetic acid (105 mg, 0.27 mmol), methyl trans-4-((4S)-fluoro-(2S)-pyrrolidinylmethoxy)cyclohexanecarboxylate (the compound synthesized in (Step 3) of Example 21) (71 mg, 0.27 mmol), HOBt (70 mg, 0.52 mmol), DMAP (catalytic amount) and EDC•HCl salt (79 mg, 0.41 mmol). The resulting solution was stirred at room temperature for 18 hours. The reaction mixture was poured in 1M HCl, followed by extraction with ethyl acetate. The extract was washed with saturated brine, dried over anhydrous magnesium sulfate and distilled under reduced pressure to remove the solvent. The residue was purified by silica gel column chromatography, whereby a crude ester was obtained. The crude ester was added with THF (3.0 ml) and 0.25M NaOH (1.6 ml, 0.4 mmol) and the mixture was stirred at room temperature for 18 hours The reaction mixture was poured in 1M HCl. The crystals thus precipitated were collected by filtration under reduced pressure. The crude crystals were purified by C-18 column chromatography (middle pressure chromatography, linear gradient water/methanol, 10%–90%) to give the title compound (69 mg, 41%) as a colorless solid.

¹H-NMR (DMSO-d₆) δ: 1.20 (m, 4H), 1.95 (m, 4H), 2.05 (m, 2H), 3.50–4.00 (m, 6H), 4.05 and 4.20 (2m, total 1H), 5.40 (m, 1H), 7.53 (m, 3H), 7.93 (m, 1H), 8.25 (dd, J=2.2,8.6 Hz, 1H), 8.81 (dd, J=5.6,9.2 Hz, 1H), 10.30 (m, 1H).

MS (ESI) m/z 611 (M+1)⁺.

Anal. Calcd for $C_{28}H_{27}ClF_3N_3O_5$ 1.0 $H_2O$: C, 53.55; H, 4.65; N, 6.69. Found: C, 53.3; H, 4.35; N, 6.68.

Example 85 trans-4-(1-(5-Chloro-2-fluoro-(4-((3-benzo(d)isothiazolylcarbonyl)amino)phenyl)acetyl)-(4S)-fluoro-(2S)-pyrrolidinylmethoxy)cyclohexanecarboxylic acid (Step 1) Synthesis of (5-chloro-2-fluoro-4-((3-benzo(d)isothiazolylcarbonyl)amino)phenyl)acetic acid

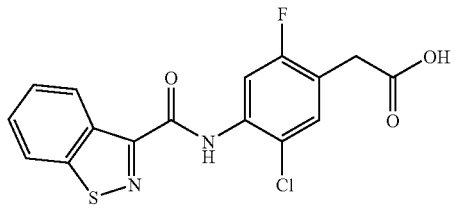

Methyl 4-amino-5-chloro-2-fluorophenylacetate (753 mg, 3.25 mmol), benzo(d)isothiazole-3-carboxylic acid (583 mg, 3.25 mmol), HOBt (834 mg, 6.18 mmol), EDC HCl (934 mg, 4.88 mmol) and DMAP (catalytic amount) were dissolved in DMF (16 ml). The resulting solution was stirred for 10 hours at 80° C. After cooling, the reaction mixture was poured in 1M HCl, followed by extraction with ethyl acetate. The extract was washed with saturated brine, dried over anhydrous magnesium sulfate and distilled under reduced pressure to remove the solvent. The residue was purified by silica gel column chromatography (middle pressure, n-hexane/ethyl acetate 9:1, 15 ml/min, φ 50×300 mm) to give ethyl (5-chloro-2-fluoro-4-((3-benzo(d)isothiazolylcarbonyl)amino)phenyl)acetate. The resulting ester was dissolved in THF/methanol (4 ml, 3:1), and to the resulting solution was added 1M NaOH (1 ml). The mixture was stirred for 18 hours at room temperature. The solvent was distilled off under reduced pressure, and the residue was poured in 1M HCl. The crystals thus precipitated were collected by filtration under reduced pressure, washed with water and dried under reduced pressure to give (5-chloro-2-fluoro-4-((3-benzo(d)isothiazolylcarbonyl)amino)phenyl) acetic acid (354 mg, 30%) as a colorless solid.

¹H-NMR (DMSO-d₆) δ: 3.68 (s, 2H), 7.65 (d, J=7.3 Hz, 1H), 7.66 (t, J=7.5 Hz, 1H), 7.73 (t, J=7.5 Hz, 1H), 7.99 (d, J=11.2 Hz, 1H), 8.38 (d, J=8.3 Hz, 1H), 8.81 (d, J=7.8 Hz, 1H), 10.30 (s, 1H).

MS (ESI) m/z 365 (M+1)⁺.

(Step 2) Synthesis of trans-4-(1-(5-chloro-2-fluoro-(4-((3-benzo(d)isothiazolylcarbonyl)amino)phenyl)acetyl)-(4S)-fluoro-(2S)-pyrrolidinylmethoxy)cyclohexanecarboxylic acid

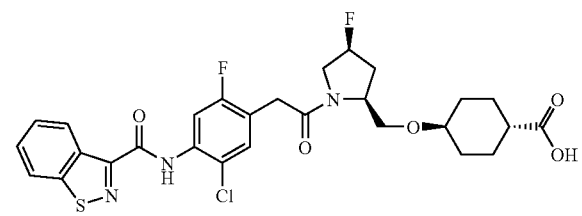

In DMF (1.2 ml) were dissolved (5-chloro-2-fluoro-4-((3-benzo(d)isothiazolylcarbonyl)amino)phenyl)acetic acid (80 mg, 0.23 mmol), methyl trans-4-((4S)-fluoro-(2S)-pyrrolidinylmethoxy)cyclohexanecarboxylate (the compound synthesized in (Step 3) of Example 21) (60 mg, 0.23 mmol), HOBt (59 mg, 0.44 mmol), DMAP (catalytic amount) and EDC•HCl (66 mg, 0.35 mmol). The resulting solution was stirred at room temperature for 18 hours. The reaction mixture was poured in 1M HCl, followed by extraction with ethyl acetate. The extract was washed with saturated brine, dried over anhydrous magnesium sulfate and distilled under reduced pressure to remove the solvent. The residue was dissolved in THF (2.1 ml) and to the resulting solution was added 0.25M NaOH (1.26 ml, 0.32 mmol). The mixture was stirred for 18 hours at room temperature. The reaction mixture was poured in ice water and acidified with 1M HCl. The crystals thus precipitated were collected by filtration under reduced pressure, washed with water and dried under reduced pressure. The crude crystals thus obtained were recrystallized from chloroform/n-hexane to give the title compound (85 mg, 64%) as a colorless solid.

¹H-NMR (DMSO-d₆) δ 1.10–1.40 (m, 6H), 1.82–2.20 (m, 6H), 3.20 (m, 1H), 3.50–4.40 (m, 6H), 5.36 (m, 1H), 7.26 (t, J=7.7 Hz, 1H), 7.64 (t, J=7.4 Hz, 1H), 7.71 (t, J=7.4 Hz, 1H), 7.94 (dd, J=4.9,8.3 Hz, 1H), 8.36 (d, J=8.3 Hz, 1H), 8.80 (d, J=8.3 Hz, 1H), 10.27 (s, 1H).

MS (ESI) m/z 575 (M+1)⁺;

Anal. Calcd for $C_{28}H_{29}ClFN_3O_5S$: C, 58.58; H, 5.13; N, 7.02. Found: C, 58.58; H, 5.13; N, 7.02.

Example 86 trans-4-(1-(4-((Benzo(d)isothiazole-3-carbonyl)amino)-5-chloro-2-fluorophenylacetyl)-(4S)-fluoro-(2S)-pyrrolidinylmethoxy)cyclohexanecarboxylic acid (Step 1) Synthesis of ethyl (2-nitrophenyl)acetate

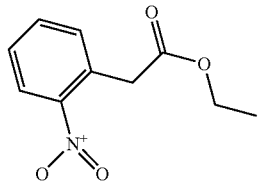

In ethanol (250 ml) was dissolved (2-nitrophenyl)acetic acid (18.5 g, 0.102 mmol), and to the resulting solution was added concentrated $H_2SO_4$ (0.1 ml). The mixture was heated under reflux for 24 hours. The reaction mixture was cooled to room temperature and then, diluted with ethyl acetate. The diluted solution was washed with a saturated aqueous solution of sodium bicarbonate and saturated brine, dried over anhydrous magnesium sulfate and distilled under reduced pressure to remove the solvent, whereby ethyl (2-nitrophenyl)acetate (17.4 g, 82%) was obtained as a colorless solid.

$^1$H-NMR (CDCl$_3$) δ 1.25 (t, J=7.1 Hz, 3H), 4.02 (s, 2H), 4.17 (q, J=7.1 Hz, 2H), 7.35 (d, J=7.6 Hz, 1H), 7.47 (dt, J=1.5,8.0 Hz, 1H), 7.59 (dt, J=1.5,7.6 Hz, 1H), 8.10 (dd, J=1,2,8.1 Hz, 1H).

MS (ESI) m/z 208 (M−1)$^+$.

(Step 2) Synthesis of ethyl benzo(d)isoxazole-3-carboxylate

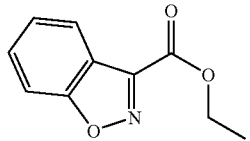

Ethyl 2-nitrophenyl)acetate (12.3 g, 58.6 mmol) and isoamyl nitrate (8.92 g, 76.1 mmol) were dissolved in ethanol (100 ml). Sodium methoxide (19.9 ml, 58.6 mmol, a 20% solution in ethanol) was added, followed by stirring at 50° C. for 1.5 hours. The reaction mixture was cooled to room temperature and neutralized with 1M HCl (30 ml), followed by extraction with ether. The extract was dried over anhydrous magnesium sulfate and distilled under reduced pressure to remove the solvent. The residue was crystallized by the addition of chloroform/n-hexane and the crystals were dried under reduced pressure for 18 hours. The crystals thus obtained were dissolved in 1,2-dimethoxyethane (100 ml) and to the resulting solution, a solution of sodium hydride (2.81 g, 70.3 mmol) in 1,2-dimethoxyethane (100 ml) was added in portions. The reaction mixture was stirred at 150° C. for 8 hours. Under cooling, the reaction mixture was poured to a saturated aqueous solution of sodium bicarbonate, followed by extraction with ether. The extract was washed with saturated brine, dried over anhydrous magnesium sulfate and distilled under reduced pressure to remove the solvent. The residue was purified by silica gel column chromatography (middle pressure chromatography system Yamazen, n-hexane/ethyl acetate 9:1, 20 ml/min, φ 80×300) to give ethyl benzo(d)isoxazole-3-carboxylate (5.75 g, 51%) as a brown solid.

$^1$H-NMR (DMSO-d$_6$) δ: 1.50 (m, 3H), 4.56 (m, 2H), 7.45 (dt, J=1.2, 6.8 Hz, 1H), 7.62 (dt, J=1.2,8.5 Hz, 1H), 7.66 (dt, J=1.0,8.5 Hz, 1H), 8.14 (dd, J=1.0,8.0 Hz, 1H).

MS (ESI) m/z 192 (M+1)$^{+\cdot}$ (Step 3) Synthesis of benzo(d)isoxazole-3-carboxylic acid

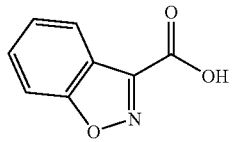

To ethyl benzo(d)isoxazole-3-carboxylate (2.0 g, 10.5 mmol) was added 50 ml of 70% $H_2SO_4$. The mixture was heated at 80° C. for 4 hours. The reaction mixture was poured in ice, followed by extraction with ether. The extract was dried over anhydrous magnesium sulfate and distilled under reduced pressure to remove the solvent, whereby benzo(d)isoxazole-3-carboxylic acid (980 mg, 57%) was obtained as a colorless solid.

$^1$H-NMR (DMSO-d$_6$) δ: 7.53 (dt, J=1.0,7.1 Hz, 1H), 7.74 (dt, J=1.2,7.1 Hz, 1H), 7.89 (dd, J=1.0,8.5 Hz, 1H), 8.10 (dt, J=1.0,8.1 Hz, 1H).

(Step 4) Synthesis of (4-((benzo(d)isoxazole-3-carbonyl)amino)-5-chloro-2-fluorophenylacetic acid

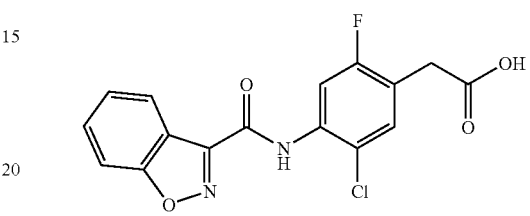

Benzo(d)isoxazole-3-carboxylic acid (475 mg, 2.91 mmol), ethyl 4-amino-5-chloro-2-fluorophenylacetate (675 mg, 2.91 mmol), HOBt (747 mg, 5.53 mmol), EDC HCl (837 mg, 4.37 mmol) and DMAP (catalytic amount) were dissolved in DMF (15 ml). The resulting solution was stirred for 24 hours at room temperature. The reaction mixture was poured in 1M HCl, followed by extraction with ethyl acetate. The extract was washed with saturated brine, dried over anhydrous magnesium sulfate and distilled under reduced pressure to remove the solvent. The residue was purified by silica gel column chromatography (middle pressure chromatography system from Yamazen, chloroform, 8 ml/min, φ 15 mm×300 mm). The ester thus obtained was added with THF (30 ml) and 0.25M NaOH (17.5 ml, 4.37 mmol), followed by stirring at room temperature for 18 hours. The reaction mixture was poured in 1M HCl to acidify the mixture. The crystals thus precipitated were collected by filtration under reduced pressure, washed with water and dried under reduced pressure to give (4-((benzo(d)isoxazole-3-carbonyl)amino)-5-chloro-2-fluorophenyl)acetic acid (100 mg, 10%) as a white solid.

$^1$H-NMR (DMSO-d$_6$) δ: 3.66 (s, 2H), 7.58 (t, J=8.0 Hz, 1H), 7.62 (d, J=7.1 Hz, 1H), 7.68 (d, J=11.4 Hz, 1H), 7.79 (d, J=9.0 Hz, 1H), 8.15 (d, J=8.8 Hz, 1H), 10.61 (d, J=4.2 Hz, 1H).

MS (ESI) m/z 349 (M+1)$^+$.

(Step 5) Synthesis of trans-4-(1-(4-((benzo(d)isothiazole-3-carbonyl)amino)-5-chloro-2-fluorophenylacetyl)-(4S)-fluoro-(2S)-pyrrolidinylmethoxy)cyclohexanecarboxylic acid

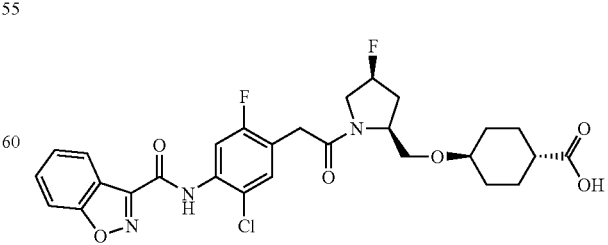

In DMF (3 ml) were dissolved (4-((benzo(d)isoxazole-3-carbonyl)amino)-5-chloro-2-fluorophenyl)acetic acid (100 mg, 0.29 mmol), methyl trans-4-((4S)-fluoro-(2S)-pyrrolidinylmethoxy)cyclohexanecarboxylate (the compound synthesized in (Step 3) of Example 21) (74 mg, 0.29 mmol), HOBt (74 mg, 0.55 mmol), DMAP (catalytic amount) and EDC·HCl salt (83 mg, 0.43 mmol). The resulting solution was stirred at room temperature for 18 hours. The reaction mixture was poured in 1M HCl, followed by extraction with ethyl acetate. The extract was washed with saturated brine, dried over anhydrous magnesium sulfate and distilled under reduced pressure to remove the solvent. The residue was purified by silica gel column chromatography. The ester thus obtained was added with THF (3.0 ml) and 0.25M NaOH (1.7 ml, 0.43 mmol), followed by stirring for 18 hours at room temperature. The reaction mixture was poured in ice water. The solution was acidified with 1M HCl. The crystals thus precipitated were collected by filtration under reduced pressure, washed with water and dried under reduced pressure to give (100 mg, 61%) as a colorless solid.

$^1$H-NMR (DMSO-d$_6$) δ: 1.05–1.50 (m, 4H), 1.95 (m, 4H), 2.04 (m, 2H), 3.50–4.00 (m, 6H), 4.05 and 4.08 (2m, total 1H), 5.40 (m, 1H), 7.52 (m, 2H), 7.63 (m, 1H), 7.79 (t, J=7.8 Hz, 1H), 7.94 (d, J=8.3 Hz, 1H), 8.16 (d, J=8.1 Hz, 1H), 10.65 (br, 1H), 12.05 (br, 1H).

MS (ESI) m/z 576 (M+1)$^+$.

Anal. Calcd for $C_{28}H_{28}ClF_2N_3O_6$: C, C, 58.39; H, 4.90; N, 7.30. Found: C, 58.19; H, 4.87; N, 7.18.

Example 87 trans-4-(1-((5-Chloro-2-fluoro-4-((1-methyl-3-indazolylcarbonyl)amino)phenyl)acetyl)-(4S)-fluoro-(2S)-pyrrolidinylmethoxy)cyclohexanecarboxylic acid (Step 1) Synthesis of methyl (2-nitrophenyl)acetate

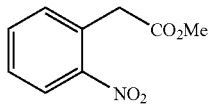

To (2-nitrophenyl)acetic acid (25.0 g, 0.14 mol) were added methanol (100 ml) and concentrated sulfuric acid (3.0 ml). The resulting mixture was heated under reflux for 10 hours. The reaction mixture was cooled to room temperature and then, distilled under reduced pressure to remove the solvent. The residue was dissolved in chloroform. The resulting solution was washed with a saturated aqueous solution of sodium bicarbonate, dried over anhydrous sodium sulfate, and distilled under reduced pressure to remove the solvent. The residue was purified by chromatography on a silica gel column, whereby from n-hexane-ethyl acetate (2:1, v/v) eluate fractions, methyl (2-nitrophenyl)acetate (26.6 g, 97%) was obtained as a yellow oil.

$^1$H-NMR (CDCl$_3$) δ: 3.72 (s, 3H), 4.03 (s, 2H), 7.36 (dd, J=7.3,1.2 Hz, 1H), 7.45 (m, 1H), 7.60 (m, 1H), 8.11 (dd, J=8.1,1.2 Hz, 1H).

(Step 2) Synthesis of methyl (2-acetamidophenyl)acetate

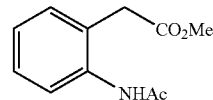

Methyl (2-nitrophenyl)acetate (26.6 g, 0.14 mol) and acetic anhydride (51.5 ml, 0.55 mol) were subjected to catalytic hydrogenation for 15 hours in toluene (150 ml) in the presence of 10% Pd/C (53.2% wet, 4.5 g). The reaction mixture was filtered to remove therefrom the catalyst, followed by washing with toluene. The filtrate was distilled under reduced pressure to remove the solvent. The residue was crystallized by the addition thereto of n-hexane and diisopropyl ether. The crystals thus precipitated were collected by filtration, washed with n-hexane, and dried under reduced pressure to give methyl (2-acetamidophenyl)acetate (24.3 g, 84%) as a pale yellow solid.

$^1$H-NMR (CDCl$_3$) δ: 2.21 (s, 3H), 3.63 (s, 2H), 3.72 (2, 3H), 7.11 (m, 1H), 7.20 (d, J=7.3 Hz, 1H), 7.30 (m, 1H), 7.83 (d, J=8.1 Hz, 1H), 8.68 (broad s, 1H).

(Step 3) Synthesis of methyl 1-acetylindazole-3-carboxylate

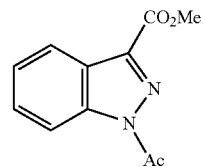

Methyl (2-acetamidophenyl)acetate (24.3 g, 0.12 mol) and acetic anhydride (24.3 ml, 0.26 mmol) were dissolved in acetic acid (60 ml). To the resulting solution, tert-butyl nitrite (90% purity, 18.6 ml, 0.14 mol) was added dropwise over 20 minutes under stirring at 90° C. After completion of the dropwise addition, the reaction mixture was stirred at 90° C. for further 1 hour. The reaction mixture was cooled to room temperature and then, poured in water (500 ml), followed by stirring for 1 hour. The crystals thus precipitated were collected by filtration under reduced pressure and dissolved in chloroform. The chloroform solution was washed with a saturated aqueous solution of sodium bicarbonate and saturated brine, dried over anhydrous sodium sulfate, and distilled under reduced pressure to remove the solvent, whereby methyl 1-acetylindazole-3-carboxylate (22.3 g, 85%) was obtained as a yellow solid.

$^1$H-NMR (CDCl$_3$) δ: 2.88 (s, 3H), 4.09 (s, 3H), 7.46 (m, 1H), 7.61 (m, 1H), 8.22 (dd, J=8.1,1.0 Hz, 1H), 8.46 (dd, J=8.6,1.0 Hz, 1H).

(Step 4) Synthesis of indazole-3-carboxylic acid

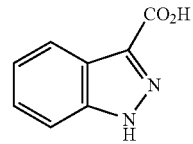

To methyl 1-acetylindazole-3-carboxylate (22.3 g, 0.10 mol) were added sodium hydroxide (8.18 g, 0.20 mol) and water (640 ml) and the resulting mixture was stirred at 60 to 70° C. for 6.5 hours. The reaction mixture was poured in concentrated HCl (30 ml). The crystals thus precipitated were collected by filtration under reduced pressure, washed with water and dried under reduced pressure to give indazole-3-carboxylic acid (17.6 g, 100%) as a pale yellow solid.

$^1$H-NMR (DMSO-$d_6$) δ: 7.29 (m, 1H), 7.44 (m, 1H), 7.65 (d, J=8.6 Hz, 1H), 8.10 (d, J=8.1 Hz, 1H), 12.96 (broad s, 1H), 13.77 (broad s, 1H).

(Step 5) Synthesis of methyl indazole-3-carboxylate

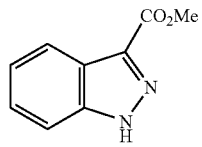

Indazole-3-carboxylic acid (5.00 g, 30.8 mmol) was dissolved in THF (200 ml) and methanol (15 ml). To the resulting solution was added (trimethylsilyl)diazomethane (a 2.0M n-hexane solution, 20 ml, 40.1 mmol) under stirring at 0° C. After stirring at room temperature for 3 hours, the reaction mixture was distilled under reduced pressure to remove the solvent. The residue was crystallized by the addition of n-hexane, and the crystals thus obtained were collected by filtration and dried under reduced pressure to give methyl indazole-3-carboxylate (3.71 g, 68%) as a colorless solid.

$^1$H-NMR (CDCl$_3$) δ: 4.07 (s, 3H), 7.34 (m, 1H), 7.47 (m, 1H), 7.70 (d, J=8.3 Hz, 1H), 8.24 (d, J=8.3 Hz, 1H), 11.83 (broad s, 1H).

MS (ESI) m/z 177 (M$^+$+1).

(Step 6) Synthesis of methyl 1-methylindazole-3-carboxylate and methyl 2-methylindazole-3-carboxylate

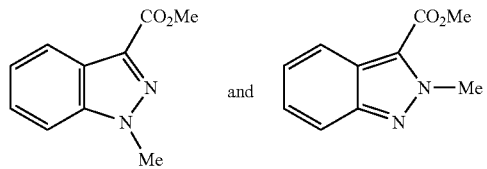

Methyl indazole-3-carboxylate (3.71 g, 21.1 mmol) was dissolved in DMF (40 ml). To the resulting solution was added sodium hydride (60% in oil, 1.01 g, 25.3 mmol) in portions under stirring at 0° C. The reaction mixture was stirred at the same temperature for 30 minutes. Methyl iodide (1.57 ml, 25.3 mmol) was added to the mixture. The resulting mixture was stirred at the same temperature for 30 minutes. A saturated aqueous solution of ammonium chloride was added and the mixture was extracted with ethyl acetate. The extract was washed with saturated brine, dried over anhydrous magnesium sulfate, and distilled under reduced pressure to remove the solvent. The residue was purified by chromatography on a silica gel column, whereby from n-hexane-ethyl acetate (3:1, v/v) eluate fractions, methyl 2-methylindazole-3-carboxylate (1.62 g, 26%) was obtained as a pale yellow solid.

$^1$H-NMR (CDCl$_3$) δ: 4.03 (s, 3H), 4.52 (s, 3H), 7.28 (m, 1H), 7.35 (m, 1H), 7.76 (d, J=8.3 Hz, 1H), 8.00 (d, J=8.3 Hz, 1H).

MS (ESI) m/z 191 (M$^+$+1).

From n-hexane-ethyl acetate (1:1, v/v) eluate fractions, 1-methylindazole-3-carboxylate (4.52 g, 73%) was obtained as a yellow solid.

$^1$H-NMR (CDCl$_3$) δ: 4.04 (s, 3H), 4.17 (s, 3H), 7.31–7.35 (m, 2H), 7.46 (d, J=4.4 Hz, 1H), 8.22 (d, J=8.1 Hz, 1H).

MS (ESI) m/z 191 (M$^+$+1).

(Step 7) Synthesis of 1-methylindazole-3-carboxylic acid

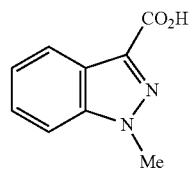

In THF (250 ml) was dissolved methyl 1-methylindazole-3-carboxylate (4.49 g, 23.6 mmol). To the resulting solution was added 0.25N NaOH (145 ml, 35.4 mmol), followed by stirring at room temperature for 24 hours. The reaction mixture was distilled under reduced pressure to remove the solvent. To the residue was added 1N HCl (145 ml). The crystals thus precipitated were collected by filtration under reduced pressure, washed with water, and dried under reduced pressure to give 1-methylindazole-3-carboxylic acid (2.81 g, 68%) as a pale yellow solid.

$^1$H-NMR (DMSO-$d_6$) δ: 4.15 (s, 3H), 7.32 (m, 1H), 7.48 (m, 1H), 7.75 (d, J=8.1 Hz, 1H), 8.08 (d, J=8.1 Hz, 1H), 12.96 (broad s, 1H).

MS (ESI) m/z 177 (M$^+$+1).

(Step 8) Synthesis of ethyl (5-chloro-2-fluoro-4-((1-methyl-3-indazolylcarbonyl)amino)phenyl)acetate

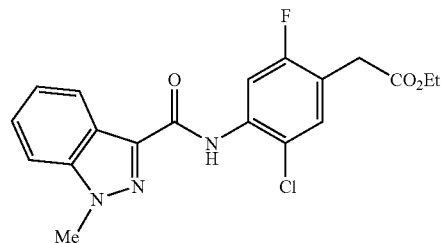

In benzene (30 ml), oxalyl chloride (0.54 ml, 6.24 mmol) was added dropwise to 1-methylindazolyl-3-carboxylic acid (1.00 g, 5.68 mmol) and DMF (44.0 μl, 0.57 mmol) under stirring at room temperature. After completion of the dropwise addition, the reaction mixture was stirred at room temperature for 1 hour. A solution of ethyl (4-amino-5-chloro-2-fluorophenyl)acetate (1.31 g, 5.68 mmol) and triethylamine (4.74 ml, 34.0 mmol) in benzene (5.0 ml), which solution had been prepared in advance, was added to the reaction mixture. The resulting mixture was heated under reflux for 4 hours. The reaction mixture was cooled to room temperature, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (3:1, v/v) eluate fractions, (5-chloro-2-fluoro-4-((1-methyl-3-indazolylcarbonyl)amino)phenyl)acetate (1.40 g, 63%) was obtained as a colorless solid.

$^1$H-NMR (CDCl$_3$) δ: 1.28 (t, J=7.1 Hz, 3H), 3.62 (s, 2H), 4.17 (s, 3H), 4.18 (q, J=7.1 Hz, 2H), 7.33–7.39 (m, 2H), 7.44–7.50 (m, 2H), 8.38 (d, J=8.3 Hz, 1H), 8.53 (d, J=11.9 Hz, 1H), 9.50 (broad s, 1H).

MS (ESI) m/z 390 (M$^+$+1).

(Step 9) Synthesis of (5-chloro-2-fluoro-4-((1-methyl-3-indazolylcarbonyl)amino)phenyl)acetic acid

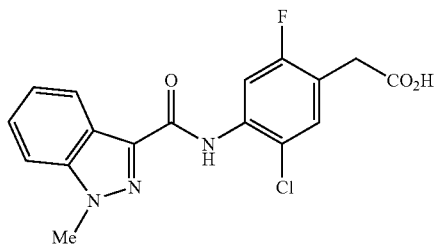

To ethyl (5-chloro-2-fluoro-4-((1-methyl-3-indazolylcarbonyl)amino)phenyl)acetate (1.40 g, 3.59 mmol) were added THF (36 ml) and 0.25N NaOH (21.5 ml, 5.39 mmol). The resulting mixture was stirred at room temperature for 6 hours. The reaction mixture was poured in 1N HCl (6.0 ml). The crystals thus precipitated were collected by filtration under reduced pressure, washed with water and dried under reduced pressure to give (5-chloro-2-fluoro-4-((1-methyl-3-indazolylcarbonyl)amino)phenyl)acetic acid (1.23 g, 95%) as a colorless solid.

$^1$H-NMR (DMSO-$d_6$) δ: 3.65 (s, 2H), 4.21 (s, 3H), 7.37 (m, 1H), 7.53 (m, 1H), 7.59 (d, J=7.3 Hz, 1H), 7.80 (d, J=8.6 Hz, 1H), 8.13 (d, J=11.4 Hz, 1H), 8.21 (d, J=8.1 Hz, 1H), 9.68 (s, 1H), 12.58 (broad s, 1H).

MS (ESI) m/z 362 (M$^+$+1).

(Step 10) Synthesis of methyl trans-4-(1-((5-chloro-2-fluoro-4-((1-methyl-3-indazolylcarbonyl)amino)phenyl)acetyl)-(4S)-fluoro-(2S)-pyrrolidinylmethoxy)cyclohexanecarboxylate

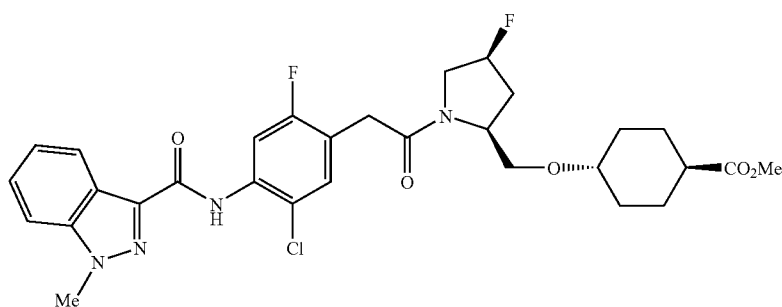

To (5-chloro-2-fluoro-4-((1-methyl-3-indazolylcarbonyl)amino)phenyl)acetic acid (200 mg, 0.55 mmol), methyl trans-4-((4S)-fluoro-(2S)-pyrrolidinylmethoxy)cyclohexanecarboxylate (the compound synthesized in (Step 3) of Example 21) (143 mg, 0.55 mmol), HOBt (15.0 mg, 0.11 mmol), and DMAP (14.0 mg, 0.11 mmol) were added DMF (5.0 ml) and EDC HCl (159 mg, 0.83 mmol). The resulting mixture was stirred at room temperature for 6 hours. Water was added to the reaction mixture, followed by extraction with ethyl acetate. The extract was washed with saturated brine, dried over anhydrous sodium sulfate, and distilled under reduced pressure to remove the solvent. The residue was purified by chromatography on a silica gel column, whereby from ethyl acetate eluate fractions, methyl trans-4-(1-((5-chloro-2-fluoro-4-((1-methyl-3-indazolylcarbonyl)amino)phenyl)acetyl)-(4S)-fluoro-(2S)-pyrrolidinylmethoxy)cyclohexanecarboxylate (332 mg, 100%) was obtained as a yellow amorphous substance.

$^1$H-NMR (CDCl$_3$) δ: 1.24–1.33 (m, 2H), 1.40–1.53 (m, 2H), 1.98–2.53 (m, 7H), 3.26–4.14 (m, 10H), 4.17 (s, 3H), 4.31 and 4.38 (each m, total 1H), 5.26 and 5.31 (each m, total 1H), 7.29–7.53 (m, 4H), 8.39 (d, J=8.3 Hz, 1H), 8.51 (m, 1H), 9.50 (broad s, 1H).

MS (ESI) m/z 604 (M$^+$+1).

(Step 11) Synthesis of trans-4-(1-((5-chloro-2-fluoro-4-((1-methyl-3-indazolylcarbonyl)amino)phenyl)acetyl)-(4S)-fluoro-(2S)-pyrrolidinylmethoxy)cyclohexanecarboxylic acid

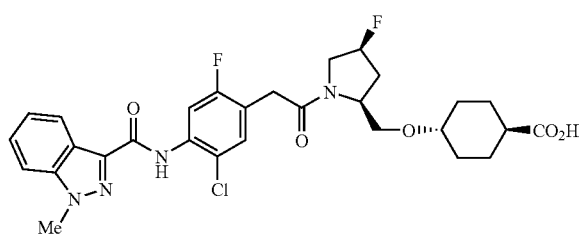

To methyl trans-4-(1-((5-chloro-2-fluoro-4-((1-methyl-3-indazolylcarbonyl)amino)phenyl)acetyl)-(4S)-fluoro-(2S)-pyrrolidinylmethoxy)cyclohexanecarboxylate (332 mg, 0.55 mmol) were added THF (5.5 ml) and 0.25N NaOH (3.30 ml, 0.82 mmol), and the resulting mixture was stirred at room temperature for 18 hours. The reaction mixture was poured in 1N HCl (1.1 ml). The crystals thus precipitated were collected by filtration under reduced pressure, washed with water and dried under reduced pressure to give the title compound (300 mg, 93%) as a colorless solid.

IR (ATR) ν 3363, 2938, 2863, 1725, 1687, 1648, 1621, 1585, 1525, 1481 cm$^{-1}$;

$^1$H-NMR (DMSO-$d_6$) δ: 1.18–1.38 (m, 4H), 1.86–2.33 (m, 7H), 3.18–3.99 (m, 7H), 4.13 and 4.35 (each m, total 1H), 4.22 (s, 3H), 5.33 and 5.42 (each m, total 1H), 7.37 (m, 1H), 7.45–7.56 (m, 2H), 7.82 (d, J=8.3 Hz, 1H), 8.08 and 8.10 (each d, J=11.4 Hz, total 1H), 8.21 (d, J=8.3 Hz, 1H), 9.71 (broad s, 1H), 12.06 (broad s, 1H).

MS (ESI) m/z 589 (M$^+$+1);

Anal. Calcd for $C_{29}H_{31}ClF_2N_4O_5 \cdot 0.25H_2O$: C, 58.68; H, 5.35; N, 9.44. Found: C, 58.46; H, 5.31; N, 9.25.

Example 88 trans-4-(1-((5-Chloro-2-fluoro-4-((2-methyl-3-indazolylcarbonyl)amino)phenyl)acetyl)-(4S)-fluoro-(2S)-pyrrolidinylmethoxy)cyclohexanecarboxylic acid (Step 1) Synthesis of 2-methylindazole-3-carboxylic acid

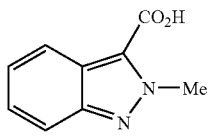

To methyl 2-methylindazole-3-carboxylate (1.59 g, 8.36 mmol) were added THF (85 ml) and 0.25N NaOH (50 ml, 12.5 mmol) and the resulting mixture was stirred at room temperature for 24 hours. The reaction mixture was distilled under reduced pressure to remove the solvent. To the residue was added water, followed by the addition of 1N HCl (50 ml). The crystals thus precipitated were collected by filtration under reduced pressure, washed with water and dried under reduced pressure to give 2-methylindazole-3-carboxylic acid (1.34 g, 91%) as a colorless solid.

$^1$H-NMR (DMSO-$d_6$) δ: 4.43 (s, 3H), 7.29 (m, 1H), 7.35 (m, 1H), 7.74 (dd, J=8.1,1.0 Hz, 1H), 7.98 (d, J=8.5 Hz, 1H), 13.59 (broad s, 1H).

MS (ESI) m/z 177 (M$^+$+1).

(Step 2) Synthesis of ethyl (5-chloro-2-fluoro-4-((2-methyl-3-indazolylcarbonyl)amino)phenyl)acetate

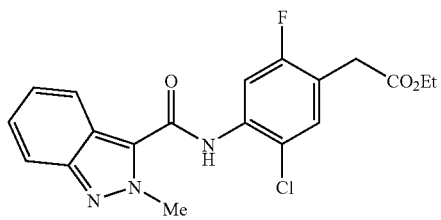

To 2-methylindazole-3-carboxylic acid (650 mg, 3.69 mmol) and DMF (29.0 μl, 0.37 mmol) was added benzene (20 ml). Under stirring at room temperature, oxalyl chloride (0.39 ml, 4.43 mmol) was added dropwise to the resulting mixture. After completion of the dropwise addition, the reaction mixture was stirred for further 1 hour at room temperature. A solution of ethyl (4-amino-5-chloro-2-fluorophenyl)acetate (855 mg, 3.69 mmol) and triethylamine (3.09 ml, 22.1 mmol) in benzene (3.0 ml), which had been prepared in advance, was added dropwise to the reaction mixture, and the mixture was heated under reflux for 16 hours. The reaction mixture was then cooled to room temperature, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (5:1, v/v) eluate fractions, ethyl (5-chloro-2-fluoro-4-((2-methyl-3-indazolylcarbonyl)amino)phenyl) acetate (390 mg, 27%) was obtained as a pale yellow solid.

$^1$H-NMR (CDCl$_3$) δ: 1.29 (t, J=7.1 Hz, 3H), 3.65 (s, 2H), 4.20 (q, J=7.1 Hz, 2H), 4.55 (s, 3H), 7.35–7.42 (m, 3H), 7.84 (d, J=8.3 Hz, 1H), 7.97 (d, J=8.1 Hz, 1H), 8.49 (d, J=11.5 Hz, 1H), 8.54 (broad s, 1H).

MS (ESI) m/z 390 (M$^+$+1).

(Step 3) Synthesis of (5-chloro-2-fluoro-4-((2-methyl-3-indazolylcarbonyl)amino)phenyl)acetic acid

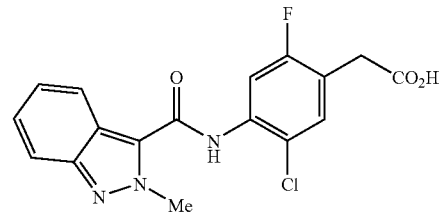

To ethyl (5-chloro-2-fluoro-4-((2-methyl-3-indazolylcarbonyl)amino)phenyl)acetate (390 mg, 1.00 mmol) were added THF (10 ml) and 0.25N NaOH (6.00 ml, 1.50 mmol). The resulting mixture was stirred at room temperature for 16 hours. The reaction mixture was poured in 1N HCl (1.5 ml). The crystals thus precipitated were collected by filtration under reduced pressure, washed with water and dried under reduced pressure to give (5-chloro-2-fluoro-4-((2-methyl-3-indazolylcarbonyl)amino)phenyl)acetic acid (1.23 g, 95%) as a brown solid.

$^1$H-NMR (DMSO-$d_6$) δ: 3.68 (s, 2H), 4.39 (s, 3H), 7.30 (m, 1H), 7.38 (m, 1H), 7.62 (d, J=7.6 Hz, 1H), 7.74–7.80 (m, 2H), 8.03 (d, J=8.3 Hz, 1H), 10.25 (broad s, 1H), 12.62 (broad s, 1H).

MS (ESI) m/z 362 (M$^+$+1).

(Step 4) Synthesis of methyl trans-4-(1-((5-chloro-2-fluoro-4-((2-methyl-3-indazolylcarbonyl)amino)phenyl)acetyl)-(4S)-fluoro-(2S)-pyrrolidinylmethoxy)cyclohexanecarboxylate

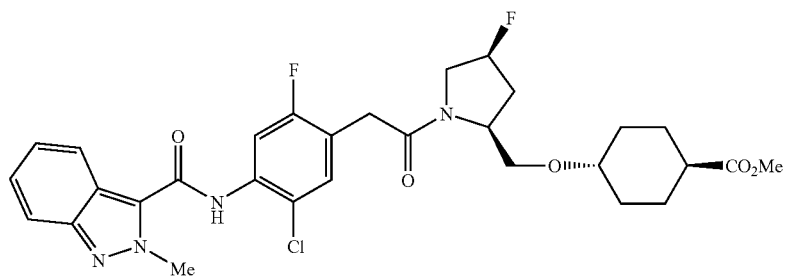

To (5-chloro-2-fluoro-4-((2-methyl-3-indazolylcarbonyl)amino)phenyl)acetic acid (200 mg, 0.55 mmol), methyl trans-4-((4S)-fluoro-(2S)-pyrrolidinylmethoxy)cyclohexanecarboxylate (the compound synthesized in (Step 3) of Example 21) (143 mg, 0.55 mmol), HOBt (15.0 mg, 0.11 mmol), and DMAP (14.0 mg, 0.11 mmol) were added DMF (5.0 ml) and EDC HCl (159 mg, 0.83 mmol). The resulting mixture was stirred at room temperature for 6 hours. To the reaction mixture was added water, followed by extraction with ethyl acetate. The extract was washed with saturated brine, dried over anhydrous sodium sulfate, and distilled under reduced pressure to remove the solvent. The residue was purified by chromatography on a silica gel column, whereby from ethyl acetate eluate fractions, methyl trans-4-(1-((5-chloro-2-fluoro-4-((2-methyl-3-indazolylcarbonyl)amino)phenyl)acetyl)-(4S)-fluoro-(2S)-pyrrolidinylmethoxy)cyclohexanecarboxylate (313 mg, 94%) was obtained as a yellow amorphous substance.

$^1$H-NMR (CDCl$_3$) δ: 1.24–1.29 (m, 2H), 1.32–1.58 (m, 2H), 1.97–2.54 (m, 7H), 3.23–4.02 (m, 10H), 4.31 and 4.38 (each m, total 1H), 4.54 (s, 3H), 5.27 and 5.32 (each m, total 1H), 7.31–7.47 (m, 3H), 7.84 (d, J=7.6 Hz, 1H), 7.96 (d, J=8.3 Hz, 1H), 8.47 (m, 1H), 8.54 (broad s, 1H).

MS (ESI) m/z 604 (M$^+$+1).

(Step 5) Synthesis of trans-4-(1-((5-chloro-2-fluoro-4-((2-methyl-3-indazolylcarbonyl)amino)phenyl)acetyl)-(4S)-fluoro-(2S)-pyrrolidinylmethoxy)cyclohexanecarboxylic acid

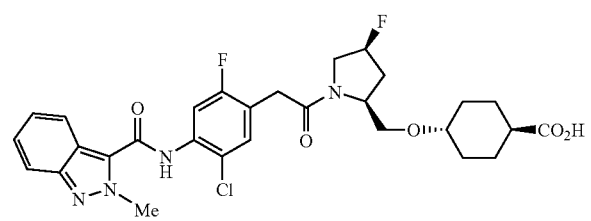

To methyl trans-4-(1-((5-chloro-2-fluoro-4-((2-methyl-3-indazolylcarbonyl)amino)phenyl)acetyl)-(4S)-fluoro-(2S)-pyrrolidinylmethoxy)cyclohexanecarboxylate (313 mg, 0.52 mmol) were added THF (5.0 ml) and 0.25N NaOH (3.11 ml, 0.78 mmol). The resulting mixture was stirred at room temperature for 18 hours. To the reaction mixture was added 1N HCl (0.85 ml). The crystals thus precipitated were collected by filtration under reduced pressure, washed with water and dried under reduced pressure to give the title compound (253 mg, 83%) as a colorless solid.

IR (ATR) ν 3409, 2942, 2861, 1725, 1681, 1646, 1621, 1587, 1521, 1454 cm$^{-1}$;

$^1$H-NMR (DMSO-d$_6$) δ: 1.16–1.42 (m, 4H), 1.86–2.33 (m, 7H), 3.19–4.36 (m, 8H), 4.39 (s, 3H), 5.33 and 5.42 (each m, total 1H), 7.31 (m, 1H), 7.38 (m, 1H), 7.49 and 7.51 (each d, J=7.1 Hz, total 1H), 7.74–7.77 (m, 2H), 8.04 (d, J=8.3 Hz, 1H), 10.27 (broad s, 1H), 12.03 (broad s, 1H).

MS (ESI) m/z 589 (M$^+$+1);

Anal. Calcd for C$_{29}$H$_{31}$ClF$_2$N$_4$O$_5$ 0.25H$_2$O: C, 58.68; H, 5.35; N, 9.44. Found: C, 58.68; H, 5.38; N, 9.32.

Example 89 trans-4-(1-((3-Chloro-4-((1-methyl-3-indazolylcarbonyl)amino)phenyl)acetyl)-(4S)-fluoro-(2S)-pyrrolidinylmethoxy)cyclohexanecarboxylic acid (Step 1) Synthesis of methyl (3-chloro-4-((1-methyl-3-indazolylcarbonyl)amino)phenyl)acetate

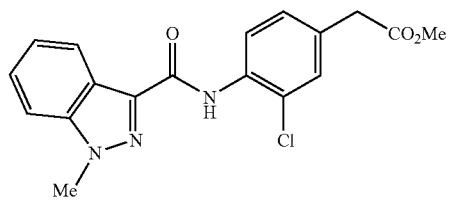

To 1-methylindazole-3-carboxylic acid (600 mg, 3.41 mmol) and DMF (27.0 µl, 0.34 mmol) was added methylene chloride (20 ml). Under stirring at room temperature, oxalyl chloride (0.36 ml, 4.09 mmol) was added dropwise to the resulting mixture. After completion of the dropwise addition, the reaction mixture was stirred at room temperature for 50 hours and the solvent was distilled off under reduced pressure. The residue was dissolved in methylene chloride (5 ml). The resulting solution was added to a solution of methyl 4-amino-3-chlorophenylacetate (680 mg, 3.41 mmol) and triethylamine (1.42 ml, 10.2 mmol) in methylene chloride (5 ml) under stirring at room temperature. The reaction mixture was heated under reflux at room temperature for 7 hours. After the reaction mixture was cooled to room temperature, water was added thereto, followed by extraction with chloroform. The extract was washed with saturated brine, dried over anhydrous sodium sulfate, and distilled under reduced pressure to remove the solvent. The residue was purified by chromatography on a silica gel column, whereby from n-hexane-ethyl acetate (2:1, v/v) eluate fractions, methyl (3-chloro-4-((1-methyl-3-indazolylcarbonyl)amino)phenyl)acetate (1.08 g, 89%) was obtained as a yellow solid.

$^1$H-NMR (CDCl$_3$) δ: 3.61 (s, 2H), 3.72 (s, 3H), 4.18 (s, 3H), 7.24 (dd, J=8.6,2.0 Hz, 1H), 7.34 (m, 1H), 7.38 (d, J=2.0 Hz, 1H), 7.45–7.50 (m, 2H), 8.41 (d, J=8.0 Hz, 1H), 8.61 (d, J=8.6 Hz, 1H), 9.47 (broad s, 1H).

MS (LCMS) m/z 358 (M$^+$+1).

(Step 2) Synthesis of (3-chloro-4-((1-methyl-3-indazolylcarbonyl)amino)phenyl)acetic acid

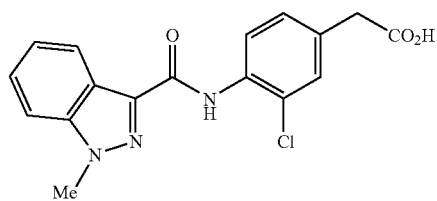

To methyl (3-chloro-4-((1-methyl-3-indazolylcarbonyl)amino)phenyl)acetate (1.08 g, 3.02 mmol) were added THF (30 ml) and 0.25N NaOH (18.1 ml, 4.53 mmol) and the resulting mixture was stirred at room temperature for 16 hours. The reaction mixture was poured in 1N HCl (5.0 ml). The crystals thus precipitated were collected by filtration under reduced pressure, washed with water, and dried under reduced pressure to give (3-chloro-4-((1-methyl-3-indazolylcarbonyl)amino)phenyl)acetic acid (0.99 g, 95%) as a brown solid.

¹H-NMR (DMSO-d₆) δ: 3.62 (s, 2H), 4.21 (s, 3H), 7.28 (dd, J=8.3,1.7 Hz, 1H), 7.35 (m, 1H), 7.47 (d, J=1.7 Hz, 1H), 7.53 (m, 1H), 7.80 (d, J=8.5 Hz, 1H), 8.11 (d, J=8.3 Hz, 1H), 8.21 (d, J=8.1 Hz, 1H), 9.69 (s, 1H), 12.49 (broad s, 1H).

MS (LCMS) m/z 344 (M⁺+1).

(Step 3) Synthesis of methyl trans-4-(1-((3-chloro-4-((1-methyl-3-indazolylcarbonyl)amino)phenyl)acetyl)-(4S)-fluoro-(2S)-pyrrolidinylmethoxy)cyclohexanecarboxylate

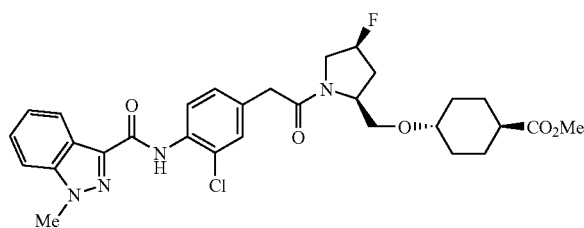

To (3-chloro-4-((1-methyl-3-indazolylcarbonyl)amino)phenyl)acetic acid (250 mg, 0.73 mmol), methyl trans-4-((4S)-fluoro-(2S)-pyrrolidinylmethoxy)cyclohexanecarboxylate (the compound synthesized in (Step 3) of Example 21) (189 mg, 0.73 mmol), HOBt (20.0 mg, 0.15 mmol), and DMAP (18.0 mg, 0.15 mmol) were added DMF (5.0 ml) and EDC HCl (209 mg, 1.09 mmol). The resulting mixture was stirred at room temperature for 17 hours. The reaction mixture was added with water, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (1:2, v/v) eluate fractions, methyl trans-4-(1-((3-chloro-4-((1-methyl-3-indazolylcarbonyl)amino)phenyl)acetyl)-(4S)-fluoro-(2S)-pyrrolidinylmethoxy)cyclohexanecarboxylate (414 mg, 97%) was obtained as a yellow amorphous substance.

¹H-NMR (CDCl₃) δ: 1.21–1.29 (m, 2H), 1.33–1.53 (m, 2H), 1.97–2.50 (m, 7H), 3.24–4.09 (m, 10H), 4.15 (s, 3H), 4.21 and 4.37 (each m, total 1H), 5.25 (m, 1H), 7.20 (m, 1H), 7.30–7.38 (m, 2H), 7.40–7.47 (m, 2H), 8.38 (d, J=8.1 Hz, 1H), 8.57 and 8.59 (each d, J=7.3 Hz, total 1H), 9.44 (broad s, 1H).

MS (ESI) m/z 586 (M⁺+1).

(Step 4) Synthesis of trans-4-(1-((3-chloro-4-((1-methyl-3-indazolylcarbonyl)amino)phenyl)acetyl)-(4S)-fluoro-(2S)-pyrrolidinylmethoxy)cyclohexanecarboxylic acid

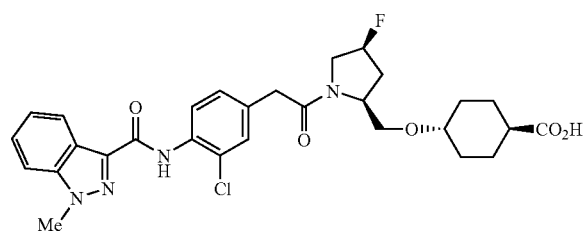

To methyl trans-4-(1-((3-chloro-4-((1-methyl-3-indazolylcarbonyl)amino)phenyl)acetyl)-(4S)-fluoro-(2S)-pyrrolidinylmethoxy)cyclohexanecarboxylate (414 mg, 0.71 mmol) were added THF (7.0 ml) and 0.25N NaOH (4.25 ml, 1.06 mmol). The resulting mixture was stirred at room temperature for 20 hours. To the reaction mixture was added 1N HCl (1.5 ml). The crystals thus precipitated were collected by filtration under reduced pressure, washed with water, and dried under reduced pressure to give the title compound (353 mg, 87%) as a colorless solid.

IR (ATR) ν 3376, 2937, 2859, 1720, 1685, 1600, 1521, 1484 cm⁻¹;

¹H-NMR (DMSO-d₆) δ: 1.14–1.41 (m, 4H), 1.85–1.99 (m, 4H), 2.08–2.26 (m, 3H), 3.16–3.88 (m, 7H), 4.14 and 4.34 (each m, total 1H), 4.21 (s, 3H), 5.32 and 5.39 (each m, total 1H), 7.24 (m, 1H), 7.35 (m, 1H), 7.42 (d J=7.6 Hz, 1H), 7.53 (m, 1H), 7.80 (d, J=8.1 Hz, 1H), 8.10 (m, 1H), 8.21 (d, J=8.1 Hz, 1H), 9.69 (s, 1H), 12.06 (broad s, 1H).

MS (ESI) m/z 572 (M⁺+1);

Anal. Calcd for C₂₉H₃₂ClFN₄O₅ 0.25H₂O: C, 60.52; H, 5.69; N, 9.73. Found: C, 60.57; H, 5.64; N, 9.50.

Example 90 trans-4-(1-(3-Chloro-4-((3-oxo-3,4-dihydro-2H-benzo(1,4)thiazine-5-yl-carbonyl)amino)phenylacetyl)-(4S)-fluoro-(2S)-pyrrolidinylmethoxy)cyclohexanecarboxylic acid (Step 1) Synthesis of trans-4-(1-(3-Chloro-4-((3-oxo-3,4-dihydro-2H-benzo(1,4)thiazine-5-yl-carbonyl)amino)phenylacetyl)-(4S)-fluoro-(2S)-pyrrolidinylmethoxy)cyclohexanecarboxylic acid

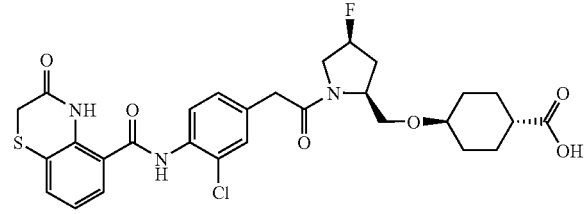

A mixture of trans-4-(1-((4-amino-3-chlorophenyl)acetyl)-(4S)-fluoro-(2S)-pyrrolidinylmethoxy)cyclohexanecarboxylic acid (500 μL of a 1.0M DMF solution, 0.50 mmol), 3-oxo-3,4-dihydro-2H-benzo(1,4)thiazine-5-carboxylic acid (105 mg, 0.5 mmol), HOBt (0.95 ml of a 1.0M DMF solution, 0.95 mmol), EDC HCl (1.5 ml of a 0.5M DMF/methylene chloride solution, 0.75 mmol) and DMAP (catalytic amount) was stirred in a screw vial for 18 hours at room temperature. The reaction mixture was diluted with chloroform (3 ml) and the diluted solution was poured in a fit syringe which had been pre-packed with acidic Hydromatrix. The syringe was washed with chloroform. The solvent was distilled off and to the residue were added THF/methanol (4 ml, 3:1) and 1M NaOH. The resulting mixture was stirred at room temperature for 18 hours. The reaction mixture was distilled and the residue was purified by high-performance liquid chromatography (ARW system) to give the title compound (15 mg, 5%) as a colorless solid.

¹H-NMR (DMSOd₆) δ: 1.10–1.40 (m, 4H), 1.90 (m, 4H), 2.12 (m, 4H), 3.20 (m, 1H), 3.40 (m, 1H), 3.56 (s, 2H), 3.65–3.90 (m, 4H), 4.11 and 4.32 (2m, total 1H), 5.32 (m, 1H), 7.14 (t, J=7.8 Hz, 1H), 7.22 (m, 1H), 7.40 (d, J=6.0 Hz, 1H), 7.51 (m, 1H), 7.59 (d, J=7.8 Hz, 1H), 7.80 (d, J=8.1 Hz, 1H).

MS (ESI) m/z 605 (M+1)⁺.

Anal. Calcd for C₂₉H₃₁ClFN₃O₆S 1.0H₂O: C, 55.99; H, 5.35; N, 6.75. Found: C, 55.85; H, 5.12; N, 6.51.

Example 91 trans-4-(1-(5-Chloro-2-fluoro-4-(1-(indolinyl)carbonylamino)phenylacetyl)-(4S)-fluoro-(2S)-pyrrolidinylmethoxy)cyclohexanecarboxylic acid (Step 1) Synthesis of methyl trans-4-(1-(5-chloro-2-fluoro-4-(1-(indolinyl)carbonylamino)phenylacetyl)-(4S)-fluoro-(2S)-pyrrolidinylmethoxy)cyclohexanecarboxylate

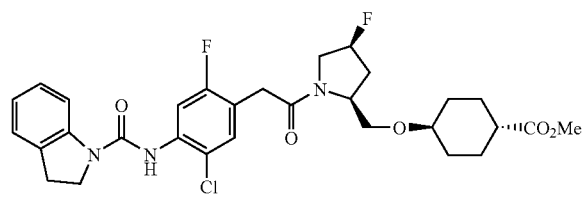

To methyl trans-4-((4S)-fluoro-(2S)-pyrrolidinylmethoxy)cyclohexanecarboxylate (the compound synthesized in (Step 3) of Example 21) (233 mg, 0.90 mmol), 5-chloro-2-fluoro-4-(1-indolinylcarbonylamino)phenylacetic acid (314 mg, 0.90 mmol) and EDC-HCl (190 mg, 0.99 mmol) were added DMF (10 ml) and HOBt (24 mg, 0.18 mmol). The resulting mixture was stirred at room temperature for 18 hours. To the reaction mixture was added water, followed by extraction with ethyl acetate. The extract was washed with saturated brine, dried over anhydrous sodium sulfate and distilled under reduced pressure to remove the solvent. The residue was purified by chromatography on a silica gel column, whereby from ethyl acetate/hexane (4/1) eluate fractions, methyl trans-4-(1-(5-chloro-2-fluoro-4-(1-(indolinyl)carbonylamino)phenylacetyl)-(4S)-fluoro-(2S)-pyrrolidinylmethoxy)cyclohexanecarboxylate (421 mg, 79%) was obtained as a colorless amorphous substance.

$^1$H-NMR (CDCl$_3$), mixture of rotamars, δ: 1.15–1.30 (m, 2H), 1.39–1.42 (m, 2H), 1.96–2.15 (m, 5H), 2.21–2.53 (series of m, 2H), 3.20–3.37 (m, overlap, 1H), 3.26 (t, J=8.8 Hz, 1H), 3.50–3.60 (m, 2H), 3.64–4.00 (series of m, overlap, 4H), 3.64 and 3.66 (s, total 3H), 4.13 (t, J=8.4 Hz, 1H), 4.27–4.40 (m, 1H), 5.18–5.36 (m, 1H), 6.98 (t, J=7.6 Hz, 1H), 7.17–7.23 (m, 3H), 7.35 (dd, J=7.2,4.0 Hz, 1H), 7.93 (d, J=8.0 Hz, 1H), 8.22 (t, J=2.4 Hz, 1H).

MS (ESI) m/z 590 (M$^+$+1).

(Step 2) Synthesis of trans-4-(1-(5-chloro-2-fluoro-4-(1-(indolinyl)carbonylamino)phenylacetyl)-(4S)-fluoro-(2S)-pyrrolidinylmethoxy)cyclohexanecarboxylic acid

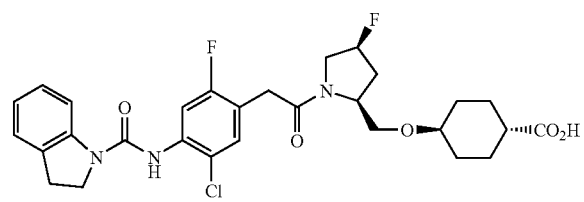

To methyl trans-4-(1-(5-chloro-2-fluoro-4-(1-(indolinyl)carbonylamino)phenylacetyl)-(4S)-fluoro-(2S)-pyrrolidinylmethoxy)cyclohexanecarboxylate (394 mg, 0.67 mmol) were added methanol-THF (1:1, 20 ml) and 0.25N NaOH (13.4 ml, 3.34 mmol). The resulting mixture was stirred at room temperature for 18 hours. To the reaction mixture was added 1N HCl to acidify the mixture, followed by extraction with chloroform/methanol (10/1, v/v). The extract was washed with saturated brine, dried over anhydrous sodium sulfate, then distilled under reduced pressure to remove the solvent. The residue was purified by chromatography on a silica gel column, whereby from chloroform/methanol (10/1) eluate fractions, the title compound (419 mg, 100%) was obtained as a colorless amorphous substance.

$^1$H-NMR (CDCl$_3$), mixture of rotamars, δ: 1.20–1.33 (m, 2H), 1.41–1.54 (m, 2H), 2.50–2.55 (series of m, 8H), 3.27 (t, J=8.0 Hz, 2H), 3.33–4.38 (series of m, 7H), 4.14 (t, J=8.8 Hz, 2H), 6.99 (t, J=7.6 Hz, 1H), 7.19–7.24 (m, 3H), 7.34–7.37 (m, 1H), 7.93 (d, J=8.4 Hz, 1H), 8.22 (t, J=11.6 Hz, 1H).

MS (ESI) m/z 576 (M$^+$+1).

Example 92 trans-4-(3-Chloro-4-(1-(6-fluoroindolinyl)carbonylamino)phenylacetyl)-(4S)-fluoro-(2S)-pyrrolidinylmethoxy)cyclohexanecarboxylic acid (Step 1) Synthesis of ethyl 3-chloro-4-(1-(6-fluoroindolinyl)carbonylamino)phenylacetate

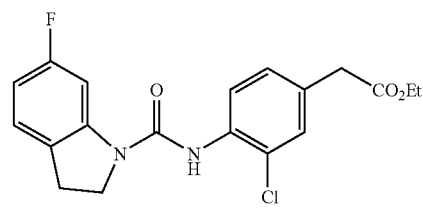

Ethyl 4-amino-3-chlorophenylacetate (520 mg, 2.43 mmol) was dissolved in THF (50 ml). Under stirring at room temperature, triphosgene (240 mg, 0.81 mmol) was added. The resulting mixture was stirred at room temperature for 1 hour. To the reaction mixture was added triethylamine (0.75 ml, 5.34 mmol), followed by the addition of a solution of 6-fluoroindoline (333 mg, 2.43 mmol) in THF (5 ml). After stirring at room temperature for 25 minutes, the reaction mixture was poured in water, followed by extraction with ethyl acetate. The extract was dried over anhydrous sodium sulfate, and distilled under reduced pressure to remove the solvent. The solid thus obtained was recrystallized from hexane/ethyl acetate to give ethyl 3-chloro-4-(1-(6-fluoroindolinyl)carbonylamino)phenylacetate (499 mg, 55%) as a colorless crystalline powder.

MS (ESI) m/z 376 (M$^+$+1).

(Step 2) Synthesis of 3-chloro-4-(1-(6-fluoroindolinyl)carbonylamino)phenylacetic acid

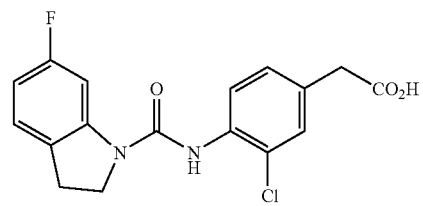

Ethyl 3-chloro-4-(1-(6-fluoroindolinyl)carbonylamino)phenylacetate (499 mg, 1.32 mmol) was dissolved in THF/methanol (1/1, 20 ml). To the resulting solution was added 0.25N NaOH (10.1 ml, 2.65 mmol), followed by stirring at room temperature for 2 hours. The reaction mixture was poured in aqueous 1N HCl and extracted with a chloroform/methanol (10/1) mixture. The extract was dried over anhydrous sodium sulfate, and distilled under reduced pressure to remove the solvent. The resulting solid was recrystallized from hexane/chloroform to give 3-chloro-4-(1-(6-fluoroindolinyl)carbonylamino)phenylacetic acid (358 mg, 78%) as a colorless crystalline powder.

$^1$H-NMR (DMSO-$d_6$) δ: 3.16 (t, J=8.8 Hz, 2H), 3.59 (s, 2H), 4.18 (t, J=8.8 Hz, 2H), 6.67 (brt, J=9.2 Hz, 1H), 7.17 (brt, J=6.4 Hz, 1H), 7.21 (d, J=8.0 Hz, 1H), 7.40 (s, 1H), 7.50 (d, J=8.0 Hz, 1H), 7.56 (dd, J=2.0,11.2 Hz, 1H), 8.32 (s, 1H).

MS (ESI) m/z 349 (M$^+$+1).

(Step 3) Synthesis of methyl trans-4-(3-chloro-4-(1-(6-fluoroindolinyl)carbonylamino)phenylacetyl)-(4S)-fluoro-(2S)-pyrrolidinylmethoxy)cyclohexanecarboxylate

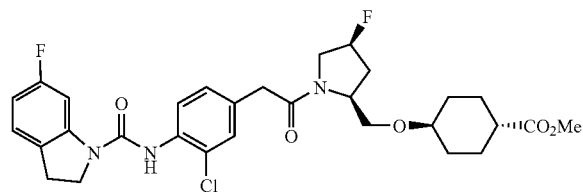

In DMF (12 ml), HOBt (28.0 mg, 0.23 mmol) was added to 3-chloro-4-(1-(6-fluoroindolinyl)carbonylamino)phenylacetic acid (358 mg, 1.03 mmol), methyl trans-4-((4S)-fluoro-(2S)-pyrrolidinylmethoxy)cyclohexanecarboxylate (the compound synthesized in (Step 3) of Example 21) (266 mg, 1.03 mmol) and EDC·HCl (216 mg, 1.13 mmol) and the resulting mixture was stirred at room temperature for 18 hours. The reaction mixture was poured in water, followed by extraction with ethyl acetate. The extract was washed with water, dried over anhydrous sodium sulfate, and distilled under reduced pressure to remove the solvent. The residue was purified by chromatography on a silica gel column, whereby from hexane/ethyl acetate (1/5) eluate fractions, methyl trans-4-(3-chloro-4-(1-(6-fluoroindolinyl)carbonylamino)phenylacetyl)-(4S)-fluoro-(2S)-pyrrolidinylmethoxy)cyclohexanecarboxylate (599 mg, 99%) was obtained as a colorless amorphous substance.

$^1$H-NMR (CDCl$_3$), mixture of rotamars, δ: 1.20–1.31 (m, 2H), 1.42–1.53 (m, 2H), 1.97–2.10 (m, 5H), 2.22–2.61 (series of m, 2H), 3.24 (t, J=8.0 Hz, 2H), 3.22–4.40 (series of m, 8H), 3.67 and 3.71 (s, total 3H), 4.20 (t, J=8.0 Hz, 2H), 5.15–5.34 (m, 1H), 6.63–6.68 (m, 1H), 7.03–7.10 (m, 2H), 7.16 (d, J=8.4 Hz, 1H), 7.34 (brs, 1H), 7.76 (dd, J=2.0, 10.4 Hz, 1H), 8.23 (t, J=8.8 Hz, 1H).

MS (ESI) m/z 590 (M$^+$+1).

(Step 4) Synthesis of trans-4-(3-chloro-4-(1-(6-fluoroindolinyl)carbonylamino)phenylacetyl)-(4S)-fluoro-(2S)-pyrrolidinylmethoxy)cyclohexanecarboxylic acid

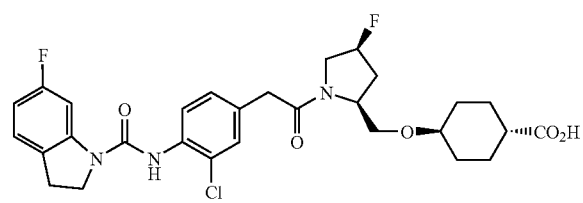

Methyl trans-4-(3-chloro-4-(1-(6-fluoroindolinyl)carbonylamino)phenylacetyl)-(4S)-fluoro-(2S)-pyrrolidinyl-methoxy)cyclohexanecarboxylate (575 mg, 0.98 mmol) was dissolved in THF/methanol (1/1, 20 ml). To the resulting solution was added 0.25N NaOH (11.7 ml, 2.92 mmol). The resulting mixture was stirred at room temperature for 18 hours. The reaction mixture was poured in 1N HCl, followed by extraction with a chloroform/methanol (10/1) mixture. The extract was dried over anhydrous sodium sulfate, and distilled under reduced pressure to remove the solvent. The residue was purified by chromatography on a silica gel column, whereby from chloroform/methanol (10/1) eluate fractions, the title compound (625 mg, 100%) was obtained as a colorless amorphous substance.

$^1$H-NMR (DMSO-$d_6$), mixture of rotamars, δ: 1.44–1.55 (m, 2H), 1.59–1.72 (m, 2H), 2.19–2.56 (series of m, 7H), 3.46 (t, J=8.0 Hz, 2H), 3.44–4.63 (series of m, 8H), 4.49 (t, J=8.4 Hz, 2H), 5.51–5.73 (m, 1H), 6.93–6.98 (m, 1H), 7.44–7.49 (m, 2H), 7.64–7.66 (m, 1H), 7.81–7.89 (m, 2H), 8.55 and 8.56 (s, total 2H) (d, J=8.4 Hz, 1H), 7.34 (brs, 1H), 7.76 (dd, J=2.0, 10.4 Hz, 1H), 8.23 (t, J=8.8 Hz, 1H)

MS (ESI) m/z 576 (M$^+$+1).

Example 93 trans-4-(1-(2-(3-Pyridyl)-6-benzoxazolylacetyl)-(4S)-fluoro-(2S)-pyrrolidinylmethoxy)cyclohexanecarboxylic acid (Step 1) Synthesis of methyl (2-(3-pyridyl)-6-benzoxazolyl)acetate

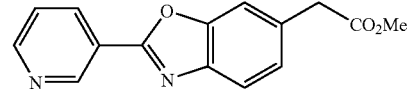

In EtOH (15 ml), pyridine-3-aldehyde (0.63 g, 5.89 mmol) and methyl 4-amino-3-hydroxyphenylacetate (1.06 g, 5.85 mmol) were stirred at room temperature for 20 hours. To the reaction mixture was added iodobenzene diacetate (2.26 g, 7.02 mmol), followed by stirring at room temperature for 20 minutes. The reaction mixture was distilled under reduced pressure to remove the solvent and the residue was dissolved in ethyl acetate. The ethyl acetate solution was washed with a saturated aqueous solution of sodium bicarbonate, dried over anhydrous sodium sulfate, and distilled under reduced pressure to remove the solvent. The residue was purified by chromatography on a silica gel column, whereby from n-hexane/ethyl acetate (1:1, v/v) eluate fractions, methyl (2-(3-pyridyl)-6-benzoxazolyl)acetate (360 mg, 23%) was obtained as a pale yellow solid.

$^1$H-NMR (CDCl$_3$) δ: 3.73 (s, 3H), 3.78 (s, 2H), 7.29 (s, 1H), 7.44–7.50 (m, 1H), 7.56–7.57 (m, 1H), 7.72–7.73 (m, 1H), 8.47–8.50 (m, 1H), 8.75–8.77 (m, 1H), 9.45–9.46 (m, 1H).

(Step 2) Synthesis of (2-(3-pyridyl)-6-benzoxazolyl)acetic acid

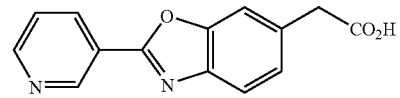

To methyl (2-(3-pyridyl)-6-benzoxazolyl)acetate (360 mg, 1.34 mmol) were added THF (8 ml) and 0.5N NaOH (8.0 ml, 4.00 mmol). The resulting mixture was stirred at room temperature for 20 hours. To the reaction mixture were added water and 1N HCl (5.0 ml, 5 mmol) to acidify the mixture, followed by extraction with ethyl acetate. The extract was washed with saturated brine, dried over anhydrous sodium sulfate, and distilled under reduced pressure to remove the solvent to give (2-(3-pyridyl)-6-benzoxazolyl)acetic acid (179 mg, 52%) as a yellow solid.

$^1$H-NMR (DMSO-$d_6$) δ: 3.78 (s, 2H), 7.34–7.36 (m, 1H), 7.62–7.79 (m, 3H), 8.52–8.55 (m, 1H), 8.80–8.82 (m, 1H), 9.35–9.36 (m, 1H).

(Step 3) Synthesis of methyl trans-4-(1-(2-(3-pyridyl)-6-benzoxazolylacetyl)-(4S)-fluoro-(2S)-pyrrolidinylmethoxy)cyclohexanecarboxylate

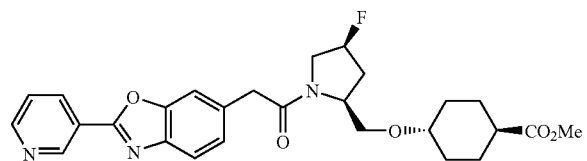

In DMF (5 ml), (2-(3-pyridyl)-6-benzoxazolyl)acetic acid (179 mg, 0.70 mmol), methyl trans-4-((4S)-fluoro-(2S)-pyrrolidinylmethoxy)cyclohexanecarboxylate (the compound synthesized in (Step 3) of Example 21) (182 mg, 0.70 mmol), EDC•HCl (202 mg, 1.05 mmol), HOBt (143 mg, 1.06 mmol), and triethylamine (147 μl, 1.05 mmol) were stirred at room temperature for 2 hours. The reaction mixture was added with water, followed by extraction with ethyl acetate. The extract was washed with saturated brine, dried over anhydrous sodium sulfate, and distilled under reduced pressure to remove the solvent. The residue was purified by chromatography on a silica gel column, whereby from chloroform-methanol (100:1 to 30:1, v/v) eluate fractions, methyl trans-4-(1-(2-(3-pyridyl)-6-benzoxazolylacetyl)-(4S)-fluoro-(2S)-pyrrolidinylmethoxy)cyclohexanecarboxylate (304 mg, 87%) was obtained as a reddish brown thick sticky liquid.

$^1$H-NMR (CDCl$_3$) δ: 1.21–1.53 (m, 4H), 1.97–2.52 (m, 7H), 3.23–3.55 (m, 2H), 3.65–4.08 (m, 8H), 4.25–4.30 and 4.40 (each m, total 1H), 5.19–5.22 and 5.32–5.35 (each m, total 1H), 7.29–7.31 (m, 1H), 7.45–7.49 (m, 1H), 7.56–7.57 (m, 1H), 7.71–7.74 (m, 1H), 8.48–8.50 (m, 1H), 8.75–8.76 (m, 1H), 9.45 (s, 1H).

MS (ESI) m/z 496 (M$^+$+1).

(Step 4) Synthesis of trans-4-(1-(2-(3-pyridyl)-6-benzoxazolylacetyl)-(4S)-fluoro-(2S)-pyrrolidinylmethoxy)cyclohexanecarboxylic acid

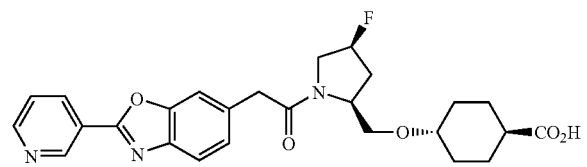

To methyl trans-4-(1-(2-(3-pyridyl)-6-benzoxazolylacetyl)-(4S)-fluoro-(2S)-pyrrolidinylmethoxy)cyclohexanecarboxylate (304 mg, 0.61 mmol) were added THF (4 ml) and 0.5N NaOH (3.7 ml, 1.85 mmol). The resulting mixture was stirred at room temperature for 2 hours. The reaction mixture was poured in ice-1N HCl. The crystals thus precipitated were collected by filtration under reduced pressure, washed with water and dried under reduced pressure to give the title compound (156 mg, 53%) as a pale yellow solid.

$^1$H-NMR (DMSO-$d_6$) δ: 1.14–1.35 (m, 4H), 1.92–2.20 (m, 7H), 3.16–3.99 (m, 7H), 4.14 and 4.34–4.36 (each m, total 1H), 5.24–5.30 and 5.38–5.44 (each m, total 1H), 7.26–7.30 (m, 1H), 7.62–7.66 (m, 2H), 7.73–7.76 (m, 1H), 8.49–8.51 (m, 1H), 8.78–8.79 (m, 1H), 9.33 (s, 1H).

MS (ESI) m/z 482 (M$^+$+1);

Anal. Calcd for $C_{26}H_{28}FN_3O_5$: C, 64.85; H, 5.86; N, 8.73. Found: C, 64.65; H, 5.92; N, 8.46.

Example 94 trans-4-(1-((2-(1-Methyl-2-pyrrolyl)-6-benzoxazolyl)acetyl)-(4S)-fluoro-(2S)-pyrrolidinylmethoxy)cyclohexanecarboxylic acid (Step 1) Synthesis of methyl (2-(1-methyl-2-pyrrolyl)-6-benzoxazolyl)acetate

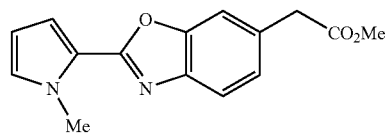

In ethanol (10 ml), 1-methylpyrrole-2-carbaldehyde (0.33 ml, 3.09 mmol) and methyl 4-amino-3-hydroxyphenylacetate (559 mg, 3.09 mmol) were stirred for 4 hours at room temperature. Iodobenzene diacetate (1.19 g, 3.70 mmol) was added to the reaction mixture. After stirring at room temperature for 30 minutes, the reaction mixture was distilled under reduced pressure to remove the solvent. The residue was purified by chromatography on a silica gel column, whereby from n-hexane-ethyl acetate (3:1, v/v) eluate fractions, methyl (2-(1-methyl-2-pyrrolyl)-6-benzoxazolyl)acetate (228 mg, 27%) was obtained as a yellow solid.

$^1$H-NMR (CDCl$_3$) δ: 3.71 (s, 3H), 3.75 (s, 2H), 4.13 (s, 3H), 6.24 (dd, J=3.9,1.7 Hz, 1H), 6.86 (m, 1H), 7.06 (dd, J=3.9,1.7 Hz, 1H), 7.20 (dd, J=8.1,1.7 Hz, 1H), 7.45 (d, J=1.0 Hz, 1H), 7.61 (d, J=8.3 Hz, 1H).

MS (ESI) m/z 270 (M$^+$).

(Step 2) Synthesis of (2-(1-methyl-2-pyrrolyl)-6-benzoxazolyl)acetic acid

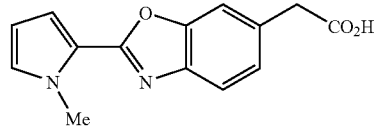

To methyl (2-(1-methyl-2-pyrrolyl)-6-benzoxazolyl)acetate (228 mg, 0.84 mmol) were added THF (8.5 ml) and 0.25N NaOH (5.10 ml, 1.27 mmol). The resulting mixture was stirred at room temperature for 5 hours. The reaction mixture was poured in 1N HCl (10 ml). The crystals thus precipitated were collected by filtration under reduced pressure, washed with water, and dried under reduced pressure to give (2-(1-methyl-2-pyrrolyl)-6-benzoxazolyl)acetic acid (144 mg, 67%) as a pale yellow solid.

¹H-NMR (DMSO-d₆) δ: 3.69 (s, 2H), 4.06 (s, 3H), 6.21 (m, 1H), 6.99 (m, 1H), 7.17 (d, J=2.2 Hz, 1H), 7.22 (d, J=8.1 Hz, 1H), 7.56 (s, 1H), 7.61 '(d, J=8.1 Hz, 1H), 12.36 (broad s, 1H).
MS (ESI) m/z 256 (M⁺).

(Step 3) Synthesis of methyl trans-4-(1-((2-(1-methyl-2-pyrrolyl)-6-benzoxazolyl)acetyl)-(4S)-fluoro-(2S)-pyrrolidinylmethoxy)cyclohexanecarboxylate

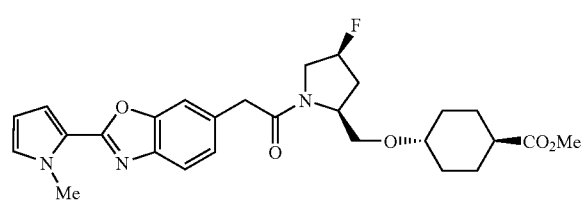

To (2-(1-methyl-2-pyrrolyl)-6-benzoxazolyl)acetic acid (144 mg, 0.56 mmol), methyl trans-4-((4S)-fluoro-(2S)-pyrrolidinylmethoxy)cyclohexanecarboxylate (the compound synthesized in (Step 3) of Example 21) (146 mg, 0.56 mmol), HOBt (15.0 mg, 0.11 mmol) and DMAP (14.0 mg, 0.11 mmol) were added DMF (6.0 ml) and EDC HCl (162 mg, 0.83 mmol). The resulting mixture was stirred at room temperature for 24 hours. To the reaction mixture was added water, followed by extraction with ethyl acetate. The extract was washed with saturated brine, dried over anhydrous sodium sulfate, and distilled under reduced pressure to remove the solvent. The residue was purified by chromatography on a silica gel column, whereby from ethyl acetate eluate fractions, methyl trans-4-(1-((2-(1-methyl-2-pyrrolyl)-6-benzoxazolyl)acetyl)-(4S)-fluoro-(2S)-pyrrolidinylmethoxy)cyclohexanecarboxylate (271 mg, 97%) was obtained as a pale yellow solid.

¹H-NMR (CDCl₃) δ: 1.20–1.33 (m, 2H), 1.39–1.54 (m, 2H), 1.97–2.51 (m, 7H), 3.26 (m, 1H), 3.35 and 3.51 (each m, total 1H), 3.65 and 3.67 (each s, total 3H), 3.69–4.06 (m, 5H), 4.24 and 4.39 (each m, total 1H), 5.24 (m, 1H), 6.24 (m, 1H), 6.86 (m, 1H), 7.06 (m, 1H), 7.18 (m, 1H), 7.44 (m, 1H), 7.60 (m, 1H).
MS (ESI) m/z 498 (M⁺+1).

(Step 4) Synthesis of trans-4-(1-((2-(1-methyl-2-pyrrolyl)-6-benzoxazolyl)acetyl)-(4S)-fluoro-(2S)-pyrrolidinylmethoxy)cyclohexanecarboxylic acid

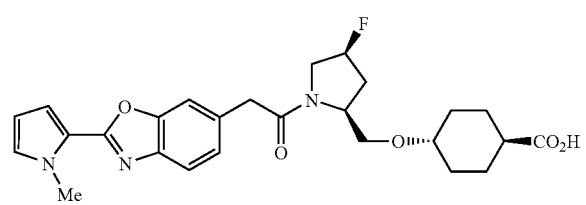

To methyl trans-4-(1-((2-(1-methyl-2-pyrrolyl)-6-benzoxazolyl)acetyl)-(4S)-fluoro-(2S)-pyrrolidinylmethoxy) cyclohexanecarboxylate (271 mg, 0.54 mmol) were added THF (5.5 ml) and 0.25N NaOH (3.27 ml, 0.82 mmol). The resulting mixture was stirred at room temperature for 3 hours. The reaction mixture was poured in 1N HCl (10 ml). The crystals thus precipitated were collected by filtration under reduced pressure, washed with water, and dried under reduced pressure to give the title compound (237 mg, 91%) as a colorless solid.

IR (ATR) ν 2938, 2861, 1718, 1644, 1627, 1575, 1523, 1423 cm⁻¹;
¹H-NMR (DMSO-d₆) δ: 1.09–1.39 (m, 4H), 1.84–2.27 (m, 7H), 3.15–4.03 (m, 7H), 4.06 (s, 3H), 4.12 and 4.32 (each m, total 1H), 5.30 and 5.36 (each m, total 1H), 6.21 (m, 1H), 6.98 (m, 1H), 7.16–7.20 (m, 2H), 7.49 and 7.51 (each m, total 1H), 7.59 and 7.60 (each d, J=8.1 Hz, total 1H), 12.01 (broad s, 1H).
MS (ESI) m/z 484 (M⁺+1);
Anal. Calcd for C₂₆H₃₀FN₃O₅: C, 64.58; H, 6.25; N, 8.69. Found: C, 64.35; H, 6.28; N, 8.49.

Example 95 trans-4-(1-(2-(1-Naphthyl)-6-benzoxazolylacetyl)-(4S)-fluoro-(2S)-pyrrolidinylmethoxy)cyclohexanecarboxylic acid (Step 1) Synthesis of methyl (2-(1-naphthyl)-6-benzoxazolyl)acetate

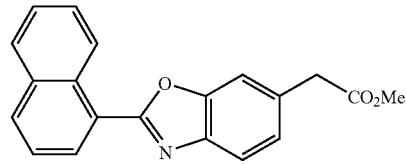

In EtOH (8 ml), 1-naphthaldehyde (263 mg, 1.68 mmol) and methyl 4-amino-3-hydroxyphenylacetate (305 mg, 1.68 mmol) were stirred at room temperature for 12 hours. Iodobenzene diacetate (651 mg, 2.02 mmol) was added to the reaction mixture, followed by stirring at room temperature for 5 minutes. After removal of the solvent by distilling the reaction mixture under reduced pressure, the residue was purified by chromatography on a silica gel column, whereby from n-hexane/ethyl acetate (6:1, v/v) eluate fractions, methyl (2-(1-naphthyl)-6-benzoxazolyl)acetate (223 mg, 42%) was obtained as a pale yellow solid.

¹H-NMR (CDCl₃) δ: 3.73 (s, 3H), 3.79 (s, 2H), 7.29–7.31 (m, 1H), 7.56–7.61 (m, 3H), 7.68–7.76 (m, 1H), 7.80–7.82 (m, 1H), 7.91–7.94 (m, 1H), 8.01–8.03 (m, 1H), 8.39–8.41 (m, 1H), 9.42–9.45 (m, 1H).
MS (ESI) m/z 318 (M⁺+1).

(Step 2) Synthesis of (2-(1-naphthyl)-6-benzoxazolyl)acetic acid

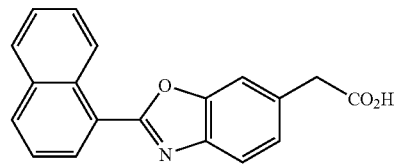

To methyl (2-(1-naphthyl)-6-benzoxazolyl)acetate (223 mg, 0.70 mmol) were added THF (4 ml) and 0.5N NaOH (4.2 ml, 2.10 mmol). The resulting mixture was stirred at room temperature for 2 days. The reaction mixture was acidified 15 with ice-1N HCl. The crystals thus precipitated were collected by filtration under reduced pressure, washed with water and dried under reduced pressure to give (2-(1-naphthyl)-6-benzoxazolyl)acetic acid (194 mg, 91%) as a pale yellow solid.

¹H-NMR (DMSO-d₆) δ: 3.78 (s, 2H), 7.34–7.36 (m, 1H), 7.65–7.78 (m, 4H), 7.84 (d, J=8.1 Hz, 1H), 8.09 (d, J=8.1 Hz, 1H), 8.21–8.23 (m, 1H), 8.43–8.45 (m, 1H), 9.40–9.42 (m, 1H).

(Step 3) Synthesis of methyl trans-4-(1-(2-(1-naphthyl)-6-benzoxazolylacetyl)-(4S)-fluoro-(2S)-pyrrolidinylmethoxy)cyclohexanecarboxylate

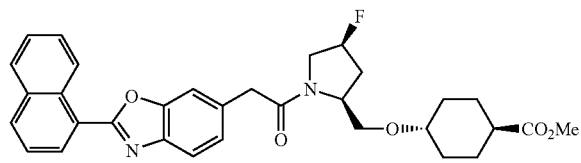

In DMF (7 ml), (2-(1-naphthyl)-6-benzoxazolyl)acetic acid (194 mg, 0.64 mmol), methyl trans-4-((4S)-fluoro-(2S)-pyrrolidinylmethoxy)cyclohexanecarboxylate (the compound synthesized in (Step 3) of Example 21) (166 mg, 0.64 mmol), EDC•HCl (184 mg, 0.96 mmol), HOBt (130 mg, 0.96 mmol), and triethylamine (134 μl, 0.96 mmol) were stirred at room temperature for 13 hours. Water was added to the reaction mixture, followed by extraction with ethyl acetate. The extract was washed with saturated brine, dried over anhydrous sodium sulfate, and distilled under reduced pressure to remove the solvent. The residue was purified by chromatography on a silica gel column with chloroform-methanol (100:1 to 60:1, v/v) eluate fractions, methyl trans-4-(1-(2-(1-naphthyl)-6-benzoxazolylacetyl)-(4S)-fluoro-(2S)-pyrrolidinylmethoxy)cyclohexanecarboxylate (310 mg, 89%) was obtained as a pale yellow solid.

¹H-NMR (CDCl₃) δ: 1.21–1.53 (m, 4H), 1.96–2.51 (m, 7H), 3.25–3.54 (m, 2H), 3.63–4.10 (m, 8H), 4.25–4.30 and 4.40 (each m, total 1H), 5.17–5.19 and 5.31–5.32 (each m, total 1H), 7.27–7.29 (m, 1H), 7.56–7.61 (m, 3H), 7.68–7.72 (m, 1H), 7.79–7.82 (m, 1H), 7.93 (d, J=8.1 Hz, 1H), 8.02 (d, J=8.1 Hz, 1H), 8.39–8.41 (m, 1H), 9.43–9.45 (m, 1H).

MS (ESI) m/z 545 (M⁺+1).

(Step 4) Synthesis of trans-4-(1-(2-(1-naphthyl)-6-benzoxazolylacetyl)-(4S)-fluoro-(2S)-pyrrolidinylmethoxy)cyclohexanecarboxylic acid

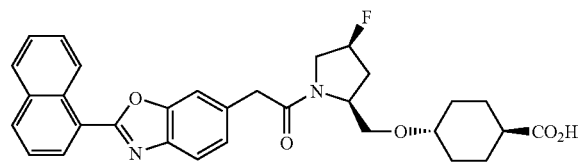

To methyl trans-4-(1-(2-(1-naphthyl)-6-benzoxazolylacetyl)-(4S)-fluoro-(2S)-pyrrolidinylmethoxy)cyclohexanecarboxylate (310 mg, 0.57 mmol) were added THF (3.0 ml) and 0.5N NaOH (3.4 ml, 1.70 mmol). The resulting mixture was stirred at room temperature for 13 hours. The reaction mixture was acidified with ice-1N HCl. The crystals thus precipitated were collected by filtration under reduced pressure, washed with water and dried under reduced pressure to give the title compound (110 mg, 33%) as a white solid.

¹H-NMR (DMSO-d₆) δ: 1.11–1.36 (m, 4H), 1.83–2.20 (m, 7H), 3.19–4.01 (m, 7H), 4.14 and 4.36–4.38 (each m, total 1H), 5.25–5.31 and 5.38–5.45 (each m, total 1H), 7.28–7.32 (m, 1H), 7.64–7.85 (m, 5H), 8.09 (d, J=8.0 Hz, 1H), 8.21 (d, J=8.0 Hz, 1H), 8.42–8.44 (m, 1H), 9.40–9.42 (m, 1H).

MS (ESI) m/z 531 (M⁺+1) ;

Anal. Calcd for C₃₁H₃₁FN₂O₅.1/2H₂O: C, 69.00; H, 5.98; N, 5.19. Found: C, 69.11; H, 5.76; N, 5.17.

Example 96 trans-4-(1-((2-(5-Chloro-1-methyl-3-indolyl)-6-benzoxazolyl)acetyl)-(4S)-fluoro-(2S)-pyrrolidinylmethoxy)cyclohexanecarboxylic acid (Step 1) Synthesis of 5-chloro-1-methylindole

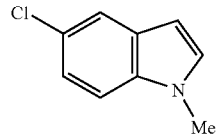

In DMF (65 ml) was dissolved 5-chloroindole (5.00 g, 33.0 mmol), followed by the addition of sodium hydride (60% in oil, 1.45 g, 36.3 mmol) in portions under stirring at 0° C. After the reaction mixture was stirred further for 30 minutes at the same temperature, methyl iodide (2.46 ml, 39.6 mmol) was added. The resulting mixture was stirred at 0° C. for 30 minutes. Ice water was added to the reaction mixture, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (3:1, v/v) eluate fractions, 5-chloro-1-methylindole (5.89 g, 100%) was obtained as a yellow oil.

¹H-NMR (CDCl₃) δ: 3.78 (s, 3H), 6.42 (d, J=3.2 Hz, 1H), 7.06 (d, J=3.2 Hz, 1H), 7.17 (dd, J=8.3 Hz, 1H), 7.23 (d, J=8.3 Hz, 1H), 7.59 (d, J=1.9 Hz, 1H).

(Step 2) Synthesis of 5-chloro-1-methylindole-3-carbaldehyde

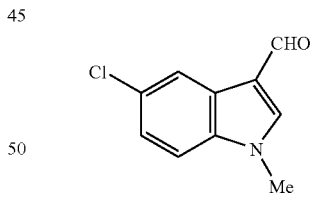

While stirring DMF (70 ml) at 0° C., phosphoryl chloride (4.97 ml, 53.3 mmol) was added dropwise in portions. After completion of the dropwise addition, the reaction mixture was stirred further for 10 minutes at the same temperature. A solution of 5-chloro-1-methylindole (5.89 g, 35.6 mmol) in DMF (10 ml) was added. The resulting mixture was stirred for cyclohexanecarboxylic time at 60° C. for 6 hours. The reaction mixture was cooled to room temperature, and added to a saturated aqueous solution of sodium bicarbonate in portions, followed by extraction with chloroform. The extract was washed with saturated brine, dried over anhydrous magnesium sulfate, and distilled under reduced pressure to remove the solvent under reduced pressure. The residue was purified by chromatography on a silica gel column, whereby from ethyl acetate eluate fractions, 5-chloro-1-methylindole-3-carbaldehyde (5.51 g, 80%) was obtained as a colorless solid.

¹H-NMR (CDCl₃) δ: 3.87 (s, 3H), 7.27 (d, J=8.5 Hz, 1H), 7.31 (dd, J=8.5,1.9 Hz, 1H), 7.69 (s, 1H), 8.30 (d, J=1.9 Hz, 1H), 9.96 (s, 1H).

MS (ESI) m/z 193 (M⁺+1).

(Step 3) Synthesis of (2-(5-chloro-1-methyl-3-indolyl)-6-benzoxazolyl)acetic acid

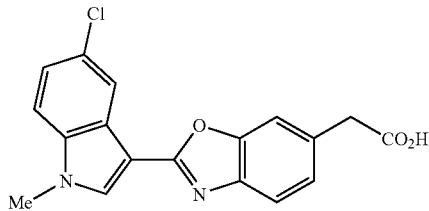

In EtOH (9.0 ml), 5-chloro-1-methylindole-3-carbaldehyde (534 mg, 2.76 mmol) and methyl 4-amino-3-hydroxyphenylacetate (500 mg, 2.76 mmol) were stirred for hours. After iodobenzene diacetate (2.03 g, 6.31 mmol) was added to the reaction mixture and the mixture was stirred at room temperature for 1 hour, the solvent was distilled off under reduced pressure. The residue was purified by chromatography on a silica gel column, whereby from n-hexane-ethyl acetate (1:1, v/v) eluate fractions, a mixture (594 mg) of methyl (2-(5-chloro-1-methyl-3-indolyl)-6-benzoxazolyl) acetate and 5-chloro-1-methylindole-3-carboxaldehyde was obtained. To the resulting mixture were added THF (17 ml) and 0.25N NaOH (10.0 ml, 2.50 mmol) and the mixture was stirred at room temperature for 23 hours. The reaction mixture was distilled under reduced pressure to remove the solvent. To the residue was added 1N HCl (10 ml), followed by extraction with chloroform-methanol (4:1, v/v). The extract was dried over anhydrous sodium sulfate and distilled under reduced pressure to remove the solvent to give (2-(5-chloro-1-methyl-3-indolyl)-6-benzoxazolyl)acetic acid (88 mg, 9%) as a brown solid.

¹H-NMR (DMSO-d₆) δ: 3.73 (s, 2H), 3.94 (s, 3H), 7.25 (dd, J=8.1,1.7 Hz, 1H), 7.36 (dd, 1H, J=8.8,1.7 Hz, 1H), 7.62–7.68 (m, 3H), 8.30 (d, J=1.7 Hz, 1H), 8.41 (s, 1H), 12.38 (broad s, 1H).

MS (ESI) m/z 341 (M⁺+1).

(Step 4) Synthesis of methyl trans-4-(1-((2-(5-chloro-1-methyl-3-indolyl)-6-benzoxazolyl)acetyl)-(4S)-fluoro-(2S)-pyrrolidinylmethoxy)cyclohexanecarboxylate

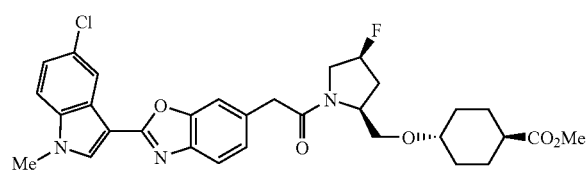

To (2-(5-chloro-1-methyl-3-indolyl)-6-benzoxazolyl)acetic acid (88.0 mg, 0.26 mmol), methyl trans-4-((4S)-fluoro-(2S)-pyrrolidinylmethoxy)cyclohexanecarboxylate (the compound synthesized in (Step 3) of Example 21) (67.0 mg, 0.26 mmol), HOBt (10.0 mg, 0.05 mmol), and DMAP (9.1 mg, 0.05 mmol) were added DMF (3.0 ml) and EDC HCl (74.0 mg, 0.39 mmol). The resulting mixture was stirred at room temperature for 14 hours. Water was added to the reaction mixture, followed by extraction with ethyl acetate. The extract was washed with saturated brine, dried over anhydrous magnesium sulfate, and distilled under reduced pressure to remove the solvent. The residue was purified by chromatography on a silica gel column, whereby from ethyl acetate eluate fractions, methyl trans-4-(1-((2-(5-chloro-1-methyl-3-indolyl)-6-benzoxazolyl)acetyl)-(4S)-fluoro-(2S)-pyrrolidinylmethoxy)cyclohexanecarboxylate (172 mg, 100%) was obtained as a yellow oil.

¹H-NMR (CDCl₃) δ: 1.21–1.34 (m, 2H), 1.40–1.57 (m, 2H), 1.97–2.51 (m, 7H), 3.27 (m, 1H), 3.36 and 3.52 (each m, total 1H), 3.64 and 3.66 (each s, total 3H), 3.67–3.86 (m, 3H), 3.89 (s, 3H), 3.91–4.15 (m, 2H), 4.26 and 4.40 (each m, total 1H), 5.26 (m, 1H), 7;21 (m, 1H), 7.27–7.31 (m, 2H), 7.51 (m, 1H), 7.65 (m, 1H), 7.92 (m, 1H), 8.44 (m, 1H).

MS (ESI) m/z 582 (M⁺+1).

(Step 5) Synthesis of trans-4-(1-((2-(5-chloro-1-methyl-3-indolyl)-6-benzoxazolyl)acetyl)-(4S)-fluoro-(2S)-pyrrolidinylmethoxy)cyclohexanecarboxylic acid

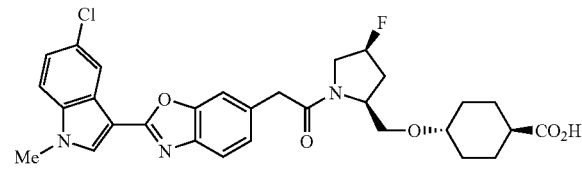

To methyl trans-4-(1-((2-(5-chloro-1-methyl-3-indolyl)-6-benzoxazolyl)acetyl)-(4S)-fluoro-(2S)-pyrrolidinylmethoxy)cyclohexanecarboxylate (172 mg, 0.30 mmol) were added THF (3.0 ml) and 0.25N NaOH (1.80 ml, 0.44 mmol). The resulting mixture was stirred at room temperature for 3 hours. The reaction mixture was poured in 1N HCl (10 ml). The crystals thus precipitated were collected by filtration under reduced pressure, washed with water, and dried under reduced pressure to give the title compound (110 mg, 65%) as a yellow solid.

IR (ATR) ν 2938, 2863, 1720, 1629, 1581, 1434 cm⁻¹;

¹H-NMR (DMSO-d₆) δ: 1.13–1.40 (m, 4H), 1.85–2.07 (m, 4H), 2.11–2.44 (m, 3H), 3.19–3.52 (m, 2H), 3.72–3.90 (m, 6H), 3.94 (s, 3H), 4.07 and 4.35 (each m, total 1H), 5.31 and 5.37 (each m, total 1H), 7.20 (m, 1H), 7.35 (dd, J=8.8, 2.0 Hz, 1H), 7.55 (d, J=8.3 Hz, 1H), 7.64–7.66 (m, 2H), 8.29 (d, J=2.0 Hz, 1H), 8.40 (s, 1H), 12.02 (broad s, 1H).

MS (ESI) m/z 568 (M⁺+1);

Anal. Calcd for C₃₀H₃₁ClFN₃O₅ 1.25H₂O: C, 61.01; H, 5.72; N, 7.12. Found: C, 61.36; H, 5.74; N, 6.37.

Example 97 trans-4-(1-((2-(1-Methyl-3-(1H-pyrrolo(2,3-b)pyridinyl))-6-benzoxazolyl)acetyl)-(4S)-fluoro-(2S)-pyrrolidinylmethoxy)cyclohexanecarboxylic acid (Step 1) Synthesis of 1-methyl-1H-pyrrolo(2,3-b)pyridine

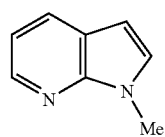

In DMF (85 ml) was dissolved 1 H-pyrrolo(2,3-b)pyridine (5.00 g, 42.3 mmol), followed by the addition of sodium hydride (60% in oil, 1.86 g, 46.6 mmol) in portions under stirring at 0° C. After stirring at 0° C. for 30 minutes, the reaction mixture was added with methyl iodide (3.16 ml, 50.8 mmol). The mixture was stirred at the same temperature for 30 minutes. Ice water was added to the reaction mixture, followed by extraction with ethyl acetate. The extract was washed with saturated brine, dried over anhydrous magnesium sulfate, and distilled under reduced pressure to remove the solvent. The residue was purified by chromatography on a silica gel column, whereby from chloroform-ethyl acetate (1:1, v/v) eluate fractions, 1-methyl-1H-pyrrolo(2,3-b)pyridine (4.87 g, 87%) was obtained as a colorless oil.

$^1$H-NMR (CDCl$_3$): 3.90 (s, 3H), 6.45 (d, J=3.4 Hz, 1H), 7.05 (dd, J=7.8,4.6 Hz, 1H), 7.18 (d, J=3.4 Hz, 1H), 7.90 (dd, J=7.8,1.5 Hz, 1H), 8.33 (dd, J=4.6,1.5 Hz, 1H).

(Step 2) Synthesis of 1-methyl-1H-pyrrolo(2,3-b)pyridine-3-carbaldehyde

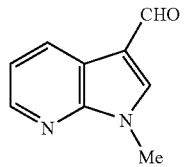

Phosphoryl chloride (5.15 ml, 55.3 mmol) was added dropwise to DMF (70 ml) under stirring at 0° C. After the reaction mixture was stirred at 0° C. for 10 minutes, a solution of 1-methyl-1H-pyrrolo(2,3-b)pyridine (4.87 g, 36.8 mmol) in DMF (5 ml) was added dropwise at the same temperature. After completion of the dropwise addition, the reaction mixture was stirred at 0° C. for 4 hours and at 60° C. for 3.5 hours. The reaction mixture was poured in ice water—a saturated aqueous solution of sodium bicarbonate to neutralize the mixture therewith, followed by extraction with chloroform. The extract was washed with saturated brine, dried over anhydrous sodium sulfate, and distilled under reduced pressure to remove the solvent. The residue was purified by chromatography on a silica gel column, whereby from ethyl acetate eluate fractions, 1-methyl-1H-pyrrolo(2,3-b)pyridine-3-carbaldehyde (4.87 g, 83%) was obtained as a yellow solid.

$^1$H-NMR (CDCl$_3$) δ: 3.98 (s, 3H), 7.28 (dd, J=7.8,4.7 Hz, 1H), 7.85 (s, 1H), 8.44 (d, J=4.7 Hz, 1H), 8.55 (d, J=7.8 Hz, 1H), 9.97 (s, 1H).

MS (ESI) m/z 160 (M$^+$–H).

(Step 3) Synthesis of (2-(1-methyl-3-(1H-pyrrolo(2,3-b)pyridinyl))-6-benzoxazolyl)acetic acid

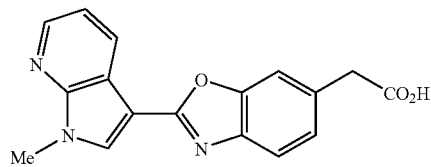

In ethanol (10 ml), 1-methyl-1H-pyrrolo(2,3-b)pyridine-3-carbaldehyde (500 mg, 3.12 mmol) and methyl 4-amino-3-hydroxyphenylacetate (566 mg, 3.12 mmol) were stirred for 20 hours at room temperature. Iodobenzene diacetate (1.21 g, 3.75 mmol) was added to the reaction mixture, followed by stirring at room temperature for 1 hour. The reaction mixture was distilled under reduced pressure to remove the solvent. The residue was purified by chromatography on a silica gel column, whereby from n-hexane-ethyl acetate (1:1, v/v) eluate fractions, a mixture (1.10 g) of methyl (2-(1-methyl-3-(1H-pyrrolo(2,3-b)pyridinyl))-6-benzoxazolyl)acetate and 1-methyl-1H-pyrrolo(2,3-b)pyridine-3-carbaldehyde was obtained as a black solid.

$^1$H-NMR (CDCl$_3$) δ: 3.74 (s, 3H), 3.79 (s, 2H), 4.02 (s, 3H), 7.25–7.32 (m, 2H), 7.52 (s, 1H), 7.67 (d, J=8.1 Hz, 1H), 8.07 (s, 1H), 8.47 (m, 1H), 8.71 (d, J=7.8 Hz, 1H).

MS (ESI) m/z 322 (M$^+$+1).

To the mixture (1.10 g) were added THF (35 ml) and 0.25N NaOH (20.6 ml, 5.15 mmol), and the resulting mixture was stirred for 2 hours at room temperature. The reaction mixture was poured in 1N HCl (20 ml). The crystals thus precipitated were collected by filtration under reduced pressure, washed with water, and dried under reduced pressure to give (2-(1-methyl-3-(1H-pyrrolo(2,3-b)pyridinyl))-6-benzoxazolyl)acetic acid (578 g, 62%) as a brown solid.

$^1$H-NMR (DMSO-d$_6$) δ: 3.74 (s, 2H), 3.96 (s, 3H), 7.26 (dd. J=8.1,1.5 Hz, 1H), 7.36 (dd, J=7.8,4.7 Hz, 1H), 7.62 (d, J=1.5 Hz, 1H), 7.65 (d, J=8.1 Hz, 1H), 8.45 (dd, J=4.7,1.5 Hz, 1H), 8.53 (s, 1H), 8.62 (dd, J=7.8,1.5 Hz, 1H), 12.37 (broad s, 1H).

MS (ESI) m/z 308 (M$^+$+1).

(Step 4) Synthesis of methyl trans-4-(1-((2-(1-methyl-3-(1H-pyrrolo(2,3-b)pyridinyl))-6-benzoxazolyl)acetyl)-(4S)-fluoro-(2S)-pyrrolidinylmethoxy)cyclohexanecarboxylate

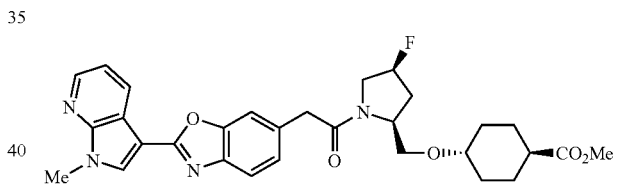

To (2-(1-methyl-3-(1H-pyrrolo(2,3-b)pyridinyl))-6-benzoxazolyl)acetic acid (250 mg, 0.81 mmol), methyl trans-4-((4S)-fluoro-(2S)-pyrrolidinylmethoxy)cyclohexanecarboxylate (the compound synthesized in (Step 3) of Example 21) (211 mg, 0.81 mmol), HOBt (22.0 mg, 0.16 mmol), and DMAP (20.0 mg, 0.16 mmol) were added DMF (8.5 ml) and EDC HCl (234 mg, 1.22 mmol). The resulting mixture was stirred at room temperature for 14 hours. Water was added to the reaction mixture, followed by extraction with ethyl acetate. The extract was washed with saturated brine, dried over anhydrous magnesium sulfate, and distilled under reduced pressure to remove the solvent. The residue was purified by chromatography on a silica gel column, whereby from ethyl acetate eluate fractions, methyl trans-4-(1-((2-(1-methyl-3-(1H-pyrrolo(2,3-b)pyridinyl))-6-benzoxazolyl)acetyl)-(4S)-fluoro-(2S)-pyrrolidinylmethoxy)cyclohexanecarboxylate (419 mg, 94%) was obtained as a yellow solid.

$^1$H-NMR (CDCl$_3$) δ: 1.18–1.34 (m, 2H), 1.39–1.53 (m, 2H), 1.97–2.51 (m, 7H), 3.27 (m, 1H), 3.36 and 3.51 (each m, total 1H), 3.98–3.64 (m, 8H), 4.01 (s, 3H), 4. 26 and 4.40 (each m, total 1H), 5.25 (m, 1H), 7.20 (m, 1H), 7.29 (m, 1H), 7.51 (m, 1H), 7.65 (dd, J=8.1, 5.6 Hz, 1H), 8.05 (d, J=1.8 Hz, 1H), 8.45 (d, J=5.6 Hz, 1H), 8.69 (dd, J=8.1,1.8 Hz, 1H).

MS (ESI) m/z 549 (M$^+$+1).

(Step 5) Synthesis of trans-4-(1-((2-(1-methyl-3-(1H-pyrrolo(2,3-b)pyridinyl))-6-benzoxazolyl)acetyl)-(4S)-fluoro-(2S)-pyrrolidinylmethoxy)cyclohexanecarboxylic acid

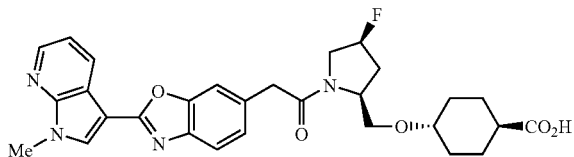

To methyl trans-4-(1-((2-(1-methyl-3-(1H-pyrrolo(2,3-b)pyridinyl))-6-benzoxazolyl)acetyl)-(4S)-fluoro-(2S)-pyrrolidinylmethoxy)cyclohexanecarboxylate (411 mg, 0.75 mmol) were added THF (7.5 ml) and 0.25N NaOH (4.50 ml, 1.12 mmol). The resulting mixture was stirred at room temperature for 19 hours. By the addition of 1N HCl, the pH of the reaction mixture was adjusted to 6. The crystals thus precipitated were collected by filtration under reduced pressure, washed with water, and dried under reduced pressure to give the title compound (281 mg, 70%) as a yellow solid.

IR (ATR) ν 2940, 2861, 1716, 1631, 1569, 1525, 1486, 1442 cm$^{-1}$;

$^1$H-NMR (DMSO-d$_6$) δ: 1.13–1.37 (m, 4H), 1.85–2.09 (m, 4H), 2.11–2.21 (m, 3H), 3.17–3.31 (m, 2H), 3.45 and 3.58 (m, total 1H), 3.72–3.92 (m, 4H), 3.96 (s, 3H), 4.15 and 4.35 (each m, total 1H), 5.32 and 5.37 (each m, total 1H), 7.21 (m, 1H), 7.35 and 7.36 (each d, J=8.1 Hz, total 1H), 7.55 and 7.57 (each s, total 1H), 7.61 and 7.62 (each d, J=8.1 Hz, total 1H), 8.44 (dd, J=4.7,1.5 Hz, 1H), 8.53 (s, 1H), 8.61 (dd, J=7.8,1.5 Hz, 1H), 11.99 (broad s, 1H).

MS (ESI) m/z 535 (M$^+$+1);

Anal. Calcd for C$_{30}$H$_{32}$FN$_3$O$_5$ 0.75H$_2$O: C, 63.55; H, 5.98; N, 10.22. Found: C, 63.67; H, 5.91; N, 10.22.

Example 98 trans-4-(1-((7-Fluoro-2-(1-methyl-3-indolyl)-6-benzoxazolyl)acetyl)-(4S)-fluoro-(2S)-pyrrolidinylmethoxy)cyclohexanecarboxylic acid (Step 1) Synthesis of methyl (7-fluoro-2-(1-methyl-3-indolyl)-6-benzoxazolyl)acetate

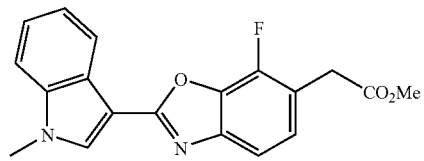

(Process A)

To 1-methylindole-3-carboxylic acid (917 mg, 5.23 mmol) was added methylene chloride (20 ml). Under stirring at 0° C., oxalyl chloride (0.68 ml, 7.85 mmol) and DMF (catalytic amount) were added. After stirring at room temperature for 1.5 hours, the reaction mixture was distilled under reduced pressure to remove the solvent. The residue was added with xylene (20 ml). Methyl (4-amino-2-fluoro-3-hydroxyphenyl)acetate (1.0 g, 5.0 mmol) and boric acid (539 mg, 8.72 mmol) were added to the resulting mixture, followed by stirring at 160° C. for 3 days. After the reaction mixture was cooled to room temperature, ice water was added thereto, followed by extraction with ethyl acetate. The extract was washed with saturated brine, dried over anhydrous sodium sulfate, and distilled under reduced pressure to remove the solvent. The residue was subjected to chromatography on a silica gel column to collect chloroform/ethyl acetate (10/1) eluate fractions and then, purified by chromatography using a thin layer plate, whereby from chloroform/acetone (10/1) eluate fractions, methyl 7-fluoro-2-(1-methyl-3-indolyl)-6-benzoxazolylacetate (62 mg, 4%) was obtained as a pale brown solid.

$^1$H-NMR (CDCl$_3$) δ: 3.73 (s, 3H), 3.81 (s, 2H), 3.88 (s, 3H), 7.15 and 7.17 (each d, each J=6.4 Hz, total 1H, amide isomers), 7.34–7.40 (m, 3H), 7.44 (d, J=8.1 Hz, 1H), 7.94 (s, 1H), 8.43 (m, 1H).

MS (ESI) m/z 339 (M$^+$+1).

(Process B)

In methanol (50 ml), 3-formyl-1-methylindole (796 mg, 5.0 mmol), methyl (4-amino-2-fluoro-3-hydroxyphenyl)acetate (1.0 g, 5.0 mmol) and Molecular Sieves 4A (10 g) were stirred at room temperature for 5 hours and then, at 70° C. for 3 hours. The reaction mixture was cooled to room temperature and iodobenzene diacetate (5.0 mmol) was added thereto. After stirring at room temperature for 14 hours, the reaction mixture was distilled under reduced pressure to remove the solvent. The residue was purified by chromatography on a silica gel column, whereby from n-hexane/ethyl acetate (3/1) eluate fractions, methyl 7-fluoro-2-(1-methyl-3-indolyl)-6-benzoxazolylacetate (860 mg, including impurities) was obtained as a pale brown solid. The compound was provided for the subsequent reaction without further purification.

(Step 2) Synthesis of (7-fluoro-2-(1-methyl-3-indolyl)-6-benzoxazolyl)acetic acid

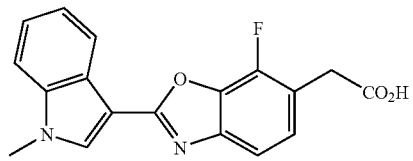

Methyl 7-fluoro-2-(1-methyl-3-indolyl)-6-benzoxazolylacetate (860 mg, the product obtained by Process A of Step 1) was dissolved in THF/methanol (20/10 ml). To the resulting solution was added 1N NaOH (20 ml), followed by stirring at room temperature for 1.5 hours. The reaction mixture was then distilled under reduced pressure to remove the solvent. To the residue thus obtained were added ether and 1N NaOH to separate the mixture into layers. The water layer was acidified with 1N HCl, followed by extraction with ethyl acetate. The extract was washed with saturated brine, dried over anhydrous sodium sulfate, and distilled under reduced pressure to remove the solvent, whereby (7-fluoro-2-(1-methyl-3-indolyl)-6-benzoxazolyl)acetic acid (350 mg, 22%) was obtained as a dark green solid. The compound was provided for the subsequent reaction without further purification.

$^1$H-NMR (CDCl$_3$-CD$_3$OD) δ: 3.56 (s, 3H), 3.91 (s, 2H), 7.36 (m, 3H), 7.79 (s, 1H), 8.26 (d, J=6.8 Hz, 1H), 9.93 (s, 1H).

MS (ESI) m/z 325 (M$^+$+1).

(Step 3) Synthesis of methyl trans-4-(1-((7-fluoro-2-(1-methyl-3-indolyl)-6-benzoxazolyl)acetyl)-(4S)-fluoro-(2S)-pyrrolidinylmethoxy)cyclohexanecarboxylate

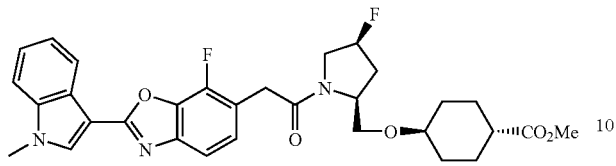

A mixture of (7-fluoro-2-(1-methyl-3-indolyl)-6-benzoxazolyl)acetic acid (350 mg, 1.08 mmol), methyl trans-4-((4S)-fluoro-(2S)-pyrrolidinylmethoxy)cyclohexanecarboxylate (the compound synthesized in (Step 3) of Example 21) (280 mg, 1.08 mmol), EDC HCl (311 mg, 1.62 mmol), HOBt (219 mg, 1.62 mmol) and triethylamine (0.75 ml, 5.40 mmol) was stirred for 7 hours in DMF (10 ml). The reaction mixture was poured in ice water, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane/ethyl acetate (3/1) eluate fractions, methyl trans-4-(1-((7-fluoro-2-(1-methyl-3-indolyl)-6-benzoxazolyl)acetyl)-(4S)-fluoro-(2S)-pyrrolidinylmethoxy)cyclohexanecarboxylate (360 mg, 59%) was obtained as a brown oil.

$^1$H-NMR (CDCl$_3$) δ: 1.21–1.65 (m, 4H), 1.95–2.56 (m, 7H), 3.21–3.39 (m, 2H), 3.56 (dd, J=8.8,6.8 Hz, 1H), 3.64 and 3.67 (each s, total 3 H, amide isomers), 3.68–3.90 (m, 3H), 3.92 (s, 3H), 4.00 and 4.03 (each s, total 1H), 4.31–4.42 (m, 1H), 5.19–5.39 (m, 1H), 7.20 (q, J=8.5 Hz, 1H), 7.36–7.48 (m, 4H), 7.98 (s, 1H), 8.45 (m, 1H).

MS (ESI) m/z 566 (M$^+$+1).

(Step 4) Synthesis of trans-4-(1-((7-fluoro-2-(1-methyl-3-indolyl)-6-benzoxazolyl)acetyl)-(4S)-fluoro-(2S)-pyrrolidinylmethoxy)cyclohexanecarboxylic acid

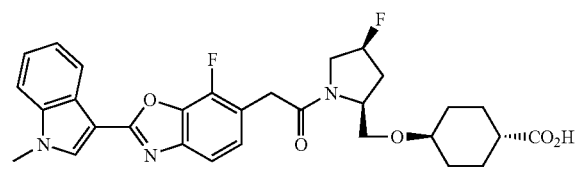

To methyl trans-4-(1-((7-fluoro-2-(1-methyl-3-indolyl)-6-benzoxazolyl)acetyl)-(4S)-fluoro-(2S)-pyrrolidinylmethoxy)cyclohexanecarboxylate (130 mg, 0.23 mmol) were added THF/methanol (10/5 ml) and 1N NaOH (4 ml). The resulting mixture was stirred at room temperature for 13 hours. The reaction mixture was distilled under reduced pressure to remove the solvent. The residue was then acidified with 1N HCl. The crystals thus precipitated were collected by filtration under reduced pressure, washed with water and dried under reduced pressure to give the title compound (93 mg, 74%) as a brown solid.

IR (ATR) ν 2941, 2864, 1716, 1628, 1583, 1504, 1442, 1369 cm$^{-1}$;

$^1$H-NMR (DMSO) δ: 1.13–1.43 (m, 5H), 1.82–2.36 (m, 7H), 3.24 (m, 1H), 3.46–3.93 (m, 4H), 3.95 (s, 3H), 4.11 and 4.15 (each s, total 1H, amide isomers), 4.42 (m, 1H), 5.25–5.50 (m, 1H), 7.22 (m, 1H), 7.35 (m, 2H), 7.48 and 7.50 (each t, J=4.4 and 3.6 Hz respectively, total 1H, amide isomers), 7.63 (d, J=6.6 Hz, 1H), 8.29 (d, J=7.3 Hz, 1H), 8.44 and 8.45 (each s, total 1H, amide isomers).

MS (ESI) m/z 522 (M$^+$+1);

Anal. Calcd for C$_{30}$H$_{31}$F$_2$N$_3$O$_5$ 1H$_2$O: C, 63.26; H, 5.84; N, 7.38. Found: C, 63.52; H, 5.77; N, 7.25.

Example 99 trans-4-(1-((2-(6-Fluoro-1-methyl-3-indolyl)-6-benzoxazolyl)acetyl)-(4S)-fluoro-(2S)-pyrrolidinylmethoxy)cyclohexanecarboxylic acid (Step 1) Synthesis of 6-fluoro-1-methylindole

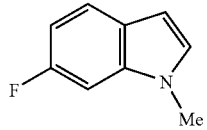

In DMF (65 ml) was dissolved 6-fluoroindole (6.10 g, 45.1 mmol). Under stirring at 0° C., sodium hydride (60% in oil, 1.45 g, 36.3 mmol) was added in portions. After stirring at 0° C. for 30 minutes, methyl iodide (2.46 ml, 39.6 mmol) was added to the reaction mixture. The reaction mixture was stirred further at the same temperature for 2.5 hours. A saturated aqueous solution of ammonium chloride was added, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (5:1, v/v) eluate fractions, 6-fluoro-1-methylindole (6.71 g, 99%) was obtained as a yellow oil.

$^1$H-NMR (CDCl$_3$) δ: 3.73 (s, 3H), 6.45 (d, J=3.2 Hz, 1H), 6.86 (ddd, J=9.8,8.5,2.2 Hz, 1H), 6.98 (dd, J=9.8,2.2 Hz, 1H), 7.01 (d, J=3.2 Hz, 1H), 7.51 (dd, J=8.5,5.3 Hz, 1H).

MS (ESI) m/z 150 (M$^+$+1).

(Step 2) Synthesis of 6-fluoro-1-methylindole-3-carbaldehyde

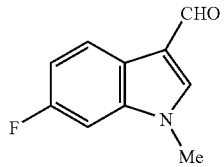

Phosphoryl chloride (5.87 ml, 63.0 mmol) was added in portions while stirring DMF (45 ml) at 0° C. After stirring at the same temperature for 20 minutes, the reaction mixture was added with a solution of 6-fluoro-1-methylindole (6.71 g, 45.0 mmol) in DMF (45 ml) at 0° C. The reaction mixture was stirred for further 0.5 hour. Ice water and 1N NaOH were added to the reaction mixture to neutralize the same, followed by extraction with ethyl acetate. The extract was washed with saturated brine, dried over anhydrous magnesium sulfate, and distilled under reduced pressure to remove the solvent. The residue was purified by chromatography on a silica gel column, whereby from ethyl acetate eluate fractions, 6-fluoro-1-methylindole-3-carbaldehyde (4.18 g, 52%) was obtained as a colorless solid.

$^1$H-NMR (CDCl$_3$) δ: 3.85 (s, 3H), 7.03–7.11 (m, 2H), 7.68 (s, 1H), 8.25 (dd, J=8.8,5.6 Hz, 1H), 9.97 (s, 1H).

MS (ESI) m/z 219 (M$^+$+1+CH$_3$CN).

(Step 3) Synthesis of methyl (2-(6-fluoro-1-methyl-3-indolyl)-6-benzoxazolyl)acetic acid

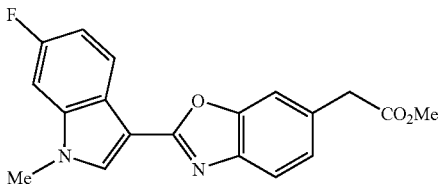

In ethanol (15 ml), 6-fluoro-1-methylindole-3-carbaldehyde (500 mg, 2.82 mmol) and methyl 4-amino-3-hydroxyphenylacetate (767 mg, 4.23 mmol) were stirred at room temperature for 2 hours. Iodobenzene diacetate (1.09 g, 3.38 mmol) was added and the mixture was stirred at room temperature for 1 hour. The reaction mixture was then distilled under reduced pressure to remove the solvent. The residue was purified chromatography on a silica gel column, whereby from n-hexane-ethyl acetate (1:1, v/v) eluate fractions, methyl (2-(6-fluoro-1-methyl-3-indolyl)-6-benzoxazolyl)acetate (889 mg, 93%) was obtained as a brown solid.

$^1$H-NMR (CDCl$_3$) δ: 3.72 (s, 3H), 3.76 (s, 2H), 3.85 (s, 3H) 7.05–7.12 (m, 2H), 7.22 (dd, J=8.1,1.5 Hz, 1H), 7.49 (d, J=1.5 Hz, 1H), 7.65 (d, J=8.1 Hz, 1H), 7.89 (s, 1H), 8.38 (dd, J=8.9,5.4 Hz, 1H).

MS (ESI) m/z 339 (M$^+$+1).

(Step 4) Synthesis of (2-(6-fluoro-1-methyl-3-indolyl)-6-benzoxazolyl)acetic acid

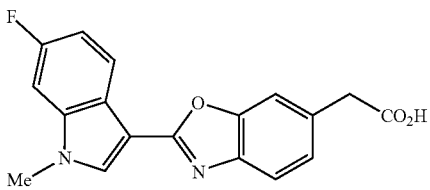

To methyl (2-(6-fluoro-1-methyl-3-indolyl)-6-benzoxazolyl)acetate (889 mg, 2.63 mmol) were added THF (25 ml) and 0.25N NaOH (15.8 ml, 3.95 mmol). The resulting mixture was stirred at room temperature for 4 hours. The reaction mixture was poured in 1N HCl (30 ml). The crystals thus precipitated were collected by filtration under reduced pressure, washed with water, and dried under reduced pressure to give (2-(6-fluoro-1-methyl-3-indolyl)-6-benzoxazolyl)acetic acid (741 mg, 87%) as a brown solid.

$^1$H-NMR (DMSO-d$_6$) δ: 3.71 (s, 2H), 3.94 (s, 3H), 7.18 (td, J=9.5,2.5 Hz, 1H), 7.23 (d, 1H, J=7.8 Hz, 1H), 7.59–7.64 (m, 3H), 7.97 (dd, J=9.5,2.5 Hz, 1H), 8.39 (s, 1H), 12.35 (broad s, 1H).

MS (ESI) m/z 325 (M$^+$+1).

(Step 5) Synthesis of methyl trans-4-(1-((2-(6-fluoro-1-methyl-3-indolyl)-6-benzoxazolyl)acetyl)-(4S)-fluoro-(2S)-pyrrolidinylmethoxy)cyclohexanecarboxylate

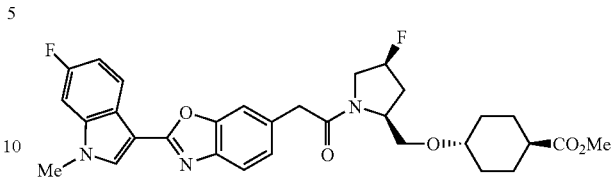

To (2-(6-fluoro-1-methyl-3-indolyl)-6-benzoxazolyl)acetic acid (200 mg, 0.62 mmol), methyl trans-4-((4S)-fluoro-(2S)-pyrrolidinylmethoxy)cyclohexanecarboxylate (the compound synthesized in (Step 3) of Example 21) (160 mg, 0.62 mmol), HOBt (17.0 mg, 0.12 mmol), and DMAP (15.0 mg, 0.12 mmol) were added DMF (6.0 ml) and EDC HCl (142 mg, 0.74 mmol). The resulting mixture was stirred at room temperature for 21 hours. Water was added to the reaction mixture, followed by extraction with ethyl acetate. The extract was washed with saturated brine, dried over anhydrous magnesium sulfate, and distilled under reduced pressure to remove the solvent. The residue was purified by chromatography on a silica gel column, whereby from ethyl acetate eluate fractions, methyl trans-4-(1-((2-(6-fluoro-1-methyl-3-indolyl)-6-benzoxazolyl)acetyl)-(4S)-fluoro-(2S)-pyrrolidinylmethoxy)cyclohexanecarboxylate (355 mg, 99%) was obtained as a yellow amorphous substance.

$^1$H-NMR (CDCl$_3$) δ: 1.16–1.32 (m, 2H), 1.38–1.51 (m, 2H), 1.95–2.48 (m, 7H), 3.24 (m, 1H), 3.34 and 3.49 (each m, total 1H), 3.62 and 3.65 (each s, total 3H), 3.83 (s, 3H), 3.90–4.06 (m, 2H), 4. 25 and 4.37 (each m, total 1H), 5.23 (m, 1H), 7.04–7.10 (m, 2H), 7.17 and 7.18 (each dd, J=7.8,1.4 Hz, total 1H), 7.46 and 7.47 (each d, J=1.4 Hz, 2H), 7.61 and 7.63 (each d, J=7.8 Hz, 1H), 7.87 (s, 1H), 8.35 (dd, J=8.5, 5.3 Hz, 1H).

MS (ESI) m/z 566 (M$^+$+1).

(Step 6) Synthesis of trans-4-(1-((2-(6-fluoro-1-methyl-3-indolyl)-6-benzoxazolyl)acetyl)-(4S)-fluoro-(2S)-pyrrolidinylmethoxy)cyclohexanecarboxylic acid

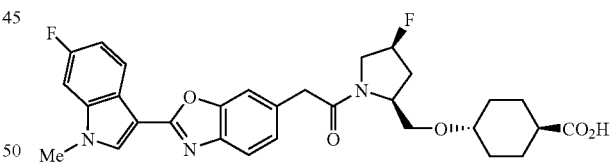

To methyl trans-4-(1-((2-(6-fluoro-1-methyl-3-indolyl)-6-benzoxazolyl)acetyl)-(4S)-fluoro-(2S)-pyrrolidinylmethoxy)cyclohexanecarboxylate (355 mg, 0.63 mmol) were added THF (6.5 ml) and 0.25N NaOH (3.77 ml, 0.94 mmol). The resulting mixture was stirred at room temperature for 15 hours. The reaction mixture was poured in 1N HCl (10 ml). The crystals thus precipitated were collected by filtration under reduced pressure, washed with water, and dried under reduced pressure to give the title compound (294 mg, 85%) as a yellow solid.

IR (ATR) ν 2938, 1712, 1616, 1577, 1434 cm$^{-1}$;

$^1$H-NMR (DMSO-d$_6$) δ: 1.09–1.39 (m, 4H), 1.84–1.93 (m, 4H), 2.06–2.44 (m, 3H), 3.16–3.99 (m, 10H), 4.13 and 4.33 (each m, total 1H), 5.30 and 5.36 (each m, total 1H), 7.12–7.21 (m, 2H), 7.49 (dd, J=9.8,2.2 Hz, 1H), 7.51 and 7.53 (each s, total 1H), 7.60 and 7.61 (each d, J=8.1 Hz, total 2H), 8.28 (dd, J=8.1,5.6 Hz, 1H), 8.30 and 8.31 (each s, total 1H), 12.03 (broad s, 1H).

MS (ESI) m/z 553 (M$^+$+2);

Anal. Calcd for $C_{30}H_{31}ClFN_3O_5$ $0.5H_2O$: C, 64.28; H, 5.75; N, 7.50. Found: C, 64.59; H, 5.77; N, 7.44.

Example 100 trans-4-(1-((2-(5-Fluoro-1-methyl-3-indolyl)-6-benzoxazolyl)acetyl)-(4S)-fluoro-(2S)-pyrrolidinylmethoxy)cyclohexanecarboxylic acid (Step 1) Synthesis of 5-fluoro-1-methylindole-3-carbaldehyde

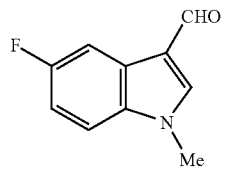

In DMF (60 ml) was dissolved 5-fluoroindole-3-carbaldehyde (5.00 g, 30.6 mmol). Under stirring at 0° C., sodium hydride (60% in oil, 1.35 g, 33.7 mmol) was added in portions. After the reaction mixture was stirred at the same temperature for 1 hour, methyl iodide (5.72 ml, 91.9 mmol) was added thereto. The resulting mixture was stirred further at 0° C. for 2 hours. A saturated aqueous solution of ammonium chloride was added to the reaction mixture to neutralize the same, followed by extraction with ethyl acetate. The extract was washed with saturated brine, dried over anhydrous magnesium sulfate, and distilled under reduced pressure to remove the solvent. The residue was purified by chromatography on a silica gel column, whereby from ethyl acetate eluate fractions, 5-fluoro-1-methylindole-3-carbaldehyde (5.42 g, 100%) was obtained as a colorless solid.

$^1$H-NMR (CDCl$_3$) δ: 3.88 (s, 3H), 7.09 (m, 1H), 7.29 (d, J=9.3,4.2 Hz, 1H), 7.71 (s, 1H), 7.98 (dd, J=9.3,2.4 Hz, 1H), 9.96 (s, 1H).

MS (ESI) m/z 178 (M$^+$+1).

(Step 2) Synthesis of (2-(5-fluoro-1-methyl-3-indolyl)-6-benzoxazolyl)acetic acid

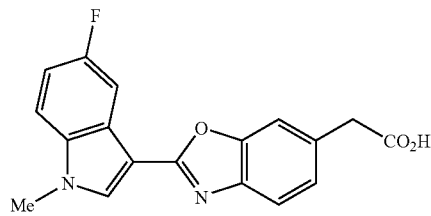

In ethanol (25 ml), 5-fluoro-1-methylindole-3-carbaldehyde (989 mg, 5.58 mmol) and methyl 4-amino-3-hydroxyphenylacetate (1.27 g, 6.99 mmol) were stirred at room temperature for 9 hours. Iodobenzene diacetate (2.16 g, 6.69 mmol) was added and the mixture was stirred further at room temperature for 18 hours. The reaction mixture was distilled under reduced pressure to remove the solvent. The residue thus obtained was purified by chromatography on a silica gel column, whereby from n-hexane-ethyl acetate (1:2, v/v) eluate fractions, a mixture (933 mg) of methyl (2-(5-fluoro-1-methyl-3-indolyl)-6-benzoxazolyl)acetate and 5-fluoro-1-methylindole-3-carboxaldehyde was obtained as a red solid.

$^1$H-NMR (CDCl$_3$) δ: 3.73 (s, 3H), 3.77 (s, 2H), 3.89 (s, 3H) 7.10 (m, 1H), 7.22–7.28 (m, 2H), 7.50 (m, 1H), 7.65 (d, J=8.1 Hz, 1H), 7.92 (s, 1H), 8.11 (dd, J=9.3, 2.4 Hz, 1H).

MS (ESI) m/z 339 (M$^+$+1).

To the mixture (933 mg) were added THF (30 ml) and 0.25N NaOH (16.6 ml, 4.15 mmol) and the resulting mixture was stirred at room temperature for 3 hours. The reaction mixture was poured in 1N HCl (30 ml). The crystals thus precipitated were collected by filtration under reduced pressure, washed with water, and dried under reduced pressure to give (2-(5-fluoro-1-methyl-3-indolyl)-6-benzoxazolyl) acetic acid (434 mg, 24%) as a brown solid.

$^1$H-NMR (DMSO-d$_6$) δ: 3.72 (s, 2H), 3.90 (s, 3H), 7.15 (td, J=9.8,2.2 Hz, 1H), 7.23 (dd, J=8.1,1.2 Hz, 1H), 7.50 (dd, J=9.8,2.2 Hz, 1H), 7.59 (d, J=1.2 Hz, 1H), 7.62 (d, J=8.1 Hz, 1H), 8.29 (dd, J=8.8,5.4 Hz, 1H), 8.33 (s, 1H), 12.37 (broad s, 1H).

MS (ESI) m/z 325 (M$^+$+1).

(Step 3) Synthesis of methyl trans-4-(1-((2-(5-fluoro-1-methyl-3-indolyl)-6-benzoxazolyl)acetyl)-(4S)-fluoro-(2S)-pyrrolidinylmethoxy)cyclohexanecarboxylate

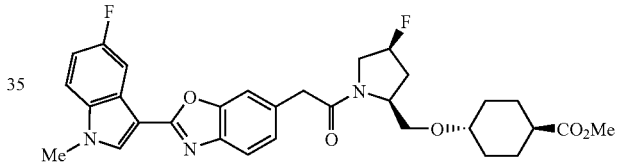

To (2-(5-fluoro-1-methyl-3-indolyl)-6-benzoxazolyl)acetic acid (200 mg, 0.62 mmol), methyl trans-4-((4S)-fluoro-(2S)-pyrrolidinylmethoxy)cyclohexanecarboxylate (the compound synthesized in (Step 3) of Example 21) (160 mg, 0.62 mmol), HOBt (17.0 mg, 0.12 mmol), and DMAP (15.0 mg, 0.12 mmol) were added DMF (6.0 ml) and EDC HCl (142 mg, 0.74 mmol). The resulting mixture was stirred at room temperature for 15 hours. Water was added to the reaction mixture, followed by extraction with ethyl acetate. The extract was washed with saturated brine, dried over anhydrous magnesium sulfate, and distilled under reduced pressure to remove the solvent. The residue was purified by chromatography on a silica gel column, whereby from ethyl acetate eluate fractions, methyl trans-4-(1-((2-(5-fluoro-1-methyl-3-indolyl)-6-benzoxazolyl)acetyl)-(4S)-fluoro-(2S)-pyrrolidinylmethoxy)cyclohexanecarboxylate (346 mg, 99%) was obtained as a yellow amorphous substance.

$^1$H-NMR (CDCl$_3$) δ: 1.17–1.34 (m, 2H), 1.39–1.53 (m, 2H), 1.97–2.51 (m, 7H), 3.26 (m, 1H), 3.35 and 3.51 (each m, total 1H), 3.64 and 3.67 (each s, total 3H), 3.90 (s, 3H), 3.91–4.13 (m, 2H), 4.26 and 4.40 (each m, total 1H), 5.24 (m, 1H), 7.09 (m, 1H), 7.19 and 7.20 (each dd, J=7.8,1.5 Hz, total 1H), 7.48 and 7.50 (each d, J=1.5 Hz, 2H), 7.63 and 7.65 (each d, J=7.8 Hz, 1H), 7.94 (s, 1H), 8.12 (dd, J=9.5,2.4 Hz, 1H).

MS (ESI) m/z 566 (M$^+$+1).

(Step 4) Synthesis of trans-4-(1-((2-(5-fluoro-1-methyl-3-indolyl)-6-benzoxazolyl)acetyl)-(4S)-fluoro-(2S)-pyrrolidinylmethoxy)cyclohexanecarboxylic acid

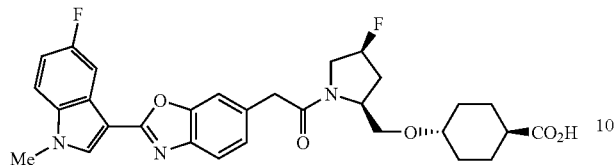

To methyl trans-4-(1-((2-(5-fluoro-1-methyl-3-indolyl)-6-benzoxazolyl)acetyl)-(4S)-fluoro-(2S)-pyrrolidinylmethoxy)cyclohexanecarboxylate (346 mg, 0.61 mmol) were added THF (6.5 ml) and 0.25N NaOH (3.67 ml, 0.92 mmol). The resulting mixture was stirred at room temperature for 15 hours. The reaction mixture was poured in 1N HCl (10 ml). The crystals thus precipitated were collected by filtration under reduced pressure, washed with water, and dried under reduced pressure to give the title compound (254 mg,. 75%) as a yellow solid.

IR (ATR) ν 2938, 1716, 1616, 1631, 1577, 1484, 1434 cm$^{-1}$;

$^1$H-NMR (DMSO-d$_6$) δ: 1.09–1.39 (m, 4H), 1.84–1.97 (m, 4H), 2.03–2.28 (m, 3H), 3.15–4.00 (m, 7H), 3.93 (s, 3H), 4.15 and 4.34 (each m, total 1H), 5.30 and 5.36 (each m, total 1H), 7.16–7.21 (m, 2H), 7.52 and 7.54 (each s, total 1H), 7.61–7.64 (m, 2H), 7.97 (dd, J=9.8,2.9 Hz, 1H), 8.36 and 8.37 (each s, total 1H), 12.03 (broad s, 1H).

MS (ESI) m/z 553 (M$^+$+1);

Anal. Calcd for C$_{30}$H$_{31}$ClFN$_3$O$_5$ 0.5H$_2$O: C, 64.28; H, 5.75; N, 7.50. Found: C, 64.54; H, 5.75; N, 7.44.

Example 101 trans-4-(1-((2-(5-Fluoro-1-methyl-3-indolyl)-7-fluoro-6-benzoxazolyl)acetyl)-(4S)-fluoro-(2S)-pyrrolidinylmethoxy)cyclohexanecarboxylic acid (Step 1) Synthesis of methyl (2-(5-fluoro-1-methyl-3-indolyl)-7-fluoro-6-benzoxazolyl)acetate

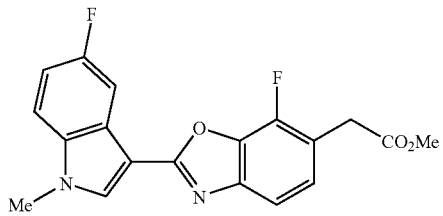

In ethanol (15 ml), Molecular Sieves 4A (1.20 g) was added to 5-fluoro-1-methylindolyl-3-carbaldehyde (515 mg, 2.91 mmol) and methyl 4-amino-2-fluoro-3-hydroxyphenylacetate (690 mg, 3.47 mmol) and the resulting mixture was stirred at room temperature for 18 hours. Iodobenzene diacetate (1.35 g, 4.10 mmol) was then added, and the resulting mixture was stirred further at room temperature for 1 hour. The reaction mixture was distilled under reduced pressure to remove the solvent. The residue was purified by chromatography on a silica gel column, whereby from hexane/ethyl acetate (1/1) eluate fractions, methyl (2-(5-fluoro-1-methyl-3-indolyl)-7-fluoro-6-benzoxazolyl)acetate (279 mg, 27%) was obtained as a brown crystalline powder.

$^1$H-NMR (CDCl$_3$) δ: 3.73 (s, 3H), 3.81 (s, 2H), 3.90 (s, 3H), 7.10 (dt, J=2.4,8.8 Hz, 1H), 7.17 (dd, J=6.4,8.0 Hz, 1H), 7.31 (dd, J=4.4,8.8 Hz, 1H), 7.44 (d, J=8.4 Hz, 1H), 7.98 (s, 1H), 8.11 (dd, J=2.4,9.6 Hz, 1H).

MS (ESI) m/z 357 (M$^+$+1).

(Step 2) Synthesis of (2-(5-fluoro-1-methyl-3-indolyl)-7-fluoro-6-benzoxazolyl)acetic acid

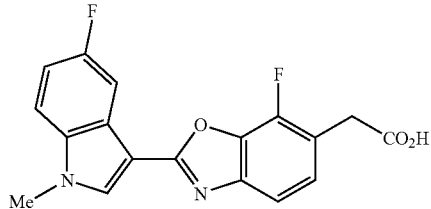

To methyl (2-(5-fluoro-1-methyl-3-indolyl)-7-fluoro-6-benzoxazolyl)acetate (279 mg, 0.78 mmol) were added THF/methanol (1/1, 20 ml) and 0.25N NaOH (9.4 ml, 2.35 mmol). The resulting mixture was stirred at room temperature for 18 hours. The reaction mixture was poured in 1N HCl to acidify the mixture therewith, followed by extraction with chloroform/methanol (10/1). The extract was dried over anhydrous sodium sulfate, and distilled under reduced pressure to remove the solvent. The crystals thus obtained were collected by filtration under reduced pressure, washed with hexane, and dried under reduced pressure to give (2-(5-fluoro-1-methyl-3-indolyl)-7-fluoro-6-benzoxazolyl)acetic acid (208 mg, 78%) as a brown crystalline powder.

$^1$H-NMR (DMSO-d$_6$) δ: 3.78 (s, 2H), 3.95 (s, 3H), 7.19–7.24 (m, 1H), 7.29 (d, J=8.0 Hz, 1H), 7.50 (d, J=8.4 Hz, 1H), 7.66 (dd, J=4.4,8.8 Hz, 1H), 7.94 (brd, J=9.6 Hz, 1H), 8.50 (brs, 1H), 12.52 (brs, 1H).

MS (ESI) m/z 342 (M$^+$+1).

(Step 3) Synthesis of methyl trans-4-(1-((2-(5-fluoro-1-methyl-3-indolyl)-7-fluoro-6-benzoxazolyl)acetyl)-(4S)-fluoro-(2S)-pyrrolidinylmethoxy)cyclohexanecarboxylate

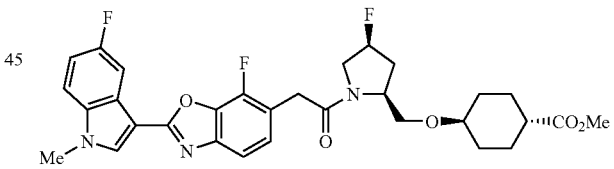

In DMF (15 ml), HOBt (16.0 mg, 0.12 mmol) was added to (2-(5-fluoro-1-methyl-3-indolyl)-7-fluoro-6-benzoxazolyl)acetic acid (202 mg, 0.59 mmol), methyl trans-4-((4S)-fluoro-(2S)-pyrrolidinylmethoxy) cyclohexanecarboxylate (the compound synthesized in (Step 3) of Example 21) (153 mg, 0.59 mmol) and EDC-HCl (124 mg, 0.65 mmol). The resulting mixture was stirred at room temperature for 17 hours. Water was added to the reaction mixture, followed by extraction with ethyl acetate. The extract was washed with saturated brine, dried over anhydrous sodium sulfate, and distilled under reduced pressure to remove the solvent. The residue was purified by chromatography on a silica gel column, whereby from hexane/ethyl acetate (1/5) eluate fractions, methyl trans-4-(1-((2-(5-fluoro-1-methyl-3-indolyl)-7-fluoro-6-benzoxazolyl)acetyl)-(4S)-fluoro-(2S)-pyrrolidinylmethoxy)cyclohexanecarboxylate (295 mg, 86%) was obtained as a colorless amorphous substance.

¹H-NMR (CDCl₃), mixture of rotamars, δ: 1.20–1.31 (m, 2H), 1.39–1.55 (m, 2H), 1.99–2.55 (series of m, 8H), 3.22–4.42 (series of m, 7H), 3.64 and 3.67 (s, total 3H), 3.90 (s, 3H), 5.19–5.40 (m, 1H), 7.08–7.13 (m, 1H), 7.20 (dd, J=8.8,15.2 Hz, 1H), 7.32 (dd, J=4.0,8.8 Hz, 1H), 7.45 (t, J=8.0 Hz, 1H), 7.98 (s, 1H), 8.11 (dd, J=2.4,9.6 Hz, 1H).

MS (ESI) m/z 584 (M⁺+1).

(Step 4) Synthesis of trans-4-(1-((2-(5-fluoro-1-methyl-3-indolyl)-7-fluoro-6-benzoxazolyl)acetyl)-(4S)-fluoro-(2S)-pyrrolidinylmethoxy)cyclohexanecarboxylic acid

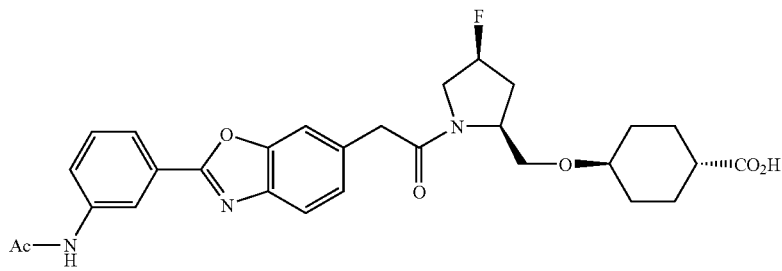

To trans-4-(1-((2-(5-fluoro-1-methyl-3-indolyl)-7-fluoro-6-benzoxazolyl)acetyl)-(4S)-fluoro-(2S)-pyrrolidinyl-methoxy)cyclohexanecarboxylate (288 mg, 0.49 mmol) were added THF/methanol (1/1, 20 ml) and 0.25N NaOH (9.9 ml, 2.45 mmol). The resulting mixture was stirred at room temperature for 17 hours. The reaction mixture was poured in 1N HCl to acidify the mixture therewith, followed by extraction with chloroform/methanol (10/1). The extract was dried over anhydrous sodium sulfate, and distilled under reduced pressure to remove the solvent. The residue was purified by chromatography on a silica gel column, whereby from chloroform/methanol (10/1) eluate fractions, the title compound (296 mg, 100%) was obtained as a colorless amorphous substance.

¹H-NMR (CDCl₃), mixture of rotamars, δ: 1.21–1.36 (m, 2H), 1.42–1.56 (m, 2H), 2.00–2.50 (series of m, 8H), 2.20 (s, 3H), 3.22–4.45 (series of m, 7H), 3.89 and 3.93 (s, total 3H), 5.20–5.40 (m, 1H), 7.10 (t, J=8.8 Hz, 1H), 7.20 (dd, J=8.0, 14.4 Hz, 1H), 7.30–7.32 (m, 1H), 7.46 (t, J=8.0 Hz, 1H), 7.99 (s, 1H), 8.10 (dd, J=2.0,9.2 Hz, 1H).

MS (ESI) m/z 570 (M⁺+1).

Example 102 trans-4-(1-(2-(1-Isoquinolinyl)-6-benzoxazoly-lacetyl)-(4S)-fluoro-(2S)-pyrrolidinylmethoxy)cyclohexanecarboxylic acid (Step 1) Synthesis of 1-isoquinolinecarbaldehyde

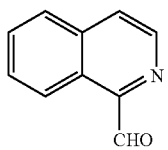

In 1,4-dioxane (20 ml) was dissolved 1-methylisoquinoline (300 mg, 2.10 mmol). To the resulting solution was added selenium dioxide (323 mg, 2.91 mmol), followed by heating under reflux for 1.5 hours under a nitrogen gas stream. After cooling to room temperature, the reaction mixture was filtered through Celite. The filtrate was distilled under reduced pressure to remove the solvent. The residue was purified by chromatography on a silica gel column, whereby from n-hexane/ethyl acetate (5:1, v/v) eluate fractions, 1-isoquinolinecarbaldehyde (252 mg, 77%) was obtained as a white solid.

¹H-NMR (CDCl₃) δ: 7.73–7.79 (m, 2H), 7.88–7.93 (m, 2H), 8.74–8.76 (m, 1H), 9.30–9.33 (m, 1H), 10.39 (s, 1H).

MS (ESI) m/z 158 (M⁺+1).

(Step 2) Synthesis of methyl (2-(1-isoquinolinyl)-6-benzoxazolyl)acetate

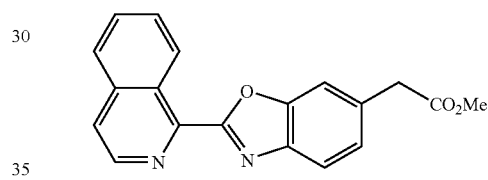

In ethanol (5 ml), 1-isoquinolinecarbaldehyde (252 mg, 1.60 mmol) and methyl 4-amino-3-hydroxyphenylacetate (349 mg, 1.93 mmol) were stirred at room temperature for 12 hours. Iodobenzene diacetate (619 mg, 1.92 mmol) was added and the reaction mixture was stirred further at room temperature for 15 minutes. The reaction mixture was distilled under reduced pressure to remove the solvent. The residue was purified by chromatography on a silica gel column, whereby from n-hexane/ethyl acetate (4:1 to 3:1, v/v) eluate fractions, methyl (2-(1-isoquinolinyl)-6-benzoxazolyl)acetate (166 mg, 33%) was obtained as a yellow amorphous substance.

¹H-NMR (CDCl₃) δ: 3.73 (s, 3H), 3.82 (s, 2H), 7.35–7.38 (m, 1H), 7.68 (m, 1H), 7.75–7.95 (m, 5H), 8.77–8.78 (m, 1H), 9.67–9.70 (m, 1H).

MS (ESI) m/z 319 (M⁺+1).

(Step 3) Synthesis of (2-(1-isoquinolinyl)-6-benzoxazolyl) acetic acid

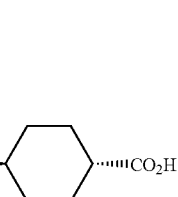

To methyl (2-(1-isoquinolinyl)-6-benzoxazolyl)acetate (166 mg, 0.52 mmol) were added THF (3 ml) and 0.5N NaOH (3.0 ml, 1.50 mmol). The resulting mixture was stirred at room temperature for 12 hours. The reaction mixture was poured in ice-1N HCl to acidify therewith. The crystals thus precipitated were collected by filtration under reduced pressure, washed with water and dried under reduced pressure to give (2-(1-isoquinolinyl)-6-benzoxazolyl)acetic acid (138 mg, 87%) as a pale brown solid.

$^1$H-NMR (DMSO-$d_6$) δ: 3.82 (s, 2H), 7.41–7.43 (m, 1H), 7.82 (s, 1H), 7.88–7.95 (m, 3H), 8.13–8.17 (m, 2H), 8.76–8.78 (m, 1H), 9.53–9.55 (m, 1H), 12.45 (broad s, 1H).

MS (ESI) m/z 305 (M$^+$+1).

(Step 4) Synthesis of methyl trans-4-(1-(2-(1-isoquinolinyl)-6-benzoxazolylacetyl)-(4S)-fluoro-(2S)-pyrrolidinylmethoxy)cyclohexanecarboxylate

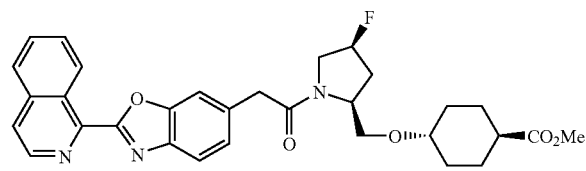

In DMF (10 ml), (2-(1-isoquinolinyl)-6-benzoxazolyl)acetic acid (138 mg, 0.45 mmol), methyl trans-4-((4S)-fluoro-(2S)-pyrrolidinylmethoxy)cyclohexanecarboxylate (the compound synthesized in (Step 3) of Example 21) (118 mg, 0.46 mmol), EDC•HCl (130 mg, 0.68 mmol), HOBt (92 mg, 0.68 mmol), and triethylamine (95 μl, 0.68 mmol) were stirred at room temperature for 15 hours. Water was added to the reaction mixture, followed by extraction with ethyl acetate. The extract was washed with saturated brine, dried over anhydrous sodium sulfate, and distilled under reduced pressure to remove the solvent. The residue was purified by chromatography on a silica gel column, whereby from toluene-acetone (4:1, v/v) eluate fractions, methyl trans-4-(1-(2-(1-isoquinolinyl)-6-benzoxazolylacetyl)-(4S)-fluoro-(2S)-pyrrolidinylmethoxy)cyclohexanecarboxylate (245 mg, 99%) was obtained as a pale yellow thick sticky liquid.

$^1$H-NMR (CDCl$_3$) δ: 1.21–1.53 (m, 4H), 1.97–2.52 (m, 7H), 3.24–3.37 and 3.50–3.54 (each m, total 2H), 3.64–4.14 (m, 8H), 4.25–4.28 and 4.39–4.41 (each m, total 1H), 5.18–5.19 and 5.31–5.33 (each m, total 1H), 7.15–7.24 (m, 1H), 7.33–7.36 (m, 1H), 7.64–7.93 (m, 5H), 8.75–8.77 (m, 1H), 9.66–9.68 (m, 1H).

MS (ESI) m/z 546.5 (M$^+$+1).

(Step 5) Synthesis of trans-4-(1-(2-(1-isoquinolinyl)-6-benzoxazolylacetyl)-(4S)-fluoro-(2S)-pyrrolidinylmethoxy)cyclohexanecarboxylic acid

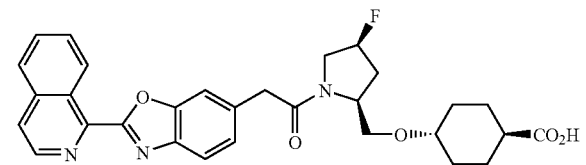

To methyl trans-4-(1-(2-(1-isoquinolinyl)-6-benzoxazolylacetyl)-(4S)-fluoro-(2S)-pyrrolidinylmethoxy)cyclohexanecarboxylate (245 mg, 0.45 mmol) were added THF (3.0 ml) and 0.5N NaOH (2.7 ml, 1.35 mmol). The resulting mixture was stirred at room temperature for 18 hours. The reaction mixture was poured in ice-1N HCl to acidify the mixture. The crystals thus precipitated were collected by filtration under reduced pressure, washed with water and dried under reduced pressure to give the title compound (175 mg, 73%) as a pale yellow solid.

$^1$H-NMR (DMSO-$d_6$) δ: 1.12–1.37 (m, 4H), 1.84–2.11 (m, 4H), 2.14–2.21 (m, 3H), 3.17–4.04 (m, 7H), 4.15 and 4.37–4.39 (each m, total 1H), 5.25–5.32 and 5.39–5.45 (each m, total 1H), 7.33–7.37 (m, 1H), 7.72–7.74 (m, 1H), 7.86–7.93 (m, 3H), 8.11–8.15 (m, 2H), 8.74–8.76 (m, 1H), 9.51–9.53 (m, 1H), 12.02 (broad s, 1H).

MS (ESI) m/z 532.5 (M$^+$+1);

Anal. Calcd for $C_{30}H_{30}FN_3O_5 \cdot 1H_2O$: C, 65.56; H, 5.87; N, 7.65. Found: C, 65.39; H, 5.94; N, 7.51.

Example 103 trans-4-(1-(7-Fluoro-2-(1-isoquinolinyl)-6-benzoxazolylacetyl)-(4S)-fluoro-(2S)-pyrrolidinylmethoxy)cyclohexanecarboxylic acid (Step 1) Synthesis of methyl (7-fluoro-2-(1-isoquinolinyl)-6-benzoxazolyl)acetate

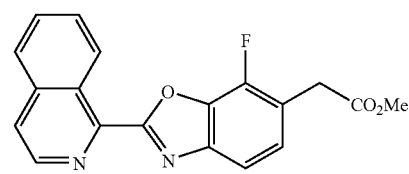

In ethanol (13 ml), isoquinoline-1-carbaldehyde (500 mg, 3.18 mmol) and methyl 4-amino-2-fluoro-3-hydroxyphenylacetate (632 mg, 3.17 mmol) were stirred at room temperature for 2 days. Iodobenzene diacetate (1.23 g, 3.82 mmol) was added, and the reaction mixture was stirred at room temperature for 10 minutes. The reaction mixture was distilled under reduced pressure to remove the solvent. The residue was purified by chromatography on a silica gel column, whereby from n-hexane/ethyl acetate (3:1, v/v) eluate fractions, methyl (7-fluoro-2-(1-isoquinolinyl)-6-benzoxazolyl)acetate (155 mg, 14%) was obtained as a red brown solid.

$^1$H-NMR (CDCl$_3$) δ: 3.74 (s, 3H), 3.87 (s, 2H), 7.30–7.33 (m, 1H), 7.66–7.94 (m, 5H), 8.78–8.79 (m, 1H), 9.58 (m, 1H).

MS (ESI) m/z 337 (M$^+$+1).

(Step 2) Synthesis of (7-fluoro-2-(1-isoquinolinyl)-6-benzoxazolyl)acetic acid

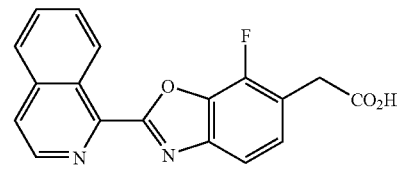

To methyl (7-fluoro-2-(1-isoquinolinyl)-6-benzoxazolyl)acetate (155 mg, 0.46 mmol) were added THF (3 ml) and 0.5N NaOH (3.0 ml, 1.50 mmol). The resulting mixture was stirred at room temperature for 1 hour. The reaction mixture was poured in ice-1N HCl to acidify the mixture therewith. The crystals thus precipitated were collected by filtration under reduced pressure, washed with water and dried under reduced pressure to give (7-fluoro-2-(1-isoquinolinyl)-6-benzoxazolyl)acetic acid (116 mg, 78%) as a brown solid.

$^1$H-NMR (DMSO-d$_6$) δ: 3.86 (s, 2H), 7.44–7.48 (m, 1H), 7.78–7.80 (m, 1H), 7.88–7.93 (m, 2H), 8.15–8.16 (m, 2H), 8.77–8.79 (m, 1H), 9.48–9.50 (m, 1H), 12.63 (broad s, 1H).

MS (ESI) m/z 323 (M$^+$+1).

(Step 3) Synthesis of methyl trans-4-(1-(7-fluoro-2-(1-isoquinolinyl)-6-benzoxazolylacetyl)-(4S)-fluoro-(2S)-pyrrolidinylmethoxy)cyclohexanecarboxylate

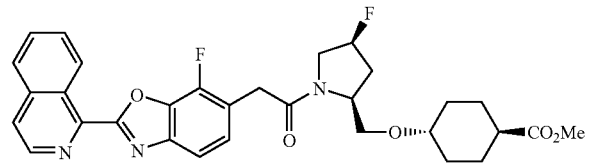

In DMF (5 ml), (7-fluoro-2-(1-isoquinolinyl)-6-benzoxazolyl)acetic acid (116 mg, 0.36 mmol), methyl trans-4-((4S)-fluoro-(2S)-pyrrolidinylmethoxy)cyclohexanecarboxylate (the compound synthesized in (Step 3) of Example 21) (93 mg, 0.36 mmol), EDC•HCl (103 mg, 0.54 mmol), HOBt (73 mg, 0.54 mmol), and triethylamine (75 μl, 0.54 mmol) were stirred at room temperature for 12 hours. The reaction mixture was poured in water. The crystals thus precipitated were collected by filtration under reduced pressure, washed with water and dried under reduced pressure to give methyl trans-4-(1-(7-fluoro-2-(1-isoquinolinyl)-6-benzoxazolylacetyl)-(4S)-fluoro-(2S)-pyrrolidinylmethoxy)cyclohexanecarboxylate (192 mg, 95%) as a brown solid.

$^1$H-NMR (CDCl$_3$) δ: 1.25–1.54 (m, 4H), 1.97–2.51 (m, 7H), 3.26–3.38 and 3.54–3.58 (each m, total 2H), 3.64–4.09 (m, 8H), 4.37–4.39 (m, 1H), 5.21 and 5.34–5.39 (each m, total 1H), 7.33–7.40 (m, 1H), 7.66–7.71 (m, 1H), 7.80–7.82 (m, 2H), 7.86–7.87 (m, 1H), 7.95 (m, 1H), 8.79–8.80 (m, 1H), 9.58–9.59 (m, 1H).

MS (ESI) m/z 564.5 (M$^+$+1).

(Step 4) Synthesis of trans-4-(1-(7-fluoro-2-(1-isoquinolinyl)-6-benzoxazolylacetyl)-(4S)-fluoro-(2S)-pyrrolidinylmethoxy)cyclohexanecarboxylic acid

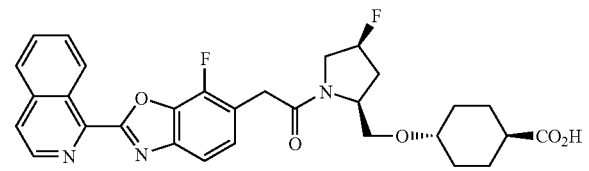

To methyl trans-4-(1-(7-fluoro-2-(1-isoquinolinyl)-6-benzoxazolylacetyl)-(4S)-fluoro-(2S)-pyrrolidinylmethoxy)cyclohexanecarboxylate (192 mg, 0.34 mmol) were added THF (4.0 ml) and 0.25N NaOH (4.0 ml, 1.00 mmol). The resulting mixture was stirred at room temperature for 13 hours. The reaction mixture was poured into ice-1N HCl to acidify the mixture therewith. The crystals thus precipitated were collected by filtration under reduced pressure, washed with water and dried under reduced pressure to give the title compound (158 mg, 84%) as a brown solid.

$^1$H-NMR (DMSO-d$_6$) δ: 1.13–1.41 (m, 4H), 1.84–2.32 (m, 7H), 3.16–4.45 (m, 7H), 5.26–5.35 and 5.40–5.49 (each m, total 1H), 7.32–7.39 (m, 1H), 7.75–7.78 (m, 1H), 7.87–7.93 (m, 2H), 8.14–8.16 (m, 2H), 8.77–8.78 (m, 1H), 9.48–9.50 (m, 1H), 12.02, (broad s, 1H).

MS (ESI) m/z 550.5 (M$^+$+1);

Anal. Calcd for C$_{30}$H$_{29}$F$_2$N$_3$O$_5$.1H$_2$O: C, 63.48; H, 5.51; N, 7.40. Found: C, 63.43; H, 5.48; N, 7.14.

Example 104 trans-4-((4S)-Fluoro-1-((2-(1-indolinyl)-6-benzoxazolyl)acetyl)-2S)-pyrrolidinylmethoxy)cyclohexanecarboxylic acid (Step 1) Synthesis of methyl (2-(1-indolinyl)-6-benzoxazolyl)acetate

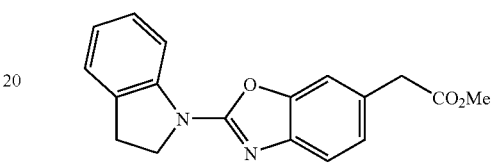

Indoline (0.34 ml, 3.0 mmol) was dissolved in THF (30 ml). To the resulting solution was added thiocarbonyldiimidazole (588 mg, 3.0 mmol), followed by stirring at room temperature for 3 hours. To the reaction mixture was added methyl 4-amino-3-hydroxyphenylacetate (544 mg, 3.0 mmol) and the resulting mixture was stirred at room temperature for 2 days. Mercuric oxide (yellow) (785 mg, 3.0 mmol) was added and the resulting mixture was stirred at 70° C. for 6 hours. After cooling to room temperature, the reaction mixture was filtered through Celite, followed by washing with methanol. The filtrate was distilled under reduced pressure to remove the solvent. The residue was purified by chromatography on a silica gel column, whereby from chloroform/ethyl acetate (10/1) eluate fractions, methyl (2-(1-indolinyl)-6-benzoxazolyl)acetate (200 mg, 22%) was obtained as a brown solid.

$^1$H-NMR (CDCl$_3$) δ 3.30: (t, J=8.6 Hz, 2H), 3.70 (s, 2H), 3.71 (s, 3H), 4.32 (t, J=8.3 Hz, 2H), 7.00 (dt, J=7.3,1.0 Hz, 1H), 7.13 (dd, J=8.1,6.4 Hz, 1H), 7.23 (d, J=6.8 Hz, 1H), 7.28 (d, J=7.3 Hz, 1H), 7.36 (d, J=1.2 Hz, 1H), 7.42 (d, J=8.1 Hz, 1H), 7.97 (d, J=8.1 Hz, 1H).

MS (ESI) m/z 309 (M$^+$+1).

(Step 2) Synthesis of (2-(1-indolinyl)-6-benzoxazolyl)acetic acid

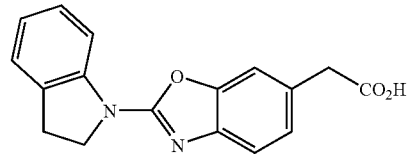

To methyl (2-(1-indolinyl)-6-benzoxazolyl)acetate (200 mg, 0.649 mmol) were added THF/methanol (6/3 ml) and 1N NaOH (3 ml). The resulting mixture was stirred at room temperature for 1.5 hours. The reaction mixture was distilled under reduced pressure to remove the solvent. To the residue was added 1N HCl to acidify the residue therewith. The crystals thus precipitated were collected by filtration under reduced pressure, washed with water and dried under reduced pressure to give (2-(1-indolinyl)-6-benzoxazolyl)acetic acid (161 mg, 84%) as a brown solid.

$^1$H-NMR (DMSO) δ: 3.27 (t, J=8.6 Hz, 2H), 3.65 (s, 2H), 4.28 (t, J=8.3 Hz, 2H), 7.00 (t, J=7.3 Hz, 1H), 7.13 (dd, J=8.1,2.0 Hz, 1H), 7.28 (t, J=6.9 Hz, 2H), 7.38 (d, J=8.1 Hz, 1H), 7.46 (s, 1H), 7.97 (d, J=7.8 Hz, 1H), 12.32 (br, 1H).

MS (ESI) m/z 249 (M$^+$+1).

(Step 3) Synthesis of methyl trans-4-((4S)-fluoro-1-((2-(1-indolinyl)-6-benzoxazolyl)acetyl)-(2S)-pyrrolidinyl-methoxy)cyclohexanecarboxylate

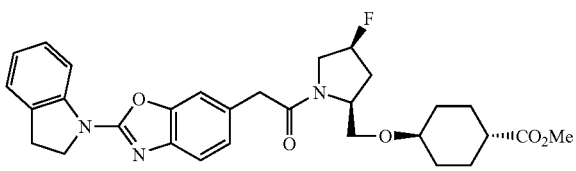

In DMF (5 ml), (2-(1-indolinyl)-6-benzoxazolyl)acetic acid (161 mg, 0.547 mmol), methyl trans-4-((4S)-fluoro-(2S)-pyrrolidinylmethoxy)cyclohexanecarboxylate (the compound synthesized in (Step 3) of Example 21) (142 mg, 0.547 mmol), EDC HCl (157 mg, 0.821 mmol), HOBt (111 mg, 0.821 mmol) and triethylamine (0.38 ml, 2.74 mmol) were stirred at room temperature for 15 hours. The reaction mixture was poured in ice water, followed by extraction with ethyl acetate. The extract was washed with saturated brine, dried over anhydrous sodium sulfate, and distilled under reduced pressure to remove the solvent. The residue was purified by chromatography on a silica gel column, whereby from chloroform/acetone (10/1) eluate fractions, methyl trans-4-((4S)-fluoro-1-((2-(1-indolinyl)-6-benzoxazolyl)acetyl)-(2S)-pyrrolidinylmethoxy)cyclohexanecarboxylate (180 mg, 61%) was obtained as a colorless oil.

$^1$H-NMR (CDCl$_3$) δ: 1.13–1.53 (m, 5H), 1.96–2.51 (m, 6H), 3.22–3.38 (m, 4H), 3.50 (t, J=8.1 Hz, 1H), 3.64 and 3.66 (each s, total 3H, amide isomers), 3.68–4.03 (m, 4H), 4.24 and 4.34 (q and m, J=7.6 Hz, total 1H, amide isomers), 4.31 (t, J=8.6 Hz, 2H), 5.24 (dq, J=53.1,4.4 Hz, 1H), 6.99 (t, J=7.3 Hz, 1H), 7.10 (m, 1H), 7.23 (d, J=7.1 Hz, 1H), 7.27 (t, J=7.6 Hz, 1H), 7.36 (dd, J=8.3,1.2 Hz, 1H), 7.40 and 7.42 (each d, each J=7.3 Hz, total 1H, amide isomers), 7.96 (d, J=8.1 Hz, 1H).

MS (ESI) m/z 536 (M$^+$+1).

(Step 4) Synthesis of trans-4-((4S)-fluoro-1-((2-(1-indolinyl)-6-benzoxazolyl)acetyl)-(2S)-pyrrolidinylmethoxy)cyclohexanecarboxylic acid

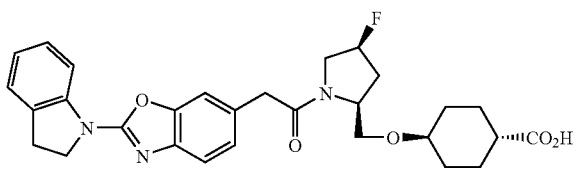

To methyl trans-4-((4S)-fluoro-1-((2-(1-indolinyl)-6-benzoxazolyl)acetyl)-(2S)-pyrrolidinylmethoxy)cyclohexanecarboxylate (180 mg, 0.336 mmol) were added THF/methanol (8/4 ml) and 1N NaOH (4 ml). After stirring at room temperature for 17 hours, the reaction mixture was distilled under reduced pressure to remove the solvent. The residue was acidified with 1N HCl. The crystals thus precipitated were collected by filtration, washed with water and dried under reduced pressure to give the title compound (147 mg, 84%) as a colorless solid.

IR (ATR) ν 2937, 2860, 1722, 1635, 1601, 1570, 1487, 1439 cm$^{-1}$;

$^1$H-NMR (DMSO-d$_6$) δ: 1.19–1.39 (m, 5H), 1.83–2.21 (m, 7H), 3.17 (t, J=9.3 Hz, 1H), 3.27 (t, J=8.6 Hz, 1H), 3.40–3.94 (m, 5H), 4.13 and 4.33 (each m, total 1H, amide isomers), 4.28 (t, J=8.6 Hz, 2H), 5.31 and 5.36 (dt and d, J=54.1, 4.4 and 54.1 Hz, respectively, total 1H, amide isomers), 6.98 (t, J=7.3 Hz, 1H), 7.09 (t, J=8.8 Hz, 1H), 7.27 (t, J=7.8 Hz, 1H), 7.29 (t, J=7.1 Hz, 1H), 7.37 (t, J=4.2 Hz, 1H), 7.40 and 7.42 (d and s, J=2.7 Hz, total 1H, amide isomers), 7.97 (d, J=8.1 Hz, 1H), 12.03 (s, 1H).

MS (ESI) m/z 522 (M$^+$+1);

Anal. Calcd for C$_{29}$H$_{32}$FN$_3$O$_{05}$ · 0.4H$_2$O: C, 65.87; H, 6.25; N, 7.95; F, 3.59. Found: C, 65.93; H, 6.27; N, 7.71; F, 3.45.

Example 105 trans-4-(1-((7-fluoro-2-(1-indolinyl)-6-benzoxazolyl)acetyl)-(4S)-fluoro-(2S)-pyrrolidinylmethoxy)cyclohexanecarboxylic acid (Step 1) Synthesis of methyl (7-fluoro-2-(1-indolinyl)-6-benzoxazolyl)acetate

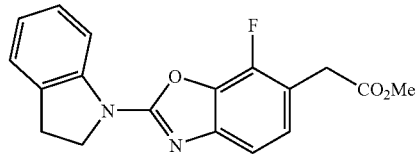

Indoline (0.49 ml, 4.36 mmol) was dissolved in THF (20 ml). To the resulting solution was added N,N'-thiocarbonyldiimidazole (863 mg, 4.36 mmol). The resulting mixture was stirred at room temperature for 14 hours. Methyl 4-amino-2-fluoro-3-hydroxyphenylacetate (1.0 g, 5.0 mmol) was added to the reaction mixture, followed by stirring at 70° C. for 1 day. Mercuric oxide (yellow) (944 mg, 4.36 mmol) was added to the reaction mixture and the resulting mixture was heated at 70° C. for 15 hours. After cooling to room temperature, the reaction mixture was filtered through Celite, followed by washing with methanol. The filtrate was distilled under reduced pressure to remove the solvent. The residue was purified by chromatography on a silica gel column, whereby from chloroform/ethyl acetate (10/1) eluate fractions, methyl (7-fluoro-2-(1-indolinyl)-6-benzoxazolyl)acetate (330 mg, 23%) was obtained as a pale brown solid.

$^1$H-NMR (CDCl$_3$) δ: 3.31 (t, J=8.5 Hz, 2H), 3.72 (s, 3H), 3.76 (s, 2H), 4.33 (t, J=8.3 Hz, 2H), 7.02 (t, J=7.3 Hz, 1H), 7.09 (t, J=6.6 Hz, 1H), 7.23 (t, J=8.0 Hz, 2H), 7.29 (d, J=8.3 Hz, 1H), 7.99 (d, J=8.0 Hz, 1H).

MS (ESI) m/z 327 (M$^+$+1).

(Step 2) Synthesis of (7-fluoro-2-(1-indolinyl)-6-benzoxazolyl)acetic acid

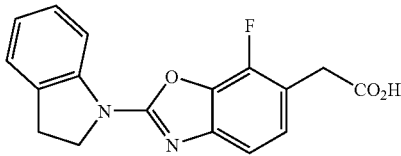

To methyl (7-fluoro-2-(1-indolinyl)-6-benzoxazolyl)acetate (330 mg, 1.01 mmol) were added THF/methanol (2:1, 12 ml) and 1N NaOH (4 ml). After stirring at room temperature for 14 hours, the reaction mixture was distilled under reduced pressure to remove the solvent. The residue was acidified with 1N HCl. The crystals thus precipitated were collected by filtration under reduced pressure, washed with water and dried under reduced pressure to give (7-fluoro-2-(1-indolinyl)-6-benzoxazolyl)acetic acid (284 mg, 90%) as a pale brown solid.

$^1$H-NMR (DMSO-$d_6$) δ: 3.28 (t, J=8.6 Hz, 2H), 3.72 (s, 2H), 4.32 (d, J=8.6 Hz, 2H), 7.03 (d, J=7.3 Hz, 1H), 7.18(t, J=6.9 Hz, 1H), 7.24 (d, J=8.1 Hz, 1H), 7.27–7.32 (m, 2H), 7.95 (d, J=7.8 Hz, 1H), 12.47 (br, 1H).

MS (ESI) m/z 313 (M$^+$+1).

(Step 3) Synthesis of methyl trans-4-(1-((7-fluoro-2-(1-indolinyl)-6-benzoxazolyl)acetyl)-(4S)-fluoro-(2S)-pyrrolidinylmethoxy)cyclohexanecarboxylate

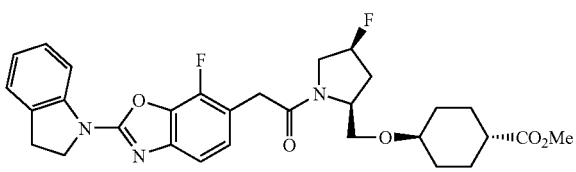

In DMF (4 ml), (7-fluoro-2-(1-indolinyl)-6-benzoxazolyl)acetic acid (156 mg, 0.50 mmol), methyl trans-4-((4S)-fluoro-(2S)-pyrrolidinylmethoxy)cyclohexanecarboxylate (the compound synthesized in (Step 3) of Example 21) (130 mg, 0.50 mmol), EDC HCl (144 mg, 0.75 mmol), HOBt (101 mg, 0.75 mmol) and triethylamine (0.35 ml, 2.50 mmol) were stirred at room temperature for 3 days. The reaction mixture was poured in ice water, followed by extraction with ethyl acetate. The extract was washed with saturated brine, dried over anhydrous sodium sulfate, and distilled under reduced pressure to remove the solvent. The residue was purified by chromatography using a thin layer plate, whereby from chloroform/acetone (10/1) eluate fractions, methyl trans-4-(1-((7-fluoro-2-(1-indolinyl)-6-benzoxazolyl)acetyl)-(4S)-fluoro-(2S)-pyrrolidinylmethoxy)cyclohexanecarboxylate (279 mg, 100%) was obtained as a brown oil.

$^1$H-NMR (CDCl$_3$) δ: 1.19–1.58 (m, 4H), 1.97–2.53 (m, 7H), 3.25 (m, 1H), 3.30 (t, J=8.8 Hz, 2H), 3.34 (m, 1H), 3.52–4.06 (m, 8 H, including amide isomers and 3.69 s, 1H), 4.32 (t, J=8.5 Hz, 2H), 4.37 (m, 1H), 5.26 and 5.30 (each dt, J=54.0, 4.4 and 53.2, 3.7 Hz, total 1H, amide isomers), 7.01 (t, J=7.6 Hz, 1H), 7.10 (q, J=7.3 Hz, 1H), 7.22 (t, J=6.3 Hz, 2H), 7.28 (t, J=7.8 Hz, 1H), 7.98 (d, J=8.1 Hz, 1H).

MS (ESI) m/z 566 (M$^+$+1).

(Step 4) Synthesis of trans-4-(1-((7-fluoro-2-(1-indolinyl)-6-benzoxazolyl)acetyl)-(4S)-fluoro-(2S)-pyrrolidinylmethoxy)cyclohexanecarboxylic acid

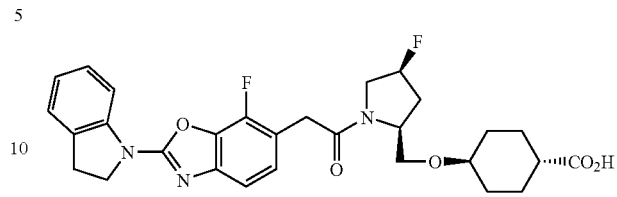

To methyl trans-4-(1-((7-fluoro-2-(1-indolinyl)-6-benzoxazolyl)acetyl)-(4S)-fluoro-(2S)-pyrrolidinylmethoxy)cyclohexanecarboxylate (279 mg, 0.50 mmol) were added THF/methanol (2:1, 15 ml) and 1N NaOH (5 ml). The resulting mixture was stirred at room temperature for 15 hours. The reaction mixture was distilled under reduced pressure to remove the solvent. The residue was acidified with 1N HCl. The crystals thus precipitated were collected by filtration under reduced pressure, washed with water and dried under reduced pressure to give the title compound (210 mg, 78%) as a colorless solid.

IR (ATR) ν 2939, 2862, 1716, 1635, 1576, 1487, 1452, 1408 cm$^{-1}$;

$^1$H-NMR (DMSO-$d_6$) δ: 1.14–1.41 (m, 4H), 1.85–2.38 (m, 7H), 3.20 (t, J=9.8 Hz, 1H), 3.29 (t, J=8.8 Hz, 2H), 3.40–4.15 (m, 6H), 4.32 (t, J=8.3 Hz, 2H), 4.37 (m, 1H), 5.33 and 5.41 (each d, J=54.9 and 53.5 Hz, total 1H, amide isomers), 7.03 (t, J=7.3 Hz, 1H), 7.08 and 7.11 (each d, each J=6.6 Hz, total 1H, amide isomers), 7.24 (dt, J=8.1, 1.9 Hz, 1H), 7.29 and 7.31 (each d, each J=7.8 Hz, total 2H, amide isomers), 7.96 (d, J=8.1 Hz, 1H), 12.05 (br, 1H).

MS (ESI) m/z 522 (M$^+$+1);

Anal. Calcd for $C_{29}H_{31}F_2N_3O_5$ 1H$_2$O: C, 62.47; H, 5.97; N, 7.54; F., 6.81. Found: C, 62.42; H, 5.87; N, 7.47; F., 6.88.

Example 106

4-(1-((2-(5-Fluoro-1-methylindolyl)-6-benzoxazolyl)acetyl)-(4S)-fluoro-(2S)-pyrrolidinylmethoxy)cyclohexylacetic acid (Step 1) Synthesis of methyl 4-((4S)-fluoro-(2S)-pyrrolidinylmethoxy)phenylacetate

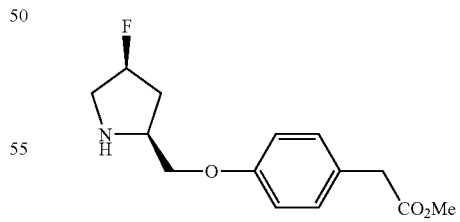

In THF (70 ml), diisopropyl azodicarboxylate (2.81 ml, 13.6 mmol) was added dropwise to N-tert-butoxycarbonyl-(4S)-fluoro-(2S)-pyrrolidinylmethanol (2.48 g, 11.3 mmol), triphenylphosphine (3.56 g, 13.6 mmol) and methyl 4-hydroxyphenylacetate (1.88 g, 11.3 mmol) at room temperature. After completion of the dropwise addition, the reaction mixture was stirred at 70° C. for 3 hours. The reaction mixture was cooled to room temperature and then, distilled under reduced pressure to remove the solvent. The residue was purified by chromatography on a silica gel column, whereby from hexane/ethyl acetate (2/1 to 4/1) eluate fractions, methyl 4-(N-tert-butoxycarbonyl-(4S)-fluoro-(2S)-pyrrolidinylmethoxy)phenylacetate was obtained. The resulting compound was dissolved into methylene chloride (50 ml). To the resulting solution was added trifluoroacetic acid (20 ml). After the resulting mixture was stirred at room temperature for 1 hour, the solvent was distilled off under reduced pressure. The residue was neutralized with a saturated aqueous solution of sodium bicarbonate, followed by extraction with a chloroform/methanol (10/1) mixture. The extract was dried over anhydrous sodium sulfate, and distilled under reduced pressure to remove the solvent. The residue was purified by chromatography on a silica gel column, whereby from chloroform/methanol (10/1) eluate fractions, methyl 4-((4S)-fluoro-(2S)-pyrrolidinylmethoxy)phenylacetate (1.89 g, 63%) was obtained as a colorless oil.

$^1$H-NMR (CDCl$_3$) δ: 1.90 (brs, 1H), 1.96–2.02 (m, 1H), 2.16–2.31 (m, 1H), 2.90–3.03 (m, 1H), 3.35 (dd, J=13.2, 20.8 Hz, 1H), 3.52 (brs, 1H), 3.56 (s, 2H), 3.67 (s, 3H), 3.96–4.04 (m, 2H), 5.16–5.30 (m, 1H), 6.87 (d, J=8.4 Hz, 2H), 7.18 (d, J=8.4 Hz, 2H).

MS (ESI) m/z 268 (M$^+$+1).

(Step 2) Synthesis of methyl 4-((4S)-fluoro-(2S)-pyrrolidinylmethoxy)cyclohexylacetate

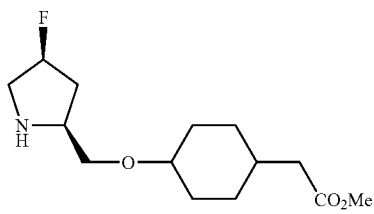

In ethanol/acetic acid (10/1, 55 ml), methyl 4-((4S)-fluoro-(2S)-pyrrolidinylmethoxy)phenylacetate (1.89 g, 7.08 mmol) and rhodium-alumina (5%, 500 mg) were subjected to catalytic hydrogenation for 18 hours at room temperature under a hydrogen gas of 4 atm. From the reaction mixture, the catalyst was filtered off. The filtrate was distilled under reduced pressure to remove the solvent. The resulting oil was poured in a saturated aqueous solution of sodium bicarbonate to neutralize the oil therewith, followed by extraction with a chloroform/methanol (10/1) mixture. The extract was dried over anhydrous sodium sulfate, and distilled under reduced pressure to remove the solvent to give methyl ((4S)-fluoro-(2S)-pyrrolidinylmethoxy)cyclohexylacetate (1.88 g, 97%) as a colorless oil.

$^1$H-NMR (CDCl$_3$), mixture of cis and trans isomers, δ: 1.23–2.16 (series of m, 10H), 2.19–2.23 (m, 4H), 2.79–2.92 (m, 1H), 3.16–3.55 (series of m, 5H), 3.65 (s, 3H), 5.30 (d, J=54.8 Hz, 1H).

MS (ESI) m/z 274 (M$^+$+1).

(Step 3) Synthesis of methyl 4-(1-((2-(5-fluoro-1-methyl-3-indolyl)-6-benzoxazolyl)acetyl)-(4S)-fluoro-(2S)-pyrrolidinylmethoxy)cyclohexylacetate

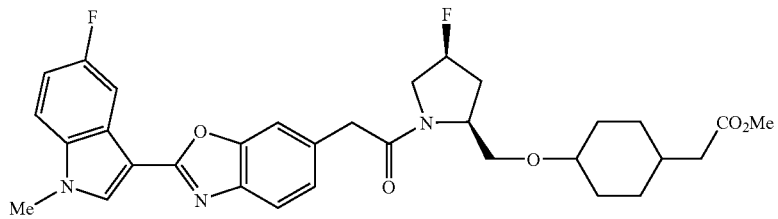

In DMF (10 ml), HOBt (18.0 mg, 0.14 mmol) was added to (2-(5-fluoro-1-methyl-3-indolyl)-6-benzoxazolyl)acetic acid (219 mg, 0.68 mmol), methyl 4-((4S)-fluoro-(2S)-pyrrolidinylmethoxy)cyclohexylacetate (185 mg, 0.68 mmol) and EDC-HCl (142 mg, 0.74 mmol). The resulting mixture was stirred at room temperature for 18 hours. Water was added to the residue, followed by extraction with ethyl acetate. The extract was washed with saturated brine, dried over anhydrous sodium sulfate, and distilled under reduced pressure to remove the solvent. The residue was purified by chromatography using thin layer silica gel, whereby from ethyl acetate eluate fractions, methyl 4-(1-((2-(5-fluoro-1-methyl-3-indolyl)-6-benzoxazolyl)acetyl)-(4S)-fluoro-(2S)-pyrrolidinylmethoxy)cyclohexylacetate (334 mg, 85%) was obtained as a colorless amorphous substance.

MS (ESI) m/z 579 (M$^+$+1).

(Step 4) Synthesis of 4-(1-((2-(5-fluoro-1-methyl-3-indolyl)-6-benzoxazolyl)acetyl)-(4S)-fluoro-(2S)-pyrrolidinylmethoxy)cyclohexylacetic acid

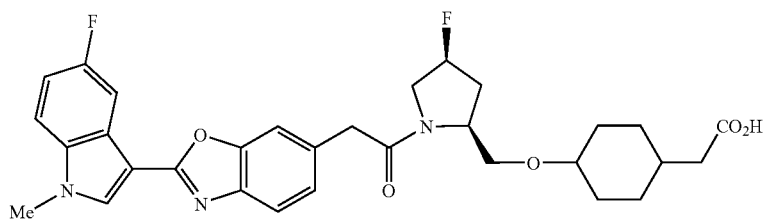

To methyl 4-(1-((2-(5-fluoro-1-methyl-3-indolyl)-6-benzoxazolyl)acetyl)-(4S)-fluoro-(2S)-pyrrolidinylmethoxy)cyclohexylacetate (315 mg, 0.54 mmol) were added THF/methanol (1/1, 20 ml) and 0.25N NaOH (10.9 ml, 2.72 mmol). The resulting mixture was stirred at room temperature for 6 hours. The reaction mixture was poured in 1N HCl to acidify the mixture therewith, followed by extraction with a chloroform/methanol (10/1) mixture. The extract was dried over anhydrous sodium sulfate, and distilled under reduced pressure to remove the solvent. The residue was purified by chromatography on a silica gel column, whereby from chloroform/methanol (10/1) eluate fractions, the title compound (260 mg, 85%) was obtained as a colorless amorphous substance.

$^1$H-NMR (DMSO-$d_6$), mixture of amide isomers, mixture of cis and trans isomers, δ: 1.53–2.60 (series of m, 14H), 3.44–4.67 (series of m, 6H), 4.24 (s, 3H), 3.22–4.45 (series of m, 7H), 5.55–5.74 (m, 1H), 7.45–7.56 (m, 2H), 7.83 (d, J=9.2 Hz, 1H), 7.91–7.94 (m, 2H), 8.28 (dd, J=2.4, 9.6 Hz, 1H), 8.66 (d J=2.8 Hz, 1H), 12.23 (brs, 1H).

MS (ESI) m/z 566 (M$^+$+1).

Example 107 trans-4-(N-(1-((5-Chloro-2-fluoro-4-((1-methyl-3-indolylcarbonyl)amino)phenyl)acetyl)-(4S)-fluoro-(2S)-pyrrolidinylmethyl)amino)cyclohexanecarboxylic acid (Step 1) Synthesis of 1-tert-butoxycarbonyl-(4S)-fluoroprolinal

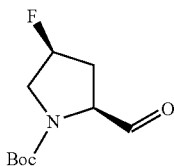

To a solution of oxalyl chloride (0.4 ml, 4.605 mmol) in methylene chloride (4.0 ml), DMSO (0.65 ml, 9.209 mmol) was added dropwise in a nitrogen gas stream and the reaction mixture was stirred at the same temperature for 15 minutes. To the reaction mixture was added a solution of 1-tert-butoxycarbonyl-(4S)-fluoro-(2S)-pyrrolidinylmethanol (504.8 mg, 2.302 mmol) in methylene chloride (5.0 ml) at −78° C. by using a syringe. The reaction mixture was stirred at the same temperature for 1 hour. To the mixture was added diisopropylethylamine (2.0 ml, 11.51 mmol) at −78° C. After stirring at the same temperature for 30 minutes, the reaction mixture was warmed to room temperature and diluted with chloroform. The chloroform solution was washed with water, dried over anhydrous sodium sulfate, and distilled under reduced pressure to remove the solvent to give 1-tert-butoxycarbonyl-(4S)-fluoroprolinal as a pale yellow amorphous substance. The resulting compound was provided for the subsequent reaction without further purification.

$^1$H-NMR (CDCl$_3$) δ: 1.43, 1.46 (total 9H, s, t-Bu), 2.16–2.49 (2H, m), 3.44–3.70 (1H, m), 3.71–3.96 (1H, m), 4.17, 4.29 (total 1H, d, J=11.4 Hz), 5.19 (1H, d, J=50.0 Hz), 9.55 and 9.60 (total 1H, s, CHO).

(Step 2) Synthesis of methyl trans-4-(N-(1-tert-butoxycarbonyl-(4S)-fluoro-(2S)-pyrrolidinylmethyl)amino)cyclohexanecarboxylate

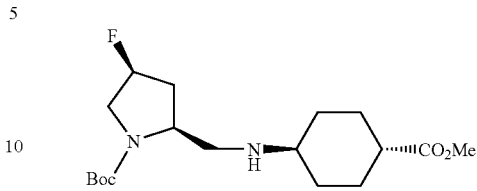

In THF (16 ml), sodium triacetoxyborohydride (1.22 g, 5.756 mmol) was added to 1-tert-butoxycarbonyl-(4S)-fluoroprolinal and methyl trans-4-aminocyclohexanecarboxylate (362.0 mg, 2.302 mmol) under stirring at 0° C. After the reaction mixture was stirred for cyclohexylcarbon 1 hour, it was diluted with chloroform. A saturated aqueous solution of sodium bicarbonate was added, followed by extraction with a chloroform-methanol (10:1, v/v) mixture. The extract was dried over anhydrous sodium sulfate, and distilled under reduced pressure to remove the solvent. The residue was purified by chromatography on a silica gel column, whereby from hexane-ethyl acetate (1:1, v/v) to chloroform-methanol (10:1, v/v) eluate fractions, methyl trans-4-(N-(1-tert-butoxycarbonyl-(4S)-fluoro-(2S)-pyrrolidinylmethyl)amino)cyclohexanecarboxylate (776.1 mg, 94% for 2 steps) was obtained as a light brown oil.

$^1$H-NMR (CDCl$_3$) δ: 0.98–1.50 (total 13H, m, including 9H, s at δ 1.45), 1.88–2.12 (5H, m), 2.13–2.30 (2H, m), 2.35–3.07 (total 4H, series of m), 3.43–4.12 (total 6H, series of m, including 3H, s at δ 3.64), 5.17 (1H, d, J=54.0 Hz).

(Step 3) Synthesis of methyl trans-4-(N-(1-tert-butoxycarbonyl-(4S)-fluoro-(2S)-pyrrolidinylmethyl)-trifluoroacetylamino)cyclohexanecarboxylate

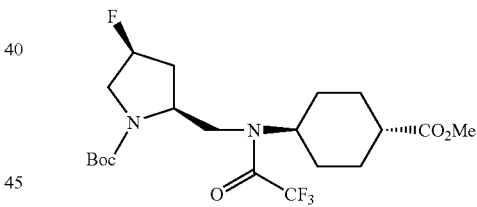

Methyl trans-4-(N-(1-tert-butoxycarbonyl-(4S)-fluoro-(2S)-pyrrolidinylmethyl)amino)cyclohexanecarboxylate (776.1 mg, 2.165 mmol) was dissolved in methylene chloride (15 ml). Under stirring at 0° C., triethylamine (0.91 ml, 6.496 mmol) and trifluoroacetic acid (0.46 ml, 3.248 mmol) were added to the resulting solution, followed by stirring for 3 hours at the same temperature. Water was added to the reaction and the mixture was extracted with ethyl acetate. The extract was dried over anhydrous sodium sulfate, and distilled under reduced pressure to remove the solvent. The residue was purified by chromatography on a silica gel column, whereby from hexane-ethyl acetate (4:1, v/v) eluate fractions, methyl trans-4-(N-(1-tert-butoxycarbonyl-(4S)-fluoro-(2S)-pyrrolidinylmethyl)-trifluoroacetylamino)cyclohexanecarboxylate (864.0 mg, 88%) was obtained as a light brown oil.

$^1$H-NMR (CDCl$_3$) δ: 0.12–2.29 (total 20H, m, including 9H, s at δ 1.42), 3.20–3.79 (total 8H, series of m, including 3H, s at δ: 3.66), 4.62 and 4.70 (total 1H, m), 5.24 (1H, br d, J=46.8 Hz).

(Step 4) Synthesis of methyl trans-4-(N-((4S)-fluoro-(2S)-pyrrolidinylmethyl)trifluoroacetylamino)cyclohexanecarboxylate

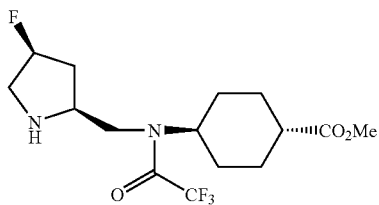

Methyl trans-4-(N-(1-tert-butoxycarbonyl-(4S)-fluoro-(2S)-pyrrolidinylmethyl)trifluoroacetylamino)cyclohexanecarboxyl ate (864.0 mg, 1.901 mmol) was dissolved in dioxane (5 ml). To the resulting solution was added 4N HCl/dioxane (20 ml) under stirring at 0° C. After stirring at room temperature for 18 hours, the reaction mixture was distilled under reduced pressure to remove the solvent to give methyl trans-4-(N-((4S)-fluoro-(2S)-pyrrolidinylmethyl)trifluoroacetylamino)cyclohexanecarboxylate as a pale yellow oil. The resulting compound was provided for the subsequent reaction without further purification.

(Step 5) Synthesis of methyl trans-4-(N-(1-((5-chloro-2-fluoro-4-((1-methyl-3-indolylcarbonyl)amino)phenyl)acetyl)-(4S)-fluoro-(2S)-pyrrolidinylmethyl)-trifluoroacetylamino)cyclohexanecarboxylate

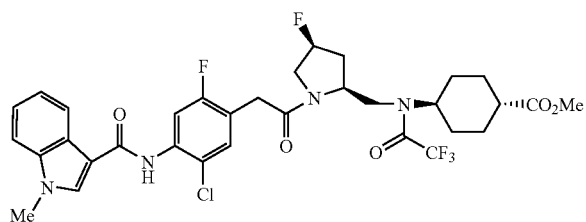

In DMF (18 ml), triethylamine (0.26 ml, 1.865 mmol) and EDC HCl (357.6 mg, 1.865 mmol) were added to methyl trans-4-(N-((4S)-fluoro-(2S)-pyrrolidinylmethyl)trifluoroacetylamino)cyclohexanecarboxyl ate (486.0 mg, 1.243 mmol), (5-chloro-2-fluoro-4-((1-methyl-3-indolylcarbonyl)amino)phenyl)acetic acid (448.7 mg, 1.243 mmol) and HOBt (33.6 mg, 0.249 mmol). The resulting mixture was stirred for cyclohexylcarbon 18 hours. The reaction mixture was diluted with ethyl acetate. The diluted mixture was washed successively with a saturated aqueous solution of sodium bicarbonate and 1N HCl, dried over anhydrous sodium sulfate, and distilled under reduced pressure to remove the solvent. The residue was purified by chromatography on a silica gel column, whereby from hexane-ethyl acetate (1:1, v/v) eluate fractions, methyl trans-4-(N-(1-((5-chloro-2-fluoro-4-((1-methyl-3-indolylcarbonyl)amino)phenyl)acetyl)-(4S)-fluoro-(2S)-pyrrolidinylmethyl)-trifluoroacetylamino)cyclohexanecarboxylate (736.9 mg, 85%) was obtained as a light brown oil.

$^1$H-NMR (CDCl$_3$) δ: 1.45–1.72 (4H, m), 1.72–1.91 (3H, m), 2.03–2.18 (2H, m), 2.29 (1H, m), 2.50 (1H, m), 3.45–4.20 (total 13H, series of m, including 3H, s at δ: 3.68, and 3H, s at δ: 3.88), 4.67 (1H, m), 5.33 (1H, br d, J=53.2 Hz), 7.28–7.45 (4H, m), 7.80 (1H, s), 8.13 (1H, m), 8.30 (1H, s), 8.52 (1H, d, J=12.0 Hz).

(Step 6) Synthesis of trans-4-(N-(1-((5-chloro-2-fluoro-4-((1-methyl-3-indolylcarbonyl)amino)phenyl)acetyl)-(4S)-fluoro-(2S)-pyrrolidinylmethyl)amino)cyclohexanecarboxylic acid

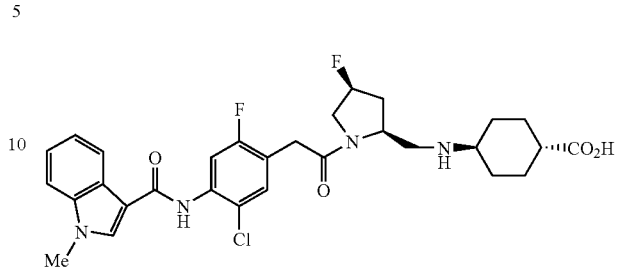

Methyl trans-4-(N-(1-((5-chloro-2-fluoro-4-((1-methyl-3-indolylcarbonyl)amino)phenyl)acetyl)-(4S)-fluoro-(2S)-pyrrolidinylmethyl)-trifluoroacetylamino)cyclohexanecarboxylate (309.1 mg, 0.443 mmol) was dissolved in THF (6.0 ml). To the resulting solution was added 0.25N NaOH (6.0 ml), followed by stirring at room temperature for 18 hours. The reaction mixture was distilled under reduced pressure to remove the solvent. The residue was neutralized with 1N HCl and then, purified by an ion exchange resin and reverse phase middle pressure column chromatography to give the title compound (51.6 mg, 20%) as a white amorphous substance.

$^1$H-NMR (CD$_3$OD) δ: 1.28–1.59 (4H, m), 2.06–2.21 (4H, m), 2.21–2.35 (2H, m), 2.35–2.59 (total 1H, m), 3.10 (1H, m), 3.78 (2H, s), 3.85–4.15 (total 5H, series of m, including 3H, s at δ: 3.91), 4.48–4.70 (3H, m), 5.42 (1H, d, J=52.7 Hz), 7.27 (1H, dd, J=8.0 Hz), 7.32 (1H, dd, J=8.0 Hz), 7.46 (1H, d, J=8.0 Hz), 7.51 (1H, d, J=8.0 Hz), 8.00 and 8.03 (total 1H, s), 8.06 (1H, s), 8.14 and 8.16 (total 1H, s), 8.34 (2H, br s);

MS (ESI) m/z 587 (M$^+$+1).

Example 108 trans-4-(N-(1-((7-Fluoro-2-(1-methyl-3-indolyl)-6-benzoxazolyl)acetyl)-(4S)-fluoro-(2S)-pyrrolidinylmethyl)amino)cyclohexanecarboxylic acid (Step 1) Synthesis of methyl trans-4-(N-(1-((7-fluoro-2-(1-methyl-3-indolyl)-6-benzoxazolyl)acetyl)-(4S)-fluoro-(2S)-pyrrolidinylmethyl)-trifluoroacetylamino)cyclohexanecarboxylate

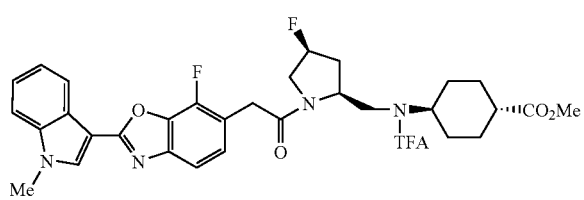

In DMF (9.0 ml), triethylamine (0.15 ml, 1.089 mmol) and EDC HCl (208.7 mg, 1.089 mmol) were added to methyl trans-4-(N-((4S)-fluoro-(2S)-pyrrolidinylmethyl)-trifluoroacetylamino)cyclohexanecarboxylate (238.7 mg, 0.726 mmol), (7-fluoro-2-(1-methyl-3-indolyl)-6-benzoxazolyl)acetic acid (235.4 mg, 0.726 mmol) and HOBt (19.6 mg, 0.145 mmol). The resulting mixture was stirred for 18 hours at room temperature. The reaction mixture was diluted with ethyl acetate. The diluted mixture was washed successively with 1N HCl and a saturated aqueous solution of sodium bicarbonate, dried over anhydrous sodium sulfate, and distilled under reduced pressure to remove the solvent. The residue was purified by chromatography on a silica gel column, whereby from hexane-ethyl acetate (1:1, v/v) eluate fractions, methyl trans-4-(N-(1-((7-fluoro-2-(1-methyl-3-indolyl)-6-benzoxazolyl)acetyl)-(4S)-fluoro-(2S)-pyrrolidinylmethyl)-trifluoroacetylamino)cyclohexanecarboxylate (100%) was obtained as a light brown oil.

$^1$H-NMR (CDCl$_3$) δ: 1.45–1.70 (5H, m), 1.72–1.89 (2H, m), 2.00–2.18 (2H, m), 2.30 (1H, m), 2.55 (1H, m), 3.50–4.17 (total 13H, series of m, including 3H, s at δ: 3.67, and 3H, s at δ: 3.92), 4.67 (1H, m), 5.32 (1H, br d, J=53.2 Hz), 7.31–7.50 (5H, m), 7.98 (1H, m), 8.44 (1H, m).

(Step 2) Synthesis of trans-4-(N-(1-((7-fluoro-2-(1-methyl-3-indolyl)-6-benzoxazolyl)acetyl)-(4S)-fluoro-(2S)-pyrrolidinylmethyl)amino)cyclohexanecarboxylic acid

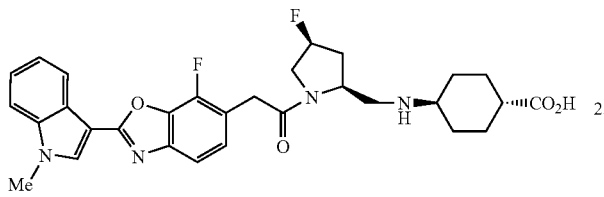

Methyl trans-4-(N-(1-((7-fluoro-2-(1-methyl-3-indolyl)-6-benzoxazolyl)acetyl)-(4S)-fluoro-(2S)-pyrrolidinylmethyl)-trifluoroacetylamino)cyclohexanecarboxylate (145.8 mg, 0.211 mmol) was dissolved in THF (4.0 ml). To the resulting solution was added 0.25N NaOH (4.0 ml), followed by stirring at room temperature for 18 hours. The reaction mixture was distilled under reduced pressure to remove the solvent. The residue was neutralized with 1N HCl and then, purified by an ion exchange resin and reverse phase middle pressure column chromatography to give the title compound (36.0 mg, 30%) as a white amorphous substance.

$^1$H-NMR (CD$_3$OD) δ: 1.20–1.56 (5H, m), 1.92–2.57 (6H, m), 3.05 (1H, m), 3.67–4.16 (total 9H, m, including 3H, s at δ: 3.94), 4.40–4.70 (1H, m), 5.43 (1H, br d, J=52.4 Hz), 7.10–7.55 (5H, m), 8.11 (1H, s), 8.30 (1H, d, J=8.0 Hz), 8.44 (1H, br s);

MS (ESI) m/z 551 (M$^+$+1).

Example 109

1-(2-(1-((5-Chloro-2-fluoro-4-((1-methyl-3-indolylcarbonyl)amino)phenyl)acetyl)-(4S)-fluoro-(2R)-pyrrolidinyl)ethyl)-4-piperidinecarboxylic acid (Step 1) Synthesis of 1-(tert-butoxycarbonyl)-(2S)-chloromethyl-(4S)-fluoropyrrolidine

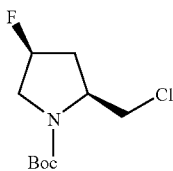

In acetonitrile (120 ml), carbon tetrachloride (3.30 ml, 34.2 mmol) was added dropwise to 1-(tert-butoxycarbonyl)-(4S)-fluoro-(2S)-pyrrolidinylmethanol (5.00 g, 22.8 mmol), potassium cyanide (2.97 g, 45.6 mmol), tributylphosphine (6.83 ml, 27.4 mmol), and 18-crown-6 (0.60 g, 2.28 mmol) under stirring at 0° C. After completion of the dropwise addition, the reaction mixture was stirred at room temperature for 19 hours and at 80° C. for 9 hours. After the reaction mixture was cooled to room temperature and the crystals thus precipitated were filtered off, the filtrate was distilled under reduced pressure to remove the solvent. The residue was purified by chromatography on a silica gel column, whereby from n-hexane-ethyl acetate (4:1, v/v) eluate fractions, 1-(tert-butoxycarbonyl)-(2S)-chloromethyl-(4S)-fluoropyrrolidine (2.05 g, 46%) was obtained as a yellow solid.

$^1$H-NMR (CDCl$_3$) δ: 1.50 (broad s, 9H), 2.16 (m, 1H), 2.53 (m, 1H), 3.41–4.17 (m, 5H), 5.24 (m, 1H).

(Step 2) Synthesis of (1-(tert-butoxycarbonyl)-(4S)-fluoro-(2R)-pyrrolidinyl)acetonitrile

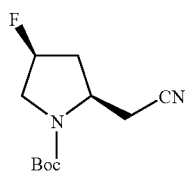

In DMSO (50 ml), 1-(tert-butoxycarbonyl)-(2S)-chloromethyl-(4S)-fluoropyrrolidine (2.01 g, 8.46 mmol) and sodium cyanide (0.83 g, 16.9 mmol) were stirred at 80° C. for 21 hours. After cooling to room temperature, the reaction mixture was added with water, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (3:1, v/v) eluate fractions, (1-(tert-butoxycarbonyl)-(4S)-fluoro-(2R)-pyrrolidinyl)acetonitrile (1.67 g, 86%) was obtained as a yellow oil.

IR (ATR) ν 2250 cm$^{-1}$;

$^1$H-NMR (CDCl$_3$) δ: 1.46 (broad s, 9H), 2.20–2.43 (m, 2H), 2.59 (m, 1H), 3.00 (m, 1H), 3.48–3.75 (m, 2H), 4.22 (m, 1H), 5.25 (m, 1H).

MS (ESI) m/z 229 (M$^+$+1).

(Step 3) Synthesis of (1-(tert-butoxycarbonyl)-(4S)-fluoro-(2R)-pyrrolidinyl)acetic acid

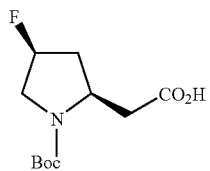

In methanol (36 ml), (1-(tert-butoxycarbonyl)-(4S)-fluoro-(2R)-pyrrolidinyl)acetonitrile (1.67 g, 7.32 mmol) and 0.25N NaOH (44 ml, 11.0 mmol) were heated under reflux for 24 hours. After cooling to room temperature, the reaction mixture was distilled under reduced pressure to remove the solvent. The residue was dissolved in water. The aqueous solution was acidified with 1N HCl, followed by extraction with ethyl acetate. The extract was dried over anhydrous magnesium sulfate, and distilled under reduced pressure to remove the solvent to give (1-(tert-butoxycarbonyl)-(4S)-fluoro-(2R)-pyrrolidinyl)acetic acid (1.37 g, 76%) as a brown solid.

$^1$H-NMR (CDCl$_3$) δ: 1.47 (s, 9H), 2.16–2.27 (m, 2H), 2.63 (m, 1H), 3.02 (m, 1H), 3.43–3.79 (m, 2H), 4.34 (m, 1H), 5.23 (m, 1H).

MS (ESI) m/z 248 (M$^+$+1).

(Step 4) Synthesis of 2-(1-(tert-butoxycarbonyl)-(4S)-fluoro-(2R)-pyrrolidinyl)ethanol

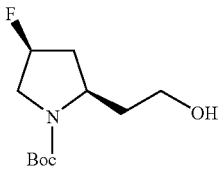

In THF (30 ml) was dissolved (1-(tert-butoxycarbonyl)(4S)-fluoro-(2R)-pyrrolidinyl)acetic acid (1.37 g, 5.54 mmol). To the resulting solution, a 10M borane-dimethyl sulfide solution (0.68 ml, 7.20 mmol) was added dropwise under stirring at 0° C. After completion of the dropwise addition, the reaction mixture was heated under reflux for 3 hours. The reaction mixture was cooled to room temperature and then, distilled under reduced pressure to remove the solvent. The residue was treated with a saturated aqueous solution of sodium bicarbonate, followed by extraction with chloroform. The extract was washed with saturated brine, dried over anhydrous sodium sulfate, and distilled under reduced pressure to remove the solvent to give 2-(1-(tert-butoxycarbonyl)-(4S)-fluoro-(2R)-pyrrolidinyl)ethanol (1.19 g, 92%) was obtained as a yellow oil.

$^1$H-NMR (CDCl$_3$) δ: 1.48 (s, 9H), 1.76–2.27 (m, 4H), 3.55–3.73 (m, 4H), 4.20–4.30 (m, 2H), 5.23 (m, 1H).

MS (ESI) m/z 234 (M$^+$+1).

(Step 5) Synthesis of ethyl 1-(2-(1-(tert-butoxycarbonyl)-(4S)-fluoro-(2R)-pyrrolidinyl)ethyl)-4-piperidinecarboxylate

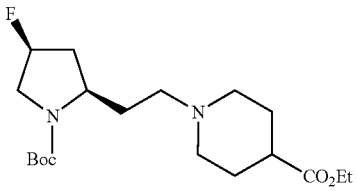

In methylene chloride (50 ml) were dissolved 2-(1-(tert-butoxycarbonyl)-(4S)-fluoro-(2R)-pyrrolidinyl)ethanol (1.19 g, 5.10 mmol) and triethylamine (1.07 ml, 7.65 mol). Under stirring at 0° C., methanesulfonyl chloride (0.43 ml, 5.61 mmol) was added dropwise to the resulting solution. After stirring at the same temperature for 1 hour, the reaction mixture was added with a saturated aqueous solution of NH$_4$Cl, followed by extraction with chloroform. The extract was washed with saturated brine, dried over anhydrous sodium sulfate, and distilled under reduced pressure to remove the solvent to afford a mesylate (1.60 g) as a yellow oil. In acetonitrile, the resulting mesylate (1.60 g), ethyl 4-piperidinacetate (1.20 ml, 7.48 mmol), and potassium carbonate (0.71 g, 5.14 mmol) were heated under reflux for 1.5 hours. The reaction mixture was cooled to room temperature. The precipitate was filtered off, and the filtrate was distilled under reduced pressure to remove the solvent. The residue was purified by chromatography on a silica gel column, whereby from chloroform-methanol (10:1, v/v) eluate fractions, ethyl 1(2-(1-(tert-butoxycarbonyl)-(4S)-fluoro-(2R)-pyrrolidinyl)ethyl)-4-piperidinecarboxylate (831 mg, 44%) was obtained as a yellow oil.

$^1$H-NMR (CDCl$_3$) δ: 1.24 (t, J=7.1 Hz, 3H), 1.46 (s, 9H), 1.62–2.47 (m, 12H), 2.83–2.90 (m, 2H), 3.49–3.93 (m, 3H), 4.12 (q, J=7.1 Hz, 2H), 4.18 (m, 1H), 5.18 (m, 1H).

MS (ESI) m/z 373 (M$^+$+1).

(Step 6) Synthesis of ethyl 1-(2-((4S)-fluoro-(2R)-pyrrolidinyl)ethyl)-4-piperidinecarboxylate

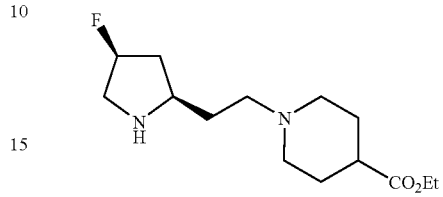

Ethyl 1-(2-(1-(tert-butoxycarbonyl)-(4S)-fluoro-(2R)-pyrrolidinyl)ethyl)-4-piperidinecarboxylate (831 mg, 2.23 mmol) was dissolved in methylene chloride (10 ml). After trifluoroacetic acid (5.0 ml) was added to the resulting solution at 0° C., the temperature of the reaction mixture was caused to rise back to room temperature and stirring was conducted for 1 hour. The reaction mixture was distilled under reduced pressure to remove the solvent. The residue thus obtained was neutralized with a saturated aqueous solution of sodium bicarbonate, followed by extraction with chloroform. The extract was washed with saturated brine, dried over anhydrous sodium sulfate, and distilled under reduced pressure to remove the solvent to give ethyl 1-(2-((4S)-fluoro-(2S)-pyrrolidinyl)ethyl)-4-piperidinecarboxylate (466 mg, 77%) as a yellow oil.

$^1$H-NMR (CDCl$_3$) δ: 1.25 (t, J=7.1 Hz, 3H), 1.68–2.16 (m, 8H), 2.21–2.35 (m, 2H), 2.40–2.58 (m, 2H), 2.80–3.07 (m, 2H), 3.29–3.76 (m, 3H), 4.13 (q, J=7.1 Hz, 2H), 4.16 (m, 1H), 5.22 (m, 1H).

MS (ESI) m/z 273 (M$^+$+1).

(Step 7) Synthesis of ethyl 1-(2-(1-((5-chloro-2-fluoro-4-((1-methyl-3-indolylcarbonyl)amino)phenyl)acetyl)-(4S)-fluoro-(2R)-pyrrolidinyl)ethyl)-4-piperidinecarboxylate

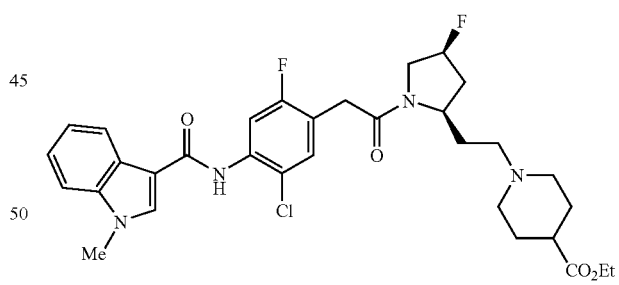

To (5-chloro-2-fluoro-4-((1-methyl-3-indolylcarbonyl)amino)phenyl)acetic acid (334 mg, 0.93 mmol), ethyl 1-(2-((4S)-fluoro-(2R)-pyrrolidinyl)ethyl)-4-piperidinecarboxylate (252 mg, 0.93 mmol), HOBt (25.0 mg, 0.19 mmol), and DMAP (23.0 mg, 0.19 mmol) were added DMF (9.0 ml) and EDC HCl (266 mg, 1.39 mmol). The resulting mixture was stirred at room temperature for 20 hours. Water was added to the reaction mixture, followed by extraction with chloroform. The extract was washed with saturated brine, dried over anhydrous sodium sulfate, and distilled under reduced pressure to remove the solvent. The residue was purified by chromatography on a silica gel column, whereby from ethyl acetate-acetone (1:1, v/v) eluate fractions, ethyl 1-(2-(1-((5-chloro-2-fluoro-4-((1-methyl-3-indolylcarbonyl)amino)

phenyl)acetyl)-(4S)-fluoro-(2R)-pyrrolidinyl)ethyl)-4-piperidinecarboxylate (269 mg, 47%) was obtained as a pale yellow amorphous substance.

¹H-NMR (CDCl₃) δ: 1.25 (t, J=7.4 Hz, 3H), 1.74–2.40 (m, 12H), 2.88–2.95 (m, 2H), 3.52–3.87 (m, 5H), 3.88 (s, 3H), 4.09–4.33 (m, 3H), 5.30 (m, 1H), 7.33–7.45 (m, 4H), 7.81 (s, 1H), 8.14 (m, 1H), 8.30 (m, 1H), 8.52 and 8.53 (each d, J=11.5 Hz, total 1H).

MS (ESI) m/z 616 (M⁺+1).

(Step 8) Synthesis of 1-(2-(1-((5-chloro-2-fluoro-4-((1-methyl-3-indolylcarbonyl)amino)phenyl)acetyl)-(4S)-fluoro-(2R)-pyrrolidinyl)ethyl)-4-piperidinecarboxylic acid

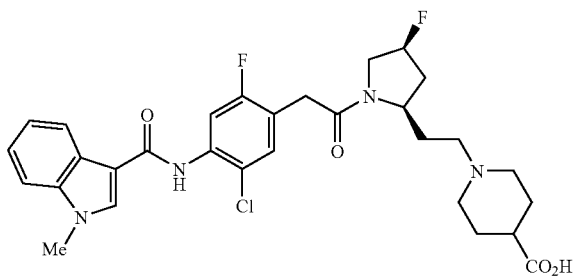

To ethyl 1-(2-(1-((5-chloro-2-fluoro-4-((1-methyl-3-indolylcarbonyl)amino)phenyl)acetyl)-(4S)-fluoro-(2R)-pyrrolidinyl)ethyl)-4-piperidinecarboxylate (269 mg, 0.44 mmol) were added THF (4.5 ml) and 0.25N NaOH (2.62 ml, 0.66 mmol). The resulting mixture was stirred at room temperature for 21 hours. The reaction mixture was distilled under reduced pressure to remove the solvent. The residue was neutralized with 1N HCl, and purified by an ion exchange resin (HP-20, Mitsubishi Chemical) to give the title compound (160 mg, 62%) as a pale yellow solid.

IR (ATR) ν 3419, 2940, 1644, 1583, 1511, 1465 cm⁻¹;

¹H-NMR (DMSO-d₆) δ: 1.45–1.58 (m, 2H), 1.74–2.36 (m, 9H), 2.73–2.87 (m, 2H), 3.41–3.87 (m, 7H), 3.88 (s, 3H), 4.09 and 4.20 (each m, total 1H), 5.32 and 5.39 (each m, total 1H), 7.21 (m, 1H), 7.27 (m, 1H), 7.44 and 7.49 (each d, J=7.6 Hz, total 1H), 7.54 (d, J=8.1 Hz, 1H), 7.71 (d, J=11.2 Hz, 1H), 8.14 (d, J=7.6 Hz, 1H), 8.30 (s, 1H), 9.29 (m, 1H).

MS (ESI) m/z 587 (M⁺+1);

Anal. Calcd for C₃₀H₃₃ClF₂N₄O₄ 0.75H₂O: C, 60.00; H, 5.79; N, 9.33. Found: C, 60.08; H, 6.00; N, 9.12.

Example 110 trans-4-(((4S)-Fluoro-1-(2-(5-fluoro-2-methylphenylamino)-7-fluoro-6-benzoxazolylacetyl)-(2S)-pyrrolidinyl)carbonylamino)cyclohexanecarboxylic acid (Step 1) Synthesis of methyl trans-4-((1-tert-butoxycarbonyl-(4S)-fluoro-(2S)-pyrrolidinylcarbonylamino)cyclohexanecarboxylate

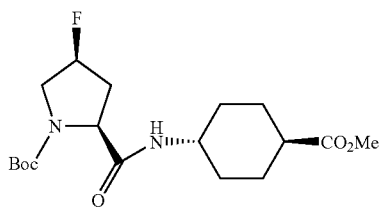

Methyl trans-4-aminocyclohexanecarboxylate (1.02 g, 6.481 mmol) and triethylamine (2.26 ml, 16.20 mmol) were dissolved in DMF (20 ml). To the resulting solution were added 1-tert-butoxycarbonyl-(4S)-fluoro-(2S)-proline (1.51 g, 6.481 mmol), HOBt (175.2 mg, 1.296 mmol) and EDC•HCl (1.86 g, 9.722 mmol) and the resulting mixture was stirred at room temperature for 18 hours. The reaction mixture was diluted with ethyl acetate. The diluted mixture was washed successively with 1N HCl and a saturated aqueous solution of sodium bicarbonate, dried over anhydrous sodium sulfate, and distilled under reduced pressure to remove the solvent. The residue was purified by chromatography on a silica gel column, whereby from hexane-ethyl acetate (1:1 to 1:3, v/v) eluate fractions, methyl trans-4-((1-tert-butoxycarbonyl-(4S)-fluoro-(2S)-pyrrolidinyl)carbonylamino)cyclohexanecarboxylate (1.21 g, 50%) was obtained as an oil.

¹H-NMR (CDCl₃) δ: 1.03–1.20 (2H, m), 1.32–1.63 (total 12H, m), 1.89–2.07 (5H, m), 2.23 (1H, m), 2.55 (1H, br s, NH), 3.45–3.84 (total 6H, m), 4.33 (1H, m), 5.18 (1H, d, J=52.0 Hz).

(Step 2) Synthesis of methyl trans-4-(((4S)-fluoro-(2S)-pyrrolidinyl)carbonylamino)cyclohexanecarboxylate

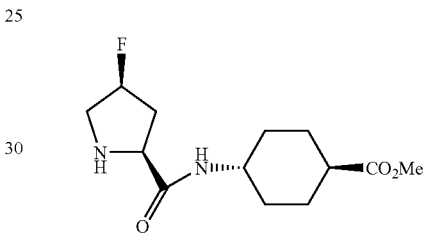

Methyl trans-4-(1-tert-butoxycarbonyl-(4S)-fluoro-(2S)-pyrrolidinylcarbonylamino)cyclohexanecarboxylate (1.21 g, 3.249 mmol) was dissolved in methylene chloride (20 ml). To the resulting solution was added trifluoroacetic acid (10 ml) at 0° C. The resulting mixture was stirred at room temperature for 3.5 hours. The reaction mixture was distilled under reduced pressure to remove the solvent. The residue was dissolved in chloroform. The chloroform solution was neutralized by washing with a saturated aqueous solution of sodium bicarbonate, followed by extraction with a chloroform-methanol (10:1, v/v) mixture. The extract was dried over anhydrous sodium sulfate, and distilled under reduced pressure to remove the solvent to give methyl trans-4-(((4S)-fluoro-(2S)-pyrrolidinyl)carbonylamino)cyclohexanecarboxylate. The resulting compound was provided for the subsequent reaction without further purification.

¹H-NMR (CDCl₃) δ: 1.07–1.35 (2H, m), 1.43–1.65 (2H, m), 1.88–2.14 (5H, m), 2.15–2.49 (3H, m), 3.06–3.38 (2H, m), 3.60–3.88 (total 5H, m), 5.16 (1H, br d, J=53.2 Hz), 7.39 (1H, br s, NH).

(Step 3) Synthesis of methyl trans-4-(((4S)-fluoro-1-(2-(5-fluoro-2-methylphenylamino)-7-fluoro-6-benzoxazolylacetyl)-(2S)-pyrrolidinyl)carbonylamino)cyclohexanecarboxylate

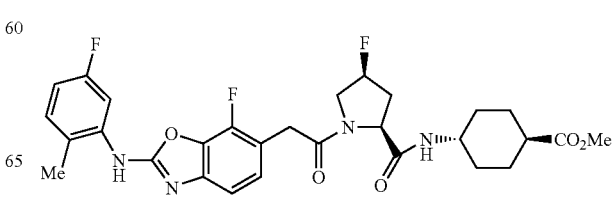

To the above-described methyl trans-4-(((4S)-fluoro-(2S)-pyrrolidinyl)carbonylamino)cyclohexanecarboxylate (81.5 mg, 0.299 mmol), 2-(5-fluoro-2-methylphenylamino)-7-fluoro-6-benzoxazolylacetic acid (92.3 mg, 0.299 mmol) and HOBt (8.1 mg, 0.060 mmol) were added DMF (4.0 ml) and EDC HCl (86.1 mg, 0.449 mmol). The resulting mixture was stirred at room temperature for 18 hours. The reaction mixture was diluted with ethyl acetate. The diluted mixture was washed with 1N HCl and a saturated aqueous solution of sodium bicarbonate, dried over anhydrous sodium sulfate, and distilled under reduced pressure to remove the solvent. The residue was purified by chromatography on a silica gel column, whereby from chloroform-methanol (20:1, v/v) eluate fractions, methyl trans-4-((4S)-fluoro-1-(2-(5-fluoro-2-methoxyphenylamino)-7-fluoro-6-benzoxazolylacetyl)-(2S)-pyrrolidinyl)carbonylamino)cyclohexanecarboxylate (10%) was obtained as a crystalline powder. The resulting compound was provided for the subsequent reaction without further purification.

$^1$H-NMR (CDCl$_3$) δ: 1.00–1.30 (2H, m), 1.42–1.63 (2H, m), 1.79–2.08 (5H, m), 2.08–2.36 (5H, m), 3.59–4.06 (total 8H, series of m), 4.59 and 4.74 (total 1H, d, J=9.6 Hz), 5.27 and 5.31 (total 1H, d, J=52.4 Hz), 6.74 (1H, m), 6.97–7.17 (2H, m), 7.22 (1H, m), 7.41 (1H, m), 8.01 (2H, m).

(Step 4) Synthesis of trans-4-(((4S)-fluoro-1-(2-(5-fluoro-2-methoxyphenylamino)-7-fluoro-6-benzoxazolylacetyl)-(2S)-pyrrolidinyl)carbonylamino)cyclohexanecarboxylic acid

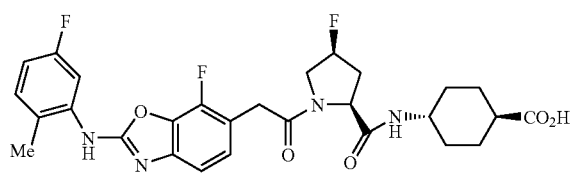

To the above-described methyl trans-4-(((4S)-fluoro-1-(2-(5-fluoro-2-methoxyphenylamino)-7-fluoro-6-benzoxazolylacetyl)-(2S)-pyrrolidinyl)carbonylamino)cyclohexanecarboxylate were added THF (4.0 ml) and 0.25N NaOH (4.0 ml). The resulting mixture was stirred at room temperature for 7 hours. The reaction mixture was distilled under reduced pressure to remove the solvent and the residue was neutralized with 1N HCl. The crystals thus precipitated were collected by filtration under reduced pressure, washed with water and dried at 50° C. under reduced pressure to give the title compound (142.5 mg, 85% for 2 steps) as a crystalline powder.

IR (ATR) ν2937, 1639, 1579, 1538 cm$^{-1}$;

$^1$H-NMR (DMSO-d$_6$) δ: 1.10–1.45 (5H, m), 1.76 (2H, m), 1.90 (2H, m), 2.04–2.50 (total 5H, m), 3.42–4.01 (total 5H, series of m), 4.40 and 4.63 (total 1H, d, J=9.6 Hz), 5.25 and 5.34 (total 1H, d, J=52.4 Hz), 6.89 (1H, m), 7.02–7.48 (4H, m), 7.90 (1H, m), 10.03 (1H, br s), 12.05 (1H, br s, CO$_2$H).

MS (ESI) m/z 559 (M$^+$+1);

Anal. Calcd for C$_{28}$H$_{29}$F$_3$N$_4$O$_5$ H$_2$O: C, 58.33; H, 5.42; N, 9.72; F, 9.89. Found: C, 58.08; H, 5.38; N, 9.45; F, 9.59.

Example 111 trans-4-((1-(5-Chloro-2-fluoro-4-((1-methyl-3-indolylcarbonyl)amino)phenylacetyl)-(4S)-fluoro-(2S)-pyrrolidinyl)carbonylamino)cyclohexanecarboxylic acid (Step 1) Synthesis of methyl trans-4-((1-tert-butoxycarbonyl-(4S)-fluoro-(2S)-pyrrolidinyl)carbonylamino)cyclohexanecarboxylate

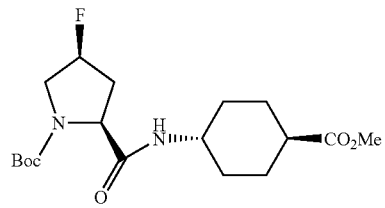

Methyl trans-4-aminocyclohexanecarboxylate (1.02 g, 6.481 mmol) was dissolved in DMF (20 ml). To the resulting solution was added triethylamine (2.26 ml, 16.20 mmol) at room temperature. After stirring for 5 minutes, 1-tert-butoxycarbonyl-(4S)-fluoro-(2S)-proline (1.51 g, 6.481 mmol), HOBt (175.2 mg, 1.296 mmol) and EDC•HCl (1.86 g, 9.722 mmol) were added to the reaction mixture. The resulting mixture was stirred for 18 hours at room temperature. The reaction mixture was diluted with ethyl acetate. The diluted mixture was washed successively with 1N HCl and a saturated aqueous solution of sodium bicarbonate, dried over anhydrous sodium sulfate, and distilled under reduced pressure to remove the solvent. The residue was purified by chromatography on a silica gel column, whereby from hexane-ethyl acetate (1:1 to 1:3, v/v) eluate fractions, methyl trans-4-((1-tert-butoxycarbonyl-(4S)-fluoro-(2S)-pyrrolidinyl)carbonylamino)cyclohexanecarboxylate (1.21 g, 50%) as an oil.

$^1$H-NMR (CDCl$_3$) δ: 1.03–1.20 (2H, m), 1.32–1.63 (total 12H, m), 1.89–2.07 (5H, m), 2.23 (1H, m), 2.55 (1H, br s, NH), 3.45–3.84 (total 6H, m), 4.33 (1H, m), 5.18 (1H, d, J=52.0 Hz).

(Step 2) Synthesis of methyl trans-4-(((4S)-fluoro-(2S)-pyrrolidinyl)carbonylamino)cyclohexanecarboxylate

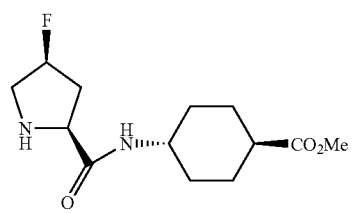

Methyl trans-4-((1-tert-butoxycarbonyl-(4S)-fluoro-(2S)-pyrrolidinylcarbonylamino)cyclohexanecarboxylate (55.3 mg, 0.148 mmol) was dissolved in methylene chloride (2.0 ml). To the resulting solution was added trifluoroacetic acid (1.0 ml) at 0° C. The resulting mixture was stirred at room temperature for 2.5 hours. The reaction mixture was distilled under reduced pressure to remove the solvent. The residue thus obtained was diluted with chloroform. The chloroform solution was neutralized with a saturated aqueous solution of sodium bicarbonate, followed by extraction with a chloroform-methanol (10:1, v/v) mixture. The extract was dried over anhydrous sodium sulfate, and distilled under reduced pressure to remove the solvent, whereby methyl trans-4-(((4S)-fluoro-(2S)-pyrrolidinyl)carbonylamino)cyclohexanecarboxylate was obtained as an amorphous substance. The resulting compound was provided for the subsequent reaction without further purification.

¹H-NMR (CDCl₃) δ: 1.07–1.35 (2H, m), 1.43–1.65 (2H, m), 1.88–2.14 (5H, m), 2.15–2.49 (3H, m), 3.06–3.38 (2H, m), 3.60–3.88 (total 5H, m), 5.16 (1H, br d, J=53.2 Hz), 7.39 (1H, br s, NH).

(Step 3) Synthesis of methyl trans-4-((1-(5-chloro-2-fluoro-4-((1-methyl-3-indolylcarbonyl)amino)phenylacetyl)-(4S)-fluoro-(2S)-pyrrolidinyl)carbonylamino)cyclohexanecarboxylate

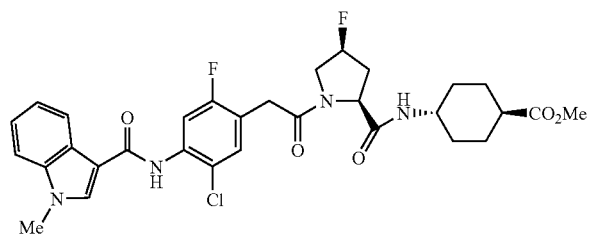

The above-described methyl trans-4-(((4S)-fluoro-(2S)-pyrrolidinyl)carbonylamino)cyclohexanecarboxylate (40.4 mg, 0.148 mmol), 5-chloro-2-fluoro-4-((1-methyl-3-indolylcarbonyl)amino)phenylacetic acid (53.6 mg, 0.148 mmol) and 1-HOBt (4.0 mg, 0.030 mmol) were dissolved in DMF (2.0 ml). To the resulting solution was added EDC HCl (42.7 mg, 0.223 mmol) and the mixture was stirred at room temperature for 18 hours. The reaction mixture was diluted with ethyl acetate. The diluted mixture was washed successively with 1N HCl and a saturated aqueous solution of sodium bicarbonate, dried over anhydrous sodium sulfate, and distilled under reduced pressure to remove the solvent. The residue was purified by chromatography on a silica gel column, whereby from chloroform-methanol (10:1, v/v) eluate fractions, methyl trans-4-((1-(5-chloro-2-fluoro-4-((1-methyl-3-indolylcarbonyl)amino)phenylacetyl)-(4S)-fluoro-(2S)-pyrrolidinyl)carbonylamino)cyclohexanecarboxylate (62.0 mg, 68% for 2 steps) was obtained as a pale yellow amorphous substance.

¹H-NMR (CDCl₃) δ: 1.00–2.32 (total 12H, series of m), 3.45–4.07 (total 11H, series of m), 4.55 and 4.71 (total 1H, d, J=10.0 Hz), 5.26 and 5.29 (total 1H, d, J=52.8 Hz), 7.27–7.45 (4H, m), 7.79 (1H, m), 8.12 (1H, m), 8.29 (1H, m), 8.54 (1H, dd, J=12.4 Hz).

(Step 4) Synthesis of trans-4-((1-(5-chloro-2-fluoro-4-((1-methyl-3-indolylcarbonyl)amino)phenylacetyl)-(4S)-fluoro-(2S)-pyrrolidinyl)carbonylamino)cyclohexanecarboxylic acid

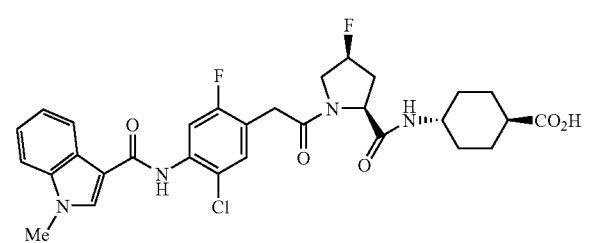

To methyl trans-4-((1-(5-chloro-2-fluoro-4-((1-methyl-3-indolylcarbonyl)amino)phenylacetyl)-(4S)-fluoro-(2S)-pyrrolidinyl)carbonylamino)cyclohexanecarboxylate (62.0 mg, 0.101 mmol) were added THF (1.5 ml) and 0.25N NaOH (1.5 ml). The resulting mixture was stirred at room temperature for 6 hours. The reaction mixture was distilled under reduced pressure to remove the solvent. The residue was neutralized with 1N HCl. The crystals thus precipitated were collected by filtration under reduced pressure, washed with water and dried at 50° C. under reduced pressure to give the title compound (56.3 mg, 93%) as a white amorphous substance.

¹H-NMR (DMSOd₆) δ: 1.11–1.42 (4H, m), 1.74 (2H, m), 1.89 (2H, m), 2.05–2.52 (3H, m), 3.37–4.01 (total 8H, series of m), 4.40 and 4.64 (total 1H, d, J=10.0 Hz), 5.25 and 5.36 (total 1H, d, J=52.4 Hz), 7.16–7.95 (total 6H, series of m), 8.15 (1H, d, J=8.0 Hz), 8.31 (1H, s), 9.31 (1H, m), 12.05 (1H, s, CO₂H).

MS (ESI) m/z 601 (M⁺+1).

Example 112 trans-4-((1-(3-Chloro-4-((1-isoquinolinylcarbonyl)amino)phenylacetyl)-(4S)-fluoro-(2S)-pyrrolidinyl)carbonylamino)cyclohexanecarboxylic acid (Step 1) Synthesis of methyl trans-4-((1-tert-butoxycarbonyl-(4S)-fluoro-(2S)-pyrrolidinyl)carbonylamino)cyclohexanecarboxylate

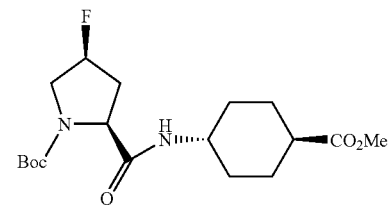

Methyl trans-4-aminocyclohexanecarboxylate (1.02 g, 6.481 mmol) was dissolved in DMF (20 ml). To the resulting solution was added triethylamine (2.26 ml, 16.20 mmol) at room temperature and the mixture was stirred for 5 minutes. To the reaction mixture were added 1-tert-butoxycarbonyl-(4S)-fluoro-(2S)-proline (1.51 g, 6.481 mmol), HOBt (175.2 mg, 1.296 mmol) and EDC•HCl (1.86 g, 9.722 mmol). The resulting mixture was stirred at room temperature for 18 hours. The reaction mixture was diluted with ethyl acetate. The diluted mixture was washed with 1N HCl and a saturated aqueous solution of sodium bicarbonate, dried over anhydrous sodium sulfate, and distilled under reduced pressure to remove the solvent. The residue was purified by chromatography on a silica gel column, whereby from hexane-ethyl acetate (1:1 to 1:3, v/v) eluate fractions, methyl trans-4-((1-tert-butoxycarbonyl-(4S)-fluoro-(2S)-pyrrolidinyl)carbonylamino)cyclohexanecarboxylate (1.21 g, 50%) was obtained as an oil.

¹H-NMR (CDCl₃) δ: 1.03–1.20 (2H, m), 1.32–1.63 (total 12H, m), 1.89–2.07 (5H, m), 2.23 (1H, m), 2.55 (1H, br s, NH), 3.45–3.84 (total 6H, m), 4.33 (1H, m), 5.18 (1H, d, J=52.0 Hz).

(Step 2) Synthesis of methyl trans-4-(((4S)-fluoro-(2S)-pyrrolidinyl)carbonylamino)cyclohexanecarboxylate

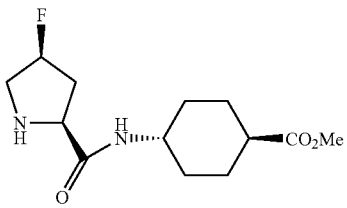

Methyl trans-4-((1-tert-butoxycarbonyl-(4S)-fluoro-(2S)-pyrrolidinyl)carbonylamino)cyclohexanecarboxylate (1.21 g, 3.249 mmol) was dissolved in methylene chloride (20 ml). To the resulting solution was added trifluoroacetic acid (10 ml) at 0° C. After stirring at room temperature for 3.5 hours, the reaction mixture was distilled under reduced pressure to remove the solvent. The residue was dissolved in chloroform. The resulting solution was neutralized with a saturated aqueous solution of sodium bicarbonate, followed by extraction with a chloroform-methanol (10:1, v/v) mixture. The extract was dried over anhydrous sodium sulfate, and distilled under reduced pressure to remove the solvent to give methyl trans-4-(((4S)-fluoro-(2S)-pyrrolidinyl)carbonylamino)cyclohexanecarboxylate as a thick sticky liquid. The resulting compound was provided for the subsequent reaction without further purification.

$^1$H-NMR (CDCl$_3$) δ: 1.07–1.35 (2H, m), 1.43–1.65 (2H, m), 1.88–2.14 (5H, m), 2.15–2.49 (3H, m), 3.06–3.38 (2H, m), 3.60–3.88 (total 5H, m), 5.16 (1H, br d, J=53.2 Hz), 7.39 (1H, br s, NH).

(Step 3) Synthesis of methyl trans-4-((1-(3-chloro-4-((1-isoquinolinylcarbonyl)amino)phenylacetyl)-(4S)-fluoro-(2S)-pyrrolidinyl)carbonylamino)cyclohexanecarboxylate

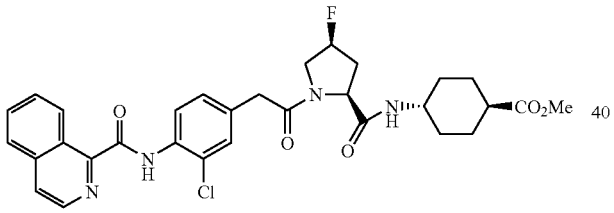

The above-described methyl trans-4-(((4S)-fluoro-(2S)-pyrrolidinyl)carbonylamino)cyclohexanecarboxylate (80.6 mg, 0.296 mmol), 3-chloro-4-((1-isoquinolinylcarbonyl)amino)phenylacetic acid (100.9 mg, 0.296 mmol) and 1-HOBt (8.0 mg, 0.059 mmol) were dissolved in DMF (4.0 ml). To the resulting solution was added EDC HCl (85.1 mg, 0.444 mmol). The resulting mixture was stirred for 18 hours at room temperature. The reaction mixture was diluted with ethyl acetate. The diluted mixture was washed successively with 1N HCl and a saturated aqueous solution of sodium bicarbonate, dried over anhydrous sodium sulfate, and distilled under reduced pressure to remove the solvent. The residue was purified by chromatography on a silica gel column, whereby from chloroform-methanol (20:1, v/v) eluate fractions, methyl trans-4-((1-(3-chloro-4-((1-isoquinolinylcarbonyl)amino)phenylacetyl)-(4S)-fluoro-(2S)-pyrrolidinyl)carbonylamino)cyclohexanecarboxylate (172.1 mg, 98%) was obtained as a thick sticky liquid.

$^1$H-NMR (CDCl$_3$) δ: 0.98–1.23 (2H, m), 1.43–1.65 (2H, m), 1.88–2.10 (6H, m), 2.24 (1H, m), 3.52–4.06 (total 8H, series of m), 4.52 and 4.74 (total 1H, d, J=9.6 Hz), 5.26 (1H, d, J=53.3 Hz), 5.96 and 6.32 (total 1H, d, J=8.5 Hz), 7.24 and 7.28 (1H, s), 7.39 and 7.44 (total 1H, s), 7.74 (2H, m), 7.89 (2H, m), 8.59 (1H, m), 8.66 (1H, d, J=8.0 Hz), 8.71 (1H, d, J=8.4 Hz), 9.70 (1H, d, J=8.4 Hz), 11.03 and 11.07 (total 1H, s).

(Step 4) Synthesis of trans-4-((1-(3-chloro-4-((1-isoquinolinylcarbonyl)amino)phenylacetyl)-(4S)-fluoro-(2S)-pyrrolidinylcarbonylamino)cyclohexanecarboxylic acid

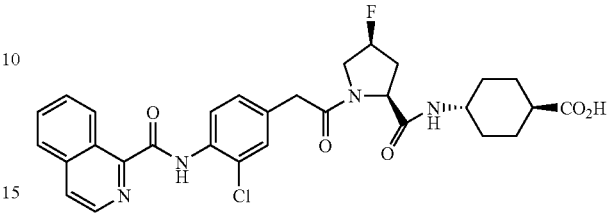

To methyl trans-4-((1-(3-chloro-4-((1-isoquinolinylcarbonyl)amino)phenylacetyl)-(4S)-fluoro-(2S)-pyrrolidinyl)carbonylamino)cyclohexanecarboxylate (172.1 mg, 0.289 mmol) were added THF (4.0 ml) and 0.25N NaOH (4.0 ml). The resulting mixture was stirred at room temperature for 7 hours. The reaction mixture was distilled under reduced pressure to remove the solvent. The residue was neutralized with 1N HCl. The crystals thus precipitated were collected by filtration under reduced pressure, washed with water and dried at 50° C. under reduced pressure to give the title compound (147.5 mg, 88%) as an amorphous substance.

IR (ATR) ν2940, 1652, 1517 cm$^{-1}$;

$^1$H-NMR (DMSO-d$_6$) δ: 1.11–1.44 (4H, m), 1.76 (2H, m), 1.90 (2H, m), 2.07–2.62 (3H, m), 3.40–3.99 (total 5H, series of m), 4.41 and 4.61 (total 1H, d, J=9.6 Hz), 5.26 and 5.34 (total 1H, d, J=53.3 Hz), 7.23–7.96 (total 5H, series of m), 8.09–8.27 (3H, m), 8.67 (1H, d, J=5.6 Hz), 9.32 (1H, d, J=8.8 Hz), 10.83 (1H, s), 12.05 (1H, br s, CO$_2$H).

MS (ESI) m/z 581 (M$^+$+1);

Anal. Calcd for C$_{30}$H$_{30}$ClFN$_4$O$_5$ 0.75H$_2$O: C, 60.61; H, 5.34; N, 9.42; Cl, 5.96; F, 3.20. Found: C, 60.50; H, 5.31; N, 9.24; Cl, 6.09; F, 2.95.

Example 113

4-((1-((5-Chloro-2-fluoro-4-(1-methyl-3-indolylcarbonylamino)phenyl)acetyl)-(4S)-fluoro-(2S)-pyrrolidinyl)carbonyl)-1-piperazinylacetic acid (Step 1) Synthesis of methyl 4-((1-((5-chloro-2-fluoro-4-(1-methyl-3-indolylcarbonylamino)phenyl)acetyl)-(4S)-fluoro-(2S)-pyrrolidinyl)carbonyl)-1-piperazinylacetate

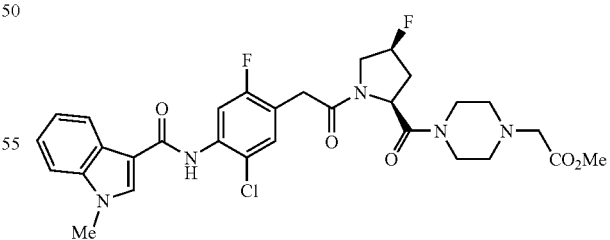

In DMF (10 ml) were dissolved (5-chloro-2-fluoro-4-(1-methyl-3-indolylcarbonylamino)phenyl)acetic acid (300 mg, 0.832 mmol) and methyl 4-(((4S)-fluoro-(2S)-pyrrolidinyl)carbonyl)-1-piperazinylacetate (300 mg, 1.10 mmol). To the resulting solution were added EDC HCl (239 mg, 1.25 mmol), DMAP (cat.), and HOBt (catalytic amount). The resulting mixture was stirred at room temperature for 12 hours. To the reaction mixture was added water (100 ml), followed by extraction with ethyl acetate. The extract was washed with saturated brine, dried over anhydrous magnesium sulfate, and distilled under reduced pressure to remove the solvent. The residue was purified by chromatography on a silica gel column, whereby from chloroform-methanol (20:1) eluate fractions, methyl 4-((1-((5-chloro-2-fluoro-4-(1-methyl-3-indolylcarbonylamino)phenyl)acetyl)-(4S)-fluoro-(2S)-pyrrolidinyl)carbonyl)-1-piperazinylacetate (419 mg, 82%) was obtained as a colorless foam.

$^1$H-NMR (CDCl$_3$) δ: 2.04–2.62 (series of m, 6H), 3.23–4.14 (series of m, 16H), 4.76–5.39 (m, 2H), 7.32–7.52 (m, 4H), 7.79 (s, 1H), 8.12 (dd, J=9.3,5.1 Hz, 1H), 8.29 (s, 1H), 8.47–8.51 (m, 1H).

MS (ESI) m/z 616 (M$^+$+1).

(Step 2) Synthesis of 4-((1-((5-Chloro-2-fluoro-4-(1-methyl-3-indolylcarbonylamino)phenyl)acetyl)-(4S)-fluoro-(2S)-pyrrolidinyl)carbonyl)-1-piperazinylacetic acid

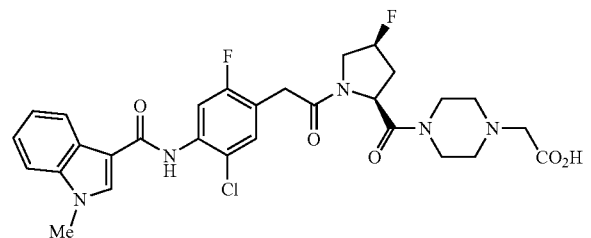

To methyl 4-((1-((5-chloro-2-fluoro-4-(1-methyl-3-indolylcarbonylamino)phenyl)acetyl)-(4S)-fluoro-(2S)-pyrrolidinyl)carbonyl)-1-piperazinylacetate (410 mg, 0.666 mmol) were added THF (10 ml) and 0.25N NaOH (5.3 ml, 1.33 mmol). The resulting mixture was stirred at room temperature for 15 hours. Water (50 ml) was added to the reaction mixture and the aqueous solution was neutralized with 1N HCl, followed by extraction with a 20% chloroform-methanol mixture (2×100 ml). The extract was dried over anhydrous magnesium sulfate and distilled under reduced pressure to remove the solvent, whereby the title compound (240 mg, 60%) was obtained as a colorless amorphous substance.

$^1$H-NMR (DMSO) δ: 2.00–4.11 (series of m, 19H), 4.92 and 5.21 (d, J=9.8 Hz, each, total 1H), 5.31 and 5.45 (m, each, total 1H), 7.20–7.30 (m, 2H), 7.41 and 7.52 (d, J=7.8 Hz, each, total 1H), 7.56 (d, J=8.3 Hz, 1H), 7.72 (d, J=11.0 Hz, 1H), 8.16 (d, J=7.8 Hz, 1H), 8.31 (s, 1H), 9.31 (s, 1H).

MS (ESI) m/z 602 (M$^+$+1);

Anal. Calcd for C$_{29}$H$_{30}$ClF$_2$N$_5$O$_5$ 3.75 H$_2$O; C, 52.02; H, 5.64; N, 10.46. Found: C, 51.59; H, 5.25; N, 10.13.

Example 114 trans-4-(1-((2-(2-Chlorophenylamino)-7-fluoro-6-benzoxazolyl)acetyl)-(4S)-fluoro-(2S)-pyrrolidinylmethoxy)cyclohexanecarboxylic acid (Step 1) Synthesis of methyl trans-4-(1-((2-(2-chlorophenylamino)-7-fluoro-6-benzoxazolyl)acetyl)-(4S)-methoxy-(2S)-pyrrolidinylmethoxy)cyclohexanecarboxylate

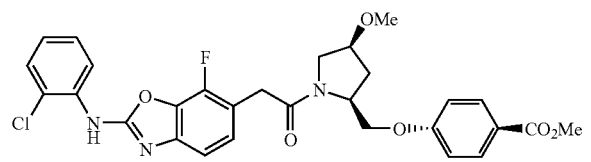

In DMF (3 ml), (2-(2-chlorophenylamino)-7-fluoro-6-benzoxazolyl)acetic acid (100 mg, 0.369 mmol), methyl trans-4-((4S)-methoxy-(2S)-pyrrolidinylmethoxy)cyclohexanecarboxylate (118 mg, 0.369 mmol), EDC HCl (106 mg, 0.554 mmol), HOBt (75 mg, 0.554 mmol) and triethylamine (0.26 ml, 1.85 mmol) were stirred at room temperature for 14 hours. The reaction mixture was poured in ice water, followed by extraction with ethyl acetate. The extract was washed with saturated brine, dried over anhydrous sodium sulfate, and distilled under reduced pressure to remove the solvent. The residue was purified by chromatography using a silica gel thin-layer plate, whereby from chloroform/acetone (10/1, v/v) eluate fractions, methyl trans-4-(1-((2-(2-chlorophenylamino)-7-fluoro-6-benzoxazolyl)acetyl)-(4S)-methoxy-(2S)-pyrrolidinylmethoxy)cyclohexanecarboxylate (151 mg, 71%) was obtained as a colorless oil.

$^1$H-NMR (CDCl$_3$) δ: 1.14–1.68 (m, 4H), 1.92–2.36 (m, 6H), 3.21–3.29 (m, 1H), 3.30 and 3.33 (each s, total 3H, amide isomers), 3.45–3.61 (m, 2H), 3.64 and 3.67 (each s, total 3H, amide isomers), 3.71(s, 1H), 3.74–4.06 (m, 5H), 4.21–4.37 (m, 1H), 7.04 (t, J=7.6 Hz, 1H), 7.14 (t, J=7.1 Hz, 1H), 7.24 (d, J=6.6 Hz, 1H), 7.36 and 7.41 (each d, J=7.8 and 8.1 Hz respectively, total 2H, amide isomers), 7.58 and 7.65 (m and br, total 1H, amide isomers), 8.52 (d, J=8.3 Hz, 1H).

MS (ESI) m/z 574 (M$^+$+1), 576 (M$^+$+3).

(Step 2) Synthesis of trans-4-(1-((2-(2-chlorophenylamino)-7-fluoro-6-benzoxazolyl)acetyl)-(4S)-methoxy-(2S)-pyrrolidinylmethoxy)cyclohexanecarboxylic acid

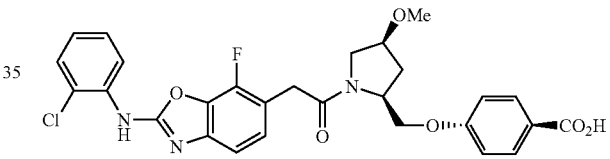

Methyl trans-4-(1-((2-(2-chlorophenylamino)-7-fluoro-6-benzoxazolyl)acetyl)-(4S)-methoxy-(2S)-pyrrolidinylmethoxy)cyclohexanecarboxylate (151 mg, 0.263 mmol) was dissolved in a THF/methanol (2:1, 6 ml) mixture. To the resulting solution was added 1N NaOH (2 ml) and the mixture was stirred at room temperature for 18 hours. The reaction mixture was distilled under reduced pressure to remove the solvent. The residue was acidified with 1N HCl. The crystals thus precipitated were collected by filtration under reduced pressure, washed with water and dried under reduced pressure. The resulting crude crystals were purified by chromatography using a silica gel thin-layer plate. The chloroform/methanol (20/1) fractions were collected and solidified with chloroform/methanol/ethyl acetate/n-hexane, whereby the title compound (80 mg, 54%) was obtained as a colorless solid.

IR (ATR) ν 3406, 2937, 2864, 1697, 1639, 1593, 1572, 1446 cm$^{-1}$;

$^1$H-NMR (DMSO) δ: 1.11–1.41 (m, 4H), 1.82–2.21 (m, 7H), 3.19 (m, 1H), 3.22 and 3.25 (each s, total 3H, amide isomers), 3.28–4.31 (m, 8H), 7.03 and 7.06 (each t, each J=7.8 Hz, total 1H, amide isomers), 7.15 (dd, J=7.8, 3.2 Hz, 1H), 7.21 (dd, J=7.8, 1.0 Hz, 1H), 7.42 (dt, J=6.6, 1.0 Hz, 1H), 7.54 (dd, J=8.1, 1.0 Hz, 1H), 8.05 (d, J=7.6 Hz, 1H).

MS (ESI) m/z 560 (M$^+$+1), 562 (M$^+$+3);

Anal. Calcd for C$_{28}$H$_{31}$ClFN$_3$O$_6$ 0.5H$_2$O: C, 59.10; H, 5.67; N, 7.38. Found: C, 59.10; H, 5.65; N, 7.20.

Example 115 trans-4-(1-((5-Chloro-2-fluoro-4-(1-methyl-3-indolylcarbonylamino)phenyl)acetyl)-(4R)-methoxy-(2S)-pyrrolidinylmethoxy)cyclohexanecarboxylic acid (Step 1) Synthesis of trans-4-(1-(tert-butoxycarbonyl)-(4R)-methoxy-(2S)-pyrrolidinylmethoxy)cyclohexanecarboxylic acid

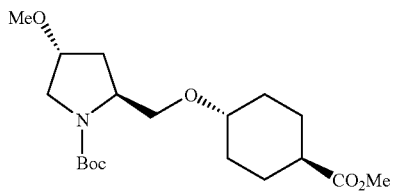

Methyl iodide (436 1, 7.00 mmol) and trans-4-(1-(tert-butoxycarbonyl)-(4R)-methoxy-(2S)-pyrrolidinylmethoxy)cyclohexanecarboxylic acid (500 mg, 1.40 mmol were dissolved in DMF (10 ml). Under stirring at 0° C., sodium hydride (112 mg, 2.80 mmol) was added to the resulting solution in portions. After stirring at the same temperature for 3 hours, the reaction mixture was added with water (50 ml), followed by extraction with ethyl acetate (200 ml). The extract was washed with saturated brine (2×100 ml), dried over anhydrous magnesium sulfate, and distilled under reduced pressure to remove the solvent. The residue was purified by chromatography on a silica gel column, whereby from chloroform-ethyl acetate (10:1) eluate fractions, methyl trans-4-(1-(tert-butoxycarbonyl)-(4R)-methoxy-(2S)-pyrrolidinylmethoxy)cyclohexanecarboxylate (441 mg, 85%) was obtained as a colorless oil.

$^1$H-NMR (CDCl$_3$) δ: 1.24 (m, 2H), 1.46 (m, 11H), 2.01–2.26 (series of m, 7H), 3.19–4.11 (series of m, 13H).

MS (ESI) m/z 372 (M$^+$+1).

(Step 2) Synthesis of methyl trans-4-(1-((5-chloro-2-fluoro-4-(1-methyl-3-indolylcarbonylamino)phenyl)acetyl)-(4R)-methoxy-(2S)-pyrrolidinylmethoxy)cyclohexanecarboxylate

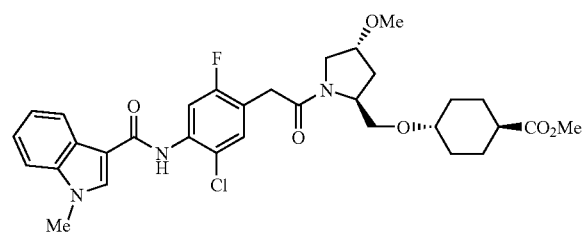

To methyl trans-4-(1-(tert-butoxycarbonyl)-(4R)-methoxy-(2S)-pyrrolidinylmethoxy)cyclohexanecarboxylate (440 mg, 1.18 mmol) were added dioxane (10 ml) and a 4N HCl/dioxane (10 ml) mixture. The resulting mixture was stirred at room temperature for 15 hours. The reaction mixture was distilled under reduced pressure to remove the solvent. The resulting solid was dissolved in DMF (10 ml) and triethylamine (821 μl, 5.90 mmol). To the resulting solution were added (5-chloro-2-fluoro-4-((1-methyl-3-indolylcarbonylamino)phenyl)acetic acid (426 mg, 1.18 mmol), EDC HCl (304 mg, 1.77 mmol), and HOBt (239 mg, 1.77 mmol). The resulting mixture was stirred at room temperature for 15 hours. To the reaction mixture were added ethyl acetate (100 ml) and H$_2$O (100 ml) to separate the ethyl acetate layer. The ethyl acetate layer was washed with saturated brine (2×100 ml), dried over anhydrous magnesium sulfate, and distilled under reduced pressure to remove the solvent. The residue was purified by chromatography on a silica gel column, whereby from chloroform-ethyl acetate (2:1) eluate fractions, methyl trans-4-(1-((5-chloro-2-fluoro-4-(1-methyl-3-indolylcarbonylamino)phenyl)acetyl)-(4R)-methoxy-(2S)-pyrrolidinylmethoxy)cyclohexanecarboxylate (401 mg, 55%) was obtained as a colorless foam.

$^1$H-NMR (CDCl$_3$) δ: 1.08–1.28 (m, 2H), 1.31–1.59 (m, 2H), 1.93–2.28 (series of m, 7H), 3.10–4.33 (series of m, 18H), 7.34–7.44 (m, 4H), 7.82 (m, 1H), 8.14 (m, 1H), 8.30 (s, 1H), 8.48–8.53 (m, 1H).

(Step 3) Synthesis of trans4-(1-((5-chloro-2-fluoro-4-(1-methyl-3-indolylcarbonylamino)phenyl)acetyl)-(4R)-methoxy-(2S)-pyrrolidinylmethoxy)cyclohexanecarboxylic acid

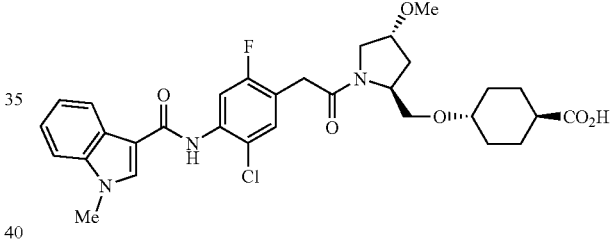

Methyl trans4-(1-((5-chloro-2-fluoro-4-(1-methyl-3-indolylcarbonylamino)phenyl)acetyl)-(4R)-methoxy-(2S)-pyrrolidinylmethoxy)cyclohexanecarboxylate (400 mg, 0.651 mmol) was dissolved in THF (5 ml). To the resulting solution was added 0.25N NaOH (5.2 ml, 1.30 mmol) and the mixture was stirred for 15 hours. The reaction mixture was poured in 1N HCl (100 ml), followed by extraction with a chloroform-methanol (5:1, 2×100 ml) mixture. The extract was dried over anhydrous magnesium sulfate and distilled under reduced pressure to remove the solvent. To the residue were added ethyl acetate and isopropyl ether to crystallize the residue. The crystals thus precipitated were collected by filtration under reduced pressure and dried under reduced pressure to give the title compound (247 mg, 63%) as a colorless amorphous substance.

$^1$H-NMR (DMSO-d$_6$) δ: 1.09–1.40 (series of m, 4H), 1.83–2.18 (series of m, 7H), 3.19–4.30 (series of m, 15H), 7.19–7.29 (m, 2H), 7.41–7.45 (m, 1H), 7.55 (d, J=7.8 Hz, 1H), 7.67–7.71 (m, 1H), 8.14 (d, J=7.8 Hz, 1H), 8.29 (s, 1H), 9.31 (s, 1H).

MS (ESI) m/z 600 (M$^+$+1);

Anal. Calcd for C$_{31}$H$_{35}$ClFN$_3$O$_6$·0.5H$_2$O: C, 61.13; H, 5.96; N, 6.90. Found: C, 61.10; H, 6.06; N, 6.64.

Example 116 trans-4-(1-((5-Chloro-2-fluoro-4-(1-methyl-3-indolylcarbonylamino)phenyl)acetyl)-(4S)-methoxy-(2S)-pyrrolidinylmethoxy)cyclohexanecarboxylic acid (Step 1) Synthesis of methyl trans-4-(1-tert-butoxycarbonyl-(4S)-methoxy-(2S)-pyrrolidinylmethoxy)cyclohexanecarboxylate

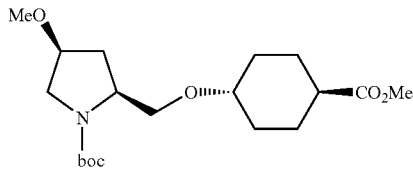

Methyl trans-4-(1-tert-butoxycarbonyl-(4S)-hydroxy-(2S)-pyrrolidinylmethoxy)cyclohexanecarboxylate (600 mg, 1.68 mmol) was dissolved in DMF (12 ml). To the resulting solution were added sodium hydride (60& in oil) (134 mg, 3.36 mmol) and methyl iodide (0.21 ml, 3.36 mmol) under stirring at 0° C. in a nitrogen gas stream. After stirring at room temperature for 14 hours, the reaction mixture was poured in ice water, followed by extraction with ethyl acetate. The extract was washed with ice water and saturated brine, dried over anhydrous sodium sulfate, and distilled under reduced pressure to remove the solvent. The residue was purified by flash column chromatography on a silica gel (Biotage flush-chromatography systems, KP-SIL 32–63 nm, 60A, n-hexane/ethyl acetate (4/1)) to give methyl trans-4-(1-tert-butoxycarbonyl-(4S)-methoxy-(2S)-pyrrolidinylmethoxy)cyclohexanecarboxylate (50 mg, 8%, more polar fraction) as a colorless oil.

$^1$H-NMR (CDCl$_3$) δ: 1.17–1.31 (m, 2H), 1.39–1.52 (m, 10H), 1.57 (s, 2H), 1.95–2.12 (m, 4H), 2.19 (d, J=13.4 Hz, 1H), 2.26 (t, J=11.2 Hz, 1H), 3.23 (m, 1H), 3.30 (s, 3H), 3.31–3.63 (m, 3H), 3.66 (s, 3H), 3.67–3.81 (m, 1H), 3.86–4.03 (m, 2H).

MS (ESI) m/z 372 (M$^+$+1).

(Step 2) Synthesis of methyl trans-4-((4S)-methoxy-(2S)-pyrrolidinylmethoxy)cyclohexanecarboxylate

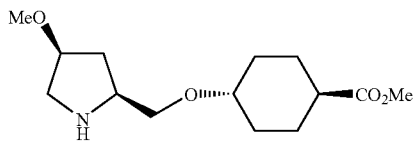

Methyl trans-4-(1-tert-butoxycarbonyl-(4S)-methoxy-(2S)-pyrrolidinylmethoxy)cyclohexanecarboxylate (50 mg, 0.135 mmol) was dissolved in methylene chloride (5 ml). To the resulting solution was added trifluoroacetic acid (0.5 ml) and the mixture was stirred at room temperature for 14 hours. The reaction mixture was distilled under reduced pressure to remove the solvent. The residue was basified with 1N NaOH, followed by extraction with methylene chloride. The extract was washed with saturated brine, dried over anhydrous sodium sulfate and distilled under reduced pressure to remove the solvent to give methyl trans-4-((4S)-methoxy-(2S)-pyrrolidinylmethoxy)cyclohexanecarboxylate (59 g, 100%) as a yellow oil.

$^1$H-NMR (CDCl$_3$) δ: 1.22–1.57 (m, 5H), 1.96–2.20 (m, 5H), 2.32 (m, 2H), 3.33 (s, 3H), 3.34–3.57 (m, 3H), 3.66 (s, 3H), 3.67–3.81 (m, 2H), 3.94 (m, 1H), 4.11 (m, 1H).

MS (ESI) m/z 272 (M$^+$+1).

(Step 3) Synthesis of methyl trans-4-(1-((5-chloro-2-fluoro-4-(1-methyl-3-indolylcarbonylamino)phenyl)acetyl)-(4S)-methoxy-(2S)-pyrrolidinylmethoxy)cyclohexanecarboxylate

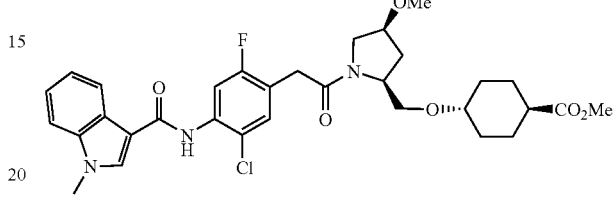

In DMF (2 ml), (5-chloro-2-fluoro-4-(1-methyl-3-indolylcarbonylamino)phenyl)acetic acid (49 mg, 0.135 mmol), methyl trans-4-((4S)-methoxy-(2S)-pyrrolidinylmethoxy)cyclohexanecarboxylate (59 mg, 0.135 mmol), EDC HCl (39 mg, 0.203 mmol), HOBt (27 mg, 0.203 mmol) and triethylamine (94 μl, 0.675 mmol) were stirred at room temperature for 20 hours. The reaction mixture was poured in ice water, followed by extraction with ethyl acetate. The extract was washed with saturated brine, dried over anhydrous sodium sulfate, and distilled under reduced pressure to remove the solvent. The residue was purified by chromatography using a silica gel thin-layer plate, whereby from chloroform/acetone (10/1) eluate fractions, methyl trans-4-(1-((5-chloro-2-fluoro-4-(1-methyl-3-indolylcarbonylamino)phenyl)acetyl)-(4S)-methoxy-(2S)-pyrrolidinylmethoxy)cyclohexanecarboxylate (117 mg, 100%) was obtained as a yellow oil.

$^1$H-NMR (CDCl$_3$) δ: 1.25 (m, 2H), 1.46 (m, 2H), 1.94–2.14 (m, 5H), 2.19–2.14 (m, 5H), 2.19–2.33 (m, 2H), 3.25 (m, 1H), 3.30 and 3.33 (each s, total 3H, amide isomers), 3.46–3.61 (m, 3H), 3.64 and 3.66 (each s, total 3H, amide isomers), 3.67–3.86 (m ,3H), 3.88 (s, 3H), 3.95 and 4.00 (each m, total 1H, amide isomers), 4.21 and (q and m, J=7.1 Hz, total 1H, amide isomers), 7.30–7.46 (m, 4H), 7.80 (s, 1H), 8.14 (d, J=5.6 Hz, 1H), 8.29 (s, 1H), 8.48 and 8.51 (each d, J=9.3 and 9.5 Hz respectively, total 1H).

MS (ESI) m/z 614 (M$^+$+1), 616 (M$^+$+3).

(Step 4) Synthesis of trans-4-(1-((5-chloro-2-fluoro-4-(1-methyl-3-indolylcarbonylamino)phenyl)acetyl)-(4S)-methoxy-(2S)-pyrrolidinylmethoxy)cyclohexanecarboxylic acid

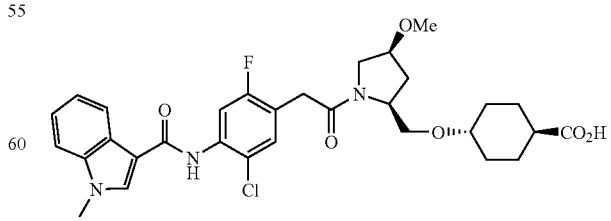

To methyl trans-4-(1-((5-chloro-2-fluoro-4-(1-methyl-3-indolylcarbonylamino)phenyl)acetyl)-(4S)-methoxy-(2S)-pyrrolidinylmethoxy)cyclohexanecarboxylate (117 mg, 0.135 mmol) were added THF/methanol (2:1, 6 ml) and 1N NaOH (2 ml). The resulting mixture was stirred at room temperature for 16 hours. The reaction mixture was distilled under reduced pressure to remove the solvent. The residue was acidified with 1N HCl. The crystals thus precipitated were collected by filtration under reduced pressure, washed with water and dried under reduced pressure to give the title compound (78 mg, 96% (3 steps)) as a colorless solid.

IR (ATR) ν 3423, 2937, 1701, 1664, 1626, 1587, 1522, 1402 cm$^{-1}$;

$^1$H-NMR (DMSO-d$_6$) δ: 1.12–1.42 (m, 4H), 1.82–2.19 (m, 7H), 3.23 and 3.26 (each s, total 3H, amide isomers), 3.44–3.83 (m, 5H), 3.89 (s, 3H), 3.94 and 4.25 (m and q, J=5.8 Hz, total 1H, amid isomers), 4.03 (br, 1H), 7.22 (t, J=7.3 hz, 1H), 7.27 (t, J=6.8 Hz, 1H), 7.42 and 7.45 (each d, each J=7.6 Hz, total 1H, amide isomers), 7.65 (d, J=8.1 Hz, 1H), 7.68 and 7.70 (d, J=11.2 and 11.0 Hz respectively, total 1H, amide isomers), 8.15 (d, J=7.8 Hz, 1H), 8.31 (d, J=2.2 Hz, 1H), 9.31 (s, 1H).

MS (ESI) m/z 600 (M$^+$+1), 602 (M$^+$+3);

Anal. Calcd for C$_{31}$H$_{35}$ClFN$_3$O$_6$ 0.8H$_2$O: C, 60.59; H, 6.00; N, 6.84. Found: C, 60.60; H, 5.97; N, 6.74.

Example 117 trans-4-((4S)-Allyloxy-1-((5-chloro-2-fluoro-4-(1-methyl-3-indolylcarbonylamino)phenyl)acetyl)-(2S)-pyrrolidinylmethoxy)cyclohexanecarboxylic acid (Step 1) Synthesis of ethyl trans-4-((4S)-allyloxy-1-(tert-butoxycarbonyl)-(2S)-pyrrolidinylmethoxy)cyclohexanecarboxylate

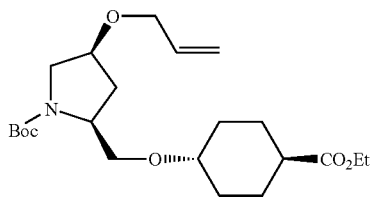

Ethyl trans-4-(1-(tert-butoxycarbonyl)-(4S)-hydroxy-(2S)-pyrrolidinylmethoxy)cyclohexanecarboxylate (810 mg, 2.18 mmol) was dissolved in DMF (15 ml). Under stirring at 0° C., allyl bromide (0.378 ml, 4.36 mmol) and sodium hydride (60% in oil, 175 mg, 4.37 mmol) were added to the resulting solution in portions. After the reaction mixture was stirred at room temperature for 2.5 hours, allyl bromide (0.189 ml, 2.18 mmol) and sodium hydride (60% in oil, 88 mg, 2.18 mmol) were added further thereto. The resulting mixture was stirred at room temperature for 2 hours. The reaction mixture was poured in ice water and then, acidified with 1N HCl. The reaction mixture was extracted with ethyl acetate. The extract was washed with saturated brine, dried over anhydrous magnesium sulfate, and distilled under reduced pressure to remove the solvent. The residue was purified by chromatography on a silica gel column, whereby from n-hexane/ethyl acetate (2:1, v/v) eluate fractions, ethyl trans-4-((4S)-allyloxy-1-(tert-butoxycarbonyl)-(2S)-pyrrolidinylmethoxy)cyclohexanecarboxylate (626 mg, 70%) was obtained as a pale yellow oil.

MS (ESI) m/z 412 (M$^+$+1).

(Step 2) Synthesis of ethyl trans-4-((4S)-allyloxy-(2S)-pyrrolidinylmethoxy)cyclohexanecarboxylate

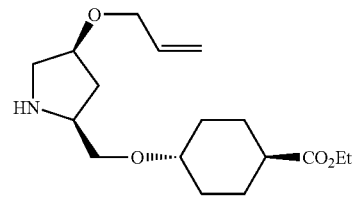

Ethyl trans-4-((4S)-allyloxy-1-(tert-butoxycarbonyl)-(2S)-pyrrolidinylmethoxy)cyclohexanecarboxylate (308 mg, 0.75 mmol) was dissolved in methylene chloride (5 ml). To the resulting solution was added trifluoroacetic acid (1 ml) and the resulting mixture was stirred at room temperature for 2 hours. The reaction mixture was distilled under reduced pressure to remove the solvent.

The residue was neutralized with a saturated aqueous solution of sodium bicarbonate. The mixture was extracted with a chloroform-methanol (5:1, v/v) mixture. The extract was washed with saturated brine, dried over anhydrous magnesium sulfate, and distilled under reduced pressure to remove the solvent to give ethyl trans-4-((4S)-allyloxy-(2S)-pyrrolidinylmethoxy)cyclohexanecarboxylate (230 mg, 99%) as a pale yellow oil.

$^1$H-NMR (CDCl$_3$) δ: 1.24 (m, total 4H), 1.45 (q, J=11.6 Hz, 2H), 1.55 (m, 1H), 1.85–1.58 (series of m, total 4H), 2.25 (m, 2H), 2.92 and 2.95 (dd, J=5.2, 2.8 Hz, each, total 1H), 3.06–3.09 (m, 1H), 3.62 (m, 2H), 3.51 (m, 2H), 4.93 (m, 2H), 4.06 (m, 1H), 4.10 (q, J=7.2 Hz, 2H), 4.46 (m, 1H), 5.15 (m, 1H), 5.25 (m, 2H), 5.88 (m, 1H).

MS (LC-MS) m/z 312 (M$^+$+1).

(Step 3) Synthesis of ethyl trans-4-((4S)-allyloxy-1-((5-chloro-2-fluoro-4-(1-methyl-3-indolylcarbonylamino)phenyl)acetyl)-(2S)-pyrrolidinylmethoxy)cyclohexanecarboxylate

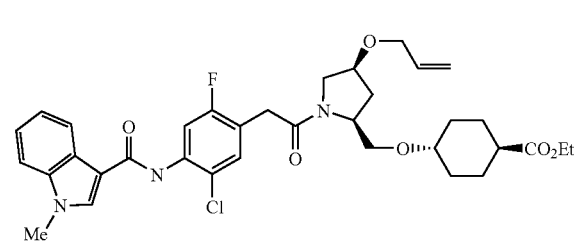

Ethyl trans-4-((4S)-allyloxy-(2S)-pyrrolidinylmethoxy) cyclohexanecarboxylate (202 mg, 0.65 mmol) and (5-chloro-2-fluoro-4-(1-methyl-3-indolylcarbonylamino) phenyl)acetic acid (234 mg, 0.65 mmol) were dissolved in DMF (7 ml). To the resulting solution were added EDC HCl (188 mg, 0.98 mmol), HOBt (2.5 mg, 0.02 mmol) and DMAP (2.5 mg, 0.02 mmol), and the resulting mixture was stirred at room temperature for 14 hours. Water was added to the reaction mixture, followed by extraction with ethyl acetate. The extract was washed with saturated brine, dried over anhydrous magnesium sulfate, and distilled under reduced pressure to remove the solvent. The residue was purified by chromatography on a silica gel column, whereby from chloroform-methanol (20:1, v/v) eluate fractions, ethyl trans-4-((4S)-allyloxy-1-((5-chloro-2-fluoro-4-(1-methyl-3-indolylcarbonylamino)phenyl)acetyl)-(2S)-pyrrolidinylmethoxy)cyclohexanecarboxylate (358 mg, 84%) was obtained as a yellow oil.

IR (ATR) ν 1724, 1643, 1514 cm$^{-1}$;

$^1$H-NMR (CDCl$_3$) δ: 1.24 (m, 3H), 1.26 (m, 2H), 1.46 (m, 2H), 1.96–2.10 (series of m, total 4H), 2.26 (m, 2H), 3.24 (m, 1H), 3.50–3.59 (series of m, total 3H), 3.72 (m, 2H), 3.82 (m, 1H), 3.89 (s, 3H), 3.96 (d, J=5.2 Hz, 1H), 4.04 (m, 1H), 4.10 (m, 3H), 4.24 (m, 1H), 4.56 (m, 1H), 5.20 (m, 1H), 5.28 (m, 1H), 5.88 (m, 1H), 7.35 (m, 2H), 7.41 (m, 2H), 7.81 (d, J=2.0 Hz, 1H), 8.13 (m, 1H), 8.30 (m, 1H), 8.50 (dd, J=12.4, 9.6 Hz, 1H).

MS (ESI) m/z 655 (M$^+$+1);

Anal. Calcd for C$_{35}$H$_{41}$ClFN$_3$O$_6$ 0.25 H$_2$O: C, 63.82; H, 6.35; N, 6.38. Found: C, 63.86; H, 6.32; N, 6.23.

(Step 4) Synthesis of trans-4-((4S)-allyloxy-1-((5-chloro-2-fluoro-4-(1-methyl-3-indolylcarbonylamino)phenyl)acetyl)-(2S)-pyrrolidinylmethoxy)cyclohexanecarboxylic acid

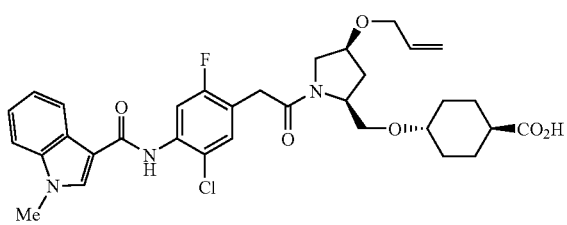

Ethyl trans-4-((4S)-allyloxy-1-((5-chloro-2-fluoro-4-(1-methyl-3-indolylcarbonylamino)phenyl)acetyl)-(2S)-pyrrolidinylmethoxy)cyclohexanecarboxylate (244 mg, 0.37 mmol) was dissolved in THF (3.5 ml). To the resulting solution was added 0.25N NaOH (3.5 ml), followed by stirring at 50° C. for 5 hours. After cooling to room temperature, the reaction mixture was concentrated under reduced pressure. The concentrate was neutralized with 1N HCl, followed by extraction with a chloroform-methanol (5:1, v/v) mixture. The extract was washed with saturated brine, dried over anhydrous magnesium sulfate, and distilled under reduced pressure to remove the solvent. The residue was purified by chromatography on silica gel column, whereby from chloroform-methanol (10:1, v/v) eluate fractions, the title compound (145 mg, 63%) was obtained as a white solid.

IR (KBr) ν 2935, 1724, 1616, 1513 cm$^{-1}$;

$^1$H-NMR (DMSO-d$_6$) δ: 1.60 (m, 2H), 1.31 (m, 2H), 1.83–1.99 (series of m, total 4H), 2.09 (m, 2H), 3.14 (mn, 1H), 3.23 (m, 1H), 3.35–3.79 (series of m, total 5H), 3.85 (s, 3H), 3.88–3.96 (series of m, total 3H), 4.02–4.13 (series of m, total 2H), 5.13 (m, 1H), 5.23 (m, 1H), 5.87 (mn, 1H), 7.20 (t, J=7.2 Hz, 1H), 7.26 (t, J=7.2 Hz, 1H), 7.40 (t, J=8.0 Hz, 1H), 7.53 (d, J=8.0 Hz, 1H), 7.67 and 7.68 (d, J=10.8 Hz, total 1H), 8.12 (d, J=8.0 Hz, 1H), 8.24 (d, J=6.0 Hz, 1H), 9.29 (s, 1H).

MS (ESI) m/z 27 (M$^+$+1);

Anal. Calcd for C$_{33}$H$_{37}$ClFN$_3$O$_6$ 0.5 H$_2$O: C, 62.41; H, 6.03; N, 6.62. Found: C, 62.33; H, 5.96; N, 6.46.

Example 118 trans-4-(1-((5-Chloro-2-fluoro-4-(1-methyl-3-indolylcarbonylamino)phenyl)acetyl)-(4S)-propoxy-(2S)-pyrrolidinylmethoxy)cyclohexanecarboxylic acid (Step 1) Synthesis of ethyl trans-4-((4S)-propoxy-(2S)-pyrrolidinylmethoxy)cyclohexanecarboxylate

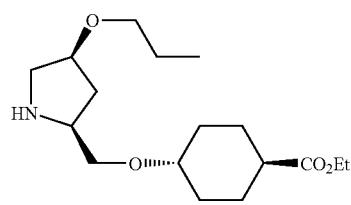

Ethyl trans-4-(1-(tert-butoxycarbonyl)-(4S)-allyloxy-(2S)-pyrrolidinylmethoxy)cyclohexanecarboxylate (318 mg, 0.77 mmol) was dissolved in ethanol (8 ml). To the resulting solution was added 5% palladium-carbon (50 mg). The resulting mixture was subjected to catalytic hydrogenation at room temperature for 48 hours under a hydrogen gas of 1 atm. After removal of the catalyst from the reaction mixture by filtration, the filtrate was distilled under reduced pressure to remove the solvent. The residue was purified by chromatography on a silica gel column, whereby from n-hexane-ethyl acetate (4:1, v/v) eluate fractions, an oil (275 mg) was obtained. The resulting oil was dissolved in methylene chloride (7 ml). Trifluoroacetic acid (2 ml) was added to the resulting solution and the mixture was stirred at room temperature for 2 hours. The reaction mixture was distilled under reduced pressure to remove the solvent. The residue was neutralized with a saturated aqueous solution of sodium bicarbonate, followed by extraction with chloroform-methanol (10:1, v/v). The extract was washed with saturated brine, dried over anhydrous magnesium sulfate, and distilled under reduced pressure to remove the solvent to afford ethyl trans-4-((4S)-propoxy-(2S)-pyrrolidinylmethoxy)cyclohexanecarboxylate (208 mg, 86%) as a yellow oil.

$^1$H-NMR (CDCl$_3$) δ: 0.91 (t, J=7.2 Hz, 3H), 1.24 (t, J=7.2 Hz, 3H), 1.27 (m, 2H), 1.38–1.66 (series of m, total 6H), 1.99 (m, 3H), 2.07 (m, 2H), 2.24 (m, 1H), 2.89 and 2.92 (d, J=5.6 Hz, each, total 1H), 3.02 and 3.05 (d, J=2.4 Hz, each, total 1H), 3.24 (m, 2H), 3.32 (dt, J=6.8, 1.2 Hz, 2H), 3.49 (m, 2H), 3.98 (m, 1H), 4.11 (q, J=7.2 Hz, 2H).

MS (ESI) m/z 314 (M$^+$+1).

(Step 2) Synthesis of ethyl trans-4-(1-((5-chloro-2-fluoro-4-(1-methyl-3-indolylcarbonylamino)phenyl)acetyl)-(4S)-propoxy-(2S)-pyrrolidinylmethoxy)cyclohexanecarboxylate

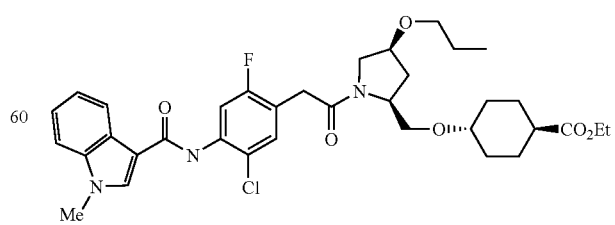

In DMF (7 ml) were dissolved (5-chloro-2-fluoro-4-((1-methyl-3-indolylcarbonyl)amino)phenyl)acetic acid (238 mg, 0.66 mmol) and ethyl trans-4-((4S)-propoxy-(2S)-pyrrolidinylmethoxy)cyclohexanecarboxylate (208 mg, 0.66 mmol). To the resulting solution were added EDC HCl (190 mg, 0.99 mmol), HOBt (5 mg, 0.04 mmol), and DMAP (5 mg, 0.04 mmol). The resulting mixture was stirred at room temperature for 14 hours. Water was added to the reaction mixture, followed by extraction with ethyl acetate. The extract was washed with saturated brine, dried over anhydrous magnesium sulfate, and distilled under reduced pressure to remove the solvent. The residue was purified by chromatography on a silica gel column, whereby from chloroform-methanol (20:1, v/v) eluate fractions, ethyl trans-4-(1-((5-chloro-2-fluoro-4-(1-methyl-3-indolylcarbonylamino)phenyl)acetyl)-(4S)-propoxy-(2S)-pyrrolidinylmethoxy)cyclohexanecarboxylate (424 mg, 98%) was obtained as a white crystalline powder.

IR (ATR) 2935, 1726, 1647, 1514 cm$^{-1}$;

$^1$H-NMR (CDCl$_3$) δ: 0.93 (m, 3H), 1.25 (m, 4H), 1.46 (m, 2H), 1.58 (m, 2H), 1.97–2.06 (series of m, total 6H), 2.24 (m, 2H), 3.24 (m, 1H), 3.35 (m, 2H), 3.43 (m, 1H), 3.49–3.59 (series of m, total 3H), 3.72 (m, 1H), 3.86 (m, 1H), 3.89 and 3.90 (series of s, total 3H), 4.02 (m, 1H), 4.11 (m, 2H), 4.26 (m, 1H), 7.35 (m, 2H), 7.41 (m, 2H), 7.81 (m, 1H), 8.14 (m, 1H), 8.30 (br s, 1H), 8.50 (m, 1H).

Anal. Calcd for C$_{35}$H$_{43}$ClFN$_3$O$_6$: C, 64.06; H, 6.61; N, 6.40. Found: C, 63.92; H, 6.70; N, 76.24.

(Step 3) trans-4-(1-((5-Chloro-2-fluoro-4-(1-methyl-3-indolylcarbonylamino)phenyl)acetyl)-(4S)-propoxy-(2S)-pyrrolidinylmethoxy)cyclohexanecarboxylic acid

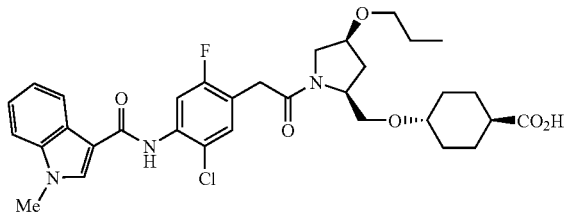

Ethyl trans-4-(1-(5-chloro-2-fluoro-4-(1-methyl-3-indolylcarbonylamino)phenylacetyl)-(4S)-propoxy-(2S)-pyrrolidinylmethoxy)cyclohexanecarboxylate (411 mg, 0.63 mmol) was dissolved in THF (5 ml). To the resulting solution was added 0.25N NaOH (5 ml). The resulting mixture was stirred at room temperature for 14 hours. The reaction mixture was concentrated under reduced pressure and acidified with 1N HCl, followed by extraction with chloroform-methanol (5:1, v/v). The extract was dried over anhydrous magnesium sulfate, and the solvent was distilled off under reduced pressure. The residue was purified by chromatography on a silica gel column, whereby from chloroform-methanol (20:1, v/v) eluate fractions, the title compound (253 mg, 64%) was obtained as a white solid.

IR (ATR) 2935, 1724, 1616, 1513 cm$^{-1}$;

$^1$H-NMR (DMSO-d$_6$) δ: 0.84 (m, 3H), 1.15 (m, 2H) 1.30 (m, 2H), 1.47 (m, 3H), 1.85–1.98 (m, 4H), 2.02 (m, 1H), 2.11 (m, 1H), 3.12 (m, 1H), 3.23 (m, 2H), 3.35 (m, 3H), 3.44–3.52 (m, 2H), 3.84 (s, 3H), 4.00 (m, 3H), 4.20 (m, 1H), 7.20 (dt, J=7.6, 2.2 Hz, 1H), 7.25 (dt, J=7.7, 2.2 Hz, 1H), 7.39 (dt, J=8.0, 3.4 Hz, 1H), 7.52 (dd, J=8.0, 2.2 Hz, 1H), 7.66 (ddd, J=11.0, 6.6, 3.4 Hz, 1H), 8.11 (dd, J=7.8, 2.2 Hz, 1H), 8.82 (m, 1H), 9.29 (s, 1H).

MS (ESI) m/z 629 (M$^+$+1);

Anal. Calcd for C$_{33}$H$_{39}$ClFN$_3$O$_6$ 0.75H$_2$O: C, 61.77; H, 6.36; N, 6.55. Found: C, 61.73; H, 6.18; N, 6.42.

Example 119 trans-4-(1-((5-Chloro-2-fluoro-4-(1-methyl-3-indolylcarbonylamino)phenyl)acetyl)-(4S)-cyclohexyloxy-(2S)-pyrrolidinylmethoxy)cyclohexanecarboxylic acid (Step 1) Synthesis of methyl trans-4-(1-tert-butoxycarbonyl-(4S)-cyclohexyloxy-(2S)-pyrrolidinylmethoxy)cyclohexanecarboxylate

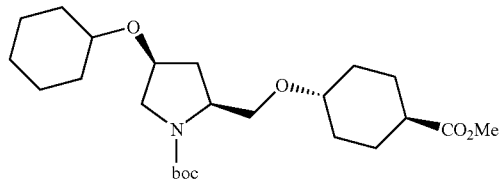

In methanol/HCl (40/1, 20.5 ml), methyl 4-((4S)-phenoxy-(2S)-pyrrolidinylmethoxy)benzoate (560 mg, 1.71 mmol) and rhodium-alumina (1.30 g) were subjected to catalytic hydrogenation at room temperature under 4 kg/cm$^2$ of hydrogen atmosphere for 4 days. From the reaction mixture, the catalyst was filtered off. The filtrate was distilled under reduced pressure to remove the solvent to give methyl 4-((4S)-cyclohexyloxy-(2S)-pyrrolidinylmethoxy)cyclohexanecarboxylate hydrochloride as a solid. The resulting compound was provided for the subsequent reaction without further purification.

In 1,4-dioxane/water (1:1, 20 ml), di-tert-butyl dicarbonate (448 mg, 2.15 mmol) was added to methyl 4-((4S)-cyclohexyloxy-(2S)-pyrrolidinylmethoxy)cyclohexanecarboxylate hydrochloride (1.71 mmol) and sodium bicarbonate (862 mg, 10.3 mmol) and the resulting mixture was stirred at room temperature for 18 hours. The reaction mixture was extracted with ethyl acetate. The extract was washed with saturated brine, dried over anhydrous sodium sulfate, and distilled under reduced pressure to remove the solvent. The residue was purified by chromatography on a silica gel column, whereby from n-hexane/ethyl acetate (2/1) eluate fractions, methyl 4-(1-tert-butoxycarbonyl-(4S)-cyclohexyloxy-(2S)-pyrrolidinylmethoxy)cyclohexanecarboxylate (642 mg, 85%) was obtained as a colorless oil.

The methyl 4-(1-tert-butoxycarbonyl-(4S)cyclohexyloxy-(2S)-pyrrolidinylmethoxy)cyclohexanecarboxylate (642 mg, 1.46 mmol) thus obtained was dissolved in methanol. To the resulting solution was added sodium methoxide (789 mg, 14.6 mmol) and the mixture was heated under reflux for 19 hours. After cooling to room temperature, the reaction mixture was distilled under reduced pressure to remove the solvent. The residue was acidified with 1N HCl, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane/ethyl acetate (20/1, v/v) eluate fractions, the target methyl trans-4-(1-tert-butoxycarbonyl-(4S)-cyclohexyloxy-(2S)-pyrrolidinylmethoxy)cyclohexanecarboxylate (90 mg, 14% (3 steps)) was obtained as a colorless oil.

In addition, a cis-isomer (90 mg, 14% (3 steps); non-polar fraction) as a colorless oil and a mixture (30 mg) of both isomers were obtained.

Trans-isomer: ¹H-NMR (CDCl₃) δ: 1.16–1.31 (m, 8H), 1.42 (s, 9H), 1.63–2.31 (m, 14H), 3.21–3.33 (m, 3H), 3.42–3.63 (m, 2H), 3.66 (s, 3H), 3.71–4.00 (m, 1H), 4.11(m, 1H);

MS (ESI) m/z 440 (M⁺+1).

Cis-isomer: ¹H-NMR (CDCl₃) δ: 1.19–1.32 (m, 8H), 1.45 (s, 9H), 1.57–2.18 (m, 13H), 2.34 (br, 1H), 3.22–3.99 (m, 1H), 4.13 (m, 1H);

MS (ESI) m/z 440 (M⁺+1).

(Step 2) Synthesis of methyl trans-4-((4S)-cyclohexyloxy-(2S)-pyrrolidinylmethoxy)cyclohexanecarboxylate

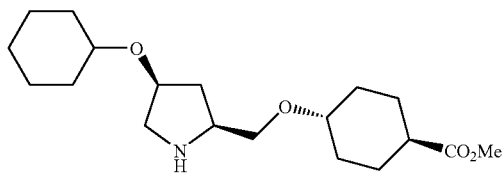

Methyl trans-4-(1-tert-butoxycarbonyl-(4S)-cyclohexyloxy-(2S)-pyrrolidinylmethoxy)cyclohexanecarboxylate (90 mg, 0.205 mmol) was dissolved in methylene chloride (10 ml). To the resulting solution was added trifluoroacetic acid (1 ml) and the mixture was stirred at room temperature for 19 hours. The reaction mixture was distilled under reduced pressure to remove the solvent. The residue was basified with methylene chloride and 1N NaOH, followed by extraction with methylene chloride. The extract was washed with saturated brine, dried over anhydrous sodium sulfate, and distilled under reduced pressure to remove the solvent whereby methyl trans-4-((4S)-cyclohexyloxy-(2S)-pyrrolidinylmethoxy)cyclohexanecarboxylate (16 mg, 23%) was obtained as a yellow oil. The resulting compound was provided for subsequent reaction without further purification.

¹H-NMR (CDCl₃) δ: 1.14–1.38 (m, 7H), 1.41–1.63 (m, 4H), 1.86 (s, 2H), 1.99–2.21 (m, 5H), 2.22–2.36 (m, 1H), 2.43 (m, 2H), 2.92–3.07 (m, 2H), 3.44–3.56 (m, 2H), 3.66 (s, 3H), 4.15 (m, 1H).

MS (ESI) m/z 340 (M⁺+1).

(Step 3) Synthesis of methyl trans-4-(1-((5-chloro-2-fluoro-4-(1-methyl-3-indolylcarbonylamino)phenyl)acetyl)-(4S)-cyclohexyloxy-(2S)-pyrrolidinylmethoxy)cyclohexanecarboxylate

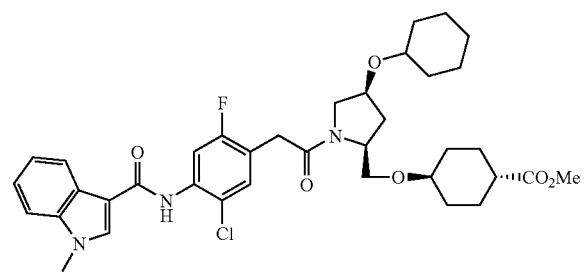

In DMF (1 ml), (5-chloro-2-fluoro-4-((1-methyl-3-indolylcarbonyl)amino)phenyl)acetic acid (17 mg, 47.1 μmol), methyl trans-4-((4S)-cyclohexyloxy-(2S)-pyrrolidinylmethoxy)-cyclohexanecarboxylate (16 mg, 47.1 μmol), EDC HCl (13.5 mg, 70.7 μmol), HOBt (9.6 mg, 70.0 μmol) and triethylamine (32.8 μl, 236 μmol) were stirred at room temperature for 17 hours. The reaction mixture was poured in ice water, followed by extraction with ethyl acetate. The extract was washed with saturated brine, dried over anhydrous sodium sulfate, and distilled under reduced pressure to remove the solvent. The residue was purified by chromatography using a silica gel thin-layer plate, whereby from chloroform/acetone (10/1, v/v) eluate fractions, methyl trans-4-(1-((5-chloro-2-fluoro-4-(1-methyl-3-indolylcarbonylamino)phenyl)acetyl)-(4S)-cyclohexyloxy-(2S)-pyrrolidinylmethoxy)cyclohexanecarboxylate (38 mg, 100%) was obtained as a colorless oil.

¹H-NMR (CDCl₃) δ: 1.19–1.32 (m, 8H), 1.38–1.52 (m, 2H), 1.72 (m, 2H), 1.83 (m, 2H), 1.94–2.31 (m, 6H), 3.20–3.34 (m, 2H), 3.42–3.59 (m, 3H), 3.64 and 3.66 (each s, total 3H, amide isomers), 3.69–3.76 (m, 2H), 3.80 (dd, J=8.6, 4.9 Hz, 1H), 3.87 (m, 1H), 3.880 and 3.883 (each s, total 3H, amide isomers), 4.18–4.28 (m, 2H), 7.33–7.42 (m, 4H), 7.80 (d, J=2.2 Hz, 1H), 8.11–8.14 (m, 1H), 8.27 and 8.29 (each s, total 1H, amide isomers), 8.47 and 8.50 (each d, each J=10.5 Hz, total 1H, amide isomers).

MS (ESI) m/z 682 (M⁺+1), 684 (M⁺+3).

(Step 4) Synthesis of trans-4-(1-((5-chloro-2-fluoro-4-(1-methyl-3-indolylcarbonylamino)phenyl)acetyl)-(4S)-cyclohexyloxy-(2S)-pyrrolidinylmethoxy)cyclohexanecarboxylic acid

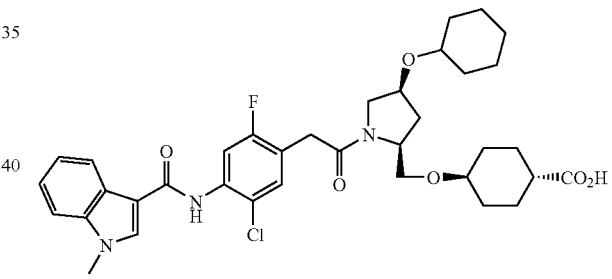

To methyl trans-4-(1-((5-chloro-2-fluoro-4-(1-methyl-3-indolylcarbonylamino)phenyl)acetyl)-(4S)-cyclohexyloxy-(2S)-pyrrolidinylmethoxy)cyclohexanecarboxylate (38 mg, 47.1 μmol) were added THF/methanol (2:1, 3 ml) and 1N NaOH (1 ml). The resulting mixture was stirred at room temperature for 13 hours. The reaction mixture was distilled under reduced pressure to remove the solvent and the residue was acidified with 1N HCl. The crystals thus precipitated were collected by filtration under reduced pressure, washed with water and dried under reduced pressure to give the title compound (34 mg, 100%) as a colorless solid.

¹H-NMR (DMSO-d₆) δ: 1.13–2.22 (m, 14H), 3.22 (m, 1H), 3.50–3.86 (m, 4H), 3.89 (s, 3H), 3.99–4.33 (m, 2H), 7.22 (t, J=7.1 Hz, 1H), 7.42 and 7.45 (each d, each J=7.1 Hz total 1H, amide isomers), 7.56 (d, J=8.3 Hz, 1H), 7.68 and 7.70 (each d, J=11.0 and 10.5 Hz respectively, total 1H, amide isomers), 8.15 (d, J=7.8 Hz, 1H), 8.30 and 8.31 (each s, total 1H, amide isomers), 9.31 (s, 1H).

MS (ESI) m/z 669 (M⁺+1), 671 (M⁺+3).

Example 120 trans-4-(1-((5-Chloro-2-fluoro-4-(1-methyl-3-indolylcarbonylamino)phenyl)acetyl)-(4S)-dimethylcarbamoylmethoxy-(2S)-pyrrolidinylmethoxy)-1-cyclohexanecarboxylic acid (Step 1) Synthesis of methyl 4-((4S)-hydroxy-(2S)-pyrrolidinylmethoxy)benzoate hydrochloride

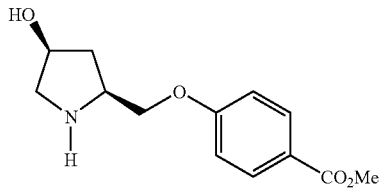

To methyl 4-(1-tert-butoxycarbonyl-(4S)-hydroxy-(2S)-pyrrolidinylmethoxy)benzoate (1.0 g, 2.85 mmol) was added 4N HCl-dioxane (10 m). The resulting mixture was stirred at room temperature for 15 hours. The reaction mixture was distilled under reduced pressure to remove the solvent. The resulting residue was crystallized by the addition of ether. The crystals thus precipitated were collected by filtration under reduced pressure, and dried under reduced pressure to give methyl 4-((4S)-hydroxy-(2S)-pyrrolidinylmethoxy)benzoate hydrochloride (660 mg, 80%) as a colorless amorphous substance.

$^1$H-NMR (DMSO-$d_6$) δ: 1.75 (m, 1H), 2.33 (m, 1H), 3.09–3.23 (m, 2H), 3.82 (s, 3H), 4.01 (m, 1H), 4.34 (m, 2H), 4.43 (m, 1H), 5.56 (d, J=3.4 Hz, 1H), 7.09 (d, J=8.8 Hz, 2H), 7.95 (d, J=8.8 Hz, 2H).

MS (ESI) m/z 252 ($M^+$+1).

(Step 2) Synthesis of methyl 4-(1-(tert-butoxycarbonyl)-(4S)-hydroxy-(2S)-pyrrolidinylmethoxy)-1-cyclohexanecarboxylate

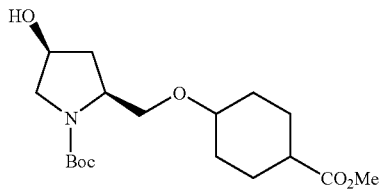

Methyl 4-((4S)-hydroxy-(2S)-pyrrolidinylmethoxy)benzoate hydrochloride (660 mg, 2.29 mmol) was dissolved in methanol-acetic acid (10:1, 33 ml). To the resulting solution was added rhodium-alumina (500 mg) and the resulting mixture was subjected to catalytic hydrogenation at room temperature for 48 hours under 4 atm. From the reaction mixture, the catalyst was filtered off. The filtrate was distilled under reduced pressure to remove the solvent. The resulting residue was dissolved in acetonitrile-water (1:1, 50 ml). To the resulting solution were added triethylamine (637 μl, 4.58 mmol) and di-tert-butyl dicarbonate (600 mg, 2.75 mmol). The resulting mixture was stirred at room temperature for 15 hours. The reaction mixture was extracted with chloroform (2×200 ml). The extract was dried over anhydrous magnesium sulfate and distilled under reduced pressure to remove the solvent. The residue was purified by chromatography on a silica gel column, whereby from chloroform-methanol (20:1) eluate fractions, methyl 4-(1-(tert-butoxycarbonyl)-(4S)-hydroxy-(2S)-pyrrolidinylmethoxy)-1-cyclohexanecarboxylate (818 mg, 100%) was obtained as a colorless oil.

$^1$H-NMR (CDCl$_3$) δ: 1.26–2.36 (series of m, 20 H), 3.34–4.21 (series of m, 8H), 4.81–5.08 (m, 2H).

(Step 3) Synthesis of methyl 4-((4S)-benzyloxymethoxy-1-(tert-butoxycarbonyl)-(2S)-pyrrolidinylmethoxy)-1-cyclohexanecarboxylate

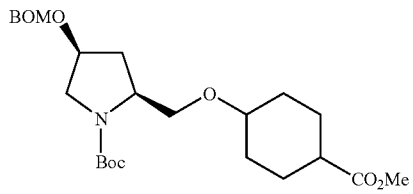

Methyl 4-(1-(tert-butoxycarbonyl)-(4S)-hydroxy-(2S)-pyrrolidinylmethoxy)-1-cyclohexanecarboxylate (818 mg, 2.29 mmol) was dissolved in methylene chloride (20 ml). To the resulting solution were added benzyl chloromethyl ether (476 μl, 3.44 mmol) and DIEA (599 μl, 3.44 mmol). The resulting mixture was heated under reflux for 15 hours. After cooling to room temperature, the reaction mixture was added with water (50 ml), followed by extraction with chloroform (200 ml). The extract was dried over anhydrous magnesium sulfate and distilled under reduced pressure to remove the solvent. The residue was purified by chromatography on a silica gel column, whereby from chloroform-ethyl acetate (10:1) eluate fractions, methyl 4-((4S)-benzyloxymethoxy-1-(tert-butoxycarbonyl)-(2S)-pyrrolidinylmethoxy)-1-cyclohexanecarboxylate (1.07 g, 98%) as a colorless oil.

MS (ESI) m/z 478 ($M^+$+1).

(Step 4) Synthesis of methyl trans-4-((4S)-benzyloxymethoxy-1-(tert-butoxycarbonyl)-(2S)-pyrrolidinylmethoxy)-1-cyclohexanecarboxylate

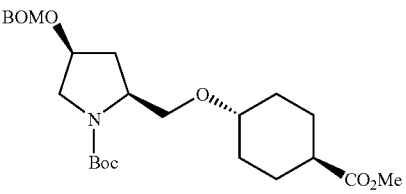

Methyl 4-((4S)-benzyloxymethoxy-1-(tert-butoxycarbonyl)-(2S)-pyrrolidinylmethoxy)-1-cyclohexanecarboxylate (1.07 g, 2.24 mmol) was dissolved in methanol (50 ml). To the resulting solution was added sodium methoxide (363 mg, 6.72 mmol). The resulting mixture was heated under reflux for 15 hours in a nitrogen gas stream. After cooling to room temperature, the reaction mixture was poured in 1N HCl (100 ml), followed by extraction with chloroform (2×200 ml). The extract was dried over anhydrous magnesium sulfate and distilled under reduced pressure to remove the solvent to give a mixture (about 1:1) of methyl 1,4-cis and trans-cyclohexanecarboxylates. The trans isomer was purified by flash column chromatography on silica gel, whereby from hexane-ethyl acetate (4:1) eluate fractions, methyl trans-4-((4S)-benzyloxymethoxy-1-(tert-butoxycarbonyl)-(2S)-pyrrolidinylmethoxy)-1-cyclohexanecarboxylate (400 mg, 37%) was obtained as a colorless oil.

$^1$H-NMR (CDCl$_3$) δ: 1.26 (m, 2H), 1.45 (m, 11H), 1.98–2.25 (m, 7H), 3.24–3.96 (series of m, total 9 H), 4.60 (s, 2H), 4.77 (m, 2H), 7.28–7.38 (m, 5H).

(Step 5) Synthesis of methyl trans-4-(1-(tert-butoxycarbonyl)-(4S)-hydroxy-(2S)-pyrrolidinylmethoxy)-1-cyclohexane carboxylate

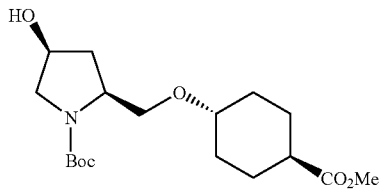

Methyl trans-4-((4S)-benzyloxymethoxy-1-(tert-butoxycarbonyl)-(2S)-pyrrolidinylmethoxy)-1-cyclohexanecarboxylate (390 mg, 0.817 mmol) was dissolved in methanol (50 ml). To the resulting solution was added 5% palladium/carbon (40 mg). The reaction mixture was subjected to catalytic hydrogenation at room temperature for 15 hours. The reaction mixture was filtered to remove the catalyst and the filtrate was distilled under reduced pressure to remove the solvent. The residue was purified by chromatography on a silica gel column, whereby from chloroform-methanol (20:1) eluate fractions, methyl trans-4-(1-(tert-butoxycarbonyl)-(4S)-hydroxy-(2S)-pyrrolidinylmethoxy)-1-cyclohexanecarboxylate (281 mg, 96%) was obtained as a colorless oil.

$^1$H-NMR (CDCl$_3$) δ: 1.28 (m, 2H), 1.46 (m, 11H), 1.86–2.36 (series of m, 7H), 3.31–3.63 (series of m, 4H), 3.66 (s, 3H), 3.92–4.21 (series of m, 3H), 4.85 and 5.06 (d, J=11.5 Hz, each, total 1H).

MS (ESI) m/z 358 (M$^+$+1).

(Step 6) Synthesis of methyl trans-4-(1-(tert-butoxycarbonyl)-(4S)-dimethylcarbamoylmethoxy-(2S)-pyrrolidinylmethoxy)-1-cyclohexanecarboxylate

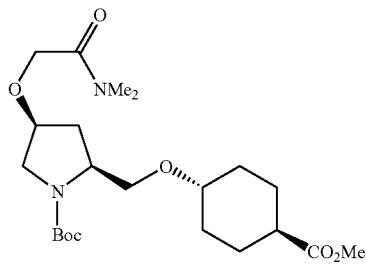

To methyl trans-4-(1-(tert-butoxycarbonyl)-(4S)-hydroxy-(2S)-pyrrolidinylmethoxy)-1-cyclohexanecarboxylate (280 mg, 0.780 mmol) were added DMF (10 ml) and N,N-dimethyl bromoacetamide (195 mg, 1.18 mmol). Under stirring at 0° C., sodium hydride (62 mg, 1.56 mmol) was added in portions. After the reaction mixture was stirred at room temperature for 1 hour, 1N HCl (50 ml) was poured therein, followed by extraction with ethyl acetate (200 ml). The extract was washed with saturated brine (2×100 ml), dried over anhydrous magnesium sulfate, and distilled under reduced pressure to remove the solvent. The residue was purified by chromatography on a silica gel column, whereby from chloroform-ethyl acetate (1:1) eluate fractions, methyl trans-4-(1-(tert-butoxycarbonyl)-(4S)-dimethylcarbamoylmethoxy-(2S)-pyrrolidinylmethoxy)-1-cyclohexanecarboxylate (247 mg, 72%) was obtained as a colorless oil.

$^1$H-NMR (CDCl$_3$) δ: 1.26 (m, 2H), 1.45 (m, 11H), 1.98 (m, 5H), 2.25 (m, 2H), 2.95 (s, 3H), 3.01 (s, 3H), 3.22 (m, 1H), 3.43 (m, 2H), 3.50–3.96 (series of m, 6H, including s, 3H, at δ: 3.66), 4.12 (m, 3H).

MS (ESI) m/z 443 (M$^+$+1).

(Step 7) Synthesis of methyl trans-4-((4S)-dimethylcarbamoylmethoxy-(2S)-pyrrolidinylmethoxy)-1-cyclohexanecarboxylate

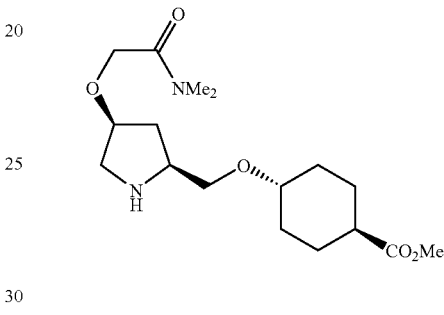

To methyl trans-4-(1-(tert-butoxycarbonyl)-(4S)-dimethylcarbamoylmethoxy-(2S)-pyrrolidinylmethoxy)-1-cyclohexanecarboxylate (245 mg, 0.554) were added dioxane (10 ml) and 4N HCl/dioxane (10 ml). The resulting mixture was stirred at room temperature for 15 hours. The reaction mixture was distilled under reduced pressure to remove the solvent, whereby methyl trans-4-((4S)-dimethylcarbamoylmethoxy-(2S)-pyrrolidinylmethoxy)-1-cyclohexanecarboxylate (210 mg, 100%) was obtained as a colorless oil.

MS (ESI) m/z 343 (M$^+$+1).

(Step 8) Synthesis of methyl trans-4-(1-((5-chloro-2-fluoro-4-(1-methyl-3-indolylcarbonylamino)phenyl)acetyl)-(4S)-dimethylcarbamoylmethoxy-(2S)-pyrrolidinylmethoxy)-1-cyclohexanecarboxylate

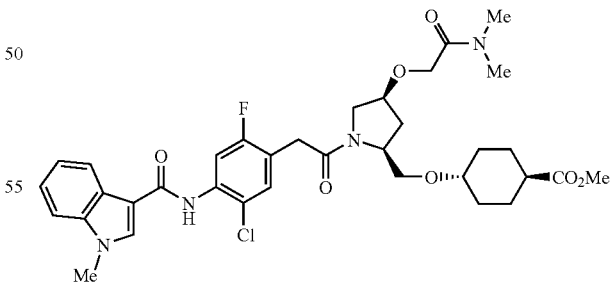

In DMF (10 ml), triethylamine (771 μl, 5.54 mmol), (5-chloro-2-fluoro-4-((1-methyl-3-indolylcarbonyl)amino)phenyl)acetic acid (200 mg, 0.554 mmol), EDC HCl (159 mg, 0.831 mmol), and HOBt (112 mg, 0.831 mmol) were added to methyl trans-4-((4S)-dimethylcarbamoylmethoxy-(2S)-pyrrolidinylmethoxy)-1-cyclohexanecarboxylate (210 mg, 0.554 mmol) and the resulting mixture was stirred at room temperature for 15 hours. To the reaction mixture were added ethyl acetate (200 ml) and water (100 ml). The organic layer thus separated was washed with saturated brine (100 ml), dried over anhydrous magnesium sulfate, and distilled under reduced pressure to remove the solvent. The residue was purified by chromatography on a silica gel column, whereby from chloroform-methanol (10:1) eluate fractions, methyl trans-4-(1-((5-chloro-2-fluoro-4-(1-methyl-3-indolylcarbonylamino)phenyl)acetyl)-(4S)-dimethylcarbamoylmethoxy-(2S)-pyrrolidinylmethoxy)-1-cyclohexanecarboxylate (288 mg, 76%) was obtained as a yellow oil.

$^1$H-NMR (CDCl$_3$) δ: 1.24 (m, 2H), 1.45 (m, 2H), 1.84–2.31 (series of m, 7H), 2.96–3.01 (m, 6H), 3.22 (m, 1H), 3.50–4.23 (series fo m, 17H), 7.27 (m, 4H), 7.80 (s, 1H), 8.12–8.14 (m, 1H), 8.29 (s, 1H), 8.49 (dd, J=12.0, 8.6 Hz, 1H).

MS (ESI) m/z 685 (M$^+$+1).

(Step 9) Synthesis of trans-4-(1-((5-chloro-2-fluoro-4-(1-methyl-3-indolylcarbonylamino)phenyl)acetyl)-(4S)-dimethylcarbamoylmethoxy-(2S)-pyrrolidinylmethoxy)-1-cyclohexanecarboxylic acid

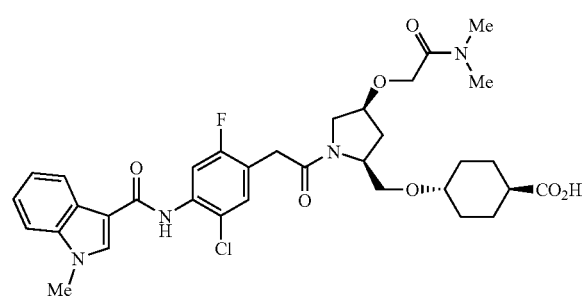

To methyl trans-4-(1-((5-chloro-2-fluoro-4-(1-methyl-3-indolylcarbonylamino)phenyl)acetyl)-(4S)-dimethylcarbamoylmethoxy-(2S)-pyrrolidinylmethoxy)-1-cyclohexanecarboxylate (280 mg, 0.409 mmol) were added THF (5 ml) and 0.25N NaOH (3.3 ml, 0.825 mmol). The resulting mixture was stirred at room temperature for 15 hours. The reaction mixture was poured in 1N HCl (100 ml), followed by extraction with chloroform-methanol (5:1, 2×100 ml). The extract was dried over anhydrous magnesium sulfate and distilled under reduced pressure to remove the solvent. The residue was dissolved in chloroform and to this solution was added hexane in portions until precipitation occurred. The crystals thus precipitated were collected by filtration under reduced pressure and dried under reduced pressure to give the title compound (180 mg, 66%) as a pale yellow solid.

$^1$H-NMR (DMSO-d$_6$) δ: 1.16–1.37 (m, 4H), 1.85–2.17 (m, 7H), 2.82 (d, J=4.4 Hz, 3H), 2.92 (d, J=6.8 Hz, 3H), 3.17–4.22 (series of m, 14H), 7.20–7.30 (m, 2H), 7.44 (dd, J=11.2, 6.8 Hz, 1H), 7.56 (d, J=8.1 Hz, 1H), 7.70 (dd, J=11.2, 6.8 Hz, 1H), 8.15 (d, J=7.8 Hz, 1H), 8.31 (s, 1H), 9.31 (s, 1H).

MS (FAB) m/z 671 (M$^+$+1);

Anal. Calcd for C$_{34}$H$_{40}$ClFN$_4$O$_7$ 0.75 H$_2$O: C, 59.64; H, 6.11; N, 8.18. Found: C, 60.03; H, 6.16; N, 7.82.

Example 121 trans-4-(1-((5-Chloro-2-fluoro-4-(1-methyl-3-indazolylcarbonylamino)phenyl)acetyl)-(4S)-methoxy-(2S)-pyrrolidinylmethoxy)cyclohexanecarboxylic acid (Step 1) Synthesis of methyl trans-4-(1-((5-chloro-2-fluoro-4-(1-methyl-3-indazolylcarbonylamino)phenyl)acetyl)-(4S)-methoxy-(2S)-pyrrolidinylmethoxy)cyclohexanecarboxylate

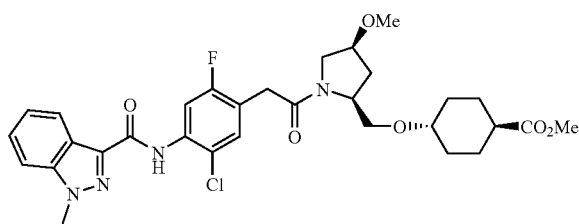

In DMF (3 ml), (5-chloro-2-fluoro-4-(1-methyl-3-indazolylcarbonylamino)phenyl)acetic acid (133 mg, 0.369 mmol), methyl trans-4-((4S)-methoxy-(2S)-pyrrolidinylmethoxy)cyclohexanecarboxylate (100 mg, 0.369 mmol), EDC HCl (106 mg, 0.554 mmol), HOBt (75 mg, 0.554 mmol) and triethylamine (0.26 ml, 1.85 mmol) were stirred at room temperature for 14 hours. The reaction mixture was poured in ice water, followed by extraction with ethyl acetate. The extract was dried over anhydrous sodium sulfate, and distilled under reduced pressure to remove the solvent. The residue was purified by chromatography using a silica gel thin-layer plate (developed in chloroform/acetone (20/1)) to give methyl trans-4-(1-((5-chloro-2-fluoro-4-(1-methyl-3-indazolylcarbonylamino)phenyl)acetyl)-(4S)-methoxy-(2S)-pyrrolidinylmethoxy) cyclohexanecarboxylate (166 mg, 73%) as a yellow oil.

$^1$H-NMR (CDCl$_3$) δ: 1.13–1.52 (m, 4H), 1.90–2.16 (m, 6H), 2.89 (m, 1H), 3.21–3.27 (m, 1H), 3.30 and 3.33 (each s, total 3H, amide isomers), 3.42–3.59 (m, 3H), 3.64 and 3.66 (each s, total 3H, amide isomers), 3.67–4.03 (m, 1H), 7.34 (m, 1H), 7.46 (s, 2H), 8.39 (d, J=8.3 Hz, 1H), 8.48 and 8.52 (each d, each J=10.0 Hz, total 1H, amide isomers), 9.49 (d, J=4.2 Hz, 1H).

MS (ESI) m/z 615 (M$^+$+1), 617 (M$^+$+3).

(Step 2) Synthesis of trans-4-(1-((5-chloro-2-fluoro-4-(1-methyl-3-indazolylcarbonylamino)phenyl)acetyl)-(4S)-methoxy-(2S)-pyrrolidinylmethoxy)cyclohexanecarboxylic acid

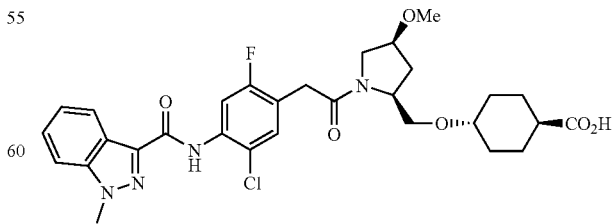

Methyl trans-4-(1-((5-chloro-2-fluoro-4-(1-methyl-3-indazolylcarbonylamino)phenyl)acetyl)-(4S)-methoxy-(2S)-pyrrolidinylmethoxy)cyclohexanecarboxylate (166 mg, 0.270 mmol) was dissolved in a THF/methanol (2:1, 6 ml) mixture. To the resulting solution was added 1N NaOH (2 ml). After the reaction mixture was stirred at room temperature for 17 hours, the solvent was distilled off under reduced pressure. To the residue was added 1N HCl. The crystals thus precipitated were collected by filtration under reduced pressure, washed with water and dried under reduced pressure to give the title compound (130 mg, 80%) as a pale yellow solid.

IR (ATR) ν 3363, 2937, 2862, 1726, 1685, 1643, 1621, 1587, 1527, 1406 cm$^{-1}$;

$^1$H-NMR (DMSO-d$_6$) δ: 1.12–1.42 (m, 4H), 1.82–2.22 (m, 7H), 3.16 (m, 1H), 3.22 and 3.26 (each s, total 3H, amide isomers), 3.43–3.99 (m, 6H), 4.02 (s, 1H), 4.21 (s, 3H), 4.24 (m, 1H), 7.37 (t, J=7.3 Hz, 1H), 7.46 and 7.50 (each d, each J=7.3 Hz, total 1H, amide isomers), 7.82 (d, J=8.3 Hz, 1H), 8.04 and 8.06 (each d, each J=11.3 Hz, 1H, amide isomers), 8.20 (d, J=8.1 Hz, 1H), 9.72 (s, 1H);

MS (ESI) m/z 601 (M$^+$+1), 603 (M$^+$+3);

Anal. Calcd for C$_{30}$H$_{34}$ClFN$_4$O$_6$ 0.5H$_2$O: C, 59.06; H, 5.78; N, 9.18; Cl, 5.81; F, 3.11. Found: C, 58.80; H, 5.64; N, 9.03; Cl, 6.00; F, 3.08.

Example 122 trans-4-((4R)-Hydroxy-1-((2-(2-methylphenylamino)-6-benzoxazolyl)acetyl)-(2S)-pyrrolidinylmethoxy)cyclohexanecarboxylic acid (Step 1) Synthesis of methyl 4-((4R)-hydroxy-(2S)-pyrrolidinylmethoxy)cyclohexanecarboxylate

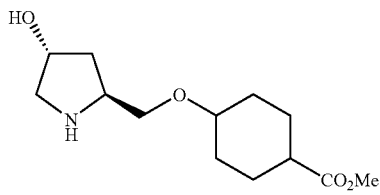

Methyl 4-(N-(tert-butoxycarbonyl)-(4R)-hydroxy-(2S)-pyrrolidinylmethoxy)benzoate (4.016 g, 11.43 mmol) was dissolved in methylene chloride (60.0 ml). Under stirring at 0° C., trifluoroacetic acid (30 ml) was added to the resulting solution. The resulting mixture was stirred at room temperature for 3 hours. The solvent was then distilled off under reduced pressure. The residue was dissolved in ethanol (80 ml), followed by catalytic hydrogenation in an autoclave for 20 hours with rhodium-alumina (5%, 1.01 g) under 9.5 kgf/cm$^2$ of hydrogen atmosphere. The reaction mixture was filtered through Celite to remove the catalyst and the solvent was distilled off under reduced pressure. The residue was dissolved in chloroform-methanol (10:1, v/v). The resulting solution was washed with a saturated aqueous solution of sodium bicarbonate, dried over anhydrous sodium sulfate, and distilled under reduced pressure to remove the solvent to give methyl 4-((4R)-hydroxy-(2S)-pyrrolidinylmethoxy)cyclohexanecarboxylate (2.46 g, 86%) as a brown oil. The resulting compound was provided for the subsequent reaction without further purification.

$^1$H-NMR (CDCl$_3$) δ: 1.10–2.45 (total 11H, series of m), 3.13–3.90 (total 9H, series of m, including 3H, s at δ: 3.65), 4.17 (1H, m), 4.65 (1H, m), 9.37 (1H, bs, NH).

(Step 2) Synthesis of methyl trans- and cis-4-(N-carbobenzoxy-(4R)-hydroxy-(2S)-pyrrolidinylmethoxy)cyclohexanecarboxylates

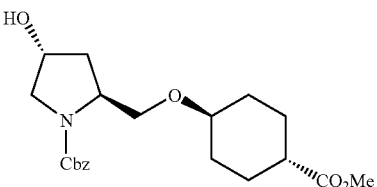

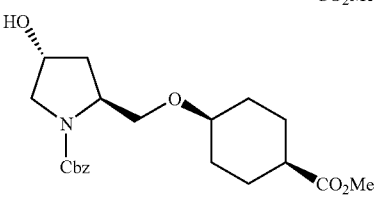

Methyl 4-((4R)-hydroxy-(2S)-pyrrolidinylmethoxy)cyclohexanecarboxylate (2.46 g, 9.790 mmol) was dissolved in methylene chloride (50.0 ml). Under stirring at 0° C., carbobenzoxy chloride (a 30 to 35% toluene solution, 8.70 ml, 14.68 mmol) and a saturated aqueous solution of sodium bicarbonate (2.5 ml) were added to the resulting solution, followed by stirring at room temperature for 2 days. The reaction mixture was diluted with chloroform. The diluted mixture was washed with 1N HCl, dried over anhydrous sodium sulfate, and distilled under reduced pressure to remove the solvent. The residue was purified by chromatography on a silica gel column, whereby from hexane-ethyl acetate (1:1, v/v) eluate fractions, a trans- and cis-diastereomer mixture was obtained. The mixture was separable by medium pressure chromatography on a silica gel column. From hexane-ethyl acetate (1:3, v/v) eluate fractions, methyl trans-4-(N-carbobenzoxy-(4R)-hydroxy-(2S)-pyrrolidinylmethoxy)cyclohexanecarboxylate (555.1 mg, 15%) and methyl cis-4-(N-carbobenzoxy-(4R)-hydroxy-(2S)-pyrrolidinylmethoxy)cyclohexanecarboxylate (2.14 g, 57%) were obtained.

$^1$H-NMR (CDCl$_3$) (trans-isomer) δ: 1.09–1.30 (2H, m), 1.31–1.52 (2H, m), 1.55–1.83 (3H, m), 1.83–2.09 (3H, m), 2.11–2.29 (2H, m), 3.13 (1H, m), 3.40–3.73 (total 7H, m, including 3H, s at δ: 3.67), 4.12 (1H, bs), 4.49 (1H, bs), 5.01–5.28 (2H, m), 7.33 (5H, m, ArH);

$^1$H-NMR (CDCl$_3$) (cis-isomer) δ: 1.30–1.51 (2H, m), 1.52–1.88 (total 6H, m), 1.90–2.12 (2H, m), 2.19 (1H, m), 2.31 (1H, m), 3.27–3.78 (total 8H, m, including 3H, s at δ: 3.64), 4.12 (1H, bs), 4.52 (1H, bs), 5.00–5.28 (2H, m), 7.31 (5H, m, ArH).

(Step 3) Synthesis of methyl trans-4-((4R)-hydroxy-(2S)-pyrrolidinylmethoxy)cyclohexanecarboxylate

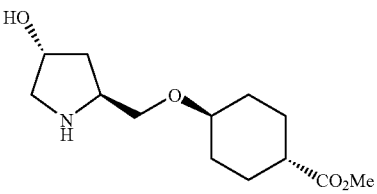

Methyl trans-4-(N-carbobenzoxy-(4R)-hydroxy-(2S)-pyrrolidinylmethoxy)cyclohexanecarboxylate (555.1 mg, 1.418 mmol) was dissolved in ethanol (11 ml). To the resulting solution was added 5% palladium/carbon (wet, 100 mg) and the mixture was subjected to catalytic reduction at room temperature under normal pressure. From the reaction mixture, the catalyst was filtered off. The filtrate was distilled under reduced pressure to remove the solvent to give methyl trans-4-((4R)-hydroxy-(2S)-pyrrolidinylmethoxy)cyclohexanecarboxylate (361.6 mg, crude). The compound was provided for the subsequent reaction without further purification.

¹H-NMR (CDCl₃) δ: 1.12–1.32 (3H, m), 1.35–1.55 (2H, m), 1.65 (1H, m), 1.74–1.93 (3H, m), 1.93–2.30 (3H, m), 2.82–3.58 (total 6H, series of m), 3.66 (3H, s, OMe), 4.40 (1H, bs).

(Step 4) Synthesis of methyl trans-4-((4R)-hydroxy-1-((2(2-methylphenylamino)-6-benzoxazolyl)acetyl)-(2S)-pyrrolidinylmethoxy)cyclohexanecarboxylate

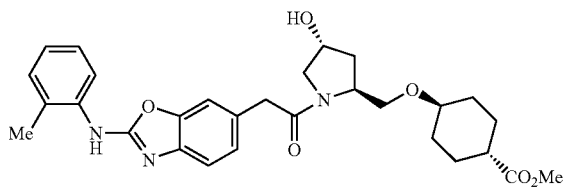

Methyl trans-4-((4R)-hydroxy-(2S)-pyrrolidinylmethoxy)cyclohexanecarboxylate (50.5 mg, 0.201 mmol), (2-(2-methylphenylamino)-6-benzoxazolyl)acetic acid (56.7 mg, 0.201 mmol), and HOBt (5.4 mg, 0.040 mmol) were dissolved in DMF (2.0 ml). To the resulting solution was added EDC HCl (57.8 mg, 0.301 mmol), followed by stirring at room temperature for 18 hours. The reaction mixture was diluted with ethyl acetate. The diluted mixture was washed with 1N HCl, dried over anhydrous sodium sulfate, and distilled under reduced pressure to remove the solvent. The residue was purified by column chromatography using a silica gel thin-layer plate, whereby from chloroform-methanol (10:1, v/v) eluate fractions, methyl trans-4-((4R)-hydroxy-1-((2-(2-methylphenylamino)-6-benzoxazolyl)acetyl)-(2S)-pyrrolidinylmethoxy)cyclohexanecarboxylate (55.5 mg, 53%) was obtained as a clear oil.

¹H-NMR (CDCl₃) δ: 1.01–1.19 (2H, m), 1.29–1.50 (2H, m), 1.79–2.06 (6H, m), 2.10–2.23 (2H, m), 2.35 (3H, s, ArMe), 3.12 (1H, m), 3.32–3.59 (3H, m), 3.61 (3H, s, OMe), 3.71 (2H, s, CH₂), 3.79 (1H, dd, J=4.4, 10.0 Hz, CH₂), 4.36 (1H, m), 4.52 (1H, m), 7.01–7.45 (total 8H, series of m, ArH, NH).

(Step 5) Synthesis of trans-4-((4R)-hydroxy-1-((2-(2-methylphenylamino)-6-benzoxazolyl)acetyl)-(2S)-pyrrolidinylmethoxy)cyclohexanecarboxylic acid

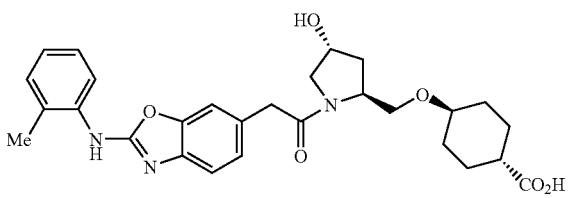

Methyl trans-4-((4R)-hydroxy-1-((2-(2-methylphenylamino)-6-benzoxazolyl)acetyl)-(2S)-pyrrolidinylmethoxy)cyclohexanecarboxylate (55.5 mg, 0.106 mmol) was dissolved in THF (1.0 ml). To the resulting solution was added 0.25N NaOH (1.0 ml), followed by stirring at room temperature for 15 hours. The reaction mixture was distilled under reduced pressure to remove the solvent. To the residue was added 1N HCl (0.3 ml). The crystals thus precipitated were collected by filtration under reduced pressure, washed with water and dried at 50° C. under reduced pressure to give the title compound (39.3 mg, 73%) as a light brown solid.

¹H-NMR (DMSO-d₆) δ: 0.98–1.39 (4H, m), 1.72–2.03 (6H, m), 2.11 (1H, m), 2.29 (3H, s, ArMe), 3.04–3.95 (8H, m), 4.09 (1H, m), 4.25, 4.32 (total 1H, m), 7.00–7.87 (total 8H, series of m, ArH, NH), 9.75 (1H, bs, CO₂H).

MS (ESI) m/z 508 (M⁺+1).

Example 123 trans-4-(1-((2-(2-Methylphenylamino)-6-benzoxazolyl)acetyl))-(4S)-phenylthio-(2S)-pyrrolidinylmethoxy)cyclohexanecarboxylic acid (Step 1) Synthesis of methyl trans-4-(N-(tert-butoxycarbonyl)-(4R)-methanesulfonyloxy-(2S)-pyrrolidinylmethoxy)cyclohexanecarboxylate

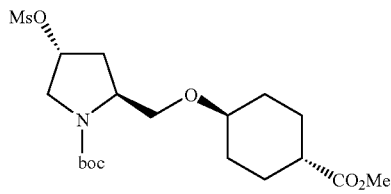

Methyl trans-4-(N-(tert-butoxycarbonyl)-(4R)-hydroxy-(2S)-pyrrolidinylmethoxy)cyclohexanecarboxylate (301.6 mg, 0.844 mmol) was dissolved in methylene chloride (6.0 ml). Under stirring at 0° C., triethylamine (0.47 ml, 3.375 mmol) and methanesulfonyl chloride (0.13 ml, 1.687 mmol) were added to the resulting solution. The reaction mixture was stirred at the same temperature for 2.5 hours. The reaction mixture was diluted with chloroform. The diluted mixture was washed with 1N HCl, dried over anhydrous sodium sulfate, and distilled under reduced pressure to remove the solvent. The residue was purified by chromatography on a silica gel column, whereby from hexane-ethyl acetate (1:1, v/v) eluate fractions, methyl trans-4-(N-(tert-butoxycarbonyl)-(4R)-methanesulfonyl-(2S)-pyrrolidinylmethoxy)cyclohexanecarboxylate (361.1 mg, 98%) was obtained as a colorless clear oil.

¹H-NMR (CDCl₃) δ: 1.12–1.27 (2H, m), 1.35–1.52 (10H, m, including 9H, s at δ: 1.45), 1.64 (1H, m), 1.90–2.05 (4H, m), 2.18–2.40 (3H, m), 3.01 (3H, s, MeSO₃), 3.17 (1H, m), 3.43–3.85 (total 7H, m, including 3H, s at δ: 3.64), 3.95–4.12 (1H, m), 5.25 (1H, m, MsOCH).

(Step 2) Synthesis of methyl trans-4-(N-(tert-butoxycarbonyl)-(4S)-phenylthio-(2S)-pyrrolidinylmethoxy)cyclohexanecarboxylate

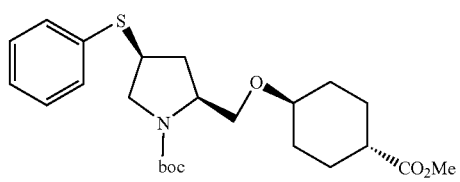

Cesium fluoride (125.9 mg, 0.829 mmol) was dried under reduced pressure at 180° C. for 40 minutes. The reaction vessel was allowed to cool down to room temperature in a nitrogen gas stream. To the reaction mixture were added DMF (2.0 ml) and thiophenol (0.11 ml, 1.078 mmol). Under stirring at room temperature, a solution of methyl trans-4-(N-(tert-butoxycarbonyl)-(4R)-methanesulfonyl-(2S)-pyrrolidinylmethoxy)cyclohexanecarboxylate (361.1 mg, 0.829 mmol) in DMF (3.5 ml) was added dropwise. The reaction mixture was stirred further for 18 hours at 50° C. and then, diluted with ethyl acetate. The diluted mixture was washed with saturated brine, dried over anhydrous sodium sulfate, and distilled under reduced pressure to remove the solvent. The residue was purified by chromatography on a silica gel column, whereby from hexane-ethyl acetate (8:1, v/v) eluate fractions, methyl trans-4-(N-(tert-butoxycarbonyl)-(4S)-phenylthio-(2S)-pyrrolidinylmethoxy)cyclohexanecarboxylate (367.2 mg, 98%) was obtained as a colorless clear oil.

$^1$H-NMR (CDCl$_3$) δ: 1.15–1.32 (2H, m, CH$_2$), 1.35–1.56 (11H, m, including 9H, s at δ: 1.46), 1.93–2.10 (5H, m, CH$_2$, CH), 2.27 (1H, m, CH$_2$), 2.45 (1H, m, CH$_2$), 3.14–3.27 (2H, m), 3.44–3.79 (total 6H, m, including 3H, s at δ: 3.67), 3.81–4.07 (2H, m), 7.20–7.45 (total 5H, series of m, ArH).

(Step 3) Synthesis of methyl trans-4-((4S)-phenylthio-(2S)-pyrrolidinylmethoxy)cyclohexanecarboxylate

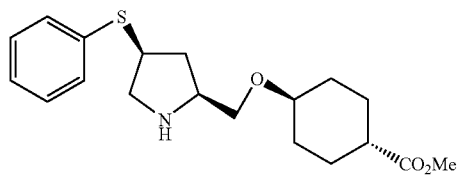

Methyl trans-4-(N-(tert-butoxycarbonyl)-(4S)-phenylthio-(2S)-pyrrolidinylmethoxy)cyclohexanecarboxylate (367.2 mg, 0.817 mmol) was dissolved in methylene chloride (7.0 ml). To the resulting solution was added trifluoroacetic acid (3.5 ml) under stirring at 0° C. The reaction mixture was stirred further at room temperature for 1.5 hours. From the reaction mixture, the solvent was distilled off under reduced pressure. The residue was diluted with chloroform, followed by washing with a saturated aqueous solution of sodium bicarbonate, drying over anhydrous sodium sulfate and distillation under reduced pressure to remove the solvent, whereby methyl trans-4-((4S)-phenylthio-(2S)-pyrrolidinylmethoxy)cyclohexanecarboxylate (256.3 mg, 90%) was obtained. The resulting compound was provided for the subsequent reaction without further purification.

$^1$H-NMR (CDCl$_3$) δ: 1.17–1.33 (2H, m), 1.35–1.55 (3H, m), 1.91–2.18 (5H, m, CH$_2$, CH, NH), 2.19–2.39 (2H, m), 2.95 (1H, dd, J=4.8, 11.6 Hz, CH$_2$), 3.13–3.33 (3H, m), 3.38–3.54 (2H, m), 3.65 (3H, s, OMe), 3.68 (1H, m), 7.11–7.40 (total 5H, series of m, ArH).

(Step 4) Synthesis of methyl trans-4-(1-((2-(2-methylphenylamino)-6-benzoxazolyl)acetyl)-(4S)-phenylthio-(2S)-pyrrolidinylmethoxy)cyclohexanecarboxylate

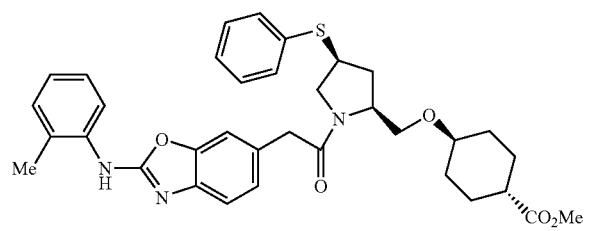

Methyl trans-4-((4S)-phenylthio-(2S)-pyrrolidinylmethoxy)cyclohexanecarboxylate (256.3 mg, 0.733 mmol), (2-(2-methylphenylamino)-6-benzoxazolyl)acetic acid (207.0 mg, 0.733 mmol), and HOBt (19.8 mg, 0.147 mmol) were dissolved in DMF (9.0 ml). Under stirring at room temperature, EDC HCl (210.9 mg, 1.100 mmol) was added. The resulting mixture was stirred further at room temperature for 18 hours. The reaction mixture was diluted with ethyl acetate. The diluted mixture was washed with 1N HCl, dried over anhydrous sodium sulfate, and distilled under reduced pressure to remove the solvent. The residue was purified by chromatography on a silica gel column, whereby from chloroform-methanol (15:1, v/v) eluate fractions, methyl trans-4-(1-((2-(2-methylphenylamino)-6-benzoxazolyl)acetyl)-(4S)-phenylthio-(2S)-pyrrolidinylmethoxy)cyclohexanecarboxylate (quantitative yield) was obtained as a light brown amorphous substance.

$^1$H-NMR (CDCl$_3$) δ: 1.04–1.29 (2H, m), 1.30–1.51 (2H, m), 2.78–2.12 (5H, m), 2.19 (1H, m), 2.34 (3H, s, ArMe), 2.37 (1H, m), 3.12 (1H, m), 3.23 (1H, dd, J=10.0 Hz), 3.49 (1H, m), 3.55–3.67 (6H, m, including 3H, s at δ: 3.61), 3.71 (1H, m), 3.88 (1H, m), 4.22 (1H, m), 6.95–7.10 (2H, m, ArH), 7.15–7.40 (9H, m, ArH), 7.90 (1H, d, J=8.0 Hz, ArH), 7.99 (1H, s, NH).

(Step 5) Synthesis of trans-4-(1-((2-(2-methylphenylamino)-6-benzoxazolyl)acetyl)-(4S)-phenylthio-(2S)-pyrrolidinylmethoxy)cyclohexanecarboxylic acid

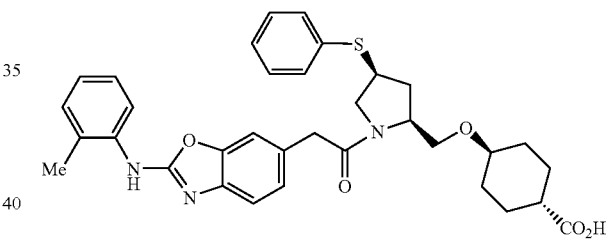

Methyl trans-4-(1-((2-(2-methylphenylamino)-6-benzoxazolyl)acetyl)-(4S)-phenylthio-(2S)-pyrrolidinylmethoxy)cyclohexanecarboxylate (187.2 mg, 0.305 mmol) was dissolved in THF (4.0 ml). To the resulting solution was added 0.25N NaOH (4.0 ml), followed by stirring at room temperature for 2 days. From the reaction mixture, the solvent was distilled off under reduced pressure. The residue was acidified with 1N HCl (1.5 ml). The crystals thus precipitated were collected by filtration under reduced pressure, washed with water and dried at 50° C. under reduced pressure to give the title compound (160.3 mg, 88%) as an amorphous substance.

IR (ATR) ν1693, 1639, 1573, 1438 cm$^{-1}$;

$^1$H-NMR (DMSO-d$_6$) δ 1.00–1.21 (2H, m), 1.22–1.38 (2H, m), 1.75–1.97 (5H, m), 2.11 (1H. m), 2.30 (3H, s, ArMe), 2.42 (1H, m), 3.01–4.15 (total 9H, series of m), 7.01 (1H, d, J=8.0 Hz, ArH), 7.08 (1H, dd, J=7.6 Hz, ArH), 7.20–7.44 (9H, m, ArH), 7.79 (1H, d, J=8.0 Hz, ArH), 9.62 (1H, br s).

MS (ESI) m/z 600 (M$^+$+1);

Anal. Calcd for C$_{34}$H$_{37}$N$_3$O$_5$S 0.5H$_2$O: C, 67.08; H, 6.29; N, 6.90; S, 5.27. Found: C, 67.02; H, 6.05; N, 6.84; S, 5.29.

Example 124 trans-4-(1-((2-(2-Methylphenylamino)-6-benzoxazolyl)acetyl)-(4S)-phenylsulfonyl-(2S)-pyrrolidinylmethoxy)cyclohexanecarboxylic acid (Step 1) Synthesis of methyl trans-4-(1-(2-(2-methylphenylamino)-6-benzoxazolylacetyl)-(4S)-phenylsulfonyl-(2S)-pyrrolidinylmethoxy)cyclohexanecarboxylate

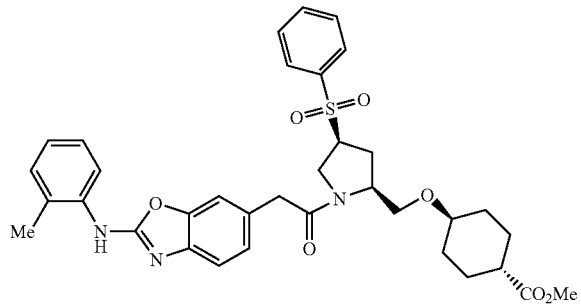

Methyl trans-4-(1-((2-(2-methylphenylamino)-6-benzoxazolyl)acetyl)-(4S)-phenylthio-(2S)-pyrrolidinylmethoxy)cyclohexanecarboxylate (282.9 mg, 0.461 mmol) was dissolved in methylene chloride (6.0 ml). To the resulting solution was added m-chloroperbenzoic acid (198.9 mg, 1.152 mmol) under stirring at 0° C. The reaction mixture was stirred at the same temperature for 3.5 hours and at room temperature for 5 hours. The reaction mixture was diluted with chloroform-methanol (10:1, v/v). The diluted mixture was washed with a saturated aqueous solution of sodium bicarbonate, dried over anhydrous sodium sulfate, and distilled under reduced pressure to remove the solvent. The residue was purified by chromatography on a silica gel column, whereby from chloroform-methanol (15:1, v/v) eluate fractions, methyl trans-4-(1-((2-(2-methylphenylamino)-6-benzoxazoly)acetyl)-(4S)-phenylsulfonyl-(2S)-pyrrolidinylmethoxy)cyclohexanecarboxylate (quantitative yield) was obtained as a light brown amorphous substance.

$^1$H-NMR (CDCl$_3$) δ: 0.95–1.55 (4H, m), 1.70–2.50 (total 10H, series of m, including total 3H, s at δ: 2.34 and 2.37), 3.00–4.34 (total 12H, series of m, including 3H, s at δ: 3.63), 6.85–8.15 (total 13H, series of m, ArH, NH).

MS (ESI) m/z 646 (M$^+$+1).

(Step 2) Synthesis of trans-4-(1-((2-(2-methylphenylamino)-6-benzoxazolyl)acetyl)-(4S)-phenylsulfonyl-(2S)-pyrrolidinylmethoxy)cyclohexanecarboxylic acid

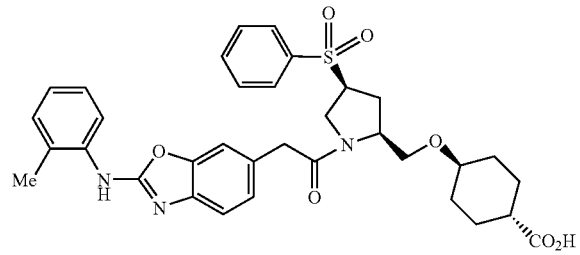

Methyl trans-4-(1-((2-(2-methylphenylamino)-6-benzoxazolyl)acetyl)-(4S)-phenylsulfonyl-(2S)-pyrrolidinylmethoxy)cyclohexanecarboxylate (297.6 mg, 0.461 mmol) was dissolved in THF (6.0 ml). To the resulting solution was added 0.25N NaOH (6.0 ml), followed by stirring at room temperature for 18 hours. From the reaction mixture, the solvent was distilled off under reduced pressure. The residue was acidified with 1N HCl (1.7 ml). The crystals thus precipitated were collected by filtration under reduced pressure, washed with water and dried at 50° C. under reduced pressure to give the title compound (268.4 mg, 92%) as an amorphous substance.

IR (ATR) ν1695, 1639, 1575, 1446 cm$^{-1}$;

$^1$H-NMR (DMSO-d$_6$) δ: 0.97–1.22 (2H, m), 1.22–1.40 (2H, m), 1.73–1.98 (4H, m), 2.07–2.25 (3H, m), 2.30 (3H, s, ArMe), 3.03–4.45 (total 9H, series of m), 6.99 (1H, d, J=8.0 Hz, ArH), 7.08 (1H, dd, J=7.2 Hz, ArH), 7.24 (4H, m, ArH), 7.65–7.96 (total 6H, series of m, ArH), 9.64 (1H, br s).

MS (ESI) m/z 632 (M$^+$+1);

Anal. Calcd for C$_{34}$H$_{37}$N$_3$O$_7$S 0.75H$_2$O: C, 63.29; H, 6.01; N, 6.51; S, 4.97. Found: C, 63.15; H, 5.71; N, 6.33; S, 4.95.

Example 125 trans-4-(1-((5-Chloro-2-fluoro-4-((1-methyl-3-indolylcarbonyl)amino)phenyl)acetyl)-(4S)-methylthio-(2S)-pyrrolidinylmethoxy)cyclohexanecarboxylic acid (Step 1) Synthesis of trans-4-(N-(tert-butoxycarbonyl)-(4S)-methylthio-(2S)-pyrrolidinylmethoxy)cyclohexanecarboxylic acid

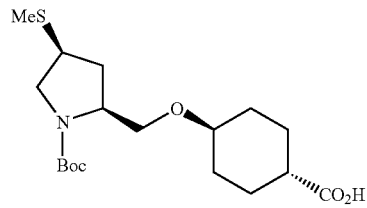

Methyl trans-4-(N-(tert-butoxycarbonyl)-(4R)-methanesulfonyloxy-(2S)-pyrrolidinylmethoxy)cyclohexanecarboxylate (95.3 mg, 0.219 mmol) was dissolved in DMF (2.0 ml). To the resulting solution was added sodium thiomethoxide (46.0 mg, 0.656 mmol) at room temperature under a nitrogen gas stream. After stirring for 18 hours at 60° C., the reaction mixture was cooled and then, diluted with ethyl acetate. The ethyl acetate solution was washed with 1N HCl, dried over anhydrous sodium sulfate and distilled under reduced pressure to remove the solvent. The residue was purified by chromatography on a silica gel column, whereby from hexane-ethyl acetate (1:1, v/v) eluate fractions, trans-4-(N-(tert-butoxycarbonyl)-(4S)-methylthio-(2S)-pyrrolidinylmethoxy)cyclohexanecarboxylic acid (77.2 mg, 95%) was obtained as a clear oil.

$^1$H-NMR (CDCl$_3$) δ: 1.17–1.34 (2H, m), 1.37–1.55 (11H, m, including 9H, s at δ: 1.46), 1.91 (1H, m), 1.96–2.10 (4H, m), 2.13 (3H, s, SMe), 2.30 (1H, m), 2.38 (1H, m), 3.07–3.18 (2H, m), 3.23 (1H, m), 3.43–4.06 (total 4H, series of m).

(Step 2) Synthesis of methyl trans-4-(N-(tert-butoxycarbonyl)-(4S)-methylthio-(2S)-pyrrolidinylmethoxy)cyclohexanecarboxylate

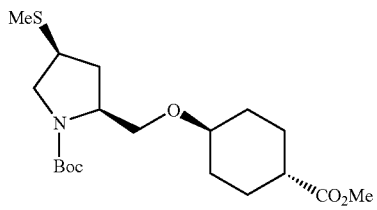

In benzene (5.0 ml) and methanol (0.5 ml) was dissolved trans-4-(N-(tert-butoxycarbonyl)-(4S)-methylthio-(2S)-pyrrolidinylmethoxy)cyclohexanecarboxylic acid (77.2 mg, 0.207 mmol). Under stirring at 0° C., trimethylsilyldiazomethane (a 2M-hexane solution, 1 ml) was added and the resulting mixture was stirred at room temperature for 30 minutes. Acetic acid was added to the reaction mixture at 0° C. From the resulting mixture, the solvent was distilled off under reduced pressure, followed by dilution with ethyl acetate. The ethyl acetate solution was washed with a saturated aqueous solution of sodium bicarbonate, dried over anhydrous sodium sulfate, and distilled under reduced pressure to remove the solvent, whereby methyl trans-4-(N-(tert-butoxycarbonyl)-(4S)-methylthio-(2S)-pyrrolidinylmethoxy)cyclohexanecarboxylate (75.6 mg, 94%) was obtained as a pale yellow oil. The compound was provided for the subsequent reaction without further purification.

$^1$H-NMR (CDCl$_3$) δ: 1.15–1.32 (2H, m), 1.36–1.54 (11H, m, including 9H, s at δ: 1.46), 1.85–2.08 (5H, m), 2.13 (3H, s, SMe), 2.26 (1H, m), 2.38 (1H, m), 3.05–3.16 (2H, m), 3.21 (1H, m), 3.42–4.05 (total 7H, series of m, including 3H, s at δ: 3.66).

(Step 3) Synthesis of methyl trans-4-((4S)-methylthio-(2S)-pyrrolidinylmethoxy)cyclohexanecarboxylate

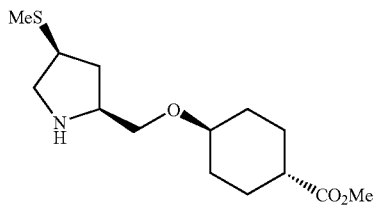

Methyl trans-4-(N-(tert-butoxycarbonyl)-(4S)-methylthio-(2S)-pyrrolidinylmethoxy)cyclohexanecarboxylate (75.6 mg, 0.195 mmol) was dissolved in methylene chloride (4.0 ml). To the resulting solution was added trifluoroacetic acid (2.0 ml) at 0° C. The resulting mixture was stirred for 2.5 hours at room temperature. From the reaction mixture, the solvent was distilled off under reduced pressure. The residue was diluted with chloroform. The chloroform solution was neutralized with a saturated aqueous solution of sodium bicarbonate, followed by extraction with a chloroform-methanol (10:1, v/v) mixture. The extract was dried over anhydrous sodium sulfate, and distilled under reduced pressure to remove the solvent, whereby methyl trans-4-((4S)-methylthio-(2S)-pyrrolidinylmethoxy)cyclohexanecarboxylate was obtained as a pale yellow oil. The compound was provided for the subsequent reaction without further purification.

$^1$H-NMR (CDCl$_3$) δ: 1.18–1.52 (6H, m), 1.94–2.12 (7H, m, including 3H, s at δ: 2.10), 2.20–2.31 (2H, m), 2.90 (1H, dd, J=8.0, 14.0 Hz), 3.11–3.32 (4H, m), 3.43 (1H, dd, J=6.2, 9.4 Hz), 3.49 (1H, dd, J=5.0, 9.4 Hz).

(Step 4) Synthesis of methyl trans-4-(1-((5-chloro-2-fluoro-4-((1-methyl-3-indolylcarbonyl)amino)phenyl)acetyl)-(4S)-methylthio-(2S)-pyrrolidinylmethoxy)cyclohexanecarboxylate

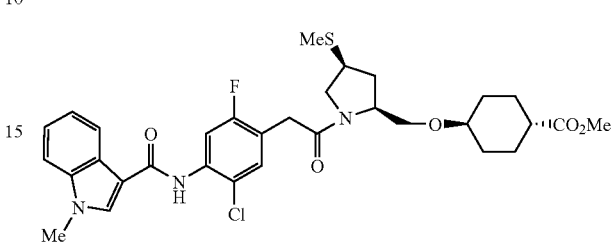

Methyl trans-4-((4S)-methylthio-(2S)-pyrrolidinylmethoxy)cyclohexanecarboxylate (161.6 mg, 0.562 mmol) was dissolved in DMF (7.0 ml). To the resulting solution were added (5-chloro-2-fluoro-4-((1-methyl-3-indolylcarbonyl)amino)phenyl)acetic acid (202.8 mg, 0.562 mmol), HOBt (15.2 mg, 0.112 mmol) and EDC HCl (161.7 mg, 0.843 mmol). The resulting mixture was stirred at room temperature for 18 hours. The reaction mixture was diluted with ethyl acetate. The diluted mixture was washed successively with 1N HCl and a saturated aqueous solution of sodium bicarbonate, dried over anhydrous sodium sulfate, and distilled under reduced pressure to remove the solvent. The residue was purified by chromatography on a silica gel column, whereby from hexane-ethyl acetate (1:2, v/v) eluate fractions, methyl trans-4-(1-((5-chloro-2-fluoro-4-((1-methyl-3-indolylcarbonyl)amino)phenyl)acetyl)-(4S)-methylthio-(2S)-pyrrolidinylmethoxy)cyclohexanecarboxylate (328.8 mg, 93%) was obtained as a pale yellow oil.

$^1$H-NMR (CDCl$_3$) δ: 1.09–1.33 (2H, m), 1.36–1.54 (2H, m), 1.90–2.11 (5H, m), 2.15 (3H, s, SMe), 2.17–2.59 (total 2H, series of m), 3.11–3.23 (2H, m), 3.30 (1H, dd, J=10.0 Hz), 3.52–3.98 (total 11H, series of m, including 3H, s at δ: 3.62 and 3H, s at 3.89), 4.19–4.44 (total 1H, m), 7.30–7.46 (4H, m), 7.81 (1H, d, J=4.4 Hz), 8.14 (1H, m), 8.30 (1H, s), 8.51 (1H, dd, J=10.8 Hz).

(Step 5) Synthesis of trans-4-(1-((5-chloro-2-fluoro-4-((1-methyl-3-indolylcarbonyl)amino)phenyl)acetyl)-(4S)-methylthio-(2S)-pyrrolidinylmethoxy)cyclohexanecarboxylic acid

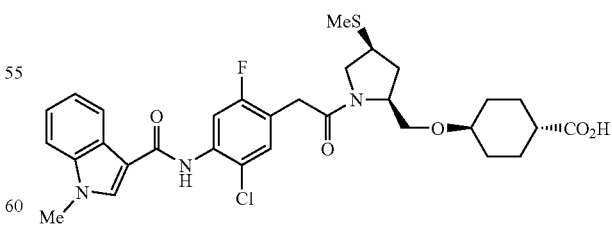

Methyl trans-4-(1-((5-chloro-2-fluoro-4-((1-methyl-3-indolylcarbonyl)amino)phenyl)acetyl)-(4S)-methylthio-(2S)-pyrrolidinylmethoxy)cyclohexanecarboxylate (146.6 mg, 0.234 mmol) was dissolved in THF (3.0 ml). To the resulting solution were added 0.25N NaOH (3.0 ml) and methanol (0.5 ml), followed by stirring at room temperature for 0.5 hour. The reaction mixture was concentrated under reduced pressure and the concentrate was neutralized with 1N HCl. The crystals thus precipitated were collected by filtration under reduced pressure, washed with water and dried at 50° C. under reduced pressure to give the title compound (135.0 mg, 94%) as a white amorphous substance.

IR (ATR) ν2935, 1641, 1517 cm$^{-1}$;

$^1$H-NMR (DMSO-d$_6$) δ: 1.08–1.43 (4H, m), 1.76–2.05 (5H, m), 2.14 (3H, s, SMe), 2.16 (1H, m), 2.35 (1H, m), 3.09–3.47 (4H, m), 3.55–3.66 (2H, m), 3.71 (1H, s), 3.80–4.38 (total 5H, series of m, including 3H, s, at δ 3.89), 7.22 (1H, dd, J=7.2 Hz), 7.28 (1H, dd, J=7.2 Hz), 7.43 (1H, d, J=7.2 Hz), 7.56 (1H, d, J=7.2 Hz), 7.70 (1H, m), 8.15 (1H, d, J=7.2 Hz), 8.31 (1H, s), 9.32 (1H, s).

MS(ESI) m/z 616 (M$^+$+1);

Anal. Calcd for C$_{31}$H$_{35}$ClFN$_3$O$_5$S 0.5H$_2$O: C, 59.56; H, 5.80; N, 6.72; Cl, 5.67; F, 3.04; S, 5.13. Found: C, 59.39; H, 5.53; N, 6.78; Cl, 5.74; F, 2.99; S, 5.12.

Example 126 trans-4-(1-((2-(5-Fluoro-2-methylphenylamino)-7-fluoro-6-benzoxazolyl)acetyl)-(4S)-methylthio-(2S)-pyrrolidinylmethoxy)cyclohexanecarboxylic acid (Step 1) Synthesis of methyl trans-4-(1-((2-(5-fluoro-2-methylphenylamino)-7-fluoro-6-benzoxazolyl)acetyl)-(4S)-methylthio-(2S)-pyrrolidinylmethoxy)cyclohexanecarboxylate

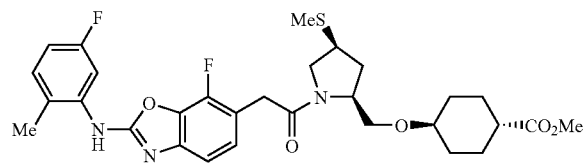

Methyl trans-4-((4S)-methylthio-(2S)-pyrrolidinylmethoxy)cyclohexanecarboxylate (169.4 mg, 0.589 mmol) was dissolved in DMF (7.0 ml). To the resulting solution were added (2-(5-fluoro-2-methylphenylamino)-7-fluoro-6-benzoxazolyl)acetic acid (187.6 mg, 0.589 mmol), HOBt (15.9 mg, 0.118 mmol) and EDC HCl (169.5 mg, 0.884 mmol). The resulting mixture was stirred at room temperature for 18 hours. The reaction mixture was diluted with ethyl acetate. The diluted mixture was washed successively with 1N HCl and a saturated aqueous solution of sodium bicarbonate, dried over anhydrous sodium sulfate, and distilled under reduced pressure to remove the solvent. The residue was purified by chromatography on a silica gel column, whereby from hexane-ethyl acetate (1:2, v/v) eluate fractions, methyl trans-4-(1-((2-(5-fluoro-2-methylphenylamino)-7-fluoro-6-benzoxazolyl)acetyl)-(4S)-methylthio-(2S)-pyrrolidinylmethoxy)cyclohexanecarboxylate (336.0 mg, 97%) was obtained as a pale yellow amorphous substance.

$^1$H-NMR (CDCl$_3$) δ: 1.10–1.35 (2H, m), 1.36–1.55 (2H, m), 1.90–2.61 (total 13H, series of m, including 3H, s at δ: 2.15 and 3H, s at δ: 2.32), 3.13–3.25 (2H, m), 3.31 (1H, dd, J=9.6 Hz), 3.54–3.80 (7H, series of m, including 3H, s at δ: 3.65), 3.87–4.00 (1H, m), 4.20–4.45 (total 1H, m), 6.75 (1H, m), 6.98 (1H, br s), 7.07–7.18 (2H, m), 7.24 (1H, m), 8.11 (1H, dd, J=2.8, 11.2 Hz).

(Step 2) Synthesis of trans-4-(1-((2-(5-fluoro-2-methylphenylamino)-7-fluoro-6-benzoxazolyl)acetyl)-(4S)-methylthio-(2S)-pyrrolidinylmethoxy)cyclohexanecarboxylic acid

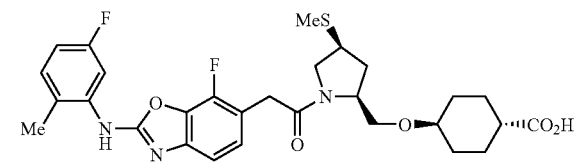

Methyl trans-4-(1-((2-(5-fluoro-2-methylphenylamino)-7-fluoro-6-benzoxazolyl)acetyl)-(4S)-methylthio-(2S)-pyrrolidinylmethoxy)cyclohexanecarboxylate (153.5 mg, 0.261 mmol) was dissolved in THF (3.0 ml). To the resulting solution was added 0.25N NaOH (3.0 ml). The resulting mixture was stirred at room temperature for 8 hours. The reaction mixture was concentrated under reduced pressure and the concentrate was neutralized with 1N HCl. The crystals thus precipitated were collected by filtration under reduced pressure, washed with water and dried at 50° C. under reduced pressure to give the title compound (138.8 mg, 93%) as a white amorphous substance.

IR (ATR) ν2935, 1639, 1577 cm$^{-1}$;

$^1$H-NMR (DMSO-d$_6$) δ: 1.05–1.43 (4H, m), 1.64–2.04 (5H, m), 2.13 (3H, s, SMe), 2.15 (1H, m), 2.30 (3H, s, ArMe), 2.33 (1H, m), 2.95–3.40 (3H, m), 3.54–3.82 (total 4H, series of m), 3.83–4.38 (total 2H, series of m), 6.90 (1H, m), 7.08 (1H, m), 7.21 (1H, dd, J=3.2,8.4 Hz), 7.26 (1H, dd, J=7.6 Hz), 7.93 (1H, dd, J=3.2, 11.2 Hz), 10.05 (1H, br s, NH), 12.05 (1H, br s, CO$_2$H).

MS(ESI) m/z 574 (M$^+$+1);

Anal. Calcd for C$_{29}$H$_{33}$F$_2$N$_3$O$_5$S 0.5H$_2$O: C, 59.78; H, 5.88; N, 7.21; F, 6.52; S, 5.50. Found: C, 59.89; H, 5.65; N, 7.21; F, 6.43; S, 5.44.

Example 127 trans-4-(1-((5-Chloro2-fluoro-4-((1-methyl-3-indazolylcarbonyl)amino)phenyl)acetyl)-(4S)-methylthio-(2S)-pyrrolidinylmethoxy)cyclohexanecarboxylic acid (Step 1) Synthesis of methyl trans-4-(1-((5-chloro 2-fluoro-4-((1-methyl-3-indazolylcarbonyl)amino)phenyl)acetyl)-(4S)-methylthio-(2S)-pyrrolidinylmethoxy)cyclohexanecarboxylate

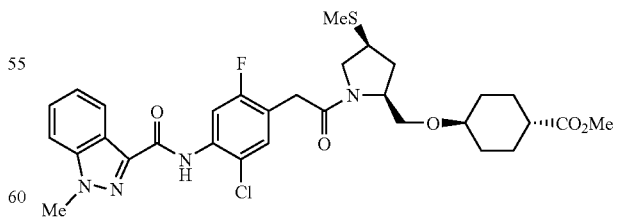

Methyl trans-4-((4S)-methylthio-(2S)-pyrrolidinylmethoxy)cyclohexylcarboxylate (163.2 mg, 0.568 mmol) was dissolved in DMF (7.0 ml). To the resulting solution were added (5-chloro-2-fluoro-4-((1-methyl-3-indazolylcarbonyl)amino)phenyl)acetic acid (205.4 mg, 0.568 mmol), HOBt (15.3 mg, 0.114 mmol) and EDC HCl (163.3 mg, 0.852 mmol), followed by stirring at room temperature for 18 hours. The reaction mixture was diluted with ethyl acetate. The diluted mixture was washed successively with 1N HCl and a saturated aqueous solution of sodium bicarbonate, dried over anhydrous sodium sulfate, and distilled under reduced pressure to remove the solvent. The residue was purified by chromatography on a silica gel column, whereby from hexane-ethyl acetate (1:2, v/v) eluate fractions, methyl trans-4-(1-((5-chloro-2-fluoro-4-((1-methyl-3-indazolylcarbonyl)amino)phenyl)acetyl)-(4S)-methylthio-(2S)-pyrrolidinylmethoxy)cyclohexanecarboxylate (348.7 mg, 97%) was obtained as a pale yellow amorphous substance.

$^1$H-NMR (CDCl$_3$) δ: 1.10–1.33 (2H, m), 1.37–1.55 (2H, m), 1.92–2.11 (5H, m), 2.15 (3H, s, SMe), 2.25 (1H, m), 2.33–2.59 (total 1H, m), 3.12–3.36 (3H, m), 3.52–3.99 (total 8H, series of m, including 3H, s at δ: 3.62), 4.17 (3H, s), 4.19–4.45 (total 1H, m), 7.29–7.42 (2H, m), 7.45–7.54 (2H, m), 8.38 (1H, d, J=8.0 Hz), 8.51 (1H, dd, J=12.0 Hz), 9.50 (1H, s).

(Step 2) Synthesis of trans-4-(1-((5-chloro-2-fluoro-4-((1-methyl-3-indazolylcarbonyl)amino)phenyl)acetyl)-(4S)-methylthio-(2S)-pyrrolidinylmethoxy)cyclohexanecarboxylic acid

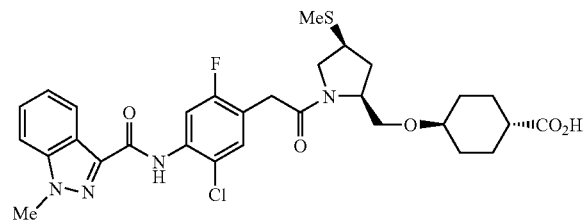

Methyl trans-4-(1-((5-chloro-2-fluoro-4-((1-methyl-3-indazolylcarbonyl)amino)phenyl)acetyl)-(4S)-methylthio-(2S)-pyrrolidinylmethoxy)cyclohexanecarboxylate (154.7 mg, 0.245 mmol) was dissolved in THF (3.0 ml). To the resulting solution were added 0.25N NaOH (3.0 ml) and methanol (1.0 ml). The resulting mixture was stirred at room temperature for 18 hours. The reaction mixture was concentrated under reduced pressure and the concentrate was neutralized with 1N HCl. The crystals thus precipitated were collected by filtration under reduced pressure, washed with water and dried at 50° C. under reduced pressure to give the title compound (132.2 mg, 87%) as a white amorphous substance.

IR (ATR) ν2937, 1621, 1529 cm$^{-1}$;

$^1$H-NMR (DMSO-d$_6$) δ: 1.07–1.42 (4H, m), 1.62–2.41 (total 10H, series of m, including 3H, s, at δ: 2.14), 2.95–3.47 (total 3H, series of m), 3.52–3.92 (total 4H, series of m), 4.00–4.39 (total 5H, series of m, including 3H, s, at δ: 4.22), 7.37 (1H, dd, J=7.6 Hz), 7.49 (1H, d, J=7.6 Hz), 7.54 (1H, dd, J=7.6 Hz), 7.83 (1H, d, J=8.4 Hz), 8.06 (1H, dd, J=6.4,11.2 Hz), 8.21 (1H, d, J=8.4 Hz), 9.73 (1H, s, NH), 12.05 (1H, br s, CO$_2$H).

MS(ESI) m/z 617 (M$^+$+1);

Anal. Calcd for C$_{30}$H$_{34}$ClFN$_4$O$_5$S 0.5H$_2$O: C, 57.55; H, 5.63; N, 8.95; Cl, 5.66; F, 3.03; S, 5.12. Found: C, 57.69; H, 5.43; N, 8.92; Cl, 5.67; F, 3.04; S, 5.18.

Example 128 trans-4-(1-((5-Chloro-2-fluoro-4-((1-methyl-3-indolylcarbonyl)amino)phenyl)acetyl)-(4S)-methanesulfonyl-(2S)-pyrrolidinylmethoxy)cyclohexanecarboxylic acid (Step 1) Synthesis of methyl trans-4-(1-((5-chloro-2-fluoro-4-((1-methyl-3-indolylcarbonyl)amino)phenyl)acetyl)-(4S)-methanesulfonyl-(2S)-pyrrolidinylmethoxy)cyclohexanecarboxylate

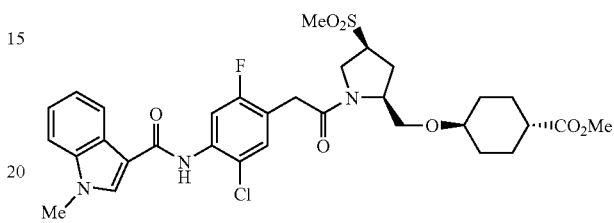

Methyl trans-4-(1-((5-chloro-2-fluoro-4-((1-methyl-3-indolylcarbonyl)amino)phenyl)acetyl)-(4S)-methylthio-(2S)-pyrrolidinylmethoxy)cyclohexanecarboxylate (182.2 mg, 0.289 mmol) was dissolved in methylene chloride (4.0 ml). To the resulting solution was added m-chloroperbenzoic acid (149.7 mg, 0.867 mmol) under stirring at 0° C. The stirring was conducted further at the same temperature for 2 hours. The reaction mixture was diluted with chloroform-methanol (10:1, v/v). The diluted mixture was washed with a saturated aqueous solution of sodium bicarbonate, dried over anhydrous sodium sulfate, and distilled under reduced pressure to remove the solvent. The residue was purified by chromatography using a silica gel thin-layer plate, whereby from chloroform-methanol (10:1, v/v) eluate fractions, methyl trans-4-(1-((5-chloro-2-fluoro-4-((1-methyl-3-indolylcarbonyl)amino)phenyl)acetyl)-(4S)-methanesulfonyl-(2S)-pyrrolidinylmethoxy)cyclohexanecarboxylate (159.1 mg, 83%) was obtained as a yellow oil.

$^1$H-NMR (CDCl$_3$) δ: 1.09–1.34 (2H, m), 1.35–1.55 (2H, m), 1.88–2.14 (5H, m), 2.27 (1H, m), 2.42–2.67 (total 1H, m), 2.92 and 2.94 (total 3H, s, SO$_2$Me), 3.14–3.33 (2H, m), 3.44–3.95 (total 11H, series of m, including total 3H, s at δ: 3.62 and 3.67, and 3H, s at 3.90), 4.04–4.60 (total 2H, series of m), 7.30–7.47 (4H, m), 7.83 (1H, s), 8.13 (1H, m), 8.31 (1H, s), 8.53 (1H, dd, J=12.0 Hz).

(Step 2) Synthesis of trans-4-(1-((5-chloro-2-fluoro-4-((1-methyl-3-indolylcarbonyl)amino)phenyl)acetyl)-(4S)-methanesulfonyl-(2S)-pyrrolidinylmethoxy)cyclohexanecarboxylic acid

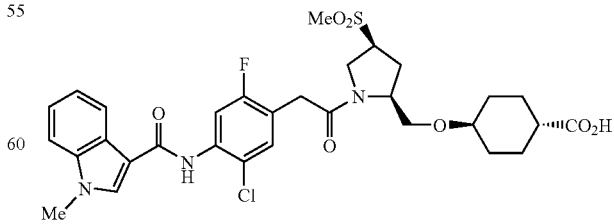

Methyl trans-4-(1-((5-chloro-2-fluoro-4-((1-methyl-3-indolylcarbonyl)amino)phenyl)acetyl)-(4S)-methanesulfonyl-(2S)-pyrrolidinylmethoxy)cyclohexanecarboxylate (159.1 mg, 0.240 mmol) was dissolved in THF (3.0 ml). To the resulting solution was added 0.25N NaOH (3.0 ml). The resulting mixture was stirred at room temperature for 4 hours. The reaction mixture was concentrated under reduced pressure. The residue was neutralized with 1N HCl. The crystals thus precipitated were collected by filtration under reduced pressure, washed with water and dried at 35° C. under reduced pressure for 3 days. The crude crystals were purified by chromatography on silica gel column, whereby from chloroform-methanol (20:1, v/v) eluate fractions, the title compound (107.4 mg, 69%) was obtained as a pale brown amorphous substance.

$^1$H-NMR (DMSO-$d_6$) δ: 1.07–1.45 (4H, m), 1.72–2.06 (5H, m), 2.06–2.49 (2H, m), 3.04 and 3.06 (total 3H, s, SO$_2$Me), 3.13–4.50 (total 12H, series of m, including 3H, s at δ: 3.89), 7.22 (1H, dd, J=7.6 Hz), 7.28 (1H, dd, J=7.6 Hz), 7.44 (1H, d, J=7.6 Hz), 7.56 (1H, d, J=7.6 Hz), 7.71 (1H, m), 8.15 (1H, d, J=7.6 Hz), 8.31 (1H, s), 9.33 (1H, s, NH), 12.09 (1H, br s, CO$_2$H).

MS(ESI) m/z 648 (M$^+$+1).

Example 129 trans-4-(1-((5-Chloro-2-fluoro-4-((1-methyl-3-indazolylcarbonyl)amino)phenyl)acetyl)-(4S)-methanesulfonyl-(2S)-pyrrolidinylmethoxy)cyclohexanecarboxylic acid (Step 1) Synthesis of methyl trans-4-(1-((5-chloro-2-fluoro-4-((1-methyl-3-indazolylcarbonyl)amino)phenyl)acetyl)-(4S)-methanesulfonyl-(2S)-pyrrolidinylmethoxy)cyclohexanecarboxylate

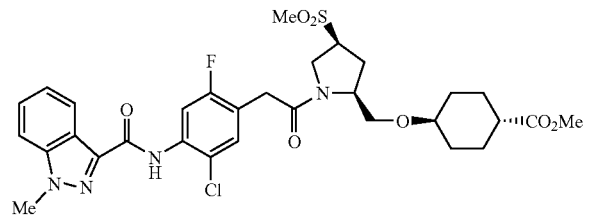

Methyl trans-4-(1-((5-chloro-2-fluoro-4-((1-methyl-3-indazolylcarbonyl)amino)phenyl)acetyl)-(4S)-methylthio-(2S)-pyrrolidinylmethoxy)cyclohexanecarboxylate (194.0 mg, 0.307 mmol) was dissolved in methylene chloride (4.0 ml). Under stirring at 0° C., m-chloroperbenzoic acid (159.1 mg, 0.922 mmol) was added to the resulting solution. Stirring was conducted further at the same temperature for 3 hours. The reaction mixture was diluted with ethyl acetate. The ethyl acetate solution was washed successively with an aqueous solution of sodium sulfite and a saturated aqueous solution of sodium bicarbonate, dried over anhydrous sodium sulfate, and distilled under reduced pressure to remove the solvent. The residue was purified by chromatography on a silica gel column, whereby from chloroform-methanol (20:1, v/v) eluate fractions, methyl trans-4-(1-((5-chloro-2-fluoro-4-((1-methyl-3-indazolylcarbonyl)amino)phenyl)acetyl)-(4S)-methanesulfonyl-(2S)-pyrrolidinylmethoxy)cyclohexanecarboxylate (quantitative yield) was obtained as a white amorphous substance.

$^1$H-NMR (CDCl$_3$) δ: 1.12–1.33 (2H, m), 1.37–1.55 (2H, m), 1.92–2.13 (4H, m), 2.20–2.67 (total 3H, series of m), 2.92 and 2.95 (total 3H, s, SO$_2$Me), 3.25 (1H, m), 3.46–3.92 (total 9H, series of m, including total 3H, s at δ: 3.63 and 3.66), 4.14 (1H, m), 4.18 (3H, s, NMe), 4.39 and 4.55 (total 1H, m), 7.30–7.42 (2H, m), 7.42–7.54 (2H, m), 8.39 (1H, d, J=8.0 Hz), 8.53 (1H, dd, J=12.4 Hz), 9.51 (1H, s).

(Step 2) Synthesis of trans-4-(1-((5-chloro-2-fluoro-4-((1-methyl-3-indazolylcarbonyl)amino)phenyl)acetyl)-(4S)-methanesulfonyl-(2S)-pyrrolidinylmethoxy)cyclohexanecarboxylic acid

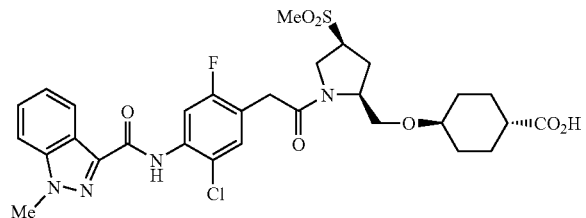

Methyl trans-4-(1-((5-chloro-2-fluoro-4-((1-methyl-3-indazolylcarbonyl)amino)phenyl)acetyl)-(4S)-methanesulfonyl-(2S)-pyrrolidinylmethoxy)cyclohexanecarboxylate (203.8 mg, 0.307 mmol) was dissolved in THF (4.0 ml). To the resulting solution were added 0.25N NaOH (4.0 ml) and methanol (0.5 ml). The resulting mixture was stirred at room temperature for 3.5 hours. The reaction mixture was concentrated under reduced pressure. After the residue was neutralized with 1N HCl, the mixture was diluted with water, followed by extraction with a chloroform-methanol (10:1, v/v) mixture. The extract was dried over anhydrous sodium sulfate and distilled under reduced pressure to remove the solvent. The residue was purified by chromatography on a silica gel column, whereby from chloroform-methanol (10:1, v/v) eluate fractions, the title compound (quantitative yield) was obtained as a white amorphous substance.

IR (ATR) ν2935, 1621, 1525 cm$^{-1}$;

$^1$H-NMR (CDCl$_3$) δ: 1.11–1.34 (2H, m), 1.38–1.57 (2H, m), 1.80–2.14 (5H, m), 2.30 (1H, m), 2.49 and 2.60 (total 1H, m), 2.92 and 2.95 (total 3H, s, SO$_2$Me), 3.25 (1H, m), 3.46–3.92 (6H, m), 4.06–4.60 (total 5H, series of m, including 3H, s at δ: 4.17), 7.29–7.42 (2H, m), 7.42–7.55 (2H, m), 8.38 (1H, d, J=8.0 Hz), 8.53 (1H, dd, J=12.0 Hz), 7.44 (1H, d, J=7.6 Hz), 7.56 (1H, d, J=7.6 Hz), 7.71 (1H, m), 8.15 (1H, d, J=7.6 Hz), 9.51 (1H, s).

MS(ESI) m/z 649 (M$^+$+1);

Anal. Calcd for C$_{30}$H$_{34}$ClFN$_4$O$_7$S 0.5H$_2$O 1.5HCl: C, 50.55; H, 5.16; N, 7.86; Cl, 12.43; F, 2.67; S, 4.50. Found: C, 50.53; H, 4.75; N, 7.62; Cl, 12.43; F, 2.62; S, 4.40.

Example 130 trans-4-(1-((5-Chloro-2-fluoro-4-(1-methyl-3-indolylcarbonylamino)phenyl)acetyl)-(2S)-pyrrolidinylmethoxy)-1-cyclohexanecarboxylic acid (Step 1) Synthesis of methyl trans-4-((2S)-pyrrolidinylmethoxy)-1-cyclohexanecarboxylate

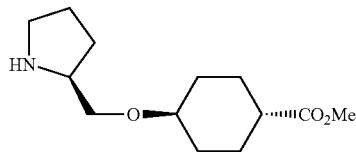

Methyl 4-((2S)-pyrrolidinylmethoxy)benzoate (2.0 g, 7.36 mmol) was dissolved in acetic acid-methanol (1:10, 55 ml). To the resulting solution was added rhodium/alumina (1 g), followed by catalytic hydrogenation at room temperature under 3.8 atm for 15 hours. From the reaction mixture, the catalyst was filtered off. The filtrate was distilled under reduced pressure to remove the solvent, whereby methyl 4-((2S)-pyrrolidinylmethoxy)-1-cyclohexanecarboxylate (1.71 g) was obtained as a colorless oil. The resulting compound was dissolved in acetonitrile-water (1:1, 40 ml). To the resulting solution were added triethylamine (1.5 ml, 10.6 mmol) and di-tert-butyl dicarbonate (1.7 g, 7.80 mmol) and the resulting mixture was stirred at room temperature for 15 hours. The reaction mixture was diluted with ethyl acetate (300 ml). The diluted mixture was washed successively with 1N HCl (100 ml) and saturated brine (100 ml), dried over anhydrous magnesium sulfate, and distilled under reduced pressure to remove the solvent, whereby methyl 4-(1-(tert-butoxycarbonyl)-(2S)-pyrrolidinylmethoxy)-1-cyclohexanecarboxylate (2.26 g) was obtained as a colorless oil. The resulting oil was dissolved in methanol (50 ml). To the resulting solution was added sodium methoxide (1.07 g, 19.9 mmol), followed by heating under reflux for 15 hours. The reaction mixture was cooled and poured in 1N HCl (100 ml), followed by extraction with chloroform (2×100 ml). The extract was dried over anhydrous magnesium sulfate and distilled under reduced pressure to remove the solvent. The oily residue was dissolved in methanol/benzene (1:4, 60 ml) and under stirring at room temperature, (trimethylsilyl)diazomethane (a 2M-hexane solution) was added in portions to the resulting solution until the disappearance of carboxylic acid was confirmed by TLC. The resulting mixture was distilled under reduced pressure to remove the solvent to give a 1:1 cis-trans mixture of methyl 4-((2S)-pyrrolidinylmethoxy)-1-cyclohexanecarboxylate as an oil. The resulting mixture was purified by flash column chromatography (Biotage) whereby from hexane-ethyl acetate (4:1) eluate fractions, the trans-isomer was obtained. The trans isomer was dissolved in trifluoroacetic acid (5 ml) and methylene chloride (5 ml). The mixture was stirred at room temperature for 15 minutes. From the reaction mixture, the solvent was distilled off under reduced pressure. The residue was neutralized with a saturated aqueous solution of sodium bicarbonate, followed by extraction with chloroform (200 ml). The extract was dried over anhydrous magnesium sulfate and distilled under reduced pressure to remove the solvent, whereby methyl trans-4-((2S)-pyrrolidinylmethoxy)-1-cyclohexanecarboxylate (504 mg) was obtained as a pale yellow oil.

$^1$H-NMR (CDCl$_3$) δ: 1.20–1.29 (m, 2H), 1.34–1.51 (m, 3H), 1.66–2.10 (series of m, 7H), 2.23–2.31 (m, 1H), 2.83–2.89 (m, 1H), 2.95–3.01 (m, 1H), 3.20–3.28 (m, 2H), 3.32–3.36 (m, 1H), 3.44–3.48 (m, 1H), 3.66 (s, 3H).

MS (ESI) m/z 242 (M$^+$+1).

(Step 2) Synthesis of methyl trans-4-(1-((5-chloro-2-fluoro-4-(1-methyl-3-indolylcarbonylamino)phenyl)acetyl)-(2S)-pyrrolidinylmethoxy)-1-cyclohexanecarboxylate

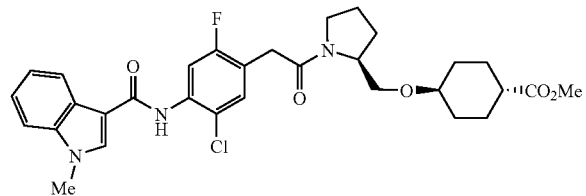

In DMF (10 ml), EDC•HCl (274 mg, 1.43 mmol), DMAP (catalytic amount), and HOBt (catalytic amount) were added to (5-chloro-2-fluoro-4-((1-methyl-3-indolylcarbonyl)amino)phenyl)acetic acid (344 mg, 0.953 mmol) and methyl trans-4-((2S)-pyrrolidinylmethoxy)-1-cyclohexanecarboxylate (230 mg, 0.953 mmol) and the resulting mixture was stirred at room temperature for 15 hours. To the reaction mixture were added ethyl acetate (200 ml) and saturated brine (100 ml). The organic layer thus separated was washed with saturated brine (100 ml), dried over anhydrous magnesium sulfate, and distilled under reduced pressure to remove the solvent. From chloroform-ethyl acetate (4:1) eluate fractions, methyl trans-4-(1-((5-chloro-2-fluoro-4-(1-methyl-3-indolylcarbonylamino)phenyl)acetyl)-(2S)-pyrrolidinylmethoxy)-1-cyclohexanecarboxylate (556 mg, 100%) was obtained as a pale yellow oil.

$^1$H-NMR (CDCl$_3$) δ: 1.12–2.32 (series of m, 13H), 3.15–4.25 (series of m, 14H), 7.32–7.44 (m, 4H), 7.81 (m, 1H), 8.14 (m, 1H), 8.29 (br s, 1H), 8.48–8.52 (m, 1H).

MS (ESI) m/z 584 (M$^+$+1).

(Step 3) Synthesis of trans-4-(1-((5-chloro-2-fluoro-4-(1-methyl-3-indolylcarbonylamino)phenyl)acetyl)-(2S)-pyrrolidinylmethoxy)-1-cyclohexanecarboxylic acid

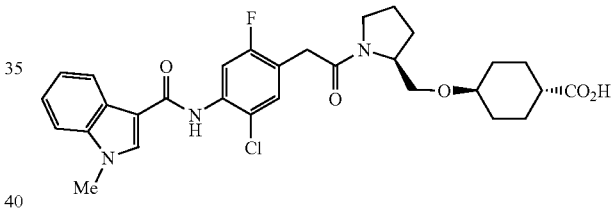

To methyl 4-(1-((5-chloro-2-fluoro-4-(1-methyl-3-indolylcarbonylamino)phenyl)acetyl)-(2S)-pyrrolidinyl methoxy)-1-cyclohexanecarboxylate (556 mg, 0.953 mmol) were added THF (10 ml) and 0.25N NaOH (10 ml, 2.50 mmol). The resulting mixture was stirred at room temperature for 15 hours. The reaction mixture was poured in 1N HCl (100 ml), followed by extraction with chloroform-methanol (5:1, 2×100 ml). The extract was dried over anhydrous magnesium sulfate and distilled under reduced pressure to remove the solvent. To the residue were added chloroform and hexane. The crystals thus precipitated were collected by filtration under reduced pressure and dried under reduced pressure to give the title compound (400 mg, 74%) as a colorless solid.

$^1$H-NMR (DMSO-d$_6$) δ: 1.13–2.34 (series of m, 13H), 3.16–4.24 (series of m, total 11H), 7.32–7.44 (m, 4H), 7.81 (s, 1H), 8.11–8.14 (m, 1H), 8.29 (s, 1H), 8.46–8.51 (m, 1H).

MS (FAB) m/z 570 (M$^+$+1);

Anal. Calcd for $C_{30}H_{33}ClN_3O_5$ 0.25 $H_2O$: C, 62.71; H, 5.88; N, 6.96. Found: C, 62.55; H, 5.99; N, 6.96.

Example 131 trans-4-(1-((2-(6-Fluoro-1-methyl-3-indolyl)-6-benzoxazolyl)acetyl)-(2S)-pyrrolidinylmethoxy)-1-cyclohexanecarboxylic acid (Step 1) Synthesis of methyl trans-4-(1-((2-(6-fluoro-1-methyl-3-indolyl)-6-benzoxazolyl)acetyl)-(2S)-pyrrolidinylmethoxy)-1-cyclohexanecarboxylate

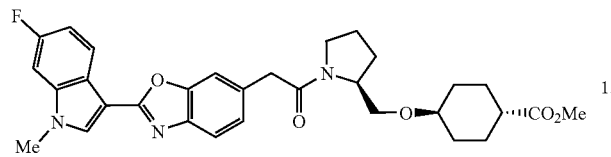

In DMF (10 ml), EDC HCl (177 mg, 0.926 mmol), DMAP (catalytic amount), and HOBt (catalytic amount) were added to (2-(6-fluoro-1-methyl-3-indolylcarbonylamino)-6-benzoxazolyl)acetic acid (200 mg, 0.617 mmol) and methyl trans-4-((2S)-pyrrolidinylmethoxy)-1-cyclohexanecarboxylate (149 mg, 0.617 mmol) and the resulting mixture was stirred at room temperature for 15 hours. To the reaction mixture were added ethyl acetate (200 ml) and saturated brine (100 ml). The organic layer thus separated was washed with saturated brine (100 ml), dried over anhydrous magnesium sulfate, and distilled under reduced pressure to remove the solvent. The residue was purified by chromatography on a silica gel column, whereby from chloroform-methanol (10:1) eluate fractions, methyl trans-4-(1-((2-(6-fluoro-1-methyl-3-indolyl)-6-benzoxazolyl)acetyl)-(2S)-pyrrolidinylmethoxy)-1-cyclohexanecarboxylate (338 mg, 100%) was obtained as a pale yellow oil.

$^1$H-NMR (CDCl$_3$) δ: 1.11–1.48 (series of m, 4H), 1.86–2.06 (m, 8H), 2.18–2.35 (m, 1H) 3.16–4.27 (series of m, 14H), 7.05–7.24 (m, 3H), 7.50–7.52 (m, 1H), 7.62–7.67 (m, 1H), 7.90 (s, 1H), 8.38 (dd, J=8.8,5.4 Hz, 1H).

MS (ESI) m/z 549 (M$^+$+1).

(Step 2) Synthesis of trans-4-(1-((2-(6-fluoro-1-methyl-3-indolyl)-6-benzoxazolyl)acetyl)-(2S)-pyrrolidinylmethoxy)-1-cyclohexanecarboxylic acid

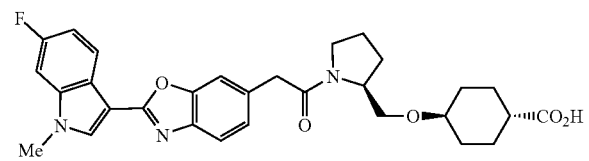

To methyl trans-4-(1-((2-(6-fluoro-1-methyl-3-indolylcarbonylamino)-6-benzoxazolyl)acetyl)-(2S)-pyrrolidinylmethoxy)-1-cyclohexanecarboxylate (338 mg, 0.617 mmol) were added THF (10 ml) and 0.25N NaOH (10 ml, 2.50 mmol). The resulting mixture was stirred at room temperature for 15 hours. The reaction mixture was poured in 1N HCl (100 ml), followed by extraction with chloroform-methanol (5:1, 2×100 ml). The extract was dried over anhydrous magnesium sulfate and distilled under reduced pressure to remove the solvent. The residue was purified by chromatography on a silica gel column, whereby from chloroform-methanol (10:1) eluate fractions, the title compound (202 mg, 49%) was obtained as a colorless amorphous substance.

$^1$H-NMR (DMSO) δ: 1.07–1.35 (m, 4H), 1.83–1.93 (m, 8H), 2.13 (m, 1H), 3.12–4.21 (series of m, 11H), 7.14–7.22 (m, 2H), 7.51–7.54 (m, 2H), 7.63 (d, J=8.1 Hz, 1H), 8.28–8.33 (m, 2H).

MS (FAB) m/z 534 (M$^+$+1);

Anal. Calcd for C$_{30}$H$_{32}$N$_3$O$_5$ 0.5 H$_2$O: C, 66.41; H, 6.13; N, 7.74. Found: C, 66.60; H, 6.23; N, 7.46.

Example 132 trans-4-(4-(5-Chloro-2-fluoro-4-((1-methyl-1H-3-indolylcarbonyl)amino)phenylacetyl)-(3S)-morpholinylmethoxy)cyclohexanecarboxylic acid (Step 1) Synthesis of methyl 4-(4-N-benzyloxycarbonyl-(3S)-morpholinylmethoxy)benzoate

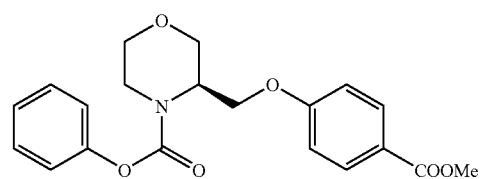

In THF (15 ml) were dissolved 4-N-benzyloxycarbonyl-(3S)-morpholinemethanol (1.42 g, 5.65 mmol), methyl 4-hydroxybenzoate (860 mg, 5.65 mmol), and triphenylphosphine (1.93 g, 7.35 mmol). To the resulting solution was added DIAD (1.44 ml, 7.35 mmol). The resulting mixture was heated under reflux for 18 hours. The reaction mixture was cooled to room temperature and distilled under reduced pressure to remove the solvent. The residue was purified by chromatography on a silica gel column (middle pressure chromatography system: YAMAZEN YFLC-5404-FC, chloroform, φ 37 mm×300 mm, 12 ml/min) to give methyl 4-(4-N-benzyloxycarbonyl-(3S)-morpholinylmethoxy)benzoate (2.18 g, 100%) as a colorless oil.

$^1$H-NMR (CDCl$_3$) δ: 3.20–4.40 (m, 9H), 3.88 (d, J=7.8 Hz, 3H), 4.96 (m, 2H), 6.88 (d, J=8.8 Hz, 2H), 7.54 (m, 5H), 7.90 (d, J=8.8 Hz, 2H).

MS (ESI) m/z, 386 (M$^+$+1).

(Step 2) Synthesis of methyl 4-(4-tert-butoxycarbonyl-(3S)-morpholinylmethoxy)cyclohexanecarboxylate

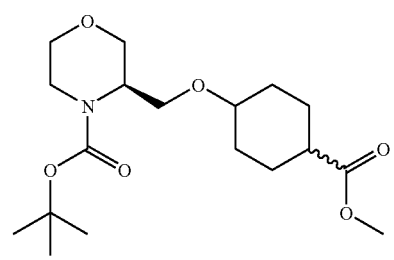

In methanol/trifluoroacetic acid (40 ml, 1:1) was dissolved methyl 4-(4-N-benzyloxycarbonyl-(3S)-morpholinylmethoxy)benzoate (2.18 g, 5.65 mmol). To the resulting solution was added 50% rhodium-alumina/carbon (1 g), followed by catalytic hydrogenation at room temperature for 48 hours under hydrogen of 5 atm. From the reaction mixture, the catalyst was filtered off. The filtrate was distilled under reduced pressure to remove the solvent. The residue was dissolved in THF (20 ml). Triethylamine (3.9 ml, 28.3 mmol) and di-tert-butyl dicarbonate (1.85 g, 8.5 mmol) were added and the resulting mixture was stirred for 18 hours at room temperature. From the reaction mixture, the solvent was distilled off under reduced pressure. Water was added to the residue and the mixture was extracted with ethyl acetate. The extract was washed with saturated brine, dried over anhydrous magnesium sulfate, and distilled under reduced pressure to remove the solvent. The residue was purified by chromatography on a silica gel column (middle pressure chromatography system: YAMAZEN YFLC-5404-FC) to give methyl 4-(4-tert-butoxycarbonyl-(3S)-morpholinylmethoxy)cyclohexanecarboxylate as a thick sticky liquid.

MS (ESI) m/z 252 (M$^+$+1).

(Step 3) Synthesis of methyl trans-4-(4-tert-butoxycarbonyl-(3S)-morpholinylmethoxy)cyclohexanecarboxylate

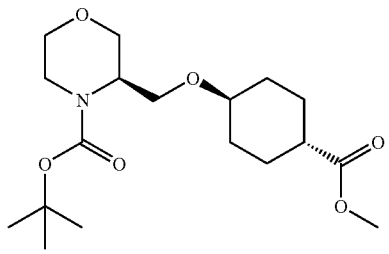

The cis- and trans-mixture of methyl 4-(4-tert-butoxycarbonyl-(3S)-morpholinylmethoxy)cyclohexanecarboxylate (450 mg, 1.21 mmol) prepared in the above-described step was separated by silica gel column chromatography (Biotage, flush chromatography No.2, 195-s, toluene/ethyl acetate, 9:1) to give methyl trans-4-(4-tert-butoxycarbonyl-(3S)-morpholinylmethoxy)cyclohexanecarboxylate (45 mg, 10%) as a colorless oil.

$^1$H-NMR (CDCl$_3$) δ: 1.28 (m, 2H), 1.42 (m, 2H), 1.48 (s, 9H), 2.05 (m, 4H), 2.28 (m, 1H), 3.02 (m, 1H), 3.25 (m, 1H), 3.48 (m, 4H), 3.65 (s, 3H), 3.70 (t, J=9.1 Hz, 1H), 3.83 (d, J=8.3 Hz, 1H), 3.96 (d, J=11.3 Hz, 2H).

MS (ESI) m/z 357 (M$^+$+1).

(Step 4) Synthesis of methyl trans-4-((3S)-morpholinylmethoxy)cyclohexanecarboxylate

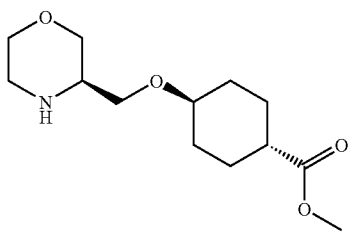

Methyl trans-4-(4-tert-butoxycarbonyl-(3S)-morpholinylmethoxy)cyclohexanecarboxylate (45 mg, 0.13 mmol) was dissolved in methylene chloride/trifluoroacetic acid (15 ml, 2:1). The resulting solution was stirred for 2 hours at room temperature. From the reaction mixture, the solvent was distilled off under reduced pressure. The residue was neutralized with a saturated aqueous solution of sodium bicarbonate. After extraction with ethyl acetate, the extract was washed with saturated brine, dried over anhydrous magnesium sulfate and distilled under reduced pressure to remove the solvent to give methyl trans-4-((3S)-morpholinylmethoxy)cyclohexanecarboxylate (29 mg, 91%) as a colorless oil.

$^1$H-NMR (DMSO) δ: 1.20 (m, 2H), 1.48 (AB type q, J=10.5 Hz, 2H), 2.05 (m, 4H), 2.88 (m, 1H), 2.95 (m, 1H), 3.00 (m, 1H), 3.20 (m, 1H), 3.25 (m, 2H), 3.40 (dd, J=4.0,8.8 Hz, 1H), 3.53 (dt, J=3.0,10.5 Hz, 1H), 3.66 (s, 3H), 3.77 (dt, J=2.5,8.8 Hz, 2H).

MS (ESI) m/z 258 (M+1)$^+$.

(Step 5) Synthesis of trans-4-(4-(5-chloro-2-fluoro-4-((1-methyl-1H-3-indolylcarbonyl)amino)phenylacetyl)-(3S)-morpholinylmethoxy)cyclohexanecarboxylic acid

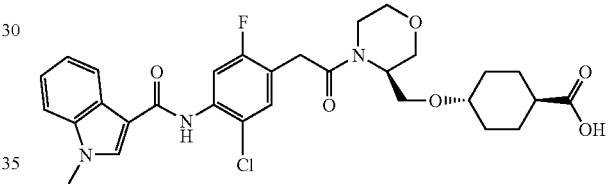

In DMF (2.5 ml), methyl trans-4-((3S)-morpholinylmethoxy)cyclohexanecarboxylate (29 mg, 0.11 mmol), (5-chloro-2-fluoro-4-((1-methyl-3-indolylcarbonyl)amino)phenyl)acetic acid (41 mg, 0.1 mmol), EDC HCl (33 mg, 0.17 mmol), HOBt (29 mg, 0.21 mmol), and DMAP (catalytic amount) were stirred for 18 hours at room temperature. The resulting mixture was diluted with ethyl acetate (50 ml). The diluted mixture was washed with 1N HCl and saturated brine, dried over anhydrous magnesium sulfate and distilled under reduced pressure. To the residue were added THF (6 ml) and 0.25M NaOH (0.68 ml, 0.17 mmol) and the mixture was stirred for 18 hours at room temperature. The reaction mixture was distilled under reduced pressure to remove the solvent. To the residue was added 1N HCl. The crystals thus precipitated were collected by filtration under reduced pressure, washed with water and dried under reduced pressure to give the title compound (57 mg, 86%) as a colorless solid.

$^1$H-NMR (DMSO-d$_6$) δ 1.20 (m, 3H), 1.35 (m, 3H), 1.92 (m, 3H), 2.18 (m, 1H), 2.90 (m, 1H), 3.52 (m, 2H), 3.50–3.85 (m, 7H), 3.88 (s, 3H), 4.05 and 4.30 (2m, total, 2H), 7.22 (t, J=7.0 Hz, 1H), 7.28 (t, J=7.5 Hz, 1H), 7.40 (dd, J=7.8 Hz, 19.1 Hz, 1H), 7.55 (d, J=8.3 Hz, 1H), 7.70 (dd, J=5.8 Hz, 10.7 Hz, 1H), 8.15 (d, J=8.6 Hz, 1H), 8.31 (s, 1H), 9.31 (s, 1H).

MS (ESI) m/z 587 (M+1)$^+$;

Anal. Calcd for $C_{30}H_{33}ClFN_3O_6$: C, 61.48; H, 5.68; N, 7.17. Found: C, 61.06; H, 5.73; N, 6.88.

Example 133 trans-4-(1-(5-Chloro-2-fluoro-4-((1-methyl-1H-3-indolylcarbonyl)amino)phenylacetyl)-(4S)-methyl-(2S)-pyrrolidinylmethoxy)cyclohexanecarboxylic acid (Step 1) Synthesis of (2R,5S)-2-phenyl-3-oxa-1-azabicyclo(3.3.0)octan-8-one

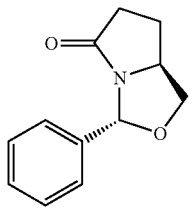

In toluene (500 ml), (5S)-hydroxymethylpyrrolidin-2-one (72 g, 0.63 mol), benzaldehyde (79.6 g, 0.75 mol) and p-toluenesulfonic acid (1.6 g, 9.4 mmol) were heated under reflux for 48 hours by using a Dean-Stark water separator. After the reaction mixture was cooled to room temperature, water (300 ml) was added thereto, followed by extraction with ethyl acetate. The extract was washed with a saturated aqueous solution of sodium bicarbonate and saturated brine, dried over anhydrous magnesium sulfate and distilled under reduced pressure to remove the solvent. The residue was distilled under reduced pressure to give (2R,5S)-2-phenyl-3-oxa-1-azabicyclo(3.3.0)octan-8-one (71 g, 56%) as a pale yellow oil.

$^1$H-NMR (CDCl$_3$) δ: 1.95 (m, 1H), 2.30 (m, 1H), 2.58 (m, 1H), 2.80 (m, 1H), 3.48 (t, J=8.0 Hz, 1H), 4.15 (m, 1H), 4.24 (m, 1H), 6.32 (s, 1H), 7.32 (m, 3H), 7.40 (m, 2H).

MS (ESI) m/z 204 (M+1)$^+$.

(Step 2) Synthesis of (2R,5S,7S)-7-methyl-2-phenyl-3-oxa-1-azabicyclo(3.3.0)octan-8-one

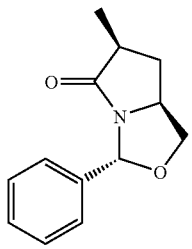

To a solution of (2R,5S)-2-phenyl-3-oxa-1-azabicyclo(3.3.0)octan-8-one (5.08 g, 25 mmol) in THF (30 ml), lithium diisopropylamide (a 2.0M solution in THF, 13.1 ml, 26.3 mmol) was added dropwise at −78° C. under stirring. After the reaction mixture was stirred at the same temperature for 15 minutes, methyl iodide (7.78 ml, 125 mmol) was added thereto and stirring was conducted further for 30 minutes at −40° C. The reaction mixture was poured in an ice-saturated aqueous solution of ammonium chloride, followed by extraction with ethyl acetate. The extract was washed with saturated brine, dried over anhydrous magnesium sulfate and distilled under reduced pressure to remove the solvent. The residue was purified by silica gel column chromatography (middle pressure Yamazen, linear gradient of n-hexane/ethyl acetate form 4:1 to 1:1, 30 ml/min, φ 50 mm×300 mm, range 0.32) to give (2R,5S,7S)-7-methyl-2-phenyl-3-oxa-1-azabicyclo(3.3.0)octan-8-one (3.8 g, 70%) as a colorless oil.

$^1$H-NMR (CDCl$_3$) δ: 1.23 (d, J=7.3 Hz, 3H), 1.54 (m, 1H), 2.62 (m, 1H), 2.95 (m, 1H, 4-H), 3.52 (t, J=7.5 Hz, 1H), 4.09 (t, J=7.5 Hz, 1H, 2-H), 4.22 (dd, J=6.5,8.0 Hz), 6.33 (s, 1H), 7.32 (m, 3H), 7.46 (m, 2H).

MS (ESI) m/z 218 (M+1)$^+$.

(Step 3) Synthesis of 1-N-benzyloxycarbonyl-(4S)-methyl-(2S)-pyrrolidinylmethanol

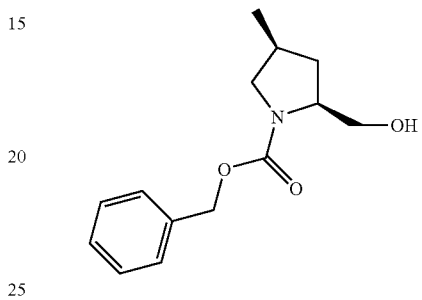

Lithium aluminum hydride (1.05 g, 26.2 mmol) was suspended in THF (10 ml). To the resulting suspension, a solution of (2R,5S,7S)-7-methyl-2-phenyl-3-oxa-1-azabicyclo(3.3.0)octan-8-one (3.79 g, 17.5 mmol) in THF (30 ml) was added dropwise under stirring at 60° C. After completion of the dropwise addition, the reaction mixture was heated under reflux for 1 hour. The reaction mixture was cooled to room temperature and then, poured in sodium thiosulfate (6.5 g, 26.2 mmol) and ice (500 cm$^3$), followed by extraction with ethyl acetate (500 ml). The extract was washed with saturated brine, dried over anhydrous magnesium sulfate and distilled under reduced pressure to remove the solvent. Ethanol/acetic acid (45 ml, 1:2) and 10% palladium carbon (400 mg) were added to the residue and the resulting mixture was subjected to catalytic reduction for 24 hours under a hydrogen gas of 3.5 atm. From the reaction mixture, the catalyst was filtered off. The filtrate was distilled under reduced pressure to remove the solvent. Toluene was added to the residue to azeotropically remove water. To the residue were added THF/water (4:1, 35 ml) and potassium carbonate (2.54 g, 18.4 mmol). Benzyloxycarbonyl chloride (a 30–35% toluene solution, 10.2 ml, 17.9 mmol) was added dropwise while stirring the resulting mixture at 0° C. After completion of the dropwise addition, the reaction mixture was stirred further for 30 minutes at the same temperature. The reaction mixture was poured in a cooled solution of ethyl acetate and a saturated aqueous solution of ammonium chloride and the mixed solution was extracted with ethyl acetate. The extract was washed with saturated brine, dried over anhydrous magnesium sulfate and distilled under reduced pressure to remove the solvent. The residue was purified by silica gel column chromatography (middle pressure Yamazen, linear gradient of n-hexane/ethyl acetate form 4:1 to 7:3, 30 ml/min, φ 50 mm×150 mm, range 0.32) to give 1-N-benzyloxycarbonyl-(4S)-methyl-(2S)-pyrrolidinylmethanol (2.46 g, 56%) as a colorless oil.

$^1$H-NMR (CDCl$_3$) δ: 1.01 (d, J=6.1 Hz, 3H), 1.12 (AB type q, J=12.5 Hz, 4-H), 1.70 (br, 1H), 2.18 (m, 2H), 2.82 (t, J=10.5 Hz), 3.63 (dd, J=7.4 Hz,11.8 Hz, 1H), 3.72 (m, 1H), 3.79 (t, J=8.5 Hz), 3.98 (m, 1H), 5.14 (s, 2H), 7.36 (m, 5H).

MS (ESI) m/z 250 (M+1)$^+$.

(Step 4) Synthesis of methyl 4-(1-N-benzyloxycarbonyl-(4S)-methyl-(2S)-pyrrolidinylmethoxy)benzoate

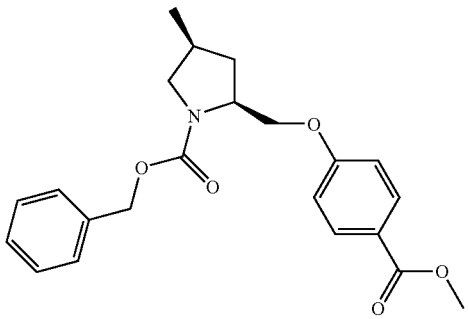

In methylene chloride (40 ml) were dissolved 1-N-benzyloxycarbonyl-(4S)-methyl-(2S)-pyrrolidinylmethanol (2.06 g, 8.26 mmol) and triethylamine (3.45 ml, 24.8 mmol). Under stirring at 0° C., methanesulfonyl chloride (1.15 ml, 14.9 mmol) was added dropwise to the resulting solution. The reaction mixture was diluted with ethyl acetate and the diluted mixture was poured in 1M HCl, followed by extraction with ethyl acetate. The extract was washed with saturated brine, dried over anhydrous magnesium sulfate and distilled under reduced pressure to remove the solvent. To the residue were added DMF (40 ml), potassium carbonate (1.71 g, 12.4 mmol) and methyl 4-hydroxybanzoate (3.77 g, 24.8 mmol). The resulting mixture was stirred at 100° C. for 2 hours. The reaction mixture was cooled to room temperature, and ether and water were added thereto, followed by extraction with ether. The extract was washed with 1M NaOH (3 times) and saturated brine, dried over anhydrous magnesium sulfate and distilled under reduced pressure to remove the solvent. The residue was purified by silica gel column chromatography, whereby from n-hexane/ethyl acetate (9:1 to 7:3) eluate fractions, 4-(1-N-benzyloxycarbonyl-(4S)-methyl-(2S)-pyrrolidinylmethoxy)benzoate (2.27 g, 72%) was obtained as a colorless oil.

$^1$H-NMR (CDCl$_3$) δ: 1.08 (m, 3H), 1.61 (m, 1H), 2.20 (m, 1H), 2.31 (m, 1H), 2.88 (t, J=10.2 Hz, 1H), 3.80–4.00 (m, 2H), 3.89 (s, 3H), 4.20 (m, 2H), 5.12 (m, 2H), 6.78 and 6.92 (d, J=8.1 Hz, total 2H), 7.32 (m, 5H), 7.90 and 7.92 (d, J=7.8 Hz, total 2H).

MS (ESI) m/z 384 (M+1)$^+$.

(Step 5) Synthesis of methyl trans-4-(1-N-tert-butoxycarbonyl-(4S)-methyl-(2S)-pyrrolidinylmethoxy)cyclohexanecarboxylate

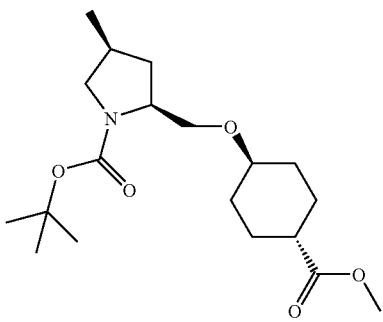

To methyl 4-(1-N-benzyloxycarbonyl-(4S)-methyl-(2S)-pyrrolidinylmethoxy)benzoate (2.27 g, 5.92 mmol) and 5% palladium carbon (389 mg) was added methanol/acetic acid (30 ml, 10:1) and the resulting mixture was subjected to catalytic reduction at room temperature under a hydrogen gas of 2 atm for 18 hours. From the reaction mixture, the catalyst was filtered off. To the filtrate were added acetic acid (10 ml) and rhodium-alumina (700 mg) and catalytic hydrogenation was effected at room temperature under a hydrogen gas of 4 atm for 24 hours. From the reaction mixture, the catalyst was filtered off. The filtrate was distilled under reduced pressure to remove the solvent. To the residue were added methylene chloride (30 ml), triethylamine (2.48 ml, 17.8 mmol) and di-tert-butyl dicarbonate (1.94 g, 8.89 mmol). The resulting mixture was stirred at room temperature for 3 hours. To the reaction mixture was added 15% citric acid, followed by extraction with chloroform. The extract was washed with saturated brine, dried over anhydrous magnesium sulfate and distilled under reduced pressure to remove the solvent. The residue was purified by silica gel column chromatography (middle pressure Yamazen, linear gradient of n-hexane/ethyl acetate form 9:1 to 1:1). To the purified product were added ethanol (50 ml) and sodium ethoxide (3.02 ml, 8.9 mmol) and the mixture was heated under reflux for 18 hours. The reaction mixture was basified with 1M NaOH. The reaction mixture was heated under reflux further for 3 hours. After cooling, the reaction mixture was distilled under reduced pressure to remove the solvent. To the residue was added 15% citric acid, followed by extraction with a chloroform/methanol mixture. The extract was dried over sodium sulfate and distilled under reduced pressure to remove the solvent. To the residue were added THF/DMF (30 ml, 2:1), ethyl iodide (2.4 ml, 29.5 mmol) and DBU (1.33 ml, 8.8 mmol) and the resulting mixture was stirred for 18 hours. To the reaction mixture was added 15% citric acid, followed by extraction with ethyl acetate. The extract was washed with saturated brine, dried over anhydrous magnesium sulfate, and distilled under reduced pressure to remove the solvent. The residue was purified by silica gel column chromatography (Biotage, KP-SIL, 32–63 m, 1000 g, n-hexane/ethyl acetate 9:1) to give methyl trans-4-(1-N-tert-butoxycarbonyl-(4S)-methyl-(2S)-pyrrolidinylmethoxy)cyclohexanecarboxylate (404 mg, 19%) as colorless oil.

$^1$H-NMR (CDCl$_3$) δ: 1.03 (d, J=6.6 Hz, 3H), 1.25 (t, J=7.3 Hz, 3H), 1.25–1.70 (m, 6H), 1.46 (s, 9H), 1.82 (m, 3H), 2.10 (m, 1H), 2.20 (m, 1H), 2.32 (m, 1H), 2.70 (t, J=10.0 Hz, 1H), 3.35–3.90 (m, 4H), 3.62 (dd, J=3.0,9.0 Hz, 1H), 4.12 (q, J=7.3 Hz, 2H).

MS (ESI) m/z 392 (M+Na)$^+$.

(Step 6) Synthesis of trans-4-(1-(5-chloro-2-fluoro-4-((1-methyl-1H-3-indolylcarbonyl)amino)phenylacetyl)-(4S)-methyl-(2S)-pyrrolidinylmethoxy)cyclohexanecarboxylic acid

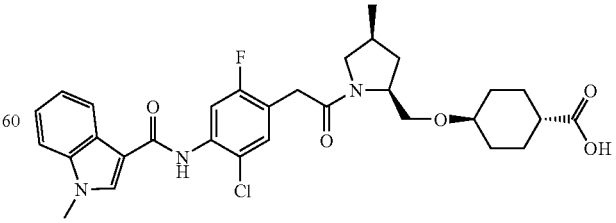

To methyl trans-4-(1-N-tert-butoxycarbonyl-(4S)-methyl-(2S)-pyrrolidinylmethoxy)cyclohexanecarboxylate (147 mg, 0.397 mmol) were added methylene chloride (15 ml) and trifluoroacetic acid (15 ml). The resulting mixture was stirred at room temperature for 1 hour. From the reaction mixture, the solvent was distilled off under reduced pressure. To the residue was added chloroform/a saturated aqueous solution of sodium bicarbonate, followed by extraction with chloroform. The extract was dried over anhydrous sodium sulfate and distilled under reduced pressure to remove the solvent. The residue was dissolved in DMF (5 ml) and (5-chloro-2-fluoro-4-((1-methyl-1H-3-indolylcarbonyl)amino)phenyl)acetic acid (143 mg, 0.397 mmol), HOBt (102 mg, 0.75 mmol), DMAP (catalytic amount) and EDC•HCl salt (114 mg, 0.6 mmol) were added to the solution. The mixture was stirred at room temperature for 18 hours. The reaction mixture was poured in 1M HCl, followed by extraction with ethyl acetate. The extract was washed with saturated brine and dried over anhydrous sodium sulfate and distilled under reduced pressure to remove the solvent. The residue was purified by column chromatography using silica gel (middle pressure Yamazen, chloroform, 10 ml/min, φ 15 mm×300 mm). To the purified product were added THF (6 ml) and 0.25M NaOH (3.6 ml, 0.9 mmol) and the mixture was stirred for 18 hours at room temperature. The reaction mixture was poured in water. The solution was acidified with 1M HCl. The crystals thus precipitated were collected by filtration under reduced pressure, washed with water and dried under reduced pressure to give the title compound (110 mg, 48%) as a colorless solid.

$^1$H-NMR (DMSO-d$_6$) δ: 1.12 (d, J=5.5 Hz, 3H), 1.10–1.50 (m, 6H), 1.85–2.15 (m, 6H), 2.60 (m, 1H), 2.90 (t, J=10.5 Hz, 1H), 3.12 (m, 1H), 3.50–4.20 (m, 5H), 2.90 (s, 3H), 7.21 (t, J=7.5 Hz, 1H), 7.29 (t, J=7.5 Hz, 1H), 7.42 (d, J=7.5 Hz, 1H), 7.57 (d, J=8.1 Hz, 1H), 7.70 (m, 1H), 8.16 (d, J=7.8 Hz, 1H), 8.32 (s, 1H).

MS (ESI) m/z 585 (M+1)$^+$;

Anal. Calcd for C$_{31}$H$_{35}$ClFN$_3$O$_5$.0.5 H$_2$O: C, 62.78; H, 6.12; N, 7.08. Found: C, 62.58; H, 5.98; N, 7.35.

Example 134 trans-4-(1-(7-Fluoro-2-(5-fluoro-2-methylphenylamino)-6-benzoxazolyl)acetyl)-(4S)-methyl-(2S)-pyrrolidinylmethoxy)cyclohexanecarboxylic acid (Step 1) Synthesis of trans4-(1-(7-fluoro-2-(5-fluoro-2-methylphenylamino)-6-benzoxazolyl)acetyl)-(4S)-methyl-(2S)-pyrrolidinylmethoxy)cyclohexanecarboxylic acid

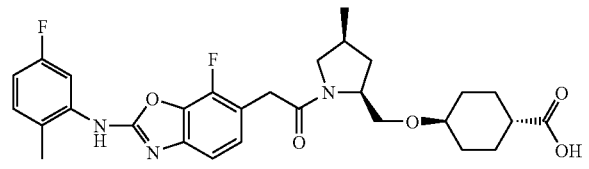

To methyl trans-4-(1-N-tert-butoxycarbonyl-(4S)-methyl-(2S)-pyrrolidinylmethoxy)cyclohexanecarboxylate (147 mg, 0.397 mmol) were added methylene chloride (15 ml) and trifluoroacetic acid (15 ml). The resulting mixture was stirred at room temperature for 1 hour. The reaction mixture was distilled under reduced pressure to remove the solvent. To the residue was added chloroform/a saturated aqueous solution of sodium bicarbonate, followed by extraction with chloroform. The extract was dried over anhydrous sodium sulfate and the reaction mixture was distilled under reduced pressure to remove the solvent. The residue was dissolved in DMF (5 ml) and to the resulting solution, 7-fluoro-2-(5-fluoro-2-methylphenylamino)-6-benzoxazolyl)acetic acid (126 mg, 0.397 mmol), HOBt (102 mg, 0.75 mmol), DMAP (catalytic amount) and EDC•HCl salt (114 mg, 0.6 mmol) were added. The resulting mixture was stirred at room temperature for 18 hours. The reaction mixture was poured in 1M HCl, followed by extraction with ethyl acetate. The extract was washed with saturated brine, dried over anhydrous magnesium sulfate and distilled under reduced pressure to remove the solvent. The residue was purified by silica gel column chromatography (middle pressure Yamazen, chloroform, 10 ml/min, φ 15 mm×300 mm). To the purified product were added THF (6 ml) and 0.25M NaOH (3.6 ml, 0.9 mmol) and the mixture was stirred for 18 hours at room temperature. The reaction mixture was poured in water. The solution was acidified with 1M HCl. The crystals thus precipitated were collected by filtration under reduced pressure, washed with water and dried under reduced pressure to give the title compound (129 mg, 60%) as a colorless solid.

$^1$H-NMR (DMSO-d$_6$) δ: 1.01 (d, J=6.0 Hz, 3H), 1.05–1.50 (m, 6H), 1.80–2.20 (m, 6H), 2.30 (s, 3H), 2.50 (m, 1H), 2.95 (t, J=9.8 Hz, 1H), 3.12 (m, 1H), 3.40–3.60 (m, 3H), 5.71 (s, 1H), 5.80–4.00 (m, 1H), 6.90 (dt, J=2.5,8.3 Hz, 1H), 7.06 (d, J=7.8 Hz, 1H), 7.20 (d, J=8.0 Hz, 1H), 7.26 (t, J=7.5 Hz, 1H), 7.92 (dd, J=2.5,11.3 Hz, 1H).

MS (ESI) m/z 542 (M+1)$^+$;

Anal. Calcd for C$_{29}$H$_{33}$F$_2$N$_3$O$_5$.0.5 H$_2$O: C, 63.26; H, 6.32; N, 7.63. Found: C, 63.34; H, 6.17; N, 7.64.

Example 135 trans-4-(1-(5-Chloro-2-fluoro-4-((1-methyl-1H-3-indazolylcarbonyl)amino)phenylacetyl)-(4S)-methyl-(2S)-pyrrolidinylmethoxy)cyclohexanecarboxylic acid (Step 1) Synthesis of trans-4-(1-(5-chloro-2-fluoro-4-((1-methyl-1H-3-indazolylcarbonyl)amino)phenylacetyl)-(4S)-methyl-(2S)-pyrrolidinylmethoxy)cyclohexanecarboxylic acid

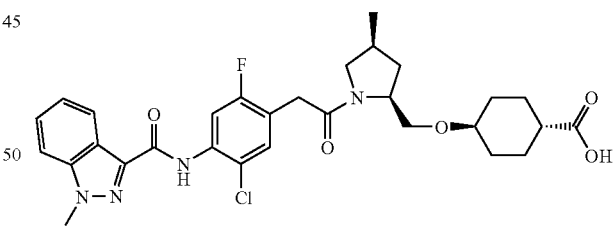

To methyl trans-4-(1-N-tert-butoxycarbonyl-(4S)-methyl-(2S)-pyrrolidinylmethoxy)cyclohexanecarboxylate (147 mg, 0.397 mmol) were added methylene chloride (15 ml) and trifluoroacetic acid (15 ml). The resulting mixture was stirred at room temperature for 1 hour. The reaction mixture was distilled under reduced pressure to remove the solvent. To the residue was added chloroform/a saturated aqueous solution of sodium bicarbonate, followed by extraction with chloroform. The extract was dried over anhydrous sodium sulfate and distilled under reduced pressure to remove the solvent. The residue was dissolved in DMF (5 ml). To the resulting solution were added (2-fluoro-5-chloro-4-((1-methyl-1H-3-indazolylcarbonyl)amino)phenyl)acetic acid (144 mg, 0.397 mmol), HOBt (102 mg, 0.75 mmol), DMAP (catalytic amount) and EDC•HCl (114 mg, 0.6 mmol) and the mixture was stirred at room temperature for 18 hours. The reaction mixture was poured in 1M HCl, followed by extraction with ethyl acetate. The extract was washed with saturated brine, dried over anhydrous magnesium sulfate, and distilled under reduced pressure to remove the solvent. The residue was purified by silica gel column chromatography (middle pressure Yamazen, chloroform, 10 ml/min, φ 15 mm×300 mm). To the purified product were added THF (6 ml) and 0.25M NaOH (3.6 ml, 0.9 mmol) and mixture was stirred for 18 hours at room temperature. The reaction mixture was poured in water and the solution was acidified with 1M HCl. The crystals thus precipitated were collected by filtration under reduced pressure, washed with water and dried under reduced pressure to give the title compound (89 mg, 38%) as a colorless solid.

$^1$H-NMR (DMSO-d$_6$) δ: 1.03 (d, J=6.1 Hz, 3H), 1.10–1.50 (m, 6H), 1.83–2.20 (m, 6H), 2.50 (m, 1H), 2.90 (t, J=9.5 Hz, 1H), 3.13 (m, 1H), 3.50–4.05 (m, 5H), 4.21 (s, 3H), 7.39 (t, J=7.5 Hz, 1H), 7.48 (d, J=7.5 Hz, 1H), 7.54 (t, J=7.5 Hz, 1H), 7.82 (d, J=8.6 Hz, 1H), 8.08 (d, J=7.5 Hz, 1H), 8.21 (d, J=8.3 Hz, 1H).

MS (ESI) m/z 586 (M+1)$^+$;

Anal. Calcd for C$_{30}$H$_{34}$ClFN$_4$O$_5$.0.75 H$_2$O: C, 60.20; H, 5.98; N, 9.36. Found: C, 60.49; H, 5.99; N, 9.10.

Example 136 trans-4-(1-((5-chloro-2-fluoro-4-((1-methyl-3-indolyl)carbonylamino)phenyl)acetyl)-(5S)-methyl-(2S)-pyrrolidinylmethoxy)cyclohexanecarboxylic acid (Step 1) Synthesis of benzyl (2S)-N-tert-butoxycarbonylamino-5-oxohexanoate

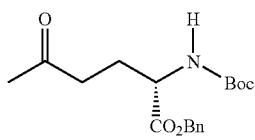

Benzyl N-tert-butoxycarbonyl-(2S)-pyroglutamate (20.5 g, 64.2 mmol) was dissolved in THF (500 ml). Methyl lithium (a 1.04M ether solution, 61.7 ml, 64.2 mmol) was added dropwise at −78° C. The temperature of the reaction mixture was caused to rise back gradually to room temperature under stirring, and the resulting mixture was stirred for 18 hours. A saturated aqueous solution of ammonium chloride was added and the resulting mixture was concentrated under reduced pressure. The concentrate was extracted with ether. The extract was washed with saturated brine, dried over anhydrous sodium sulfate, and distilled under reduced pressure to remove the solvent. The residue was purified by chromatography on a silica gel column, whereby from hexane/ethyl acetate (3/1) eluate fractions, benzyl (2S)-N-tert-butoxycarbonylamino-5-oxohexanoate (8.37 g, 39%) was obtained as a yellow oil.

$^1$H-NMR (CDCl$_3$) δ: 1.43 (s, 9H), 1.61–2.15 (series of m, 3H), 2.09 (s, 3H), 2.41–2.55 (m, 2H), 4.30 (brs, 1H), 4.70 (d, J=5.6 Hz, 1H), 5.12–5.21 (m, 2H), 7.29–7.37 (m, 5H);

MS (ESI) m/z 336 (M$^+$+H).

(Step 2) Synthesis of N-tert-butoxycarbonyl-(5S)-methyl-(2S)-pyrrolidinylmethanol

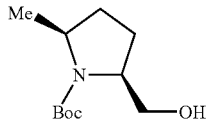

To (2S)-N-tert-butoxycarbonylamino-5-oxohexanoate (7.61 g, 22.7 mmol) were added methylene chloride (50 ml) and trifluoroacetic acid (20 ml). The mixture was stirred at room temperature for 1 hour. The reaction mixture was distilled under reduced pressure to remove the solvent. Toluene was added to the residue to azeotropically remove excessive trifluoroacetic acid under reduced pressure. To the residue were added 10%-palladium/carbon (500 mg) and methanol (100 ml) to conduct catalytic reduction at room temperature under normal pressure. From the reaction mixture, the catalyst was filtered off and the filtrate was distilled under reduced pressure to remove the solvent to obtain a brown oil. To the resulting oil were added ditert-butyl dicarbonate (7.43 g, 34.0 mmol), methanol/water (6/1, 140 ml) and 1N NaOH (56.7 ml, 56.7 mmol). The resulting mixture was stirred at room temperature for 30 minutes. The reaction mixture was concentrated under reduced pressure, followed by extraction with a chloroform/methanol (10/1) mixture. The extract was dried over anhydrous sodium sulfate, and distilled under reduced pressure to remove the solvent. The residue was purified by chromatography on a silica gel column, whereby from hexane/ethyl acetate (1/3) eluate fractions, an oil was obtained. The oil was dissolved in THF (100 ml) and under stirring at room temperature, borane-dimethyl sulfide (an about 10M solution, 4.54 ml, 45.4 mmol) was added. The resulting mixture was stirred at 60° C. for 1 hour. After cooling, ice water and 1N HCl were added, followed by extraction with ethyl acetate. The extract was washed with saturated brine, dried over anhydrous sodium sulfate, and distilled under reduced pressure to remove the solvent. The residue was purified by chromatography on a silica gel column, whereby from hexane/ethyl acetate (1/1) eluate fractions, N-tert-butoxycarbonyl-(5S)-methyl-(2S)-pyrrolidinylmethanol (2.03 g, total 42%) was obtained as a colorless oil.

$^1$H-NMR (CDCl$_3$) δ: 1.17 (d, J=6.0 Hz, 3H), 1.48 (s, 9H), 1.48–1.64 (m, 2H), 1.90–2.11 (m, 2H), 3.52–3.57 (m, 1H), 3.68–3.70 (m, 1H), 3.94–4.13 (m, 2H).

(Step 3) Synthesis of methyl 4-(N-tert-butoxycarbonyl-(5S)-methyl-(2S)-pyrrolidinylmethoxy)benzoate

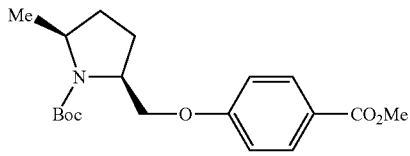

In THF (50 ml were dissolved N-tert-butoxycarbonyl-(5S)-methyl-(2S)-pyrrolidinylmethanol (2.02 g, 9.38 mmol), triphenylphosphine (2.95 g, 11.3 mmol) and methyl 4-hydroxybenzoate (1.43 g, 9.38 mmol). To the resulting solution was added diisopropyl azodicarboxylate (2.14 ml, 10.3 mmol) and the mixture was stirred at room temperature for 18 hours. The reaction mixture was distilled under reduced pressure to remove the solvent. The residue was purified by chromatography on a silica gel column, whereby from hexane/ethyl acetate (3/1) eluate fractions, methyl 4-(N-tert-butoxycarbonyl-(5S)-methyl-(2S)-pyrrolidinylmethoxy)benzoate (3.27 g, 100%) was obtained as a colorless oil.

¹H-NMR (CDCl₃) δ: 1.24 (brs, 3H), 1.49 (s, 9H), 1.55–1.70 (m, 2H), 1.94–2.11 (m, 2H), 3.88 (s, 3H), 3.88 (overlap, 1H), 4.06–4.20 (m, 2H), 6.93–6.96 (m, 2H), 7.97 (d, J=8.8 Hz, 2H).

MS (ESI) m/z 350 (M⁺+H).

(Step 4) Synthesis of methyl trans-4-((5S)-methyl-(2S)-pyrrolidinylmethoxy)cyclohexanecarboxylate

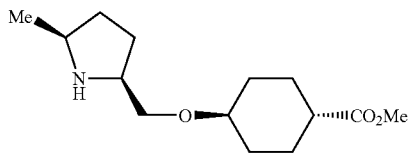

In methanol/acetic acid (10/1, 55 ml), methyl 4-(N-tert-butoxycarbonyl-(5S)-methyl-(2S)-pyrrolidinylmethoxy) benzoate (3.27 g, 9.34 mmol) and 5% rhodium-alumina (0.52 g) were stirred at room temperature for 18 hours under a hydrogen gas of 20 atm. From the reaction mixture, the catalyst was filtered off and then, the solvent was distilled off under reduced pressure. The residue was purified by chromatography on a silica gel column, whereby from hexane/ethyl acetate (3/1) eluate fractions, methyl 4-((5S)-methyl-(2S)-pyrrolidinylmethoxy)cyclohexanecarboxylate (1.74 g, 52%) was obtained as a colorless oil. Under a nitrogen gas stream, methyl 4-((5S)-methyl-(2S)-pyrrolidinylmethoxy)cyclohexanecarboxylate (1.73 g, 4.87 mmol) was dissolved in methanol (50 ml). To the resulting solution was added sodium methoxide (800 mg, 14.6 mmol) and the mixture was stirred for 24 hours. After cooling, 1N HCl was added and the resulting mixture was concentrated under reduced pressure. The concentrate was extracted with a chloroform/methanol (10/1) mixture. The extract was dried over anhydrous sodium sulfate and distilled under reduced pressure to remove the solvent. The residue was dissolved in benzene/methanol (5/1, 30 ml). Under stirring at 0° C., trimethylsilyldiazomethane (a 2.0M hexane solution) was added dropwise to the solution. After completion of the dropwise addition, the reaction mixture was stirred at room temperature for 2 hours. The reaction mixture was then distilled under reduced pressure to remove the solvent, and the residue was purified by flash column chromatography using silica gel, whereby from hexane/ethyl acetate (8/1) eluate fractions, methyl trans-4-(N-tert-butoxycarbonyl-(5S)-methyl-(2S)-pyrrolidinylmethoxy)cyclohexanecarboxylate (700 mg, 40%) was obtained as an oil. The product was dissolved into methylene chloride (30 ml), and trifluoroacetic acid (10 ml) was added to the resulting solution. The mixture was stirred at room temperature for 7 hours. From the reaction mixture, the solvent was distilled off under reduced pressure. To the residue was added a saturated aqueous solution of sodium bicarbonate, followed by extraction with chloroform/methanol (10/1). The extract was dried over anhydrous sodium sulfate, and distilled under reduced pressure to remove the solvent to give methyl trans-4-((5S)-methyl-(2S)-pyrrolidinylmethoxy)cyclohexanecarboxylate (502 mg, 100%) as a pale yellow oil.

¹H-NMR (CDCl₃) δ: 1.17 (d, J=6.0 Hz, 3H), 1.94–1.33 (m, 3H), 1.41–1.54 (m, 3H), 1.76–1.90 (m, 2H), 1.98–2.08 (m, 3H), 2.22–2.29 (m, 3H), 3.14–3.30 (m, 3H), 3.39 (dd, J=6.4, 9.2 Hz, 1H), 3.52 (dd, J=4.4,9.6 Hz, 1H), 3.66 (s, 3H).

(Step 5) Synthesis of methyl trans-4-(1-((5-chloro-2-fluoro-4-((1-methyl-3-indolyl)carbonylamino)phenyl)acetyl)-(5S)-methyl-(2S)-pyrrolidinylmethoxy)cyclohexanecarboxylate

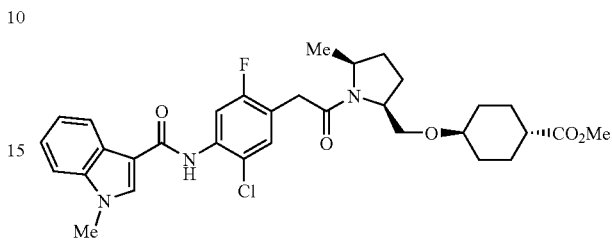

In DMF (10 ml), HOBt (21.0 mg, 0.16 mmol) was added to (5-chloro-2-fluoro-4-((1-methyl-3-indolylcarbonyl)amino)phenyl)acetic acid (283 mg, 0.78 mmol), methyl trans-4-((5S)-methyl-(2S)-pyrrolidinylmethoxy)cyclohexylcarboxylate (205 mg, 0.78 mmol) and EDC-HCl (165 mg, 0.86 mmol) and the resulting mixture was stirred for cyclohexylcarbon 18 hours. The reaction mixture was poured in water, followed by extraction with ethyl acetate. The extract was washed with water, dried over anhydrous sodium sulfate, and distilled under reduced pressure to remove the solvent. The residue was purified by chromatography using a silica gel thinlayer plate, whereby from hexane/ethyl acetate (1/5) eluate fractions, methyl trans-4-(1-((5-chloro-2-fluoro-4-((1-methyl-3-indolyl)carbonylamino)phenyl)acetyl)-(5S)-methyl (2S)-pyrrolidinylmethoxy)cyclohexanecarboxylate (404 mg, 86%) was obtained as a colorless amorphous substance.

¹H-NMR (CDCl₃), mixture of rotamars, δ: 1.20–1.34 (m, overlap, 2H), 1.29 and 1.33 (d, J=6.4 Hz, total 3H), 1.42–2.31 (series of m, 11H), 3.23–3.27 (m, 1H), 3.44–3.51 (m, 1H), 3.66–3.83 (m, 3H), 3.66 and 3.68 (s, total 3H), 4.14 (brs, 2H), 7.35–7.37 (m, 2H), 7.42–7.44 (m, 2H), 7.82 (s, 1H), 8.13–8.16 (m, 1H), 8.30 (s, 1H), 8.49 and 8.52 (d, J=4.8 Hz, total 1H).

MS (ESI) m/z 598 (M⁺+1).

(Step 6) Synthesis of trans-4-(1-((5-chloro-2-fluoro-4-((1-methyl-3-indolyl)carbonylamino)phenyl)acetyl)-(5S)-methyl-(2S)-pyrrolidinylmethoxy)cyclohexanecarboxylic acid

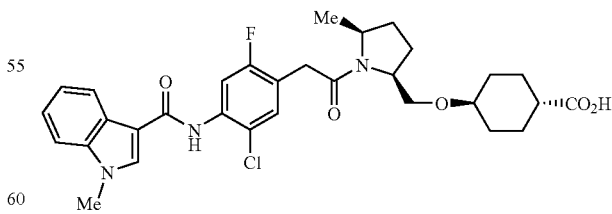

Methyl trans-4-(1-((5-chloro-2-fluoro-4-((1-methyl-3-indolyl)carbonylamino)phenyl)acetyl)-(5S)-methyl-(2S)-pyrrolidinylmethoxy)cyclohexanecarboxylate (388 mg, 0.65 mmol) was dissolved in THF/methanol (1/1, 20 ml). To the resulting solution was added 0.25N NaOH (7.80 ml, 1.95 mmol) and the resulting mixture was stirred at room temperature for 18 hours. The reaction mixture was poured in 1N HCl, followed by extraction with a chloroform/methanol (10/1) mixture. The extract was dried over anhydrous sodium sulfate, and distilled under reduced pressure to remove the solvent. The residue was purified by chromatography on a silica gel column, whereby from chloroform/methanol (15/1) eluate fractions, the title compound (389 mg, 100%) was obtained as a colorless amorphous substance.

$^1$H-NMR (CDCl$_3$), mixture of rotamars, δ 1.15–1.27 (m, overlap, 2H), 1.22 and 1.26 (d, J=6.0 Hz, total 3H), 1.37–2.30 (series of m, 11H), 3.16–3.22 (m, 1H), 3.35–3.45 (m, 1H), 3.52–3.79 (m, 3H), 3.82 (s, 3H), 4.09 (brs, 2H), 7.26–7.31 (m, 2H), 7.34–7.37 (m, 2H), 7.75 (s, 1H), 8.05–8.08 (m, 1H), 8.23 (s, 1H), 8.41 and 8.44 (d, J=5.6 Hz, total 1H).

MS (ESI) m/z 584 (M$^+$+1);

Anal. calcd for C$_{31}$H$_{35}$ClFN$_3$O$_5$.1/4H$_2$O: C, 63.26; H, 6.08; N, 7.14. Found: C, 63.33; H, 6.18; N, 7.14.

Example 137 trans-4-(1-((2-(5-Fluoro-2-methylphenylamino)-7-fluoro-6-benzoxazolyl)acetyl)-(5S)-methyl-(2S)-pyrrolidinylmethoxy)cyclohexanecarboxylic acid (Step 1) Synthesis of methyl trans-4-(1-((2-(5-fluoro-2-methylphenylamino)-7-fluoro-6-benzoxazolyl)acetyl)-(5S)-methyl-(2S)-pyrrolidinylmethoxy)cyclohexanecarboxylate

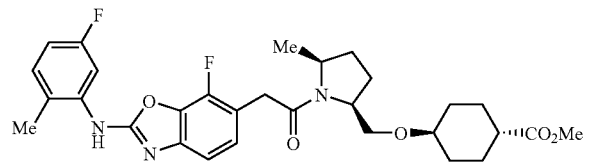

In DMF (10 ml) were dissolved (2-(5-fluoro-2-methylphenylamino)-7-fluoro-6-benzoxazolyl)acetic acid (182 mg, 0.57 mmol), methyl trans-4-((5S)-methyl-(2S)-pyrrolidinylmethoxy)cyclohexylcarboxylate (146 mg, 0.57 mmol) and EDC-HCl (121 mg, 0.63 mmol). To the resulting solution was added HOBt (15.0 mg, 0.11 mmol), and the resulting mixture was stirred at room temperature for 18 hours. The reaction mixture was poured in water, followed by extraction with ethyl acetate. The extract was washed with water, dried over anhydrous sodium sulfate, and distilled under reduced pressure to remove the solvent. The residue was purified by chromatography using a silica gel thin-layer plate (TLC), whereby from hexane-ethyl acetate (1/5) eluate fractions, methyl trans-4-(1-((2-(5-fluoro-2-methylphenylamino)-7-fluoro-6-benzoxazolyl)acetyl)-(5S)-methyl-(2S)-pyrrolidinylmethoxy)cyclohexanecarboxylate (276 mg, 87%) was obtained as a colorless amorphous substance.

$^1$H-NMR (CDCl$_3$), mixture of rotamars, δ: 1.22–2.24 (series of m, 13H), 1.31 and 1.33 (d, J=6.4 Hz, total 3H), 3.20–3.29 (m, 1H), 3.43–3.52 (m, 1H), 3.63–3.83 (series of m, 3H), 3.67 and 3.68 (s, total 3H), 3.89 (s, 1H), 4.17 (brs, 2H), 6.74–6.78 (m, 1H), 7.10–7.17 (m, 2H), 7.23 and 7.26 (d, J=2.0 Hz, total 1H), 8.09 and 8.12 (d, J=4.0 Hz, total 1H).

MS (ESI) m/z 556 (M$^+$+2).

(Step 2) Synthesis of trans-4-(1-((2-(5-fluoro-2-methylphenylamino)-7-fluoro-6-benzoxazolyl)acetyl)-(5S)-methyl-(2S)-pyrrolidinylmethoxy)cyclohexanecarboxylic acid

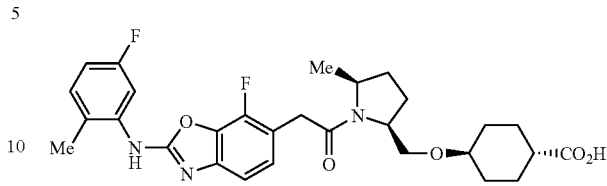

Methyl trans-4-(1-((2-(5-fluoro-2-methylphenylamino)-7-fluoro-6-benzoxazolyl)acetyl)-(5S)-methyl-(2S)-pyrrolidinylmethoxy)cyclohexanecarboxylate (264 mg, 0.48 mmol) was dissolved in THF/methanol (1/1, 20 ml). To the resulting solution was added 0.25N NaOH (5.70 ml, 1.43 mmol) and the mixture was stirred at room temperature for 17 hours. The reaction mixture was poured in 1N HCl, followed by extraction with a chloroform/methanol (10/1) mixture. The extract was dried over anhydrous sodium sulfate, and distilled under reduced pressure to remove the solvent. The residue was purified by chromatography on a silica gel column, whereby from chloroform/methanol (15/1) eluate fractions, the title compound (173 mg, 67%) was obtained as a colorless amorphous substance.

$^1$H-NMR (CDCl$_3$), mixture of rotamars, δ: 1.14–2.25 (series of m, 13H), 1.31 and 1.33 (d, J=6.4 Hz, total 3H), 3.15–3.21 (m, 1H), 3.35–3.44 (m, 1H), 3.58–3.75 (series of m, 3H), 3.82 (s, 1H), 4.10 (brs, 2H), 6.68–6.72 (m, 1H), 7.03–7.14 (m, 3H), 7.80–7.83 (m, 1H).

MS (ESI) m/z 542 (M$^+$+1);

Anal. calcd. for C$_{29}$H$_{33}$ClF$_2$N$_3$O$_5$: C, 64.31; H, 6.14; N, 7.76. Found: C, 64.02; H, 6.25; N, 7.52.

Example 138 trans-4-(1-(5-Chloro-2-fluoro-4-((1-methyl-1H-3-indolylcarbonyl)amino)phenylacetyl)-(4S)-methoxymethyl-(2S)-pyrrolidinylmethoxy)cyclohexanecarboxylic acid (Step 1) Synthesis of (2R,5S,7S)-7-methoxymethyl-2-phenyl-3-oxa-1-azabicyclo(3.3.0)octan-8-one

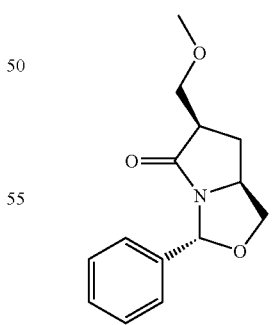

To a solution of lithium diisopropylamide (110 mmol, 100 ml of THF, prepared from diisopropylamine (15.6 ml, 110 mmol) and n-butyl lithium (70.1 ml, 1.57M, 110 mmol)) was added (2R,5S)-2-phenyl-3-oxa-1-azabicyclo(3.3.0)octan-8-one (10.2 g, 50 mmol) under stirring at −78° C. After stirring at the same temperature for 1 hour, a solution of chloromethyl methyl ether (5.7 ml, 75 mmol) in THF (50 ml) was added to the reaction mixture and stirring was conducted further at −78° C. for 90 minutes. The reaction mixture was poured in a saturated aqueous solution of ammonium chloride, followed by extraction with ethyl acetate. The extract was washed with saturated brine, dried over anhydrous magnesium sulfate and distilled under reduced pressure to remove the solvent. The residue was purified by silica gel column chromatography (middle pressure Yamazen, linear gradient of n-hexane/ethyl acetate from 9:1 to 7:3, 30 ml/min, φ 80 mm×300 mm, range 0.08) to give (2R,5S,7S)-7-methoxymethyl-2-phenyl-3-oxa-1-azabicyclo(3.3.0)octan-8-one (1.06 g, 9%) as a colorless oil.

$^1$H-NMR (CDCl$_3$) δ: 1.94 (m, 1H, H-6), 2.52 (m, 1H, H-6), 3.09 (m, 1H, H-7), 3.38 (s, 3H, OMe), 3.53 (t, J=8.1 Hz, 1H, H-4), 3.58 (dd, J=4.0,9.5 Hz, 1H, CH$_2$OMe), 3.67 (dd, J=5.4 Hz, 9.4 Hz, 1H, CH$_2$OMe), 4.08 (m, 1H, H-5), 4.22 (AB type d, J=6.4 Hz, 1H, H-4), 6.30 (s, 1H, H-2), 7.32 (m, 3H, Ph), 7.43 (d, J=6.6 Hz,2H, Ph).

MS (ESI) m/z 248 (M+1)$^+$.

(Step 2) Synthesis of 1-N-benzyloxycarbonyl-(4S)-methoxymethyl-(2S)-pyrrolidinylmethanol

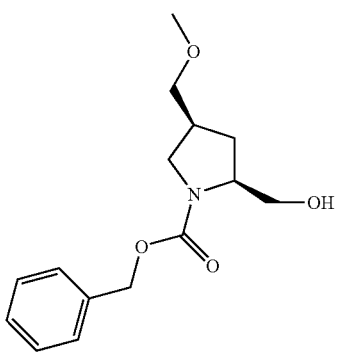

Lithium aluminum hydride (0.56 ml, 12.8 mmol) was suspended in THF (7 ml). To the resulting suspension was added a solution of (2R,5S,7S)-7-methoxymethyl-2-phenyl-3-oxa-1-azabicyclo(3.3.0)octan-8-one (2.11 g, 8.5 mmol) in THF (10 ml) under stirring at 60° C. The reaction mixture was heated under reflux for 1 hour. The reaction mixture was cooled and sodium thiosulfate (6.5 g, 26.2 mmol) and water (10 ml) were added thereto. The reaction mixture was filtered through Celite under reduced pressure. From the filtrate, the solvent was distilled off under reduced pressure. To the residue were added ethanol (10 ml), acetic acid (20 ml) and palladium-carbon and the resulting mixture was subjected to catalytic hydrogenation under normal pressure for 3 days. The reaction mixture was filtered to remove the catalyst and then the solvent was removed from the filtrate under reduced pressure. To the residue were added THF/water (4:1, 20 ml) and potassium carbonate (2.35 g, 17 mmol). Under stirring of the mixture at 0° C., benzyloxycarbonyl chloride (a 30 to 35% toluene solution, 9.7 ml, 17 mmol) was added. The reaction mixture was stirred further at room temperature for 24 hours. The reaction mixture was poured in ethyl acetate and a saturated aqueous solution of ammonium chloride, followed by extraction with ethyl acetate. The extract was washed with saturated brine, dried over anhydrous magnesium sulfate and distilled under reduced pressure to remove the solvent. The residue was purified by silica gel column chromatography (middle pressure Yamazen, linear gradient of n-hexane/ethyl acetate from 4:1 to 1:9, 30 ml/min, φ 50 mm×150 mm, range 0.32) to give 1-N-benzyloxycarbonyl-(4S)-methoxymethyl-(2S)-pyrrolidinylmethanol (1.61 g, 69%) as a colorless oil.

$^1$H-NMR (CDCl$_3$) δ: 3.01 (m, 1H, 3-H), 2.18 (m, 1H, 3-H), 2.40 (m, 1H, 4-H), 3.08 (t, J=10.5 Hz, 1H, 5-H), 3.30 (m, 1H, CH$_2$OMe), 3.31 (s, 3H, OMe), 3.38 (dd, J=4.5,9.1 Hz, 1H, CH$_2$OMe), 3.62 (dd, J=7.2, 11.7 Hz, 1H, CH$_2$OH), 3.70 (m, 1H, CH$_2$OH), 3.81 (t, J=9.0 Hz, 1H, 5-H), 4.00 (m, 1H, 2-H), 4.88 (br, 1H, OH), 5.12 (AB type d, J=13.0 Hz, 2H), 7.35 (m, 5H, Ph).

MS (ESI) m/z 280 (M+1)$^+$.

(Step 3) Synthesis of methyl 4-(1-N-benzyloxycarbonyl-(4S)-methoxymethyl-(2S)-pyrrolidinylmethoxy)benzoate

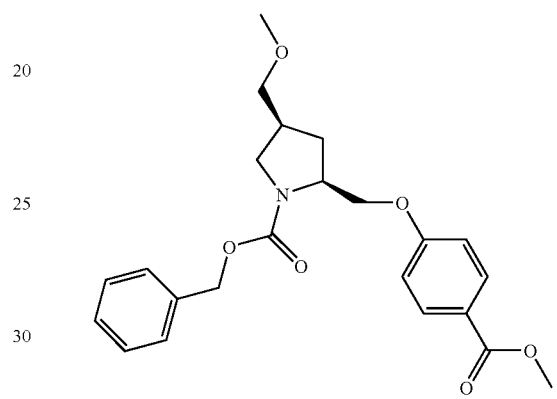

In methylene chloride (20 ml) were dissolved 1-N-benzyloxycarbonyl-(4S)-methoxymethyl-(2S)-pyrrolidinylmethanol (1.6 g, 5.7 mmol) and triethylamine (4.8 ml, 34 mmol). To the resulting solution was added a solution of methanesulfonyl chloride (1.6 ml, 21 mmol) in methylene chloride (8 ml) under stirring at 0° C. The reaction mixture was stirred for 1 hour at the same temperature. The reaction mixture was diluted with ethyl acetate and the solution was poured in 1M HCl. The mixed solution was extracted with ethyl acetate. The extract was washed with saturated brine, dried over anhydrous magnesium sulfate and distilled under reduced pressure to remove the solvent. The residue was dissolved in DMF (28 ml) and to the resulting solution were added potassium carbonate (1.2 g, 8.6 mmol) and methyl 4-hydroxybenzoate (2.6 g, 17 mmol). The resulting mixture was stirred at 100° C. for 2 hours. After cooling, ether and water were added to the reaction mixture, followed by extraction with ether. The extract was washed with 1M NaOH (3 times), dried over anhydrous magnesium sulfate and distilled under reduced pressure to remove the solvent. The residue was purified by silica gel column chromatography (middle pressure Yamazen, linear gradient of n-hexane/ethyl acetate from 9:1 to 7:3, φ 50 mm×300 mm) to give methyl 4-(1-N-benzyloxycarbonyl-(4S)-methoxymethyl-(2S)-pyrrolidinylmethoxy)benzoate (1.46 g, 62%) as a colorless oil.

$^1$H-NMR (CDCl$_3$) δ: 1.78 (m, 1H), 2.32 (m, 1H), 2.48 (m, 1H), 3.10 (t, J=10.2 Hz, 1H), 3.30 (s, 3H), 3.42 (m, 3H), 3.85 (s, 3H), 4.20 (m, 3H), 5.10 (m, 2H), 6.90 (m, 2H), 7.32 (m, 5H), 7.90 (m, 2H).

MS (ESI) m/z 414 (M+1)$^+$.

(Step 4) Synthesis of methyl trans-4-(1-N-tert-butoxycarbonyl-(4S)-methoxymethyl-(2S)-pyrrolidinylmethoxy)cyclohexanecarboxylate

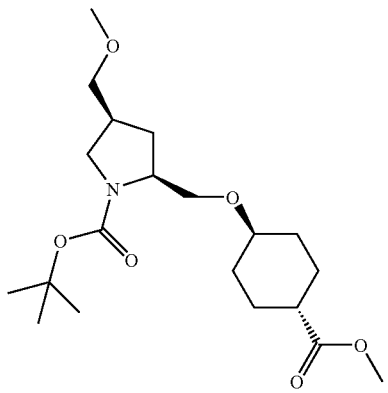

In a methanol/acetic acid (100 ml, 10:1) mixed solvent, methyl 4-(1-N-benzyloxycarbonyl-(4S)-methoxymethyl-(2S)-pyrrolidinylmethoxy)benzoate (1.45 g, 3.51 mmol) and 10% palladium-carbon (300 mg) were subjected to catalytic hydrogenation for 3 hours at room temperature under normal pressure. From the reaction mixture, the catalyst was filtered off. To the filtrate were added acetic acid (10 ml) and rhodium/aluminum (435 mg) and the mixture was subjected to catalytic hydrogenation for 24 hours under a hydrogen gas of 4 atom. From the reaction mixture, the catalyst was filtered off and the filtrate was distilled under reduced pressure to remove the solvent. The residue was dissolved in methylene chloride (18 ml) and to the resulting solution, triethylamine (1.47 ml, 10.5 mmol) and di-tert-butyl-dicarbonate (1.15 g, 5.3 mmol) were added. Stirring was conducted for 6 hours at room temperature. The reaction mixture was poured in a 15% aqueous citric acid solution, followed by extraction with chloroform. The extract was washed with saturated brine and dried over anhydrous magnesium sulfate. After removal of the solvent by distillation under reduced pressure, the residue was dissolved in methanol and sodium methoxide (285 mg, 5.27 mmol) was added to the solution. The resulting mixture was heated under reflux for 18 hours. After cooling, the reaction mixture was poured in a saturated aqueous solution of citric acid, followed by extraction with chloroform. The extract was dried over anhydrous sodium sulfate. After removal of the solvent by distillation under reduced pressure, the residue was dissolved in methanol/benzene (1:4, 18 ml). Under stirring at 0° C., trimethylsilyldiazomethane (2.64 ml, a 2.0M n-hexane solution, 5.27 mmol) was added to the solution. The reaction mixture was stirred further for 3 hours at room temperature, followed by distillation under reduced pressure to remove the solvent. The residue was purified by medium-pressure column chromatography using silica gel (Biotage, KP-SIL, 32–63 μm, 75M, n-hexane/ethyl acetate 4:1 v/v) to give methyl trans-4-(1-N-tert-butoxycarbonyl-(4S)-methoxymethyl-(2S)-pyrrolidinylmethoxy)cyclohexane carboxylate (473 mg, 35%) as colorless oil.

$^1$H-NMR (CDCl$_3$) δ: 1.25 (m, 3H), 1.48 (s, 9H), 2.00 (m, 4H), 2.20 (m, 2H), 2.38 (m, 1H), 2.92 (t, J=9.5 Hz, 1H), 3.20 (m, 1H), 3.33 (s, 3H), 3.40–3.90 (m, 8H), 3.62 (s, 3H).

MS (ESI) m/z 386 (M+1)$^+$.

(Step 5) Synthesis of trans-4-(1-(5-chloro-2-fluoro-4-((1-methyl-1H-3-indolylcarbonyl)amino)phenylacetyl)-(4S)-methoxymethyl-(2S)-pyrrolidinylmethoxy)cyclohexanecarboxylic acid

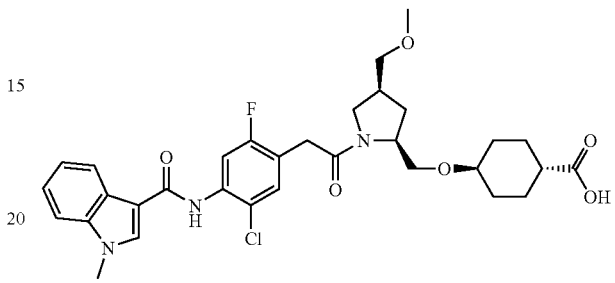

In methylene chloride (15 ml) was dissolved methyl trans-4-(1-N-tert-butoxycarbonyl-(4S)-methoxymethyl-(2S)-pyrrolidinylmethoxy)cyclohexanecarboxylate (157 mg, 0.406 mmol). To the resulting solution was added trifluoroacetic acid (15 ml). The resulting mixture was stirred at room temperature for 2 hours. The reaction mixture was distilled under reduced pressure to remove the solvent and the residue was dissolved in chloroform/a saturated aqueous solution of sodium bicarbonate, followed by extraction with chloroform. The extract was dried over anhydrous sodium sulfate, and distilled under reduced pressure to remove the solvent. The residue was dissolved in DMF (2 ml). To the resulting solution were added (5-chloro-2-fluoro-4-((1-methyl-1H-3-indolylcarbonyl)amino)phenyl]acetic acid (146 mg, 0.406 mmol), HOBt (104 mg, 0.77 mmol), DMAP (catalytic amount) and EDC•HCl salt (117 mg, 0.61 mmol). The resulting mixture was stirred at room temperature for 18 hours. The reaction mixture was poured in 1M HCl, followed by extraction with ethyl acetate. The extract was washed with saturated brine, dried over anhydrous magnesium sulfate and distilled under reduced pressure to remove the solvent. The residue was purified by medium-pressure silica gel column chromatography (middle pressure Yamazen, chloroform/methanol 10:0 to 20:1, 20 ml/min, φ 50 mm×150 mm). The purified product was dissolved in THF (4 ml) and 0.25M NaOH (2.4 ml, 0.61 mmol) was added to the solution. The resulting mixture was stirred for 18 hours at room temperature. The reaction mixture was acidified with 1M HCl. The crystals thus precipitated were collected by filtration under reduced pressure, washed with water and dried under reduced pressure to give the title compound (140 mg, 56%) as a colorless solid.

$^1$H-NMR (DMSO-d$_6$) δ: 1.20–2.80 (m, 15H), 3.10–4.30 (m, 7H), 3.30 (s, 3H), 3.90 (s, 3H), 7.21 (t, J=7.5 Hz, 1H), 7.27 (t, J=7.5 Hz, 1H), 7.41 (d, J=7.3 Hz, !H), 7.55 (d, J=8.1 Hz, 1H), 7.70 (d, J=11.2 Hz, 1H), 8.14 (d, J=7.5 Hz, 1H), 8.31 (s, 1H), 9.30 (s, 1H).

MS (ESI) m/z 615 (M+1)$^+$;

Anal. Calcd for $C_{30}H_{32}ClF_2N_3O_5 \cdot 0.75H_2O$: C, 59.90; H, 5.61; N, 7.31. Found: C, 59.97; H, 5.55; N, 7.31.

Example 139 trans-4-(1-(5-Chloro-2-fluoro-4-((1-methyl-1H-indazole-3-indazolylcarbonyl)amino)phenylacetyl)-(4S)-methoxymethyl-(2S)-pyrrolidinylmethoxy)cyclohexanecarboxylic acid (Step 1) Synthesis of trans-4-(1-(5-chloro-2-fluoro-4-((1-methyl-1H-indazolylcarbonyl)amino)phenylacetyl)-(4S)-methoxymethyl-(2S)-pyrrolidinylmethoxy)cyclohexanecarboxylic acid

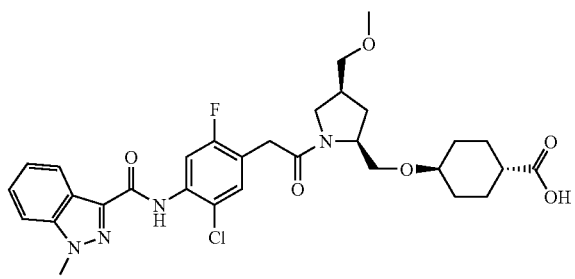

To a solution of methyl trans-4-(1-N-tert-butoxycarbonyl-(4S)-methoxymethyl-(2S)-pyrrolidinylmethoxy)cyclohexanecarboxylate (157 mg, 0.406 mmol) in methylene chloride (15 ml), trifluoroacetic acid (15 ml) was added. The resulting mixture was stirred at room temperature for 2 hours. The reaction mixture was distilled under reduced pressure to remove the solvent. To the residue was added chloroform/a saturated aqueous solution of sodium bicarbonate, followed by extraction with chloroform. The extract was dried over anhydrous sodium sulfate and distilled under reduced pressure to remove the solvent. The residue was dissolved in DMF (2 ml) and (5-chloro-2-fluoro-4-((1-methyl-1H-indazolylcarbonyl)amino)phenyl)acetic acid (147 mg, 0.406 mmol), HOBt (104 mg, 0.77 mmol), DMAP (catalytic amount) and EDC•HCl salt (117 mg, 0.61 mmol) were added to the solution. The resulting mixture was stirred at room temperature for 18 hours. The reaction mixture was poured in 1M HCl, followed by extraction with ethyl acetate. The extract was washed with saturated brine, dried over anhydrous magnesium sulfate, and distilled under reduced pressure to remove the solvent. The residue was purified by silica gel column chromatography (middle pressure Yamazen, chloroform/methanol 10:0 to 20:1, 20 ml/min, φ 50 mm×150 mm). The purified product was dissolved in THF (4 ml) and 0.25M NaOH (2.4 ml, 0.61 mmol) was added to the solution. The resulting mixture was stirred for 18 hours at room temperature. The reaction mixture was acidified with 1M HCl. The crystals thus precipitated were collected by filtration under reduced pressure, washed with water and dried under reduced pressure, whereby a white solid (154 mg, 62%) was obtained.

$^1$H-NMR (DMSO-$d_6$) δ: 1.20–2.80 (m, 15H), 3.10–4.30 (m, 7H), 3.30 (s, 3H), 3.90 (s, 3H), 7.37 (t, J=7.5 Hz, 1H), 7.46 (d, J=7.1 Hz, 1H), 7.53 (t, J=8.0 Hz, 1H), 7.82 (d, J=8.3 Hz, 1H), 8.06 (d, J=11.5 Hz, 1H), 8.20 (d, J=7.6 Hz, 1H), 9.71 (s, 1H).

MS (ESI) m/z 616 (M+1)$^+$;

Anal. Calcd for $C_{31}H_{36}ClFN_4O_6 \cdot 0.25H_2O$: C, 62.13; H, 6.11; N, 6.79. Found: C, 62.04; H, 6.15; N, 6.75.

Example 140 trans-4-(1-(7-Fluoro-2-(5-fluoro-2-methylphenylamino)-6-benzoxazolylacetyl)-(4S)-methoxymethyl-(2S)-pyrrolidinylmethoxy)cyclohexanecarboxylic acid (Step 1) Synthesis of trans-4-(1-(7-fluoro-2-(5-fluoro-2-methylphenylamino)-6-benzoxazolylacetyl)-(4S)-methoxymethyl-(2S)-pyrrolidinylmethoxy)cyclohexanecarboxylic acid

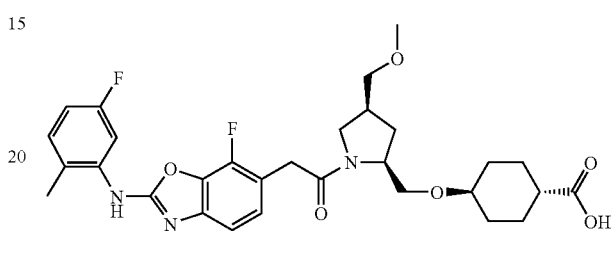

To a solution of methyl trans-4-(1-N-tert-butoxycarbonyl-(4S)-methoxymethyl-(2S)-pyrrolidinylmethoxy)cyclohexanecarboxylate (157 mg, 0.406 mmol) in methylene chloride (15 ml), trifluoroacetic acid (15 ml) was added. The resulting mixture was stirred at room temperature for 2 hours. The reaction mixture was distilled under reduced pressure to remove the solvent. The residue was dissolved in chloroform/saturated aqueous solution of sodium bicarbonate, followed by extraction with chloroform. The extract was dried over anhydrous sodium sulfate and distilled under reduced pressure to remove the solvent. The residue was dissolved in DMF (2 ml). To the resulting solution were added 7-fluoro-2-(5-fluoro-2-methylphenylamino)-6-benzoxazolacetic acid (147 mg, 0.406 mmol), HOBt (104 mg, 0.77 mmol), DMAP (catalytic amount) and EDC•HCl salt (129 mg, 0.61 mmol). The mixture was stirred at room temperature for 18 hours. The reaction mixture was poured in 1M HCl, followed by extraction with ethyl acetate. The extract was washed with saturated brine, dried over anhydrous magnesium sulfate and distilled under reduced pressure to remove the solvent. The residue was purified by silica gel column chromatography (middle pressure Yamazen, chloroform/methanol 10:0 to 20:1, 20 ml/min, φ 50 mm×150 mm). The purified product was dissolved in THF (4 ml) and 0.25 M NaOH (2.4 ml, 0.61 mmol) was added to the solution. The resulting mixture was stirred for 18 hours at room temperature. The reaction mixture was acidified with 1M HCl. The crystals thus precipitated were collected by filtration under reduced pressure, washed with water and dried under reduced pressure to give the title compound (110 mg, 47%) as a colorless solid.

$^1$H-NMR (DMSO-$d_6$) δ: 1.20–1.60 (m, 6H), 1.80–3.80 (m, 9H), 2.31 (s, 3H), 3.10–4.30 (m, 7H), 3.25 (s, 3H), 6.88 (dt, J=2.4,8.5 Hz, 1H), 7.05 (t, J=7.5 Hz, 1H), 7.20 (d, J=8.1 Hz, 1H), 7.25 (t, J=7.5 Hz, 1H), 7.92 (d, J=10.8 Hz, 1H).

MS (ESI) m/z 572 (M+1)$^+$;

Anal. Calcd for $C_{30}H_{35}F_2N_3O_6 \cdot 0.25H_2O$: C, 62.54; H, 6.21; N, 7.29. Found: C, 62.46; H, 6.23; N, 7.29.

Example 141 trans-4-((1-(5-Chloro-2-fluoro-4-((1-methyl-3-indolyl)carbonylamino)phenyl)acetyl)-(5S)-methoxymethyl-(2S)-pyrrolidinylmethoxy)cyclohexanecarboxylic acid (Step 1) Synthesis of (2S)-benzyloxymethyl-N-tert-butoxycarbonyl-(5S)-hydroxymethylpyrrolidine

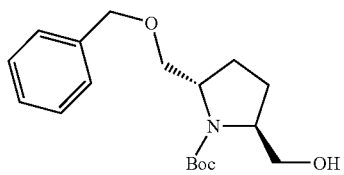

In methanol/THF/water (5/3/2, 100 ml) was dissolved (2S)-benzoyloxymethyl-(5S)-benzyloxymethyl-N-tert-butoxycarbonylpyrrolidine (3.34 g, 7.85 mmol). To the resulting solution was added 1N NaOH (25.0 ml, 25.0 mmol) and the resulting mixture was stirred at room temperature for 7 hours. The reaction mixture was concentrated under reduced pressure. The residue was extracted with chloroform/methanol (10/1). The extract was dried over anhydrous sodium sulfate, and distilled under reduced pressure to remove the solvent. The residue was purified by chromatography on a silica gel column, whereby from hexane/ethyl acetate (3/1 to EtOAc) eluate fractions, (2S)-benzyloxymethyl-N-tert-butoxycarbonyl-(5S)-hydroxymethylpyrrolidine (1.46 g, 58%) was obtained as a colorless oil.

$^1$H-NMR (CDCl$_3$) δ: 1.41 (s, 9H), 1.57 (brs, 1H), 1.95–1.97 (m, 2H), 2.05–2.18 (m, 1H), 3.36 (t, J=8.4 Hz, 1H), 3.56–3.62 (m, 2H), 3.67–3.72 (m, 2H), 3.95 (brs, 1H), 4.03 (brs, 1H), 4.51 (s, 1H), 7.28–7.37 (m, 5H).

MS (FAB) m/z 322 (M$^+$+1).

(Step 2) Synthesis of (2S)-benzyloxymethyl-N-tert-butoxycarbonyl-(5S)-methoxymethylpyrrolidine

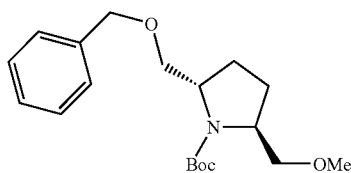

In DMF (50 ml) was dissolved (2S)-benzyloxymethyl-N-tert-butoxycarbonyl-(5S)-hydroxymethylpyrrolidine (1.46 g, 4.55 mmol). Under stirring at 0° C., sodium hydride (60% in oil, 218 mg, 5.46 mmol) was added to the resulting solution in portions. After stirring at the same temperature for 10 minutes, methyl iodide (1.42 ml, 22.8 mmol) was added and the resulting mixture was stirred further at room temperature for 18 hours. The reaction mixture was poured in 1N HCl, followed by extraction with ether. The extract was washed with water, dried over anhydrous sodium sulfate, and distilled under reduced pressure to remove the solvent. The residue was purified by chromatography on a silica gel column, whereby from hexane/ethyl acetate (5/1) eluate fractions, (2S)-benzyloxymethyl-N-tert-butoxycarbonyl-(5S)-methoxymethylpyrrolidine (1.13 g, 74%) was obtained as a colorless oil.

$^1$H-NMR (CDCl$_3$), mixture of rotamers, δ: 1.40 and 1.47 (s, total 9H), 1.86–2.02 (m, 4H), 3.20–3.68 (series of m, 4H), 3.34 (s, 3H), 3.86–4.00 (m, 2H), 4.46–4.58 (m, 2H), 7.27–7.34 (m, 5H).

(Step 3) Synthesis of N-tert-butoxycarbonyl-(5S)-hydroxymethyl-(2S)-methoxymethylpyrrolidine

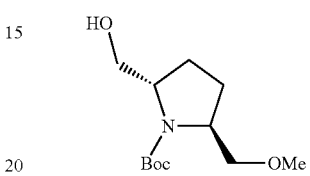

In methanol (30 ml), (2S)-benzyloxymethyl-N-tert-butoxycarbonyl-(5S)-methoxymethylpyrrolidine (1.12 g, 3.34 mmol) and 10% palladium/carbon (163 mg) were subjected to catalytic hydrogenation at room temperature under normal pressure for 18 hours. From the reaction mixture, the catalyst was filtered off and the filtrate was distilled under reduced pressure to remove the solvent, whereby N-tert-butoxycarbonyl-(5S)-hydroxymethyl-(2S)-methoxymethylpyrrolidine (866 mg, 100%) was obtained as a colorless oil.

$^1$H-NMR (CDCl$_3$) δ: 1.49 (s, 9H), 1.57–1.70 (m, 1H), 1.87–1.98 (m, 2H), 2.014–2.14 (m, 1H), 3.17–4.02 (series of m, 6H), 3.35 (s, 3H).

(Step 4) Synthesis of methyl 4-(N-tert-butoxycarbonyl-(5S)-methoxymethyl-(2S)-pyrrolidinylmethoxy)benzoate

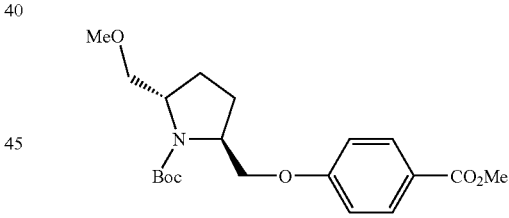

In THF (30 ml) were dissolved N-tert-butoxycarbonyl-(5S)-hydroxymethyl-(2S)-methoxymethylpyrrolidine (865 mg, 3.53 mmol), triphenylphosphine (1.11 g, 4.23 mmol) and methyl 4-hydroxybenzoate (536 mg, 3.53 mmol). To the resulting solution was added DIAD (803 μl, 3.88 mmol) and the resulting mixture was stirred at 60° C. for 2 hours. After cooling to room temperature, the reaction mixture was distilled under reduced pressure to remove the solvent. The residue was purified by chromatography on a silica gel column, whereby from hexane/ethyl acetate (3/1) eluate fractions, methyl 4-(N-tert-butoxycarbonyl-(5S)-methoxymethyl-(2S)-pyrrolidinylmethoxy)benzoate (1.13 g, 84%) was obtained as a colorless oil.

$^1$H-NMR (CDCl$_3$), mixture of rotamers, δ: 1.48 (s, 9H), 1.94–2.14 (m, 4H), 3.26–4.27 (series of m, 6H), 3.36 (s, 3H), 3.88 and 3.89 (s, total 3H), 6.93 and 6.96 (d, J=8.8 Hz, total 2H), 7.96 and 7.99 (d, J=4.0 Hz, total 2H).

(Step 5) Synthesis of methyl trans-4-(N-tert-butoxycarbonyl-(5S)-methoxymethyl-(2S)-pyrrolidinylmethoxy)cyclohexanecarboxylate

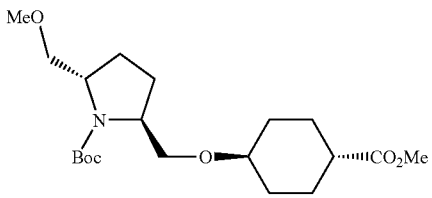

In ethanol/acetic acid (10/1, 55 ml), methyl 4-(N-tert-butoxycarbonyl-(5S)-methoxymethyl-(2S)-pyrrolidinylmethoxy)benzoate (1.02 g, 2.69 mml) and 5% rhodium-alumina (500 mg) were subjected to catalytic hydrogenation at room temperature for 2.5 hours under a hydrogen gas of 8 atom. From the reaction mixture, the catalyst was filtered off and the filtrate was distilled under reduced pressure to remove the solvent. The residue was purified by chromatography on a silica gel column, whereby from hexane/ethyl acetate (3/1) eluate fractions, methyl 4-(N-tert-butoxycarbonyl-(5S)-methoxymethyl-(2S)-pyrrolidinylmethoxy)cyclohexanecarboxylate (771 mg, 74%) was obtained as a colorless oil. The oil was dissolved in methanol (770 mg, 1.20 mmol). To the resulting solution was added sodium methoxide (324 mg, 5.99 mmol), followed by heating under reflux for 18 hours. After cooling, the reaction mixture was neutralized with 1N HCl, followed by extraction with a chloroform/methanol (10/1) mixture. The extract was dried over anhydrous sodium sulfate, and distilled under reduced pressure to remove the solvent to give an oil. The oil was dissolved in a benzene/methanol (10/1, 22 ml) mixture, followed by the dropwise addition of trimethylsilyl diazomethane (a 2.0M hexane solution, 0.50 ml, 0.25 mmol). After the reaction mixture was stirred at room temperature for 1 hour, the solvent was distilled off under reduced pressure. The residue was purified by flash column chromatography using silica gel, whereby from hexane/ethyl acetate (5/1) eluate fractions, methyl trans-4-(N-tert-butoxycarbonyl-(5S)-methoxymethyl-(2S)-pyrrolidinylmethoxy)cyclohexanecarboxylate (178 mg, 23%) was obtained as a colorless oil.

MS (ESI) m/z 386 (M$^+$+1).

(Step 6) Synthesis of methyl trans-4-((5S)-methoxymethyl-(2S)-pyrrolidinylmethoxy)cyclohexanecarboxylate

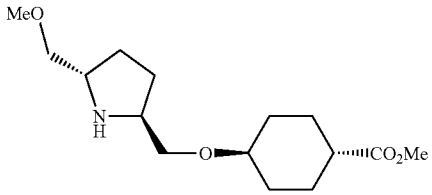

Methyl trans-4-(N-tert-butoxycarbonyl-(5S)-methoxymethyl-(2S)-pyrrolidinylmethoxy) cyclohexanecarboxylate (175 mg, 0.45 mmol) was dissolved in methylene chloride (20 ml). To the resulting solution was added trifluoroacetic acid (7 ml). The resulting mixture was stirred at room temperature for 30 minutes. The reaction mixture was distilled under reduced pressure to remove the solvent. The residue was neutralized with a saturated aqueous solution of sodium bicarbonate, followed by extraction with a chloroform/methanol (10/1) mixture. The extract was dried over anhydrous sodium sulfate, and distilled under reduced pressure to remove the solvent, whereby methyl trans-4-((5S)-methoxymethyl-(2S)-pyrrolidinylmethoxy)-cyclohexanecarboxylate (130 mg, 100%) was obtained as a pale yellow oil.

MS (ESI) m/z 286 (M$^+$+1).

(Step 7) Synthesis of methyl trans-4-(1-((5-chloro-2-fluoro-4-((1-methyl-3-indolyl)carbonylamino)phenyl)acetyl)-(5S)-methoxymethyl-(2S)-pyrrolidinylmethoxy)cyclohexanecarboxylate

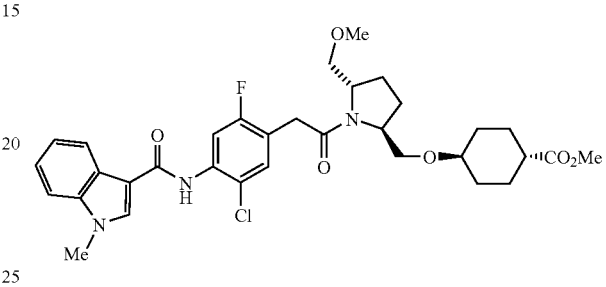

In DMF (10 ml), HOBt (18.2 mg, 0.14 mmol) was added to (5-chloro-2-fluoro-4-((1-methyl-3-indolylcarbonyl)amino)phenyl)acetic acid (162 mg, 0.45 mmol), methyl trans-4-((5S)-methoxymethyl-(2S)-pyrrolidinylmethoxy) cyclohexanecarboxylate (128 mg, 0.45 mmol) and EDC•HCl (103 mg, 0.54 mmol) and the resulting mixture was stirred at room temperature for 18 hours. The reaction mixture was poured in water, followed by extraction with ethyl acetate. The extract was washed with water, dried over anhydrous sodium sulfate, and distilled under reduced pressure to remove the solvent. The residue was purified by chromatography on a silica gel column, whereby from hexane-ethyl acetate (1/5) eluate fractions, methyl trans-4-((1-(5-chloro-2-fluoro-4-((1-methyl-3-indolyl)carbonylamino)phenyl)acetyl)-(5S)-methoxymethyl-(2S)-pyrrolidinylmethoxy)cyclohexanecarboxylate (244 mg, 87%) was obtained as a colorless amorphous substance.

$^1$H-NMR (CDCl$_3$), mixture of rotamars, δ: 1.09–2.25 (series of m, 12H), 3.05–4.20 (series of m, 10H), 3.27 and 3.31 (s, total 3H), 3.55 and 3.61 (s, total 3H), 3.84 (s, 3H), 7.28–7.32 (m, 2H), 7.36–7.41 (m, 2H), 7.76 (d, J=2.4 Hz, 1H), 8.01–8.10 (m, 1H), 8.24 (s, 1H), 8.43 and 8.46 (s, total 1H).

MS (ESI) m/z 628 (M$^+$+1)

(Step 8) Synthesis of trans-4-(1-((5-chloro-2-fluoro-4-((1-methyl-3-indolyl)carbonylamino)phenyl)acetyl)-(5S)-methoxymethyl-(2S)-pyrrolidinylmethoxy)cyclohexanecarboxylic acid

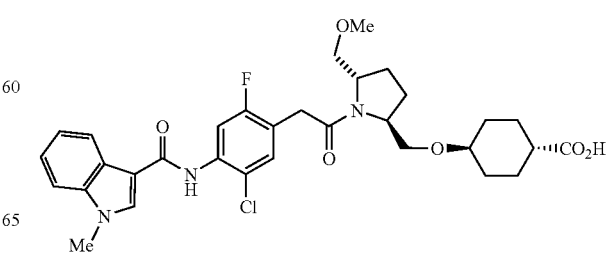

In THF/methanol (1/1, 20 ml) was dissolved methyl trans-4-(1-((5-chloro-2-fluoro-4-((1-methyl-3-indolyl)carbonylamino)phenyl)acetyl)-(5S)-methoxymethyl-(2S)-pyrrolidinylmethoxy)cyclohexanecarboxylate (241 mg, 0.39 mmol). To the resulting solution was added 0.25N NaOH (7.67 ml, 1.92 mmol). The resulting mixture was stirred at room temperature for 18 hours. The reaction mixture was poured in 1N HCl, followed by extraction with a chloroform/methanol (10/1) mixture. The extract was dried over anhydrous sodium sulfate, and distilled under reduced pressure to remove the solvent. The residue was purified by chromatography on a silica gel column, whereby from chloroform/methanol (15/1) eluate fractions, the title compound (204 mg, 87%) was obtained as a colorless amorphous substance.

$^1$H-NMR (CDCl$_3$), mixture of rotamars, δ: 1.05–2.32 (series of m, 12H), 3.10–4.25 (series of m, 10H), 3.30 and 3.35 (s, total 3H), 3.85 and 3.86 (s, total 3H), 7.30–7.35 (m, 2H), 7.38–7.44 (m, 2H), 7.79 (d, J=1.2 Hz, 1H), 8.08–8.12 (m, 1H), 8.28 (s, 1H), 8.45 and 8.48 (d, J=6.0 Hz, total 1H).

MS (ESI) m/z 613 (M$^+$+1);

Anal. calcd for C$_{32}$H$_{37}$ClFN$_3$O$_6$: C, 62.59; H, 6.07; N, 6.84. Found: C, 62.45; H, 6.30; N, 6.65.

Example 142 trans-4-(1-((5-Chloro-2-fluoro-4-(1-methyl-3-indolylcarbonylamino)phenyl)acetyl)-(4S)-(N-methylacetamido)-(2S)-pyrrolidinylmethoxy)-1-cyclohexanecarboxylic acid (Step 1) Synthesis of methyl trans-4-((4S)-azido-1-(tert-butoxycarbonyl)-(2S)-pyrrolidinylmethoxy)-1-cyclohexanecarboxylate

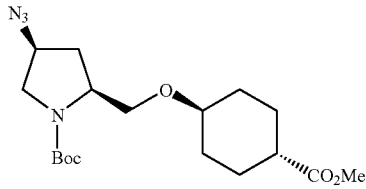

Methyl trans-4-(1-(tert-butoxycarbonyl)-(4S)-methanesulfonyloxy-(2S)-pyrrolidinylmethoxy)-1-cyclohexanecarboxylate (530 mg, 1.22 mmol) was dissolved in DMF (10 ml) and LiN$_3$ (119 mg, 2.43 mmol) was added to the resulting solution. The mixture was stirred at 80° C. for 5 hours. After cooling, the reaction mixture was diluted with ethyl acetate (300 ml). The ethyl acetate solution was washed with saturated brine, dried over anhydrous magnesium sulfate and distilled under reduced pressure to remove the solvent. The residue was purified by chromatography on a silica gel column, whereby from chloroform-ethyl acetate (20:1 to 10:1) eluate fractions, methyl trans-4-((4S)-azido-1-(tert-butoxycarbonyl)-(2S)-pyrrolidinylmethoxy)-1-cyclohexanecarboxylate (423 mg, 91%) was obtained as a pale yellow oil.

$^1$H-NMR (CDCl$_3$) δ: 1.21–1.30 (m, 2H), 1.46 (m, 11 H, including s, 9H, at δ: 1.46), 2.00–2.36 (series of m, 7H), 3.20–4.13 (series of m, 10H, including s, 3H, at δ: 3.66).

(Step 2) Synthesis of methyl trans-4-((4S)-amino-1-(tert-butoxycarbonyl)-(2S)-pyrrolidinylmethoxy)-1-cyclohexanecarboxylate

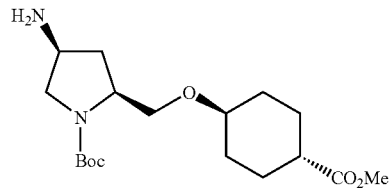

In methanol (20 ml), 5% palladium/carbon (400 mg) was added to methyl trans-4-((4S)-azido-1-(tert-butoxycarbonyl)-(2S)-pyrrolidinylmethoxy)-1-cyclohexanecarboxylate (420 mg, 1.10 mmol) and catalytic hydrogenation was effected for 15 hours at room temperature under normal pressure. After removal of the catalyst by filtration, the filtrate was distilled under reduced pressure to remove the solvent, whereby methyl trans-4-((4S)-amino-1-(tert-butoxycarbonyl)-(2S)-pyrrolidinylmethoxy)-1-cyclohexanecarboxylate (391 mg, 100%) was obtained as a pale yellow oil.

MS (ESI) m/z 357 (M$^+$+1).

(Step 3) Synthesis of methyl trans-4-(1-(tert-butoxycarbonyl)-(4S)-trifluoroacetamido-(2S)-pyrrolidinylmethoxy)-1-cyclohexanecarboxylate

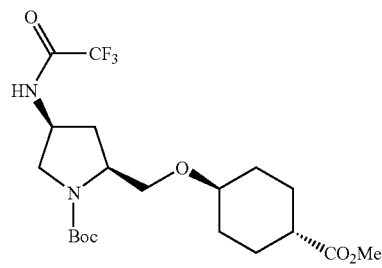

Methyl trans-4-((4S)-amino-1-(tert-butoxycarbonyl)-(2S)-pyrrolidinylmethoxy)-1-cyclohexanecarboxylate (390 mg, 1.09 mmol) was dissolved in methylene chloride (10 ml). Under stirring at 0° C., diisopropylethylamine (381 μl, 2.19 mmol) and trifluoroacetic anhydride (227 μl, 1.64 mmol) were added to the resulting solution. After stirring for 2 hours at the same temperature, the reaction mixture was added with water (50 ml), followed by extraction with ethyl acetate (200 ml). The extract was washed with saturated brine (100 ml), dried over anhydrous magnesium sulfate, and distilled under reduced pressure to remove the solvent. The residue was purified by chromatography on a silica gel column, whereby from chloroform-ethyl acetate (10:1) eluate fractions, methyl trans-4-(1-(tert-butoxycarbonyl)-(4S)-trifluoroacetamido-(2S)-pyrrolidinylmethoxy)-1-cyclohexanecarboxylate (375 mg, 76%) was obtained as a yellow oil.

$^1$H-NMR (CDCl$_3$) δ: 1.22–2.50 (series of m, 20H), 3.27–3.69 (series of m, 7H, including s, 3H, at d 3.67), 3.96–4.15 (m, 2H), 4.62 (m, 1H), 8.45 and 8.56 (m, each, total 1H).

MS (ESI) m/z 453 (M$^+$+1).

(Step 4) Synthesis of methyl trans-4-(1-(tert-butoxycarbonyl)-(4S)-N-methyltrifluoroacetamido-(2S)-pyrrolidinylmethoxy)-1-cyclohexanecarboxylate

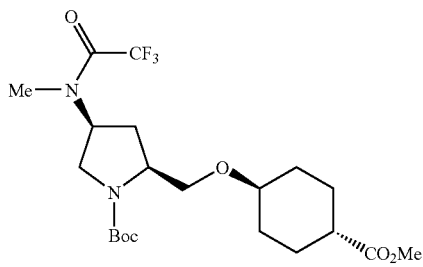

In DMF (10 ml) were dissolved methyl trans-4-(1-(tert-butoxycarbonyl)-(4S)-trifluoroacetamido-(2S)-pyrrolidinylmethoxy)-1-cyclohexanecarboxylate (375 mg, 0.829 mmol) and MeI (258 μl, 4.15 mmol). To the resulting solution was added sodium hydride (40 mg, 0.995 mmol) in portions under stirring at 0° C. After stirring for 1 hour at the same temperature, the reaction mixture was added with 1N HCl (50 ml), followed by extraction with ethyl acetate (200 ml). The extract was washed with saturated brine (100 ml), dried over anhydrous magnesium sulfate, and distilled under reduced pressure to remove the solvent. The residue was purified by chromatography on a silica gel column, whereby from chloroform-ethyl acetate (10:1) eluate fractions, methyl trans-4-(1-(tert-butoxycarbonyl)-(4S)-N-methyltrifluoroacetamido-(2S)-pyrrolidinylmethoxy)-1-cyclohexanecarboxylate (202 mg, 52%) was obtained as a yellow oil.

MS (ESI) m/z 467 (M$^+$+1).

(Step 5) Synthesis of methyl trans-4-(1-(tert-butoxycarbonyl)-(4S)-N-methylacetamido-(2S)-pyrrolidinylmethoxy)-1-cyclohexanecarboxylate

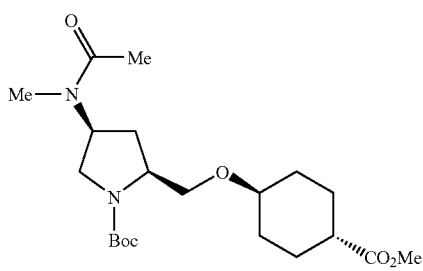

Methyl trans-4-(1-(tert-butoxycarbonyl)-(4S)-N-methyltrifluoroacetamido-(2S)-pyrrolidinylmethoxy)-1-cyclohexanecarboxylate (200 mg, 0.429 mmol) was dissolved in THF-methanol (5:1, 6 ml). To the resulting solution was added a 2M aqueous solution (4 ml) of $Na_2CO_3$. After stirring for 3 hours, the reaction mixture was diluted with ethyl acetate (100 ml). The ethyl acetate solution was washed with saturated brine (100 ml), dried over anhydrous magnesium sulfate and distilled under reduced pressure to remove the solvent. The residue was dissolved in methylene chloride (20 ml). To the resulting solution were added triethylamine (119 μl, 0.859 mmol) and acetylene chloride (46 μl, 0.644 mmol) under stirring at 0° C. The reaction mixture was stirred at room temperature for hour and diluted with ethyl acetate (100 ml). The diluted mixture was washed with saturated brine (100 ml), dried over anhydrous magnesium sulfate, and distilled under reduced pressure to remove the solvent. The residue was purified by chromatography on a silica gel column, whereby from chloroform-methanol (20:1) eluate fractions, methyl trans-4-(1-(tert-butoxycarbonyl)-(4S)-N-methylacetamido-(2S)-pyrrolidinylmethoxy)-1-cyclohexanecarboxylate (90 mg, 51%) was obtained as a colorless oil.

$^1$H-NMR (CDCl$_3$) δ: 1.25 (m, 2H), 1.45 (m, 11H), 1.98–2.29 (series of m, 10H), 2.86 and 2.92 (s, each, total 3H), 3.02–3.30 (m, 2H), 3.62–3.92 (series of m, 7H, including s, 3H, at δ: 3.66), 4.29 and 5.14 (m, each, total 1H).

(Step 6) Synthesis of methyl trans-4-((4S)-N-methylacetamido-(2S)-pyrrolidinylmethoxy)-1-cyclohexanecarboxylate hydrochloride

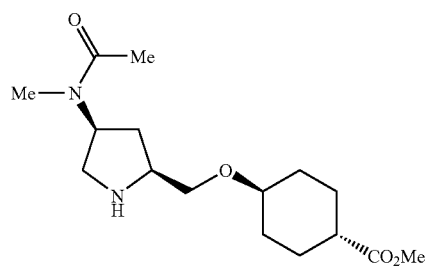

Methyl trans-4-(1-(tert-butoxycarbonyl)-(4S)-N-methylacetamido-(2S)-pyrrolidinylmethoxy)-1-cyclohexanecarboxylate (90 mg, 0.218 mmol) was dissolved in dioxane (5 ml). To the resulting solution was added a 4N HCl/dioxane solution (10 ml). The resulting mixture was stirred at room temperature for 5 hours. The reaction mixture was distilled under reduced pressure to remove the solvent, whereby methyl trans-4-((4S)-N-methylacetamido-(2S)-pyrrolidinylmethoxy)-1-cyclohexanecarboxylate hydrochloride (80 mg) was obtained as a pale yellow oil.

MS (ESI) m/z 313 (M$^+$+1).

(Step 7) Synthesis of methyl trans-4-(1-((5-chloro-2-fluoro-4-(1-methyl-3-indolylcarbonylamino)phenyl)acetyl)-(4S)-(N-methylacetamido)-(2S)-pyrrolidinylmethoxy)-1-cyclohexanecarboxylate

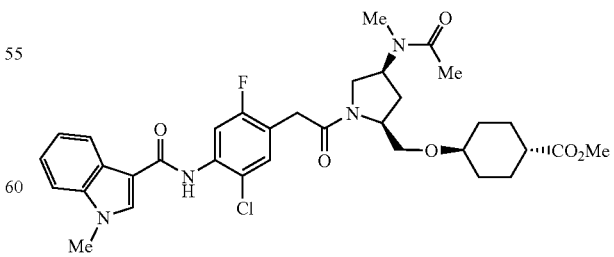

Methyl trans-4-((4S)-N-methylacetamido-(2S)-pyrrolidinylmethoxy)-1-cyclohexanecarboxylate hydrochloride (80 mg, crude) was dissolved in DMF (10 ml). To the resulting solution were added 5-chloro-2-fluoro-4-(1-methyl-3-indolylcarbonylamino)phenyl)acetic acid (79 mg, 0.218 mg), triethylamine (303 μl, 2.18 mmol), EDC HCl (63 mg, 0.327 mmoll), and HOBt (44 mg, 0.327 mmol). The resulting mixture was stirred at room temperature for 15 hours. To the reaction mixture were added ethyl acetate (100 ml) and water (100 ml) to separate an ethyl acetate layer. The ethyl acetate layer was washed with saturated brine (100 ml), dried over anhydrous magnesium sulfate, and distilled under reduced pressure to remove the solvent. The residue was purified by chromatography on a silica gel column, whereby from chloroform-methanol (10:1) eluate fractions, methyl trans-4-(1-((5-chloro-2-fluoro-4-(1-methyl-3-indolylcarbonylamino)phenyl)acetyl)-(4S)-(methylacetamido)-(2S)-pyrrolidinylmethoxy)-1-cyclohexanecarboxylate (120 mg, 84%) was obtained as a yellow thick sticky liquid.

$^1$H-NMR (CDCl$_3$) δ: 1.07–2.23 (series of m, 14H), 2.87 and 2.94 (s, each, total 3H), 3.18 (m, 2H), 3.40–3.95 (series of m, 11H), 4.25 (m, 1H), 4.36 and 5.22 (m, each, total 1H), 7.33–7.42 (m, 4H), 7.82 (s, 1H), 8.13–8.15 (m, 1H), 8.29 (s, 1H), 8.49–8.54 (m, 1H).

MS (ESI) m/z 655 (M$^+$+1).

(Step 8) Synthesis of trans-4-(1-((5-chloro-2-fluoro-4-(1-methyl-3-indolylcarbonylamino)phenyl)acetyl)-(4S)-(N-methylacetamido)-(2S)-pyrrolidinylmethoxy)-1-cyclohexanecarboxylic acid

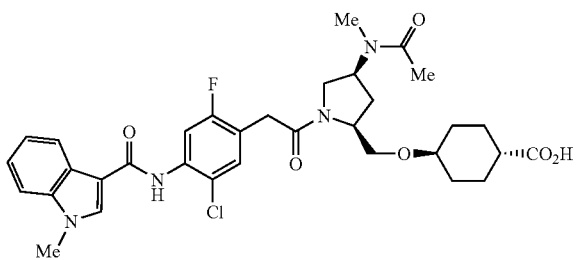

Methyl trans-4-(1-((5-chloro-2-fluoro-4-(1-methyl-3-indolylcarbonylamino)phenyl)acetyl)-(4S)-(methylacetamido)-(2S)-pyrrolidinylmethoxy)-1-cyclohexanecarboxylate (115 mg, 0.176 mmol) was dissolved in THF (5 ml). To the resulting solution was added 0.25N NaOH (4 ml, 1 mmol). After stirring at room temperature for 15 hours, the reaction mixture was poured in 1N HCl (100 ml), followed by extraction with chloroform-methanol (5:1, 2×100 ml). The extract was dried over anhydrous magnesium sulfate and distilled under reduced pressure to remove the solvent. The residue was dissolved in chloroform. Hexane was added to the resulting solution until precipitation of crystals occurred. The solid thus precipitated was collected by filtration under reduced pressure and dried to give the title compound (87 mg, 77%) as a pale yellow amorphous substance.

$^1$H-NMR (DMSO-d$_6$) δ: 1.14–1.38 (m, 4H), 1.87–2.16 (m, 10H), 2.75 and 2.91 (s, each, total 3H), 3.17–5.05 (series of m, 12H), 7.20–7.30 (m, 2H), 7.40–7.44 (m, 1H), 7.56 (d, J=8.1 Hz, 1H), 7.70 (m, 1H), 8.15 (d, J=7.8 Hz, 1H), 8.31 (s, 1H), 9.31 (s, 1H).

MS (ESI) m/z 642 (M$^+$+1);

Anal. Calcd for $C_{33}H_{38}ClFN_4O_6$, C, 61.82; H, 5.97; N, 8.74. Found: C, 59.72; H, 6.26; N, 7.68.

Example 143 trans-4-(1-(5-Chloro-2-fluoro-4-(1-methyl-3-indolylcarbonylamino)phenylacetyl)-4,4-difluoro-(2S)-pyrrolidinylmethoxy)cyclohexanecarboxylic acid and cis-4-(1-(5-chloro-2-fluoro-4-(1-methyl-3-indolylcarbonylamino)phenylacetyl)-4,4-difluoro-(2S)-pyrrolidinylmethoxy)cyclohexanecarboxylic acid (Step 1) Synthesis of methyl 4-(1-(5-chloro-2-fluoro-4-(1-methyl-3-indolylcarbonylamino)phenylacetyl)-4,4-difluoro-(2S)-pyrrolidinylmethoxy)cyclohexanecarboxylate

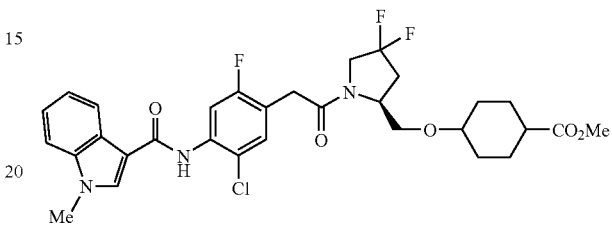

In DMF (5 ml) were dissolved (5-chloro-2-fluoro-4-((1-methyl-3-indolylcarbonylamino)phenyl)acetic acid (208 mg, 0.58 mmol) and methyl 4-(4,4-difluoro-(2S)-pyrrolidinylmethoxy)cyclohexanecarboxylate (160 mg, 0.58 mmol). To the resulting solution were added EDC HCl (167 mg, 0.87 mmol), HOBt (2.5 mg, 0.02 mmol), and DMAP (2.5 mg, 0.02 mmol), and the resulting mixture was stirred at room temperature for 14 hours. The reaction mixture was diluted with ethyl acetate. The diluted mixture was washed with saturated brine, dried over anhydrous magnesium sulfate, and distilled under reduced pressure to remove the solvent. The residue was purified by chromatography on a silica gel column, whereby from chloroform-methanol (30:1, v/v) eluate fractions, methyl 4-(1-(5-chloro-2-fluoro-4-(1-methyl-3-indolylcarbonylamino)phenylacetyl)-4,4-difluoro-(2S)-pyrrolidinylmethoxy)cyclohexanecarboxylate (a mixture of two diastereomers) (335 mg, 93%) was obtained as a pale brown crystalline powder.

IR (ATR) ν 1726, 1658, 1518 cm$^{-1}$;

$^1$H-NMR (CDCl$_3$) δ: 1.26 (m, 1H), 1.46 (m, 2H), 1.63–1.85 (series of m, total 5H), 1.99 (m, 2H), 2 35 (m, 1H), 2.55 (m, 2H), 3.51 (m, 1H), 3.58 (dd, J=10.8,6.8 Hz, 1H), 3.66 and 3.67 (s, total 3H), 3.71 (m, 1H), 3.83 (m, 1H), 3.88 (s, 3H), 4.49 (m, 1H), 7.33–7.42 (series of m, total 4H), 7.80–7.81 (series of s, total 1H), 8.00 (s, 1H), 8.12 (m, 1H), 8.30 (s, 1H), 8.49–8.55 (series of d, J=12.0 Hz, total 1H).

MS (LC-MS) m/z 621 (M$^+$1)

(Step 2) Synthesis of trans-4-(1-(5-chloro-2-fluoro-4-(1-methyl-3-indolylcarbonylamino)phenylacetyl)-4,4-difluoro-(2S)-pyrrolidinylmethoxy)cyclohexanecarboxylic acid and cis-4-(1-(5-chloro-2-fluoro-4-(1-methyl-3-indolylcarbonylamino)phenylacetyl)-4,4-difluoro-(2S)-pyrrolidinylmethoxy)cyclohexanecarboxylic acid

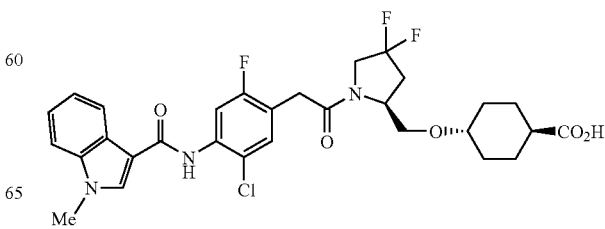

To methyl 4-(1-(5-chloro-2-fluoro-4-(1-methyl-3-indolylcarbonylamino)phenylacetyl)-4,4-difluoro-(2S)-pyrrolidinylmethoxy)cyclohexanecarboxylate (620 mg, 0.53 mmol) were added THF (4.5 ml) and 0.25N NaOH (4.5 ml). The resulting mixture was stirred at room temperature for 14 hours. The reaction mixture was distilled under reduced pressure to remove the solvent. The residue was acidified with 1N HCl, followed by extraction with chloroform-methanol (5:1, v/v). The extract was washed with saturated brine, dried over anhydrous magnesium sulfate, and distilled under reduced pressure to remove the solvent. By chromatography using a silica gel thin-layer plate (Whatman TLC), two diastereomers were separated from the residue, whereby from chloroform-methanol (40:1, v/v×3) eluate fractions, trans-4-(1-(5-chloro-2-fluoro-4-(1-methyl-3-indolylcarbonylamino)phenylacetyl)-4,4-difluoro-(2S)-pyrrolidinylmethoxy)cyclohexanecarboxylic acid (53 mg, 16%) was obtained as a white solid.

IR (ATR) ν 1653, 1518 cm$^{-1}$;
$^1$H-NMR (DMSO-d$_6$) δ: 1.11–1.31 (series of m, total 3H), 1.44 (m, 2H), 1.99 (m, 4H), 2.25 (m, 1H), 2.52 (m, 2H), 3.18 (m, 1H), 3.54 (m, 2H), 3.72 (m, 1H), 3.85 (s, 3H), 3.90 (m, 1H), 4.46 (m, 1H), 7.34 (m, 3H), 7.38 (m, 2H), 7.80 (s, 1H), 8.11 (m, 1H), 8.29 (s, 1H), 8.51 (dd, J=12.0,6.0 Hz, 1H), 8.49 and 8.50 (d, J=12.0 Hz, total 1H).

MS (ESI) m/z 607 (M$^+$+1).

The further elution gave cis-4-(1-(5-chloro-2-fluoro-4-(1-methyl-3-indolylcarbonylamino)phenylacetyl)-4,4-difluoro-(2S)-pyrrolidinylmethoxy)cyclohexanecarboxylic acid (246 mg, 67%) as a white solid.

IR (KBr) ν 1653, 1521 cm$^{-1}$;
$^1$H-NMR (DMSO-d$_6$) δ 1.47 (m, 2H), 1.65–1.86 (series of m, total 6H), 2.34 (m, 1H), 2.51–2.60 (series of m, total 2H), 3.44 (m, 2H), 3.52 and 3.58 (AB q, J=12.3 Hz, 2H), 3.75 (m, 1H), 3.83 (m, 1H), 3.85 (s, 3H), 3.93 (m, 1H), 4.49 (m, 1H), 7.34 (m, 3H), 7.39 (d, J=6.4 Hz, 2H), 7.79 and 7.81 (s, total 1H), 8.11 (m, 1H), 8.28 (s, 1H), 8.48 (d, J=12.0 Hz, 1H).

MS (ESI) m/z 607 (M$^+$+1);

Anal. Calcd for C$_{30}$H$_{31}$ClF$_3$N$_3$O$_5$ H$_2$O: C, 57.74; H, 5.33; N, 6.73. Found: C, 57.55; H, 5.06; N, 6.52.

Example 144 trans-4-((2S)-((5-Chloro-2-fluoro-4-(1-methyl-3-indolylcarbonylamino)phenyl)-N-methylacetamido)-1-propoxy)-1-cyclohexanecarboxylic acid (Step 1) Synthesis of methyl 4-((2S)-N-methylamino-1-propoxy)-1-cyclohexanecarboxylate

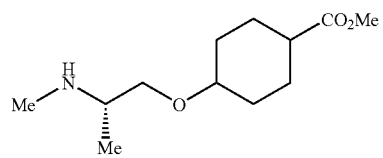

In methanol (30 ml), rhodium/alumina (2 g) was added to methyl 4-((2S)-N-methylamino-1-propoxy)benzoate (1.83 g, 8.20 mmol) and trifluoroacetic acid (1.9 ml, 24.6 mmol) and the resulting mixture was subjected to catalytic hydrogenation for 15 hours under a hydrogen gas of 20 atom. From the reaction mixture, the catalyst was filtered off and the filtrate was distilled under reduced pressure to remove the solvent. The residue was basified with a saturated aqueous solution of sodium bicarbonate, followed by extraction with chloroform (2×100 ml). The extract was dried over anhydrous magnesium sulfate and distilled under reduced pressure to remove the solvent, whereby methyl 4-((2S)-N-methylamino-1-propoxy)-1-cyclohexanecarboxylate (1.56 g, 83%) was obtained as a pale yellow oil.

$^1$H-NMR (CDCl$_3$) δ: 0.99–1.02 (m, 3H), 1.20–2.03 (series of m, 8H), 2.24–2.44 (m, 4H), 2.74 (m, 1H), 3.18–3.44 (series of m, 3H), 3.67 (m, 3H).

MS (ESI) m/z 230 (M$^+$+1).

(Step 2) Synthesis of methyl 4-((2S)-(N-(tert-butoxycarbonyl)-N-methylamino)-1-propoxy)-1-cyclohexanecarboxylate

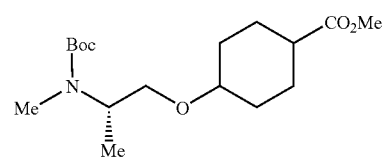

The methyl 4-((2S)-N-methylamino-1-propoxy)-1-cyclohexanecarboxylate obtained in the above-described step was dissolved in acetonitrile (25 ml) and water (25 ml). To the resulting solution were added triethylamine (1.9 ml, 13.5 mmol) and di-tert-butyl dicarbonate (2.2 g, 10.1 mmol). The resulting mixture was stirred at room temperature for 15 hours. The reaction mixture was extracted with ethyl acetate (100 ml). The extract was washed with saturated brine (100 ml), dried over anhydrous magnesium sulfate, and distilled under reduced pressure to remove the solvent. The residue was purified by chromatography on a silica gel column, whereby from hexane-ethyl acetate (4:1) eluate fractions, methyl 4-((2S)-(N-(tert-butoxycarbonyl)-N-methylamino)-1-propoxy)-1-cyclohexanecarboxylate (1.83 g, 82%) was obtained as a colorless oil.

$^1$H-NMR (CDCl$_3$) δ: 1.09–1.12 (m, 3H), 1.24–2.33 (series of m, 18H), 2.75 (m, 3H), 3.20–3.44 (m, 3H), 3.66 (m, 3H), 4.10–4.34 (m, 1H).

MS (ESI) m/z 330 (M$^+$+1).

(Step 3) Synthesis of methyl trans-4-((2S)-(N-(tert-butoxycarbonyl)-N-methylamino)-1-propoxy)-1-cyclohexanecarboxylate

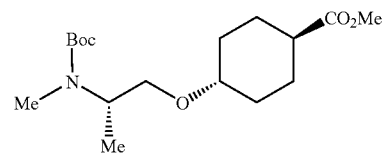

Methyl 4-((2S)-(N-(tert-butoxycarbonyl)-N-methylamino)-1-propoxy)-1-cyclohexanecarboxylate (1.83 g, 5.56 mmol) was dissolved in dry methanol (30 ml). To the resulting solution was added sodium methoxide (900 mg, 16.7 mmol) and the mixture was heated under reflux for 15 hours. After cooling to room temperature, the reaction mixture was poured in 1N HCl (100 ml), followed by extraction with ethyl acetate (2×100 ml). The extract was washed with saturated brine (100 ml), dried over anhydrous magnesium sulfate, and distilled under reduced pressure to remove the solvent. The residue was dissolved in a 20% methanol-benzene mixture (20 ml) and to the resulting solution, trimethylsilyldiazomethane (a 2.0M hexane solution) was added in portions until the disappearance of raw material carboxylic acid was confirmed on TLC. From the reaction mixture, the solvent was distilled off under reduced pressure. The residue was purified by chromatography on a silica gel column, whereby from hexane-ethyl acetate (4:1) eluate fractions, methyl trans-4-((2S)-(N-(tert-butoxycarbonyl)-N-methylamino)-1-propoxy)-1-cyclohexanecarboxylate (786 mg, 43%) was obtained as a colorless oil.

$^{1}$H-NMR (CDCl$_{3}$) δ: 1.09 (d, J=6.8 Hz, 3H), 1.21 (m, 2H), 1.46 (m, 11 H, including s, 9H, at δ: 1.46), 2.02 (m, 4H), 2.26 (m, 1H), 2.73 (br s, 3H), 3.18–3.47 (m, 3H), 3.66 (s, 3H), 4.11–4.34 (m, 1H).

MS (ESI) m/z 330 (M$^{+}$+1).

(Step 4) Synthesis of methyl trans-4-((2S)-methylamino-1-propoxy)-1-cyclohexanecarboxylate hydrochloride

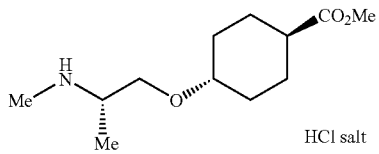

HCl salt

Methyl trans-4-((2S)-(N-(tert-butoxycarbonyl)-N-methylamino)-1-propoxy)-1-cyclohexanecarboxylate (786 mg, 2.39 mmol) was dissolved in dioxane (10 ml). To the resulting solution was added a 4N HCl/dioxane solution (15 ml). The mixture was stirred at room temperature for 15 hours. The reaction mixture was distilled under reduced pressure to remove the solvent. The residue was solidified by treating it with ether, whereby methyl trans-4-((2S)-methylamino-1-propoxy)-1-cyclohexanecarboxylate hydrochloride (500 mg, 79%) was obtained as a colorless amorphous substance.

$^{1}$H-NMR (DMSO) δ: 1.16–1.24 (m, 5H), 1.31–1.40 (m, 2H), 1.87–1.91 (m, 2H), 1.96–1.99 (m, 2H), 2.24–2.30 (m, 1H), 2.49 (s, 3H), 3.21–3.28 (m, 2H), 3.47–3.60 (series of m, 7H), 8.73 (br s, 2H).

MS (ESI) m/z 230 (M$^{+}$+1).

(Step 5) Synthesis of methyl trans-4-((2S)-((5-chloro-2-fluoro-4-(1-methyl-3-indolylcarbonylamino)phenyl)-N-methylacetamido)-1-propoxy)-1-cyclohexanecarboxylate

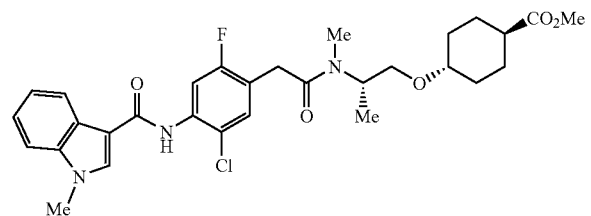

Methyl trans-4-((2S)-methylamino-1-propoxy)-1-cyclohexanecarboxylate hydrochloride (200 mg, 0.753 mmol) and (5-chloro-2-fluoro-4-(1-methyl-3-indolylcarbonylamino)phenyl)acetic acid (272 mg, 0.753 mmol) were dissolved in DMF (10 ml). To the resulting solution were added and triethylamine (523 μl, 3.76 mmol), EDC HCl (217 mg, 1.13 mmol), and HOBt (153 mg, 1.13 mmol). The resulting mixture was stirred at room temperature for 15 hours. To the reaction mixture were added ethyl acetate (100 ml) and water (100 ml) to separate it into layers. The ethyl acetate layer thus separated was washed with saturated brine (2×100 ml), dried over anhydrous magnesium sulfate, and distilled under reduced pressure to remove the solvent. The residue was purified by chromatography on a silica gel column, whereby from chloroform-methanol (10:1) eluate fractions, methyl trans-4-((2S)-((5-chloro-2-fluoro-4-(1-methyl-3-indolylcarbonylamino)phenyl)-N-methylacetamido)-1-propoxy)-1-cyclohexanecarboxylate (400 mg, 93%) was obtained as a yellow viscous oil.

$^{1}$H-NMR (CDCl$_{3}$) δ: 1.11–1.14 (m, 3H), 1.15–1.29 (m, 2H), 1.40–1.49 (m, 2H), 2.00 (m, 4H), 2.21–2.30 (m, 1H), 2.81 and 2.90 (s, each, total 3H), 3.17 (m, 1H), 3.36–3.49 (m, 2H), 3.59–3.89 (series of m, 8H, including s, 3H, at δ: 3.85), 4.12 and 4.80 (m, each, total 1H), 7.31–7.41 (m, 4H), 7.78 (d, J=1.7 Hz, 1H), 8.13 (dd, J=6.1,3.2 Hz, 1H), 8.27 (s, 1H), 8.49 (d, J=12.9 Hz, 1H).

MS (ESI) m/z 572 (M$^{+}$+1).

(Step 6) Synthesis of trans-4-((2S)-((5-chloro-2-fluoro-4-(1-methyl-3-indolylcarbonylamino)phenyl)-N-methylacetamido)-1-propoxy)-1-cyclohexanecarboxylic acid

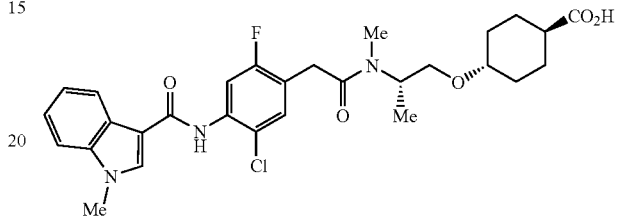

Methyl trans-4-((2S)-((5-chloro-2-fluoro-4-(1-methyl-3-indolylcarbonylamino)phenyl)-N-methylacetamido)-1-propoxy)-1-cyclohexanecarboxylate (400 mg, 0.699 mmol) was dissolved in THF (10 ml). To the resulting solution was added 0.25N NaOH (5.6 ml, 1.40 mmol). The resulting mixture was stirred at room temperature for 15 hours. The reaction mixture was poured in 1N HCl (50 ml), followed by extraction with chloroform (2×100 ml). The extract was dried over anhydrous magnesium sulfate and distilled under reduced pressure to remove the solvent. The residue was dissolved in chloroform. Hexane was added to the resulting solution in portions to cause crystallization. The crystals thus precipitated were collected by filtration under reduced pressure and dried to give the title compound (260 mg, 67%) as a colorless amorphous substance.

$^{1}$H-NMR (DMSO-d$_{6}$) δ: 1.01–1.34 (series of m, 7H), 1.89 (m, 4H), 2.15 (m, 1H), 2.70 and 2.90 (s, each, total 3H, due to double bond character of the C(O)—N bond in amide), 3.21–3.92 (series of m, 8H), 4.18 and 4.61 (m, each, 1H, due to double bond character of the C(O)—N bond in amide), 7.20–7.69 (series of m, 5H), 8.16 (m, 1H), 8.31 (s, 1H), 9.30 (s, 1H), 12.04 (s, 1H).

MS (FAB) m/z 558 (M$^{+}$+1);

Anal. Calcd for C$_{29}$H$_{33}$ClFN$_{3}$O$_{5}$: C, 62.42; H, 5.96; N, 7.53. Found: C, 62.09; H, 6.09; N, 7.26.

Example 145 trans-4-((2S)-((7-Fluoro-2-((5-fluoro-2-methylphenyl)amino)-6-benzoxazolyl)-N-methylacetamido)-1-propoxy)-1-cyclohexanecarboxylic acid (Step 1) Synthesis of methyl trans-4-((2S)-((7-fluoro-2-((5-fluoro-2-methylphenyl)amino)-6-benzoxazolyl)-N-methylacetamido)-1-propoxy)-1-cyclohexanecarboxylate

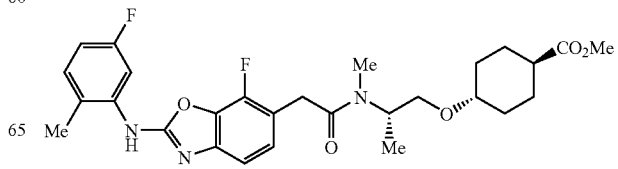

In DMF (10 ml), triethylamine (523 µl, 3.76 mmol), EDC HCl (217 mg, 1.13 mmol), and HOBt (153 mg, 1.13 mmol) were added to methyl trans-4-((2S)-N-methylamino-1-propoxy)-1-cyclohexanecarboxylate hydrochloride (200 mg, 0.753 mmol) and methyl 7-fluoro-2-((5-fluoro-2-methylphenyl)amino)-6-benzoxazolyl)acetate (239 mg, 0.753 mmol) and the resulting mixture was stirred at room temperature for 15 hours. To the reaction mixture were added ethyl acetate (100 ml) and water (100 ml) to separate it into layers. The ethyl acetate layer thus obtained was washed with saturated brine (2×100 ml), dried over anhydrous magnesium sulfate, and distilled under reduced pressure to remove the solvent. The residue was purified by chromatography on a silica gel column, whereby from chloroform-methanol (20:1) eluate fractions, methyl trans-4-((2S)-((7-fluoro-2-((5-fluoro-2-methylphenyl)amino)-6-benzoxazolyl)-N-methylacetamido)-1-propoxy)-1-cyclohexanecarboxylate (399 mg, 100%) was obtained as a yellow viscous oil.

$^1$H-NMR (CDCl$_3$) δ: 1.08–1.48 (m, 7H), 1.99 (m, 4H), 2.28 (m, 4H), 2.77–3.94 (series of m, 11H), 4.19 and 4.83 (m, each, total 1H), 6.73 (m, 1H), 7.03–7.21 (m, 3H), 7.44 (m, 1H), 8.00–8.04 (m 1H).

MS (ESI) m/z 572 (M$^+$+1).

(Step 2) Synthesis of trans-4-((2S)-((7-fluoro-2-((5-fluoro-2-methylphenyl)amino)-6-benzoxazolyl)-N-methylacetamido)-1-propoxy)-1-cyclohexanecarboxylic acid

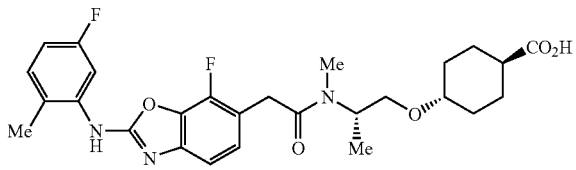

Methyl trans-4-((2S)-(7-fluoro-2-((5-fluoro-2-methylphenyl)amino)-6-benzoxazolyl)-N-methylacetamido)-1-propoxy)-1-cyclohexanecarboxylate (399 mg, 0.753 mmol) was dissolved in THF (10 ml). To the resulting solution was added 0.25N NaOH (6 ml, 1.50 mmol). The resulting mixture was stirred at room temperature for 15 hours. The reaction mixture was poured in 1N HCl (50 ml), followed by extraction with chloroform (2×100 ml). The extract was dried over anhydrous magnesium sulfate and distilled under reduced pressure to remove the solvent. The residue was dissolved in chloroform. Hexane was added until the precipitation of a solid occurred. The precipitate thus obtained was collected by filtration under reduced pressure and dried to give the title compound (210 mg, 54%) as a colorless amorphous substance.

$^1$H-NMR (DMSO-d$_6$) δ: 1.00–1.40 (series of m, 7H), 1.89 (m, 4H), 2.15 (m, 1H), 2.30 (s, 3H), 2.69 and 2.90 (s, each, total 3H, due to double bond character of the C(O)—N in amide), 3.19 (m, 1H), 3.33–3.47 (m, 4H), 3.73–3.84 (m, 2H), 4.19 and 4.63 (m, each, total 1H, due to double bond character of the C(O)—N in amide), 6.89 (dt, J=8.3,2.7 Hz, 1H), 7.03 and 7.07 (t, J=7.8 Hz, total 1H, due to double bond character of the C(O)—N in amide), 7.21 (d, J=7.8 Hz, 1H), 7.27 (t, J=7.8 Hz, 1H), 7.94 (dd, J=11.5,2.5 Hz, 1H), 10.04 (br s, 1H), 12.06 (br s, 1H).

MS (FAB) m/z 516 (M$^+$+1);

Anal. Calcd for C$_{27}$H$_{31}$F$_2$N$_3$O$_5$: C, 62.90; H, 6.06; N, 8.15. Found: C, 62.92; H, 6.25; N, 7.86.

Example 146

4-(1-((2-(5-Fluoro-2-methylphenylamino)-6-benzoxazolyl)acetyl)-(4S)-fluoro-(2S)-pyrrolidinylmethoxy) benzoic acid (Step 1) Synthesis of methyl (2-(5-fluoro-2-methylphenylamino)-6-benzoxazolyl)acetate

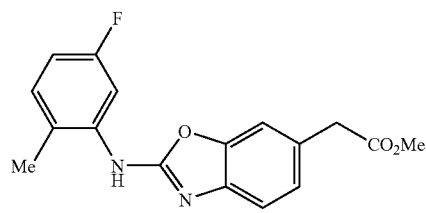

In methanol (50 ml), 5-fluoro-2-methylphenyl isothiocyanate (2.00 g, 12.0 mmol) was added to methyl 4-amino-3-hydroxyphenylacetate (2.17 g, 12.0 mmol) and the resulting mixture was stirred at room temperature for 27 hours. Mercuric oxide (yellow) (3.12 g, 14.4 mmol) was added to the reaction mixture, followed by stirring at 70° C. for 4 hours. After cooling to room temperature, the reaction mixture was filtered through Celite, followed by washing with methanol. The filtrate was distilled under reduced pressure to remove the solvent. The residue was purified by chromatography on a silica gel column, whereby from chloroform/ethyl acetate (10/1) eluate fractions, methyl (2-(5-fluoro-2-methylphenylamino)-6-benzoxazolyl)acetate (1.73 g, 46%) was obtained as a brown oil.

$^1$H-NMR (CDCl$_3$) δ: 2.13 (s, 3H), 3.705 (s, 2H), 3.711 (s, 3H), 6.74 (dt, J=8.3,2.7 Hz, 1H), 6.81 (br, 1H), 7.15 (dd, J=8.1, 1.7 Hz, 2H), 7.31 (d, J=1.2 Hz, 1H), 7.44 (d, J=8.1 Hz, 1H), 8.09 (dd, J=11.0,2.7 Hz, 1H).

MS (ESI) m/z 315 (M$^+$+1).

(Step 2) Synthesis of (2-(5-fluoro-2-methylphenylamino)-6-benzoxazolyl)acetic acid

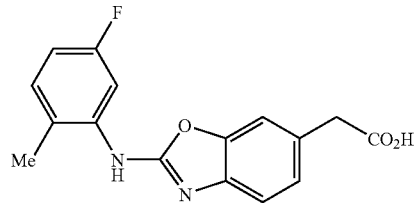

Methyl (2-(5-fluoro-2-methylphenylamino)-6-benzoxazolyl)acetate (1.73 g, 5.50 mmol) was dissolved in THF/methanol (2:1, 30 ml). To the resulting solution was added 1N NaOH (20 ml) and the mixture was stirred at room temperature for 3.5 hours. The reaction mixture was distilled under reduced pressure to remove the solvent. The residue was acidified with 1N HCl. The crystals thus precipitated were collected by filtration under reduced pressure, washed with water and dried under reduced pressure to give (2-(5-fluoro-2-methylphenylamino)-6-benzoxazolyl)acetic acid (1.60 g, 97%) was obtained as a colorless crystalline powder.

$^1$H-NMR (DMSO-d$_6$) δ: 2.49 (s, 3H), 3.64 (d, J=1.7 Hz, 2H), 6.87 (dt, J=8.3,1.5 Hz, 1H), 7.11 (d, J=8.1 Hz, 1H), 7.25 (t, J=7.3 Hz, 1H), 7.37 (d, J=8.1 Hz, 1H), 7.41 (s, 1H), 7.95 and 7.98 (each s, total 1H, amide isomers), 9.80 (br, 1H).

MS (ESI) m/z 301 (M⁺+1).

(Step 3) Synthesis of methyl 4-(1-((2-(5-fluoro-2-methylphenylamino)-6-benzoxazolyl)acetyl)-(4S)-fluoro-(2S)-pyrrolidinylmethoxy)benzoate

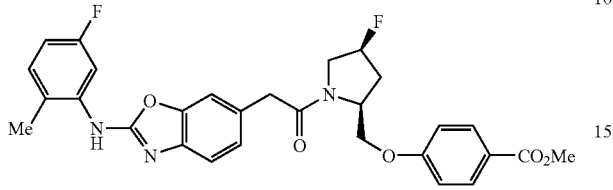

In DMF (5 ml), (2-(5-fluoro-2-methylphenylamino)-6-benzoxazoyl)acetic acid (300 mg, 1.0 mmol), methyl 4-((4S)-fluoro-(2S)-pyrrolidinylmethoxy)benzoate (253 mg, 1.0 mmol), EDC HCl (288 mg, 1.5 mmol), HOBt (203 mg, 1.5 mmol) and triethylamine (0.70 ml, 5.0 mmol) were stirred at room temperature for 17 hours. The reaction mixture was poured into ice water, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane/ethyl acetate (1/4) eluate fractions, methyl 4-(1((2-(5-fluoro-2-methylphenylamino)-6-benzoxazolyl)acetyl)-(4S)-fluoro-(2S)-pyrrolidinylmethoxy)benzoate (630 mg, 100%) was obtained as a colorless amorphous substance.

¹H-NMR (CDCl₃) δ: 2.05–2.62 (m, 5H), 3.73 (d, J=3.9 Hz, 2H), 3.80 (m, 1H), 3.86 (s, 3H), 3.90–4.10 (m, 2H), 4.46–4.68 (m, 2H), 5.23–5.38 (m, 1H), 6.73 (dt, J=8.1,2.4 Hz, 1H), 6.86 and 6.98 (each d, each J=8.8 Hz, total 2H, amide isomers), 7.12 (m, 3H), 7.26 (s, 1H), 7.29 (t, J=9.0 Hz, 1H), 7.43 (t, J=8.1 Hz, 1H), 7.95 and 7.99 (each d, each J=8.8 Hz, total 2H, amide isomers), 8.05 and 8.08 (each s, total 1H, amide isomers).

MS (ESI) m/z 536 (M⁺+1).

(Step 4) Synthesis of 4-(1-((2-(5-fluoro-2-methylphenylamino)-6-benzoxazolyl)acetyl)-(4S)-fluoro-(2S)-pyrrolidinylmethoxy)benzoic acid

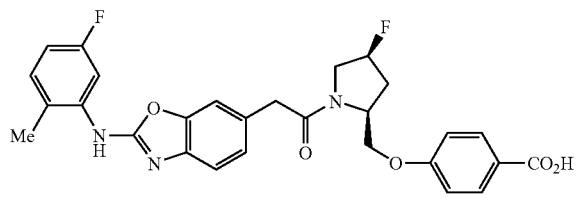

Methyl 4-(1-((2-(5-fluoro-2-methylphenylamino)-6-benzoxazolyl)acetyl)-(4S)-fluoro-(2S)-pyrrolidinylmethoxy) benzoate (630 mg, 1.0 mmol) was dissolved in THF/methanol (20/10 ml). To the resulting solution was added 1N NaOH (20 ml). The resulting mixture was stirred at room temperature for 23 hours. From the reaction mixture, the solvent was distilled off under reduced pressure. The residue was acidified with 1N HCl. The crystals thus precipitated were collected by filtration under reduced pressure, washed with water and dried under reduced pressure to give the title compound (501 mg, 96%) as a pale pink solid.

IR (ATR) ν 2983, 1684, 1639, 1604, 1576, 1541, 1508, 1423 cm⁻¹;

¹H-NMR (DMSO-d₆) δ: 2.24 (m, 2H), 2.30 (s, 3H), 3.67–4.10 (m, 5H), 4.21–4.71 (m, 2H), 5.38 and 5.45 (each d, J=54.6 and 53.1 Hz respectively, total 1H, amide isomers), 6.87 (dt, J=8.5,2.2 Hz, 1H), 7.03–7.13 (m, 3H), 7.25 (t, J=7.6 Hz, 1H), 7.36 and 7.39 (each s, total 2H, amide isomers), 7.87 (dd, J=9.0,2.2 Hz, 2H), 7.95 (d, J=11.0 Hz, 1H), 9.80 (br, 1H).

MS (ESI) m/z 522 (M⁺+1).

Anal. Calcd for C₂₈H₂₅FN₃O₅.0.7H₂O.0.4HCl: C, 61.29; H, 4.92; N, 7.66; Cl, 2.58; F, 6.92. Found: C, 61.13; H, 4.74; N, 7.38; Cl, 2.57; F, 6.87.

Example 147

4-(1-((3-Chloro-4-((1-methyl-3-indolylcarbonyl)amino)phenyl)acetyl)-(4S)-fluoro-(2S)-pyrrolidinylmethoxy)benzoic acid (Step 1) Synthesis of ethyl (3-chloro-4-((1-methyl-3-indolylcarbonyl)amino)phenyl)acetate

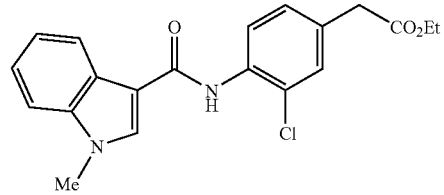

In DMF (20 ml), EDC HCl (1.44 g, 7.49 mmol) was added to 1-methyl-3-indolylcarboxylic acid (1.01 g, 5.71 mmol), ethyl 4-amino-3-chlorophenylacetate (1.22 g, 5.71 mmol), HOBt (0.86 g, 6.34 mmol), and DMAP (0.14 g, 1.15 mmol) and the resulting mixture was stirred at 70° C. for 18 hours. After cooling to room temperature, the reaction mixture was added with water, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (1:1, v/v) eluate fractions, ethyl (3-chloro-4-((1-methyl-3-indolylcarbonyl)amino)phenyl) acetate (639 mg, 30%) was obtained as a yellow solid.

¹H-NMR (CDCl₃) δ: 1.27 (t, J=7.1 Hz, 3H), 3.58 (s, 2H), 3.89 (s, 3H), 4.17 (q, J=7.1 Hz, 2H), 7.24 (dd, J=8.3,2.0 Hz, 1H), 7.32–7.43 (m, 4H), 7.81 (s, 1H), 8.16 (m, 1H), 8.28 (broad s, 1H), 8.59 (d, J=8.3 Hz, 1H).

MS (ESI) m/z 371 (M⁺+1).

(Step 2) Synthesis of (3-chloro-4-((1-methyl-3-indolylcarbonyl)amino)phenyl)acetic acid

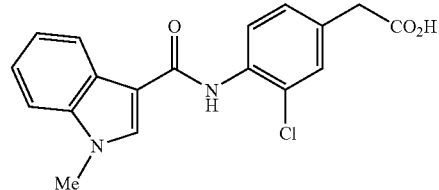

Ethyl (3-chloro-4-((1-methyl-3-indolylcarbonyl)amino) phenyl)acetate (639 mg, 1.72 mmol) was dissolved in THF (17.5 ml). To the resulting solution was added 0.25N NaOH (10.3 ml, 2.58 mmol), followed by stirring at room temperature for 4 hours. The reaction mixture was poured in 1N HCl (15 ml). The crystals thus precipitated were collected by filtration under reduced pressure, washed with water and dried under reduced pressure to give (3-chloro-4-((1-methyl-3-indolylcarbonyl)amino)phenyl)acetic acid (549 mg, 93%) as a colorless solid.

$^1$H-NMR (DMSO-$d_6$) δ: 3.61 (s, 2H), 3.89 (s, 3H), 7.17–7.28 (m, 3H), 7.43 (d, J=1.7 Hz, 1H), 7.53 (d, J=8.3 Hz, 1H), 7.69 (d, J=8.3 Hz, 1H), 8.14 (d, J=7.8 Hz, 1H), 8.26 (s, 1H), 9.26 (s, 1H).

(Step 3) Synthesis of methyl 4-(1-((3-chloro-4-((1-methyl-3-indolylcarbonyl)amino)phenyl)acetyl)-(4S)-fluoro-(2S)-pyrrolidinylmethoxy)benzoate

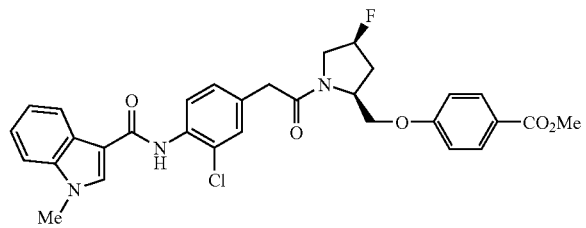

In DMF (5.0 ml), EDC HCl (161 mg, 0.84 mmol) was added to (3-chloro-4-((1-methyl-3-indolylcarbonyl)amino)phenyl)acetic acid (240 mg, 0.70 mmol), methyl 4-((4S)-fluoro-(2S)-pyrrolidinylmethoxy)benzoate (177 mg, 0.70 mmol), HOBt (114 mg, 0.84 mmol), and DMAP (17.0 mg, 0.14 mmol) and the resulting mixture was stirred at room temperature for 24 hours. Water was added to the reaction mixture, followed by extraction with ethyl acetate. The extract was washed with saturated brine, dried over anhydrous sodium sulfate, and distilled under reduced pressure to remove the solvent. The residue was purified by chromatography on a silica gel column, whereby from ethyl acetate eluate fractions, methyl 4-(1-((3-chloro-4-((1-methyl-3-indolylcarbonyl)amino)phenyl)acetyl)-(4S)-fluoro-(2S)-pyrrolidinylmethoxy)benzoate (176 mg, 43%) was obtained as a pale yellow amorphous substance.

$^1$H-NMR (CDCl$_3$) δ: 2.03–2.69 (m, 2H), 3.59 (d, J=15.2 Hz, 1H), 3.64 (d, J=15.2 Hz, 1H), 3.68–4.19(m, 9H, including singlet, 3H, at δ: 3.86, and singlet, 3H, at δ: 3.87), 4.47–4.63 (m, 2H), 5.36 (m, 1H), 6.98 (d, J=8.8 Hz, 2H), 7.18 (d, J=8.3 Hz, 1H), 7.32–7.42 (m, 4H), 7.80 (s, 1H), 7.95 (d, J=8.8 Hz, 2H), 8.13 (m, 1H), 8.27 (broad s, 1H), 8.56 (m, 1H).

MS (ESI) m/z 578 (M$^+$+1).

(Step 4) Synthesis of 4-(1-((3-chloro-4-((1-methyl-3-indolylcarbonyl)amino)phenyl)acetyl)-(4S)-fluoro-(2S)-pyrrolidinylmethoxy)benzoic acid

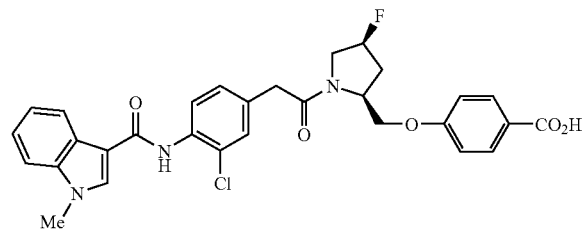

Methyl 4-(1-((3-chloro-4-((1-methyl-3-indolylcarbonyl)amino)phenyl)acetyl)-(4S)-fluoro-(2S)-pyrrolidinylmethoxy)benzoate (176 mg, 0.30 mmol) was dissolved in THF (3.0 ml). To the resulting solution was added 0.25N NaOH (1.83 ml, 0.45 mmol). The resulting mixture was stirred at room temperature for 19 hours and at 60° C. for 5 hours. The reaction mixture was poured in 1N HCl (5.0 ml). The crystals thus precipitated were collected by filtration under reduced pressure, washed with water and dried under reduced pressure precipitate to give the title compound (120 mg, 71%) as a colorless solid.

IR (ATR) ν 1708, 1650, 1604, 1579, 1511, 1469 cm$^{-1}$;

$^1$H-NMR (DMSOd$_6$) δ: 2.26–2.33 (m, 2H), 3.69 (d, J=15.9 Hz, 1H), 3.75 (d, J=15.9 Hz, 1H), 3.80–3.97 (m, 7H, including singlet, 3H, at δ: 3.89), 4.40–4.44 (m, 2H), 5.46 (m, 1H), 7.07 (d, J=8.8 Hz, 2H), 7.18–7.28 (m, 2H), 7.39 and 7.42 (each broad s, total 1H), 7.53 (d, J=8.1 Hz, 1H), 7.70 (d, J=8.1 Hz, 1H), 7.87 (d, J=8.8 Hz, 2H), 8.14 (d, J=7.8 Hz, 1H), 8.26 (s, 1H), 9.26 (s, 1H), 12.60 (broad s, 1H).

MS (ESI) m/z 564 (M$^+$+1);

Anal. Calcd for $C_{30}H_{27}ClFN_3O_5$: C, 63.89; H, 4.83; N, 7.45. Found: C, 63.50; H, 5.01; N, 7.13.

Example 148

3-Amino-4-((4S)-fluoro-1-((2-methylphenylamino)-6-benzoxazolylacetyl)-(2S)-pyrrolidinylmethoxy)benzoic acid (Step 1) Synthesis of methyl 4-((4S)-fluoro-1-((2-methylphenylamino)-6-benzoxazolylacetyl)-(2S)-pyrrolidinylmethoxy)-3-nitrobenzoate

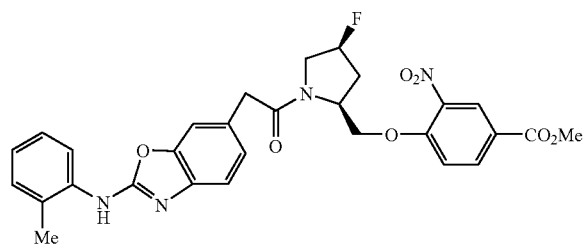

In DMF (10 ml) were dissolved ((2-methylphenylamino)-6-benzoxazolyl)acetic acid (391 mg, 1.38 mmol) and methyl 4-((4S)-fluoro-(2S)-pyrrolidinylmethoxy)-3-nitrobenzoate (412 mg, 1.38 mmol). To the resulting solution were added EDC HCl (405 mg, 2.11 mmol), HOBt (2.5 mg, 0.02 mmol), and DMAP (2.5 mg, 0.02 mmol), and the resulting mixture was stirred at room temperature for 18 hours. To the reaction mixture was added water, followed by extraction with ethyl acetate. The extract was washed with saturated brine, dried over anhydrous sodium sulfate, and distilled under reduced pressure to remove the solvent. The residue was purified by chromatography on a silica gel column, whereby from chloroform-methanol (20:1, v/v) eluate fractions, methyl 4-((4S)-fluoro-1-((2-methylphenylamino)-6-benzoxazolylacetyl)-(2S)-pyrrolidinylmethoxy-3-nitrobenzoate (460 mg, 59%) was obtained as a yellow solid.

$^1$H-NMR (CDCl$_3$) δ: 2.12 (m, 2H), 2.34 (s, 3H), 2.67 (d, J=17.2 Hz, 1H), 3.73 (m, 1H), 3.82 (m, 1H), 3.92 (s, 3H), 4.03 (m, 1H), 4.11 (m, 1H), 4.58 (br, 1H), 4.72 (br, 1H), 5.31 (d, J=58.1 Hz, 1H), 6.73 (m, 1H), 6.94 (m, 1H), 7.09 (m, 2H), 7.25 (m, 2H), 7.32 (m, 3H), 8.08 (m, 1H), 8.16 (m, 1H).

(Step 2) Synthesis of methyl 3-amino-4-((4S)-fluoro-1-((2-methylphenylamino)-6-benzoxazolylacetyl)-(2S)-pyrrolidinylmethoxy)benzoate

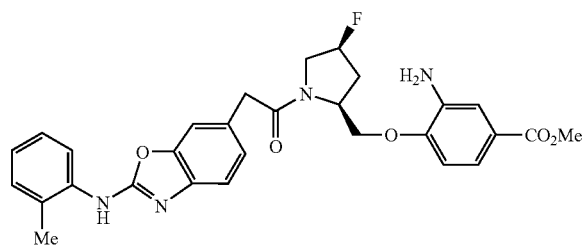

In ethanol (5 ml) and THF (2 ml), methyl 4-((4S)-fluoro-1-((2-methylphenylamino-6-benzoxazolylacetyl)-(2S)-pyrrolidinylmethoxy-3-nitrobenzoate (460 mg, 0.82 mmol) and 5% palladium-carbon (500 mg) were subjected to catalytic hydrogenation for 60 hours under normal pressure. From the reaction mixture, the catalyst was filtered off and the filtrate was distilled under reduced pressure to remove the solvent. The residue was purified by chromatography on a silica gel column, whereby from chloroform-methyl ester (10:1, v/v) eluate fractions, methyl 3-amino-4-((4S)-fluoro-1-((2-methylphenylamino)-6-benzoxazolylacetyl)-(2S)-pyrrolidinylmethoxy)benzoate (192 mg, 44%) was obtained as a brown solid.

IR (KBr) ν 1708, 1639, 1573 cm$^{-1}$;

$^1$H-NMR (CDCl$_3$) δ: 2.12 (m, 2H), 2.36 (s, 3H), 2.47 (dd, J=16.0,21.5 Hz, 1H), 3.73 (m, 2H), 3.84 (s, 3H), 4.11 (br, 1H), 4.16 (m, 1H), 4.40 (dd, J=4.8,8.8 Hz, 1H), 4.49 (br, 1H), 4.73 (br, 1H), 5.33 (series of dt, J=4.4,52.8 Hz, total 1H), 6.90 (m, 1H), 7.08 (d, J=7.2 Hz, 2H), 7.23 (m, 2H), 7.30 (d, J=7.2 Hz, 1H), 7.36 (dd, J=11.2,12.8 Hz, 1H), 7.43 (m, 1H), 8.09 (d, J=8.0 Hz, 2H).

MS (ESI) m/z 533 (M$^+$+H);

Anal. Calcd for C$_{29}$H$_{29}$FN$_4$O$_5$ 2.5H$_2$O: C, 60.30; H, 5.93; N, 9.70. Found: C, 60.48; 11.2, H, 5.13; N, 9.26.

(Step 3) Synthesis of 3-amino-4-((4S)-fluoro-1-((2-methylphenylamino)-6-benzoxazolylacetyl)-(2S)-pyrrolidinylmethoxy)benzoic acid

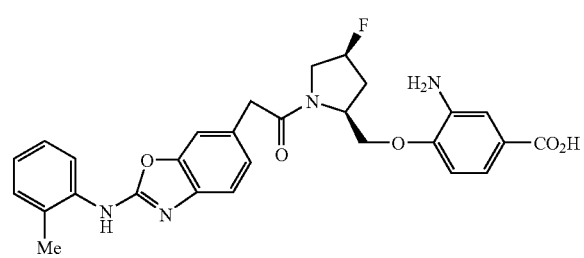

Methyl 3-amino-4-((4S)-fluoro-1-((2-methylphenylamino-6-benzoxazolylacetyl)-(2S)-pyrrolidinylmethoxy)benzoate (191 mg, 0.36 mmol) was dissolved in THF (3 ml).

To the resulting solution was added 0.25N NaOH (3 ml), and the resulting mixture was heated under reflux for 5 hours. After cooling, the reaction mixture was concentrated under reduced pressure to remove the solvent and the residue was diluted with a chloroform-methanol mixture (5:1, v/v). The solution was washed with 1N HCl, dried over anhydrous magnesium sulfate, and distilled under a reduced pressure to remove the solvent. The residue was purified by chromatography on a silica gel column, whereby from chloroform-methanol (5:1, v/v) eluate fractions, the title compound (76 mg, 41%) was obtained as a brown solid.

IR (ATR) ν 1639, 1573 cm$^{-1}$;

$^1$H-NMR (DMSO-d$_6$) δ: 2.27 (s, 3H), 2.49 (s, 1H), 3.7–4.1 (series of m, total 4H), 4.24 (m, 2H), 4.46 (m, 2H), 5.42 (series of d, J=53.2 Hz, total 1H), 6.86 (d, J=8.0 Hz, 1H), 7.04 (t, J=14.4 Hz, 2H), 7.05 (s, 1H), 7.14 (m, 1H), 7.22 (m, total 3H), 7.33 (d, J=5.6 Hz, 1H), 7.78 (d, J=8.4 Hz, 2H), 9.67 (br, 1H).

MS (ESI) 519 (M$^+$+1).

Example 149

4-(1-(3-Chloro-4-((1-methyl-3-indolylcarbonyl)amino)phenylacetyl)-(4S)-fluoro-(2S)-pyrrolidinylmethoxy)-2-methoxybenzoic acid (Step 1) Synthesis of ethyl 4-(1-(3-chloro-4-((1-methyl-3-indolylcarbonyl)amino)phenylacetyl)-(4S)-fluoro-(2S)-pyrrolidinylmethoxy)-2-methoxybenzoate

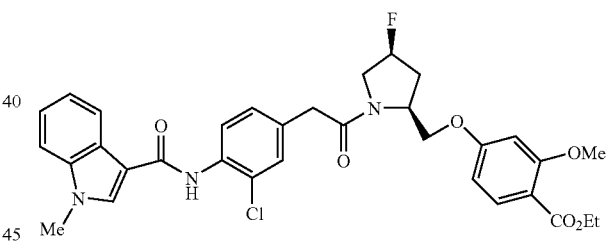

In DMF (14 ml), EDC HCl (173.2 mg, 0.904 mmol) was added to ethyl 4-((4S)-fluoro-(2S)-pyrrolidinylmethoxy)-2-methoxybenzoate (179.1 mg, 0.602 mmol), 3-chloro-4-((1-methyl-3-indolylcarbonyl)amino)phenylacetic acid (206.4 mg, 0.602 mmol) and HOBt (32.6 mg, 0.241 mmol) and the resulting mixture was stirred at room temperature for 18 hours. The reaction mixture was diluted with ethyl acetate. The diluted mixture was washed successively with 1N HCl and a saturated aqueous solution of sodium bicarbonate, dried over anhydrous sodium sulfate, and distilled under reduced pressure to remove the solvent. The residue was purified by chromatography on a silica gel column, whereby from chloroform-methanol (25:1, v/v) eluate fractions, ethyl 4-(1-(3-chloro-4-((1-methyl-3-indolylcarbonyl)amino)phenylacetyl)-(4S)-fluoro-(2S)-pyrrolidinylmethoxy)-2-methoxybenzoate (100%) was obtained as an amorphous substance.

$^1$H-NMR (CDCl$_3$) δ: 1.35 (3H, t, J=7.6 Hz, OCH$_2$Me), 1.72–2.70 (total 2H, series of m), 3.52–4.18 (total 11H, series of m, including 3H, s, at δ: 3.34 and 3H, s at δ: 3.92), 4.30 (2H, q, J=7.6 Hz, OCH$_2$Me), 4.50–4.66 (2H, m), 5.31 (1H, d, J=52.4 Hz), 6.40–6.64 (total 2H, m), 7.20 (1H, m), 7.29–7.45 (4H, m), 7.75–7.88 (2H, m), 8.14 (1H, m), 8.25 (1H, m), 8.57 (1H, m).

Example 150

6-(1-(3-Chloro-4-(1-methyl-3-indolyl)carbonylaminophenylacetyl)-(4S)-fluoro-(2S)-pyrrolidinylmethoxy)nicotinic acid (Step 1) Synthesis of methyl 6-(1-(3-chloro-4-(1-methyl-3-indolyl)carbonylaminophenylacetyl)-(4S)-fluoro-(2S)-pyrrolidinylmethoxy)nicotinate

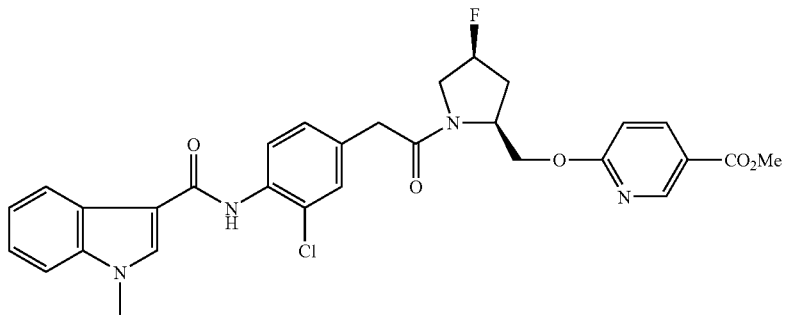

(Step 2) Synthesis of 4-(1-(3-chloro-4-((1-methyl-3-indolylcarbonyl)amino)phenylacetyl)-(4S)-fluoro-(2S)-pyrrolidinylmethoxy)-2-methoxybenzoic acid

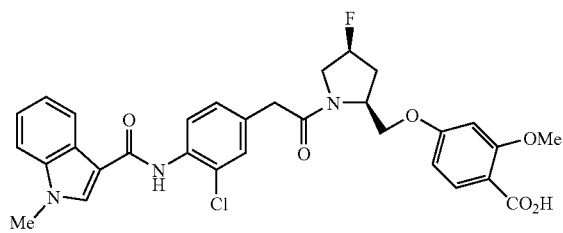

Ethyl 4-(1-(3-chloro-4-((1-methyl-3-indolylcarbonyl)amino)phenylacetyl)-(4S)-fluoro-(2S)-pyrrolidinylmethoxy)-2-methoxybenzoate (374.6 mg, 0.602 mmol) was dissolved in THF (8.0 ml). To the resulting solution was added 0.25N NaOH (8.0 ml), followed by stirring at room temperature for 18 hours. The reaction mixture was concentrated. The concentrate was then neutralized with 1N HCl (2.5 ml). The crystals thus precipitated were collected by filtration under reduced pressure, washed with water and dried at 50° C. under reduced pressure to give the title compound (345.8 mg, 97%) as an amorphous substance.

IR (ATR) ν1608, 1511 cm$^{-1}$;

$^1$H-NMR (DMSO-d$_6$) δ 2.15–2.40 (2H, m), 3.40–4.78 (total 13H, m, including 3H, s at δ: 3.84 and 3H, s at δ: 3.91), 5.42, 5.49 (total 1H, br d, J=52.0 Hz), 6.50–6.80 (2H, m), 7.23 (3H, m), 7.44 (1H, d, J=10.0 Hz), 7.57 (1H, d, J=10.0 Hz), 7.70 (2H, m), 8.16 (1H, m), 8.29 (1H, s), 9.32 (1H, m), 12.15 (1H, br s, CO$_2$H).

MS (ESI) m/z 594 (M$^+$+1);

Anal. Calcd for C$_{31}$H$_{29}$ClFN$_3$O$_6$·H$_2$O: C, 60.83; H, 5.11; N, 6.87; Cl, 5.79; F, 3.10. Found: C, 60.53; H, 5.01; N, 6.71; Cl, 5.69; F, 3.09.

Methyl 6-(1-tert-butoxycarbonyl-(4S)-fluoro-(2S)-pyrrolidinylmethoxy)nicotinate (197 mg, 0.50 mmol) was dissolved in methylene chloride (10 ml). Under stirring at 0° C., trifluoroacetic acid (10 ml) was added and the resulting mixture was stirred at room temperature for 30 minutes. From the reaction mixture, the solvent was distilled off under reduced pressure. To the residue was added a saturated aqueous solution of sodium bicarbonate, followed by extraction with methylene chloride. The extract was washed with saturated brine, dried over anhydrous sodium sulfate, and distilled under reduced pressure to remove the solvent. The residue was provided for the subsequent reaction without further purification. In THF (5.0 ml) and acetonitrile (5.0 ml), EDC·HCl (144 mg, 0.75 mmol) was added to the resulting compound, (3-chloro-4-(1-methyl-3-indolyl)carbonylaminophenyl)acetic acid (171 mg, 0.5 mmol), HOBt (70 mg, 0.5 mmol), and triethylamine (208 μl, 1.5 mmol) at 0° C. The resulting mixture was stirred at room temperature for 16 hours. Water was added to the reaction mixture, followed by extraction with ethyl acetate. The extract was washed with a saturated aqueous solution of sodium bicarbonate and a 2M aqueous solution of citric acid, dried over anhydrous sodium sulfate, and distilled under reduced pressure to remove the solvent. The residue was purified by chromatography using a silica gel thin-layer plate (TLC), whereby from chloroform-methanol (95:5, v/v) eluate fractions, methyl 6-(1-(3-chloro-4-(1-methyl-3-indolyl)carbonylaminophenylacetyl)-(4S)-fluoro-(2S)-pyrrolidinylmethoxy)nicotinate (330 mg, 100%) was obtained as a colorless oil.

$^1$H-NMR (CDCl$_3$) δ: 2.10–2.55 (m, 2H), 3.55–4.05 (m, 10H), 4.25–4.85 (m, 3H), 5.24–5.37 (m, 1H), 6.78 (t, J=8.8 Hz, 1H), 7.25–7.44 (m, 5H), 7.80 (d, J=4.6 Hz, 1H), 8.13–8.25 (m, 3H), 8.54–8.59 (m, 1H), 8.80–8.86 (m, 1H).

(Step 2) Synthesis of 6-(1-(3-chloro-4-(1-methyl-3-indolyl)carbonylaminophenylacetyl)-(4S)-fluoro-(2S)-pyrrolidinylmethoxy)nicotinic acid

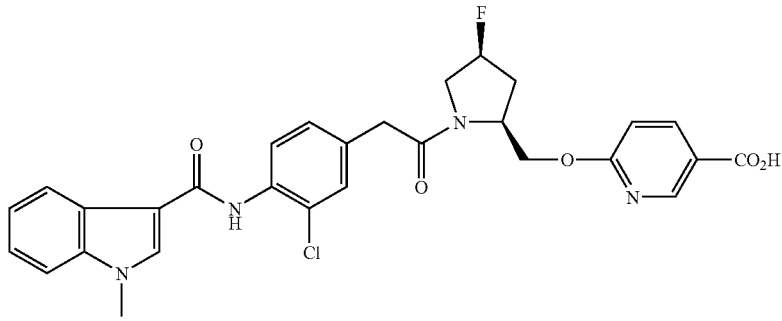

Methyl 6-(1-(3-chloro-4-(1-methyl-3-indolyl)carbonylaminophenylacetyl)-(4S)-fluoro-(2S)-pyrrolidinylmethoxy)nicotinate (330 mg, 0.5 mmol) was dissolved in THF (10 ml) and methanol (15 ml). To the resulting solution was added 1N NaOH (1.0 ml, 1.0 mmol). The resulting mixture was stirred at 70° C. for 18 hours. After cooling, the reaction mixture was acidified with water and 1N HCl. The crystals thus precipitated were collected by filtration under reduced pressure, washed with water and dried under reduced pressure to give the title compound (270 mg, 96%) as a white solid.

IR (ATR) ν 2983, 1600, 1511, 1222 cm$^{-1}$;

$^1$H-NMR (DMSO-d$_6$) δ: 2.20–2.40 (m, 2H), 3.50–4.00 (m, 7H), 4.10–4.80 (m, 3H), 5.38–5.52 (m, 1H), 6.90–6.93 (m, 1H), 7.18–7.28 (m, 1H), 7.41 (s, 1H), 7.54 (d, J=8.3 Hz, 1H), 7.65–7.68 (m, 1H), 8.14–8.20 (m, 2H), 8.26 (s, 1H), 8.68–8.73 (m, 1H), 9.29 (s, 1H).

MS (FAB) m/z 565 (M+H)$^+$;

Anal. calcd for $C_{29}H_{26}ClFN_4O_5$ 0.5 H$_2$O: C, 60.68; H, 4.74; N, 9.76. Found: C, 60.49; H, 4.72; N, 9.56.

Example 151

4-(3,4-Dehydro-1-((2-(2-methylphenylamino)-6-benzoxazolyl)acetyl)-(2S)-pyrrolidinylmethoxy)benzoic acid (Step 1) Synthesis of methyl 4-(3,4-dehydro-1-((2-(2-methylphenylamino)-6-benzoxazolyl)acetyl)-(2S)-pyrrolidinylmethoxy)benzoate

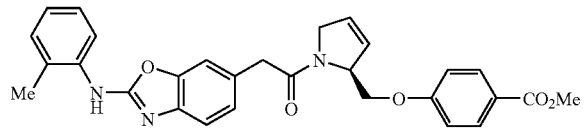

In DMF (7.5 ml) were dissolved (2-(2-methylphenylamino)-6-benzoxazolyl)acetic acid (223 mg, 0.79 mmol), methyl 4-(3,4-dehydro-(2S)-pyrrolidinylmethoxy)benzoate (184 mg, 0.79 mmol), HOBt (21.0 mg, 0.16 mmol), and triethylamine (0.16 ml, 1.15 mmol). To the resulting solution was added EDC HCl (227 mg, 1.15 mmol) and the resulting mixture was stirred at room temperature for 12 hours. To the reaction mixture was added water, followed by extraction with ethyl acetate. The extract was washed with saturated brine, dried over anhydrous sodium sulfate, and distilled under reduced pressure to remove the solvent. The residue was purified by chromatography on a silica gel column, whereby from ethyl acetate eluate fractions, methyl 4-(3,4-dehydro-1-((2-(2-methylphenylamino)-6-benzoxazolyl)acetyl)-(2S)-pyrrolidinylmethoxy)benzoate (331 mg, 84%) was obtained as a yellow solid.

$^1$H-NMR (CDCl$_3$) δ: 2.37 (s, 3H), 3.71 (s, 2H), 3.84 (s, 3H), 4.20 (m, 1H), 4.31–4.35 (m, 2H), 4.42 (dd, J=9.5,5.4 Hz, 1H), 5.10 (m, 1H), 5.87–5.95 (m, 2H), 6.86 (d, J=8.8 Hz, 2H), 7.05–7.09 (m, 2H), 7.16 (d, J=1.2 Hz, 1H), 7.22 (d, J=8.1 Hz, 1H), 7.31 (t, J=8.1 Hz, 1H), 7.37 (d, J=8.1 Hz, 1H), 7.93 (d, J=8.8 Hz, 2H), 8.19 (d, J=7.6 Hz, 1H).

MS (ESI) 498 (M$^+$+1).

(Step 2) Synthesis of 4-(3,4-dehydro-1-((2-(2-methylphenylamino)-6-benzoxazolyl)acetyl)-(2S)-pyrrolidinylmethoxy)benzoic acid

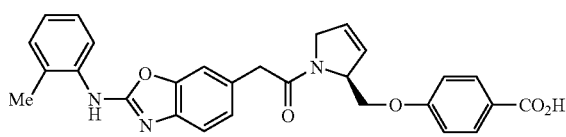

Methyl 4-(3,4-dehydro-1-((2-(2-methylphenylamino)-6-benzoxazolyl)acetyl)-(2S)-pyrrolidinylmethoxy)benzoate (331 mg, 0.67 mmol) was dissolved in THF (7.0 ml). To the resulting solution was added 0.25N NaOH (4.00 ml, 1.00 mmol), followed by stirring at room temperature for 6 hours. The reaction mixture was poured in 1N HCl (10 ml). The crystals thus precipitated were collected by filtration under reduced pressure, washed with water and dried under reduced pressure to give the title compound (241 mg, 75%) as a pale yellow solid.

IR (ATR) ν 3060, 2921, 1681, 1639, 1604, 1573, 1509, 1423 cm$^{-1}$;

$^1$H-NMR (DMSO-d$_6$) δ: 2.29 (s, 3H), 3.71 (s, 2H), 4.23–4.25 (m, 2H), 4.33 (m, 1H), 4.22 (m, 1H), 5.18 (broad s, 1H), 5.96–6.02 (m, 2H), 6.96 (d, J=8.8 Hz, 2H), 7.02–7.09 (m, 2H), 7.21–7.23 (m, 3H), 7.30 (broad s, 1H), 7.79 (d, J=8.3 Hz, 1H), 7.85 (d, J=8.8 Hz, 2H), 9.63 (broad s, 1H).

MS (FAB) 484 (M$^+$+1);

Anal. Calcd for $C_{28}H_{25}N_3O_5$ 0.5H$_2$O: C, 68.28; H, 5.32; N, 8.53. Found: C, 68.03; H, 5.35; N, 8.42.

Example 152

4-((3S)-Methoxy-1-((2-(2-methylphenylamino)-6-benzoxazolyl)acetyl)-(2R)-pyrrolidinylmethoxy)benzoic acid (Step 1) Synthesis of methyl 4-(1-(tert-butoxycarbonyl)-(3S)-methoxy-(2R)-pyrrolidinylmethoxy)benzoate

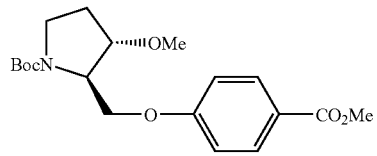

Methyl 4-((3S)-hydroxy-(2R)-pyrrolidinylmethoxy)benzoate (501 mg, 1.43 mmol) was dissolved in DMF (7.5 ml). To the resulting solution was added sodium hydride (60% in oil, 68 mg, 1.71 mmol) in portions under stirring at 0° C. After stirring at 0° C. for 30 minutes, methyl iodide (0.27 ml, 4.28 mmol) was added. The resulting mixture was stirred at the same temperature for 1 hour. A saturated aqueous solution of ammonium chloride was added, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (3:1, v/v) eluate fractions, methyl 4-(1-(tert-butoxycarbonyl)-(3S)-methoxy-(2R)-pyrrolidinylmethoxy)benzoate (569 mg, 100%) was obtained as a yellow oil.

$^1$H-NMR (CDCl$_3$) δ: 1.48 (broad s, 9H), 1.95–2.19 (m, 2H), 3.34 (s. 3H), 3.38–3.54 (m, 2H), 3.89 (s, 3H), 3.93–4.30 (m, 4H), 6.96 (d, J=8.6 Hz, 2H), 7.98 (d, J=8.6 Hz, 2H).

(Step 2) Synthesis of methyl 4-((3S)-methoxy-(2R)-pyrrolidinylmethoxy)benzoate

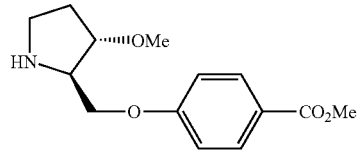

Methyl 4-(1-(tert-butoxycarbonyl)-(3S)-methoxy-(2R)-pyrrolidinylmethoxy)benzoate (569 mg, 1.56 mmol) was dissolved in methylene chloride (10 ml). To the resulting solution was added trifluoroacetic acid (5.0 ml) under stirring at 0° C. The resulting mixture was stirred at room temperature for 3 hours. From the reaction mixture, the solvent was distilled off under reduced pressure. The residue was neutralized with a saturated aqueous solution of sodium bicarbonate, followed by extraction with chloroform. The extract was dried over anhydrous sodium sulfate and distilled under reduced pressure to remove the solvent, whereby methyl 4-((3S)-methoxy-(2R)-pyrrolidinylmethoxy)benzoate (356 mg, 86%) was obtained as a yellow oil.

$^1$H-NMR (CDCl$_3$) δ: 1.86–2.01 (m, 3H), 3.02–3.15 (m, 2H), 3.35 (s. 3H), 3.45 (m, 1H), 3.81 (m, 1H), 3.88 (s, 3H), 3.95–4.02 (m, 2H), 6.92 (d, J=8.0 Hz, 2H), 7.98 (d, J=8.0 Hz, 2H).

(Step 3) Synthesis of methyl 4-((3S)-methoxy-1-((2-(2-methylphenylamino)-6-benzoxazolylacetyl)-(2R)-pyrrolidinylmethoxy)benzoate

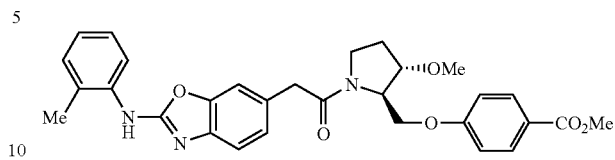

In DMF (7.0 ml), EDC HCl (193 mg, 1.01 mmol) was added to (2-(2-methylphenylamino)-6-benzoxazolyl)acetic acid (189 mg, 0.67 mmol), methyl 4-((3S)-methoxy-(2R)-pyrrolidinylmethoxy)benzoate (178 mg, 0.67 mmol), HOBt (18.0 mg, 0.13 mmol), and triethylamine (0.14 ml, 1.01 mmol) and the resulting mixture was stirred at room temperature for 24 hours. The reaction mixture was diluted with ethyl acetate. The diluted mixture was washed with saturated brine, dried over anhydrous sodium sulfate, and distilled under reduced pressure to remove the solvent. The residue was purified by chromatography on a silica gel column, whereby from ethyl acetate eluate fractions, methyl 4-((3S)-methoxy-1-((2-(2-methylphenylamino)-6-benzoxazolylacetyl)-(2R)-pyrrolidinylmethoxy)benzoate (384 mg, 100%) was obtained as a pale yellow amorphous substance.

$^1$H-NMR (CDCl$_3$) δ: 2.11 (m, 1H), 2.23 (m, 1H), 2.36 (s, 3H), 3.30 (s, 3H), 3.56–3.68 (m, 2H), 3.71 (s, 2H), 3.85 (s, 3H), 3.98 (m, 1H), 4.10 (dd, J=10.0,6.8 Hz, 1H), 4.29 (dd, J=10.0,3.2 Hz, 1H), 4.44 (m, 1H), 6.91 (d, J=9.0 Hz, 2H), 7.04–7.08 (m, 2H), 7.19 (d, J=2.2 Hz, 1H), 7.21 (m, 1H), 7.29 (m, 1H), 7.34 (d, J=7.9 Hz, 1H), 7.94 (d, J=9.0 Hz, 2H), 7.98 (d, J=8.1 Hz, 1H), 8.01 (broad s, 1H).

MS (ESI) m/z 530 (M$^+$+1).

(Step 4) Synthesis of 4-((3S)-methoxy-1-((2-(2-methylphenylamino)-6-benzoxazolyl)acetyl)-(2R)-pyrrolidinylmethoxy)benzoic acid

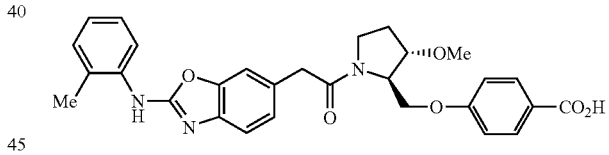

Methyl 4-((3S)-methoxy-1-((2-(2-methylphenylamino)-6-benzoxazolylacetyl)-(2R)-pyrrolidinylmethoxy)benzoate (384 mg, 0.73 mmol) was dissolved in THF (7.5 ml). To the resulting solution was added 0.25N NaOH (4.40 ml, 1.09 mmol), followed by stirring at room temperature for 5 hours. The reaction mixture was poured in 1N HCl (10 ml). The crystals thus precipitated were collected by filtration under reduced pressure, washed with water and dried under reduced pressure to give the title compound (300 mg, 80%) as a brown solid.

IR (ATR) ν 2927, 1681, 1639, 1604, 1575, 1486, 1438 cm$^{-1}$;

$^1$H-NMR (DMSO-d$_6$) δ: 2.08 (m, 1H), 2.22 (m, 1H), 2.30 (s, 3H), 3.22 (s, 3H), 3.60 (m, 1H), 3.67 (m, 1H), 3.73 (s, 2H), 3.91 (m, 1H), 3.97 (m, 1H), 4,21–4.23 (m, 2H), 7.00–7.08 (m, 4H), 7.22–7.25 (m, 3H), 7.31 (broad s, 1H), 7.81 (d, J=8.3 Hz, 1H), 7.87 (d, J=8.6 Hz, 2H), 9.59 (broad s, 1H).

MS (FAB) m/z 516 (M$^+$+1);

Anal. Calcd for C$_{29}$H$_{29}$N$_3$O$_6$ H$_2$O: C, 65.28; H, 5.86; N, 7.88. Found: C, 65.57; H, 5.95; N, 7.87.

Example 153

4-(1-(2-(2-Methylphenylamino)-6-benzoxazolylacetyl)-(4R)-thiazolidinylmethoxy)benzoic acid (Step 1) Synthesis of methyl 4-(1-(2-(2-methylphenylamino)-6-benzoxazolylacetyl)-(4R)-thiazolidinylmethoxy)benzoate

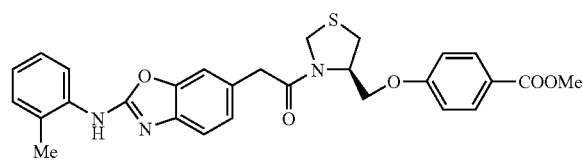

Methyl 4-((4R)-thiazolidinylmethoxy)benzoate (354 mg, 1.4 mmol), (2-(2-methylphenylamino)-6-benzoxazolyl)acetic acid (395 mg, 1.4 mmol), HOBt (189 mg, 1.4 mmol), and triethylamine (583 μl, 4.2 mmol) were dissolved in methylene chloride (15 ml). Under stirring at 0° C., EDC•HCl (403 mg, 2.1 mmol) was added. The reaction mixture was stirred at room temperature for 16 hours. From the reaction mixture, the solvent was distilled off under reduced pressure. Water was added to the residue, followed by extraction with ethyl acetate. The extract was washed successively with a saturated aqueous solution of sodium bicarbonate, a 2M aqueous solution of citric acid, and a saturated aqueous solution of sodium bicarbonate, dried over anhydrous sodium sulfate, and distilled under reduced pressure to remove the solvent. The residue was purified by chromatography on a silica gel column, whereby from n-hexane-ethyl acetate (1:1, v/v) eluate fractions, methyl 4-(1-(2-(2-methylphenylamino)-6-benzoxazolylacetyl)-(4R)-thiazolidinylmethoxy)benzoate (600 mg, 83%) was obtained as a yellow oil.

$^1$H-NMR (CDCl$_3$) δ: 2.34 and 2.36 (total 3H, each s), 3.05–3.18 (m, 2H), 3.80–4.94 (m, 10H), 6.81–7.41 (m, 9H), 7.97 (d, J=8.8 Hz, 2H), 8.06 (d, J=8.0 Hz, 1H).

(Step 2) Synthesis of 4-(1-(2-(2-methylphenylamino)-6-benzoxazolylacetyl)-(4R)-thiazolidinylmethoxy)benzoic acid

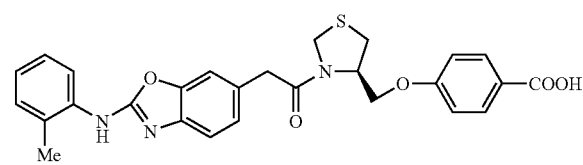

Methyl 4-(1-(2-(2-methylphenylamino)-6-benzoxazolylacetyl)-(4R)-thiazolidinylmethoxy)benzoate (600 mg, 1.16 mmol) was dissolved in THF (5.0 ml) and ethanol (3.0 ml). To the resulting solution was added 1N NaOH (1.5 ml, 1.5 mmol). The resulting mixture was stirred at 70° C. for 18 hours. After cooling, the reaction mixture was distilled under reduced pressure to remove the solvent. The residue was acidified with 1N HCl. The crystals thus precipitated were collected by filtration under reduced pressure, washed with water and dried under reduced pressure to give the title compound (560 mg, 96%) as a white crystalline powder.

IR (KBr) ν 2987, 2900, 1639, 1575, 1241, 754 cm$^{-1}$;
$^1$H-NMR (DMSO-d$_6$) δ: 2.30 (s, 3H), 3.05–3.30 (m, 3H), 3.70–4.30 (m, 3H), 4.56–5.00 (m, 3H), 7.06–7.33 (m, 9H), 7.80–7.88 (m, 3H).
MS (FAB) m/z 504 (M$^+$+1);
Anal. calcd for C$_{27}$H$_{25}$N$_3$O$_5$S: C, 64.40; H, 5.00; N, 8.34; S, 6.37. Found: C, 63.76; H, 4.98; N, 8.18; S, 6.17.

Example 154

4-(2-((2-(2-Methylphenylamino)-6-benzoxazolyl)-N-methylacetamido)ethoxy)benzoic acid (Step 1) Synthesis of methyl 4-(2-(N-methylamino)ethoxy)benzoate

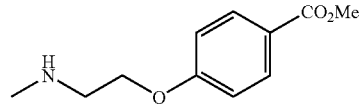

In THF (100 ml) was dissolved N-(tert-butoxycarbonyl)-2-(methylamino)ethanol (3.03 g, 17.3 mmol). To the resulting solution was added methyl 4-hydroxybenzoate (2.77 g, 18.2 mmol) and under stirring at 0° C. in a nitrogen gas stream, triphenylphosphine (6.35 g, 24.2 mmol) and DIAD (3.5 ml, 24.5 mmol) were added. The resulting mixture was stirred further at room temperature for 18 hours. From the reaction mixture, the solvent was distilled off under reduced pressure. Water was added to the residue, followed by extraction with ethyl acetate. The extract was washed with saturated brine, dried over anhydrous magnesium sulfate, and distilled under reduced pressure to remove the solvent. The residue was purified by chromatography on a silica gel column, whereby from n-hexane-ethyl acetate (4:1, v/v) eluate fractions, methyl 4-(2-(N-(tert-butoxycarbonyl)-N-methylamino)ethoxy)benzoate (4.09 g, 76%) was obtained as a yellow oil. The resulting compound (933 mg, 3.01 mmol) was dissolved in methylene chloride (3 ml). To the resulting solution was added trifluoroacetic acid (1 ml) under stirring at 0° C. The reaction mixture was stirred further at room temperature for 2 hours. From the reaction mixture, the solvent was distilled off under reduced pressure. The residue was neutralized with a saturated aqueous solution of sodium bicarbonate, followed by extraction with a chloroform-methanol mixture (5:1, v/v). The extract was washed with a saturated aqueous solution of sodium bicarbonate, dried over anhydrous magnesium sulfate, and distilled under reduced pressure to remove the solvent, whereby methyl 4-(2-(N-methylamino)ethoxy)benzoate (618 mg, 98%) was obtained as a yellow oil.

$^1$H-NMR (CDCl$_3$) δ: 2.54 (s, 3H), 3.02 (dd, J=5.0 Hz, 2H), 3.88 (d, J=6.0 Hz, 3H), 4.14 (dd, J=5.0 Hz, 2H), 6.80 (d, J=8.8 Hz, 1H), 6.91 (d, J=9.0 Hz, 1H), 7.91 (d, J=9.0 Hz, 1H), 7.98 (d, J=8.8 Hz, 1H).

(Step 2) Synthesis of methyl 4-(2-((2-(2-methylphenylamino)-6-benzoxazolyl)N-methylacetamido)ethoxy)benzoate

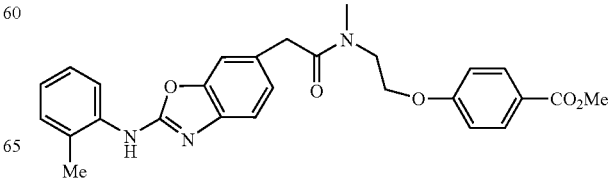

In DMF (6 ml) were dissolved 2-(2-methylphenylamino)-6-benzoxazolylacetic acid (154 mg, 0.55 mmol) and methyl 4-(2-(N-methylamino)ethoxy)benzoate (117 mg, 0.55 mmol). To the resulting solution were added EDC HCl (157 mg, 0.81 mmol), HOBt (5 mg, 0.04 mmol), and DMAP (5 mg, 0.04 mmol). The resulting mixture was stirred at room temperature for 18 hours. Water was added to the reaction mixture, followed by extraction with ethyl acetate. The extract was washed with saturated brine, dried over anhydrous magnesium sulfate, and distilled under reduced pressure to remove the solvent. The residue was purified by chromatography on a silica gel column, whereby from chloroform-methanol (10:1, v/v) eluate fractions, methyl 4-(2-((2-(2-methylphenylamino)-6-benzoxazolyl)-N-methylacetamido)ethoxy)benzoate (207 mg, 80%) was obtained as a yellow oil.

IR (ATR) ν 1710, 1631, 1573 cm$^{-1}$;
$^1$H-NMR (CDCl$_3$) δ: 2.36 (s, 3H), 3.16 (series of d, J=2.4 Hz, total 2H), 3.79 (m, 3H), 3.87 (d, J=2.4 Hz, 2H), 3.87 (d, J=2.4 Hz, 2H), 3.92 (m, 1H), 4.23 (series of t, J=4.8 Hz, total 1H), 6.87 (m, 2H), 7.07 (t, J=6.4 Hz, 1H), 7.22 (m, 1H), 7.30 (m, 1H), 7.37 (d, J=8.0 Hz, 1H), 7.95 (m, 2H), 8.04 (br, 2H), 8.07 (d, J=7.2 Hz, 1H).

MS(ESI) m/z 474 (M+H)$^+$;
Anal. Calcd for C$_{27}$H$_{27}$FN$_3$O$_5$·H$_2$O: C, 65.98; H, 5.95; N, 8.55. Found: C, 65.98; H, 5.73; N, 7.68.

(Step 3) Synthesis of 4-(2-((2-(2-methylphenylamino)-6-benzoxazolyl)-N-methylacetamido)ethoxy)benzoic acid

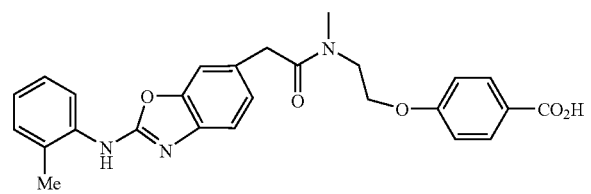

Methyl 4-(2-((2-(2-methylphenylamino)-6-benzoxazolyl)-N-methylacetamido)ethoxy)benzoate (206.9 mg, 0.44 mmol) was dissolved in THF (5 ml). To the resulting solution was added 0.25N NaOH (5 ml), and the resulting mixture was stirred at room temperature for 2 hours. To the reaction mixture was added NaOH (500 mg), followed by heating under reflux for 3 hours. After cooling, the reaction mixture was distilled under reduced pressure to remove the solvent. The residue was diluted with a chloroform-methanol mixture (5:1, v/v). The solution was washed with 1N HCl, dried over anhydrous magnesium sulfate, and distilled under reduced pressure to remove the solvent. The residue was purified by chromatography on a silica gel column, whereby from chloroform-methanol (20:1, v/v) eluate fractions, the title compound (101 mg, 51%) was obtained as a pale red solid.

IR (ATR) ν 1683, 1637, 1604, 1573 cm$^{-1}$;
$^1$H-NMR (CDCl$_3$) δ: 2.34 (s, 3H), 3.47 (s, 2H), 3.71 (q, J=7.2 Hz, 2H), 3.77 (s, 2H), 3.91 (m, 1H), 4.20 (m, 3H), 6.78 (d, J=8.0 Hz, 1H), 6.83 (d, J=8.8 Hz, 1H), 7.07 (m, 2H), 7.22 (m, 2H), 7.32 (m, 1H), 7.62 (m, 1H), 7.74 (d, J=8.0 Hz, 1H), 8.02 (t, J=9.2 Hz, 2H).

MS (ESI) m/z 460 (M+H)$^+$;
Anal. Calcd for C$_{26}$H$_{25}$FN$_3$O$_5$·H$_2$O: C, 65.45; H, 5.70; N, 8.80. Found: C, 65.35; H, 5.72; N, 8.25.

Example 155

4-((4R)-Methoxy-1-((2-(2-methylphenylamino)-6-benzoxazolyl)acetyl)-(3S)-pyrrolidinyloxy)benzoic acid (Step 1) Synthesis of 1-benzyl-(3S,4S)-dihydroxy-2,5-dioxopyrrolidine

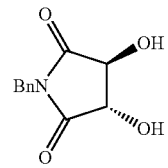

In xylene (500 ml), D-tartaric acid (25.0 g, 0.17 mol) and benzylamine (19.6 g, 0.18 mmol) were heated under reflux for 18 hours by using a Dean-Stark water separator. After cooling, the reaction mixture was distilled under reduced pressure to remove the solvent, whereby 1-benzyl-(3S,4S)-dihydroxy-2,5-dioxopyrrolidine (33.7 g, 90%) was obtained as a brown solid.

IR (KBr) ν 3291, 1710, 1434 cm$^{-1}$;
$^1$H-NMR (CD$_3$OD) δ: 4.40 (s, 2H), 4.64 (s, 2H), 7.25–7.33 (m, 5H).
MS (FAB) m/z 222 (M$^+$+1).

(Step 2) Synthesis of 1-benzyl-(3R,4R)-dihydroxypyrrolidine

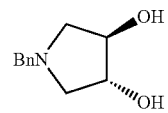

Under stirring at 0° C., 1-benzyl-(3S,4S)-dihydroxy-2,5-dioxopyrrolidine (17.3 g, 78.3 mmol) was added to a suspension of lithium aluminum hydride (8.91 g, 235 mmol) in THF (500 ml). The reaction mixture was heated under reflux for 18 hours. After the reaction mixture was cooled to 0° C., ethyl acetate (50 ml) was added thereto. The resulting mixture was stirred for 30 minutes and then, ice water was added. The reaction mixture was filtered through Celite. The filtrate was dried over anhydrous magnesium sulfate, and distilled under reduced pressure to remove the solvent to give 1-benzyl-(3R,4R)-dihydroxypyrrolidine (9.60 g, 63%) as a red oil.

$^1$H-NMR (CDCl$_3$) δ: 2.45–2.47 (m, 2H), 2.94–2.98 (m, 2H), 3.63 (s, 2H), 4.08 (s, 2H), 7.24–7.33 (m, 5H).
MS (ESI) m/z 194 (M$^+$+1).

(Step 3) Synthesis of 1-(tert-butoxycarbonyl)-(3R,4R)-dihydroxypyrrolidine

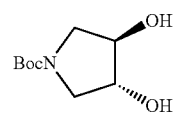

In ethyl acetate (400 ml), 5% palladium/carbon (53.1% wet, 4.20 g) was added to 1-benzyl-(3R,4R)-dihydroxypyrrolidine (9.60 g, 49.7 mmol) and di-tert-butyl dicarbonate (10.8 g, 49.7 mmol) and the resulting mixture was subjected to catalytic hydrogenation at room temperature under normal pressure for 14 hours. From the reaction mixture, the catalyst was filtered off and the filtrate was distilled under reduced pressure to remove the solvent, whereby 1-(tert-butoxycarbonyl)-(3R,4R)-dihydroxypyrrolidine (5.64 g, 35%) was obtained as a colorless solid.

$^1$H-NMR (CDCl$_3$) δ: 1.39 (s, 9H), 3.11 (dd, J=11.3,3.4 Hz, 2H), 3.34–3.38 (m, 2H), 3.86–3.87 (m, 2H), 5.03–5.04 (m, 2H).

MS (ESI) m/z 189 (M$^+$+1-CH$_3$).

(Step 4) Synthesis of 1-(tert-butoxycarbonyl)-(4R)-(tert-butyldimethylsilyloxy)-(3R)-hydroxypyrrolidine

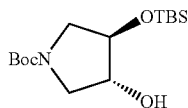

To a solution of 1-(tert-butoxycarbonyl)-(3R,4R)-dihydroxypyrrolidine (5.64 g, 27.8 mmol) in THF (50 ml) was added sodium hydride (60% in oil, 1.10 g, 27.5 mmol) in portions under stirring at 0° C. The reaction mixture was stirred at room temperature for 4 hours. To the reaction mixture was added tert-butyldimethylsilyl chloride (TBSCl) (4.15 g, 27.5 mmol), followed by stirring for 3 hours. To the reaction mixture was added a saturated aqueous solution of ammonium chloride, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (2:1, v/v) eluate fractions, 1-(tert-butoxycarbonyl)-(4R)-(tert-butyldimethylsilyloxy)-(3R)-hydroxypyrrolidine (5.27 g, 60%) was obtained as a colorless oil.

$^1$H-NMR (CDCl$_3$) δ: 0.07 (s, 3H), 0.08 (s, 3H), 0.87 (s, 9H), 1.46 (s, 9H), 3.20–3.36 (m, 2H), 3.52–3.65 (m, 2H), 4.06–4.12 (m, 2H).

MS (ESI) m/z 318 (M$^+$+1).

(Step 5) Synthesis of methyl 4-(1-(tert-butoxycarbonyl)-(4R)-(tert-butyldimethylsilyloxy)-(3S)-pyrrolidinyloxy)benzoate

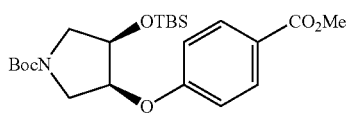

In THF (15 ml), DIAD (3.60 ml, 18.3 mmol) was added to 1-(tert-butoxycarbonyl)-(4R)-(tert-butyldimethylsilyloxy)-(3R)-hydroxypyrrolidine (5.27 g, 16.6 mmol), methyl 4-hydroxybenzoate (2.53 g, 16.6 mmol), and triphenylphosphine (4.79 g, 18.3 mmol) and the resulting mixture was heated under reflux for 6 hours. The reaction mixture was cooled to room temperature, and distilled under reduced pressure to remove the solvent. The residue was purified by chromatography on a silica gel column, whereby from n-hexane-ethyl acetate (5:1, v/v) eluate fractions, methyl 4-(1-(tert-butoxycarbonyl)-(4R)-(tert-butyldimethylsilyloxy)-(3S)-pyrrolidinyloxy)benzoate and a small amount of methyl 4-hydroxybenzoate were obtained as a yellow oil.

$^1$H-NMR (CDCl$_3$) δ: –0.05 (s, 3H), 0.03 (s, 3H), 0.81 (s, 9H), 1.47 (s, 9H), 3.38 (m, 1H), 3.48–3.64 (m, 2H), 3.72 (m, 1H), 3.89 (s, 3H), 4.43 (m, 1H), 4.72 (m, 1H), 6.92 (d, J=8.8 Hz, 2H), 7.97 (d, J=8.8 Hz, 2H).

MS (ESI) m/z 437 (M$^+$+1-CH$_3$).

(Step 6) Synthesis of methyl 4-(1-(tert-butoxycarbonyl)-(4R)-hydroxy-(3S)-pyrrolidinyloxy)benzoate

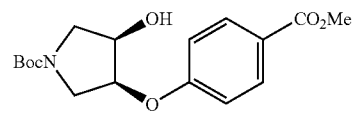

To the above-described methyl 4-(1-(tert-butoxycarbonyl)-(4R)-(tert-butyldimethylsilyloxy)-(3S)-pyrrolidinyloxy)benzoate and small amount of methyl 4-hydroxybenzoate (total 4.75 g) was added acetic acid-water-THF (3:1:1, v/v, 50 ml). The resulting mixture was stirred at room temperature for 23 hours. The reaction mixture was neutralized with a saturated aqueous solution of sodium bicarbonate, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (1:1, v/v) eluate fractions, methyl 4-(1-(tert-butoxycarbonyl)-(4R)-hydroxy-(3S)-pyrrolidinyloxy)benzoate (3.86 g, 71% for 2 steps) was obtained as a colorless oil.

$^1$H-NMR (CDCl$_3$) δ: 1.45 (broad s, 9H), 2.45 (m, 1H), 3.39–3.58 (m, 2H), 3.68–3.82 (m, 2H), 3.90 (s, 3H), 4.49 (m, 1H), 4.80 (m, 1H), 6.96 (d, J=8.1 Hz, 2H), 8.00–8.03 (m, 2H).

MS (ESI) m/z 323 (M$^+$+1-CH$_3$).

(Step 7) Synthesis of methyl 4-(1-(tert-butoxycarbonyl)-(4R)-methoxy-(3S)-pyrrolidinyloxy)benzoate

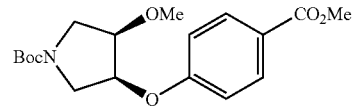

In THF (10 ml), sodium hydride (60% in oil, 72.0 mg, 1.79 mmol) was added in portions to methyl 4-(1-(tert-butoxycarbonyl)-(4R)-hydroxy-(3S)-pyrrolidinyloxy)benzoate (505 mg, 1.50 mmol) and methyl iodide (0.30 ml, 1.79 mmol) under stirring at 0° C. The resulting mixture was stirred further at the same temperature for 2 hours. To the reaction mixture was added a saturated aqueous solution of ammonium chloride, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (3:1, v/v) eluate fractions, methyl 4-(1-(tert-butoxycarbonyl)-(4R)-methoxy-(3S)-pyrrolidinyloxy)benzoate (657 mg, 100%) was obtained as a colorless oil.

¹H-NMR (CDCl₃) δ: 1.45 (broad s, 9H), 3.41 (s, 3H), 3.44–3.72 (m, 4H), 3.89 (s, 3H), 4.04 (m, 1H), 4.87 (m, 1H), 6.96 (d, J=8.0 Hz, 2H), 7.98–8.00 (m, 2H).

(Step 8) Synthesis of methyl 4-((4R)-methoxy-(3S)-pyrrolidinyloxy)benzoate

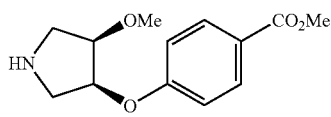

Methyl 4-(1-(tert-butoxycarbonyl)-(4R)-methoxy-(3S)-pyrrolidinyloxy)benzoate (601 mg, 1.71 mmol) was dissolved in methylene chloride (10 ml). To the resulting solution was added trifluoroacetic acid (5 ml) under stirring at 0° C. The reaction mixture was stirred further for 2.5 hours at room temperature. From the reaction mixture, the solvent was distilled off under reduced pressure. The residue was neutralized with a saturated aqueous solution of sodium bicarbonate, followed by extraction with chloroform. The extract was dried over anhydrous sodium sulfate and distilled under reduced pressure to remove the solvent, whereby methyl 4-((4R)-methoxy-(3S)-pyrrolidinyloxy)benzoate (339 mg, 79%) was obtained as a yellow oil.

¹H-NMR (CDCl₃) δ: 3.11–3.20 (m, 3H), 3.28 (dd, J=12.5, 5.6 Hz, 1H), 3.38 (s, 3H), 3.89 (s, 3H), 3.99 (m, 1H), 4.79 (m, 1H), 6.96 (d, J=8.5 Hz, 2H), 7.98 (d, J=8.5 Hz, 2H).

(Step 9) Synthesis of methyl 4-((4R)-methoxy-1-((2-(2-methylphenylamino)-6-benzoxazolyl)acetyl)-(3S)-pyrrolidinyloxy)benzoate

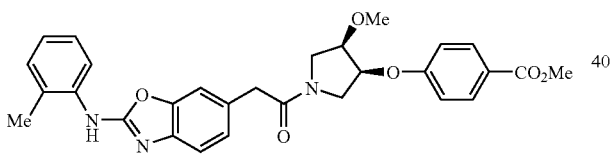

In DMF (5.0 ml), EDC HCl (192 mg, 1.00 mmol) was added to (2-(2-methylphenylamino)-6-benzoxazolyl)acetic acid (189 mg, 0.67 mmol), methyl 4-((4R)-methoxy-(3S)-pyrrolidinyloxy)benzoate (168 mg, 0.67 mmol), HOBt (18.0 mg, 0.13 mmol), and triethylamine (0.14 ml, 1.00 mmol) and the resulting mixture was stirred at room temperature for 24 hours. Water was added to the reaction mixture, followed by extraction with ethyl acetate. The extract was dried over anhydrous sodium sulfate, and distilled under reduced pressure to remove the solvent. The residue was purified by chromatography on a silica gel column, whereby from ethyl acetate eluate fractions, methyl 4-((4R)-methoxy-1-((2-(2-methylphenylamino)-6-benzoxazolyl)acetyl)-(3S)-pyrrolidinyloxy)benzoate (345 mg, 100%) was obtained as a yellow oil.

¹H-NMR (CDCl₃) δ: 2.34 (s, 3H), 3.36 (s, 3H), 3.54–3.81 (m, 6H), 3.84 and 3.87 (each s, total 3H), 4.05 (m, 1H), 4.88 (m, 1H), 6.88–6.93 (m, 2H), 7.02–7.08 (m, 4H), 7.20–7.37 (m, 4H), 7.90–7.99 (m, 4H).

MS (ESI) m/z 516 (M⁺+1)

(Step 10) Synthesis of 4-((4R)-methoxy-1-((2-(2-methylphenylamino)-6-benzoxazolyl)acetyl)-(3S)-pyrrolidinyloxy)benzoic acid

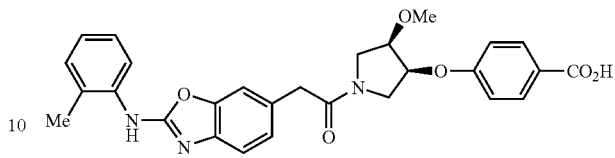

Methyl 4-((4R)-methoxy-1-((2-(2-methylphenylamino)-6-benzoxazolyl)acetyl)-(3S)-pyrrolidinyloxy)benzoate (345 mg, 0.67 mmol) was dissolved in THF (7.0 ml). To the resulting solution was added 0.25N NaOH (4.01 ml, 1.00 mmol). The resulting mixture was stirred at room temperature for 7 hours. The reaction mixture was poured in 1N HCl (3.0 ml). The crystals thus precipitated were collected by filtration under reduced pressure, washed with water, and dried under reduced pressure to give the title compound (218 mg, 65%) as a colorless solid.

IR (ATR) ν 2935, 1683, 1639, 1602, 1575, 1508, 1440 cm⁻¹;

¹H-NMR (DMSO-d₆) δ: 2.30 (s, 3H), 3.52 and 3.28 (each s, total 3H), 3.41–3.65 (m, 2H), 3.68 and 3.71 (each s, total 2H), 3.79–3.99 (m, 2H), 4.12 and 4.19 (each m, total 1H), 5.11 and 5.17 (each m, total 1H), 7.03–7.11 (m, 4H), 7.22–7.28 (m, 3H), 7.31 (d, J=8.8 Hz, 1H), 7.79 (d, J=7.9 Hz, 1H), 7.88 (d, J=8.8 Hz, 2H), 9.85 (broad s, 1H).

MS (FAB) m/z 502 (M⁺+1);

Anal. Calcd for $C_{28}H_{27}N_3O_6$ 1.5$H_2O$: C, 63.63; H, 5.72; N, 7.95. Found: C, 63.69; H, 5.55; N, 8.01.

Example 156 trans-4-(1-((2-(5-Fluoro-2-methylphenylamino)-7-fluoro-6-benzoxazolyl)acetyl)-(2S)-methoxymethyl-(4R)-pyrrolidinyloxy)cyclohexanecarboxylic acid (Step 1) Synthesis of 1-tert-butoxycarbonyl-(2S)-tert-butyldiphenylsilyloxymethyl-(4S)-(4-nitrobenzoyloxy)pyrrolidine

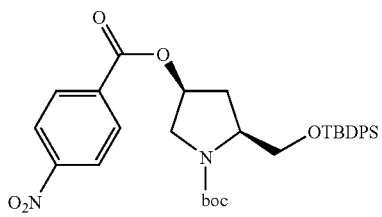

In THF (300 ml), DIAD (4.53 ml, 23.0 mmol) was added to 1-tert-butoxycarbonyl-(2S)-tert-butyldiphenylsilyloxymethyl-(4R)-hydroxypyrrolidine (10.51 g, 23.0 mmol), 4-nitrobenzoic acid (3.85 g, 23.0 mmol) and triphenylphosphine (6.03 g, 23.0 mmol) and the resulting mixture was stirred at room temperature for 2 hours. From the reaction mixture, the solvent was distilled off under reduced pressure. The residue was purified by chromatography on a silica gel column, whereby from n-hexane/ethyl acetate (5/1) eluate fractions, 1-tert-butoxycarbonyl-(2S)-tert-butyldiphenylsilyloxymethyl-(4S)-(4-nitrobenzoyloxy)pyrrolidine (15.39 g, 100%) was obtained as a colorless amorphous substance.

¹H-NMR (CDCl₃) δ: 1.02 (s, 9H), 1.36 and 1.45 (each s, total 9H, amide isomers), 2.39–2.64 (m, 2H), 3.44–3.78 (m, 2H), 3.87 (dd, J=13.0,5.4 Hz, 1H), 3.98–4.24 (m, 2H), 5.56 (br, 1H), 7.26 (m, 2H), 7.28–7.41 (m, 4H), 7.51–7.65 (m, 4H), 8.01 (d, J=8.1 Hz, 2H), 8.16 (d, J=7.8 Hz, 2H).

MS (ESI) m/z 606 (M⁺+1).

(Step 2) Synthesis of 1-tert-butoxycarbonyl-(4S)-hydroxy-(2S)-(4-nitrobenzoyloxymethyl)pyrrolidine

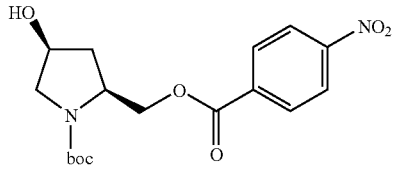

In THF (500 ml) was dissolved 1-tert-butoxycarbonyl-(2S)-tert-butyldiphenylsilyloxymethyl-(4S)-(4nitrobenzoyloxy)pyrrolidine (15.4 g, 24.5 mmol). To the resulting solution was added a 1.0M tetrabutylammonium fluoride-THF solution (25.4 ml, 25.4 mmol) under stirring at 0° C. The temperature of the reaction mixture was gradually raised back to room temperature, at which stirring was conducted for 14 hours. Water was added to the reaction mixture, followed by extraction with ethyl acetate. The extract was washed with saturated brine, dried over anhydrous sodium sulfate and distilled under reduced pressure to remove the solvent. The residue was purified by chromatography on a silica gel column, whereby from n-hexane/ethyl acetate (2/1) and chloroform/acetone eluate fractions, 1-tert-butoxycarbonyl-(4S)-hydroxy-(2S)-(4-nitrobenzoyloxymethyl) pyrrolidine (2.53 g, 27.2%) was obtained as a colorless oil.

¹H-NMR (CDCl₃) δ: 1.45 (s, 9H), 1.90–2.16 (m, 2H), 2.24 (m, 1H), 3.42 (d, J=12.2 Hz, 1H), 3.68–3.80 (m, 1H), 4.22 and 4.36 (each br, total 1H, amide isomers), 4.51–4.72 (m, 3H), 8.23–8.29 (m, 4H).

MS (ESI) m/z 367 (M⁺+1).

(Step 3) Synthesis of ethyl 4-(1-tert-butoxycarbonyl-(2S)-(4-nitrobenzoyloxymethyl)-(4R)-pyrrolidinyloxy)benzoate

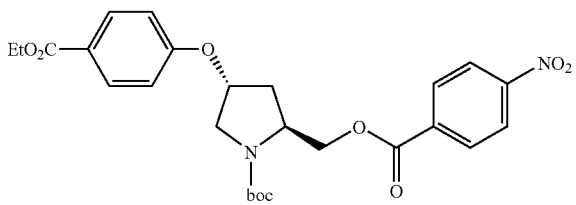

In THF (100 ml), DIAD (1.36 ml, 6.91 mmol) was added to 1-tert-butoxycarbonyl-(4S)-hydroxy-(2S)-(4-nitrobenzoyloxymethyl)pyrrolidine (2.53 g, 6.91 mmol), ethyl 4-hydroxybenzoate (1.15 g, 6.91 mmol) and triphenylphosphine (1.81 g, 6.91 mmol) and the resulting mixture was stirred at room temperature for 14 hours. The reaction mixture was distilled under reduced pressure to remove the solvent. The residue was purified by chromatography on a silica gel column, and chloroform/ethyl acetate (5/1) eluate fractions were collected, followed by flash chromatography on a silica gel column (ϕ 4×40 cm, chloroform/ethyl acetate (5/1)) to give ethyl 4-(1-tert-butoxycarbonyl-(2S)-(4-nitrobenzoyloxymethyl)-(4R)-pyrrolidinyloxy)benzoate (2.55 g, 72%) as a colorless oil.

¹H-NMR (CDCl₃) δ: 1.38 (dt, J=7.1,2.0 Hz, 3H), 1.56 (s, 9H), 2.12–2.32 (m, 2H), 2.44 (m, 1H), 3.60 (dd, J=12.2,4.4 Hz, 1H), 3.83 and 3.99 (each br, total 1H, amide isomers), 4.35 (dq, J=7.1,2.0 Hz, 2H), 4.41–4.62 (m, 2H), 4.96 (s, 1H), 6.86 (d, J=6.8 Hz, 2H), 7.99 (d, J=7.3 Hz, 2H), 8.19 (d, J=7.3 Hz, 2H), 8.27 (d, J=8.3 Hz, 1H), 8.28 (d, J=7.3 Hz, 1H).

MS (ESI) m/z 515 (M⁺+1).

(Step 4) Synthesis of ethyl 4-(1-tert-butoxycarbonyl-(2S)-hydroxymethyl-(4R)-pyrrolidinyloxy)benzoate

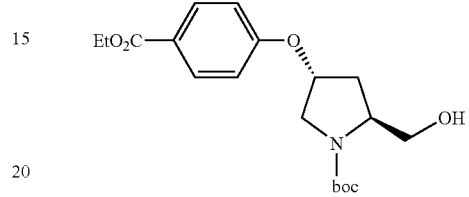

In ethanol (100 ml), potassium carbonate (685 mg, 4.96 mmol) was added to ethyl 4-(1-tert-butoxycarbonyl-(2S)-(4-nitrobenzoyloxymethyl)-(4R)-pyrrolidinyloxy)benzoate (2.55 g, 4.96 mmol) and the resulting mixture was stirred at room temperature for 24 hours. From the reaction mixture, the solvent was distilled off under reduced pressure. The residue was purified by chromatography on a silica gel column, whereby from chloroform/ethyl acetate (5/1) eluate fractions, ethyl 4-(1-tert-butoxycarbonyl-(2S)-hydroxymethyl-(4R)-pyrrolidinyloxy)benzoate (1.36 g, 75%) was obtained as a colorless oil.

¹H-NMR (CDCl₃) δ: 1.38 (t, J=7.1 Hz, 3H), 1.46 (s, 9H), 1.89 (br, 1H), 2.34 (m, 1H), 3.58–3.97 (m, 4H), 4.05–4.26 (m, 1H), 4.35 (q, J=7.1 Hz, 2H), 4.69 and 4.88 (each br, total 1H, amide isomers), 6.87 (d, J=8.8 Hz, 2H), 8.00 (d, J=8.5 Hz, 2H).

MS (ESI) m/z 366 (M⁺+1).

(Step 5) Synthesis of ethyl 4-((2S)-hydroxymethyl-(4R)-pyrrolidinyloxy)benzoate hydrochloride

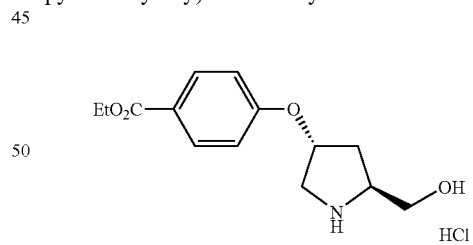

Ethyl 4-(1-tert-butoxycarbonyl-(2S)-hydroxymethyl-(4R)-pyrrolidinyloxy)benzoate (1.36 g, 3.72 mmol) was dissolved in dioxane (50 ml). To the resulting solution was added a 4N HCl/dioxane solution (30 ml) and the mixture was stirred at room temperature for 3.5 hours. The reaction mixture was distilled under reduced pressure to remove the solvent, whereby ethyl 4-((2S)-hydroxymethyl-(4R)-pyrrolidinyloxy)benzoate hydrochloride (1.21 g, 100%) was obtained as a brown oil. The resulting compound was provided for the subsequent reaction without further purification.

(Step 6) Synthesis of ethyl 4-((2S)-hydroxymethyl-(4R)-pyrrolidinyloxy)cyclohexanecarboxylate hydrochloride

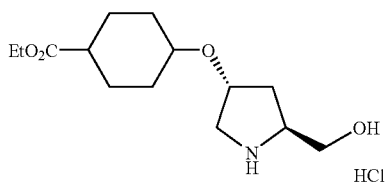

In ethanol (30 ml), ethyl 4-((2S)-hydroxymethyl-(4R)-pyrrolidinyloxy)benzoate hydrochloride (1.21 g, 3.72 mmol) and rhodium/alumina (1.2 g) were subjected to catalytic hydrogenation at room temperature for 3 days under 4 kg/cm² of a hydrogen gas. From the reaction mixture, the catalyst was filtered off and the filtrate was distilled under reduced pressure to remove the solvent, whereby ethyl 4-((2S)-hydroxymethyl-(4R)-pyrrolidinyloxy)cyclohexanecarboxylate hydrochloride as a brown oil. The resulting compound was provided for the subsequent reaction without further purification.

(Step 7) Synthesis of ethyl 4-(1-tert-butoxycarbonyl-(2S)-hydroxymethyl-(4R)-pyrrolidinyloxy)cyclohexanecarboxylate

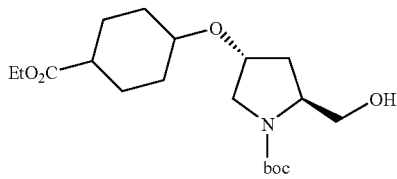

In dioxane (30 ml), di-tert-butyl dicarbonate (812 mg, 3.72 mmol) was added to ethyl 4-((2S)-hydroxymethyl-(4R)-pyrrolidinyloxy)cyclohexanecarboxylate hydrochloride (3.72 mmol) and a saturated aqueous solution of sodium bicarbonate (10 ml) and the resulting mixture was stirred at room temperature for 2 days. Ethyl acetate was added to the reaction mixture. The resulting mixture was washed saturated brine, dried over anhydrous sodium sulfate, and distilled under reduced pressure to remove the solvent to give ethyl 4-(1-tert-butoxycarbonyl-(2S)-hydroxymethyl-carboxylate-(4R)-pyrrolidinyloxy)cyclohexanecarboxylate (1.28 g, 93% (3 steps)) as a brown oil. The resulting compound was provided for the subsequent reaction without further purification.

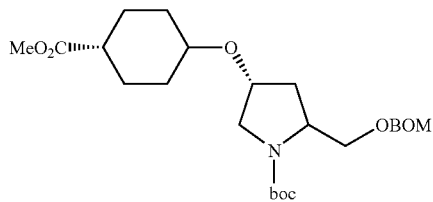

Ethyl 4-(1-tert-butoxycarbonyl-(2S)-hydroxymethyl-(4R)-pyrrolidinyloxy)cyclohexanecarboxylate (1.28 g, 3.45 mmol) was dissolved in methylene chloride (30 ml). To the resulting solution were added N,N-diisopropylethylamine (1.20 ml, 6.90 mmol) and benzyloxycarbonyl chloride (HOMCl) (0.72 ml, 5.18 mmol). The resulting mixture was stirred at room temperature for 14 hours in a nitrogen gas stream. The reaction mixture was poured in water, followed by extraction with methylene chloride. The extract was washed with 1N HCl and a saturated aqueous solution of sodium bicarbonate, dried over anhydrous sodium sulfate, and distilled under reduced pressure to remove the solvent. The residue was purified by chromatography on a silica gel column, whereby from n-hexane/ethyl acetate (2/1) eluate fractions, ethyl 4-(1-tert-butoxycarbonyl-(2S)-benzyloxymethyloxymethyl-(4R)-pyrrolidinyloxy)cyclohexanecarboxylate (1.02 g, 60%) was obtained as a colorless oil. The resulting compound was isomerized in the subsequent step.

In ethanol, sodium ethoxide (1.41 g, 20.7 mmol) was added to ethyl 4-(1-tert-butoxycarbonyl-(2S)-benzyloxymethyloxymethyl-(4R)-pyrrolidinyloxy)cyclohexanecarboxylate (1.02 g, 2.07 mmol). The resulting mixture was heated under reflux for 13 hours. After the reaction mixture was cooled to room temperature, the solvent was distilled off under reduced pressure. The residue was acidified with 1N HCl, followed by extraction with ethyl acetate. The extract was washed with saturated brine, dried over anhydrous sodium sulfate, and distilled under reduced pressure to remove the solvent. The residue was dissolved in methanol/toluene (1:10, 22 ml). To the resulting solution was added a 2.0M hexane solution (1.04 ml, 2.07 mmol) of trimethylsilyldiazomethane. The resulting mixture was stirred at room temperature for 5 hours. The reaction mixture was distilled under reduced pressure to remove the solvent. The residue was purified by flash chromatography on a silica gel column (φ 3×30 cm, eluted in: n-hexane/ethyl acetate (10/1)) and by chromatography using a silica gel thin-layer plate (TLC) (developed in n-hexane/ethyl acetate (10/1)) to give methyl trans-4-(1-tert-butoxycarbonyl-(2S)-benzyloxymethyloxymethyl-(4R)-pyrrolidinyloxy)cyclohexanecarboxylate (326 mg, 33% (2 steps)) as a colorless oil.

$^1$H-NMR (CDCl$_3$) δ: 1.20–1.30 (m, 3H), 1.39–1.51 (m, 11H), 1.92–2.22 (m, 6H), 2.25 (tt, J=11.8,2.9 Hz, 1H), 3.24 (tt, J=10.3,3.7 Hz, 1H), 3.30–3.64 (m, 2H), 3.66 (s, 3H), 3.75 (br, 1H), 4.02 and 4.09 (each br, total 1H, amide isomers), 4.21 (br, 1H), 4.58 (s, 2H), 4.73 (d, J=4.6 Hz, 2H), 7.29 (m, 1H), 7.33 (s, 2H), 7.34 (s, 2H).

MS (ESI) m/z 478 (M$^+$+1).

(Step 9) Synthesis of methyl trans-4-(1-tert-butoxycarbonyl-(2S)-hydroxymethyl-(4R)-pyrrolidinyloxy)cyclohexanecarboxylate

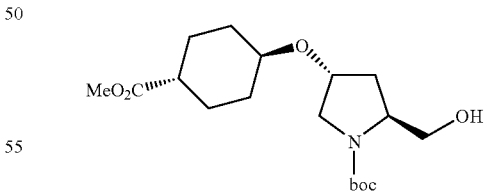

In methanol (10 ml), methyl trans-4-(1-tert-butoxycarbonyl-(2S)-benzyloxymethyloxymethyl-(4R)-pyrrolidinyloxy)cyclohexanecarboxylate (326 mg, 0.683 mmol) and 5% palladium/carbon (wet.) (326 mg) were subjected to catalytic hydrogenation at room temperature for 14 hours. From the reaction mixture, the catalyst was filtered off and the filtrate was distilled under reduced pressure to remove the solvent to give methyl trans-4-(1-tert-butoxycarbonyl-(2S)-hydroxymethyl-(4R)-pyrrolidinyloxy)cyclohexanecarboxylate (247 mg, 100%) as a colorless oil. The resulting compound was provided for the subsequent reaction without further purification.

$^1$H-NMR (CDCl$_3$) δ: 1.21–1.33 (m, 3H), 1.39 (m, 1H), 1.47 (s, 9H), 1.61–1.71 (m, 1H), 1.95–2.10 (m, 5H), 2.26 (m, 1H), 3.24 (m, 1H), 3.33–3.51 (m, 2H), 3.53 and 3.56 (each d, J=6.8 and 7.1 Hz respectively, total 1H, amide isomers), 3.66 (s, 3H), 3.68 (m, 1H), 4.09 (br, 2H).

MS (ESI) m/z 358 (M$^+$+1).

(Step 10) Synthesis of methyl trans-4-(1-tert-butoxycarbonyl-(2S)-methoxymethyl-(4R)-pyrrolidinyloxy)cyclohexanecarboxylate

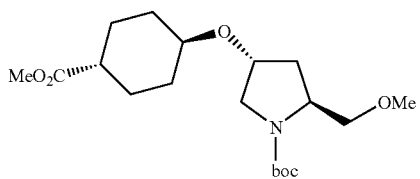

Methyl trans-4-(1-tert-butoxycarbonyl-(2S)-hydroxymethyl-(4R)-pyrrolidinyloxy)cyclohexanecarboxylate (247 mg, 0.683 mmol) was dissolved in DMF (5 ml). To the resulting solution was added sodium hydride (60% in oil, 55 mg, 1.37 mmol) in portions under stirring at 0° C. in a nitrogen gas stream. After the reaction mixture was stirred at the same temperature for 30 minutes, methyl iodide (85 μl, 1.37 mmol) was added thereto. Stirring was conducted further at the same temperature for 4 hours. Sodium hydride (60% in oil, 55 mg, 1.37 mmol) and methyl iodide (85 μl, 1.37 mmol) were added and the mixture was stirred at room temperature for 14 hours. The reaction mixture was poured in water, followed by extraction with chloroform. The extract was washed with a saturated aqueous solution of sodium bicarbonate and saturated brine, dried over anhydrous sodium sulfate, and distilled under reduced pressure to remove the solvent. The residue was purified by chromatography on a silica gel column, whereby from n-hexane/ethyl acetate(2/1) eluate fractions, trans-4-(1-tert-butoxycarbonyl-(2S)-methoxymethyl-(4R)-pyrrolidinyloxy)cyclohexanecarboxylate (260 mg, 100%) was obtained as a colorless oil.

$^1$H-NMR (CDCl$_3$) δ: 1.20–1.32 (m, 3H), 1.39–1.52 (m, 10H), 1.91–2.13 (m, 6H), 2.21–2.29 (m, 1H), 3.25 (m, 1H), 3.34 (s, 3H), 3.37–3.53 (m, 4H), 3.66 (s, 3H), 3.79 and 4.05 (each br, total 1H, amide isomers), 4.14 and 4.21 (each br, total 1H, amide isomers).

MS (ESI) m/z 372 (M$^+$+1).

(Step 11) Synthesis of methyl trans-4-((2S)-methoxymethyl-(4R)-pyrrolidinyloxy)cyclohexanecarboxylate

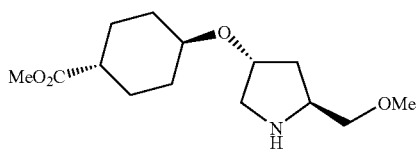

Methyl trans-4-(1-tert-butoxycarbonyl-(2S)-methoxymethyl-(4R)-pyrrolidinyloxy)cyclohexanecarboxylate (260 mg, 0.70 mmol) was dissolved in methylene chloride (10 ml). To the resulting solution was added trifluoroacetic acid (2 ml) and the mixture was stirred at room temperature for 14 hours. From the reaction mixture, the solvent was distilled off under reduced pressure. The residue was basified with 1N NaOH, followed by extraction with methylene chloride. The extract was washed with saturated brine, dried over anhydrous sodium sulfate and distilled under reduced pressure to remove the solvent, whereby methyl trans-4-((2S)-methoxymethyl-(4R)-pyrrolidinyloxy)cyclohexanecarboxylate (150 mg, 81%) was obtained as a yellow oil.

$^1$H-NMR (CDCl$_3$) δ: 1.21–2.39 (m, 1H), 2.87 (dd, J=11.5, 3.2 Hz, 1H), 3.05 (dd, J=11.5, 4.9 Hz, 1H), 3.20–3.34 (m, 2H), 3.35 (s, 3H), 3.48 (m, 2H), 3.66 (s, 3H), 4.07 and 4.14 (each br, total 1H, amide isomers).

MS (ESI) m/z 272 (M$^+$+1).

(Step 12) Synthesis of methyl trans-4-(1-((2-(5-fluoro-2-methylphenylamino)-7-fluoro-6-benzoxazolyl)acetyl)-(2S)-methoxymethyl-(4R)-pyrrolidinyloxy)cyclohexanecarboxylate

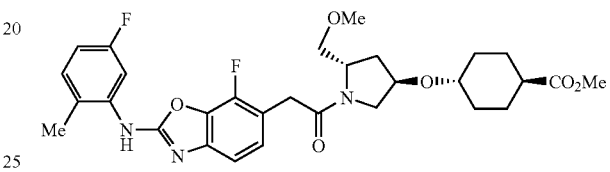

In DMF (2 ml), (2-(5-fluoro-2-methylphenylamino)-7-fluoro-6-benzoxazolyl)acetic acid (59 mg, 0.184 mmol), methyl trans-4-((2S)-methoxymethyl-(4R)-pyrrolidinyloxy)cyclohexanecarboxylate (50 mg, 0.184 mmol), EDC HCl (53 mg, 0.276 mmol), HOBT (37 mg, 0.276 mmol) and triethylamine (128 μl, 0.920 mmol) were stirred at room temperature for 3 days. Water was added to the reaction mixture, followed by extraction with ethyl acetate. The extract was washed with saturated brine, and heated under reflux over anhydrous sodium sulfate. After cooling, the reaction mixture was distilled under reduced pressure to remove the solvent. The residue was purified by column chromatography using a silica gel thin-layer plate (chloroform/acetone (7/1) eluent) to give methyl trans-4-(1-((2-(5-fluoro-2-methylphenylamino)-7-fluoro-6-benzoxazolyl)acetyl)-(2S)-methoxymethyl-(4R)-pyrrolidinyloxy)cyclohexanecarboxylate (99 mg, 94%) as a yellow oil.

$^1$H-NMR (CDCl$_3$) δ: 1.17–1.58 (m, 4H), 1.91–2.29 (m, 6H), 2.30 (s, 3H), 3.24 (m, 1H), 3.31 and 3.36 (each s, total 3H, amide isomers), 3.38–3.53 (m, 3H), 3.65 and 3.66 (s, 3H), 3.67–3.70 (m, 1H), 3.72 (s, 2H), 3.81–3.92 (m, 1H), 4.35–4.39 (m, 2H), 6.74 (dt, J=8.1,2.2 Hz, 1H), 7.09–7.16 (m, 2H), 7.22 (d, J=8.1 Hz, 1H), 8.06 (dd, J=11.0,2.4 Hz, 1H).

MS (ESI) m/z 572 (M$^+$+1).

(Step 13) Synthesis of trans-4-(1-((2-(5-fluoro-2-methylphenylamino)-7-fluoro-6-benzoxazolyl)acetyl)-(2S)-methoxymethyl-(4R)-pyrrolidinyloxy)cyclohexanecarboxylic acid

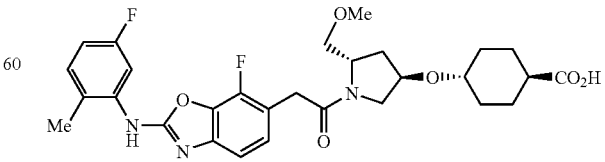

Methyl trans-4-(1-((2-(5-fluoro-2-methylphenylamino)-7-fluoro-6-benzoxazolyl)acetyl)-(2S)-methoxymethyl-(4R)-pyrrolidinyloxy)cyclohexanecarboxylate (99 mg, 0.173 mmol) was dissolved in THF/methanol (4/2 ml). To the resulting solution was added 1N NaOH (2 ml). After stirring at room temperature for 13 hours, the reaction mixture was distilled under reduced pressure to remove the solvent. To the residue was added 1N HCl. The crystals thus precipitated were collected by filtration under reduced pressure, washed with water and dried under reduced pressure. The crude crystals were purified by column chromatography using a silica gel thin-layer plate (TLC) (chloroform/methanol (20/1) developing solution) to give the title compound (61 mg, 63%) as a colorless solid.

$^1$H-NMR (DMSO-$d_6$) δ: 1.12–1.41 (m, 5H), 1.86–2.20 (m, 6H), 2.30 (s, 3H), 3.23 (s, 3H), 3.38–3.98 (m, 7H), 4.09 and 4.31 (each m, total 2H, amide isomers), 6.89(dt, J=8.3, 2.9 Hz, 1H), 7.09 (d, J=7.8 Hz, 1H), 7.19 and 7.20 (each d, each J=8.1 Hz, total 1H, amide isomers), 7.26 (t, J=7.8 Hz, 1H), 7.89–7.93 (m, 1H), 10.05 (br, 1H), 12.06 (br, 1H).

MS (ESI) m/z 558 (M$^+$+1).

Example 157 trans-4-(1-((5-Chloro-2-fluoro-4-(1-methyl-3-indolylcarbonylamino)phenyl)acetyl)-(2S)-methoxymethyl-(4R)-pyrrolidinylmethoxy)cyclohexanecarboxylic acid (Step 1) Synthesis of methyl trans-4-(1-((5-chloro-2-fluoro-4-(1-methyl-3-indolylcarbonylamino)phenyl)acetyl)-(2S)-methoxymethyl-(4R)-pyrrolidinylmethoxy)cyclohexanecarboxylate

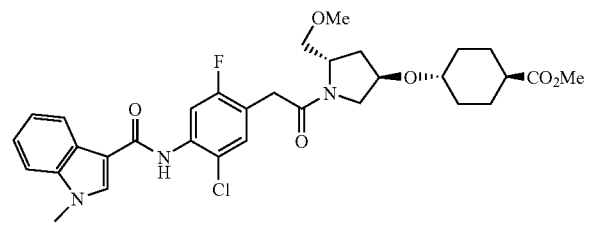

In DMF (2 ml), (5-chloro-2-fluoro-4-(1-methyl-3-indolylcarbonylamino)phenyl)acetic acid (66 mg, 0.184 mmol), methyl trans-4-((2S)-methoxymethyl-(4R)-pyrrolidinylmethoxy) cyclohexanecarboxylate (50 mg, 0.184 mmol), EDC HCl (53 mg, 0.276 mmol), HOBt (37 mg, 0.276 mmol) and triethylamine (128 µl, 0.920 mmol) were stirred at room temperature for 3 days. The reaction mixture was poured in ice water, followed by extraction. The extract was washed with ice water and saturated brine, dried over anhydrous sodium sulfate, and distilled under reduced pressure to remove the solvent. The residue was purified by chromatography using a silica gel thin-layer plate (TLC) (developed with chloroform/acetone (7/1)) to give methyl trans-4-(1-((5-chloro-2-fluoro-4-(1-methyl-3-indolylcarbonylamino)phenyl)acetyl)-(2S)-methoxymethyl (4R)-pyrrolidinylmethoxy)cyclohexanecarboxylate (99 mg, 88%) as a yellow oil.

$^1$H-NMR (CDCl$_3$) δ: 1.22–1.56 (m, 4H), 1.92–2.38 (m, 6H), 3.21–3.32 (m, 1H), 3.33 and 3.35 (each s, total 3H, amide isomers), 3.37–3.49 (m, 2H), 3.61 (d, J=5.4 Hz, 1H), 3.64 and 3.66 (each s, total 3H, amide isomers), 3.67–3.72 (m, 2H), 3.84 (m, 1H), 3.88 (s, 3H), 4.23–4.39 (m, 2H), 7.33–7.45 (m, 4H), 7.81 (s, 1H), 8.14 (m, 1H), 8.29 (s, 1H), 8.49 and 8.50 (each d, each J=12.0 Hz, total 1H, amide isomers).

MS (ESI) m/z 614 (M$^+$+1), 616 (M$^+$+3).

(Step 2) Synthesis of trans-4-(1-((5-chloro-2-fluoro-4-(1-methyl-3-indolylcarbonylamino)phenyl)acetyl)-(2S)-methoxymethyl-(4R)-pyrrolidinylmethoxy)cyclohexanecarboxylic acid

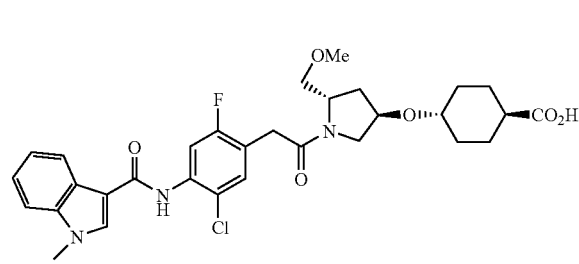

Methyl trans-4-(1-((5-chloro-2-fluoro-4-(1-methyl-3-indolylcarbonylamino)phenyl)acetyl)-(2S)-methoxymethyl (4R)-pyrrolidinylmethoxy)cyclohexanecarboxylate (99 mg, 0.161 mmol) was dissolved in THF/methanol (2:1, 6 ml). To the resulting solution was added 1N NaOH (2 ml). After stirring at room temperature for 13 hours, the reaction mixture was distilled under reduced pressure to remove the solvent. The residue was acidified with 1N HCl. The crystals thus precipitated were collected by filtration under reduced pressure, washed with water and dried under reduced pressure. The crude crystals were purified by chromatography using a silica gel thin-layer plate (TLC) (developed in chloroform/methanol (20/1)) to give the title compound (35 mg, 36%) as a colorless solid.

IR (ATR) ν 3417, 2935, 1724, 1641, 1620, 1518, 1404 cm$^{-1}$;

$^1$H-NMR (DMSO) δ: 1.11–1.41 (m, 4H), 1.87–2.19 (m, 7H), 3.24 (s, 3H), 3.31 (s, 1H), 3.35–3.56 (m, 3H), 3.67 (s, 2H), 3.68–3.86 (m, 1H), 3.89 (s, 3H), 4.09 and 4.33 (each m, total 2H, amide isomers), 7.21 (t, J=6.9 Hz, 1H), 7.27 (dt, J=8.1,1.0 Hz, 1H), 7.45 (t, J=7.3 Hz, 1H), 7.55 (d, J=8.3 Hz, 1H), 7.69 and 7.70 (each d, J=11.0 and 11.3 Hz respectively, total 1H, amide isomers), 8.14 (d, J=7.6 Hz, 1H), 8.31 (s, 1H), 9.31 (s, 1H), 12.05 (br, 1H).

MS (ESI) m/z 600 (M$^+$+1)., 602 (M$^+$+3);

Anal. Calcd for $C_{31}H_{35}ClFN_3O_6$ 0.6H$_2$O: C, 60.95; H, 5.97; Cl, 5.80;F, 3.11; N, 6.88. Found: C, 60.79; H, 5.99; Cl, 5.83; F, 3.02; N, 6.83.

Example 158 trans-4-(1-((5-Chloro-2-fluoro-4-(1-methyl-3-indazolylcarbonylamino)phenyl)acetyl)-(2S)-methoxymethyl-(4R)-pyrrolidinylmethoxy)cyclohexanecarboxylic acid (Step 1) Synthesis of methyl trans-4-(1-((5-chloro-2-fluoro-4-(1-methyl-3-indazolylcarbonylamino)phenyl)acetyl)-(2S)-methoxymethyl-(4R)-pyrrolidinylmethoxy)cyclohexanecarboxylate

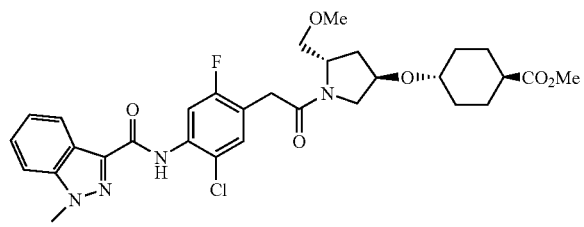

In DMF (2 ml), (5-chloro-2-fluoro-4-(1-methyl-3-indazolylcarbonylamino)phenyl)acetic acid (137 mg, 0.380 mmol), methyl trans-4-((2S)-methoxymethyl-(4R)-pyrrolidinyloxy)cyclohexanecarboxylate (103 mg, 0.380 mmol), EDC HCl (109 mg, 0.570 mmol), HOBt (77 mg, 0.570 mmol) and triethylamine (0.26 ml, 1.9 mmol) were stirred at room temperature for 21 hours. The reaction mixture was poured in ice water, followed by extraction with ethyl acetate. The extract was washed with ice water and saturated brine, dried over anhydrous sodium sulfate and distilled under reduced pressure to remove the solvent. The residue was purified by chromatography using a silica gel thin-layer plate (TLC) (chloroform/acetone (7/1) developing solution) to give methyl trans-4-(1-((5-chloro-2-fluoro-4-(1-methyl-3-indazolylcarbonylamino)phenyl)acetyl)-(2S)-methoxymethyl-(4R)-pyrrolidinylmethoxy)cyclohexanecarboxylate (198 mg, 85%) as a colorless oil.

$^1$H-NMR (CDCl$_3$) δ: 1.15–1.51 (m, 4H), 1.78 and 1.80 (each s, total 2H, amide isomers), 1.91–2.29 (m, 6H), 3.25 (m, 1H), 3.32 and 3.36 (each s, total 3H, amide isomers), 3.38–3.50 (m, 2H), 3.62 and 3.66 (each s, total 3H, amide isomers), 3.69 (m, 1H), 3.87 (s, 1H), 3.90 (s, 3H), 4.25–4.39 (m, 2H), 7.22 (t, J=7.3 Hz, 1H), 7.35–7.46 (m, 4H), 8.01 (s, 1H), 8.43 and 8.44 (each d, each J=3.2 Hz, total 1H, amide isomers).

MS (ESI) m/z 615 (M$^+$+1), 617 (M$^+$+3).

(Step 2) Synthesis of trans-4-(1-((5-chloro-2-fluoro-4-(1-methyl-3-indazolylcarbonylamino)phenyl)acetyl)-(2S)-methoxymethyl-(4R)-pyrrolidinylmethoxy)cyclohexanecarboxylic acid

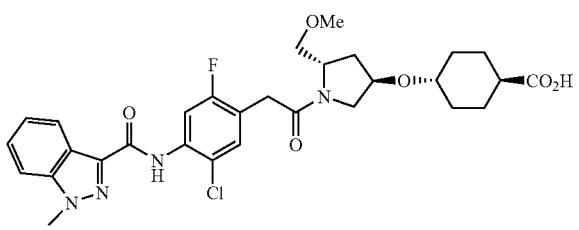

Methyl trans-4-(1-((5-chloro-2-fluoro-4-(1-methyl-3-indazolylcarbonylamino)phenyl)acetyl)-(2S)-methoxymethyl (4R)-pyrrolidinylmethoxy)cyclohexanecarboxylate (198 mg, 0.322 mmol) was dissolved in THF/methanol (2:1, 12 ml). To the resulting solution was added 1N NaOH (4 ml). After stirring at room temperature for 13 hours, the reaction mixture was distilled under reduced pressure to remove the solvent. The residue was acidified with 1N HCl. The crystals thus precipitated were collected by filtration under reduced pressure, washed with water and dried under reduced pressure to give the title compound (145 mg, 75%) as a colorless amorphous substance.

IR (ATR) ν 3361, 2939, 2864, 1724, 1685, 1620, 1529, 1408 cm$^{-1}$;

$^1$H-NMR (DMSO-d$_6$) δ: 1.13–1.43 (m, 4H), 1.84–2.21 (m, 7H), 3.25 (s, 3H), 3.34–3.57 (m, 4H), 3.68 (d, J=4.4 Hz, 2H), 3.74 (q, J=18.6 Hz, 1H), 4.09 and 4.35 (each m, total 2H, amide isomers), 4.22 (s, 3H), 7.38 (t, J=6.8 Hz, 1H), 7.51 (t, J=7.8 Hz, 1H), 7.54 (t, J=7.8 Hz, 1H), 7.83 (d, J=8.5 Hz, 1H), 8.07 (dd, J=11.2,1.2 Hz, 1H), 8.21 (dd, J=8.1,1.2 Hz, 1H), 9.72 (s, 1H), 12.07 (br, 1H).

MS (ESI) m/z 601 (M$^+$+1) 603 (M$^+$+3);

Anal. Calcd for C$_{30}$H$_{34}$ClFN$_4$O$_6$ 0.5H$_2$O 0.1HCl: C, 58.71; H, 5.76; Cl, 6.35; F, 3.10; N, 9.13. Found: C, 58.83; H, 5.66; Cl, 6.60; F, 3.06; N, 9.14.

Example 159

4-(1-((2-(5-Fluoro-2-methylphenylamino)-7-fluoro-6-benzoxazolyl)acetyl)-(2S)-methoxymethyl-(4R)-pyrrolidinyloxy)benzoic acid (Step 1) Synthesis of methyl 4-(1-((2-(5-fluoro-2-methylphenylamino)-7-fluoro-6-benzoxazolyl)acetyl)-(2S)-methoxymethyl-(4R)-pyrrolidinyloxy)benzoate

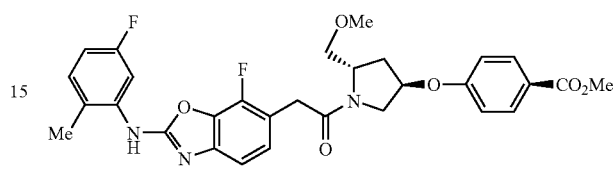

In DMF (2 ml), (2-(5-fluoro-2-methylphenylamino)-7-fluoro-6-benzoxazolyl)acetic acid (127 mg, 0.400 mmol), methyl 4-((2S)-methoxymethyl-(4R)-pyrrolidinyloxy)benzoate (106 mg, 0.400 mmol), EDC HCl (115 mg, 0.600 mmol), HOBt (81 mg, 0.600 mmol) and triethylamine (0.28 ml, 2.00 mmol) were stirred at room temperature for 21 hours. The reaction mixture was poured in ice water, followed by extraction with ethyl acetate. The extract was washed with saturated brine, dried over anhydrous sodium sulfate and distilled under reduced pressure to remove the solvent. The residue was purified by chromatography using a silica gel thin-layer plate (TLC) (chloroform/acetone (5/1) developing solution) to give methyl 4-(1-((2-(5-fluoro-2-methylphenylamino)-7-fluoro-6-benzoxazolyl)acetyl)-(2S)-methoxymethyl-(4R)-pyrrolidinyloxy)benzoate (118 mg, 52%) as a colorless amorphous substance.

$^1$H-NMR (CDCl$_3$) δ: 2.23–2.43 (m, 5H; including 2.32 ppm., s, 3H), 3.35 and 3.39 (each s, total 3H, amide isomers), 3.46–3.92 (m, 8H; including 3.79 ppm., s, 3H), 4.40 and 4.47 (each m, total 1H, amide isomers), 5.02 (m, 1H), 6.72–6.85 (m, 3H), 7.05 (br, 1H), 7.13 (d, J=8.3 Hz, 1H), 7.15 (d, J=7.3 Hz, 1H), 7.20 (d, J=8.0 Hz, 1H), 7.92 (d, J=9.0 Hz, 2H), 8.12 (dd, J=11.0,2.7 Hz, 1H).

MS (ESI) m/z 566 (M$^+$+1).

(Step 2) Synthesis of 4-(1-((2-(5-fluoro-2-methylphenylamino)-7-fluoro-6-benzoxazolyl)acetyl)-(2S)-methoxymethyl-(4R)-pyrrolidinyloxy)benzoic acid

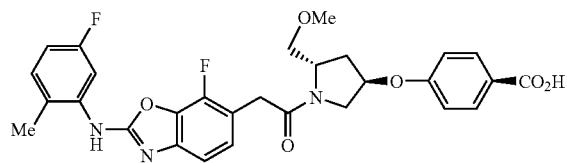

Methyl 4-(1-((2-(5-fluoro-2-methylphenylamino)-7-fluoro-6-benzoxazolyl)acetyl)-(2S)-methoxymethyl-(4R)-pyrrolidinyloxy)benzoate (118 mg, 0.209 mmol) was dissolved in THF/methanol (2:1, 12 ml). To the resulting solution was added 1N NaOH (4 ml). After stirring at room temperature for 18 hours, the reaction mixture was distilled under reduced pressure to remove the solvent. The residue was acidified with 1N HCl. The crystals thus precipitated were collected by filtration under reduced pressure, washed with water and dried under reduced pressure to give the title compound (92 mg, 80%) as a colorless solid.

IR (ATR) ν 2939, 1684, 1639, 1604, 1577, 1506, 1452, 1244 cm$^{-1}$;

$^1$H-NMR (DMSO-d$_6$) δ: 2.17 (m, 1H), 2.30 (s, 3H), 2.32 (m, 1H), 3.32 and 3.35 (each s, total 3H, amide isomers), 3.48 (m, 1H), 3.51–3.58 (m, 1H), 3.73 (d, J=7.6 Hz, 1H), 3.79 (d, J=10.2 Hz, 1H), 3.82–4.00 (m, 2H), 4.22 and 4.50 (each m, total 1H, amide isomers), 5.13 and 5.18 (each m, total 1H, amide isomers), 6.89 (dt, J=8.5, 1.7 Hz, 1H), 7.00 and 7.01 (each d, each J=7.6 Hz, total 2H, amide isomers), 7.06 and 7.09 (each d, J=7.1 and 4.4 Hz respectively, total 1H, amide isomers), 7.19 (d, J=8.8 Hz, 1H), 7.26 (t, J=7.8 Hz, 1H), 7.88 (d, J=8.3 Hz, 2H), 7.92 (d, J=11.0 Hz, 1H), 10.03 (br, 1H), 12.63 (br, 1H).

MS (ESI) m/z 552 (M$^+$+1);

Anal. Calcd for C$_{29}$H$_{27}$FN$_3$O$_6$ 0.5H$_2$O: C, 62.14; H, 5.03; F, 6.78; N, 7.50. Found: C, 62.33; H, 5.01; F, 6.70; N, 7.40.

Example 160

4-(1-(2-(5-Fluoro-2-methylphenylamino)-7-fluoro-6-benzoxazolylacetyl)-(3R)-pyrrolidinyloxy)cyclohexanecarboxylic acid (Step 1) Synthesis of ethyl 4-(1-benzyl-(3R)-pyrrolidinyloxy)benzoate

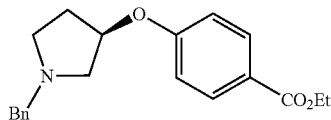

In THF (30 ml), DIAD (5.2 ml, 36.7 mmol) was added to 1-benzyl-(2S)-hydroxypyrrolidine (5.0 g, 28.2 mmol), ethyl 4-hydroxybenzoate (4.6 g, 28 mmol), and triphenylphosphine (9.6 g, 36.7 mmol) under stirring at 0° C. The reaction mixture was stirred at room temperature for 18 hours. From the reaction mixture, the solvent was distilled off under reduced pressure. The residue was purified by chromatography on a silica gel column, whereby from n-hexane-ethyl acetate (4:1 to 1:1, v/v) eluate fractions, ethyl 4-(1-benzyl-(3R)-pyrrolidinyloxy)benzoate (5.8 g, 64%) was obtained as an amorphous substance.

$^1$H-NMR (CDCl$_3$) δ: 1.36 (t, J=7.1 Hz, 3H), 1.67 (br s, 1H), 1.95–2.04 (m, 1H), 2.30–2.33 (m, 1H), 2.58–2.62 (m, 1H), 2.73–2.78 (m, 2H), 2.96–3.00 (m, 1H), 3.67 (AB q, J=7.0 Hz, 2H), 4.33 (q, J=7.1 Hz, 2H), 4.86–4.89 (m, 1H), 6.83 (d, J=9.0 Hz, 2H), 7.25–7.32 (m, 5H), 7.96 (d, J=9.0 Hz, 2H).

(Step 2) Synthesis of ethyl 4-(1-tert-butoxycarbonyl-(3R)-pyrrolidinyloxy)cyclohexanecarboxylate

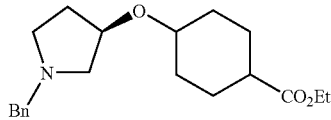

In ethanol (10 ml) and acetic acid (1.0 ml), ethyl 4-(1-benzyl-(3R)-pyrrolidinyloxy)benzoate (3.8 g, 11.7 mmol) and 5% rhodium/alumina (1.9 g) were subjected to catalytic hydrogenation for 24 hours under a hydrogen gas of 5 atom. From the reaction mixture, the catalyst was filtered off, and the filtrate was distilled under reduced pressure to remove the solvent. The residue was purified by chromatography on a silica gel column, whereby from n-hexane-ethyl acetate (5:1 to 4:1, v/v) eluate fractions, ethyl 4-(1-tert-butoxycarbonyl-(3R)-pyrrolidinyloxy)cyclohexanecarboxylate (1.9 g, 47%) was obtained as a pale yellow oil.

(Step 3) Synthesis of ethyl trans-4-(1-tert-butoxycarbonyl-(3R)-pyrrolidinyloxy)cyclohexanecarboxylate

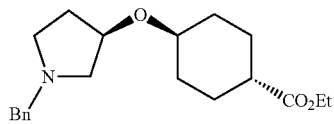

Ethyl 4-(1-tert-butoxycarbonyl-(3R)-pyrrolidinyloxy)cyclohexanecarboxylate (1.7 g, 4.98 mmol) and sodium methoxide (a 20% ethanol solution) (3.5 ml) were heated under reflux for 3 hours in ethanol (15 ml). After cooling, the reaction mixture was diluted with water, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane-ethyl acetate (4:1, v/v) eluate fractions, ethyl trans-4-(1-tert-butoxycarbonyl-(3R)-pyrrolidinyloxy)cyclohexanecarboxylate (280 mg, 16%) was obtained as a colorless oil.

$^1$H-NMR (CDCl$_3$) δ: 1.20–1.35 (m, 5H), 1.40–1.50 (m, 11H), 1.80–2.05 (m, 6H), 2.20–2.30 (m, 1H), 3.20–3.50 (m, 5H), 4.10–4.20 (m, 3H).

(Step 4) Synthesis of ethyl 4-(1-(2-(5-fluoro-2-methylphenylamino)-7-fluoro-6-benzoxazolylacetyl)-(3R)-pyrrolidinyloxy)cyclohexanecarboxylate

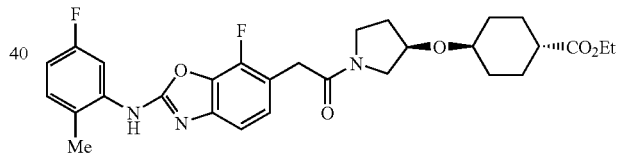

Ethyl trans-4-(1-tert-butoxycarbonyl-(3R)-pyrrolidinyloxy)cyclohexanecarboxylate (280 mg, 0.82 mmol) was dissolved in methylene chloride (5.0 ml). Under stirring at 0° C., trifluoroacetic acid (5.0 ml) was added to the resulting solution. The reaction mixture was stirred at room temperature for 0.5 hour. From the reaction mixture, the solvent was distilled off under reduced pressure. The residue was neutralized with a saturated aqueous solution of sodium bicarbonate, followed by extraction with methylene chloride. The extract was washed with saturated brine, dried over anhydrous sodium sulfate, and distilled under reduced pressure to remove the solvent (the resulting product was used to the subsequent reaction without further purification). In THF (5.0 ml) and acetonitrile (5.0 ml), EDC•HCl (119 mg, 0.62 mmol) were added to the residue (0.41 mmol), (2-(5-fluoro-2-methylphenylamino)-7-fluoro-6-benzoxazolyl)acetic acid (130 mg, 0.41 mmol), HOBt (84 mg, 0.41 mmol), and triethylamine (170 μl, 1.23 mmol) under ice cooling at 0° C. The reaction mixture was stirred at room temperature for 16 hours, and distilled under reduced pressure to remove the solvent. The residue was diluted with water, followed by extraction with ethyl acetate. The extract was washed successively with a saturated aqueous solution of sodium bicarbonate, a 2M aqueous solution of citric acid, and a saturated aqueous solution of sodium bicarbonate, dried over anhydrous sodium sulfate, and distilled under reduced pressure to remove the solvent. The residue was purified by column chromatography using a silica gel thin-layer plate (TLC) (n-hexane-ethyl acetate (1:3, v/v) developing solution) to give ethyl 4-(1-(2-(5-fluoro-2-methylphenylamino)-7-fluoro-6-benzoxazolylacetyl)-(3R)-pyrrolidinyloxy)cyclohexanecarboxylate (170 mg, 77%) as a colorless oil.

$^1$H-NMR (CDCl$_3$) δ: 1.19–1.38 (m, 5H), 1.39–1.55 (m, 2H), 1.85–2.10 (m, 6H), 2.19–2.30 (m, 1H), 2.31 (s, 3H), 3.20–3.32 (m, 1H), 3.50–3.80 (m, 6H), 4.07–4.14 (m, 2H), 4.20–4.27 (m, 1H), 6.73–6.77 (m, 1H), 7.02 (br s, 1H), 7.12–7.26 (m, 4H), 8.08–8.11 (m, 1H).

(Step 5) Synthesis of 4-(1-(2-(5-fluoro-2-methylphenylamino)-7-fluoro-6-benzoxazolylacetyl)-(3R)-pyrrolidinyloxy)cyclohexanecarboxylic acid

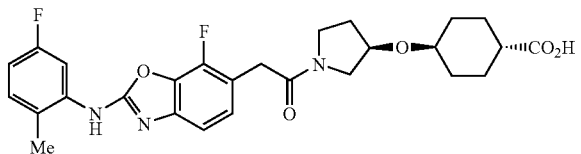

Ethyl 4-(1-(2-(5-fluoro-2-methylphenylamino)-7-fluoro-6-benzoxazolylacetyl)-(3R)-pyrrolidinyloxy)cyclohexanecarboxylate (170 mg, 0.31 mmol) was dissolved in THF (5.0 ml) and methanol (3.0 ml). To the resulting solution was added 1N NaOH (1.0 ml, 1.0 mmol). The resulting mixture was stirred at 70° C. for 18 hours. The reaction mixture was cooled and distilled under reduced pressure to remove the solvent. The residue was neutralized with 1N HCl. The crystals thus precipitated were collected by filtration under reduced pressure, washed with water and dried under reduced pressure to give the title compound (140 mg, 87%) as a white solid.

IR (KBr) ν 2940, 1639, 1610, 1577, 1454, 1070 cm$^{-1}$;

$^1$H-NMR (DMSO-d$_6$) δ: 1.10–1.25 (m, 2H), 1.30–1.45 (m, 2H), 1.80–2.00 (m, 6H), 2.10–2.20 (m, 1H), 2.29 (s, 3H), 3.30–3.80 (m, 7H), 4.20–4.29 (m, 1H), 6.86–6.91 (m, 1H), 7.09 (t, J=6.8 Hz, 1H), 7.20–7.27 (m, 2H), 7.92 (d, J=11.4 Hz, 1H).

MS (FAB) m/z 514 (M+H)$^+$;

Anal. Calcd for C$_{27}$H$_{29}$F$_2$N$_3$O$_5$ 0.8H$_2$O: C, 61.43; H, 5.84; N, 7.96. Found: C, 61.64; H, 5.79; N, 7.77.

Example 161 trans-4-(1-((7-Fluoro-2-(1-methyl-3-indolyl)-6-benzoxazolyl)acetyl)-(2S)-methoxymethyl-(4R)-pyrrolidinylmethoxy)cyclohexanecarboxylic acid (Step 1) Synthesis of methyl trans-4-(1-((7-fluoro-2-(1-methyl-3-indolyl)-6-benzoxazolyl)acetyl)-(2S)-methoxymethyl-(4R)-pyrrolidinylmethoxy)cyclohexanecarboxylate

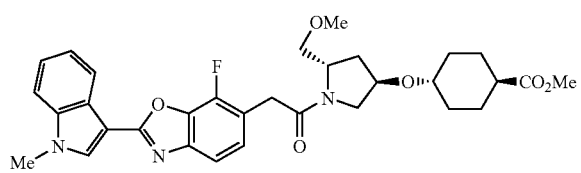

In DMF (2 ml), (7-fluoro-2-(1-methyl-3-indolyl)-6-benzoxazolyl)acetic acid (122 mg, 0.376 mmol), methyl trans-4-((2S)-methoxymethyl-(4R)-pyrrolidinyloxy)cyclohexanecarboxylate (102 mg, 0.376 mmol), EDC HCl (108 mg, 0.564 mmol), HOBt (76 mg, 0.564 mmol) and triethylamine (0.26 ml, 1.88 mmol) were stirred at room temperature for 21 hours. The reaction mixture was poured in ice water, followed by extraction with ethyl acetate. The extract was washed with ice water and saturated brine, dried over anhydrous sodium sulfate and distilled under reduced pressure to remove the solvent. The residue was purified by chromatography using a silica gel thin-layer plate (TLC) (chloroform/acetone (10/1) developing solution) to give methyl trans-4-(1-((7-fluoro-2-(1-methyl-3-indolyl)-6-benzoxazolyl)acetyl)-(2S)-methoxymethyl-(4R)-pyrrolidinylmethoxy)cyclohexanecarboxylate (175 mg, 84%) as a brown oil.

$^1$H-NMR (CDCl$_3$) δ: 1.18–1.53 (m, 4H), 1.82 (s, 1H), 1.93–2.31 (m, 7H), 3.25 (m, 1H), 3.33 and 3.34 (each s, total 3H, amide isomers), 3.42 (d, J=9.8 Hz, 2H), 3.61 and 3.63 (each s, total 3H, amide isomers), 3.65 (s, 1H), 3.66–3.88 (m, 2H), 4.15 (s, 3H), 4.23–4.34 (m, 2H), 7.33 (t, J=6.1 Hz, 1H), 7.39 (d, J=7.3 Hz, 1H), 7.45 (m, 2H), 8.37 (d, J=8.1 Hz, 1H), 8.49 and 8.51 (each d, each J=11.7 Hz, total 1H, amide iosmers), 9.48 (s, 1H).

MS (ESI) m/z 578 (M$^+$+1).

(Step 2) Synthesis of trans-4-(1-((7-fluoro-2-(1-methyl-3-indolyl)-6-benzoxazolyl)acetyl)-(2S)-methoxymethyl-(4R)-pyrrolidinylmethoxy)cyclohexanecarboxylic acid

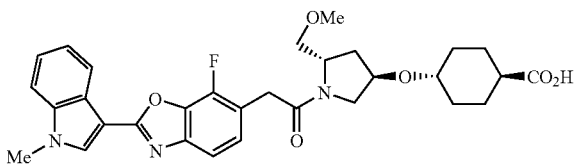

Methyl trans-4-(1-((7-fluoro-2-(1-methyl-3-indolyl)-6-benzoxazolyl)acetyl)-(2S)-methoxymethyl-(4R)-pyrrolidinylmethoxy)cyclohexanecarboxylate (175 mg, 0.324 mmol) was dissolved in THF/methanol (8/4 ml). To the resulting solution was added 1N NaOH (4 ml). After stirring at room temperature for 15 hours, the reaction mixture was distilled under reduced pressure to remove the solvent. The residue was acidified with 1N HCl. The crystals thus precipitated were collected by filtration under reduced pressure, washed with water and dried under reduced pressure to give the title compound (129 mg, 73%) as a colorless solid.

IR (ATR) ν 2937, 2864, 1724, 1626, 1583, 1502, 1442, 1369 cm$^{-1}$;

$^1$H-NMR (DMSO-d$_6$) δ: 1.10–1.41 (m, 4H), 1.83–2.19 (m, 7H), 3.24 (s, 3H), 3.7–3.38 (m, 1H), 3.42 (d, J=4.7 Hz, 2H), 3.51 and 3.55 (each dd, J=10.7,4.2 and 10.7,2.9 Hz respectively, total 1H, amide isomers), 3.70 (dd, J=10.5,5.4 Hz, 1H), 3.81 (s, 3H), 3.91 (s, 3H), 4.10 and 4.34 (each m, total 2H, amide isomers), 7.22 (t, J=6.6 Hz, 1H), 7.33 (dq, J=7.1,1.0 Hz, 1H), 7.35 (dq, J=7.1,1.0 Hz, 1H), 7.47 and 7.48 (each d, J=8.1 and 8.3 Hz respectively, total 1H, amide isomers), 7.63 (dd, J=6.8,1.5 Hz, 1H), 8.29 (dd, J=6.3,1.5 Hz, 1H), 8.44 (s, 1H), 12.05 (s, 1H).

MS (ESI) m/z 564 (M$^+$+1);

Anal. Calcd for C$_{31}$H$_{34}$FN$_3$O$_6$ 0.5H$_2$O: C, 65.02; H, 6.16; F, 3.32; N, 7.34. Found: C, 64.72; H, 6.15; F, 3.21; N, 7.28.

Example 162

4-(1-(5-Chloro-2-fluoro-4-(1-methyl-3-indolyl)carbonylaminophenylacetyl)-(3R)-pyrrolidinylmethoxy)benzoic acid (Step 1) Synthesis of 1-benzyl-(3R)-cyanopyrrolidine

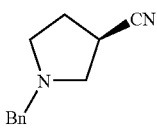

In methylene chloride (25 ml) were dissolved 1-benzyl-(3S)-hydroxypyrrolidine (4.0 g, 22.6 mmol) and triethylamine (9.1 ml, 66 mmol). Methanesulfonyl chloride (3.76 g, 33 mmol) was added dropwise under stirring at 0° C. After completion of the dropwise addition, the reaction mixture was stirred at room temperature for hour, and then distilled under reduced pressure to remove the solvent. The residue was purified by chromatography on a silica gel column, whereby from n-hexane:ethyl acetate (1:4, v/v) eluate fractions, the resulting product was obtained as a pale yellow oil. The oil was dissolved in DMSO (25 ml), and to the resulting solution was added sodium cyanide (6.0 g, 113 mmol). The resulting mixture was stirred at 60° C. for 18 hours. The reaction mixture was poured in water, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane:ethyl acetate (3:1 to 1:1, v/v) eluate fractions, 1-benzyl-(3R)-cyanopyrrolidine (3.2 g, 77%) was obtained as a pale yellow oil.

$^1$H-NMR (CDCl$_3$) δ: 2.05–2.30 (m, 2H), 2.58–2.70 (m, 3H), 2.80–3.05 (m, 2H), 3.64 (AB q, J=12.9 Hz, 2H), 7.25–7.34 (m, 5H).

(Step 2) Synthesis of methyl 1-benzyl-(3R)-pyrrolidinylcarboxylate

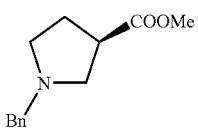

In concentrated HCl (15 ml), 1-benzyl-(3R)-cyanopyrrolidine (2.0 g, 10.75 mmol) was heated under reflux for 0.5 hour. After cooling, the reaction mixture was distilled under reduced pressure to remove the solvent. The residue was dissolved in methanol (10 ml). Under stirring at −50° C., and thionyl chloride (2.6 ml) was added. The mixture was stirred further at room temperature for 18 hours. From the reaction mixture, the solvent was distilled off under reduced pressure. The residue was neutralized with a saturated aqueous solution of sodium bicarbonate, followed by extraction with chloroform. The extract was washed with saturated brine, dried over anhydrous sodium sulfate, and distilled under reduced pressure to remove the solvent. The residue was purified by chromatography on a silica gel column, whereby from n-hexane:ethyl acetate (2:1 to 1:2, v/v) eluate fractions, methyl 1-benzyl-(3R)-pyrrolidinylcarboxylate (1.6 g, 70%) was obtained as a colorless oil.

$^1$H-NMR (CDCl$_3$) δ: 2.08–2.12 (m, 2H), 2.50–2.69 (m, 3H), 2.88–3.03 (m, 2H), 3.62 (s, 3H), 3.67 (s, 3H), 7.25–7.32 (m, 5H).

(Step 3) Synthesis of methyl 1-tert-butoxycarbonyl-(3R)-pyrrolidinylcarboxylate

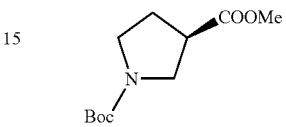

Methyl 1-benzyl-(3R)-pyrrolidinylcarboxylate (1.6 g, 7.3 mmol) and palladium hydroxide-carbon (300 mg) were subjected to catalytic hydrogenation in methanol (15 ml) under normal pressure for 18 hours. From the reaction mixture, the catalyst was filtered off, and the filtrate was distilled under reduced pressure to remove the solvent, whereby a colorless oil was obtained. The oil was dissolved in methylene chloride (20 ml). To the resulting solution were added di-tert-butyl dicarbonate (2.0 g, 9.5 mmol) and triethylamine (2.0 ml). The resulting mixture was stirred at room temperature for 6 hours. From the reaction mixture, the solvent was distilled off under reduced pressure. The residue was purified by chromatography on a silica gel column, whereby from n-hexane:ethyl acetate (5:1 to 1:1, v/v) eluate fractions, methyl 1-tert-butoxycarbonyl-(3R)-pyrrolidinylcarboxylate (1.2 g, 72%) was obtained as a colorless oil.

$^1$H-NMR (CDCl$_3$) δ: 1.46 (s, 9H), 2.12 (br s, 2H), 3.04–3.06 (m, 1H), 3.33–3.36 (m, 1H), 3.48–3.70 (m, 3H), 3.71 (s, 3H).

(Step 4) Synthesis of 1-tert-butoxycarbonyl-(3R)-pyrrolidinylcarboxylic acid

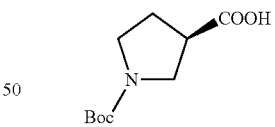

Methyl 1-tert-butoxycarbonyl-(3R)-pyrrolidinylcarboxylate (1.6 g, 6.98 mmol) was dissolved in THF (15 ml) and methanol (7 ml). To the resulting solution was added 1N NaOH (10 ml, 10 mmol). The mixture was stirred at 70° C. for 18 hours. The reaction mixture was cooled and distilled under reduced pressure to remove the solvent. The residue was neutralized with 1N HCl. The crystals thus precipitated were collected by filtration under reduced pressure, washed with water and dried under reduced pressure to give 1-tert-butoxycarbonyl-(3R)-pyrrolidinylcarboxylic acid (1.5 g, 80%) as a white crystalline solid.

$^1$H-NMR (CDCl$_3$) δ: 1.46 (s, 9H), 2.10–2.20 (m, 2H), 3.08–3.11 (m, 1H), 3.36–3.62 (m, 4H).

(Step 5) Synthesis of 1-tert-butoxycarbonyl-(3R)-pyrrolidinemethanol

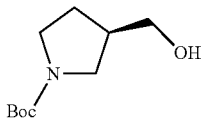

In THF (15 ml), borane-dimethyl sulfide (a 1.0M THF solution) (8.0 ml, 8.0 mmol) was added to 1-tert-butoxycarbonyl-(3R)-pyrrolidinylcarboxylic acid (1.1 g, 5.11 mmol) under stirring at 0° C. The reaction mixture was stirred at room temperature for 3 hours and then, heated under reflux for 3 hours. After cooling, the reaction mixture was distilled under reduced pressure to remove the solvent. Water was added the residue, followed by extraction with ethyl acetate. The extract was washed with water, dried over anhydrous sodium sulfate, and distilled under reduced pressure to remove the solvent to give 1tert-butoxycarbonyl-(3R)-pyrrolidinemethanol (1.2 g, 100%) as a colorless oil.

$^1$H-NMR (CDCl$_3$) δ: 1.45 (s, 9H), 1.80–2.00 (m, 1H), 2.30–2.45 (m, 1H), 3.05–3.15 (m, 1H), 3.20–3.70 (m, 6H).

(Step 6) Synthesis of ethyl 4-(1-tert-butoxycarbonyl-(3R)-pyrrolidinylmethoxy)benzoate

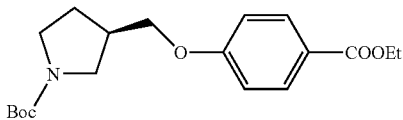

In THF (15 ml), DIAD (1.34 g, 6.64 mmol) was added to 1-tert-butoxycarbonyl-(3R)-pyrrolidinemethanol (1.1 g, 5.11 mmol), ethyl 4-hydroxybenzoate (848 mg, 5.11 mmol), and triphenylphosphine (1.74 g, 6.64 mmol) under stirring at 0° C. The reaction mixture was stirred further at room temperature for 18 hours. From the reaction mixture, the solvent was distilled off under reduced pressure. The residue was purified by chromatography on a silica gel column, whereby from n-hexane:ethyl acetate (1:1, v/v) eluate fractions, ethyl 4-(1-tert-butoxycarbonyl-(3R)-pyrrolidinylmethoxy)benzoate (800 mg, 45%) was obtained as a pale yellow oil.

$^1$H-NMR (CDCl$_3$) δ: 1.38 (t, J=7.1 Hz, 3H), 1.75–1.85 (m, 1H), 2.00–2.15 (m, 1H), 2.62–2.75 (m, 1H), 3.15–3.65 (m, 4H), 3.85–4.05 (m, 2H), 4.34 (q, J=7.1 Hz, 2H), 6.90 (d, J=8.5 Hz, 2H), 7.99 (d, J=8.5 Hz, 2H).

(Step 7) Synthesis of ethyl 4-(1-((5-chloro-2-fluoro-4-(1-methyl-3-indolyl)carbonylaminophenyl)acetyl)-(3R)-pyrrolidinylmethoxy)benzoate

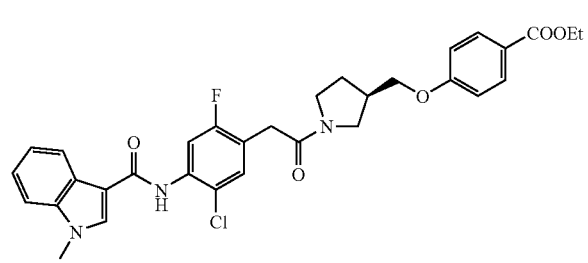

Ethyl 4-(1-tert-butoxycarbonyl-(3R)-pyrrolidinylmethoxy)benzoate (150 mg, 0.42 mmol) was dissolved in methylene chloride (5.0 ml). To the resulting solution was added trifluoroacetic acid (5.0 ml) under stirring at 0° C. The reaction mixture was stirred further at room temperature for 0.5 hour. From the reaction mixture, the solvent was distilled off under reduced pressure. The residue was neutralized with a saturated aqueous solution of sodium bicarbonate, followed by extraction with methylene chloride. The extract was washed with saturated brine, dried over anhydrous sodium sulfate, and distilled under reduced pressure to remove the solvent. The resulting residue was provided for the subsequent reaction without further purification. In THF (5.0 ml) and acetonitrile (5.0 ml), EDC•HCl (144 mg, 0.75 mmol) was added to the resulting oil, (5-chloro-2-fluoro-4-(1-methyl3-indolyl)carbonylaminophenyl)acetic acid (180 mg, 0.5 mmol), HOBt (70 mg, 0.5 mmol), and triethylamine (208 μl, 1.5 mmol) at 0° C. The resulting mixture was stirred for 16 hours. From the reaction mixture, the solvent was distilled off under reduced pressure. Water was added to the residue, followed by extraction with ethyl acetate. The extract was washed successively with a saturated aqueous solution of sodium bicarbonate, a 2M aqueous solution of citric acid, and a saturated aqueous solution of sodium bicarbonate, dried over anhydrous sodium sulfate, and distilled under reduced pressure to remove the solvent. The residue was purified by chromatography using a silica gel thin-layer plate (TLC), whereby from n-hexane:ethyl acetate (1:4, v/v) eluate fractions, methyl 4-(1-(5-chloro-2-fluoro-4-(1-methyl-3-indolyl)carbonylaminophenylacetyl)-(3R)-pyrrolidinylmethoxy)benzoate (140 mg, 55%) was obtained as a colorless oil.

$^1$H-NMR (CDCl$_3$) δ: 1.32–1.39 (m, 3H), 1.80–2.30 (m, 2H), 2.62–2.88 (m, 1H), 3.35–4.10 (m, 8H), 4.20–4.40 (m, 2H), 6.88 (d, J=7.1 Hz, 2H), 7.34–7.45 (m, 4H), 7.81 (d, J=7.1 Hz, 1H), 7.99 (d, J=7.1 Hz, 2H), 8.12–8.14 (m, 1H), 8.25–8.30 (m, 1H), 8.48–8.53 (m, 1H).

(Step 8) Synthesis of 4-(1-((5-chloro-2-fluoro-4-(1-methyl-3-indolyl)carbonylaminophenylacetyl)-(3R)-pyrrolidinylmethyloxy)benzoic acid

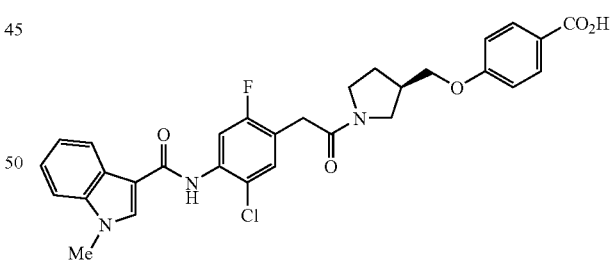

Ethyl 4-(1-((5-chloro-2-fluoro-4-(1-methyl-3-indolyl)carbonylaminophenylacetyl)-(3R)-pyrrolidinylmethyloxy)benzoate (140 mg, 0.24 mmol) was dissolved in THF (10 ml) and methanol (5.0 ml). To the resulting solution was added 1N NaOH (1.0 ml, 1.0 mmol). The resulting mixture was stirred at 70° C. for 18 hours. The reaction mixture was distilled under reduced pressure to remove the solvent. The residue was diluted with water, and then acidified with 1N HCl. The crystals thus precipitated were collected by filtration under reduced pressure, washed with water and dried under reduced pressure to give the title compound (160 mg, 100%) as a white crystalline solid.

¹H-NMR (DMSO-d₆) δ: 1.70–2.20 (m, 2H), 2.60–2.80 (m, 1H), 3.20–3.90 (m, 9H), 4.02–4.18 (m, 2H), 7.03–7.06 (m, 2H), 7.20–7.29 (m, 2H), 7.47 (dd, J=2.7,7.5, 1H), 7.56 (d, J=8.0 Hz, 1H), 7.70 (dd, J=2.9,11.2 Hz, 1H), 7.88–7.91 (m, 1H), 8.15 (d, J=7.5 Hz, 1H), 8.31 (s, 1H), 9.31 (d, J=2.9 Hz, 1H).

MS (ESI) m/z 564 (M +H)⁺.

Example 163 trans-4-(1-(5-Chloro-2-fluoro-4-(1-methyl-3-indolyl)carbonylaminophenylacetyl)-(3R)-pyrrolidinylmethyloxy)cyclohexanecarboxylic acid (Step 1) Synthesis of ethyl 4-(1-tert-butoxycarbonyl-(3R)-pyrrolidinylmethoxy)cyclohexanecarboxylate

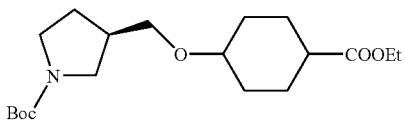

Ethyl 4-(1-tert-butoxycarbonyl-(3R)-pyrrolidinylmethoxy)benzoate (650 mg, 1.86 mmol) and 5% rhodium-alumina (300 mg) were subjected to catalytic hydrogenation in ethanol (10 ml) and acetic acid (1.0 ml) under a hydrogen gas of 5 atm for 24 hours. From the reaction mixture, the catalyst was filtered off, and the filtrate was distilled under reduced pressure to remove the solvent, whereby ethyl 4-(1-tert-butoxycarbonyl-3R-pyrrolidinylmethoxy)cyclohexanecarboxylate (660 mg, 100%) was obtained as a colorless oil. The resulting compound was provided for the subsequent reaction without further purification.

(Step 2) Synthesis of methyl cis- and trans-4-(1-tert-butoxycarbonyl-(3R)-pyrrolidinylmethoxy)cyclohexanecarboxylates

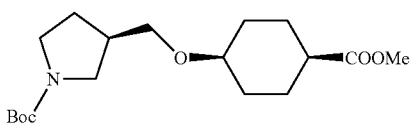

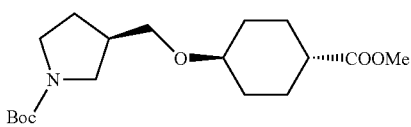

Ethyl 4-(1-tert-butoxycarbonyl-(3R)-pyrrolidinylmethoxy)cyclohexanecarboxylate (640 mg, 1.91 mmol) and a sodium ethoxide ethanol solution (4.0 mmol) were heated under reflux for 3 hours in ethanol (20 ml). After cooling, the reaction mixture was distilled under reduced pressure to remove the solvent. The residue was diluted with ethyl acetate. The ethyl acetate solution was washed with saturated brine, dried over anhydrous sodium sulfate, and distilled under reduced pressure to remove the solvent to give 4-(1-tert-butoxycarbonyl-3R-pyrrolidinylmethoxy)cyclohexanecarboxylic acid. The resulting product was dissolved in toluene (16 ml) and methanol (4.0 ml). Trimethylsilyldiazomethane (a 2.0M hexane solution) (1.4 ml) was added dropwise to the resulting solution. After stirring at room temperature for 1 hour, the reaction mixture was distilled under reduced pressure to remove the solvent. The residue was purified by flash column chromatography using a silica gel, whereby from n-hexane:ethyl acetate (4:1, v/v) eluate fractions, methyl 4-(1-tert-butoxycarbonyl-(3R)-pyrrolidinylmethoxy)cyclohexanecarboxylate (270 mg, 41% for cis-isomer, 120 mg, 18% for trans-isomer) was obtained as a colorless oil.

Cis isomer; ¹H-NMR (CDCl₃) δ: 1.39–2.00 (m, 19H), 2.30–2.50 (m, 2H), 3.00–3.10 (m, 1H), 3.22–3.55 (m, 6H), 3.66 (s, 3H).

Trans isomer; ¹H-NMR (CDCl₃) δ: 1.18–1.28 (m, 2H), 1.40–1.55 (m, 11H), 1.90–2.10 (m, 6H), 2.20–2.50 (m, 2H), 3.00–3.55 (m, 7H), 3.66 (s, 3H).

(Step 3) Synthesis of methyl trans-4-(1-((5-chloro-2-fluoro-4-(1-methyl-3-indolyl)carbonylaminophenyl)acetyl)-(3R)-pyrrolidinylmethyloxy)cyclohexanecarboxylate

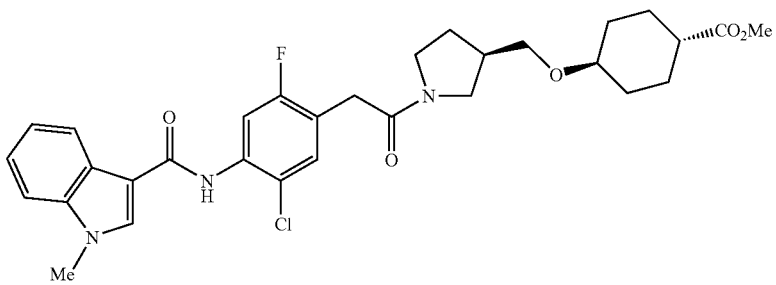

Methyl trans-4-(1-tert-butoxycarbonyl-(3R)-pyrrolidinylmethoxy)cyclohexanecarboxylate (120 mg, 0.35 mmol) was dissolved in methylene chloride (5.0 ml). To the resulting solution was added trifluoroacetic acid (5.0 ml) under stirring at 0° C. The reaction mixture was stirred further at room temperature for 0.5 hour. From the reaction mixture, the solvent was distilled off under reduced pressure. A saturated aqueous solution of sodium bicarbonate was added to the residue, followed by extraction with methylene chloride. The extract was washed with saturated brine, dried over anhydrous sodium sulfate, and distilled under reduced pressure to remove the solvent. The crude product thus obtained was provided for the subsequent reaction without further purification. In THF (5.0 ml) and acetonitrile (5.0 ml), EDC•HCl (100 mg, 0.52 mmol) was added to the crude product, (5-chloro-2-fluoro-4-(1-methyl-3-indolyl)carbonylaminophenyl)acetic acid (126 mg, 0.35 mmol), HOBt (48 mg, 0.35 mmol), and triethylamine (139 μl, 1.0 mmol) under stirring at 0° C. The reaction mixture was stirred further at room temperature for 16 hours. From the reaction mixture, the solvent was distilled off under reduced pressure. The residue was diluted with water, followed by extraction with ethyl acetate. The extract was washed successively with a saturated aqueous solution of sodium bicarbonate, a 2M aqueous solution of citric acid, and a saturated aqueous solution of sodium bicarbonate, dried over anhydrous sodium sulfate, and distilled under reduced pressure to remove the solvent. The residue was purified by chromatography using a silica gel thin-layer plate (TLC), whereby from n-hexane:ethyl acetate (1:7, v/v) eluate fractions, methyl trans-4-(1-((5-chloro-2-fluoro-4-(1-methyl-3-indolyl)carbonylaminophenyl)acetyl)-(3R)-pyrrolidinylmethyloxy)cyclohexanecarboxylate (110 mg, 54%) was obtained as a colorless oil.

$^1$H-NMR (CDCl$_3$) δ: 1.10–1.31 (m, 2H), 1.35–1.50 (m, 2H), 1.52–1.85 (m, 2H), 1.90–2.10 (m, 6H), 2.15–2.30 (m, 1H), 2.40–2.60 (m, 1H), 3.20–3.80 (m, 10H), 3.89 (s, 3H), 7.33–7.44 (s, 4H), 7.80 (s, 1H), 8.12–8.14 (m, 1H), 8.29 (s, 1H), 8.48–8.52 (m, 1H).

(Step 4) Synthesis of trans-4-(1-((5-chloro-2-fluoro-4-(1-methyl-3-indolyl)carbonylaminophenyl)acetyl)-(3R)-pyrrolidinylmethoxy)cyclohexanecarboxylic acid Methyl trans-4-(1-((5-chloro-2-fluoro-4-(1-methyl-3-indolyl)carbonylaminophenylacetyl)-(3R)-pyrrolidinylmethoxy)cyclohexanecarboxylate (110 mg, 0.2 mmol) was dissolved in THF (10 ml) and methanol (5.0 ml). To the resulting solution was added 1N NaOH (1.0 ml, 1.0 mmol). The resulting mixture was stirred at 70° C. for 18 hours. After cooling, the reaction mixture was distilled under reduced pressure to remove the solvent. The residue was neutralized with 1N HCl. The crystals thus precipitated were collected by filtration under reduced pressure, washed with water and dried under reduced pressure to give the title compound (100 mg, 100%) as a white crystalline solid.

IR (ATR) ν 1614, 1517, 1403, 1099 cm$^{-1}$;

$^1$H-NMR (DMSOd$_6$) δ: 1.10–1.21 (m, 2H), 1.30–1.40 (m, 2H), 1.50–1.75 (m, 1H), 1.80–2.05 (m, 5H), 2.10–2.40 (m, 2H), 3.05–3.80 (m, 9H), 3.89 (s, 3H), 7.19–7.29 (m, 2H), 7.45 (d, J=7.3 Hz, 1H), 7.55 (d, J=8.3 Hz, 1H), 7.69 (d, J=11.0 Hz, 1H), 8.15 (d, J=7.8 Hz, 1H), 8.30 (s, 1H), 9.31 (s, 1H).

MS (FAB) m/z 570 (M+H)$^+$;

Anal. calcd for C$_{30}$H$_{33}$ClFN$_3$O$_5$: C, 63.21; H, 5.83; N, 7.37; Cl, 6.22; F, 3.33. Found: C, 62.86; H, 5.71; N, 7.15; Cl, 5.99; F, 3.19.

Example 164 trans-4-(1-((5-Chloro-2-fluoro-4-((1-methyl-3-indolylcarbonyl)amino)phenyl)acetyl)-(5R)-methoxymethyl-(2S)-pyrrolidinylmethoxy)cyclohexanecarboxylic acid (Step 1) Synthesis of (5S)-benzyloxymethyl-N-tert-butoxycarbonyl-(2S)-pyrrolidinecarbaldehyde

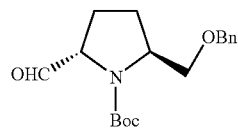

To a solution of oxalyl chloride (1.58 ml, 18.1 mmol) in methylene chloride (30 ml) was added dropwise DMSO (1.93 ml, 27.2 mmol) under stirring at −78° C. To the reaction mixture, a solution of (5S)-benzyloxymethyl-N-tert-butoxycarbonyl-(2S)-pyrrolidinemethanol (2.91 g, 9.05 mmol) in methylene chloride (20 ml) was added at the same temperature. At a reaction temperature raised from −78° C. to −40° C., stirring was conducted for 3 hours. Triethylamine (6.31 ml, 45.3 mmol) was added to the reaction mixture, and the mixture was stirred at 40° C. for 2 hours. The reaction mixture was diluted with a saturated aqueous solution of ammonium chloride, followed by extraction with chloroform. The extract was washed with saturated brine, dried over anhydrous sodium sulfate, and distilled under reduced pressure to remove the solvent. The residue was purified by chromatography on a silica gel column, whereby from n-hexane/ethyl acetate (4:1, v/v) eluate fractions, (5S)-benzyloxymethyl-N-tert-butoxycarbonyl-(2S)-pyrrolidinecarbaldehyde (2.90 g, 100%) was obtained as a pale yellow oil.

$^1$H-NMR (CDCl$_3$) δ: 1.42 and 1.43 (each s, total 9H), 1.85–2.04 (m, 3H), 2.16–2.35 (m, 1H), 3.41–3.45 and 3.55–3.59 (each m, total 1H), 3.61–3.63 (m, 1H), 4.07–4.30 (m, 2H), 4.48–4.57 (m, 2H), 7.27–7.35 (m, 5H), 9.52 and 9.58 (each s, total 1H).

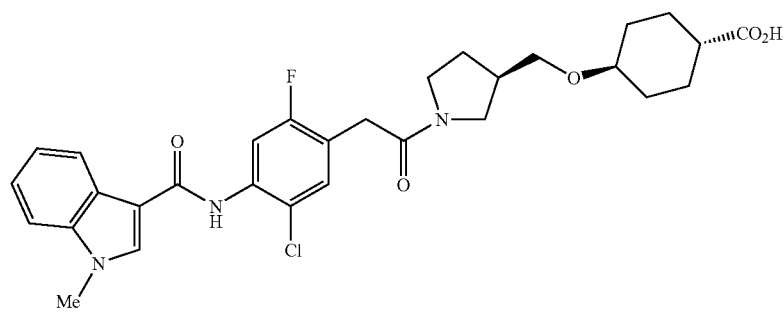

(Step 2) Synthesis of (2S)-benzyloxymethyl-N-tert-butoxycarbonyl-(5R)-hydroxymethylpyrrolidine and (2S)-benzyloxymethyl-N-tert-butoxycarbonyl-(5S)-hydroxymethylpyrrolidine

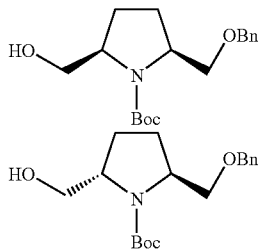

In methanol (30 ml) was dissolved (5S)-benzyloxymethyl-N-tert-butoxycarbonyl-(2S)-pyrrolidinecarbaldehyde (2.90 g, 9.08 mmol). To the resulting solution was added potassium carbonate (1.50 g, 10.9 mmol) and the mixture was heated under reflux for 10 hours. After cooling to room temperature, the reaction mixture was distilled under reduced pressure to remove the solvent. Water was added to the residue, followed by extraction with ethyl acetate. The extract was washed with saturated brine, dried over anhydrous sodium sulfate, and distilled under reduced pressure to remove the solvent, whereby (5S)-benzyloxymethyl-N-tert-butoxycarbonylpyrrolidinecarbaldehyde (2.52 g) was obtained. In methanol (20 ml), sodium borohydride (0.60 g, 15.9 mmol) was added to (5S)-benzyloxymethyl-N-tert-butoxycarbonylpyrrolidinecarbaldehyde (2.52 g, 7.89 mmol) under stirring at 0° C., while adding thereto. The reaction mixture was stirred at room temperature for 20 hours. The mixture was concentrated under reduced pressure to remove the solvent. Water was added to the residue, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane/ethyl acetate (3:1, v/v) eluate fractions, (2S)-benzyloxymethyl-N-tert-butoxycarbonyl-(5R)-hydroxymethylpyrrolidine (1.42 g, 56%) was obtained as a pale yellow oil.

$^1$H-NMR (CDCl$_3$) (2S,5R) δ: 1.43 (s, 9H), 1.87–2.01 (m, 4H), 3.44–3.52 (m, 2H), 3.74–3.78 (m, 1H), 3.92–4.01 (m, 2H), 4.50–4.57 (m, 1H), 4.70 (m, 1H), 7.27–7.37 (m, 5H).

In addition, (2S)-benzyloxymethyl-N-tert-butoxycarbonyl-(5S)-hydroxymethylpyrrolidine (0.65 g, 26%) was obtained as a pale yellow oil.

$^1$H-NMR (CDCl$_3$) (2S,5S) δ: 1.41 (s, 9H), 1.93–2.16 (m, 4H), 3.33–3.38 (m, 1H), 3.52–3.60 (m, 2H), 3.66–3.72 (m, 1H), 3.95–4.02 (m, 2H), 4.29 (m, 1H), 4.48–4.54 (m, 2H), 7.28–7.36 (m, 5H).

(Step 3) Synthesis of (2S)-benzyloxymethyl-N-tert-butoxycarbonyl-(5R)-methoxymethylpyrrolidine

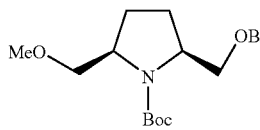

In DMF (5 ml) were suspended (2S)-benzyloxymethyl-N-tert-butoxycarbonyl-(5R)-hydroxymethylpyrrolidine (190 mg, 0.59 mmol) and sodium hydride (28 mg, 1.17 mmol). To the resulting suspension was added methyl iodide (44 μl, 0.71 mmol) under stirring at 0° C. The reaction mixture was stirred further at room temperature for 2 days. Water was added to the reaction mixture, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane/ethyl acetate (5:1, v/v) eluate fractions, (2S)-benzyloxymethyl-N-tert-butoxycarbonyl-(5R)-methoxymethylpyrrolidine (183 mg, 92%) was obtained as a colorless oil.

$^1$H-NMR (CDCl$_3$) δ: 1.44 (s, 9H), 1.87–1.99 (m, 4H), 3.28–3.34 (m, total 5 H, including s, 3H, at δ: 3.31), 3.49 (m, 1H), 3.51–3.61 (m, 1H), 3.96 (m, 2H), 4.52 (s, 2H), 7.25–7.33 (m, 5H).

(Step 4) Synthesis of N-tert-butoxycarbonyl-(5R)-methoxymethyl-(2S)-pyrrolidinemethanol

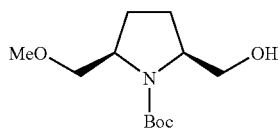

In methanol (10 ml) was dissolved (2S)-benzyloxymethyl-N-tert-butoxycarbonyl-(5R)-methoxymethylpyrrolidine (183 mg, 0.55 mmol). In the presence of 10% palladium-carbon (40 mg, ca. 20 wt %), the resulting solution was subjected to catalytic hydrogenation for 15 hours. From the reaction mixture, the catalyst was filtered off and the filtrate was distilled under reduced pressure to remove the solvent. The residue was purified by chromatography on a silica gel column, whereby from n-hexane/ethyl acetate (2:1, v/v) eluate fractions, N-tert-butoxycarbonyl-(5R)-methoxymethyl-(2S)-pyrrolidinemethanol (116 mg, 87%) was obtained as a colorless oil.

$^1$H-NMR (CDCl$_3$) δ: 1.48 (s, 9H), 1.87–2.01 (m, 4H), 3.36 (s, 3H), 3.38–3.39 (m, 1H), 3.45–3.51 (m, 1H), 3.78–3.99 (m, 3H), 4.66–4.69 (m, 1H).

(Step 5) Synthesis of methyl 4-((5R)-methoxymethyl-(2S)-pyrrolidinylmethoxy)benzoate

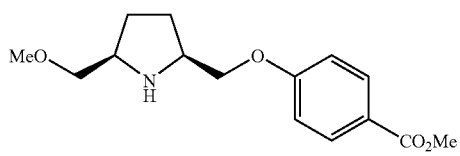

In THF (20 ml), DIAD (1.14 ml, 5.79 mmol) was added to N-tert-butoxycarbonyl-(5R)-methoxymethyl-(2S)-pyrrolidinemethanol (950 mg, 3.87 mmol), methyl 4-hydroxybenzoate (648 mg, 4.26 mmol) and triphenylphosphine (1.22 g, 4.65 mmol) and the resulting mixture was heated under reflux for 10 hours. After cooling to room temperature, the reaction mixture was distilled under reduced pressure to remove the solvent. The residue was purified by chromatography on a silica gel column, whereby from n-hexane/ethyl acetate (6:1, v/v) eluate fractions, methyl 4-(N-tert-butoxycarbonyl-(5R)-methoxymethyl-(2S)-pyrrolidinylmethoxy)benzoate (1.62 g) was obtained.

The resulting product (1.62 g) was dissolved in methylene chloride (15 ml). To the resulting solution was added trifluoroacetic acid (15 ml). The reaction mixture was stirred at room temperature for 17 hours. The reaction mixture was made basic with a saturated aqueous solution of sodium bicarbonate, followed by extraction with chloroform. The extract was washed with saturated brine, dried over anhydrous sodium sulfate, and distilled under reduced pressure to remove the solvent. The residue was purified by chromatography on a silica gel column, whereby from chloroform/methanol (20:1, v/v) eluate fractions, methyl 4-((5R)-methoxymethyl-(2S)-pyrrolidinylmethoxy)benzoate (1.03 g, 95% for 2 steps) was obtained as a pale yellow oil.

$^1$H-NMR (CDCl$_3$) δ: 1.49–2.01 (m, 5H), 3.27–3.33 (m, 1H), 3.37–3.44 (m, total 5H, including s, 3H, at δ: 3.37), 3.53–3.59 (m, 1H), 3.87–4.00 (m, total 5H, including s, 3H, at δ: 3.88), 6.09 (d, J=8.8 Hz, 2H), 7.97 (d, J=8.8 Hz, 2H).

(Step 6) Synthesis of methyl 4-(N-tert-butoxycarbonyl-(5R)-methoxymethyl-(2S)-pyrrolidinylmethoxy)cyclohexanecarboxylate

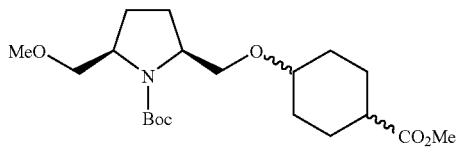

Methyl 4-((5R)-methoxymethyl-(2S)-pyrrolidinylmethoxy)benzoate (1.03 g, 3.69 mmol) was dissolved in methanol/trifluoroacetic acid (21 ml, 20:1, v/v). To the resulting solution was added rhodium-alumina (0.50 g) and the resulting mixture was subjected to catalytic hydrogenation for 1 day under a hydrogen gas of 10 atm. From the reaction mixture, the catalyst was filtered off and the filtrate was distilled under reduced pressure to remove the solvent, whereby methyl 4-((5R)-methoxymethyl-(2S)-pyrrolidinylmethoxy)cyclohexanecarboxylate trifluoroacetate (1.15 g) was obtained.

To the resulting product (1.15 g) were added dioxane/a saturated aqueous solution of sodium bicarbonate (30 ml, 1:1, v/v) and di-tert-butyl dicarbonate (0.81 g, 3.71 mmol) and the resulting mixture was stirred at room temperature for 2 hours. The reaction mixture was acidified with 1N HCl, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane/ethyl acetate (5:1, v/v) eluate fractions, methyl 4-(N-tert-butoxycarbonyl-(5R)-methoxymethyl-(2S)-pyrrolidinylmethoxy)cyclohexanecarboxylate (1.32 g, 93% for 2 steps) was obtained as a colorless oil.

$^1$H-NMR (CDCl$_3$) δ: 1.46 (s, 9H), 1.64–1.67 (m, 2H), 1.80–1.98 (m, 6H), 2.10–2.34 (m, 5H), 3.32–3.39 (m, total 5 H, including s, 3H, at δ: 3.35), 3.46–3.63 (m, 3H), 3.67 (s, 3H), 3.91 (m, 2H).

(Step 7) Synthesis of methyl trans-4-(N-tert-butoxycarbonyl-(5R)-methoxymethyl-(2S)-pyrrolidinylmethoxy)cyclohexanecarboxylate and methyl cis4-(N-tert-butoxycarbonyl-(5R)-methoxymethyl-(2S)-pyrrolidinylmethoxy)cyclohexanecarboxylate

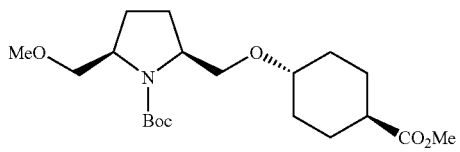

-continued

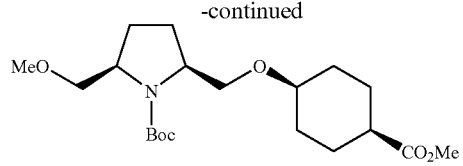

Methyl 4-(N-tert-butoxycarbonyl-(5R)-methoxymethyl-(2S)-pyrrolidinylmethoxy)cyclohexanecarboxylate (1.32 g, 3.42 mmol) was dissolved in methanol (10 ml). To the resulting solution was added sodium methoxide (0.55 g, 10.2 mmol) and the mixture was heated under reflux for 20 hours. After cooling to the room temperature, the reaction mixture was concentrated under reduced pressure to remove the solvent. The residue was added with water, followed by extraction with ethyl acetate. The extract was washed with saturated brine, dried over anhydrous sodium sulfate, and distilled under reduced pressure to remove the solvent, whereby a crude product was obtained. The crude product was dissolved in methanol/benzene (10 ml, 1:4, v/v). To the resulting solution was added trimethylsilyldiazomethane (a 2.0M hexane solution, 680 μl, 1.36 mmol) and the mixture was stirred further at room temperature for 3 hours. From the reaction mixture, the solvent was distilled off under reduced pressure. The residue was purified by flash column chromatography using a silica gel, whereby from n-hexane/ethyl acetate (7:1, v/v) eluate fractions, methyl trans-4-(N-tert-butoxycarbonyl-(5R)-methoxymethyl-(2S)-pyrrolidinylmethoxy)cyclohexanecarboxylate (321 mg, 24%) was obtained as a pale yellow oil.

$^1$H-NMR (CDCl$_3$) (1,4-trans): δ: 1.22–1.33 (m, 2H), 1.41–1.51 (m, total 11 H, including s, 9H, at δ: 1.46), 1.87–2.07 (m, 8H), 2.24–2.29 (m, 1H), 3.17–3.63 (m, total 8H, including s, 3H, at δ: 3.35), 3.66 (s, 3H), 3.87–3.97 (m, 2H).

In addition, methyl cis-4-(N-tert-butoxycarbonyl-(5R)-methoxymethyl-(2S)-pyrrolidinylmethoxy)cyclohexanecarboxylate (349 mg, 26%) was obtained as a colorless oil.

$^1$H-NMR (CDCl$_3$) : (1,4-cis) : δ: 1.43–1.52 (m, total 11H, including s, 9H, at δ: 1.46), 1.64–1.67 (m, 2H), 1.79–1.97 (m, 8H), 2.32–2.36 (m, 1H), 3.29–3.52 (m, total 8H, including s, 3H, at δ: 3.35), 3.66 (s, 3H), 3.88–3.94 (m, 2H).

(Step 8) Synthesis of methyl trans-4-((5R)-methoxymethyl (2S)-pyrrolidinylmethoxy)cyclohexanecarboxylate

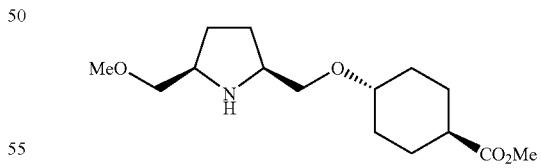

Methyl trans-4-(N-tert-butoxycarbonyl-(5R)-methoxymethyl-(2S)-pyrrolidinylmethoxy)cyclohexanecarboxylate (321 mg, 0.83 mmol) was dissolved in methylene chloride (3 ml). To the resulting solution was added trifluoroacetic acid (3 ml) and the mixture was stirred at room temperature for 1 hour. The reaction mixture was made basic with a saturated aqueous solution of sodium bicarbonate, followed by extraction with chloroform. The extract was washed with saturated brine, dried over anhydrous sodium sulfate, and distilled under reduced pressure to remove the solvent to give methyl trans-4-((5R)-methoxymethyl-(2S)-pyrrolidinylmethoxy)cyclohexanecarboxylate (240 mg, 100%) as a pale yellow oil.

¹H-NMR (CDCl₃) δ: 1.21–1.33 (m, 2H), 1.41–1.50 (m, 2H), 1.80–1.86 (m, 3H), 1.99–2.09 (m, 5H), 2.23–2.30 (m, 1H), 3.18–3.26 (m, 1H), 3.29–3.44 (m, total 8H, including s, 3H, at δ: 3.36), 3.49–3.52 (m, 1H), 3.66 (s, 3H).

(Step 9) Synthesis of methyl trans-4-(1-((5-chloro-2-fluoro-4-((1-methyl-3-indolylcarbonyl)amino)phenyl)acetyl)-(5R)-methoxymethyl-(2S)-pyrrolidinylmethoxy)cyclohexanecarboxylate

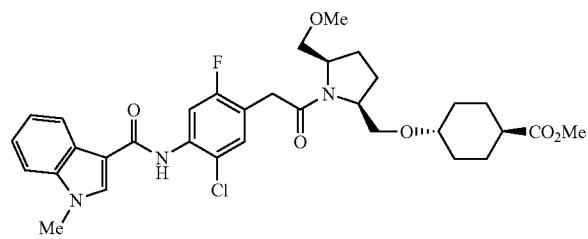

In DMF (5 ml), (5-chloro-2-fluoro-4-((1-methyl-3-indolylcarbonyl)amino)phenyl)acetic acid (168 mg, 0.47 mmol), methyl trans-4-((5R)-methoxymethyl-(2S)-pyrrolidinylmethoxy)cyclohexanecarboxylate (133 mg, 0.47 mmol), EDC HCl (134 mg, 0.70 mmol), HOBt (94 mg, 0.70 mmol), and triethylamine (100 μl, 0.71 mmol) were stirred at room temperature for 20 hours. The reaction mixture was diluted with water, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane/ethyl acetate (1:1 to 4:5, v/v) eluate fractions, methyl trans-4-(1-((5-chloro-2-fluoro-4-((1-methyl-3-indolylcarbonyl)amino)phenyl)acetyl)-(5R)-methoxymethyl-(2S)-pyrrolidinylmethoxy)cyclohexanecarboxylate (251 mg, 86%) was obtained as a pale yellow oil.

¹H-NMR (CDCl₃) δ: 1.14–1.32 (m, 2H), 1.40–1.53 (m, 2H), 1.85–2.10 (m, 8H), 2.23–2.32 (m, 1H), 3.20–3.25 (m, 1H), 3.39–3.84 (m, 12H), 3.87 (s, 3H), 4.11–4.24 (m, 2H), 7.30–7.42 (m, 4H), 7.79 (s, 1H), 8.11–8.15 (m, 1H), 8.28 (s, 1H), 8.49 (dd, J=1.5,12.0 Hz, 1H).

MS (ESI) m/z 628.5 (M⁺+1).

(Step 10) Synthesis of trans-4-(1-((5-chloro-2-fluoro-4-((1-methyl-3-indolylcarbonyl)amino)phenyl)acetyl)-(5R)-methoxymethyl-(2S)-pyrrolidinylmethoxy)cyclohexanecarboxylic acid

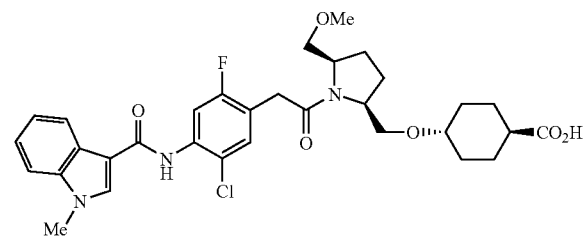

Methyl trans-4-(1-((5-chloro-2-fluoro-4-((1-methyl-3-indolylcarbonyl)amino)phenyl)acetyl)-(5R)-methoxymethyl-(2S)-pyrrolidinylmethoxy)cyclohexanecarboxylate (251 mg, 0.40 mmol) was dissolved in THF (3 ml). To the resulting solution was added 0.5N NaOH (3.0 ml, 1.50 mmol) and the resulting mixture was stirred at room temperature for 15 hours. The reaction mixture was poured in ice-1N HCl. The crystals thus precipitated were collected by filtration under reduced pressure. The crude crystals were purified by chromatography on a silica gel column, whereby from chloroform/methanol (50:1 to 20:1, v/v) eluate fractions, the title compound (160 mg, 65%) was obtained as a white solid.

¹H-NMR (DMSO-d₆) δ: 1.14–1.40 (m, 4H), 1.74–1.90 (m, 8H), 2.06–2.17 (m, 1H), 3.16–3.55 (m, 8H), 3.79–3.84 (m, 2H), 3.88 (s, 3H), 3.99–4.06 (m, 1H), 4.18–4.25 (m, 1H), 7.18–7.28 (m, 2H), 7.40–7.43 (m, 1H), 7.55 (d, J=8.1 Hz, 1H), 7.66–7.69 (m, 1H), 8.14 (d, J=8.1 Hz, 1H), 8.30 (s, 1H), 9.30 (s, 1H), 12.02 (broad s, 1H).

MS (ESI) m/z 614 (M⁺+1).

Anal. Calcd for C₃₂H₃₇ClFN₃O₆: C, 62.59; H, 6.07; N, 6.84; F, 3.09; Cl, 5.77. Found: C, 62.43; H, 6.20; N, 6.59; F, 2.93; Cl, 5.47.

Example 165 trans-4-(1-((2-(5-Fluoro-2-methylphenylamino)-7-fluoro-6-benzoxazolyl)acetyl)-(5R)-methoxymethyl-(2S)-pyrrolidinylmethoxy)cyclohexanecarboxylic acid (Step 1) Synthesis of methyl trans-4-(1-((2-(5-fluoro-2-methylphenylamino)-7-fluoro-6-benzoxazolyl)acetyl)-(5R)-methoxymethyl-(2S)-pyrrolidinylmethoxy)cyclohexanecarboxylate

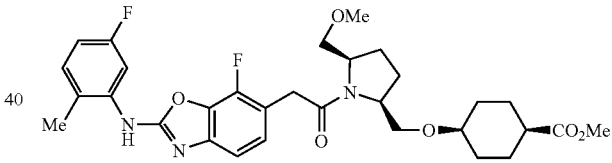

In DMF (5 ml), (2-(5-fluoro-2-methylphenylamino)-7-fluoro-6-benzoxazolyl)acetic acid (123 mg, 0.39 mmol), methyl trans-4-((5R)-methoxymethyl-(2S)-pyrrolidinylmethoxy)cyclohexanecarboxylate (110 mg, 0.39 mmol), EDC HCl (110 mg, 0.57 mmol), HOBt (78 mg, 0.58 mmol), and triethylamine (80 μl, 0.57 mmol) were stirred at room temperature for 20 hours. The reaction mixture was diluted with water, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane/ethyl acetate (1:1, v/v) eluate fractions, methyl trans-4-(1-((2-(5-fluoro-2-methylphenylamino)-7-fluoro-6-benzoxazolyl)acetyl)-(5R)-methoxymethyl-(2S)-pyrrolidinylmethoxy)cyclohexanecarboxylate (223 mg, 99%) was obtained as a pale yellow oil.

¹H-NMR (CDCl₃) δ: 1.20–1.33 (m, 2H), 1.40–1.53 (m, 2H), 1.86–2.11 (m, 8H), 2.23–2.27 (m, 1H), 2.30 (s, 3H), 3.19–3.28 (m, 1H), 3.34–3.71 (m, total 10H), 3.83–3.97 (m, 2H), 4.19–4.25 (m, 2H), 6.72–6.76 (m, 1H), 7.05–7.35 (m, 4H), 8.04–8.07 (dd, J=2.4,10.7 Hz, 1H).

MS (ESI) m/z 586.4 (M⁺+1).

(Step 2) Synthesis of trans-4-(1-((2-(5-fluoro-2-methylphenylamino)-7-fluoro-6-benzoxazolyl)acetyl)-(5R)-methoxymethyl-(2S)-pyrrolidinylmethoxy)cyclohexanecarboxylic acid

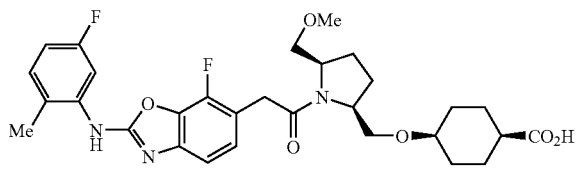

Methyl trans-4-(1-((2-(5-fluoro-2-methylphenylamino)-7-fluoro-6-benzoxazolyl)acetyl)-(5R)-methoxymethyl-(2S)-pyrrolidinylmethoxy)cyclohexanecarboxylate (223 mg, 0.38 mmol) was dissolved in THF (3 ml). To the resulting solution was added 0.5N NaOH (3.0 ml, 1.50 mmol). The resulting mixture was stirred at room temperature for 15 hours. The reaction mixture poured in ice-1N HCl, followed by extraction with ethyl acetate. The extract was washed with saturated brine, dried over anhydrous sodium sulfate, and distilled under reduced pressure to remove the solvent. The crude crystals were recrystallized from n-hexane/ethyl acetate to give the title compound (169 mg, 78%) as a white solid.

$^1$H-NMR (DMSO-$d_6$) δ: 1.13–1.36 (m, 4H), 1.75–1.94 (m, 8H), 2.14 (m, 1H), 2.28 (s, 3H), 3.15–3.53 (m, 8H), 3.86–3.88 (m, 2H), 3.90–4.02 (m, 1H), 4.21–4.23 (m, 1H), 6.86–6.89 (m, 1H), 7.02–7.04 (m, 1H), 7.18–7.26 (m, 2H), 7.90–7.93 (m, 1H).

MS (ESI) m/z 572 (M$^+$+1).

Anal. Calcd for $C_{30}H_{35}F_2N_3O_6$: C, 63.04; H, 6.17; N, 7.35; F, 6.65. Found: C, 63.01; H, 6.35; N, 6.96; F, 6.28.

Example 166 trans-4-(1-((5-Chloro-2-fluoro-4-((1-methyl-3-indazolylcarbonyl)amino)phenyl)acetyl)-(5R)-methoxymethyl-(2S)-pyrrolidinylmethoxy)cyclohexanecarboxylic acid (Step 1) Synthesis of methyl trans-4-(1-((5-chloro-2-fluoro-4-((1-methyl-3-indazolylcarbonyl)amino)phenyl)acetyl)-(5R)-methoxymethyl-(2S)-pyrrolidinylmethoxy)cyclohexanecarboxylate

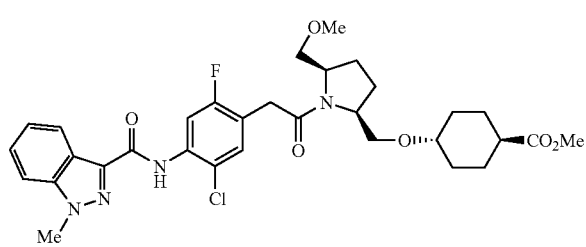

In DMF (3 ml), (5-chloro-2-fluoro-4-((1-methyl-3-indazolylcarbonyl)amino)phenyl)acetic acid (56 mg, 0.15 mmol), methyl trans-4-((5R)-methoxymethyl-(2S)-pyrrolidinylmethoxy)cyclohexanecarboxylate (60 mg, 0.15 mmol), EDC HCl (45 mg, 0.23 mmol), HOBt (32 mg, 0.24 mmol), and triethylamine (33 µl, 0.24 mmol) were stirred at room temperature for 2 days. The reaction mixture was diluted with water, followed by extraction with ethyl acetate. The extract was washed with saturated brine, dried over anhydrous sodium sulfate, and distilled under reduced pressure to remove the solvent. The residue was purified by chromatography on a silica gel column, whereby from chloroform/methanol (40:1, v/v) eluate fractions, methyl trans-4-(1-((5-chloro-2-fluoro-4-((1-methyl-3-indazolylcarbonyl)amino)phenyl)acetyl)-(5R)-methoxymethyl-(2S)-pyrrolidinylmethoxy)cyclohexanecarboxylate (101 mg, 100%) was obtained as a colorless oil.

$^1$H-NMR (CDCl$_3$) δ: 1.21–1.32 (m, 2H), 1.41–1.53 (m, 2H), 1.85–2.05 (m, 8H), 2.23–2.32 (m, 1H), 3.20–3.25 (m, 1H), 3.35–3.84 (m, 12H), 4.13–4.26 (m, total 5H, including s, 3H at δ: 4.16), 7.31–7.39 (m, 2H), 7.44–7.49 (m, 2H), 8.39 (d, J=8.3 Hz, 1H), 8.51 (d, J=11.7 Hz, 1H), 9.49 (s, 1H).

(Step 2) Synthesis of trans-4-(1-((5-chloro-2-fluoro-4-((1-methyl-3-indazolylcarbonyl)amino)phenyl)acetyl)-(5R)-methoxymethyl-(2S)-pyrrolidinylmethoxy)cyclohexanecarboxylic acid

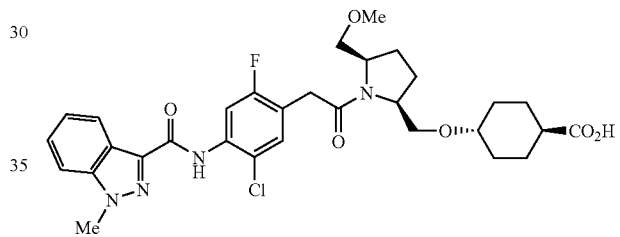

Methyl trans-4-(1-((5-chloro-2-fluoro-4-((1-methyl-3-indazolylcarbonyl)amino)phenyl)acetyl)-(5R)-methoxymethyl-(2S)-pyrrolidinylmethoxy)cyclohexanecarboxylate (101 mg, 0.16 mmol) was dissolved in THF (2 ml). To the resulting solution was added 0.5N NaOH (1.0 ml, 0.50 mmol) and the mixture was stirred at room temperature for 15 hours. The reaction mixture was poured in ice-1N HCl, followed by extraction with ethyl acetate. The extract was washed with saturated brine, dried over anhydrous sodium sulfate, and distilled under reduced pressure to remove the solvent. The residue was purified by chromatography on a silica gel column, whereby from chloroform/methanol (40:1, v/v) eluate fractions, the title compound (78 mg, 79%) was obtained as a white solid.

$^1$H-NMR (DMSO-$d_6$) δ: 1.11–1.48 (m, 4H), 1.74–2.01 (m, 8H), 2.14–2.17 (m, 1H), 3.16–3.55 (m, 8H), 3.80–3.89 (m, 2H), 3.97–4.07 (m, 1H), 4.17–4.26 (m, total 4H, including s, 3H at δ: 4.21), 7.34–7.38 (m, 1H), 7.45–7.48 (m, 1H), 7.51–7.55 (m, 1H), 7.81 (d, J=8.6 Hz, 1H), 8.03–8.07 (m, 1H), 8.20 (d, J=8.3 Hz, 1H), 9.71 (s, 1H), 12.06 (broad s, 1H).

MS (LC) m/z 614.8 (M$^+$+1). 613.6 (M$^+$−1).

Anal. Calcd for $C_{31}H_{36}ClFN_4O_6$: C, 60.53; H, 5.90; N, 9.11; F, 3.09; Cl, 5.76. Found: C, 60.56; H, 5.97; N, 8.71; F, 3.07; Cl, 5.70.

Example 167 trans-4-(1-((2-(5-Fluoro-2-methylphenylamino)-7-fluoro-6-benzoxazolyl)acetyl)-(5S)-methoxymethyl-(2S)-pyrrolidinylmethoxy)cyclohexanecarboxylic acid (Step 1) Synthesis of methyl trans-4-(1-((2-(5-fluoro-2-methylphenylamino)-7-fluoro-6-benzoxazolyl)acetyl)-(5S)-methoxymethyl-(2S)-pyrrolidinylmethoxy)cyclohexanecarboxylate

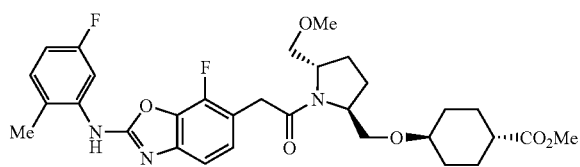

In DMF (10 ml) were dissolved (2-(5-fluoro-2-methylphenylamino)-7-fluoro-6-benzoxazolyl)acetic acid (228 mg, 0.71 mmol), methyl trans-4-((5S)-methoxymethyl-(2S)-pyrrolidinylmethoxy)cyclohexanecarboxylate (186 mg, 0.65 mmol) and EDC-HCl (163 mg, 0.85 mmol). To the resulting solution was added HOBt (26.0 mg, 0.20 mmol), and the resulting mixture was stirred at room temperature for 18 hours. The reaction mixture was poured in water, followed by extraction with ethyl acetate. The extract was washed with water (three times), dried over anhydrous sodium sulfate, and distilled under reduced pressure to remove the solvent. The residue was purified by column chromatography using a silica gel thin-layer plate (TLC), whereby from hexane-ethyl acetate (1/3) eluate fractions, methyl trans-4-(1-((2-(5-fluoro-2-methylphenylamino)-7-fluoro-6-benzoxazolyl)acetyl)-(5S)-methoxymethyl-(2S)-pyrrolidinylmethoxy)cyclohexanecarboxylate (331 mg, 87%) was obtained as a colorless amorphous substance.

$^1$H-NMR (CDCl$_3$), mixture of rotamers, δ: 1.12–2.32 (series of m, 12H), 2.31 and 2.32 (s, total 3H), 3.11–4.25 (series of m, 10H), 3.30, 3.31 and 3.39 (s, total 3H), 3.63 and 3.67 (s, total 3H), 6.73–6.78 (m, 1H), 7.11–7.16 (m, 2H), 7.23–7.27 (m, 2H), 8.07–8.12 (m, 1H).

MS (ESI) m/z 586 (M$^+$+1).

(Step 2) Synthesis of trans-4-(1-((2-(5-fluoro-2-methylphenylamino)-7-fluoro-6-benzoxazolyl)acetyl)-(5S)-methoxymethyl-(2S)-pyrrolidinylmethoxy)cyclohexanecarboxylic acid

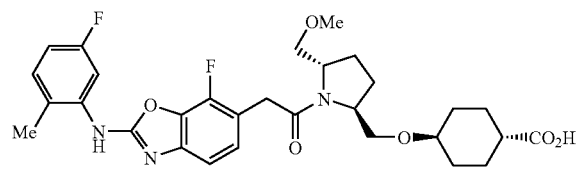

Methyl trans-4-(1-((2-(5-fluoro-2-methylphenylamino)-7-fluoro-6-benzoxazolyl)acetyl)-(5S)-methoxymethyl-(2S)-pyrrolidinylmethoxy)cyclohexanecarboxylate (313 mg, 0.53 mmol) was dissolved in THF/methanol (1/1, 20 ml). To the resulting solution was added aqueous 0.25N NaOH (12.8 ml, 3.20 mmol) and the resulting mixture was stirred at room temperature for 18 hours. The reaction mixture was poured in 1N HCl, followed by extraction with a chloroform/methanol mixture (10/1). The extract was dried over anhydrous sodium sulfate, and distilled under reduced pressure to remove the solvent. The residue was purified by chromatography on a silica gel column, whereby from chloroform/methanol (15/1) eluate fractions, the title compound (288 mg, 94%) was obtained as a colorless amorphous substance.

$^1$H-NMR (CDCl$_3$), mixture of rotamars, δ: 1.10–2.26 (series of m, 12H), 2.29 and 2.31 (s, total 3H), 3.07–4.28 (series of m, 11H), 2.29 and 3.31 (s, total 3H), 7.30–7.35 (m, 2H), 6.76 (dt, J=2.0,8.0 Hz, 1H), 7.11–7.21 (series of m, 3H), 7.11–7.21 (series of m, 3H), 7.82 and 7.90 (d, J=6.4 Hz, total 1H).

MS (ESI) m/z 571 (M$^+$+1);

Anal. calcd for C$_{30}$H$_{35}$F$_2$N$_3$O$_6$: C, 63.04; H, 6.17; N, 7.35. Found: C, 63.29; H, 6.32; N, 7.35.

Example 168 trans-4-(1-((5-Chloro-2-fluoro-4-((1-methyl-3-indazolyl)carbonyl)aminophenyl)acetyl)-(5S)-methoxymethyl-(2S)-pyrrolidinylmethoxy)cyclohexanecarboxylic acid (Step 1) Synthesis of methyl trans-4-(1-((5-chloro-2-fluoro-4-((1-methyl-3-indazolyl)carbonyl)aminophenyl)acetyl)-(5S)-methoxymethyl-(2S)-pyrrolidinylmethoxy)cyclohexanecarboxylate

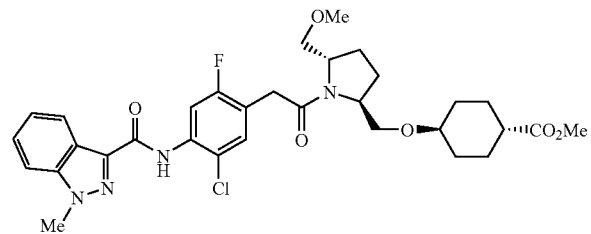

In DMF (10 ml), HOBt (29.0 mg, 0.21 mmol) was added to (5-chloro-2-fluoro-4-((1-methyl-3-indazolyl)carbonyl)aminophenyl)acetic acid (280 mg, 0.78 mmol), methyl trans-4-((5S)-methoxymethyl-(2S)-pyrrolidinylmethoxy)cyclohexanecarboxylate (201 mg, 0.70 mmol) and EDC-HCL (175 mg, 0.92 mmol) and the resulting mixture was stirred at room temperature for 18 hours. The reaction mixture was poured in water, followed by extraction with ethyl acetate. The extract was washed with water (three times), dried over anhydrous sodium sulfate, and distilled under reduced pressure to remove the solvent. The residue was purified by chromatography using a silica gel thin-layer plate (TLC), whereby from hexane/ethyl acetate (1/5) eluate fractions, methyl trans-4-(1-((5-chloro-2-fluoro-4-((1-methyl-3-indazolyl)carbonyl)aminophenyl)acetyl)-(5S)-methoxymethyl-(2S)-pyrrolidinylmethoxy)cyclohexanecarboxylate (322 mg, 73%) was obtained as a colorless amorphous substance.

$^1$H-NMR (CDCl$_3$), mixture of rotamars, δ: 1.10–2.30 (series of m, 12H), 3.13–4.25 (series of m, 10H), 3.33 and 3.37 (s, total 3H), 3.61 and 3.67 (s, total 3H), 4.18 (s, 3H), 7.33–7.37 (m, 1H), 7.43–7.51 (m, 3H), 8.40 (d, J=8.0 Hz, 1H), 8.50 and 8.53 (d, J=12.0 Hz, total 1H), 9.50 (s, 1H).

MS (ESI) m/z 629 (M$^+$+1).

(Step 2) Synthesis of trans-4-(1-((5-chloro-2-fluoro-4-((1-methyl-3-indazolyl)carbonyl)aminophenyl)acetyl)-(5S)-methoxymethyl-(2S)-pyrrolidinylmethoxy)cyclohexanecarboxylic acid

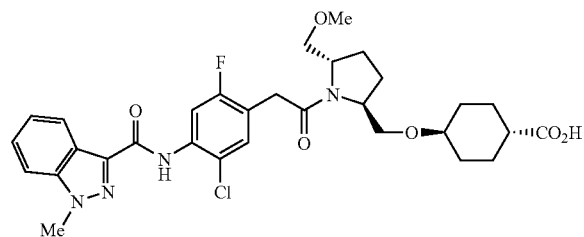

Methyl trans-4-(1-((5-chloro-2-fluoro-4-((1-methyl-3-indazolyl)carbonyl)aminophenyl)acetyl)-(5S)-methoxymethyl-(2S)-pyrrolidinylmethoxy)cyclohexanecarboxylate (305 mg, 0.49 mmol) was dissolved in THF/methanol (1/1, 20 ml). To the resulting solution was added 0.25N NaOH (11.6 ml, 2.91 mmol) and the mixture was stirred at room temperature for 18 hours. The reaction mixture was poured in 1N HCl, followed by extraction with a chloroform/methanol mixture (10/1). The extract was dried over anhydrous sodium sulfate, and distilled under reduced pressure to remove the solvent. The residue was purified by chromatography on a silica gel column, whereby from chloroform/methanol (15/1) eluate fractions, the title compound (311 mg, 100%) was obtained as a colorless amorphous substance.

$^1$H-NMR (CDCl$_3$), mixture of rotamars, δ: 1.10–2.35 (series of m, 12H), 3.14–4.26 (series of m, 12H), 3.32 and 3.37 (s, total 3H), 8.37–8.40 (m, 1H), 8.49 and 8.52 (s, total 1H), 9.50 (s, 1H).

MS (ESI) m/z 615 (M$^+$+1);

Anal. calcd for C$_{31}$H$_{36}$ClFN$_4$O$_6$: C, 60.53; H, 5.90; N, 9.11. Found: C, 60.67; H, 6.07; N, 8.80.

Example 169 trans-4-(1-((5-Chloro-2-fluoro-4-((1-methyl-3-indazolylcarbonyl)amino)phenyl)acetyl)-(3S)-methoxy-(2R)-pyrrolidinylmethoxy)cyclohexanecarboxylic acid (Step 1) Synthesis of N-benzyloxycarbonyl-(2R)-tert-butyldimethylsilyloxymethyl-(3S)-methoxypyrrolidine

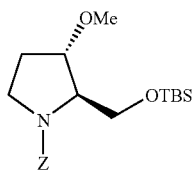

In DMF (10 ml), methyl iodide (0.53 ml, 8.51 mmol) was added to N-benzyloxycarbonyl-(2R)-tert-butyldimethylsilyloxymethyl-(3S)-hydroxypyrrolidine (2.60 g, 7.11 mmol) and sodium hydride (0.34 g, 14.2 mmol) under stirring at 0° C. The reaction mixture was stirred further at the same temperature for 13 hours. Water was added to the reaction mixture, followed by extraction with ethyl acetate. The extract was washed with saturated brine, dried over anhydrous sodium sulfate, and distilled under reduced pressure to remove the solvent. The residue was purified by chromatography on a silica gel column, whereby from n-hexane/ethyl acetate (6:1, v/v) eluate fractions, N-benzyloxycarbonyl-(2R)-tert-butyldimethylsilyloxymethyl-(3S)-methoxypyrrolidine (2.73 g, 100%) as a colorless oil.

$^1$H-NMR (CDCl$_3$) δ: 0.05 (s, 6H), 0.90 and 0.93 (each s, total 9H), 2.02–2.08 (m, 2H), 3.35–3.37 (each s, total 3H), 3.41–3.64 (m, 3H), 3.75–3.98 (m, 3H), 5.08–5.27 (m, 2H), 7.32–7.40 (m, 5H).

(Step 2) Synthesis of N-benzyloxycarbonyl-(3S)-methoxy-(2R)-pyrrolidinemethanol

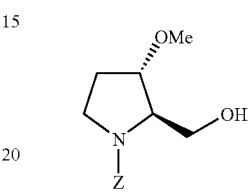

In THF (15 ml) was dissolved N-benzyloxycarbonyl-(2R)-tert-butyldimethylsilyloxymethyl-(3S)-methoxypyrrolidine (2.73 g, 7.19 mmol). To the resulting solution was added tetrabutylammonium fluoride (TBAF) (a 1M THF solution, 14.4 ml, 14.4 mmol) under stirring at 0° C. The reaction mixture was stirred further at room temperature for 18 hours. The reaction mixture was concentrated under reduced pressure. To the residue was added 1N HCl, followed by extraction with ethyl acetate. The extract was washed with saturated brine, dried over anhydrous sodium sulfate, and distilled under reduced pressure to remove the solvent. The residue was purified by chromatography on a silica gel column, whereby from chloroform/methanol (20:1, v/v) eluate fractions, N-benzyloxycarbonyl-(3S)-methoxy-(2R)-pyrrolidinemethanol (2.01 g, 100%) was obtained as a colorless oil.

$^1$H-NMR (CDCl$_3$) δ: 1.98 (m, 2H), 3.34 (s, 3H), 3.41–3.74 (m, 5H), 3.88 and 4.01 (each m, total 1H), 5.14 (s, 2H), 7.30–7.36 (m, 5H).

MS (ESI) m/z 265.9 (M$^+$+1).

(Step 3) Synthesis of methyl 4-((3S)-methoxy-(2R)-pyrrolidinylmethoxy)benzoate

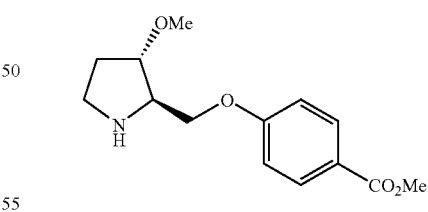

In THF (20 ml), DIAD (1.69 ml, 8.58 mmol) was added to N-benzyloxycarbonyl-(3S)-methoxy-(2R)-pyrrolidinemethanol (1.90 g, 7.16 mmol), methyl 4-hydroxybenzoate (1.20 g, 7.89 mmol) and triphenylphosphine (2.25 g, 8.58 mmol) and the resulting mixture was heated under reflux for 12 hours. After cooling to room temperature, the reaction mixture was distilled under reduced pressure to remove the solvent. The residue was purified by chromatography on a silica gel column, whereby from n-hexane/ethyl acetate (1:1, v/v) eluate fractions, methyl 4-(N-benzyloxycarbonyl-(3S)-methoxy-(2R)-pyrrolidinylmethoxy)

benzoate was obtained. The resulting compound was dissolved in methanol (50 ml), followed by the addition of 10% palladium-carbon (1.50 g). The mixture was subjected to catalytic hydrogenation for 20 hours under normal pressure. From the reaction mixture, the catalyst was filtered off and the filtrate was distilled under reduced pressure to remove the solvent. The residue was purified by chromatography on a silica gel column, whereby from chloroform/methanol (30:1, v/v) eluate fractions, methyl 4-((3S)-methoxy-(2R)-pyrrolidinylmethoxy)benzoate (1.39 g, 73% for 2 steps) was obtained as a brown oil.

$^1$H-NMR (CDCl$_3$) δ: 1.87–2.01 (m, 2H), 3.03–3.18 (m, 2H), 3.35 (s, 3H), 3.43–3.47 (m, 1H), 3.79–3.82 (m, 1H), 3.89 (s, 3H), 3.95–4.02 (m, 2H), 6.91–6.93 (m, 2H), 7.97–8.00 (m, 2H).

(Step 4) Synthesis of methyl 4-(N-tert-butoxycarbonyl-(3S)-methoxy-(2R)-pyrrolidinylmethoxy)cyclohexanecarboxylate

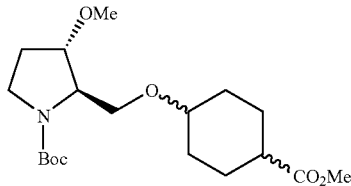

Methyl 4-((3S)-methoxy-(2R)-pyrrolidinylmethoxy)benzoate (1.39 g, 5.24 mmol) was dissolved in methanol/acetic acid (22 ml, 10:1, v/v). To the resulting solution was added rhodium/alumina (0.55 g) and the mixture was subjected to catalytic hydrogenation for 2 days under a hydrogen gas of 10 atom. From the reaction mixture, the catalyst was filtered off and the filtrate was distilled under reduced pressure to remove the solvent. The residue was dissolved into chloroform. The resulting solution was washed with a saturated aqueous solution of sodium bicarbonate, dried over anhydrous sodium sulfate, and distilled under reduced pressure to remove the solvent to give methyl 4-((3S)-methoxy-(2R)-pyrrolidinylmethoxy)cyclohexanecarboxylate (1.42 g). The resulting product (1.42 g), di-tert-butyl dicarbonate (1.26 g, 5.77 mmol), and DMAP (0.06 g, 0.49 mmol) were stirred at room temperature for 20 hours in acetonitrile (20 ml). From the reaction mixture, the solvent was distilled off under reduced pressure. The residue was purified by chromatography on a silica gel column, whereby from n-hexane/ethyl acetate (4:1 to 3:1, v/v) eluate fractions, methyl 4-(N-tert-butoxycarbonyl-(3S)-methoxy-(2R)-pyrrolidinylmethoxy)cyclohexanecarboxylate (1.67 g, 86% for 2 steps) was obtained as a pale yellow oil.

MS (ESI) m/z 372 (M$^+$+1).

(Step 5) Synthesis of methyl trans-4-((3S)-methoxy-(2R)-pyrrolidinylmethoxy)cyclohexanecarboxylate

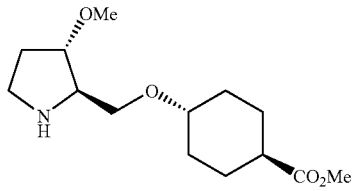

Methyl 4-(N-tert-butoxycarbonyl-(3S)-methoxy-(2R)-pyrrolidinylmethoxy)cyclohexanecarboxylate (1.67 g, 4.50 mmol) was dissolved in methanol (15 ml). To the resulting solution was added sodium methoxide (0.73 g, 13.5 mmol). The resulting mixture was heated under reflux for 24 hours. After cooling to room temperature, the reaction mixture was concentrated under reduced pressure. The residue was acidified with 1N HCl, followed by extraction with ethyl acetate. The extract was washed with saturated brine, dried over anhydrous sodium sulfate, and distilled under reduced pressure to remove the solvent. The residue was dissolved in methanol/benzene (20 ml, 1:4, v/v), followed by the addition of trimethylsilyldiazomethane (a 2.0M hexane solution, 1.10 ml, 1.10 mmol). The resulting mixture was stirred further at room temperature for 2 hours. From the reaction mixture, the solvent was distilled off under reduced pressure. The residue was purified by chromatography on a silica gel column, whereby from n-hexane/ethyl acetate (2:1, v/v) eluate fractions, methyl trans-4-(N-tert-butoxycarbonyl-(3S)-methoxy-(2R)-pyrrolidinylmethoxy)cyclohexanecarboxylate was obtained as a colorless oil. The resulting compound (60 g) was dissolved in methylene chloride (3 ml). To the resulting solution was added trifluoroacetic acid (3 ml). The resulting mixture was stirred at room temperature for 1 hour. The reaction mixture was made basic with a saturated aqueous solution of sodium bicarbonate, followed by extraction with chloroform. The extract was washed with saturated brine, dried over anhydrous sodium sulfate, and distilled under reduced pressure to remove the solvent, whereby methyl trans-4-((3S)-methoxy-(2R)-pyrrolidinylmethoxy)cyclohexanecarboxylate (40 mg, 3% for 3 steps) was obtained as a brown oil.

$^1$H-NMR (CDCl$_3$) δ: 1.21–1.29 (m, 2H), 1.42–1.52 (m, 2H), 1.72–2.08 (m, 6H), 2.23–2.31 (m, 1H), 2.99–3.02 (m, 2H), 3.15–3.51 (m, total 8H, including s, 3H, at δ: 3.31), 3.64–3.66 (m, total 4H, including s, 3H, at δ: 3.66).

(Step 6) Synthesis of methyl trans-4-(1-((5-chloro-2-fluoro-4-((1-methyl-3-indolylcarbonyl)amino)phenyl)acetyl)-(3S)-methoxy-(2R)-pyrrolidinylmethoxy)cyclohexanecarboxylate

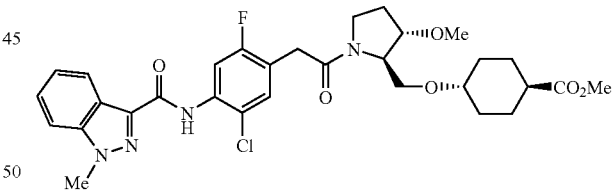

In DMF (3 ml), (5-chloro-2-fluoro-4-((1-methyl-3-indolylcarbonyl)amino)phenyl)acetic acid (53 mg, 0.15 mmol), methyl trans-4-((3S)-methoxy-(2R)-pyrrolidinylmethoxy)cyclohexanecarboxylate (40 mg, 0.15 mmol), EDC HCl (42 mg, 0.22 mmol), HOBt (30 mg, 0.22 mmol), and triethylamine (31 µl, 0.22 mmol) were stirred at room temperature for 3 hours. The reaction mixture was poured into water. The crystals thus precipitated were collected by filtration under reduced pressure. The crude crystals were purified by chromatography on a silica gel column, whereby from chloroform/methanol (60:1, v/v) eluate fractions, methyl trans-4-(1-((5-chloro-2-fluoro-4-((1-methyl-3-indolylcarbonyl)amino)phenyl)acetyl)-(3S)-methoxy-(2R)-pyrrolidinylmethoxy)cyclohexanecarboxylate (70 mg, 77%) was obtained as a colorless oil.

$^1$H-NMR (CDCl$_3$) δ: 1.12–1.26 (m, 2H), 1.38–1.52 (m, 2H), 1.94–2.07 (m, 5H), 2.16–2.28 (m, 2H), 3.17–3.24 (m, 1H), 3.33 (s, 3H), 3.44–3.74 (m, total 9H, including s, 3H, at δ: 3.62), 3.84–3.89 (m, 1H), 4.17 (s, 3H), 4.22–4.25 (m, 1H), 7.31–7.49 (m, 4H), 8.38 (d, J=8.1 Hz, 1H), 8.51 (d, J=11.8 Hz, 1H), 9.49 (s, 1H).

MS (ESI) m/z 614.8 (M$^+$+1).

(Step 7) Synthesis of trans-4-(1-((5-chloro-2-fluoro-4-((1-methyl-3-indolylcarbonyl)amino)phenyl)acetyl)-(3S)-methoxy-(2R)-pyrrolidinylmethoxy)cyclohexanecarboxylic acid

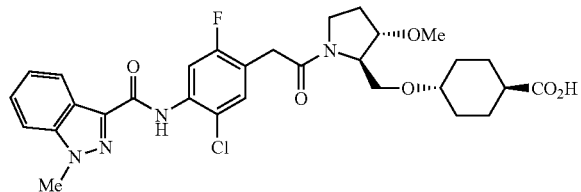

Methyl trans-4-(1-((5-chloro-2-fluoro-4-((1-methyl-3-indolylcarbonyl)amino)phenyl)acetyl)-(3S)-methoxy-(2R)-pyrrolidinylmethoxy)cyclohexanecarboxylate (70 mg, 0.11 mmol) was dissolved in THF (1.5 ml). To the resulting solution was added 0.25N NaOH (1.4 ml, 0.35 mmol) and the mixture was stirred at room temperature for 2 hours. The reaction mixture was poured in ice-1N HCl. The crystals thus precipitated were collected by filtration under reduced pressure, washed with water and dried under reduced pressure to give the title compound (57 mg, 83%) as a white solid.

$^1$H-NMR (CDCl$_3$) δ: 1.13–1.37 (m, 4H), 1.85–2.18 (m, 7H), 3.15–3.84 (m, 11H), 3.95–3.96 and 4.11–4.14 (each m, total 1H), 4.22 (s, 3H), 7.35–7.39 (m, 1H), 7.50–7.56 (m, 2H), 7.82 (d, J=8.6 Hz, 1H), 8.07 (d, J=11.3 Hz, 1H), 8.21 (d, J=8.3 Hz, 1H), 9.72 (s, 1H), 12.10 (broad s, 1H).

MS (LC) m/z 600.8 (M$^+$+1), 599.4 (M$^+$−1);

Anal. Calcd for $C_{30}H_{34}ClFN_4O_6$: C, 59.95; H, 5.70; N, 9.32; F, 3.16; Cl, 5.90. Found: C, 59.71; H, 5.85; N, 8.89; F, 3.00; Cl, 5.88.

Example 170 trans-4-(1-(2,5-Dichloro-4-((1-methyl-1H-3-indolylcarbonyl)amino)phenylacetyl)-(4S)-methoxy-(2S)-pyrrolidinylmethoxy)cyclohexanecarboxylic acid (Step 1) Synthesis of trans-4-(1-(2,5-dichloro-4-((1-methyl-1H-3-indolylcarbonyl)amino)phenylacetyl)-(4S)-methoxy-(2S)-pyrrolidinylmethoxy)cyclohexanecarboxylic acid

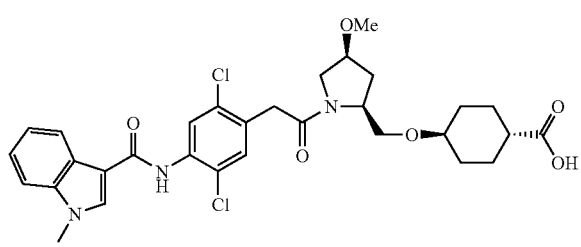

In DMF (2 ml) was dissolved methyl trans-4-(N-tert-butoxycarbonyl-(4S)-methoxy-(2S)-pyrrolidinylmethoxy)cyclohexanecarboxylate (100 mg, 0.37 mmol). To the resulting solution were added (2,5-dichloro-4-((1-methyl-1H-3-indolylcarbonyl)amino)phenyl)acetic acid (140 mg, 0.37 mmol), HOBt (95 mg, 0.70 mmol), DMAP (catalytic amount) and EDC•HCl salt (107 mg, 0.56 mmol). The resulting mixture was stirred at room temperature for 18 hours. The reaction mixture was poured in 1M HCl, followed by extraction with ethyl acetate three times. The extract was washed with saturated brine, dried over anhydrous magnesium sulfate and distilled under reduced pressure to remove the solvent. The residue was purified by silica gel column chromatography (middle pressure Yamazen, chloroform/methanol 10:0 to 97:3, 20 ml/min, φ 50 mm×150 mm). The purified ester was dissolved in THF (4 ml) and to the resulting solution was added 0.25M NaOH (2.4 ml, 0.61 mmol). The resulting mixture was stirred for 18 hours at room temperature. From the reaction mixture, the solvent was distilled off under reduced pressure. The residue was crystallized by the addition of 1M HCl. The crystals thus precipitated were collected by filtration under reduced pressure, washed with water and dried under reduced pressure to give the title compound (150 mg, 66%) as a colorless solid.

$^1$H-NMR (DMSO-d$_6$) δ: 1.10–1.40 (m, 4H), 1.80–2.20 (m, 8H), 3.15–4.30 (m, 8H), 3.28 (s, 3H), 3.90 (s, 3H), 7.21 (t, J=7.5 Hz, 1H), 7.28 (t, J=7.5 Hz, 1H), 7.50 (d, J=15.2 Hz, 1H), 7.56 (d, J=8.3 Hz, 1H), 7.88 (d, J=4.1 Hz, 1H), 8.15 (d, J=8.0 Hz, 1H), 8.31 (s, 1H), 9.39 (s, 1H).

MS (ESI) m/z 617 (M+1)$^+$;

Anal. Calcd for $C_{31}H_{35}Cl_2N_3O_6 \cdot 0.5H_2O$: C, 59.52; H, 5.80; N, 6.72. Found: C, 59.36; H, 5.72; N, 6.68.

Example 171 trans-4-(1-(5-Chloro-2-fluoro-4-((3-benzo(d)isothiazolylcarbonyl)amino)phenylacetyl)-(4S)-methoxy-(2S)-pyrrolidinylmethoxy)cyclohexanecarboxylic acid (Step 1) Synthesis of trans-4-(1-(5-chloro-2-fluoro-4-((3-benzo(d)isothiazolylcarbonyl)amino)phenylacetyl)-(4S)-methoxy-(2S)-pyrrolidinylmethoxy)cyclohexanecarboxylic acid

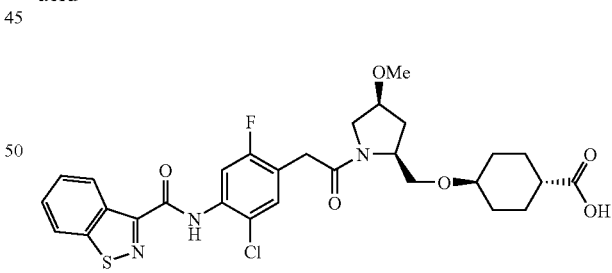

In DMF (2 ml) was dissolved methyl trans-4-(N-tert-butoxycarbonyl-(4S)-methoxy-(2S)-pyrrolidinylmethoxy)cyclohexanecarboxylate (100 mg, 0.37 mmol). To the resulting solution were added (3-benzo(d)isothiazolylcarbonyl)amino)phenylacetic acid (135 mg, 0.37 mmol), HOBt (95 mg, 0.70 mmol), DMAP (catalytic amount) and EDC•HCl salt (107 mg, 0.56 mmol). The resulting mixture was stirred at room temperature for 18 hours. The reaction mixture was poured in 1M HCl, followed by extraction with ethyl acetate three times. The extract was washed with saturated brine, dried over anhydrous magnesium sulfate and distilled under reduced pressure to remove the solvent. The residue was purified by silica gel column chromatography (middle pressure Yamazen, chloroform/methanol 10:0 to 97:3, 20 ml/min, φ 50 mm×150 mm). The purified ester was dissolved in THF (4 ml) and to the resulting solution was added 0.25M NaOH (2.4 ml, 0.61 mmol). After stirring for 18 hours at room temperature, the reaction mixture was distilled under reduced pressure to remove the solvent. The residue was crystallized by the addition of 1M HCl. The crystals thus precipitated were collected by filtration under reduced pressure, washed with water and dried under reduced pressure to give the title compound (150 mg, 67%) as a colorless solid.

$^1$H-NMR (DMSO-$d_6$) δ: 1.10–1.40 (m, 4H), 1.80–2.20 (m, 8H), 3.15–4.30 (m, 8H), 3.28 (s, 3H), 7.51 (dd, J=7.0 Hz, 1H), 7.66 (t, J=7.5 Hz, 1H), 7.73 (t, J=7.5 Hz, 1H), 7.95 (dd, J=6.0,10.6 Hz, 1H), 8.38 (d, J=8.1 Hz, 1H), 8.81 (d, J=8.3 Hz, 1H), 10.30 (s, 1H), 12.05 (s, 1H).

MS (ESI) m/z 605 (M+1)$^+$;

Anal. Calcd for $C_{29}H_{31}ClFN_3O_6S \cdot 0.5H_2O$: C,56.81; H, 5.26; N, 6.85. Found: C, 56.78; H, 5.15; N, 6.86

Example 172 trans-4-(1-((5-Chloro-2-fluoro-4-(3-indazolylcarbonylamino)phenyl)acetyl)-(4S)-fluoro-(2S)-pyrrolidinylmethoxy)cyclohexanecarboxylic acid (Step 1) Synthesis of methyl 1-(4-methoxybenzyl)-3-indazolylcarboxylate

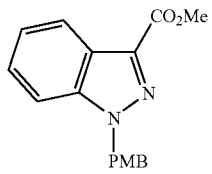

Methyl 3-indazolylcarboxylate (2.0 g, 11.4 mmol) was dissolved in DMF (20 ml). To the resulting solution were added 4-methoxybenzyl chloride (1.7 ml, 12.5 mmol) and potassium carbonate (2.35 g, 17.0 mmol). The resulting mixture was stirred at 80° C. for 15 hours. After cooling, the reaction mixture was poured in water (50 ml), followed by extraction with ethyl acetate (200 ml). The extract was washed with saturated brine (2×100 ml), dried over anhydrous magnesium sulfate, and distilled under reduced pressure to remove the solvent. The residue was purified by chromatography on a silica gel column, whereby from hexane-ethyl acetate (4:1) eluate fractions, methyl 1-(4-methoxybenzyl)-3-indazolylcarboxylate (polar fractions, 838 mg, 25%) was obtained as a pale yellow oil and 2(4-methoxybenzyl) isomer (non-polar fractions, 500 mg, 15%) was obtained as a pale yellow oil.

$^1$H-NMR (CDCl$_3$) δ: 3.76 (s, 3H), 4.05 (s, 3H), 5.64 (s, 2H), 6.82 (d, J=8.5 Hz, 2H), 7.20 (d, J=8.5 Hz, 2H), 7.30 (dd, J=8.1,4.2 Hz, 1H), 7.36–7.37 (m, 2H), 8.23 (dd, J=8.1, 1.0 Hz, 1H).

MS (ESI) m/z 297 (M$^+$+1).

(Step 2) Synthesis of 1-(4-methoxybenzyl)-3-indazolylcarboxylic acid

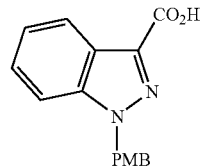

Methyl 1-(4-methoxybenzyl)-3-indazolylcarboxylate (830 mg, 2.80 mmol) was dissolved in THF (22 ml). To the resulting solution was added 0.25N NaOH (22 ml, 5.60 mmol). The resulting mixture was stirred for 15 hours at room temperature. The reaction mixture was poured in 1N HCl (50 ml), followed by extraction with chloroform (2×100 ml). The extract was dried over anhydrous magnesium sulfate and distilled under reduced pressure to remove the solvent. The residue was dissolved in chloroform and hexane was added to the resulting solution until precipitation appeared. The crystals thus precipitated were collected by filtration under reduced pressure and dried for 12 hours under reduced pressure to give 1-(4-methoxybenzyl)-3-indazolylcarboxylicacid (630 mg, 80%) as a colorless amorphous substance.

$^1$H-NMR (DMSO-$d_6$) δ: 3.70 (s, 3H), 5.69 (s, 2H), 6.88 (d, J=8.8 Hz, 2H), 7.26 (d, J=8.8 Hz, 2H), 7.29–7.32 (m, 1H), 7.43–7.48 (m, 1H), 7.84 (d, J=8.6 Hz, 1H), 8.08 (d, J=8.6 Hz, 1H), 13.06 (br s, 1H).

MS (ESI) m/z 283 (M$^+$+1).

(Step 3) Synthesis of ethyl (5-chloro-2-fluoro-4-(1-(4-methoxybenzyl)-3-indazolylcarbonylamino)phenyl)acetate

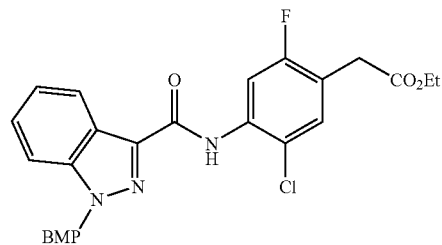

In methylene chloride (10 ml) was dissolved 1-(4-methoxybenzyl)-3-indazolylcarboxylic acid (630 mg, 2.23 mmol). To the resulting solution were added oxalyl chloride (292 μl, 3.53 mmol) and DMF (1 drop). The resulting mixture was stirred until the mixture became uniform. From the reaction mixture, the solvent was distilled off under reduced pressure. The residue was dissolved in methylene chloride (20 ml). Ethyl (4-amino-5-chloro-2-fluorophenyl) acetate (517 mg, 2.23 mmol) and triethylamine (621 μl, 4.46 mmol) were added to the resulting solution. The resulting mixture was heated under reflux for 15 hours. After cooling, the reaction mixture was added with water (50 ml), followed by extraction with chloroform (200 ml). The extract was dried over anhydrous magnesium sulfate and distilled under reduced pressure to remove the solvent. The residue was purified by chromatography on a silica gel column, whereby from hexane-ethyl acetate (4:1) eluate fractions, ethyl (5-chloro-2-fluoro-4-(1-(4-methoxybenzyl)-3-indazolylcarbonylamino)phenyl)acetate (881 mg, 80%) was obtained as a pale yellow amorphous substance.

¹H-NMR (CDCl₃) δ: 1.27 (t, J=7.1 Hz, 3H), 3.62 (s, 2H), 3.77 (s, 3H), 4.19 (q, J=7.1 H, 2H), 5.59 (s, 2H), 6.85 (d, J=8.8 Hz, 2H), 7.22 (d, J=8.8 Hz, 2H), 7.24–7.42 (m, 4H), 8.39 (d, J=8.1 Hz, 1H), 8.54 (d, J=11.7 Hz, 1H), 9.56 (s, 1H).

MS (ESI) m/z 496 (M⁺+1).

(Step 4) Synthesis of ethyl (5-chloro-2-fluoro-4-(3-indazolylcarbonylamino)phenyl)acetate

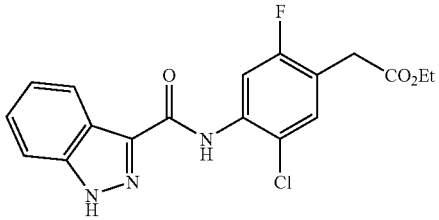

A mixture of anisole (288 μl, 2.66 mmol), trifluoroacetic acid (10 ml), and ethyl (5-chloro-2-fluoro-4-(1-(4-methoxybenzyl)-3-indazolylcarbonylamino)phenyl)acetate (880 mg, 1.77 mmol) was heated under reflux for 15 hours. After cooling, the reaction mixture was distilled under reduced pressure to remove the solvent. Water (50 ml) was added to the residue. The crystals thus precipitated were collected by filtration under reduced pressure and washed with water. The crude crystals thus obtained were recrystallized from chloroform-methanol, whereby ethyl (5-chloro-2-fluoro-4-(3-indazolylcarbonylamino)phenyl)acetate (531 mg, 80%) was obtained as a colorless crystalline powder.

¹H-NMR (DMSO-d₆) δ: 1.20 (t, J=7.1 Hz, 3H), 3.75 (s, 2H), 4.12 (q, J=7.1 Hz, 2H), 7.34 (t, J=7.8 Hz, 1H), 7.49 (dt, J=8.1,1.0 Hz, 1H), 7.63 (d, J=7.8 Hz, 1H), 7.71 (d, J=8.1 Hz, 1H), 8.16 (d, J=11.5 Hz, 1H), 8.21 (d, J=8.1 Hz, 1H), 9.79 (s, 1H).

MS (ESI) m/z 376 (M⁺+1).

(Step 5) Synthesis of (5-chloro-2-fluoro-4-(3-indazolylcarbonylamino)phenyl)acetic acid

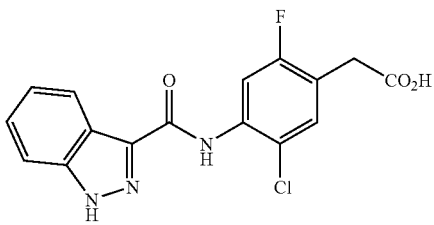

Ethyl (5-chloro-2-fluoro-4-(3-indazolylcarbonylamino) phenyl)acetate (531 mg, 1.41 mmol) was dissolved in methanol (50 ml). To the resulting solution was added 0.25N NaOH (12 ml, 3 mmol). The resulting mixture was stirred at room temperature for 15 hours. The reaction mixture was poured in 1N HCl (100 ml). The crystals thus precipitated were collected by filtration under reduced pressure, washed with water and dried under reduced pressure for 15 hours to give (5-chloro-2-fluoro-4-(3-indazolylcarbonylamino)phenyl)acetic acid (480 mg, 98%) as a colorless crystalline powder.

¹H-NMR (DMSO-₆) δ: 3.63 (s, 2H), 7.34 (t, J=7.6 Hz, 1H), 7.49 (t, J=7.6 Hz, 1H), 7.62 (m, 1H), 7.72 (d, J=8.3 Hz, 1H), 8.13 (d, J=11.2 Hz, 1H), 8.21 (d, J=8.1 Hz, 1H), 9.79 (s, 1H), 13.96 (br s, 1H).

(Step 6) Synthesis of methyl trans-4-(1-((5-chloro-2-fluoro-4-(3-indazolylcarbonylamino)phenyl)acetyl)-(4S)-fluoro-(2S)-pyrrolidinylmethoxy)cyclohexanecarboxylate

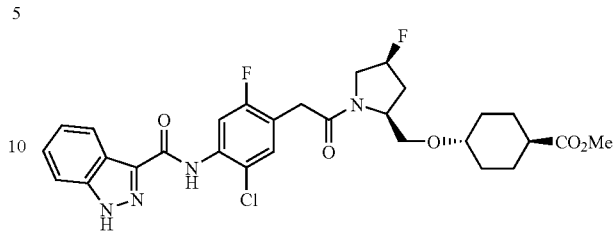

In DMF (10 ml) were dissolved (5-chloro-2-fluoro-4-(3-indazolylcarbonylamino)phenyl)acetic acid (300 mg, 0.863 mmol) and methyl trans-4-((4S)-fluoro-(2S)-pyrrolidinylmethoxy)cyclohexanecarboxylate (the compound synthesized in (Step 3) of Example 21) (224 mg, 0.863 mmol). To the resulting solution were added EDC HCl (248 mg, 1.29 mmol), HOBt (catalytic amount), and DMAP (catalytic amount). The resulting mixture was stirred at room temperature for 15 hours. To the reaction mixture were added ethyl acetate (200 m) and water (200 ml). The ethyl acetate layer was washed with saturated brine (2×100 ml), dried over anhydrous magnesium sulfate, and distilled under reduced pressure to remove the solvent. The residue was purified by chromatography on a silica gel column, whereby from chloroform-methanol (20:1) eluate fractions, trans-4-(1-((5-chloro-2-fluoro-4-(3-indazolylcarbonylamino)phenyl)acetyl)-(4S)-fluoro-(2S)-pyrrolidinylmethoxy)cyclohexanecarboxylate (223 mg, 44%) was obtained as a colorless solid.

¹H-NMR (DMSO-d₆) δ: 1.20–1.35 (m, 2H), 1.36–1.54 (m, 2H), 1.96–2.12 (m, 4H), 2.20–2.58 (m, 3H), 3.24–4.12 (series of m, 10H), 4.36 and 4.47 (m, each, total 1H, due to double bond character of the C(O)—N bond in amide), 5.25 and 5.38 (m, each, total 1H, due to double bond character of the C(O)—N bond in amide), 7.26 (m, 1H), 7.36–7.40 (m, 1H), 7.47–7.49 (m, 1H), 8.20 (t, J=13.4 Hz, 1H), 8.33 (d, J=8.1 Hz, 1H), 9.50 (d, J=8.1 Hz, 1H), 11.7 (s, 1H).

MS (ESI) m/z 589 (M⁺+1).

(Step 7) Synthesis of trans-4-(1-((5-chloro-2-fluoro-4-(3-indazolylcarbonylamino)phenyl)acetyl)-(4S)-fluoro-(2S)-pyrrolidinylmethoxy)cyclohexanecarboxylic acid

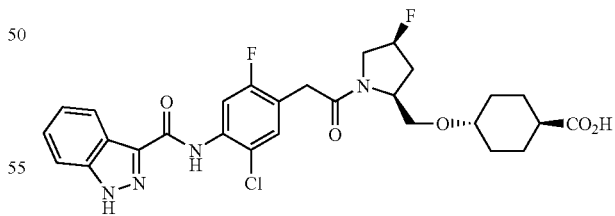

Methyl trans-4-(1-((5-chloro-2-fluoro-4-(3-indazolylcarbonylamino)phenyl)acetyl)-(4S)-fluoro-(2S)-pyrrolidinylmethoxy)cyclohexanecarboxylate (223 mg, 0.379 mmol) was dissolved in THF (5 ml). To the resulting solution was added 0.25N NaOH (4 ml, 1 mmol). The resulting mixture was stirred at room temperature for 15 hours. The reaction mixture was poured in 1N HCl (100 ml), followed by extraction with a chloroform-methanol mixture (5:1, 2×100 ml). The extract was dried over anhydrous magnesium sulfate and distilled under reduced pressure to remove the solvent. The residue was purified by chromatography on a silica gel column, whereby from chloroform-methanol (10:1 to 5:1) eluate fractions, the title compound (125 mg, 57%) was obtained as a colorless amorphous substance.

¹H-NMR (DMSO-d₆) δ: 1.17–1.38 (m, 4H), 1.86–2.23 (series of m, 7H), 3.17–4.37 (series of m, 8H), 5.26–5.49 (m, 1H), 7.34 (t, J=7.6 Hz, 1H), 7.48–7.53 (m, 2H), 7.72 (d, J=8.3 Hz, 1H), 8.12 (dd, J=11.5,4.9 Hz, 1H), 8.22 (d, J=8.3 Hz, 1H), 9.79 (s, 1H), 13.90 (br s, 1H).

MS (ESI) m/z 575 (M⁺+1);

Anal. Calcd for C₂₈H₂₉ClF₂N₄O₅: C, 58.49; H, 5.08; N, 9.74. Found: C, 58.32; H, 5.28; N, 9.22.

Example 173 trans-4-(1-((5-Chloro-2-fluoro-4-((1-methyl-3-indolylcarbonyl)amino)phenyl)acetyl)-(5R)-isopropyl-(2S)-pyrrolidinylmethoxy)cyclohexanecarboxylic acid (Step 1) Synthesis of benzyl (2S)-(N-(tert-butoxycarbonyl)amino-6-methyl-5-oxo)heptanoate

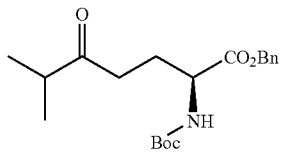

In THF (60 ml), isopropylmagnesium chloride (a 2.0M ether solution, 15.0 ml, 30.0 mmol) was added to benzyl 1-(tert-butoxycarbonyl)-L-pyroglutamate (8.02 g, 25.1 mmol) under stirring at –78° C. After stirring at the same temperature for 2.5 hours, the reaction mixture was acidified with a saturated aqueous solution of ammonium chloride and 1N HCl at the same temperature. The resulting mixture was stirred at room temperature for 14 hours. The reaction mixture was concentrated under reduced pressure to remove the solvent, followed by extraction with ethyl acetate. The extract was washed with saturated brine, dried over anhydrous magnesium sulfate, and distilled under reduced pressure to remove the solvent. The residue was purified by Biotage's flash column chromatography on silica gel, whereby from n-hexane/ethyl acetate (6:1, v/v) eluate fractions, benzyl (2S)-((tert-butoxycarbonyl)amino-6-methyl-5-oxo)heptanoate (1.79 g, 20%) was obtained as a pale yellow oil.

¹H-NMR (CDCl₃) δ: 1.05 (d, J=7.0 Hz, 6H), 1.43 (s, 9H), 1.92 (m, 1H), 2.10 (m, 1H), 2.42–2.58 (m, 3H), 4.31 (m, 1H), 5.09 (m, 1H), 5.13 and 5.20 (AB q, J=12.2 Hz, 2H), 7.35 (m, 5H);

MS (ESI) m/z 364 (M⁺+1).

(Step 2) Synthesis of (5S)-benzyloxycarbonyl-2-isopropyl-1-pyrrolidine hydrochloride

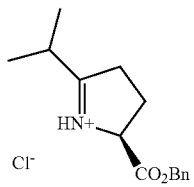

To benzyl (2S)-((tert-butoxycarbonyl)amino-6-methyl5-oxo)heptanoate (3.83 g, 10.5 mmol) was added 4.0N HCl (a dioxane solution, 6 ml). The resulting mixture was stirred for 3 hours at room temperature. The reaction mixture was distilled under reduced pressure to remove the solvent to give (5S)-benzyloxycarbonyl-2-isopropyl-1-pyrrolidine hydrochloride (3.05 g, 100%) as a brown oil.

¹H-NMR (CDCl₃) δ: 1.35 (d, J=7.2 Hz, 6H), 3.48 (m, 1H), 2.72 (m, 1H), 2.42–2.58 (m, 3H), 3.56 (m, 1H), 5.21 and 5.25 (AB q, J=7.7 Hz, 2H), 7.33–7.41 (m, 5H).

(Step 3) Synthesis of 1-(tert-butoxycarbonyl)-(5R)-isopropyl-L-proline

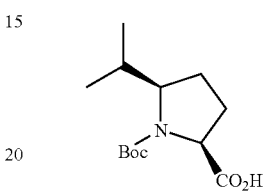

In ethanol (20 ml) was dissolved (5S)-benzyloxycarbonyl-2-isopropyl-1-pyrrolidine hydrochloride (3.05 g, 10.5 mmol). To the resulting solution was added 10% palladium-carbon (750 mg) and the mixture was subjected to catalytic hydrogenation at room temperature under normal pressure for 18 hours. After removal of the catalyst by filtration, the filtrate was distilled under reduced pressure to remove the solvent, whereby a brown solid was obtained. The resulting product was dissolved in acetonitrile-water (1:1, v/v, 50 ml). To the resulting solution were added di-tert-butyl dicarbonate (2.29 g, 10.5 mmol) and triethylamine (2.93 ml, 21.0 mmol) and the mixture was stirred at room temperature for 2 hours. The reaction mixture was concentrated under reduced pressure to remove the solvent. To the residue was added 1N HCl, followed by extraction with ethyl acetate. The extract was washed with saturated brine, dried over anhydrous magnesium sulfate, and distilled under reduced pressure to remove the solvent. The residue was purified by chromatography on a silica gel column, whereby from n-hexane/ethyl acetate (1:1, v/v) eluate fractions, 1-(tert-butoxycarbonyl)-(5R)-isopropyl-L-proline (2.18 g, 81%) was obtained as a white solid.

¹H-NMR (CDCl₃) δ: 0.91 (m, 6H), 1.48 (s, 9H), 1.80–1.86 (m, 2H), 1.95–2.35 (series of m, total 4H), 3.73 (m, 1H), 4.34 (br s, 1H).

MS (ESI) m/z 258 (M⁺+1).

(Step 4) Synthesis of 1-(tert-butoxycarbonyl)-(5R)-isopropyl-(2S)-pyrrolidinylmethanol

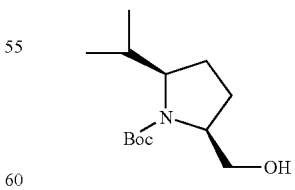

In THF (40 ml) was dissolved 1-(tert-butoxycarbonyl)-(5R)-isopropyl-L-proline (2.18 g, 8.48 mmol). To the resulting solution was added borane-dimethyl sulfide (1.70 ml, 17.0 mmol). The resulting mixture was stirred at 60° C. for 2 hours. The reaction mixture was added with water at 0° C. and then, distilled under reduced pressure to remove the solvent. To the residue was added 1N HCl, followed by extraction with ethyl acetate. The extract was washed with saturated brine, dried over anhydrous magnesium sulfate, and distilled under reduced pressure to remove the solvent. The residue was purified by chromatography on a silica gel column, whereby from n-hexane/ethyl acetate (3:1, v/v) eluate fractions, 1-(tert-butoxycarbonyl)-(5R)-isopropyl (2S)-pyrrolidinylmethanol (530 mg, 96%) was obtained as a colorless oil.

$^1$H-NMR (CDCl$_3$) δ: 0.86 (d, J=6.8 Hz, 3H), 0.92 (d, J=6.8 Hz, 3H), 1.47 (s, 9H), 1.65 and 1.67 (s, total, 1H), 1.74 (m, 3H), 1.99 (m, 1H), 3.52 (t, J=9.6 Hz, 1H), 3.66 (m, 2H), 4.00 (m, 1H), 5.06 (m, 1H).

MS (ESI) m/z 244 (M$^+$+1).

(Step 5) Synthesis of methyl 4-(1-(tert-butoxycarbonyl)-(5R)-isopropyl-(2S)-pyrrolidinylmethoxy)benzoate

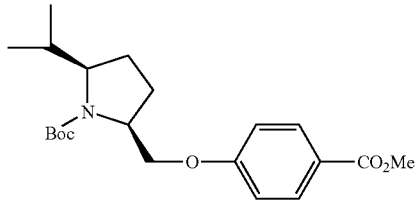

In THF (30 ml), DIAD (1.85 ml, 9.39 mmol) was added dropwise to 1-(tert-butoxycarbonyl)-(5R)-isopropyl-(2S)-pyrrolidinylmethanol (1.90 g, 7.81 mmol), triphenylphosphine (2.46 ml, 9.38 mmol), and methyl 4-hydroxybenzoate (1.19 g, 7.82 mmol). After completion of the dropwise addition, the reaction mixture was stirred at room temperature for 14 hours. From the reaction mixture, the solvent was distilled off under reduced pressure. The residue was purified by chromatography on a silica gel column, whereby from n-hexane/ethyl acetate (4:1, v/v) eluate fractions, methyl 4-(1-(tert-butoxycarbonyl)-(5R)-isopropyl-(2S)-pyrrolidinylmethoxy)benzoate (2.97 g, 100%) was obtained as a pale yellow oil.

$^1$H-NMR (CDCl$_3$) δ: 0.86 and 0.90 (d, J=6.8 Hz, total 6H, due to double bond character of C(O)—N bond in amide), 1.26–1.44 (m, 1H), 1.47 (s, 9H), 1.79 (m, 2H), 1.98 (m, 3H), 3.63 (m, 1H), 3.88 (s, 3H), 4.16 (m, 1H), 4.23 (m, 1H), 6.94 (d, J=8.8 Hz, 2H), 7.97 (d, J=8.8 Hz, 2H).

MS (ESI) m/z 378 (M$^+$+1).

(Step 6) Synthesis of methyl 4-(1-(tert-butoxycarbonyl)-(5R)-isopropyl-(2S)-pyrrolidinylmethoxy)cyclohexanecarboxylate

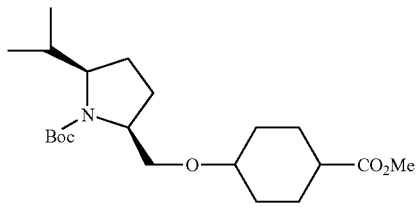

Methyl 4-(1-(tert-butoxycarbonyl)-(5R)-isopropyl-(2S)-pyrrolidinylmethoxy)benzoate (2.97 g, 7.81 mmol) was dissolved in methylene chloride (15 ml). To the resulting solution was added trifluoroacetic acid (3.5 ml). After stirring for 3 hours at room temperature, the reaction mixture was distilled under reduced pressure to remove the solvent, whereby a yellow oil was obtained. The resulting yellow oil was dissolved in ethanol (35 ml). To the resulting solution was added rhodium-alumina (1.40 g) and catalytic hydrogenation was effected for 14 hours under a hydrogen gas of 12 atm. After removal of the catalyst by filtration, the filtrate was distilled under reduced pressure to remove the solvent, whereby a pale brown solid (1.60 g) was obtained. The resulting compound was dissolved in acetonitrile-water (1:1, v/v, 40 ml). To the resulting solution were added di-tert-butyl dicarbonate (1.23 g, 5.63 mmol) and triethylamine (786 µl, 5.64 mmol) and the mixture was stirred at room temperature for 2 hours. The reaction mixture was concentrated under reduced pressure to remove the solvent. To the residue was added 1N HCl, followed by extraction with ethyl acetate. The extract was washed with a saturated aqueous solution of sodium bicarbonate, dried over anhydrous magnesium sulfate, and distilled under reduced pressure to remove the solvent, whereby methyl 4-(1-(tert-butoxycarbonyl)-(5R)-isopropyl-(2S)-pyrrolidinylmethoxy)cyclohexanecarboxylate (a pale yellow oil, 2.18 g, 100%) was obtained as a mixture of cis-trans isomers (ca 4:1, determined from $^1$H-NMR spectrum).

$^1$H-NMR (CDCl$_3$) δ: 0.81 and 0.88 (d, J=6.8 Hz, total 6H, due to double bond character of C(O)—N bond in amide), 1.45 (s, 9H), 1.47–1.74 (series of m, total 4H), 1.79–1.92 (series of m, total 6H), 2.04 (s, 3H), 2.34 (m, 1H), 3.23 (m, 1H), 3.47 (m, 1H), 3.56 (m, 2H), 3.67 (s, 3H), 3.91 (m, 1H).

(Step 7) Synthesis of methyl trans-4-((5R)-isopropyl-(2S)-pyrrolidinylmethoxy)cyclohexanecarboxylate

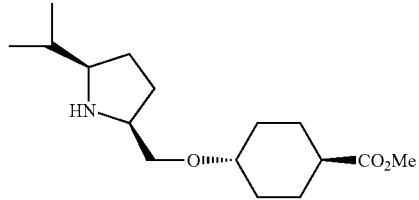

Methyl 4-(1-(tert-butoxycarbonyl)-(5R)-isopropyl(2S)-pyrrolidinylmethoxy)cyclohexanecarboxylate (2.18 g, 5.54 mmol) and sodium methoxide (914 mg, 16.9 mmol) were heated under reflux for 14 hours in methanol (50 ml). After cooling to room temperature, the reaction mixture was concentrated under reduced pressure. To the residue was added 1N HCl, followed by extraction with ethyl acetate. The extract was washed with a saturated aqueous solution of sodium bicarbonate, dried over anhydrous magnesium sulfate, and distilled under reduced pressure to remove the solvent, whereby a yellow oil was obtained. The resulting oil was dissolved in benzene (40 ml) and methanol (10 ml). To the resulting solution was added a 2M hexane solution (1.4 ml, 2.8 mmol) of trimethylsilyldiazomethane and the resulting mixture was stirred at room temperature for 2 hours. After addition of acetic acid (500 µl, 0.30 mmol), the solvent was distilled off under reduced pressure. The residue was purified by chromatography on a silica gel column, whereby from n-hexane/ethyl acetate (6:1) eluate fractions, a trans isomer was obtained as a pale yellow oil (740 mg). The resulting product was dissolved in methylene chloride (12 ml). To the resulting solution was added trifluoroacetic acid (3 ml), and the mixture was stirred at room temperature for 2 hours. From the reaction mixture, the solvent was distilled off under reduced pressure. The residue was neutralized with a saturated aqueous solution of sodium bicarbonate, followed by extraction with chloroform-methanol (5:1, v/v). The extract was washed with saturated brine, dried over anhydrous magnesium sulfate, and distilled under reduced pressure to remove the solvent, whereby methyl trans-4-((5R)-isopropyl-(2S)-pyrrolidinylmethoxy)cyclohexanecarboxylate (567 mg, 35%) was obtained as a pale yellow solid.

$^1$H-NMR (CDCl$_3$) δ: 0.97 (d, J=6.4 Hz, 3H), 1.11 (d, J=6.4 Hz, 3H), 1.25 (m, 2H), 1.47 (m, 2H), 1.72 (m, 1H), 1.81 (m, 1H), 1.89–2.11 (series of m, total 7H), 2.26 (tt, J=11.6,3.6 Hz, 1H), 3.17 (m, 1H), 3.33 (tt, J=10.4,3.6 Hz, 1H), 3.64 (m, 1H), 3.66 (s, 3H), 3.76 (m, 2H).

MS (ESI) m/z 284 (M$^+$+1).

(Step 8) Synthesis of methyl trans-4-(1-((5-chloro-2-fluoro-4-((1-methyl-3-indolylcarbonyl)amino)phenyl)acetyl)-(5R)-isopropyl-(2S)-pyrrolidinylmethoxy)cyclohexanecarboxylate

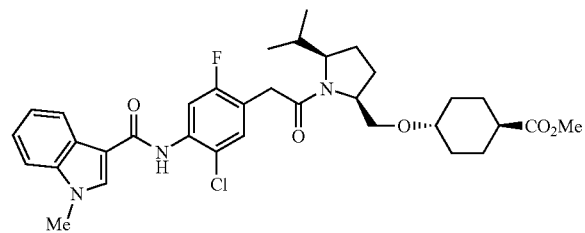

In DMF (5 ml), EDC HCl (151 mg, 0.81 mmol), HOBt (2.5 mg, 0.02 mmol), and DMAP (2.5 mg, 0.02 mmol) were added to (5-chloro-2-fluoro-4-((1-methyl-3-indolylcarbonyl)amino)phenyl)acetic acid (171 mg, 0.54 mmol) and methyl trans-4-((5R)-isopropyl-(2S)-pyrrolidinylmethoxy) cyclohexanecarboxylate (152 mg, 0.54 mmol) and the resulting mixture was stirred at room temperature for 14 hours. Water was added to the reaction mixture, followed by extraction with ethyl acetate. The extract was washed with saturated brine, dried over anhydrous magnesium sulfate, and distilled under reduced pressure to remove the solvent. The residue was purified by chromatography on a silica gel column, whereby from chloroform-methanol (40:1, v/v) eluate fractions, methyl trans-4-(1-((5-chloro-2-fluoro-4-((1-methyl-3-indolylcarbonyl)amino)phenyl)acetyl)-(5R)-isopropyl-(2S)-pyrrolidinylmethoxy)cyclohexanecarboxylate (159 mg, 50%) was obtained as a pale yellow oil.

IR (ATR) ν 2945, 1730, 1637, 1514, 1400 cm$^{-1}$;

$^1$H-NMR (CDCl$_3$) δ: 0.73 and 0.87 (d, J=6.8 Hz, total 3H, due to double bond character of C(O)—N bond in amide), 0.81 and 0.94 (d, J=6.8 Hz, total 3H, due to double bond character of C(O)—N bond in amide), 1.19 (m, 2H), 1.39 (m, 2H), 1.64 (m, 1H), 1.84–2.00 (series of m, total 6H), 1.96 (s, 3H), 2.21 (m, 1H), 2.28 (m, 1H), 3.16 (m, 1H), 3.34 (m, 2H), 3.45 (m, 1H), 3.58 (s, 3H), 3.71 (m, 1H), 3.96 (m, 1H), 4.08 (m, 2H), 7.25 (m, 2H), 7.30 (m, 2H), 7.69 (m, 1H), 8.05 (dd, J=6.0, 2.8 Hz, 1H), 8.18 (s, 1H), 8.39 and 8.41 (d, J=12.0 Hz, total 1H, due to double bond character of C(O)—N bond in amide).

MS (ESI) m/z 626 (M$^+$+1);

Anal. Calcd for C$_{34}$H$_{41}$ClFN$_3$O$_5$ 0.75 H$_2$O: C, 63.84; H, 6.70; N, 6.57. Found: C, 63.66; H, 6.59; N, 6.54.

(Step 9) Synthesis of trans-4-(1-((5-chloro-2-fluoro-4((1-methyl-3-indolylcarbonyl)amino)phenyl)acetyl)-(5R)-isopropyl-(2S)-pyrrolidinylmethoxy)cyclohexanecarboxylic acid

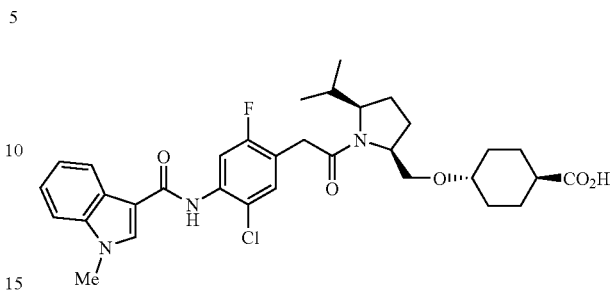

In THF (2 ml) and methanol (1 ml) was dissolved methyl trans-4-(1-((5-chloro-2-fluoro-4-((1-methyl-3-indolylcarbonyl)amino)phenyl)acetyl)-(5R)-isopropyl-(2S)-pyrrolidinylmethoxy)cyclohexanecarboxylate (100 mg, 0.16 mmol). To the resulting solution was added 0.25N NaOH (2 ml), and the resulting mixture was heated under reflux for 2 hours at room temperature. After cooling to room temperature, the reaction mixture was concentrated under reduced pressure to remove the solvent. The concentrate was acidified with 1N HCl. The crystals thus precipitated were collected by filtration under reduced pressure, washed with water and dried under reduced pressure to give the title compound (81 mg, 83%) as a white solid.

IR (ATR) ν 2937, 1724, 1620, 1514, 1402 cm$^{-1}$;

$^1$H-NMR (DMSO-d$_6$) δ: 0.75 and 0.90 (d, J=6.4 Hz, total 3H, due to double bond character of C(O)—N bond in amide), 0.80 and 0.96 (d, J=6.4 Hz, total 3H, due to double bond character of C(O)—N bond in amide), 1.13–1.23 (m, 3H), 1.33 (m, 2H), 1.71 (m, 2H), 1.88 (m, 4H), 1.98 (m, 2H), 2.11 (m, 1H), 2.21 (m, 1H), 3.21 (m, 3H), 3.72 (m, 2H), 4.16 (m, 1H), 7.18 (t, J=7.2 Hz, 1H), 7.32 (d, J=7.2 Hz, 1H), 7.47 (d, J=8.0 Hz, 1H), 7.75 (d, J=11.2 Hz, 1H), 8.12 (d, J=7.6 Hz, 1H), 8.24 (s, 1H), 9.07 (s, 1H).

MS (ESI) m/z 612 (M$^+$+1);

Anal. Calcd for C$_{33}$H$_{39}$ClF$_2$N$_3$O$_5$: C, 64.75; H, 6.42; N, 6.86. Found: C, 64.54; H, 6.50; N, 6.73.

Test 1: In vitro Evaluation of Test Compounds

In vitro Evaluation Test (1)

CHO cells forcedly expressed by the transduction of integrins haα$_4$ and β$_1$ were seeded in a Coster 3599 plate (3×10$^4$ cells/100 μl/well) and they were cultured for 2 days. After the medium was washed with buffer A* twice, 50 μl/well of Eu$^{3+}$-hVCAM-1 D1D7-IgG diluted to 2 riM with an assay buffer ** was added. To the resulting well was added 50 μl/well of a test compound diluted with 2% DMS0-assay buffer (in the presence or absence of 6% human serum albumin) (to a well subjected to Scatchard analysis was added a solution diluted in another manner). After stirring for 5 minutes on a plate mixer, the plate was allowed to stand at room temperature for 1 hour. Then, the plate was washed four times with the buffer A and added with 100 μl/well of an enhancement reagent (DELFIA). The plate was shaken for 5 minutes on a plate mixer, followed by measurement of fluorescence intensity by a time-resolved fluorometer (DELFIA Wallac). From the binding ratio available by the following calculation formula: $((F_T - F_{NS}) - (F_T - F_{NS}))/(F_T - F_{NS}) \times 100$, the IC$_{50}$ (concentration inhibiting 50% of binding of CHO cells with hVCAM-1 D1D7-IgG) of the test compound was determined. In the above formula, F$_T$ means the fluorescence intensity of the well free of the test compound, $F_{NS}$ means the fluorescence intensity of the well free of the test compound and anti-hα$_4$ antibody (SG/73), and $F_I$ means the fluorescence intensity of the well containing the test compound. The Kd indicating the binding strength and Bmax (maximum binding) were estimated within a range of 0.06 to 20 nM in accordance with the Scatchard analysis method. The results are shown in Table 1.

The value Ki was calculated based on:

$$Ki = \frac{IC_{50}}{1 + \frac{[L]}{Kd}}$$

((L) means a ligand concentration).

(* buffer A: 25 mM HEPES (pH 7.5), 150 mM NaCl, 1 mM Ca$^{2+}$, 1 MM Mg$^{2+}$, 4 mM Mn$^{2+}$; ** assay buffer: 25 mM HEPES (pH 7.5), 150 mM NaCl, 1 mM Ca$^{2+}$, 1 mM Mg$^{2+}$, 4 mM Mn$^{2+}$, 0.1% BSA, 20 μM DTPA, with/without 6% ALBUMIN, HUMAN SERUM (C/N A-1653, SIGMA))

In vitro Evaluation Test (2)

In a 96-well microplate, hVCAM-1 D1D7-IgG (600 ng/ml in TSM) was immobilized at 4° C. (50 μl/well). After blocking by the addition of 100 μl/well of a 2% BSA-TSM solution, 150 μl/well (2.1×10$^5$/well) of Jurkat cells labeled with BCECF-AM and 50 μl/well of a test compound were added and the plate was allowed to stand at 37° C. for 1 hour. The test compound was adjusted to have a final concentration of 0.1 ng/ml to 100 ng/ml (0.5% DMSO). The well was filled with the below-described medium and sealed with a plate seal (product of Sumitomo Bakelite). The plate was then turned inside out and allowed to stand at room temperature for 30 minutes. Then, unbound cells were removed. After suction of the medium, the cells were solubilized with a 0.1% NP-40 solution and fluorescence intensity was measured by a fluorescence reader (excited at 485 nm/measured at 550 nM). From the binding ratio available by the following formula: $((F_T-F_{NS})-(F_I-F_{NS}))/(F_T-F_{NS})\times100$, the IC$_{50}$ (concentration inhibiting 50% of the binding of hVCAM-1 D1D7-IgG with Jarkat cells) of the test compound was determined. In the above equation, $F_T$ means the fluorescence intensity of the well free of the test compound, $F_{NS}$ means the fluorescence intensity of the well free of the test compound and hVCAM-1 D$_1$D7-IgG, and $F_I$ means the luorescence intensity of the well containing the test compound.

(TMS: 25 mM Tris-HCl (pH 8.0)-150 mM NaCl-2 mM MgCl$_2$; medium: RPMI (FACS-free); BCEFC-AM (Dojin Kagaku))

TABLE 1

| Example | Ki (nM) |
|---|---|
| 1 | 30 |
| 2 | 17 |
| 3 | 40 |
| 6 | 14 |
| 7 | 7.1 |
| 8 | 24 |
| 15 | 2.2 |
| 18 | 7.8 |
| 20 | 3.9 |
| 21 (Isomer G) | 382 |

TABLE 1-continued

| Example | Ki (nM) |
|---|---|
| 21 (Isomer H) | 2.5 |
| 22 (Isomer B) | 3.5 |
| 24 (Isomer A) | 14 |
| 25 (Isomer A) | 18 |
| 26 (Isomer A) | 2 |
| 30 | 40 |
| 31 | 16 |
| 33 | 31 |
| 34 | 26 |
| 36 | 1.5 |
| 37 | 6.9 |
| 38 | 0.43 |
| 39 | 2.1 |
| 40 | 1.9 |
| 41 | 3.8 |
| 43 | 6 |
| 44 | 2 |
| 45 | 8.8 |
| 46 | 37 |
| 47 | 5.8 |
| 49 | 4.4 |
| 50 | 13 |
| 52 | 10 |
| 53 | 32 |
| 54 | 5.6 |
| 55 | 8.5 |
| 56 | 2.1 |
| 57 | 7.3 |
| 59 | 7.2 |
| 60 | 6.3 |
| 61 | 2.3 |
| 62 | 3.4 |
| 63 | 3.1 |
| 64 | 0.31 |
| 65 | 4 |
| 69 | 34 |
| 70 | 7.2 |
| 71 | 18 |
| 72 | 4.4 |
| 73 | 51 |
| 74 | 7.7 |
| 75 | 21 |
| 76 | 1.6 |
| 78 | 14 |
| 79 | 4.5 |
| 80 | 12 |
| 81 | 25 |
| 82 | 18 |
| 83 | 1.9 |
| 85 | 6.4 |
| 87 | 9.1 |
| 89 | 3.6 |
| 91 | 2 |
| 92 | 2.7 |
| 95 | 34 |
| 96 | 20 |
| 98 | 3.6 |
| 99 | 17 |
| 100 | 5.5 |
| 101 | 8.1 |
| 102 | 47 |
| 104 | 20 |
| 105 | 42 |
| 107 | 11 |
| 108 | 21 |
| 109 | 25 |
| 110 | 7 |
| 111 | 2.6 |
| 112 | 6.5 |
| 114 | 4.8 |
| 115 | 30 |
| 116 | 2.5 |
| 117 | 5.1 |
| 118 | 6.9 |
| 119 | 5.9 |
| 120 | 1.9 |
| 121 | 3.9 |

TABLE 1-continued

| Example | Ki (nM) |
| --- | --- |
| 122 | 29 |
| 123 | 5.8 |
| 124 | 1.4 |
| 125 | 6.5 |
| 126 | 2 |
| 127 | 9.7 |
| 128 | 2.7 |
| 129 | 1.5 |
| 130 | 8.8 |
| 131 | 17 |
| 133 | 22 |
| 134 | 3.1 |
| 135 | 19 |
| 136 | 5.4 |
| 137 | 5.6 |
| 138 | 15 |
| 139 | 9.1 |
| 140 | 1.8 |
| 141 | 21 |
| 142 | 18 |
| 143 | 17 |
| 144 | 48 |
| 145 | 18 |
| 146 | 21 |
| 147 | 40 |
| 150 | 10 |
| 151 | 37 |
| 155 | 20 |
| 156 | 43 |
| 159 | 47 |
| 160 | 61 |
| 163 | 39 |
| 164 | 6.4 |
| 165 | 2.9 |
| 166 | 7.9 |
| 167 | 0.87 |
| 168 | 59 |
| 169 | 16 |
| 170 | 4.3 |
| 171 | 5 |
| 172 | 6.8 |
| 173 | 10 |

Test 2: In vivo Evaluation of Test Compounds

Transmigration Test of Eosinophils in the Mice Actively Sensitized with ascaris (*Ascaris suum* Antigen in Pigs):

It has been reported that eosinophil transmigration was induced by active sensitization with ascaris (Int. Arch. Immunol., 8, 11–18(1995)). Test compounds were evaluated in accordance with the method described in this literature. Test compounds were each orally or subcutaneously administered two or three times a day. The total cell count and eosinophil count in BALF 48 hours after sensitization were calculated and effects were compare between the test-compound-administered group and a test-compound-free group.

Inhibitory Action Against Pleurisy of Rat Sensitized with Compound 48/80:

By intrapleurally inoculating 7-week-old male CD/IGS rats (Charles River Japan) with 50 μg of Compound 48/80 (Sigma), pleurisy was caused. The pleural exudate for 24 hours was collected together with the buffer and the number of eosophils in the exudate was counted. The test compound was orally or subcutaneously administered once or twice by using a proper solvent such as 0.5% MC (aqueous solution of methyl cellulose). Effects of it were compared with those of a test-compound-free group.

Test 3: Evaluation of Oral Bioavailability by Mouse Bioassay

A test compound was suspended or dissolved in a proper administration medium to give a concentration of 1 mg/ml. To 7 to 9 week old female Balb/C mice, 10 mg/kg of the resulting suspension or solution was orally administered. Fifteen minutes after the administration, blood was collected from the postcava under anesthesia with ether and the serum was separated from it. The concentration of each test compound was determined by estimating the serum level from a calibration curve obtained with VCAM-1/VLA-4 inhibitory activity as an index or measuring the concentration by using LC/MS/MS. The results are shown in Table 2.

TABLE 2

Mouse Bioassay Evaluation Results

| Example No. | Dose/kg | Blood level (ng/ml) |
| --- | --- | --- |
| 25 (Isomer A) | 10 | 1094 |
| 24 (Isomer A) | 10 | 2179 |
| 36 | 10 | 1099 |
| 37 | 10 | 3687 |
| 39 | 10 | 5157 |
| 43 | 10 | 1194 |
| 44 | 10 | 912 |
| 49 | 10 | 508 |
| 55 | 10 | 2029 |
| 61 | 10 | 3316 |
| 62 | 10 | 3196 |
| 63 | 10 | 8551 |
| 65 | 10 | 11473 |
| 70 | 10 | 2803 |
| 71 | 10 | 7339 |
| 72 | 10 | 1878 |
| 74 | 10 | 14058 |
| 79 | 10 | 9372 |
| 83 | 10 | 1536 |
| 87 | 10 | 15144 |
| 89 | 10 | 10871 |
| 91 | 10 | 2957 |
| 92 | 10 | 1987 |
| 98 | 10 | 2211 |
| 100 | 10 | 533 |
| 101 | 10 | 3144 |
| 114 | 10 | 3450 |
| 115 | 10 | 888 |
| 116 | 10 | 9405 |
| 117 | 10 | 2927 |
| 118 | 10 | 5733 |
| 121 | 10 | 4406 |
| 123 | 10 | 705 |
| 125 | 10 | 2570 |
| 130 | 10 | 3591 |
| 136 | 10 | 2504 |
| 138 | 10 | 1264 |
| 139 | 10 | 2428 |
| 141 | 10 | 8824 |
| 155 | 10 | 571 |
| 164 | 10 | 2301 |
| 165 | 10 | 816 |
| 166 | 10 | 3068 |
| 169 | 10 | 21769 |
| 170 | 10 | 3363 |
| 171 | 10 | 2732 |
| 172 | 10 | 848 |
| 173 | 10 | 3473 |

Evaluation Example 4: Tests on Pharmacokinetics and Oral Bioavailability

The pharmacokinetic parameter of the test compound orally administered to rats or dogs are described below. The results are shown in Table 3.

TABLE 3

Evaluation of pharmacokinetics and oral bioavailability

| Tested | Example | Dose/kg | AUC[1] (ng · h/ml) | F[2] (%) | CLtot[3] (mL/min/kg) |
|---|---|---|---|---|---|
| Rat | 20 (Isomer A) | 2.0 | 152 | 35 | 73 |
|  | 21 (Isomer H) | 5.0 | 14931 | 52 | 3.3 |
| Dog | 20 (Isomer A) | 2.0 | 776 | 44 | 19.1 |
|  | 21 (Isomer H) | 2.0 | 759.9 | 40 | 17.9 |

[1]AUC (ng · h/ml): total area under the plasma concentration (measured by LC/MS/MS method) versus time curve;
[2]F (%): oral bioavailability;
[3]CLtot (mL/min/kg): apparent plasma clearance

INDUSTRIAL APPLICABILITY

The invention compounds or salts thereof selectively inhibit the binding of cell adhesion molecules to VLA-4 and exhibit high oral bioavailability so that they are usable as a preventive or remedy for various diseases mediated by migration and adhesion of leukocytes such as inflammatory diseases, autoimmune diseases, metastasis, bronchial asthma, rhinostenosis, diabetes, arthritis, psoriasis, multiple sclerosis, inflammatory intestinal diseases, and rejection upon transplantation. They are highly effective when orally administered and can be administered for a long period of time so that they are of high clinical utility.

The invention claimed is:

1. A compound represented by formula (I):

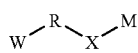

(I)

wherein W represents $W^A$-$A^1$-$W^B$- in which, $W^A$ represents a monovalent aryl group which may be substituted or a monovalent heterocyclic group which may be substituted, $A^1$ represents —$NR^1$—, a single bond, —C(O)—, —C(O)$NR^1$—, a substituted or unsubstituted vinylene group, an ethynylene group, —$CR^{1a}R^{1b}$—O—, —$CR^{1a}$=$CR^{1b}$—C(O)$NR^1$ or —$CR^{1a}$=$CR^{1b}$—C(O)— (in which, $R^1$ represents a hydrogen atom or a lower alkyl group, and $R^{1a}$ and $R^{1b}$ each independently represents a hydrogen atom or a lower alkyl group), and $W^B$ represents a divalent aryl group which may be substituted or a divalent heterocyclic group which may be substituted);

R represents a single bond, —NH—, —$OCH_2$—, an alkenylene group or —$(CH_2)_n$— (in which, n stands for 1 or 2);

X represents —C(O)—, —$CH_2$— or —$S(O)_2$—, and

M represents formula (iii)

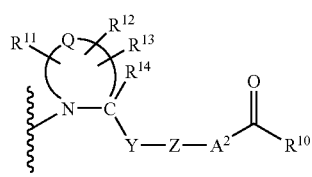

(iii)

(in which,

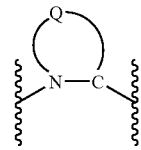

(iii-a)

represents a divalent 5-membered heterocyclic group (in which the nitrogen atom is bonded to X and Q represents a carbon), $R^{11}$, $R^{12}$ and $R^{13}$ each independently represents a hydrogen atom, a hydroxyl group, an amino group, a halogen atom, a cyano group, a carboxyl group, an alkoxycarbonyl group, a carbamoyl group, a substituted or unsubstituted mono- or dialkylaminocarbonyl group, a substituted or unsubstituted alkyl group, a substituted or unsubstituted aryl group, a substituted or unsubstituted heteroaryl group, a substituted or unsubstituted alkoxy group, a substituted or unsubstituted mono- or dialkylamino group, a substituted or unsubstituted cycloalkylamino group, a substituted or unsubstituted alkylsulfonylamino group, a substituted or unsubstituted arylsulfonylamino group, a substituted or unsubstituted aryloxy group, a substituted or unsubstituted heteroaryloxy group, a substituted or unsubstituted benzyloxy group, a substituted or unsubstituted alkylthio group, a substituted or unsubstituted cycloalkylthio group, a substituted or unsubstituted arylthio group, a substituted or unsubstituted alkylsulfonyl group, a substituted or unsubstituted cycloalkylsulfonyl group, or a substituted or unsubstituted arylsulfonyl group, or $R^{11}$ and $R^{12}$ or $R^{12}$ and $R^{13}$ may be coupled to form, together with the atom constituting the heterocyclic group to which $R^{11}$ to $R^{13}$ are bonded, a 3 to 7-membered cyclic hydrocarbon or heterocycle (which may have, on the ring thereof, 1 to 3 substituents selected from a hydroxyl group, halogen atoms, an amino group, alkyl groups, alkoxy groups, aryl groups, aryloxy groups, alkylamino groups, a benzyloxy group and heteroaryl groups), $R^{14}$ represents a hydrogen atom or a substituted or unsubstituted lower alkyl group, Y represents a single bond, —C(O)—, —C(O)NH—, or a linear or branched divalent aliphatic $C_{1-12}$ hydrocarbon group which may have a $C_{3-6}$ spiro ring or may have one or more carbon atoms substituted with —O—, —S—, —$S(O)_2$—, —C(O)— or —$NY^1$— (in which, $Y^1$ represents a hydrogen atom or a lower alkyl group), Z represents a substituted or unsubstituted arylene group, a substituted or unsubstituted heteroarylene group or a substituted or unsubstituted cycloalkylene group, $A^2$ represents a single bond, an alkenylene group, an alkynylene group, —$(CH_2)_t$— or —$O(CH_2)_v$— (in which, t stands for 1, 2 or 3 and v stands for 0, 1, 2 or 3), and $R^{10}$ represents a hydroxyl or a lower alkoxy group or salt thereof.

2. A compound or salt according to claim 1, wherein W represents formula (i):

$$W^1\text{-}A^1\text{-}W^2\text{-} \qquad (i)$$

(wherein,

W$^1$ represents a substituted or unsubstituted aryl group or a substituted or unsubstituted monovalent heterocyclic group, A$^1$ represents —NR$^1$—, a single bond, —C(O)—, —C(O)NR$^1$—, a substituted or unsubstituted vinylene group, an ethynylene group, —CR$^{1a}$R$^{1b}$—O—, —CR$^{1a}$=R$^{1b}$—C(O)NR$^1$— or —CR$^{1a}$=R$^{1b}$—C(O)— (in which, R$^1$ represents a hydrogen atom or a lower alkyl group, and R$^{1a}$ and R$^{1b}$ each independently represents a hydrogen atom or a lower alkyl group), and W$^2$ represents a substituted or unsubstituted divalent bicyclic heterocyclic group).

3. The compound or salt according to claim 2, wherein W$^2$ represents formula (i-a):

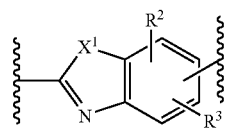

(i-a)

(wherein, the bonding on the left side is to A$^1$, the bonding on the right side is to R, X$^1$ represents an oxygen or sulfur atom, and R$^2$ and R$^3$ each independently represents a hydrogen atom, a halogen atom, a lower alkyl group, a hydroxyl group, a lower alkoxy group or an amino group, with the proviso that A$^1$ is not —NR$^1$— when W$^2$ is (i-b) or (i-c)).

4. The compound or salt according to claim 2, wherein W$^2$ is formula (i-b):

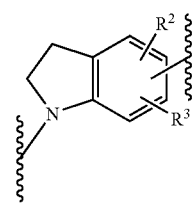

(i-b)

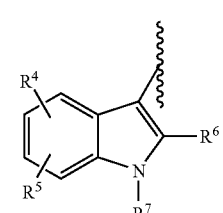

(ii-a)

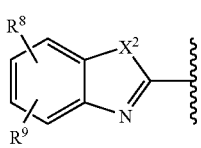

(ii-b)

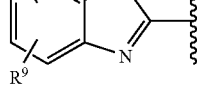

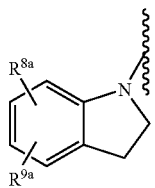

(ii-c)

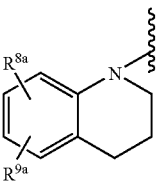

(ii-d)

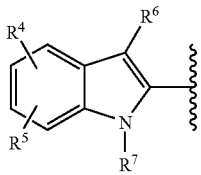

(ii-e)

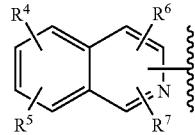

(ii-f)

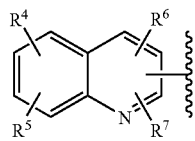

(ii-g)

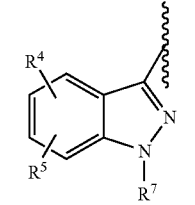

(ii-h)

(ii-i)

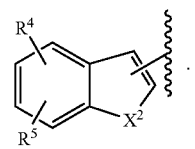

(ii-j)

5. The compound or salt according to claim 2, wherein $W^2$ is formula (i-c)

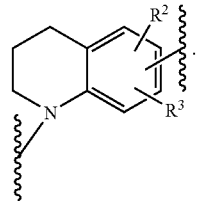

(i-c)

6. A compound or salt according to claim 1, wherein $A^1$ represents a single bond, —NH, or —C(O)NH—.

7. A compound or salt according to claim 1, wherein $W^2$ represents formula (iii-a) and the formula (iii-a) represents a pyrrolidine ring.

8. A compound or salt according to claim 1, wherein Y represents —CH$_2$O—, —CH$_2$S—, —CH$_2$S(O)$_2$—, —(CH$_2$)$_2$—, —CH=CH—, —C≡C— or —CH$_2$NY$^1$—.

9. A compound or salt according to claim 1, wherein Y represents —CH$_2$O—.

10. A compound or salt according to any one of claim 1, wherein $A^2$ represents a single bond and $R^{10}$ represents a hydroxyl or lower alkoxy group.

11. A compound or salt according to claim 3, wherein $W^2$ represents formula (i-a) and in the formula (i-a), $X^1$ represents an oxygen atom and the bonding on the right side is to R at the 6-position of benzoxazole.

12. The compound of claim 1, wherein W represents formula (ii):

$$W^3-A^1-W^4-$$ (ii)

(wherein, $W^3$ represents a substituted or unsubstituted monovalent bicyclic heterocyclic group, $A^1$ represents —NR$^1$—, a single bond, —C(O)—, —C(O)NR$^1$—, a substituted or unsubstituted vinylene group, an ethynylene group, —CR$^{1a}$R$^{1b}$—O—, —CR$^{1a}$CR$^{1b}$=C(O)NR$^1$— or —CR$^{1a}$=CR$^{1b}$—C(O)— (in which, R$^1$ represents a hydrogen atom or a lower alkyl group, and R$^{1a}$ and R$^{1b}$ each independently represents a hydrogen atom or a lower alkyl group), and $W^4$ represents a substituted or unsubstituted arylene group or a substituted or unsubstituted divalent monocyclic heterocyclic group).

13. The compound of claim 12, wherein $W^3$ represents any one of the following formulas (ii-a) to (ii-j):

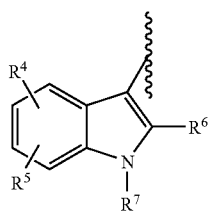

(ii-a)

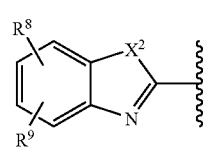

(ii-b)

-continued

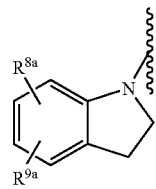

(ii-c)

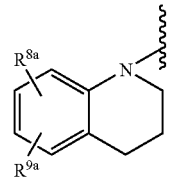

(ii-d)

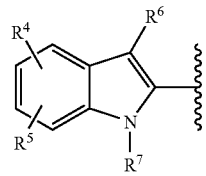

(ii-e)

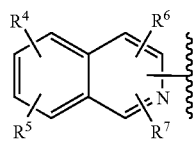

(ii-f)

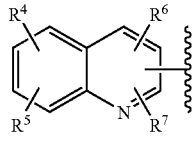

(ii-g)

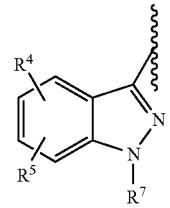

(ii-h)

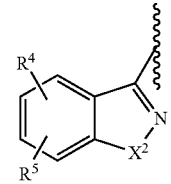

(ii-i)

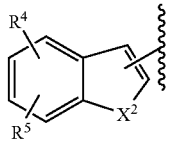

(ii-j)

(in which, $X^2$ represents an oxygen or sulfur atom, $R^4$ and $R^5$ each independently represents a hydrogen atom, a halogen atom, a lower alkyl group, a hydroxyl group, a lower alkoxy group or an amino group, $R^6$ and $R^7$ each independently represents a hydrogen atom or a lower alkyl group, and $R^8$, $R^9$, $R^{8a}$ and $R^{9a}$ each independently represents a hydrogen atom, a halogen atom, a lower alkyl group, a hydroxyl group, a lower alkoxy group or an amino group, with the proviso that when $W^3$ represents (ii-c) or (ii-d), $A^1$ does not represents —$NR^1$—).

14. A pharmaceutical composition comprising:
the compound of claim 1 or its salt, and
a pharmaceutically acceptable carrier.

15. The composition of claim 14, further comprising at least one other drug selected from the group consisting of an anti-inflammatory, anti-arthritic, adrenocortical steroid, immunosuppressant, antipsoriatic, bronchodilator, bronchial asthma drug, and antidiabetic drug(s).

16. The composition of claim 14 in a form suitable for parenteral administration.

17. The composition of claim 14 in a form suitable for oral administration.

18. A method of treating a condition, wherein said condition is selected from the group consisting of bronchial asthma, allergic rhinitis, type-1 diabetes, rheumatoid arthritis, multiple sclerosis, inflammatory bowel disease, and allograft rejection upon transplantation which is associated with VLA-4 mediated cell adhesion, said method comprising administering to a subject in need thereof an effective amount of the compound according to claim 1.

19. The method of claim 18, wherein said condition is selected from the group consisting of bronchial asthma, allergic rhinitis type 1 diabetes, rheumatoid arthritis, multiple sclerosis, inflammatory bowel disease and allograft rejection upon transplantation.

20. The method of claim 18, wherein said effective amount ranges from 0.1 mg to 1,000 mg.

21. A method for making a pharmaceutical composition comprising admixing the compound or salt of claim 1 with at least one pharmaceutically acceptable carrier.

* * * * *